US008796256B2

(12) United States Patent (10) Patent No.: US 8,796,256 B2
Bignan et al. (45) Date of Patent: Aug. 5, 2014

(54) SUBSTITUTED THIAZOLIDINEDIONE INDAZOLES, INDOLES AND BENZOTRIAZOLES AS ESTROGEN-RELATED RECEPTOR-α MODULATORS

(75) Inventors: Gilles Bignan, Bridgewater, NJ (US); Wing Cheung, Horsham, PA (US); Micheal Gaul, Yardley, PA (US); Hui Huang, Monroe, NJ (US); Xun Li, New Hope, PA (US); Raymond Patch, Yardley, PA (US); Sharmila Patel, Jamison, PA (US); Mark Player, Phoenixville, PA (US); Guozhang Xu, Bensalem, PA (US); Bao-Ping Zhao, West Windsor, NJ (US); Jian Liu, Manalapan, NJ (US)

(73) Assignee: Janssen Pharmaceutica NV, Beerse (BE)

( * ) Notice: Subject to any disclaimer, the term of this patent is extended or adjusted under 35 U.S.C. 154(b) by 559 days.

(21) Appl. No.: 13/114,084

(22) Filed: May 24, 2011

(65) Prior Publication Data
US 2011/0294780 A1 Dec. 1, 2011

Related U.S. Application Data

(60) Provisional application No. 61/347,953, filed on May 25, 2010.

(51) Int. Cl.
*C07D 417/06* (2006.01)
(52) U.S. Cl.
USPC .......... 514/210.21; 514/217.1; 514/218; 514/228.2; 514/234.2; 514/254.02; 514/304; 514/306; 514/322; 514/338; 514/369; 544/58.7; 544/74; 544/105; 544/133; 544/369; 546/133; 546/138; 546/199; 546/270.1; 548/122; 548/131; 548/134; 548/181
(58) Field of Classification Search
None
See application file for complete search history.

(56) References Cited

U.S. PATENT DOCUMENTS

| | | | |
|---|---|---|---|
| 5,811,439 A | 9/1998 | Ogawa et al. | |
| 8,263,781 B2 * | 9/2012 | Bignan et al. | 548/184 |
| 2006/0014812 A1 | 1/2006 | Player et al. | |
| 2007/0249589 A1 | 10/2007 | Aebi et al. | |

FOREIGN PATENT DOCUMENTS

| | | |
|---|---|---|
| WO | WO 98/27113 A2 | 6/1998 |
| WO | WO 2004/006846 A2 | 1/2004 |
| WO | WO 2004/007491 A1 | 1/2004 |

OTHER PUBLICATIONS

Kumar et al., "Serum glucose and triglyceride lowering activity of some novel glitazones against dexamethasone-induced hyperlipidemia and insulin resistance.", Indian Journal of Pharmacology, Dec. 2007, pp. 299-302, vol. 39(6), XP000002657538.
International Search Report relating to corresponding International Patent Application No. PCT/US2011/037571, filed May 23, 2011. Date of Mailing of International Search Report: Sep. 5, 2011.
Written Opinion of the International Searching Authority relating to corresponding International Patent Application No. PCT/US2011/037571, filed May 23, 2011. Date of Mailing of Written Opinion: Sep. 5, 2011.
Aranda et al., "Nuclear Hormone Receptors and Gene Expression.", Physiol. Rev., 2001, pp. 1269-1304, vol. 81(3).
Ariazi et al., "Estrogen-related Receptor α and Estrogen-related Receptor γ Associate with Unfavorable and Favorable Biomarkers, Respectively, in Human Breast Cancer 1.", Cancer Res., 2002, pp. 6510-6518, vol. 62.
Baicchi et al., "Synthesis, Properties, and Reactions of 1H-Indazol-3-ols and 1,2-Dihydro-3H-indazol-3-ones.", Synthesis, 1978, pp. 633-648, vol. 9.
Berge et al., "Pharmaceutical Salts.", J. Pharm. Sci., 1977, vol. 66(1), pp. 1-19.
Bonnelye et al., "Estrogen Receptor-Related Receptor α Impinges on the Estrogen Axis in Bone: Potential Function in Osteoporosis.", Endocrinology, 2002, pp. 3658-3670, vol. 143(9).

(Continued)

*Primary Examiner* — Kamal Saeed
(74) *Attorney, Agent, or Firm* — Jeremy K. McKown

(57) ABSTRACT

The present invention relates to compounds of Formula (I),

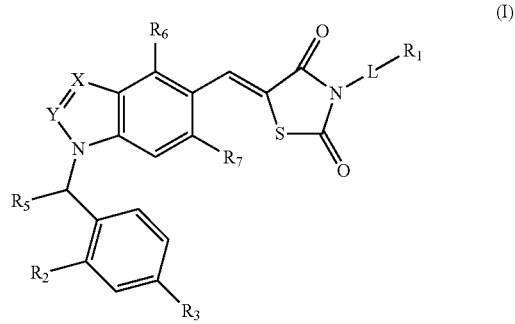

methods for preparing these compounds, compositions, intermediates and derivatives thereof and for treating a condition including but not limited to ankylosing spondylitis, atherosclerosis, arthritis (such as rheumatoid arthritis, infectious arthritis, childhood arthritis, psoriatic arthritis, reactive arthritis), bone-related diseases (including those related to bone formation), breast cancer (including those unresponsive to anti-estrogen therapy), cardiovascular disorders, cartilage-related disease (such as cartilage injury/loss, cartilage degeneration, and those related to cartilage formation), chondrodysplasia, chondrosarcoma, chronic back injury, chronic bronchitis, chronic inflammatory airway disease, chronic obstructive pulmonary disease, diabetes, disorders of energy homeostasis, gout, pseudogout, lipid disorders, metabolic syndrome, multiple myeloma, obesity, osteoarthritis, osteogenesis imperfecta, osteolytic bone metastasis, osteomalacia, osteoporosis, Paget's disease, periodontal disease, polymyalgia rheumatica, Reiter's syndrome, repetitive stress injury, hyperglycemia, elevated blood glucose level, and insulin resistance.

28 Claims, No Drawings

(56) References Cited

OTHER PUBLICATIONS

Bonnelye et al., "The ERR-1 Orphan Receptor Is a Transcriptional Activator Expressed During Bone Development.", Mol. Endocrin, 1997, pp. 905-916, vol. 11.
Bonnelye, et al., "The Orphan Nuclear Estrogen Receptor—related Receptor a (ERRα) Is Expressed throughout Osteoblast Differentiation and Regulates Bone Formation in Vitro.", J. Cell Biol. 2001, pp. 971-984, vol. 153.
Calabretta et al., "Sodium Cyanoborohydride Reduction of (Benzyloxycarbonyl)- and (tert-Butoxycarbonyl)hydrazones.", Synthesis, 1991, pp. 536-539, vol. 7.
Dess, D.B. and Martin, J.C., "A Useful as 12-I-5 Triacetoxyperiodinane (the Dess-Martin Periodinane) for the Selective Oxidation of Primary or Secondary Alcohols and a Variety of Related 12-I-5 Species[1a].", J. Am. Chem. Soc., 1991, pp. 7277-7287, vol. 113.
Geffken et al., "Synthesis and Properties of 3-Alkoxy(hydroxy)thiazolidin-2,4-diones.", Chem. Sci., 1987, pp. 1202-1206, vol. 42.
Giguere et al., "Identification of a new class of steroid hormone receptors.", Nature, 1988, pp. 91-94, vol. 331.
Giguere, V., "Orphan Nuclear Receptors: From Gene to Function*.", Endocrine Rev., 1999, pp. 689-725, vol. 20(5).
Giguere, V., "To ERR in the estrogen pathway.", Trends in Endocrinol. Metab., 2002, pp. 220-225, vol. 13.
Gould P.L., "Salt Selection for Basic Drugs.", International J. Pharm., 1986, pp. 201-217, vol. 33.
Grundy et al., "Definition of Metabolic Syndrome: Report of the National Heart, Lung, and Blood Institute/American Heart Association Conference on Scientific Issues Related to Definition.", Circulation, 2004, pp. 433-438, vol. 109(3).
Hatsuda, M. and Seki, M., "A Practical Synthesis of Highly Functionalized Aryl Nitriles Through Cyanation of Aryl Bromides Employing Heterogeneous Pd/C.", Tetrahedron Lett., 2005, pp. 1849-1853, vol. 46(11).
Hong et al., "Hormone-independent Transcriptional Activation and Coactivator Binding by Novel Orphan Nuclear Receptor ERR3*.", J. Biol. Chem. 1999, pp. 22618-22626, vol. 274.
Huskens et al., "Observation of Sterotopic Group Recognition in Chiral Borate Complexes in Solution.", Eur. J. Org. Chem. 1999, pp. 1775-1786.
Jones, P.L. and Y.B. Shi., "N-CoR-HDAC Corepressor Complexes: Roles in Transcriptional Regulation by Nuclear Hormone Receptors.", Curr. Top. Microbiol. Immunol., 2003, pp. 237-268, vol. 274.
Kamei et al., "PPARγ coactivator 1β ERR ligand 1 is an ERR protein ligand, whose expression induces a high-energy expenditure and antagonizes obesity.", Proc. Natl. Acad. Sci., 2003, pp. 12378-12383, 100(21), USA.
Korach, K. S., "Insights from the Study of Animals Lacking Functional Estrogen Receptor.", Science, Jan. 1994, pp. 1524-1527, vol. 266.
Kraus et al., "Estrogen-related Receptor α1 Actively Antagonizes Estrogen Receptor-regulated Transcription in MCF-7 Mammary Cells*.", J. Biol. Chem., 2002, pp. 24826-24834, vol. 272.
Lee, D.G., "Lean Tetraacetate.", Oxidation, vol. 1, 1969, pp. 56-80, Augustine, R.L. Editor, Marcel Dekker, New York.
Luo et al., "Reduced Fat Mass in Mice Lacking Orphan Nuclear Receptor Estrogen-Related Receptor α.", Mol. Cell. Biol., 2003, pp. 7947-7956, vol. 23(22).
March, J., *Advanced Organic Chemistry. Reactions, Mechanisms and Structure*, 2nd Ed, McGraw-Hill Co.: New York, 1977; pp. 835.
McKenna et al., "Nuclear Receptor Coregulators: Cellular and Molecular Biology.", Endocrine Rev., 1999, pp. 321-344, vol. 20.
Miller et al., "Reductions with Dialkylaluminum Hydrides.", J. Org. Chem., 1959, pp. 627-630, vol. 24.
Mitsunobu, O., "The Use of Diethyl Azodicarboxylate and Triphenylphosphine in Synthesis and Transformation of Natural Products.", Synthesis 1981, pp. 1-28, vol. 1.

Moffat, J.G., "Sulfoxide-Carbodiimide and Related Oxidations.", Oxidation, 1971, pp. 1-64, vol. 2; Augustine, R.L. and Trecker, D.J., Eds.; Marcel Dekker: New York.
Mowry, D.T., "The Preparation of Nitriles.", Chem Rev., 1948, vol. 42, pp. 189-283.
Murray, R.W. and Jeyaraman, R., "Dioxiranes: Synthesis and Reactions of Methyldiones.", J. Org. Chem, 1985, pp. 2847-2853, vol. 50(16).
Nicolaou et al., "New Uses for the Burgess Reagent in Chemical Synthesis: Methods for the Facile and Steroselective Formation of Sulfamidates, lycosylamines, and Sulfamides.", Chemistry—A European Journal, 2004, pp. 5581-5606, vol. 10(22).
Olefsky, J.M., "Minireview Prologue. Nuclear Receptor Minireview Series*.", J. Biol. Chem., 2001, pp. 36863-36864, vol. 276(40).
Pacifici, R.J., "Estrogen, Cytokines, and Pathogenesis of Postmenopausal Osteoporosis.", Bone Miner. Res., 1996, pp. 1043-1051, vol. 11(8).
Rochette-Egly et al., "Retinoic Acid Receptor β: Immunodetection and Phosphorylation on Tyrosine Residues.", Mol. Endocrinol., 1992, pp. 2197-2209, vol. 6.
Rochette-Egly et al., "Stimulation of RARa Activation Function AF-1 through Binding to the General Transcription Factor TFIIH and Phosphorylation by CDK7.", Cell, 1997, pp. 97-107, vol. 90.
Schareina et al., "Potassium hexacyanoferrate(II)- an new cyanating agent for the palladium-catalyzed cyanation or aryl halides.", Chem Commun., 2004, pp. 1388-1389, vol. 12.
Singh et al., "Recent Advances in Nucleophilic Fluorination Reactions of Organic Compounds Using Deoxofluor and DAST.", Synthesis, 2002, pp. 2561-2578, vol. 17.
Sladek et al., "The Orphan Nuclear Receptor Estrogen-Related Receptor α Is a Transcriptional Regulator of the Human Medium-Chain Acyl Coenzyme a Dehydrogenase Gene.", Mol. Cell. Biol. 1997, pp. 5400-5409, vol. 17.
Stepaneko et al., "Enantioselective reduction of prochiral ketones using spiroborate esters as catalysts.", Tetrahedron Lett., 2007, pp. 5799-5802, vol. 48(33).
Sumi, D. and L.J. Ignarro, "Estrogen-related receptor α1 up-regulates endothelial nitric oxide synthase expression.", Proc Natl. Acad. Sci. 2003, pp. 14451-14456, vol. 100.
Turner et al., "Skeletal Effects of Estrogen.", Endocrine Rev. 1994, pp. 275-300, vol. 15(3).
Vanacker et al., "Transcriptional targets shared by estrogen receptor-related receptors (ERRs) and estrogen receptor (ER) α, but not by ERβ.", The EMBO Journal, 1999, pp. 4270-4279, vol. 18.
Van ES, T. and Staskun, B., "Reductions with Raney alloy in acid solution.", Journal of the Chemical Society (Resumed), 1965, pp. 5775-5777.
Vega, R.B. and D.P. Kelly, "A Role for Estrogen-related Receptor α in the Control of Mitochondrial Fatty Acid β-Oxidation during Brown Adipocyte Differentiation*.", J. Biol. Chem. 1997, pp. 31693-31699, vol. 272.
Weissman et al., "Ligand-free Palladium Catalyzed Cyanation of Aryl Halides.", J. Org. Chem., 2005, pp. 1508-1510, vol. 70(4).
Windahl et al., "Increased cortical bone mineral content but unchanged trabecular bone mineral density in female ERβ—/— mice.", J. Clin. Invest., 1999, pp. 895-901, vol. 104(7).
Wu et al., "1-Acyl-2-alkylhydrazines by the Reduction of Acylhydrazones.", Synthesis, Apr. 1995, pp. 435-438, vol. 04.
Wurtz et al., "A canonical structure for ligand-binding domain of nuclear receptors.", Nat. Struct. Biol.,1996, pp. 87-94, vol. 3.
Xu et al., "Structural basis for antagonist mediated recruitment of nuclear co-repressors by PPARa.", Nature 2002, pp. 813-817, vol. 415 (6873).
Yang, C. and Williams, "Palladium-Catalyzed Cyanation of Aryl Bromides Promoted by Low-Level Organotin Compounds.", J.M., Org. Lett., pp. 2837-28402004, vol. 6(17).
Zhang, Z. and C.T. Teng, "Estrogen Receptor-related Receptor α1 Interacts with Coactivator and Constitutively Activates the Estrogen Response Elements of the Human Lactoferrin Gene*.", J. Biol. Chem., 2000, pp. 20837-20846, vol. 275(27).

* cited by examiner

SUBSTITUTED THIAZOLIDINEDIONE INDAZOLES, INDOLES AND BENZOTRIAZOLES AS ESTROGEN-RELATED RECEPTOR-α MODULATORS

CROSS REFERENCE TO RELATED APPLICATIONS

This application claims the benefit of U.S. Provisional Application 61/347,953, filed on May 25, 2010, which is incorporated by reference herein in its entirety.

FIELD OF THE INVENTION

The present invention relates to certain novel compounds, methods for preparing compounds, compositions, intermediates and derivatives thereof and for treating conditions such as cancer, arthritis, inflammatory airway disease, and metabolic disorders. More particularly, the compounds of the present invention are Estrogen Related Receptor alpha (ERR-α) modulators useful for treating, ameliorating, or inhibiting the progression of disease states, disorders, and conditions mediated by ERR-α activity.

BACKGROUND OF THE INVENTION

Nuclear receptors are members of a superfamily of transcription factors. The members of this family share structural similarities and regulate a diverse set of biological effects (Olefsky, J. M. J. Biol. Chem. 2001, 276(40), 36863-36864). Ligands activate or repress these transcription factors that control genes involved in metabolism, differentiation and reproduction (Laudet, V. and H. Gronmeyer. The Nuclear Receptor Factbooks. 2002, San Diego: Academic Press). Presently, the human genome project has identified about 48 members for this family and cognate ligands have been identified for about 28 of them (Giguere, V. Endocrine Rev. 1999, 20(5), 689-725). This protein family is composed of modular structural domains that can be interchanged within the members of the family without loss of function. A typical nuclear receptor contains a hypervariable N-terminus, a conserved DNA binding domain (DBD), a hinge region, and a conserved ligand-binding domain (LBD). The function of the DBD is targeting of the receptor to specific DNA sequences (Nuclear Hormone Receptor (NHR) response elements or NREs), and the function of the LBD is recognition of its cognate ligand. Within the sequence of the nuclear receptor there are regions involved in transcriptional activation. The Activation Function 1 (AF-1) domain is situated at the N-terminus and constitutively activates transcription (Rochette-Egly, C. et al. Cell 1997, 90, 97-107; Rochette-Egly, C. et al. Mol. Endocrinol. 1992, 6, 2197-2209), while the Activation Function 2 (AF-2) domain is embedded within the LBD and its transcriptional activation is ligand dependent (Wurtz, J. M. et al. Nat. Struct. Biol. 1996, 3, 87-94). Nuclear receptors can exist as monomers, homodimers or heterodimers and bind to direct or inverted nucleotide repeats (Laudet and Gronmeyer, 2002; Aranda, A. and A. Pascual. Physiol. Rev. 2001, 81(3), 1269-1304).

The members of this family exist either in an activated or repressed basal biological state. The basic mechanism of gene activation involves ligand dependent exchange of co-regulatory proteins. These co-regulatory proteins are referred to as co-activators or co-repressors (McKenna, L. J. et al. Endocrine Rev. 1999, 20, 321-344). A nuclear receptor in the repressed state is bound to its DNA response element and is associated with co-repressor proteins that recruit histone deacetylases (HDACs) (Jones, P. L. and Y. B. Shi. Curr. Top. Microbiol. Immunol. 2003, 274, 237-268). In the presence of an agonist there is an exchange of co-repressors with co-activators that in turn recruit transcription factors that assemble into an ATP dependent chromatin-remodeling complex. Histones are hyper-acetylated, causing the nucleosome to unfold, and repression is alleviated. The AF-2 domain acts as the ligand dependent molecular switch for the exchange of co-regulatory proteins. In the presence of an agonist the AF-2 domain undergoes a conformational transition and presents a surface on the LBD for interaction with co-activator proteins. In the absence of an agonist or in the presence of an antagonist the AF-2 domain presents a surface that promotes interactions with co-repressor proteins. The interaction surfaces on the LBD for both co-activators, and co-repressors overlap and provide a conserved molecular mechanism for gene activation or repression that is shared by the members of this family of transcription factors (Xu, H. E. et al. Nature 2002, 415 (6873), 813-817).

Natural ligands that modulate the biological activity of nuclear receptors have been identified for only approximately one half of known nuclear receptors. Receptors for which no natural ligand has been identified are termed "orphan receptors." The discovery of ligands or compounds that interact with an orphan receptor will accelerate the understanding of the role of the nuclear receptors in physiology and disease and facilitate the pursuit of new therapeutic approaches. Estrogen related receptors (ERRs) constitutes a sub-class of these receptors where no ligand has been identified.

ERR-α (also known as ERR-1), an orphan receptor, is the first of the three identified members of the estrogen receptor related subfamily of orphan nuclear receptors (ERR-α, β, γ). The ERR subfamily is closely related to the estrogen receptors (ER-α and ER-β). ERR-α and ERR-β were first isolated by a low stringency hybridization screen (Giguere, V. et al. Nature 1988, 331, 91-94) followed later with the discovery of ERR-γ (Hong, H. et al. J. Biol. Chem. 1999, 274, 22618-22626). The ERRs and ERs share sequence similarity with the highest homology observed in their DBDs, approximately 60%, and all interact with the classical DNA estrogen response element. Recent biochemical evidence suggested that the ERRs and ERs share target genes, including pS2, lactoferin, aromatase and osteopontin, and share co-regulator proteins (Giguere, V. Trends in Endocrinol. Metab. 2002, 13, 220-225; Vanacker, J. M. et al. EMBO J. 1999, 18, 4270-4279; Kraus, R. J. et al. J. Biol. Chem. 2002, 272, 24286-24834; Hong et al., 1999; Zhang, Z. and C. T. Teng. J. Biol. Chem. 2000, 275, 20387-20846). Therefore, one of the main functions of ERR is to regulate the response of estrogen responsive genes. The effect of the steroid hormone estrogen is primarily mediated in the breast, bone and endometrium. Thus, the identification of compounds that will interact with ERRs should provide a benefit for the treatment of bone related disease, breast cancer and reproduction.

ERR-α is shown to be present both in normal and breast cancer tissue (Ariazi, E. A. et al. Cancer Res. 2002, 62, 6510-6518). It has been reported that the main function of ERR-α in normal breast tissue is that of a repressor for estrogen responsive genes. In breast cancers or cell lines that are non-estrogen responsive (ER-α negative), ERR-α has been reported to be in an activated state (Ariazi et al., 2002). Therefore, compounds that will interact with ERR-α may be useful agents for the treatment of breast cancer that is ER-α negative and non-responsive to classical anti-estrogenic therapy, or may be used as an adjunct agent for anti-estrogen responsive breast cancers. These agents may act as antagonists by reducing the biological activity of ERR-α in these particular tissues.

Many post-menopausal women experience osteoporosis, a condition that is a result of the reduction of estrogen production. Reduction of estrogen levels results in an increase of bone loss (Turner, R. T. et al. Endocrine Rev. 1994, 15(3), 275-300). An anabolic effect on bone development has been observed on the administration of estrogens to postmenopausal patients with osteoporosis (Pacifici, R. J. Bone Miner. Res. 1996, 11(8), 1043-1051) but the molecular mechanism is unknown since ER-α and ER-β knock-out animals have minor skeletal defects, where the action of estrogens is typically mediated (Korach, K. S. Science 1994, 266, 1524-1527; Windahl, S. H. et al. J. Clin. Invest. 1999, 104(7), 895-901). Expression of ERR-α in bone is regulated by estrogen (Bonnelye, E. et al. Mol. Endocrin. 1997, 11, 905-916; Bonnelye, E. et al. J. Cell Biol. 2001, 153, 971-984). ERR-α is maintained throughout osteoblast differentiation stages. Over-expression of ERR-α in rat calvaria osteoblasts, an accepted model of bone differentiation, results in an increase of bone nodule formation, while treatment of rat calvaria osteoblasts with ERR-α antisense results in a decrease of bone nodule formation. ERR-α also regulates osteopontin, a protein believed to be involved in bone matrix formation. Therefore compounds that will modulate ERR-α by increasing its activity can have an anabolic effect for the regeneration of bone density and provide a benefit over current approaches that prevent bone loss, but have no anabolic effect. Such compounds can enhance the activity of the receptor by two possible mechanisms: i) enhancing the association of the receptor with proteins that enhance its activity or improve the stability of the receptor; and ii) increasing the intracellular concentrations of the receptor and consequently increasing its activity. Conversely, with respect to bone diseases that are a result of abnormal bone growth, compounds that will interact with ERR-α and decrease its biological activity may provide a benefit for the treatment of these diseases by retarding bone growth. Antagonism of the association of the receptor with co-activator proteins decreases the activity of the receptor.

ERR-α is also present in cardiac, adipose, and muscle tissue and forms a transcriptional active complex with the PGC-1 co-activator family, co-activators implicated with energy homeostasis, mitochondria biogenesis, hepatic gluconeogenesis and in the regulation of genes involved in fatty acid beta-oxidation (Kamei, Y. et al. Proc. Natl. Acad. Sci. USA 2003, 100(21), 12378-12383). ERR-α regulates the expression of the medium chain acyl-CoA dehydrogenase promoter (MCAD). Medium chain acyl-CoA dehydrogenase is a gene involved in the initial reaction in fatty acid beta-oxidation. It is believed that in the adipose tissue ERR-α regulates energy expenditure through the regulation of MCAD (Sladek, R. et al. Mol. Cell. Biol. 1997, 17, 5400-5409; Vega, R. B. and D. P. Kelly. J. Biol. Chem. 1997, 272, 31693-31699). In antisense experiments in rat calvaria osteoblasts, in addition to the inhibition of bone nodule formation, there was an increase in adipocyte differentiation markers including aP2 and PPAR-γ (Bonnelye, E. et al. Endocrinology 2002, 143, 3658-3670). Recently an ERR-α knockout model has been described that exhibited reduced fat mass relative to the wild type and DNA chip analysis data indicated alteration of the expression levels of genes involved in adipogenesis and energy metabolism (Luo, J. et al. Mol. Cell. Biol. 2003, 23(22), 7947-7956). More recently it has been shown that ERR-α regulates the expression of endothelial nitric oxide synthase, a gene that has a protective mechanism against arteriosclerosis (Sumi, D. and L. J. Ignarro. Proc Natl. Acad. Sci. 2003, 100, 14451-14456). The biochemical evidence supports the involvement of ERR-α in metabolic homeostasis and differentiation of cells into adipocytes. Therefore, compounds interacting with ERR-α can affect energy homeostasis and may therefore provide a benefit for the treatment of obesity and metabolic syndrome related disease indications, including arteriosclerosis and diabetes (Grundy, S. M. et al. Circulation 2004, 109(3), 433-438).

There is a continuing need for new ERR-α inverse agonists. There is also a need for ERR-α inverse agonists useful for the treatment of conditions including but not limited to ankylosing spondylitis, artherosclerosis, arthritis (such as rheumatoid arthritis, infectious arthritis, childhood arthritis, psoriatic arthritis, reactive arthritis), bone-related diseases (including those related to bone formation), breast cancer (including those unresponsive to anti-estrogen therapy), cardiovascular disorders, cartilage-related disease (such as cartilage injury/loss, cartilage degeneration, and those related to cartilage formation), chondrodysplasia, chondrosarcoma, chronic back injury, chronic bronchitis, chronic inflammatory airway disease, chronic obstructive pulmonary disease, diabetes, disorders of energy homeostasis, gout, pseudogout, lipid disorders, metabolic syndrome, multiple myeloma, obesity, osteoarthritis, osteogenesis imperfecta, osteolytic bone metastasis, osteomalacia, osteoporosis, Paget's disease, periodontal disease, polymyalgia rheumatica, Reiter's syndrome, repetitive stress injury, hyperglycemia, elevated blood glucose level, and insulin resistance.

SUMMARY OF THE INVENTION

In its many embodiments, the present invention provides novel compounds useful as, for example, ERR-α inverse agonists, methods of preparing such compounds, pharmaceutical compositions comprising one or more such compounds, methods of preparing pharmaceutical compositions comprising one or more such compounds, and methods of treatment, inhibition or amelioration of one or more diseases associated with ERR-α using such compounds or pharmaceutical compositions.

One aspect of the present invention features a compound of Formula (I)

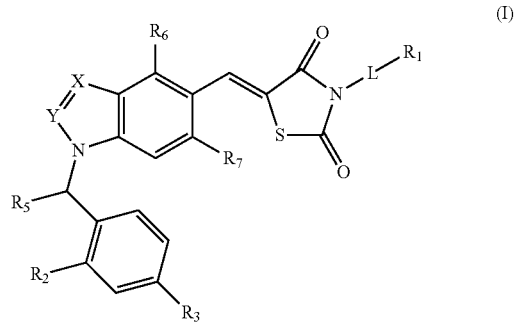

wherein
X is N, or CR$_4$;
Y is N, or CH; with the proviso that when Y is CH, X is CH;
L is a bond or optionally substituted C$_{1-4}$alkyl;
  wherein said optionally substituted C$_{1-4}$alkyl may be substituted with one to four groups, said groups independently selected from hydroxyl, oxo, halo, amino, —C(O)OH, and —C(O)O—C$_{1-2}$alkyl;

$R_1$ is selected from H, hydroxyl, amino, guanidinyl, —N($R^a$)$R^b$, —S(O)$_2$—$R^c$, optionally substituted alkoxyl, optionally substituted $C_{2-6}$alkenyl, optionally substituted aryl, optionally substituted cycloalkyl, and optionally substituted heterocyclyl;

wherein $R^a$ is $C_{1-4}$alkyl, —$C_{1-4}$alkyl-OH, optionally nitro-substituted heteroaryl, —C(O)—$C_{1-2}$alkyl with $C_{1-2}$alkyl optionally substituted with halo, or —S(O)$_2$—$R^d$; wherein $R^d$ is —N($R^b$)$R^e$, optionally halo-substituted $C_{1-4}$alkyl, optionally trifluoromethyl-substituted aryl, optionally alkoxyl-substituted heterocyclyl, or heteroaryl wherein said heteroaryl is optionally substituted with halo, $C_{1-4}$alkyl, —C(O)O—$R^b$ or NHC(O)—$R^b$;

wherein $R^c$ is amino, $C_{1-4}$alkyl, —NH$R^b$, or —NHC(O)—$R^b$;

wherein said optionally substituted alkoxyl may be substituted with one to three groups, said groups independently selected from guanidinyl, —N($R^b$)$R^e$, $C_{1-4}$alkyl, —$C_{1-4}$alkyl-O$R^b$, —$C_{1-4}$alkyl-C(O)O$R^b$, and —$C_{1-4}$alkyl-heterocyclyl;

wherein said optionally substituted $C_{2-6}$alkenyl may be substituted with —C(O)O$R^b$;

wherein said optionally substituted aryl may be substituted with one to two groups, said groups independently selected from halo, —CF$_3$, and —C(O)O$R^b$;

wherein said optionally substituted heteroaryl may be substituted with one to three groups, said groups independently selected from halo, $C_{1-4}$ alkyl, —O$R^b$, —N($R^b$)$R^e$, —C(O)O$R^b$, —$C_{1-2}$alkyl-heteroaryl, —S(O)$_2R^b$, optionally halo-substituted —S(O)$_2$—$C_{1-2}$alkyl, —S(O)$_2$-heterocyclyl, —N($R^b$)C(O)—$C_{1-3}$alkyl, and optionally halo-substituted —N($R^b$)S(O)$_2$—$C_{1-2}$alkyl;

wherein said optionally substituted cycloalkyl may be substituted with one to three groups, said groups independently selected from halo, —O$R^b$, —C(O)O$R^b$, —C(O)N($R^b$)$R^e$, —N($R^b$)$R^e$, —N($R^b$)C(O)O$R^e$, —C(O)N($R^b$)—S(O)$_2$—$R^e$, and —$C_{1-4}$alkyl-N($R^b$)$R^e$;

wherein said optionally substituted heterocyclyl may be substituted with one to five groups, said groups independently selected from halo, oxo, —O$R^b$, optionally halo-substituted $C_{1-4}$alkyl, —$C_{1-4}$alkyl-O$R^b$, —C(O)O$R^b$, —C(O)$R^b$, —$C_{1-4}$alkyl-C(O)O$R^b$, —$C_{1-4}$alkyl-CN, —$C_{1-4}$alkyl-C(O)N($R^b$)$R^e$, —$C_{1-4}$alkyl-S(O)$_2R^b$, —N($R^b$)$R^e$, —N($R^b$)C(O)—O$R^e$, —C(O)N($R^b$)$R^e$, —$C_{1-4}$alkyl-N($R^b$)$R^e$, —S(O)$_2$N($R^b$)$R^e$, —C(O$R^b$)—$C_{1-4}$alkyl-O$R^e$, and —N($R^b$)C(O)-cycloalkyl;

wherein $R^b$, $R^e$ are independently selected from H and $C_{1-4}$alkyl;

$R_2$ is halo-substituted $C_{1-3}$alkyl, or alternatively $R_2$ is linked together to $R_5$ to form a cycloalkyl fused to the phenyl ring to which $R_2$ is shown attached;

$R_3$ is halo, cyano, halo-substituted $C_{1-3}$alkyl, or $C_{1-4}$alkoxyl;

$R_4$ is H, hydroxyl, halo, $C_{1-4}$alkyl, $C_{1-4}$alkoxyl, optionally substituted phenyl, cyano, or —C(O)NH$_2$, $R_5$ is H, or alternatively $R_5$ is linked together to $R_2$ to form a cycloalkyl fused to the phenyl ring to which $R_2$ is shown attached;

$R_6$ is H or F; and $R_7$ is H or F;

or an enantiomer, diastereomer, cis-trans isomer, racemate, prodrug or pharmaceutically acceptable salt thereof.

Furthermore, the present invention includes a compound of Formula (I), wherein $R_1$, $R_2$, $R_3$, $R_4$, $R_5$, $R_6$, $R_7$, L, X, and Y are as described above, with the proviso that when $R_6$ is F, $R_7$ is H;

or an enantiomer, diastereomer, cis-trans isomer, racemate, prodrug or pharmaceutically acceptable salt thereof.

Another aspect of the present invention features a pharmaceutical composition comprising at least one compound of Formula (I) and at least one pharmaceutically acceptable carrier.

The present invention also features a method of treating a subject suffering from or diagnosed with a disease, disorder, or condition mediated by ERR-α activity, comprising administering to the subject a therapeutically effective amount of at least one compound of Formula (I). Such disease, disorder, or condition can include bone-related disease, bone formation, breast cancer (including those unresponsive to anti-estrogen therapy), cartilage formation, cartilage injury, cartilage loss, cartilage degeneration, cartilage injury, ankylosing spondylitis, chronic back injury, gout, osteoporosis, osteolytic bone metastasis, multiple myeloma, chondrosarcoma, chondrodysplasia, osteogenesis imperfecta, osteomalacia, Paget's disease, polymyalgia rheumatica, pseudogout, arthritis, rheumatoid arthritis, infectious arthritis, osteoarthritis, psoriatic arthritis, reactive arthritis, childhood arthritis, Reiter's syndrome, repetitive stress injury, periodontal disease, chronic inflammatory airway disease, chronic bronchitis, chronic obstructive pulmonary disease, metabolic syndrome, obesity, disorders of energy homeostasis, diabetes, lipid disorders, cardiovascular disorders, artherosclerosis, hyperglycemia, elevated blood glucose level, and insulin resistance. The therapeutically effective amount of the compound of Formula (I) can be from about 0.1 mg/day to about 5000 mg/day for an average human.

The present invention further features a process for making a pharmaceutical composition comprising admixing any of the compounds according to Formula (I) and a pharmaceutically acceptable carrier.

Additional embodiments and advantages of the invention will become apparent from the detailed discussion, schemes, examples, and claims below.

DETAILED DESCRIPTION OF THE INVENTION

This invention relates to novel ERR-α modulators and compositions thereof for the treatment, amelioration, or inhibition of numerous conditions, including but not limited to cancer, arthritis, inflammatory airway disease, bone-related diseases, metabolic disorders, and associated symptoms or complications thereof.

One aspect of the present invention features a compound of Formula (I)

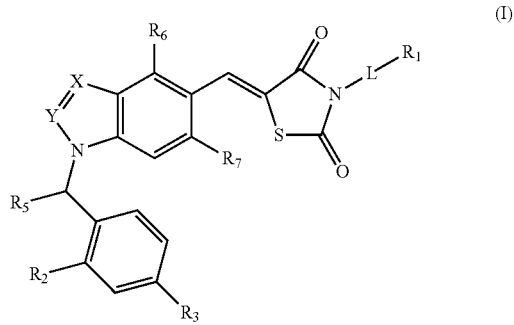

wherein
X is N, or CR$_4$;
Y is N, or CH; with the proviso that when Y is CH, X is CH;

L is a bond or optionally substituted $C_{1-4}$alkyl;

wherein said optionally substituted $C_{1-4}$alkyl may be substituted with one to four groups, said groups independently selected from hydroxyl, oxo, halo, amino, —C(O)OH, and —C(O)O—$C_{1-2}$alkyl;

$R_1$ is selected from H, hydroxyl, amino, guanidinyl, —N($R^a$)$R^b$, —S(O)$_2$—$R^c$, optionally substituted alkoxyl, optionally substituted $C_{2-6}$alkenyl, optionally substituted aryl, optionally substituted cycloalkyl, and optionally substituted heterocyclyl;

wherein $R^a$ is $C_{1-4}$alkyl, —$C_{1-4}$alkyl-OH, optionally nitro-substituted heteroaryl, —C(O)—$C_{1-2}$alkyl with $C_{1-2}$alkyl optionally substituted with halo, or —S(O)$_2$—$R^d$; wherein $R^d$ is —N($R^b$)$R^e$, optionally halo-substituted $C_{1-4}$alkyl, optionally trifluoromethyl-substituted aryl, optionally alkoxyl-substituted heterocyclyl, or heteroaryl wherein said heteroaryl is optionally substituted with halo, $C_{1-4}$alkyl, —C(O)O—$R^b$ or NHC(O)—$R^b$;

wherein $R^c$ is amino, $C_{1-4}$alkyl, —NH$R^b$, or —NHC(O)—$R^b$;

wherein said optionally substituted alkoxyl may be substituted with one to three groups, said groups independently selected from guanidinyl, —N($R^b$)$R^e$, $C_{1-4}$alkyl, —$C_{1-4}$alkyl-O$R^b$, —$C_{1-4}$alkyl-C(O)O$R^b$, and —$C_{1-4}$alkyl-heterocyclyl;

wherein said optionally substituted $C_{2-6}$alkenyl may be substituted with —C(O)O$R^b$;

wherein said optionally substituted aryl may be substituted with one to two groups, said groups independently selected from halo, —CF$_3$, and —C(O)O$R^b$;

wherein said optionally substituted heteroaryl may be substituted with one to three groups, said groups independently selected from halo, $C_{1-4}$ alkyl, —O$R^b$, —N($R^b$)$R^e$, —C(O)O$R^b$, —$C_{1-2}$alkyl-heteroaryl, —S(O)$_2$$R^b$, optionally halo-substituted —S(O)$_2$—$C_{1-2}$alkyl, —S(O)$_2$-heterocyclyl, —N($R^b$)C(O)—$C_{1-3}$alkyl, and optionally halo-substituted —N($R^b$)S(O)$_2$—$C_{1-2}$alkyl;

wherein said optionally substituted cycloalkyl may be substituted with one to three groups, said groups independently selected from halo, —O$R^b$, —C(O)O$R^b$, —C(O)N($R^b$)$R^e$, —N($R^b$)$R^e$, —N($R^b$)C(O)O$R^e$, —C(O)N($R^b$)—S(O)$_2$—$R^e$, and —$C_{1-4}$alkyl-N($R^b$)$R^e$;

wherein said optionally substituted heterocyclyl may be substituted with one to five groups, said groups independently selected from halo, oxo, —O$R^b$, optionally halo-substituted $C_{1-4}$alkyl, —$C_{1-4}$alkyl-O$R^b$, —C(O)O$R^b$, —C(O)$R^b$, —$C_{1-4}$alkyl-C(O)O$R^b$, —$C_{1-4}$alkyl-CN, —$C_{1-4}$alkyl-C(O)N($R^b$)$R^e$, —$C_{1-4}$alkyl-S(O)$_2$$R^b$, —N($R^b$)$R^e$, —N($R^b$)C(O)—O$R^e$, —C(O)N($R^b$)$R^e$, —$C_{1-4}$alkyl-N($R^b$)$R^e$, —S(O)$_2$N($R^b$)$R^e$, —C(O$R^b$)—$C_{1-4}$alkyl-O$R^e$, and —N($R^b$)C(O)-cycloalkyl;

wherein $R^b$, $R^e$ are independently selected from H and $C_{1-4}$alkyl;

$R_2$ is halo-substituted $O_{1-3}$alkyl, or alternatively $R_2$ is linked together to $R_5$ to form a cycloalkyl fused to the phenyl ring to which $R_2$ is shown attached;

$R_3$ is halo, cyano, halo-substituted $C_{1-3}$alkyl, or $C_{1-4}$alkoxyl;

$R_4$ is H, hydroxyl, halo, $C_{1-4}$alkyl, $C_{1-4}$alkoxyl, optionally substituted phenyl, cyano, or —C(O)NH$_2$;

$R_5$ is H, or alternatively $R_5$ is linked together to $R_2$ to form a cycloalkyl fused to the phenyl ring to which $R_2$ is shown attached;

$R_6$ is H or F; and $R_7$ is H or F;

or an enantiomer, diastereomer, cis-trans isomer, racemate, prodrug or pharmaceutically acceptable salt thereof.

Furthermore, the present invention includes a compound of Formula (I), wherein $R_1$, $R_2$, $R_3$, $R_4$, $R_5$, $R_6$, $R_7$, L, X, and Y are as described above, with the proviso that when $R_6$ is F, $R_7$ is H;

or an enantiomer, diastereomer, cis-trans isomer, racemate, prodrug or pharmaceutically acceptable salt thereof.

In particular, the present invention includes a cis-trans isomer of the compound of Formula (I), which has the following structure, wherein $R_1$, $R_2$, $R_3$, $R_4$, $R_5$, $R_6$, $R_7$, L, X, and Y are as described above:

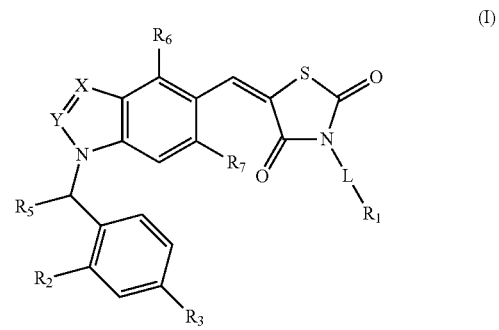

(I)

Particularly, the present invention includes a compound of Formula (I) wherein compound of claim 1 wherein X is N or CR4;

Y is N or CH; with the proviso that when Y is CH, X is CH;

L is a bond or optionally substituted $C_{1-4}$alkyl;

wherein said optionally substituted $C_{1-4}$alkyl may be substituted with one to four groups, said groups independently selected from hydroxyl, oxo, halo, amino, —C(O)OH, and —C(O)O—$C_{1-2}$alkyl;

$R_1$ is selected from

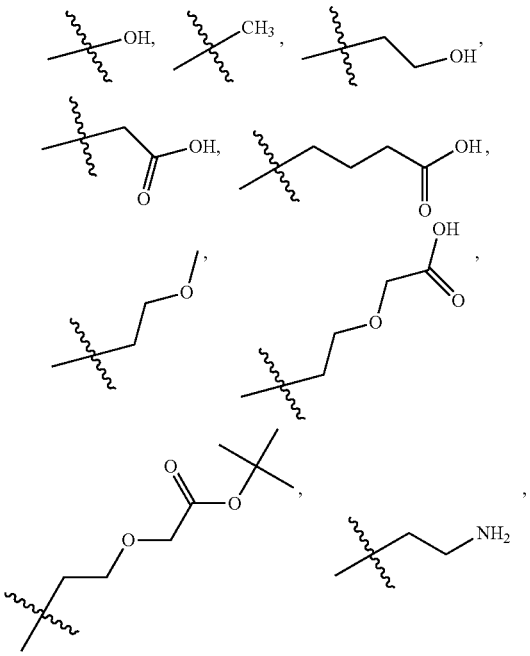

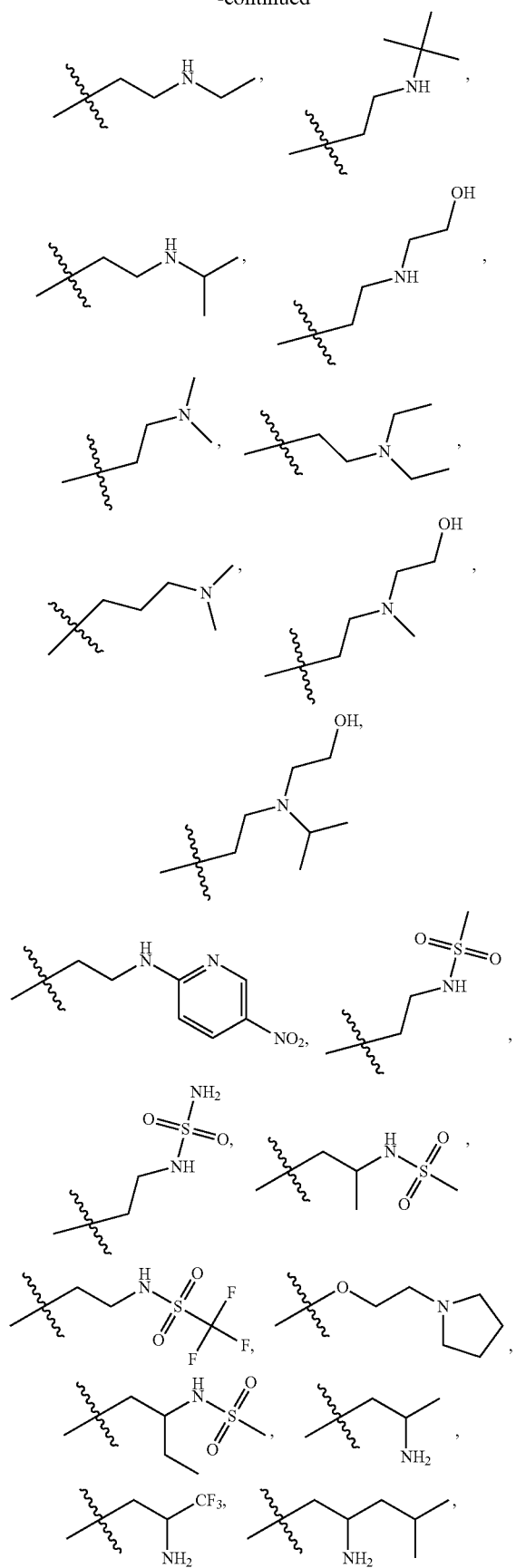
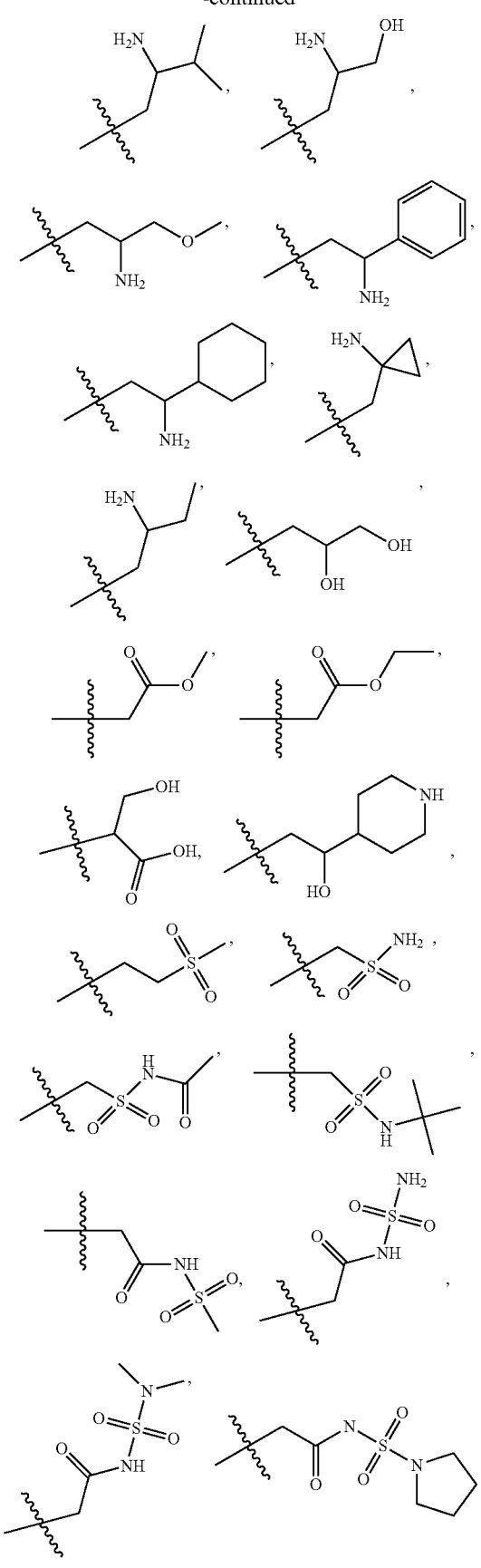

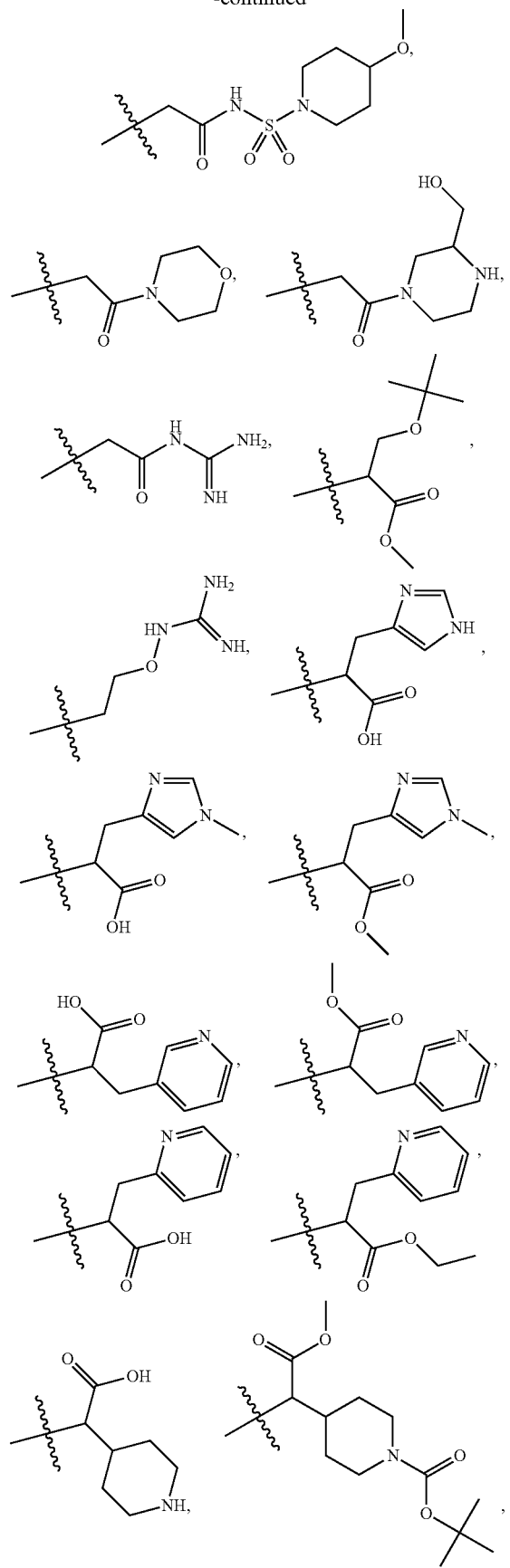
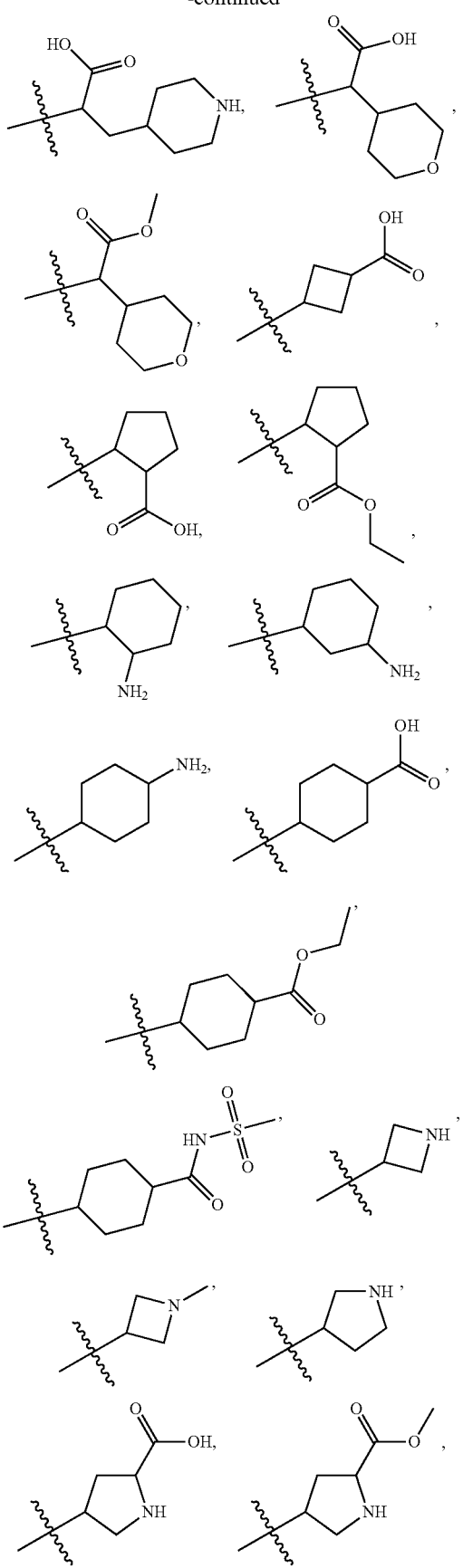

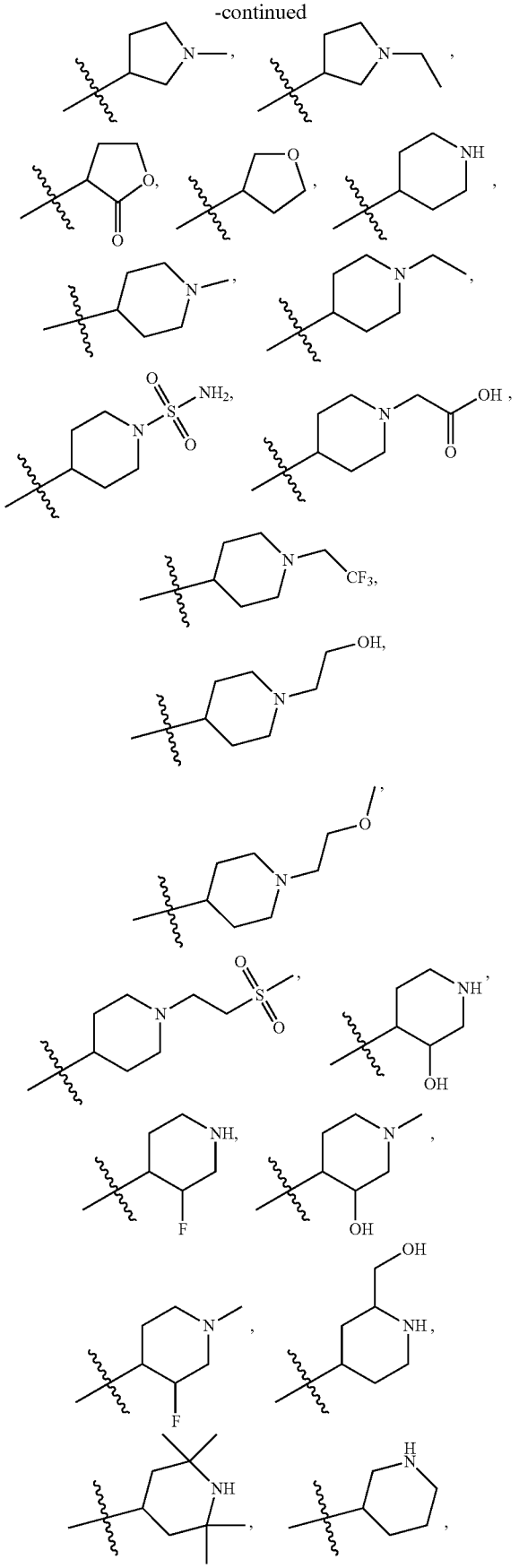
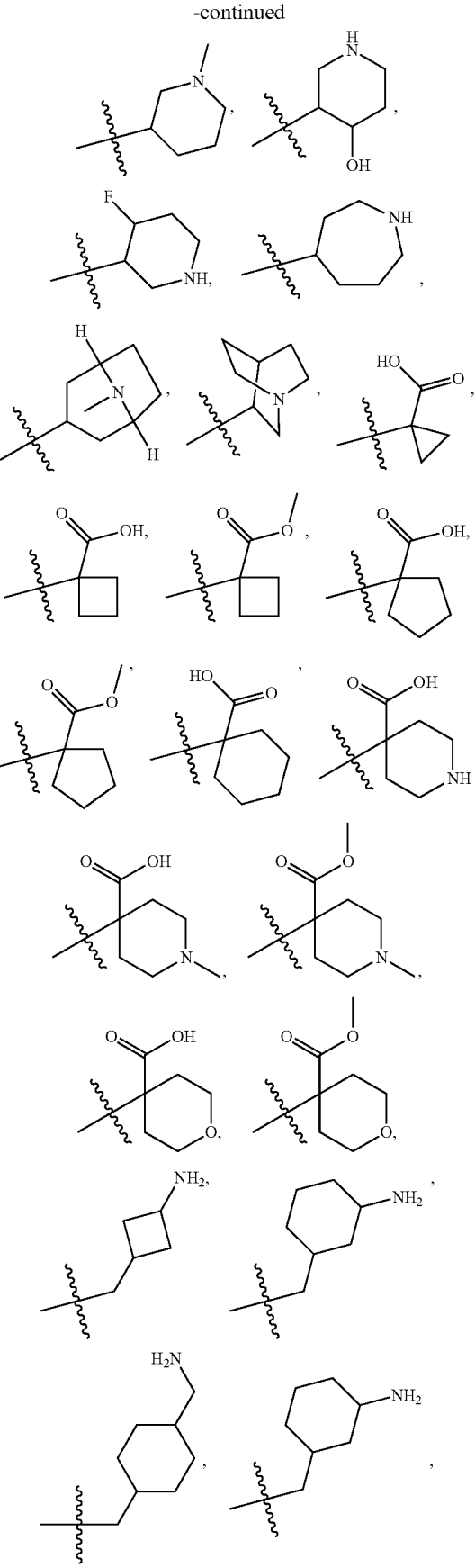

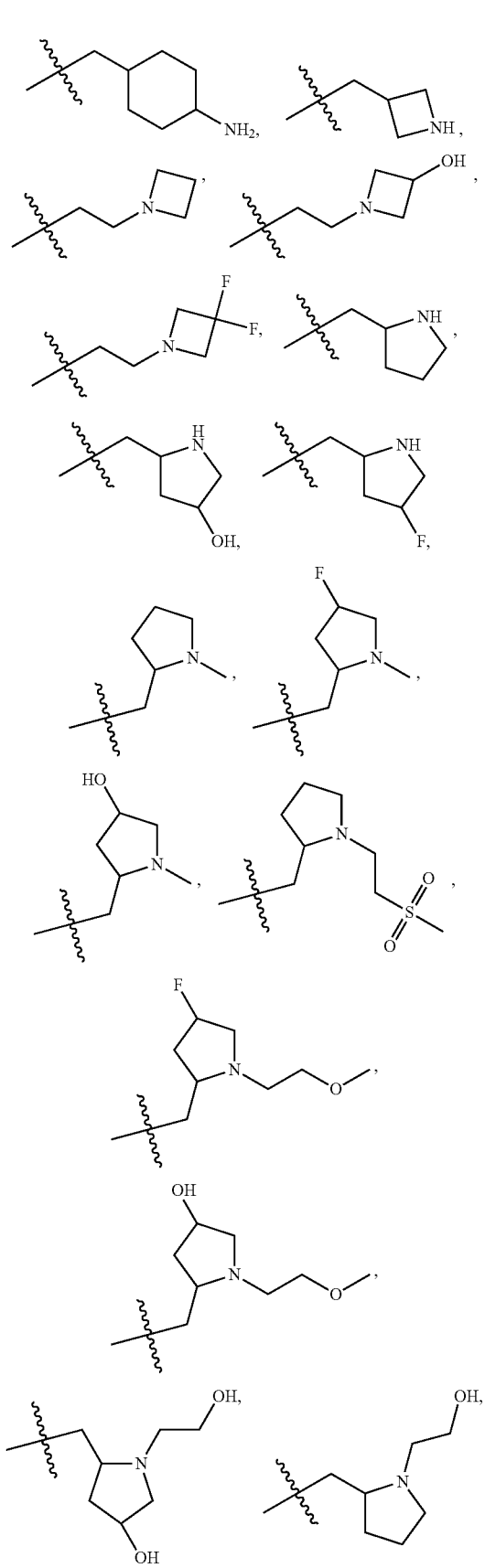
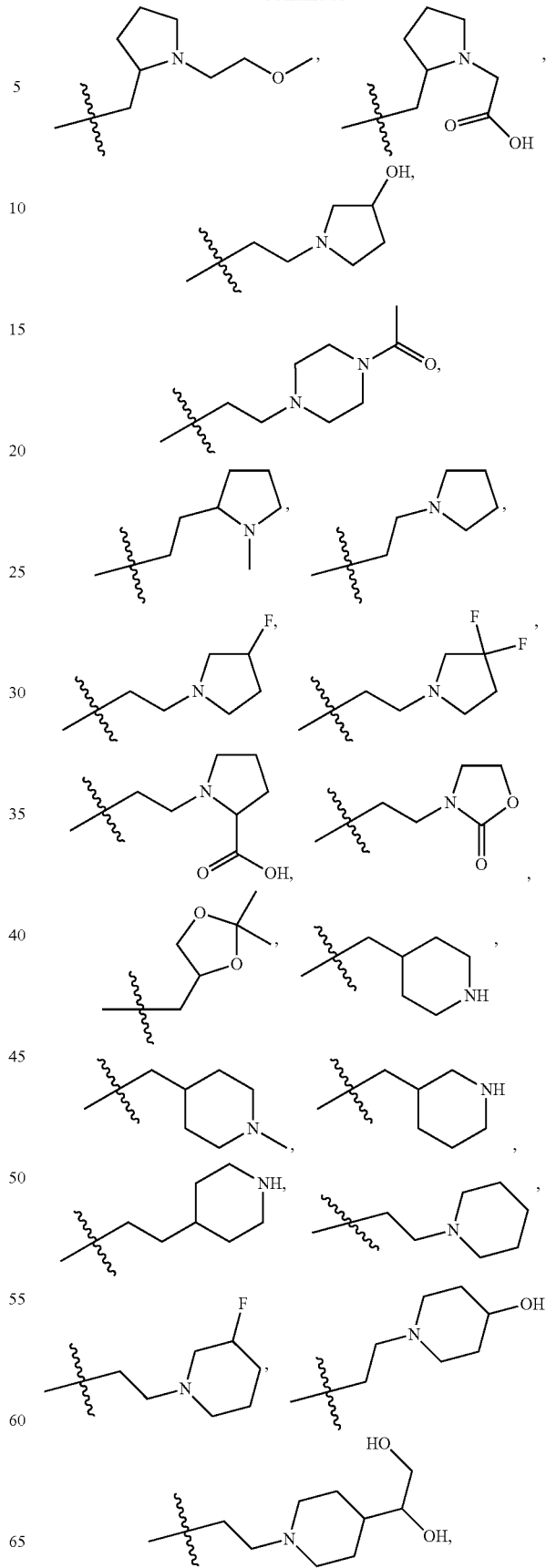

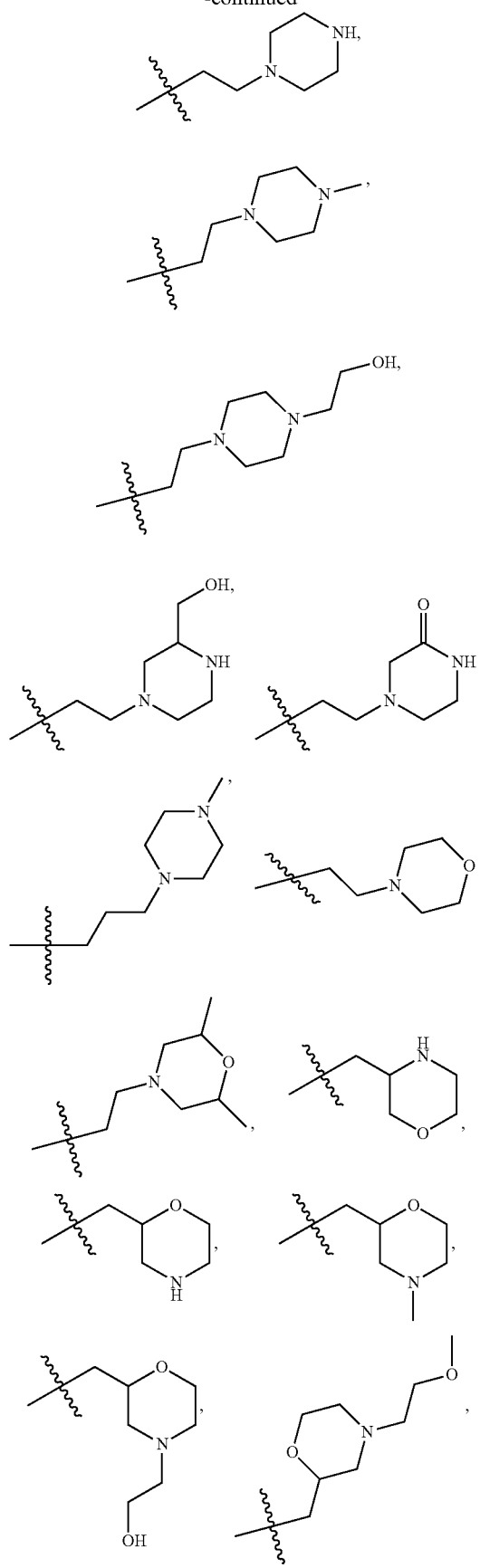
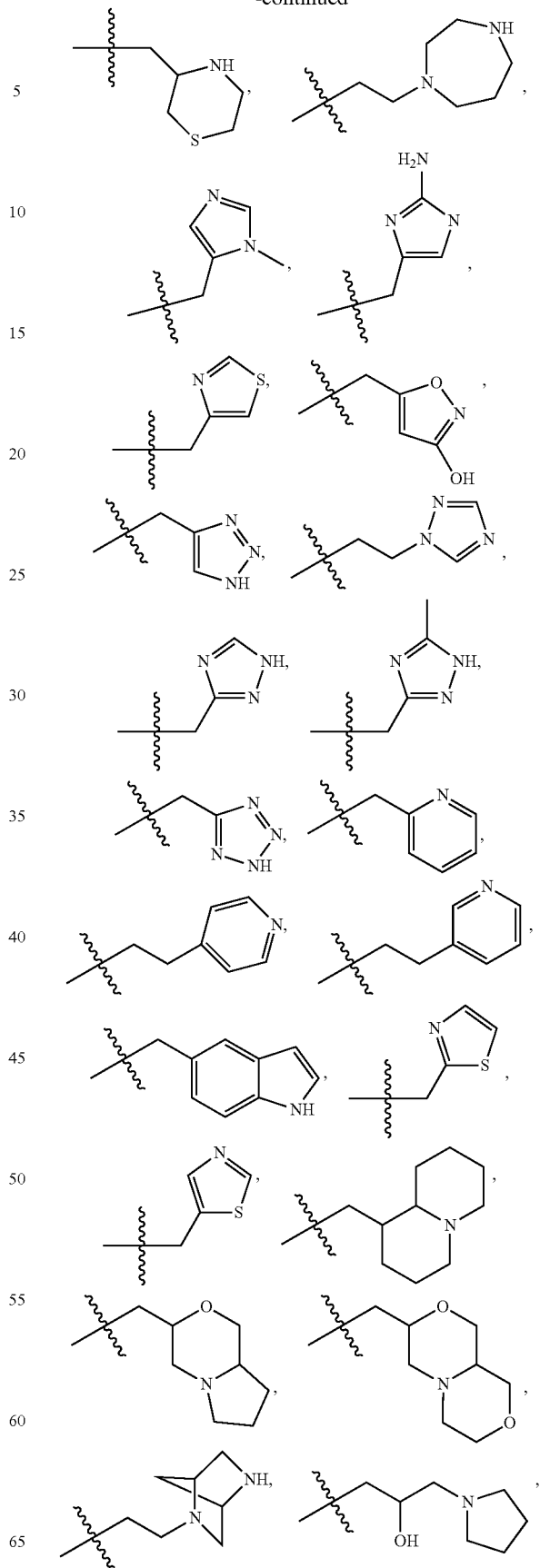

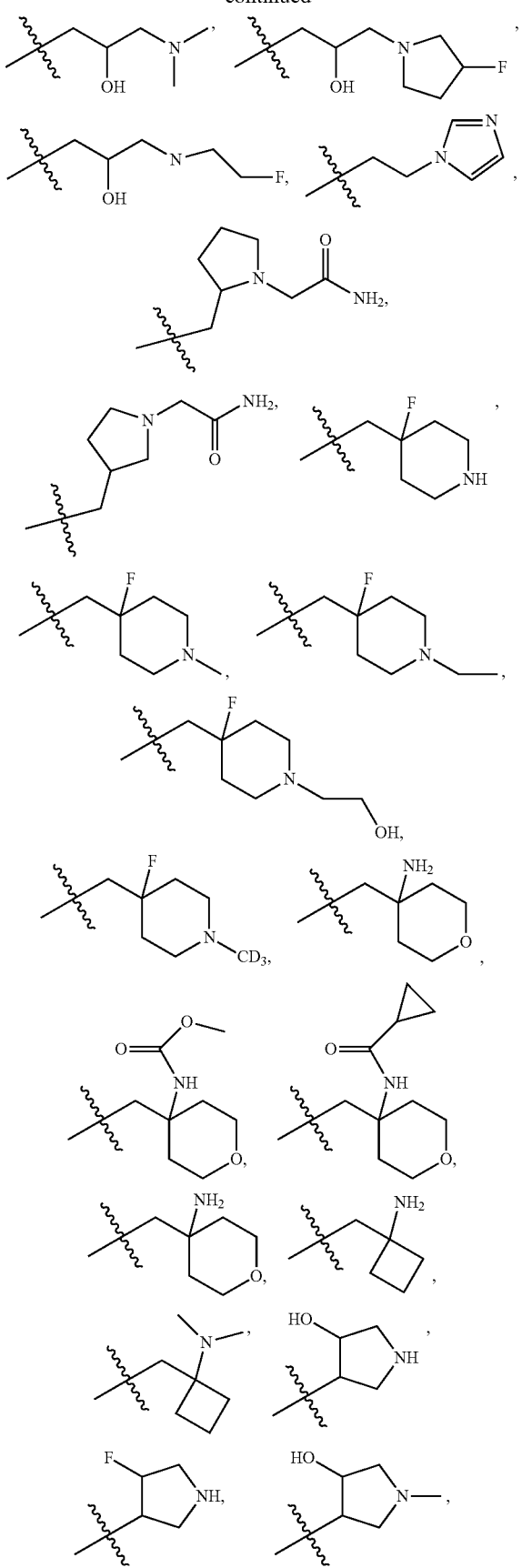
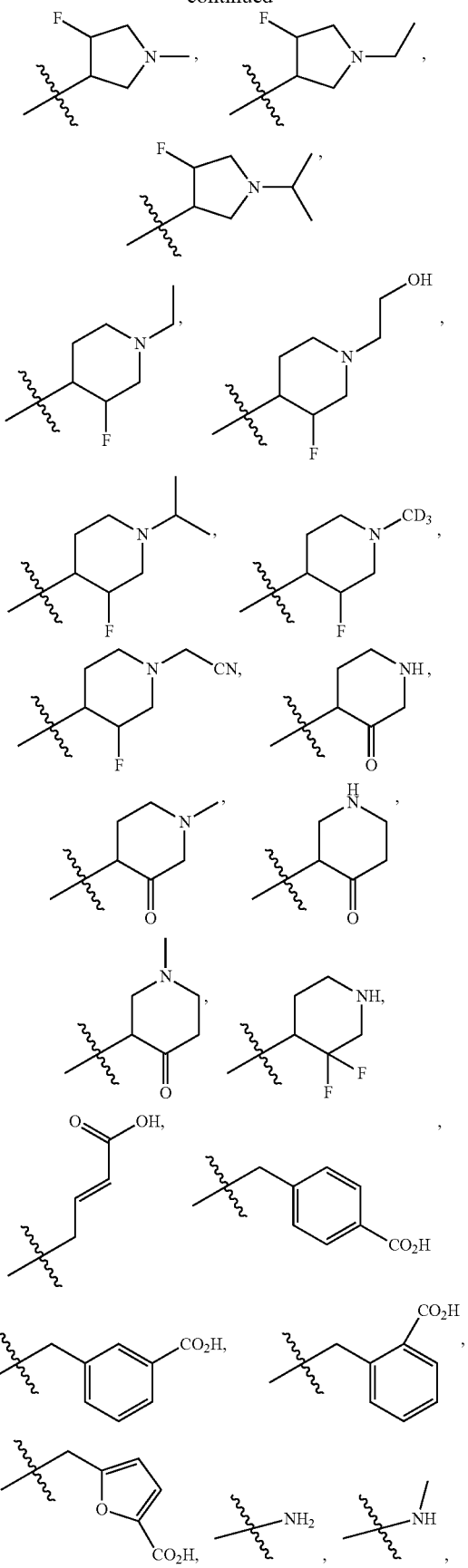

-continued
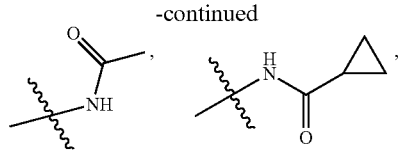
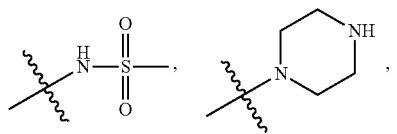
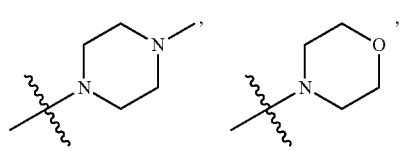
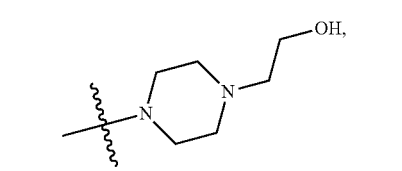
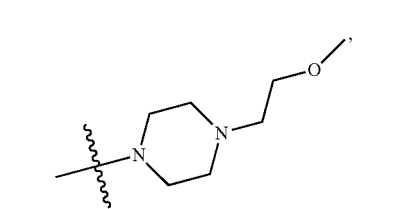
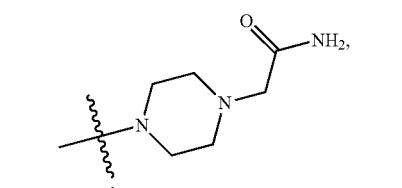
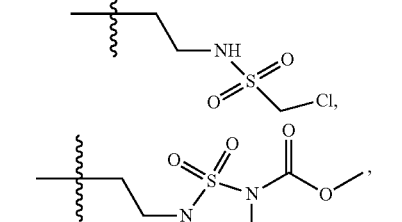
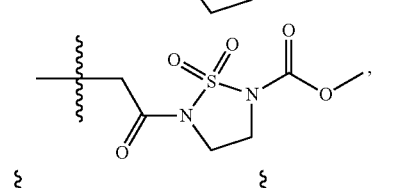
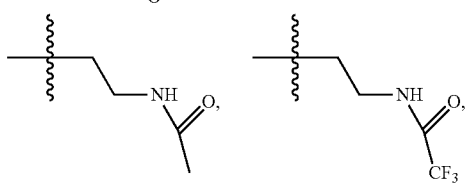
-continued
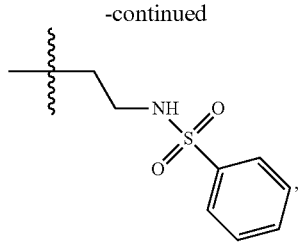
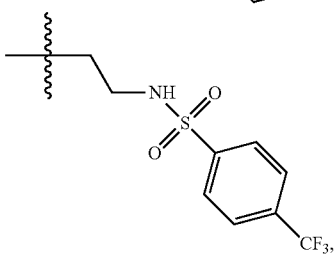
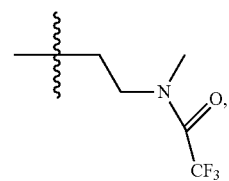
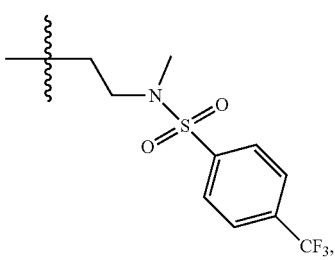
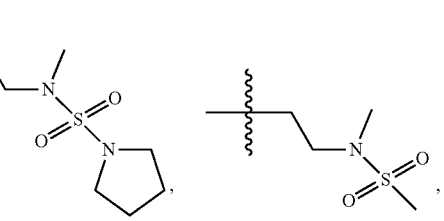
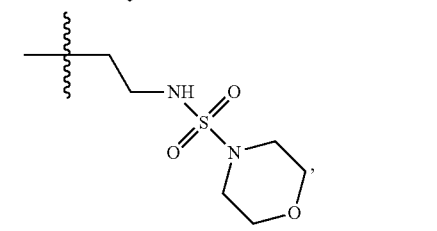
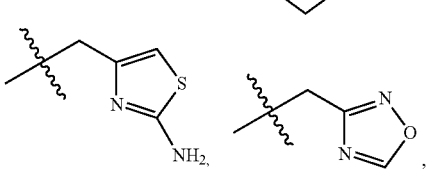

-continued

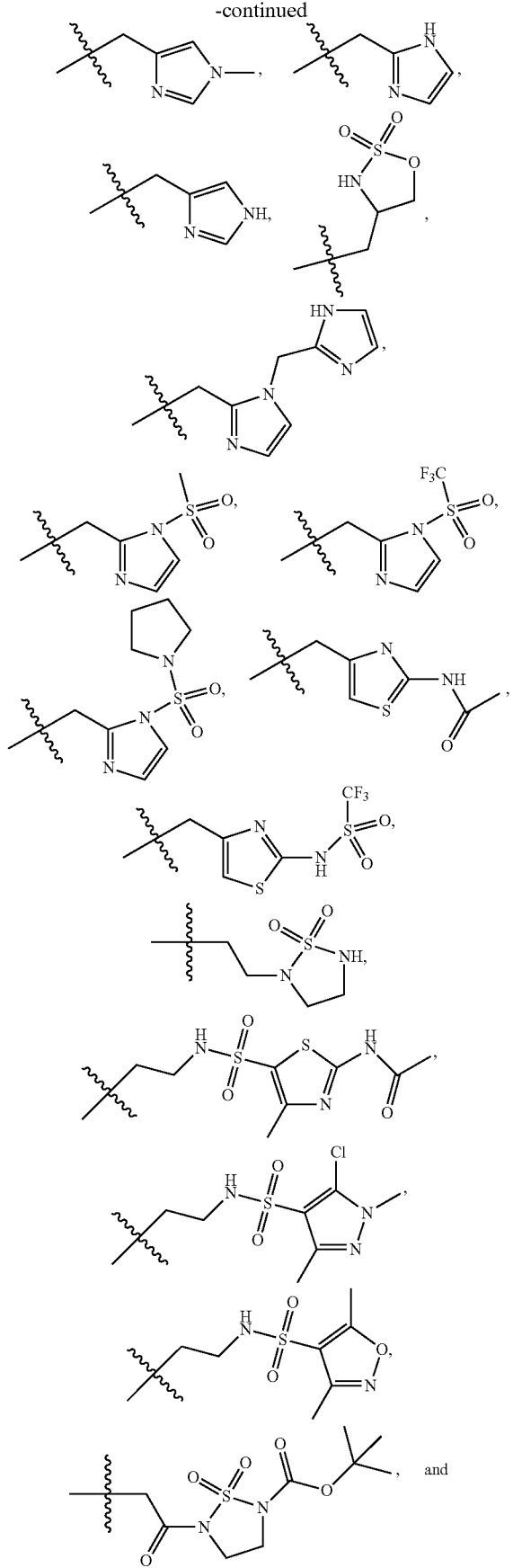

$R_2$ is halo-substituted $C_{1-3}$alkyl;
$R_3$ is halo or halo-substituted $C_{1-3}$alkyl;
$R_4$ is H or halo
$R_5$ is H;
$R_6$ is H or F; and
$R_7$ is H or F;
or an enantiomer, diastereomer, cis-trans isomer, racemate, prodrug or pharmaceutically acceptable salt thereof.

In another embodiment, the present invention includes a compound of Formula (I) wherein
X is N or CR4;
Y is N or CH; with the proviso that when Y is CH, X is CH;
L is a bond or optionally substituted $C_{1-4}$alkyl;
wherein said optionally substituted $C_{1-4}$alkyl may be substituted with one to four groups, said groups independently selected from hydroxyl, oxo, halo, amino, —C(O)OH, and —C(O)O—$C_{1-2}$alkyl;
$R_2$ is $CF_3$;
$R_3$ is F, Cl, $CF_3$ or $OCH_3$;
$R_4$ is H, hydroxyl, Cl, $OCH_3$ or $CH_3$;
$R_5$ is H;
$R_6$ is H; and
$R_7$ is H.

In another embodiment, the present invention includes a compound of Formula (I) wherein
X is N or $CR_4$;
Y is N;
$R_3$ is $C_1$, $CF_3$ or $OCH_3$; and
$R_4$ is H, Cl, or $CH_3$.

In another embodiment, the present invention includes a compound of Formula (I) wherein
X is N or $CR_4$;
Y is N;
L is a bond;
$R_3$ is $C_1$, $CF_3$ or $OCH_3$; and
$R_4$ is H, Cl, or $CH_3$.

In another embodiment, the present invention includes a compound of Formula (I) wherein
X is N or $CR_4$;
Y is N;
L is optionally substituted $C_{1-4}$alkyl;
wherein said optionally substituted $C_{1-4}$alkyl may be substituted with one to four groups, said groups independently selected from hydroxyl, oxo, halo, amino, —C(O)OH, and —C(O)O—$C_{1-2}$alkyl;
$R_3$ is $C_1$, $CF_3$ or $OCH_3$; and
$R_4$ is H, Cl, or $CH_3$.

In one embodiment of formula (I) X is CH; and Y is N.

More particularly, the present invention includes a compound of Formula (I) wherein
X is N or $CR_4$;
Y is N;
$R_2$ is $CF_3$;
$R_3$ is $C_1$, $CF_3$ or $OCH_3$;
$R_4$ is H, Cl, or $CH_3$;
$R_5$ is H;
$R_6$ is H; and
$R_7$ is H;

or an enantiomer, diastereomer, cis-trans isomer, racemate, prodrug or pharmaceutically acceptable salt thereof.

In an embodiment, the present invention includes a compound of Formula (I) wherein
X is CH;
Y is N;
$R_2$ is $CF_3$;
$R_3$ is $C_1$, $CF_3$, or $OCH_3$;
$R_5$ is H;
$R_6$ is H; and
$R_7$ is H.

In another embodiment, the present invention includes a compound of Formula (I) wherein
X is N;
Y is N;
$R_2$ is $CF_3$;
$R_3$ is $C_1$, $CF_3$, or $OCH_3$;
$R_5$ is H;
$R_6$ is H; and
$R_7$ is H.

In yet another embodiment, the present invention includes a compound of Formula (I) wherein
X is CH;
$R_2$ is $CF_3$;
$R_3$ is Cl, or $CF_3$;
$R_5$ is H;
$R_6$ is H; and
$R_7$ is H.
$R_1$ is selected from H,

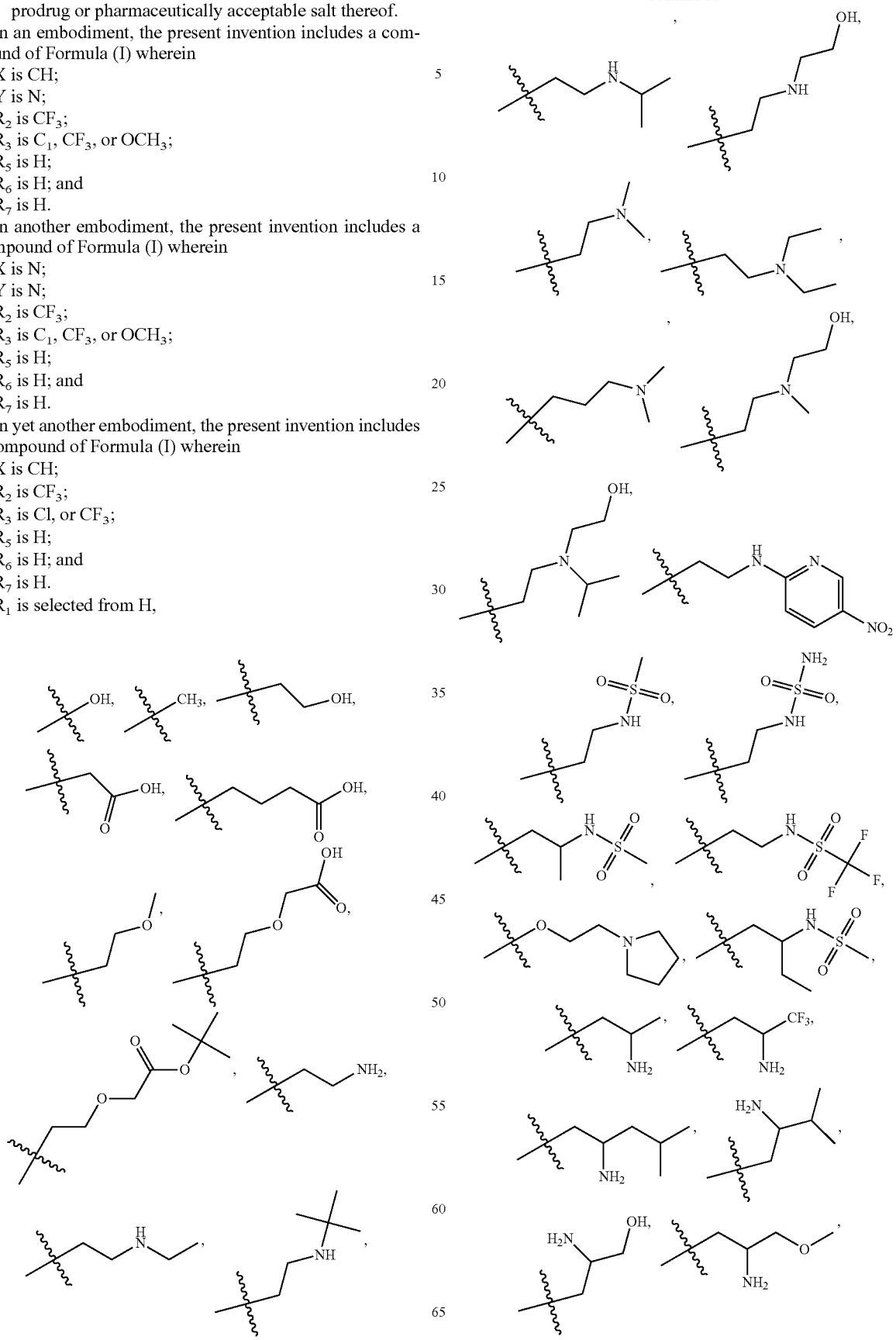

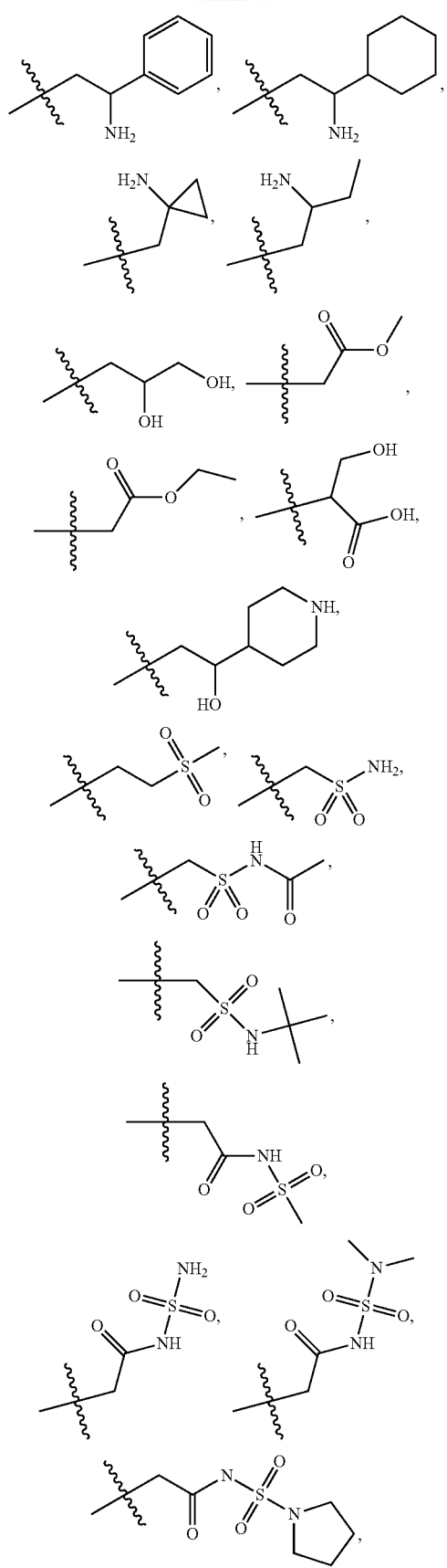
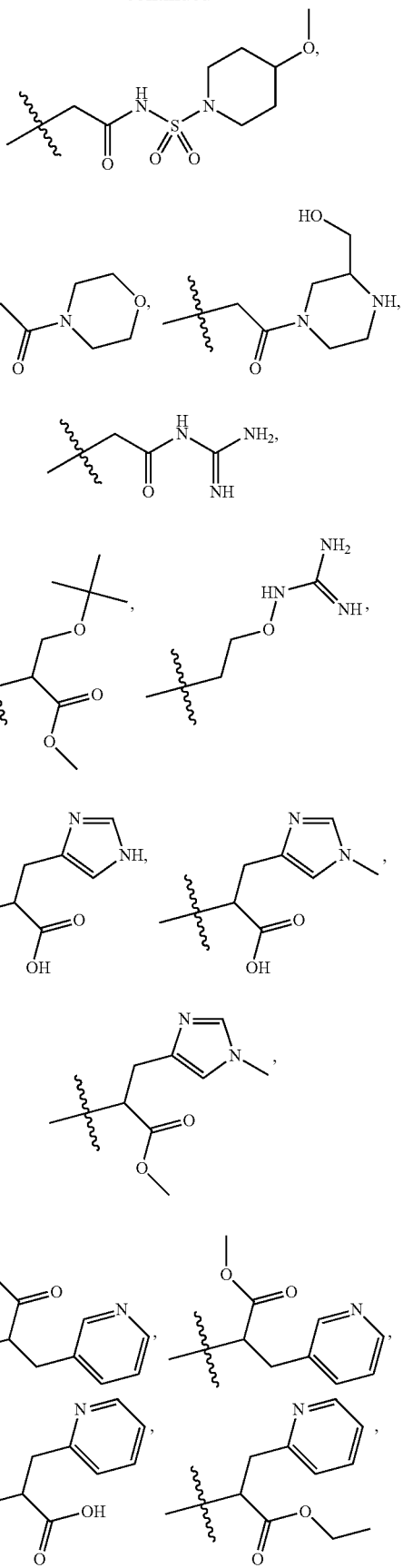

29
-continued
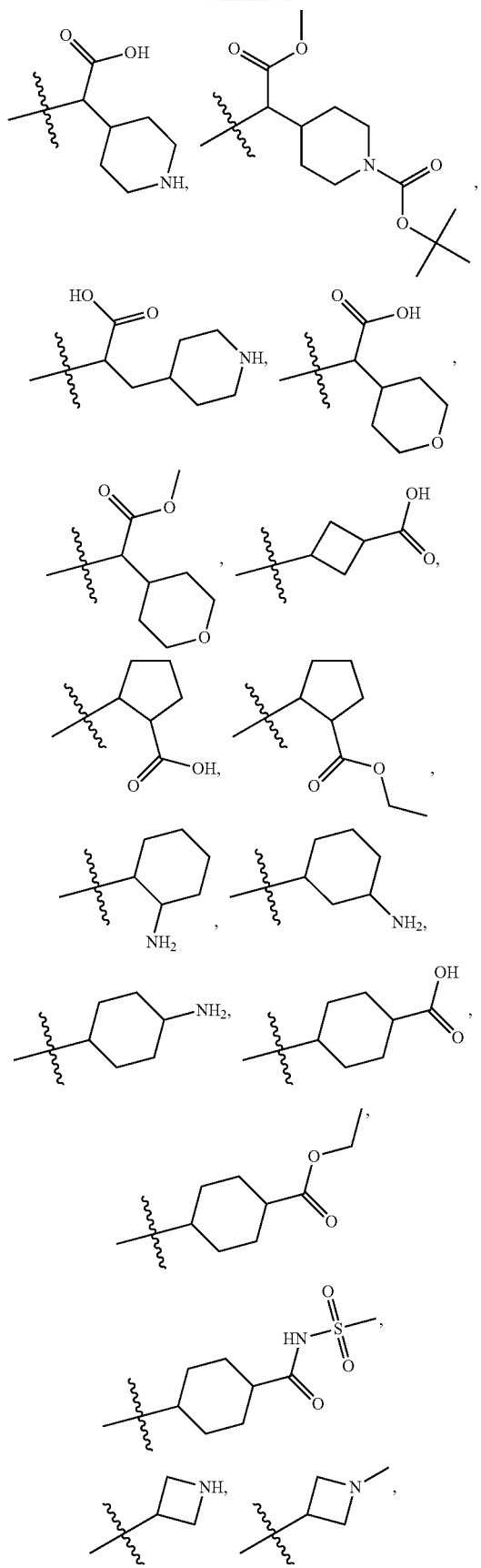
30
-continued
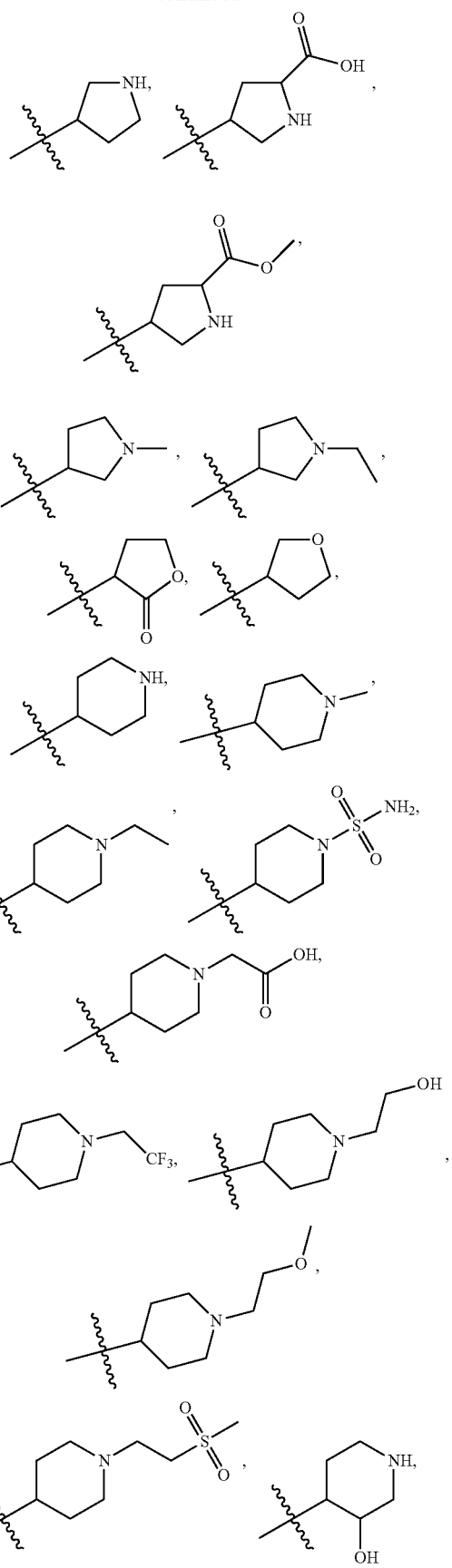

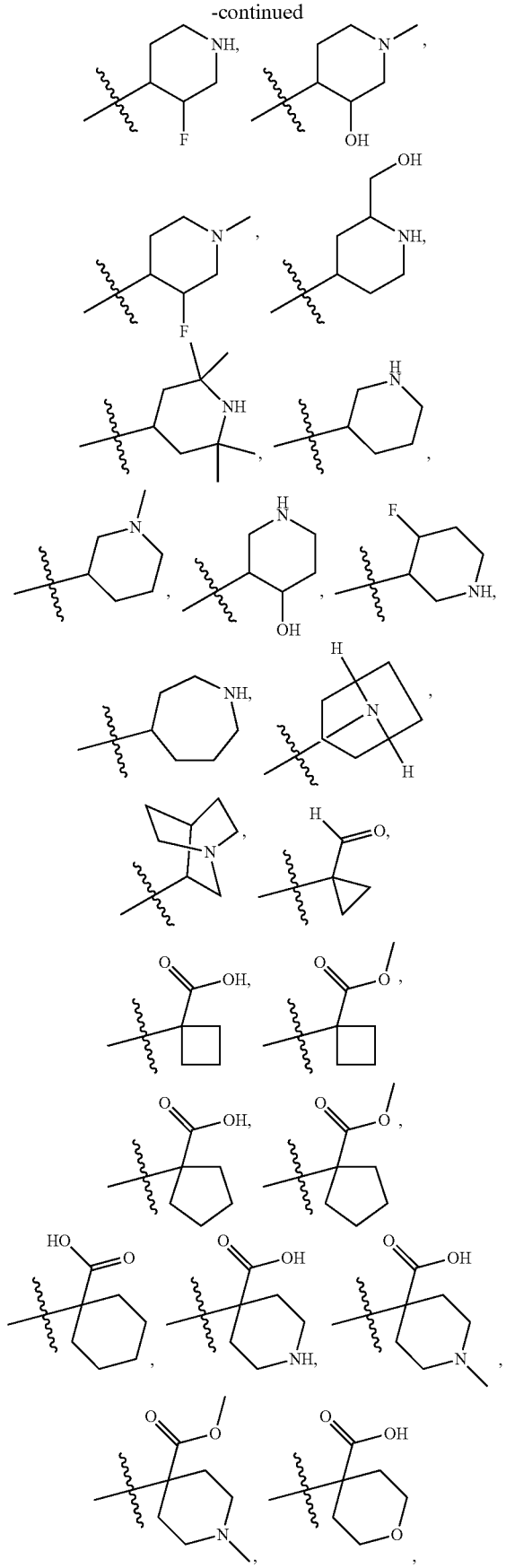
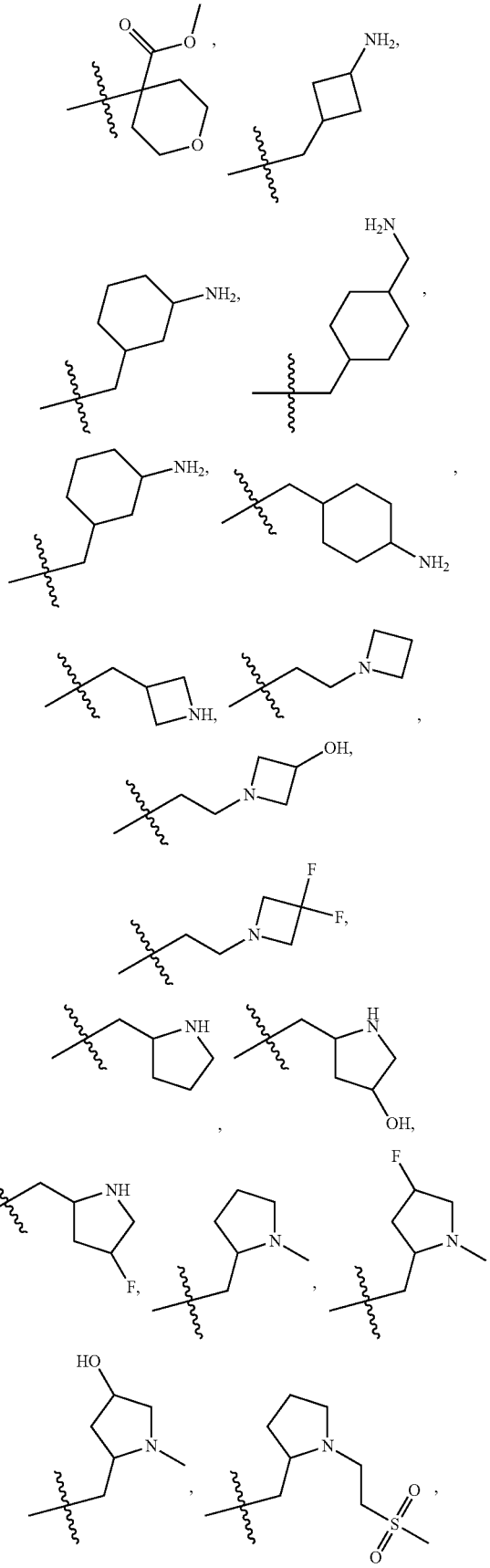

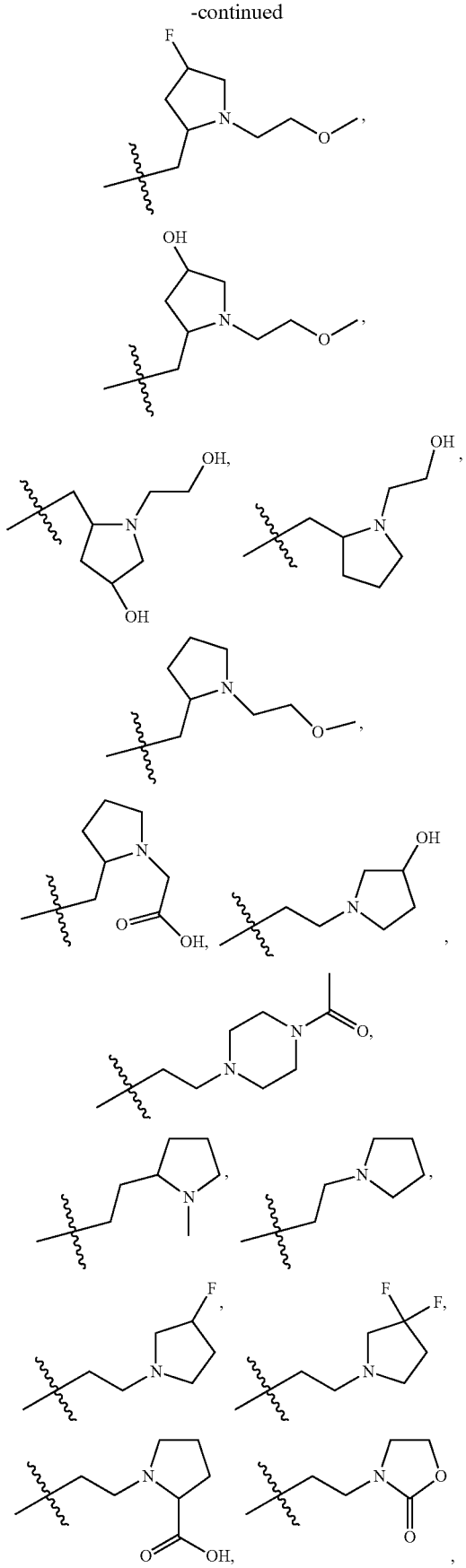
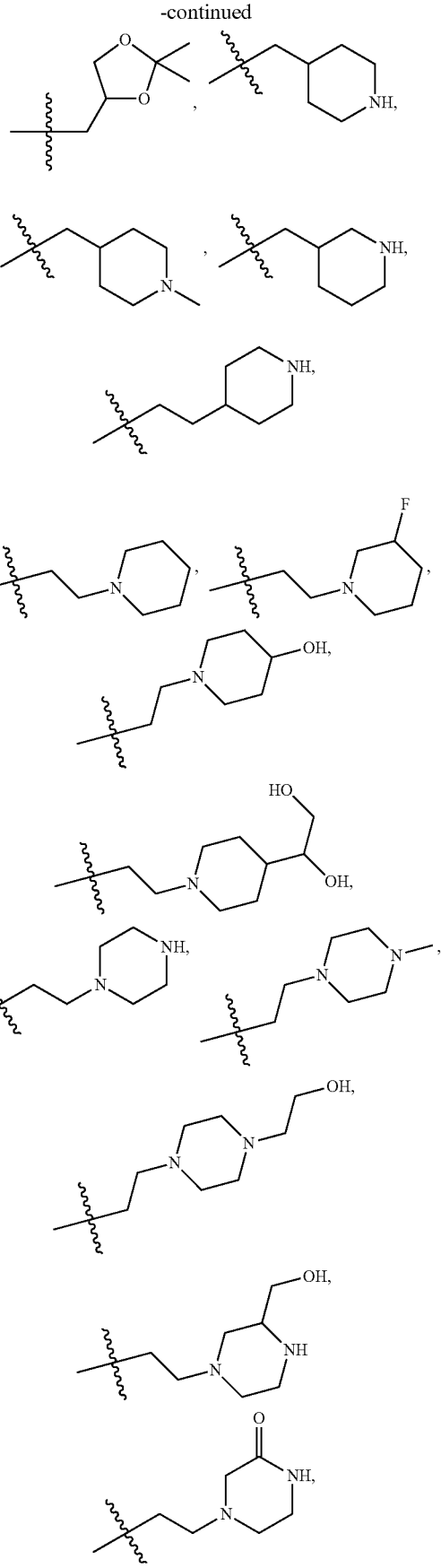

35
-continued
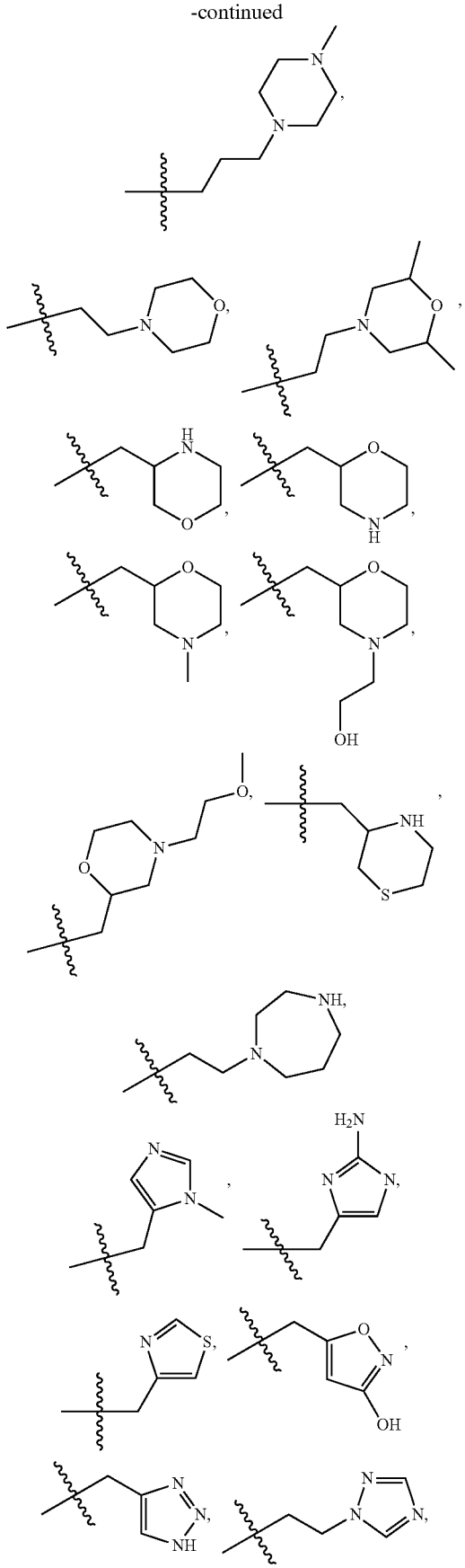
36
-continued
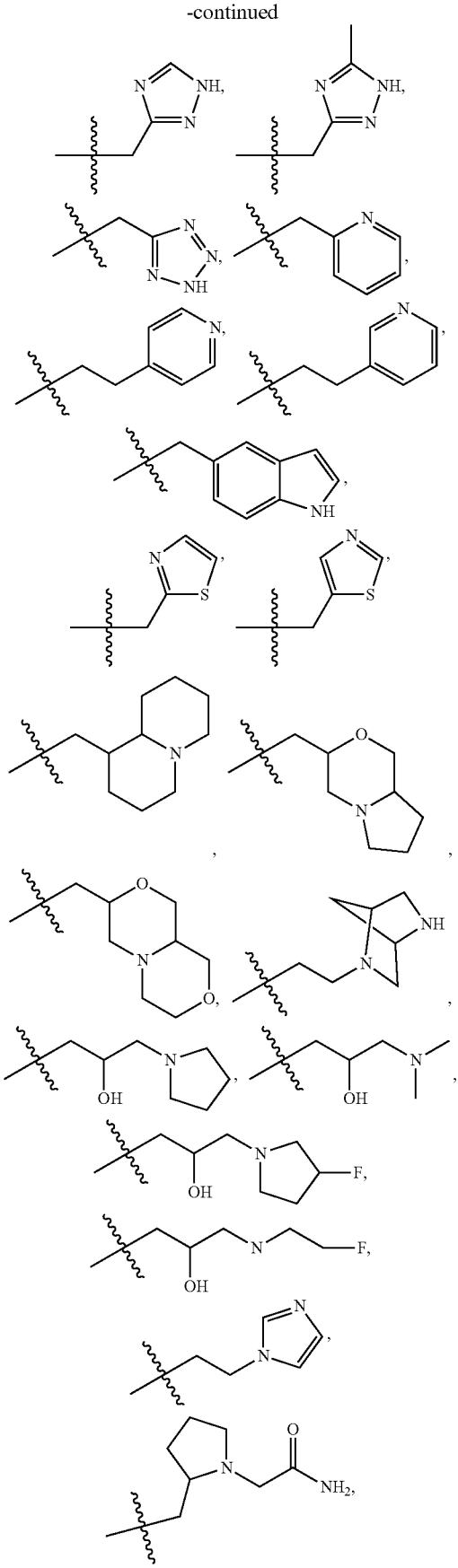

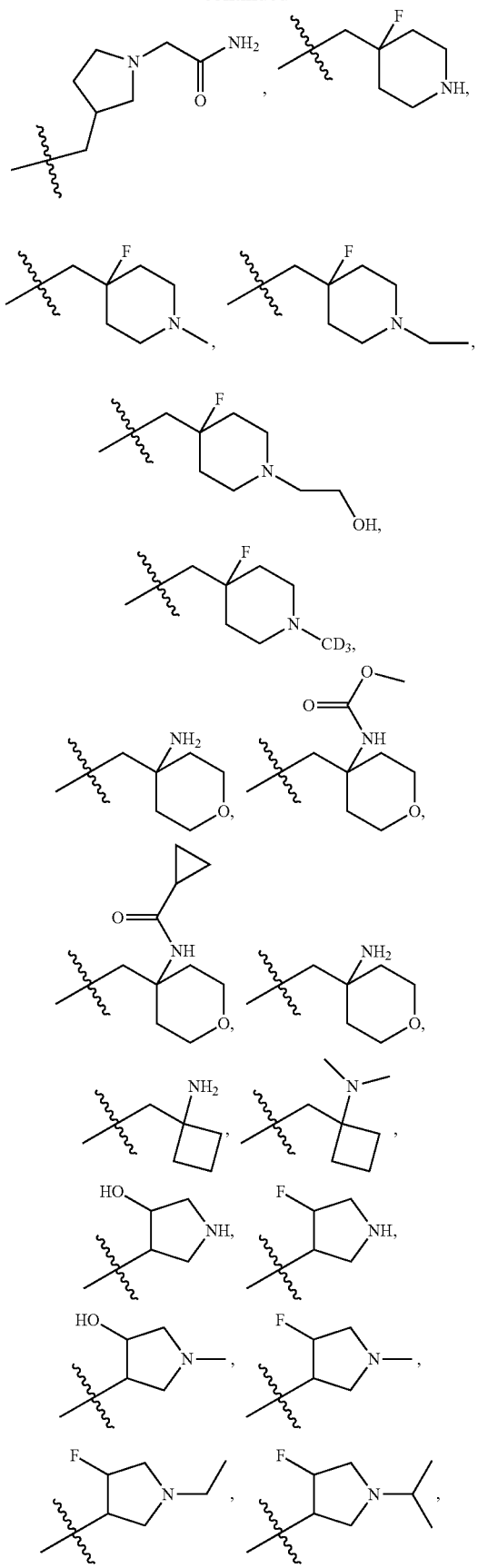
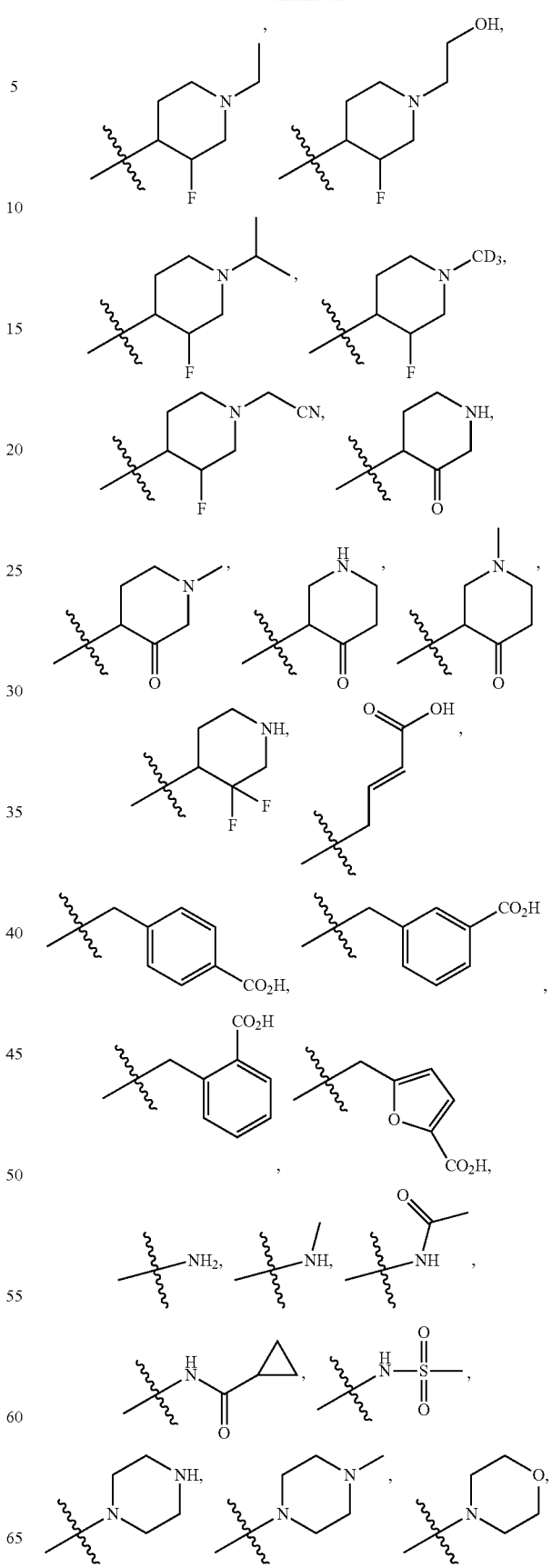

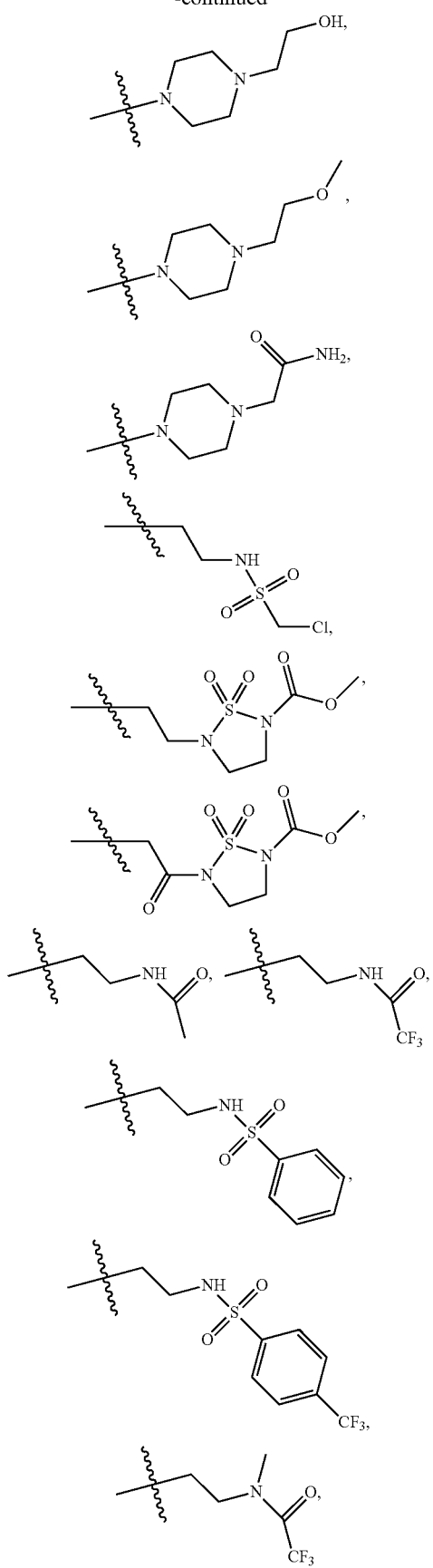
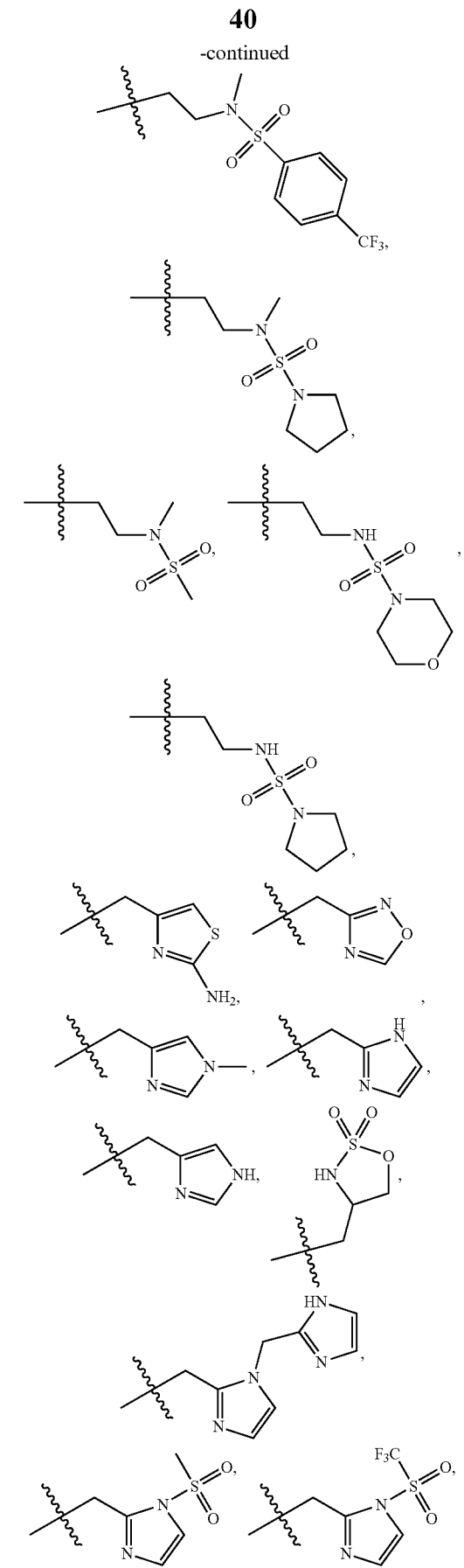

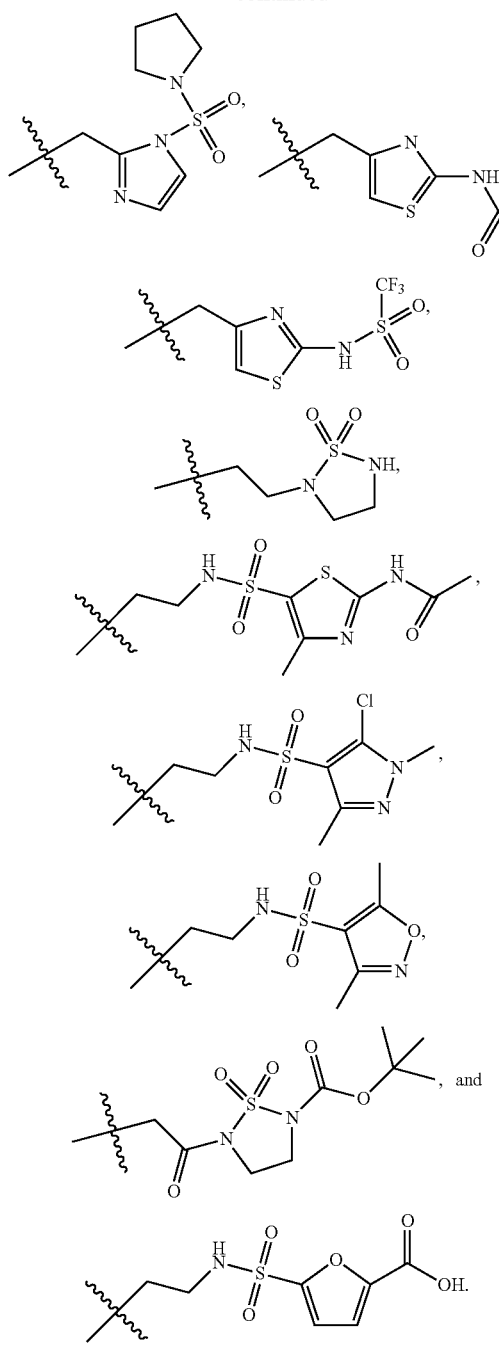
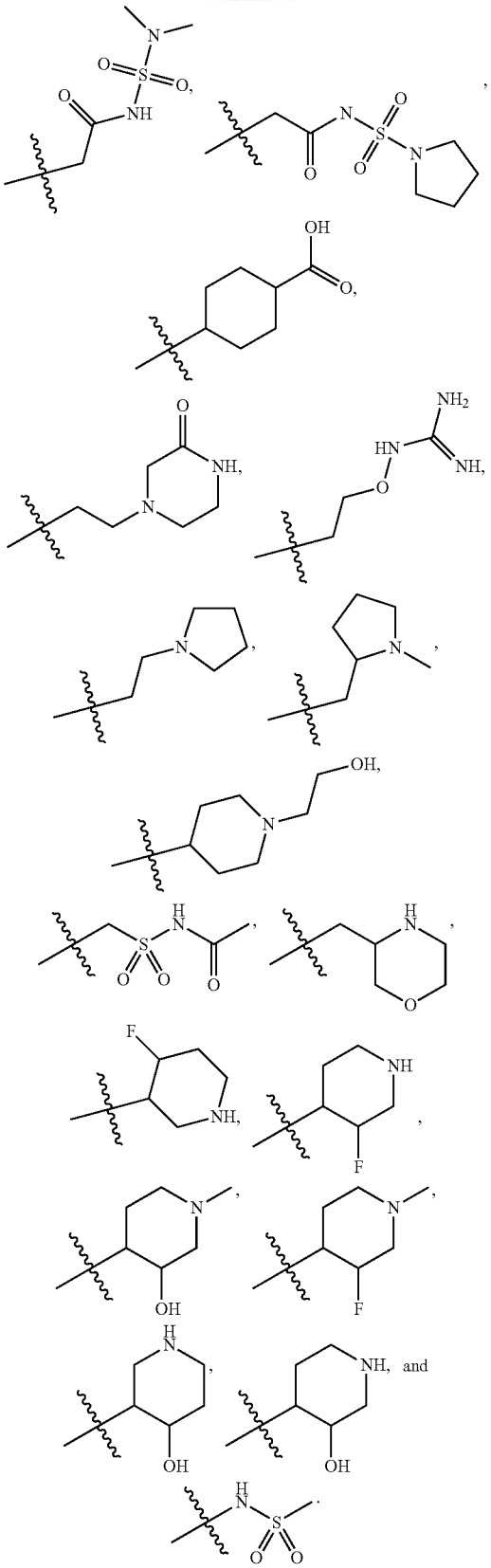
In certain embodiments of the present invention, $R_1$ is selected from:
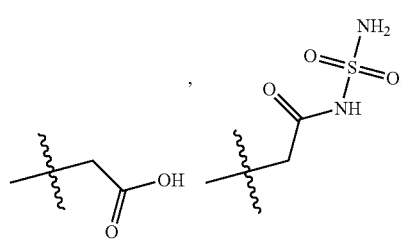
Furthermore, certain embodiments of the present invention include compounds of Formula (I) wherein X is N or CR$_4$;

Y is N or CH; with the proviso that when Y is CH, X is CH;

L is a bond or optionally substituted C$_{1-4}$alkyl;

wherein said optionally substituted C$_{1-4}$alkyl may be substituted with one to four groups, said groups independently selected from hydroxyl, oxo, halo, amino, —C(O)OH, and —C(O)O—C$_{1-2}$alkyl;

R$_1$ is selected from

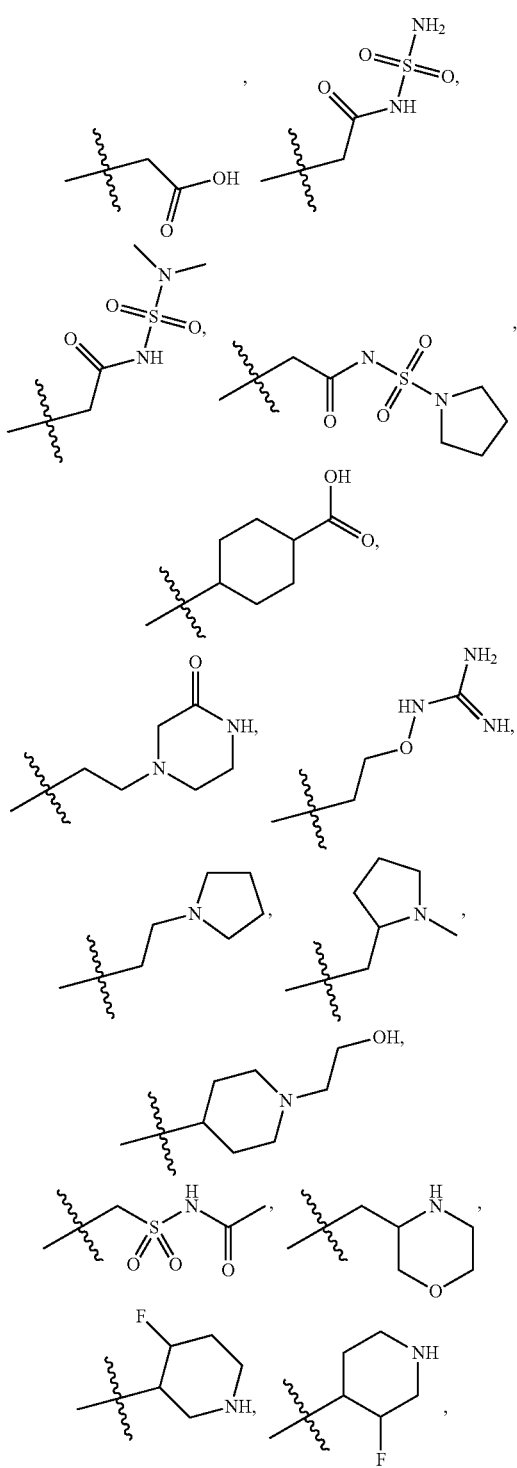

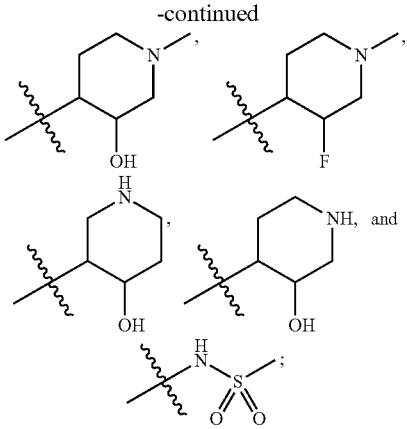

R$_2$ is halo-substituted C$_{1-3}$alkyl;

R$_3$ is halo or halo-substituted C$_{1-3}$alkyl;

R$_4$ is H or halo

R$_5$ is H;

R$_6$ is H or F; and

R$_7$ is H or F.

Other embodiments of the present invention include compounds of Formula (I) wherein X is N or CR$_4$;

Y is N or CH; with the proviso that when Y is CH, X is CH;

L is a bond or optionally substituted C$_{1-4}$alkyl;

wherein said optionally substituted C$_{1-4}$alkyl may be substituted with one to four groups, said groups independently selected from hydroxyl, oxo, halo, amino, —C(O)OH, and —C(O)O—C$_{1-2}$alkyl;

R$_2$ is CF$_3$;

R$_3$ is F, Cl, CF$_3$ or OCH$_3$;

R$_4$ is H, hydroxyl, Cl, OCH$_3$ or CH$_3$;

R$_5$ is H;

R$_6$ is H; and

R$_7$ is H.

Another embodiment of the present invention includes compounds of Formula (I) wherein X is N or CR$_4$;

Y is N;

R$_3$ is C$_1$, CF$_3$ or OCH$_3$; and

R$_4$ is H, Cl, or CH$_3$.

In one embodiment, the present invention includes compounds of Formula (I) wherein X is N or CR$_4$;

Y is N;

L is a bond;

R$_3$ is C$_1$, CF$_3$ or OCH$_3$; and

R$_4$ is H, Cl, or CH$_3$.

In one embodiment, the present invention includes compounds of Formula (I) wherein X is N or CR$_4$;

Y is N;

L is optionally substituted C$_{1-4}$alkyl;

wherein said optionally substituted C$_{1-4}$alkyl may be substituted with one to four groups, said groups independently selected from hydroxyl, oxo, halo, amino, —C(O)OH, and —C(O)O—C$_{1-2}$alkyl;

R$_3$ is C$_1$, CF$_3$ or OCH$_3$; and

R$_4$ is H, Cl, or CH$_3$.

In one embodiment, the present invention includes compounds of Formula (I) wherein X is N, or CR$_4$;

Y is N;

$R_2$ is halo-substituted $C_{1-3}$alkyl;
$R_3$ is halo or halo-substituted $C_{1-3}$alkyl;
$R_4$ is H or halo;
$R_5$ is H;
$R_6$ is H; and
$R_7$ is H;
or an enantiomer, diastereomer, cis-trans isomer, racemate, prodrug or pharmaceutically acceptable salt thereof.

Even more so, certain embodiments of the present invention include compounds of Formula (I) wherein X is $CR_4$; and $R_4$ is H.

In certain embodiments of the present invention, $R_1$ is selected from:

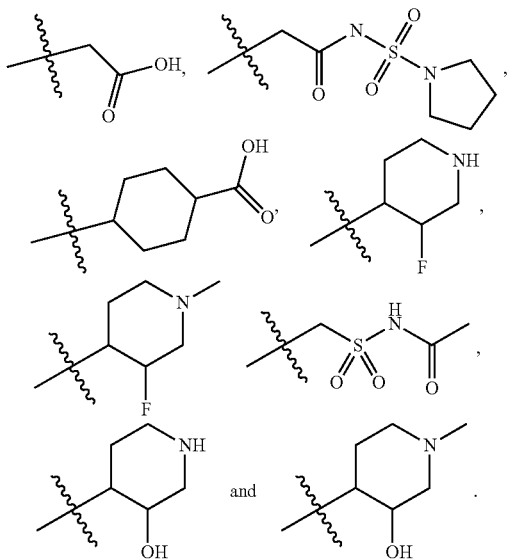

Furthermore, certain embodiments of the present invention include compounds of Formula (I) wherein
X is N or $CR_4$;
Y is N or CH; with the proviso that when Y is CH, X is CH;
L is a bond or optionally substituted $C_{1-4}$alkyl;
wherein said optionally substituted $C_{1-4}$alkyl may be substituted with one to four groups, said groups independently selected from hydroxyl, oxo, halo, amino, —C(O)OH, and —C(O)O—$C_{1-2}$alkyl;
$R_1$ is selected from

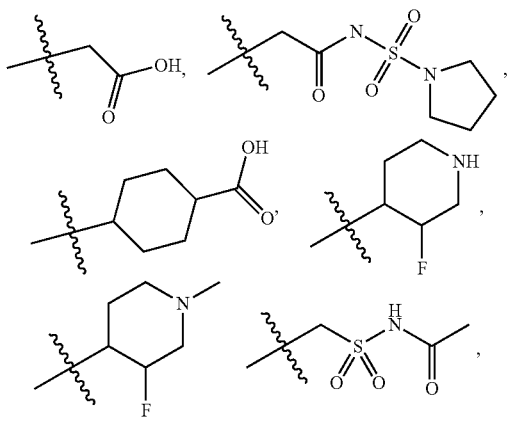

$R_2$ is halo-substituted $C_{1-3}$alkyl;
$R_3$ is halo or halo-substituted $C_{1-3}$alkyl;
$R_4$ is H or halo
$R_5$ is H;
$R_6$ is H or F; and
$R_7$ is H or F.

Other embodiments of the present invention include compounds of Formula (I) wherein
X is N or $CR_4$;
Y is N or CH; with the proviso that when Y is CH, X is CH;
L is a bond or optionally substituted $C_{1-4}$alkyl;
wherein said optionally substituted $C_{1-4}$alkyl may be substituted with one to four groups, said groups independently selected from hydroxyl, oxo, halo, amino, —C(O)OH, and —C(O)O—$C_{1-2}$alkyl;
$R_2$ is $CF_3$;
$R_3$ is F, Cl, $CF_3$ or $OCH_3$;
$R_4$ is H, hydroxyl, Cl, $OCH_3$ or $CH_3$;
$R_5$ is H;
$R_6$ is H; and
$R_7$ is H.

Another embodiment of the present invention includes compounds of Formula (I) wherein
X is N or $CR_4$;
Y is N;
$R_3$ is $C_1$, $CF_3$ or $OCH_3$; and
$R_4$ is H, Cl, or $CH_3$.

In one embodiment, the present invention includes compounds of Formula (I) wherein
X is N or $CR_4$;
Y is N;
L is a bond;
$R_3$ is $C_1$, $CF_3$ or $OCH_3$; and
$R_4$ is H, Cl, or $CH_3$.

In one embodiment, the present invention includes compounds of Formula (I) wherein
X is N or $CR_4$;
Y is N;
L is optionally substituted $C_{1-4}$alkyl;
wherein said optionally substituted $C_{1-4}$alkyl may be substituted with one to four groups, said groups independently selected from hydroxyl, oxo, halo, amino, —C(O)OH, and —C(O)O—$C_{1-2}$alkyl;
$R_3$ is $C_1$, $CF_3$ or $OCH_3$; and
$R_4$ is H, Cl, or $CH_3$.

In one embodiment, the present invention includes compounds of Formula (I) wherein
X is N, or $CR_4$;
Y is N;
$R_2$ is halo-substituted $C_{1-3}$alkyl;
$R_3$ is halo or halo-substituted $C_{1-3}$alkyl;
$R_4$ is H or halo;
$R_5$ is H;
$R_6$ is H; and
$R_7$ is H;
or an enantiomer, diastereomer, cis-trans isomer, racemate, prodrug or pharmaceutically acceptable salt thereof.

In one embodiment, the present invention includes compounds of Formula (I) wherein said optional $C_{1-4}$alkyl substituent, of said optionally substituted heterocyclyl, is substituted with deuterium.

It is an embodiment of the present invention to provide a compound selected from:

[(5Z)-5-({1-[4-Chloro-2-(trifluoromethyl)benzyl]-1H-benzotriazol-5-yl}methylidene)-2,4-dioxo-1,3-thiazolidin-3-yl]acetic acid;

[(5Z)-5-({1-[4-Chloro-2-(trifluoromethyl)benzyl]-3-chloro-1H-indazol-5-yl}methylidene)-2,4-dioxo-1,3-thiazolidin-3-yl]acetic acid;

[(5Z)-5-({1-[4-Chloro-2-(trifluoromethyl)benzyl]-1H-indazol-5-yl}methylidene)-2,4-dioxo-1,3-thiazolidin-3-yl]acetic acid;

2-[(5Z)-5-({1-[4-Chloro-2-(trifluoromethyl)benzyl]-1H-indazol-5-yl}methylidene)-2,4-dioxo-1,3-thiazolidin-3-yl]-N-(pyrrolidin-1-ylsulfonyl)acetamide;

(5Z)-5-({1-[4-chloro-2-(trifluoromethyl)benzyl]-1H-indazol-5-yl}methylidene)-3-(trans-3-hydroxy-1-methylpiperidin-4-yl)-1,3-thiazolidine-2,4-dione;

(5Z)-5-({1-[4-chloro-2-(trifluoromethyl)benzyl]-1H-indazol-5-yl}methylidene)-3-(trans-3-fluoro-1-methylpiperidin-4-yl)-1,3-thiazolidine-2,4-dione;

(5Z)-5-({1-[4-chloro-2-(trifluoromethyl)benzyl]-1H-indazol-5-yl}methylidene)-3-(trans-3-hydroxypiperidin-4-yl)-1,3-thiazolidine-2,4-dione;

(5Z)-5-({1-[4-chloro-2-(trifluoromethyl)benzyl]-3-methyl-1H-indazol-5-yl}methylidene)-3-(trans-3-fluoropiperidin-4-yl)-1,3-thiazolidine-2,4-dione;

(5Z)-5-({1-[4-chloro-2-(trifluoromethyl)benzyl]-3-methyl-1H-indazol-5-yl}methylidene)-3-(trans-3-fluoro-1-methylpiperidin-4-yl)-1,3-thiazolidine-2,4-dione;

N-({[(5Z)-5-({1-[4-Chloro-2-(trifluoromethyl)benzyl]-1H-indazol-5-yl}methylidene)-2,4-dioxo-1,3-thiazolidin-3-yl]methyl}sulfonyl)acetamide;

(5Z)-5-({1-[4-Chloro-2-(trifluoromethyl)benzyl]-1H-indazol-5-yl}methylidene)-3-[(3S)-morpholin-3-ylmethyl]-1,3-thiazolidine-2,4-dione;

1-{2-[(5Z)-5-({1-[4-Chloro-2-(trifluoromethyl)benzyl]-1H-indazol-5-yl}methylidene)-2,4-dioxo-1,3-thiazolidin-3-yl]ethoxy}guanidine;

(5Z)-5-({1-[2,4-Bis(trifluoromethyl)benzyl]-1H-indazol-5-yl}methylidene)-3-(cis-4-fluoropiperidin-3-yl)-1,3-thiazolidine-2,4-dione;

(5Z)-5-({1-[4-Chloro-2-(trifluoromethyl)benzyl]-1H-indazol-5-yl}methylidene)-3-(cis-4-fluoropiperidin-3-yl)-1,3-thiazolidine-2,4-dione;

2-[(5Z)-5-({1-[4-Chloro-2-(trifluoromethyl)benzyl]-1H-indazol-5-yl}methylidene)-2,4-dioxo-1,3-thiazolidin-3-yl]-N-sulfamoylacetamide;

(5Z)-5-({1-[4-Chloro-2-(trifluoromethyl)benzyl]-1H-indazol-5-yl}methylidene)-3-(2H-tetrazol-5-ylmethyl)-1,3-thiazolidine-2,4-dione;

(5Z)-5-({1-[4-Chloro-2-(trifluoromethyl)benzyl]-1H-indazol-5-yl}methylidene)-3-[1-(2-hydroxyethyl)piperidin-4-yl]-1,3-thiazolidine-2,4-dione;

(5Z)-5-({1-[4-Chloro-2-(trifluoromethyl)benzyl]-1H-indazol-5-yl}methylidene)-3-(2-pyrrolidin-1-ylethyl)-1,3-thiazolidine-2,4-dione;

(5Z)-5-({1-[4-Chloro-2-(trifluoromethyl)benzyl]-1H-indazol-5-yl}methylidene)-3-{[(2S)-1-methylpyrrolidin-2-yl]methyl}-1,3-thiazolidine-2,4-dione;

N-[(5Z)-5-({1-[4-Chloro-2-(trifluoromethyl)benzyl]-1H-indazol-5-yl}methylidene)-2,4-dioxo-1,3-thiazolidin-3-yl]methanesulfonamide;

(5Z)-5-({1-[4-Chloro-2-(trifluoromethyl)benzyl]-1H-indazol-5-yl}methylidene)-3-(trans-4-hydroxypiperidin-3-yl)-1,3-thiazolidine-2,4-dione;

(5Z)-5-({1-[4-Chloro-2-(trifluoromethyl)benzyl]-1H-indazol-5-yl}methylidene)-3-(trans-3-fluoropiperidin-4-yl)-1,3-thiazolidine-2,4-dione;

(5Z)-5-({1-[4-Chloro-2-(trifluoromethyl)benzyl]-1H-indazol-5-yl}methylidene)-3-[(3R,4R)-3-fluoropiperidin-4-yl]-1,3-thiazolidine-2,4-dione;

(5Z)-5-({1-[4-Chloro-2-(trifluoromethyl)benzyl]-1H-indazol-5-yl}methylidene)-3-[(3S,4S)-3-fluoropiperidin-4-yl]-1,3-thiazolidine-2,4-dione;

(5Z)-5-({1-[4-Chloro-2-(trifluoromethyl)benzyl]-1H-indazol-5-yl}methylidene)-3-[(3R,4R)-3-fluoro-1-methylpiperidin-4-yl]-1,3-thiazolidine-2,4-dione;

(5Z)-5-({1-[4-Chloro-2-(trifluoromethyl)benzyl]-1H-indazol-5-yl}methylidene)-3-[(3S,4S)-3-fluoro-1-methylpiperidin-4-yl]-1,3-thiazolidine-2,4-dione; and (5Z)-5-({1-[4-Chloro-2-(trifluoromethyl)benzyl]-1H-indazol-5-yl}methylidene)-3-[(trans)-3-fluoro-1-(2-hydroxyethyl)piperidin-4-yl]-1,3-thiazolidine-2,4-dione.

Particularly, the present invention provides a compound selected from:

[(5Z)-5-({1-[4-Chloro-2-(trifluoromethyl)benzyl]-1H-benzotriazol-5-yl}methylidene)-2,4-dioxo-1,3-thiazolidin-3-yl]acetic acid;

[(5Z)-5-({1-[4-Chloro-2-(trifluoromethyl)benzyl]-3-chloro-1H-indazol-5-yl}methylidene)-2,4-dioxo-1,3-thiazolidin-3-yl]acetic acid;

N-({[(5Z)-5-({1-[4-Chloro-2-(trifluoromethyl)benzyl]-1H-indazol-5-yl}methylidene)-2,4-dioxo-1,3-thiazolidin-3-yl]methyl}sulfonyl)acetamide;

(5Z)-5-({1-[4-Chloro-2-(trifluoromethyl)benzyl]-1H-indazol-5-yl}methylidene)-3-(morpholin-3-ylmethyl)-1,3-thiazolidine-2,4-dione;

1-{2-[(5Z)-5-({1-[4-Chloro-2-(trifluoromethyl)benzyl]-1H-indazol-5-yl}methylidene)-2,4-dioxo-1,3-thiazolidin-3-yl]ethoxy}guanidine;

N-[(5Z)-5-({1-[4-Chloro-2-(trifluoromethyl)benzyl]-1H-indazol-5-yl}methylidene)-2,4-dioxo-1,3-thiazolidin-3-yl]methanesulfonamide;

(5Z)-5-({1-[4-chloro-2-(trifluoromethyl)benzyl]-1H-indazol-5-yl}methylidene)-3-(trans-3-hydroxy-1-methylpiperidin-4-yl)-1,3-thiazolidine-2,4-dione;

(5Z)-5-({1-[4-chloro-2-(trifluoromethyl)benzyl]-1H-indazol-5-yl}methylidene)-3-(trans-3-fluoro-1-methylpiperidin-4-yl)-1,3-thiazolidine-2,4-dione;

(5Z)-5-({1-[4-chloro-2-(trifluoromethyl)benzyl]-1H-indazol-5-yl}methylidene)-3-(trans-3-hydroxypiperidin-4-yl)-1,3-thiazolidine-2,4-dione;

(5Z)-5-({1-[4-chloro-2-(trifluoromethyl)benzyl]-3-methyl-1H-indazol-5-yl}methylidene)-3-(trans-3-fluoropiperidin-4-yl)-1,3-thiazolidine-2,4-dione;

(5Z)-5-({1-[4-chloro-2-(trifluoromethyl)benzyl]-3-methyl-1H-indazol-5-yl}methylidene)-3-(trans-3-fluoro-1-methyl piperidin-4-yl)-1,3-thiazolidine-2,4-dione;

(5Z)-5-({1-[4-Chloro-2-(trifluoromethyl)benzyl]-1H-indazol-5-yl}methylidene)-3-(trans-4-hydroxypiperidin-3-yl)-1,3-thiazolidine-2,4-dione;

(5Z)-5-({1-[4-Chloro-2-(trifluoromethyl)benzyl]-1H-indazol-5-yl}methylidene)-3-(trans-3-fluoropiperidin-4-yl)-1,3-thiazolidine-2,4-dione;

(5Z)-5-({1-[4-Chloro-2-(trifluoromethyl)benzyl]-1H-indazol-5-yl}methylidene)-3-[(3R,4R)-3-fluoropiperidin-4-yl]-1,3-thiazolidine-2,4-dione;

(5Z)-5-({1-[4-Chloro-2-(trifluoromethyl)benzyl]-1H-indazol-5-yl}methylidene)-3-[(3S,4S)-3-fluoropiperidin-4-yl]-1,3-thiazolidine-2,4-dione;
(5Z)-5-({1-[4-Chloro-2-(trifluoromethyl)benzyl]-1H-indazol-5-yl}methylidene)-3-[(3R,4R)-3-fluoro-1-methylpiperidin-4-yl]-1,3-thiazolidine-2,4-dione;
(5Z)-5-({1-[4-Chloro-2-(trifluoromethyl)benzyl]-1H-indazol-5-yl}methylidene)-3-[(3S,4S)-3-fluoro-1-methylpiperidin-4-yl]-1,3-thiazolidine-2,4-dione; and
(5Z)-5-({1-[4-Chloro-2-(trifluoromethyl)benzyl]-1H-indazol-5-yl}methylidene)-3-[(trans)-3-fluoro-1-(2-hydroxyethyl)piperidin-4-yl]-1,3-thiazolidine-2,4-dione.

More particularly, the present invention provides a compound selected from:

[(5Z)-5-({1-[4-Chloro-2-(trifluoromethyl)benzyl]-1H-benzotriazol-5-yl}methylidene)-2,4-dioxo-1,3-thiazolidin-3-yl]acetic acid;
(5Z)-5-({1-[4-chloro-2-(trifluoromethyl)benzyl]-1H-indazol-5-yl}methylidene)-3-(trans-3-fluoro-1-methylpiperidin-4-yl)-1,3-thiazolidine-2,4-dione;
(5Z)-5-({1-[4-chloro-2-(trifluoromethyl)benzyl]-3-methyl-1H-indazol-5-yl}methylidene)-3-(trans-3-fluoropiperidin-4-yl)-1,3-thiazolidine-2,4-dione;
(5Z)-5-({1-[4-chloro-2-(trifluoromethyl)benzyl]-3-methyl-1H-indazol-5-yl}methylidene)-3-(trans-3-fluoro-1-methylpiperidin-4-yl)-1,3-thiazolidine-2,4-dione;
(5Z)-5-({1-[4-Chloro-2-(trifluoromethyl)benzyl]-1H-indazol-5-yl}methylidene)-3-(trans-3-fluoropiperidin-4-yl)-1,3-thiazolidine-2,4-dione;
(5Z)-5-({1-[4-Chloro-2-(trifluoromethyl)benzyl]-1H-indazol-5-yl}methylidene)-3-[(3R,4R)-3-fluoropiperidin-4-yl]-1,3-thiazolidine-2,4-dione;
(5Z)-5-({1-[4-Chloro-2-(trifluoromethyl)benzyl]-1H-indazol-5-yl}methylidene)-3-[(3S,4S)-3-fluoropiperidin-4-yl]-1,3-thiazolidine-2,4-dione;
(5Z)-5-({1-[4-Chloro-2-(trifluoromethyl)benzyl]-1H-indazol-5-yl}methylidene)-3-[(3R,4R)-3-fluoro-1-methylpiperidin-4-yl]-1,3-thiazolidine-2,4-dione;
(5Z)-5-({1-[4-Chloro-2-(trifluoromethyl)benzyl]-1H-indazol-5-yl}methylidene)-3-[(3S,4S)-3-fluoro-1-methylpiperidin-4-yl]-1,3-thiazolidine-2,4-dione; and
(5Z)-5-({1-[4-Chloro-2-(trifluoromethyl)benzyl]-1H-indazol-5-yl}methylidene)-3-[(trans)-3-fluoro-1-(2-hydroxyethyl)piperidin-4-yl]-1,3-thiazolidine-2,4-dione.

Another aspect of the present invention features a pharmaceutical composition comprising at least one compound of Formula (I) and at least one pharmaceutically acceptable carrier. Particularly, a pharmaceutical composition of the present invention can further comprise at least one additional agent, drug, medicament, antibody and/or inhibitor for treating, ameliorating or inhibiting the progression of an ERR-α mediated disease. A pharmaceutical composition of the present invention comprises a compound selected from:

[(5Z)-5-({1-[4-Chloro-2-(trifluoromethyl)benzyl]-1H-benzotriazol-5-yl}methylidene)-2,4-dioxo-1,3-thiazolidin-3-yl]acetic acid;
[(5Z)-5-({1-[4-Chloro-2-(trifluoromethyl)benzyl]-3-chloro-1H-indazol-5-yl}methylidene)-2,4-dioxo-1,3-thiazolidin-3-yl]acetic acid;
[(5Z)-5-({1-[4-Chloro-2-(trifluoromethyl)benzyl]-1H-indazol-5-yl}methylidene)-2,4-dioxo-1,3-thiazolidin-3-yl]acetic acid;
2-[(5Z)-5-({1-[4-Chloro-2-(trifluoromethyl)benzyl]-1H-indazol-5-yl}methylidene)-2,4-dioxo-1,3-thiazolidin-3-yl]-N-(pyrrolidin-1-ylsulfonyl)acetamide;
(5Z)-5-({1-[4-chloro-2-(trifluoromethyl)benzyl]-1H-indazol-5-yl}methylidene)-3-(trans-3-hydroxy-1-methylpiperidin-4-yl)-1,3-thiazolidine-2,4-dione;
(5Z)-5-({1-[4-chloro-2-(trifluoromethyl)benzyl]-1H-indazol-5-yl}methylidene)-3-(trans-3-fluoro-1-methylpiperidin-4-yl)-1,3-thiazolidine-2,4-dione;
(5Z)-5-({1-[4-chloro-2-(trifluoromethyl)benzyl]-1H-indazol-5-yl}methylidene)-3-(trans-3-hydroxypiperidin-4-yl)-1,3-thiazolidine-2,4-dione;
(5Z)-5-({1-[4-chloro-2-(trifluoromethyl)benzyl]-3-methyl-1H-indazol-5-yl}methylidene)-3-(trans-3-fluoropiperidin-4-yl)-1,3-thiazolidine-2,4-dione;
(5Z)-5-({1-[4-chloro-2-(trifluoromethyl)benzyl]-3-methyl-1H-indazol-5-yl}methylidene)-3-(trans-3-fluoro-1-methylpiperidin-4-yl)-1,3-thiazolidine-2,4-dione;
N-({[(5Z)-5-({1-[4-Chloro-2-(trifluoromethyl)benzyl]-1H-indazol-5-yl}methylidene)-2,4-dioxo-1,3-thiazolidin-3-yl]methyl}sulfonyl)acetamide;
(5Z)-5-({1-[4-Chloro-2-(trifluoromethyl)benzyl]-1H-indazol-5-yl}methylidene)-3-[(3S)-morpholin-3-ylmethyl]-1,3-thiazolidine-2,4-dione;
1-{2-[(5Z)-5-({1-[4-Chloro-2-(trifluoromethyl)benzyl]-1H-indazol-5-yl}methylidene)-2,4-dioxo-1,3-thiazolidin-3-yl]ethoxy}guanidine;
(5Z)-5-({1-[2,4-Bis(trifluoromethyl)benzyl]-1H-indazol-5-yl}methylidene)-3-(cis-4-fluoropiperidin-3-yl)-1,3-thiazolidine-2,4-dione;
(5Z)-5-({1-[4-Chloro-2-(trifluoromethyl)benzyl]-1H-indazol-5-yl}methylidene)-3-(cis-4-fluoropiperidin-3-yl)-1,3-thiazolidine-2,4-dione;
2-[(5Z)-5-({1-[4-Chloro-2-(trifluoromethyl)benzyl]-1H-indazol-5-yl}methylidene)-2,4-dioxo-1,3-thiazolidin-3-yl]-N-sulfamoylacetamide;
(5Z)-5-({1-[4-Chloro-2-(trifluoromethyl)benzyl]-1H-indazol-5-yl}methylidene)-3-(2H-tetrazol-5-ylmethyl)-1,3-thiazolidine-2,4-dione;
(5Z)-5-({1-[4-Chloro-2-(trifluoromethyl)benzyl]-1H-indazol-5-yl}methylidene)-3-[1-(2-hydroxyethyl)piperidin-4-yl]-1,3-thiazolidine-2,4-dione;
(5Z)-5-({1-[4-Chloro-2-(trifluoromethyl)benzyl]-1H-indazol-5-yl}methylidene)-3-(2-pyrrolidin-1-ylethyl)-1,3-thiazolidine-2,4-dione;
(5Z)-5-({1-[4-Chloro-2-(trifluoromethyl)benzyl]-1H-indazol-5-yl}methylidene)-3-{[(2S)-1-methylpyrrolidin-2-yl]methyl}-1,3-thiazolidine-2,4-dione;
N-[(5Z)-5-({1-[4-Chloro-2-(trifluoromethyl)benzyl]-1H-indazol-5-yl}methylidene)-2,4-dioxo-1,3-thiazolidin-3-yl]methanesulfonamide;
(5Z)-5-({1-[4-Chloro-2-(trifluoromethyl)benzyl]-1H-indazol-5-yl}methylidene)-3-(trans-4-hydroxypiperidin-3-yl)-1,3-thiazolidine-2,4-dione;
(5Z)-5-({1-[4-Chloro-2-(trifluoromethyl)benzyl]-1H-indazol-5-yl}methylidene)-3-(trans-3-fluoropiperidin-4-yl)-1,3-thiazolidine-2,4-dione;
(5Z)-5-({1-[4-Chloro-2-(trifluoromethyl)benzyl]-1H-indazol-5-yl}methylidene)-3-[(3R,4R)-3-fluoropiperidin-4-yl]-1,3-thiazolidine-2,4-dione;
(5Z)-5-({1-[4-Chloro-2-(trifluoromethyl)benzyl]-1H-indazol-5-yl}methylidene)-3-[(3S,4S)-3-fluoropiperidin-4-yl]-1,3-thiazolidine-2,4-dione;
(5Z)-5-({1-[4-Chloro-2-(trifluoromethyl)benzyl]-1H-indazol-5-yl}methylidene)-3-[(3R,4R)-3-fluoro-1-methylpiperidin-4-yl]-1,3-thiazolidine-2,4-dione;
(5Z)-5-({1-[4-Chloro-2-(trifluoromethyl)benzyl]-1H-indazol-5-yl}methylidene)-3-[(3S,4S)-3-fluoro-1-methylpiperidin-4-yl]-1,3-thiazolidine-2,4-dione; and (5Z)-5-({1-[4-Chloro-2-(trifluoromethyl)benzyl]-1H-indazol-5-yl}methylidene)-3-[(trans)-3-fluoro-1-(2-hydroxyethyl)piperidin-4-yl]-1,3-thiazolidine-2,4-dione.

Particularly, a pharmaceutical composition of the present invention comprises at least a compound selected from:

[(5Z)-5-({1-[4-Chloro-2-(trifluoromethyl)benzyl]-1H-benzotriazol-5-yl}methylidene)-2,4-dioxo-1,3-thiazolidin-3-yl]acetic acid;

[(5Z)-5-({1-[4-Chloro-2-(trifluoromethyl)benzyl]-3-chloro-1H-indazol-5-yl}methylidene)-2,4-dioxo-1,3-thiazolidin-3-yl]acetic acid;

N-({[(5Z)-5-({1-[4-Chloro-2-(trifluoromethyl)benzyl]-1H-indazol-5-yl}methylidene)-2,4-dioxo-1,3-thiazolidin-3-yl]methyl}sulfonyl)acetamide;

(5Z)-5-({1-[4-Chloro-2-(trifluoromethyl)benzyl]-1H-indazol-5-yl}methylidene)-3-(morpholin-3-ylmethyl)-1,3-thiazolidine-2,4-dione;

1-{2-[(5Z)-5-({1-[4-Chloro-2-(trifluoromethyl)benzyl]-1H-indazol-5-yl}methylidene)-2,4-dioxo-1,3-thiazolidin-3-yl]ethoxy}guanidine;

N-[(5Z)-5-({1-[4-Chloro-2-(trifluoromethyl)benzyl]-1H-indazol-5-yl}methylidene)-2,4-dioxo-1,3-thiazolidin-3-yl]methanesulfonamide;

(5Z)-5-({1-[4-chloro-2-(trifluoromethyl)benzyl]-1H-indazol-5-yl}methylidene)-3-(trans-3-hydroxy-1-methylpiperidin-4-yl)-1,3-thiazolidine-2,4-dione;

(5Z)-5-({1-[4-chloro-2-(trifluoromethyl)benzyl]-1H-indazol-5-yl}methylidene)-3-(trans-3-fluoro-1-methylpiperidin-4-yl)-1,3-thiazolidine-2,4-dione;

(5Z)-5-({1-[4-chloro-2-(trifluoromethyl)benzyl]-1H-indazol-5-yl}methylidene)-3-(trans-3-hydroxypiperidin-4-yl)-1,3-thiazolidine-2,4-dione;

(5Z)-5-({1-[4-chloro-2-(trifluoromethyl)benzyl]-3-methyl-1H-indazol-5-yl}methylidene)-3-(trans-3-fluoropiperidin-4-yl)-1,3-thiazolidine-2,4-dione;

(5Z)-5-({1-[4-chloro-2-(trifluoromethyl)benzyl]-3-methyl-1H-indazol-5-yl}methylidene)-3-(trans-3-fluoro-1-methyl piperidin-4-yl)-1,3-thiazolidine-2,4-dione;

(5Z)-5-({1-[4-Chloro-2-(trifluoromethyl)benzyl]-1H-indazol-5-yl}methylidene)-3-(trans-4-hydroxypiperidin-3-yl)-1,3-thiazolidine-2,4-dione;

(5Z)-5-({1-[4-Chloro-2-(trifluoromethyl)benzyl]-1H-indazol-5-yl}methylidene)-3-(trans-3-fluoropiperidin-4-yl)-1,3-thiazolidine-2,4-dione;

(5Z)-5-({1-[4-Chloro-2-(trifluoromethyl)benzyl]-1H-indazol-5-yl}methylidene)-3-[(3R,4R)-3-fluoropiperidin-4-yl]-1,3-thiazolidine-2,4-dione;

(5Z)-5-({1-[4-Chloro-2-(trifluoromethyl)benzyl]-1H-indazol-5-yl}methylidene)-3-[(3S,4S)-3-fluoropiperidin-4-yl]-1,3-thiazolidine-2,4-dione;

(5Z)-5-({1-[4-Chloro-2-(trifluoromethyl)benzyl]-1H-indazol-5-yl}methylidene)-3-[(3R,4R)-3-fluoro-1-methylpiperidin-4-yl]-1,3-thiazolidine-2,4-dione;

(5Z)-5-({1-[4-Chloro-2-(trifluoromethyl)benzyl]-1H-indazol-5-yl}methylidene)-3-[(3S,4S)-3-fluoro-1-methylpiperidin-4-yl]-1,3-thiazolidine-2,4-dione; and (5Z)-5-({1-[4-Chloro-2-(trifluoromethyl)benzyl]-1H-indazol-5-yl}methylidene)-3-[(trans)-3-fluoro-1-(2-hydroxyethyl)piperidin-4-yl]-1,3-thiazolidine-2,4-dione.

More particularly, a pharmaceutical composition of the present invention comprises at least a compound selected from:

[(5Z)-5-({1-[4-Chloro-2-(trifluoromethyl)benzyl]-1H-benzotriazol-5-yl}methylidene)-2,4-dioxo-1,3-thiazolidin-3-yl]acetic acid;

(5Z)-5-({1-[4-chloro-2-(trifluoromethyl)benzyl]-1H-indazol-5-yl}methylidene)-3-(trans-3-fluoro-1-methylpiperidin-4-yl)-1,3-thiazolidine-2,4-dione;

(5Z)-5-({1-[4-chloro-2-(trifluoromethyl)benzyl]-3-methyl-1H-indazol-5-yl}methylidene)-3-(trans-3-fluoropiperidin-4-yl)-1,3-thiazolidine-2,4-dione;

(5Z)-5-({1-[4-chloro-2-(trifluoromethyl)benzyl]-3-methyl-1H-indazol-5-yl}methylidene)-3-(trans-3-fluoro-1-methylpiperidin-4-yl)-1,3-thiazolidine-2,4-dione;

(5Z)-5-({1-[4-Chloro-2-(trifluoromethyl)benzyl]-1H-indazol-5-yl}methylidene)-3-(trans-3-fluoropiperidin-4-yl)-1,3-thiazolidine-2,4-dione;

(5Z)-5-({1-[4-Chloro-2-(trifluoromethyl)benzyl]-1H-indazol-5-yl}methylidene)-3-[(3R,4R)-3-fluoropiperidin-4-yl]-1,3-thiazolidine-2,4-dione;

(5Z)-5-({1-[4-Chloro-2-(trifluoromethyl)benzyl]-1H-indazol-5-yl}methylidene)-3-[(3S,4S)-3-fluoropiperidin-4-yl]-1,3-thiazolidine-2,4-dione;

(5Z)-5-({1-[4-Chloro-2-(trifluoromethyl)benzyl]-1H-indazol-5-yl}methylidene)-3-[(3R,4R)-3-fluoro-1-methylpiperidin-4-yl]-1,3-thiazolidine-2,4-dione;

(5Z)-5-({1-[4-Chloro-2-(trifluoromethyl)benzyl]-1H-indazol-5-yl}methylidene)-3-[(3S,4S)-3-fluoro-1-methylpiperidin-4-yl]-1,3-thiazolidine-2,4-dione; and (5Z)-5-({1-[4-Chloro-2-(trifluoromethyl)benzyl]-1H-indazol-5-yl}methylidene)-3-[(trans)-3-fluoro-1-(2-hydroxyethyl)piperidin-4-yl]-1,3-thiazolidine-2,4-dione.

The present invention also features a method of treating a subject suffering from or diagnosed with a disease, disorder, or condition mediated by ERR-α activity, comprising administering to the subject a therapeutically effective amount of at least one compound of Formula (I).

The present invention also features a method for inhibiting the progression of an ERR-α-mediated condition in a subject in need thereof, comprising administering to said subject a therapeutically effective amount of at least one compound of Formula (I).

The present invention also features a method for treating a prediabetic condition in a subject in need thereof, comprising administering to said subject a therapeutically effective amount of at least one compound of Formula (I).

Such disease, disorder, or condition can include, but is not limited to ankylosing spondylitis, artherosclerosis, arthritis (such as rheumatoid arthritis, infectious arthritis, childhood arthritis, psoriatic arthritis, reactive arthritis), bone-related diseases (including those related to bone formation), breast cancer (including those unresponsive to anti-estrogen therapy), cardiovascular disorders, cartilage-related disease (such as cartilage injury/loss, cartilage degeneration, and those related to cartilage formation), chondrodysplasia, chondrosarcoma, chronic back injury, chronic bronchitis, chronic inflammatory airway disease, chronic obstructive pulmonary disease, diabetes, disorders of energy homeostasis, gout, pseudogout, lipid disorders, metabolic syndrome, multiple myeloma, obesity, osteoarthritis, osteogenesis imperfecta, osteolytic bone metastasis, osteomalacia, osteoporosis, Paget's disease, periodontal disease, polymyalgia rheumatica, Reiter's syndrome, repetitive stress injury, hyperglycemia, elevated blood glucose level, and insulin resistance.

According to one aspect of the invention, the disclosed compounds and compositions are useful for the amelioration of symptoms associated with, the treatment of, and inhibiting the progression of, the following conditions and diseases: bone-related disease, bone formation, cartilage formation, cartilage loss, cartilage degeneration, cartilage injury, ankylosing spondylitis, chronic back injury, gout, osteoporosis, osteolytic bone metastasis, multiple myeloma, chondrosarcoma, chondrodysplasia, osteogenesis imperfecta, osteomalacia, Paget's disease, polymyalgia rheumatica, pseudogout, arthritis, rheumatoid arthritis, infectious arthritis, osteoarthritis, psoriatic arthritis, reactive arthritis, childhood arthritis, Reiter's syndrome, and repetitive stress injury.

According to another aspect of the invention, the disclosed compounds and compositions are useful for the amelioration of symptoms associated with, the treatment of, and/or inhibiting the progression of, the following conditions and diseases: periodontal disease, chronic inflammatory airway disease, chronic bronchitis, and chronic obstructive pulmonary disease.

According to a further aspect of the invention, the disclosed compounds and compositions are useful for the amelioration of symptoms associated with, the treatment of, and/or inhibiting the progression of breast cancer.

According to yet another aspect of the invention, the disclosed compounds and compositions are useful for the amelioration of symptoms associated with, the treatment of, and/or inhibiting the progression of, the following conditions and diseases: metabolic syndrome, obesity, disorders of energy homeostasis, diabetes, lipid disorders, cardiovascular disorders, artherosclerosis, hyperglycemia, elevated blood glucose level, and insulin resistance.

Particularly, a method of the present invention comprises administering to the subject a therapeutically effective amount of (a) at least one compound of Formula (I); and (b) at least one additional agent selected from a second ERR-α inverse agonist, an ERR-α antagonist, a glucokinase modulator, an anti-diabetic agent, an anti-obesity agent, a lipid lowering agent, an anti-thrombotic agent, direct thrombin inhibitor, and a blood pressure lowering agent, said administration being in any order. More particularly, the additional agent in (b) is a second ERR-α inverse agonist different from the compound in (a). More particularly, the additional agent in (b) is an anti-obesity agent selected from CB1 antagonists, monoamine reuptake inhibitors, and lipase inhibitors. More particularly, the additional agent in (b) is selected from rimonabant, sibutramine, and orlistat.

The present invention also features a method for treating or inhibiting the progression of one or more ERR-α-mediated conditions, said method comprising administering to a patient in need of treatment a pharmaceutically effective amount of a composition of the invention.

It is a further embodiment of the invention to provide a process for making a pharmaceutical composition comprising admixing any of the compounds according to Formula (I) and a pharmaceutically acceptable carrier.

The invention also features pharmaceutical compositions which include, without limitation, one or more of the disclosed compounds, and pharmaceutically acceptable carriers or excipients.

In a further embodiment of the invention, a method for treating or ameliorating an ERR-α-mediated condition in a subject in need thereof comprises administering to the subject a therapeutically effective amount of at least one compound of Formula (I), wherein the therapeutically effective amount of the compound of Formula (I) is from about 0.1 mg/dose to about 5 g/dose. In particular, the therapeutically effective amount of the compound of Formula (I) is from about 0.5 mg/dose to about 1000 mg/dose. More particularly, the therapeutically effective amount of the compound of Formula (I) is from about 1 mg/dose to about 100 mg/dose. In a further embodiment of the invention, the number of doses per day of a compound of Formula (I) is from 1 to 3 doses. In a further embodiment of the invention, the therapeutically effective amount of the compound of Formula (I) is from about 0.001 mg/kg/day to about 30 mg/kg/day. More particularly, the therapeutically effective amount of the compound of Formula (I) is from about 0.01 mg/kg/day to about 2 mg/kg/day.

In a further embodiment of the invention, a method for inhibiting the progression of an ERR-α-mediated condition in a subject in need thereof comprises administering to the subject a therapeutically effective amount of at least one compound of Formula (I), wherein the therapeutically effective amount of the compound of Formula (I) is from about 0.1 mg/dose to about 5 g/dose. In particular, the therapeutically effective amount of the compound of Formula (I) is from about 1 mg/dose to about 100 mg/dose. In a further embodiment of the invention, the number of doses per day of a compound of Formula (I) is from 1 to 3 doses. In a further embodiment of the invention, the therapeutically effective amount of the compound of Formula (I) is from about 0.001 mg/kg/day to about 30 mg/kg/day. More particularly, the therapeutically effective amount of the compound of Formula (I) is from about 0.01 mg/kg/day to about 2 mg/kg/day.

In yet another embodiment of the invention, a method for treating a prediabetic condition in a subject in need thereof, comprises administering to said subject a therapeutically effective amount of at least one compound of Formula (I), wherein the therapeutically effective amount of the compound of Formula (I) is from about 0.1 mg/dose to about 5 g/dose. In particular, the therapeutically effective amount of the compound of Formula (I) is from about 1 mg/dose to about 100 mg/dose. In a further embodiment of the invention, the number of doses per day of a compound of Formula (I) is from 1 to 3 doses. In a further embodiment of the invention, the therapeutically effective amount of the compound of Formula (I) is from about 0.001 mg/kg/day to about 30 mg/kg/day. More particularly, the therapeutically effective amount of the compound of Formula (I) is from about 0.01 mg/kg/day to about 2 mg/kg/day.

The invention is further described below.

A) Terms

Some terms are defined below and by their usage throughout this disclosure.

Unless otherwise noted, "alkyl" as used herein, whether used alone or as part of a substituent group, refers to a saturated, branched, or straight-chain monovalent hydrocarbon radical derived by the removal of one hydrogen atom from a single carbon atom of a parent alkane. Typical alkyl groups include, but are not limited to, methyl; ethyls; propyls such as propan-1-yl, propan-2-yl; butyls such as butan-1-yl, butan-2-yl, 2-methyl-propan-1-yl, 2-methyl-propan-2-yl, and the like. In preferred embodiments, the alkyl groups are $C_{1-6}$alkyl, with $C_{1-3}$alkyl being particularly preferred. "Alkoxyl" radicals are oxygen ethers formed from the previously described straight or branched chain alkyl groups.

As used herein, "halo" or "halogen" shall mean chlorine, bromine, fluorine and iodine. "Halo substituted" shall mean a group substituted with at least one halogen atom, preferably substituted with a least one fluoro atom. Suitable examples include, but are not limited to —$CF_3$, —$CH_2$—$CHF_2$, —$CH_2$—$CF_3$, and the like.

As used herein, "deuterium substituted" shall mean a group substituted with at least one deuterium atom. Suitable examples include, but are not limited to —$CD_3$, —$CH_2$—$CHD_2$, —$CH_2$—$CD_3$, and the like.

The term "guanidinyl" is defined as the radical of structure

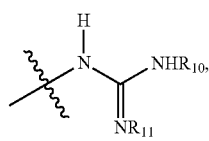

wherein $R_{10}$ and $R_{11}$ are independently selected from H, and/or $C_{1-4}$-alkyl.

The term "cycloalkyl," as used herein, refers to a stable, saturated or partially saturated monocyclic or bicyclic ring system containing from 3 to 8 ring carbons and preferably 5 to 7 ring carbons. Examples of such cyclic alkyl rings include cyclopropyl, cyclobutyl, cyclopentyl, cyclohexyl or cycloheptyl.

The term "alkenyl" refers to an unsaturated branched, straight-chain or cyclic monovalent hydrocarbon radical, which has at least one carbon-carbon double bond, derived by the removal of one hydrogen atom from a single carbon atom of a parent alkene. The radical may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

The term "heteroaryl" refers to a monovalent heteroaromatic radical derived by the removal of one hydrogen atom from a single atom of a parent heteroaromatic ring system. Typical heteroaryl groups include monocyclic and bicyclic systems where one or both rings is heteroaromatic. Heteroaromatic rings may contain 1-4 heteroatoms selected from O, N, and S. Examples include but are not limited to, radicals derived from carbazole, furan, imidazole, indazole, indole, indolizine, isoindole, isoquinoline, isothiazole, isoxazole, naphthyridine, oxadiazole, oxazole, purine, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

The term "aryl," as used herein, refers to aromatic groups comprising a stable six-membered monocyclic, or ten-membered bicyclic or fourteen-membered tricyclic aromatic ring system which consists of carbon atoms. Examples of aryl groups include, but are not limited to, phenyl or naphthalenyl.

The term "heterocyclyl" or "heterocycle" is a 3- to 12-member saturated or partially saturated single (monocyclic), bicyclic, or fused ring system which consists of carbon atoms and from 1 to 6 heteroatoms selected from N, O and S. The heterocyclyl group may be attached at any heteroatom or carbon atom which results in the creation of a stable structure. The bicyclic heterocyclyl group include systems where one or both rings include heteroatoms. Examples of heterocyclyl groups include, but are not limited to, 2-imidazoline, imidazolidine; morpholine, oxazoline, oxazolidine, 2-pyrroline, 3-pyrroline, pyrrolidine, pyridone, pyrimidone, piperazine, piperidine, indoline, tetrahydrofuran, 2-pyrroline, 3-pyrroline, 2-imidazoline, 2-pyrazoline, indolinone, thiomorpholine, tetrahydropyran, tetrahydroquinoline, tetrahydroquinazoline, [1,2,5]thiadiazolidine 1,1-dioxide, [1,2,3] oxathiazolidine 2,2-dioxide, and the like.

The term "oxo" whether used alone or as part of a substituent group refers to an O= to either a carbon or a sulfur atom. For example, phthalimide and saccharin are examples of compounds with oxo substituents.

The term "cis-trans isomer" refers to stereoisomeric olefins or cycloalkanes (or hetero-analogues) which differ in the positions of atoms (or groups) relative to a reference plane: in the cis-isomer the atoms of highest priority are on the same side; in the trans-isomer they are on opposite sides.

The term "substituted" refers to a radical in which one or more hydrogen atoms are each independently replaced with the same or different substituent(s).

With reference to substituents, the term "independently" means that when more than one of such substituent is possible, such substituents may be the same or different from each other.

The term "composition" is intended to encompass a product comprising the specified ingredients in the specified amounts, as well as any product which results, directly or indirectly, from combinations of the specified ingredients in the specified amounts.

The term "subject" as used herein, refers to an animal, preferably a mammal, most preferably a human, who is the object of treatment, observation or experiment.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

The term "inverse agonist" as used herein refers to compounds or substances that have the ability to decrease the constitutive level of receptor activation in the absence of an agonist instead of only blocking the activation induced by agonist binding at the receptor.

Metabolic disorders, diseases, or conditions include, but are not limited to, diabetes, obesity, and associated symptoms or complications thereof. They include such conditions as IDDM (insulin-dependent diabetes mellitus), NIDDM (non insulin-dependent diabetes mellitus), IGT (Impaired Glucose Tolerance), IFG (Impaired Fasting Glucose), Syndrome X (or Metabolic Syndrome), hyperglycemia, elevated blood glucose level, and insulin resistance. A condition such as IGT or IFG is also known as a "prediabetic condition" or "prediabetic state."

Methods are known in the art for determining effective doses for therapeutic and prophylactic purposes for the disclosed pharmaceutical compositions or the disclosed drug combinations, whether or not formulated in the same composition. For therapeutic purposes, the term "therapeutically effective amount" as used herein, means that amount of each active compound or pharmaceutical agent, alone or in combination, that elicits the biological or medicinal response in a tissue system, animal or human that is being sought by a researcher, veterinarian, medical doctor or other clinician, which includes alleviation of the symptoms of the disease or disorder being treated. For prophylactic purposes (i.e., inhibiting the onset or progression of a disorder), the term "therapeutically effective amount" refers to that amount of each active compound or pharmaceutical agent, alone or in combination, that treats or inhibits in a subject the onset or progression of a disorder as being sought by a researcher, veterinarian, medical doctor or other clinician. Thus, the present invention provides combinations of two or more drugs wherein, for example, (a) each drug is administered in an independently therapeutically or prophylactically effective amount; (b) at least one drug in the combination is administered in an amount that is sub-therapeutic or sub-prophylactic if administered alone, but is therapeutic or prophylactic when administered in combination with the second or additional drugs according to the invention; or (c) both (or more) drugs are administered in an amount that is sub-therapeutic or sub-prophylactic if administered alone, but are therapeutic or prophylactic when administered together.

The term "pharmaceutically acceptable salt" refers to non-toxic pharmaceutically acceptable salts (Ref. International J. Pharm., 1986, 33, 201-217; J. Pharm. Sci., 1997 (January), 66, 1, 1). Other salts well known to those in the art may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

B) Compounds

Representative compounds of the present invention are listed in Table I below:

TABLE I

| STRUCTURE | COMPOUND # | NAME |
|---|---|---|
| 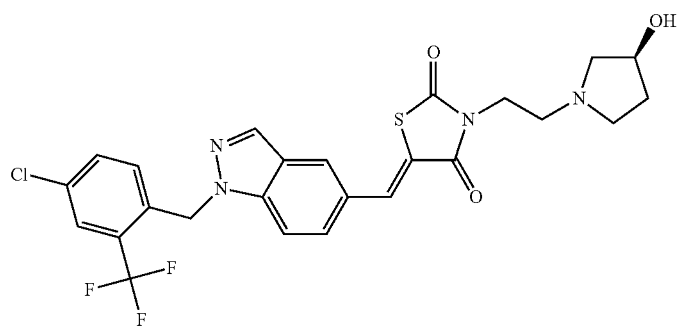 [SMILES: O=C1S/C(=C\c2ccc3c(cnn3Cc3ccc(Cl)cc3C(F)(F)F)c2)C(=O)N1CCN1CC[C@H](O)C1] | 1 | (5Z)-5-({1-[4-Chloro-2-(trifluoromethyl)benzyl]-1H-indazol-5-yl}methylidene)-3-{2-[(3S)-3-fluoro-pyrrolidin-1-yl]ethyl}-1,3-thiazolidine-2,4-dione |
| 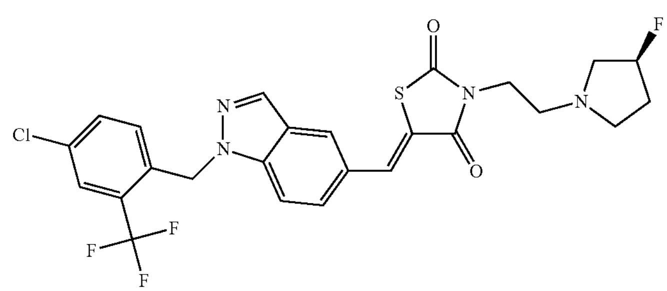 [SMILES: O=C1S/C(=C\c2ccc3c(cnn3Cc3ccc(Cl)cc3C(F)(F)F)c2)C(=O)N1CCN1CC[C@H](F)C1] | 2 | (5Z)-5-({1-[4-Chloro-2-(trifluoromethyl)benzyl]-1H-indazol-5-yl}methylidene)-3-{2-[(3S)-3-fluoro-pyrrolidin-1-yl]ethyl}-1,3-thiazolidine-2,4-dione |
| 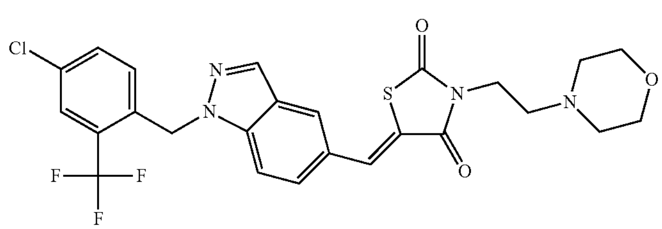 | 3 | (5Z)-5-({1-[4-Chloro-2-(trifluoromethyl)benzyl]-1H-indazol-5-yl}methylidene)-3-(2-morpholin-4-ylethyl)-1,3-thiazolidine-2,4-dione |
| 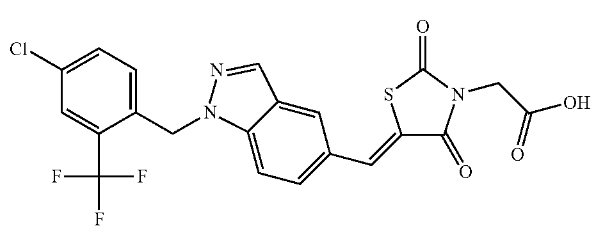 [SMILES: O=C(O)CN1C(=O)S/C(=C\c2ccc3c(cnn3Cc3ccc(Cl)cc3C(F)(F)F)c2)C1=O] | 4 | (5Z)-5-{[1-(4-Chloro-2-trifluoromethylbenzyl)-1H-indazol-5-yl]methylidene}-2,4-dioxothiazolidin-3-ylacetic acid |

TABLE I-continued

| STRUCTURE | COMPOUND # | NAME |
|---|---|---|
| 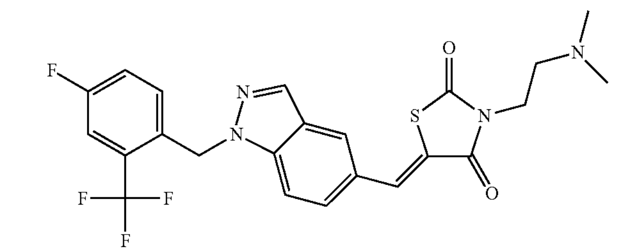 | 5 | (5Z)-3-[2-(Dimethylamino)ethyl]-5-[(1-{[4-fluoro-2-(trifluoromethyl)phenyl]methyl}-1H-indazol-5-yl)methylidene]-1,3-thiazolidine-2,4-dione |
| 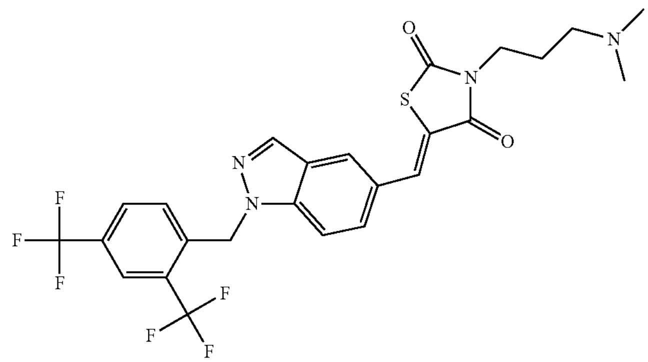 [SMILES: CN(C)CCCN1C(=O)S/C(=C\c2ccc3c(cnn3Cc3ccc(C(F)(F)F)cc3C(F)(F)F)c2)C1=O] | 6 | (5Z)-5-[(1-{[2,4-Bis(trifluoromethyl)phenyl]methyl}-1H-indazol-5-yl)methylidene]-3-[3-(dimethylamino)propyl]-1,3-thiazolidine-2,4-dione |
| 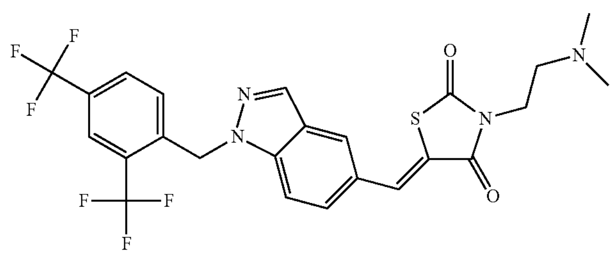 | 7 | (5Z)-5-[(1-{[2,4-Bis(trifluoromethyl)phenyl]methyl}-1H-indazol-5-yl)methylidene]-3-[2-(dimethylamino)ethyl]-1,3-thiazolidine-2,4-dione |
| 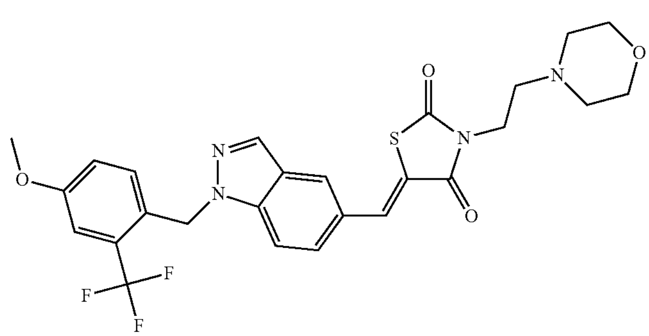 [SMILES: COc1ccc(Cn2ncc3cc(/C=C4\SC(=O)N(CCN5CCOCC5)C4=O)ccc32)c(C(F)(F)F)c1] | 8 | (5Z)-5-[(1-{[4-(Methyloxy)-2-(trifluoromethyl)phenyl]methyl}-1H-indazol-5-yl)methylidene]-3-(2-morpholin-4-ylethyl)-1,3-thiazolidine-2,4-dione |
| 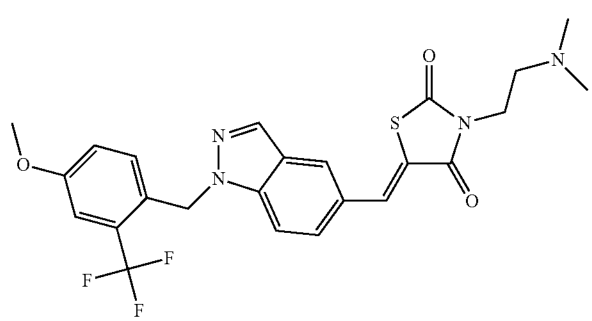 | 9 | (5Z)-3-[2-(Dimethylamino)ethyl]-5-[(1-{[4-(methyloxy)-2-(trifluoromethyl)phenyl]methyl}-1H-indazol-5-yl)methylidene]-1,3-thiazolidine-2,4-dione |

TABLE I-continued

| STRUCTURE | COMPOUND # | NAME |
|---|---|---|
| 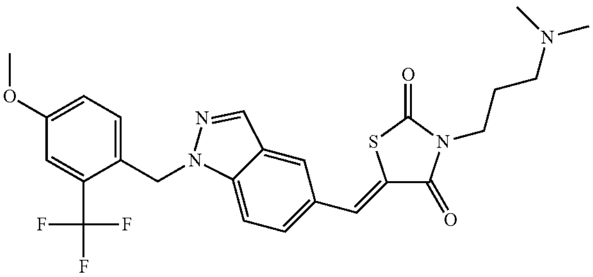 [SMILES: COc1ccc(Cn2ncc3cc(/C=C4\SC(=O)N(CCCN(C)C)C4=O)ccc32)c(C(F)(F)F)c1] | 10 | (5Z)-3-[3-(Dimethylamino)propyl]-5-[(1-{[4-(methyloxy)-2-(trifluoromethyl)phenyl]methyl}-1H-indazol-5-yl)methylidene]-1,3-thiazolidine-2,4-dione |
| 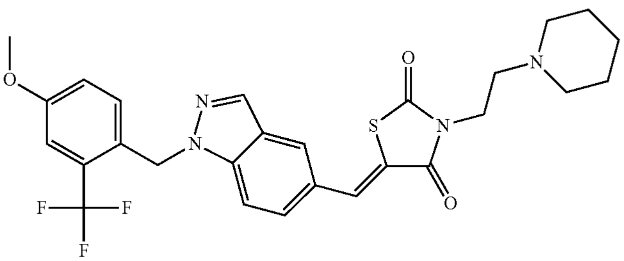 [SMILES: COc1ccc(Cn2ncc3cc(/C=C4\SC(=O)N(CCN5CCCCC5)C4=O)ccc32)c(C(F)(F)F)c1] | 11 | (5Z)-5-[(1-{[4-(Methyloxy)-2-(trifluoromethyl)phenyl]methyl}-1H-indazol-5-yl)methylidene]-3-(2-piperidin-1-ylethyl)-1,3-thiazolidine-2,4-dione |
| 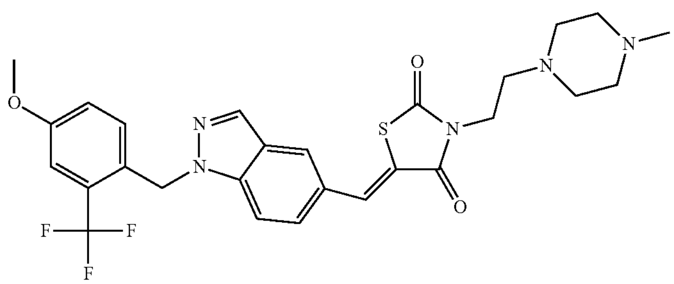 [SMILES: COc1ccc(Cn2ncc3cc(/C=C4\SC(=O)N(CCN5CCN(C)CC5)C4=O)ccc32)c(C(F)(F)F)c1] | 12 | (5Z)-5-[(1-{[4-(Methyloxy)-2-(trifluoromethyl)phenyl]methyl}-1H-indazol-5-yl)methylidene]-3-[2-(4-methylpiperazin-1-yl)ethyl]-1,3-thiazolidine-2,4-dione |
| 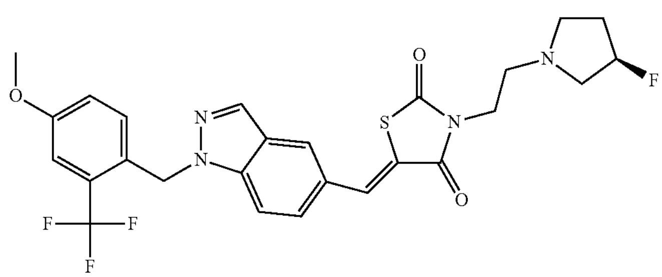 [SMILES: COc1ccc(Cn2ncc3cc(/C=C4\SC(=O)N(CCN5CC[C@@H](F)C5)C4=O)ccc32)c(C(F)(F)F)c1] | 13 | (5Z)-3-{2-[(3R)-3-Fluoropyrrolidin-1-yl]ethyl}-5-[(1-{[4-(methyloxy)-2-(trifluoromethyl)phenyl]methyl}-1H-indazol-5-yl)methylidene]-1,3-thiazolidine-2,4-dione |
| 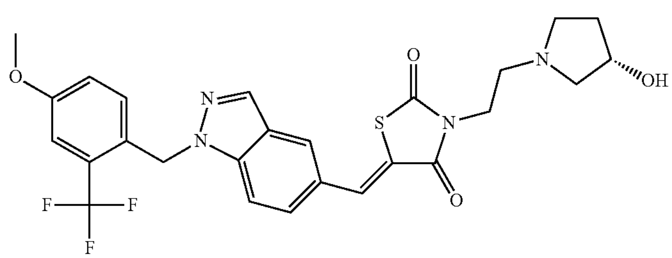 [SMILES: COc1ccc(Cn2ncc3cc(/C=C4\SC(=O)N(CCN5CC[C@H](O)C5)C4=O)ccc32)c(C(F)(F)F)c1] | 14 | (5Z)-3-{2-[(3S)-3-Hydroxypyrrolidin-1-yl]ethyl}-5-({1-[4-methoxy-2-(trifluoromethyl)benzyl]-1H-indazol-5-yl}methylidene)-1,3-thiazolidine-2,4-dione |

TABLE I-continued

| STRUCTURE | COMPOUND # | NAME |
|---|---|---|
| 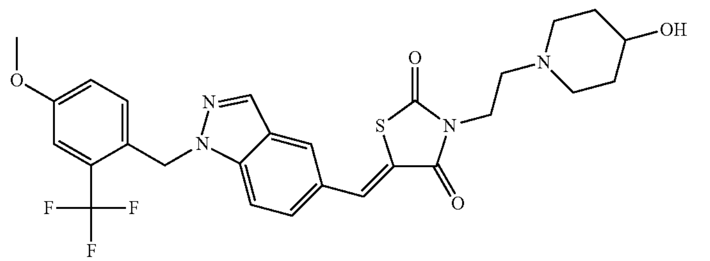 [SMILES: COc1ccc(Cn2ncc3cc(/C=C4\SC(=O)N(CCN5CCC(O)CC5)C4=O)ccc32)c(C(F)(F)F)c1] | 15 | (5Z)-3-[2-(4-Hydroxypiperidin-1-yl)ethyl]-5-({1-[4-methoxy-2-(trifluoromethyl)benzyl]-1H-indazol-5-yl}methylidene)-1,3-thiazolidine-2,4-dione |
| 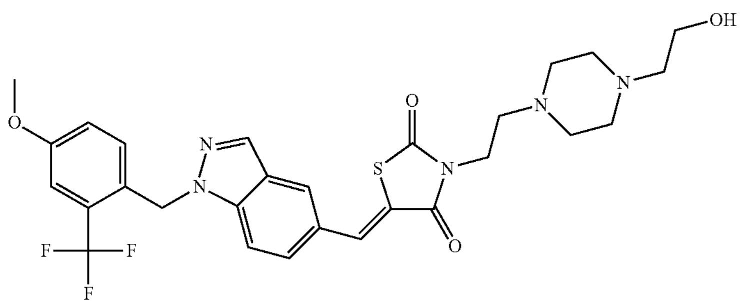 [SMILES: COc1ccc(Cn2ncc3cc(/C=C4\SC(=O)N(CCN5CCN(CCO)CC5)C4=O)ccc32)c(C(F)(F)F)c1] | 16 | (5Z)-3-{2-[4-(2-Hydroxyethyl)piperazin-1-yl]ethyl}-5-({1-[4-methoxy-2-(trifluoromethyl)benzyl]-1H-indazol-5-yl}methylidene)-1,3-thiazolidine-2,4-dione |
| 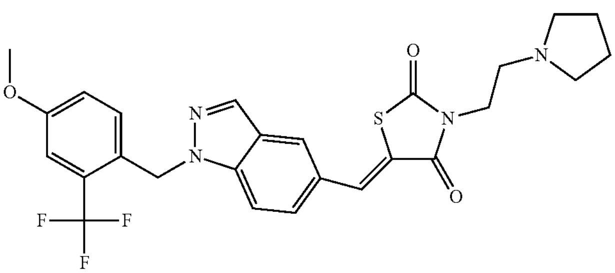 [SMILES: COc1ccc(Cn2ncc3cc(/C=C4\SC(=O)N(CCN5CCCC5)C4=O)ccc32)c(C(F)(F)F)c1] | 17 | (5Z)-5-({1-[4-Methoxy-2-(trifluoromethyl)benzyl]-1H-indazol-5-yl}methylidene)-3-(2-pyrrolidin-1-ylethyl)-1,3-thiazolidine-2,4-dione |
| 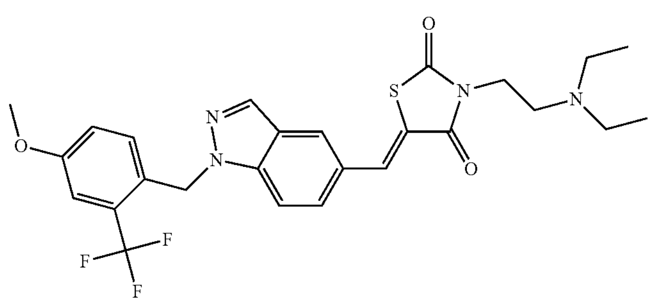 [SMILES: CCN(CC)CCN1C(=O)S/C(=C\c2ccc3c(cnn3Cc3ccc(OC)cc3C(F)(F)F)c2)C1=O] | 18 | (5Z)-3-[2-(Diethylamino)ethyl]-5-({1-[4-methoxy-2-(trifluoromethyl)benzyl]-1H-indazol-5-yl}methylidene)-1,3-thiazolidine-2,4-dione |
| 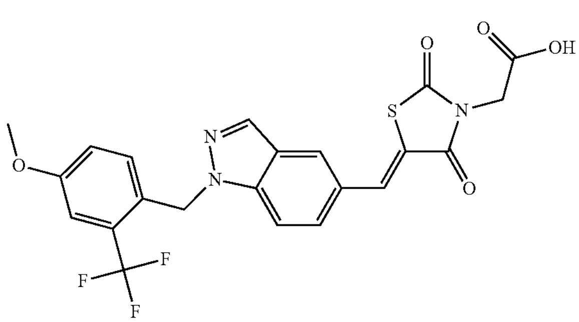 [SMILES: COc1ccc(Cn2ncc3cc(/C=C4\SC(=O)N(CC(=O)O)C4=O)ccc32)c(C(F)(F)F)c1] | 19 | [(5Z)-5-({1-[4-Methoxy-2-(trifluoromethyl)benzyl]-1H-indazol-5-yl}methylidene)-2,4-dioxo-1,3-thiazolidin-3-yl]acetic acid |

TABLE I-continued

| STRUCTURE | COMPOUND # | NAME |
|---|---|---|
| 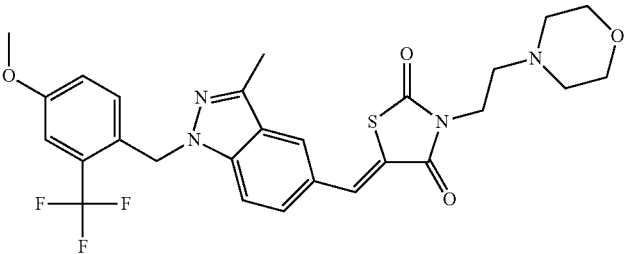 [SMILES: COc1ccc(Cn2nc(C)c3cc(/C=C4\SC(=O)N(CCN5CCOCC5)C4=O)ccc32)c(C(F)(F)F)c1] | 20 | (5Z)-5-({1-[4-Methoxy-2-(trifluoromethyl)benzyl]-3-methyl-1H-indazol-5-yl}methylidene)-3-(2-morpholin-4-ylethyl)-1,3-thiazolidine-2,4-dione |
| 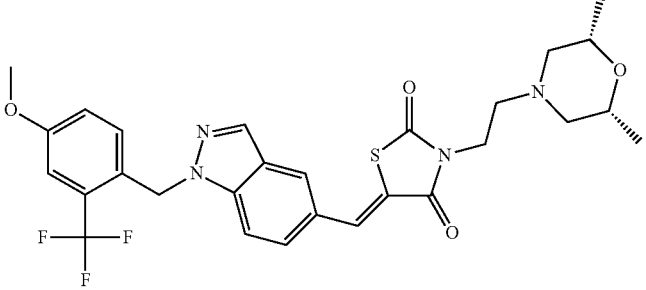 [SMILES: COc1ccc(Cn2ncc3cc(/C=C4\SC(=O)N(CCN5C[C@@H](C)O[C@@H](C)C5)C4=O)ccc32)c(C(F)(F)F)c1] | 21 | (5Z)-3-{2-[cis-2,6-Dimethylmorpholin-4-yl]ethyl}-5-({1-[4-methoxy-2-(trifluoromethyl)benzyl]-1H-indazol-5-yl)methylidene)-1,3-thiazolidine-2,4-dione |
| 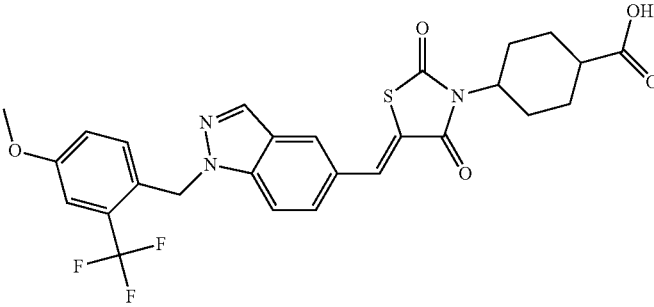 | 22 | 4-[(5Z)-5-({1-[4-Methoxy-2-(trifluoromethyl)benzyl]-1H-indazol-5-yl}methylidene)-2,4-dioxo-1,3-thiazolidin-3-yl)cyclohexanecarboxylic acid |
| 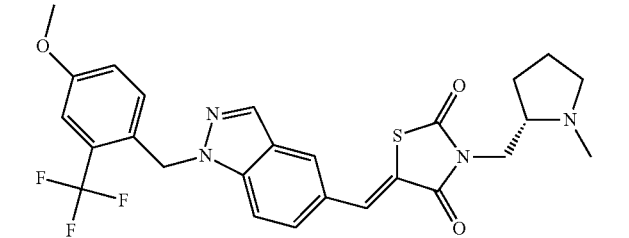 [SMILES: COc1ccc(Cn2ncc3cc(/C=C4\SC(=O)N(C[C@@H]5CCCN5C)C4=O)ccc32)c(C(F)(F)F)c1] | 23 | (5Z)-5-({1-[4-Methoxy-2-(trifluoromethyl)benzyl]-1H-indazol-5-yl}methylidene)-3-{[(2S)-1-methylpyrrolidin-2-yl]methyl}-1,3-thiazolidine-2,4-dione |
| 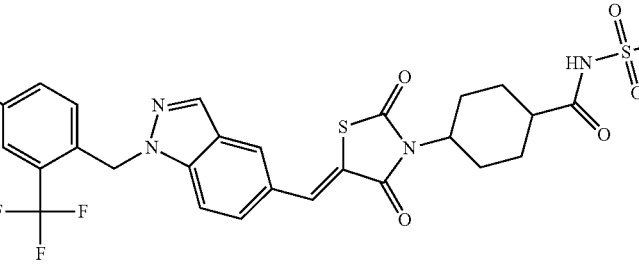 | 24 | 4-[(5Z)-5-({1-[4-Methoxy-2-(trifluoromethyl)benzyl]-1H-indazol-5-yl}methylidene)-2,4-dioxo-1,3-thiazolidin-3-yl]-N-(methylsulfonyl)cyclohexanecarboxamide |

TABLE I-continued

| STRUCTURE | COMPOUND # | NAME |
|---|---|---|
| 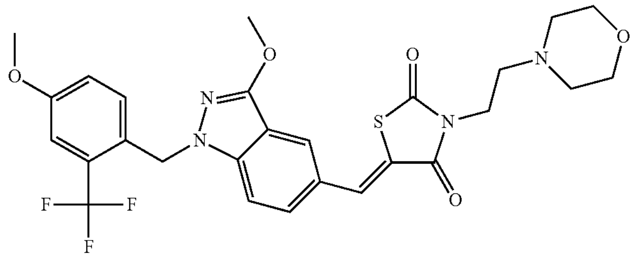 [SMILES: COc1ccc(Cn2nc(OC)c3cc(/C=C4\SC(=O)N(CCN5CCOCC5)C4=O)ccc32)c(C(F)(F)F)c1] | 25 | (5Z)-5-({3-Methoxy-1-[4-methoxy-2-(trifluoromethyl)benzyl]-1H-indazol-5-yl}methylidene)-3-(2-morpholin-4-ylethyl)-1,3-thiazolidine-2,4-dione |
| 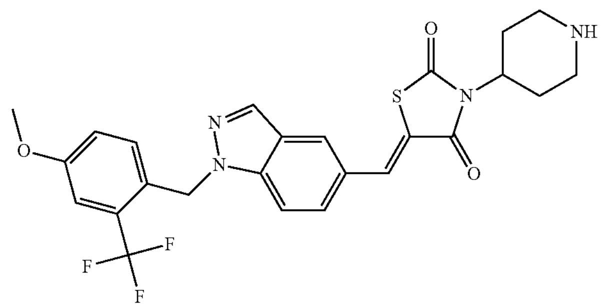 [SMILES: COc1ccc(Cn2ncc3cc(/C=C4\SC(=O)N(C5CCNCC5)C4=O)ccc32)c(C(F)(F)F)c1] | 26 | (5Z)-5-({1-[4-Methoxy-2-(trifluoromethyl)benzyl]-1H-indazol-5-yl}methylidene)-3-piperidin-4-yl-1,3-thiazolidine-2,4-dione |
| 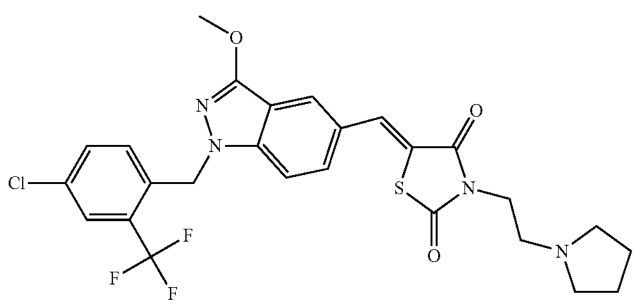 [SMILES: COc1nn(Cc2ccc(Cl)cc2C(F)(F)F)c2ccc(/C=C3\SC(=O)N(CCN4CCCC4)C3=O)cc12] | 27 | (5Z)-5-({1-[4-Chloro-2-(trifluoromethyl)benzyl]-3-methoxy-1H-indazol-5-yl}methylidene)-3-(2-pyrrolidin-1-ylethyl)-1,3-thiazolidine-2,4-dione |
| 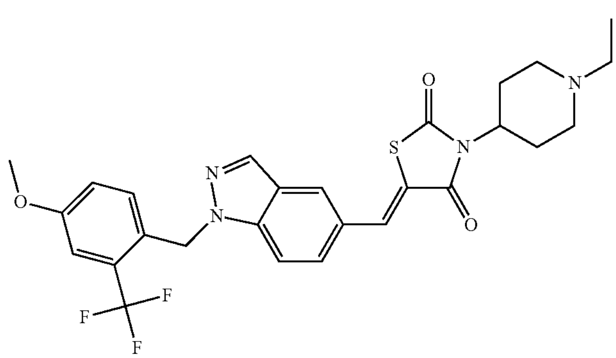 [SMILES: CCN1CCC(N2C(=O)S/C(=C\c3ccc4c(cnn4Cc4ccc(OC)cc4C(F)(F)F)c3)C2=O)CC1] | 28 | (5Z)-3-(1-Ethylpiperidin-4-yl)-5-({1-[4-methoxy-2-(trifluoromethyl)benzyl]-1H-indazol-5-yl}methylidene)-1,3-thiazolidine-2,4-dione |
| 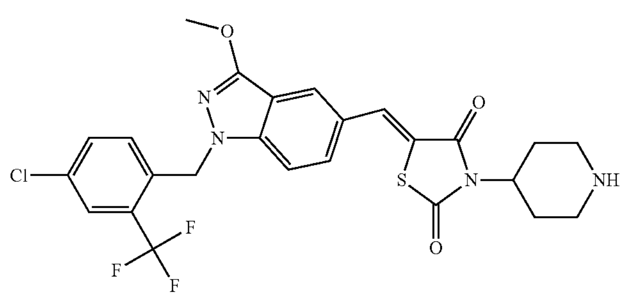 [SMILES: COc1nn(Cc2ccc(Cl)cc2C(F)(F)F)c2ccc(/C=C3\SC(=O)N(C4CCNCC4)C3=O)cc12] | 29 | (5Z)-5-({1-[4-Chloro-2-(trifluoromethyl)benzyl]-3-methoxy-1H-indazol-5-yl}methylidene)-3-piperidin-4-yl-1,3-thiazolidine-2,4-dione |

TABLE I-continued

| STRUCTURE | COMPOUND # | NAME |
|---|---|---|
| 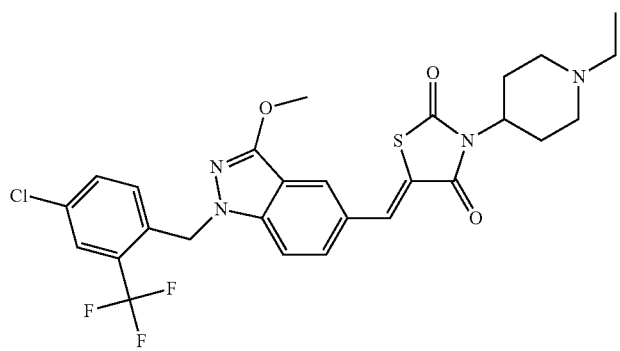 [SMILES: CCN1CCC(N2C(=O)S/C(=C\c3ccc4c(c3)c(OC)nn4Cc3ccc(Cl)cc3C(F)(F)F)C2=O)CC1] | 30 | (5Z)-5-({1-[4-Chloro-2-(trifluoromethyl)benzyl]-3-methoxy-1H-indazol-5-yl}methylidene)-3-(1-ethylpiperidin-4-yl)-1,3-thiazolidine-2,4-dione |
| 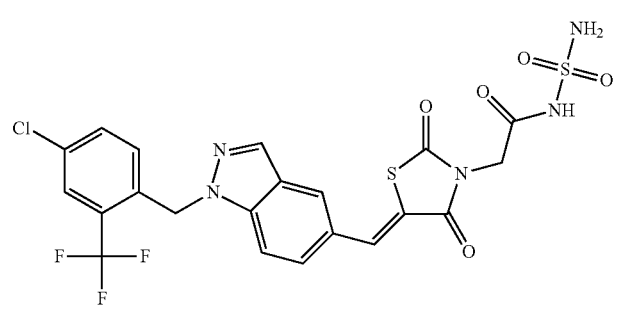 [SMILES: NS(=O)(=O)NC(=O)CN1C(=O)S/C(=C\c2ccc3c(cnn3Cc3ccc(Cl)cc3C(F)(F)F)c2)C1=O] | 31 | 2-[(5Z)-5-({1-[4-Chloro-2-(trifluoromethyl)benzyl]-1H-indazol-5-yl}methylidene)-2,4-dioxo-1,3-thiazolidin-3-yl]-N-sulfamoylacetamide |
| 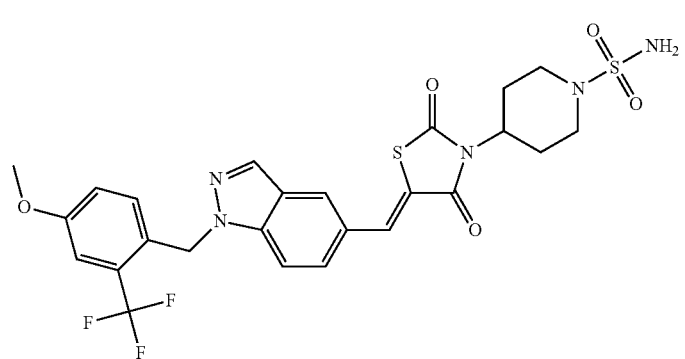 [SMILES: COc1ccc(Cn2ncc3cc(/C=C4\SC(=O)N(C5CCN(S(N)(=O)=O)CC5)C4=O)ccc32)c(C(F)(F)F)c1] | 32 | 4-[(5Z)-5-({1-[4-Methoxy-2-(trifluoromethyl)benzyl]-1H-indazol-5-yl}methylidene)-2,4-dioxo-1,3-thiazolidin-3-yl]piperidine-1-sulfonamide |
| 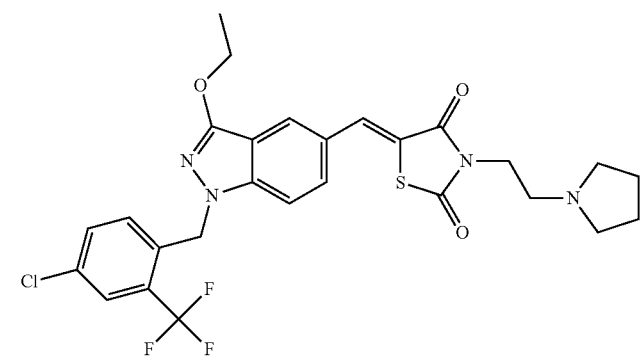 [SMILES: CCOc1nn(Cc2ccc(Cl)cc2C(F)(F)F)c2ccc(/C=C3\SC(=O)N(CCN4CCCC4)C3=O)cc12] | 33 | (5Z)-5-({1-[4-Chloro-2-(trifluoromethyl)benzyl]-3-ethoxy-1H-indazol-5-yl}methylidene)-3-(2-pyrrolidin-1-ylethyl)-1,3-thiazolidine-2,4-dione |

TABLE I-continued

| STRUCTURE | COMPOUND # | NAME |
|---|---|---|
| 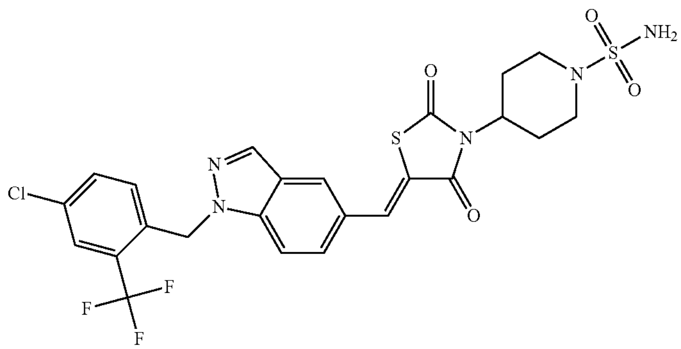 [SMILES: NS(=O)(=O)N1CCC(N2C(=O)S/C(=C\c3ccc4c(cnn4Cc4ccc(Cl)cc4C(F)(F)F)c3)C2=O)CC1] | 34 | 4-[(5Z)-5-({1-[4-Chloro-2-(trifluoromethyl)benzyl]-1H-indazol-5-yl}methylidene)-2,4-dioxo-1,3-thiazolidin-3-yl]piperidine-1-sulfonamide |
| 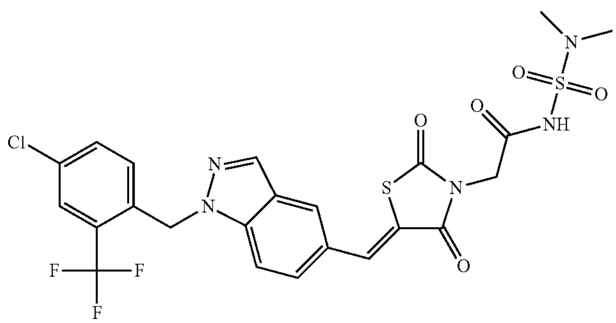 [SMILES: CN(C)S(=O)(=O)NC(=O)CN1C(=O)S/C(=C\c2ccc3c(cnn3Cc3ccc(Cl)cc3C(F)(F)F)c2)C1=O] | 35 | 2-[(5Z)-5-({1-[4-Chloro-2-(trifluoromethyl)benzyl]-1H-indazol-5-yl}methylidene)-2,4-dioxo-1,3-thiazolidin-3-yl]-N-(dimethylsulfamoyl)acetamide |
| 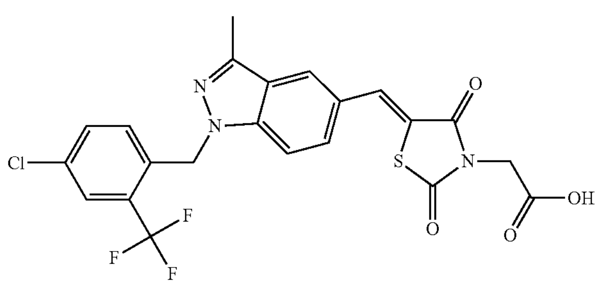 [SMILES: Cc1nn(Cc2ccc(Cl)cc2C(F)(F)F)c2ccc(/C=C3\SC(=O)N(CC(=O)O)C3=O)cc12] | 36 | [(5Z)-5-({1-[4-Chloro-2-(trifluoromethyl)benzyl]-3-methyl-1H-indazol-5-yl}methylidene)-2,4-dioxo-1,3-thiazolidin-3-yl]acetic acid |
| 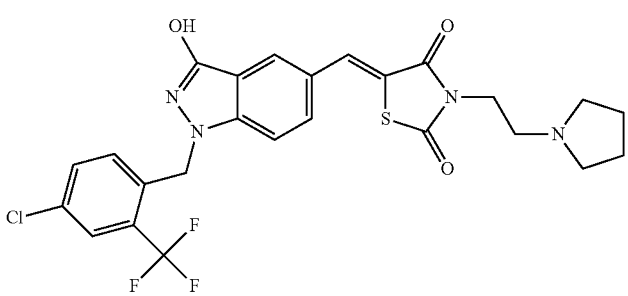 [SMILES: O=C1S/C(=C\c2ccc3c(c2)c(O)nn3Cc2ccc(Cl)cc2C(F)(F)F)C(=O)N1CCN1CCCC1] | 37 | (5Z)-5-({1-[4-Chloro-2-(trifluoromethyl)benzyl]-3-oxo-2,3-dihydro-1H-indazol-5-yl}methylidene)-3-(2-pyrrolidin-1-ylethyl)-1,3-thiazolidine-2,4-dione |
| 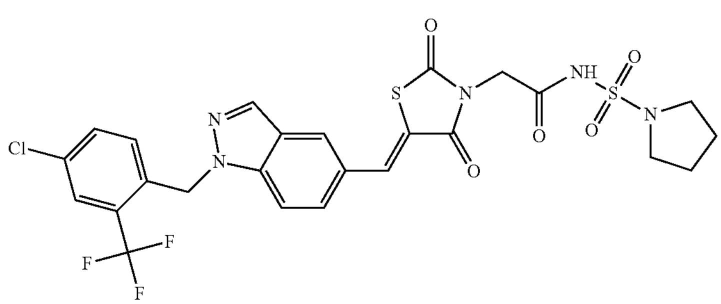 [SMILES: O=C(CN1C(=O)S/C(=C\c2ccc3c(cnn3Cc3ccc(Cl)cc3C(F)(F)F)c2)C1=O)NS(=O)(=O)N1CCCC1] | 38 | 2-[(5Z)-5-({1-[4-Chloro-2-(trifluoromethyl)benzyl]-1H-indazol-5-yl}methylidene)-2,4-dioxo-1,3-thiazolidin-3-yl]-N-(pyrrolidin-1-ylsulfonyl)acetamide |

TABLE I-continued

| STRUCTURE | COMPOUND # | NAME |
|---|---|---|
| 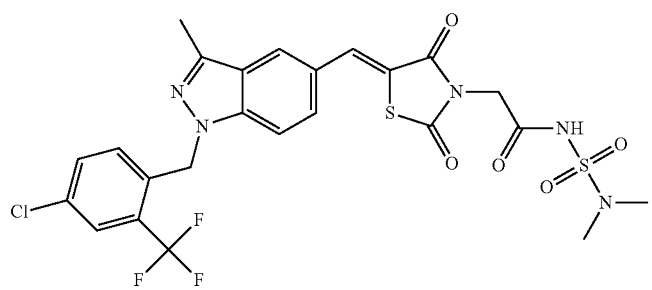 [SMILES: Cc1nn(Cc2ccc(Cl)cc2C(F)(F)F)c2ccc(/C=C3\SC(=O)N(CC(=O)NS(=O)(=O)N(C)C)C3=O)cc12] | 39 | 2-[(5Z)-5-({1-[4-Chloro-2-(trifluoromethyl)benzyl]-3-methyl-1H-indazol-5-yl}methylidene)-2,4-dioxo-1,3-thiazolidin-3-yl]-N-(dimethylsulfamoyl)acetamide |
| 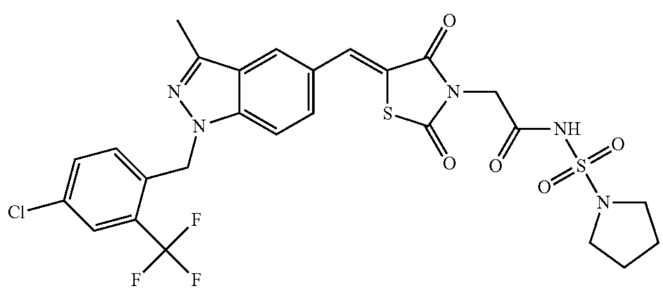 [SMILES: Cc1nn(Cc2ccc(Cl)cc2C(F)(F)F)c2ccc(/C=C3\SC(=O)N(CC(=O)NS(=O)(=O)N4CCCC4)C3=O)cc12] | 40 | 2-[(5Z)-5-({1-[4-Chloro-2-(trifluoromethyl)benzyl]-3-methyl-1H-indazol-5-yl}methylidene)-2,4-dioxo-1,3-thiazolidin-3-yl]-N-(pyrrolidin-1-ylsulfonyl)acetamide |
| 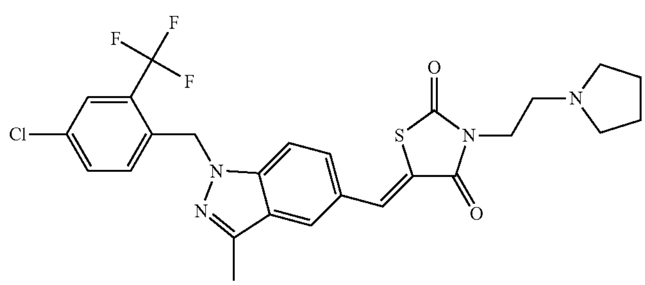 [SMILES: Cc1nn(Cc2ccc(Cl)cc2C(F)(F)F)c2ccc(/C=C3\SC(=O)N(CCN4CCCC4)C3=O)cc12] | 41 | (5Z)-5-({1-[4-Chloro-2-(trifluoromethyl)benzyl]-3-methyl-1H-indazol-5-yl}methylidene)-3-(2-pyrrolidin-1-ylethyl)-1,3-thiazolidine-2,4-dione |
| 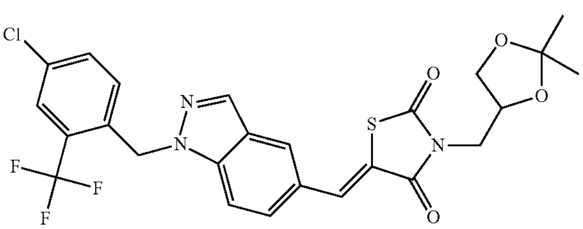 [SMILES: CC1(C)OCC(CN2C(=O)S/C(=C\c3ccc4c(cnn4Cc4ccc(Cl)cc4C(F)(F)F)c3)C2=O)O1] | 42 | (5Z)-5-({1-[4-Chloro-2-(trifluoromethyl)benzyl]-1H-indazol-5-yl}methylidene)-3-[(2,2-dimethyl-1,3-dioxolan-4-yl)methyl]-1,3-thiazolidine-2,4-dione |
| 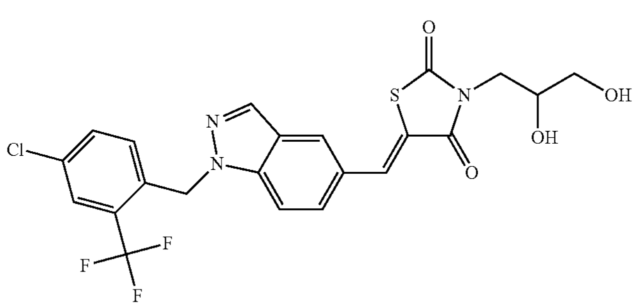 [SMILES: O=C1S/C(=C\c2ccc3c(cnn3Cc3ccc(Cl)cc3C(F)(F)F)c2)C(=O)N1CC(O)CO] | 43 | (5Z)-5-({1-[4-Chloro-2-(trifluoromethyl)benzyl]-1H-indazol-5-yl}methylidene)-3-(2,3-dihydroxypropyl)-1,3-thiazolidine-2,4-dione |

TABLE I-continued

| STRUCTURE | COMPOUND # | NAME |
|---|---|---|
| 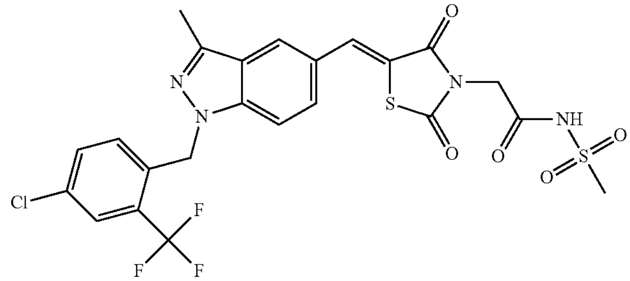 [SMILES: Cc1nn(Cc2ccc(Cl)cc2C(F)(F)F)c2ccc(/C=C3\SC(=O)N(CC(=O)NS(C)(=O)=O)C3=O)cc12] | 44 | 2-[(5Z)-5-({1-[4-Chloro-2-(trifluoromethyl)benzyl]-3-methyl-1H-indazol-5-yl}methylidene)-2,4-dioxo-1,3-thiazolidin-3-yl]-N-(methylsulfonyl)acetamide |
| 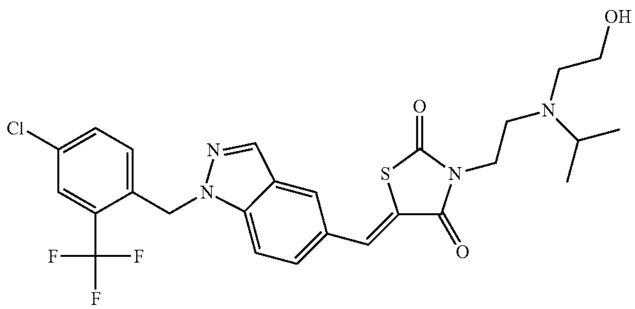 [SMILES: CC(C)N(CCO)CCN1C(=O)S/C(=C\c2ccc3c(cnn3Cc3ccc(Cl)cc3C(F)(F)F)c2)C1=O] | 45 | (5Z)-5-({1-[4-Chloro-2-(trifluoromethyl)benzyl]-1H-indazol-5-yl}methylidene)-3-{2-[(2-hydroxyethyl)(1-methylethyl)amino]ethyl}-1,3-thiazolidine-2,4-dione |
| 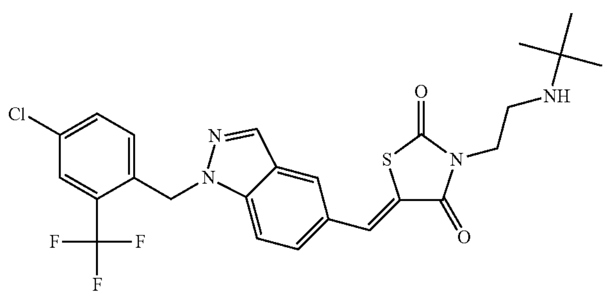 [SMILES: CC(C)(C)NCCN1C(=O)S/C(=C\c2ccc3c(cnn3Cc3ccc(Cl)cc3C(F)(F)F)c2)C1=O] | 46 | (5Z)-3-[2-(tert-Butylamino)ethyl]-5-({1-[4-chloro-2-(trifluoromethyl)benzyl]-1H-indazol-5-yl}methylidene)-1,3-thiazolidine-2,4-dione |
| 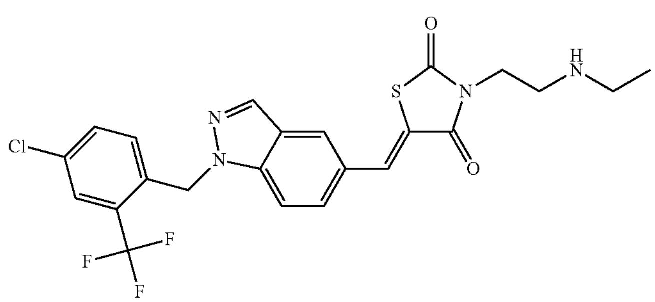 [SMILES: CCNCCN1C(=O)S/C(=C\c2ccc3c(cnn3Cc3ccc(Cl)cc3C(F)(F)F)c2)C1=O] | 47 | (5Z)-5-({1-[4-Chloro-2-(trifluoromethyl)benzyl]-1H-indazol-5-yl}methylidene)-3-[2-(ethylamino)ethyl]-1,3-thiazolidine-2,4-dione |
| 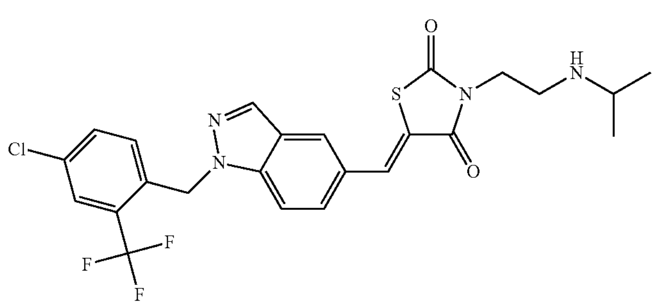 [SMILES: CC(C)NCCN1C(=O)S/C(=C\c2ccc3c(cnn3Cc3ccc(Cl)cc3C(F)(F)F)c2)C1=O] | 48 | (5Z)-5-({1-[4-Chloro-2-(trifluoromethyl)benzyl]-1H-indazol-5-yl}methylidene)-3-{2-[(1-methylethyl)amino]ethyl}-1,3-thiazolidine-2,4-dione |

TABLE I-continued

| STRUCTURE | COMPOUND # | NAME |
|---|---|---|
| 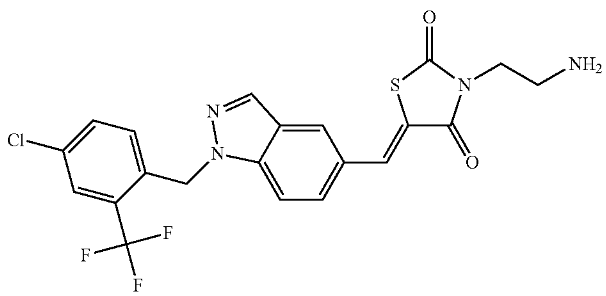 [SMILES: NCCN1C(=O)S/C(=C\c2ccc3c(cnn3Cc3ccc(Cl)cc3C(F)(F)F)c2)C1=O] | 49 | 3-(2-Aminoethyl)-(5Z)-5-({1-[4-chloro-2-(trifluoromethyl)benzyl]-1H-indazol-5-yl}methylidene)-1,3-thiazolidine-2,4-dione |
| 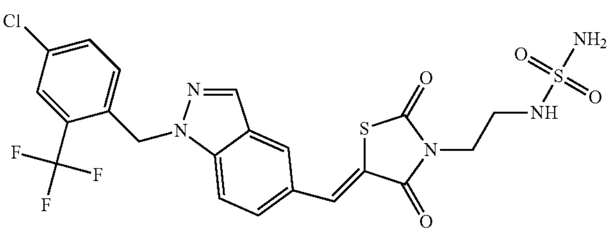 [SMILES: NS(=O)(=O)NCCN1C(=O)S/C(=C\c2ccc3c(cnn3Cc3ccc(Cl)cc3C(F)(F)F)c2)C1=O] | 50 | N-{2-[(5Z)-5-({1-[4-Chloro-2-(trifluoromethyl)benzyl]-1H-indazol-5-yl}methylidene)-2,4-dioxo-1,3-thiazolidin-3-yl]ethyl}sulfamide |
| 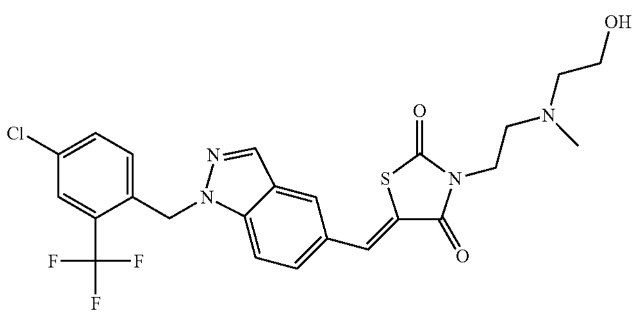 [SMILES: CN(CCO)CCN1C(=O)S/C(=C\c2ccc3c(cnn3Cc3ccc(Cl)cc3C(F)(F)F)c2)C1=O] | 51 | (5Z)-5-({1-[4-Chloro-2-(trifluoromethyl)benzyl]-1H-indazol-5-yl}methylidene)-3-{2-[(2-hydroxyethyl)(methyl)amino]ethyl}-1,3-thiazolidine-2,4-dione |
| 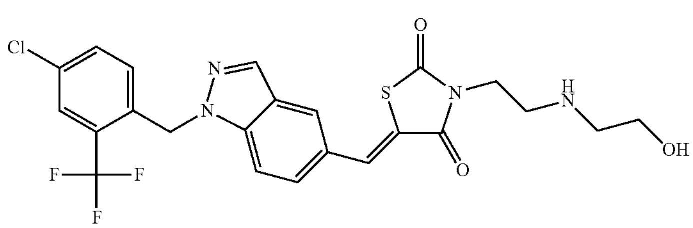 [SMILES: O=C1S/C(=C\c2ccc3c(cnn3Cc3ccc(Cl)cc3C(F)(F)F)c2)C(=O)N1CCNCCO] | 52 | (5Z)-5-({1-[4-Chloro-2-(trifluoromethyl)benzyl]-1H-indazol-5-yl}methylidene)-3-{2-[(2-hydroxyethyl)amino]ethyl}-1,3-thiazolidine-2,4-dione |
| 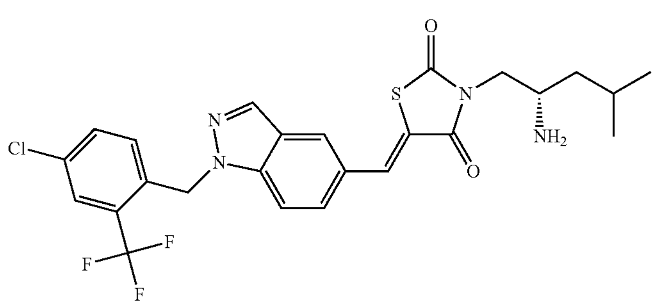 [SMILES: CC(C)C[C@H](N)CN1C(=O)S/C(=C\c2ccc3c(cnn3Cc3ccc(Cl)cc3C(F)(F)F)c2)C1=O] | 53 | (5Z)-3-[(2S)-2-Amino-4-methylpentyl]-5-({1-[4-chloro-2-(trifluoromethyl)benzyl]-1H-indazol-5-yl}methylidene)-1,3-thiazolidine-2,4-dione |

TABLE I-continued

| STRUCTURE | COMPOUND # | NAME |
|---|---|---|
| 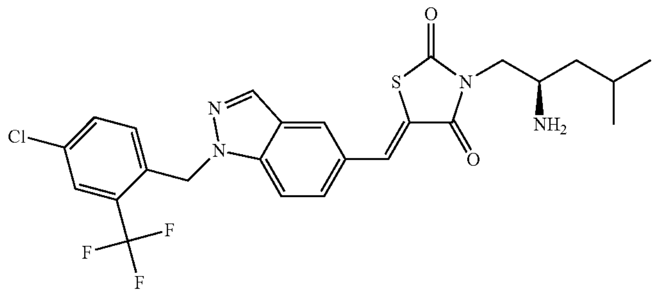 [SMILES: CC(C)C[C@@H](N)CN1C(=O)S/C(=C\c2ccc3c(cnn3Cc3ccc(Cl)cc3C(F)(F)F)c2)C1=O] | 54 | (5Z)-3-[(2R)-2-Amino-4-methylpentyl]-5-({1-[4-chloro-2-(trifluoromethyl)benzyl]-1H-indazol-5-yl}methylidene)-1,3-thiazolidine-2,4-dione |
| 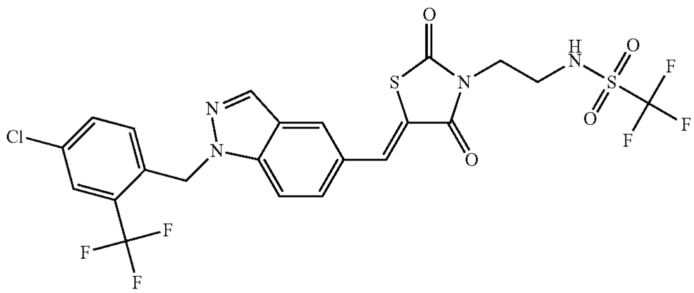 [SMILES: O=C1S/C(=C\c2ccc3c(cnn3Cc3ccc(Cl)cc3C(F)(F)F)c2)C(=O)N1CCNS(=O)(=O)C(F)(F)F] | 55 | N-{2-[(5Z)-5-({1-[4-Chloro-2-(trifluoromethyl)benzyl]-1H-indazol-5-yl}methylidene)-2,4-dioxo-1,3-thiazolidin-3-yl]ethyl}-1,1,1-trifluoromethanesulfonamide |
| 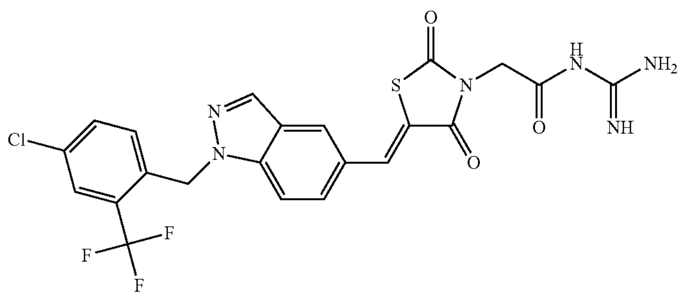 [SMILES: N=C(N)NC(=O)CN1C(=O)S/C(=C\c2ccc3c(cnn3Cc3ccc(Cl)cc3C(F)(F)F)c2)C1=O] | 56 | N-Carbamimidoyl-2-[(5Z)-5-({1-[4-chloro-2-(trifluoromethyl)benzyl]-1H-indazol-5-yl}methylidene)-2,4-dioxo-1,3-thiazolidin-3-yl]acetamide |
| 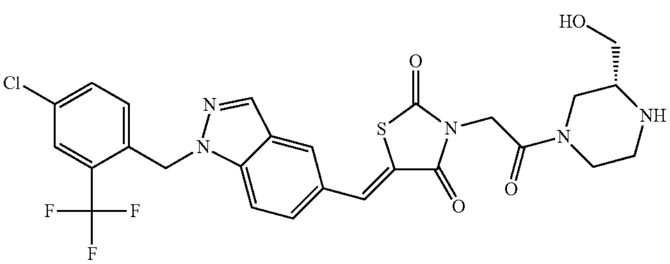 [SMILES: O=C(CN1C(=O)S/C(=C\c2ccc3c(cnn3Cc3ccc(Cl)cc3C(F)(F)F)c2)C1=O)N1CCN[C@@H](CO)C1] | 57 | (5Z)-5-({1-[4-Chloro-2-(trifluoromethyl)benzyl]-1H-indazol-5-yl}methylidene)-3-{2-[(3R)-3-(hydroxymethyl)piperazin-1-yl]-2-oxoethyl}-1,3-thiazolidine-2,4-dione |
| 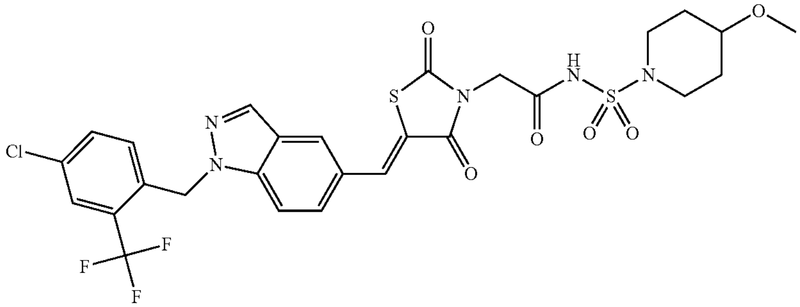 [SMILES: COC1CCN(S(=O)(=O)NC(=O)CN2C(=O)S/C(=C\c3ccc4c(cnn4Cc4ccc(Cl)cc4C(F)(F)F)c3)C2=O)CC1] | 58 | 2-[(5Z)-5-({1-[4-chloro-2-(trifluoromethyl)benzyl]-1H-indazol-5-yl}methylidene)-2,4-dioxo-1,3-thiazolidin-3-yl]-N-[(4-methoxypiperidin-1-yl)sulfonyl]acetamide |

TABLE I-continued

| STRUCTURE | COMPOUND # | NAME |
|---|---|---|
| 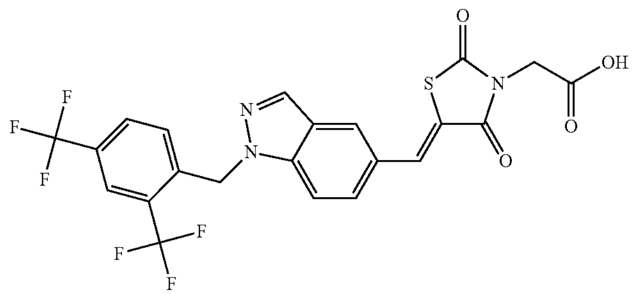 [SMILES: O=C(O)CN1C(=O)S/C(=C\c2ccc3c(cnn3Cc3ccc(C(F)(F)F)cc3C(F)(F)F)c2)C1=O] | 59 | [(5Z)-5-({1-[2,4-Bis(trifluoromethyl)benzyl]-1H-indazol-5-yl}methylidene)-2,4-dioxo-1,3-thiazolidin-3-yl]acetic acid |
| 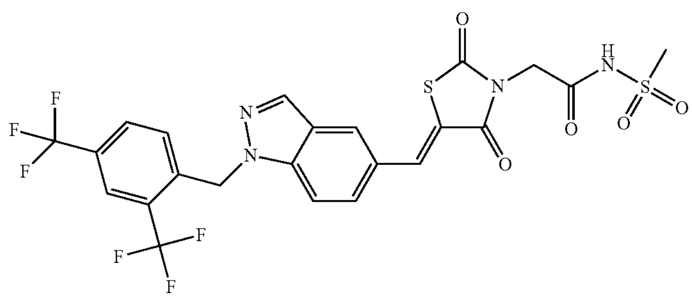 [SMILES: CS(=O)(=O)NC(=O)CN1C(=O)S/C(=C\c2ccc3c(cnn3Cc3ccc(C(F)(F)F)cc3C(F)(F)F)c2)C1=O] | 60 | 2-[(5Z)-5-({1-[2,4-Bis(trifluoromethyl)benzyl]-1H-indazol-5-yl}methylidene)-2,4-dioxo-1,3-thiazolidin-3-yl]-N-(methylsulfonyl)acetamide |
| 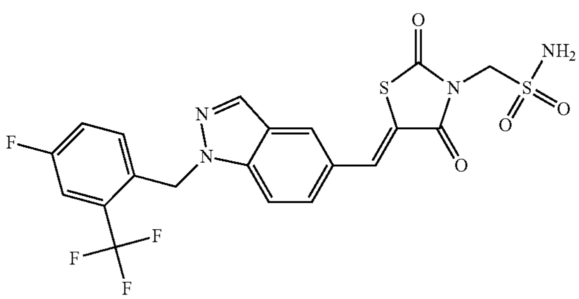 [SMILES: NS(=O)(=O)CN1C(=O)S/C(=C\c2ccc3c(cnn3Cc3ccc(F)cc3C(F)(F)F)c2)C1=O] | 61 | 1-[(5Z)-5-({1-[4-Fluoro-2-(trifluoromethyl)benzyl]-1H-indazol-5-yl}methylidene)-2,4-dioxo-1,3-thiazolidin-3-yl]methanesulfonamide |
| 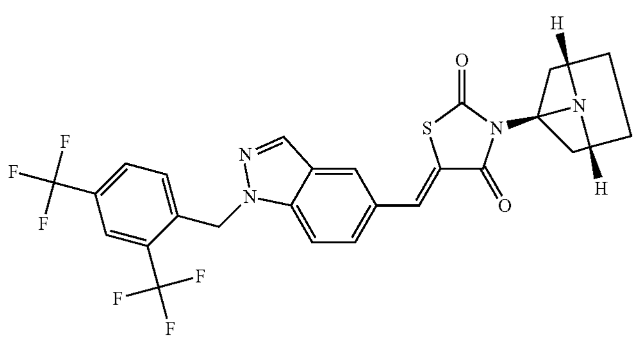 [SMILES: O=C1S/C(=C\c2ccc3c(cnn3Cc3ccc(C(F)(F)F)cc3C(F)(F)F)c2)C(=O)N1[C@@]12C[C@H]3CC[C@@H](C1)N32] | 62 | (5Z)-5-({1-[2,4-Bis(trifluoromethyl)benzyl]-1H-indazol-5-yl}methylidene)-3-[(3-exo)-8-methyl-8-azabicyclo[3.2.1]oct-3-yl]-1,3-thiazolidine-2,4-dione |
| 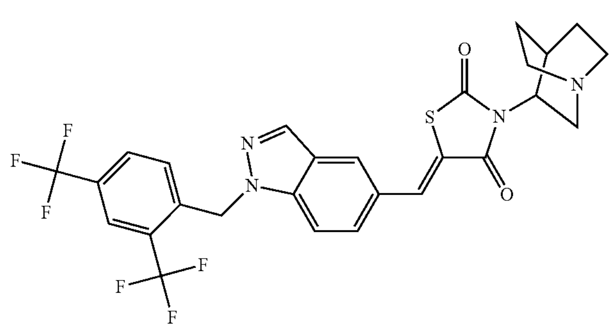 [SMILES: O=C1S/C(=C\c2ccc3c(cnn3Cc3ccc(C(F)(F)F)cc3C(F)(F)F)c2)C(=O)N1C1CN2CCC1CC2] | 63 | (5Z)-3-(1-Azabicyclo[2.2.2]oct-3-yl)-5-({1-[2,4-bis(trifluoromethyl)benzyl]-1H-indazol-5-yl}methylidene)-1,3-thiazolidine-2,4-dione |

TABLE I-continued

| STRUCTURE | COMPOUND # | NAME |
|---|---|---|
| 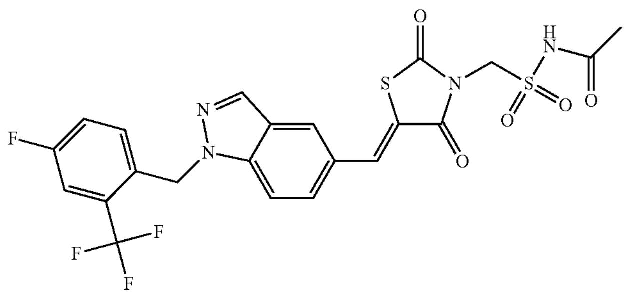 [SMILES: CC(=O)NS(=O)(=O)CN1C(=O)S/C(=C\c2ccc3c(cnn3Cc3ccc(F)cc3C(F)(F)F)c2)C1=O] | 64 | N-({[(5Z)-5-({1-[4-Fluoro-2-(trifluoromethyl)benzyl]-1H-indazol-5-yl}methylidene)-2,4-dioxo-1,3-thiazolidin-3-yl)methyl}sulfonyl)acetamide |
| 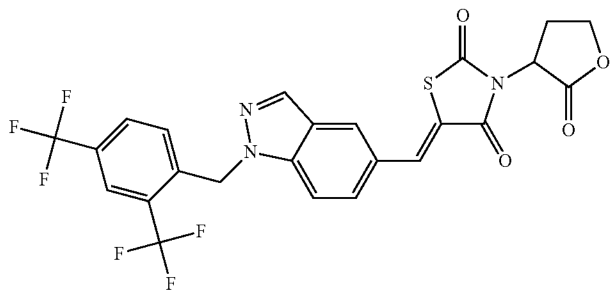 [SMILES: O=C1OCCC1N1C(=O)S/C(=C\c2ccc3c(cnn3Cc3ccc(C(F)(F)F)cc3C(F)(F)F)c2)C1=O] | 65 | (5Z)-5-({1-[2,4-Bis(trifluoromethyl)benzyl]-1H-indazol-5-yl}methylidene)-3-(2-oxotetrahydrofuran-3-yl)-1,3-thiazolidine-2,4-dione |
| 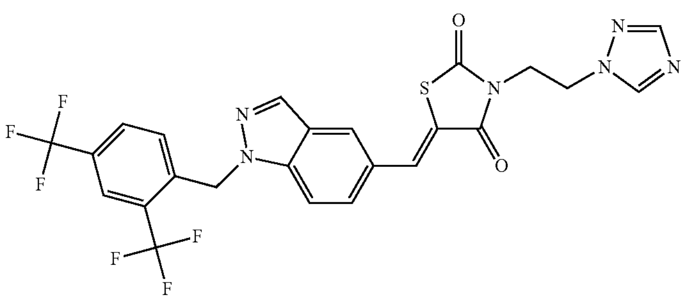 [SMILES: O=C1S/C(=C\c2ccc3c(cnn3Cc3ccc(C(F)(F)F)cc3C(F)(F)F)c2)C(=O)N1CCn1cncn1] | 66 | (5Z)-5-({1-[2,4-Bis(trifluoromethyl)benzyl]-1H-indazol-5-yl}methylidene)-3-[2-(1H-1,2,4-triazol-1-yl)ethyl]-1,3-thiazolidine-2,4-dione |
| 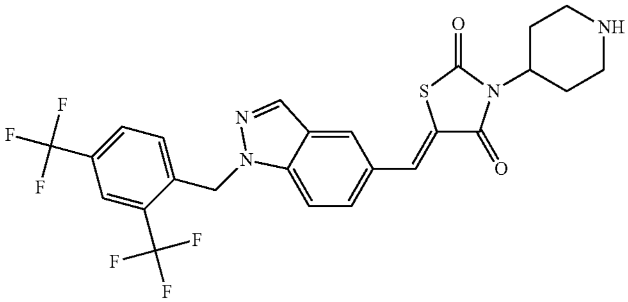 [SMILES: O=C1S/C(=C\c2ccc3c(cnn3Cc3ccc(C(F)(F)F)cc3C(F)(F)F)c2)C(=O)N1C1CCNCC1] | 67 | (5Z)-5-({1-[2,4-Bis(trifluoromethyl)benzyl]-1H-indazol-5-yl}methylidene)-3-piperidin-4-yl-1,3-thiazolidine-2,4-dione |
| 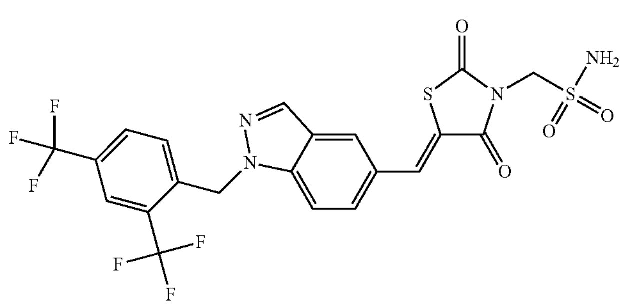 [SMILES: NS(=O)(=O)CN1C(=O)S/C(=C\c2ccc3c(cnn3Cc3ccc(C(F)(F)F)cc3C(F)(F)F)c2)C1=O] | 68 | 1-[(5Z)-5-({1-[2,4-Bis(trifluoromethyl-benzyl]-1H-indazol-5-yl}methylidene)-2,4-dioxo-1,3-thiazolidin-3-yl]methanesulfonamide |

TABLE I-continued

| STRUCTURE | COMPOUND # | NAME |
|---|---|---|
| 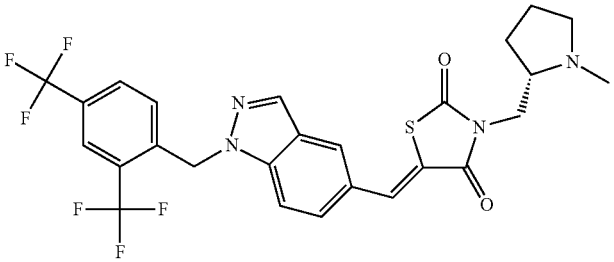 [SMILES: CN1CCC[C@H]1CN1C(=O)S/C(=C\c2ccc3c(cnn3Cc3ccc(C(F)(F)F)cc3C(F)(F)F)c2)C1=O] | 69 | (5Z)-5-({1-[2,4-Bis(trifluoromethyl)benzyl]-1H-indazol-5-yl}methylidene)-3-{[(2S)-1-methylpyrrolidin-2-yl]methyl}-1,3-thiazolidine-2,4-dione |
| 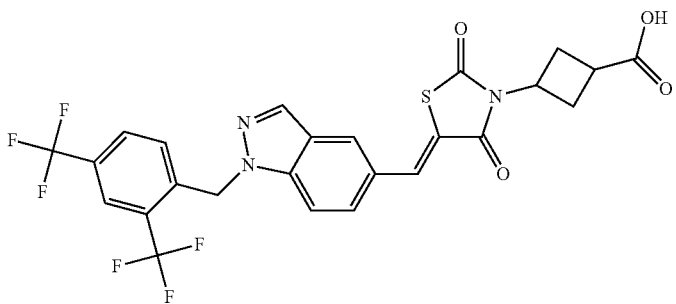 [SMILES: O=C(O)C1CC(N2C(=O)S/C(=C\c3ccc4c(cnn4Cc4ccc(C(F)(F)F)cc4C(F)(F)F)c3)C2=O)C1] | 70 | 3-[(5Z)-5-({1-[2,4-Bis(trifluoromethyl)benzyl]-1H-indazol-5-yl}methylidene)-2,4-dioxo-1,3-thiazolidin-3-yl]cyclobutanecarboxylic acid |
| 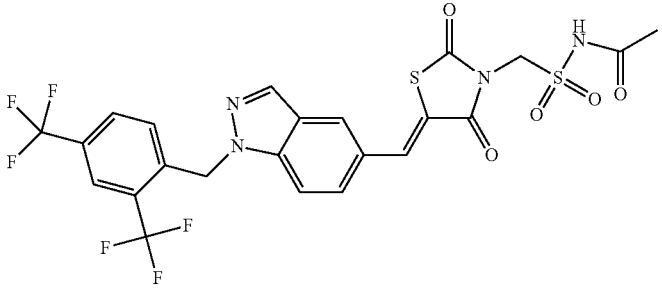 [SMILES: CC(=O)NS(=O)(=O)CN1C(=O)S/C(=C\c2ccc3c(cnn3Cc3ccc(C(F)(F)F)cc3C(F)(F)F)c2)C1=O] | 71 | N-({[(5Z)-5-({1-[2,4-Bis(trifluoromethyl)benzyl]-1H-indazol-5-yl}methylidene)-2,4-dioxo-1,3-thiazolidin-3-yl]methyl}sulfonyl)acetamide |
| 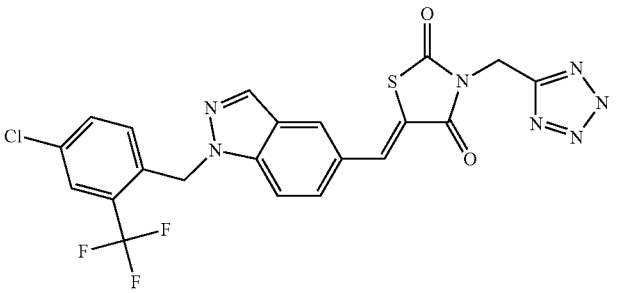 [SMILES: O=C1S/C(=C\c2ccc3c(cnn3Cc3ccc(Cl)cc3C(F)(F)F)c2)C(=O)N1Cc1nn[nH]n1] | 72 | (5Z)-5-({1-[4-Chloro-2-(trifluoromethyl)benzyl]-1H-indazol-5-yl}methylidene)-3-(2H-tetrazol-5-ylmethyl)-1,3-thiazolidine-2,4-dione |
| 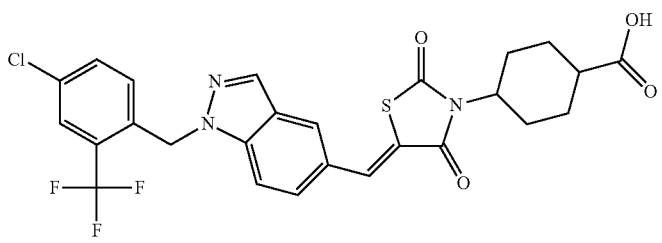 [SMILES: O=C(O)C1CCC(N2C(=O)S/C(=C\c3ccc4c(cnn4Cc4ccc(Cl)cc4C(F)(F)F)c3)C2=O)CC1] | 73 | 4-[(5Z)-5-({1-[4-Chloro-2-(trifluoromethyl)benzyl]-1H-indazol-5-yl}methylidene)-2,4-dioxo-1,3-thiazolidin-3-yl]cyclohexanecarboxylic acid |

TABLE I-continued

| STRUCTURE | COMPOUND # | NAME |
|---|---|---|
| 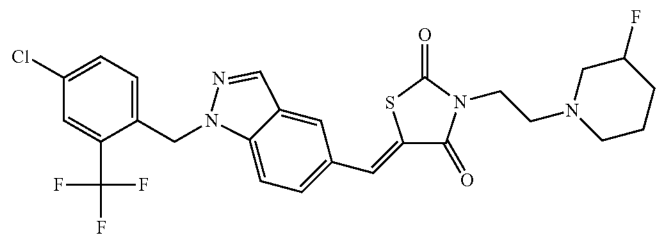 [SMILES: O=C1S/C(=C\c2ccc3c(cnn3Cc3ccc(Cl)cc3C(F)(F)F)c2)C(=O)N1CCN1CCCC(F)C1] | 74 | (5Z)-5-({1-[4-Chloro-2-(trifluoromethyl)benzyl]-1H-indazol-5-yl}methylidene)-3-[2-(3-fluoropiperidin-1-yl)ethyl]-1,3-thiazolidine-2,4-dione |
| 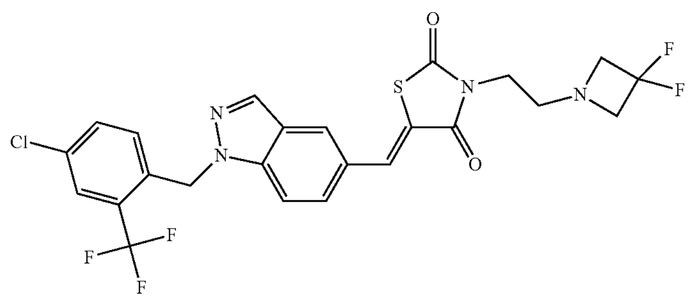 [SMILES: O=C1S/C(=C\c2ccc3c(cnn3Cc3ccc(Cl)cc3C(F)(F)F)c2)C(=O)N1CCN1CC(F)(F)C1] | 75 | (5Z)-5-({1-[4-Chloro-2-(trifluoromethyl)benzyl]-1H-indazol-5-yl}methylidene)-3-[2-(3,3-difluoroazetidin-1-yl)ethyl]-1,3-thiazolidine-2,4-dione |
| 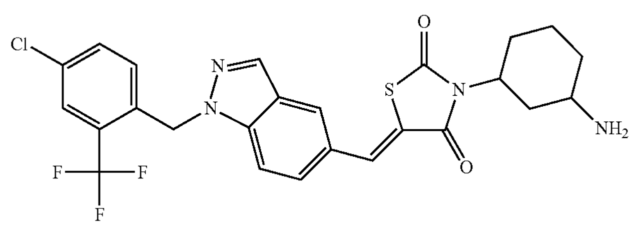 [SMILES: NC1CCCC(N2C(=O)S/C(=C\c3ccc4c(cnn4Cc4ccc(Cl)cc4C(F)(F)F)c3)C2=O)C1] | 76 | (5Z)-3-(3-Aminocyclohexyl)-5-({1-[4-chloro-2-(trifluoromethyl)benzyl]-1H-indazol-5-yl}methylidene)-1,3-thiazolidine-2,4-dione |
| 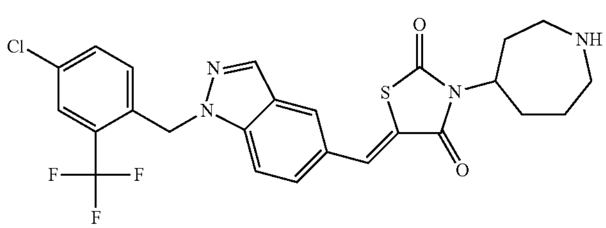 [SMILES: O=C1S/C(=C\c2ccc3c(cnn3Cc3ccc(Cl)cc3C(F)(F)F)c2)C(=O)N1C1CCCNCC1] | 77 | (5Z)-3-Azepan-4-yl-5-({1-[4-chloro-2-(trifluoromethyl)benzyl]-1H-indazol-5-yl}methylidene)-1,3-thiazolidine-2,4-dione |
| 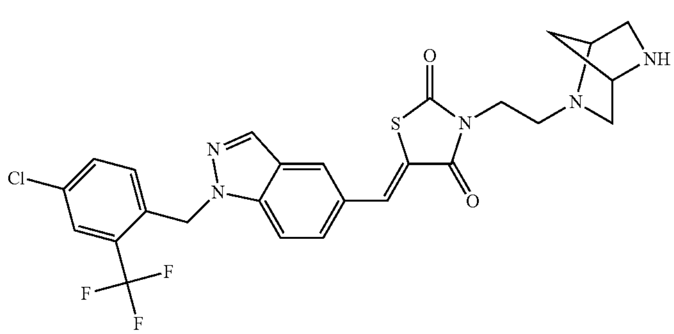 [SMILES: O=C1S/C(=C\c2ccc3c(cnn3Cc3ccc(Cl)cc3C(F)(F)F)c2)C(=O)N1CCN1CC2CC1CN2] | 78 | (5Z)-5-({1-[4-Chloro-2-(trifluoromethyl)benzyl]-1H-indazol-5-yl}methylidene)-3-[2-(1S,4S)-(2,5-diazabicyclo[2.2.1]hept-2-yl)ethyl]-1,3-thiazolidine-2,4-dione |

TABLE I-continued

| STRUCTURE | COMPOUND # | NAME |
|---|---|---|
| 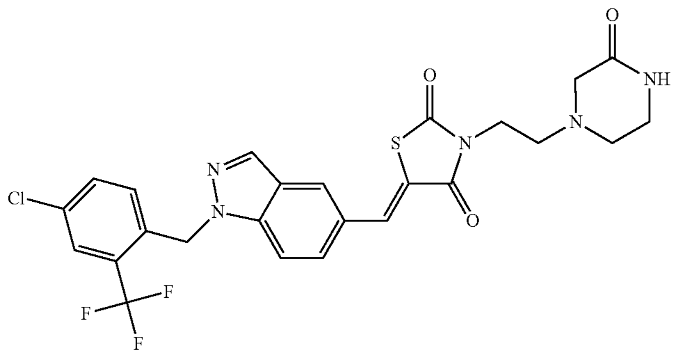 [SMILES: O=C1CN(CCN2C(=O)S/C(=C\c3ccc4c(cnn4Cc4ccc(Cl)cc4C(F)(F)F)c3)C2=O)CCN1] | 79 | (5Z)-5-({1-[4-Chloro-2-(trifluoromethyl)benzyl]-1H-indazol-5-yl}methylidene)-3-[2-(3-oxopiperazin-1-yl)ethyl]-1,3-thiazolidine-2,4-dione |
| 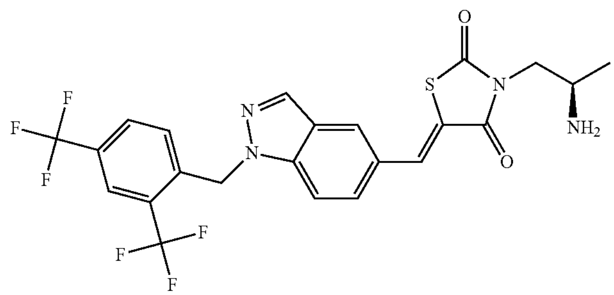 [SMILES: C[C@@H](N)CN1C(=O)S/C(=C\c2ccc3c(cnn3Cc3ccc(C(F)(F)F)cc3C(F)(F)F)c2)C1=O] | 80 | (5Z)-3-[(2R)-2-Aminopropyl]-5-({1-[2,4-bis(trifluoromethyl)benzyl]-1H-indazol-5-yl}methylidene)-1,3-thiazolidine-2,4-dione |
| 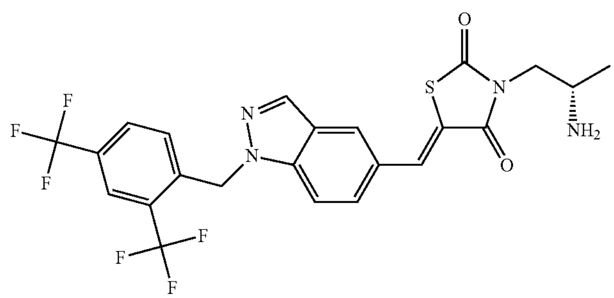 [SMILES: C[C@H](N)CN1C(=O)S/C(=C\c2ccc3c(cnn3Cc3ccc(C(F)(F)F)cc3C(F)(F)F)c2)C1=O] | 81 | (5Z)-3-[(2S)-2-Aminopropyl]-5-({1-[2,4-bis(trifluoromethyl)benzyl]-1H-indazol-5-yl}methylidene)-1,3-thiazolidine-2,4-dione |
| 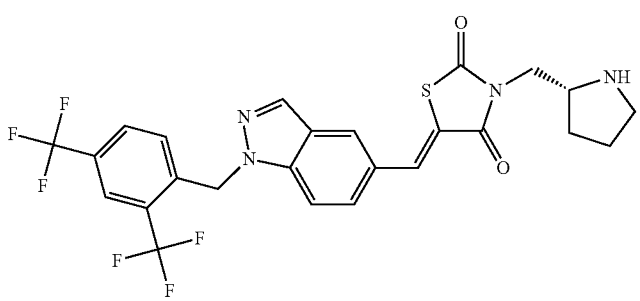 [SMILES: O=C1S/C(=C\c2ccc3c(cnn3Cc3ccc(C(F)(F)F)cc3C(F)(F)F)c2)C(=O)N1C[C@H]1CCCN1] | 82 | (5Z)-5-({1-[2,4-Bis(trifluoromethyl)benzyl]-1H-indazol-5-yl}methylidene)-3-[(2R)-pyrrolidin-2-ylmethyl]-1,3-thiazolidine-2,4-dione |
| 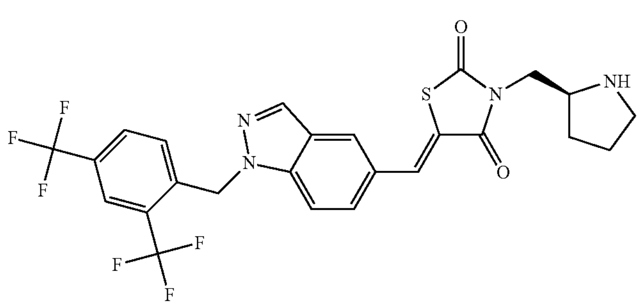 [SMILES: O=C1S/C(=C\c2ccc3c(cnn3Cc3ccc(C(F)(F)F)cc3C(F)(F)F)c2)C(=O)N1C[C@@H]1CCCN1] | 83 | (5Z)-5-({1-[2,4-Bis(trifluoromethyl)benzyl]-1H-indazol-5-yl}methylidene)-3-[(2S)-pyrrolidin-2-ylmethyl]-1,3-thiazolidine-2,4-dione |

TABLE I-continued

| STRUCTURE | COMPOUND # | NAME |
|---|---|---|
| 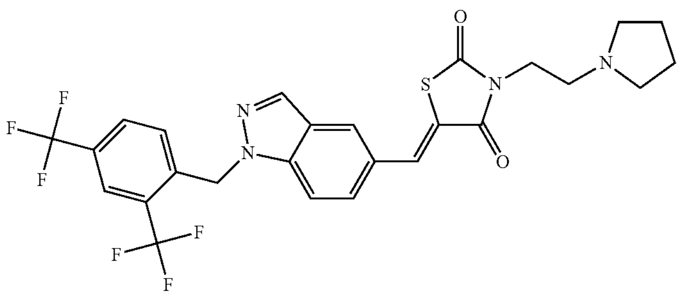 [SMILES: O=C1S/C(=C\c2ccc3c(cnn3Cc3ccc(C(F)(F)F)cc3C(F)(F)F)c2)C(=O)N1CCN1CCCC1] | 84 | (5Z)-5-({1-[2,4-Bis(trifluoromethyl)benzyl]-1H-indazol-5-yl}methylidene)-3-(2-pyrrolidin-1-ylethyl)-1,3-thiazolidine-2,4-dione |
| 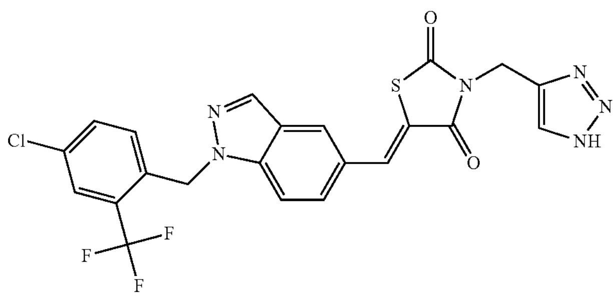 [SMILES: O=C1S/C(=C\c2ccc3c(cnn3Cc3ccc(Cl)cc3C(F)(F)F)c2)C(=O)N1Cc1c[nH]nn1] | 85 | (5Z)-5-({1-[4-Chloro-2-(trifluoromethyl)benzyl]-1H-indazol-5-yl}methylidene)-3-(1H-1,2,3-triazol-4-ylmethyl)-1,3-thiazolidine-2,4-dione |
| 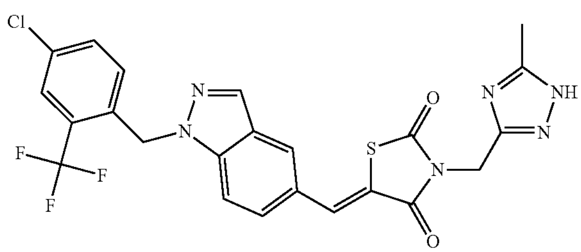 [SMILES: Cc1nc(CN2C(=O)S/C(=C\c3ccc4c(cnn4Cc4ccc(Cl)cc4C(F)(F)F)c3)C2=O)n[nH]1] | 86 | (5Z)-5-({1-[4-Chloro-2-(trifluoromethyl)benzyl]-1H-indazol-5-yl}methylidene)-3-[(5-methyl-1H-1,2,4-triazol-3-yl)methyl]-1,3-thiazolidine-2,4-dione |
| 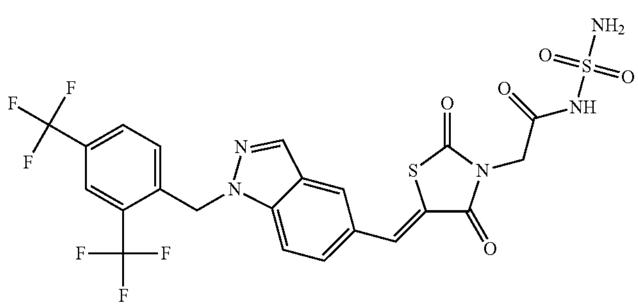 [SMILES: NS(=O)(=O)NC(=O)CN1C(=O)S/C(=C\c2ccc3c(cnn3Cc3ccc(C(F)(F)F)cc3C(F)(F)F)c2)C1=O] | 87 | 2-[(5Z)-5-({1-[2,4-Bis(trifluoromethyl)benzyl]-1H-indazol-5-yl}methylidene)-2,4-dioxo-1,3-thiazolidin-3-yl]-N-sulfamoylacetamide |
| 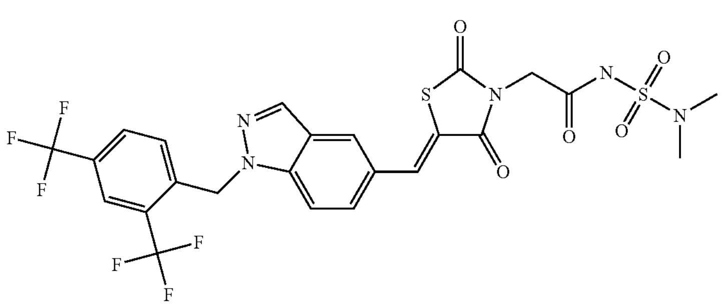 [SMILES: CN(C)S(=O)(=O)NC(=O)CN1C(=O)S/C(=C\c2ccc3c(cnn3Cc3ccc(C(F)(F)F)cc3C(F)(F)F)c2)C1=O] | 88 | 2-[(5Z)-5-({1-[2,4-Bis(trifluoromethyl)benzyl]-1H-indazol-5-yl}methylidene)-2,4-dioxo-1,3-thiazolidin-3-yl]-N-(dimethylsulfamoyl)acetamide |

TABLE I-continued

| STRUCTURE | COMPOUND # | NAME |
|---|---|---|
| 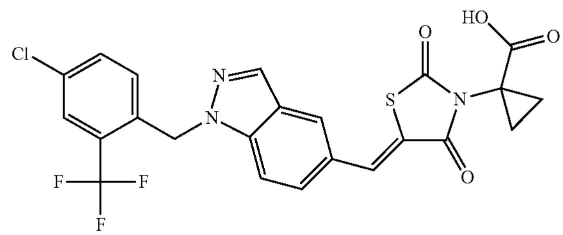 [SMILES: O=C1S/C(=C\c2ccc3c(cnn3Cc3ccc(Cl)cc3C(F)(F)F)c2)C(=O)N1C1(C(=O)O)CC1] | 89 | 1-[(5Z)-5-({1-[4-Chloro-2-(trifluoromethyl)benzyl]-1H-indazol-5-yl}methylidene)-2,4-dioxo-1,3-thiazolidin-3-yl]cyclopropanecarboxylic acid |
| 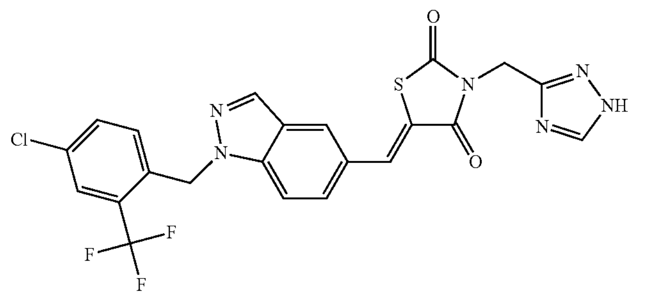 [SMILES: O=C1S/C(=C\c2ccc3c(cnn3Cc3ccc(Cl)cc3C(F)(F)F)c2)C(=O)N1Cc1nc[nH]n1] | 90 | (5Z)-5-({1-[4-Chloro-2-(trifluoromethyl)benzyl]-1H-indazol-5-yl}methylidene)-3-(1H-1,2,4-triazol-3-ylmethyl)-1,3-thiazolidine-2,4-dione |
| 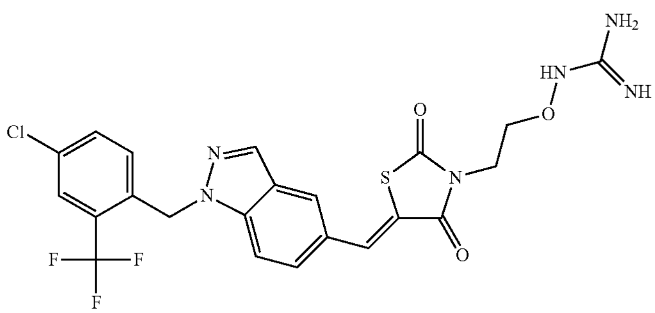 [SMILES: N=C(N)NOCCN1C(=O)S/C(=C\c2ccc3c(cnn3Cc3ccc(Cl)cc3C(F)(F)F)c2)C1=O] | 91 | 1-{2-[(5Z)-5-({1-[4-Chloro-2-(trifluoromethyl)benzyl]-1H-indazol-5-yl}methylidene)-2,4-dioxo-1,3-thiazolidin-3-yl]ethoxy}guanidine |
| 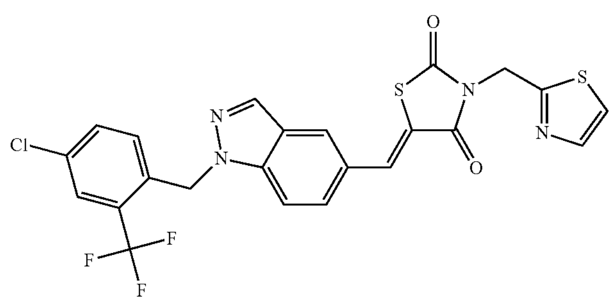 [SMILES: O=C1S/C(=C\c2ccc3c(cnn3Cc3ccc(Cl)cc3C(F)(F)F)c2)C(=O)N1Cc1nccs1] | 92 | (5Z)-5-({1-[4-Chloro-2-(trifluoromethyl)benzyl]-1H-indazol-5-yl}methylidene)-3-(1,3-thiazol-2-ylmethyl)-1,3-thiazolidine-2,4-dione |
| 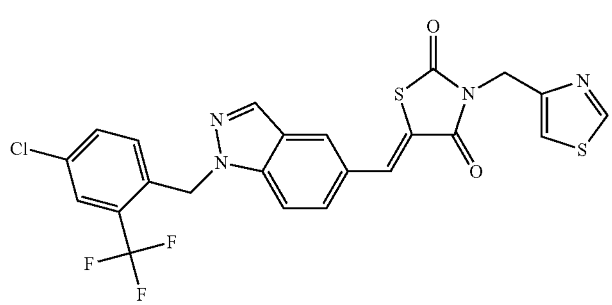 [SMILES: O=C1S/C(=C\c2ccc3c(cnn3Cc3ccc(Cl)cc3C(F)(F)F)c2)C(=O)N1Cc1cscn1] | 93 | (5Z)-5-({1-[4-Chloro-2-(trifluoromethyl)benzyl]-1H-indazol-5-1,3-thiazolidine-2,4-dione |

TABLE I-continued

| STRUCTURE | COMPOUND # | NAME |
|---|---|---|
| 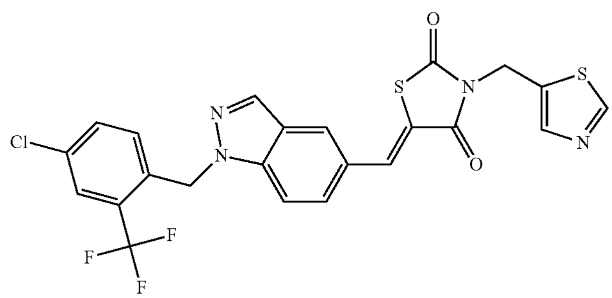 [SMILES: O=C1S/C(=C\c2ccc3c(cnn3Cc3ccc(Cl)cc3C(F)(F)F)c2)C(=O)N1Cc1cncs1] | 94 | (5Z)-5-({1-[4-Chloro-2-(trifluoromethyl)benzyl]-1H-indazol-5-yl}methylidene)-3-(1,3-thiazol-5-ylmethyl)-1,3-thiazolidine-2,4-dione |
| 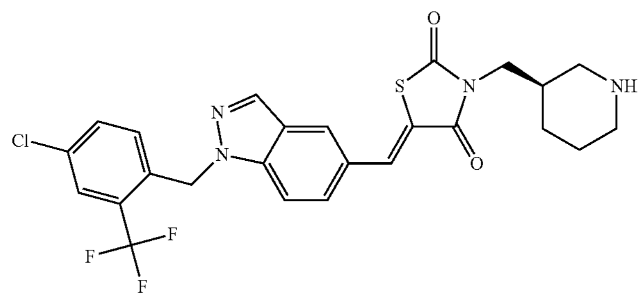 [SMILES: O=C1S/C(=C\c2ccc3c(cnn3Cc3ccc(Cl)cc3C(F)(F)F)c2)C(=O)N1C[C@@H]1CCCNC1] | 95 | (5Z)-5-({1-[4-Chloro-2-(trifluoromethyl)benzyl]-1H-indazol-5-yl}methylidene)-3-[(3R)-piperidin-3-ylmethyl]-1,3-thiazolidine-2,4-dione |
| 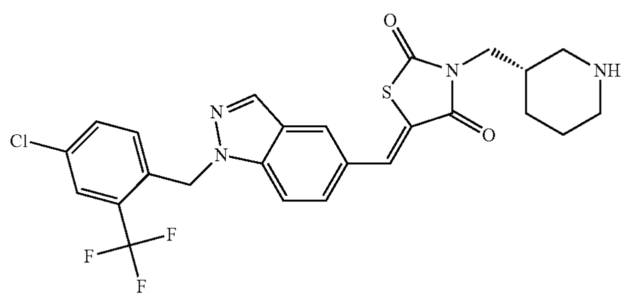 [SMILES: O=C1S/C(=C\c2ccc3c(cnn3Cc3ccc(Cl)cc3C(F)(F)F)c2)C(=O)N1C[C@H]1CCCNC1] | 96 | (5Z)-5-({1-[4-Chloro-2-(trifluoromethyl)benzyl]-1H-indazol-5-yl}methylidene)-3-[(3S)-piperidin-3-ylmethyl]-1,3-thiazolidine-2,4-dione |
| 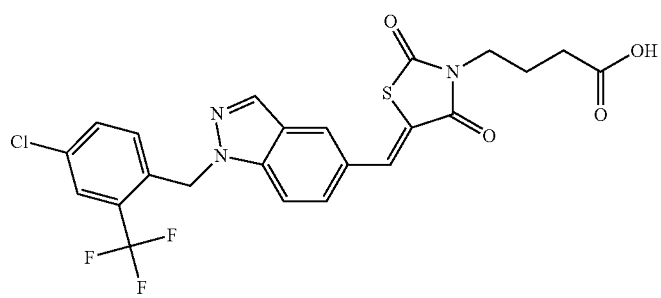 [SMILES: O=C(O)CCCN1C(=O)S/C(=C\c2ccc3c(cnn3Cc3ccc(Cl)cc3C(F)(F)F)c2)C1=O] | 97 | 4-[(5Z)-5-({1-[4-Chloro-2-(trifluoromethyl)benzyl]-1H-indazol-5-yl}methylidene)-2,4-dioxo-1,3-thiazolidin-3-yl]butanoic acid |
| 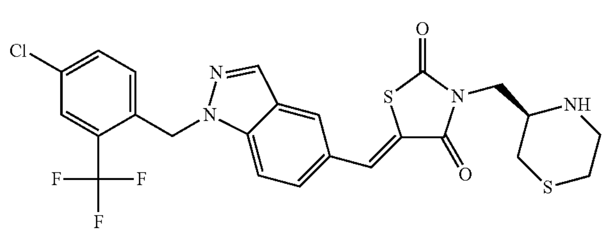 [SMILES: O=C1S/C(=C\c2ccc3c(cnn3Cc3ccc(Cl)cc3C(F)(F)F)c2)C(=O)N1C[C@@H]1CSCCN1] | 98 | (5Z)-5-({1-[4-Chloro-2-(trifluoromethyl)benzyl]-1H-indazol-5-yl}methylidene)-3-[(3R)-thiomorpholin-3-ylmethyl]-1,3-thiazolidine-2,4-dione |

TABLE I-continued

| STRUCTURE | COMPOUND # | NAME |
|---|---|---|
| 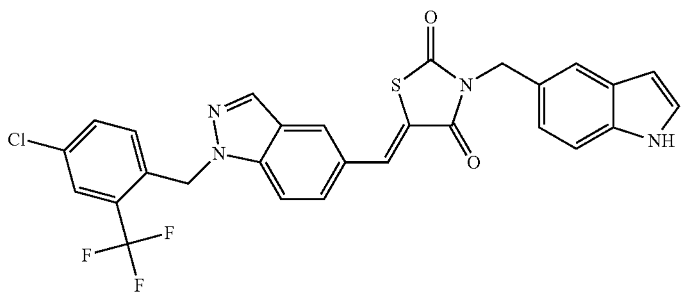 [SMILES: O=C1S/C(=C\c2ccc3c(cnn3Cc3ccc(Cl)cc3C(F)(F)F)c2)C(=O)N1Cc1ccc2[nH]ccc2c1] | 99 | 2-[(5Z)-5-({1-[2,4-Bis(trifluoromethyl)benzyl]-1H-indazol-5-yl}methylidene)-2,4-dioxo-1,3-thiazolidin-3-yl]-N-sulfamoylacetamide |
| 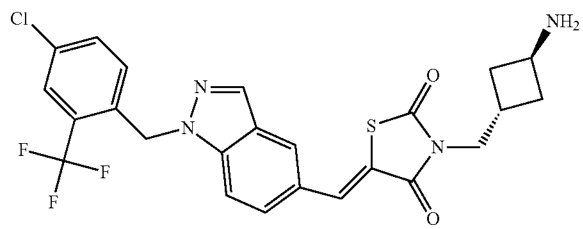 [SMILES: N[C@H]1C[C@H](CN2C(=O)S/C(=C\c3ccc4c(cnn4Cc4ccc(Cl)cc4C(F)(F)F)c3)C2=O)C1] | 100 | (5Z)-3-[(trans-3-Aminocyclobutyl)methyl]-5-({1-[4-chloro-2-(trifluoromethyl)benzyl]-1H-indazol-5-yl}methylidene)-1,3-thiazolidine-2,4-dione |
| 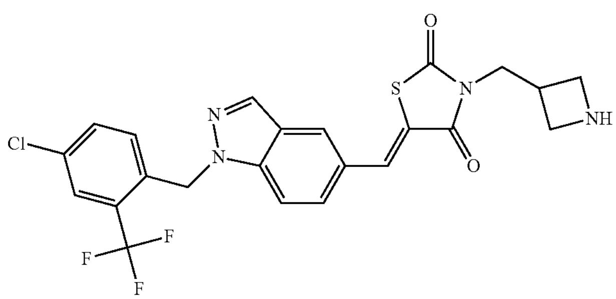 [SMILES: O=C1S/C(=C\c2ccc3c(cnn3Cc3ccc(Cl)cc3C(F)(F)F)c2)C(=O)N1CC1CNC1] | 101 | (5Z)-3-(Azetidin-3-ylmethyl)-5-({1-[4-chloro-2-(trifluoromethyl)benzyl]-1H-indazol-5-yl}methylidene)-1,3-thiazolidine-2,4-dione |
| 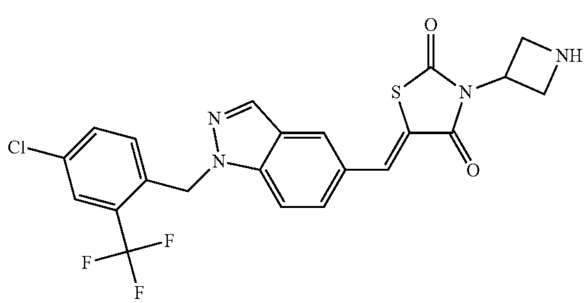 [SMILES: O=C1S/C(=C\c2ccc3c(cnn3Cc3ccc(Cl)cc3C(F)(F)F)c2)C(=O)N1C1CNC1] | 102 | (5Z)-3-Azetidin-3-yl-5-({1-[4-chloro-2-(trifluoromethyl)benzyl]-1H-indazol-5-yl}methylidene)-1,3-thiazolidine-2,4-dione |
| 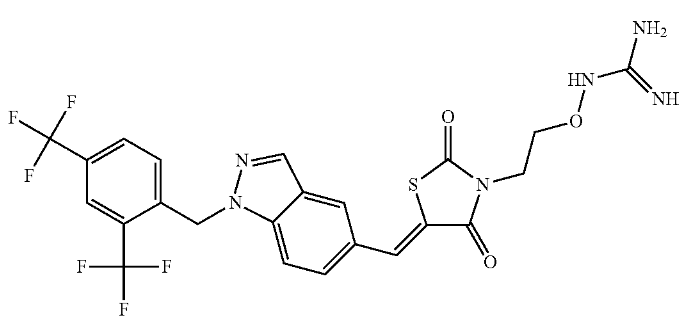 [SMILES: N=C(N)NOCCN1C(=O)S/C(=C\c2ccc3c(cnn3Cc3ccc(C(F)(F)F)cc3C(F)(F)F)c2)C1=O] | 103 | 1-{2-[(5Z)-5-({1-[2,4-Bis(trifluoromethyl)benzyl]-1H-indazol-5-yl}methylidene)-2,4-dioxo-1,3-thiazolidin-3-yl]ethoxy}guanidine |

TABLE I-continued

| STRUCTURE | COMPOUND # | NAME |
|---|---|---|
| 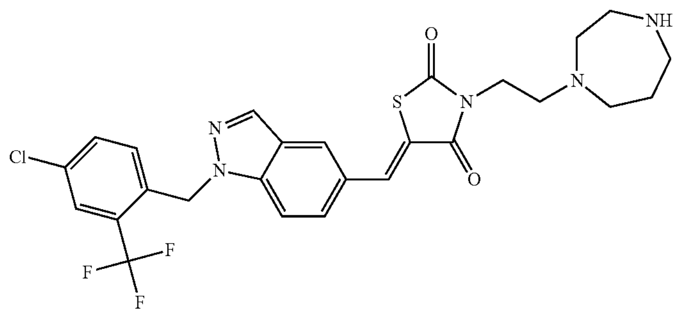 [SMILES: O=C1S/C(=C\c2ccc3c(cnn3Cc3ccc(Cl)cc3C(F)(F)F)c2)C(=O)N1CCN1CCCNCC1] | 104 | (5Z)-5-({1-[4-Chloro-2-(trifluoromethyl)benzyl]-1H-indazol-5-yl}methylidene)-3-[2-(1,4-diazepan-1-yl)ethyl]-1,3-thiazolidine-2,4-dione |
| 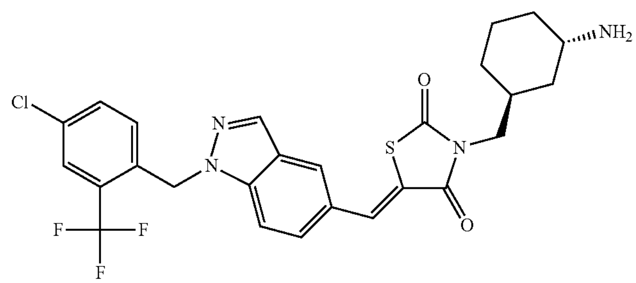 [SMILES: N[C@H]1CCC[C@H](CN2C(=O)S/C(=C\c3ccc4c(cnn4Cc4ccc(Cl)cc4C(F)(F)F)c3)C2=O)C1] | 105 | (5Z)-3-{[(1S,3S)-3-Aminocyclohexyl]methyl}-5-({1-[4-chloro-2-(trifluoromethyl)benzyl]-1H-indazol-5-yl}methylidene)-1,3-thiazolidine-2,4-dione |
| 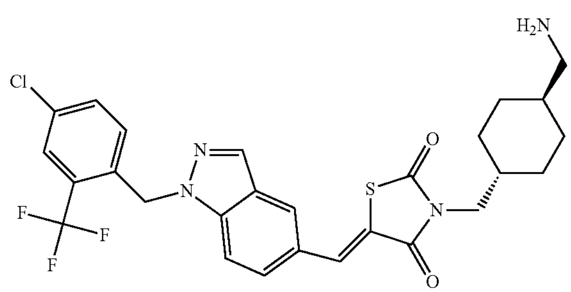 [SMILES: NC[C@H]1CC[C@H](CN2C(=O)S/C(=C\c3ccc4c(cnn4Cc4ccc(Cl)cc4C(F)(F)F)c3)C2=O)CC1] | 106 | (5Z)-3-{[trans-4-(Aminomethyl)cyclohexyl]methyl}-5-({1-[4-chloro-2-(trifluoromethyl)benzyl]-1H-indazol-5-yl}methylidene)-1,3-thiazolidine-2,4-dione |
| 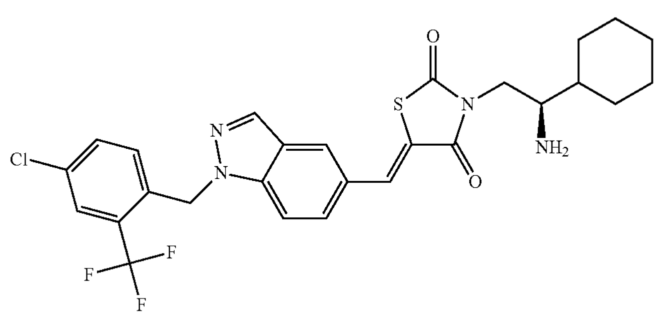 [SMILES: N[C@@H](CN1C(=O)S/C(=C\c2ccc3c(cnn3Cc3ccc(Cl)cc3C(F)(F)F)c2)C1=O)C1CCCCC1] | 107 | (5Z)-3-[(2R)-2-Amino-2-cyclohexylethyl]-5-({1-[4-chloro-2-(trifluoromethyl)benzyl]-1H-indazol-5-yl}methylidene)-1,3-thiazolidine-2,4-dione |
| 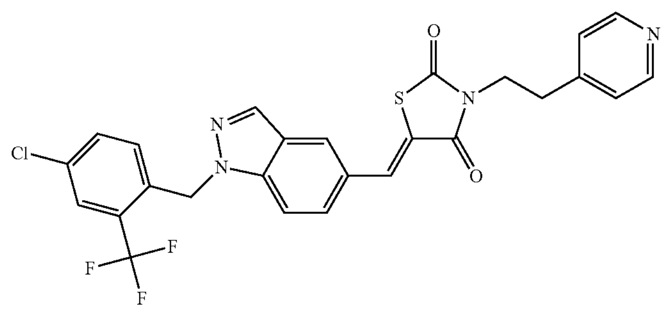 [SMILES: O=C1S/C(=C\c2ccc3c(cnn3Cc3ccc(Cl)cc3C(F)(F)F)c2)C(=O)N1CCc1ccncc1] | 108 | (5Z)-5-({1-[4-Chloro-2-(trifluoromethyl)benzyl]-1H-indazol-5-yl}methylidene)-3-(2-pyridin-4-ylethyl)-1,3-thiazolidine-2,4-dione |

TABLE I-continued

| STRUCTURE | COMPOUND # | NAME |
|---|---|---|
| 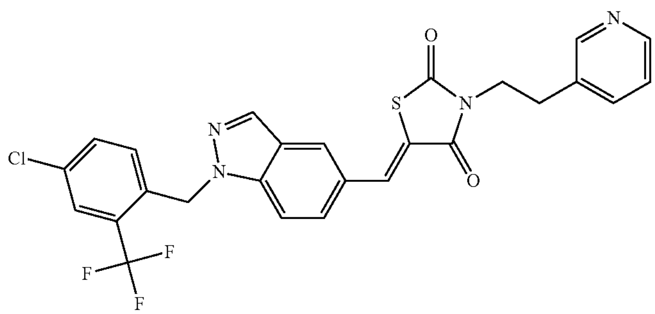 [SMILES: O=C1S/C(=C\c2ccc3c(cnn3Cc3ccc(Cl)cc3C(F)(F)F)c2)C(=O)N1CCc1cccnc1] | 109 | (5Z)-5-({1-[4-Chloro-2-(trifluoromethyl)benzyl]-1H-indazol-5-yl}methylidene)-3-(2-pyridin-3-ylethyl)-1,3-thiazolidine-2,4-dione |
| 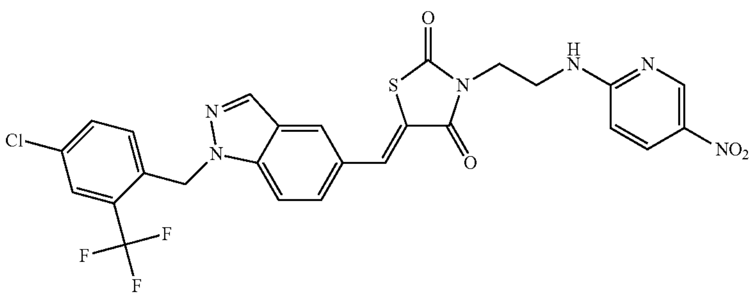 [SMILES: O=C1S/C(=C\c2ccc3c(cnn3Cc3ccc(Cl)cc3C(F)(F)F)c2)C(=O)N1CCNc1ccc([N+](=O)[O-])cn1] | 110 | (5Z)-5-({1-[4-Chloro-2-(trifluoromethyl)benzyl]-1H-indazol-5-yl}methylidene)-3-{2-[(5-nitropyridin-2-yl)amino]ethyl}-1,3-thiazolidine-2,4-dione |
| 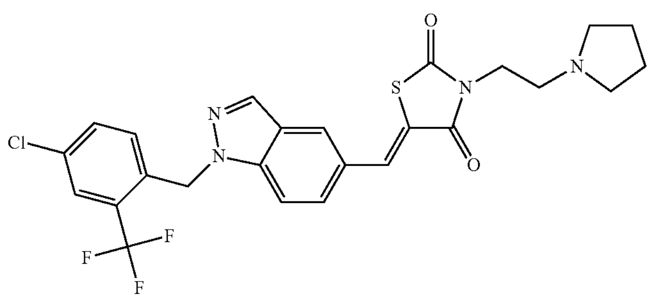 [SMILES: O=C1S/C(=C\c2ccc3c(cnn3Cc3ccc(Cl)cc3C(F)(F)F)c2)C(=O)N1CCN1CCCC1] | 111 | (5Z)-5-({1-[4-Chloro-2-(trifluoromethyl)benzyl]-1H-indazol-5-yl}methylidene)-3-(2-pyrrolidin-1-ylethyl)-1,3-thiazolidine-2,4-dione |
| 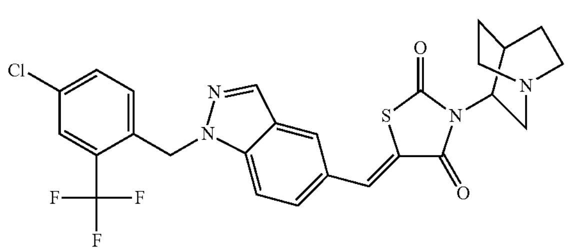 [SMILES: O=C1S/C(=C\c2ccc3c(cnn3Cc3ccc(Cl)cc3C(F)(F)F)c2)C(=O)N1C1CN2CCC1CC2] | 112 | (5Z)-3-(1-Azabicyclo[2.2.2]oct-3-yl)-5-({1-[4-chloro-2-(trifluoromethyl)benzyl]-1H-indazol-5-yl}methylidene)-1,3-thiazolidine-2,4-dione |
| 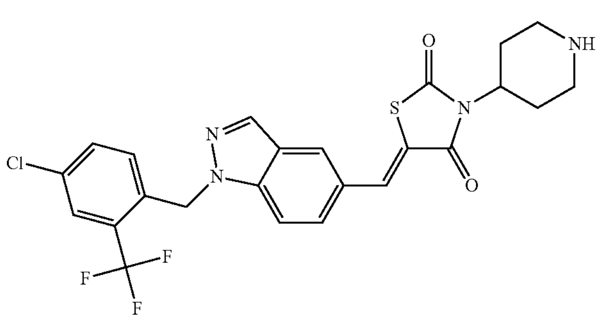 [SMILES: O=C1S/C(=C\c2ccc3c(cnn3Cc3ccc(Cl)cc3C(F)(F)F)c2)C(=O)N1C1CCNCC1] | 113 | (5Z)-5-({1-[4-Chloro-2-(trifluoromethyl)benzyl]-1H-indazol-5-yl}methylidene)-3-piperidin-4-yl-1,3-thiazolidine-2,4-dione |

TABLE I-continued

| STRUCTURE | COMPOUND # | NAME |
|---|---|---|
| 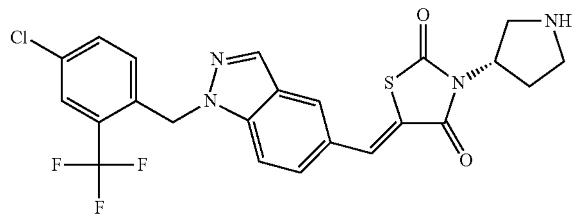 [SMILES: O=C1S/C(=C\c2ccc3c(cnn3Cc3ccc(Cl)cc3C(F)(F)F)c2)C(=O)N1[C@H]1CCNC1] | 114 | (5Z)-5-({1-[4-Chloro-2-(trifluoromethyl)benzyl]-1H-indazol-5-yl}methylidene)-3-[(3S)-pyrrolidin-3-yl]-1,3-thiazolidine-2,4-dione |
| 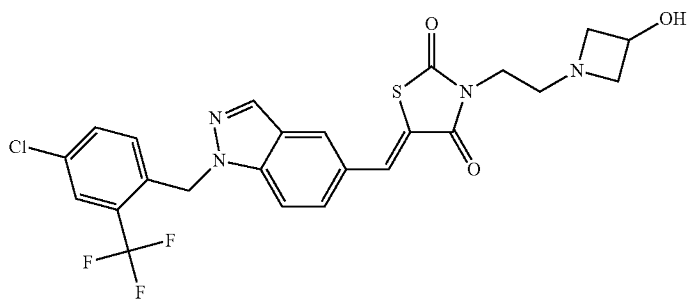 [SMILES: O=C1S/C(=C\c2ccc3c(cnn3Cc3ccc(Cl)cc3C(F)(F)F)c2)C(=O)N1CCN1CC(O)C1] | 115 | (5Z)-5-({1-[4-Chloro-2-(trifluoromethyl)benzyl]-1H-indazol-5-yl}methylidene)-3-[2-(3-hydroxyazetidin-1-yl)ethyl]-1,3-thiazolidine-2,4-dione |
| 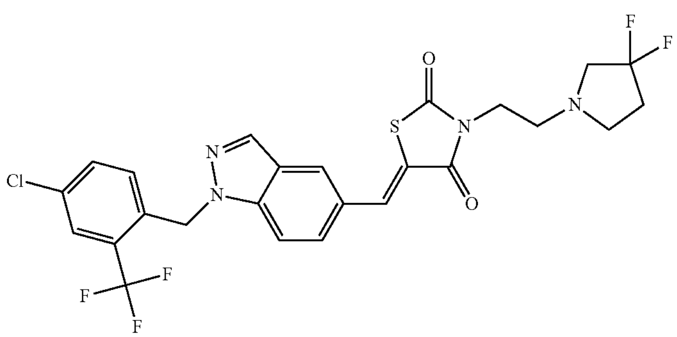 [SMILES: O=C1S/C(=C\c2ccc3c(cnn3Cc3ccc(Cl)cc3C(F)(F)F)c2)C(=O)N1CCN1CCC(F)(F)C1] | 116 | (5Z)-5-({1-[4-Chloro-2-(trifluoromethyl)benzyl]-1H-indazol-5-yl}methylidene)-3-[2-(3,3-difluoropyrrolidin-1-yl)ethyl]-1,3-thiazolidine-2,4-dione |
| 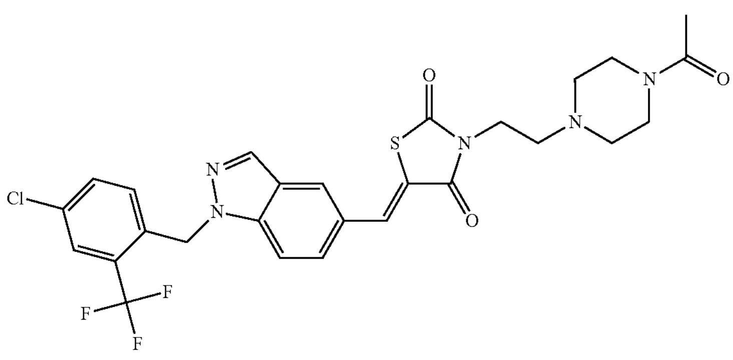 [SMILES: CC(=O)N1CCN(CCN2C(=O)S/C(=C\c3ccc4c(cnn4Cc4ccc(Cl)cc4C(F)(F)F)c3)C2=O)CC1] | 117 | (5Z)-3-[2-(4-Acetylpiperazin-1-yl)ethyl]-5-({1-[4-chloro-2-(trifluoromethyl)benzyl]-1H-indazol-5-yl}methylidene)-1,3-thiazolidine-2,4-dione |
| 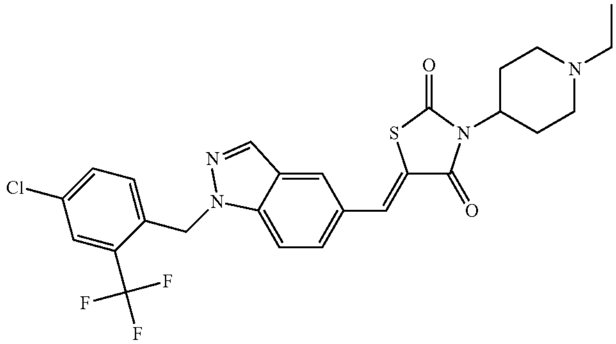 [SMILES: CCN1CCC(N2C(=O)S/C(=C\c3ccc4c(cnn4Cc4ccc(Cl)cc4C(F)(F)F)c3)C2=O)CC1] | 118 | (5Z)-5-({1-[4-Chloro-2-(trifluoromethyl)benzyl]-1H-indazol-5-yl}methylidene)-3-(1-ethylpiperidin-4-yl)-1,3-thiazolidine-2,4-dione |

TABLE I-continued

| STRUCTURE | COMPOUND # | NAME |
|---|---|---|
| 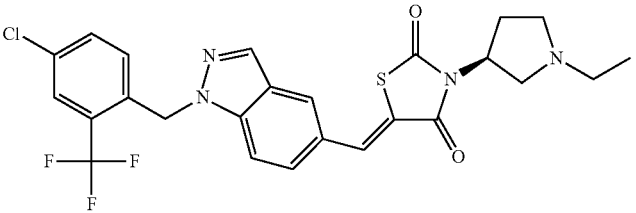 [SMILES: CCN1CC[C@H](N2C(=O)S/C(=C\c3ccc4c(cnn4Cc4ccc(Cl)cc4C(F)(F)F)c3)C2=O)C1] | 119 | (5Z)-5-({1-[4-Chloro-2-(trifluoromethyl)benzyl]-1H-indazol-5-yl}methylidene)-3-[(3S)-1-ethylpyrrolidin-3-yl]-1,3-thiazolidine-2,4-dione |
| 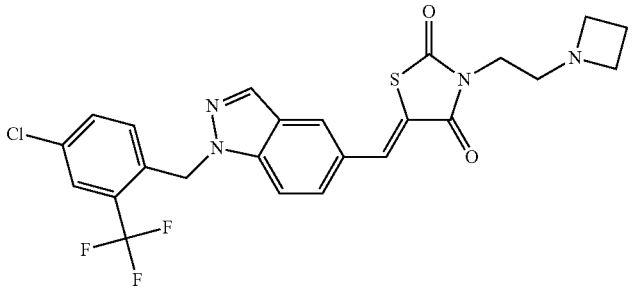 [SMILES: O=C1S/C(=C\c2ccc3c(cnn3Cc3ccc(Cl)cc3C(F)(F)F)c2)C(=O)N1CCN1CCC1] | 120 | (5Z)-3-(2-Azetidin-1-ylethyl)-5-({1-[4-chloro-2-(trifluoromethyl)benzyl]-1H-indazol-5-yl}methylidene)-1,3-thiazolidine-2,4-dione |
| 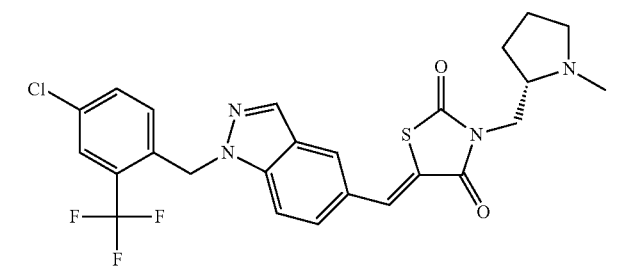 [SMILES: CN1CCC[C@H]1CN1C(=O)S/C(=C\c2ccc3c(cnn3Cc3ccc(Cl)cc3C(F)(F)F)c2)C1=O] | 121 | (5Z)-5-({1-[4-Chloro-2-(trifluoromethyl)benzyl]-1H-indazol-5-yl}methylidene)-3-{[(2S)-1-methylpyrrolidin-2-yl]methyl}-1,3-thiazolidine-2,4-dione |
| 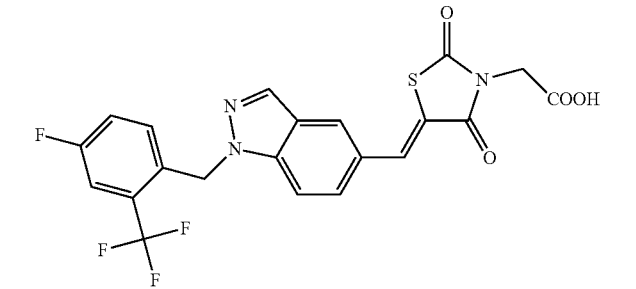 [SMILES: O=C(O)CN1C(=O)S/C(=C\c2ccc3c(cnn3Cc3ccc(F)cc3C(F)(F)F)c2)C1=O] | 122 | [(5Z)-5-({1-[4-Fluoro-2-(trifluoromethyl)benzyl]-1H-indazol-5-yl}methylidene)-2,4-dioxo-1,3-thiazolidin-3-yl]acetic acid |
| 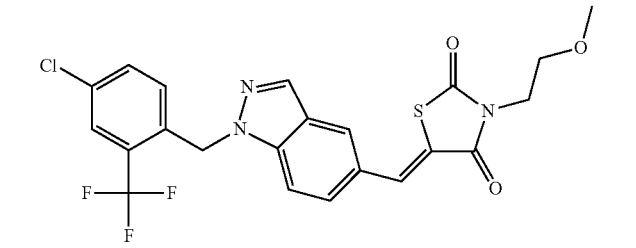 [SMILES: COCCN1C(=O)S/C(=C\c2ccc3c(cnn3Cc3ccc(Cl)cc3C(F)(F)F)c2)C1=O] | 123 | (5Z)-5-({1-[4-Chloro-2-(trifluoromethyl)benzyl]-1H-indazol-5-yl}methylidene)-3-(2-methoxyethyl)-1,3-thiazolidine-2,4-dione |
| 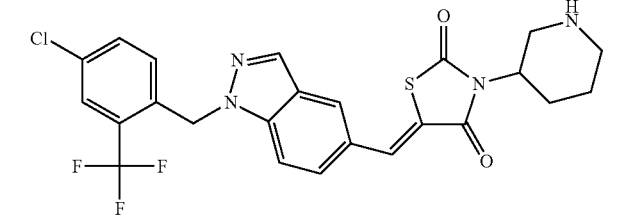 [SMILES: O=C1S/C(=C\c2ccc3c(cnn3Cc3ccc(Cl)cc3C(F)(F)F)c2)C(=O)N1C1CCCNC1] | 124 | (5Z)-5-({1-[4-Chloro-2-(trifluoromethyl)benzyl]-1H-indazol-5-yl}methylidene)-3-piperidin-3-yl-1,3-thiazolidine-2,4-dione |

TABLE I-continued

| STRUCTURE | COMPOUND # | NAME |
|---|---|---|
| 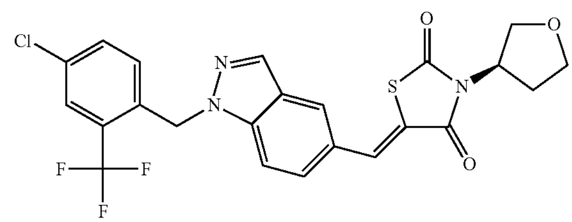 [SMILES: O=C1S/C(=C\c2ccc3c(cnn3Cc3ccc(Cl)cc3C(F)(F)F)c2)C(=O)N1[C@@H]1CCOC1] | 125 | (5Z)-5-({1-[4-Chloro-2-(trifluoromethyl)benzyl]-1H-indazol-5-yl}methylidene)-3-[(3R)-tetrahydrofuran-3-yl]-1,3-thiazolidine-2,4-dione |
| 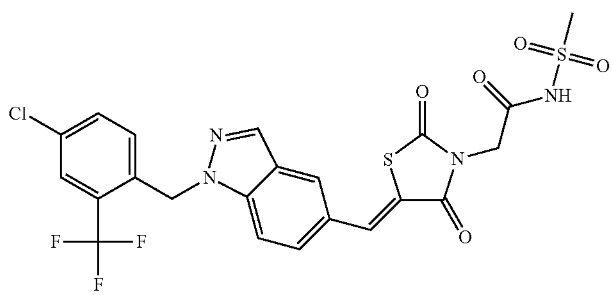 [SMILES: CS(=O)(=O)NC(=O)CN1C(=O)S/C(=C\c2ccc3c(cnn3Cc3ccc(Cl)cc3C(F)(F)F)c2)C1=O] | 126 | 2-[(5Z)-5-({1-[4-Chloro-2-(trifluoromethyl)benzyl]-1H-indazol-5-yl}methylidene)-2,4-dioxo-1,3-thiazolidin-3-yl]-N-(methylsulfonyl)acetamide |
| 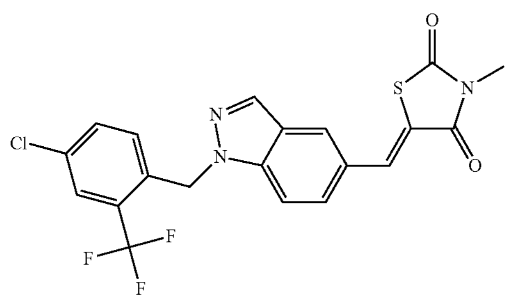 [SMILES: CN1C(=O)S/C(=C\c2ccc3c(cnn3Cc3ccc(Cl)cc3C(F)(F)F)c2)C1=O] | 127 | (5Z)-5-({1-[4-Chloro-2-(trifluoromethyl)-benzyl]-1H-indazol-5-yl}methylidene)-3-methyl-1,3-thiazolidine-2,4-dione |
| 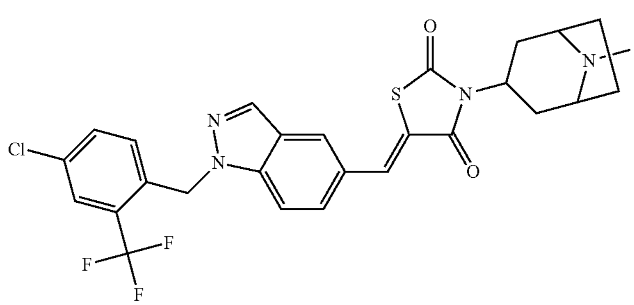 [SMILES: CN1C2CCC1CC(N1C(=O)S/C(=C\c3ccc4c(cnn4Cc4ccc(Cl)cc4C(F)(F)F)c3)C1=O)C2] | 128 | (5Z)-5-({1-[4-Chloro-2-(trifluoromethyl)benzyl]-1H-indazol-5-yl}methylidene)-3-(8-methyl-8-azabicyclo[3.2.1]oct-3-yl)-1,3-thiazolidine-2,4-dione |
| 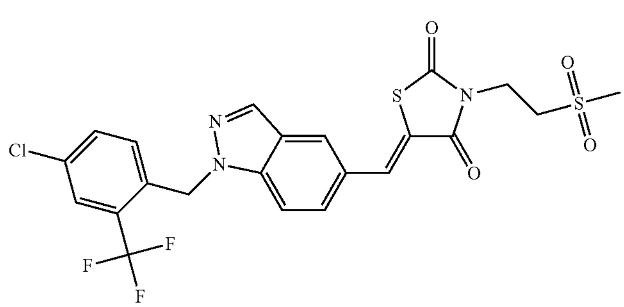 [SMILES: CS(=O)(=O)CCN1C(=O)S/C(=C\c2ccc3c(cnn3Cc3ccc(Cl)cc3C(F)(F)F)c2)C1=O] | 129 | (5Z)-5-({1-[4-Chloro-2-(trifluoromethyl)benzyl]-1H-indazol-5-yl}methylidene)-3-[2-(methylsulfonyl)ethyl]-1,3-thiazolidine-2,4-dione |

TABLE I-continued

| STRUCTURE | COMPOUND # | NAME |
|---|---|---|
| 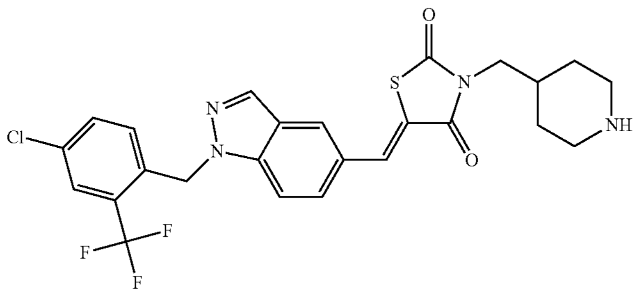 [SMILES: O=C1S/C(=C\c2ccc3c(cnn3Cc3ccc(Cl)cc3C(F)(F)F)c2)C(=O)N1CC1CCNCC1] | 130 | (5Z)-5-({1-[4-Chloro-2-(trifluoromethyl)benzyl]-1H-indazol-5-yl}methylidene)-3-(piperidin-4-ylmethyl)-1,3-thiazolidine-2,4-dione |
| 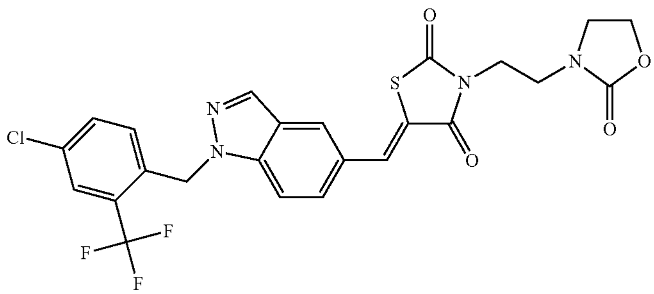 [SMILES: O=C1OCCN1CCN1C(=O)S/C(=C\c2ccc3c(cnn3Cc3ccc(Cl)cc3C(F)(F)F)c2)C1=O] | 131 | (5Z)-5-({1-[4-Chloro-2-(trifluoromethyl)benzyl]-1H-indazol-5-yl}methylidene)-3-[2-(2-oxo-1,3-oxazolidin-3-yl)ethyl]-1,3-thiazolidine-2,4-dione |
| 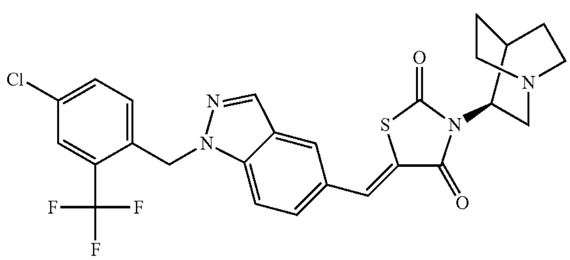 [SMILES: O=C1S/C(=C\c2ccc3c(cnn3Cc3ccc(Cl)cc3C(F)(F)F)c2)C(=O)N1[C@@H]1CN2CCC1CC2] | 132 | (5Z)-3-[(3S)-1-Azabicyclo[2.2.2]oct-3-yl]-5-({1-[4-chloro-2-(trifluoromethyl)benzyl]-1H-indazol-5-yl}methylidene)-1,3-thiazolidine-2,4-dione |
| 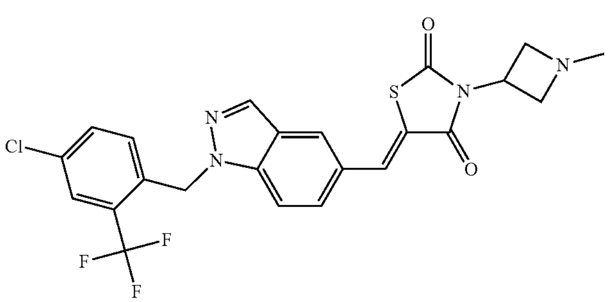 [SMILES: CN1CC(N2C(=O)S/C(=C\c3ccc4c(cnn4Cc4ccc(Cl)cc4C(F)(F)F)c3)C2=O)C1] | 133 | (5Z)-5-({1-[4-Chloro-2-(trifluoromethyl)benzyl]-1H-indazol-5-yl}methylidene)-3-(1-methylazetidin-3-yl)-1,3-thiazolidine-2,4-dione |
| 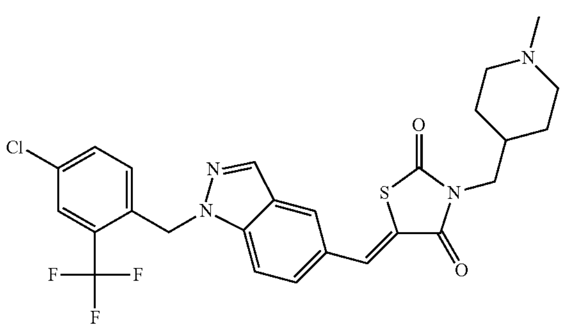 [SMILES: CN1CCC(CN2C(=O)S/C(=C\c3ccc4c(cnn4Cc4ccc(Cl)cc4C(F)(F)F)c3)C2=O)CC1] | 134 | (5Z)-5-({1-[4-Chloro-2-(trifluoromethyl)benzyl]-1H-indazol-5-yl}methylidene)-3-[(1-methylpiperidin-4-yl)methyl]-1,3-thiazolidine-2,4-dione |

TABLE I-continued

| STRUCTURE | COMPOUND # | NAME |
|---|---|---|
| 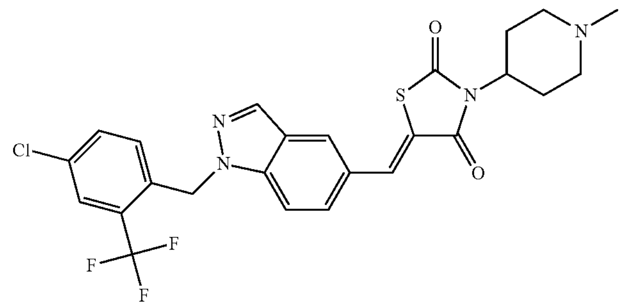 [SMILES: CN1CCC(N2C(=O)S/C(=C\c3ccc4c(cnn4Cc4ccc(Cl)cc4C(F)(F)F)c3)C2=O)CC1] | 135 | (5Z)-5-({1-[4-Chloro-2-(trifluoromethyl)benzyl]-1H-indazol-5-yl}methylidene)-3-(1-methylpiperidin-4-yl)-1,3-thiazolidine-2,4-dione |
| 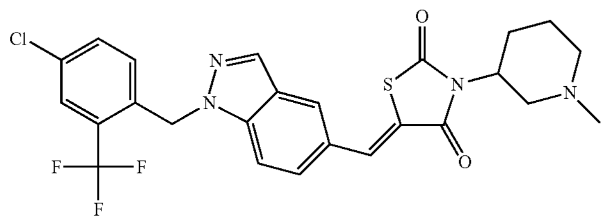 [SMILES: CN1CCCC(N2C(=O)S/C(=C\c3ccc4c(cnn4Cc4ccc(Cl)cc4C(F)(F)F)c3)C2=O)C1] | 136 | (5Z)-5-({1-[4-Chloro-2-(trifluoromethyl)benzyl]-1H-indazol-5-yl}methylidene)-3-(1-methylpiperidin-3-yl)-1,3-thiazolidine-2,4-dione |
| 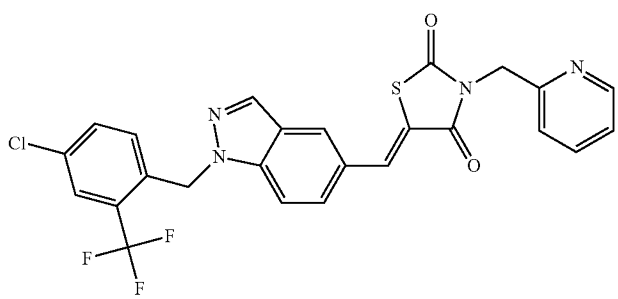 [SMILES: O=C1S/C(=C\c2ccc3c(cnn3Cc3ccc(Cl)cc3C(F)(F)F)c2)C(=O)N1Cc1ccccn1] | 137 | (5Z)-5-({1-[4-Chloro-2-(trifluoromethyl)benzyl]-1H-indazol-5-yl}methylidene)-3-(pyridin-2-ylmethyl)-1,3-thiazolidine-2,4-dione |
| 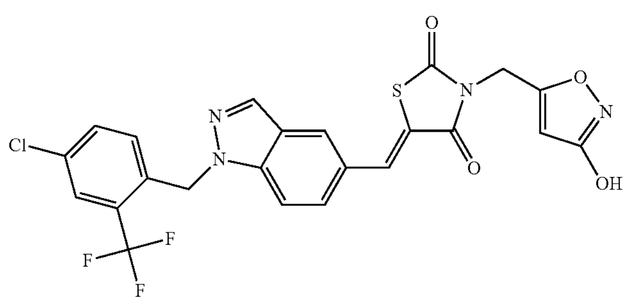 [SMILES: O=C1S/C(=C\c2ccc3c(cnn3Cc3ccc(Cl)cc3C(F)(F)F)c2)C(=O)N1Cc1cc(O)no1] | 138 | (5Z)-5-({1-[4-Chloro-2-(trifluoromethyl)benzyl]-1H-indazol-5-yl}methylidene)-3-[(3-hydroxyisoxazol-5-yl)methyl]-1,3-thiazolidine-2,4-dione |
| 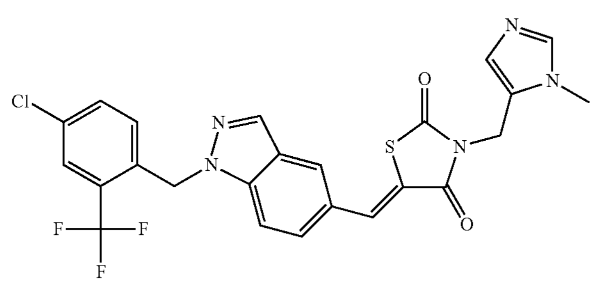 [SMILES: Cn1cncc1CN1C(=O)S/C(=C\c2ccc3c(cnn3Cc3ccc(Cl)cc3C(F)(F)F)c2)C1=O] | 139 | (5Z)-5-({1-[4-Chloro-2-(trifluoromethyl)benzyl]-1H-indazol-5-yl}methylidene)-3-[(1-methyl-1H-imidazol-5-yl)methyl]-1,3-thiazolidine-2,4-dione |

TABLE I-continued

| STRUCTURE | COMPOUND # | NAME |
|---|---|---|
| 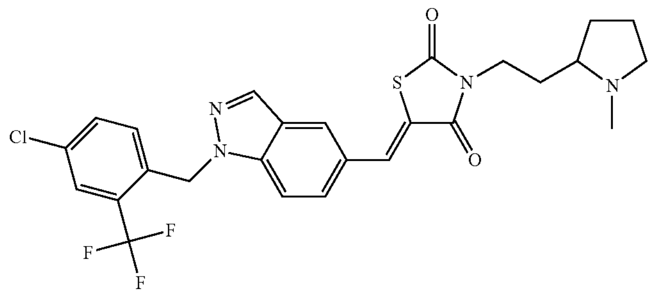 | 140 | (5Z)-5-({1-[4-Chloro-2-(trifluoromethyl)benzyl]-1H-indazol-5-yl}methylidene)-3-[2-(1-methylpyrrolidin-2-yl)ethyl]-1,3-thiazolidine-2,4-dione |
| 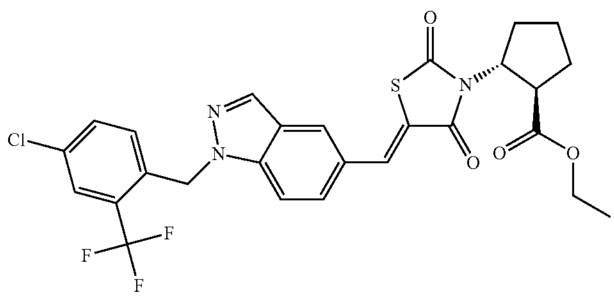 [SMILES: CCOC(=O)[C@@H]1CCC[C@H]1N1C(=O)S/C(=C\c2ccc3c(cnn3Cc3ccc(Cl)cc3C(F)(F)F)c2)C1=O] | 141 | Ethyl (1R,2R)-2-[(5Z)-5-({1-[4-chloro-2-(trifluoromethyl)benzyl]-1H-indazol-5-yl}methylidene)-2,4-dioxo-1,3-thiazolidin-3-yl]cyclopentanecarboxylate |
| 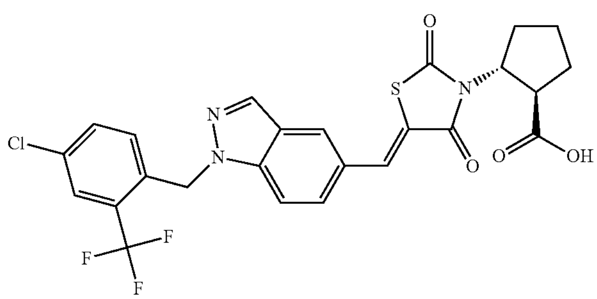 [SMILES: O=C(O)[C@@H]1CCC[C@H]1N1C(=O)S/C(=C\c2ccc3c(cnn3Cc3ccc(Cl)cc3C(F)(F)F)c2)C1=O] | 142 | (1R,2R)-2-[(5Z)-5-({1-[4-Chloro-2-(trifluoromethyl)benzyl]-1H-indazol-5-yl}methylidene)-2,4-dioxo-1,3-thiazolidin-3-yl]cyclopentanecarboxylic acid |
| 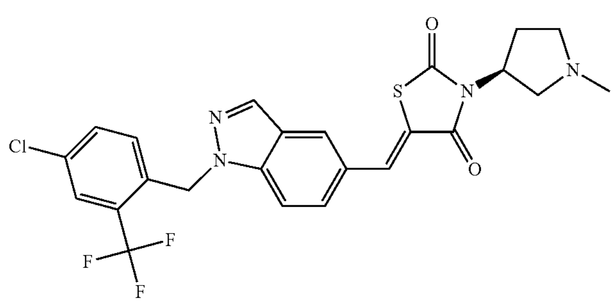 [SMILES: CN1CC[C@H](N2C(=O)S/C(=C\c3ccc4c(cnn4Cc4ccc(Cl)cc4C(F)(F)F)c3)C2=O)C1] | 143 | (5Z)-5-({1-[4-Chloro-2-(trifluoromethyl)benzyl]-1H-indazol-5-yl}methylidene)-3-[(3S)-1-methylpyrrolidin-3-yl]-1,3-thiazolidine-2,4-dione |
| 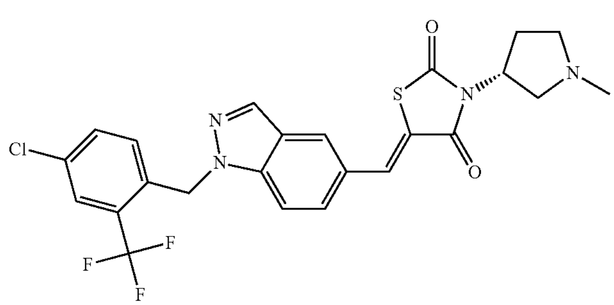 [SMILES: CN1CC[C@@H](N2C(=O)S/C(=C\c3ccc4c(cnn4Cc4ccc(Cl)cc4C(F)(F)F)c3)C2=O)C1] | 144 | (5Z)-5-({1-[4-Chloro-2-(trifluoromethyl)benzyl]-1H-indazol-5-yl}methylidene)-3-[(3R)-1-methylpyrrolidin-3-yl]-1,3-thiazolidine-2,4-dione |

TABLE I-continued

| STRUCTURE | COMPOUND # | NAME |
|---|---|---|
| 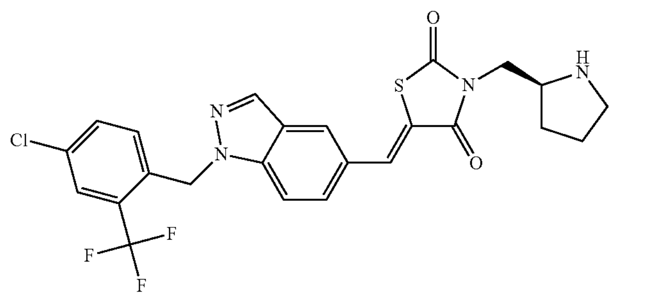 [SMILES: O=C1S/C(=C\c2ccc3c(cnn3Cc3ccc(Cl)cc3C(F)(F)F)c2)C(=O)N1C[C@@H]1CCCN1] | 145 | (5Z)-5-({1-[4-Chloro-2-(trifluoromethyl)benzyl]-1H-indazol-5-yl}methylidene)-3-[(2S)-pyrrolidin-2-ylmethyl]-1,3-thiazolidine-2,4-dione |
| 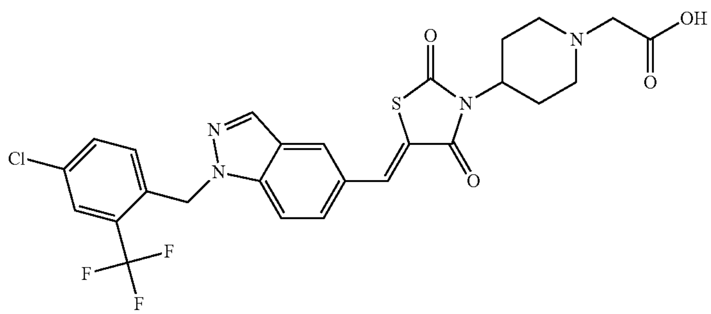 [SMILES: O=C(O)CN1CCC(N2C(=O)S/C(=C\c3ccc4c(cnn4Cc4ccc(Cl)cc4C(F)(F)F)c3)C2=O)CC1] | 146 | {4-[(5Z)-5-({1-[4-Chloro-2-(trifluoromethyl)benzyl]-1H-indazol-5-yl}methylidene)-2,4-dioxo-1,3-thiazolidin-3-yl]piperidin-1-yl}acetic acid |
| 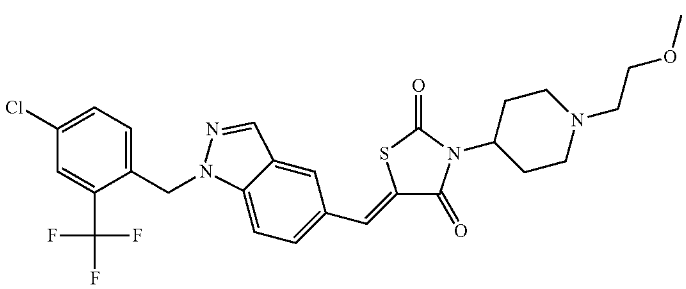 [SMILES: COCCN1CCC(N2C(=O)S/C(=C\c3ccc4c(cnn4Cc4ccc(Cl)cc4C(F)(F)F)c3)C2=O)CC1] | 147 | (5Z)-5-({1-[4-Chloro-2-(trifluoromethyl)benzyl]-1H-indazol-5-yl}methylidene)-3-[1-(2-methoxyethyl)piperidin-4-yl]-1,3-thiazolidine-2,4-dione |
| 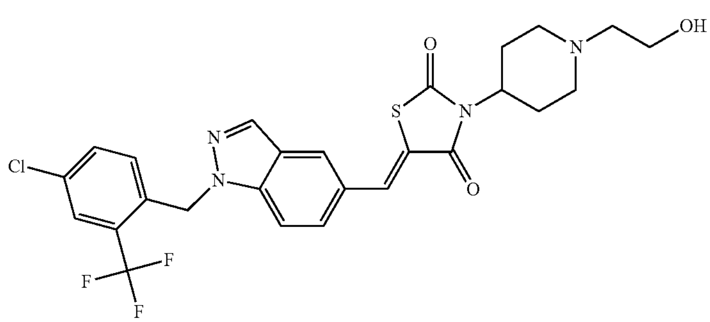 [SMILES: O=C1S/C(=C\c2ccc3c(cnn3Cc3ccc(Cl)cc3C(F)(F)F)c2)C(=O)N1C1CCN(CCO)CC1] | 148 | (5Z)-5-({1-[4-Chloro-2-(trifluoromethyl)benzyl]-1H-indazol-5-yl}methylidene)-3-[1-(2-hydroxyethyl)piperidin-4-yl]-1,3-thiazolidine-2,4-dione |
| 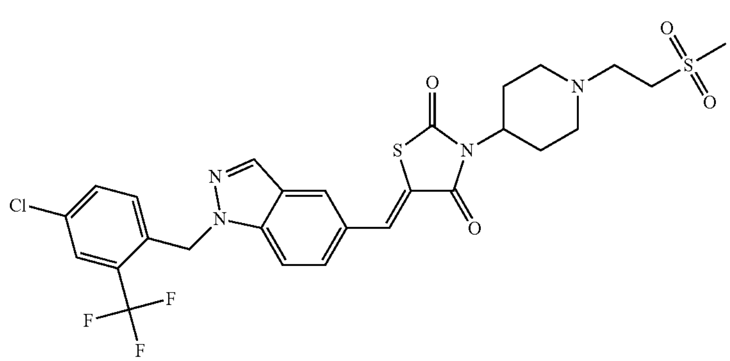 [SMILES: CS(=O)(=O)CCN1CCC(N2C(=O)S/C(=C\c3ccc4c(cnn4Cc4ccc(Cl)cc4C(F)(F)F)c3)C2=O)CC1] | 149 | (5Z)-5-({1-[4-Chloro-2-(trifluoromethyl)benzyl]-1H-indazol-5-yl}methylidene)-3-{1-[2-(methylsulfonyl)ethyl]piperidin-4-yl}-1,3-thiazolidine-2,4-dione |

TABLE I-continued

| STRUCTURE | COMPOUND # | NAME |
|---|---|---|
| 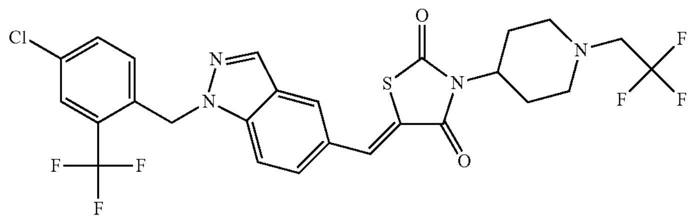 [SMILES: O=C1S/C(=C\c2ccc3c(cnn3Cc3ccc(Cl)cc3C(F)(F)F)c2)C(=O)N1C1CCN(CC(F)(F)F)CC1] | 150 | (5Z)-5-({1-[4-Chloro-2-(trifluoromethyl)benzyl]-1H-indazol-5-yl}methylidene)-3-[1-(2,2,2-trifluoroethyl)piperidin-4-yl]-1,3-thiazolidine-2,4-dione |
| 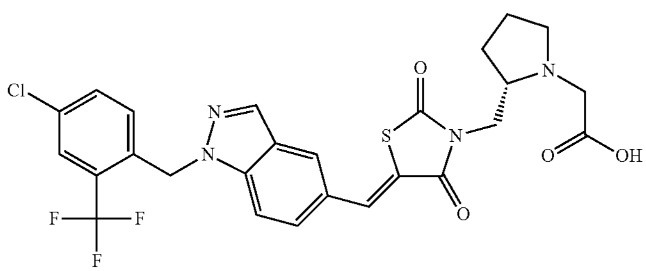 [SMILES: O=C(O)CN1CCC[C@H]1CN1C(=O)S/C(=C\c2ccc3c(cnn3Cc3ccc(Cl)cc3C(F)(F)F)c2)C1=O] | 151 | [(2S)-2-{[(5Z)-5-({1-[4-Chloro-2-(trifluoromethyl)benzyl]-1H-indazol-5-yl}methylidene)-2,4-dioxo-1,3-thiazolidin-3-yl]methyl}pyrrolidin-1-yl]acetic acid |
| 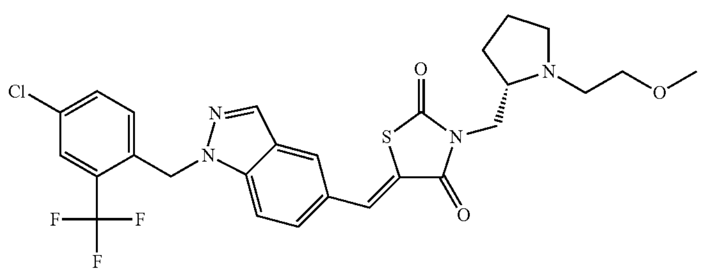 [SMILES: COCCN1CCC[C@H]1CN1C(=O)S/C(=C\c2ccc3c(cnn3Cc3ccc(Cl)cc3C(F)(F)F)c2)C1=O] | 152 | (5Z)-5-({1-[4-Chloro-2-(trifluoromethyl)benzyl]-1H-indazol-5-yl}methylidene)-3-{[(2S)-1-(2-methoxyethyl)pyrrolidin-2-yl]methyl}-1,3-thiazolidine-2,4-dione |
| 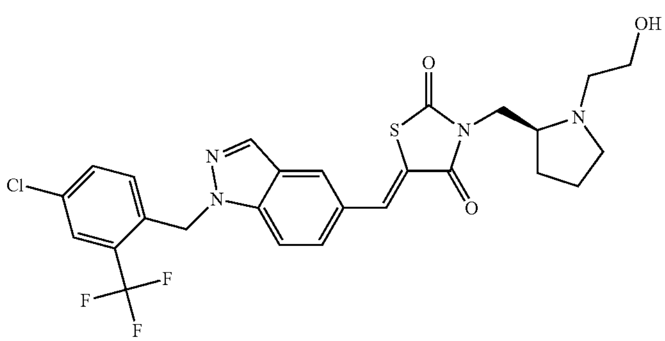 [SMILES: O=C1S/C(=C\c2ccc3c(cnn3Cc3ccc(Cl)cc3C(F)(F)F)c2)C(=O)N1C[C@@H]1CCCN1CCO] | 153 | (5Z)-5-({1-[4-Chloro-2-(trifluoromethyl)benzyl]-1H-indazol-5-yl}methylidene)-3-{[(2S)-1-(2-hydroxyethyl)pyrrolidin-2-yl]methyl}-1,3-thiazolidine-2,4-dione |
| 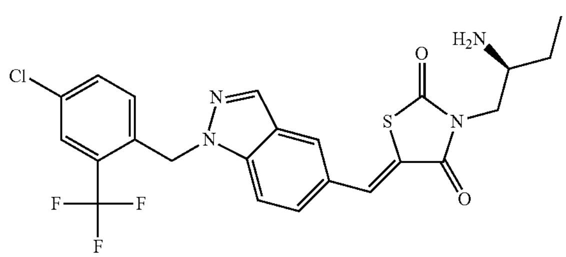 [SMILES: CC[C@H](N)CN1C(=O)S/C(=C\c2ccc3c(cnn3Cc3ccc(Cl)cc3C(F)(F)F)c2)C1=O] | 154 | 3-[(2S)-2-Aminobutyl]-(5Z)-5-({1-[4-chloro-2-(trifluoromethyl)benzyl]-1H-indazol-5-yl}methylidene)-1,3-thiazolidine-2,4-dione |

TABLE I-continued

| STRUCTURE | COMPOUND # | NAME |
|---|---|---|
| 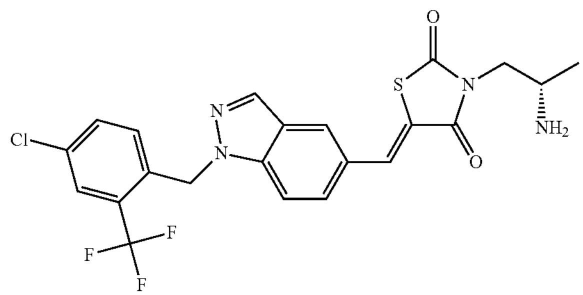 [SMILES: C[C@H](N)CN1C(=O)S/C(=C\c2ccc3c(cnn3Cc3ccc(Cl)cc3C(F)(F)F)c2)C1=O] | 155 | 3-[(2S)-2-Aminopropyl]-(5Z)-5-({1-[4-chloro-2-(trifluoromethyl)benzyl]-1H-indazol-5-yl}methylidene)-1,3-thiazolidine-2,4-dione |
| 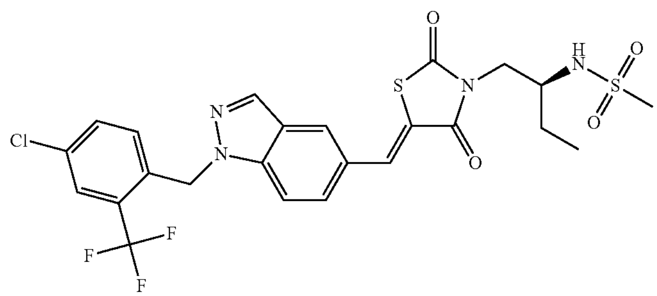 [SMILES: CC[C@@H](CN1C(=O)S/C(=C\c2ccc3c(cnn3Cc3ccc(Cl)cc3C(F)(F)F)c2)C1=O)NS(C)(=O)=O] | 156 | N-[(1S)-1-{[(5Z)-5-({1-[4-Chloro-2-(trifluoromethyl)benzyl]-1H-indazol-5-yl}methylidene)-2,4-dioxo-1,3-thiazolidin-3-yl]methyl}propyl]methanesulfonamide |
| 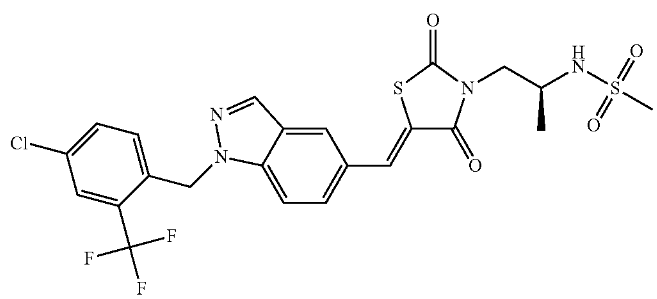 [SMILES: C[C@@H](CN1C(=O)S/C(=C\c2ccc3c(cnn3Cc3ccc(Cl)cc3C(F)(F)F)c2)C1=O)NS(C)(=O)=O] | 157 | N-{(1S)-2-[(5Z)-5-({1-[4-Chloro-2-(trifluoromethyl)benzyl]-1H-indazol-5-yl}methylidene)-2,4-dioxo-1,3-thiazolidin-3-yl]-1-methylethyl}methanesulfonamide |
| 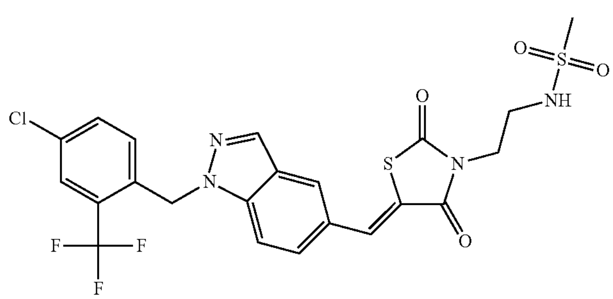 [SMILES: CS(=O)(=O)NCCN1C(=O)S/C(=C\c2ccc3c(cnn3Cc3ccc(Cl)cc3C(F)(F)F)c2)C1=O] | 158 | N-{2-[(5Z)-5-({1-[4-Chloro-2-(trifluoromethyl)benzyl]-1H-indazol-5-yl}methylidene)-2,4-dioxo-1,3-thiazolidin-3-yl]ethyl}methanesulfonamide |
| 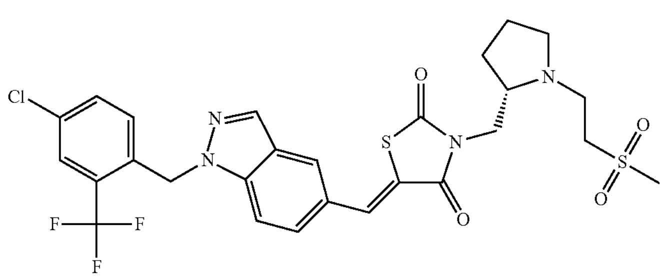 [SMILES: CS(=O)(=O)CCN1CCC[C@H]1CN1C(=O)S/C(=C\c2ccc3c(cnn3Cc3ccc(Cl)cc3C(F)(F)F)c2)C1=O] | 159 | (5Z)-5-({1-[4-Chloro-2-(trifluoromethyl)benzyl]-1H-indazol-5-yl}methylidene)-3-({(2S)-1-[2-(methylsulfonyl)ethyl]pyrrolidin-2-yl}methyl)-1,3-thiazolidine-2,4-dione |

TABLE I-continued

| STRUCTURE | COMPOUND # | NAME |
|---|---|---|
| 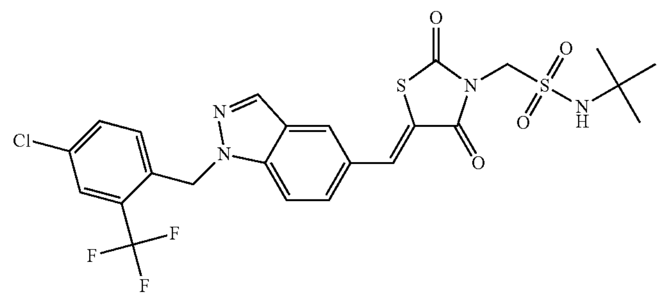 [SMILES: CC(C)(C)NS(=O)(=O)CN1C(=O)S/C(=C\c2ccc3c(cnn3Cc3ccc(Cl)cc3C(F)(F)F)c2)C1=O] | 160 | N-tert-Butyl-1-[(5Z)-5-({1-[4-chloro-2-(trifluoromethyl)benzyl]-1H-indazol-5-yl}methylidene)-2,4-dioxo-1,3-thiazolidin-3-yl]methanesulfonamide |
| 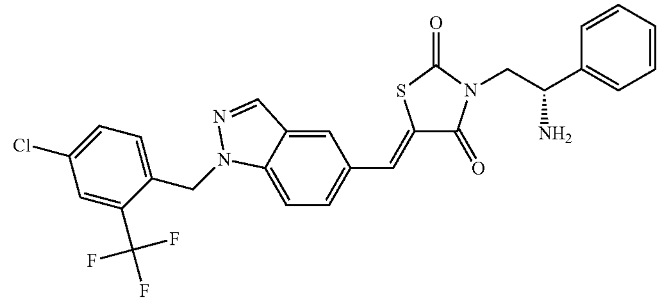 [SMILES: N[C@H](CN1C(=O)S/C(=C\c2ccc3c(cnn3Cc3ccc(Cl)cc3C(F)(F)F)c2)C1=O)c1ccccc1] | 161 | (5Z)-3-[(2S)-2-Amino-2-phenylethyl]-5-({1-[4-chloro-2-(trifluoromethyl)benzyl]-1H-indazol-5-yl}methylidene)-1,3-thiazolidine-2,4-dione |
| 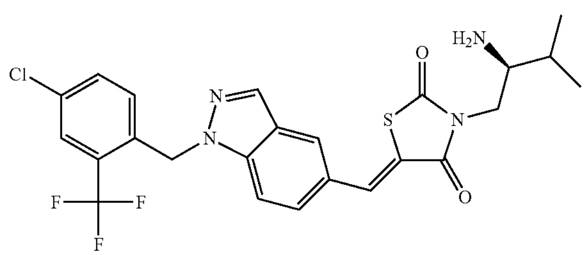 [SMILES: CC(C)[C@H](N)CN1C(=O)S/C(=C\c2ccc3c(cnn3Cc3ccc(Cl)cc3C(F)(F)F)c2)C1=O] | 162 | (5Z)-3-[(2S)-2-Amino-3-methylbutyl]-5-({1-[4-chloro-2-(trifluoromethyl)benzyl]-1H-indazol-5-yl}methylidene)-1,3-thiazolidine-2,4-dione |
| 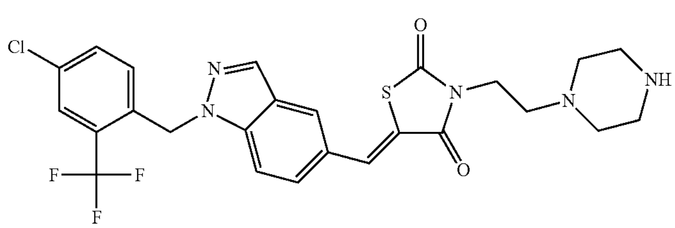 [SMILES: O=C1S/C(=C\c2ccc3c(cnn3Cc3ccc(Cl)cc3C(F)(F)F)c2)C(=O)N1CCN1CCNCC1] | 163 | (5Z)-5-({1-[4-Chloro-2-(trifluoromethyl)benzyl]-1H-indazol-5-yl}methylidene)-3-(2-piperazin-1-ylethyl)-1,3-thiazolidine-2,4-dione |
| 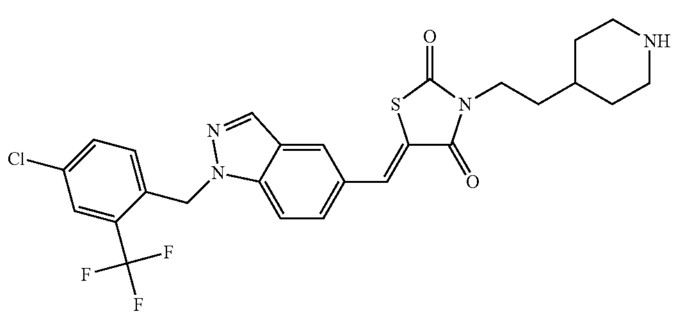 [SMILES: O=C1S/C(=C\c2ccc3c(cnn3Cc3ccc(Cl)cc3C(F)(F)F)c2)C(=O)N1CCC1CCNCC1] | 164 | (5Z)-5-({1-[4-Chloro-2-(trifluoromethyl)benzyl]-1H-indazol-5-yl}methylidene)-3-(2-piperidin-4-ylethyl)-1,3-thiazolidine-2,4-dione |

TABLE I-continued

| STRUCTURE | COMPOUND # | NAME |
|---|---|---|
| 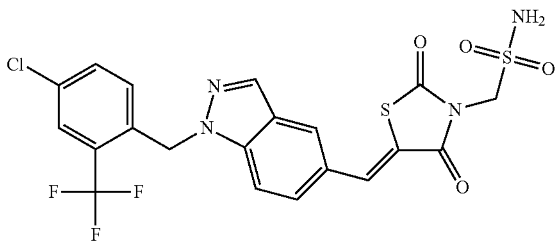 [SMILES: NS(=O)(=O)CN1C(=O)S/C(=C\c2ccc3c(cnn3Cc3ccc(Cl)cc3C(F)(F)F)c2)C1=O] | 165 | 1-[(5Z)-5-({1-[4-Chloro-2-(trifluoromethyl)benzyl]-1H-indazol-5-yl}methylidene)-2,4-dioxo-1,3-thiazolidin-3-yl]methanesulfonamide |
| 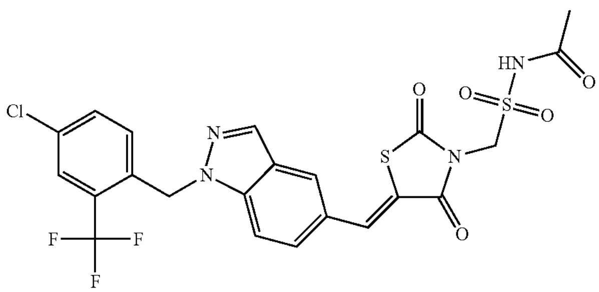 [SMILES: CC(=O)NS(=O)(=O)CN1C(=O)S/C(=C\c2ccc3c(cnn3Cc3ccc(Cl)cc3C(F)(F)F)c2)C1=O] | 166 | N-({[(5Z)-5-({1-[4-Chloro-2-(trifluoromethyl)benzyl]-1H-indazol-5-yl}methylidene)-2,4-dioxo-1,3-thiazolidin-3-yl]methyl}sulfonyl)acetamide |
| 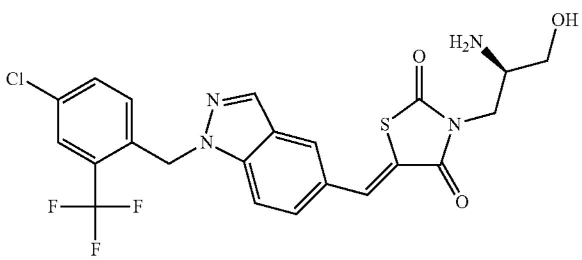 [SMILES: N[C@@H](CO)CN1C(=O)S/C(=C\c2ccc3c(cnn3Cc3ccc(Cl)cc3C(F)(F)F)c2)C1=O] | 167 | (5Z)-3-[(2R)-2-Amino-3-hydroxypropyl]-5-({1-[4-chloro-2-(trifluoromethyl)benzyl]-1H-indazol-5-yl}methylidene)-1,3-thiazolidine-2,4-dione |
| 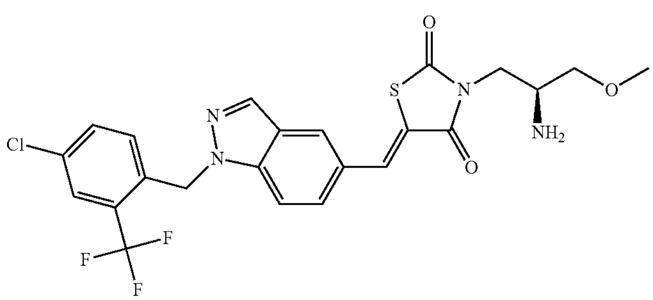 [SMILES: COC[C@@H](N)CN1C(=O)S/C(=C\c2ccc3c(cnn3Cc3ccc(Cl)cc3C(F)(F)F)c2)C1=O] | 168 | (5Z)-3-[(2S)-2-Amino-3-methoxypropyl]-5-({1-[4-chloro-2-(trifluoromethyl)benzyl]-1H-indazol-5-yl}methylidene)-1,3-thiazolidine-2,4-dione |
| 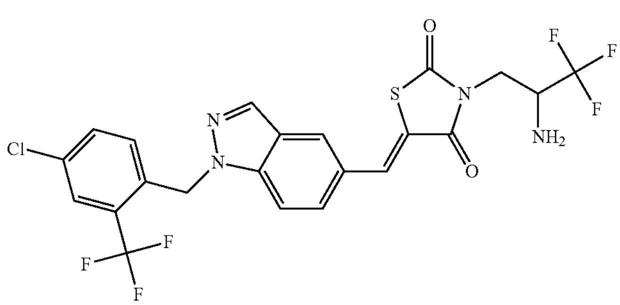 [SMILES: NC(CN1C(=O)S/C(=C\c2ccc3c(cnn3Cc3ccc(Cl)cc3C(F)(F)F)c2)C1=O)C(F)(F)F] | 169 | (5Z)-3-(2-Amino-3,3,3-trifluoropropyl)-5-({1-[4-chloro-2-(trifluoromethyl)benzyl]-1H-indazol-5-yl}methylidene)-1,3-thiazolidine-2,4-dione |

TABLE I-continued

| STRUCTURE | COMPOUND # | NAME |
|---|---|---|
| 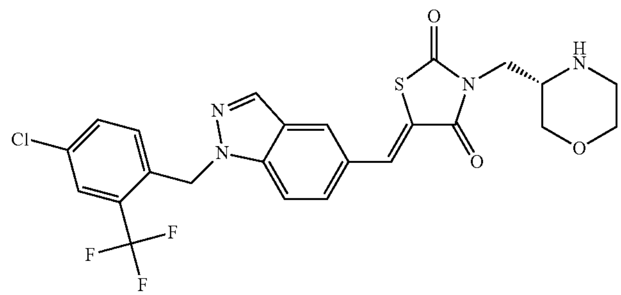 [SMILES: O=C1S/C(=C\c2ccc3c(cnn3Cc3ccc(Cl)cc3C(F)(F)F)c2)C(=O)N1C[C@H]1COCCN1] | 170 | (5Z)-5-({1-[4-Chloro-2-(trifluoromethyl)benzyl]-1H-indazol-5-yl}methylidene)-3-[(3S)-morpholin-3-ylmethyl]-1,3-thiazolidine-2,4-dione |
| 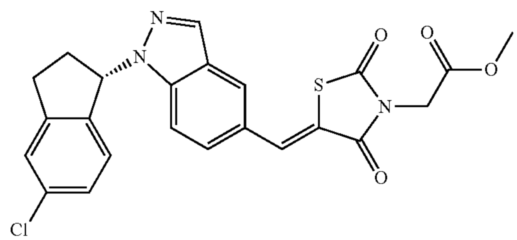 [SMILES: COC(=O)CN1C(=O)S/C(=C\c2ccc3c(cnn3[C@H]3CCc4cc(Cl)ccc43)c2)C1=O] | 171 | Methyl [(5Z)-5-({1-[(1S)-5-chloro-2,3-dihydro-1H-inden-1-yl]-1H-indazol-5-yl}methylidene)-2,4-dioxo-1,3-thiazolidin-3-yl]acetate |
| 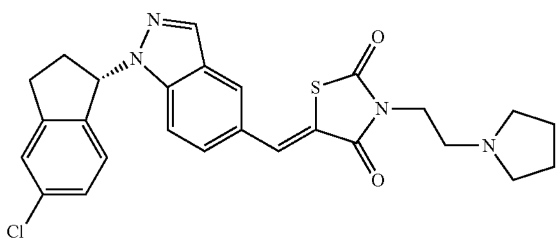 [SMILES: O=C1S/C(=C\c2ccc3c(cnn3[C@H]3CCc4cc(Cl)ccc43)c2)C(=O)N1CCN1CCCC1] | 172 | (5Z)-5-({1-[(1S)-5-Chloro-2,3-dihydro-1H-inden-1-yl]-1H-indazol-5-yl}methylidene)-3-(2-pyrrolidin-1-ylethyl)-1,3-thiazolidine-2,4-dione |
| 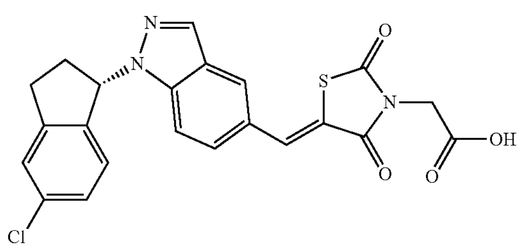 [SMILES: O=C(O)CN1C(=O)S/C(=C\c2ccc3c(cnn3[C@H]3CCc4cc(Cl)ccc43)c2)C1=O] | 173 | [(5Z)-5-({1-[(1S)-5-Chloro-2,3-dihydro-1H-inden-1-yl]-1H-indazol-5-yl}methylidene)-2,4-dioxo-1,3-thiazolidin-3-yl]acetic acid |
| 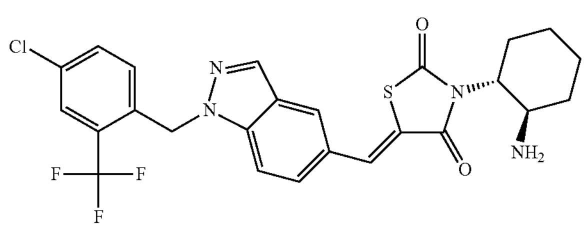 [SMILES: N[C@@H]1CCCC[C@H]1N1C(=O)S/C(=C\c2ccc3c(cnn3Cc3ccc(Cl)cc3C(F)(F)F)c2)C1=O] | 174 | (5Z)-3-[(1R,2R)-2-Aminocyclohexyl]-5-({1-[4-chloro-2-(trifluoromethyl)benzyl]-1H-indazol-5-yl}methylidine)-1,3-thiazolidine-2,4-dione |
| 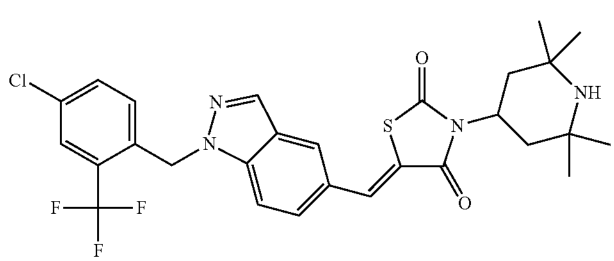 [SMILES: CC1(C)CC(N2C(=O)S/C(=C\c3ccc4c(cnn4Cc4ccc(Cl)cc4C(F)(F)F)c3)C2=O)CC(C)(C)N1] | 175 | (5Z)-5-({1-[4-Chloro-2-(trifluoromethyl)benzyl]-1H-indazol-5-yl}methylidene)-3-(2,2,6,6-tetramethylpiperidin-4-yl)-1,3-thiazolidine-2,4-dione |

| STRUCTURE | COMPOUND # | NAME |
|---|---|---|
| 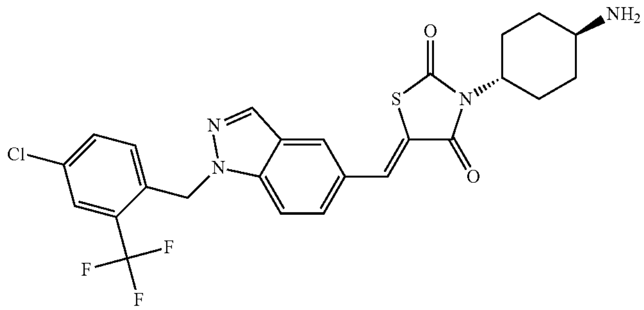 [SMILES: N[C@H]1CC[C@H](N2C(=O)S/C(=C\c3ccc4c(cnn4Cc4ccc(Cl)cc4C(F)(F)F)c3)C2=O)CC1] | 176 | (5Z)-3-(trans-4-Aminocyclohexyl)-5-({1-[4-chloro-2-(trifluoromethyl)benzyl]-1H-indazol-5-yl}methylidene)-1,3-thiazolidine-2,4-dione |
| 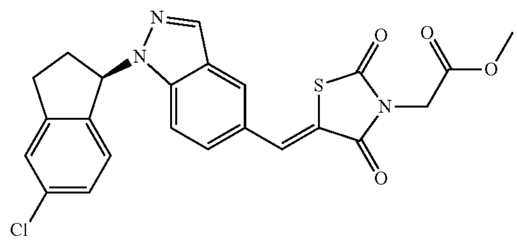 [SMILES: COC(=O)CN1C(=O)S/C(=C\c2ccc3c(cnn3[C@@H]3CCc4cc(Cl)ccc43)c2)C1=O] | 177 | Methyl [(5Z)-5-({1-[(1R)-5-chloro-2,3-dihydro-1H-inden-1-yl]-1H-indazol-5-yl}methylidene)-2,4-dioxo-1,3-thiazolidin-3-yl]acetate |
| 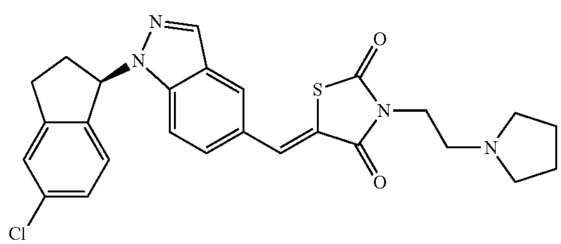 [SMILES: O=C1S/C(=C\c2ccc3c(cnn3[C@@H]3CCc4cc(Cl)ccc43)c2)C(=O)N1CCN1CCCC1] | 178 | (5Z)-5-({1-[(1R)-5-Chloro-2,3-dihydro-1H-inden-1-yl]-1H-indazol-5-yl}methylidene)-3-(2-pyrrolidin-1-ylethyl)-1,3-thiazolidine-2,4-dione |
| 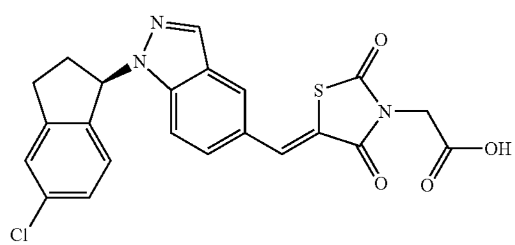 [SMILES: O=C(O)CN1C(=O)S/C(=C\c2ccc3c(cnn3[C@@H]3CCc4cc(Cl)ccc43)c2)C1=O] | 179 | [(5Z)-5-({1-[(1R)-5-Chloro-2,3-dihydro-1H-inden-1-yl]-1H-indazol-5-yl}methylidene)-2,4-dioxo-1,3-thiazolidin-3-yl]acetic acid |
| 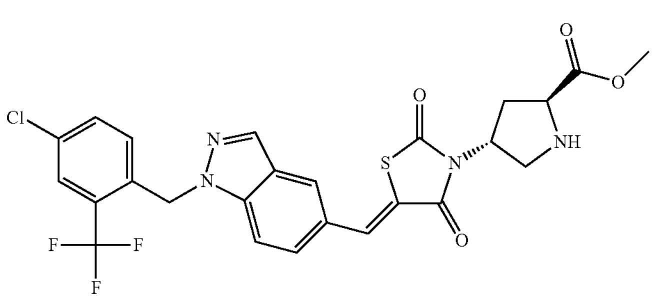 [SMILES: COC(=O)[C@@H]1C[C@@H](N2C(=O)S/C(=C\c3ccc4c(cnn4Cc4ccc(Cl)cc4C(F)(F)F)c3)C2=O)CN1] | 180 | Methyl (4R)-4-[(5Z)-5-({1-[4-chloro-2-(trifluoromethyl)benzyl]-1H-indazol-5-yl}methylidene)-2,4-dioxo-1,3-thiazolidin-3-yl]-L-prolinate |

TABLE I-continued

| STRUCTURE | COMPOUND # | NAME |
|---|---|---|
| 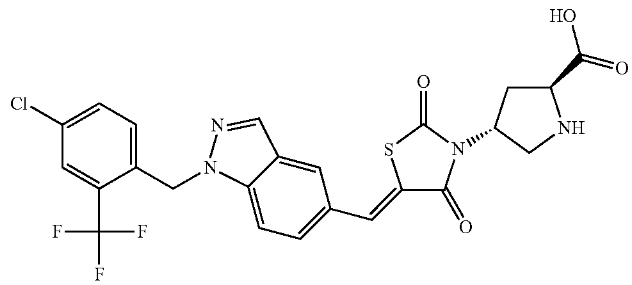 [SMILES: O=C(O)[C@@H]1C[C@@H](N2C(=O)S/C(=C\c3ccc4c(cnn4Cc4ccc(Cl)cc4C(F)(F)F)c3)C2=O)CN1] | 181 | (4R)-4-[(5Z)-5-({1-[4-Chloro-2-(trifluoromethyl)benzyl]-1H-indazol-5-yl}methylidene)-2,4-dioxo-1,3-thiazolidin-3-yl]-L-proline |
| 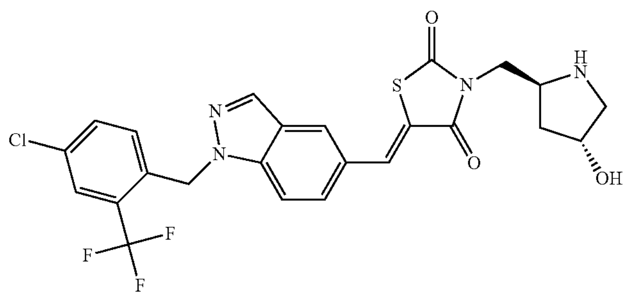 [SMILES: O=C1S/C(=C\c2ccc3c(cnn3Cc3ccc(Cl)cc3C(F)(F)F)c2)C(=O)N1C[C@@H]1C[C@@H](O)CN1] | 182 | (5Z)-5-({1-[4-Chloro-2-(trifluoromethyl)benzyl]-1H-indazol-5-yl}methylidene)-3-{[(2S,4R)-4-hydroxypyrrolidin-2-yl]methyl}-1,3-thiazolidine-2,4-dione |
| 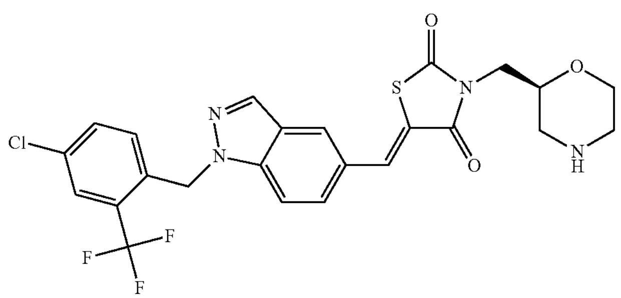 [SMILES: O=C1S/C(=C\c2ccc3c(cnn3Cc3ccc(Cl)cc3C(F)(F)F)c2)C(=O)N1C[C@@H]1CNCCO1] | 183 | (5Z)-5-({1-[4-Chloro-2-(trifluoromethyl)benzyl]-1H-indazol-5-yl}methylidine)-3-[(2S)-morpholin-2-ylmethyl]-1,3-thiazolidine-2,4-dione |
| 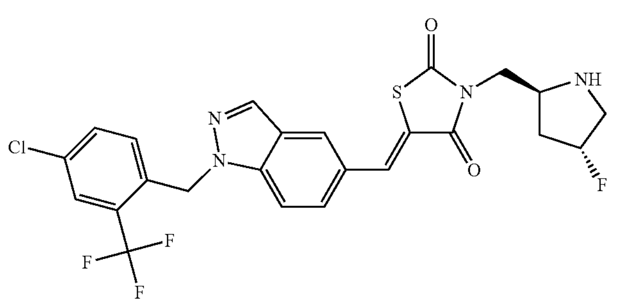 [SMILES: O=C1S/C(=C\c2ccc3c(cnn3Cc3ccc(Cl)cc3C(F)(F)F)c2)C(=O)N1C[C@@H]1C[C@@H](F)CN1] | 184 | (5Z)-5-({1-[4-Chloro-2-(trifluoromethyl)benzyl]-1H-indazol-5-yl}methylidene)-3-{[(2S,4R)-4-fluoropyrrolidin-2-yl]methyl}-1,3-thiazolidine-2,4-dione |
| 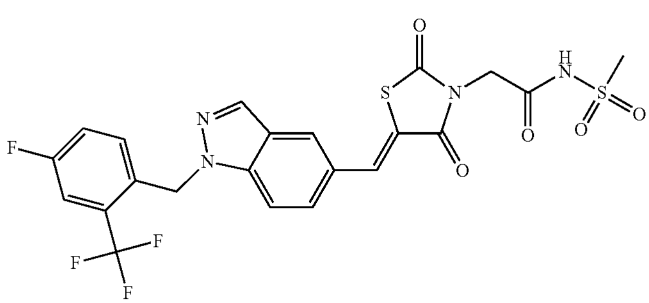 [SMILES: CS(=O)(=O)NC(=O)CN1C(=O)S/C(=C\c2ccc3c(cnn3Cc3ccc(F)cc3C(F)(F)F)c2)C1=O] | 185 | 2-[(5Z)-5-({1-[4-Fluoro-2-(trifluoromethyl)benzyl]-1H-indazol-5-yl}methylidene)-2,4-dioxo-1,3-thiazolidin-3-yl]-N-(methylsulfonyl)acetamide |

TABLE I-continued

| STRUCTURE | COMPOUND # | NAME |
|---|---|---|
| 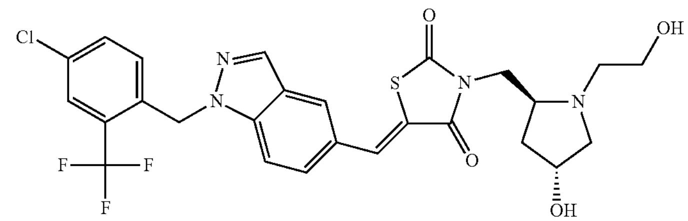 [SMILES: O=C1S/C(=C\c2ccc3c(cnn3Cc3ccc(Cl)cc3C(F)(F)F)c2)C(=O)N1C[C@@H]1C[C@@H](O)CN1CCO] | 186 | (5Z)-5-({1-[4-Chloro-2-(trifluoromethyl)benzyl]-1H-indazol-5-yl}methylidene)-3-{[(2S,4R)-4-hydroxy-1-(2-hydroxyethyl)pyrrolidin-2-yl]methyl}-1,3-thiazolidine-2,4-dione |
| 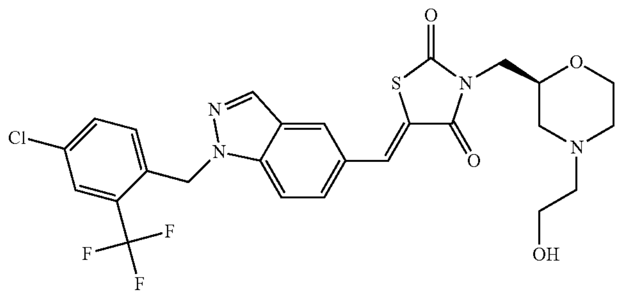 [SMILES: O=C1S/C(=C\c2ccc3c(cnn3Cc3ccc(Cl)cc3C(F)(F)F)c2)C(=O)N1C[C@@H]1CN(CCO)CCO1] | 187 | (5Z)-5-({1-[4-Chloro-2-(trifluoromethyl)benzyl]-1H-indazol-5-yl}methylidene)-3-{[(2S)-4-(2-hydroxyethyl)morpholin-2-yl]methyl}-1,3-thiazolidine-2,4-dione |
| 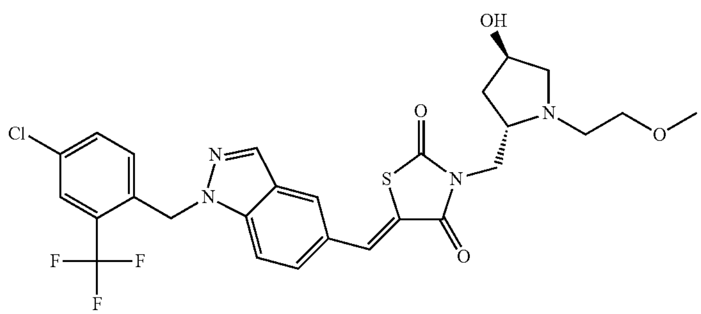 [SMILES: COCCN1C[C@H](O)C[C@H]1CN1C(=O)S/C(=C\c2ccc3c(cnn3Cc3ccc(Cl)cc3C(F)(F)F)c2)C1=O] | 188 | (5Z)-5-({1-[4-Chloro-2-(trifluoromethyl)benzyl]-1H-indazol-5-yl}methylidene)-3-{[(2S,4R)-4-hydroxy-1-(2-methoxyethyl)pyrrolidin-2-yl]methyl}-1,3-thiazolidine-2,4-dione |
| 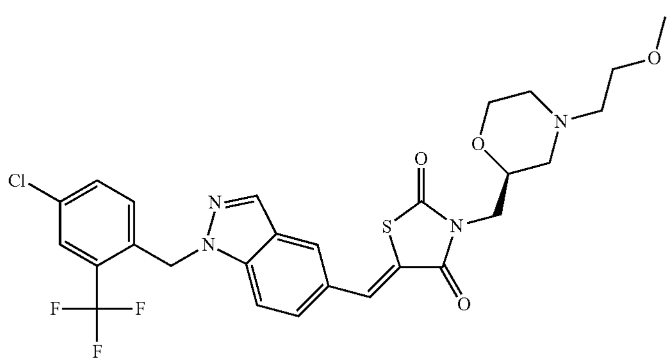 [SMILES: COCCN1CCO[C@H](CN2C(=O)S/C(=C\c3ccc4c(cnn4Cc4ccc(Cl)cc4C(F)(F)F)c3)C2=O)C1] | 189 | (5Z)-5-({1-[4-Chloro-2-(trifluoromethyl)benzyl]-1H-indazol-5-yl}methylidene)-3-{[(2S)-4-(2-methoxyethyl)morpholin-2-yl]methyl}-1,3-thiazolidine-2,4-dione |
| 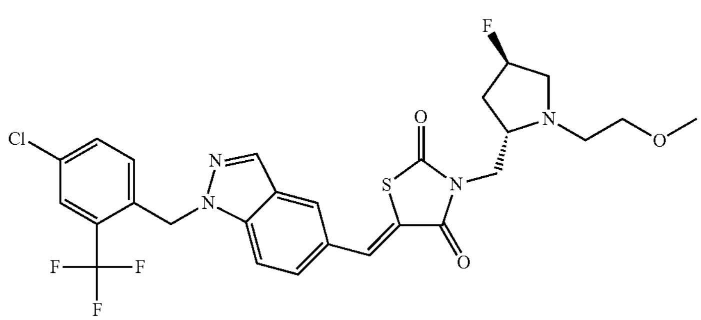 [SMILES: COCCN1C[C@H](F)C[C@H]1CN1C(=O)S/C(=C\c2ccc3c(cnn3Cc3ccc(Cl)cc3C(F)(F)F)c2)C1=O] | 190 | (5Z)-5-({1-[4-Chloro-2-(trifluoromethyl)benzyl]-1H-indazol-5-yl}methylidene)-3-{[(2S,4R)-4-fluoro-1-(2-methoxyethyl)pyrrolidin-2-yl]methyl}-1,3-thiazolidine-2,4-dione |

TABLE I-continued

| STRUCTURE | COMPOUND # | NAME |
|---|---|---|
| 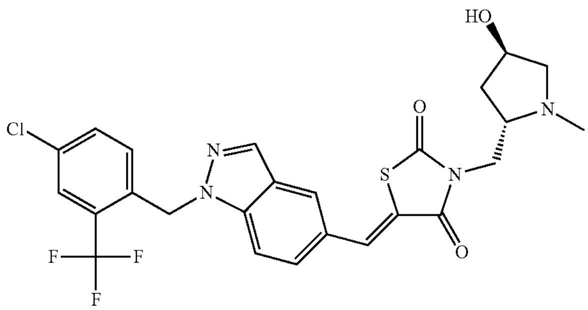 [SMILES: CN1C[C@H](O)C[C@H]1CN1C(=O)S/C(=C\c2ccc3c(cnn3Cc3ccc(Cl)cc3C(F)(F)F)c2)C1=O] | 191 | (5Z)-5-({1-[4-Chloro-2-(trifluoromethyl)benzyl]-1H-indazol-5-yl}methylidene)-3-{[(2S,4R)-4-hydroxy-1-methylpyrrolidin-2-yl]methyl}-1,3-thiazolidine-2,4-dione |
| 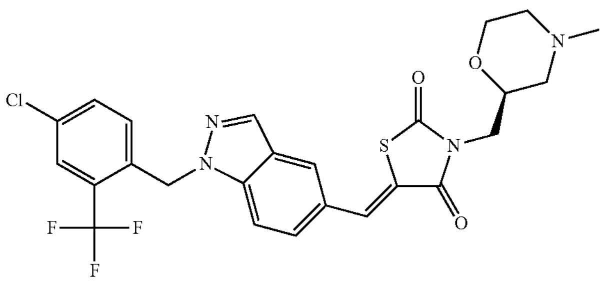 [SMILES: CN1CCO[C@H](CN2C(=O)S/C(=C\c3ccc4c(cnn4Cc4ccc(Cl)cc4C(F)(F)F)c3)C2=O)C1] | 192 | (5Z)-5-({1-[4-Chloro-2-(trifluoromethyl)benzyl]-1H-indazol-5-yl}methylidene)-3-{[(2S)-4-methylmorpholin-2-yl]methyl}-1,3-thiazolidine-2,4-dione |
| 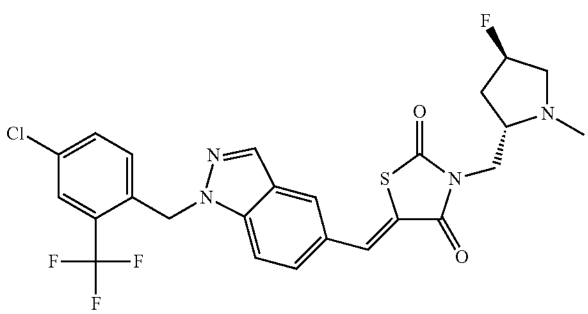 [SMILES: CN1C[C@H](F)C[C@H]1CN1C(=O)S/C(=C\c2ccc3c(cnn3Cc3ccc(Cl)cc3C(F)(F)F)c2)C1=O] | 193 | (5Z)-5-({1-[4-Chloro-2-(trifluoromethyl)benzyl]-1H-indazol-5-yl}methylidene)-3-{[(2S,4R)-4-fluoro-1-methylpyrrolidin-2-yl]methyl}-1,3-thiazolidine-2,4-dione |
| 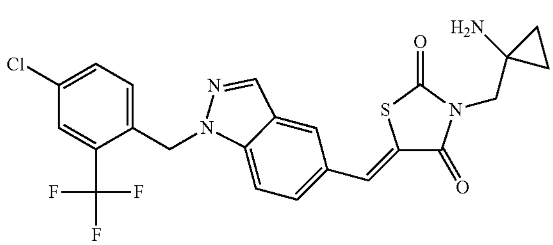 [SMILES: NC1(CN2C(=O)S/C(=C\c3ccc4c(cnn4Cc4ccc(Cl)cc4C(F)(F)F)c3)C2=O)CC1] | 194 | (5Z)-3-[(1-Aminocyclopropyl)methyl]-5-({1-[4-chloro-2-(trifluoromethyl)benzyl]-1H-indazol-5-yl}methylidene)-1,3-thiazolidine-2,4-dione |
| 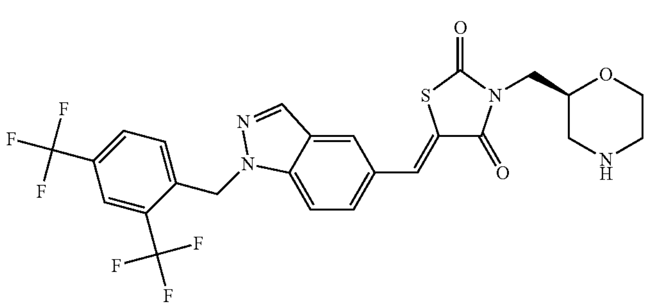 [SMILES: O=C1S/C(=C\c2ccc3c(cnn3Cc3ccc(C(F)(F)F)cc3C(F)(F)F)c2)C(=O)N1C[C@@H]1CNCCO1] | 195 | (5Z)-5-({1-[2,4-Bis(trifluoromethyl)benzyl]-1H-indazol-5-yl}methylidene)-3-[(2S)-morpholin-2-ylmethyl]-1,3-thiazolidine-2,4-dione |

TABLE I-continued

| STRUCTURE | COMPOUND # | NAME |
|---|---|---|
| 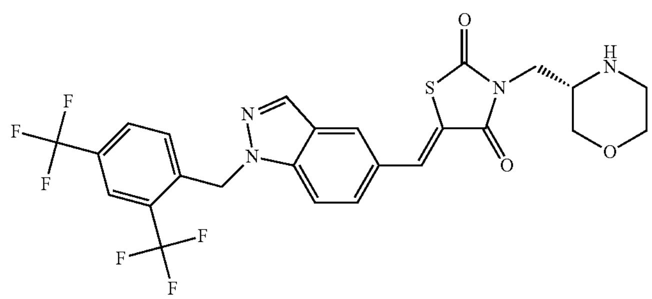 [SMILES: O=C1S/C(=C\c2ccc3c(cnn3Cc3ccc(C(F)(F)F)cc3C(F)(F)F)c2)C(=O)N1C[C@H]1COCCN1] | 196 | (5Z)-5-({1-[2,4-Bis(trifluoromethyl)benzyl]-1H-indazol-5-yl}methylidene)-3-[(3S)-morpholin-3-ylmethyl]-1,3-thiazolidine-2,4-dione |
| 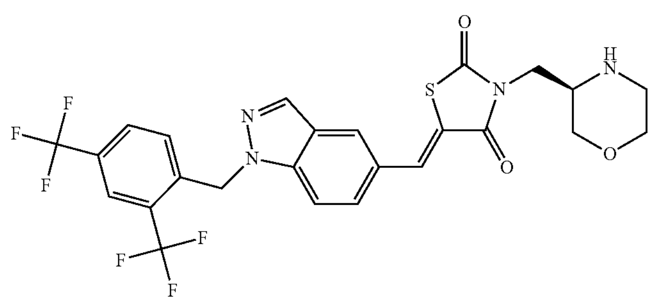 [SMILES: O=C1S/C(=C\c2ccc3c(cnn3Cc3ccc(C(F)(F)F)cc3C(F)(F)F)c2)C(=O)N1C[C@@H]1COCCN1] | 197 | (5Z)-5-({1-[2,4-Bis(trifluoromethyl)benzyl]-1H-indazol-5-yl}methylidene)-3-[(3R)-morpholin-3-ylmethyl]-1,3-thiazolidine-2,4-dione |
| 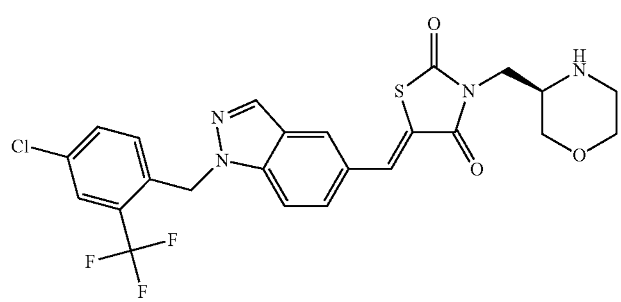 [SMILES: O=C1S/C(=C\c2ccc3c(cnn3Cc3ccc(Cl)cc3C(F)(F)F)c2)C(=O)N1C[C@@H]1COCCN1] | 198 | (5Z)-5-({1-[4-Chloro-2-(trifluoromethyl)benzyl]-1H-indazol-5-yl}methylidene)-3-[(3R)-morpholin-3-ylmethyl]-1,3-thiazolidine-2,4-dione |
| 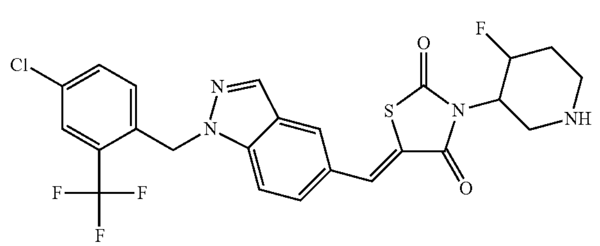 [SMILES: O=C1S/C(=C\c2ccc3c(cnn3Cc3ccc(Cl)cc3C(F)(F)F)c2)C(=O)N1C1CNCCC1F] | 199 | (5Z)-5-({1-[4-Chloro-2-(trifluoromethyl)benzyl]-1H-indazol-5-yl}methylidene)-3-(cis-4-fluoropiperidin-3-yl)-1,3-thiazolidine-2,4-dione |
| 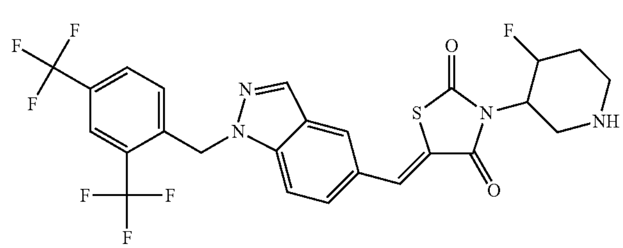 [SMILES: O=C1S/C(=C\c2ccc3c(cnn3Cc3ccc(C(F)(F)F)cc3C(F)(F)F)c2)C(=O)N1C1CNCCC1F] | 200 | (5Z)-5-({1-[2,4-Bis(trifluoromethyl)benzyl]-1H-indazol-5-yl}methylidene)-3-(cis-4-fluoropiperidin-3-yl)-1,3-thiazolidine-2,4-dione |

TABLE I-continued

| STRUCTURE | COMPOUND # | NAME |
|---|---|---|
| 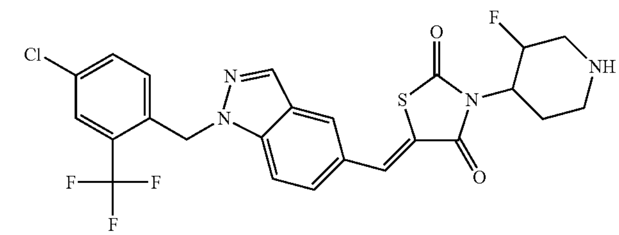 [SMILES: O=C1S/C(=C\c2ccc3c(cnn3Cc3ccc(Cl)cc3C(F)(F)F)c2)C(=O)N1C1CCNCC1F] | 201 | (5Z)-5-({1-[4-Chloro-2-(trifluoromethyl)benzyl]-1H-indazol-5-yl}methylidene)-3-(cis-3-fluoropiperidin-4-yl)-1,3-thiazolidine-2,4-dione |
| 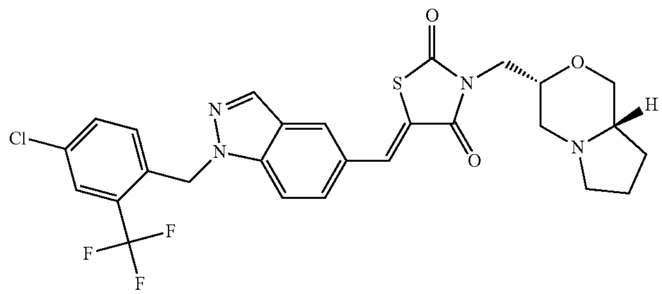 [SMILES: O=C1S/C(=C\c2ccc3c(cnn3Cc3ccc(Cl)cc3C(F)(F)F)c2)C(=O)N1C[C@H]1CN2CCC[C@H]2CO1] | 202 | (5Z)-5-({1-[4-Chloro-2-(trifluoromethyl)benzyl]-1H-indazol-5-yl}methylidene)-3-[(3R,8aS)-hexahydro-1H-pyrrolo[2,1-c][1,4]oxazin-3-ylmethyl]-1,3-thiazolidine-2,4-dione |
| 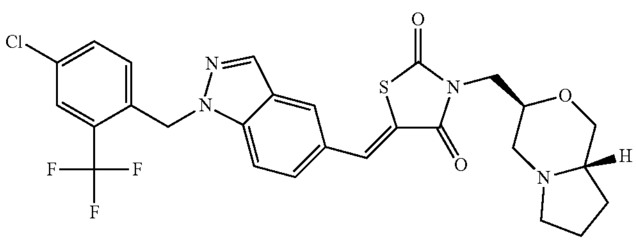 [SMILES: O=C1S/C(=C\c2ccc3c(cnn3Cc3ccc(Cl)cc3C(F)(F)F)c2)C(=O)N1C[C@@H]1CN2CCC[C@H]2CO1] | 203 | (5Z)-5-({1-[4-Chloro-2-(trifluoromethyl)benzyl]-1H-indazol-5-yl}methylidene)-3-[(3S,8aS)-hexahydro-1H-pyrrolo[2,1-c][1,4]oxazin-3-ylmethyl]-1,3-thiazolidine-2,4-dione |
| 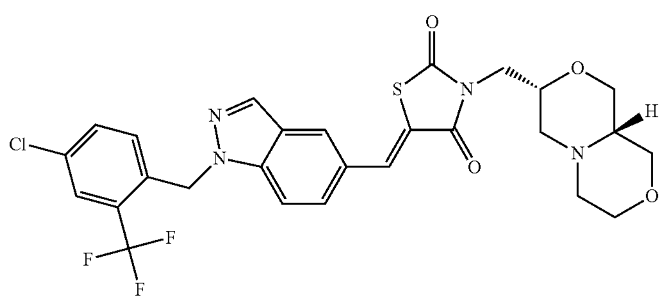 [SMILES: O=C1S/C(=C\c2ccc3c(cnn3Cc3ccc(Cl)cc3C(F)(F)F)c2)C(=O)N1C[C@H]1CN2CCOC[C@H]2CO1] | 204 | (5Z)-5-({1-[4-Chloro-2-(trifluoromethyl)benzyl]-1H-indazol-5-yl}methylidene)-3-[(3R,9aS)-hexahydro-1H-[1,4]oxazino[3,4-c][1,4]oxazin-3-ylmethyl]-1,3-thiazolidine-2,4-dione |
| 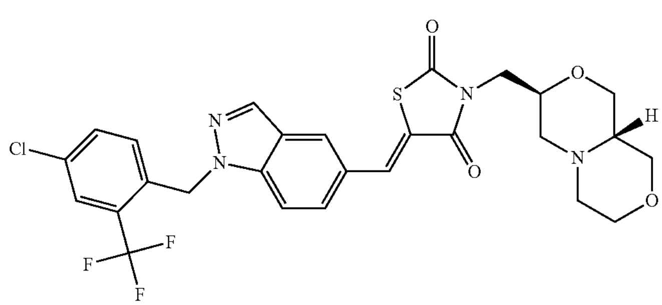 [SMILES: O=C1S/C(=C\c2ccc3c(cnn3Cc3ccc(Cl)cc3C(F)(F)F)c2)C(=O)N1C[C@@H]1CN2CCOC[C@H]2CO1] | 205 | (5Z)-5-({1-[4-Chloro-2-(trifluoromethyl)benzyl]-1H-indazol-5-yl}methylidene)-3-[(3S,9aS)-hexahydro-1H-[1,4]oxazino[3,4-c][1,4]oxazin-3-ylmethyl]-1,3-thiazolidine-2,4-dione |

TABLE I-continued

| STRUCTURE | COMPOUND # | NAME |
|---|---|---|
| 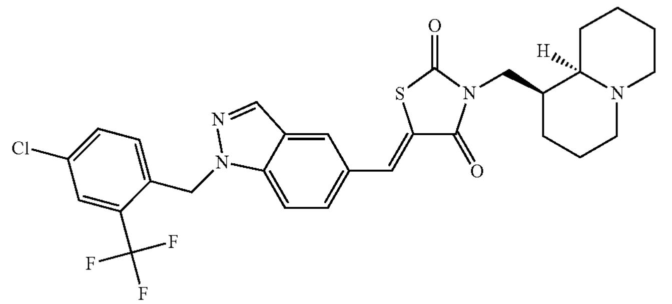 [SMILES: O=C1S/C(=C\c2ccc3c(cnn3Cc3ccc(Cl)cc3C(F)(F)F)c2)C(=O)N1C[C@@H]1CCCN2CCCC[C@H]12] | 206 | (5Z)-5-({1-[4-Chloro-2-(trifluoromethyl)benzyl]-1H-indazol-5-yl}methylidene)-3-[(1S,9aR)-octahydro-2H-quinolizin-1-ylmethyl]-1,3-thiazolidine-2,4-dione |
| 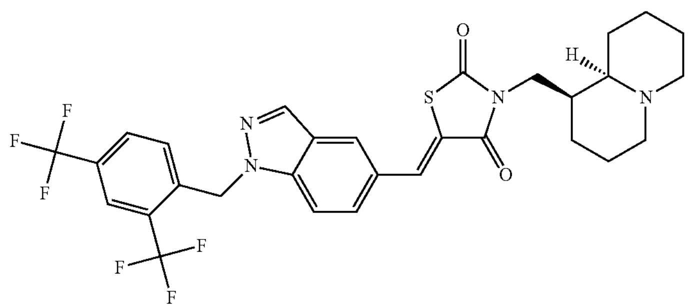 [SMILES: O=C1S/C(=C\c2ccc3c(cnn3Cc3ccc(C(F)(F)F)cc3C(F)(F)F)c2)C(=O)N1C[C@@H]1CCCN2CCCC[C@H]12] | 207 | (5Z)-5-({1-[2,4-Bis(trifluoromethyl)benzyl]-1H-indazol-5-yl}methylidene)-3-[(1S,9aR)-octahydro-2H-quinolizin-1-ylmethyl]-1,3-thiazolidine-2,4-dione |
| 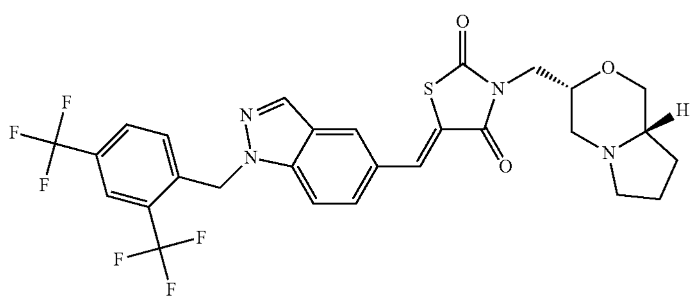 [SMILES: O=C1S/C(=C\c2ccc3c(cnn3Cc3ccc(C(F)(F)F)cc3C(F)(F)F)c2)C(=O)N1C[C@H]1CN2CCC[C@H]2CO1] | 208 | (5Z)-5-({1-[2,4-Bis(trifluoromethyl)benzyl]-1H-indazol-5-yl}methylidene)-3-[(3R,8aS)-hexahydro-1H-pyrrolo[2,1-c][1,4]oxazin-3-ylmethyl]-1,3-thiazolidine-2,4-dione |
| 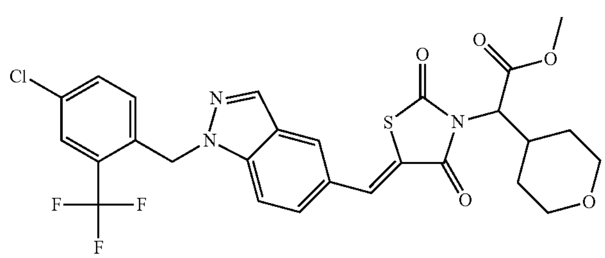 [SMILES: COC(=O)C(C1CCOCC1)N1C(=O)S/C(=C\c2ccc3c(cnn3Cc3ccc(Cl)cc3C(F)(F)F)c2)C1=O] | 209 | Methyl [(5Z)-5-({1-[4-chloro-2-(trifluoromethyl)benzyl]-1H-indazol-5-yl}methylidene)-2,4-dioxo-1,3-thiazolidin-3-yl](tetrahydro-2H-pyran-4-yl)acetate |
| 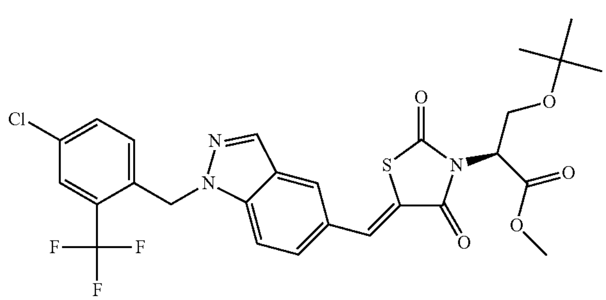 [SMILES: COC(=O)[C@H](COC(C)(C)C)N1C(=O)S/C(=C\c2ccc3c(cnn3Cc3ccc(Cl)cc3C(F)(F)F)c2)C1=O] | 210 | Methyl (2S)-3-tert-butoxy-2-[(5Z)-5-({1-[4-chloro-2-(trifluoromethyl)benzyl]-1H-indazol-5-yl}methylidene)-2,4-dioxo-1,3-thiazolidin-3-yl]propanoate |

TABLE I-continued

| STRUCTURE | COMPOUND # | NAME |
|---|---|---|
| 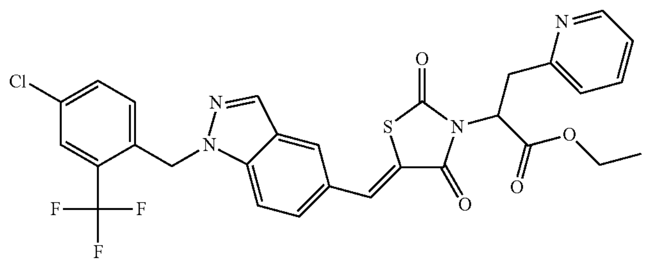 [SMILES: CCOC(=O)C(Cc1ccccn1)N1C(=O)S/C(=C\c2ccc3c(cnn3Cc3ccc(Cl)cc3C(F)(F)F)c2)C1=O] | 211 | Ethyl 2-[(5Z)-5-({1-[4-chloro-2-(trifluoromethyl)benzyl]-1H-indazol-5-yl}methylidene)-2,4-dioxo-1,3-thiazolidin-3-yl]-3-pyridin-2-ylpropanoate |
| 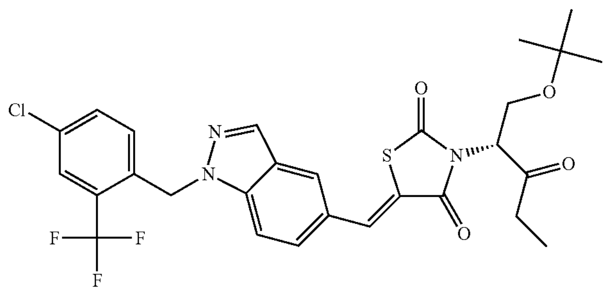 [SMILES: CCC(=O)[C@@H](COC(C)(C)C)N1C(=O)S/C(=C\c2ccc3c(cnn3Cc3ccc(Cl)cc3C(F)(F)F)c2)C1=O] | 212 | Methyl (2R)-3-tert-butoxy-2-[(5Z)-5-({1-[4-chloro-2-(trifluoromethyl)benzyl]-1H-indazol-5-yl}methylidene)-2,4-dioxo-1,3-thiazolidin-3-yl]propanoate |
| 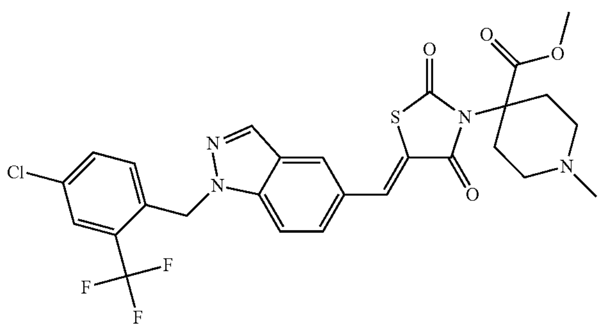 [SMILES: COC(=O)C1(N2C(=O)S/C(=C\c3ccc4c(cnn4Cc4ccc(Cl)cc4C(F)(F)F)c3)C2=O)CCN(C)CC1] | 213 | Methyl 4-[(5Z)-5-({1-[4-chloro-2-(trifluoromethyl)benzyl]-1H-indazol-5-yl}methylidene)-2,4-dioxo-1,3-thiazolidin-3-yl]-1-methylpiperidine-4-carboxylate |
| 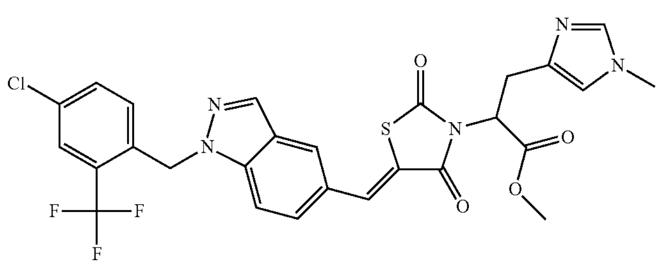 [SMILES: COC(=O)C(Cc1cn(C)cn1)N1C(=O)S/C(=C\c2ccc3c(cnn3Cc3ccc(Cl)cc3C(F)(F)F)c2)C1=O] | 214 | Methyl 2-[(5Z)-5-({1-[4-chloro-2-(trifluoromethyl)benzyl]-1H-indazol-5-yl}methylidene)-2,4-dioxo-1,3-thiazolidin-3-yl]-3-(1-methyl-1H-imidazol-4-yl)propanoate |
| 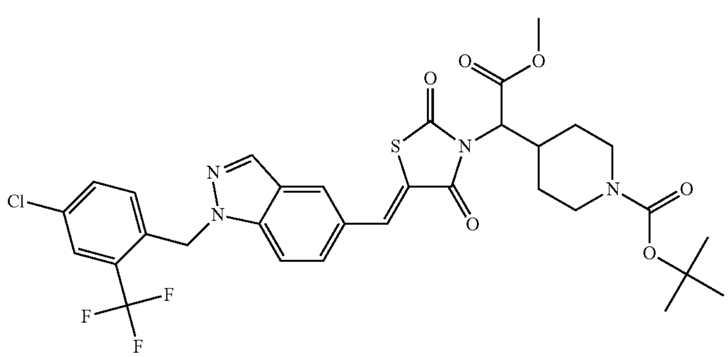 [SMILES: COC(=O)C(C1CCN(C(=O)OC(C)(C)C)CC1)N1C(=O)S/C(=C\c2ccc3c(cnn3Cc3ccc(Cl)cc3C(F)(F)F)c2)C1=O] | 215 | tert-Butyl 4-{1-[(5Z)-5-({1-[4-chloro-2-(trifluoromethyl)benzyl]-1H-indazol-5-yl}methylidene)-2,4-dioxo-1,3-thiazolidin-3-yl]-2-methoxy-2-oxoethyl}piperidine-1-carboxylate |

TABLE I-continued

| STRUCTURE | COMPOUND # | NAME |
|---|---|---|
| 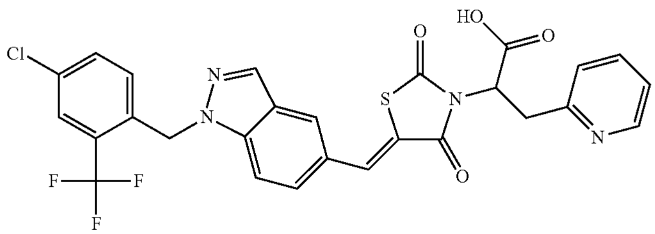 [SMILES: O=C(O)C(Cc1ccccn1)N1C(=O)S/C(=C\c2ccc3c(cnn3Cc3ccc(Cl)cc3C(F)(F)F)c2)C1=O] | 216 | 2-[(5Z)-5-({1-[4-Chloro-2-(trifluoromethyl)benzyl]-1H-indazol-5-yl}methylidene)-2,4-dioxo-1,3-thiazolidin-3-yl]-3-pyridin-2-ylpropanoic acid |
| 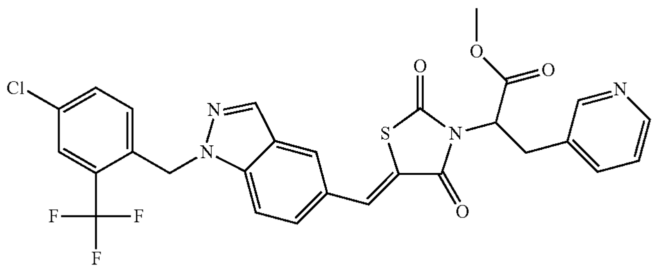 [SMILES: COC(=O)C(Cc1cccnc1)N1C(=O)S/C(=C\c2ccc3c(cnn3Cc3ccc(Cl)cc3C(F)(F)F)c2)C1=O] | 217 | Methyl 2-[(5Z)-5-({1-[4-chloro-2-(trifluoromethyl)benzyl]-1H-indazol-5-yl}methylidene)-2,4-dioxo-1,3-thiazilidin-3-yl]-3-pyridin-3-ylpropanoate |
| 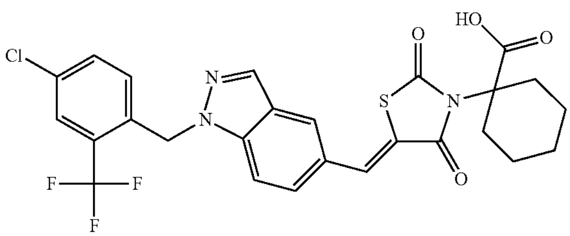 [SMILES: O=C1S/C(=C\c2ccc3c(cnn3Cc3ccc(Cl)cc3C(F)(F)F)c2)C(=O)N1C1(C(=O)O)CCCCC1] | 218 | 1-[(5Z)-5-({1-[4-Chloro-2-(trifluoromethyl)benzyl]-1H-indazol-5-yl}methylidene)-2,4-dioxo-1,3-thiazolidin-3-yl]cyclohexanecarboxylic acid |
| 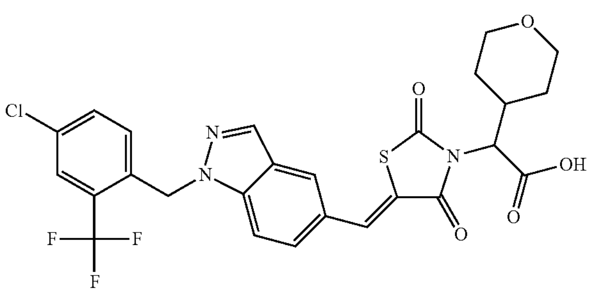 [SMILES: O=C(O)C(C1CCOCC1)N1C(=O)S/C(=C\c2ccc3c(cnn3Cc3ccc(Cl)cc3C(F)(F)F)c2)C1=O] | 219 | [(5Z)-5-({1-[4-Chloro-2-(trifluoromethyl)benzyl]-1H-indazol-5-yl}methylidene)-2,4-dioxo-1,3-thiazolidin-3-yl](tetrahydro-2H-pyran-4-yl)acetic acid |
| 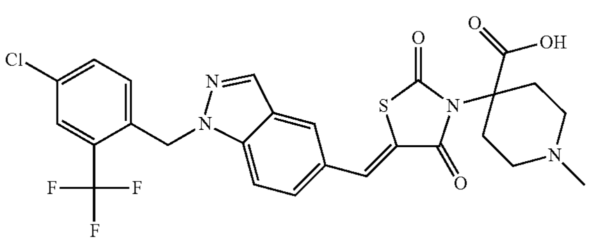 [SMILES: CN1CCC(C(=O)O)(N2C(=O)S/C(=C\c3ccc4c(cnn4Cc4ccc(Cl)cc4C(F)(F)F)c3)C2=O)CC1] | 220 | 4-[(5Z)-5-({1-[4-Chloro-2-(trifluoromethyl)benzyl]-1H-indazol-5-yl}methylidene)-2,4-dioxo-1,3-thiazolidin-3-yl]-1-methylpiperidine-4-carboxylic acid |
| 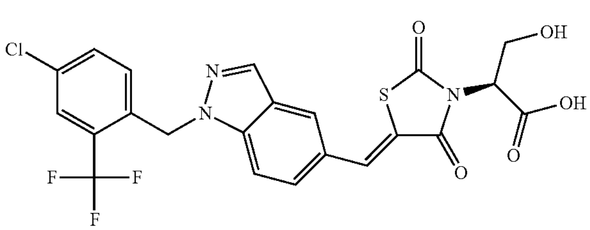 [SMILES: O=C(O)[C@H](CO)N1C(=O)S/C(=C\c2ccc3c(cnn3Cc3ccc(Cl)cc3C(F)(F)F)c2)C1=O] | 221 | (2S)-2-[(5Z)-5-({1-[4-Chloro-2-(trifluoromethyl)benzyl]-1H-indazol-5-yl}methylidene)-2,4-dioxo-1,3-thiazolidin-3-yl]-3-hydroxypropanoic acid |

TABLE I-continued

| STRUCTURE | COMPOUND # | NAME |
|---|---|---|
| 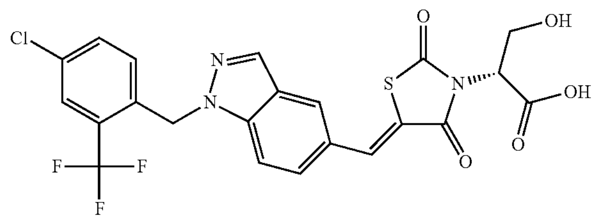 [SMILES: O=C(O)[C@@H](CO)N1C(=O)S/C(=C\c2ccc3c(cnn3Cc3ccc(Cl)cc3C(F)(F)F)c2)C1=O] | 222 | (2R)-2-[(5Z)-5-({1-[4-Chloro-2-(trifluoromethyl)benzyl]-1H-indazol-5-yl}methylidene)-2,4-dioxo-1,3-thiazolidin-3-yl]-3-hydroxypropanoic acid |
| 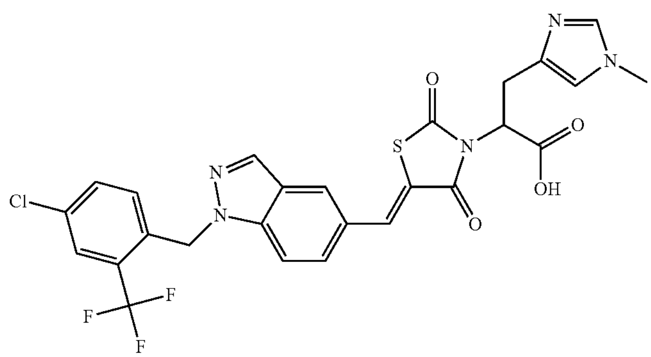 [SMILES: Cn1cnc(CC(C(=O)O)N2C(=O)S/C(=C\c3ccc4c(cnn4Cc4ccc(Cl)cc4C(F)(F)F)c3)C2=O)c1] | 223 | 2-[(5Z)-5-({1-[4-Chloro-2-(trifluoromethyl)benzyl]-1H-indazol-5-yl}methylidene)-2,4-dioxo-1,3-thiazolidin-3-yl]-3-(1-methyl-1H-imidazol-4-yl)propanoicacid |
| 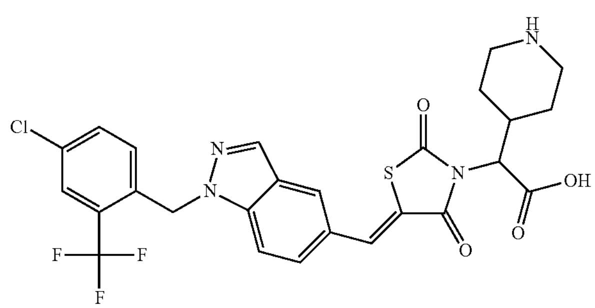 [SMILES: O=C(O)C(C1CCNCC1)N1C(=O)S/C(=C\c2ccc3c(cnn3Cc3ccc(Cl)cc3C(F)(F)F)c2)C1=O] | 224 | [(5Z)-5-({1-[4-Chloro-2-(trifluoromethyl)benzyl]-1H-indazol-5-yl}methylidene)-2,4-dioxo-1,3-thiazolidin-3-yl](piperidin-4-yl)acetic acid |
| 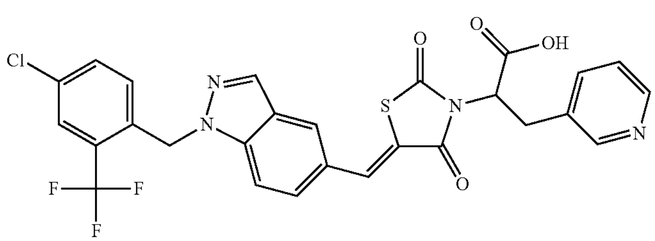 [SMILES: O=C(O)C(Cc1cccnc1)N1C(=O)S/C(=C\c2ccc3c(cnn3Cc3ccc(Cl)cc3C(F)(F)F)c2)C1=O] | 225 | 2-[(5Z)-5-({1-[4-Chloro-2-(trifluoromethyl)benzyl]-1H-indazol-5-yl}methylidene)-2,4-dioxo-1,3-thiazolidin-3-yl]-3-pyridin-3-ylpropanoic acid |
| 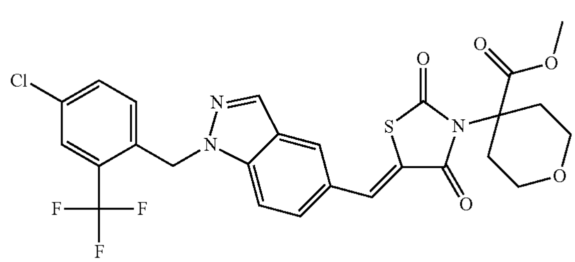 [SMILES: COC(=O)C1(N2C(=O)S/C(=C\c3ccc4c(cnn4Cc4ccc(Cl)cc4C(F)(F)F)c3)C2=O)CCOCC1] | 226 | Methyl 4-[(5Z)-5-({1-[4-chloro-2-(trifluoromethyl)benzyl]-1H-indazol-5-yl}methylidene)-2,4-dioxo-1,3-thiazolidin-3-yl]tetrahydro-2H-pyran-4-carboxylate |

TABLE I-continued

| STRUCTURE | COMPOUND # | NAME |
|---|---|---|
| 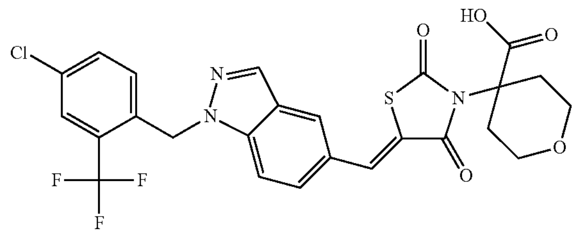 | 227 | 4-[(5Z)-5-({1-[4-Chloro-2-(trifluoromethyl)benzyl]-1H-indazol-5-yl}methylidene)-2,4-dioxo-1,3-thiazolidin-3-yl]tetrahydro-2H-pyran-4-carboxylic acid |
| 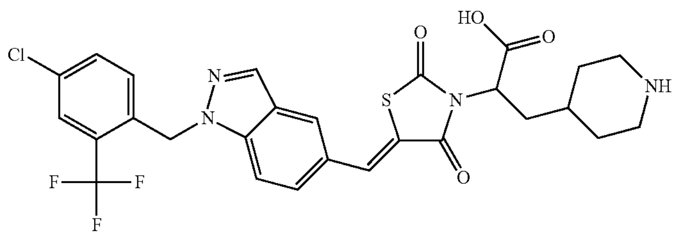 [SMILES: O=C(O)C(CC1CCNCC1)N1C(=O)S/C(=C\c2ccc3c(cnn3Cc3ccc(Cl)cc3C(F)(F)F)c2)C1=O] | 228 | 2-[(5Z)-5-({1-[4-Chloro-2-(trifluoromethyl)benzyl]-1H-indazol-5-yl}methylidene)-2,4-dioxo-1,3-thiazolidin-3-yl]-3-piperidin-4-ylpropanoic acid |
| 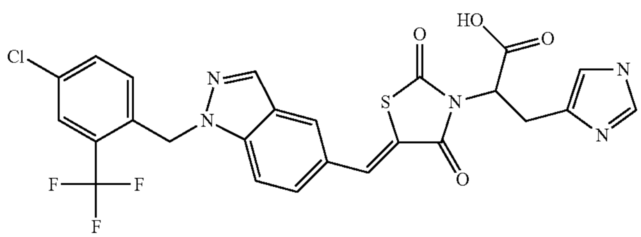 [SMILES: O=C(O)C(Cc1c[nH]cn1)N1C(=O)S/C(=C\c2ccc3c(cnn3Cc3ccc(Cl)cc3C(F)(F)F)c2)C1=O] | 229 | 2-[(5Z)-5-({1-[4-Chloro-2-(trifluoromethyl)benzyl]-1H-indazol-5-yl}methylidene)-2,4-dioxo-1,3-thiazolidin-3-yl]-3-(1H-imidazol-4-yl)propanoic acid |
| 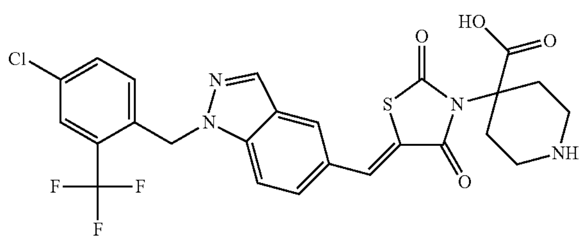 [SMILES: O=C1S/C(=C\c2ccc3c(cnn3Cc3ccc(Cl)cc3C(F)(F)F)c2)C(=O)N1C1(C(=O)O)CCNCC1] | 230 | 4-[(5Z)-5-({1-[4-Chloro-2-(trifluoromethyl)benzyl]-1H-indazol-5-yl}methylidene)-2,4-dioxo-1,3-thiazolidin-3-yl]piperidine-4-carboxylic acid |
| 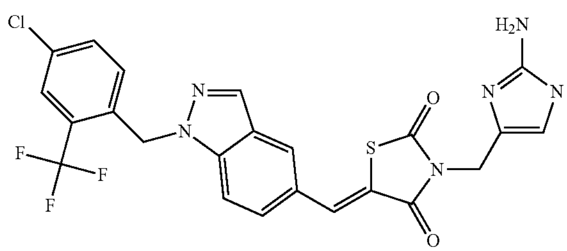 [SMILES: Nc1nc(CN2C(=O)S/C(=C\c3ccc4c(cnn4Cc4ccc(Cl)cc4C(F)(F)F)c3)C2=O)c[nH]1] | 231 | (5Z)-3-[(2-Amino-1H-imidazol-4-yl)methyl]-5-({1-[4-chloro-2-(trifluoromethyl)benzyl]-1H-indazol-5-yl}methylidene)-1,3-thiazolidine-2,4-dione |
| 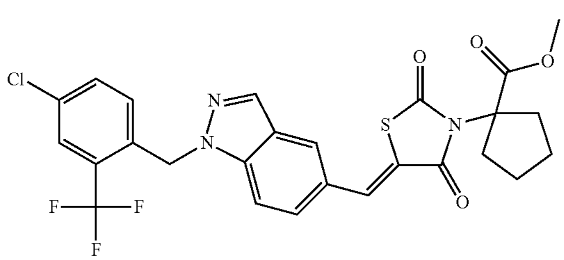 [SMILES: COC(=O)C1(N2C(=O)S/C(=C\c3ccc4c(cnn4Cc4ccc(Cl)cc4C(F)(F)F)c3)C2=O)CCCC1] | 232 | Methyl 1-[(5Z)-5-({1-[4-chloro-2-(trifluoromethyl)benzyl]-1H-indazol-5-yl}methylidene)-2,4-dioxo-1,3-thiazolidin-3-yl]cyclopentanecarboxylate |

TABLE I-continued

| STRUCTURE | COMPOUND # | NAME |
|---|---|---|
| 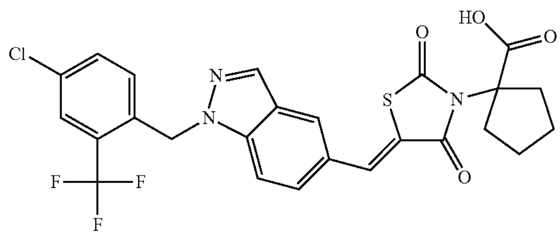 [SMILES: O=C1S/C(=C\c2ccc3c(cnn3Cc3ccc(Cl)cc3C(F)(F)F)c2)C(=O)N1C1(C(=O)O)CCCC1] | 233 | 1-[(5Z)-5-({1-[4-Chloro-2-(trifluoromethyl)benzyl]-1H-indazol-5-yl}methylidene)-2,4-dioxo-1,3-thiazolidin-3-yl]cyclopentanecarboxylic acid |
| 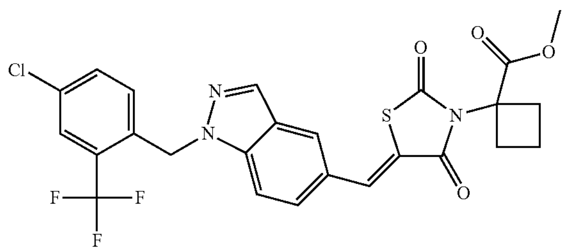 [SMILES: COC(=O)C1(N2C(=O)S/C(=C\c3ccc4c(cnn4Cc4ccc(Cl)cc4C(F)(F)F)c3)C2=O)CCC1] | 234 | Methyl 1-[(5Z)-5-({1-[4-chloro-2-(trifluoromethyl)benzyl]-1H-indazol-5-yl}methylidene)-2,4-dioxo-1,3-thiazolidin-3-yl]cyclobutanecarboxylate |
| 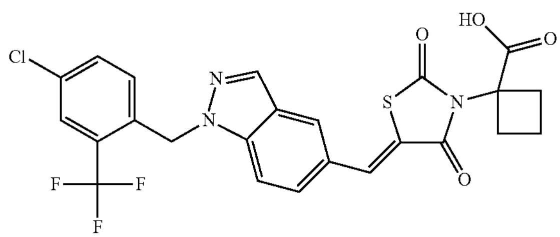 [SMILES: O=C1S/C(=C\c2ccc3c(cnn3Cc3ccc(Cl)cc3C(F)(F)F)c2)C(=O)N1C1(C(=O)O)CCC1] | 235 | 1-[(5Z)-5-({1-[4-Chloro-2-(trifluoromethyl)benzyl]-1H-indazol-5-yl}methylidene)-2,4-dioxo-1,3-thiazolidin-3-yl]cyclobutanecarboxylic acid |
| 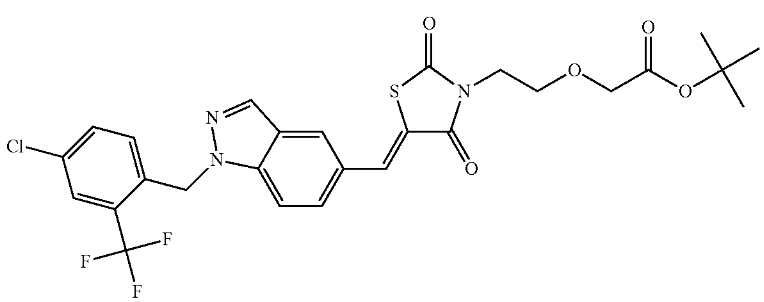 [SMILES: CC(C)(C)OC(=O)COCCN1C(=O)S/C(=C\c2ccc3c(cnn3Cc3ccc(Cl)cc3C(F)(F)F)c2)C1=O] | 236 | tert-Butyl {2-[(5Z)-5-({1-[4-chloro-2-(trifluoromethyl)benzyl]-1H-indazol-5-yl}methylidene)-2,4-dioxo-1,3-thiazolidin-3-yl]ethoxy}acetate |
| 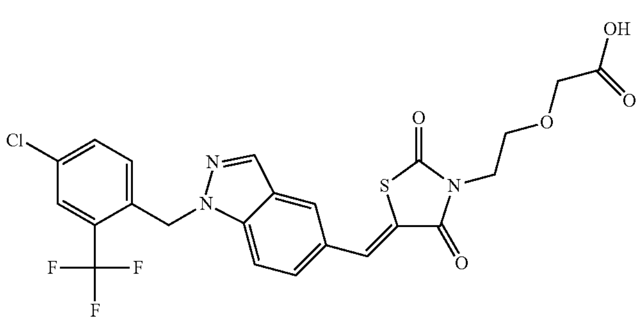 [SMILES: O=C(O)COCCN1C(=O)S/C(=C\c2ccc3c(cnn3Cc3ccc(Cl)cc3C(F)(F)F)c2)C1=O] | 237 | {2-[(5Z)-5-({1-[4-Chloro-2-(trifluoromethyl)benzyl]-1H-indazol-5-yl}methylidene)-2,4-dioxo-1,3-thiazolidin-3-yl]ethoxy}acetic acid |

TABLE I-continued

| STRUCTURE | COMPOUND # | NAME |
|---|---|---|
| 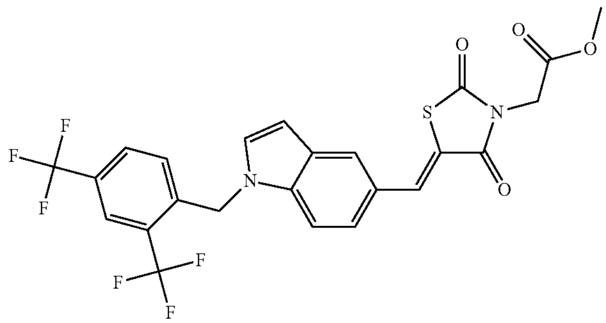 [SMILES: COC(=O)CN1C(=O)S/C(=C\c2ccc3c(ccn3Cc3ccc(C(F)(F)F)cc3C(F)(F)F)c2)C1=O] | 238 | Methyl {(5Z)-5-[(1-{[2,4-bis(trifluoromethyl)phenyl]methyl}-1H-indol-5-yl)methylidene]-2,4-dioxo-1,3-thiazolidin-3-yl}acetate |
| 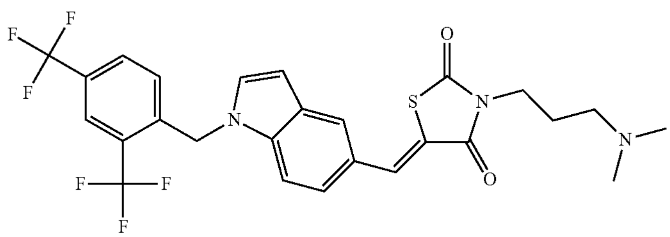 [SMILES: CN(C)CCCN1C(=O)S/C(=C\c2ccc3c(ccn3Cc3ccc(C(F)(F)F)cc3C(F)(F)F)c2)C1=O] | 239 | (5Z)-5-[(1-{[2,4-Bis(trifluoromethyl)phenyl]methyl}-1H-indol-5-yl)methylidene]-3-[3-(dimethylamino)propyl]-1,3-thiazolidine-2,4-dione |
| 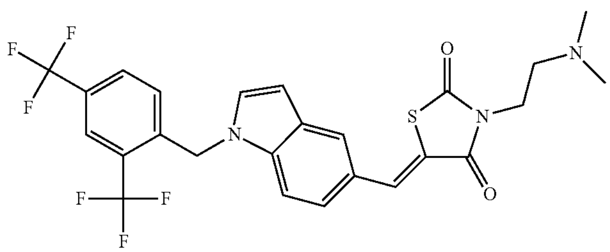 [SMILES: CN(C)CCN1C(=O)S/C(=C\c2ccc3c(ccn3Cc3ccc(C(F)(F)F)cc3C(F)(F)F)c2)C1=O] | 240 | (5Z)-5-[(1-{[2,4-Bis(trifluoromethyl)phenyl]methyl}-1H-indol-5-yl)methylidene]-3-[2-(dimethylamino)ethyl]-1,3-thiazolidine-2,4-dione |
| 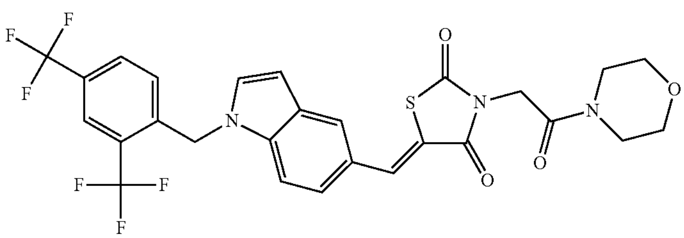 [SMILES: O=C(CN1C(=O)S/C(=C\c2ccc3c(ccn3Cc3ccc(C(F)(F)F)cc3C(F)(F)F)c2)C1=O)N1CCOCC1] | 241 | (5Z)-5-[(1-{[2,4-Bis(trifluoromethyl)phenyl]methyl}-1H-indol-5-yl)methylidene]-3-(2-morpholin-4-yl-2-oxoethyl)-1,3-thiazolidine-2,4-dione |
| 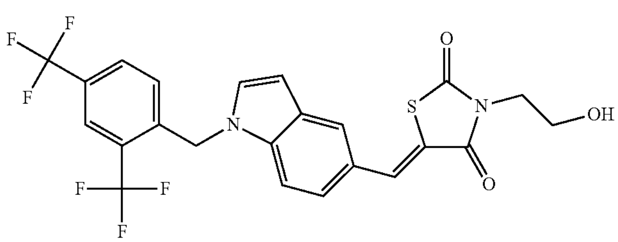 [SMILES: O=C1S/C(=C\c2ccc3c(ccn3Cc3ccc(C(F)(F)F)cc3C(F)(F)F)c2)C(=O)N1CCO] | 242 | (5Z)-5-[(1-{[2,4-Bis(trifluoromethyl)phenyl]methyl}-1H-indol-5-yl)methylidene]-3-(2-hydroxyethyl)-1,3-thiazolidine-2,4-dione |
| 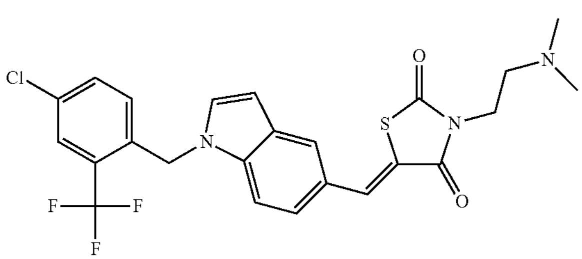 [SMILES: CN(C)CCN1C(=O)S/C(=C\c2ccc3c(ccn3Cc3ccc(Cl)cc3C(F)(F)F)c2)C1=O] | 243 | (5Z)-5-[(1-{[4-Chloro-2-(trifluoromethyl)phenyl]methyl}-1H-indol-5-yl)methylidene]-3-[2-(dimethylamino)ethyl]-1,3-thiazolidine-2,4-dione |

TABLE I-continued

| STRUCTURE | COMPOUND # | NAME |
|---|---|---|
| 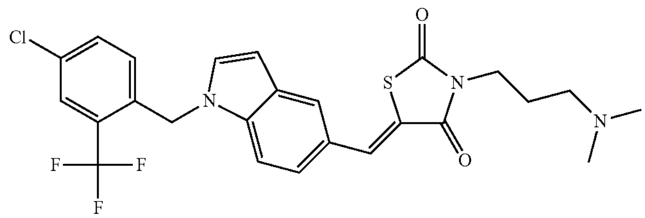 [SMILES: CN(C)CCCN1C(=O)S/C(=C\c2ccc3c(ccn3Cc3ccc(Cl)cc3C(F)(F)F)c2)C1=O] | 244 | (5Z)-5-[(1-{[4-Chloro-2-(trifluoromethyl)phenyl]methyl}-1H-indol-5-yl)methylidene]-3-[3-(dimethylamino)-propyl]-1,3-thiazolidine-2,4-dione |
| 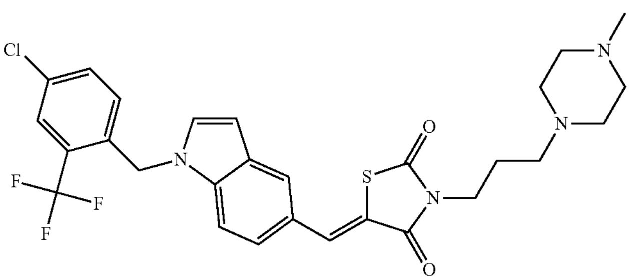 [SMILES: CN1CCN(CCCN2C(=O)S/C(=C\c3ccc4c(ccn4Cc4ccc(Cl)cc4C(F)(F)F)c3)C2=O)CC1] | 245 | (5Z)-5-[(1-{[4-Chloro-2-(trifluoromethyl)phenyl]methyl}-1H-indol-5-yl)methylidene]-3-[3-(4-methylpiperazin-1-yl)propyl]-1,3-thiazolidine-2,4-dione |
| 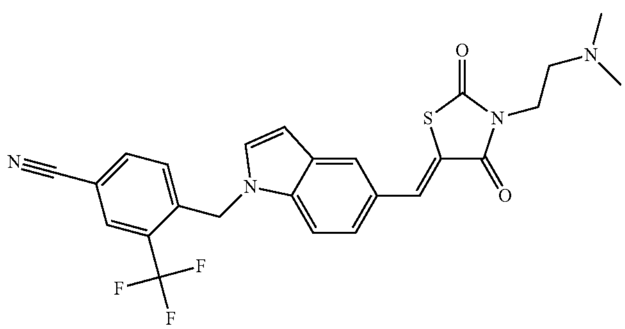 [SMILES: CN(C)CCN1C(=O)S/C(=C\c2ccc3c(ccn3Cc3ccc(C#N)cc3C(F)(F)F)c2)C1=O] | 246 | 4-({5-[(Z)-{3-[2-(Dimethylamino)ethyl]-2,4-dioxo-1,3-thiazolidin-5-ylidene}methyl]-1H-indol-1-yl}methyl)-3-(trifluoromethyl)benzonitrile |
| 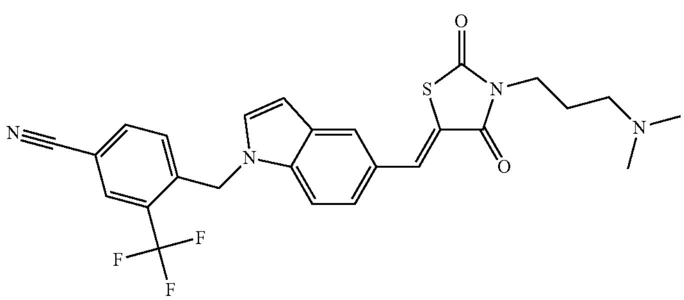 [SMILES: CN(C)CCCN1C(=O)S/C(=C\c2ccc3c(ccn3Cc3ccc(C#N)cc3C(F)(F)F)c2)C1=O] | 247 | 4-({5-[(Z)-{3-[3-(Dimethylamino)propyl]-2,4-dioxo-1,3-thiazolidin-5-ylidene}methyl]-1H-indol-1-yl}methyl)-3-(trifluoromethyl)benzonitrile |
| 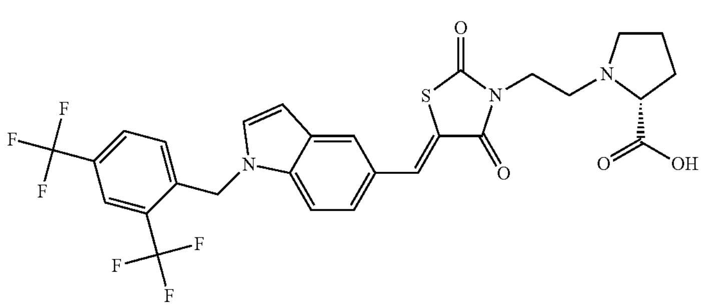 [SMILES: O=C(O)[C@H]1CCCN1CCN1C(=O)S/C(=C\c2ccc3c(ccn3Cc3ccc(C(F)(F)F)cc3C(F)(F)F)c2)C1=O] | 248 | 1-{2-[(5Z)-5-({1-[2,4-Bis(trifluoromethyl)benzyl]-1H-indol-5-yl}methylidene)-2,4-dioxo-1,3-thiazolidin-3-yl]ethyl}-D-proline |

TABLE I-continued

| STRUCTURE | COMPOUND # | NAME |
|---|---|---|
| 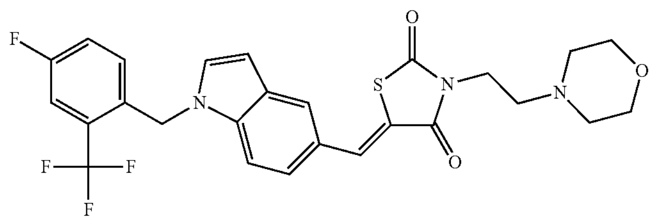 [SMILES: O=C1S/C(=C\c2ccc3c(ccn3Cc3ccc(F)cc3C(F)(F)F)c2)C(=O)N1CCN1CCOCC1] | 249 | (5Z)-5-[(1-{[4-Fluoro-2-(trifluoromethyl)phenyl]methyl}-1H-indol-5-yl)methylidene]-3-(2-morpholin-4-ylethyl)-1,3-thiazolidine-2,4-dione |
| 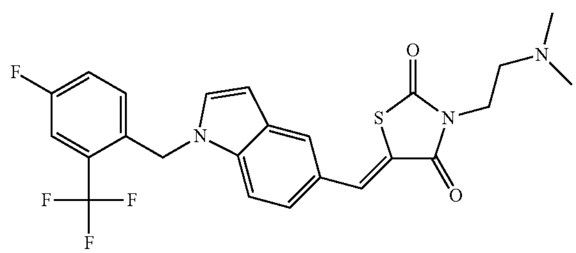 [SMILES: CN(C)CCN1C(=O)S/C(=C\c2ccc3c(ccn3Cc3ccc(F)cc3C(F)(F)F)c2)C1=O] | 250 | (5Z)-3-[2-(Dimethylamino)ethyl]-5-[(1-{[4-fluoro-2-(trifluoromethyl)phenyl]methyl}-1H-indol-5-yl)methylidene]-1,3-thiazolidine-2,4-dione |
| 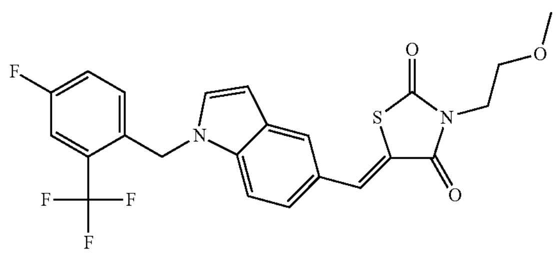 [SMILES: COCCN1C(=O)S/C(=C\c2ccc3c(ccn3Cc3ccc(F)cc3C(F)(F)F)c2)C1=O] | 251 | (5Z)-5-[(1-{[4-Fluoro-2-(trifluoromethyl)phenyl]methyl}-1H-indol-5-yl)methylidene]-3-[2-(methyloxy)ethyl]-1,3-thiazolidine-2,4-dione |
| 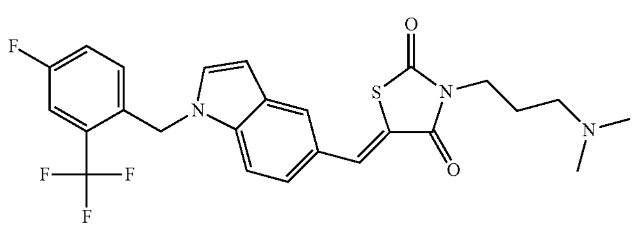 [SMILES: CN(C)CCCN1C(=O)S/C(=C\c2ccc3c(ccn3Cc3ccc(F)cc3C(F)(F)F)c2)C1=O] | 252 | (5Z)-3-[3-(Dimethylamino)propyl]-5-[(1-{[4-fluoro-2-(trifluoromethyl)phenyl]methyl}-1H-indol-5-yl)methylidene]-1,3-thiazolidine-2,4-dione |
| 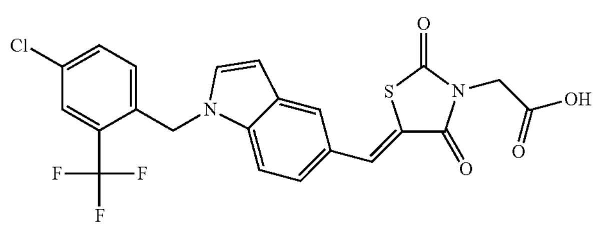 [SMILES: O=C(O)CN1C(=O)S/C(=C\c2ccc3c(ccn3Cc3ccc(Cl)cc3C(F)(F)F)c2)C1=O] | 253 | [(5Z)-5-({1-[4-Chloro-2-(trifluoromethyl)benzyl]-1H-indol-5-yl}methylidene)-2,4-dioxo-1,3-thiazolidin-3-yl]acetic acid |
| 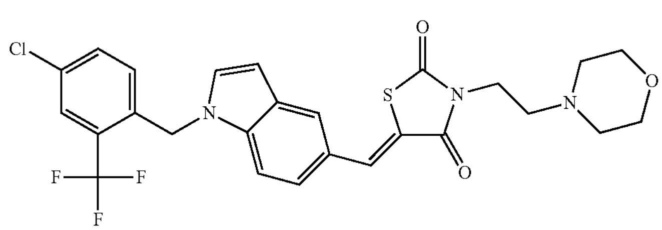 [SMILES: O=C1S/C(=C\c2ccc3c(ccn3Cc3ccc(Cl)cc3C(F)(F)F)c2)C(=O)N1CCN1CCOCC1] | 254 | (5Z)-5-({1-[4-Chloro-2-(trifluoromethyl)benzyl]-1H-indol-5-yl}methylidene)-3-(2-morpholin-4-ylethyl)-1,3-thiazolidine-2,4-dione |

TABLE I-continued

| STRUCTURE | COMPOUND # | NAME |
|---|---|---|
| 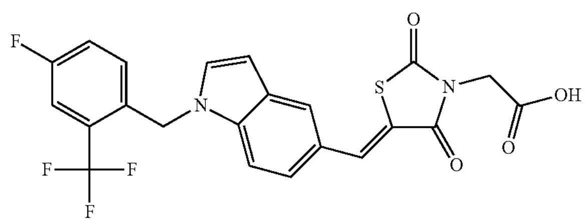 [SMILES: O=C(O)CN1C(=O)S/C(=C\c2ccc3c(ccn3Cc3ccc(F)cc3C(F)(F)F)c2)C1=O] | 255 | [(5Z)-5-({1-[4-Fluoro-2-(trifluoromethyl)benzyl]-1H-indol-5-yl}methylidene)-2,4-dioxo-1,3-thiazolidin-3-yl]acetic acid |
| 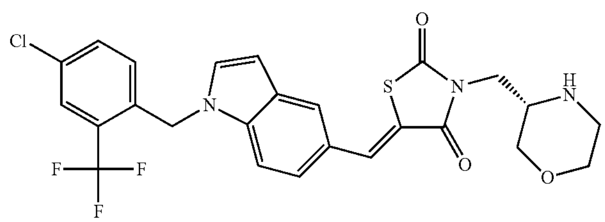 [SMILES: O=C1S/C(=C\c2ccc3c(ccn3Cc3ccc(Cl)cc3C(F)(F)F)c2)C(=O)N1C[C@H]1COCCN1] | 256 | (5Z)-5-({1-[4-Chloro-2-(trifluoromethyl)benzyl]-1H-indol-5-yl}methylidene)-3-[(3S)-morpholin-3-ylmethyl]-1,3-thiazolidine-2,4-dione |
| 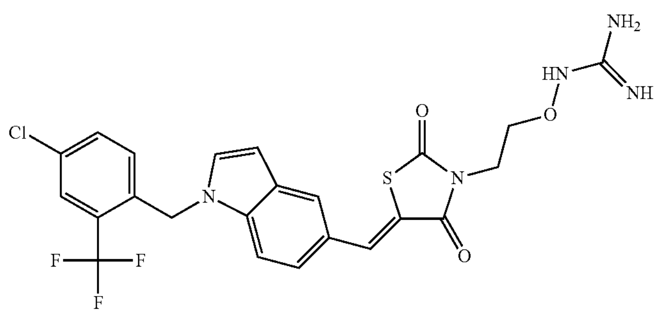 | 257 | 1-{2-[(5Z)-5-({1-[4-Chloro-2-(trifluoromethyl)benzyl]-1H-indol-5-yl}methylidene)-2,4-dioxo-1,3-thiazolidin-3-yl]ethoxy}guanidine |
| 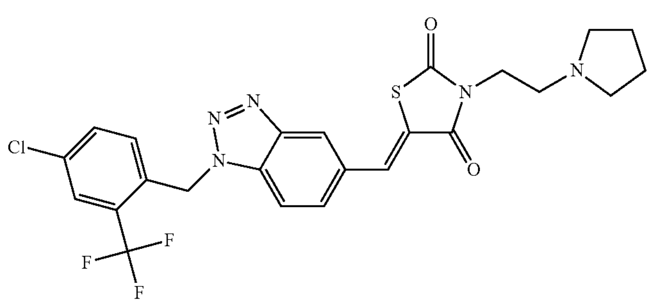 | 258 | (5Z)-5-({1-[4-Chloro-2-(trifluoromethyl)benzyl]-1H-benzotriazol-5-yl}methylidene)-3-(2-pyrrolidin-1-ylmethyl)-1,3-thiazolidine-2,4-dione |
| 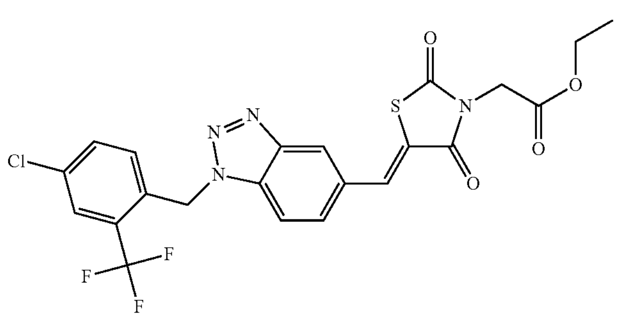 [SMILES: CCOC(=O)CN1C(=O)S/C(=C\c2ccc3c(c2)nnn3Cc2ccc(Cl)cc2C(F)(F)F)C1=O] | 259 | Ethyl [(5Z)-5-({1-[4-chloro-2-(trifluoromethyl)benzyl]-1H-benzotriazol-5-yl}methylidene)-2,4-dioxo-1,3-thiazolidin-3-yl]acetate |

TABLE I-continued

| STRUCTURE | COMPOUND # | NAME |
|---|---|---|
| 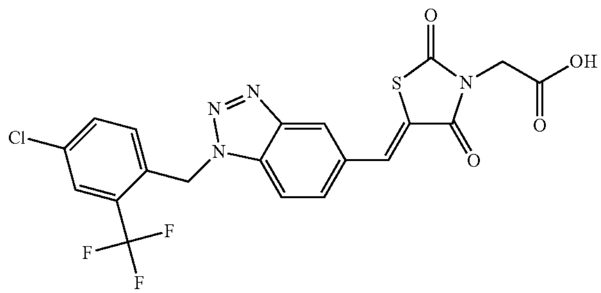 [SMILES: O=C(O)CN1C(=O)S/C(=C\c2ccc3c(c2)nnn3Cc2ccc(Cl)cc2C(F)(F)F)C1=O] | 260 | [(5Z)-5-({1-[4-Chloro-2-(trifluoromethyl)benzyl]-1H-benzotriazol-5-yl}methylidene)-2,4-dioxo-1,3-thiazolidin-3-yl]acetic acid |
| 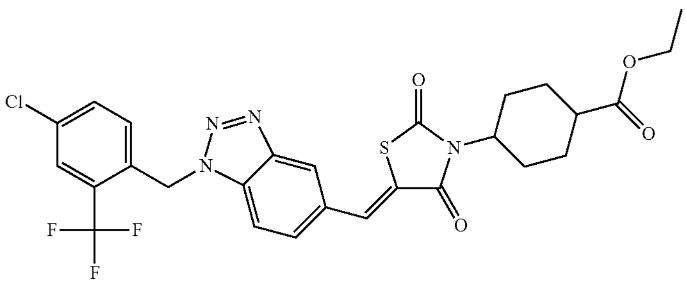 [SMILES: CCOC(=O)C1CCC(N2C(=O)S/C(=C\c3ccc4c(c3)nnn4Cc3ccc(Cl)cc3C(F)(F)F)C2=O)CC1] | 261 | Ethyl 4-[(5Z)-5-({1-[4-chloro-2-(trifluoromethyl)benzyl]-1H-benzotriazol-5-yl}methylidene)-2,4-dioxo-1,3-thiazolidin-3-yl]cyclohexanecarboxylate |
| 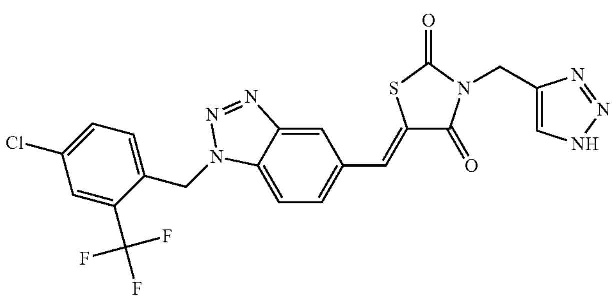 [SMILES: O=C1S/C(=C\c2ccc3c(c2)nnn3Cc2ccc(Cl)cc2C(F)(F)F)C(=O)N1Cc1c[nH]nn1] | 262 | (5Z)-5-({1-[4-Chloro-2-(trifluoromethyl)benzyl]-1H-benzotriazol-5-yl}methylidene)-3-(1H-1,2,3-triazol-4-ylmethyl)-1,3-thiazolidine-2,4-dione |
| 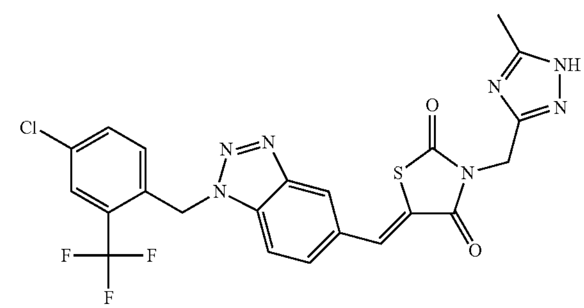 [SMILES: Cc1nc(CN2C(=O)S/C(=C\c3ccc4c(c3)nnn4Cc3ccc(Cl)cc3C(F)(F)F)C2=O)n[nH]1] | 263 | (5Z)-5-({1-[4-Chloro-2-(trifluoromethyl)benzyl]-1H-benzotriazol-5-yl}methylidene)-3-[(5-methyl-1H-1,2,4-triazol-3-yl)methyl]-1,3-thiazolidine-2,4-dione |
| 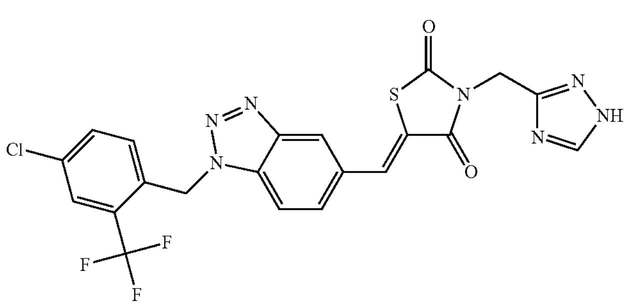 [SMILES: O=C1S/C(=C\c2ccc3c(c2)nnn3Cc2ccc(Cl)cc2C(F)(F)F)C(=O)N1Cc1nc[nH]n1] | 264 | (5Z)-5-({1-[4-Chloro-2-(trifluoromethyl)benzyl]-1H-benzotriazol-5-yl}methylidene)-3-(1H-1,2,4-triazol-3-ylmethyl)-1,3-thiazolidine-2,4-dione |

TABLE I-continued

| STRUCTURE | COMPOUND # | NAME |
|---|---|---|
| 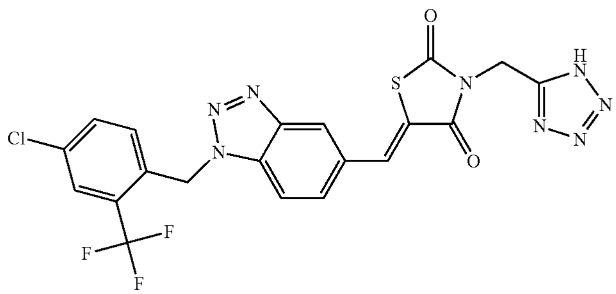 [SMILES: O=C1S/C(=C\c2ccc3c(c2)nnn3Cc2ccc(Cl)cc2C(F)(F)F)C(=O)N1Cc1nnn[nH]1] | 265 | (5Z)-5-({1-[4-Chloro-2-(trifluoromethyl)benzyl]-1H-benzotriazol-5-yl}methylidene)-3-(1H-tetrazol-5-ylmethyl)-1,3-thiazolidine-2,4-dione |
| 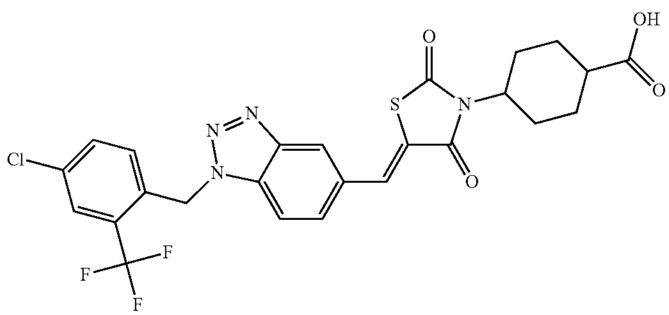 [SMILES: O=C(O)C1CCC(N2C(=O)S/C(=C\c3ccc4c(c3)nnn4Cc3ccc(Cl)cc3C(F)(F)F)C2=O)CC1] | 266 | 4-[(5Z)-5-({1-[4-Chloro-2-(trifluoromethyl)benzyl]-1H-benzotriazol-5-yl}methylidene)-2,4-dioxo-1,3-thiazolidin-3-yl]cyclohexanecarboxylic acid |
| 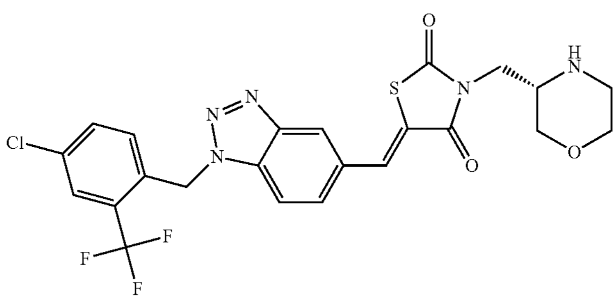 [SMILES: O=C1S/C(=C\c2ccc3c(c2)nnn3Cc2ccc(Cl)cc2C(F)(F)F)C(=O)N1C[C@H]1COCCN1] | 267 | (5Z)-5-({1-[4-Chloro-2-(trifluoromethyl)benzyl]-1H-benzotriazol-5-yl}methylidene)-3-[(3S)-morpholin-3-ylmethyl]-1,3-thiazolidine-2,4-dione |
| 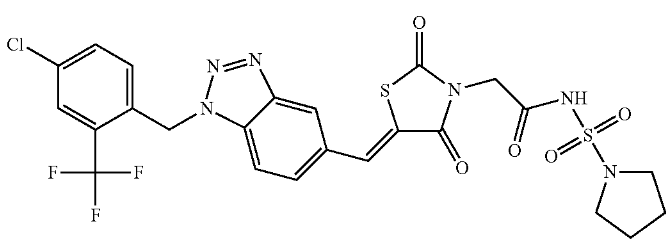 [SMILES: O=C(CN1C(=O)S/C(=C\c2ccc3c(c2)nnn3Cc2ccc(Cl)cc2C(F)(F)F)C1=O)NS(=O)(=O)N1CCCC1] | 268 | 2-[(5Z)-5-({1-[4-Chloro-2-(trifluoromethyl)benzyl]-1H-benzotriazol-5-yl}methylidene)-2,4-dioxo-1,3-thiazolidin-3-yl]-N-(pyrrolidin-1-ylsulfonyl)acetamide |
| 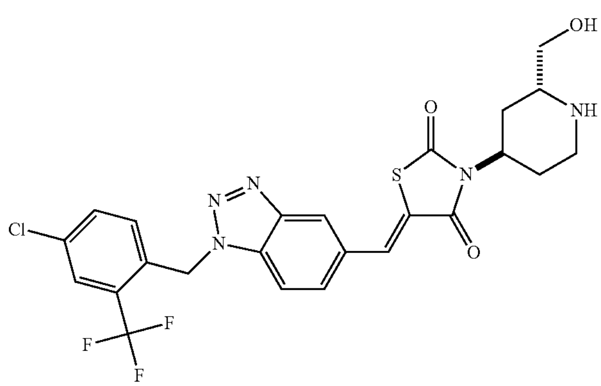 | 269 | (5Z)-5-({1-[4-Chloro-2-(trifluoromethyl)benzyl]-1H-indazol-5-yl}methylidene)-3-[trans-2-(hydroxymethyl)piperidin-4-yl]-1,3-thiazolidine-2,4-dione |

TABLE I-continued

| STRUCTURE | COMPOUND # | NAME |
|---|---|---|
| 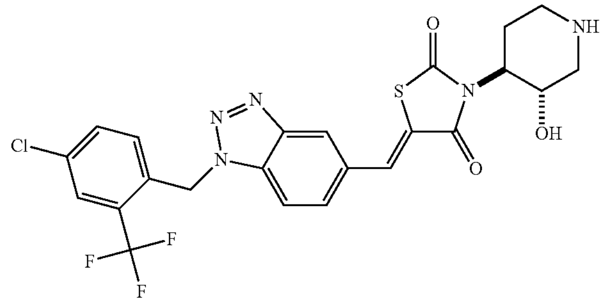 | 270 | (5Z)-5-({1-[4-Chloro-2-(trifluoromethyl)-benzyl]-1H-indazol-5-yl}methylidene)-3-[trans-3-hydroxypiperidin-4-yl]-1,3-thiazolidine-2,4-dione |
| 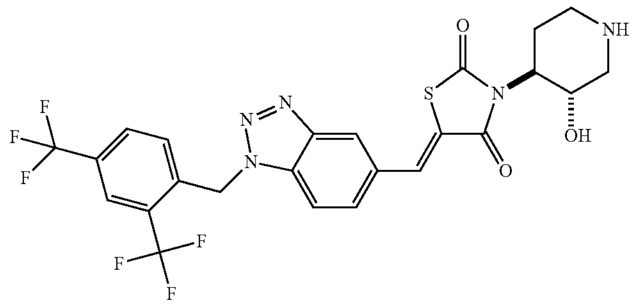 | 271 | (5Z)-5-({1-[2,4-Bis(trifluoromethyl)benzyl]-1H-indazol-5-yl}methylidene)-3-[trans-3-hydroxypiperidin-4-yl]-1,3-thiazolidine-2,4-dione |
| 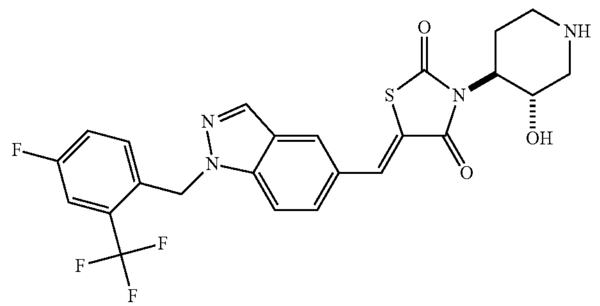 | 272 | (5Z)-5-({1-[4-Fluoro-2-(trifluoromethyl)-benzyl]-1H-indazol-5-yl}methylidene)-3-[trans-3-hydroxypiperidin-4-yl]-1,3-thiazolidine-2,4-dione |
| 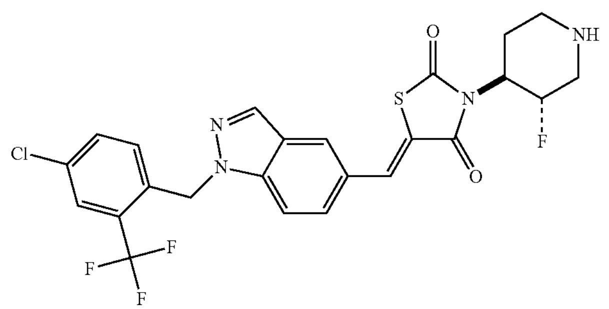 | 273 | (5Z)-5-({1-[4-Chloro-2-(trifluoromethyl)benzyl]-1H-indazol-5-yl}methylidene)-3-(trans-3-fluoropiperidin-4-yl)-1,3-thiazolidine-2,4-dione |
| 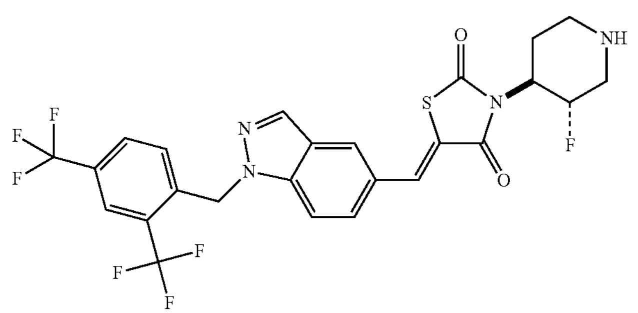 | 274 | (5Z)-5-({1-[2,4-Bis(trifluoromethyl)benzyl]-1H-indazol-5-yl}methylidene)-3-(trans-3-fluoropiperidin-4-yl)-1,3-thiazolidine-2,4-dione |

TABLE I-continued

| STRUCTURE | COMPOUND # | NAME |
|---|---|---|
| 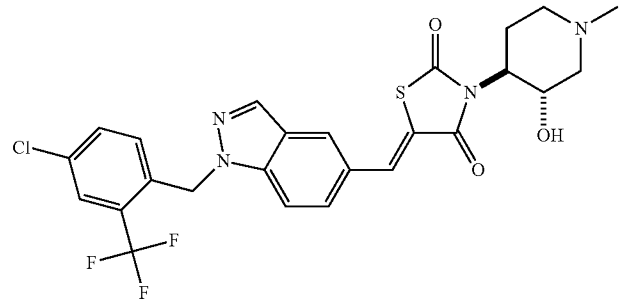 | 275 | (5Z)-5-({1-[4-Chloro-2-(trifluoromethyl)-benzyl]-1H-indazol-5-yl}methylidene)-3-[trans-3-hydroxy-1-methylpiperidin-4-yl]-1,3-thiazolidine-2,4-dione |
| 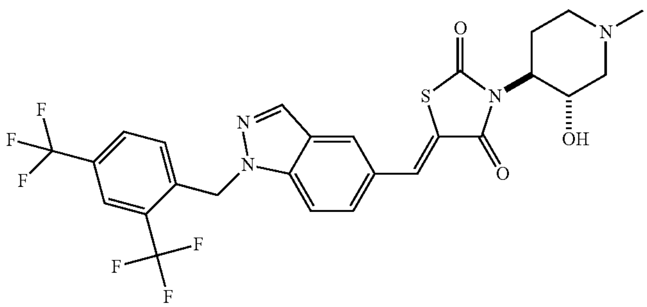 | 276 | (5Z)-5-({1-[2,4-Bis(trifluoromethyl)benzyl]-1H-indazol-5-yl}methylidene)-3-[trans-3-hydroxy-1-methylpiperidin-4-yl]-1,3-thiazolidine-2,4-dione |
| 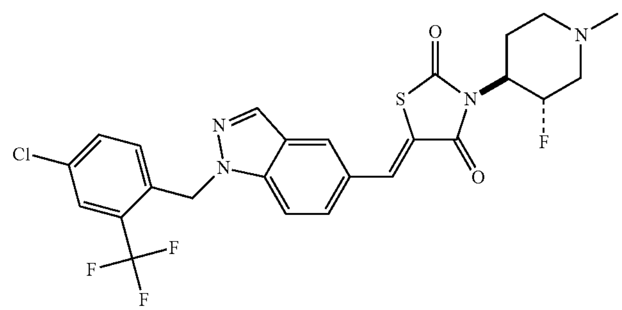 | 277 | (5Z)-5-({1-[4-Chloro-2-(trifluoromethyl)benzyl]-1H-indazol-5-yl}methylidene)-3-(trans-3-fluoro-1-methylpiperidin-4-yl)-1,3-thiazolidine-2,4-dione |
| 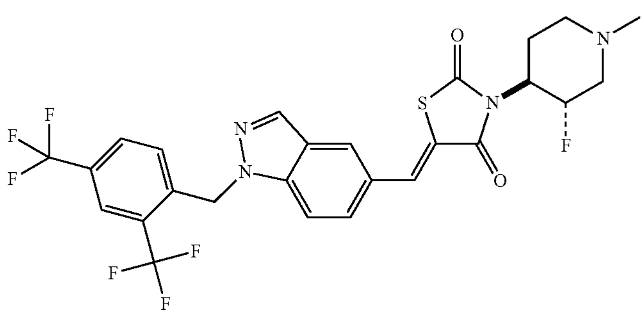 | 278 | (5Z)-5-({1-[2,4-Bis(trifluoromethyl)benzyl]-1H-indazol-5-yl}methylidene)-3-(trans-3-fluoro-1-methylpiperidin-4-yl)-1,3-thiazolidine-2,4-dione |
| 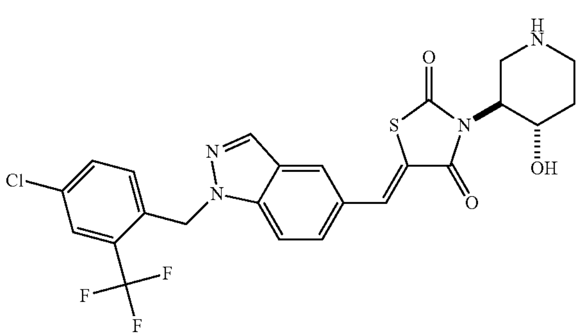 | 279 | (5Z)-5-({1-[4-Chloro-2-(trifluoromethyl)-benzyl]-1H-indazol-5-yl}methylidene)-3-[trans-4-hydroxypiperidin-3-yl]-1,3-thiazolidine-2,4-dione |

TABLE I-continued

| STRUCTURE | COMPOUND # | NAME |
|---|---|---|
| 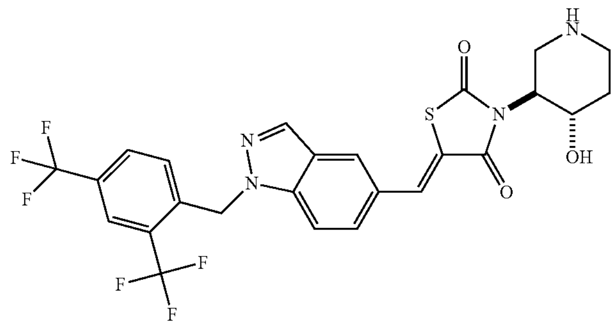 | 280 | (5Z)-5-({1-[2,4-Bis(trifluoromethyl)benzyl]-1H-indazol-5-yl}methylidene)-3-[trans-4-hydroxypiperidin-3-yl]-1,3-thiazolidine-2,4-dione |
| 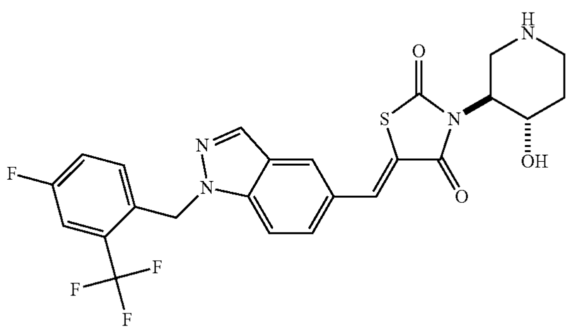 | 281 | (5Z)-5-({1-[4-Fluoro-2-(trifluoromethyl)-benzyl]-1H-indazol-5-yl}methylidene)-3-[trans-4-hydroxypiperidin-3-yl]-1,3-thiazolidine-2,4-dione |
| 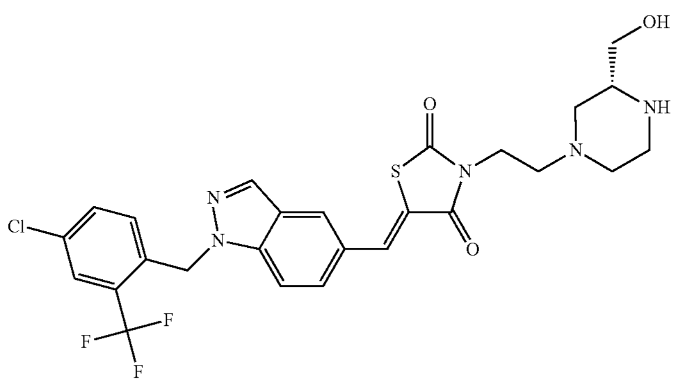 [SMILES: O=C1S/C(=C\c2ccc3c(cnn3Cc3ccc(Cl)cc3C(F)(F)F)c2)C(=O)N1CCN1CCN[C@@H](CO)C1] | 282 | (5Z)-5-({1-[4-Chloro-2-(trifluoromethyl)benzyl]-1H-indazol-5-yl}methylidene)-3-{2-[(3R)-3-(hydroxymethyl)piperazin-1-yl]ethyl}-1,3-thiazolidine-2,4-dione |
| 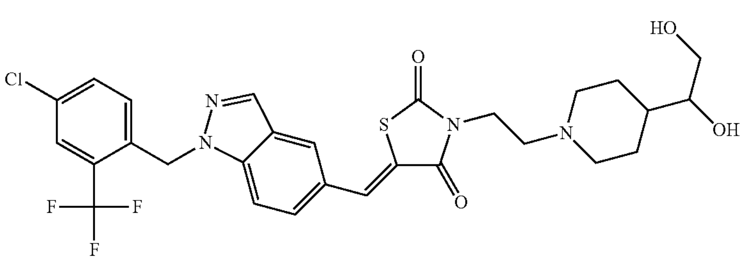 [SMILES: O=C1S/C(=C\c2ccc3c(cnn3Cc3ccc(Cl)cc3C(F)(F)F)c2)C(=O)N1CCN1CCC(C(O)CO)CC1] | 283 | (5Z)-5-({1-[4-Chloro-2-(trifluoromethyl)benzyl]-1H-indazol-5-yl}methylidene)-3-{2-[4-(1,2-dihydroxyethyl)piperidin-1-yl]ethyl}-1,3-thiazolidine-2,4-dione |

TABLE I-continued

| STRUCTURE | COMPOUND # | NAME |
|---|---|---|
| 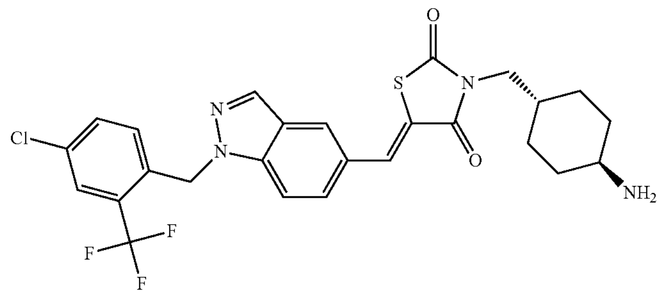 [SMILES: N[C@H]1CC[C@H](CN2C(=O)S/C(=C\c3ccc4c(cnn4Cc4ccc(Cl)cc4C(F)(F)F)c3)C2=O)CC1] | 284 | (5Z)-3-[(trans-4-Aminocyclohexyl)methyl]-5-({1-[4-chloro-2-(trifluoromethyl)benzyl]-1H-indazol-5-yl}methylidene)-1,3-thiazolidine-2,4-dione |
| 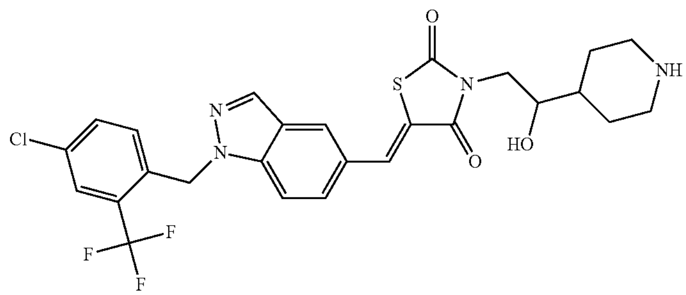 [SMILES: O=C1S/C(=C\c2ccc3c(cnn3Cc3ccc(Cl)cc3C(F)(F)F)c2)C(=O)N1CC(O)C1CCNCC1] | 285 | (5Z)-5-({1-[4-Chloro-2-(trifluoromethyl)benzyl]-1H-indazol-5-yl}methylidene)-3-(2-hydroxy-2-piperidin-4-ylethyl)-1,3-thiazolidine-2,4-dione |
| 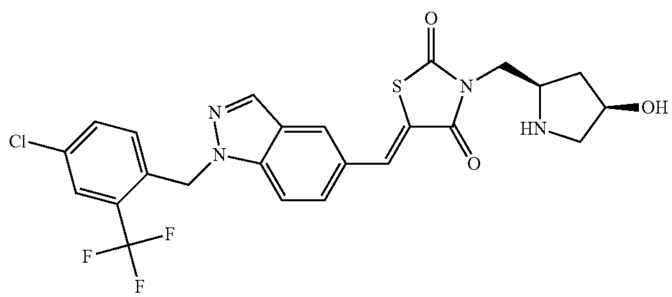 [SMILES: O=C1S/C(=C\c2ccc3c(cnn3Cc3ccc(Cl)cc3C(F)(F)F)c2)C(=O)N1C[C@H]1C[C@@H](O)CN1] | 286 | (5Z)-5-({1-[4-Chloro-2-(trifluoromethyl)benzyl]-1H-indazol-5-yl}methylidene)-3-{[(2S,4S)-4-hydroxypyrrolidin-2-yl]methyl}-1,3-thiazolidine-2,4-dione |
| 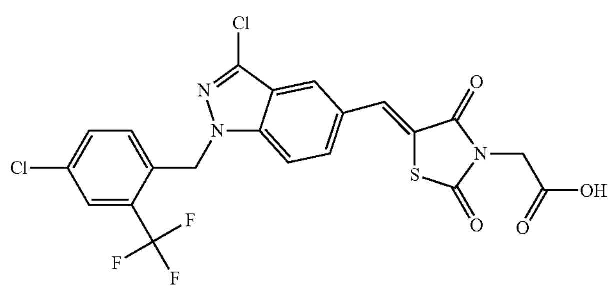 [SMILES: O=C(O)CN1C(=O)S/C(=C\c2ccc3c(c2)c(Cl)nn3Cc2ccc(Cl)cc2C(F)(F)F)C1=O] | 287 | [(5Z)-5-({1-[4-Chloro-2-(trifluoromethyl)benzyl]-3-chloro-1H-indazol-5-yl}methylidene)-2,4-dioxo-1,3-thiazolidin-3-yl]acetic acid |
| 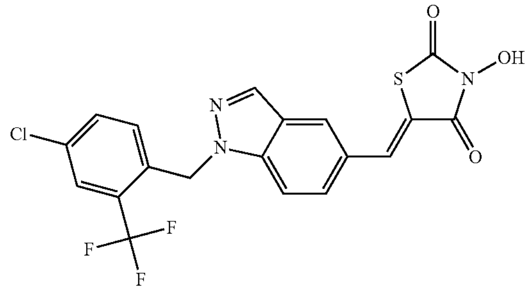 [SMILES: O=C1S/C(=C\c2ccc3c(cnn3Cc3ccc(Cl)cc3C(F)(F)F)c2)C(=O)N1O] | 288 | (5Z)-5-({1-[4-Chloro-2-(trifluoromethyl)benzyl]-1H-indazol-5-yl}methylidene)-3-hydroxy-1,3-thiazolidine-2,4-dione |

TABLE I-continued

| STRUCTURE | COMPOUND # | NAME |
|---|---|---|
| 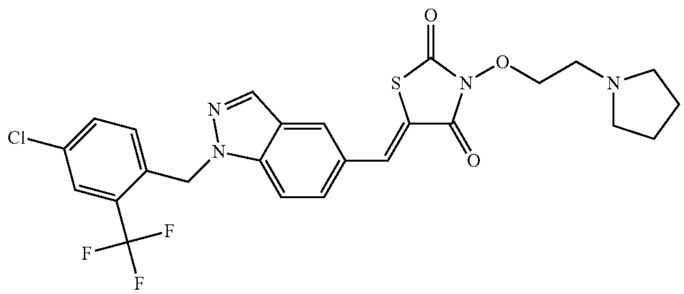 [SMILES: O=C1S/C(=C\c2ccc3c(cnn3Cc3ccc(Cl)cc3C(F)(F)F)c2)C(=O)N1OCCN1CCCC1] | 289 | (5Z)-5-({1-[4-Chloro-2-(trifluoromethyl)benzyl]-1H-indazol-5-yl}methylidene)-3-(2-pyrrolidin-1-ylethoxy)-1,3-thiazolidine-2,4-dione |
| 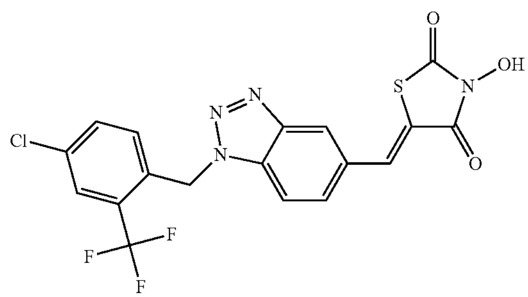 [SMILES: O=C1S/C(=C\c2ccc3c(c2)nnn3Cc2ccc(Cl)cc2C(F)(F)F)C(=O)N1O] | 290 | (5Z)-5-({1-[4-Chloro-2-(trifluoromethyl)benzyl]-1H-benzotriazol-5-yl}methylidene)-3-hydroxy-1,3-thiazolidine-2,4-dione |
| 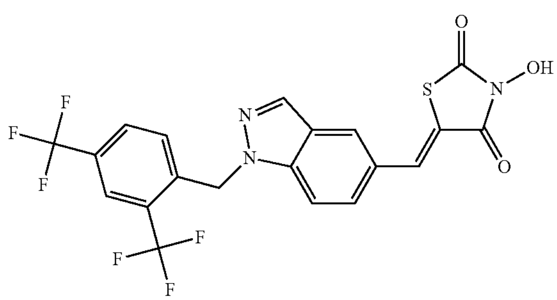 [SMILES: O=C1S/C(=C\c2ccc3c(cnn3Cc3ccc(C(F)(F)F)cc3C(F)(F)F)c2)C(=O)N1O] | 291 | (5Z)-5-({1-[2,4-Bis(trifluoromethyl)benzyl]-1H-indazol-5-yl}methylidene)-3-hydroxy-1,3-thiazolidine-2,4-dione |
| 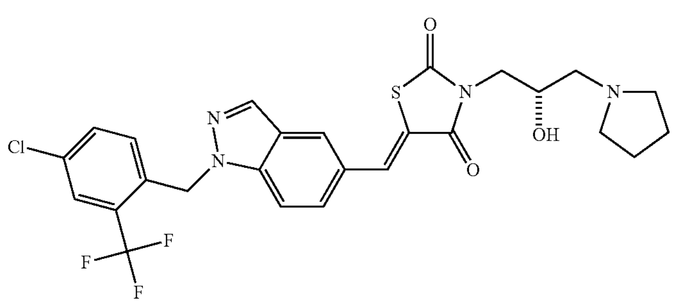 [SMILES: O=C1S/C(=C\c2ccc3c(cnn3Cc3ccc(Cl)cc3C(F)(F)F)c2)C(=O)N1C[C@@H](O)CN1CCCC1] | 292 | (5Z)-5-({1-[4-Chloro-2-(trifluoromethyl)benzyl]-1H-indazol-5-yl}methylidene)-3-[(2S)-2-hydroxy-3-pyrrolidin-1-ylpropyl]-1,3-thiazolidine-2,4-dione |
| 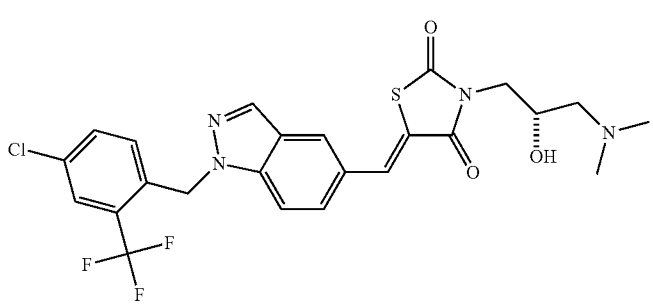 [SMILES: CN(C)C[C@H](O)CN1C(=O)S/C(=C\c2ccc3c(cnn3Cc3ccc(Cl)cc3C(F)(F)F)c2)C1=O] | 293 | (5Z)-5-({1-[4-Chloro-2-(trifluoromethyl)benzyl]-1H-indazol-5-yl}methylidene)-3-[(2S)-3-(dimethylamino)-2-hydroxypropyl]-1,3-thiazolidine-2,4-dione |

TABLE I-continued

| STRUCTURE | COMPOUND # | NAME |
|---|---|---|
| 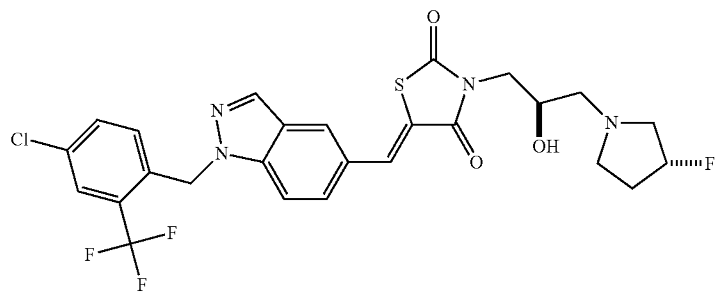 [SMILES: O=C1S/C(=C\c2ccc3c(cnn3Cc3ccc(Cl)cc3C(F)(F)F)c2)C(=O)N1C[C@H](O)CN1CC[C@@H](F)C1] | 294 | (5Z)-5-({1-[4-Chloro-2-(trifluoromethyl)benzyl]-1H-indazol-5-yl}methylidene)-3-{(2R)-3-[(3R)-3-fluoropyrrolidin-1-yl]-2-hydroxypropyl}-1,3-thiazolidine-2,4-dione |
| 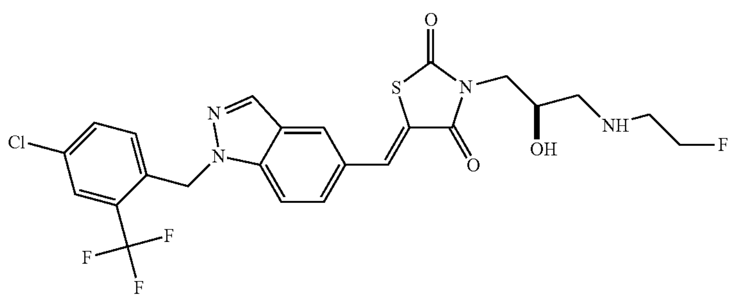 [SMILES: O=C1S/C(=C\c2ccc3c(cnn3Cc3ccc(Cl)cc3C(F)(F)F)c2)C(=O)N1C[C@H](O)CNCCF] | 295 | (5Z)-5-({1-[4-Chloro-2-(trifluoromethyl)benzyl]-1H-indazol-5-yl}methylidene)-3-{(2R)-3-[(2-fluoroethyl)amino]-2-hydroxypropyl}-1,3-thiazolidine-2,4-dione |
| 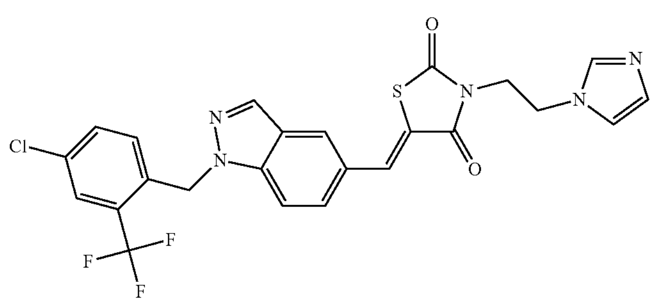 [SMILES: O=C1S/C(=C\c2ccc3c(cnn3Cc3ccc(Cl)cc3C(F)(F)F)c2)C(=O)N1CCn1ccnc1] | 296 | (5Z)-5-({1-[4-Chloro-2-(trifluoromethyl)benzyl]-1H-indazol-5-yl}methylidene)-3-[2-(1H-imidazol-1-yl)ethyl]-1,3-thiazolidine-2,4-dione |
| 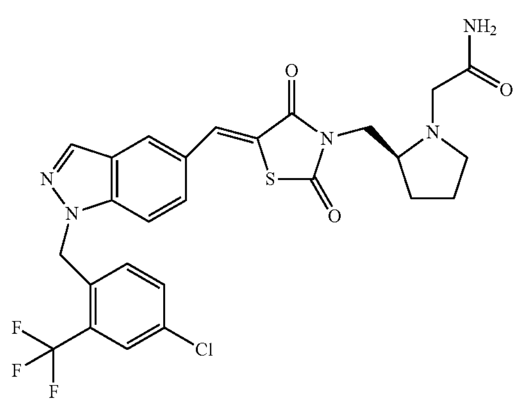 [SMILES: NC(=O)CN1CCC[C@H]1CN1C(=O)S/C(=C\c2ccc3c(cnn3Cc3ccc(Cl)cc3C(F)(F)F)c2)C1=O] | 297 | 2-[(2S)-2-{[(5Z)-5-({1-[4-Chloro-2-(trifluoromethyl)benzyl]-1H-indazol-5-yl}methylidene)-2,4-dioxo-1,3-thiazolidin-3-yl]methyl}pyrrolidin-1-yl]acetamide |

TABLE I-continued

| STRUCTURE | COMPOUND # | NAME |
|---|---|---|
| 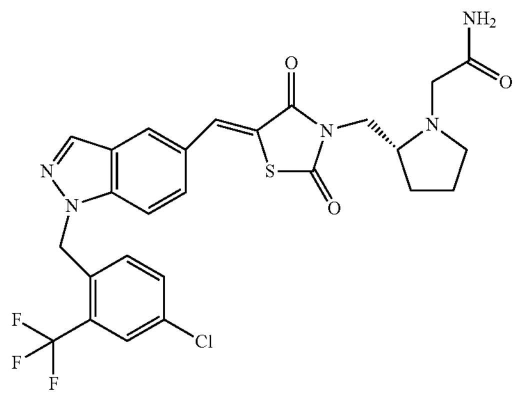 [SMILES: NC(=O)CN1CCC[C@@H]1CN1C(=O)S/C(=C\c2ccc3c(cnn3Cc3ccc(Cl)cc3C(F)(F)F)c2)C1=O] | 298 | 2-[(2R)-2-{[(5Z)-5-({1-[4-Chloro-2-(trifluoromethyl)benzyl]-1H-indazol-5-yl}methylidene)-2,4-dioxo-1,3-thiazolidin-3-yl]methyl}pyrrolidin-1-yl]acetamide |
| 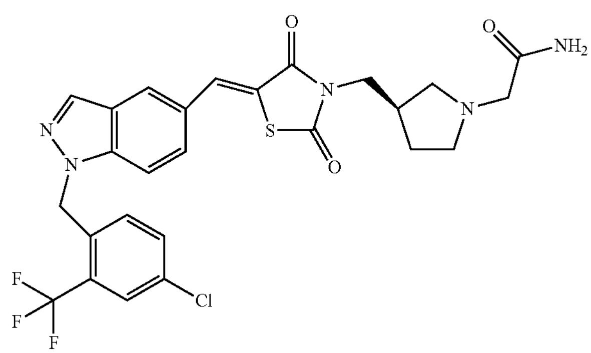 [SMILES: NC(=O)CN1CC[C@@H](CN2C(=O)S/C(=C\c3ccc4c(cnn4Cc4ccc(Cl)cc4C(F)(F)F)c3)C2=O)C1] | 299 | 2-[(3R)-3-{[(5Z)-5-({1-[4-Chloro-2-(trifluoromethyl)benzyl]-1H-indazol-5-yl}methylidene)-2,4-dioxo-1,3-thiazolidin-3-yl]methyl}pyrrolidin-1-yl]acetamide |
| 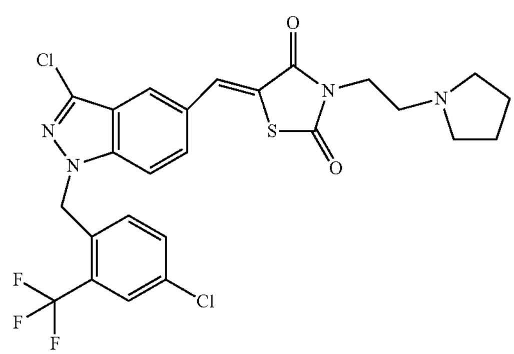 [SMILES: O=C1S/C(=C\c2ccc3c(c2)c(Cl)nn3Cc2ccc(Cl)cc2C(F)(F)F)C(=O)N1CCN1CCCC1] | 300 | (5Z)-5-({3-Chloro-1-[4-chloro-2-(trifluoromethyl)benzyl]-1H-indazol-5-yl}methylidene)-3-(2-pyrrolidin-1-ylethyl)-1,3-thiazolidine-2,4-dione |
| 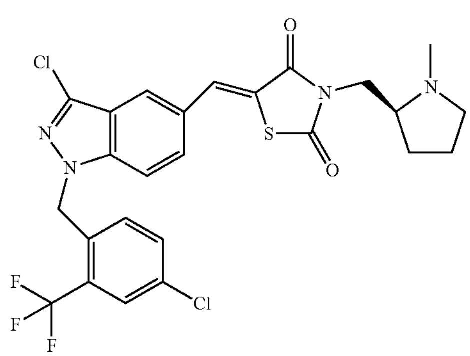 [SMILES: CN1CCC[C@H]1CN1C(=O)S/C(=C\c2ccc3c(c2)c(Cl)nn3Cc2ccc(Cl)cc2C(F)(F)F)C1=O] | 301 | (5Z)-5-({3-Chloro-1-[4-chloro-2-(trifluoromethyl)benzyl]-1H-indazol-5-yl}methylidene)-3-{[(2S)-1-methylpyrrolidin-2-yl]methyl}-1,3-thiazolidine-2,4-dione |

TABLE I-continued

| STRUCTURE | COMPOUND # | NAME |
|---|---|---|
| 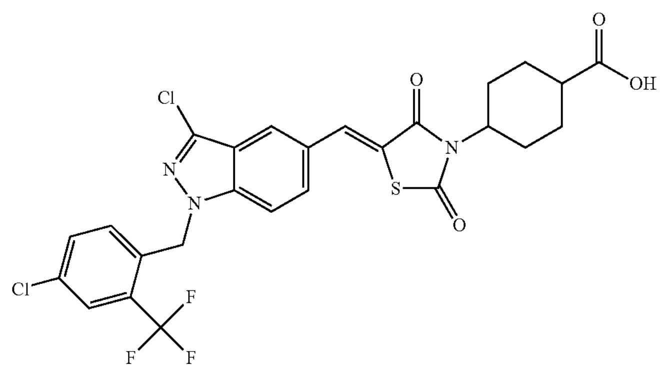 [SMILES: O=C(O)C1CCC(N2C(=O)S/C(=C\c3ccc4c(c3)c(Cl)nn4Cc3ccc(Cl)cc3C(F)(F)F)C2=O)CC1] | 302 | 4-[(5Z)-5-({3-Chloro-1-[4-chloro-2-(trifluoromethyl)benzyl]-1H-indazol-5-yl}methylidene)-2,4-dioxo-1,3-thiazolidin-3-yl]cyclohexanecarboxylic acid |
| 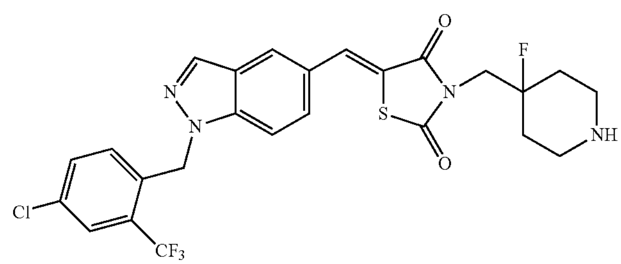 [SMILES: O=C1S/C(=C\c2ccc3c(cnn3Cc3ccc(Cl)cc3C(F)(F)F)c2)C(=O)N1CC1(F)CCNCC1] | 303 | (5Z)-5-({1-[4-Chloro-2-(trifluoromethyl)benzyl]-1H-indazol-5-yl}methylidene)-3-[(4-fluoropiperidin-4-yl)methyl]-1,3-thiazolidine-2,4-dione |
| 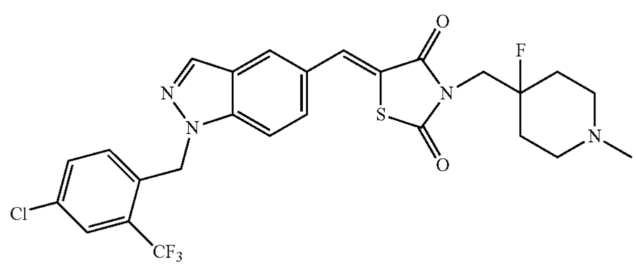 [SMILES: CN1CCC(F)(CN2C(=O)S/C(=C\c3ccc4c(cnn4Cc4ccc(Cl)cc4C(F)(F)F)c3)C2=O)CC1] | 304 | (5Z)-5-({1-[4-Chloro-2-(trifluoromethyl)benzyl]-1H-indazol-5-yl}methylidene)-3-[(4-fluoro-1-methylpiperidin-4-yl)methyl]-1,3-thiazolidine-2,4-dione |
| 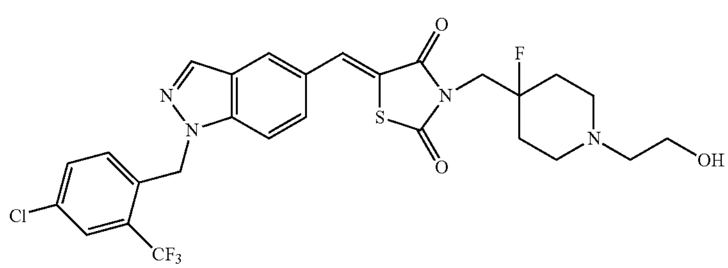 [SMILES: O=C1S/C(=C\c2ccc3c(cnn3Cc3ccc(Cl)cc3C(F)(F)F)c2)C(=O)N1CC1(F)CCN(CCO)CC1] | 305 | (5Z)-5-({1-[4-Chloro-2-(trifluoromethyl)benzyl]-1H-indazol-5-yl}methylidene)-3-{[4-fluoro-1-(2-hydroxyethyl)piperidin-4-yl]methyl}-1,3-thiazolidine-2,4-dione |
| 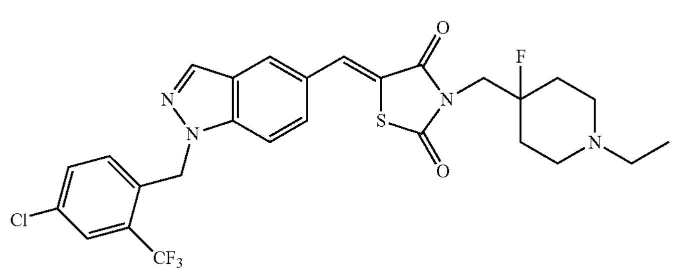 [SMILES: CCN1CCC(F)(CN2C(=O)S/C(=C\c3ccc4c(cnn4Cc4ccc(Cl)cc4C(F)(F)F)c3)C2=O)CC1] | 306 | (5Z)-5-({1-[4-Chloro-2-(trifluoromethyl)benzyl]-1H-indazol-5-yl}methylidene)-3-[(1-ethyl-4-fluoropiperidin-4-yl)methyl]-1,3-thiazolidine-2,4-dione |

TABLE I-continued

| STRUCTURE | COMPOUND # | NAME |
|---|---|---|
| 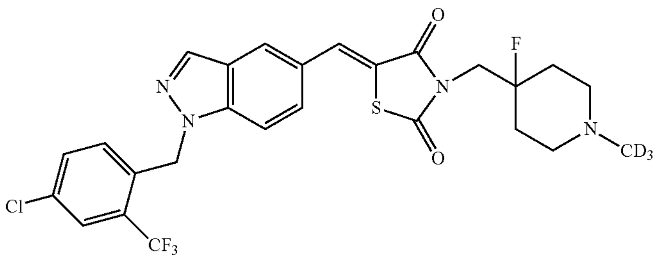 [SMILES: [2H]C([2H])([2H])N1CCC(F)(CN2C(=O)S/C(=C\c3ccc4c(cnn4Cc4ccc(Cl)cc4C(F)(F)F)c3)C2=O)CC1] | 307 | (5Z)-5-({1-[4-Chloro-2-(trifluoromethyl)benzyl]-1H-indazol-5-yl}methylidene)-3-{[4-fluoro-1-($^2$H$_3$)methylpiperidin-4-yl]methyl}-1,3-thiazolidine-2,4-dione |
| 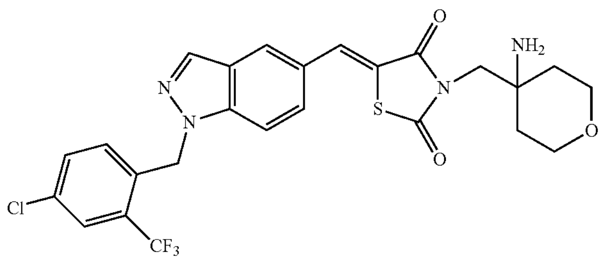 [SMILES: NC1(CN2C(=O)S/C(=C\c3ccc4c(cnn4Cc4ccc(Cl)cc4C(F)(F)F)c3)C2=O)CCOCC1] | 308 | (5Z)-3-[(4-Aminotetrahydro-2H-pyran-4-yl)methyl]-5-({1-[4-chloro-2-(trifluoromethyl)benzyl]-1H-indazol-5-yl}methylidene)-1,3-thiazolidine-2,4-dione |
| 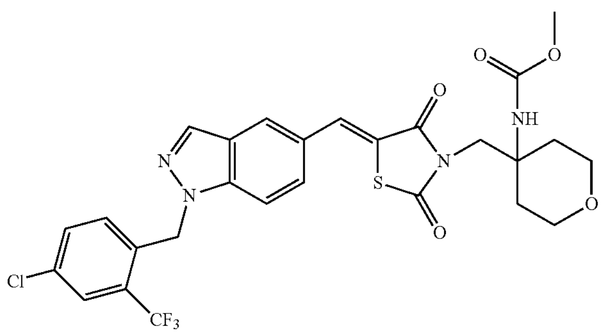 [SMILES: COC(=O)NC1(CN2C(=O)S/C(=C\c3ccc4c(cnn4Cc4ccc(Cl)cc4C(F)(F)F)c3)C2=O)CCOCC1] | 309 | Methyl (4-{[(5Z)-5-({1-[4-chloro-2-(trifluoromethyl)benzyl]-1H-indazol-5-yl}methylidene)-2,4-dioxo-1,3-thiazolidin-3-yl]methyl}tetrahydro-2H-pyran-4-yl)carbamate |
| 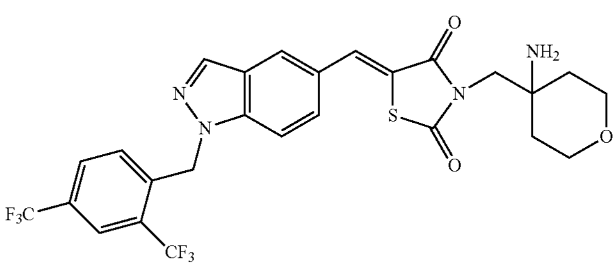 [SMILES: NC1(CN2C(=O)S/C(=C\c3ccc4c(cnn4Cc4ccc(C(F)(F)F)cc4C(F)(F)F)c3)C2=O)CCOCC1] | 310 | (5Z)-3-[(4-Aminotetrahydro-2H-pyran-4-yl)methyl]-5-({1-[2,4-bis(trifluoromethyl)benzyl]-1H-indazol-5-yl}methylidene)-1,3-thiazolidine-2,4-dione |
| 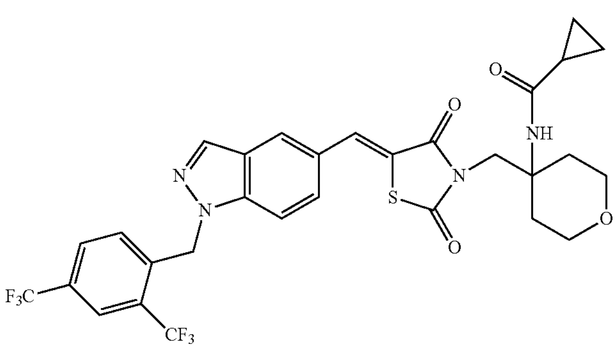 [SMILES: O=C(NC1(CN2C(=O)S/C(=C\c3ccc4c(cnn4Cc4ccc(C(F)(F)F)cc4C(F)(F)F)c3)C2=O)CCOCC1)C1CC1] | 311 | N-(4-{[(5Z)-5-({1-[2,4-Bis(trifluoromethyl)benzyl]-1H-indazol-5-yl}methylidene)-2,4-dioxo-1,3-thiazolidin-3-yl]methyl}tetrahydro-2H-pyran-4-yl)cyclopropanecarboxamide |

TABLE I-continued

| STRUCTURE | COMPOUND # | NAME |
|---|---|---|
| 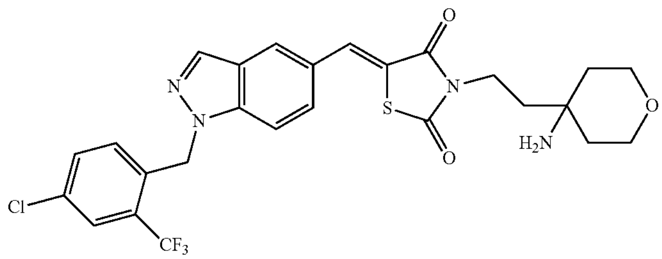 [SMILES: NC1(CCN2C(=O)S/C(=C\c3ccc4c(cnn4Cc4ccc(Cl)cc4C(F)(F)F)c3)C2=O)CCOCC1] | 312 | (5Z)-3-[2-(4-Aminotetrahydro-2H-pyran-4-yl)ethyl]-5-({1-[4-chloro-2-(trifluoromethyl)benzyl]-1H-indazol-5-yl}methylidene)-1,3-thiazolidine-2,4-dione |
| 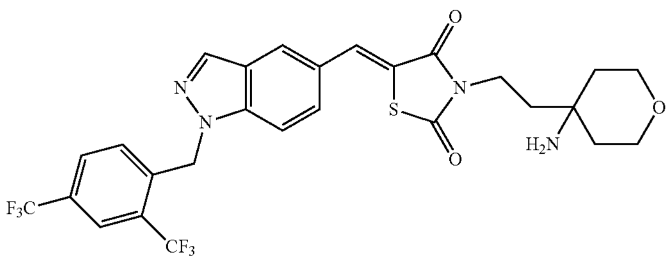 [SMILES: NC1(CCN2C(=O)S/C(=C\c3ccc4c(cnn4Cc4ccc(C(F)(F)F)cc4C(F)(F)F)c3)C2=O)CCOCC1] | 313 | (5Z)-3-[2-(4-Aminotetrahydro-2H-pyran-4-yl)ethyl]-5-({1-[2,4-bis(trifluoromethyl)benzyl]-1H-indazol-5-yl}methylidene)-1,3-thiazolidine-2,4-dione |
| 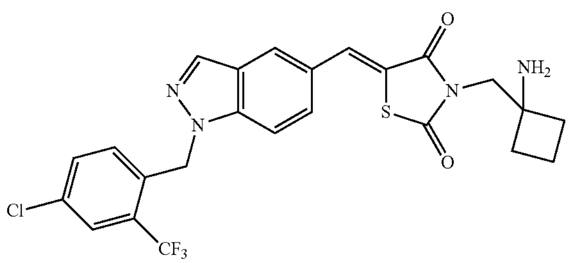 [SMILES: NC1(CN2C(=O)S/C(=C\c3ccc4c(cnn4Cc4ccc(Cl)cc4C(F)(F)F)c3)C2=O)CCC1] | 314 | (5Z)-3-[(1-Aminocyclobutyl)methyl]-5-({1-[4-chloro-2-(trifluoromethyl)benzyl]-1H-indazol-5-yl}methylidene)-1,3-thiazolidine-2,4-dione |
| 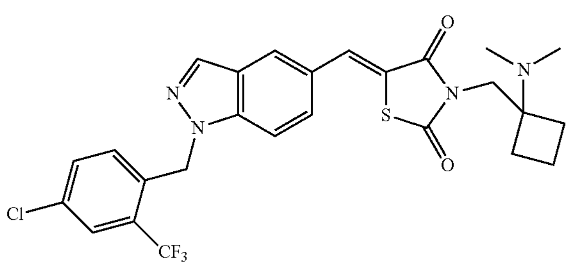 [SMILES: CN(C)C1(CN2C(=O)S/C(=C\c3ccc4c(cnn4Cc4ccc(Cl)cc4C(F)(F)F)c3)C2=O)CCC1] | 315 | (5Z)-5-({1-[4-Chloro-2-(trifluoromethyl)benzyl]-1H-indazol-5-yl}methylidene)-3-{[1-(dimethylamino)cyclobutyl]methyl}-1,3-thiazolidine-2,4-dione |
| 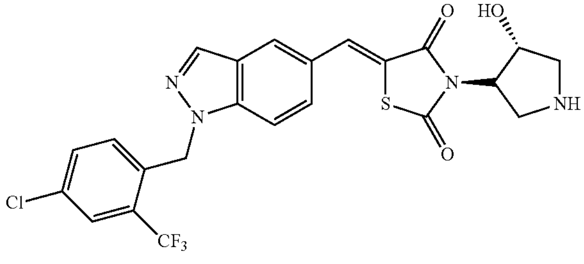 | 316 | (5Z)-5-({1-[4-Chloro-2-(trifluoromethyl)benzyl]-1H-indazol-5-yl}methylidene)-3-[trans-4-hydroxypyrrolidin-3-yl]-1,3-thiazolidine-2,4-dione |

TABLE I-continued

| STRUCTURE | COMPOUND # | NAME |
|---|---|---|
| 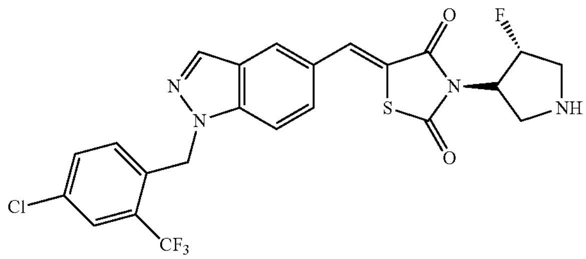 | 317 | (5Z)-5-({1-[4-Chloro-2-(trifluoromethyl)benzyl]-1H-indazol-5-yl}methylidene)-3-[trans-4-fluoropyrrolidin-3-yl]-1,3-thiazolidine-2,4-dione |
| 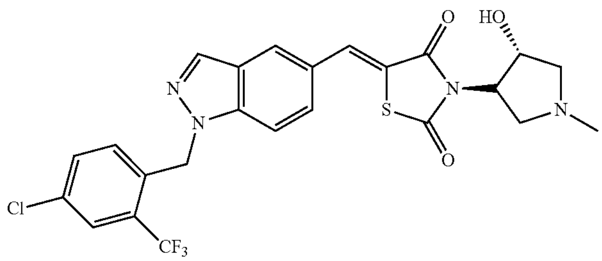 | 318 | (5Z)-5-({1-[4-Chloro-2-(trifluoromethyl)benzyl]-1H-indazol-5-yl}methylidene)-3-[trans-4-hydroxy-1-methylpyrrolidin-3-yl]-1,3-thiazolidine-2,4-dione |
| 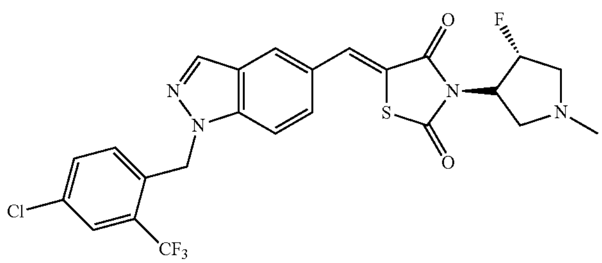 | 319 | (5Z)-5-({1-[4-Chloro-2-(trifluoromethyl)benzyl]-1H-indazol-5-yl}methylidene)-3-[trans-4-fluoro-1-methylpyrrolidin-3-yl]-1,3-thiazolidine-2,4-dione |
| 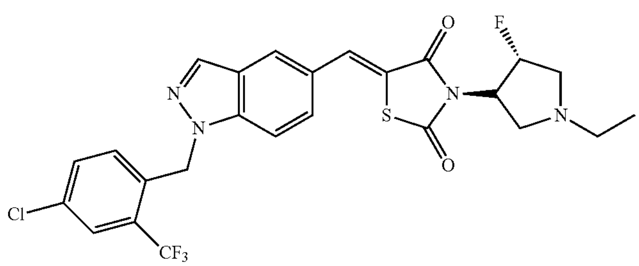 | 320 | (5Z)-5-({1-[4-Chloro-2-(trifluoromethyl)benzyl]-1H-indazol-5-yl}methylidene)-3-[trans-1-ethyl-4-fluoropyrrolidin-3-yl]-1,3-thiazolidine-2,4-dione |
| 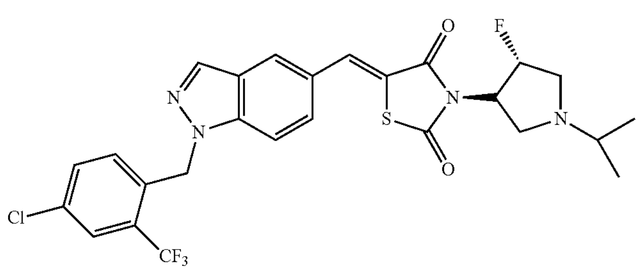 | 321 | (5Z)-5-({1-[4-Chloro-2-(trifluoromethyl)benzyl]-1H-indazol-5-yl}methylidene)-3-[trans-4-fluoro-1-(1-methylethyl)pyrrolidin-3-yl]-1,3-thiazolidine-2,4-dione |

TABLE I-continued

| STRUCTURE | COMPOUND # | NAME |
|---|---|---|
| 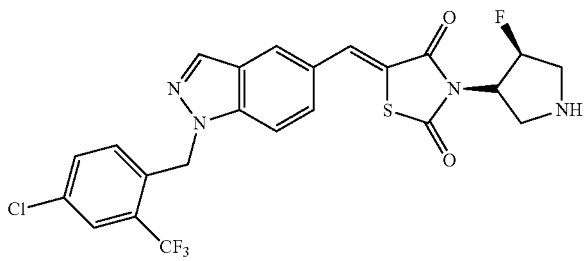 | 322 | (5Z)-5-({1-[4-Chloro-2-(trifluoromethyl)benzyl]-1H-indazol-5-yl}methylidene)-3-[cis-4-fluoropyrrolidin-3-yl]-1,3-thiazolidine-2,4-dione |
| 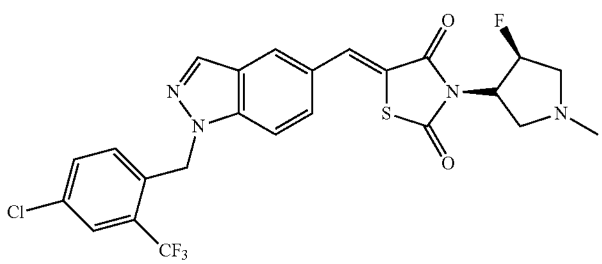 | 323 | (5Z)-5-({1-[4-Chloro-2-(trifluoromethyl)benzyl]-1H-indazol-5-yl}methylidene)-3-[cis-4-fluoro-1-methylpyrrolidin-3-yl]-1,3-thiazolidine-2,4-dione |
| 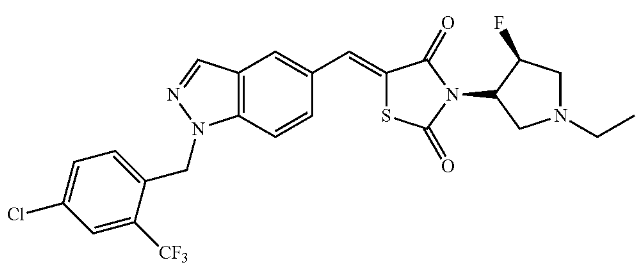 | 324 | (5Z)-5-({1-[4-Chloro-2-(trifluoromethyl)benzyl]-1H-indazol-5-yl}methylidene)-3-[cis-1-ethyl-4-fluoropyrrolidin-3-yl]-1,3-thiazolidine-2,4-dione |
| 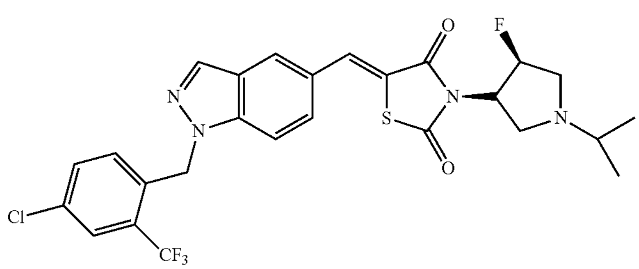 | 325 | (5Z)-5-({1-[4-Chloro-2-(trifluoromethyl)benzyl]-1H-indazol-5-yl}methylidene)-3-[cis-4-fluoro-1-(1-methylethyl)pyrrolidin-3-yl]-1,3-thiazolidine-2,4-dione |
| 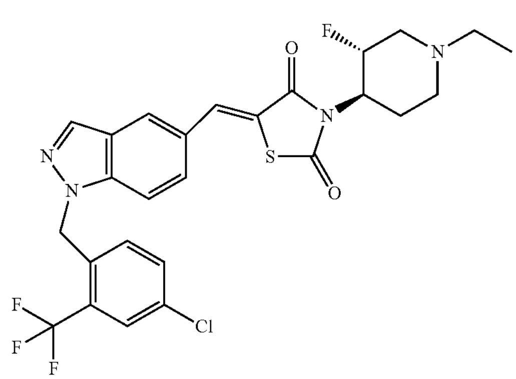 [SMILES: CCN1CC[C@@H](N2C(=O)S/C(=C\c3ccc4c(cnn4Cc4ccc(Cl)cc4C(F)(F)F)c3)C2=O)[C@H](F)C1] | 326 | (5Z)-5-({1-[4-Chloro-2-(trifluoromethyl)benzyl]-1H-indazol-5-yl}methylidene)-3-[trans-1-ethyl-3-fluoropiperidin-4-yl]-1,3-thiazolidine-2,4-dione |

TABLE I-continued

| STRUCTURE | COMPOUND # | NAME |
|---|---|---|
| 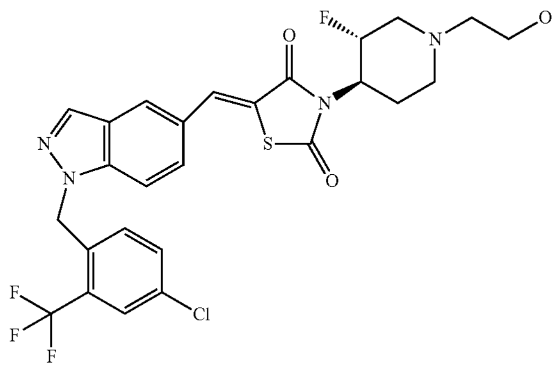 [SMILES: O=C1S/C(=C\c2ccc3c(cnn3Cc3ccc(Cl)cc3C(F)(F)F)c2)C(=O)N1[C@@H]1CCN(CCO)C[C@H]1F] | 327 | (5Z)-5-({1-[4-Chloro-2-(trifluoromethyl)benzyl]-1H-indazol-5-yl}methylidene)-3-[trans-3-fluoro-1-(2-hydroxyethyl)piperidin-4-yl]-1,3-thiazolidine-2,4-dione |
| 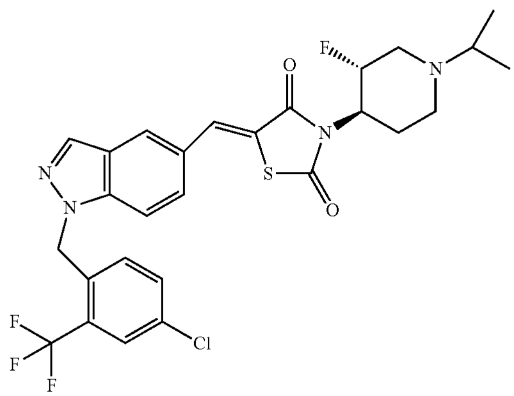 [SMILES: CC(C)N1CC[C@@H](N2C(=O)S/C(=C\c3ccc4c(cnn4Cc4ccc(Cl)cc4C(F)(F)F)c3)C2=O)[C@H](F)C1] | 328 | (5Z)-5-({1-[4-Chloro-2-(trifluoromethyl)benzyl]-1H-indazol-5-yl}methylidene)-3-[trans-3-fluoro-1-(1-methylethyl)piperidin-4-yl]-1,3-thiazolidine-2,4-dione |
| 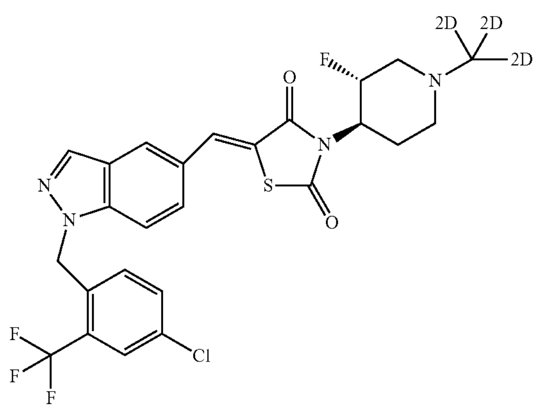 | 329 | (5Z)-5-({1-[4-Chloro-2-(trifluoromethyl)benzyl]-1H-indazol-5-yl}methylidene)-3-[trans-3-fluoro-1-(1,1,1-d$_3$)-methylpiperidin-4-yl]-1,3-thiazolidine-2,4-dione |
| 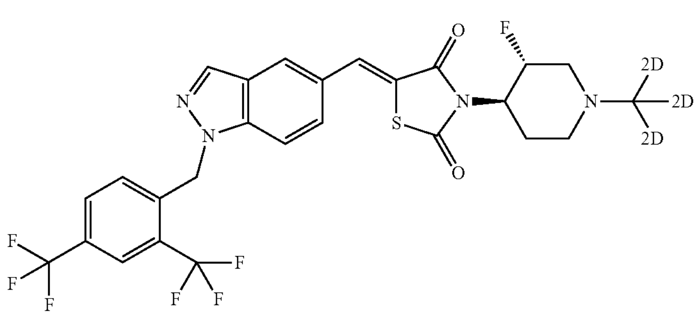 | 330 | (5Z)-5-({1-[2,4-Bis(trifluoromethyl)benzyl]-1H-indazol-5-yl}methylidene)-3-[trans-3-fluoro-1-(1,1,1-d$_3$)-methylpiperidin-4-yl]-1,3-thiazolidine-2,4-dione |

TABLE I-continued

| STRUCTURE | COMPOUND # | NAME |
|---|---|---|
| 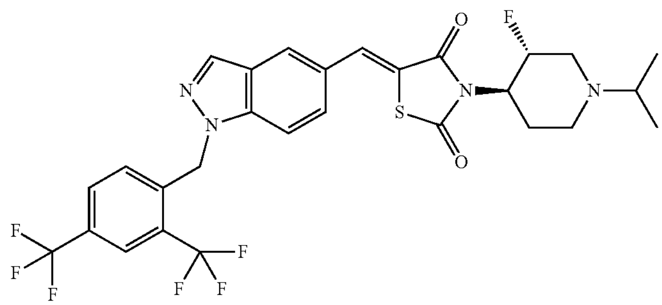 [SMILES: CC(C)N1CC[C@@H](N2C(=O)S/C(=C\c3ccc4c(cnn4Cc4ccc(C(F)(F)F)cc4C(F)(F)F)c3)C2=O)[C@H](F)C1] | 331 | (5Z)-5-({1-[2,4-Bis(trifluoromethyl)benzyl]-1H-indazol-5-yl}methylidene)-3-[trans-3-fluoro-1-(1-methylethyl)piperidin-4-yl]-1,3-thiazolidine-2,4-dione |
| 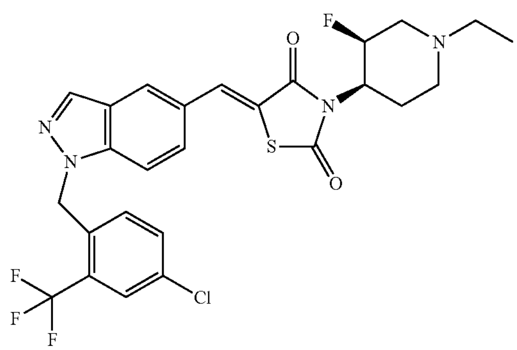 [SMILES: CCN1CC[C@@H](N2C(=O)S/C(=C\c3ccc4c(cnn4Cc4ccc(Cl)cc4C(F)(F)F)c3)C2=O)[C@@H](F)C1] | 332 | (5Z)-5-({1-[4-Chloro-2-(trifluoromethyl)benzyl]-1H-indazol-5-yl}methylidene)-3-[cis-1-ethyl-3-fluoropiperidin-4-yl]-1,3-thiazolidine-2,4-dione |
| 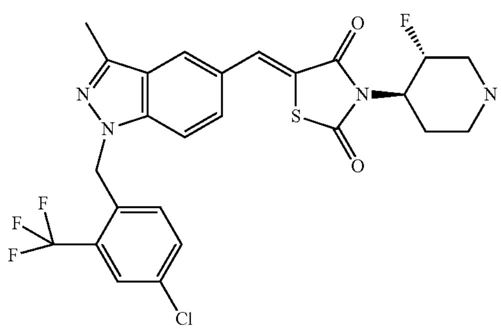 [SMILES: Cc1nn(Cc2ccc(Cl)cc2C(F)(F)F)c2ccc(/C=C3\SC(=O)N([C@@H]4CCNC[C@H]4F)C3=O)cc12] | 333 | (5Z)-5-({1-[4-Chloro-2-(trifluoromethyl)benzyl]-3-methyl-1H-indazol-5-yl}methylidene)-3-[trans-3-fluoropiperidin-4-yl]-1,3-thiazolidine-2,4-dione |
| 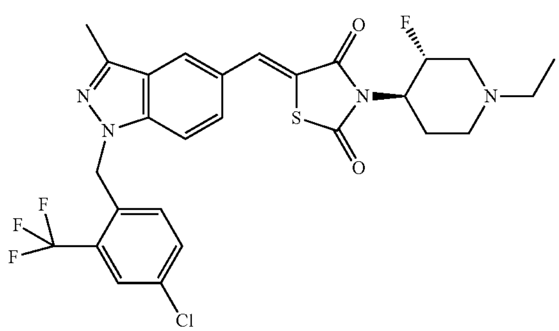 [SMILES: CCN1CC[C@@H](N2C(=O)S/C(=C\c3ccc4c(c3)c(C)nn4Cc3ccc(Cl)cc3C(F)(F)F)C2=O)[C@H](F)C1] | 334 | (5Z)-5-({1-[4-Chloro-2-(trifluoromethyl)benzyl]-3-methyl-1H-indazol-5-yl}methylidene)-3-[trans-1-ethyl-3-fluoropiperidin-4-yl]-1,3-thiazolidine-2,4-dione |

TABLE I-continued

| STRUCTURE | COMPOUND # | NAME |
|---|---|---|
| 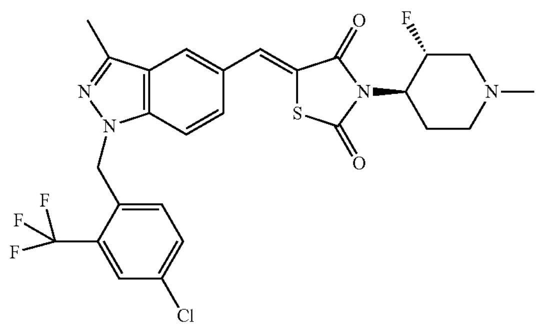 [SMILES: Cc1nn(Cc2ccc(Cl)cc2C(F)(F)F)c2ccc(/C=C3\SC(=O)N([C@@H]4CCN(C)C[C@H]4F)C3=O)cc12] | 335 | (5Z)-5-({1-[4-Chloro-2-(trifluoromethyl)benzyl]-3-methyl-1H-indazol-5-yl}methylidene)-3-[trans-3-fluoro-1-methylpiperidin-4-yl]-1,3-thiazolidine-2,4-dione |
| 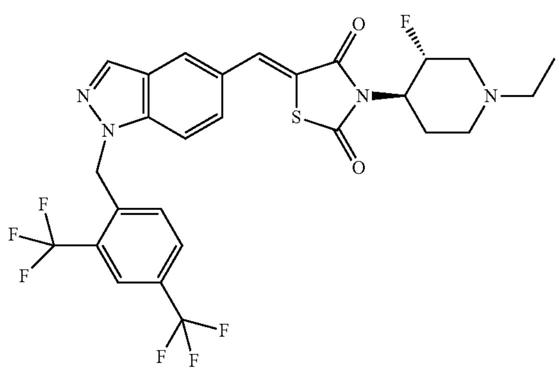 [SMILES: CCN1CC[C@@H](N2C(=O)S/C(=C\c3ccc4c(cnn4Cc4ccc(C(F)(F)F)cc4C(F)(F)F)c3)C2=O)[C@H](F)C1] | 336 | (5Z)-5-({1-[2,4-Bis(trifluoromethyl)benzyl]-1H-indazol-5-yl}methylidene)-3-[trans-1-ethyl-3-fluoropiperidin-4-yl]-1,3-thiazolidine-2,4-dione |
| 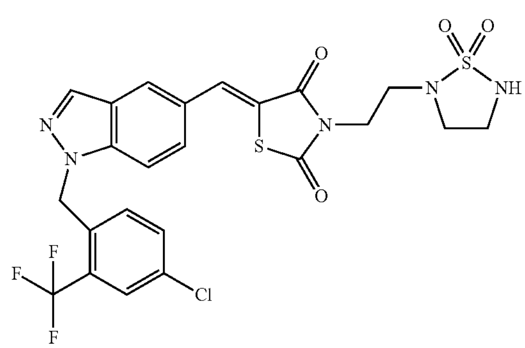 [SMILES: O=C1S/C(=C\c2ccc3c(cnn3Cc3ccc(Cl)cc3C(F)(F)F)c2)C(=O)N1CCN1CCNS1(=O)=O] | 337 | (5Z)-5-({1-[4-Chloro-2-(trifluoromethyl)benzyl]-1H-indazol-5-yl}methylidene)-3-[2-(1,1-dioxido-1,2,5-thiadiazolidin-2-yl)ethyl]-1,3-thiazolidine-2,4-dione |
| 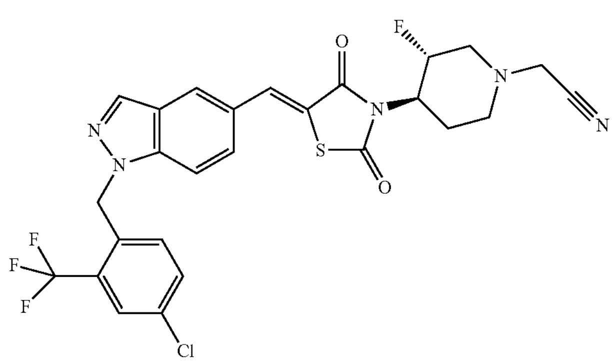 [SMILES: N#CCN1CC[C@@H](N2C(=O)S/C(=C\c3ccc4c(cnn4Cc4ccc(Cl)cc4C(F)(F)F)c3)C2=O)[C@H](F)C1] | 338 | trans-4-[(5Z)-5-({1-[4-Chloro-2-(trifluoromethyl)benzyl]-1H-indazol-5-yl}methylidene)-2,4-dioxo-1,3-thiazolidin-3-yl]-3-fluoropiperidin-1-yl}acetonitrile |

TABLE I-continued

| STRUCTURE | COMPOUND # | NAME |
|---|---|---|
| 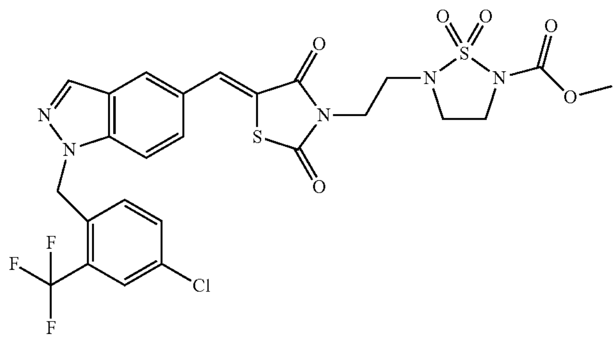 [SMILES: COC(=O)N1CCN(CCN2C(=O)S/C(=C\c3ccc4c(cnn4Cc4ccc(Cl)cc4C(F)(F)F)c3)C2=O)S1(=O)=O] | 339 | Methyl 5-{2-[(5Z)-5-({1-[4-chloro-2-(trifluoromethyl)benzyl]-1H-indazol-5-yl}methylidene)-2,4-dioxo-1,3-thiazolidin-3-yl]ethyl}-1,2,5-thiadiazolidine-2-carboxylate 1,1-dioxide |
| 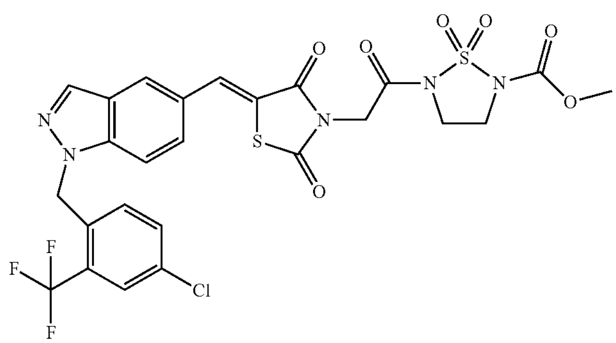 [SMILES: COC(=O)N1CCN(C(=O)CN2C(=O)S/C(=C\c3ccc4c(cnn4Cc4ccc(Cl)cc4C(F)(F)F)c3)C2=O)S1(=O)=O] | 340 | Methyl 5-{[(5Z)-5-({1-[4-chloro-2-(trifluoromethyl)benzyl]-1H-indazol-5-yl}methylidene)-2,4-dioxo-1,3-thiazolidin-3-yl]acetyl}-1,2,5-thiadiazolidine-2-carboxylate 1,1-dioxide |
| 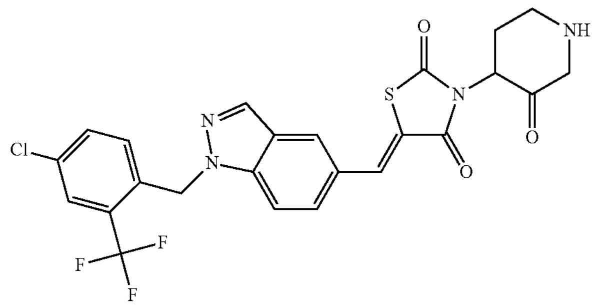 [SMILES: O=C1CNCCC1N1C(=O)S/C(=C\c2ccc3c(cnn3Cc3ccc(Cl)cc3C(F)(F)F)c2)C1=O] | 341 | (5Z)-5-({1-[4-Chloro-2-(trifluoromethyl)benzyl]-1H-indazol-5-yl}methylidene)-3-(3-oxopiperidin-4-yl)-1,3-thiazolidine-2,4-dione |
| 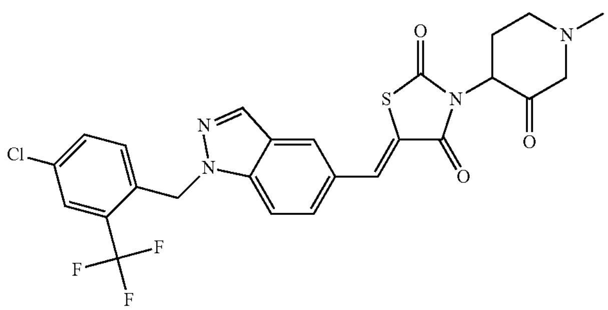 [SMILES: CN1CCC(N2C(=O)S/C(=C\c3ccc4c(cnn4Cc4ccc(Cl)cc4C(F)(F)F)c3)C2=O)C(=O)C1] | 342 | (5Z)-5-({1-[4-Chloro-2-(trifluoromethyl)benzyl]-1H-indazol-5-yl}methylidene)-3-(1-methyl-3-oxopiperidin-4-yl)-1,3-thiazolidine-2,4-dione |

TABLE I-continued

| STRUCTURE | COMPOUND # | NAME |
|---|---|---|
| 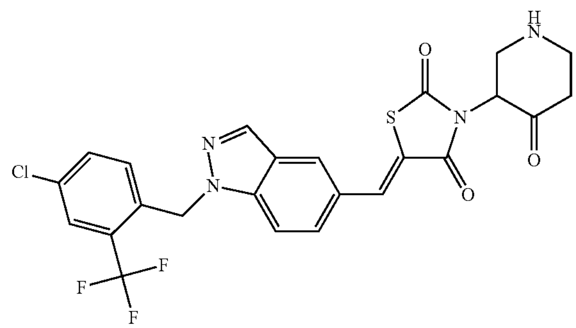 [SMILES: O=C1CCNCC1N1C(=O)S/C(=C\c2ccc3c(cnn3Cc3ccc(Cl)cc3C(F)(F)F)c2)C1=O] | 343 | (5Z)-5-({1-[4-Chloro-2-(trifluoromethyl)benzyl]-1H-indazol-5-yl}methylidene)-3-(4-oxopiperidin-3-yl)-1,3-thiazolidine-2,4-dione |
| 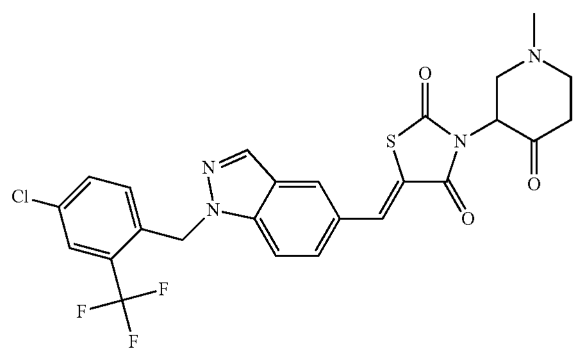 [SMILES: CN1CCC(=O)C(N2C(=O)S/C(=C\c3ccc4c(cnn4Cc4ccc(Cl)cc4C(F)(F)F)c3)C2=O)C1] | 344 | (5Z)-5-({1-[4-Chloro-2-(trifluoromethyl)benzyl]-1H-indazol-5-yl}methylidene)-3-(1-methyl-4-oxopiperidin-3-yl)-1,3-thiazolidine-2,4-dione |
| 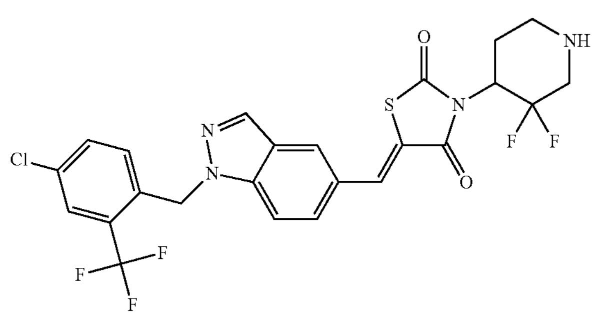 [SMILES: O=C1S/C(=C\c2ccc3c(cnn3Cc3ccc(Cl)cc3C(F)(F)F)c2)C(=O)N1C1CCNCC1(F)F] | 345 | (5Z)-5-({1-[4-Chloro-2-(trifluoromethyl)benzyl]-1H-indazol-5-yl}methylidene)-3-(3,3-difluoropiperidin-4-yl)-1,3-thiazolidine-2,4-dione |
| 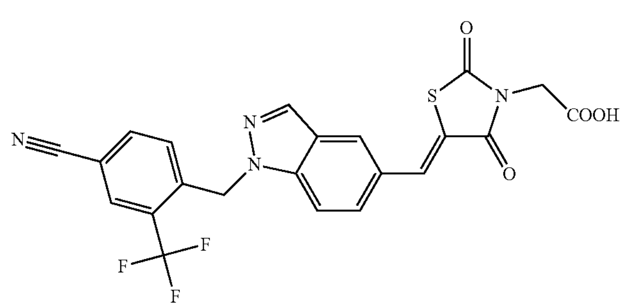 [SMILES: N#Cc1ccc(Cn2ncc3cc(/C=C4\SC(=O)N(CC(=O)O)C4=O)ccc32)c(C(F)(F)F)c1] | 346 | [(5Z)-5-({1-[4-Cyano-2-(trifluoromethyl)benzyl]-1H-indazol-5-yl}methylidene)-2,4-dioxo-1,3-thiazolidin-3-yl]acetic acid |

TABLE I-continued

| STRUCTURE | COMPOUND # | NAME |
|---|---|---|
| 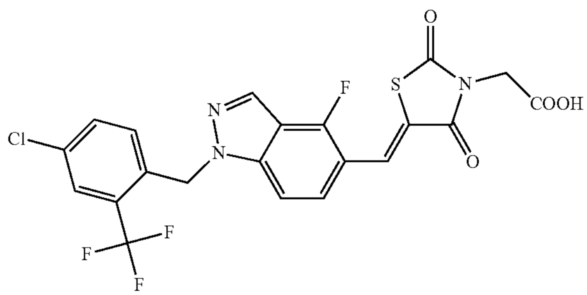 [SMILES: O=C(O)CN1C(=O)S/C(=C\c2ccc3c(cnn3Cc3ccc(Cl)cc3C(F)(F)F)c2F)C1=O] | 347 | [(5Z)-5-({1-[4-Chloro-2-(trifluoromethyl)benzyl]-4-fluoro-1H-indazol-5-yl}methylidene)-2,4-dioxo-1,3-thiazolidin-3-yl]acetic acid |
| 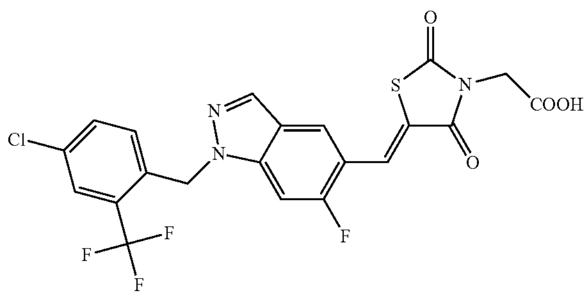 [SMILES: O=C(O)CN1C(=O)S/C(=C\c2cc3cnn(Cc4ccc(Cl)cc4C(F)(F)F)c3cc2F)C1=O] | 348 | [(5Z)-5-({1-[4-Chloro-2-(trifluoromethyl)benzyl]-6-fluoro-1H-indazol-5-yl}methylidene)-2,4-dioxo-1,3-thiazolidin-3-yl]acetic acid |
| 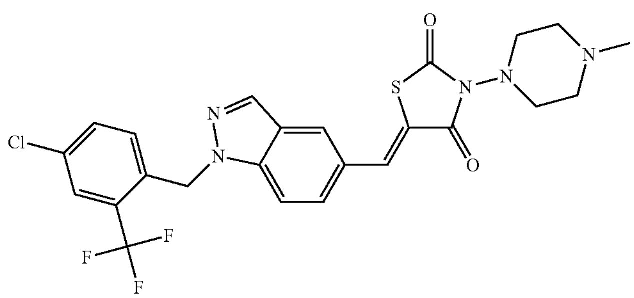 [SMILES: CN1CCN(N2C(=O)S/C(=C\c3ccc4c(cnn4Cc4ccc(Cl)cc4C(F)(F)F)c3)C2=O)CC1] | 349 | (5Z)-5-({1-[4-Chloro-2-(trifluoromethyl)benzyl]-1H-indazol-5-yl}methylidene)-3-(4-methylpiperazin-1-yl)-1,3-thiazolidine-2,4-dione |
| 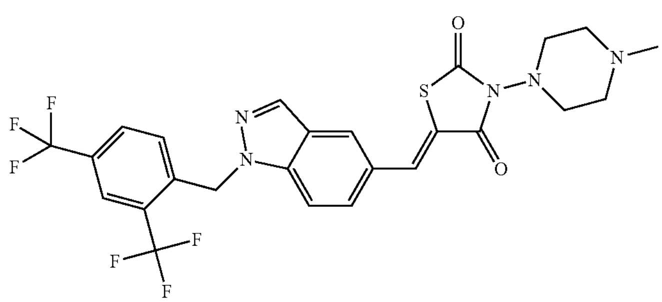 [SMILES: CN1CCN(N2C(=O)S/C(=C\c3ccc4c(cnn4Cc4ccc(C(F)(F)F)cc4C(F)(F)F)c3)C2=O)CC1] | 350 | (5Z)-5-({1-[2,4-Bis(trifluoromethyl)benzyl]-1H-indazol-5-yl}methylidene)-3-(4-methylpiperazin-1-yl)-1,3-thiazolidine-2,4-dione |
| 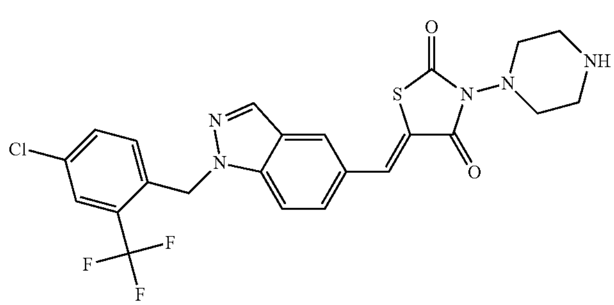 [SMILES: O=C1S/C(=C\c2ccc3c(cnn3Cc3ccc(Cl)cc3C(F)(F)F)c2)C(=O)N1N1CCNCC1] | 351 | (5Z)-5-({1-[4-Chloro-2-(trifluoromethyl)benzyl]-1H-indazol-5-yl}methylidene)-3-piperazin-1-yl-1,3-thiazolidine-2,4-dione |

TABLE I-continued

| STRUCTURE | COMPOUND # | NAME |
|---|---|---|
| 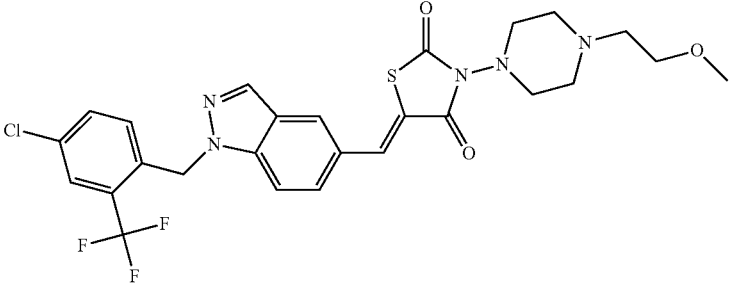 [SMILES: COCCN1CCN(N2C(=O)S/C(=C\c3ccc4c(cnn4Cc4ccc(Cl)cc4C(F)(F)F)c3)C2=O)CC1] | 352 | (5Z)-5-({1-[4-Chloro-2-(trifluoromethyl)benzyl]-1H-indazol-5-yl}methylidene)-3-[4-(2-methoxyethyl)piperazin-1-yl]-1,3-thiazolidine-2,4-dione |
| 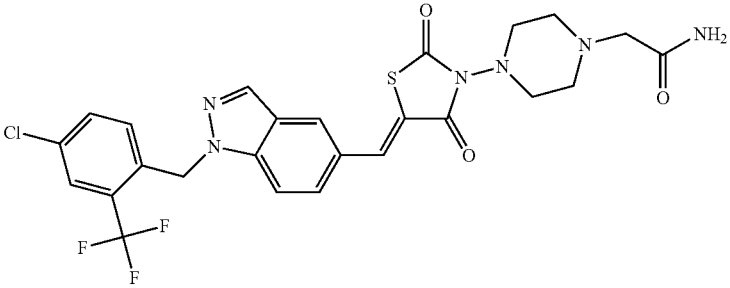 [SMILES: NC(=O)CN1CCN(N2C(=O)S/C(=C\c3ccc4c(cnn4Cc4ccc(Cl)cc4C(F)(F)F)c3)C2=O)CC1] | 353 | 2-{4-[(5Z)-5-({1-[4-Chloro-2-(trifluoromethyl)benzyl]-1H-indazol-5-yl}methylidene)-2,4-dioxo-1,3-thiazolidin-3-yl]piperazin-1-yl}acetamide |
| 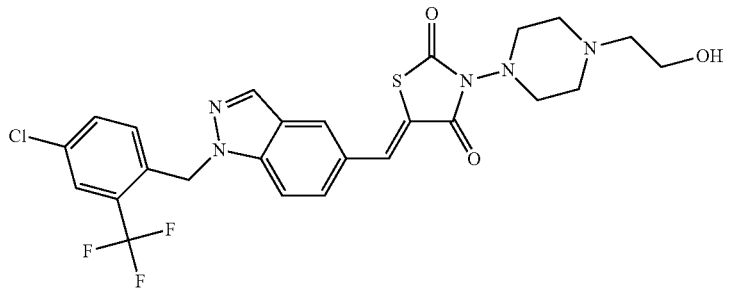 [SMILES: O=C1S/C(=C\c2ccc3c(cnn3Cc3ccc(Cl)cc3C(F)(F)F)c2)C(=O)N1N1CCN(CCO)CC1] | 354 | (5Z)-5-({1-[4-Chloro-2-(trifluoromethyl)benzyl]-1H-indazol-5-yl}methylidene)-3-[4-(2-hydroxyethyl)piperazin-1-yl]-1,3-thiazolidine-2,4-dione |
| 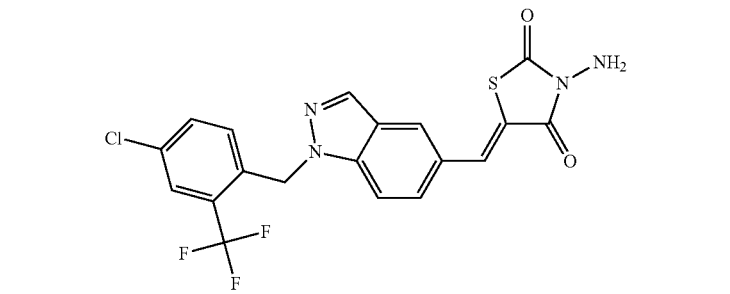 [SMILES: NN1C(=O)S/C(=C\c2ccc3c(cnn3Cc3ccc(Cl)cc3C(F)(F)F)c2)C1=O] | 355 | (5Z)-3-Amino-5-({1-[4-chloro-2-(trifluoromethyl)benzyl]-1H-indazol-5-yl}methylidene)-1,3-thiazolidine-2,4-dione |
| 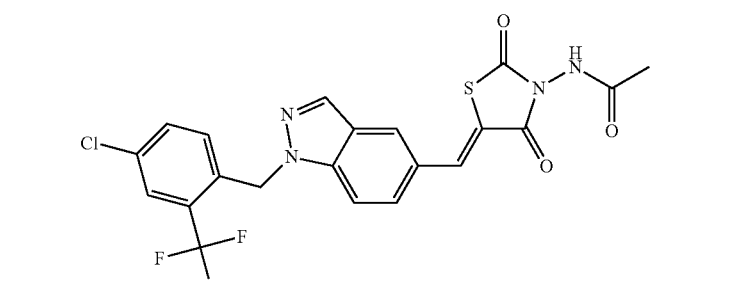 | 356 | N-[(5Z)-5-({1-[4-Chloro-2-(trifluoromethyl)benzyl]-1H-indazol-5-yl}methylidene)-2,4-dioxo-1,3-thiazolidin-3-yl]acetamide |

TABLE I-continued

| STRUCTURE | COMPOUND # | NAME |
|---|---|---|
| 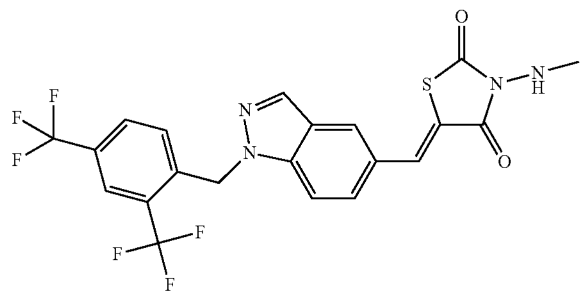 [SMILES: CNN1C(=O)S/C(=C\c2ccc3c(cnn3Cc3ccc(C(F)(F)F)cc3C(F)(F)F)c2)C1=O] | 357 | (5Z)-5-({1-[2,4-Bis(trifluoromethyl)benzyl]-1H-indazol-5-yl}methylidene)-3-(methylamino)-1,3-thiazolidine-2,4-dione |
| 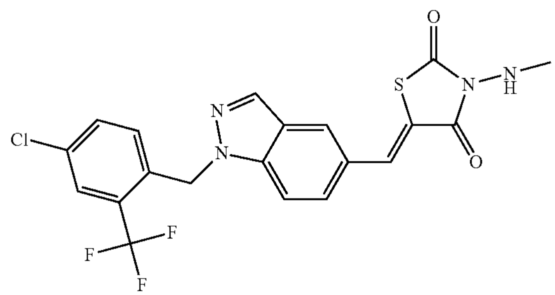 [SMILES: CNN1C(=O)S/C(=C\c2ccc3c(cnn3Cc3ccc(Cl)cc3C(F)(F)F)c2)C1=O] | 358 | (5Z)-5-({1-[4-Chloro-2-(trifluoromethyl)benzyl]-1H-indazol-5-yl}methylidene)-3-(methylamino)-1,3-thiazolidine-2,4-dione |
| 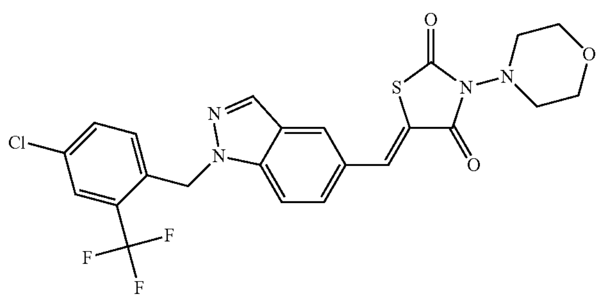 [SMILES: O=C1S/C(=C\c2ccc3c(cnn3Cc3ccc(Cl)cc3C(F)(F)F)c2)C(=O)N1N1CCOCC1] | 359 | (5Z)-5-({1-[4-Chloro-2-(trifluoromethyl)benzyl]-1H-indazol-5-yl}methylidene)-3-morpholin-4-yl-1,3-thiazolidine-2,4-dione |
| 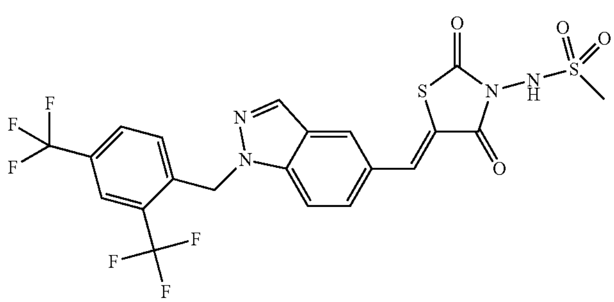 [SMILES: CS(=O)(=O)NN1C(=O)S/C(=C\c2ccc3c(cnn3Cc3ccc(C(F)(F)F)cc3C(F)(F)F)c2)C1=O] | 360 | N-[(5Z)-5-({1-[2,4-Bis(trifluoromethyl)benzyl]-1H-indazol-5-yl}methylidene)-2,4-dioxo-1,3-thiazolidin-3-yl]methanesulfonamide |
| 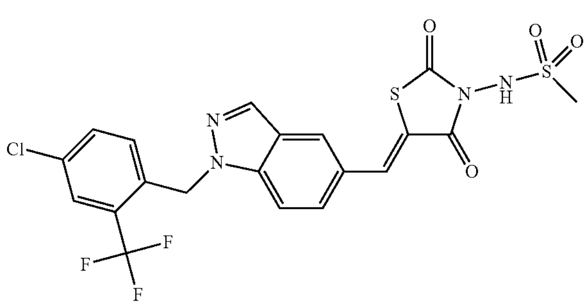 [SMILES: CS(=O)(=O)NN1C(=O)S/C(=C\c2ccc3c(cnn3Cc3ccc(Cl)cc3C(F)(F)F)c2)C1=O] | 361 | N-[(5Z)-5-({1-[4-Chloro-2-(trifluoromethyl)benzyl]-1H-indazol-5-yl}methylidene)-2,4-dioxo-1,3-thiazolidin-3-yl]methanesulfonamide |

TABLE I-continued

| STRUCTURE | COMPOUND # | NAME |
|---|---|---|
| 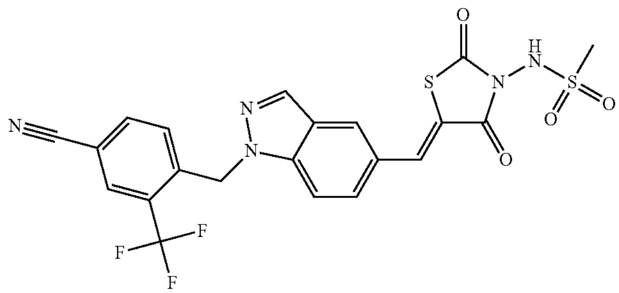 [SMILES: CS(=O)(=O)NN1C(=O)S/C(=C\c2ccc3c(cnn3Cc3ccc(C#N)cc3C(F)(F)F)c2)C1=O] | 362 | N-[(5Z)-5-({1-[4-Cyano-2-(trifluoromethyl)benzyl]-1H-indazol-5-yl}methylidene)-2,4-dioxo-1,3-thiazolidin-3-yl]methanesulfonamide |
| 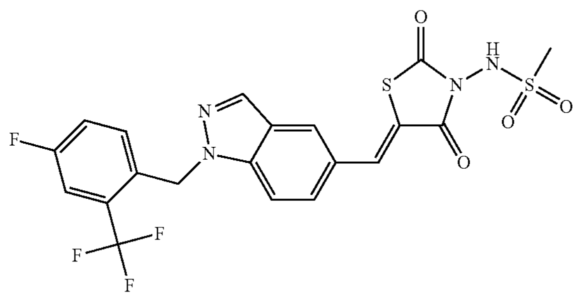 [SMILES: CS(=O)(=O)NN1C(=O)S/C(=C\c2ccc3c(cnn3Cc3ccc(F)cc3C(F)(F)F)c2)C1=O] | 363 | N-[(5Z)-5-({1-[4-Fluoro-2-(trifluoromethyl)benzyl]-1H-indazol-5-yl}methylidene)-2,4-dioxo-1,3-thiazolidin-3-yl]methanesulfonamide |
| 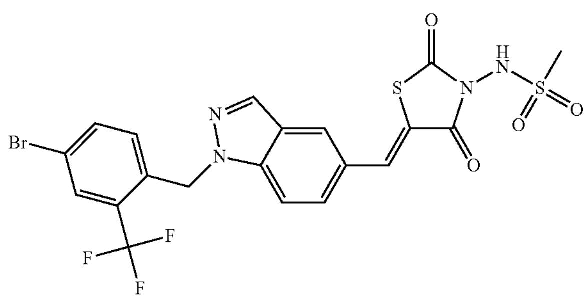 [SMILES: CS(=O)(=O)NN1C(=O)S/C(=C\c2ccc3c(cnn3Cc3ccc(Br)cc3C(F)(F)F)c2)C1=O] | 364 | N-[(5Z)-5-({1-[4-Bromo-2-(trifluoromethyl)benzyl]-1H-indazol-5-yl}methylidene)-2,4-dioxo-1,3-thiazolidin-3-yl]methanesulfonamide |
| 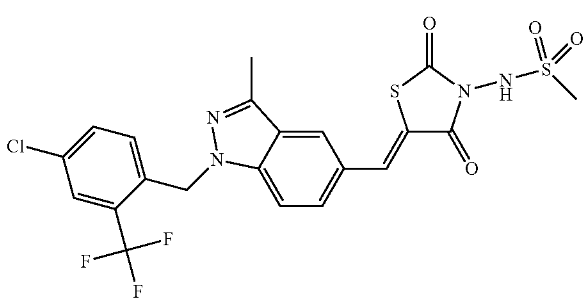 | 365 | N-[(5Z)-5-({1-[4-Chloro-2-(trifluoromethyl)benzyl]-3-methyl-1H-indazol-5-yl}methylidene)-2,4-dioxo-1,3-thiazolidin-3-yl]methanesulfonamide |
| 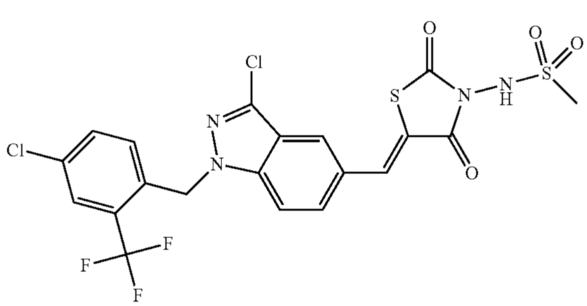 [SMILES: CS(=O)(=O)NN1C(=O)S/C(=C\c2ccc3c(c2)c(Cl)nn3Cc2ccc(Cl)cc2C(F)(F)F)C1=O] | 366 | N-[(5Z)-5-({3-Chloro-1-[4-chloro-2-(trifluoromethyl)benzyl]-1H-indazol-5-yl}methylidene)-2,4-dioxo-1,3-thiazolidin-3-yl]methanesulfonamide |

TABLE I-continued

| STRUCTURE | COMPOUND # | NAME |
|---|---|---|
| 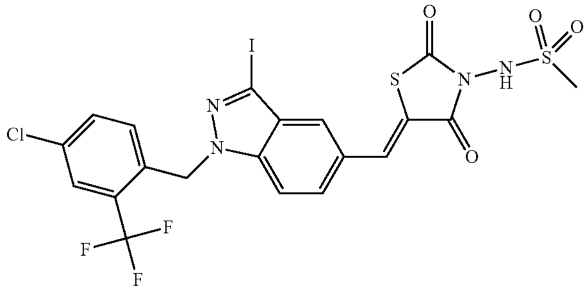 | 367 | N-[(5Z)-5-({1-[4-Chloro-2-(trifluoromethyl)benzyl]-3-iodo-1H-indazol-5-yl}methylidene)-2,4-dioxo-1,3-thiazolidin-3-yl]methanesulfonamide |
| 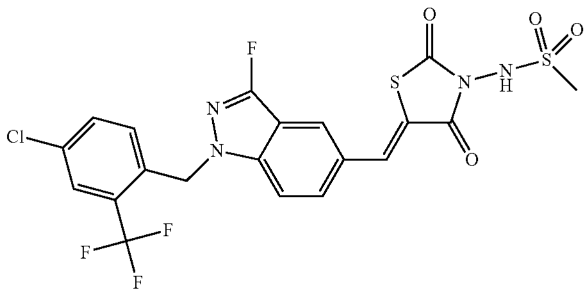 [SMILES: CS(=O)(=O)NN1C(=O)S/C(=C\c2ccc3c(c2)c(I)nn3Cc2ccc(Cl)cc2C(F)(F)F)C1=O] | 368 | N-[(5Z)-5-({1-[4-Chloro-2-(trifluoromethyl)benzyl]-3-fluoro-1H-indazol-5-yl}methylidene)-2,4-dioxo-1,3-thiazolidin-3-yl]methanesulfonamide |
| 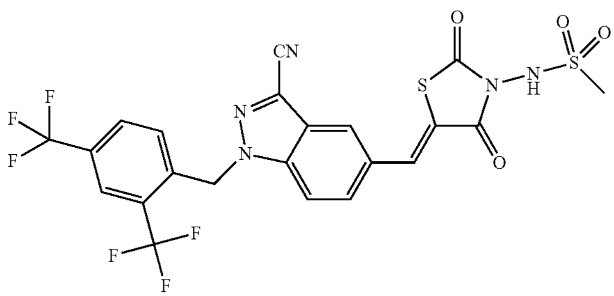 [SMILES: CS(=O)(=O)NN1C(=O)S/C(=C\c2ccc3c(c2)c(C#N)nn3Cc2ccc(C(F)(F)F)cc2C(F)(F)F)C1=O] | 369 | N-[(5Z)-5-({1-[2,4-Bis(trifluoromethyl)benzyl]-3-cyano-1H-indazol-5-yl}methylidene)-2,4-dioxo-1,3-thiazolidin-3-yl]methanesulfonamide |
| 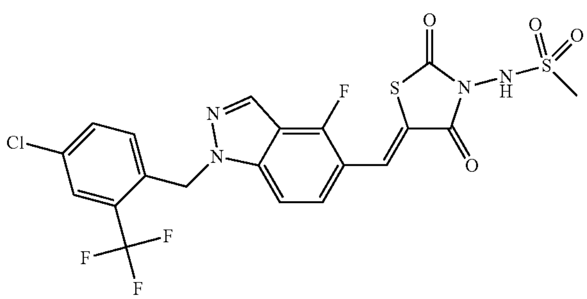 [SMILES: CS(=O)(=O)NN1C(=O)S/C(=C\c2ccc3c(cnn3Cc3ccc(Cl)cc3C(F)(F)F)c2F)C1=O] | 370 | N-[(5Z)-5-({1-[4-Chloro-2-(trifluoromethyl)benzyl]-4-fluoro-1H-indazol-5-yl}methylidene)-2,4-dioxo-1,3-thiazolidin-3-yl]methanesulfonamide |
| 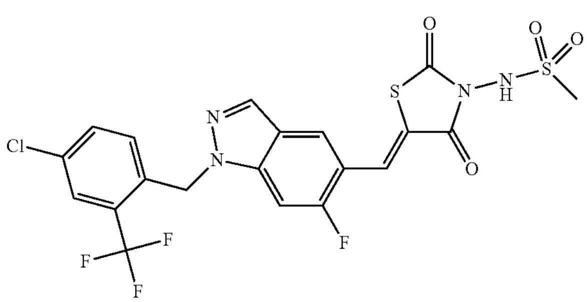 [SMILES: CS(=O)(=O)NN1C(=O)S/C(=C\c2cc3cnn(Cc4ccc(Cl)cc4C(F)(F)F)c3cc2F)C1=O] | 371 | N-[(5Z)-5-({1-[4-Chloro-2-(trifluoromethyl)benzyl]-6-fluoro-1H-indazol-5-yl}methylidene)-2,4-dioxo-1,3-thiazolidin-3-yl]methanesulfonamide |

TABLE I-continued

| STRUCTURE | COMPOUND # | NAME |
|---|---|---|
| 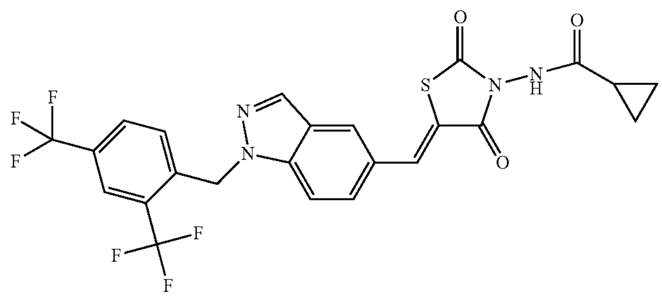 [SMILES: O=C(NN1C(=O)S/C(=C\c2ccc3c(cnn3Cc3ccc(C(F)(F)F)cc3C(F)(F)F)c2)C1=O)C1CC1] | 372 | N-[(5Z)-5-({1-[2,4-Bis(trifluoromethyl)benzyl]-1H-indazol-5-yl}methylidene)-2,4-dioxo-1,3-thiazolidin-3-yl]cyclopropanecarboxamide |
| 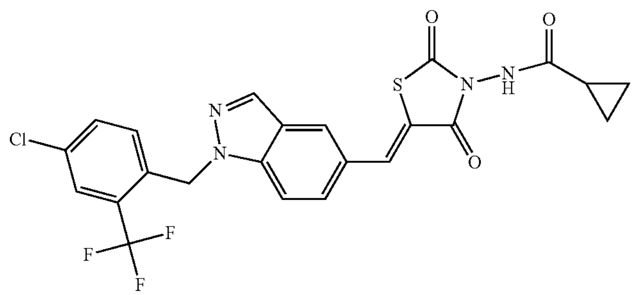 [SMILES: O=C(NN1C(=O)S/C(=C\c2ccc3c(cnn3Cc3ccc(Cl)cc3C(F)(F)F)c2)C1=O)C1CC1] | 373 | N-[(5Z)-5-({1-[4-Chloro-2-(trifluoromethyl)benzyl]-1H-indazol-5-yl}methylidene)-2,4-dioxo-1,3-thiazolidin-3-yl]cyclopropanecarboxamide |
| 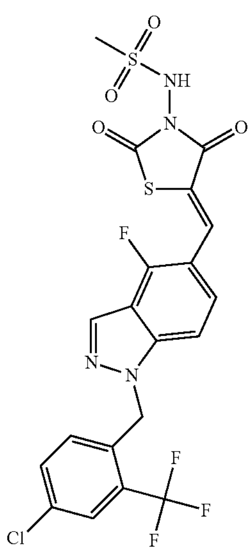 [SMILES: CS(=O)(=O)NN1C(=O)S/C(=C\c2ccc3c(cnn3Cc3ccc(Cl)cc3C(F)(F)F)c2F)C1=O] | 374 | N-[(5Z)-5-({1-[4-Chloro-2-(trifluoromethyl)benzyl]-4-fluoro-1H-indazol-5-yl}methylidene)-2,4-dioxo-1,3-thiazolidin-3-yl]methanesulfonamide |
| 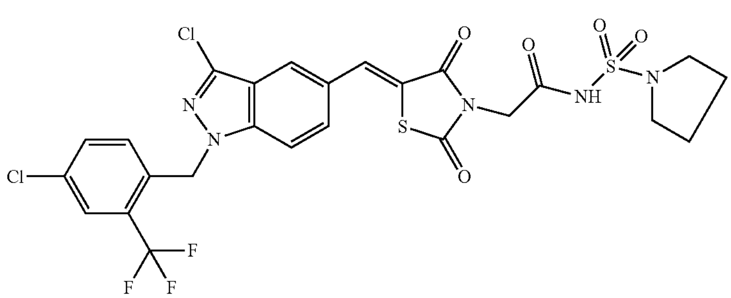 [SMILES: O=C(CN1C(=O)S/C(=C\c2ccc3c(c2)c(Cl)nn3Cc2ccc(Cl)cc2C(F)(F)F)C1=O)NS(=O)(=O)N1CCCC1] | 375 | 2-[(5Z)-5-({3-Chloro-1-[4-chloro-2-(trifluoromethyl)benzyl]-1H-indazol-5-yl}methylidene)-2,4-dioxo-1,3-thiazolidin-3-yl]-N-(pyrrolidin-1-ylsulfonyl)acetamide |

TABLE I-continued

| STRUCTURE | COMPOUND # | NAME |
|---|---|---|
| 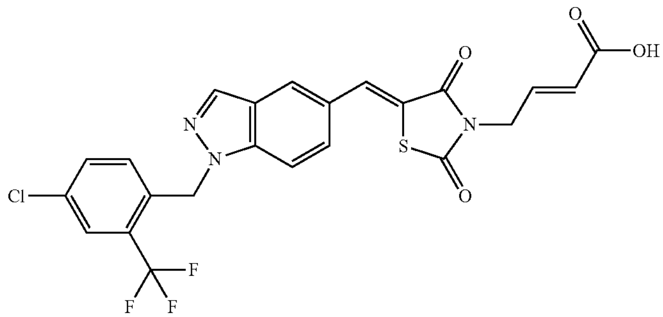 [SMILES: O=C(O)/C=C/CN1C(=O)S/C(=C\c2ccc3c(cnn3Cc3ccc(Cl)cc3C(F)(F)F)c2)C1=O] | 376 | (2E)-4-[(5Z)-5-({1-[4-Chloro-2-(trifluoromethyl)benzyl]-1H-indazol-5-yl}methylidene)-2,4-dioxo-1,3-thiazolidin-3-yl]but-2-enoic acid |
| 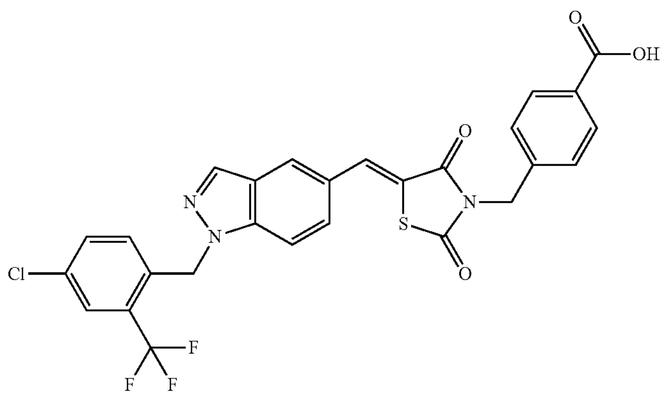 [SMILES: O=C(O)c1ccc(CN2C(=O)S/C(=C\c3ccc4c(cnn4Cc4ccc(Cl)cc4C(F)(F)F)c3)C2=O)cc1] | 377 | 4-{[(5Z)-5-({1-[4-Chloro-2-(trifluoromethyl)benzyl]-1H-indazol-5-yl}methylidene)-2,4-dioxo-1,3-thiazolidin-3-yl]methyl}benzoic acid |
| 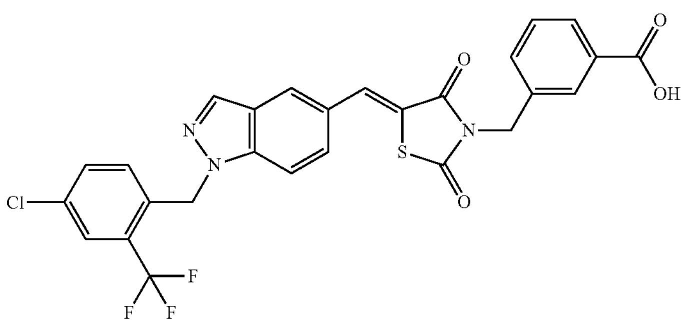 [SMILES: O=C(O)c1cccc(CN2C(=O)S/C(=C\c3ccc4c(cnn4Cc4ccc(Cl)cc4C(F)(F)F)c3)C2=O)c1] | 378 | 3-{[(5Z)-5-({1-[4-Chloro-2-(trifluoromethyl)benzyl]-1H-indazol-5-yl}methylidene)-2,4-dioxo-1,3-thiazolidin-3-yl]methyl}benzoic acid |
| 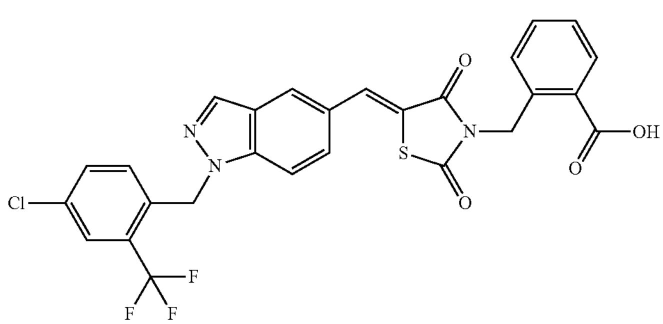 [SMILES: O=C(O)c1ccccc1CN1C(=O)S/C(=C\c2ccc3c(cnn3Cc3ccc(Cl)cc3C(F)(F)F)c2)C1=O] | 379 | 2-{[(5Z)-5-({1-[4-Chloro-2-(trifluoromethyl)benzyl]-1H-indazol-5-yl}methylidene)-2,4-dioxo-1,3-thiazolidin-3-yl]methyl}benzoic acid |

TABLE I-continued

| STRUCTURE | COMPOUND # | NAME |
|---|---|---|
| 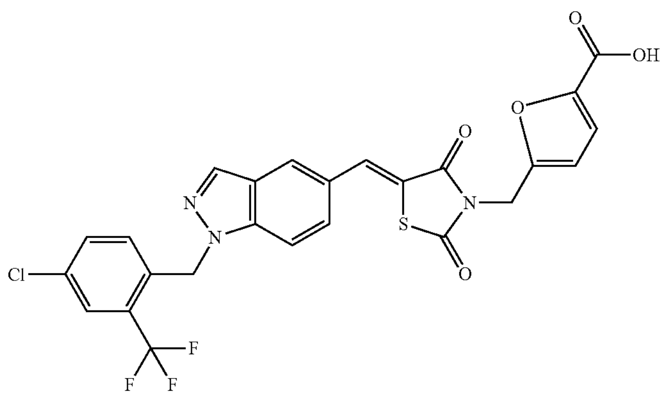 [SMILES: O=C(O)c1ccc(CN2C(=O)S/C(=C\c3ccc4c(cnn4Cc4ccc(Cl)cc4C(F)(F)F)c3)C2=O)o1] | 380 | 5-{[(5Z)-5-({1-[4-Chloro-2-(trifluoromethyl)benzyl]-1H-indazol-5-yl}methylidene)-2,4-dioxo-1,3-thiazolidin-3-yl]methyl}furan-2-carboxylic acid |
| 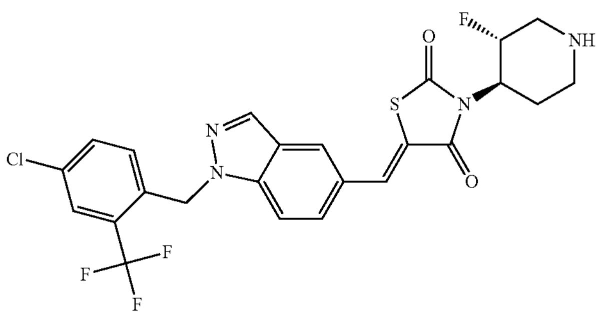 [SMILES: O=C1S/C(=C\c2ccc3c(cnn3Cc3ccc(Cl)cc3C(F)(F)F)c2)C(=O)N1[C@@H]1CCNC[C@H]1F] | 381 | (5Z)-5-({1-[4-Chloro-2-(trifluoromethyl)benzyl]-1H-indazol-5-yl}methylidene)-3-[(3R,4R)-3-fluoropiperidin-4-yl]-1,3-thiazolidine-2,4-dione |
| 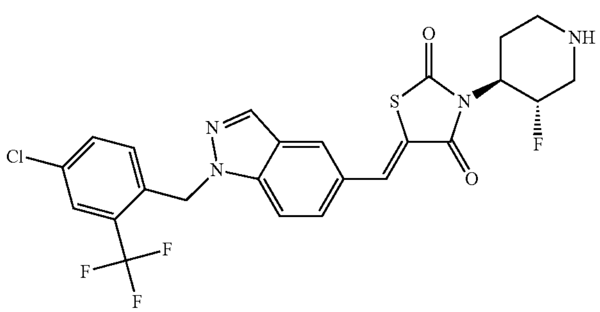 [SMILES: O=C1S/C(=C\c2ccc3c(cnn3Cc3ccc(Cl)cc3C(F)(F)F)c2)C(=O)N1[C@H]1CCNC[C@@H]1F] | 382 | (5Z)-5-({1-[4-Chloro-2-(trifluoromethyl)benzyl]-1H-indazol-5-yl}methylidene)-3-[(3S,4S)-3-fluoropiperidin-4-yl]-1,3-thiazolidine-2,4-dione |
| 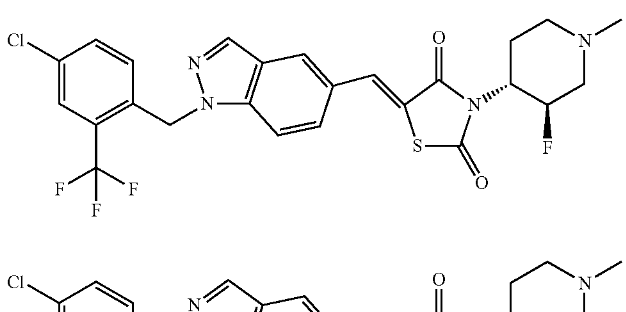 | 383 | (5Z)-5-({1-[4-Chloro-2-(trifluoromethyl)benzyl]-1H-indazol-5-yl}methylidene)-3-[(3R,4R)-3-fluoro-1-methylpiperidin-4-yl]-1,3-thiazolidine-2,4-dione |
| 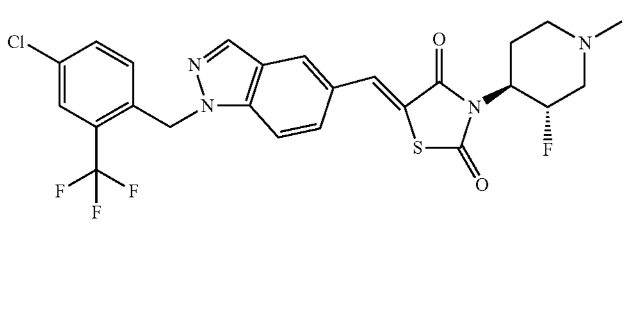 [SMILES: CN1CC[C@H](N2C(=O)S/C(=C\c3ccc4c(cnn4Cc4ccc(Cl)cc4C(F)(F)F)c3)C2=O)[C@@H](F)C1] | 384 | (5Z)-5-({1-[4-Chloro-2-(trifluoromethyl)benzyl]-1H-indazol-5-yl}methylidene)-3-[(3S,4S)-3-fluoro-1-methylpiperidin-4-yl]-1,3-thiazolidine-2,4-dione |

TABLE I-continued

| STRUCTURE | COMPOUND # | NAME |
|---|---|---|
| 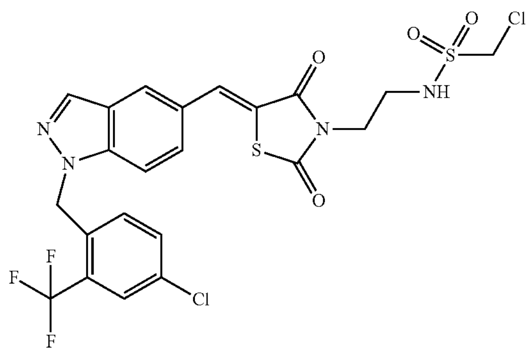 [SMILES: O=C1S/C(=C\c2ccc3c(cnn3Cc3ccc(Cl)cc3C(F)(F)F)c2)C(=O)N1CCNS(=O)(=O)CCl] | 385 | 1-Chloro-N-{2-[(5Z)-5-({1-[4-chloro-2-(trifluoromethyl)benzyl]-1H-indazol-5-yl}methylidene)-2,4-dioxo-1,3-thiazolidin-3-yl]ethyl}methanesulfonamide |
| 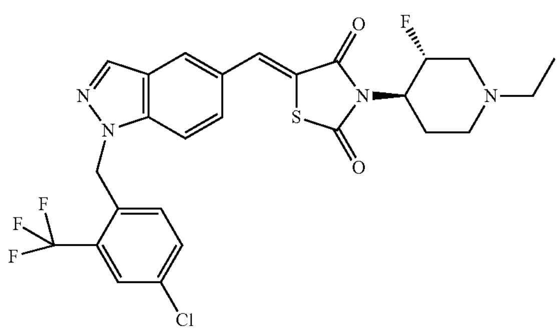 [SMILES: CCN1CC[C@@H](N2C(=O)S/C(=C\c3ccc4c(cnn4Cc4ccc(Cl)cc4C(F)(F)F)c3)C2=O)[C@H](F)C1] | 386 | (5Z)-5-({1-[4-Chloro-2-(trifluoromethyl)benzyl]-1H-indazol-5-yl}methylidene)-3-[(3R,4R)-1-ethyl-3-fluoropiperidin-4-yl]-1,3-thiazolidine-2,4-dione |
| 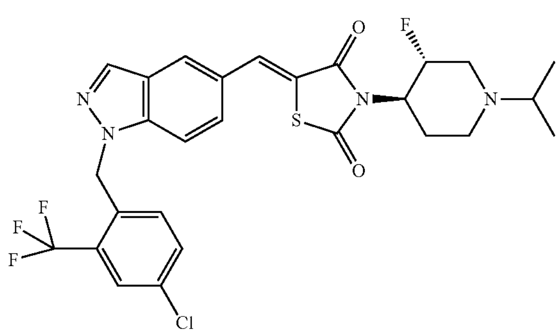 [SMILES: CC(C)N1CC[C@@H](N2C(=O)S/C(=C\c3ccc4c(cnn4Cc4ccc(Cl)cc4C(F)(F)F)c3)C2=O)[C@H](F)C1] | 387 | (5Z)-5-({1-[4-Chloro-2-(trifluoromethyl)benzyl]-1H-indazol-5-yl}methylidene)-3-[(3R,4R)-3-fluoro-1-(1-methylethyl)piperidin-4-yl]-1,3-thiazolidine-2,4-dione |
| 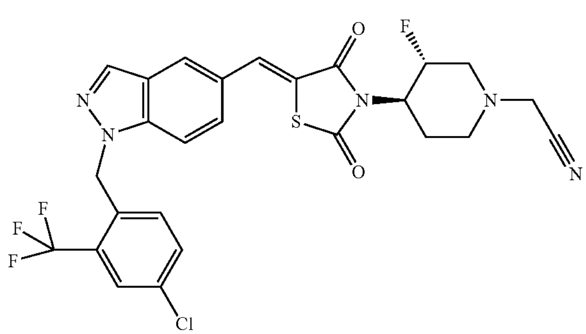 [SMILES: N#CCN1CC[C@@H](N2C(=O)S/C(=C\c3ccc4c(cnn4Cc4ccc(Cl)cc4C(F)(F)F)c3)C2=O)[C@H](F)C1] | 388 | {(3R,4R)-4-[(5Z)-5-({1-[4-Chloro-2-(trifluoromethyl)benzyl]-1H-indazol-5-yl}methylidene)-2,4-dioxo-1,3-thiazolidin-3-yl]-3-fluoropiperidin-1-yl}acetonitrile |

TABLE I-continued

| STRUCTURE | COMPOUND # | NAME |
|---|---|---|
| 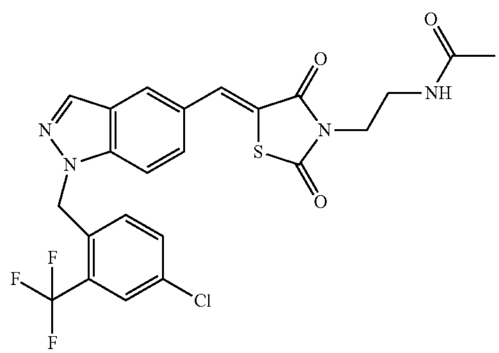 [SMILES: CC(=O)NCCN1C(=O)S/C(=C\c2ccc3c(cnn3Cc3ccc(Cl)cc3C(F)(F)F)c2)C1=O] | 389 | N-{2-[(5Z)-5-({1-[4-Chloro-2-(trifluoromethyl)benzyl]-1H-indazol-5-yl}methylidene)-2,4-dioxo-1,3-thiazolidin-3-yl]ethyl}acetamide |
| 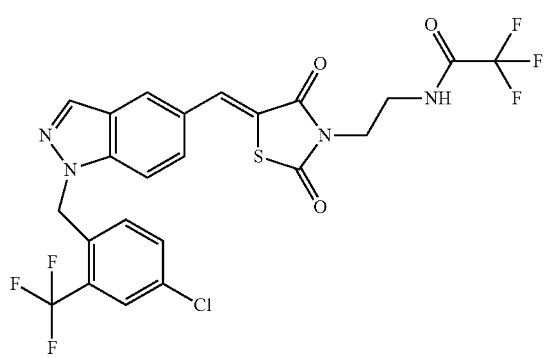 [SMILES: O=C1S/C(=C\c2ccc3c(cnn3Cc3ccc(Cl)cc3C(F)(F)F)c2)C(=O)N1CCNC(=O)C(F)(F)F] | 390 | N-{2-[(5Z)-5-({1-[4-Chloro-2-(trifluoromethyl)benzyl]-1H-indazol-5-yl}methylidene)-2,4-dioxo-1,3-thiazolidin-3-yl]ethyl}-2,2,2-trifluoroacetamide |
| 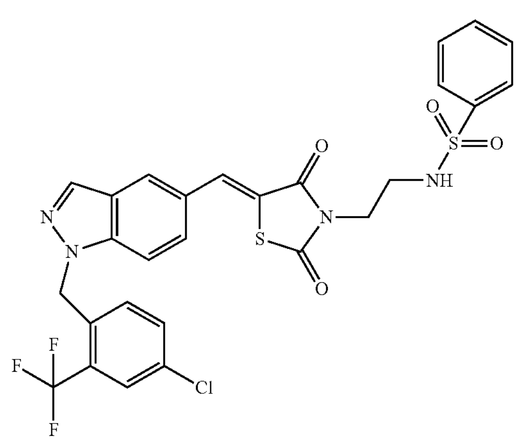 [SMILES: O=C1S/C(=C\c2ccc3c(cnn3Cc3ccc(Cl)cc3C(F)(F)F)c2)C(=O)N1CCNS(=O)(=O)c1ccccc1] | 391 | N-{2-[(5Z)-5-({1-[4-Chloro-2-(trifluoromethyl)benzyl]-1H-indazol-5-yl}methylidene)-2,4-dioxo-1,3-thiazolidin-3-yl]ethyl}benzenesulfonamide |

TABLE I-continued

| STRUCTURE | COMPOUND # | NAME |
|---|---|---|
| 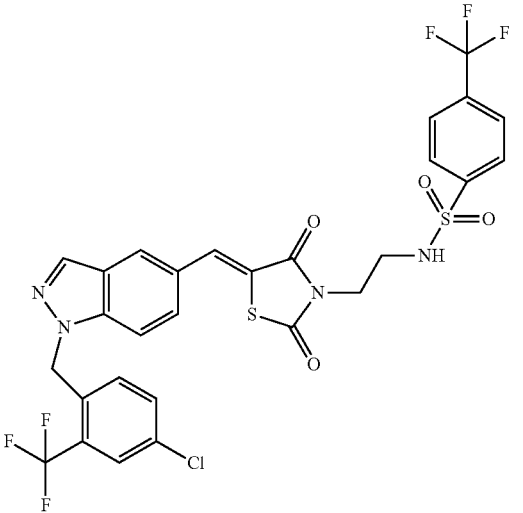 [SMILES: O=C1S/C(=C\c2ccc3c(cnn3Cc3ccc(Cl)cc3C(F)(F)F)c2)C(=O)N1CCNS(=O)(=O)c1ccc(C(F)(F)F)cc1] | 392 | N-{2-[(5Z)-5-({1-[4-Chloro-2-(trifluoromethyl)benzyl]-1H-indazol-5-yl}methylidene)-2,4-dioxo-1,3-thiazolidin-3-yl]ethyl}-4-(trifluoromethyl)benzenesulfonamide |
| 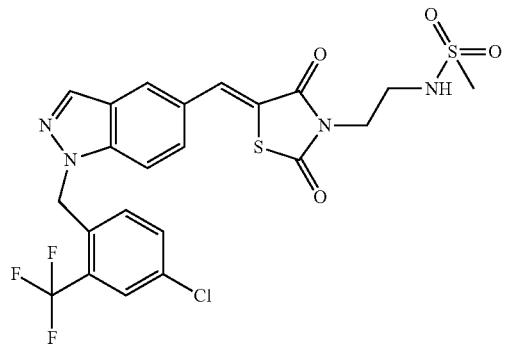 [SMILES: CS(=O)(=O)NCCN1C(=O)S/C(=C\c2ccc3c(cnn3Cc3ccc(Cl)cc3C(F)(F)F)c2)C1=O] | 393 | N-{2-[(5Z)-5-({1-[4-Chloro-2-(trifluoromethyl)benzyl]-1H-indazol-5-yl}methylidene)-2,4-dioxo-1,3-thiazolidin-3-yl]ethyl}methanesulfonamide |
| 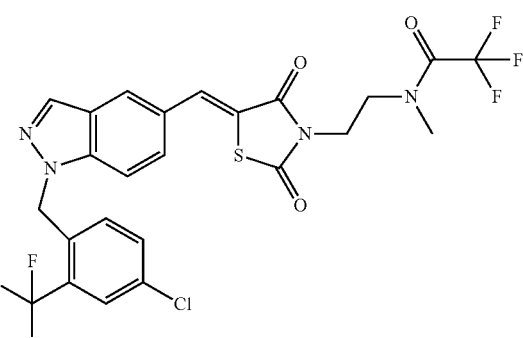 | 394 | N-{2-[(5Z)-5-({1-[4-Chloro-2-(trifluoromethyl)benzyl]-1H-indazol-5-yl}methylidene)-2,4-dioxo-1,3-thiazolidin-3-yl]ethyl}-2,2,2-trifluoro-N-methylacetamide |
| 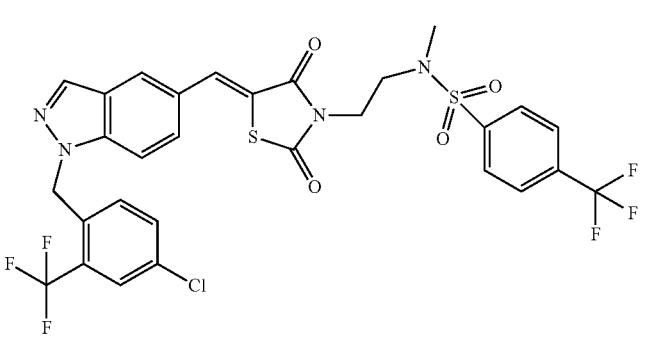 [SMILES: CN(CCN1C(=O)S/C(=C\c2ccc3c(cnn3Cc3ccc(Cl)cc3C(F)(F)F)c2)C1=O)S(=O)(=O)c1ccc(C(F)(F)F)cc1] | 395 | N-{2-[(5Z)-5-({1-[4-Chloro-2-(trifluoromethyl)benzyl]-1H-indazol-5-yl}methylidene)-2,4-dioxo-1,3-thiazolidin-3-yl]ethyl}-N-methyl-4-(trifluoromethyl)benzenesulfonamide |

TABLE I-continued

| STRUCTURE | COMPOUND # | NAME |
|---|---|---|
| 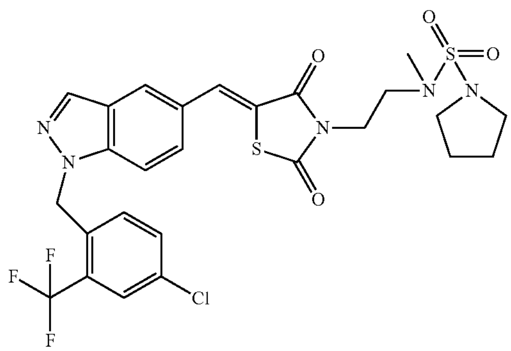 [SMILES: CN(CCN1C(=O)S/C(=C\c2ccc3c(cnn3Cc3ccc(Cl)cc3C(F)(F)F)c2)C1=O)S(=O)(=O)N1CCCC1] | 396 | N-{2-[(5Z)-5-({1-[4-Chloro-2-(trifluoromethyl)benzyl]-1H-indazol-5-yl}methylidene)-2,4-dioxo-1,3-thiazolidin-3-yl]ethyl}-N-methylpyrrolidine-1-sulfonamide |
| 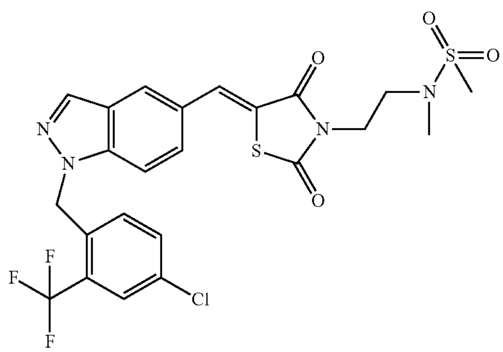 [SMILES: CN(CCN1C(=O)S/C(=C\c2ccc3c(cnn3Cc3ccc(Cl)cc3C(F)(F)F)c2)C1=O)S(C)(=O)=O] | 397 | N-{2-[(5Z)-5-({1-[4-Chloro-2-(trifluoromethyl)benzyl]-1H-indazol-5-yl}methylidene)-2,4-dioxo-1,3-thiazolidin-3-yl]ethyl}-N-methylmethanesulfonamide |
| 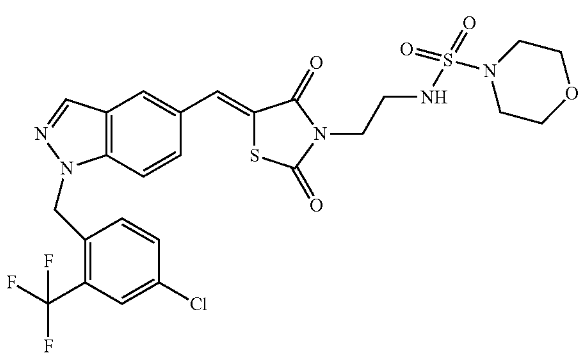 [SMILES: O=C1S/C(=C\c2ccc3c(cnn3Cc3ccc(Cl)cc3C(F)(F)F)c2)C(=O)N1CCNS(=O)(=O)N1CCOCC1] | 398 | N-{2-[(5Z)-5-({1-[4-Chloro-2-(trifluoromethyl)benzyl]-1H-indazol-5-yl}methylidene)-2,4-dioxo-1,3-thiazolidin-3-yl]ethyl}morpholine-4-sulfonamide |
| 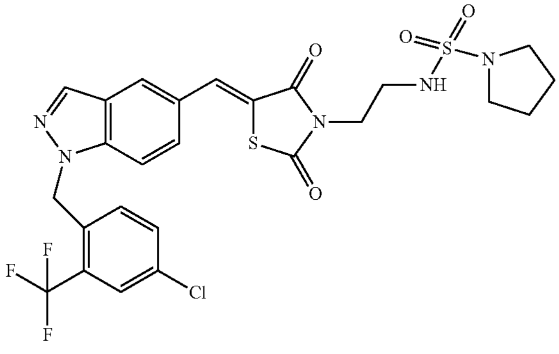 [SMILES: O=C1S/C(=C\c2ccc3c(cnn3Cc3ccc(Cl)cc3C(F)(F)F)c2)C(=O)N1CCNS(=O)(=O)N1CCCC1] | 399 | N-{2-[(5Z)-5-({1-[4-Chloro-2-(trifluoromethyl)benzyl]-1H-indazol-5-yl}methylidene)-2,4-dioxo-1,3-thiazolidin-3-yl]ethyl}pyrrolidine-1-sulfonamide |

TABLE I-continued

| STRUCTURE | COMPOUND # | NAME |
|---|---|---|
| 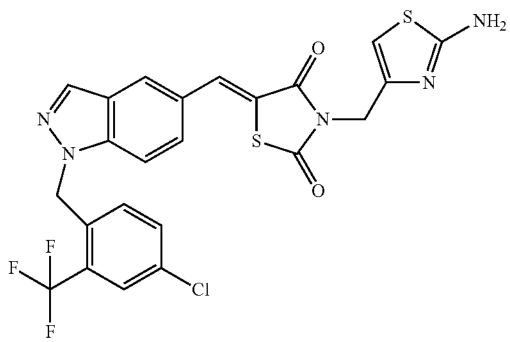 [SMILES: Nc1nc(CN2C(=O)S/C(=C\c3ccc4c(cnn4Cc4ccc(Cl)cc4C(F)(F)F)c3)C2=O)cs1] | 400 | (5Z)-3-[(2-Amino-1,3-thiazol-4-yl)methyl]-5-({1-[4-chloro-2-(trifluoromethyl)benzyl]-1H-indazol-5-yl}methylidene)-1,3-thiazolidine-2,4-dione |
| 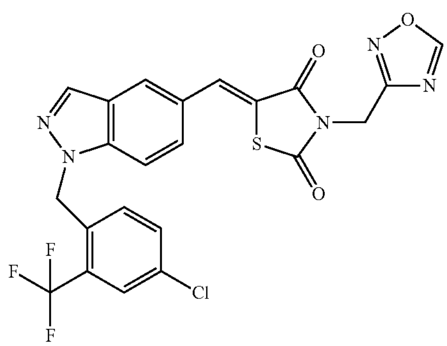 [SMILES: O=C1S/C(=C\c2ccc3c(cnn3Cc3ccc(Cl)cc3C(F)(F)F)c2)C(=O)N1Cc1ncon1] | 401 | (5Z)-5-({1-[4-Chloro-2-(trifluoromethyl)benzyl]-1H-indazol-5-yl}methylidene)-3-(1,2,4-oxadiazol-3-ylmethyl)-1,3-thiazolidine-2,4-dione |
| 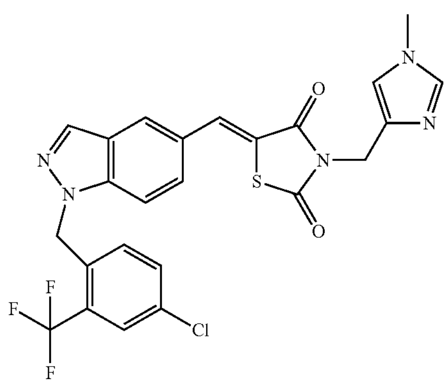 [SMILES: Cn1cnc(CN2C(=O)S/C(=C\c3ccc4c(cnn4Cc4ccc(Cl)cc4C(F)(F)F)c3)C2=O)c1] | 402 | (5Z)-5-({1-[4-Chloro-2-(trifluoromethyl)benzyl]-1H-indazol-5-yl}methylidene)-3-[(1-methyl-1H-imidazol-4-yl)methyl]-1,3-thiazolidine-2,4-dione |
| 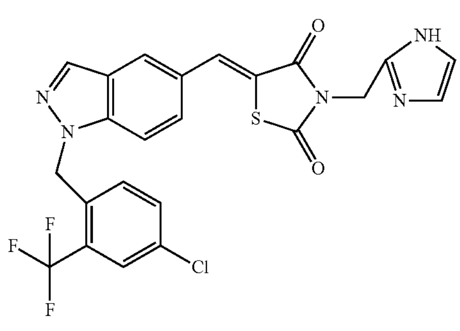 [SMILES: O=C1S/C(=C\c2ccc3c(cnn3Cc3ccc(Cl)cc3C(F)(F)F)c2)C(=O)N1Cc1ncc[nH]1] | 403 | (5Z)-5-({1-[4-Chloro-2-(trifluoromethyl)benzyl]-1H-indazol-5-yl}methylidene)-3-(1H-imidazol-2-ylmethyl)-1,3-thiazolidine-2,4-dione |

TABLE I-continued

| STRUCTURE | COMPOUND # | NAME |
|---|---|---|
| 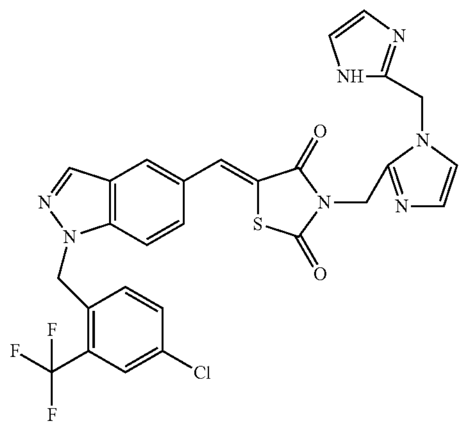 [SMILES: O=C1S/C(=C\c2ccc3c(cnn3Cc3ccc(Cl)cc3C(F)(F)F)c2)C(=O)N1Cc1nccn1Cc1ncc[nH]1] | 404 | (5Z)-5-({1-[4-Chloro-2-(trifluoromethyl)benzyl]-1H-indazol-5-yl}methylidene)-3-{[1-(1H-imidazol-2-ylmethyl)-1H-imidazol-2-yl]methyl}-1,3-thiazolidine-2,4-dione |
| 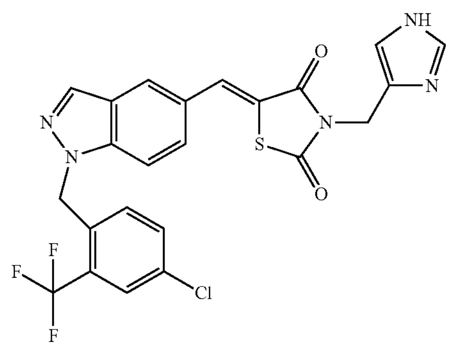 [SMILES: O=C1S/C(=C\c2ccc3c(cnn3Cc3ccc(Cl)cc3C(F)(F)F)c2)C(=O)N1Cc1c[nH]cn1] | 405 | (5Z)-5-({1-[4-Chloro-2-(trifluoromethyl)benzyl]-1H-indazol-5-yl}methylidene)-3-(1H-imidazol-4-ylmethyl)-1,3-thiazolidine-2,4-dione |
| 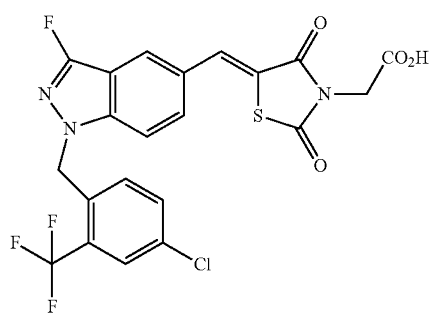 [SMILES: O=C(O)CN1C(=O)S/C(=C\c2ccc3c(c2)c(F)nn3Cc2ccc(Cl)cc2C(F)(F)F)C1=O] | 406 | [(5Z)-5-({1-[4-Chloro-2-(trifluoromethyl)benzyl]-3-fluoro-1H-indazol-5-yl}methylidene)-2,4-dioxo-1,3-thiazolidin-3-yl]acetic acid |
| 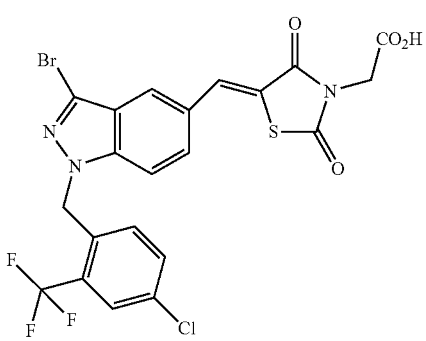 [SMILES: O=C(O)CN1C(=O)S/C(=C\c2ccc3c(c2)c(Br)nn3Cc2ccc(Cl)cc2C(F)(F)F)C1=O] | 407 | [(5Z)-5-({3-Bromo-1-[4-chloro-2-(trifluoromethyl)benzyl]-1H-indazol-5-yl}methylidene)-2,4-dioxo-1,3-thiazolidin-3-yl]acetic acid |

US 8,796,256 B2

225 226

TABLE I-continued

| STRUCTURE | COMPOUND # | NAME |
|---|---|---|
| 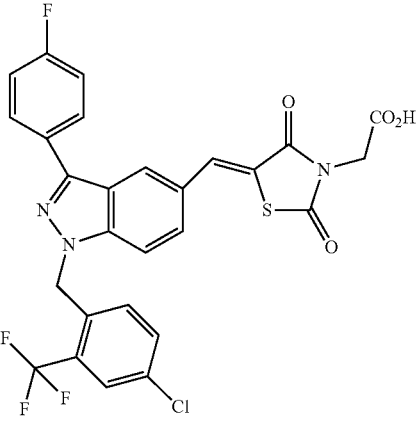 [SMILES: O=C(O)CN1C(=O)S/C(=C\c2ccc3c(c2)c(-c2ccc(F)cc2)nn3Cc2ccc(Cl)cc2C(F)(F)F)C1=O] | 408 | [(5Z)-5-({1-[4-Chloro-2-(trifluoromethyl)benzyl]-3-(4-fluorophenyl)-1H-indazol-5-yl}methylidene)-2,4-dioxo-1,3-thiazolidin-3-yl]acetic acid |
| 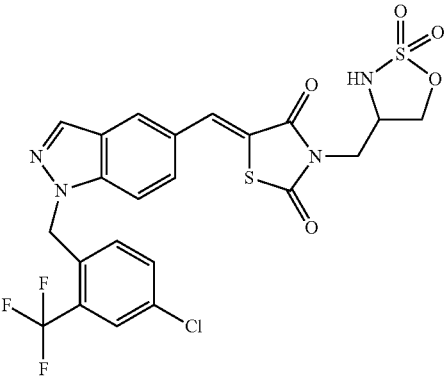 [SMILES: O=C1S/C(=C\c2ccc3c(cnn3Cc3ccc(Cl)cc3C(F)(F)F)c2)C(=O)N1CC1COS(=O)(=O)N1] | 409 | (5Z)-5-({1-[4-Chloro-2-(trifluoromethyl)benzyl]-1H-indazol-5-yl}methylidene)-3-[(2,2-dioxido-1,2,3-oxathiazolidin-4-yl)methyl]-1,3-thiazolidine-2,4-dione |
| 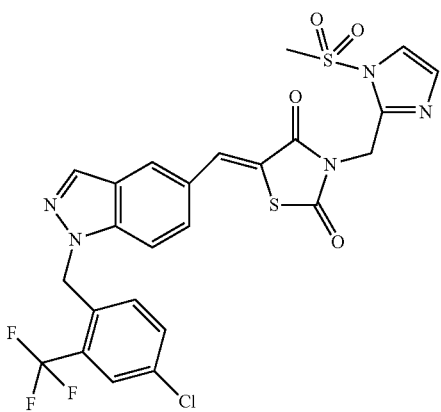 [SMILES: CS(=O)(=O)n1ccnc1CN1C(=O)S/C(=C\c2ccc3c(cnn3Cc3ccc(Cl)cc3C(F)(F)F)c2)C1=O] | 410 | (5Z)-5-({1-[4-Chloro-2-(trifluoromethyl)benzyl]-1H-indazol-5-yl}methylidene)-3-{[1-(methylsulfonyl)-1H-imidazol-2-yl]methyl}-1,3-thiazolidine-2,4-dione |

TABLE I-continued

| STRUCTURE | COMPOUND # | NAME |
|---|---|---|
| 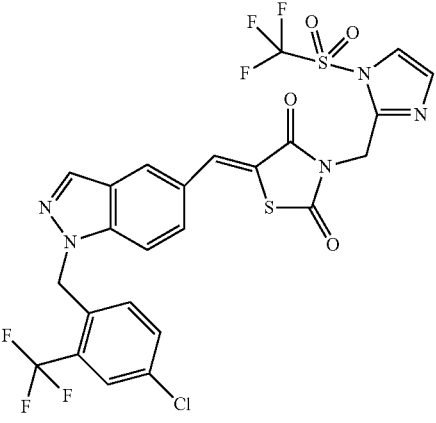 [SMILES: O=C1S/C(=C\c2ccc3c(cnn3Cc3ccc(Cl)cc3C(F)(F)F)c2)C(=O)N1Cc1nccn1S(=O)(=O)C(F)(F)F] | 411 | (5Z)-5-({1-[4-Chloro-2-(trifluoromethyl)benzyl]-1H-indazol-5-yl}methylidene)-3-({1-[(trifluoromethyl)sulfonyl]-1H-imidazol-2-yl}methyl)-1,3-thiazolidine-2,4-dione |
| 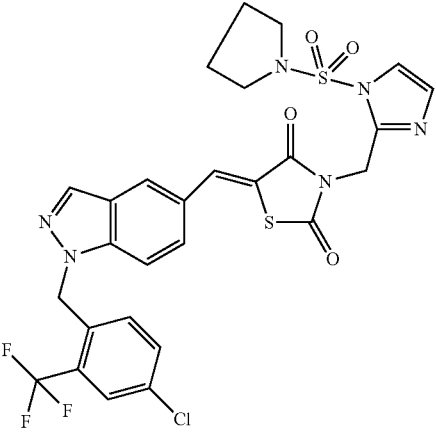 [SMILES: O=C1S/C(=C\c2ccc3c(cnn3Cc3ccc(Cl)cc3C(F)(F)F)c2)C(=O)N1Cc1nccn1S(=O)(=O)N1CCCC1] | 412 | (5Z)-5-({1-[4-Chloro-2-(trifluoromethyl)benzyl]-1H-indazol-5-yl}methylidene)-3-{[1-(pyrrolidin-1-ylsulfonyl)-1H-imidazol-2-yl]methyl}-1,3-thiazolidine-2,4-dione |
| 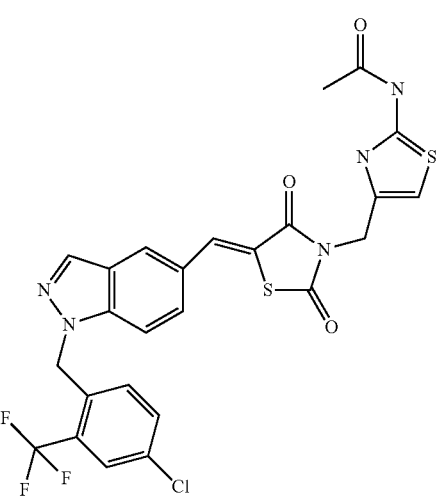 | 413 | N-(4-{[(5Z)-5-({1-[4-Chloro-2-(trifluoromethyl)benzyl]-1H-indazol-5-yl}methylidene)-2,4-dioxo-1,3-thiazolidin-3-yl]methyl}-1,3-thiazol-2-yl)acetamide |

TABLE I-continued

| STRUCTURE | COMPOUND # | NAME |
|---|---|---|
| 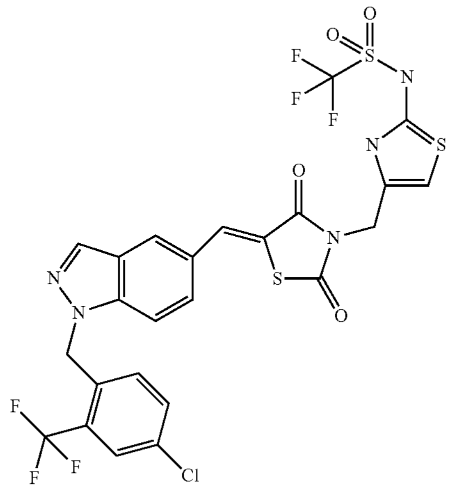 | 414 | N-(4-{[(5Z)-5-({1-[4-Chloro-2-(trifluoromethyl)benzyl]-1H-indazol-5-yl}methylidene)-2,4-dioxo-1,3-thiazolidin-3-yl]methyl}-1,3-thiazol-2-yl)-1,1,1-trifluoromethanesulfonamide |
| 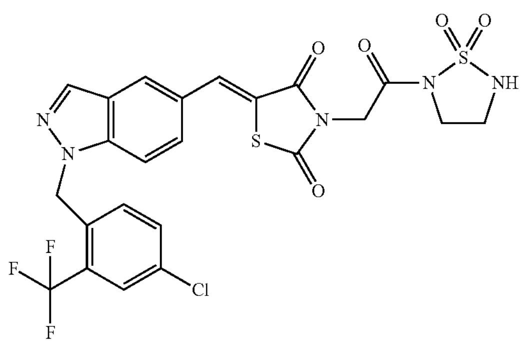 [SMILES: O=C1S/C(=C\c2ccc3c(cnn3Cc3ccc(Cl)cc3C(F)(F)F)c2)C(=O)N1CC(=O)N1CCNS1(=O)=O] | 415 | tert-Butyl 5-{[(5Z)-5-({1-[4-chloro-2-(trifluoromethyl)benzyl]-1H-indazol-5-yl}methylidene)-2,4-dioxo-1,3-thiazolidin-3-yl]acetyl}-1,2,5-thiadiazolidine-2-carboxylate 1,1-dioxide |
| 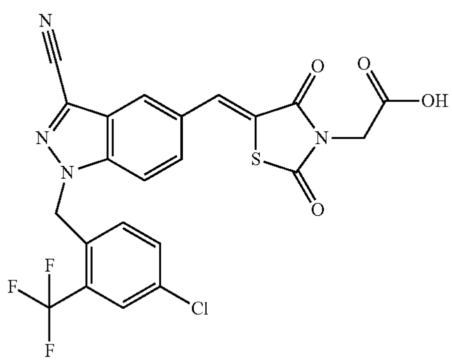 [SMILES: N#Cc1nn(Cc2ccc(Cl)cc2C(F)(F)F)c2ccc(/C=C3\SC(=O)N(CC(=O)O)C3=O)cc12] | 416 | [(5Z)-5-({1-[4-Chloro-2-(trifluoromethyl)benzyl]-3-cyano-1H-indazol-5-yl}methylidene)-2,4-dioxo-1,3-thiazolidin-3-yl]acetic acid |
| 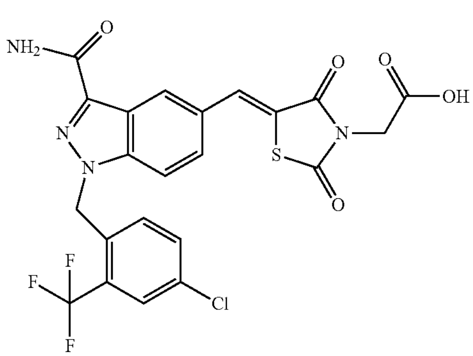 [SMILES: NC(=O)c1nn(Cc2ccc(Cl)cc2C(F)(F)F)c2ccc(/C=C3\SC(=O)N(CC(=O)O)C3=O)cc12] | 417 | [(5Z)-5-({3-Carbamoyl-1-[4-chloro-2-(trifluoromethyl)benzyl]-1H-indazol-5-yl}methylidene)-2,4-dioxo-1,3-thiazolidin-3-yl]acetic acid |

TABLE I-continued

| STRUCTURE | COMPOUND # | NAME |
|---|---|---|
| 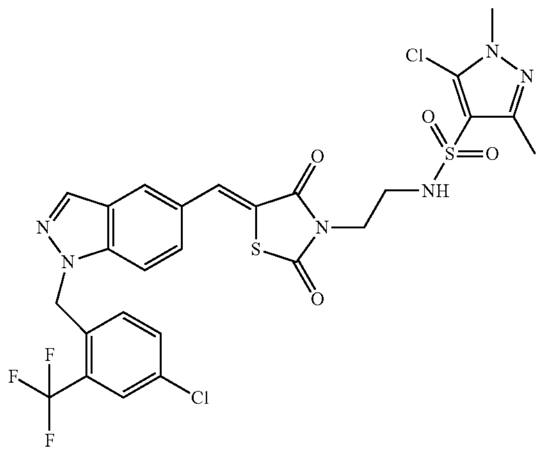 [SMILES: Cc1nn(C)c(Cl)c1S(=O)(=O)NCCN1C(=O)S/C(=C\c2ccc3c(cnn3Cc3ccc(Cl)cc3C(F)(F)F)c2)C1=O] | 418 | 5-Chloro-N-{2-[(5Z)-5-({1-[4-chloro-2-(trifluoromethyl)benzyl]-1H-indazol-5-yl}methylidene)-2,4-dioxo-1,3-thiazolidin-3-yl]ethyl}-1,3-dimethyl-1H-pyrazole-4-sulfonamide |
| 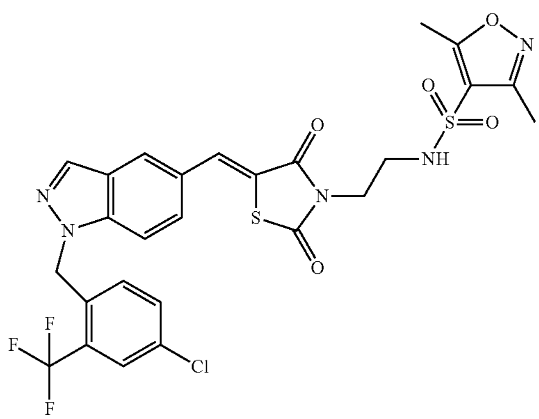 [SMILES: Cc1noc(C)c1S(=O)(=O)NCCN1C(=O)S/C(=C\c2ccc3c(cnn3Cc3ccc(Cl)cc3C(F)(F)F)c2)C1=O] | 419 | N-{2-[(5Z)-5-({1-[4-Chloro-2-(trifluoromethyl)benzyl]-1H-indazol-5-yl}methylidene)-2,4-dioxo-1,3-thiazolidin-3-yl]ethyl}-3,5-dimethylisoxazole-4-sulfonamide |
| 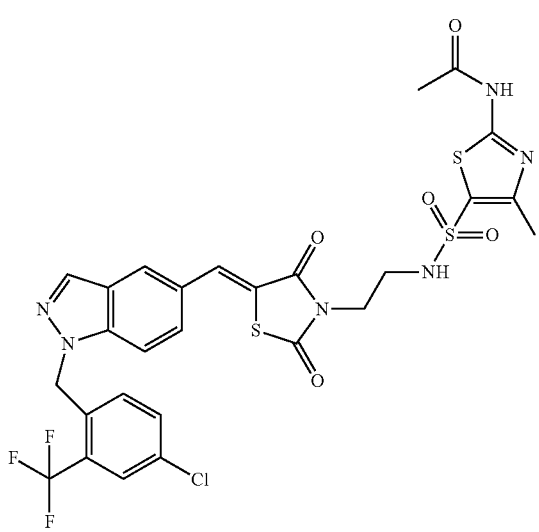 [SMILES: CC(=O)Nc1nc(C)c(S(=O)(=O)NCCN2C(=O)S/C(=C\c3ccc4c(cnn4Cc4ccc(Cl)cc4C(F)(F)F)c3)C2=O)s1] | 420 | N-[5-({2-[(5Z)-5-({1-[4-Chloro-2-(trifluoromethyl)benzyl]-1H-indazol-5-yl}methylidene)-2,4-dioxo-1,3-thiazolidin-3-yl]ethyl}sulfamoyl)-4-methyl-1,3-thiazol-2-yl]acetamide |

TABLE I-continued

| STRUCTURE | COMPOUND # | NAME |
|---|---|---|
| 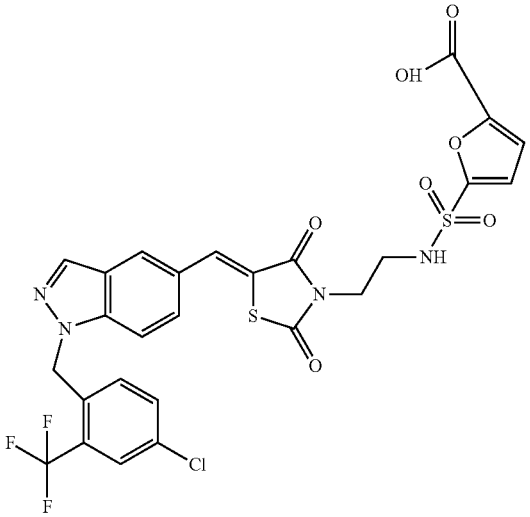 [SMILES: O=C(O)c1ccc(S(=O)(=O)NCCN2C(=O)S/C(=C\c3ccc4c(cnn4Cc4ccc(Cl)cc4C(F)(F)F)c3)C2=O)o1] | 421 | 5-({2-[(5Z)-5-({1-[4-Chloro-2-(trifluoromethyl)benzyl]-1H-indazol-5-yl}methylidene)-2,4-dioxo-1,3-thiazolidin-3-yl]ethyl}sulfamoyl)furan-2-carboxylic acid |

C) Synthesis

The invention provides methods of making the disclosed compounds according to traditional organic synthetic methods as well as matrix or combinatorial synthetic methods. Schemes 1 to 9 describe suggested synthetic routes. Using the scheme, the guidelines below, and the examples, a person of skill in the art may develop analogous or similar methods for a given compound that is within the invention. These methods are representative of the synthetic schemes, but are not to be construed as limiting the scope of the invention.

Where the compounds according to this invention have at least one chiral center, they may accordingly exist as enantiomers. Where the compounds possess two or more chiral centers, they may additionally exist as diastereomers. Where the processes for the preparation of the compounds according to the invention give rise to mixtures of stereoisomers, these isomers may be separated by conventional techniques such as preparative chromatography. The compounds may be prepared in racemic form or as individual enantiomers or diasteromers by either stereospecific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. It is to be understood that all stereoisomers, racemic mixtures, diastereomers, geometric isomers, and enantiomers thereof are encompassed within the scope of the present invention.

Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Examples of the described synthetic routes include Schemes 1-9, Examples 1 through 427, and General Procedures A-Y. Compounds analogous to the target compounds of these examples can be made according to similar routes. The disclosed compounds are useful as pharmaceutical agents as described herein.

Abbreviations or acronyms useful herein include:
AIBN (2,2'-azobisisobutyronitrile)
Al—Ni (aluminum-nickel)
aq (aqueous)
Boc (tert-butoxycarbonyl)
BOP (benzotriazol-1-yloxy)tris(dimethylamino)phosphonium hexyluorophosphate)
BuLi (butyllithium)
CDI (1,1'-carbonyldiimidazole)
Deoxofluor® ([Bis(2-methoxyethyl)aminosulfur Trifluoride])
DAST (Diethylaminosulfur Trifluoride)
DIBAL-H (diisobutylaluminum hydride)
DCE (1,2-dichloroethane)
DCM (dichloromethane)
DEAD (diethyl azidodicarboxylate)
DIAD (diisopropyl azidodicarboxylate)
DIPEA (diisopropylethylamine)
DMAC (dimethylacetamide)
DMAP (4-(dimethylamino)pyridine)
DME (ethylene glycol dimethyl ether)
DMF (dimethylformamide)
DMPU (1,3-dimethyl-3,4,5,6-tetrahydro-2(1H)-pyrimidinone)
DMSO (methyl sulfoxide)
EDC (N-(3-dimethylaminopropyl)-N'-ethylcarbodiimide)
EDCI (1-(3-dimethylaminopropyl)-3-ethylcarbodiimide hydrochloride)
Et (ethyl)
EtOAc (ethyl acetate)
h (hour(s))
HATU (O-(7-azabenzotriazol-1-yl)-N,N,N',N'-tetramethyluronium hexafluorophosphate)
HCl (hydrochloric acid)

HMPA (hexamethylphosphoramide)
HOBt (1-hydroxybenzotriazole monohydrate)
HPLC (high performance liquid chromatography)
LAH (lithium aluminum hydride)
LCMS (high pressure liquid chromatography with mass spectrometer)
LDA (lithium diisopropylamide)
LHMDS (lithium hexamethyl disilazide)
MCPBA (3-chloroperbenzoic acid)
Me (methyl)
MeCN (acetonitrile)
MeOH (methyl alcohol)
mg (milligram)
MOM (methoxymethyl)
NaHMDS (sodium hexamethyl disilazide)
NaO$^t$Bu (sodium tert-butoxide)
NBS (N-bromosuccinimide)
NCS (N-chlorosuccinimide)
NMP (N-methylpyrrolidinone)
N,N-DMA (N,N-dimethylacetamide)
Py (Pyridine)
rt (room temperature)
PS—PPh$_3$ (polymer-bound triphenylphosphine)
sat'd (saturated)
SPE (solid phase extraction)
TBTU (O-benzotriazol-1-yl-N,N,N',N'-tetramethyluronium hexafluorophosphate)
TEMPO (2,2,6,6-tetramethyl-1-piperidinyloxy, free radical)
TES (triethylsilane)
TFA (trifluoroacetic acid);
THF (tetrahydrofuran)
THP (tetrahydropyranyl)
TLC (thin layer chromatography)
TZD (2,4-thiazolidinedione)

General Guidance

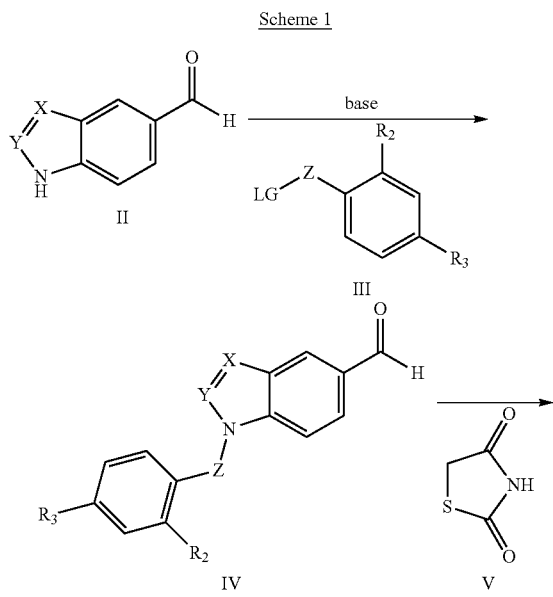

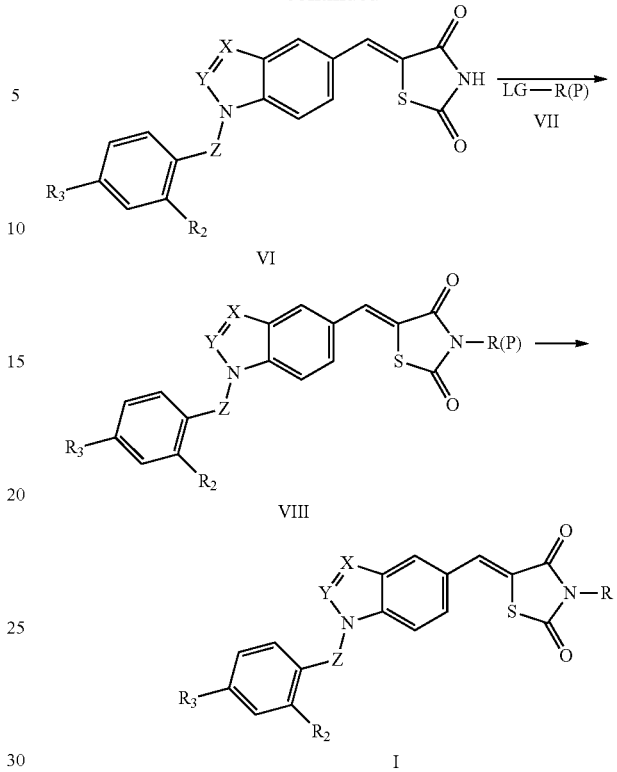

The compounds I, wherein Z is CHR$_5$, and R is R$_1$ with X, Y, R$_1$, R$_2$, R$_3$ and R$_5$ are defined as in above Formula (I), may be synthesized as outlined by the general synthetic route illustrated in Scheme 1. Treatment of an appropriate 1H-indazole-5-carbaldehyde II, 1H-indole-5-carbaldehyde II or 1H-benzotriazole-5-carbaldehyde II and an appropriately substituted benzyl derivative III, a known compound or compound prepared by known methods, wherein LG is a suitably selected leaving group such as Cl, Br, I, tosylate, mesylate, and the like, both of which are either commercially available or can be made from commercially available starting materials, with a base such as K$_2$CO$_3$, Os$_2$CO$_3$, KOH, NaH, and the like, in a solvent such as NMP, DMF, THF, and the like, at a temperature preferably between 25-150° C. can provide the substituted 1-benzyl-1H-indazole-5-carbaldehyde IV, 1-benzyl-1H-indole-5-carbaldehyde IV, or 1-benzyl-1H-benzotriazole-5-carbaldehyde IV. Knoevenagel reaction of aldehydes IV with 2,4-thiazolidinedione V can provide compounds VI. (For a review of Knoevenagel reactions, see: Jones, G. The Knoevenagel Reaction. Org. React. 1967, 15, 204-599.) The Knoevenagel condensation between aldehydes IV and 2,4-thiazolidinedione V is typically performed in the presence of a catalytic amount of base such as piperidine and an acid such as benzoic acid in an aprotic solvent such as toluene at a temperature preferably between 100-200° C. The reaction may also be performed with a base such as sodium acetate in a solvent such as acetonitrile at a temperature preferably between 50-150° C., or in the presence of ammonium acetate in acetic acid at a temperature preferably between 50-150° C. The compounds VI are reacted with a compound VII, a known compound or compound prepared by known methods, wherein R is a substituted alkyl group which may optionally bear a suitable functional protecting group (P) (such as those described in *Protective Groups in Organic Chemistry*, J. F. W. McOmie, Ed.; Plenum Press: 1973; and T. W. Greene & P. G.

M. Wuts, *Protective Groups in Organic Synthesis*, 3rd ed.; John Wiley & Sons, Inc.: New York, 1999) and LG is a suitably selected leaving group such as Cl, Br, I, tosylate, mesylate, and the like (as described in: March, J. *Advanced Organic Chemistry. Reactions, Mechanisms and Structure*, 2nd ed.; McGraw-Hill Co.: New York, 1977; pp 326) in the presence of a base such as $K_2CO_3$, $Et_3N$, DIPEA, and the like, in an organic solvent such as MeOH, MeCN, DCM, THF, and the like, at a temperature preferably between 25-80° C., to yield compounds VIII. Appropriate deprotection of compounds VIII, provides the corresponding compound I. In the case where the R is substituted with one or more amine groups, suitable protecting groups such as Boc, Cbz, and the like may be incorporated, which may be deprotected under appropriate conditions known to those skilled in the art to afford a compound of Formula (I) of the present invention. For example, Boc-protected amines may be deprotected under acidic conditions using reagents such as HCl, TFA, and the like. Likewise, Cbz-protected amines may be deprotected under acidic conditions or hydrogenolysis. In the case where R is substituted with carboxyl groups, suitable protecting groups such as methyl, ethyl and t-butyl esters and the like may be incorporated, which may be deprotected under acidic conditions such as HCl, TFA and the like. In the case where R is substituted with hydroxyl groups, suitable protecting groups such as MOM, THP, t-butyl ethers and the like may be incorporated, which may be deprotected under acidic conditions such as HCl, TFA and the like. The unmasked functionalities generated by deprotection may be subjected to further chemical transformations according to methods known in the art, to provide additional derivatives of I. When an optional functional protecting group is not present in compounds VII, then the Knoevenagel reaction affords compounds I directly.

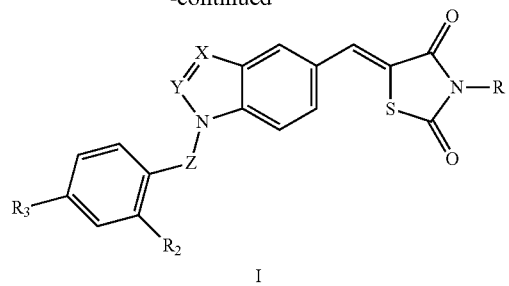

I

Alternatively, the compounds I, wherein Z is $CHR_5$, and R is $R_1$ with X, Y, $R_1$, $R_2$, $R_3$ and $R_5$ are defined as in above Formula (I), may be synthesized as outlined by the general synthetic route illustrated in Scheme 2. Accordingly, reaction of a suitable compound IX, a known compound or compound prepared by known methods, wherein R is a substituted alkyl group which may optionally bear a suitable functional protecting group (P), thioglycolic acid X, and CU, in a solvent such as DCM and the like, at a temperature preferably between 20-50° C., can provide N-alkyl TZD derivatives XI (Geffken, D. Z. *Naturforsch., B: Chem. Sci.* 1987, 42, 1202-6). Knoevenagel reactions of XI with compounds IV using conditions set forth in Scheme I, can provide compounds VIII, which, when suitably deprotected, can provide compounds I. The unmasked functionalities generated upon deprotection may be subjected to further chemical transformations according to methods known in the art, to provide additional derivatives of I. When an optional functional protecting group is not present in compounds XI, then the Knoevenagel reaction affords compounds of I directly.

Scheme 2

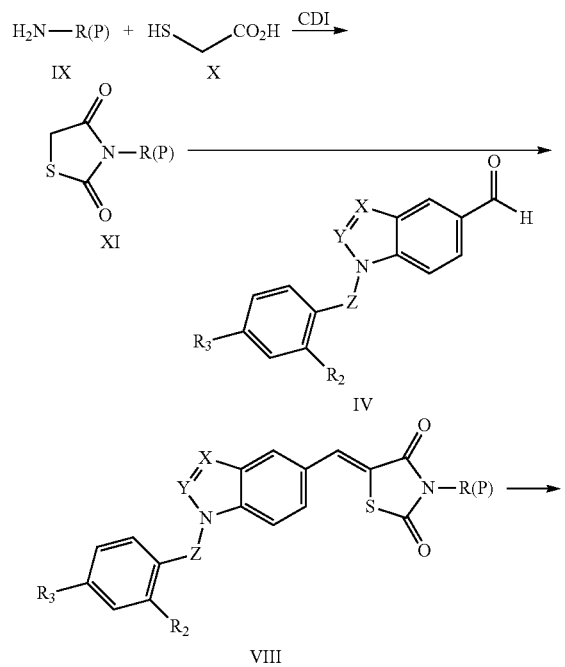

Scheme 3

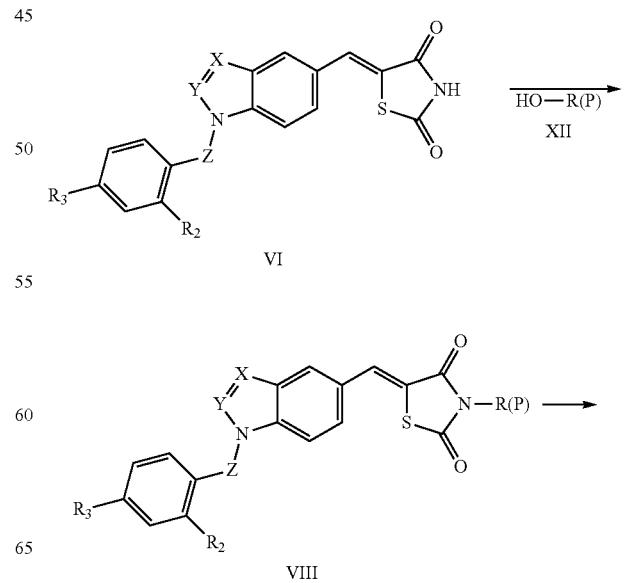

-continued

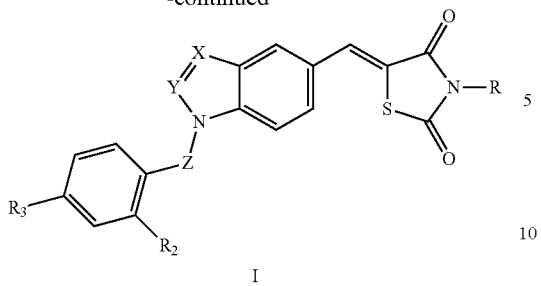

I

-continued

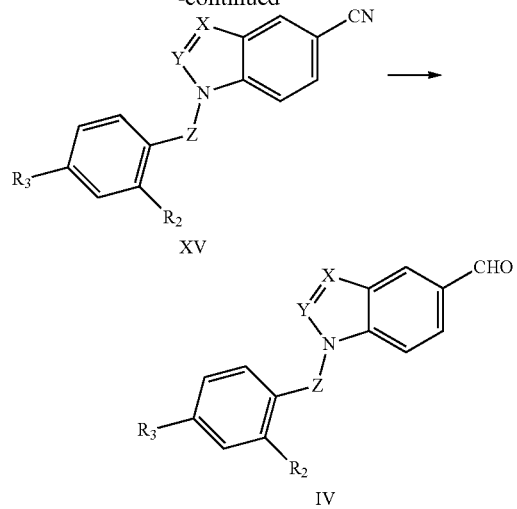

The compounds I, wherein Z is $CHR_5$, and R is $R_1$ with X, Y, $R_1$, $R_2$, $R_3$ and $R_5$ are defined as in above Formula (I), may alternatively be synthesized as outlined by the general synthetic route illustrated in Scheme 3. Accordingly, a suitable compound VI, prepared as described in Scheme 1, wherein Z is $CHR_5$, and R is $R_1$ with X, Y, $R_2$ and $R_3$ are defined as in above Formula (I), is reacted under Mitsunobu conditions (for a review, see: Mitsunobu, O. *Synthesis* 1981, 1-28) with compounds XII, wherein R is a substituted alkyl group which may optionally bear a suitable functional protecting group (P), in the presence of triphenylphosphine or a resin-bound triphenylphosphine equivalent, such as PS—$PPh_3$ and an azido coupling reagent such as DIAD or DEAD and the like, in an organic solvent such as THF, MeCN, N,N-DMA, and the like, at a temperature preferably between 25-100° C., to yield compounds VIII. Appropriate deprotection of VIII, using the synthetic routes as described in Scheme 1, can provide the corresponding compound I. The unmasked functionalities generated by deprotection may be subjected to further chemical transformations according to methods known in the art, to provide additional derivatives of I. When an optional functional protecting group is not present in compounds XII, then the Mitsunobu reaction affords compounds I directly.

Scheme 4

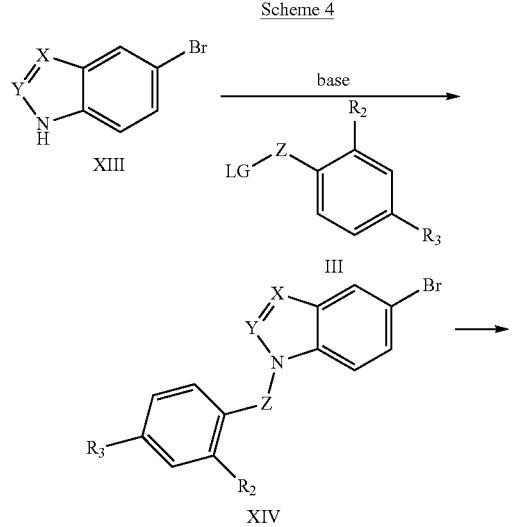

The compounds IV, wherein Z is $CHR_5$, X is $CR_4$, Y is N, $R_4$ is $C_{1-4}$alkyl, and $R_1$, $R_2$, $R_3$ and $R_5$ are defined as in above Formula (I), may be synthesized as outlined by the general synthetic route illustrated in Scheme 4. Treatment of an appropriate 5-bromo-3-alkyl-1H-indazole XIII, and an appropriately substituted benzyl derivative III, as defined in Scheme 1 with a base such as $K_2CO_3$, $Cs_2CO_3$, KOH, NaH, and the like, in a solvent such as NMP, DMF, THF, and the like, at a temperature preferably between 25-150° C. can provide the substituted 5-bromo-3-alkyl-1-benzyl-1H-indazoles XIV. Treatment of bromoindazoles XIV with cyanating reagents such as CuCN (for review, see: Mowry, D. T. *Chem. Rev.*, 1948, 42, 189-283), KCN (Yang, C. and Williams, J. M., *Org. Lett.*, 2004, 6, 2837-40), $K_4Fe(CN)_6.3H_2O$ (Schareina, T. et al., *Chem. Commun.*, 2004, 1388-9 and Weissman, S. A., et al., *J. Org. Chem.*, 2005, 70, 1508-10), $Zn(CN)_2$ (Hatsuda, M. and Seki, M. *Tetrahedron Lett.*, 2005, 46, 1849-53) and the like and suitable catalysts such as CuI, $Pd(OAc)_2$, $Pd(PPh_3)_4$, $Pd(dppf)Cl_2$, $Pd_2(dba)_3$ and the like in a solvent such as NMP, N,N-DMA, DMF, toluene, and the like, at a temperature preferably between 80-200° C. can provide the substituted 5-cyano-3-alkyl-1-benzyl-1H-indazoles XV. Partial reduction of cyanoindazoles XV can provide the substituted 3-alkyl-1-benzyl-1H-indazole-5-carbaldehydes IV (see: March, J. *Advanced Organic Chemistry. Reactions, Mechanisms and Structure*, $2^{nd}$ Ed, McGraw-Hill Co.: New York, 1977; pp 835). In particular, this reduction can be carried out with suitable reducing agents such as DIBAL-H in an organic solvent such as THF, toluene, and the like at a temperature of −78° C. (Miller, A. E. G., et al., *J. Org. Chem.*, 1959, 24, 627-30) or Ni—Al in a solvent mixture of $HCO_2H$ and water at a temperature preferably between 100-110° C. (van Es, T. and Staskun, B., *J. Chem. Soc.*, 1965, 5775-7) to provide the substituted 3-alkyl-1-benzyl-1H-indazole-5-carbaldehydes IV. Aldehydes IV can be transformed to provide compounds of Formula (I) utilizing the synthetic routes as described in Schemes 1-3.

Scheme 5

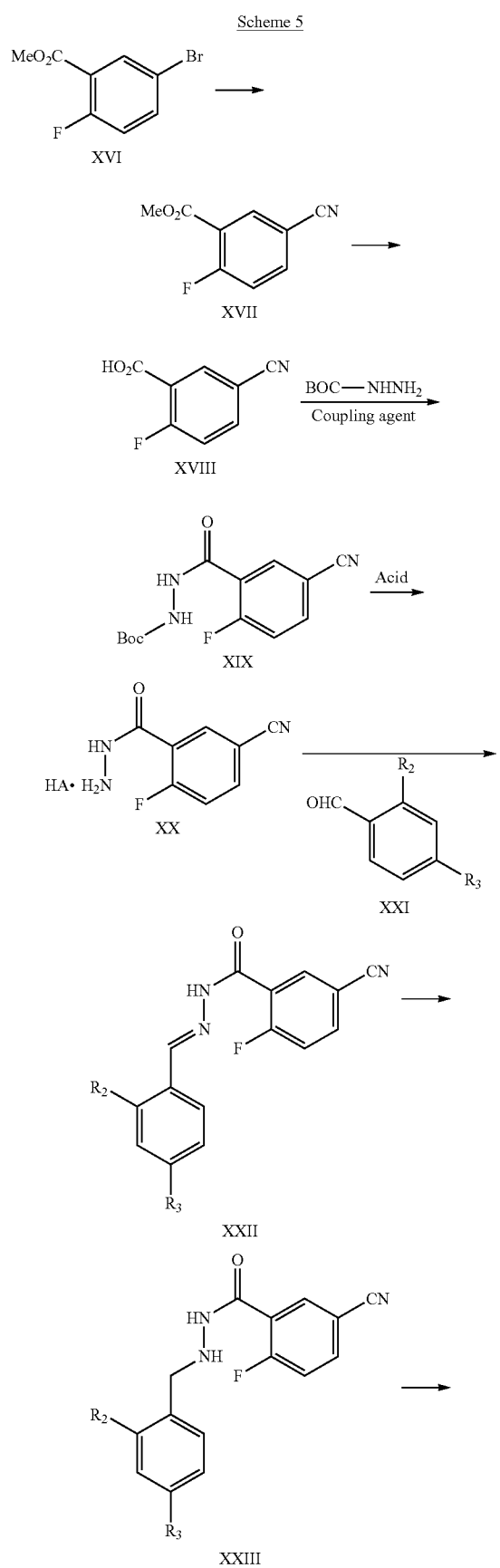

The compounds XV, wherein X is C—O—R, R is H or optionally substituted $C_{1-4}$alkyl, Y is N, Z is $CH_2$, and $R_2$, and $R_3$ are defined as in above Formula (I), may be synthesized as outlined by the general synthetic route illustrated in Scheme 5. (A review of the preparation and chemistry of 1H-indazol-3-ols is provided in Baiocchi, L., et al., *Synthesis* 1978, 633-648.) Treatment of bromobenzoate XVI with cyanating reagents utilizing the synthetic routes as described in Scheme 4 can provide cyanobenzoate XVII, which can be selectively hydrolyzed by treatment with bases such as LiOH in a solvent mixture of THF and water at an ambient temperature to give cyanobenzoic acid XVIII. Reaction of cyanobenzoic acid XVIII and BOC-hydrazide with conventional coupling agents (for a review, see: M. Bodansky and A. Bodansky, *The Practice of Peptide Synthesis*, Springer-Verlag: New York, 1984) such as EDCI, CU, HATU, TBTU and the like in organic solvents such as DCM, THF, N,N-DMA and the like at ambient temperature can provide acylhydrazide XIX. Treatment of BOC-hydrazide XIX with acids such as HCl in anhydrous solvents such as THF, dioxane, and the like, or TFA, neat or in solvents such as DCM, and the like, can provide the deprotected hydrazide XX as the corresponding acid salt. Condensation of hydrazide XX with substituted benzaldehydes XXI, where $R_2$ and $R_3$ are defined as in Formula (I), in solvents such as EtOH, toluene, dioxane, and the like, at temperatures preferably between 80 and 120° C. can provide acylhydrazones XXII. Treatment of acylhydrazones XXII with reducing agents such as $NaCNBH_3$ in anhydrous solvents such as THF, dioxane, and the like (Calabretta, R., et al., *Synthesis,* 1991, 536-9), or with TFA and TES, in solvents such as DCM and the like (Wu, P-L., et al., *Synthesis,* 1995, 435-8), can provide substituted benzylhydrazides XXIII. Cyclization of benzylhydrazides XXIII can be effected under basic conditions in the presence of copper powder in refluxing pentanol (Baiocchi, L., et al., *Synthesis* 1978, 633-648) or thermally in the absence of base, at temperatures preferably between 100 and 220° C. in solvents such as DMF, N,N-DMA, NMP, and the like, to provide compounds XV, wherein X is C—O—R, R is H, Y is N, Z is $CH_2$, and $R_2$ and $R_3$ are defined as in above Formula (I). Further reaction of XV, thusly prepared, and a compound XXIV, a known compound or compound prepared by known methods, wherein LG is a suitably selected leaving group such as Cl, Br, I, tosylate, mesylate, diazo and the like, with a base such as $K_2CO_3$, $Cs_2CO_3$, KOH, NaH, and the like, in a solvent such as NMP, DMF, THF, and the like, at a temperature preferably between 25-150° C. can provide compounds XV, wherein X is C—O—R, R is $C_{1-4}$alkyl, Y is N, Z is $CH_2$, and $R_2$ and $R_3$ are defined as in above Formula (I). Nitriles XV can be converted to aldehydes IV, utilizing the synthetic routes as described in Scheme 4, and can subsequently be transformed to provide compounds of Formula (I) utilizing the synthetic routes as described in Schemes 1-3.

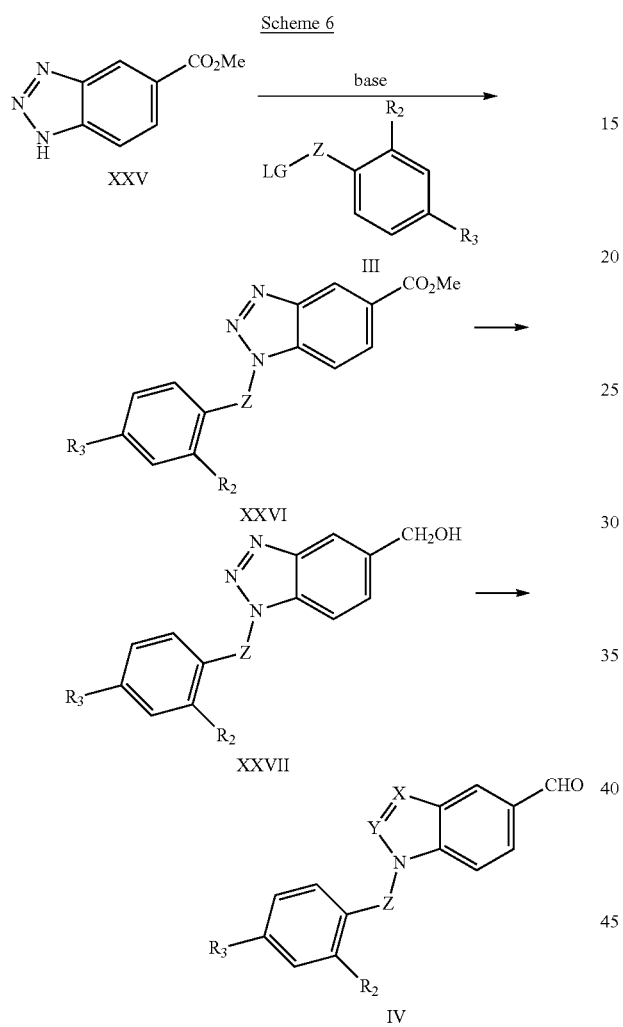

The compounds IV, wherein X is N, Y is N, Z is $CHR_5$, and $R_2$, $R_3$, and $R_5$ are defined as in above Formula (I), may be synthesized as outlined by the general synthetic route illustrated in Scheme 6. Treatment of benzotriazole ester XXV and an appropriately substituted benzyl derivative III, as defined in Scheme 1 with a base such as $K_2CO_3$, $Cs_2CO_3$, KOH, NaH, and the like, in a solvent such as NMP, DMF, THF, and the like, at a temperature preferably between 25-150° C. can provide the substituted 1-benzyl-1H-benzotriazole-5-carboxylates XXVI. Reaction of esters XXVI with conventional reducing agents (see: Hudlicky, M. *Reductions in Organic Chemistry*, Ellis Horwood, Ltd.: Chichester, UK, 1984) such as LAH, DIBAL-H and the like, in solvents such as THF, DME, and the like at temperatures preferably between −20 to 50° C. can provide 5-hydroxymethyl benzotriazole XXVII. Oxidation of alcohols XXVII (for various methods see: Moffat, J. G. in *Oxidation*, Vol. 2; Augustine, R.

L. and Trecker, D. J., Eds.; Marcel Dekker: New York, 1971; pp 1-64; and Lee, D. G. in *Oxidation*, Vol. 1; Augustine, R. L., Ed.; Marcel Dekker New York, 1969; pp 56-80) with oxidizing agents such as PCC, $MnO_2$, Dess-Martin periodinane (Dess, D. B. and Martin, J. C., *J. Am. Chem. Soc.*, 1991, 113, 7277-87), and the like, in solvents such as DCM, DCE and the like at temperatures preferably between 20-80° C. can provide 1-benzyl-1H-benzotriazole-5-carbaldehydes IV. Aldehydes IV can be transformed to provide compounds of Formula (I) utilizing the synthetic routes as described in Schemes 1-3.

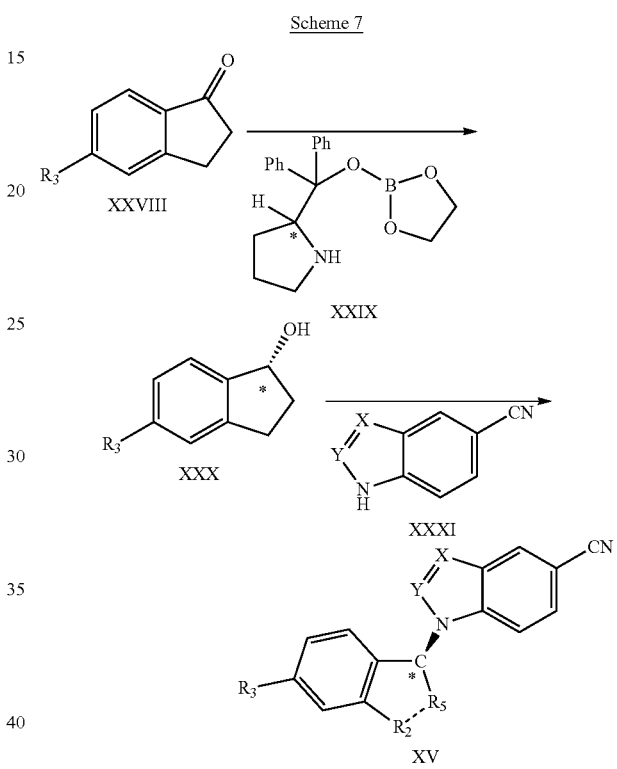

The compounds XV, wherein X is $CR_4$, and $R_5$ taken together with $R_2$ to form —$CHCH_2CH_2$—, and Y, $R_3$ and $R_4$ are defined as in above Formula (I), may be synthesized as outlined by the general synthetic route illustrated in Scheme 7. Reduction of indan-1-one XXVIII with a reducing reagent such as borane dimethylsulfide complex at the presence of a chiral spiroborate ester such as compound XXIX yields chiral alcohol XXX (Stepanenko, V., et al., *Tetrahedron Lett.*, 2007, 48, 5799-5802). Alcohol XXX is then reacted under Mitsunobu conditions with compounds XXXI, in the presence of a tri-substituted phosphine such as tributylphosphine or triphenylphosphine and the like, and an azido coupling reagent such as DIAD or DEAD and the like, in an organic solvent such as toluene, THF, MeCN, N,N-DMA, and the like, at a temperature preferably between 25-100° C., to yield compounds XV. Nitriles XV can be converted to aldehydes IV, utilizing the synthetic routes as described in Scheme 4, and can subsequently be transformed to provide compounds of Formula (I) utilizing the synthetic routes as described in Schemes 1-3.

Scheme 8

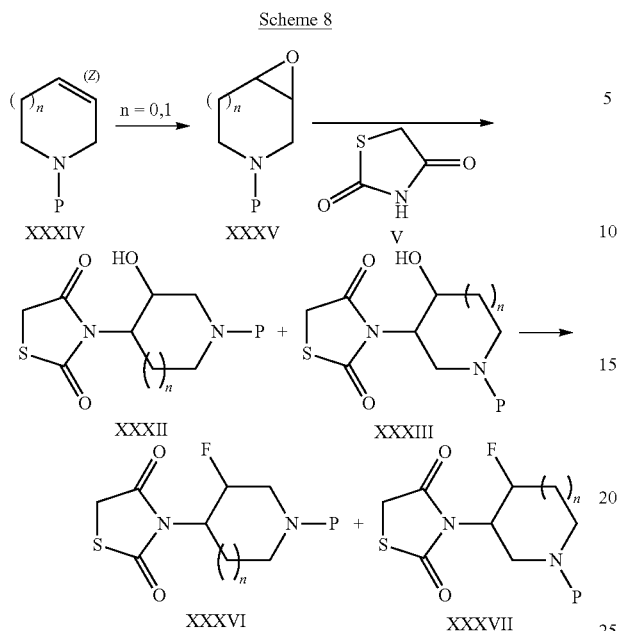

The compounds XXXVI and XXXVII, wherein P is a suitable amine protecting group as defined for Formula VII, may be synthesized as outlined by the general synthetic route illustrated in Scheme 8. Epoxidation (for a general review of epoxidation chemistry, see: Swern, D. in *Organic Peroxides*, Vol. II; Swern, D., Ed.; Wiley-Interscience: New York, 1971; pp 355-533) of appropriately protected compound of formula XXIV, wherein n is an integer from 0 to 1, with an oxidizing reagent, such as MCPBA in a solvent such as DCM, or dimethyldioxirane (Murray, R. W. and Jeyaraman, R., *J. Org. Chem.*, 1985, 50, 2847-53) in solvents such as DCM, CHCl$_3$, MeCN, and the like, at a temperature preferably between 5-50° C., provides the N-protected epoxide XXXV. Reaction of oxirane XXXV with 1,3-thiazolidine-2,4-dione V with or without the presence of a phase transfer reagent, such as tetraethylammonium chloride or tetrabutylammonium bromide, and the like in solvents such as DMF, DMAC, and the like at temperatures preferably between 140 to 200° C. in a microwave reactor provides one isomer when n is 0,3-(4-hydroxy-pyrrolidin-3-yl)-thiazolidine-2,4-dione and the two readily separable (silica gel chromatography) regioisomers when n is 1,3-hydroxy-4-(2,4-dioxo-1,3-thiazolidin-3-yl)piperidine XXXII and 4-hydroxy-3-(2,4-dioxo-1,3-thiazolidin-3-yl)piperidine) XXXIII. Fluorination (for a general review of fluorination, see: *Synthesis*, 2002, 2561-2578 and references cited herein) of each hydroxyl derivative XXXII and XXXIII, wherein n is an integrator from 0 to 1, with a fluorinating reagent, such as DAST or Deoxofluor®, in a solvent such as DCM, EtOAc, Py, and the like, at a temperature preferably between −78° C. and reflux, provides the N-protected fluoro regioisomer XXXVI and XXXVII, respectively. The N-alkyl TZD derivatives XXXVI and XXXVII can be further transformed to provide compounds of above Formula (I) using the synthetic routes as described in Schemes 2.

Scheme 9

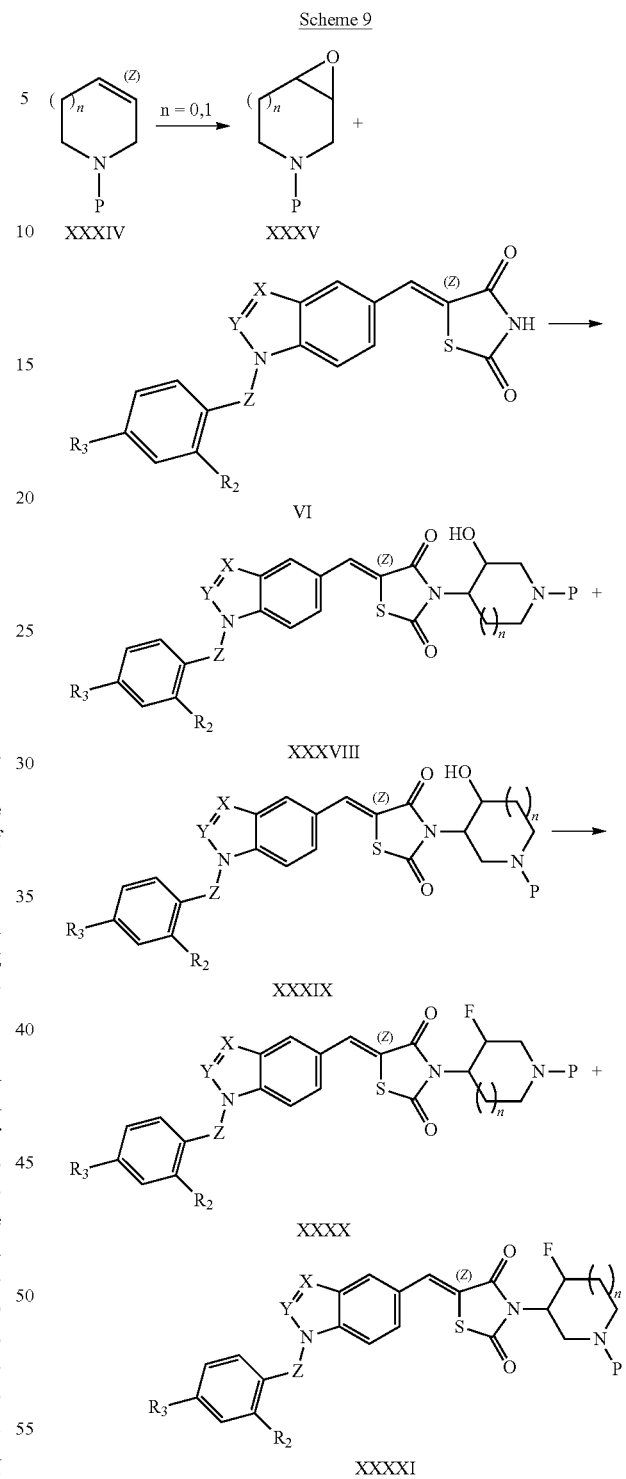

The compounds XXXX and XXXXI, wherein P is a suitable amine protecting group as defined for Formula VII, may be synthesized as outlined by the general synthetic route illustrated in Scheme 9. Epoxidation (for a general review of epoxidation chemistry, see: Swern, D. in *Organic Peroxides*, Vol. II; Swern, D., Ed.; Wiley-Interscience: New York, 1971; pp 355-533) of appropriately protected compound of formula XXXIV, wherein n is an integer from 0 to 1, with an oxidizing reagent, such as MCPBA in a solvent such as DCM, or dimethyldioxirane (Murray, R. W. and Jeyaraman, R., *J. Org. Chem.*, 1985, 50, 2847-53) in solvents such as DCM, CHCl$_3$, MeCN, and the like, at a temperature preferably between 5-50° C., provides the N-protected epoxide XXXV. Reaction of oxirane XXXV with the derivative VI with or without the presence of a phase transfer reagent, such as tetraethylammonium chloride, tetrabutylammonium bromide, and the like in solvents such as DMF, DMAC, and the like at temperatures preferably between 140 to 200° C. in a microwave reactor provides one isomer when n is 0, compound of formula XXXVIII and the two readily separable (Chiral chromatography) regioisomers when n is 1, compounds of formula XXXVIII and XXXIX. Fluorination (for a general review of fluorination, see: *Synthesis*, 2002, 2561-2578 and references cited herein) of each hydroxyl derivatives XXXVIII and XXXIX, wherein n is an integer from 0 to 1, with a fluorinating reagent, such as DAST or Deoxofluor®, in a solvent such as DCM, EtOAc, Py, and the like, at a temperature preferably between −78° C. and reflux, provides the corresponding N-protected fluoro regioisomers XXXX and XXXXI, respectively.

N-alkyl TZD derivatives XXXX and XXXXI can be further deprotected to provide compounds of above Formula (I) using the synthetic routes as described in Schemes 1-3.

EXAMPLES

General Procedure A: A solution of the heteroarylcarbaldehyde (1H-indazole-5-carbaldehyde, 1H-indole-5-carbaldehyde or 1H-benzotriazole-5-carbaldehyde; 52.0 mmol), heteroaryl bromide (3-methyl-5-bromo-1H-indazole; 52.0 mmol) or heteroaryl carboxylic ester (methyl 1H-benzotriazole-5-carboxylate; 52.0 mmol) and an appropriately substituted benzyl bromide (62.1 mmol) in DMF (120 mL) was treated with Cs$_2$CO$_3$ (17 g, 52.1 mmol), and the mixture was heated at 90° C. for 16 h. The reaction was cooled to rt and partitioned between EtOAc and H$_2$O. The organic phase was washed with water (3×), brine, dried (Na$_2$SO$_4$) and concentrated in vacuo. Silica gel chromatography (EtOAc/hexane or DCM/hexane) afforded the desired substituted 1-benzyl-1H-heteroarylcarbaldehyde or 1-benzyl-1H-heteroaryl bromide isomer.

General Procedure B: A mixture of the heteroarylcarbaldehyde (1H-indazole-5-carbaldehyde or 1H-indole-5-carbaldehyde; 3.0 mmol) or heteroaryl bromide (3-methyl-5-bromo-1H-indazole; 3.0 mmol), an appropriately substituted benzyl bromide (3.6 mmol), powdered KOH (3.6 mmol) and tetrabutylammonium bromide (0.6 mmol) in THF (15 mL) was stirred at rt for 1 h. The mixture was diluted with ether, filtered and concentrated. The resultant residue was purified by silica gel chromatography (EtOAc/hexane or DCM/hexane) to afford the desired substituted 1-benzyl-1H-heteroarylcarbaldehyde or 1-benzyl-1H-heteroaryl bromide isomer.

General Procedure C. To a mixture of thiazolidine-2,4-dione (5.0 mmol), an aliphatic alcohol (6 mmol) and Ph$_3$P (6 mmol), in THF (10 mL) was added a solution of DIAD (1.18 mL) in THF (5 mL), and the solution was heated at 70° C. for 12 h. The reaction was cooled to rt and concentrated in vacuo. Purification of the resultant residue by silica gel chromatography (DCM/MeOH) afforded the 3-alkyl-1,3-thiazolidine-2,4-dione.

General Procedure D. A mixture of the amine HCl salt (1.4 mmol) and DIPEA (4.2 mmol) in DCM (10 mL) was stirred for 10 min at rt. To the resultant homogeneous solution was added thioglycolic acid (1.4 mmol) and 1,1'-carbonyldiimidazole (CU, 2.8 mmol) [bubbles formed], and the reaction mixture was stirred at rt for 12 h. The mixture was extracted with DCM and sat'd NaHCO$_3$ solution. The aqueous layer was further extracted with EtOAc and the combined organic phase was washed with brine, dried (Na$_2$SO$_4$) and concentrated in vacuo. Purification of the resultant residue by silica gel chromatography (EtOAc/haxanes) afforded the desired 3-alkylated 1,3-thiazolidine-2,4-dione product.

General Procedure E. A mixture of thiazolidine-2,4-dione (1.0 mmol), substituted 1-benzyl-1H-heteroarylcarbaldehyde from Procedure A or B (1.0 mmol), NH$_4$OAc (2.0 mmol) and acetic acid (2.0 mL) and was heated at 110° C. for 12 h. After cooling to rt, the precipitated product was collected by filtration, washed extensively with water and triturated with EtOAc/hexane to afford the desired pure 5-[1-(substituted benzyl)-1H-heteroar-5-ylmethylene]-1,3-thiazolidine-2,4-dione product.

General Procedure F. A mixture of the thiazolidine-2,4-dione (substituted as in Procedure C or D; 1.0 mmol), substituted 1-benzyl-1H-heteroarylcarbaldehyde from Procedure A or B (1.0 mmol), NH$_4$OAc (2.0 mmol) and acetic acid (2.0 mL) and was heated at 110° C. for 12 h. The reaction was cooled to rt and concentrated in vacuo. Purification of the resultant residue by silica gel chromatography (DCM/MeOH) afforded the desired 5-[1-(substituted benzyl)-1H-heteroar-5-ylmethylene]-(3-alkylated)-1,3-thiazolidine-2,4-dione product.

General Procedure F1. To the mixture of thiazolidine-2,4-dione (1.0 mmol), substituted 1-benzyl-1H-heteroarylcarbaldehyde from Procedure A or B (1.0 mmol) in toluene was added catalytic amounts of benzoic acid and piperidine. The mixture was stirred at 150° C. with a Dean-Stark apparatus for 20 h. After cooling down, solvent was evaporated and the crude was purified by flash chromatography.

General Procedure G. (A) A mixture of 5-[1-(substituted benzyl)-1H-heteroar-5-ylmethylene]-1,3-thiazolidine-2,4-dione from Procedure E (0.19 mmol), K$_2$CO$_3$ (2.27 mmol) and either 1-bromo-2-chloroethane or 1-bromo-3-chloropropane (1.89 mmol) in DMF (2 mL) was stirred at 80° C. for 3 h, then cooled to rt. The mixture was partitioned between EtOAc and water and the organic extracts were washed with brine, dried (Na$_2$SO$_4$) and concentrated to afford the crude 3-(2-chloroethyl)-1,3-thiazolidine-2,4-dione product which was used directly without further purification.

(B) A portion of the crude 3-(2-chloroethyl)-1,3-thiazolidine-2,4-dione (0.056 mmol) was dissolved in DMF (1 mL). To this solution was added the secondary amine (10 equiv.) and the resulting mixture was stirred at 70° C. for 1 h. After cooling to rt, the reaction was partitioned between EtOAc and water. The organic extracts were dried (Na$_2$SO$_4$) and concentrated in vacuo and the resultant residue was purified by silica gel chromatography (DCM/MeOH) to afford the desired product.

General Procedure H. A mixture of 5-[1-(substituted benzyl)-1H-heteroar-5-ylmethylene]-1,3-thiazolidine-2,4-dione from Procedure E (0.2 mmol), K$_2$CO$_3$ (0.48 mmol) and aminoalkyl chloride hydrochloride (0.24 mmol) in DMF (2 mL) was stirred at 70° C. for 3 h. After cooling to rt, the reaction was partitioned between EtOAc and water. The organic extracts were dried (Na$_2$SO$_4$) and concentrated in vacuo and the resultant residue was purified by silica gel chromatography (DCM/MeOH) to afford the desired product.

General Procedure I. (A) A mixture of 5-[1-(substituted benzyl)-1H-heteroar-5-ylmethylene]-1,3-thiazolidine-2,4-dione from Procedure E (1 mmol), tert-butyl bromoacetate (1.5 mmol) and K$_2$CO$_3$ (3 mmol) in DMF (4 mL) was stirred at 90° C. for 1 h, then cooled to rt. Water (12 mL) was added to the mixture, producing a milky suspension; ether (4 mL) was then added affording a triphasic mixture (the solid product was suspended in the ether phase). After removal of the aqueous phase, hexane (2 mL) was added and the mixture was filtered and washed with ether/hexane (1:2) to afford the pure 5-[1-(substituted benzyl)-1H-heteroar-5-ylmethylene]-(2,4-dioxo-1,3-thiazolidin-3-yl)acetic acid tert-butyl ester as a slightly yellow-tinted white powder.

(B) A solution of the above ester (0.82 mmol) in DCM (5 mL) and TFA (5 mL) was stirred at rt for 2 h, then concentrated in vacuo. The solid thus obtained was boiled in MeCN (10 mL) for 5 min, then allowed to cool to rt. The product was filtered and washed with MeCN to afford the 5-[1-(substituted benzyl)-1H-heteroar-5-ylmethylene]-(2,4-dioxo-1, 3-thiazolidin-3-yl)acetic acid as an off-white powder.

General Procedure J. To a mixture of 5-[1-(substituted benzyl)-1H-heteroar-5-ylmethylene]-1,3-thiazolidine-2,4-dione from Procedure E (0.25 mmol), an aliphatic alcohol (0.375 mmol) and $Ph_3P$ (0.375 mmol), in THF (2 mL) was added DIAD (0.375 mmol) and the solution was stirred at rt for 2 h. The reaction was concentrated in vacuo and the resultant residue was purified by silica gel chromatography (DCM/MeOH) to afford the desired 5-[1-(substituted benzyl)-1H-heteroar-5-ylmethylene]-(3-alkylated)-1,3-thiazolidine-2,4-dione product.

General Procedure K. To a mixture of 5-[1-(substituted benzyl)-1H-heteroar-5-ylmethylene]-1,3-thiazolidine-2,4-dione from Procedure E (0.1 mmol), an aliphatic alcohol (0.2 mmol) and $PS-Ph_3P$ (1.6 mmol/g; 2.4 equiv), in THF (2 mL) was added DIAD (0.2 mmol) and the solution was stirred at 60° C. for 1-3 h. After cooling to rt, the reaction was filtered and concentrated and the resultant residue was purified by silica gel chromatography (DCM/MeOH) to afford the desired 5-[1-(substituted benzyl)-1H-heteroar-5-ylmethylene]-(3-alkylated)-1,3-thiazolidine-2,4-dione product.

General Procedure L. A mixture of the 5-[1-(substituted benzyl)-1H-heteroar-5-ylmethylene]-(2,4-dioxo-1,3-thiazolidin-3-yl)acetic acid from Procedure I (0.1 mmol) and CDI (0.2 mmol) in THF (2 mL) was stirred at rt over night. To the resultant homogeneous solution was added the sulfamide (0.15 mmol) followed by DBU (3 mmol), and the solution was stirred for 1 h. The mixture was then acidified to pH 3 with 10% aq. HCl, and the aqueous phase was removed. DCM (4 mL) was added to the organic phase, which was then dried ($Na_2SO_4$) and purified by silica gel chromatography (DCM/MeOH) to afford the 5-[1-(substituted benzyl)-1H-heteroar-5-ylmethylene]-(2,4-dioxo-1,3-thiazolidin-3-yl)acetyl sulfamide.

General Procedure M. The BOC-protected intermediate or tert-butyl ester (1 mmol) was treated with TFA/DCM (0.3; 0.7 v/v). The mixture was stirred at rt for 2-4 h and concentrated in vacuo. The residue was partitioned between EtOAc and a sat'd aq. $NaHCO_3$ solution. The organic phase was dried and evaporated to afford the desired product, which could be further purified by silica gel chromatography (DCM/EtOAc/MeOH) or reverse phase HPLC (MeCN/water/formic acid).

General Procedure N. A solution of BOO intermediate (0.2 mmol) in THF (2 mL) was treated with 4.0N HCl in 1,4-dioxane (2 mL) and stirred at rt for 12 h. The mixture was diluted with ether, and the resultant precipitate was filtered, washed extensively with ether and dried to afford the corresponding product as the amine HCl salt.

General Procedure O. A mixture of the ester (0.67 mmol), 10% aq. HCl (5 mL) and dioxane (10 mL) was heated at 95° C. for 24 h (or until judged complete as monitored by LCMS). After cooling to rt, the reaction was concentrated in vacuo The resultant residue was triturated with a mixture of MeCN/ether (1:2) to afford the solid carboxylic acid, which was filtered and washed with ether.

General Procedure P. A mixture of the aryl bromide (3 mmol), $K_4Fe(CN)_6 \cdot 3H_2O$ (0.66 mmol), $Na_2CO_3$ (3 mmol) and $Pd(OAc)_2$ (0.5 mol %) in N,N-DMA (5 mL) was purged with $N_2$ and heated at 130° C. for 2 h. The mixture was cooled to rt, diluted with ether and filtered. The organic solution was extracted with water (3×), dried ($K_2CO_3$) and concentrated to afford the crude aryl cyanide, which was purified by silica gel chromatography (DCM/hexane) or (EtOAc/hexane).

General Procedure Q. A mixture of the aryl nitrile (3.18 mmol), Al—Ni alloy (1.6 g), formic acid (70 mL) and water (7 mL) was heated to a mild reflux. After 1 h, a second portion of Al—Ni alloy (0.8 g) was added and heating was maintained for an additional 0.5 h. The reaction was partially cooled and filtered through a pad of diatomaceous earth; the inorganics were washed with MeCN and the combined organics were concentrated in vacuo. The resultant residue was purified by silica gel chromatography (DCM) to afford the aryl aldehyde, which was sufficiently pure for subsequent reactions.

General Procedure R. To a solution of the amine (0.04 mmol) in THF/MeOH (1:1 v/v, 1 mL) was added formaldehyde (30%)/0 in water, 1.5 equiv) and sodium cyanoborohydride (2 equiv). The mixture was stirred at rt for 2 h. Solvent was evaporated and the residue was purified by preparative HPLC to afford the desired product.

General Procedure R2. To a solution of the amine (0.07 mmol) in DCM (2 mL) was added formaldehyde (30%)/0 in water, 10 equiv) and then sodium triacetoxyborohydride (2 equiv). The mixture was stirred at rt for 12 h. Solvent was evaporated and the residue was purified by silica gel chromatography (DCM/MeOH) to afford the desired product.

General Procedure R3. To a solution of the amine (0.09 mmol) in MeCN (2 mL) was added potassium carbonate (20 equiv.) and the acyl chloride (1.3 equiv). The mixture was stirred at rt for 12 h. Solvent was evaporated and the residue was purified silica gel chromatography (DCM/MeOH) to afford the desired product.

General Procedure S. A mixture of the amine or TZD (0.8 mmol), $K_2CO_3$ (1.2 mmol) and alkyl halide (1 mmol) in DMF (5 mL) was stirred at 60° C. for 3 h. After cooling to rt, the reaction was partitioned between DCM and water. The organic extracts were dried ($Na_2SO_4$) and concentrated in vacuo and the resultant residue was purified by silica gel chromatography (DCM/MeOH) or by preparative HPLC to afford the desired product.

General Procedure T. A solution of the acid or acyl sulfamide (0.1 mmol) in THF (1 mL) was treated with ethanolamine or diethanolamine (2 equiv) and the mixture was stirred at rt for 1 h. Ether (10 mL) was then added, and the resulting precipitate was filtered, washed with ether and dried to afford the pure ethanolamine or diethanolamine salt.

General Procedure U. A solution of the amine (0.05 mmol) in DCM (1 mL) was treated with an acylating or sulfonylating agent (2 equiv) and triethylamine (2 equiv), and the mixture was stirred at rt for 10 min. Solvent was evaporated and the resultant residue was purified by silica gel chromatography (EtOAc/hexane) to afford the sulfonamide.

General Procedure V. A solution of the sulfonamide or 3-aminothiazolidine-2,4-dione (1 mmol) in acetic anhydride (5 mL) was treated with zinc chloride (50 mg). The mixture was stirred at 50° C. for 1 h. Solvent was evaporated and the residue was partitioned between DCM and water. The organic extracts were washed with brine, dried ($Na_2SO_4$) and concentrated to afford the crude acylsulfonamide, which was then purified by recrystallization from methanol.

General Procedure W. To a mixture of either a 5-[1-(substituted benzyl)-1H-heteroar-5-ylmethylene]-1,3-thiazolidine-2,4-dione from Procedure E or a 5-substituted-1H-indazole (2.24 mmol), an aliphatic alcohol (4.48 mmol) and Bu₃P (4.48 mmol), in toluene (20 mL) was added 1,1'-azobis(N,N-dimethylformamide (4.48 mmol) and the solution was stirred at 80° C. for 4 h. After cooling to rt, the mixture was diluted with EtOAc and extracted with water (3×), dried (Na₂SO₄) and concentrated in vacuo. Purification of the resultant residue by silica gel chromatography (hexane/EtOAc or DCM/MeOH) afforded the desired product (either 5-[1-(substituted benzyl)-1H-heteroar-5-ylmethylene]-(3-alkylated)-1,3-thiazolidine-2,4-dione or 5-substituted-1-alkylated-1H-indazole, respectively).

General Procedure X. (A) A mixture of 5-[1-(substituted benzyl)-1H-heteroar-5-ylmethylene]-1,3-thiazolidine-2,4-dione from Procedure E (0.45 mmol), K₂CO₃ (0.59 mmol) and a substituted benzenesulfonic acid oxiranylmethyl ester (0.54 mmol) in DMF (5 mL) was stirred at 50° C. for 4 h. After cooling to rt, the reaction was partitioned between EtOAc and water. The organic extracts were dried (Na₂SO₄) and concentrated in vacuo and the resultant residue was purified by silica gel chromatography (Heptane/EtOAc) to afford the desired product. (B) A mixture of the above oxiranyl (0.085 mmol) with an alkylamine (0.25 mmol) and DIPEA (0.25 mmol) in EtOH (1 mL), THF (0.5 mL) and MeOH (0.5 mL) was stirred at 70° C. for 4 h. After cooling to rt, the reaction mixture was concentrated in vacuo and the resultant residue was purified by silica gel chromatography (DCM/MeOH) to afford the desired product.

General Procedure Y. To a solution of the alkyl hydrazine and mercapto-acetic acid (1 eq.) in CH₂Cl₂ was added 1,1'-carbonyldiimidazole (1.2 eq.). The mixture was stirred at rt for 1-3 days. Solvent was evaporated and the crude was purified by flash chromatography to give the 3-alkylamino-thiazolidine-2,4-diones.

Example 1

(5Z)-5-({1-[4-Chloro-2-(trifluoromethyl)benzyl]-1H-indazol-5-yl}methylidene)-3-{2-[(3S)-3-hydroxypyrrolidin-1-yl]ethyl}-1,3-thiazolidine-2,4-dione

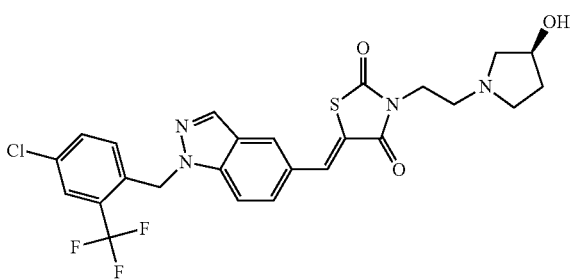 [SMILES: O=C1S/C(=C\c2ccc3c(cnn3Cc3ccc(Cl)cc3C(F)(F)F)c2)C(=O)N1CCN1CC[C@H](O)C1]

(A) [4-Chloro-2-(trifluoromethyl)benzyl]-1H-indazol-5-carbaldehyde was prepared from 4-chloro-2-(trifluoromethyl)benzyl bromide and 1H-indazol-5-carbaldehyde following General Procedure A.

(B) [(5Z)-5-({1-[4-Chloro-2-(trifluoromethyl)benzyl]-1H-indazol-5-yl}methylidene)-2,4-dioxo-1,3-thiazolidine was prepared from [4-chloro-2-(trifluoromethyl)benzyl]-1H-indazol-5-carbaldehyde following General Procedure E.

(C) (5Z)-5-({1-[4-Chloro-2-(trifluoromethyl)benzyl]-1H-indazol-5-yl}methylidene)-3-{2-[(3S)-3-hydroxypyrrolidin-1-yl]ethyl}-1,3-thiazolidine-2,4-dione was prepared from [(5Z)-5-({1-[4-chloro-2-(trifluoromethyl)benzyl]-1H-indazol-5-yl}methylidene)-2,4-dioxo-1,3-thiazolidine, 1-bromo-2-chloroethane and (3S)-3-hydroxypyrrolidine following General Procedure G.

¹H NMR (400 MHZ, CDCl₃): δ 8.16 (s, 1H), 8.10 (s, 1H), 7.93 (m, 1H), 7.70 (d, 1H), 7.59 (d, 1H), 7.23-7.34 (m, 2H), 6.62 (d, 1H), 5.78 (s, 2H), 4.51 (m, 1H), 3.92-4.09 (m, 2H), 3.39-3.83 (m, 4H), 3.03-3.23 (m, 2H), 2.01-2.17 (m, 2H).

LC/MS: mass calcd. for C₂₅H₂₂ClF₃N₄O₃S: 550.11. found 551.2 [M+H]⁺

Example 2

(5Z)-5-({1-[4-Chloro-2-(trifluoromethyl)benzyl]-1H-indazol-5-yl}methylidene)-3-{2-[(3S)-3-fluoropyrrolidin-1-yl]ethyl}-1,3-thiazolidine-2,4-dione

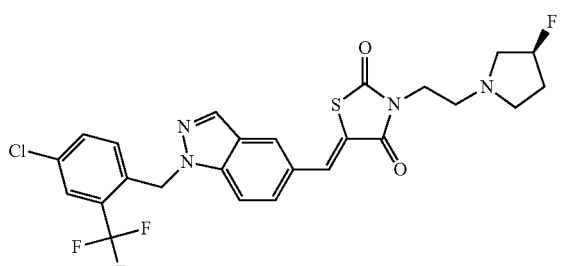

(5Z)-5-({1-[4-Chloro-2-(trifluoromethyl)benzyl]-1H-indazol-5-yl}methylidene)-3-{2-[(3S)-3-fluoropyrrolidin-1-yl]ethyl}-1,3-thiazolidine-2,4-dione was prepared from [(5Z)-5-({1-[4-chloro-2-(trifluoromethyl)benzyl]-1H-indazol-5-yl}methylidene)-2,4-dioxo-1,3-thiazolidine (from Example 1), 1-bromo-2-chloroethane and (3S)-3-fluoropyrrolidine following General Procedure G.

¹H NMR (400 MHz, CDCl₃): δ 8.17 (s, 1H), 8.11 (s, 1H), 7.89-7.97 (m, 1H), 7.70 (d, 1H), 7.59 (d, 1H), 7.25-7.35 (m, 2H), 6.63 (d, 1H), 5.78 (s, 2H), 5.16-5.41 (m, 1H), 3.57-4.11 (m, 6H), 3.08-3.24 (m, 2H), 2.32 (m, 2H).

LC/MS: mass calcd. for C₂₅H₂₁ClF₄N₄O₂S: 552.10. found 553.3 [M+H]⁺

Example 3

(5Z)-5-({1-[4-Chloro-2-(trifluoromethyl)benzyl]-1H-indazol-5-yl}methylidene)-3-(2-morpholin-4-ylethyl)-1,3-thiazolidine-2,4-dione

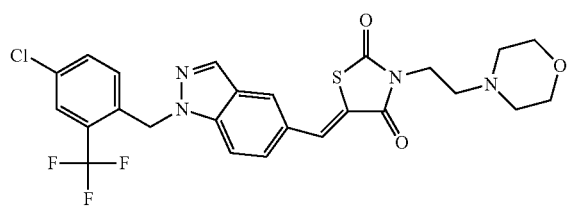 [SMILES: O=C1S/C(=C\c2ccc3c(cnn3Cc3ccc(Cl)cc3C(F)(F)F)c2)C(=O)N1CCN1CCOCC1]

(5Z)-5-({1-[4-Chloro-2-(trifluoromethyl)benzyl]-1H-indazol-5-yl}methylidene)-3-(2-morpholin-4-ylethyl)-1,3-thiazolidine-2,4-dione was prepared from [(5Z)-5-({1-[4-chloro-2-(trifluoromethyl)benzyl]-1H-indazol-5- yl}methylidene)-2,4-dioxo-1,3-thiazolidine and 4-(2-chloroethyl)-morpholine hydrochloride following General Procedure H.

¹H NMR (400 MHz, CDCl₃): δ 8.22 (s, 1H), 8.01 (s, 1H), 7.97 (s, 1H), 7.71 (s, 1H), 7.49-7.56 (m, 1H), 7.35 (dd, 2H), 6.67 (d, 1H), 5.80 (s, 2H), 3.90 (t, 2H), 3.66 (t, 4H), 2.64 (t, 2H), 2.52 (br. s., 4H).

LC/MS: mass calcd. for $C_{25}H_{22}ClF_3N_4O_3S$: 550.11. found 551.3 [M+H]⁺

Example 4

[(5Z)-5-({1-[4-Chloro-2-(trifluoromethyl)benzyl]-1H-indazol-5-yl}methylidene)-2,4-dioxo-1,3-thiazolidin-3-yl]acetic acid

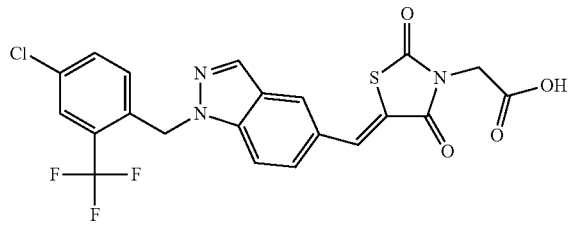 [SMILES: O=C(O)CN1C(=O)S/C(=C\c2ccc3c(cnn3Cc3ccc(Cl)cc3C(F)(F)F)c2)C1=O]

[(5Z)-5-({1-[4-Chloro-2-(trifluoromethyl)benzyl]-1H-indazol-5-yl}methylidene)-2,4-dioxo-1,3-thiazolidin-3-yl]acetic acid was prepared from [(5Z)-5-({1-[4-chloro-2-(trifluoromethyl)benzyl]-1H-indazol-5-yl}methylidene)-2,4-dioxo-1,3-thiazolidine (from Example 1) following General Procedure I.

¹H NMR (400 MHz, DMSO-d₆): δ 8.36 (s, 1H), 8.19 (s, 1H), 8.13 (s, 1H), 7.87 (d, 1H), 7.80 (d, 1H), 7.66-7.72 (m, 1H), 7.64 (dd, 1H), 6.76 (d, 1H), 5.85 (s, 2H), 4.37 (s, 2H).

LC/MS: mass calcd. for $C_{21}H_{13}ClF_3N_3O_4S$: 495.03. found 496.2 [M+H]⁺

Example 5

(5Z)-3-[2-(Dimethylamino)ethyl]-5-[(1-{[4-fluoro-2-(trifluoromethyl)phenyl]-methyl}-1H-indazol-5-yl)methylidene]-1,3-thiazolidine-2,4-dione

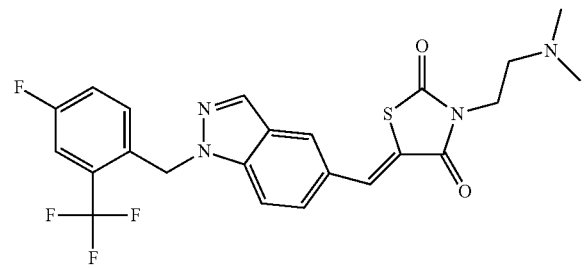 [SMILES: CN(C)CCN1C(=O)S/C(=C\c2ccc3c(cnn3Cc3ccc(F)cc3C(F)(F)F)c2)C1=O]

(A) [4-Fluoro-2-(trifluoromethyl)benzyl]-1H-indazol-5-carbaldehyde was prepared from 4-fluoro-2-(trifluoromethyl)benzyl bromide and 1H-indazol-5-carbaldehyde following General Procedure A.

(B) [(5Z)-5-({1-[4-Fluoro-2-(trifluoromethyl)benzyl]-1H-indazol-5-yl}methylidene)-2,4-dioxo-1,3-thiazolidine was prepared from [4-fluoro-2-(trifluoromethyl)benzyl]-1H-indazol-5-carbaldehyde following General Procedure E.

(C) (5Z)-3-[2-(Dimethylamino)ethyl]-5-[(1-{[4-fluoro-2-(trifluoromethyl)phenyl]-methyl}-1H-indazol-5-yl)methylidene]-1,3-thiazolidine-2,4-dione was prepared from [(5Z)-5-({1-[4-fluoro-2-(trifluoromethyl)benzyl]-1H-indazol-5-yl}methylidene)-2,4-dioxo-1,3-thiazolidine and 2-chloro-N,N-dimethylethylamine hydrochloride following General Procedure H.

¹H NMR (400 MHz, DMSO-d₆): δ 8.36 (s, 1H), 8.17 (s, 1H), 8.08 (s, 1H), 7.81 (d, 1H), 7.73 (dd, 1H), 7.69 (m, 1H), 7.45 (m, 1H), 6.87 (m, 1H), 5.86 (s, 2H), 3.77 (t, 2H), 2.48 (t, 2H), 2.17 (s, 6H).

LC/MS: mass calcd. for $C_{23}H_{20}F_4N_4O_2S$: 492.12. found 493.4 [M+H]⁺

Example 6

(5Z)-5-[(1-{[2,4-Bis(trifluoromethyl)phenyl]methyl}-1H-indazol-5-yl)methylidene]-3-[3-(dimethylamino)propyl]-1,3-thiazolidine-2,4-dione

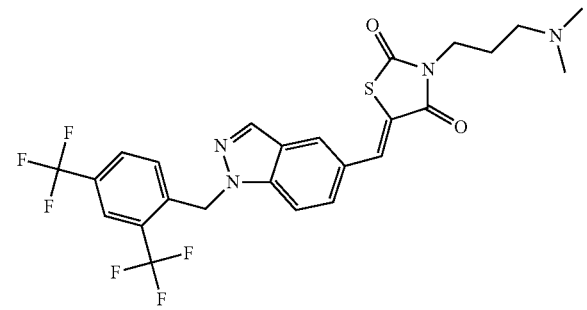 [SMILES: CN(C)CCCN1C(=O)S/C(=C\c2ccc3c(cnn3Cc3ccc(C(F)(F)F)cc3C(F)(F)F)c2)C1=O]

(A) [2,4-bis-(trifluoromethyl)benzyl]-1H-indazol-5-carbaldehyde was prepared from 2,4-bis-(trifluoromethyl)benzyl bromide and 1H-indazol-5-carbaldehyde following General Procedure A.

(B) [(5Z)-5-({1-[2,4-bis-(trifluoromethyl)benzyl]-1H-indazol-5-yl}methylidene)-2,4-dioxo-1,3-thiazolidine was prepared from [2,4-bis-(trifluoromethyl)benzyl]-1H-indazol-5-carbaldehyde following General Procedure E.

(C) (5Z)-5-[(1-{[2,4-bis-(trifluoromethyl)phenyl]methyl}-1H-indazol-5-yl)methylidene]-3-[3-(dimethylamino)propyl]-1,3-thiazolidine-2,4-dione was prepared from [(5Z)-5-({1-[2,4-bis-(trifluoromethyl)benzyl]-1H-indazol-5-yl}methylidene)-2,4-dioxo-1,3-thiazolidine and 3-dimethylamino-1-propyl chloride hydrochloride following General Procedure H.

¹H NMR (400 MHz, CDCl₃): δ 8.24 (s, 1H), 8.01 (s, 1H), 7.98 (br. s, 2H), 7.63 (d, 1H), 7.53 (dd, 1H), 7.35 (d, 1H), 6.83 (d, 1H), 5.89 (s, 2H), 3.83 (t, 2H), 2.34 (t, 2H), 2.21 (s, 6H), 1.84 (m, 2H).

LC/MS: mass calcd. for $C_{25}H_{22}F_6N_4O_2S$: 556.14. found 557.4 [M+H]⁺

Example 7

(5Z)-5-[(1-{[2,4-Bis(trifluoromethyl)phenyl]methyl}-1H-indazol-5-yl)methylidene]-3-[2-(dimethylamino)ethyl]-1,3-thiazolidine-2,4-dione

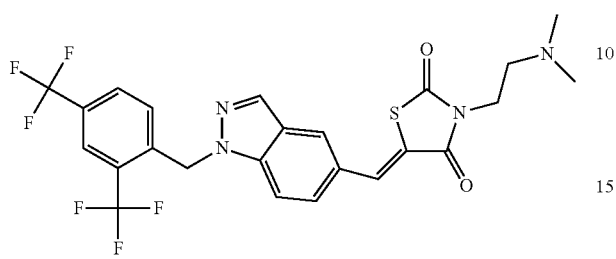

(5Z)-5-[(1-{[2,4-Bis(trifluoromethyl)phenyl]methyl}-1H-indazol-5-yl)methylidene]-3-[2-(dimethylamino)ethyl]-1,3-thiazolidine-2,4-dione was prepared from [(5Z)-5-({1-[2,4-bis-(trifluoromethyl)benzyl]-1H-indazol-5-yl}methylidene)-2,4-dioxo-1,3-thiazolidine (from Example 6) and 2-chloro-N,N-dimethylethylamine hydrochloride following General Procedure H.

$^1$H NMR (400 MHz, CDCl$_3$): δ 8.24 (s, 1H), 8.01 (s, 1H), 7.99 (s, 1H), 7.97 (s, 1H), 7.63 (d, 1H), 7.52 (dd, 1H), 7.35 (d, 1H), 6.83 (d, 1H), 5.89 (s, 2H), 3.88 (t, 2H), 2.58 (t, 2H), 2.29 (s, 6H).

LC/MS: mass calcd. for C$_{24}$H$_{20}$F$_6$N$_4$O$_2$S: 542.12. found 543.4 [M+H]$^+$

Example 8

(5Z)-5-[(1-{[4-(Methyloxy)-2-(trifluoromethyl)phenyl]methyl}-1H-indazol-5-yl)methylidene]-3-(2-morpholin-4-ylethyl)-1,3-thiazolidine-2,4-dione

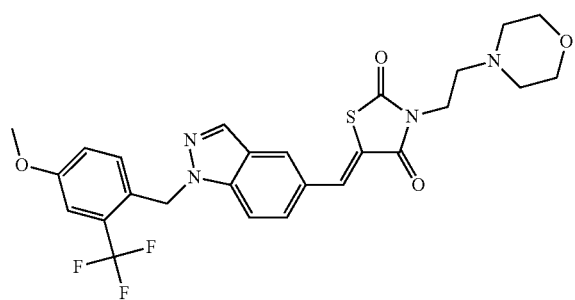 [SMILES: COc1ccc(Cn2ncc3cc(/C=C4\SC(=O)N(CCN5CCOCC5)C4=O)ccc32)c(C(F)(F)F)c1]

(A) [4-methoxy-2-(trifluoromethyl)benzyl]-1H-indazol-5-carbaldehyde was prepared from 4-methoxy-2-(trifluoromethyl)benzyl bromide and 1H-indazol-5-carbaldehyde following General Procedure A.
(B) [(5Z)-5-({1-[4-Methoxy-2-(trifluoromethyl)benzyl]-1H-indazol-5-yl}methylidene)-2,4-dioxo-1,3-thiazolidine was prepared from [4-methoxy-2-(trifluoromethyl)benzyl]-1H-indazol-5-carbaldehyde following General Procedure E.
(C) (5Z)-5-[(1-{[4-(Methyloxy)-2-(trifluoromethyl)phenyl]methyl}-1H-indazol-5-yl)methylidene]-3-(2-morpholin-4-ylethyl)-1,3-thiazolidine-2,4-dione was prepared from [(5Z)-5-({1-[4-Methoxy-2-(trifluoromethyl)benzyl]-1H-indazol-5-yl}methylidene)-2,4-dioxo-1,3-thiazolidine and 4-(2-chloroethyl)morpholine hydrochloride following General Procedure H.

$^1$H NMR (400 MHz, CD$_3$OD): δ 8.26 (s, 1H), 8.12 (s, 2H), 7.63 (dd, 1H), 7.56 (d, 1H), 7.27 (d, 1H), 7.01 (dd, 1H), 6.73 (d, 1H), 5.80 (s, 2H), 4.20 (t, 2H), 4.09 (br, 2H), 3.81 (s, 3H), 3.71 (br, 2H), 3.53 (t, 2H).

LC/MS: mass calcd. for C$_{26}$H$_{25}$F$_3$N$_4$O$_4$S: 546.15. found 547.2 [M+H]$^+$

Example 9

(5Z)-3-[2-(Dimethylamino)ethyl]-5-[(1-{[4-(methyloxy)-2-(trifluoromethyl)phenyl]methyl}-1H-indazol-5-yl)methylidene]-1,3-thiazolidine-2,4-dione

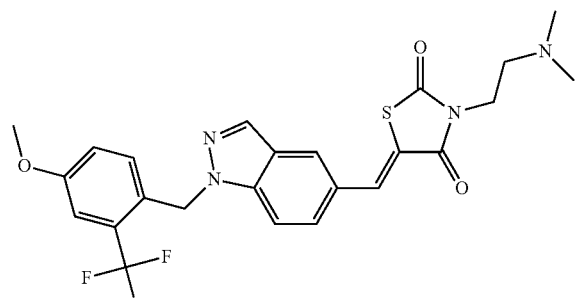

(5Z)-3-[2-(Dimethylamino)ethyl]-5-[(1-{[4-(methyloxy)-2-(trifluoromethyl)phenyl]methyl}-1H-indazol-5-yl)methylidene]-1,3-thiazolidine-2,4-dione was prepared from [(5Z)-5-({1-[4-methoxy-2-(trifluoromethyl)benzyl]-1H-indazol-5-yl}methylidene)-2,4-dioxo-1,3-thiazolidine (from Example 8) and 2-chloro-N,N-dimethylethylamine hydrochloride following General Procedure H.

$^1$H NMR (400 MHz, CD$_3$OD): δ 8.26 (d, 1H), 8.11 (br, 2H), 7.62 (dd, 1H), 7.56 (d, 1H), 7.27 (d, 1H), 7.01 (dd, 1H), 6.73 (d, 1H), 5.80 (s, 2H), 4.17 (t, 2H), 3.81 (s, 3H), 3.51 (t, 2H), 3.01 (s, 6H).

LC/MS: mass calcd. for C$_{24}$H$_{23}$F$_3$N$_4$O$_3$S: 504.14. found 505.2 [M+H]$^+$

Example 10

(5Z)-3-[3-(Dimethylamino)propyl]-5-[(1-{[4-(methyloxy)-2-(trifluoromethyl)phenyl]methyl}-1H-indazol-5-yl)methylidene]-1,3-thiazolidine-2,4-dione

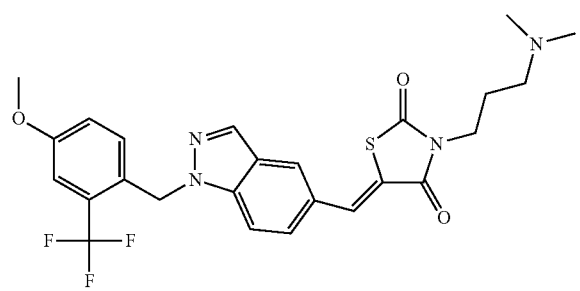 [SMILES: COc1ccc(Cn2ncc3cc(/C=C4\SC(=O)N(CCCN(C)C)C4=O)ccc32)c(C(F)(F)F)c1]

(5Z)-3-[3-(Dimethylamino)propyl]-5-[(1-{[4-(methyloxy)-2-(trifluoromethyl)phenyl]methyl}-1H-indazol-5-yl)

methylidene]-1,3-thiazolidine-2,4-dione was prepared from [(5Z)-5-({1-[4-methoxy-2-(trifluoromethyl)benzyl]-1H-indazol-5-yl}methylidene)-2,4-dioxo-1,3-thiazolidine (from Example 8) and 3-dimethylamino-1-propyl chloride hydrochloride following General Procedure H.

$^1$H NMR (400 MHz, CD$_3$OD): δ 8.25 (s, 1H), 8.05 (s, 1H), 7.60 (d, 1H), 7.53 (d, 1H), 7.27 (m, 2H), 7.00 (m, 1H), 6.72 (m, 1H), 5.78 (s, 2H), 3.88 (t, 2H), 3.81 (s, 3H), 3.22 (t, 2H), 2.91 (s, 6H), 2.13 (m, 2H).

LC/MS: mass calcd. for C$_{25}$H$_{25}$F$_3$N$_4$O$_3$S: 518.16. found 519.3 [M+H]$^+$ Example 11

(5Z)-5-[(1-{[4-(Methyloxy)-2-(trifluoromethyl)phenyl]methyl}-1H-indazol-5-yl)methylidene]-3-(2-piperidin-1-ylethyl)-1,3-thiazolidine-2,4-dione

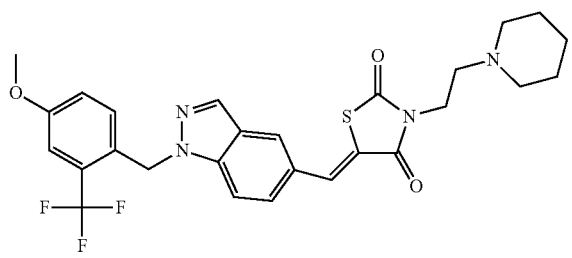 [SMILES: COc1ccc(Cn2ncc3cc(/C=C4\SC(=O)N(CCN5CCCCC5)C4=O)ccc32)c(C(F)(F)F)c1]

(5Z)-5-[(1-{[4-(Methyloxy)-2-(trifluoromethyl)phenyl]methyl}-1H-indazol-5-yl)methylidene]-3-(2-piperidin-1-ylethyl)-1,3-thiazolidine-2,4-dione was prepared from [(5Z)-5-({1-[4-methoxy-2-(trifluoromethyl)benzyl]-1H-indazol-5-yl}methylidene)-2,4-dioxo-1,3-thiazolidine (from Example 8) and 1-(2-chloroethyl)piperidine hydrochloride following General Procedure H.

$^1$H NMR (400 MHz, CDCl$_3$): δ 8.19 (s, 1H), 8.00 (s, 1H), 7.95 (m, 1H), 7.50 (dd, 1H), 7.36 (d, 1H), 7.23 (d, 1H), 6.88 (dd, 1H), 6.71 (d, 1H), 5.76 (s, 2H), 3.89 (t, 2H), 3.80 (s, 3H), 2.58 (t, 2H), 2.45 (br, 4H), 1.54 (m, 4H), 1.41 (m, 2H).

LC/MS: mass calcd. for C$_{27}$H$_{27}$F$_3$N$_4$O$_3$S: 544.18. found 545.3 [M+H]$^+$ Example 12

(5Z)-5-[(1-{[4-(Methyloxy)-2-(trifluoromethyl)phenyl]methyl}-1H-indazol-5-yl)methylidene]-3-[2-(4-methyl piperazin-1-yl)ethyl]-1,3-thiazolidine-2,4-dione

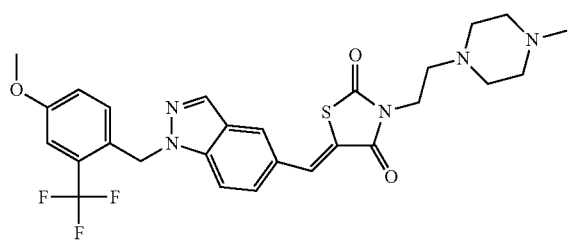 [SMILES: COc1ccc(Cn2ncc3cc(/C=C4\SC(=O)N(CCN5CCN(C)CC5)C4=O)ccc32)c(C(F)(F)F)c1]

(5Z)-5-[(1-{[4-(Methyloxy)-2-(trifluoromethyl)phenyl]methyl}-1H-indazol-5-yl)methylidene]-3-[2-(4-methylpiperazin-1-yl)ethyl]-1,3-thiazolidine-2,4-dione was prepared from [(5Z)-5-({1-[4-methoxy-2-(trifluoromethyl)benzyl]-1H-indazol-5-yl}methylidene)-2,4-dioxo-1,3-thiazolidine (from Example 8) and 2-(4-methylpiperazin-1-yl)ethanol following General Procedure J.

$^1$H NMR (400 MHz, CDCl$_3$): δ 8.15 (d, 1H), 8.09 (m, 1H), 7.92 (s, 1H), 7.56 (dd, 1H), 7.29 (d, 1H), 7.22 (d, 1H), 6.86 (dd, 1H), 6.67 (d, 1H), 5.75 (s, 2H), 3.98 (br, 2H), 3.79 (s, 3H), 3.73 (br, 2H), 3.45 (br, 2H), 3.15 (t, 2H), 2.50 (br, 4H), 2.34 (s, 3H).

LC/MS: mass calcd. for C$_{17}$H$_{28}$F$_3$N$_5$O$_3$S: 559.19. found 560.3 [M+H]$^+$ Example 13

(5Z)-3-{2-[(3R)-3-Fluoropyrrolidin-1-yl]ethyl}-5-[(1-{[4-(methyloxy)-2-(trifluoromethyl)phenyl]methyl}-1H-indazol-5-yl)methylidene]-1,3-thiazolidine-2,4-dione

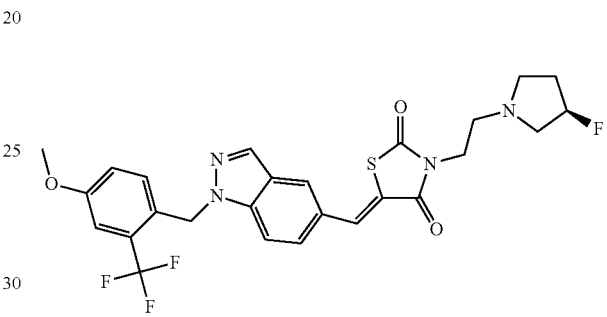

(5Z)-3-{2-[(3R)-3-Fluoropyrrolidin-1-yl]ethyl}-5-[(1-{[4-(methyloxy)-2-(trifluoro-methyl)phenyl]methyl}-1H-indazol-5-yl)methylidene]-1,3-thiazolidine-2,4-dione was prepared from [(5Z)-5-({1-[4-methoxy-2-(trifluoromethyl)benzyl]-1H-indazol-5-yl}methylidene)-2,4-dioxo-1,3-thiazolidine (from Example 8), 1-bromo-2-chloroethane and (3R)-3-fluoropyrrolidine following General Procedure G.

$^1$H NMR (400 MHz, CDCl$_3$): δ 8.16 (s, 1H), 8.10 (s, 1H), 7.93 (m, 1H), 7.57 (d, 1H), 7.30 (d, 1H), 7.23 (d, 1H), 6.86 (dd, 1H), 6.67 (d, 1H), 5.75 (s, 2H), 5.28 (m, 1H), 3.92-4.14 (m, 2H), 3.80 (s, 3H), 3.72 (m, 2H), 3.01-3.21 (m, 4H), 2.01-2.40 (2H).

LC/MS: mass calcd. for C$_{26}$H$_{24}$F$_4$N$_4$O$_3$S: 548.15. found 549.2 [M+H]$^+$ Example 14

(5Z)-3-{2-[(3S)-3-Hydroxypyrrolidin-1-yl]ethyl}-5-({1-[4-methoxy-2-(trifluoromethyl)benzyl]-1H-indazol-5-yl}methylidene)-1,3-thiazolidine-2,4-dione

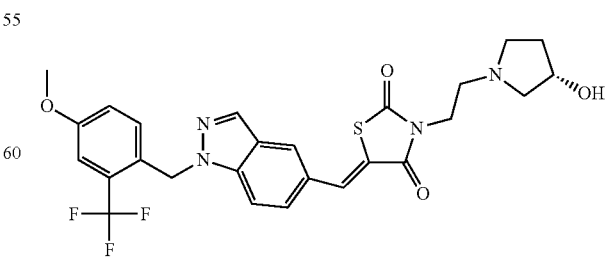

(5Z)-3-{2-[(3S)-3-Hydroxypyrrolidin-1-yl]ethyl}-5-({1-[4-methoxy-2-(trifluoromethyl)benzyl]-1H-indazol-5- yl}methylidene)-1,3-thiazolidine-2,4-dione was prepared from [(5Z)-5-({1-[4-methoxy-2-(trifluoromethyl)benzyl]-1H-indazol-5-yl}methylidene)-2,4-dioxo-1,3-thiazolidine (from Example 8), 1-bromo-2-chloroethane and (3S)-3-hydroxypyrrolidine following General Procedure G.

$^1$H NMR (400 MHz, CDCl$_3$): δ 8.15 (d, 1H), 8.09 (s, 1H), 7.94 (d, 1H), 7.57 (d, 1H), 7.29 (d, 1H), 7.23 (d, 1H), 6.86 (dd, 1H), 6.66 (d, 1H), 5.75 (s, 2H), 4.53 (m, 1H), 3.95-4.12 (m, 2H), 3.79 (s, 3H), 3.42-3.78 (m, 4H), 3.14 (m, 2H), 2.01-2.34 (m, 2H).

LC/MS: mass calcd. for $C_{26}H_{25}F_3N_4O_4S$: 546.15. found 547.3 [M+H]$^+$

Example 15

(5Z)-3-[2-(4-Hydroxypiperidin-1-yl)ethyl]-5-({1-[4-methoxy-2-(trifluoromethyl)benzyl]-1H-indazol-5-yl}methylidene)-1,3-thiazolidine-2,4-dione

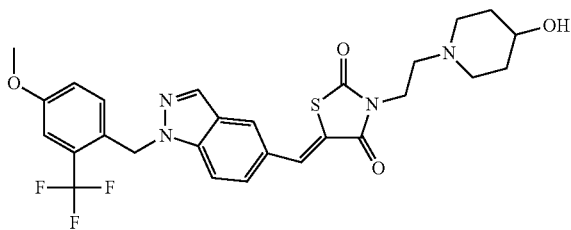 [SMILES: COc1ccc(Cn2ncc3cc(/C=C4\SC(=O)N(CCN5CCC(O)CC5)C4=O)ccc32)c(C(F)(F)F)c1]

(5Z)-3-[2-(4-Hydroxypiperidin-1-yl)ethyl]-5-({1-[4-methoxy-2-(trifluoromethyl)benzyl]-1H-indazol-5-yl}methylidene)-1,3-thiazolidine-2,4-dione was prepared from [(5Z)-5-({1-[4-methoxy-2-(trifluoromethyl)benzyl]-1H-indazol-5-yl}methylidene)-2,4-dioxo-1,3-thiazolidine (from Example 8), 1-bromo-2-chloroethane and 4-hydroxypiperidine following General Procedure G.

$^1$H NMR (400 MHz, CDCl$_3$): δ 8.15 (m, 1H), 8.09 (m, 1H), 7.91 (s, 1H), 7.56 (dd, 1H), 7.29 (d, 1H), 7.22 (d, 1H), 6.86 (dd, 1H), 6.66 (d, 1H), 5.75 (s, 2H), 3.91-4.08 (m, 3H), 3.80 (s, 3H), 3.52 (br. s, 2H), 3.30 (br. s, 2H), 3.15 (t, 2H), 1.52-2.04 (m, 4H).

LC/MS: mass calcd. for $C_{27}H_{27}F_3N_4O_4S$: 560.17. found 561.3 [M+H]$^+$

Example 16

(5Z)-3-{2-[4-(2-Hydroxyethyl)piperazin-1-yl]ethyl}-5-({1-[4-methoxy-2-(trifluoromethyl)benzyl]-1H-indazol-5-yl}methylidene)-1,3-thiazolidine-2,4-dione

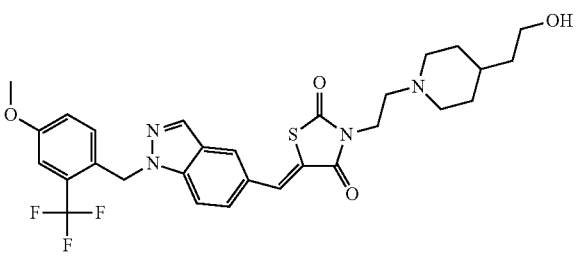 [SMILES: COc1ccc(Cn2ncc3cc(/C=C4\SC(=O)N(CCN5CCC(CCO)CC5)C4=O)ccc32)c(C(F)(F)F)c1]

(5Z)-3-{2-[4-(2-Hydroxyethyl)piperazin-1-yl]ethyl}-5-({1-[4-methoxy-2-(trifluoromethyl)benzyl]-1H-indazol-5-yl}methylidene)-1,3-thiazolidine-2,4-dione was prepared from [(5Z)-5-({1-[4-methoxy-2-(trifluoromethyl)benzyl]-1H-indazol-5-yl}methylidene)-2,4-dioxo-1,3-thiazolidine (from Example 8), 1-bromo-2-chloroethane and 1-(2-hydroxyethyl)piperazine following General Procedure G.

$^1$H NMR (400 MHz, CD$_3$OD): δ 8.20 (m, 1H), 8.19 (m, 1H), 7.90 (s, 1H), 7.67 (dd, 1H), 7.45 (d, 1H), 7.27 (d, 1H), 7.00 (dd, 1H), 6.67 (d, 1H), 5.78 (s, 2H), 4.00 (m, 2H), 3.91 (m, 2H), 3.81 (s, 3H), 3.69 (br. s, 2H), 3.20-3.52 (m, 10H).

LC/MS: mass calcd. for $C_{28}H_{30}F_3N_5O_4S$: 589.20. found 590.3 [M+H]$^+$

Example 17

(5Z)-5-({1-[4-Methoxy-2-(trifluoromethyl)benzyl]-1H-indazol-5-yl}methylidene)-3-(2-pyrrolidin-1-ylethyl)-1,3-thiazolidine-2,4-dione

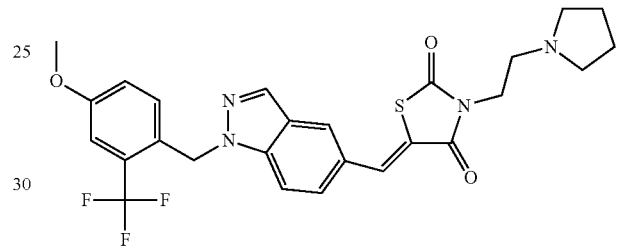

(5Z)-5-({1-[4-Methoxy-2-(trifluoromethyl)benzyl]-1H-indazol-5-yl}methylidene)-3-(2-pyrrolidin-1-ylethyl)-1,3-thiazolidine-2,4-dione was prepared from [(5Z)-5-({1-[4-methoxy-2-(trifluoromethyl)benzyl]-1H-indazol-5-yl}methylidene)-2,4-dioxo-1,3-thiazolidine (from Example 8) and 1-(2-chloroethyl)pyrrolidine hydrochloride following General Procedure H.

$^1$H NMR (400 MHz, CDCl$_3$): δ 8.19 (d, 1H), 8.01 (s, 1H), 7.94 (m, 1H), 7.48 (dd, 1H), 7.36 (d, 1H), 7.23 (d, 1H), 6.88 (dd, 1H), 6.71 (d, 1H), 5.76 (s, 2H), 3.92 (t, 2H), 3.80 (s, 3H), 2.76 (t, 2H), 2.59 (m, 4H), 1.77 (m, 4H).

LC/MS: mass calcd. for $C_{26}H_{25}F_3N_4O_3S$: 530.16. found 531.3 [M+H]$^+$

Example 18

(5Z)-3-[2-(Diethylamino)ethyl]-5-({1-[4-methoxy-2-(trifluoromethyl)benzyl]-1H-indazol-5-yl}methylidene)-1,3-thiazolidine-2,4-dione

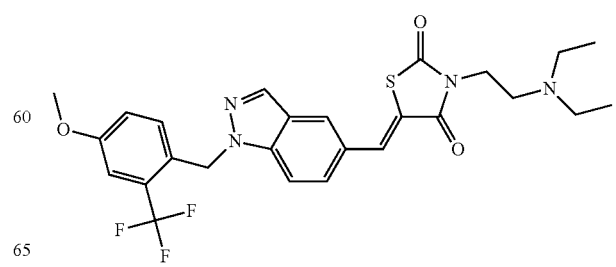

(5Z)-3-[2-(Diethylamino)ethyl]-5-({1-[4-methoxy-2-(trifluoromethyl)benzyl]-1H-indazol-5-yl}methylidene)-1,3-thiazolidine-2,4-dione was prepared from [(5Z)-5-({1-[4-methoxy-2-(trifluoromethyl)benzyl]-1H-indazol-5-yl}methylidene)-2,4-dioxo-1,3-thiazolidine (from Example 8) and N,N-diethylaminoethyl chloride hydrochloride following General Procedure H.

$^1$H NMR (400 MHz, CDCl$_3$): δ 8.19 (d, 1H), 8.00 (s, 1H), 7.95 (m, 1H), 7.49 (dd, 1H), 7.36 (d, 1H), 7.23 (d, 1H), 6.88 (dd, 1H), 6.71 (d, 1H), 5.76 (s, 2H), 3.84 (t, 2H), 3.80 (s, 3H), 2.70 (t, 2H), 2.56 (q, 4H), 1.01 (t, 6H).

LC/MS: mass calcd. for $C_{26}H_{27}F_3N_4O_3S$: 532.18. found 533.3 [M+H]$^+$

Example 19

[(5Z)-5-({1-[4-Chloro-2-(trifluoromethyl)benzyl]-1H-indazol-5-yl}methylidene)-2,4-dioxo-1,3-thiazolidin-3-yl]acetic acid

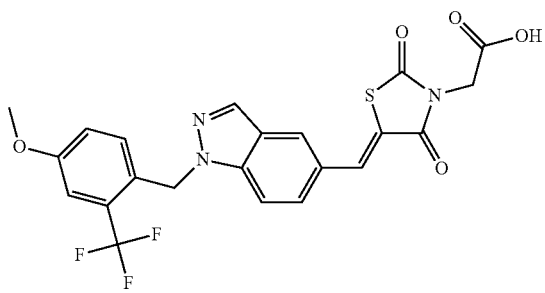 [SMILES: COc1ccc(Cn2ncc3cc(/C=C4\SC(=O)N(CC(=O)O)C4=O)ccc32)c(C(F)(F)F)c1]

[(5Z)-5-({1-[4-Methoxy-2-(trifluoromethyl)benzyl]-1H-indazol-5-yl}methylidene)-2,4-dioxo-1,3-thiazolidin-3-yl]acetic acid was prepared from [(5Z)-5-({1-[4-methoxy-2-(trifluoromethyl)benzyl]-1H-indazol-5-yl}methylidene)-2,4-dioxo-1,3-thiazolidine (from Example 8) following General Procedure I.

$^1$H NMR (400 MHz, DMSO-d$_6$): δ 13.46 (br. s, 1H), 8.35 (s, 1H), 8.20 (s, 1H), 8.15 (s, 1H), 7.78 (d, 1H), 7.69 (dd, 1H), 7.28 (d, 1H), 7.14 (dd, 1H), 6.81 (d, 1H), 5.79 (s, 2H), 4.39 (s, 2H), 3.80 (s, 3H).

LC/MS: mass calcd. for $C_{22}H_{16}F_3N_3O_6S$: 491.08. found 492.3 [M+H]$^+$

Example 20

(5Z)-5-({1-[4-Methoxy-2-(trifluoromethyl)benzyl]-3-methyl-1H-indazol-5-yl}methylidene)-3-(2-morpholin-4-ylethyl)-1,3-thiazolidine-2,4-dione

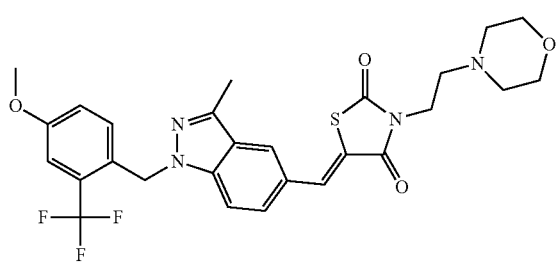 [SMILES: COc1ccc(Cn2nc(C)c3cc(/C=C4\SC(=O)N(CCN5CCOCC5)C4=O)ccc32)c(C(F)(F)F)c1]

(A) 5-Bromo-1-[4-methoxy-2-(trifluoromethyl)benzyl]-3-methyl-1H-indazole was prepared from 4-methoxy-2-(trifluoromethyl)benzyl bromide and 5-bromo-3-methyl-1H-indazole following General Procedure A.

(B) 1-[4-Methoxy-2-(trifluoromethyl)benzyl]-3-methyl-1H-indazol-5-carbonitrile was prepared from 5-bromo-1-[4-methoxy-2-(trifluoromethyl)benzyl]-3-methyl-1H-indazole following General Procedure P (C) 1-[4-Methoxy-2-(trifluoromethyl)benzyl]-3-methyl-1H-indazol-5-carbaldehyde was prepared from 1-[4-methoxy-2-(trifluoromethyl)benzyl]-3-methyl-1H-indazol-5-carbonitrile following General Procedure Q.

(D) [(5Z)-5-({1-[4-Methoxy-2-(trifluoromethyl)benzyl]-3-methyl-1H-indazol-5-yl}methylidene)-2,4-dioxo-1,3-thiazolidine was prepared from [4-methoxy-2-(trifluoromethyl)benzyl]-3-methyl-1H-indazol-5-carbaldehyde following General Procedure E.

(E) (5Z)-5-({1-[4-Methoxy-2-(trifluoromethyl)benzyl]-3-methyl-1H-indazol-5-yl}methylidene)-3-(2-morpholin-4-ylethyl)-1,3-thiazolidine-2,4-dione was prepared from [(5Z)-5-({1-[4-methoxy-2-(trifluoromethyl)benzyl]-3-methyl-1H-indazol-5-yl}methylidene)-2,4-dioxo-1,3-thiazolidine and 4-(2-chloroethyl)morpholine hydrochloride following General Procedure H.

$^1$H NMR (400 MHz, DMSO-d$_6$): δ 9.82 (br. s, 1H), 8.13 (d, 1H), 7.72 (d, 1H), 7.66 (dd, 1H), 7.27 (d, 1H), 7.14 (dd, 1H), 6.82 (d, 1H), 5.70 (s, 2H), 3.92-4.13 (m, 3H), 3.80 (s, 3H), 3.54-3.71 (m, 3H), 3.44-3.53 (m, 1H), 3.09-3.24 (m, 1H), 2.55 (s, 3H).

LCMS: mass calcd. for $C_{27}H_{27}F_3N_4O_4S$: 560.17. found 561.2 [M+H]$^+$

Example 21

(5Z)-3-{2-[cis-2,6-Dimethylmorpholin-4-yl]ethyl}-5-({1-[4-methoxy-2-(trifluoromethyl)benzyl]-1H-indazol-5-yl}methylidene)-1,3-thiazolidine-2,4-dione

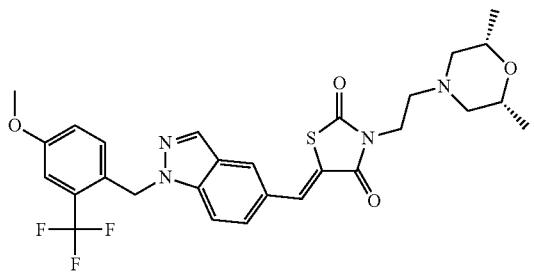

(5Z)-3-{2-[cis-2,6-Dimethylmorpholin-4-yl]ethyl}-5-({1-[4-methoxy-2-(trifluoromethyl)benzyl]-1H-indazol-5-yl}methylidene)-1,3-thiazolidine-2,4-dione was prepared from [(5Z)-5-({1-[4-methoxy-2-(trifluoromethyl)-benzyl]-1H-indazol-5-yl}methylidene)-2,4-dioxo-1,3-thiazolidine (from Example 8), 1-bromo-2-chloroethane and cis-2,6-dimethylmorpholine following General Procedure G.

$^1$H NMR (400 MHz, DMSO-d$_6$): δ 8.27 (s, 1H), 8.15 (s, 1H), 7.82 (s, 1H), 7.67 (dd, 1H), 7.66 (d, 1H), 7.27 (d, 1H), 7.13 (dd, 1H), 6.76 (d, 1H), 5.77 (s, 2H), 4.03-4.23 (m, 1H), 3.87 (br. s, 2H), 3.79 (s, 3H), 3.47-3.66 (m, 2H), 3.04-3.21 (m, 1H), 1.02-1.19 (m, 6H).

LCMS: mass calcd. for $C_{28}H_{29}F_3N_4O_4S$: 574.19. found 575.1 [M+H]$^+$

Example 22

4-[(5Z)-5-({1-[4-Methoxy-2-(trifluoromethyl)benzyl]-1H-indazol-5-yl}methylidene)-2,4-dioxo-1,3-thiazolidin-3-yl]cyclohexanecarboxylic acid

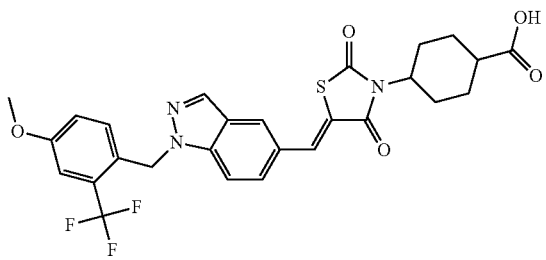 [SMILES: COc1ccc(Cn2ncc3cc(/C=C4\SC(=O)N(C5CCC(C(=O)O)CC5)C4=O)ccc32)c(C(F)(F)F)c1]

(A) [(5Z)-5-({1-[4-Methoxy-2-(trifluoromethyl)benzyl]-1H-indazol-5-yl}methylidene)-2,4-dioxo-1,3-thiazolidine (from Example 8) and 4-hydroxycyclohexanecarboxylic acid ethyl ester were reacted following General Procedure J to afford [(5Z)-5-({1-[4-methoxy-2-(trifluoromethyl)benzyl]-1H-indazol-5-yl}methylidene)-2,4-dioxo-1,3-thiazolidin-3-yl]cyclohexanecarboxylic acid ethyl ester.

(B) [(5Z)-5-({1-[4-Methoxy-2-(trifluoromethyl)benzyl]-1H-indazol-5-yl}methylidene)-2,4-dioxo-1,3-thiazolidin-3-yl]cyclohexanecarboxylic acid ethyl ester was hydrolyzed following General Procedure O to provide 4-[(5Z)-5-({1-[4-methoxy-2-(trifluoromethyl)benzyl]-1H-indazol-5-yl}methylidene)-2,4-dioxo-1,3-thiazolidin-3-yl]cyclohexanecarboxylic acid.

$^1$H NMR (400 MHz, DMSO-$d_6$): δ 12.25 (br. s, 1H), 8.33 (s, 1H), 8.14 (d, 1H), 8.03 (d, 1H), 7.76 (d, 1H), 7.65 (ddd, 1H), 7.27 (d, 1H), 7.14 (dd, 1H), 6.80 (d, 1H), 5.78 (s, 2H), 4.05-4.27 (m, 1H), 3.80 (s, 3H), 1.94-2.30 (m, 5H), 1.69-1.85 (m, 1H), 1.31-1.68 (m, 3H).

LCMS: mass calcd. for $C_{27}H_{24}F_3N_3O_6S$: 559.14. found 560.0 [M+H]$^+$

Example 23

(5Z)-5-({1-[4-Methoxy-2-(trifluoromethyl)benzyl]-1H-indazol-5-yl}methylidene)-3-{[(2S)-1-methylpyrrolidin-2-yl]methyl}-1,3-thiazolidine-2,4-dione

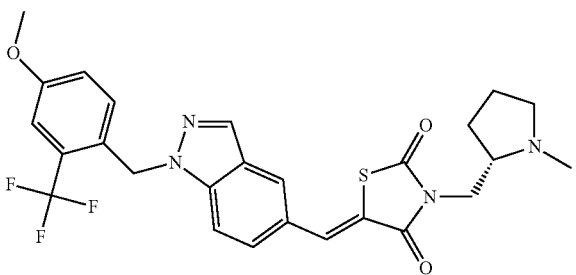 [SMILES: COc1ccc(Cn2ncc3cc(/C=C4\SC(=O)N(C[C@@H]5CCCN5C)C4=O)ccc32)c(C(F)(F)F)c1]

(A) {[(2S)-1-methylpyrrolidin-2-yl]methyl}-1,3-thiazolidine-2,4-dione was prepared from (2S)-1-methylpyrrolidin-2-yl]methyl alcohol and 1,3-thiazolidine-2,4-dione following General Procedure C.

(B) (5Z)-5-({1-[4-Methoxy-2-(trifluoromethyl)benzyl]-1H-indazol-5-yl}methylidene)-3-{[(2S)-1-methylpyrrolidin-2-yl]methyl}-1,3-thiazolidine-2,4-dione was prepared from {[(2S)-1-methylpyrrolidin-2-yl]methyl}-1,3-thiazolidine-2,4-dione and [4-methoxy-2-(trifluoromethyl)benzyl]-1H-indazol-5-carbaldehyde (from Example 8) following General Procedure F. Treatment with HCl in ether afforded the corresponding HCl salt.

$^1$H NMR (400 MHz, DMSO-$d_6$): δ 9.78-10.25 (br. m, 1H), 8.31-8.38 (m, 1H), 8.14-8.22 (m, 1H), 8.05-8.14 (m, 1H), 7.73-7.83 (m, 1H), 7.62-7.72 (m, 1H), 7.28 (d, 1H), 7.14 (dd, 1H), 6.84 (d, 1H), 5.79 (s, 2H), 4.01-4.16 (m, 2H), 3.80 (s, 3H), 3.50-3.68 (m, 2H), 3.05-3.19 (m, 1H), 2.95 (d, 2H), 2.76-2.87 (m, 1H), 2.10-2.28 (m, 1H), 1.63-2.06 (m, 3H).

LCMS: mass calcd. for $C_{26}H_{26}F_3N_4O_3S$: 530.16. found 531.3 [M+H]$^+$

Example 24

4-[(5Z)-5-({1-[4-Methoxy-2-(trifluoromethyl)benzyl]-1H-indazol-5-yl}methylidene)-2,4-dioxo-1,3-thiazolidin-3-yl]-N-(methylsulfonyl)cyclohexanecarboxamide

4-[(5Z)-5-({1-[4-Methoxy-2-(trifluoromethyl)benzyl]-1H-indazol-5-yl}methylidene)-2,4-dioxo-1,3-thiazolidin-3-yl]-N-(methylsulfonyl)cyclohexanecarboxamide was prepared from 4-[(5Z)-5-({1-[4-methoxy-2-(trifluoromethyl)benzyl]-1H-indazol-5-yl}methylidene)-2,4-dioxo-1,3-thiazolidin-3-yl]cyclohexanecarboxylic acid (Example 22) following General Procedure L using methanesulfonic acid amide in place of the sulfamide.

$^1$H NMR (400 MHz, DMSO-$d_6$): δ 11.64 (br. s, 1H), 8.33 (s, 1H), 8.14 (d, 1H), 8.03 (d, 1H), 7.76 (d, 1H), 7.65 (ddd, 1H), 7.27 (d, 1H), 7.14 (dd, 1H), 6.80 (dd, 1H), 5.78 (s, 2H), 4.08-4.25 (m, 1H), 3.80 (s, 3H), 3.25 (d, 3H), 2.54-2.70 (m, 1H), 2.22-2.43 (m, 2H), 2.02-2.22 (m, 2H), 1.95 (br. d, 1H), 1.79 (br. d, 1H), 1.37-1.70 (m, 3H).

LCMS: mass calcd. for $C_{28}H_{27}F_3N_4O_6S_2$: 636.67. found 637.0 [M+H]$^+$

Example 25

(5Z)-5-({3-Methoxy-1-[4-methoxy-2-(trifluoromethyl)benzyl]-1H-indazol-5-yl}methylidene)-3-(2-morpholin-4-ylethyl)-1,3-thiazolidine-2,4-dione

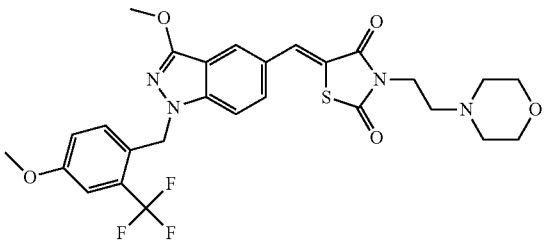 [SMILES: COc1ccc(Cn2nc(OC)c3cc(/C=C4\SC(=O)N(CCN5CCOCC5)C4=O)ccc32)c(C(F)(F)F)c1]

(A) Methyl 5-cyano-2-fluorobenzoate was prepared from methyl 5-bromo-2-fluorobenzoate following General Procedure P.

(B) A mixture of methyl 5-cyano-2-fluorobenzoate (0.018 mol), LiOH (0.02 mol), THF (35 mL) and water (7 mL)

was stirred at rt for 2 h. The solution was acidified with conc. HCl and concentrated to dryness to afford crude 5-cyano-2-fluorobenzoic acid, which was used directly without further purification.

(C) A mixture of the crude 5-cyano-2-fluorobenzoic acid, tert-butyl carbazate (0.02 mol) and EDCI (0.02 mol) in DCM (30 mL) was stirred overnight at rt. The reaction was then extracted with water, dried ($K_2CO_3$) and concentrated in vacuo. Purification by silica gel chromatography (DCM/MeOH) afforded 2-(5-cyano-2-fluorobenzoyl)hydrazinecarboxylic acid tert-butyl ester.

(D) 2-(5-Cyano-2-fluorobenzoyl)hydrazinecarboxylic acid tert-butyl ester was deprotected following General Procedure N to afford (5-cyano-2-fluorobenzoyl)hydrazine.

(E) A mixture of (5-cyano-2-fluorobenzoyl)hydrazine (1 mmol) and 4-methoxy-2-trifluoromethylbenzaldehyde (1.25 mmol) was refluxed in EtOH (10 mL) for 1 h, then cooled to 5° C. The precipitate that formed was filtered and washed with cold EtOH to afford 5-cyano-2-fluorobenzoic acid (4-methoxy-2-trifluoromethylbenzylidene)hydrazide.

(F) To a suspension of 5-cyano-2-fluoro-benzoic acid (4-methoxy-2-trifluoromethylbenzylidene)hydrazide (0.64 mmol) in DCM (3 mL) was added TES (0.5 mL) followed by TFA (1.5 mL), and the resulting solution was stirred at rt for 3 h, then concentrated. The residual syrup was taken up in DCM (10 mL) and extracted successively with 0.1N NaOH and water, dried ($K_2CO_3$) and concentrated. Purification by silica gel chromatography (DCM/MeOH) afforded 5-cyano-2-fluorobenzoic acid 2-(4-methoxy-2-trifluoromethylbenzyl)hydrazide.

(G) A solution of 5-cyano-2-fluorobenzoic acid 2-(4-methoxy-2-trifluoromethylbenzyl)hydrazide (0.6 mmol) in N,N-DMA (2 mL) was heated at 120° C. for 3 h, then cooled to rt. Water (10 mL) was gradually added, and the resultant precipitate was filtered and washed with water to afford 3-hydroxy-1-(4-methoxy-2-trifluoromethylbenzyl)-1H-indazole-5-carbonitrile.

(H) Treatment of 3-hydroxy-1-(4-methoxy-2-trifluoromethylbenzyl)-1H-indazole-5-carbonitrile following General Procedure Q provided 3-hydroxy-1-(4-methoxy-2-trifluoromethylbenzyl)-1H-indazole-5-carbaldehyde.

(I) A mixture of 3-hydroxy-1-(4-methoxy-2-trifluoromethylbenzyl)-1H-indazole-5-carbaldehyde (0.5 mmol), $K_2CO_3$ (1.7 mmol) and iodomethane (1 mmol) in DMF (3 mL) was stirred at rt overnight. The reaction was diluted with water (5 mL) and extracted with ether (3×), dried (anhydrous $Na_2SO_4$) and concentrated. Purification of the resultant residue by silica gel chromatography afforded 3-methoxy-1-(4-methoxy-2-trifluoromethylbenzyl)-1H-indazole-5-carbaldehyde.

(J) Reaction of 3-methoxy-1-(4-methoxy-2-trifluoromethyl-benzyl)-1H-indazole-5-carbaldehyde with 1,3-thiazolidine-2,4-dione following General Procedure E provided (5Z)-5-({3-methoxy-1-[4-methoxy-2-(trifluoromethyl)benzyl]-1H-indazol-5-yl}methylidene)-1,3-thiazolidine-2,4-dione.

(K) (5Z)-5-({3-Methoxy-1-[4-methoxy-2-(trifluoromethyl)benzyl]-1H-indazol-5-yl}methylidene)-3-(2-morpholin-4-ylethyl)-1,3-thiazolidine-2,4-dione was prepared from (5Z)-5-({3-methoxy-1-[4-methoxy-2-(trifluoromethyl)-benzyl]-1H-indazol-5-yl}methylidene)-1,3-thiazolidine-2,4-dione and 4-(2-chloroethyl)morpholine hydrochloride following General Procedure H.

$^1$H NMR (400 MHz, DMSO-$d_6$): δ 10.12 (br. s, 1H), 8.11 (s, 1H), 8.00 (s, 1H), 7.66 (s, 2H), 7.27 (d, 1H), 7.14 (dd, 1H), 6.81 (d, 1H), 5.61 (s, 2H), 4.02-4.15 (m, 2H), 4.01 (s, 3H), 3.80 (s, 3H), 3.53-3.74 (m, 4H), 3.01-3.24 (m, 2H).

LCMS: mass calcd. for $C_{27}H_{27}F_3N_4O_6S$: 576.17. found 577.2 [M+H]$^+$

Example 26

(5Z)-5-({1-[4-Methoxy-2-(trifluoromethyl)benzyl]-1H-indazol-5-yl}methylidene)-3-piperidin-4-yl-1,3-thiazolidine-2,4-dione

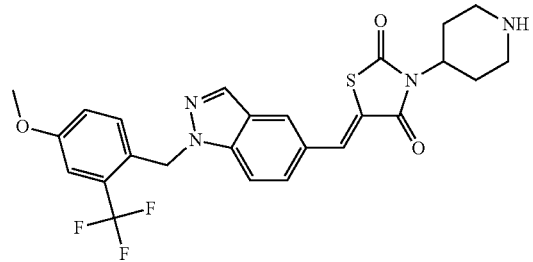 [SMILES: COc1ccc(Cn2ncc3cc(/C=C4\SC(=O)N(C5CCNCC5)C4=O)ccc32)c(C(F)(F)F)c1]

(A) 1,1-Dimethylethyl 4-{(5Z)-5-[(1-{[4-methoxy-2-(trifluoromethyl)phenyl]-methyl}-1H-indazol-5-yl)methylidene]-2,4-dioxo-1,3-thiazolidin-3-yl}piperidine-1-carboxylate was prepared from (5Z)-5-({1-[4-methoxy-2-(trifluoromethyl)benzyl]-1H-indazol-5-yl}methylidene)-2,4-dioxo-1,3-thiazolidine (from Example 8) and 4-hydroxypiperidine-1-carboxylic acid tert-butyl ester following General Procedure J.

(B) (5Z)-5-({1-[4-Methoxy-2-(trifluoromethyl)benzyl]-1H-indazol-5-yl}methylidene)-3-piperidin-4-yl-1,3-thiazolidine-2,4-dione was prepared from 1,1-dimethylethyl 4-{(5Z)-5-[(1-{[4-methoxy-2-(trifluoromethyl)phenyl]methyl}-1H-indazol-5-yl)methylidene]-2,4-dioxo-1,3-thiazolidin-3-yl}piperidine-1-carboxylate following General Procedure N.

$^1$H NMR (400 MHz, DMSO-$d_6$): δ 8.86 (br. s, 1H), 8.41 (br. s, 1H), 8.34 (s, 1H), 8.15 (s, 1H), 8.06 (s, 1H), 7.76 (d, 1H), 7.66 (dd, 1H), 7.28 (d, 1H), 7.14 (dd, 1H), 6.83 (d, 1H), 5.78 (s, 2H), 4.39-4.61 (m, 1H), 3.80 (s, 3H), 3.38 (d, 2H), 3.34 (s, 2H), 2.97-3.17 (m, 2H), 1.92 (d, 2H).

LCMS: mass calcd. for $C_{26}H_{23}F_3N_4O_3S$: 516.14. found 517.2 [M+H]$^+$

Example 27

(5Z)-5-({1-[4-Chloro-2-(trifluoromethyl)benzyl]-3-methoxy-1H-indazol-5-yl}methylidene)-3-(2-pyrrolidin-1-ylethyl)-1,3-thiazolidine-2,4-dione

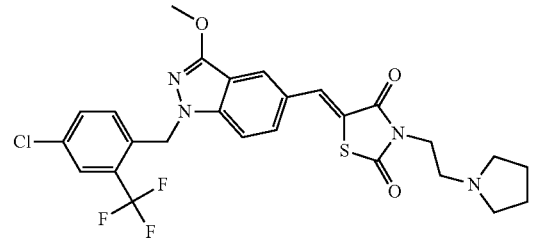 [SMILES: COc1nn(Cc2ccc(Cl)cc2C(F)(F)F)c2ccc(/C=C3\SC(=O)N(CCN4CCCC4)C3=O)cc12]

(A) A mixture of (5-cyano-2-fluorobenzoyl)hydrazine (from Example 25; 3.54 mmol) and 4-chloro-2-trifluoromethylbenzaldehyde (3.9 mmol) was refluxed in EtOH (15 mL) for 1 h, then cooled to 5° C. The precipitate that formed was filtered and washed with cold EtOH to afford 5-cyano-2-fluorobenzoic acid (4-methoxy-2-trifluoromethylbenzylidene)hydrazide.

(B) To a suspension of 5-cyano-2-fluoro-benzoic acid (4-chloro-2-trifluoromethylbenzylidene)hydrazide (2.67 mmol) in DCM (10 mL) was added TES (2 mL) followed by TFA (6 mL), and the resulting solution was stirred at rt overnight, then concentrated. The residual syrup was taken up in DCM (10 mL) and extracted successively with 0.1N NaOH and water, dried (anhydrous $Na_2SO_4$) and concentrated. Purification by silica gel chromatography (DCM/MeOH) afforded 5-cyano-2-fluorobenzoic acid 2-(4-chloro-2-trifluoromethylbenzyl)hydrazide.

(C) A solution of 5-cyano-2-fluorobenzoic acid 2-(4-chloro-2-trifluoromethylbenzyl)hydrazide (1.6 mmol) in N,N-DMA (6 mL) was heated at 120° C. for 3 h, then cooled to rt. Water (10 mL) was gradually added, and the resultant precipitate was extracted into DCM and concentrated in vacuo. The crude solid was triturated with ether/DCM (1:1) to afford 1-(4-chloro-2-trifluoromethylbenzyl)-3-hydroxy-1H-indazole-5-carbonitrile.

(D) A mixture of 1-(4-chloro-2-trifluoromethylbenzyl)-3-hydroxy-1H-indazole-5-carbonitrile (0.85 mmol), $K_2CO_3$ (2.6 mmol) and iodomethane (1.7 mmol) in DMF (4 mL) was stirred at rt overnight. The reaction was diluted with water (6 mL) and extracted with ether (3×), dried (anhydrous $Na_2SO_4$) and concentrated. Purification of the resultant residue by silica gel chromatography (hexane/ether) afforded 1-(4-chloro-2-trifluoromethylbenzyl)-3-methoxy-1H-indazole-5-carbonitrile.

(E) Treatment of 1-(4-chloro-2-trifluoromethylbenzyl)-3-methoxy-1H-indazole-5-carbonitrile following General Procedure Q provided 1-(4-chloro-2-trifluoromethylbenzyl)-3-methoxy-1H-indazole-5-carbaldehyde.

(F) Reaction of 1-(4-chloro-2-trifluoromethylbenzyl)-3-methoxy-1H-indazole-5-carbaldehyde with 1,3-thiazolidine-2,4-dione following General Procedure E provided (5Z)-5-({1-[4-chloro-2-(trifluoromethyl)benzyl]-3-methoxy-1H-indazol-5-yl}methylidene)-1,3-thiazolidine-2,4-dione.

(G) (5Z)-5-({1-[4-Chloro-2-(trifluoromethyl)benzyl]-3-methoxy-1H-indazol-5-yl}methylidene)-3-(2-pyrrolidin-1-ylethyl)-1,3-thiazolidine-2,4-dione was prepared from (5Z)-5-({1-[4-chloro-2-(trifluoromethyl)benzyl]-3-methoxy-1H-indazol-5-yl}methylidene)-1,3-thiazolidine-2,4-dione and 1-(2-hydroxyethyl)pyrrolidine following General Procedure J.

$^1$H NMR (400 MHz, DMSO-$d_6$): δ 9.69 (br. s, 1H), 8.11 (s, 1H), 8.01 (s, 1H), 7.89 (d, 1H), 7.69 (s, 2H), 7.66 (dd, 1H), 6.82 (d, 1H), 5.69 (s, 2H), 3.93-4.07 (m, 5H), 3.52-3.65 (m, 2H), 3.41-3.52 (m, 2H), 3.03-3.20 (m, 2H), 1.95-2.10 (m, 2H), 1.78-1.94 (m, 2H).

LCMS: mass calcd. for $C_{26}H_{24}ClF_3N_4O_3S$: 564.12. found 565.2 [M+H]$^+$

Example 28

(5Z)-3-(1-Ethylpiperidin-4-yl)-5-({1-[4-methoxy-2-(trifluoromethyl)benzyl]-1H-indazol-5-yl}methylidene)-1,3-thiazolidine-2,4-dione

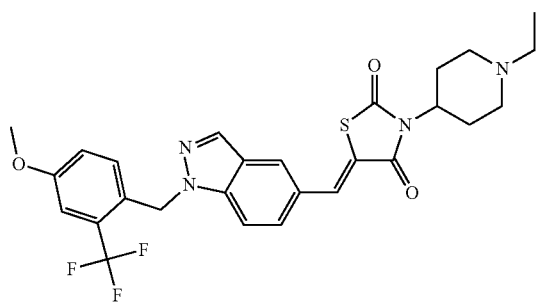 [SMILES: CCN1CCC(N2C(=O)S/C(=C\c3ccc4c(cnn4Cc4ccc(OC)cc4C(F)(F)F)c3)C2=O)CC1]

(5Z)-3-(1-Ethylpiperidin-4-yl)-5-({1-[4-methoxy-2-(trifluoromethyl)benzyl]-1H-indazol-5-yl}methylidene)-1,3-thiazolidine-2,4-dione was prepared from (5Z)-5-({1-[4-methoxy-2-(trifluoromethyl)benzyl]-1H-indazol-5-yl}methylidene)-3-piperidin-4-yl-1,3-thiazolidine-2,4-dione (Example 26) and ethyl iodide following General Procedure S.

$^1$H NMR (400 MHz, DMSO-$d_6$): δ 9.30 (br. s, 1H), 8.34 (s, 1H), 8.15 (s, 1H), 8.07 (s, 1H), 7.77 (d, 1H), 7.67 (dd, 1H), 7.28 (d, 1H), 7.14 (dd, 1H), 6.83 (d, 1H), 5.79 (s, 2H), 4.41-4.57 (m, 1H), 3.80 (s, 3H), 3.58 (br. d, 2H), 2.96-3.18 (m, 4H), 2.54-2.63 (m, 2H), 2.00 (br. d, 2H), 1.23 (t, 3H).

LCMS: mass calcd. for $C_{27}H_{27}F_3N_4O_3S$: 544.18. found 545.3 [M+H]$^+$

Example 29

(5Z)-5-({1-[4-Chloro-2-(trifluoromethyl)benzyl]-3-methoxy-1H-indazol-5-yl}methylidene)-3-piperidin-4-yl-1,3-thiazolidine-2,4-dione

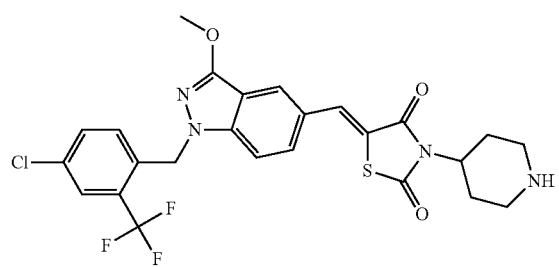 [SMILES: COc1nn(Cc2ccc(Cl)cc2C(F)(F)F)c2ccc(/C=C3\SC(=O)N(C4CCNCC4)C3=O)cc12]

(A) 1,1-Dimethylethyl 4-{(5Z)-5-[(1-{[4-chloro-2-(trifluoromethyl)phenyl]-methyl}-3-methoxy-1H-indazol-5-yl)methylidene]-2,4-dioxo-1,3-thiazolidin-3-yl}piperidine-1-carboxylate was prepared from (5Z)-5-({1-[4-chloro-2-(trifluoromethyl)benzyl]-3-methoxy-1H-indazol-5-yl}methylidene)-1,3-thiazolidine-2,4-dione (from Example 27) and 4-hydroxypiperidine-1-carboxylic acid tert-butyl ester following General Procedure J.

(B) (5Z)-5-({1-[4-Chloro-2-(trifluoromethyl)benzyl]-3-methoxy-1H-indazol-5-yl}methylidene)-3-piperidin-4-yl-1,3-thiazolidine-2,4-dione hydrochloride was prepared from 1,1-dimethylethyl 4-{(5Z)-5-[(1-{[4-chloro-2-(trifluoromethyl)phenyl]methyl}-3-methoxy-1H-indazol-5-yl)methylidene]-2,4-dioxo-1,3- thiazolidin-3-yl}piperidine-1-carboxylate following General Procedure N.

$^1$H NMR (400 MHz, DMSO-d$_6$): δ 8.79 (br. d, 1H), 8.37 (br. q, 1H), 8.07 (s, 1H), 7.98 (s, 1H), 7.89 (d, 1H), 7.60-7.75 (m, 3H), 6.81 (d, 1H), 5.69 (s, 2H), 4.43-4.61 (m, 1H), 4.01 (s, 3H), 3.39 (br. d, 2H), 2.98-3.20 (m, 2H), 1.92 (br. d, 2H).

LCMS: mass calcd. for C$_{25}$H$_{22}$ClF$_3$N$_4$O$_3$S: 550.11. found 551.2 [M+H]$^+$ Example 30

(5Z)-5-({1-[4-Chloro-2-(trifluoromethyl)benzyl]-3-methoxy-1H-indazol-5-yl}methylidene)-3-(1-ethylpiperidin-4-yl)-1,3-thiazolidine-2,4-dione

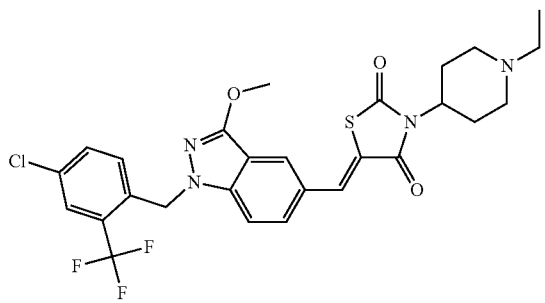 [SMILES: CCN1CCC(N2C(=O)S/C(=C\c3ccc4c(c3)c(OC)nn4Cc3ccc(Cl)cc3C(F)(F)F)C2=O)CC1]

(5Z)-5-({1-[4-Chloro-2-(trifluoromethyl)benzyl]-3-methoxy-1H-indazol-5-yl}methylidene)-3-(1-ethylpiperidin-4-yl)-1,3-thiazolidine-2,4-dione was prepared from (5Z)-5-({1-[4-chloro-2-(trifluoromethyl)benzyl]-3-methoxy-1H-indazol-5-yl}methylidene)-3-piperidin-4-yl-1,3-thiazolidine-2,4-dione (Example 29) and ethyl iodide following General Procedure S.

$^1$H NMR (400 MHz, DMSO-d$_6$): δ 9.24 (br. s, 1H), 8.08 (s, 1H), 7.98 (s, 1H), 7.89 (d, 1H), 7.56-7.76 (m, 3H), 6.81 (d, 1H), 5.69 (s, 2H), 4.51 (m, 1H), 4.01 (s, 3H), 3.58 (br. d, 2H), 2.99-3.19 (m, 4H), 2.55-2.66 (m, 2H), 2.00 (br. d, 2H), 1.23 (t, 3H).

LCMS: mass calcd. for C$_{27}$H$_{26}$ClF$_3$N$_4$O$_3$S: 578.14. found 579.3 [M+H]$^+$ Example 31

2-[(5Z)-5-({1-[4-Chloro-2-(trifluoromethyl)benzyl]-1H-indazol-5-yl}methylidene)-2,4-dioxo-1,3-thiazolidin-3-yl]-N-sulfamoylacetamide

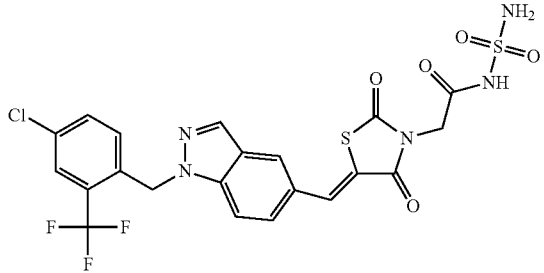 [SMILES: NS(=O)(=O)NC(=O)CN1C(=O)S/C(=C\c2ccc3c(cnn3Cc3ccc(Cl)cc3C(F)(F)F)c2)C1=O]

2-[(5Z)-5-({1-[4-Chloro-2-(trifluoromethyl)benzyl]-1H-indazol-5-yl}methylidene)-2,4-dioxo-1,3-thiazolidin-3-yl]-N-sulfamoylacetamide was prepared from [(5Z)-5-({1-[4-chloro-2-(trifluoromethyl)benzyl]-1H-indazol-5-yl}methylidene)-2,4-dioxo-1,3-thiazolidin-3-yl]acetic acid (Example 4) and sulfamide following General Procedure L.

$^1$H NMR (400 MHz, DMSO-d$_6$): δ 11.93 (s, 1H), 8.38 (s, 1H), 8.21 (s, 1H), 8.14 (s, 1H), 7.89 (d, 1H), 7.83 (d, 1H), 7.71 (dd, 1H), 7.66 (dd, 1H), 7.62 (s, 2H), 6.78 (d, 1H), 5.88 (s, 2H), 4.39 (s, 2H).

LCMS: mass calcd. for C$_{21}$H$_{15}$ClF$_3$N$_5$O$_5$S$_2$: 573.02. found 573.7 [M+H]$^+$ Example 32

4-[(5Z)-5-({1-[4-Methoxy-2-(trifluoromethyl)benzyl]-1H-indazol-5-yl}methylidene)-2,4-dioxo-1,3-thiazolidin-3-yl]piperidine-1-sulfonamide

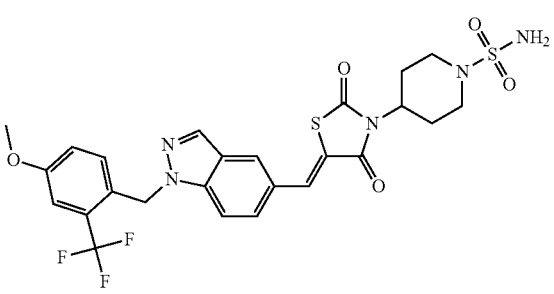 [SMILES: COc1ccc(Cn2ncc3cc(/C=C4\SC(=O)N(C5CCN(S(N)(=O)=O)CC5)C4=O)ccc32)c(C(F)(F)F)c1]

(A) To a solution of tert-butanol (0.9 mmol) in DCM (1 mL) was added chlorosulfonyl isocyanate (0.5 mmol) and the solution was stirred for 5 min. (5Z)-5-({1-[4-Methoxy-2-(trifluoromethyl)benzyl]-1H-indazol-5-yl}methylidene)-3-piperidin-4-yl-1,3-thiazolidine-2,4-dione hydrochloride (Example 26; 0.2 mmol) was then added to this solution, followed by triethylamine (1 mmol) and the mixture was stirred for 1 h. The reaction was extracted with water, dried (Na$_2$SO$_4$), concentrated and purified by silica gel chromatography (DCM/MeOH) to afford 1,1-dimethylethyl [(4-{(5Z)-5-[(1-{[4-methoxy-2-(trifluoromethyl)phenyl]methyl}-1H-indazol-5-yl)methylidene]-2,4-dioxo-1,3-thiazolidin-3-yl}piperidin-1-yl)sulfonyl]carbamate.

(B) 4-[(5Z)-5-({1-[4-Methoxy-2-(trifluoromethyl)benzyl]-1H-indazol-5-yl}methylidene)-2,4-dioxo-1,3-thiazolidin-3-yl]piperidine-1-sulfonamide was prepared from 1,1-dimethylethyl [(4-{(5Z)-5-[(1-{[4-methoxy-2-(trifluoromethyl)phenyl]methyl}-1H-indazol-5-yl)methylidene]-2,4-dioxo-1,3-thiazolidin-3-yl}piperidin-1-yl)sulfonyl]carbamate following General Procedure N.

$^1$H NMR (400 MHz, DMSO-d$_6$): δ 8.34 (s, 1H), 8.15 (s, 1H), 8.07 (s, 1H), 7.76 (d, 1H), 7.67 (dd, 1H), 7.27 (d, 1H), 7.14 (dd, 1H), 7.10 (t, 1H), 6.85 (s, 2H), 6.81 (d, 1H), 5.78 (s, 2H), 4.14-4.31 (m, 1H), 3.80 (s, 3H), 3.60 (br. d, 2H), 2.55-2.66 (m, 2H), 2.29-2.44 (m, 2H), 1.81 (br. d, 2H).

LCMS: mass calcd. for C$_{26}$H$_{24}$F$_3$N$_6$O$_6$S$_2$: 595.12. found 595.8 [M+H]$^+$

Example 33

(5Z)-5-({1-[4-Chloro-2-(trifluoromethyl)benzyl]-3-ethoxy-1H-indazol-5-yl}methylidene)-3-(2-pyrrolidin-1-ylethyl)-1,3-thiazolidine-2,4-dione

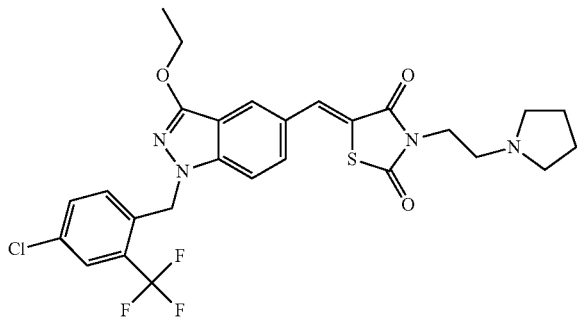 [SMILES: CCOc1nn(Cc2ccc(Cl)cc2C(F)(F)F)c2ccc(/C=C3\SC(=O)N(CCN4CCCC4)C3=O)cc12]

(A) A mixture of 5-bromo-2-fluorobenzoic acid (3 mmol), tert-butyl carbazate (3.6 mol) and EDCI (3.6 mol) in DCM (15 mL) was stirred overnight at rt. The reaction was then extracted with water, dried (anhydrous $Na_2SO_4$) and concentrated in vacuo. Purification by silica gel chromatography (DCM) afforded 2-(5-bromo-2-fluorobenzoyl)hydrazinecarboxylic acid tert-butyl ester as a white solid.

(B) 2-(5-Bromo-2-fluorobenzoyl)hydrazinecarboxylic acid tert-butyl ester was deprotected following General Procedure N to afford (5-bromo-2-fluorobenzoyl)hydrazine hydrochloride.

(C) A mixture of (5-bromo-2-fluorobenzoyl)hydrazine hydrochloride (3.15 mmol) and 4-chloro-2-trifluoromethylbenzaldehyde (3.34 mmol) was refluxed in EtOH (15 mL) for 1 h, then cooled to 5° C. The precipitate that formed was filtered and washed with cold EtOH to afford 5-bromo-2-fluorobenzoic acid (4-chloro-2-trifluoromethyl-benzylidene)hydrazide as a slightly yellow white solid.

(D) To a suspension of 5-bromo-2-fluorobenzoic acid (4-chloro-2-trifluoromethylbenzylidene)hydrazide (2.8 mmol) in DCM (10 mL) was added TES (2 mL) followed by TFA (6 mL), and the resulting solution was stirred at rt overnight, then concentrated. The residual syrup was taken up in DCM (10 mL) and extracted successively with sat'd $NaHCO_3$ and water, dried (anhydrous $Na_2SO_4$) and concentrated. Purification by silica gel chromatography (hexane/DCM) afforded 5-bromo-2-fluorobenzoic acid N'-(4-chloro-2-trifluoromethylbenzyl)hydrazide as a white powder.

(E) A solution of 5-bromo-2-fluorobenzoic acid N'-(4-chloro-2-trifluoromethylbenzyl)hydrazide (2.15 mmol) in N,N-DMA (12 mL) was heated in a microwave reactor at 220° C. for 3 h, then cooled to rt. Saturated aq. $NaHCO_3$ (5 mL) was added, followed by water (50 mL) and the resultant precipitate was filtered and washed with water to afford crude 5-bromo-1-(4-chloro-2-trifluoromethylbenzyl)-3-hydroxy-1H-indazole, which was used directly without further purification.

(F) A mixture of 5-bromo-1-(4-chloro-2-trifluoromethylbenzyl)-3-hydroxy-1H-indazole (0.58 mmol), $K_2CO_3$ (1.74 mmol) and ethyl iodide (1.16 mmol) in DMF (4 mL) was stirred at rt overnight. The reaction was diluted with water (6 mL) and extracted with ether (3×), dried (anhydrous $Na_2SO_4$) and concentrated. Purification of the resultant residue by silica gel chromatography (hexane/EtOAc) afforded 5-bromo-1-(4-chloro-2-trifluoromethylbenzyl)-3-ethoxy-1H-indazole as a pale yellow white solid.

(G) 1-(4-Chloro-2-trifluoromethylbenzyl)-3-ethoxy-1H-indazole-5-carbonitrile was prepared from 5-bromo-1-(4-chloro-2-trifluoromethylbenzyl)-3-ethoxy-1H-indazole following General Procedure P.

(H) 1-(4-Chloro-2-trifluoromethylbenzyl)-3-ethoxy-1H-indazole-5-carbaldehyde was prepared from 1-(4-chloro-2-trifluoromethylbenzyl)-3-ethoxy-1H-indazole-5-carbonitrile following General Procedure Q.

(I) Reaction of 1-(4-chloro-2-trifluoromethylbenzyl)-3-ethoxy-1H-indazole-5-carbaldehyde with 1,3-thiazolidine-2,4-dione following General Procedure E provided (5Z)-5-({1-[4-chloro-2-(trifluoromethyl)benzyl]-3-ethoxy-1H-indazol-5-yl}methylidene)-1,3-thiazolidine-2,4-dione.

(J) (5Z)-5-({1-[4-Chloro-2-(trifluoromethyl)benzyl]-3-ethoxy-1H-indazol-5-yl}methylidene)-3-(2-pyrrolidin-1-ylethyl)-1,3-thiazolidine-2,4-dione was prepared from (5Z)-5-({1-[4-chloro-2-(trifluoromethyl)benzyl]-3-ethoxy-1H-indazol-5-yl}methylidene)-1,3-thiazolidine-2,4-dione and 1-(2-hydroxyethyl)pyrrolidine following General Procedure J.

$^1$H NMR (400 MHz, DMSO-$d_6$): δ 9.75 (br. s, 1H), 8.11 (s, 1H), 8.02 (s, 1H), 7.89 (d, 1H), 7.63-7.73 (m, 3H), 6.81 (d, 1H), 5.68 (s, 2H), 4.37 (q, 2H), 4.01 (br. t, 2H), 3.52-3.65 (m, 2H), 3.47 (br. q, 2H), 3.04-3.19 (m, 2H), 1.95-2.11 (m, 2H), 1.78-1.95 (m, 2H), 1.40 (t, 3H).

LCMS: mass calcd. for $C_{27}H_{26}ClF_3N_4O_3S$: 578.14. found 579.2 [M+H]$^+$

Example 34

4-[(5Z)-5-({1-[4-Chloro-2-(trifluoromethyl)benzyl]-1H-indazol-5-yl}methylidene)-2,4-dioxo-1,3-thiazolidin-3-yl]piperidine-1-sulfonamide

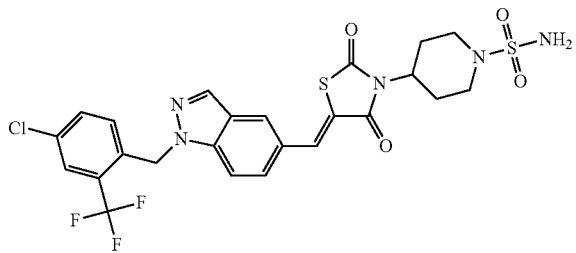 [SMILES: NS(=O)(=O)N1CCC(N2C(=O)S/C(=C\c3ccc4c(cnn4Cc4ccc(Cl)cc4C(F)(F)F)c3)C2=O)CC1]

(A) 1,1-Dimethylethyl 4-{(5Z)-5-[(1-{[4-chloro-2-(trifluoromethyl)phenyl]-methyl}-1H-indazol-5-yl)methylidene]-2,4-dioxo-1,3-thiazolidin-3-yl}piperidine-1-carboxylate was prepared from [(5Z)-5-({1-[4-chloro-2-(trifluoromethyl)benzyl]-1H-indazol-5-yl}methylidene)-2,4-dioxo-1,3-thiazolidine (from Example 1) and 4-hydroxypiperidine-1-carboxylic acid tert-butyl ester following General Procedure J.

(B) (5Z)-5-({1-[4-Chloro-2-(trifluoromethyl)benzyl]-1H-indazol-5-yl}methylidene)-3-piperidin-4-yl-1,3-thiazolidine-2,4-dione hydrochloride was prepared by the deprotection of 1,1-dimethylethyl 4-{(5Z)-5-[(1-{[4-chloro-2-(trifluoromethyl)phenyl]-methyl}-1H-indazol-5-yl)methylidene]-2,4-dioxo-1,3-thiazolidin-3-yl}piperidine-1-carboxylate following General Procedure N.

(C) To a solution of tert-butanol (1.8 mmol) in DCM (2 mL) was added chlorosulfonyl isocyanate (1 mmol) and the solution was stirred for 5 min. (5Z)-5-({1-[4-Chloro-2-(trifluoromethyl)benzyl]-1H-indazol-5-yl}methylidene)-3-piperidin-4-yl-1,3-thiazolidine-2,4-dione hydrochloride (0.23 mmol) was then added to this solution, followed by triethylamine (2 mmol) and the mixture was stirred for 1 h. The reaction was extracted with water, dried (anhydrous $Na_2SO_4$), concentrated and purified by silica gel chromatography (DCM/MeOH) to afford 1,1-dimethylethyl [(4-{(5Z)-5-[(1-{[4-chloro-2-(trifluoromethyl)phenyl]-methyl}-1H-indazol-5-yl)methylidene]-2,4-dioxo-1,3-thiazolidin-3-yl}piperidin-1-yl)sulfonyl]carbamate.

(D) 1,1-Dimethylethyl [(4-{(5Z)-5-[(1-{[4-chloro-2-(trifluoromethyl)phenyl]-methyl}-1H-indazol-5-yl)methylidene]-2,4-dioxo-1,3-thiazolidin-3-yl}piperidin-1-yl)sulfonyl]carbamate was deprotected following General Procedure N to afford 4-[(5Z)-5-({1-[4-chloro-2-(trifluoromethyl)-benzyl]-1H-indazol-5-yl}methylidene)-2,4-dioxo-1,3-thiazolidin-3-yl]piperidine-1-sulfonamide.

$^1$H NMR (400 MHz, DMSO-$d_6$): δ 8.37 (s, 1H), 8.17 (s, 1H), 8.07 (s, 1H), 7.89 (d, 1H), 7.81 (d, 1H), 7.60-7.74 (m, 2H), 6.85 (s, 2H), 6.78 (d, 1H), 5.87 (s, 2H), 4.14-4.31 (m, 1H), 3.57-3.65 (m, 2H), 2.56-2.65 (m, 2H), 2.34-2.43 (m, 2H), 1.81 (br. d, 1H).

LCMS: mass calcd. for $C_{24}H_{21}ClF_3N_5O_4S_2$: 599.07. found 599.9 [M+H]$^+$ Example 35

2-[(5Z)-5-({1-[4-Chloro-2-(trifluoromethyl)benzyl]-1H-indazol-5-yl}methylidene)-2,4-dioxo-1,3-thiazolidin-3-yl]-N-(dimethylsulfamoyl)acetamide

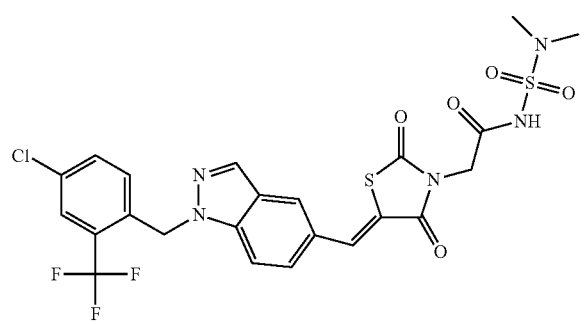 [SMILES: CN(C)S(=O)(=O)NC(=O)CN1C(=O)S/C(=C\c2ccc3c(cnn3Cc3ccc(Cl)cc3C(F)(F)F)c2)C1=O]

2-[(5Z)-5-({1-[4-Chloro-2-(trifluoromethyl)benzyl]-1H-indazol-5-yl}methylidene)-2,4-dioxo-1,3-thiazolidin-3-yl]-N-(dimethylsulfamoyl)acetamide was prepared from [(5Z)-5-({1-[4-chloro-2-(trifluoromethyl)benzyl]-1H-indazol-5-yl}methylidene)-2,4-dioxo-1,3-thiazolidin-3-yl]acetic acid (Example 4) and N,N-dimethylsulfamide following General Procedure L.

$^1$H NMR (400 MHz, DMSO-$d_6$): δ 12.01 (s, 1H), 8.38 (s, 1H), 8.21 (s, 1H), 8.15 (s, 1H), 7.89 (d, 1H), 7.83 (d, 1H), 7.71 (d, 1H), 7.66 (dd, 1H), 6.79 (d, 1H), 5.88 (s, 2H), 4.46 (s, 2H), 2.81 (s, 6H).

LCMS: mass calcd. for $C_{23}H_{19}ClF_3N_5O_5S_2$: 601.05. found 601.8 [M+H]$^+$ Example 36

[(5Z)-5-({1-[4-Chloro-2-(trifluoromethyl)benzyl]-3-methyl-1H-indazol-5-yl}methylidene)-2,4-dioxo-1,3-thiazolidin-3-yl]acetic acid

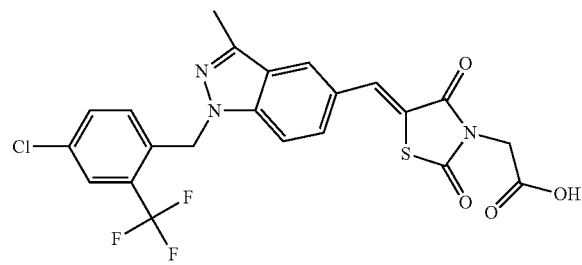 [SMILES: Cc1nn(Cc2ccc(Cl)cc2C(F)(F)F)c2ccc(/C=C3\SC(=O)N(CC(=O)O)C3=O)cc12]

(A) 5-Bromo-1-[4-chloro-2-(trifluoromethyl)benzyl]-3-methyl-1H-indazole was prepared from 4-chloro-2-(trifluoromethyl)benzyl bromide and 5-bromo-3-methyl-1H-indazole following General Procedure A.

(B) 1-[4-Chloro-2-(trifluoromethyl)benzyl]-3-methyl-1H-indazol-5-carbonitrile was prepared from 5-bromo-1-[4-chloro-2-(trifluoromethyl)benzyl]-3-methyl-1H-indazole following General Procedure P.

(C) 1-[4-Chloro-2-(trifluoromethyl)benzyl]-3-methyl-1H-indazol-5-carbaldehyde was prepared from 1-[4-chloro-2-(trifluoromethyl)benzyl]-3-methyl-1H-indazol-5-carbonitrile following General Procedure Q.

(D) [(5Z)-5-({1-[4-Chloro-2-(trifluoromethyl)benzyl]-3-methyl-1H-indazol-5-yl}methylidene)-2,4-dioxo-1,3-thiazolidine was prepared from [4-chloro-2-(trifluoromethyl)benzyl]-3-methyl-1H-indazol-5-carbaldehyde following General Procedure E.

(E) [(5Z)-5-({1-[4-Chloro-2-(trifluoromethyl)benzyl]-3-methyl-1H-indazol-5-yl}methylidene)-2,4-dioxo-1,3-thiazolidin-3-yl]acetic acid was prepared from [(5Z)-5-({1-[4-chloro-2-(trifluoromethyl)benzyl]-3-methyl-1H-indazol-5-yl}methylidene)-2,4-dioxo-1,3-thiazolidine following General Procedure I.

$^1$H NMR (400 MHz, DMSO-$d_6$): δ 13.46 (br. s, 1H), 8.11-8.17 (m, 2H), 7.88 (d, 1H), 7.73-7.80 (m, 1H), 7.61-7.71 (m, 2H), 6.77 (d, 1H), 5.79 (s, 2H), 4.40 (s, 2H), 2.55 (s, 3H).

LCMS: mass calcd. for $C_{22}H_{16}ClF_3N_3O_4S$: 509.04. found 510.0 [M+H]$^+$

Example 37

(5Z)-5-({1-[4-Chloro-2-(trifluoromethyl)benzyl]-3-oxo-2,3-dihydro-1H-indazol-5-yl}methylidene)-3-(2-pyrrolidin-1-ylethyl)-1,3-thiazolidine-2,4-dione

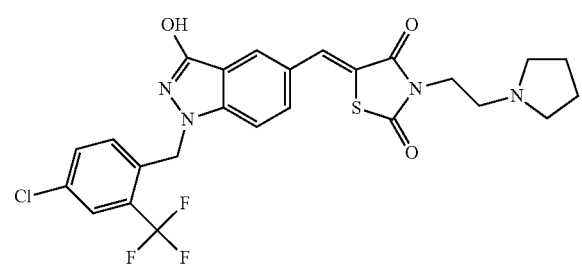 [SMILES: O=C1S/C(=C\c2ccc3c(c2)c(O)nn3Cc2ccc(Cl)cc2C(F)(F)F)C(=O)N1CCN1CCCC1]

(A) 3-(2-Pyrrolidin-1-ylethyl)-1,3-thiazolidine-2,4-dione was prepared from 1,3-thiazolidine-2,4-dione and 1-(2-hydroxyethyl)pyrrolidine following General Procedure C.

(B) 1-(4-chloro-2-trifluoromethylbenzyl)-3-hydroxy-1H-indazole-5-carbonitrile (from Example 27) was converted to 1-(4-chloro-2-trifluoromethylbenzyl)-3-hydroxy-1H-indazole-5-carbaldehyde following General Procedure Q.

(C) Reaction of 3-(2-pyrrolidin-1-ylethyl)-1,3-thiazolidine-2,4-dione and 1-(4-chloro-2-trifluoromethylbenzyl)-3-hydroxy-1H-indazole-5-carbaldehyde following General Procedure F afforded (5Z)-5-({1-[4-chloro-2-(trifluoromethyl)benzyl]-3-oxo-2,3-dihydro-1H-indazol-5-yl}methylidene)-3-(2-pyrrolidin-1-ylethyl)-1,3-thiazolidine-2,4-dione.

$^1$H NMR (400 MHz, DMSO-$d_6$): δ 11.43 (s, 1H), 9.98 (br. s, 1H), 8.07 (s, 1H), 8.03 (s, 1H), 7.87 (d, 1H), 7.61-7.73 (m, 3H), 6.88 (d, 1H), 5.61 (s, 2H), 4.01 (t, 2H), 3.52-3.65 (m, 2H), 3.47 (br. q, 2H), 3.00-3.18 (m, 2H), 1.93-2.10 (m, 2H), 1.78-1.93 (m, 2H).

LCMS: mass calcd. for $C_{26}H_{22}ClF_3N_4O_3S$: 550.11. found 551.2 [M+H]$^+$

Example 38

2-[(5Z)-5-({1-[4-Chloro-2-(trifluoromethyl)benzyl]-1H-indazol-5-yl}methylidene)-2,4-dioxo-1,3-thiazolidin-3-yl]-N-(pyrrolidin-1-ylsulfonyl)acetamide

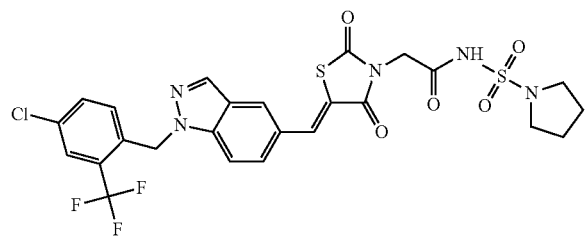 [SMILES: O=C(CN1C(=O)S/C(=C\c2ccc3c(cnn3Cc3ccc(Cl)cc3C(F)(F)F)c2)C1=O)NS(=O)(=O)N1CCCC1]

2-[(5Z)-5-({1-[4-Chloro-2-(trifluoromethyl)benzyl]-1H-indazol-5-yl}methylidene)-2,4-dioxo-1,3-thiazolidin-3-yl]-N-(pyrrolidin-1-ylsulfonyl)acetamide was prepared from [(5Z)-5-({1-[4-chloro-2-(trifluoromethyl)benzyl]-1H-indazol-5-yl}methylidene)-2,4-dioxo-1,3-thiazolidin-3-yl]acetic acid (Example 4) and pyrrolidin-1-ylsulfonic acid amide following General Procedure L. The corresponding ethanolamine salt was prepared following General Procedure T.

$^1$H NMR (400 MHz, DMSO-$d_6$): δ 8.37 (s, 1H), 8.18 (s, 1H), 8.08 (s, 1H), 7.89 (d, 1H), 7.81 (d, 1H), 7.70 (dd, 1H), 7.66 (dd, 1H), 7.48 (br. s, 2H), 6.77 (d, 1H), 5.87 (s, 2H), 5.12 (t, 1H), 4.04 (s, 2H), 3.56 (q, 2H), 2.94-3.03 (m, 3H), 2.80-2.87 (m, 2H), 1.60 (ddd, 4H).

LCMS: mass calcd. for $C_{26}H_{21}ClF_3N_6O_6S_2$: 627.06. found 627.8 [M+H]$^+$

Example 39

2-[(5Z)-5-({1-[4-Chloro-2-(trifluoromethyl)benzyl]-3-methyl-1H-indazol-5-yl}methylidene)-2,4-dioxo-1,3-thiazolidin-3-yl]-N-(dimethylsulfamoyl)acetamide

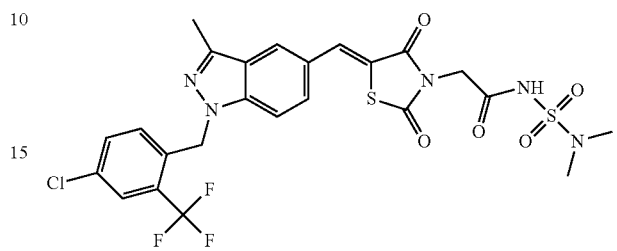

2-[(5Z)-5-({1-[4-Chloro-2-(trifluoromethyl)benzyl]-3-methyl-1H-indazol-5-yl}methylidene)-2,4-dioxo-1,3-thiazolidin-3-yl]-N-(dimethylsulfamoyl)acetamide was prepared from [(5Z)-5-({1-[4-chloro-2-(trifluoromethyl)benzyl]-3-methyl-1H-indazol-5-yl}methylidene)-2,4-dioxo-1,3-thiazolidin-3-yl] acetic acid (Example 36) and N,N-dimethylsulfamide following General Procedure L.

$^1$H NMR (400 MHz, DMSO-$d_6$): δ 12.01 (br. s, 1H), 8.15 (s, 1H), 8.12 (s, 1H), 7.88 (d, 1H), 7.76 (d, 1H), 7.61-7.73 (m, 2H), 6.77 (d, 1H), 5.79 (s, 2H), 4.34 (br. s, 2H), 2.70 (br. s, 6H), 2.55 (s, 3H).

LCMS: mass calcd. for $C_{24}H_{21}ClF_3N_5O_5S_2$: 615.06. found 615.8 [M+H]$^+$

Example 40

2-[(5Z)-5-({1-[4-Chloro-2-(trifluoromethyl)benzyl]-3-methyl-1H-indazol-5-yl}methylidene)-2,4-dioxo-1,3-thiazolidin-3-yl]-N-(pyrrolidin-1-ylsulfonyl)acetamide

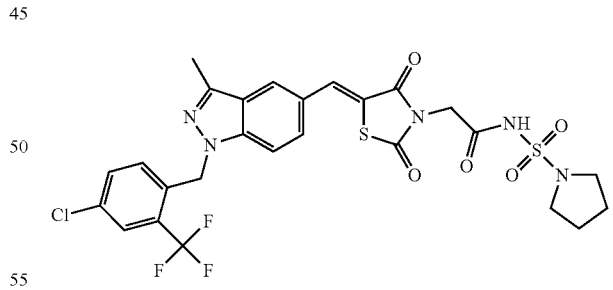

2-[(5Z)-5-({1-[4-Chloro-2-(trifluoromethyl)benzyl]-3-methyl-1H-indazol-5-yl}methylidene)-2,4-dioxo-1,3-thiazolidin-3-yl]-N-(pyrrolidin-1-ylsulfonyl)acetamide was prepared from [(5Z)-5-({1-[4-chloro-2-(trifluoromethyl)benzyl]-3-methyl-1H-indazol-5-yl}methylidene)-2,4-dioxo-1,3-thiazolidin-3-yl]acetic acid (Example 36) and pyrrolidin-1-ylsulfonic acid amide following General Procedure L. The corresponding ethanolamine salt was prepared following General Procedure T.

$^1$H NMR (400 MHz, DMSO-$d_6$): δ 8.13 (s, 1H), 8.08 (s, 1H), 7.88 (d, 1H), 7.77 (s, 1H), 7.74 (s, 1H), 7.68 (d, 1H), 7.63-7.67 (m, 1H), 7.49 (br. s, 2H), 6.76 (d, 1H), 5.78 (s, 2H), 5.12 (t, 1H), 4.04 (s, 2H), 3.56 (q, 2H), 3.00 (br. t, 4H), 2.84 (t, 2H), 2.55 (s, 3H), 1.60 (ddd, 4H).

LCMS: mass calcd. for $C_{26}H_{23}ClF_3N_5O_5S_2$: 641.08. found 641.9 $[M+H]^+$

Example 41

(5Z)-5-({1-[4-Chloro-2-(trifluoromethyl)benzyl]-3-methyl-1H-indazol-5-yl}methylidene)-3-(2-pyrrolidin-1-ylethyl)-1,3-thiazolidine-2,4-dione

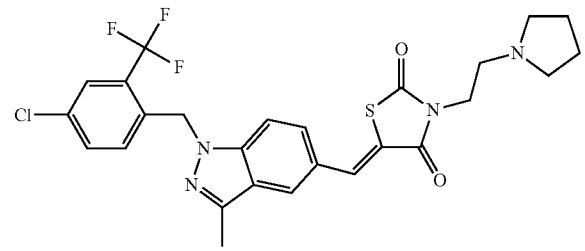 [SMILES: Cc1nn(Cc2ccc(Cl)cc2C(F)(F)F)c2ccc(/C=C3\SC(=O)N(CCN4CCCC4)C3=O)cc12]

(5Z)-5-({1-[4-Chloro-2-(trifluoromethyl)benzyl]-3-methyl-1H-indazol-5-yl}methylidene)-3-(2-pyrrolidin-1-yl-ethyl)-1,3-thiazolidine-2,4-dione was prepared from [(5Z)-5-({1-[4-Chloro-2-(trifluoromethyl)benzyl]-3-methyl-1H-indazol-5-yl}methylidene)-2,4-dioxo-1,3-thiazolidine (from Example 36) and 1-(2-chloroethyl)pyrrolidine hydrochloride following General Procedure H.

$^1$H NMR (400 MHz, DMSO-d$_6$): δ 9.87 (br. s, 1H), 8.14 (s, 1H), 8.11 (s, 1H), 7.89 (d, 1H), 7.72-7.80 (m, 1H), 7.63-7.71 (m, 2H), 6.80 (d, 1H), 5.79 (s, 2H), 4.02 (t, 2H), 3.53-3.67 (m, 2H), 3.47 (m, 2H), 3.02-3.19 (m, 2H), 2.55 (s, 3H), 1.95-2.09 (m, 2H), 1.77-1.94 (m, 2H).

LCMS: mass calcd. for $C_{26}H_{24}ClF_3N_4O_2S$: 548.13. found 549.1 $[M+H]^+$

Example 42

(5Z)-5-({1-[4-Chloro-2-(trifluoromethyl)benzyl]-1H-indazol-5-yl}methylidene)-3-[(2,2-dimethyl-1,3-dioxolan-4-yl)methyl]-1,3-thiazolidine-2,4-dione

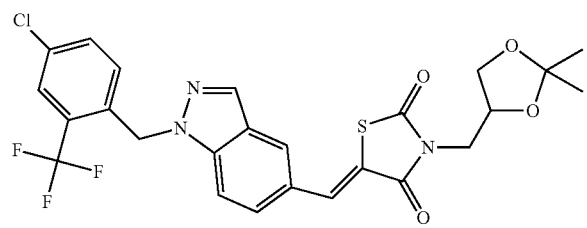 [SMILES: CC1(C)OCC(CN2C(=O)S/C(=C\c3ccc4c(cnn4Cc4ccc(Cl)cc4C(F)(F)F)c3)C2=O)O1]

(5Z)-5-({1-[4-Chloro-2-(trifluoromethyl)benzyl]-1H-indazol-5-yl}methylidene)-3-[(2,2-dimethyl-1,3-dioxolan-4-yl)methyl]-1,3-thiazolidine-2,4-dione was prepared from [(5Z)-5-({1-[4-chloro-2-(trifluoromethyl)-benzyl]-1H-indazol-5-yl}methylidene)-2,4-dioxo-1,3-thiazolidine (from Example 1) and (2,2-dimethyl-[1,3]dioxolan-4-yl)methanol following General Procedure J.

$^1$H NMR (400 MHz, DMSO-d$_6$): δ 8.38 (s, 1H), 8.18 (s, 1H), 8.11 (s, 1H), 7.89 (d, 1H), 7.81 (d, 1H), 7.70 (dd, 1H), 7.66 (dd, 1H), 6.78 (d, 1H), 5.87 (s, 2H), 4.28-4.41 (m, 1H), 4.03 (dd, 1H), 3.76-3.85 (m, 2H), 3.71 (dd, 1H), 1.34 (s, 3H), 1.24 (s, 3H).

LCMS: mass calcd. for $C_{25}H_{21}ClF_3N_3O_4S$: 551.09. found 552.0 $[M+H]^+$

Example 43

(5Z)-5-({1-[4-Chloro-2-(trifluoromethyl)benzyl]-1H-indazol-5-yl}methylidene)-3-(2,3-dihydroxypropyl)-1,3-thiazolidine-2,4-dione

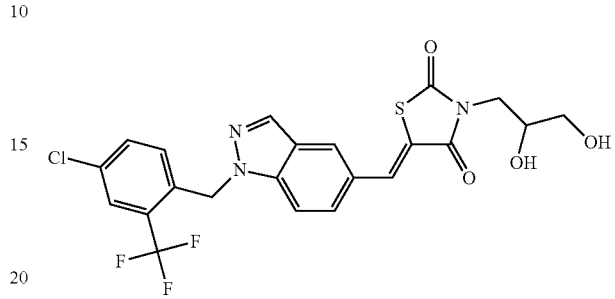

A solution of (5Z)-5-({1-[4-chloro-2-(trifluoromethyl)benzyl]-1H-indazol-5-yl}methylidene)-3-[(2,2-dimethyl-1,3-dioxolan-4-yl)methyl]-1,3-thiazolidine-2,4-dione (Example 42; 0.1 mmol) in dioxane (3 mL) was treated with 10% aq. HCl (0.5 mL) and stirred at 45° C. overnight. Concentration of the reaction in vacuo gave a pale yellow solid which was triturated with ether to afford pure (5Z)-5-({1-[4-chloro-2-(trifluoromethyl)benzyl]-1H-indazol-5-yl}methylidene)-3-(2,3-dihydroxypropyl)-1,3-thiazolidine-2,4-dione as a pale yellow crystalline solid.

$^1$H NMR (400 MHz, DMSO-d$_6$): δ 8.37 (s, 1H), 8.17 (s, 1H), 8.07 (s, 1H), 7.89 (d, 1H), 7.81 (d, 1H), 7.70 (dd, 1H), 7.66 (dd, 1H), 6.78 (d, 1H), 5.87 (s, 2H), 5.02 (d, 1H), 4.74 (t, 1H), 3.76-3.89 (m, 1H), 3.60-3.75 (m, 2H), 3.35-3.46 (m, 2H).

LCMS: mass calcd. for $C_{22}H_{17}ClF_3N_3O_4S$: 511.06. found 512.0 $[M+H]^+$

Example 44

2-[(5Z)-5-({1-[4-Chloro-2-(trifluoromethyl)benzyl]-3-methyl-1H-indazol-5-yl}methylidene)-2,4-dioxo-1,3-thiazolidin-3-yl]-N-(methylsulfonyl)acetamide

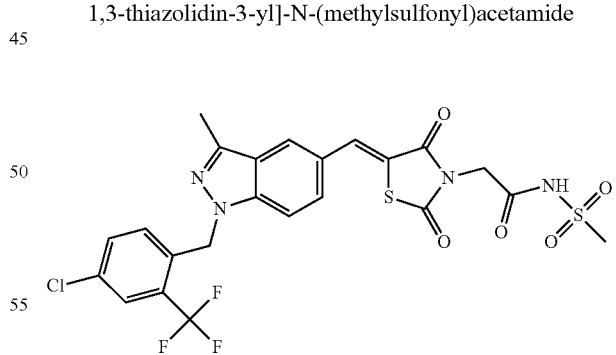

2-[(5Z)-5-({1-[4-Chloro-2-(trifluoromethyl)benzyl]-3-methyl-1H-indazol-5-yl}methylidene)-2,4-dioxo-1,3-thiazolidin-3-yl]-N-(methylsulfonyl)-acetamide was prepared from [(5Z)-5-({1-[4-chloro-2-(trifluoromethyl)-benzyl]-3-methyl-1H-indazol-5-yl}methylidene)-2,4-dioxo-1,3-thiazolidin-3-yl]acetic acid (Example 36) following General Procedure L, using methanesulfonic acid amide in place of the sulfamide. The corresponding diethanolamine salt was prepared following General Procedure T.

¹H NMR (400 MHz, DMSO-d₆): δ 8.22 (br. s, 2H), 8.13 (s, 1H), 8.08 (s, 1H), 7.88 (d, 1H), 7.76 (d, 1H), 7.62-7.71 (m, 2H), 6.75 (d, 1H), 5.79 (s, 2H), 5.17 (t, 2H), 4.06 (s, 2H), 3.64 (q, 4H), 2.99 (t, 4H), 2.71 (s, 3H), 2.55 (s, 3H).

LCMS: mass calcd. for $C_{23}H_{18}ClF_3N_4O_6S_2$: 586.04. found 586.9 [M+H]⁺

Example 45

(5Z)-5-({1-[4-Chloro-2-(trifluoromethyl)benzyl]-1H-indazol-5-yl}methylidene)-3-{2-[(2-hydroxyethyl)(1-methylethyl)amino]ethyl}-1,3-thiazolidine-2,4-dione

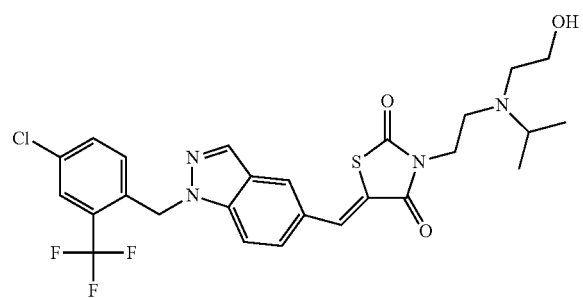 [SMILES: CC(C)N(CCO)CCN1C(=O)S/C(=C\c2ccc3c(cnn3Cc3ccc(Cl)cc3C(F)(F)F)c2)C1=O]

(5Z)-5-({1-[4-Chloro-2-(trifluoromethyl)benzyl]-1H-indazol-5-yl}methylidene)-3-{2-[(2-hydroxyethyl)(1-methylethyl)amino]ethyl}-1,3-thiazolidine-2,4-dione was prepared from [(5Z)-5-({1-[4-chloro-2-(trifluoromethyl)benzyl]-1H-indazol-5-yl}methylidene)-2,4-dioxo-1,3-thiazolidine (from Example 1) and N,N-bis(2-hydroxyethyl)isopropyl amine following General Procedure J.

¹H NMR (400 MHz, DMSO-d₆): δ 9.35 (br. s, 1H), 8.38 (s, 1H), 8.20 (s, 1H), 8.12 (s, 1H), 7.90 (d, 1H), 7.82 (d, 1H), 7.70 (dd, 1H), 7.67 (dd, 1H), 6.81 (d, 1H), 5.87 (s, 2H), 5.47 (br. s, 1H), 4.08 (br. t, 2H), 3.77 (m, 4H), 3.37-3.46 (m, 3H), 3.27-3.33 (m, 1H), 3.08-3.24 (m, 1H), 1.27 (d, 6H).

LCMS: mass calcd. for $C_{26}H_{26}ClF_3N_4O_3S$: 566.14. found 567.2 [M+H]⁺

Example 46

(5Z)-3-[2-(tert-Butylamino)ethyl]-5-({1-[4-chloro-2-(trifluoromethyl)benzyl]-1H-indazol-5-yl}methylidene)-1,3-thiazolidine-2,4-dione

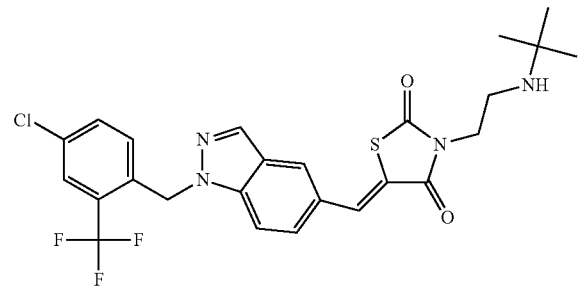 [SMILES: CC(C)(C)NCCN1C(=O)S/C(=C\c2ccc3c(cnn3Cc3ccc(Cl)cc3C(F)(F)F)c2)C1=O]

(5Z)-3-[2-(tert-Butylamino)ethyl]-5-({1-[4-chloro-2-(trifluoromethyl)benzyl]-1H-indazol-5-yl}methylidene)-1,3-thiazolidine-2,4-dione was prepared from [(5Z)-5-({1-[4-chloro-2-(trifluoromethyl)benzyl]-1H-indazol-5-yl}methylidene)-2,4-dioxo-1,3-thiazolidine (from Example 1) and 2-(N-tert-butylamino)ethanol following General Procedure J.

¹H NMR (400 MHz, DMSO-d₆): δ 8.69 (br. s, 2H), 8.38 (d, 1H), 8.20 (s, 1H), 8.13 (s, 1H), 7.90 (d, 1H), 7.82 (d, 1H), 7.71 (dd, 1H), 7.67 (dd, 1H), 6.81 (d, 1H), 5.87 (s, 2H), 4.00 (t, 2H), 3.07-3.24 (m, 2H), 1.29 (s, 9H).

LCMS: mass calcd. for $C_{26}H_{24}ClF_3N_4O_2S$: 536.13. found 537.0 [M+H]⁺

Example 47

(5Z)-5-({1-[4-Chloro-2-(trifluoromethyl)benzyl]-1H-indazol-5-yl}methylidene)-3-[2-(ethylamino)ethyl]-1,3-thiazolidine-2,4-dione

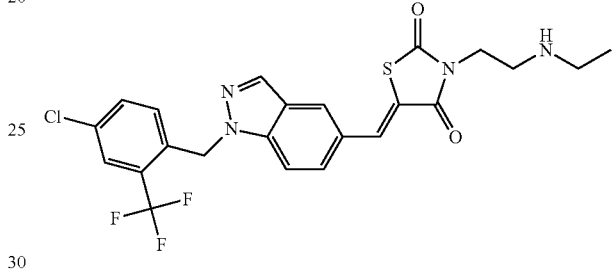

(5Z)-5-({1-[4-Chloro-2-(trifluoromethyl)benzyl]-1H-indazol-5-yl}methylidene)-3-[2-(ethylamino)ethyl]-1,3-thiazolidine-2,4-dione was prepared from [(5Z)-5-({1-[4-chloro-2-(trifluoromethyl)benzyl]-1H-indazol-5-yl}methylidene)-2,4-dioxo-1,3-thiazolidine (from Example 1) and 2-(ethylamino)ethanol following General Procedure K.

¹H NMR (400 MHz, DMSO-d₆): δ 8.54 (br. s, 2H), 8.38 (s, 1H), 8.20 (s, 1H), 8.12 (s, 1H), 7.90 (d, 1H), 7.79-7.86 (m, 1H), 7.71 (dd, 1H), 7.67 (dd, 1H), 6.82 (d, 1H), 5.87 (s, 2H), 3.96 (t, 2H), 3.22 (br. s, 2H), 3.00 (br. s, 2H), 1.17 (t, 3H).

LCMS: mass calcd. for $C_{23}H_{20}ClF_3N_4O_2S$: 508.09. found 509.1 [M+H]⁺

Example 48

(5Z)-5-({1-[4-Chloro-2-(trifluoromethyl)benzyl]-1H-indazol-5-yl}methylidene)-3-{2-[(1-methylethyl)amino]ethyl}-1,3-thiazolidine-2,4-dione

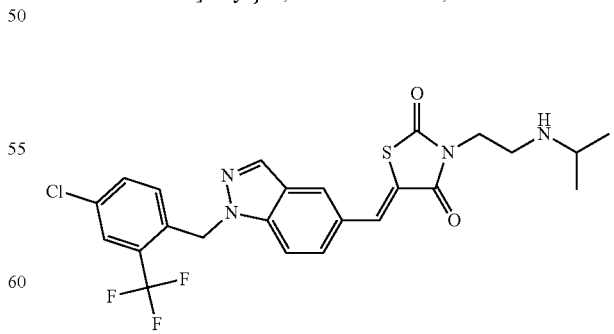

(5Z)-5-({1-[4-Chloro-2-(trifluoromethyl)benzyl]-1H-indazol-5-yl}methylidene)-3-{2-[(1-methylethyl)amino]ethyl}-1,3-thiazolidine-2,4-dione was prepared from [(5Z)-5-({1-[4-chloro-2-(trifluoromethyl)benzyl]-1H-indazol-5- yl}methylidene)-2,4-dioxo-1,3-thiazolidine (from Example 1) and 2-(isopropylamino)ethanol following General Procedure K.

$^1$H NMR (400 MHz, DMSO-$d_6$): δ 8.50 (br. s, 2H), 8.38 (s, 1H), 8.20 (s, 1H), 8.13 (s, 1H), 7.90 (d, 1H), 7.82 (d, 1H), 7.71 (dd, 1H), 7.67 (dd, 1H), 6.82 (d, 1H), 5.87 (s, 2H), 3.96 (t, 2H), 3.35-3.44 (m, 1H), 3.22 (br. s, 2H), 1.22 (d, 6H).

LCMS: mass calcd. for $C_{24}H_{22}ClF_3N_4O_2S$: 522.11. found 523.0 [M+H]$^+$

Example 49

3-(2-Aminoethyl)-(5Z)-5-({1-[4-chloro-2-(trifluoromethyl)benzyl]-1H-indazol-5-yl}methylidene)-1,3-thiazolidine-2,4-dione

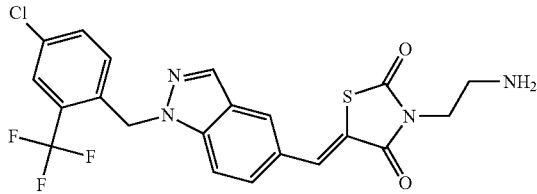 [SMILES: NCCN1C(=O)S/C(=C\c2ccc3c(cnn3Cc3ccc(Cl)cc3C(F)(F)F)c2)C1=O]

(A) 1,1-Dimethylethyl (2-{(5Z)-5-[(1-{[4-chloro-2-(trifluoromethyl)phenyl]-methyl}-1H-indazol-5-yl)methylidene]-2,4-dioxo-1,3-thiazolidin-3-yl}ethyl)carbamate was prepared from [(5Z)-5-({1-[4-chloro-2-(trifluoromethyl)benzyl]-1H-indazol-5-yl}methylidene)-2,4-dioxo-1,3-thiazolidine (from Example 1) and N-(tert-butoxycarbonyl)ethanolamine following General Procedure J.

(B) 3-(2-Aminoethyl)-(5Z)-5-({1-[4-chloro-2-(trifluoromethyl)benzyl]-1H-indazol-5-yl}methylidene)-1,3-thiazolidine-2,4-dione hydrochloride was prepared by the deprotection of 1,1-dimethylethyl (2-{(5Z)-5-[(1-{[4-chloro-2-(trifluoromethyl)phenyl]methyl}-1H-indazol-5-yl)methylidene]-2,4-dioxo-1,3-thiazolidin-3-yl}ethyl)carbamate following General Procedure M.

$^1$H NMR (400 MHz, DMSO-$d_6$): δ 8.38 (s, 1H), 8.19 (s, 1H), 8.10 (s, 1H), 7.86-7.98 (m, 3H), 7.77-7.85 (m, 1H), 7.63-7.73 (m, 2H), 6.81 (d, 1H), 5.87 (s, 2H), 3.92 (br. s., 2H), 3.07 (m, 2H).

LC/MS: mass calcd. for $C_{21}H_{16}ClF_3N_4O_2S$: 480.06. found 481.3 [M+1]$^+$ Example 50

N-{2-[(5Z)-5-({1-[4-Chloro-2-(trifluoromethyl)benzyl]-1H-indazol-5-yl}methylidene)-2,4-dioxo-1,3-thiazolidin-3-yl]ethyl}sulfamide

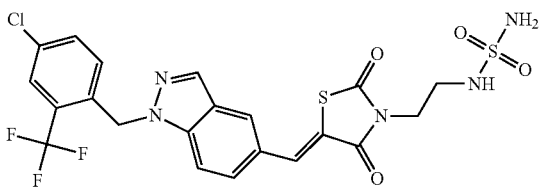 [SMILES: NS(=O)(=O)NCCN1C(=O)S/C(=C\c2ccc3c(cnn3Cc3ccc(Cl)cc3C(F)(F)F)c2)C1=O]

(A) To a solution of tert-butanol (2.45 mmol) in DCM (3 mL) was added chlorosulfonyl isocyanate (1.36 mmol) and the solution was stirred for 5 min. 3-(2-Aminoethyl)-5-({1-[4-chloro-2-(trifluoromethyl)benzyl]-1H-indazol-5-yl}methylidene)-1,3-thiazolidine-2,4-dione hydrochloride (0.34 mmol) was then added to this solution, followed by triethylamine (2.72 mmol) and the mixture was stirred for 1 h. The reaction was diluted with DCM, extracted with water, dried (anhydrous $Na_2SO_4$), concentrated and purified by silica gel chromatography (DCM/MeOH) to afford 1,1-dimethylethyl {[(2-{(5Z)-5-[(1-{[4-chloro-2-(trifluoromethyl)phenyl]methyl}-1H-indazol-5-yl)methylidene]-2,4-dioxo-1,3-thiazolidin-3-yl}ethyl)amino]sulfonyl}-carbamate.

(B) 1,1-Dimethylethyl {[(2-{(5Z)-5-[(1-{[4-chloro-2-(trifluoromethyl)phenyl]-methyl}-1H-indazol-5-yl)methylidene]-2,4-dioxo-1,3-thiazolidin-3-yl}ethyl)amino]sulfonyl}carbamate was deprotected following General Procedure N to provide N-{2-[(5Z)-5-({1-[4-chloro-2-(trifluoromethyl)benzyl]-1H-indazol-5-yl}methylidene)-2,4-dioxo-1,3-thiazolidin-3-yl]ethyl}sulfamide.

$^1$H NMR (400 MHz, DMSO-$d_6$): δ 8.37 (d, 1H), 8.17 (s, 1H), 8.06 (s, 1H), 7.89 (d, 1H), 7.81 (d, 1H), 7.69 (dd, 1H), 7.66 (dd, 1H), 6.82 (t, 1H), 6.78 (d, 1H), 6.56 (s, 2H), 5.87 (s, 2H), 3.79 (t, 2H), 3.15 (q, 2H).

LCMS: mass calcd. for $C_{21}H_{17}ClF_3N_5O_4S_2$: 559.04. found 571.9 [M+H+Na]$^+$ Example 51

(5Z)-5-({1-[4-Chloro-2-(trifluoromethyl)benzyl]-1H-indazol-5-yl}methylidene)-3-{2-[(2-hydroxyethyl)(methyl)amino]ethyl}-1,3-thiazolidine-2,4-dione

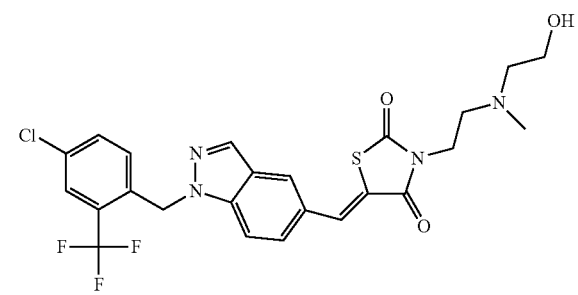 [SMILES: CN(CCO)CCN1C(=O)S/C(=C\c2ccc3c(cnn3Cc3ccc(Cl)cc3C(F)(F)F)c2)C1=O]

(5Z)-5-({1-[4-Chloro-2-(trifluoromethyl)benzyl]-1H-indazol-5-yl}methylidene)-3-{2-[(2-hydroxyethyl)(methyl)amino]ethyl}-1,3-thiazolidine-2,4-dione was prepared from [(5Z)-5-({1-[4-chloro-2-(trifluoromethyl)benzyl]-1H-indazol-5-yl}methylidene)-2,4-dioxo-1,3-thiazolidine (from Example 1) and N-methyldiethanolamine following General Procedure K.

$^1$H NMR (400 MHz, DMSO-$d_6$): δ 9.57 (br. s, 1H), 8.38 (s, 1H), 8.20 (s, 1H), 8.11 (s, 1H), 7.90 (d, 1H), 7.82 (d, 1H), 7.70 (dd, 1H), 7.67 (dd, 1H), 6.81 (d, 1H), 5.87 (s, 2H), 5.40 (br. t, 1H), 4.06 (br. t, 2H), 3.67-3.80 (m, 2H), 3.46-3.60 (m, 1H), 3.36-3.43 (m, 2H), 3.12-3.25 (m, 1H), 2.88 (d, 3H).

LCMS: mass calcd. for $C_{24}H_{22}ClF_3N_4O_3S$: 538.11. found 539.1 [M+H]$^+$

Example 52

(5Z)-5-({1-[4-Chloro-2-(trifluoromethyl)benzyl]-1H-indazol-5-yl}methylidene)-3-{2-[(2-hydroxy-ethyl)amino]ethyl}-1,3-thiazolidine-2,4-dione

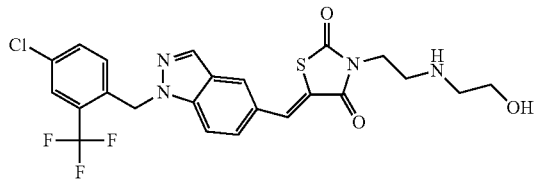 [SMILES: O=C1S/C(=C\c2ccc3c(cnn3Cc3ccc(Cl)cc3C(F)(F)F)c2)C(=O)N1CCNCCO]

(5Z)-5-({1-[4-Chloro-2-(trifluoromethyl)benzyl]-1H-indazol-5-yl}methylidene)-3-{2-[(2-hydroxyethyl)amino]ethyl}-1,3-thiazolidine-2,4-dione was prepared from [(5Z)-5-({1-[4-chloro-2-(trifluoromethyl)benzyl]-1H-indazol-5-yl}methylidene)-2,4-dioxo-1,3-thiazolidine (from Example 1) and diethanolamine following General Procedure K.

$^1$H NMR (400 MHz, DMSO-$d_6$): δ 8.66 (br. s, 1H), 8.38 (s, 1H), 8.20 (s, 1H), 8.11 (s, 1H), 7.90 (d, 1H), 7.82 (d, 1H), 7.71 (dd, 1H), 7.67 (dd, 1H), 6.82 (d, 1H), 5.87 (s, 1H), 5.32 (t, 1H), 4.01 (t, 1H), 3.65 (q, 2H), 3.25 (br. s, 2H), 3.05 (br. s, 2H).

LCMS: mass calcd. for $C_{23}H_{20}ClF_3N_4O_3S$: 524.09. found 425.1 $[M+H]^+$

Example 53

(5Z)-3-[(2S)-2-Amino-4-methylpentyl]-5-({1-[4-chloro-2-(trifluoromethyl)benzyl]-1H-indazol-5-yl}methylidene)-1,3-thiazolidine-2,4-dione

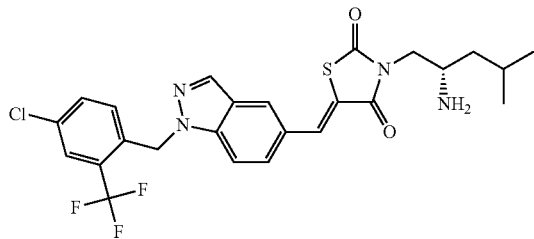 [SMILES: CC(C)C[C@H](N)CN1C(=O)S/C(=C\c2ccc3c(cnn3Cc3ccc(Cl)cc3C(F)(F)F)c2)C1=O]

(A) (5Z)-3-[(2S)-2-(tert-butyloxycarbonyl)amino-4-methylpentyl]-5-({1-[4-chloro-2-(trifluoromethyl)benzyl]-1H-indazol-5-yl}methylidene)-1,3-thiazolidine-2,4-dione was prepared from [(5Z)-5-({1-[4-chloro-2-(trifluoromethyl)benzyl]-1H-indazol-5-yl}methylidene)-2,4-dioxo-1,3-thiazolidine (from Example 1) and Boc-L-leucinol following General Procedure K.

(B) (5Z)-3-[(2S)-2-Amino-4-methylpentyl]-5-({1-[4-chloro-2-(trifluoromethyl)benzyl]-1H-indazol-5-yl}methylidene)-1,3-thiazolidine-2,4-dione was prepared from (5Z)-3-[(2S)-2-(tert-butyloxycarbonyl)amino-4-methylpentyl]-5-({1-[4-chloro-2-(trifluoromethyl)benzyl]-1H-indazol-5-yl}methylidene)-1,3-thiazolidine-2,4-dione following General Procedure N.

$^1$H NMR (400 MHz, DMSO-$d_6$): δ 8.38 (s, 1H), 8.20 (s, 1H), 8.11 (s, 1H), 7.96 (br. s, 3H), 7.90 (d, 1H), 7.82 (d, 1H), 7.71 (dd, 1H), 7.67 (dd, 1H), 6.82 (d, 1H), 5.88 (s, 1H), 3.87 (dd, 1H), 3.79 (dd, 1H), 3.38-3.49 (m, 1H), 1.71-1.85 (m, 1H), 1.38-1.55 (m, 2H), 0.94 (d, 3H), 0.92 (d, 3H).

LCMS: mass calcd. for $C_{25}H_{24}ClF_3N_4O_2S$: 536.13. found 537.1 $[M+H]^+$

Example 54

(5Z)-3-[(2R)-2-Amino-4-methylpentyl]-5-({1-[4-chloro-2-(trifluoromethyl)benzyl]-1H-indazol-5-yl}methylidene)-1,3-thiazolidine-2,4-dione

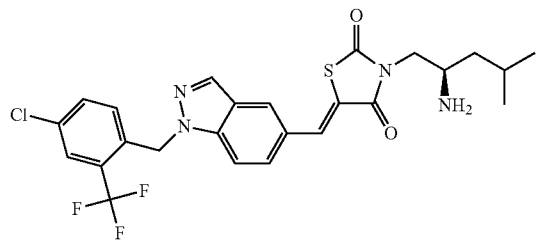

(A) (5Z)-3-[(2R)-2-(tert-butyloxycarbonyl)amino-4-methylpentyl]-5-({1-[4-chloro-2-(trifluoromethyl)benzyl]-1H-indazol-5-yl}methylidene)-1,3-thiazolidine-2,4-dione was prepared from [(5Z)-5-({1-[4-chloro-2-(trifluoromethyl)benzyl]-1H-indazol-5-yl}methylidene)-2,4-dioxo-1,3-thiazolidine (from Example 1) and Boc-D-leucinol following General Procedure K.

(B) (5Z)-3-[(2R)-2-Amino-4-methylpentyl]-5-({1-[4-chloro-2-(trifluoromethyl)benzyl]-1H-indazol-5-yl}methylidene)-1,3-thiazolidine-2,4-dione was prepared from (5Z)-3-[(2R)-2-(tert-butyloxycarbonyl)amino-4-methylpentyl]-5-({1-[4-chloro-2-(trifluoromethyl)benzyl]-1H-indazol-5-yl}methylidene)-1,3-thiazolidine-2,4-dione following General Procedure N.

$^1$H NMR (400 MHz, DMSO-$d_6$): δ 8.38 (s, 1H), 8.20 (s, 1H), 8.11 (s, 1H), 7.96 (br. s, 3H), 7.90 (d, 1H), 7.82 (d, 1H), 7.71 (dd, 1H), 7.67 (dd, 1H), 6.82 (d, 1H), 5.88 (s, 1H), 3.87 (dd, 1H), 3.79 (dd, 1H), 3.38-3.49 (m, 1H), 1.71-1.85 (m, 1H), 1.38-1.55 (m, 2H), 0.94 (d, 3H), 0.92 (d, 3H).

LCMS: mass calcd. for $C_{26}H_{24}ClF_3N_4O_2S$: 536.13. found 537.1 $[M+H]^+$

Example 55

N-{2-[(5Z)-5-({1-[4-Chloro-2-(trifluoromethyl)benzyl]-1H-indazol-5-yl}methylidene)-2,4-dioxo-1,3-thiazolidin-3-yl]ethyl}-1,1,1-trifluoromethanesulfonamide

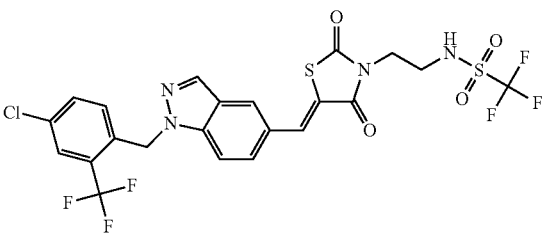 [SMILES: O=C1S/C(=C\c2ccc3c(cnn3Cc3ccc(Cl)cc3C(F)(F)F)c2)C(=O)N1CCNS(=O)(=O)C(F)(F)F]

To a cooled (−78° C.) solution of 3-(2-aminoethyl)-5-({1-[4-chloro-2-(trifluoromethyl)benzyl]-1H-indazol-5-yl}methylidene)-1,3-thiazolidine-2,4-dione hydrochloride (Example 49; 0.1 mmol), triethylamine (0.3 mmol) and DCM (1.5 mL) was added triflic anhydride (0.15 mmol), and the resultant mixture was allowed to warm to rt. After 1 h, the mixture was extracted with 1N HCl, dried (anhydrous Na$_2$SO$_4$) and concentrated. The residue was purified by silica gel chromatography to afford N-{2-[(5Z)-5-({1-[4-chloro-2-(trifluoromethyl)benzyl]-1H-indazol-5-yl}methylidene)-2,4-dioxo-1,3-thiazolidin-3-yl]ethyl}-1,1,1-trifluoromethanesulfonamide as a white powder, which was converted to the corresponding ethanolamine salt following General Procedure T.

$^1$H NMR (400 MHz, DMSO-d$_6$): δ 8.37 (s, 1H), 8.16 (s, 1H), 8.05 (s, 1H), 7.89 (d, 1H), 7.81 (d, 1H), 7.69 (dd, 1H), 7.65 (dd, 1H), 7.46 (br. s, 2H), 6.74 (d, 1H), 5.87 (s, 2H), 5.11 (t, 1H), 3.63 (t, 2H), 3.55 (q, 2H), 3.12 (t, 2H), 2.84 (t, 2H).

LCMS: mass calcd. for C$_{22}$H$_{16}$ClF$_6$N$_4$O$_4$S$_2$: 612.01. found 613.1 [M+H]$^+$ Example 56

N-Carbamimidoyl-2-[(5Z)-5-({1-[4-chloro-2-(trifluoromethyl)benzyl]-1H-indazol-5-yl}methylidene)-2,4-dioxo-1,3-thiazolidin-3-yl]acetamide

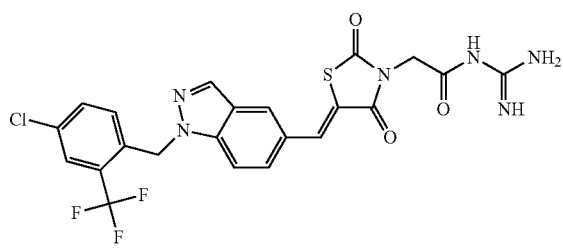 [SMILES: N=C(N)NC(=O)CN1C(=O)S/C(=C\c2ccc3c(cnn3Cc3ccc(Cl)cc3C(F)(F)F)c2)C1=O]

(A) A mixture of [(5Z)-5-({1-[4-chloro-2-(trifluoromethyl)benzyl]-1H-indazol-5-yl}methylidene)-2,4-dioxo-1,3-thiazolidin-3-yl]acetic acid (Example 4; 0.091 mmol) and CDI (0.18 mmol) in THF (2 mL) was stirred at rt overnight. tert-Butoxycarbonylguanidine (0.18 mmol) was then added and the mixture was stirred for 1 h, acidified (pH~5) with 1% aq. HCl and extracted with DCM. The organic phase was dried (anhydrous Na$_2$SO$_4$) and concentrated and the resultant residue was purified by silica gel chromatography (DCM/MeOH; 0.1% HOAc) to afford 1,1-dimethylethyl {[({(5Z)-5-[(1-{[4-chloro-2-(trifluoromethyl)phenyl]methyl}-1H-indazol-5-yl)methylidene]-2,4-dioxo-1,3-thiazolidin-3-yl}acetyl)amino](imino)methyl}-carbamate.

(B) N-Carbamimidoyl-2-[(5Z)-5-({1-[4-chloro-2-(trifluoromethyl)benzyl]-1H-indazol-5-yl}methylidene)-2,4-dioxo-1,3-thiazolidin-3-yl]acetamide was prepared from 1,1-dimethylethyl {[({(5Z)-5-[(1-{[4-chloro-2-(trifluoromethyl)phenyl]methyl}-1H-indazol-5-yl)methylidene]-2,4-dioxo-1,3-thiazolidin-3-yl}acetyl)amino](imino)methyl}carbamate following General Procedure N.

$^1$H NMR (400 MHz, DMSO-d$_6$): δ 12.07 (br. s, 1H), 8.55-8.08 (br. hump, 4H), 8.39 (s, 1H), 8.22 (s, 1H), 8.17 (s, 1H), 7.90 (d, 1H), 7.80-7.85 (m, 1H), 7.72 (dd, 1H), 7.67 (dd, 1H), 6.79 (d, 1H), 5.88 (s, 2H), 4.64 (s, 2H).

LCMS: mass calcd. for C$_{22}$H$_{16}$ClF$_3$N$_6$O$_3$S: 536.06. found 536.9 [M+H]$^+$ Example 57

(5Z)-5-({1-[4-Chloro-2-(trifluoromethyl)benzyl]-1H-indazol-5-yl}methylidene)-3-{2-[(3R)-3-(hydroxymethyl)piperazin-1-yl]-2-oxoethyl}-1,3-thiazolidine-2,4-dione

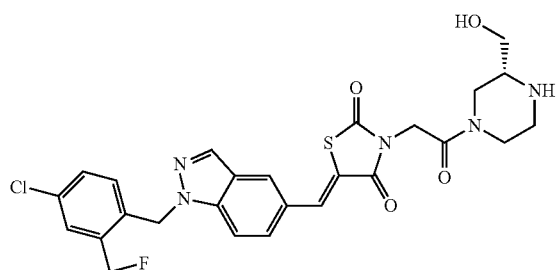

(A) A mixture of [(5Z)-5-({1-[4-chloro-2-(trifluoromethyl)benzyl]-1H-indazol-5-yl}methylidene)-2,4-dioxo-1,3-thiazolidin-3-yl]acetic acid (Example 4; 0.1 mmol) and CDI (0.2 mmol) in THF (2 mL) was stirred at 40° C. for 3 h, then cooled to rt. 1,1-Dimethylethyl (2R)-2-(hydroxymethyl)piperazine-1-carboxylate (0.2 mmol) was added and the solution was stirred overnight. The reaction was then concentrated in vacuo and the resultant residue was purified by silica gel chromatography (DCM/MeOH) to provide 1,1-dimethylethyl (2R)-4-({(5Z)-5-[(1-{[4-chloro-2-(trifluoromethyl)phenyl]methyl}-1H-indazol-5-yl)methylidene]-2,4-dioxo-1,3-thiazolidin-3-yl}acetyl)-2-(hydroxymethyl)piperazine-1-carboxylate.

(B) Deprotection of 1,1-dimethylethyl (2R)-4-({(5Z)-5-[(1-{[4-chloro-2-(trifluoromethyl)phenyl]methyl}-1H-indazol-5-yl)methylidene]-2,4-dioxo-1,3-thiazolidin-3-yl}acetyl)-2-(hydroxymethyl)piperazine-1-carboxylate following General Procedure N provided (5Z)-5-({1-[4-chloro-2-(trifluoromethyl)benzyl]-1H-indazol-5-yl}methylidene)-3-{2-[(3R)-3-(hydroxymethyl)piperazin-1-yl]-2-oxoethyl}-1,3-thiazolidine-2,4-dione hydrochloride.

$^1$H NMR (400 MHz, DMSO-d$_6$): δ 9.19-9.36 (m, 1H), 8.86-9.04 (m, 1H), 8.38 (s, 1H), 8.21 (s, 1H), 8.12 (s, 1H), 7.90 (d, 1H), 7.83 (d, 1H), 7.71 (dd, 1H), 7.67 (dd, 1H), 6.79 (d, 1H), 5.88 (s, 2H), 5.54 (dt, 1H), 4.76-4.91 (m, 1H), 4.53-4.69 (m, 1H), 4.22-4.35 (m, 1H), 3.98-4.14 (m, 1H), 3.42-3.77 (m, 3H), 2.87-3.33 (m, 4H).

LCMS: mass calcd. for C$_{26}$H$_{23}$ClF$_3$N$_6$O$_4$S: 593.11. found 593.9 [M+H]$^+$

Example 58

2-[(5Z)-5-({1-[4-Chloro-2-(trifluoromethyl)benzyl]-1H-indazol-5-yl}methylidene)-2,4-dioxo-1,3-thiazolidin-3-yl]-N-[(4-methoxypiperidin-1-yl)sulfonyl]acetamide

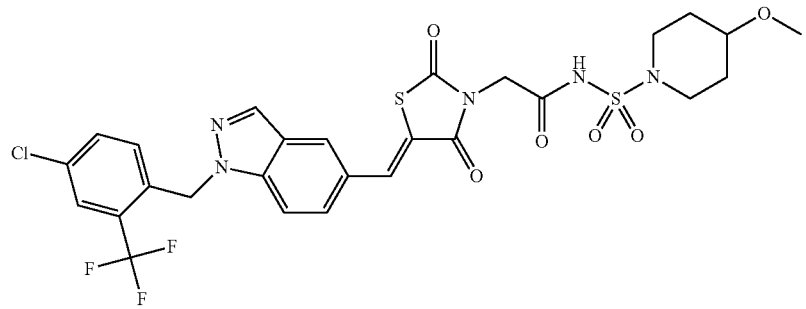 [SMILES: COC1CCN(S(=O)(=O)NC(=O)CN2C(=O)S/C(=C\c3ccc4c(cnn4Cc4ccc(Cl)cc4C(F)(F)F)c3)C2=O)CC1]

2-[(5Z)-5-({1-[4-Chloro-2-(trifluoromethyl)benzyl]-1H-indazol-5-yl}methylidene)-2,4-dioxo-1,3-thiazolidin-3-yl]-N-[(4-methoxypiperidin-1-yl)sulfonyl]acetamide was prepared from [(5Z)-5-({1-[4-chloro-2-(trifluoromethyl)benzyl]-1H-indazol-5-yl}methylidene)-2,4-dioxo-1,3-thiazolidin-3-yl]acetic acid (Example 4) and 4-methoxypiperidin-1-ylsulfonic acid amide following General Procedure L. The corresponding ethanolamine salt was prepared following General Procedure T.

$^1$H NMR (400 MHz, DMSO-$d_6$): δ 8.37 (s, 1H), 8.20 (s, 1H), 8.09 (s, 1H), 7.89 (s, 1H), 7.81 (d, 1H), 7.72 (d, 1H), 7.66 (d, 1H), 7.60 (br. s, 2H), 6.76 (d, 1H), 5.87 (s, 2H), 5.13 (t, 1H), 4.03 (s, 2H), 3.51-3.63 (m, 2H), 3.06-3.23 (m, 2H), 2.93 (s, 3H), 2.80-2.92 (m, 3H), 1.65-1.79 (m, 2H), 1.19-1.35 (m, 2H).

LCMS: mass calcd. for $C_{27}H_{26}ClF_3N_6O_6S_2$: 671.09. found 671.8 [M+H]$^+$

Example 59

[(5Z)-5-({1-[2,4-Bis(trifluoromethyl)benzyl]-1H-indazol-5-yl}methylidene)-2,4-dioxo-1,3-thiazolidin-3-yl]acetic acid

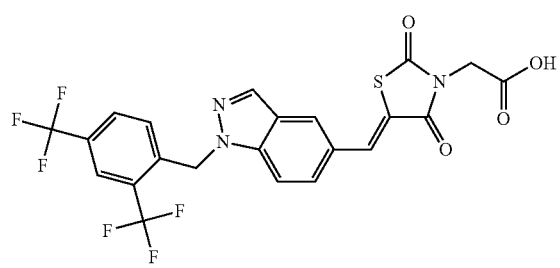 [SMILES: O=C(O)CN1C(=O)S/C(=C\c2ccc3c(cnn3Cc3ccc(C(F)(F)F)cc3C(F)(F)F)c2)C1=O]

[(5Z)-5-({1-[2,4-Bis(trifluoromethyl)benzyl]-1H-indazol-5-yl}methylidene)-2,4-dioxo-1,3-thiazolidin-3-yl]acetic acid was prepared from [(5Z)-5-({1-[2,4-bis(trifluoromethyl)benzyl]-1H-indazol-5-yl}methylidene)-2,4-dioxo-1,3-thiazolidine (from Example 6) following General Procedure I.

$^1$H NMR (400 MHz, DMSO-$d_6$): δ 8.39 (s, 1H), 8.20 (s, 1H), 8.14 (s, 1H), 8.10 (s, 1H), 7.96 (d, 1H), 7.83 (d, 1H), 7.70 (dd, 1H), 6.91 (d, 1H), 5.97 (s, 2H), 4.37 (s, 2H).

LCMS: mass calcd. for $C_{22}H_{13}F_6N_3O_4S$: 529.05. found 530.0 [M+H]$^+$

Example 60

2-[(5Z)-5-({1-[2,4-Bis(trifluoromethyl)benzyl]-1H-indazol-5-yl}methylidene)-2,4-dioxo-1,3-thiazolidin-3-yl]-N-(methylsulfonyl)acetamide

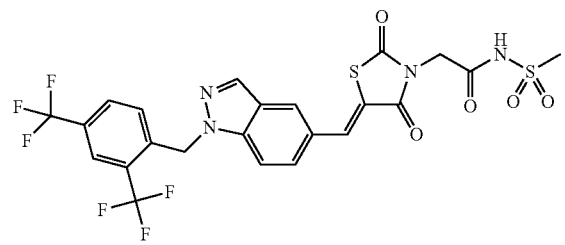 [SMILES: CS(=O)(=O)NC(=O)CN1C(=O)S/C(=C\c2ccc3c(cnn3Cc3ccc(C(F)(F)F)cc3C(F)(F)F)c2)C1=O]

2-[(5Z)-5-({1-[2,4-Bis(trifluoromethyl)benzyl]-1H-indazol-5-yl}methylidene)-2,4-dioxo-1,3-thiazolidin-3-yl]-N-(methylsulfonyl)acetamide was prepared from [(5Z)-5-({1-[2,4-bis(trifluoromethyl)benzyl]-1H-indazol-5-yl}methylidene)-2,4-dioxo-1,3-thiazolidin-3-yl]acetic acid (Example 59) following General Procedure L, using methanesulfonic acid amide in place of the sulfamide.

$^1$H NMR (400 MHz, DMSO-$d_6$): δ 8.42 (s, 1H), 8.23 (s, 1H), 8.15 (s, 1H), 8.13 (s, 1H), 7.98 (d, 1H), 7.86 (d, 1H), 7.73 (dd, 1H), 6.94 (d, 1H), 6.00 (s, 2H), 4.45 (s, 2H), 3.25 (s, 3H).

LC/MS: mass calcd. for $C_{23}H_{16}F_6N_4O_5S_2$, 606.05. found 607.4 [M+1]$^+$

Example 61

1-[(5Z)-5-({1-[4-Fluoro-2-(trifluoromethyl)benzyl]-1H-indazol-5-yl}methylidene)-2,4-dioxo-1,3-thiazolidin-3-yl]methanesulfonamide

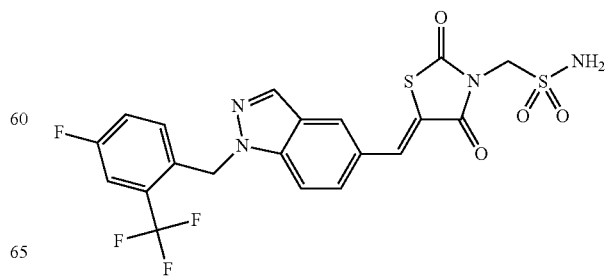

(A) N-tert-Butyl-1-[(5Z)-5-({1-[4-fluoro-2-(trifluoromethyl)benzyl]-1H-indazol-5-yl}methylidene)-2,4-dioxo-1,3-thiazolidin-3-yl]methanesulfonamide was prepared from [(5Z)-5-({1-[4-fluoro-2-(trifluoromethyl)benzyl]-1H-indazol-5-yl}methylidene)-2,4-dioxo-1,3-thiazolidine (from Example 5) and N-tert-butyl-1-chloromethanesulfonamide following General Procedure H.

(B) 1-[(5Z)-5-({1-[4-Fluoro-2-(trifluoromethyl)benzyl]-1H-indazol-5-yl}methylidene)-2,4-dioxo-1,3-thiazolidin-3-yl]methanesulfonamide was prepared from N-tert-butyl-1-[(5Z)-5-({1-[4-fluoro-2-(trifluoromethyl)benzyl]-1H-indazol-5-yl}methylidene)-2,4-dioxo-1,3-thiazolidin-3-yl]methanesulfonamide using the same method as described in Procedure M, but at a reaction temperature of 50° C.

$^1$H NMR (400 MHz, DMSO-$d_6$): δ 8.36 (s, 1H), 8.19 (s, 1H), 8.13 (s, 1H), 7.81 (d, 1H), 7.66-7.75 (m, 1H), 7.44 (t, 1H), 7.36 (br. s., 2H), 6.81-6.94 (m, 1H), 5.84 (br. s., 2H), 4.87 (s, 2H).

LC/MS: mass calcd. for $C_{20}H_{14}F_4N_4O_4S_2$: 514.04. found 515.2 [M+1]$^+$ Example 62

(5Z)-5-({1-[2,4-Bis(trifluoromethyl)benzyl]-1H-indazol-5-yl}methylidene)-3-[(3-exo)-8-methyl-8-azabicyclo[3.2.1]oct-3-yl]-1,3-thiazolidine-2,4-dione

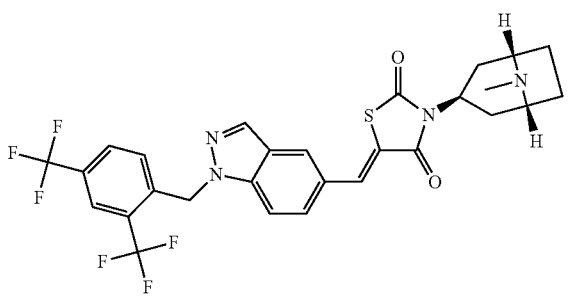 [SMILES: CN1[C@@H]2CC[C@H]1C[C@H](N1C(=O)S/C(=C\c3ccc4c(cnn4Cc4ccc(C(F)(F)F)cc4C(F)(F)F)c3)C1=O)C2]

(A) [(3-exo)-8-methyl-8-azabicyclo[3.2.1]oct-3-yl]-1,3-thiazolidine-2,4-dione was prepared from 1,3-thiazolidine-2,4-dione and [(3-endo)-3-hydroxy-8-methyl-8-azabicyclo[3.2.1]octane] following General Procedure C.

(B) (5Z)-5-({1-[2,4-Bis(trifluoromethyl)benzyl]-1H-indazol-5-yl}methylidene)-3-[(3-exo)-8-methyl-8-azabicyclo[3.2.1]oct-3-yl]-1,3-thiazolidine-2,4-dione was prepared from [(3-exo)-8-methyl-8-azabicyclo[3.2.1]oct-3-yl]-1,3-thiazolidine-2,4-dione and [2,4-bis(trifluoromethyl)benzyl]-1H-indazol-5-carbaldehyde (from Example 6) following General Procedure F.

$^1$H NMR (400 MHz, CDCl$_3$): δ 8.24 (s, 1H), 7.82-8.12 (m, 3H), 7.63 (d, 1H), 7.51 (d, 1H), 7.35 (d, 1H), 6.83 (d, 1H), 5.89 (br. s., 2H), 4.55-4.76 (m, 1H), 3.30 (br. s., 2H), 2.66 (br. t, 2H), 2.49 (s, 3H), 1.98-2.22 (m, 2H), 1.73 (br. d, 2H), 1.32-1.48 (m, 2H).

LCMS: mass calcd. for $C_{28}H_{24}F_6N_4O_2S$: 594.15. found 595.5 [M+H]$^+$

Example 63

(5Z)-3-(1-Azabicyclo[2.2.2]oct-3-yl)-5-({1-[2,4-bis(trifluoromethyl)benzyl]-1H-indazol-5-yl}methylidene)-1,3-thiazolidine-2,4-dione

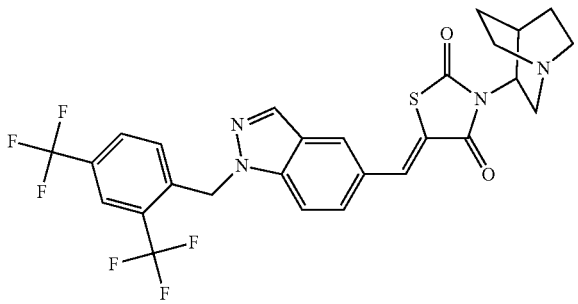 [SMILES: O=C1S/C(=C\c2ccc3c(cnn3Cc3ccc(C(F)(F)F)cc3C(F)(F)F)c2)C(=O)N1C1CN2CCC1CC2]

(A) 3-(1-Azabicyclo[2.2.2]oct-3-yl)-1,3-thiazolidine-2,4-dione was prepared from 1,3-thiazolidine-2,4-dione and 3-hydroxy-1-azabicyclo[2.2.2]octane following General Procedure C.

(B) (5Z)-3-(1-Azabicyclo[2.2.2]oct-3-yl)-5-({1-[2,4-bis(trifluoromethyl)benzyl]-1H-indazol-5-yl}methylidene)-1,3-thiazolidine-2,4-dione was prepared from 3-(1-azabicyclo[2.2.2]oct-3-yl)-1,3-thiazolidine-2,4-dione and [2,4-bis(trifluoromethyl)benzyl]-1H-indazol-5-carbaldehyde (from Example 6) following General Procedure F.

$^1$H NMR (400 MHz, CDCl$_3$): δ 8.24 (s, 1H), 7.88-8.12 (m, 3H), 7.64 (d, 1H), 7.43-7.56 (m, 1H), 7.35 (d, 1H), 6.84 (d, 1H), 5.89 (s, 2H), 4.56 (dd, 1H), 3.95 (dd, 1H), 3.26-3.47 (m, 1H), 3.09 (t, 1H), 2.72-2.98 (m, 3H), 1.95 (m, 2H), 1.53-1.74 (m, 1H), 1.35-1.52 (m, 1H), 1.26 (m, 1H).

LCMS: mass calcd. for $C_{27}H_{22}F_6N_4O_2S$: 580.14. found 622.5 [M+MeCN+H]$^+$ Example 64

N-({[(5Z)-5-({1-[4-Fluoro-2-(trifluoromethyl)benzyl]-1H-indazol-5-yl}methylidene)-2,4-dioxo-1,3-thiazolidin-3-yl]methyl}sulfonyl)acetamide

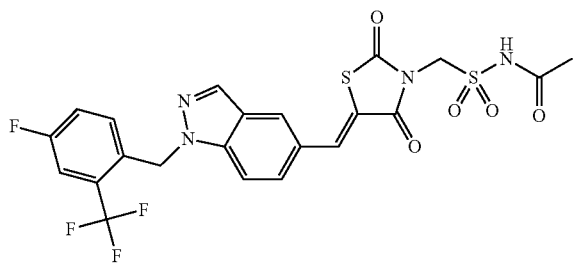 [SMILES: CC(=O)NS(=O)(=O)CN1C(=O)S/C(=C\c2ccc3c(cnn3Cc3ccc(F)cc3C(F)(F)F)c2)C1=O]

N-({[(5Z)-5-({1-[4-Fluoro-2-(trifluoromethyl)benzyl]-1H-indazol-5-yl}methylidene)-2,4-dioxo-1,3-thiazolidin-3- yl]methyl}sulfonyl)acetamide was prepared from 1-[(5Z)-5-({1-[4-fluoro-2-(trifluoromethyl)benzyl]-1H-indazol-5-yl}methylidene)-2,4-dioxo-1,3-thiazolidin-3-yl]methanesulfonamide (Example 61) following General Procedure V.

$^1$H NMR (400 MHz, DMSO-d$_6$): δ 12.06 (s, 1H), 8.38 (s, 1H), 8.23 (s, 1H), 8.22 (s, 1H), 7.84 (d, 1H), 7.69-7.76 (m, 2H), 7.46 (td, 1H), 6.90 (dd, 1H), 5.87 (s, 2H), 5.25 (s, 2H), 2.01 (s, 3H).

LC/MS: mass calcd. for $C_{22}H_{16}F_4N_4O_6S_2$, 556.05. found 557.4 [M+1]$^+$

Example 65

(5Z)-5-({1-[2,4-Bis(trifluoromethyl)benzyl]-1H-indazol-5-yl}methylidene)-3-(2-oxotetrahydrofuran-3-yl)-1,3-thiazolidine-2,4-dione

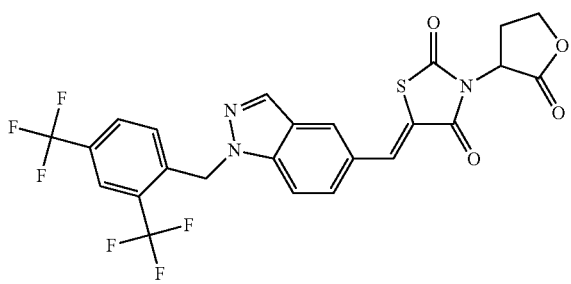 [SMILES: O=C1OCCC1N1C(=O)S/C(=C\c2ccc3c(cnn3Cc3ccc(C(F)(F)F)cc3C(F)(F)F)c2)C1=O]

(A) To a hot solution of 1,3-thiazolidine-2,4-dione (50 mmol) in EtOH (12.5 mL) was added a solution of KOH (55 mmol) in EtOH (12.5 mL) and the mixture was stirred at 70° C. for 1 h, then allowed to cool to rt. The reaction was then cooled in an ice-bath, and the resulting precipitate was collected by filtration and washed with cold EtOH and dried to afford the potassium salt of 1,3-thiazolidine-2,4-dione as a white solid.

(B) A mixture of the potassium salt of 1,3-thiazolidine-2,4-dione (1 mmol) and 2-bromobutyrolactone (1.2 mmol) in DMF (5 mL) was stirred at 100° C. for 1 h, then concentrated in vacuo. Purification of the residue by silica gel chromatography afforded 3-(2-oxotetrahydrofuran-3-yl)-1,3-thiazolidine-2,4-dione as an oil.

(C) (5Z)-5-({1-[2,4-Bis(trifluoromethyl)benzyl]-1H-indazol-5-yl}methylidene)-3-(2-oxotetrahydrofuran-3-yl)-1,3-thiazolidine-2,4-dione was prepared from 3-(2-oxotetrahydrofuran-3-yl)-1,3-thiazolidine-2,4-dione and [2,4-bis(trifluoromethyl)benzyl]-1H-indazol-5-carbaldehyde (from Example 6) following General Procedure F.

$^1$H NMR (400 MHz, CDCl$_3$): δ 8.26 (s, 1H), 8.06 (s, 1H), 7.99 (s, 2H), 7.64 (d, 1H), 7.46-7.56 (m, 1H), 7.37 (d, 1H), 6.85 (d, 1H), 5.90 (s, 2H), 5.22 (t, 1H), 4.66 (td, 1H), 4.41 (td, 1H), 2.77 (dddd, 1H), 2.61 (dddd, 1H).

LCMS: mass calcd. for $C_{24}H_{15}F_6N_3O_4S$: 555.07. found 597.5 [M+MeCN+H]$^+$

Example 66

(5Z)-5-({1-[2,4-Bis(trifluoromethyl)benzyl]-1H-indazol-5-yl}methylidene)-3-[2-(1H-1,2,4-triazol-1-yl)ethyl]-1,3-thiazolidine-2,4-dione

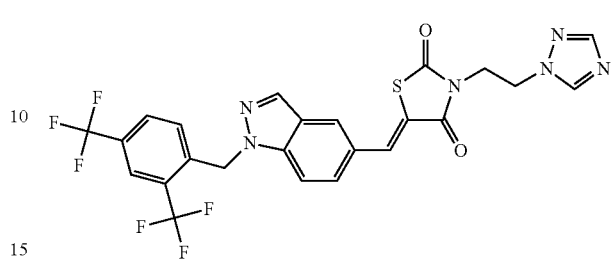

A mixture of [(5Z)-5-({1-[2,4-bis(trifluoromethyl)benzyl]-1H-indazol-5-yl}methylidene)-2,4-dioxo-1,3-thiazolidine (from Example 6; 0.064 mmol), 1-(2-chloroethyl)-1H-[1,2,4]triazole (0.096 mmol), K$_2$CO$_3$ (0.128 mmol) in DMF (1 mL) was heated in a microwave reactor at 140° C. for 10 min, then cooled to rt and concentrated in vacuo. The resultant residue was purified by silica gel chromatography (DCM/MeOH) to afford (5Z)-5-({1-[2,4-bis(trifluoromethyl)benzyl]-1H-indazol-5-yl}methylidene)-3-[2-(1H-1,2,4-triazol-1-yl)ethyl]-1,3-thiazolidine-2,4-dione as a yellow solid.

$^1$H NMR (400 MHz, CDCl$_3$): δ 8.25 (s, 1H), 8.07 (s, 1H), 7.91-8.03 (m, 3H), 7.64 (d, 1H), 7.51 (dd, 1H), 7.36 (d, 1H), 6.83 (d, 1H), 5.89 (s, 2H), 4.54 (t, 2H), 4.23 (t, 2H).

LCMS: mass calcd. for $C_{24}H_{16}F_6N_6O_2S$: 566.10. found 567.4 [M+H]$^+$

Example 67

(5Z)-5-({1-[2,4-Bis(trifluoromethyl)benzyl]-1H-indazol-5-yl}methylidene)-3-piperidin-4-yl-1,3-thiazolidine-2,4-dione

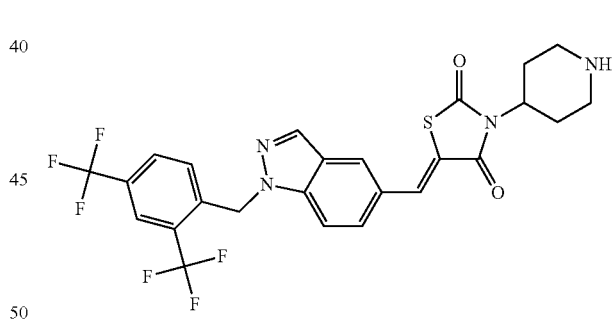

(A) 4-(2,4-Dioxothiazolidin-3-yl)-piperidine-1-carboxylic acid tert-butyl ester was prepared from 1,3-thiazolidine-2,4-dione and 4-hydroxypiperidine-1-carboxylic acid tert-butyl ester following General Procedure C.

(B) Reaction of 4-(2,4-dioxothiazolidin-3-yl)-piperidine-1-carboxylic acid tert-butyl ester and [2,4-bis(trifluoromethyl)benzyl]-1H-indazol-5-carbaldehyde (from Example 6) following General Procedure F afforded 1,1-dimethylethyl 4-{(5Z)-5-[(1-{[2,4-bis(trifluoromethyl)phenyl]-methyl}-1H-indazol-5-yl)methylidene]-2,4-dioxo-1,3-thiazolidin-3-yl}piperidine-1-carboxylate directly, as the hydroacetate salt.

$^1$H NMR (400 MHz, CD$_3$OD): δ 8.30 (s, 1H), 8.12 (s, 1H), 8.05 (s, 3H), 7.79 (d, 1H), 7.56-7.68 (m, 3H), 6.87 (d, 1H), 5.98 (s, 2H), 4.60 (tt, 1H), 3.49 (dd, 2H), 3.09 (td, 2H), 2.73 (dd, 1H), 2.66 (dd, 1H), 1.96 (d, 2H), 1.93 (s, 3H).

LCMS: mass calcd. for $C_{25}H_{20}F_6N_4O_2S$: 554.12. found 596.5 $[M+MeCN+H]^+$

Example 68

1-[(5Z)-5-({1-[2,4-Bis(trifluoromethyl)benzyl]-1H-indazol-5-yl}methylidene)-2,4-dioxo-1,3-thiazolidin-3-yl]methanesulfonamide

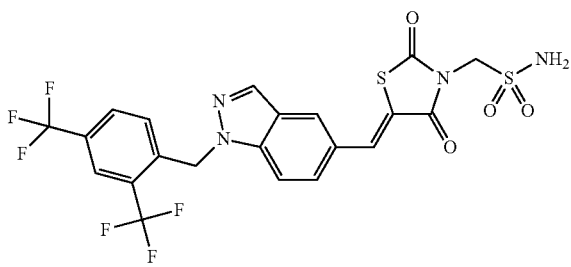 [SMILES: NS(=O)(=O)CN1C(=O)S/C(=C\c2ccc3c(cnn3Cc3ccc(C(F)(F)F)cc3C(F)(F)F)c2)C1=O]

(A) N-tert-Butyl-1-[(5Z)-5-({1-[2,4-bis(trifluoromethyl)benzyl]-1H-indazol-5-yl}methylidene)-2,4-dioxo-1,3-thiazolidin-3-yl]methanesulfonamide was prepared from [(5Z)-5-({1-[2,4-bis(trifluoromethyl)benzyl]-1H-indazol-5-yl}methylidene)-2,4-dioxo-1,3-thiazolidine (from Example 6) and N-tert-butyl-1-chloromethanesulfonamide following General Procedure H.

(B) 1-[(5Z)-5-({1-[2,4-bis(trifluoromethyl)benzyl]-1H-indazol-5-yl}methylidene)-2,4-dioxo-1,3-thiazolidin-3-yl]methanesulfonamide was prepared from N-tert-butyl-1-[(5Z)-5-({1-[2,4-bis(trifluoromethyl)-benzyl]-1H-indazol-5-yl}methylidene)-2,4-dioxo-1,3-thiazolidin-3-yl]methanesulfonamide using the same method as described in Procedure M, but at a reaction temperature of 50° C.

$^1$H NMR (400 MHz, DMSO-d$_6$): δ 8.39 (s, 1H), 8.21 (s, 1H), 8.14 (s, 1H), 8.10 (br. s., 1H), 7.96 (d, 1H), 7.84 (d, 1H), 7.71 (d, 1H), 7.37 (s, 1H), 6.92 (d, 1H), 5.97 (br. s., 2H), 4.88 (s, 2H).

LC/MS: mass calcd. for $C_{21}H_{14}F_6N_4O_4S_2$, 564.04. found 565.2 $[M+1]^+$

Example 69

(5Z)-5-({1-[2,4-Bis(trifluoromethyl)benzyl]-1H-indazol-5-yl}methylidene)-3-{[(2S)-1-methylpyrrolidin-2-yl]methyl}-1,3-thiazolidine-2,4-dione

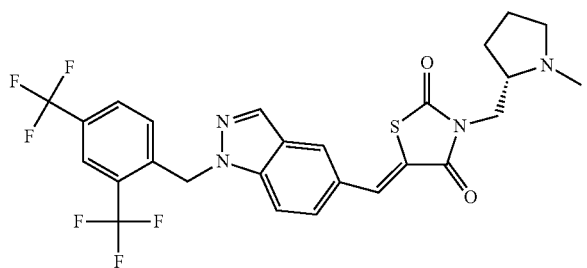 [SMILES: CN1CCC[C@H]1CN1C(=O)S/C(=C\c2ccc3c(cnn3Cc3ccc(C(F)(F)F)cc3C(F)(F)F)c2)C1=O]

(5Z)-5-({1-[2,4-Bis(trifluoromethyl)benzyl]-1H-indazol-5-yl}methylidene)-3-{[(2S)-1-methylpyrrolidin-2-yl]methyl}-1,3-thiazolidine-2,4-dione was prepared from {[(2S)-1-methylpyrrolidin-2-yl]methyl}-1,3-thiazolidine-2,4-dione (from Example 23) and [2,4-bis(trifluoromethyl)benzyl]-1H-indazol-5-carbaldehyde (from Example 6) following General Procedure F.

$^1$H NMR (400 MHz, CDCl$_3$): δ 8.24 (d, 1H), 8.02 (s, 1H), 7.98 (br. s., 2H), 7.63 (d, 1H), 7.53 (dd, 1H), 7.36 (d, 1H), 6.83 (d, 1H), 5.89 (s, 2H), 3.88 (dd, 1H), 3.81 (dd, 1H), 3.10-3.20 (m, 1H), 2.57-2.70 (m, 1H), 2.48 (s, 3H), 2.28 (td, 1H), 1.66-1.98 (m, 4H).

LCMS: mass calcd. for $C_{26}H_{22}F_6N_4O_2S$: 568.14. found 569.5 $[M+H]^+$

Example 70

3-[(5Z)-5-({1-[2,4-Bis(trifluoromethyl)benzyl]-1H-indazol-5-yl}methylidene)-2,4-dioxo-1,3-thiazolidin-3-yl]cyclobutanecarboxylic acid

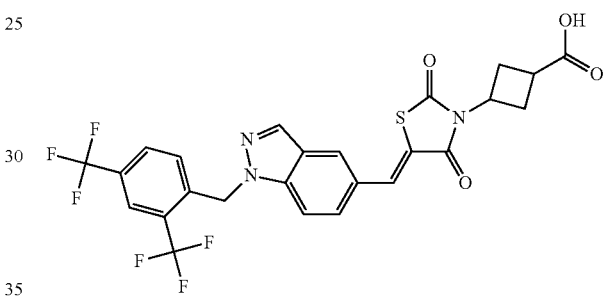

(A) Ethyl 3-(2,4-dioxo-1,3-thiazolidin-3-yl)cyclobutanecarboxylate was prepared from 1,3-thiazolidine-2,4-dione and ethyl 3-hydroxycyclobutanecarboxylate following General Procedure C.

(B) Ethyl 3-[(5Z)-5-({1-[2,4-bis(trifluoromethyl)benzyl]-1H-indazol-5-yl}methylidene)-2,4-dioxo-1,3-thiazolidin-3-yl]cyclobutanecarboxylate was prepared from ethyl 3-(2,4-dioxo-1,3-thiazolidin-3-yl)cyclobutanecarboxylate and [2,4-bis(trifluoromethyl)benzyl]-1H-indazol-5-carbaldehyde (from Example 6) following General Procedure F.

(C) 3-[(5Z)-5-({1-[2,4-Bis(trifluoromethyl)benzyl]-1H-indazol-5-yl}methylidene)-2,4-dioxo-1,3-thiazolidin-3-yl]cyclobutanecarboxylic acid was prepared from the hydrolysis of ethyl 3-[(5Z)-5-({1-[2,4-bis(trifluoromethyl)benzyl]-1H-indazol-5-yl}methylidene)-2,4-dioxo-1,3-thiazolidin-3-yl]cyclobutanecarboxylate following General Procedure O.

$^1$H NMR (400 MHz, CDCl$_3$): δ 8.25 (d, 1H), 8.01 (s, 1H), 7.96-8.00 (m, 2H), 7.64 (d, 1H), 7.48-7.57 (m, 1H), 7.36 (d, 1H), 6.84 (d, 1H), 5.89 (s, 2H), 5.13-5.30 (m, 1H), 3.29-3.42 (m, 1H), 3.15-3.29 (m, 2H), 2.58-2.74 (m, 2H).

LCMS: mass calcd. for $C_{25}H_{17}F_6N_3O_4S$: 569.08. found 570.4 $[M+H]^+$

Example 71

N-({[(5Z)-5-({1-[2,4-Bis(trifluoromethyl)benzyl]-1H-indazol-5-yl}methylidene)-2,4-dioxo-1,3-thiazolidin-3-yl]methyl}sulfonyl)acetamide

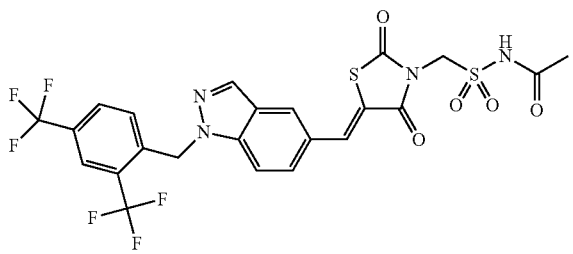 [SMILES: CC(=O)NS(=O)(=O)CN1C(=O)S/C(=C\c2ccc3c(cnn3Cc3ccc(C(F)(F)F)cc3C(F)(F)F)c2)C1=O]

N-({[(5Z)-5-({1-[2-4-Bis(trifluoromethyl)benzyl]-1H-indazol-5-yl}methylidene)-2,4-dioxo-1,3-thiazolidin-3-yl]methyl}sulfonyl)acetamide was prepared from 1-[(5Z)-5-({1-[2,4-bis(trifluoromethyl)benzyl]-1H-indazol-5-yl}methylidene)-2,4-dioxo-1,3-thiazolidin-3-yl]methanesulfonamide (Example 68) following General Procedure V.

$^1$H NMR (400 MHz, DMSO-d$_6$): δ 12.06 (br. s., 1H), 8.42 (s, 1H), 8.25 (s, 1H), 8.22 (s, 2H), 8.13 (s, 1H), 7.98 (d, 1H), 7.87 (d, 1H), 7.74 (dd, 1H), 6.96 (d, 1H), 6.00 (s, 2H), 5.25 (s, 2H), 2.01 (s, 3H).

LC/MS: mass calcd. for $C_{23}H_{16}F_6N_4O_5S_2$, 606.05. found 607.4 [M+1]$^+$

Example 72

(5Z)-5-({1-[4-Chloro-2-(trifluoromethyl)benzyl]-1H-indazol-5-yl}methylidene)-3-(2H-tetrazol-5-ylmethyl)-1,3-thiazolidine-2,4-dione

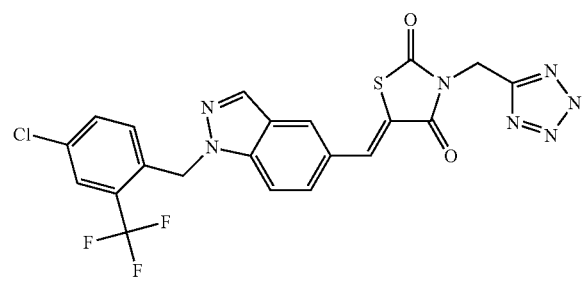 [SMILES: O=C1S/C(=C\c2ccc3c(cnn3Cc3ccc(Cl)cc3C(F)(F)F)c2)C(=O)N1Cc1nn[nH]n1]

(A) A mixture of thiazolidine-2,4-dione (4.27 mmol), bromoacetonitrile (4.27 mmol), K$_2$CO$_3$ (4.27 mmol) and acetone (5 mL) was stirred at rt for 12 h. The solution was filtered and the filtrate was concentrated in vacuo to afford crude (2,4-dioxo-1,3-thiazolidin-3-yl)acetonitrile, which was used directly without further purification.

(B) A mixture of AlCl$_3$ (2.56 mmol) and NaN$_3$ (11.3 mmol) in anhydrous THF (4 mL) was stirred at rt for 15 min, then cooled to 0° C. The crude (2,4-dioxo-1,3-thiazolidin-3-yl)acetonitrile (2.56 mmol) was added, and the resulting mixture was refluxed for 12 h. The reaction was diluted with EtOAc and extracted with 1N HCl. The organic layer was dried (anhydrous Na$_2$SO$_4$) and concentrated in vacuo to afford crude 3-(2H-tetrazol-5-ylmethyl)-1,3-thiazolidine-2,4-dione, which was used directly without further purification.

(C) (5Z)-5-({1-[4-Chloro-2-(trifluoromethyl)benzyl]-1H-indazol-5-yl}methylidene)-3-(2H-tetrazol-5-ylmethyl)-1,3-thiazolidine-2,4-dione was prepared from [4-chloro-2-(trifluoromethyl)benzyl]-1H-indazol-5-carbaldehyde (from Example 1) and 3-(2H-tetrazol-5-ylmethyl)-1,3-thiazolidine-2,4-dione following General Procedure E.

$^1$H NMR (400 MHz, DMSO-d$_6$): δ 8.39 (s, 1H), 8.21 (s, 1H), 8.16 (s, 1H), 7.86-7.91 (m, 1H), 7.79-7.86 (m, 1H), 7.72 (dd, 1H), 7.66 (dd, 1H), 6.80 (d, 1H), 5.88 (s, 2H), 5.19 (s, 2H).

LC/MS: mass calcd. for $C_{21}H_{13}ClF_3N_7O_2S$: 519.05. found 520.0 [M+H]$^+$

Example 73

4-[(5Z)-5-({1-[4-Chloro-2-(trifluoromethyl)benzyl]-1H-indazol-5-yl}methylidene)-2,4-dioxo-1,3-thiazolidin-3-yl]cyclohexanecarboxylic acid

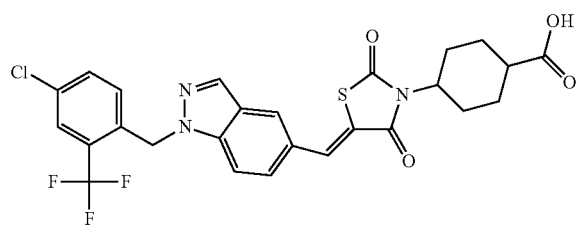 [SMILES: O=C(O)C1CCC(N2C(=O)S/C(=C\c3ccc4c(cnn4Cc4ccc(Cl)cc4C(F)(F)F)c3)C2=O)CC1]

(A) [(5Z)-5-({1-[4-Chloro-2-(trifluoromethyl)benzyl]-1H-indazol-5-yl}methylidene)-2,4-dioxo-1,3-thiazolidine (from Example 1) and 4-hydroxycyclohexanecarboxylic acid ethyl ester were reacted following General Procedure J to afford [(5Z)-5-({1-[4-chloro-2-(trifluoromethyl)benzyl]-1H-indazol-5-yl}methylidene)-2,4-dioxo-1,3-thiazolidin-3-yl]cyclohexanecarboxylic acid ethyl ester.

(B) [(5Z)-5-({1-[4-Chloro-2-(trifluoromethyl)benzyl]-1H-indazol-5-yl}methylidene)-2,4-dioxo-1,3-thiazolidin-3-yl]cyclohexanecarboxylic acid ethyl ester was hydrolyzed following General Procedure 0 to provide 4-[(5Z)-5-({1-[4-chloro-2-(trifluoromethyl)benzyl]-1H-indazol-5-yl}methylidene)-2,4-dioxo-1,3-thiazolidin-3-yl]cyclohexanecarboxylic acid.

(C) 4-[(5Z)-5-({1-[4-Chloro-2-(trifluoromethyl)benzyl]-1H-indazol-5-yl}methylidene)-2,4-dioxo-1,3-thiazolidin-3-yl]cyclohexanecarboxylic acid was converted to the ethanolamine salt as described in Procedure L.

$^1$H NMR (400 MHz, DMSO-d$_6$): δ 8.36 (s, 1H), 8.15 (s, 1H), 8.04 (s, 1H), 7.89 (s, 1H), 7.80 (d, 1H), 7.60-7.74 (m, 2H), 6.77 (d, 1H), 5.86 (s, 2H), 4.13 (t, 1H), 3.43 (t, 2H), 2.66 (t, 2H), 1.92-2.22 (m, 5H), 1.73 (d, 2H), 1.28-1.48 (m, 2H).

LC/MS: mass calcd. for $C_{26}H_{21}ClF_3N_3O_4S$: 563.09. found 564.0 [M+H]$^+$

Example 74

(5Z)-5-({1-[4-Chloro-2-(trifluoromethyl)benzyl]-1H-indazol-5-yl}methylidene)-3-[2-(3-fluoropiperidin-1-yl)ethyl]-1,3-thiazolidine-2,4-dione

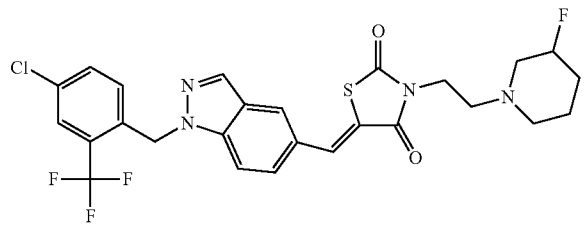 [SMILES: O=C1S/C(=C\c2ccc3c(cnn3Cc3ccc(Cl)cc3C(F)(F)F)c2)C(=O)N1CCN1CCCC(F)C1]

(5Z)-5-({1-[4-Chloro-2-(trifluoromethyl)benzyl]-1H-indazol-5-yl}methylidene)-3-[2-(3-fluoropiperidin-1-yl)ethyl]-1,3-thiazolidine-2,4-dione was prepared from [(5Z)-5-({1-[4-chloro-2-(trifluoromethyl)benzyl]-1H-indazol-5-yl}methylidene)-2,4-dioxo-1,3-thiazolidine (from Example 1), 1-bromo-2-chloroethane and 3-fluoropiperidine following General Procedure G.

$^1$H NMR (400 MHz, CDCl$_3$): δ 8.18-8.22 (m, 1H), 8.12 (s, 1H), 7.91 (s, 1H), 7.71 (d, 1H), 7.60 (dd, 1H), 7.32 (dd, 1H), 7.24-7.30 (m, 1H), 6.62 (d, 1H), 5.80 (s, 2H), 4.15-4.94 (m, 3H), 3.88-4.11 (m, 2H), 3.34-3.86 (m, 2H), 3.03-3.24 (m, 2H), 1.58-2.17 (m, 3H).

LC/MS: mass calcd. for C$_{26}$H$_{23}$ClF$_4$N$_4$O$_2$S: 566.12. found 567.1 [M+H]$^+$

Example 75

(5Z)-5-({1-[4-Chloro-2-(trifluoromethyl)benzyl]-1H-indazol-5-yl}methylidene)-3-[2-(3,3-difluoroazetidin-1-yl)ethyl]-1,3-thiazolidine-2,4-dione

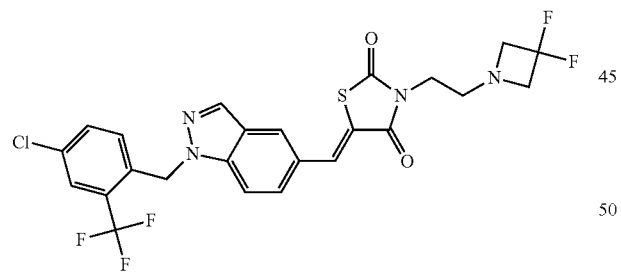

(5Z)-5-({1-[4-Chloro-2-(trifluoromethyl)benzyl]-1H-indazol-5-yl}methylidene)-3-[2-(3-fluoropiperidin-1-yl)ethyl]-1,3-thiazolidine-2,4-dione was prepared from [(5Z)-5-({1-[4-chloro-2-(trifluoromethyl)benzyl]-1H-indazol-5-yl}methylidene)-2,4-dioxo-1,3-thiazolidine (from Example 1), 1-bromo-2-chloroethane and 3,3-difluoroazetidine following General Procedure G.

$^1$H NMR (400 MHz, CDCl$_3$): δ 8.18 (s, 1H), 8.12 (s, 1H), 7.87 (s, 1H), 7.71 (d, 1H), 7.59 (dd, 1H), 7.32 (dd, 1H), 7.29 (d, 1H), 6.64 (d, 1H), 5.79 (s, 2H), 4.48 (t, 4H), 4.07-4.14 (m, 2H), 3.11-3.18 (m, 2H).

LC/MS: mass calcd. for C$_{24}$H$_{18}$ClF$_5$N$_4$O$_2$S: 556.08. found 556.9 [M+H]$^+$

Example 76

(5Z)-3-(3-Aminocyclohexyl)-5-({1-[4-chloro-2-(trifluoromethyl)benzyl]-1H-indazol-5-yl}methylidene)-1,3-thiazolidine-2,4-dione

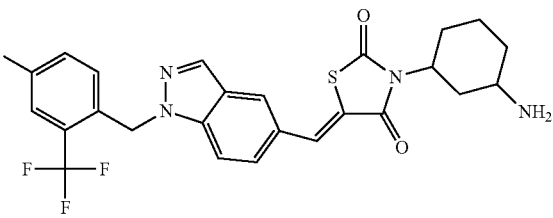

(A) 1,1-Dimethylethyl (3-{5-[1-(4-chloro-2-trifluoromethylbenzyl)-1H-indazol-5-ylmethylene]-2,4-dioxo-1,3-thiazolidin-3-yl}cyclohexyl)-carbamate was prepared from [(5Z)-5-({1-[4-chloro-2-(trifluoromethyl)benzyl]-1H-indazol-5-yl}methylidene)-2,4-dioxo-1,3-thiazolidine (from Example 1) and 1,1-dimethylethyl (3-hydroxycyclohexyl)carbamate following General Procedure J.

(B) (5Z)-3-(3-Aminocyclohexyl)-5-({1-[4-chloro-2-(trifluoromethyl)benzyl]-1H-indazol-5-yl}methylidene)-1,3-thiazolidine-2,4-dione was prepared from 1,1-dimethylethyl (3-{5-[1-(4-chloro-2-trifluoromethylbenzyl)-1H-indazol-5-ylmethylene]-2,4-dioxo-1,3-thiazolidin-3-yl}cyclohexyl)carbamate following General Procedure M.

$^1$H NMR (400 MHz, CDCl$_3$): δ 8.16-8.22 (m, 1H), 7.87-7.96 (m, 2H), 7.66-7.74 (m, 1H), 7.40-7.51 (m, 1H), 7.27-7.35 (m, 2H), 6.66 (d, 1H), 5.75 (s, 2H), 4.27-4.47 (m, 1H), 4.18 (br. s., 2H), 3.29 (br. s., 1H), 2.47-2.70 (m, 1H), 2.06-2.27 (m, 2H), 1.98 (br. s., 1H), 1.60-1.86 (m, 2H), 1.46 (br. s., 1H).

LC/MS: mass calcd. for C$_{25}$H$_{22}$ClF$_3$N$_4$O$_2$S: 534.11. found 535.1 [M+H]$^+$

Example 77

(5Z)-3-Azepan-4-yl-5-({1-[4-chloro-2-(trifluoromethyl)benzyl]-1H-indazol-5-yl}methylidene)-1,3-thiazolidine-2,4-dione

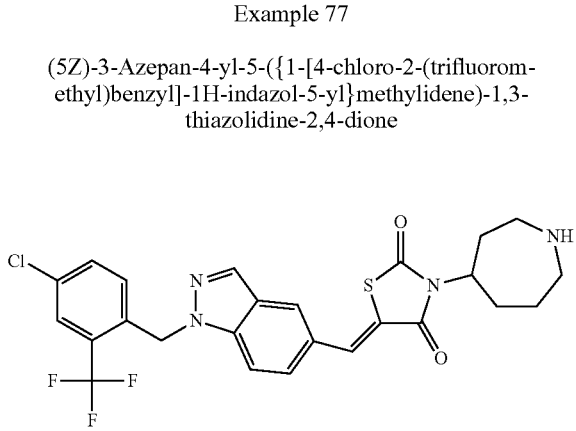

(A) 1,1-Dimethylethyl 4-{5-[1-(4-chloro-2-trifluoromethylbenzyl)-1H-indazol-5-ylmethylene]-2,4-dioxo-1,3-thiazolidin-3-yl}-azepane-1-carboxylate was prepared from [(5Z)-5-({1-[4-chloro-2-(trifluoromethyl)benzyl]-1H-indazol-5-yl}methylidene)-2,4-dioxo-1,3-thiazolidine (from Example 1) and 1,1-dimethylethyl 4-hydroxyazepane-1-carboxylate following General Procedure J.

(B) (5Z)-3-Azepan-4-yl-5-({1-[4-chloro-2-(trifluoromethyl)benzyl]-1H-indazol-5-yl}methylidene)-1,3-thiazolidine-2,4-dione was prepared from 1,1-dimethylethyl 4-{5-[1-(4-chloro-2-trifluoromethylbenzyl)-1H-indazol-5-ylmethylene]-2,4-dioxo-1,3-thiazolidin-3-yl}azepane-1-carboxylate following General Procedure M.

$^1$H NMR (400 MHz, CDCl$_3$): δ 8.21 (s, 1H), 7.99 (s, 1H), 7.94 (s, 1H), 7.72 (d, 1H), 7.48 (dd, 1H), 7.34 (d, 2H), 6.68 (d, 1H), 5.79 (s, 2H), 4.94 (br. s., 2H), 4.57-4.74 (m, 1H), 3.56-3.75 (m, 1H), 3.37-3.56 (m, 1H), 3.16-3.37 (m, 2H), 2.57-2.70 (m, 1H), 2.39 (q, 1H), 2.22-2.33 (m, 1H), 2.08-2.21 (m, 1H), 1.98-2.08 (m, 1H), 1.84-1.98 (m, 1H), 1.37-1.46 (m, 1H).

LC/MS: mass calcd. for C$_{25}$H$_{22}$ClF$_3$N$_4$O$_2$S: 534.11. found 535.3 [M+H]$^+$ Example 78

(5Z)-5-({1-[4-Chloro-2-(trifluoromethyl)benzyl]-1H-indazol-5-yl}methylidene)-3-[2-(1S,4S)-(2,5-diazabicyclo[2.2.1]hept-2-yl)ethyl]-1,3-thiazolidine-2,4-dione

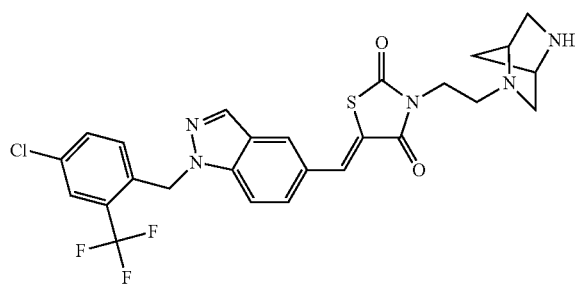 [SMILES: O=C1S/C(=C\c2ccc3c(cnn3Cc3ccc(Cl)cc3C(F)(F)F)c2)C(=O)N1CCN1CC2CC1CN2]

(A) 1,1-Dimethylethyl 5-(2-{5-[1-(4-chloro-2-trifluoromethylbenzyl)-1H-indazol-5-ylmethylene]-2,4-dioxo-1,3-thiazolidin-3-yl}ethyl)-(1S,4S)-2,5-diazabicyclo[2.2.1]heptane-2-carboxylate was prepared from [(5Z)-5-({1-[4-chloro-2-(trifluoromethyl)benzyl]-1H-indazol-5-yl}methylidene)-2,4-dioxo-1,3-thiazolidine (from Example 1), 1-bromo-2-chloroethane and 1,1-dimethylethyl (1S,4S)-2,5-diazabicyclo[2.2.1]heptane-2-carboxylate following General Procedure G.

(B) (5Z)-5-({1-[4-Chloro-2-(trifluoromethyl)benzyl]-1H-indazol-5-yl}methylidene)-3-[2-((1S,4S)-2,5-diazabicyclo[2.2.1]hept-2-yl)ethyl]-1,3-thiazolidine-2,4-dione was prepared from 1,1-dimethylethyl 5-(2-{5-[1-(4-chloro-2-trifluoromethylbenzyl)-1H-indazol-5-ylmethylene]-2,4-dioxo-1,3-thiazolidin-3-yl}ethyl)-(1S,4S)-2,5-diazabicyclo[2.2.1]heptane-2-carboxylate following General Procedure M.

$^1$H NMR (400 MHz, CDCl$_3$): δ 8.19 (s, 1H), 8.11 (s, 1H), 7.86 (br. s., 1H), 7.71 (s, 1H), 7.59 (d, 1H), 7.24-7.38 (m, 2H), 6.62 (d, 1H), 5.78 (br. s., 2H), 5.51 (br. s., 3H), 4.87 (br. s., 1H), 4.36-4.60 (m, 1H), 4.07-4.19 (m, 1H), 3.83-3.96 (m, 1H), 3.61-3.83 (m, 3H), 3.42 (br. s., 1H), 3.00-3.29 (m, 3H), 2.06-2.35 (m, 2H).

LC/MS: mass calcd. for C$_{26}$H$_{23}$ClF$_3$N$_5$O$_2$S: 561.12. found 562.1 [M+H]$^+$ Example 79

(5Z)-5-({1-[4-Chloro-2-(trifluoromethyl)benzyl]-1H-indazol-5-yl}methylidene)-3-[2-(3-oxopiperazin-1-yl)ethyl]-1,3-thiazolidine-2,4-dione

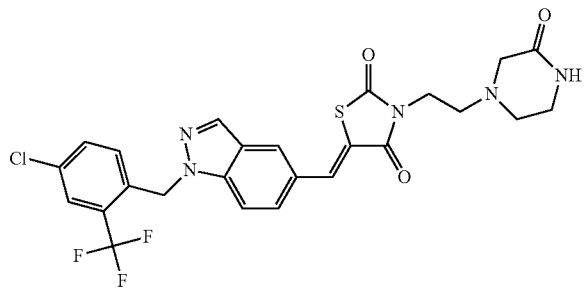 [SMILES: O=C1CN(CCN2C(=O)S/C(=C\c3ccc4c(cnn4Cc4ccc(Cl)cc4C(F)(F)F)c3)C2=O)CCN1]

(5Z)-5-({1-[4-Chloro-2-(trifluoromethyl)benzyl]-1H-indazol-5-yl}methylidene)-3-[2-(3-oxopiperazin-1-yl)ethyl]-1,3-thiazolidine-2,4-dione was prepared from [(5Z)-5-({1-[4-chloro-2-(trifluoromethyl)benzyl]-1H-indazol-5-yl}methylidene)-2,4-dioxo-1,3-thiazolidine (from Example 1), 1-bromo-2-chloroethane and piperazin-2-one following General Procedure G.

$^1$H NMR (400 MHz, CDCl$_3$): δ 8.18 (s, 1H), 8.11 (s, 1H), 7.91 (s, 1H), 7.71 (d, 1H), 7.58 (dd, 1H), 7.32 (dd, 1H), 7.28 (d, 1H), 6.63 (d, 1H), 6.30 (br. s., 1H), 5.79 (s, 2H), 4.15 (br. s., 2H), 4.01 (br. s., 2H), 3.52 (br. s., 2H), 3.12-3.21 (m, 2H), 1.61 (br. s., 2H).

LC/MS: mass calcd. for C$_{25}$H$_{21}$ClF$_3$N$_5$O$_3$S: 563.10. found 564.0 [M+H]$^+$ Example 80

(5Z)-3-[(2R)-2-Aminopropyl]-5-({1-[2,4-bis(trifluoromethyl)benzyl]-1H-indazol-5-yl}methylidene)-1,3-thiazolidine-2,4-dione

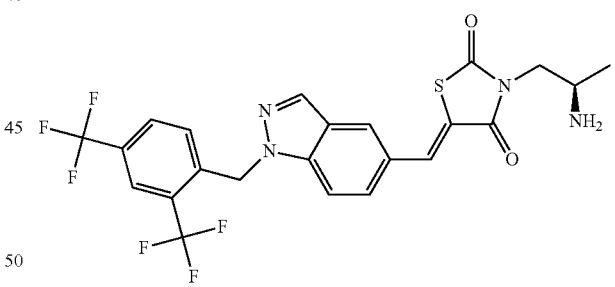

(A) 1,1-Dimethylethyl [2-(5-{[1-(2,4-bis-trifluoromethylbenzyl)-1H-indazol-5-yl]methylene}-2,4-dioxo-1,3-thiazolidin-3-yl)-(1R)-1-methylethyl]-carbamate was prepared from [(5Z)-5-({1-[2,4-bis-(trifluoromethyl)benzyl]-1H-indazol-5-yl}methylidene)-2,4-dioxo-1,3-thiazolidine (from Example 6) and 1,1-dimethylethyl (1R)-(2-hydroxy-1-methylethyl)carbamate following General Procedure J.

(B) (5Z)-3-[(2R)-2-Aminopropyl]-5-({1-[2,4-bis(trifluoromethyl)benzyl]-1H-indazol-5-yl}methylidene)-1,3-thiazolidine-2,4-dione was prepared from 1,1-dimethylethyl [2-(5-{[1-(2,4-bis-trifluoromethylbenzyl)-1H-indazol-5-yl]methylene}-2,4-dioxo-1,3-thiazolidin-3-yl)-(1R)-1-methylethyl]-carbamate following General Procedure M.

$^1$H NMR (400 MHz, CDCl$_3$): δ 8.23 (s, 1H), 7.97-8.02 (m, 3H), 7.63 (d, 1H), 7.52 (dd, 1H), 7.35 (d, 1H), 6.83 (d, 1H), 5.89 (s, 2H), 3.72-3.79 (m, 2H), 3.35-3.47 (m, 1H), 1.24 (d, 3H).

LC/MS: mass calcd. for C$_{23}$H$_{18}$F$_6$N$_4$O$_2$S: 528.11. found 529.0 [M+H]$^+$ Example 81

(5Z)-3-[(2S)-2-Aminopropyl]-5-({1-[2,4-bis(trifluoromethyl)benzyl]-1H-indazol-5-yl}methylidene)-1,3-thiazolidine-2,4-dione

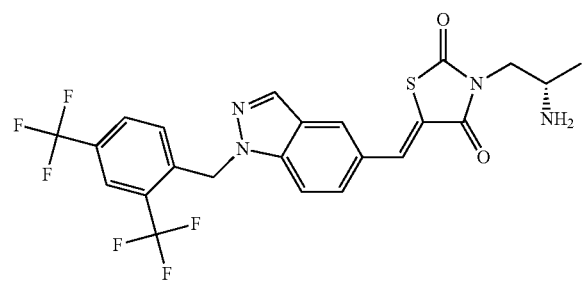 [SMILES: C[C@H](N)CN1C(=O)S/C(=C\c2ccc3c(cnn3Cc3ccc(C(F)(F)F)cc3C(F)(F)F)c2)C1=O]

(A) 1,1-Dimethylethyl [2-(5-{[1-(2,4-bis-trifluoromethylbenzyl)-1H-indazol-5-yl]methylene}-2,4-dioxo-1,3-thiazolidin-3-yl)-(1S)-1-methylethyl]-carbamate was prepared from [(5Z)-5-({1-[2,4-bis-(trifluoromethyl)benzyl]-1H-indazol-5-yl}methylidene)-2,4-dioxo-1,3-thiazolidine (from Example 6) and 1,1-dimethylethyl (1S)-(2-hydroxy-1-methylethyl)carbamate following General Procedure J.

(B) (5Z)-3-[(2S)-2-Aminopropyl]-5-({1-[2,4-bis(trifluoromethyl)benzyl]-1H-indazol-5-yl}methylidene)-1,3-thiazolidine-2,4-dione was prepared from 1,1-dimethylethyl [2-(5-{[1-(2,4-bis-trifluoromethylbenzyl)-1H-indazol-5-yl]methylene}-2,4-dioxo-1,3-thiazolidin-3-yl)-(1S)-1-methylethyl]-carbamate following General Procedure M.

$^1$H NMR (400 MHz, CDCl$_3$): δ 8.19 (s, 1H), 7.92-7.98 (m, 3H), 7.62 (d, 1H), 7.46 (dd, 1H), 7.30 (d, 1H), 6.82 (d, 1H), 5.86 (s, 2H), 3.83-3.96 (m, 2H), 3.60-3.70 (m, 1H), 1.34 (d, 3H).

LC/MS: mass calcd. for C$_{23}$H$_{18}$F$_6$N$_4$O$_2$S: 528.11. found 529.0 [M+H]$^+$ Example 82

(5Z)-5-({1-[2,4-Bis(trifluoromethyl)benzyl]-1H-indazol-5-yl}methylidene)-3-[(2R)-pyrrolidin-2-ylmethyl]-1,3-thiazolidine-2,4-dione

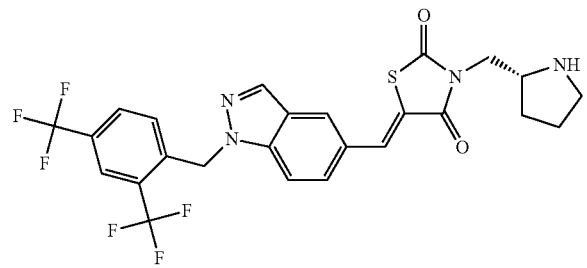 [SMILES: O=C1S/C(=C\c2ccc3c(cnn3Cc3ccc(C(F)(F)F)cc3C(F)(F)F)c2)C(=O)N1C[C@H]1CCCN1]

(A) 1,1-Dimethylethyl (2R)-2-(5-{[1-(2,4-Bis-trifluoromethylbenzyl)-1H-indazol-5-yl]methylene}-2,4-dioxo-1,3-thiazolidin-3-ylmethyl)pyrrolidine-1-carboxylate was prepared from [(5Z)-5-({1-[2,4-bis(trifluoromethyl)benzyl]-1H-indazol-5-yl}methylidene)-2,4-dioxo-1,3-thiazolidine (from Example 6) and 1,1-dimethylethyl (2R)-2-hydroxymethylpyrrolidine-1-carboxylate following General Procedure J.

(B) (5Z)-5-({1-[2,4-Bis(trifluoromethyl)benzyl]-1H-indazol-5-yl}methylidene)-3-[(2R)-pyrrolidin-2-ylmethyl]-1,3-thiazolidine-2,4-dione was prepared from 1,1-dimethylethyl (2R)-2-(5-{[1-(2,4-bis-trifluoromethylbenzyl)-1H-indazol-5-yl]methylene}-2,4-dioxo-1,3-thiazolidin-3-ylmethyl)pyrrolidine-1-carboxylate following General Procedure M.

$^1$H NMR (400 MHz, CDCl$_3$): δ 8.21 (s, 1H), 7.99 (d, 2H), 7.91-7.96 (m, 1H), 7.63 (d, 1H), 7.44-7.52 (m, 1H), 7.33 (d, 1H), 6.83 (d, 1H), 5.87 (s, 2H), 4.22 (dd, 1H), 4.12 (dd, 1H), 3.78-3.98 (m, 1H), 3.52-3.72 (m, 1H), 3.30-3.50 (m, 1H), 2.15-2.36 (m, 2H), 2.02-2.13 (m, 1H), 1.89-2.02 (m, 1H).

LC/MS: mass calcd. for C$_{25}$H$_{20}$F$_6$N$_4$O$_2$S: 554.12. found 555.2 [M+H]$^+$ Example 83

(5Z)-5-({1-[2,4-Bis(trifluoromethyl)benzyl]-1H-indazol-5-yl}methylidene)-3-[(2S)-pyrrolidin-2-ylmethyl]-1,3-thiazolidine-2,4-dione

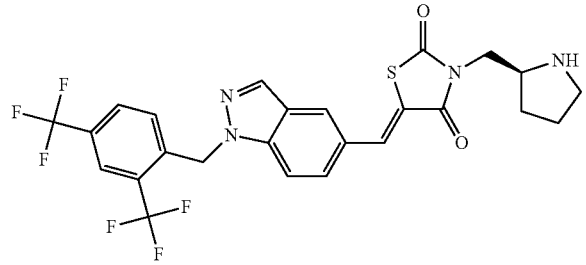 [SMILES: O=C1S/C(=C\c2ccc3c(cnn3Cc3ccc(C(F)(F)F)cc3C(F)(F)F)c2)C(=O)N1C[C@@H]1CCCN1]

(A) 1,1-Dimethylethyl (2S)-2-(5-{[1-(2,4-Bis-trifluoromethylbenzyl)-1H-indazol-5-yl]methylene}-2,4-dioxo-1,3-thiazolidin-3-ylmethyl)pyrrolidine-1-carboxylate was prepared from [(5Z)-5-({1-[2,4-bis(trifluoromethyl)benzyl]-1H-indazol-5-yl}methylidene)-2,4-dioxo-1,3-thiazolidine (from Example 6) and 1,1-dimethylethyl (2S)-2-hydroxymethylpyrrolidine-1-carboxylate following General Procedure J.

(B) (5Z)-5-({1-[2,4-Bis(trifluoromethyl)benzyl]-1H-indazol-5-yl}methylidene)-3-[(2S)-pyrrolidin-2-ylmethyl]-1,3-thiazolidine-2,4-dione was prepared from 1,1-dimethylethyl (2S)-2-(5-{[1-(2,4-bis-trifluoromethylbenzyl)-1H-indazol-5-yl]methylene}-2,4-dioxo-1,3-thiazolidin-3-ylmethyl)pyrrolidine-1-carboxylate following General Procedure M.

$^1$H NMR (400 MHz, CDCl$_3$): δ 8.21 (s, 1H), 7.98 (s, 2H), 7.94 (s, 1H), 7.63 (d, 1H), 7.48 (dd, 1H), 7.32 (d, 1H), 6.82 (d, 1H), 5.87 (s, 2H), 4.09 (dd, 1H), 3.98 (dd, 1H), 3.66-3.79 (m, 1H), 3.41-3.53 (m, 1H), 3.10-3.30 (m, 1H), 2.02-2.23 (m, 2H), 1.89-2.02 (m, 1H), 1.75-1.89 (m, 1H).

LC/MS: mass calcd. for C$_{25}$H$_{20}$F$_6$N$_4$O$_2$S: 554.12. found 555.2 [M+H]$^+$

Example 84

(5Z)-5-({1-[2,4-Bis(trifluoromethyl)benzyl]-1H-indazol-5-yl}methylidene)-3-(2-pyrrolidin-1-yl-ethyl)-1,3-thiazolidine-2,4-dione

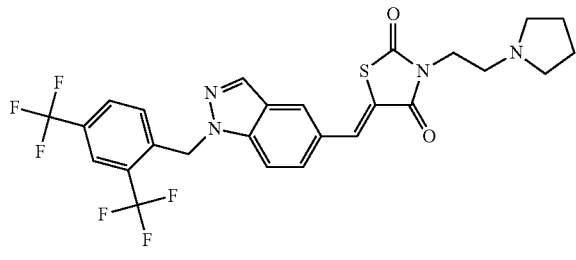 [SMILES: O=C1S/C(=C\c2ccc3c(cnn3Cc3ccc(C(F)(F)F)cc3C(F)(F)F)c2)C(=O)N1CCN1CCCC1]

(5Z)-5-({1-[2,4-Bis(trifluoromethyl)benzyl]-1H-indazol-5-yl}methylidene)-3-(2-pyrrolidin-1-ylethyl)-1,3-thiazolidine-2,4-dione was prepared from [(5Z)-5-({1-[2,4-bis-(trifluoromethyl)benzyl]-1H-indazol-5-yl}methylidene)-2,4-dioxo-1,3-thiazolidine (from Example 6), 1-bromo-2-chloroethane and pyrrolidine following General Procedure G.

$^1$H NMR (400 MHz, CDCl$_3$): δ 8.19 (s, 1H), 8.12 (s, 1H), 7.97 (s, 1H), 7.93 (s, 1H), 7.61 (d, 2H), 7.22-7.33 (m, 1H), 6.79 (d, 1H), 5.88 (s, 2H), 3.96-4.09 (m, 2H), 3.58 (t, 2H), 3.48 (t, 2H), 3.10-3.19 (m, 2H), 1.87-2.04 (m, 4H).

LC/MS: mass calcd. for C$_{26}$H$_{22}$F$_6$N$_4$O$_2$S: 568.14. found 569.0 [M+H]$^+$

Example 85

(5Z)-5-({1-[4-Chloro-2-(trifluoromethyl)benzyl]-1H-indazol-5-yl}methylidene)-3-(1H-1,2,3-triazol-4-ylmethyl)-1,3-thiazolidine-2,4-dione

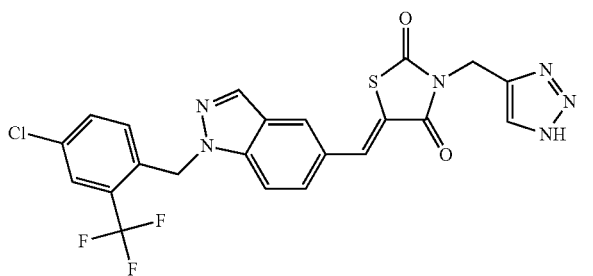 [SMILES: O=C1S/C(=C\c2ccc3c(cnn3Cc3ccc(Cl)cc3C(F)(F)F)c2)C(=O)N1Cc1c[nH]nn1]

(A) 3-(1H-1,2,3-Triazol-4-ylmethyl)-1,3-thiazolidine-2,4-dione was prepared from 4-aminomethyl-(1H)-1,2,3-triazole hydrochloride following General Procedure D.

(B) (5Z)-5-({1-[4-Chloro-2-(trifluoromethyl)benzyl]-1H-indazol-5-yl}methylidene)-3-(1H-1,2,3-triazol-4-ylmethyl)-1,3-thiazolidine-2,4-dione was prepared from [4-chloro-2-(trifluoromethyl)benzyl]-1H-indazol-5-carbaldehyde (from Example 1) and 3-(1H-1,2,3-triazol-4-ylmethyl)-1,3-thiazolidine-2,4-dione following General Procedure F.

$^1$H NMR (400 MHz, CDCl$_3$): δ 8.22 (s, 1H), 8.06 (s, 1H), 7.96 (s, 1H), 7.78 (s, 1H), 7.72 (d, 1H), 7.50 (dd, 1H), 7.31-7.38 (m, 2H), 6.68 (d, 1H), 5.80 (s, 2H), 5.09 (s, 2H).

LC/MS: mass calcd. for C$_{22}$H$_{14}$ClF$_3$N$_6$O$_2$S: 518.05. found 519.0 [M+H]$^+$

Example 86

(5Z)-5-({1-[4-Chloro-2-(trifluoromethyl)benzyl]-1H-indazol-5-yl}methylidene)-3-[(5-methyl-1H-1,2,4-triazol-3-yl)methyl]-1,3-thiazolidine-2,4-dione

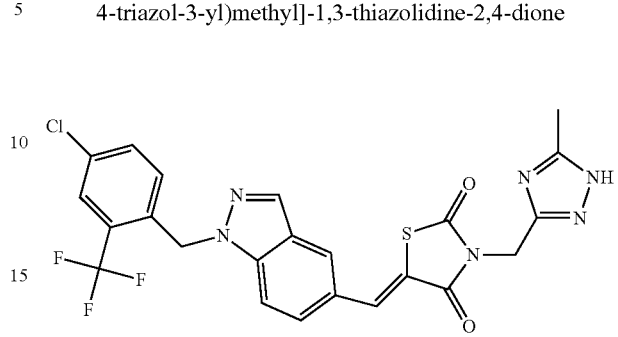

(A) 3-(5-Methyl-1H-1,2,4-triazol-3-ylmethyl)-1,3-thiazolidine-2,4-dione was prepared from 3-aminomethyl-5-methyl-(1H)-1,2,4-triazole following General Procedure D.

(B) (5Z)-5-({1-[4-Chloro-2-(trifluoromethyl)benzyl]-1H-indazol-5-yl}methylidene)-3-[(5-methyl-1H-1,2,4-triazol-3-yl)methyl]-1,3-thiazolidine-2,4-dione was prepared from [4-chloro-2-(trifluoromethyl)benzyl]-1H-indazol-5-carbaldehyde (from Example 1) and 3-(5-methyl-1H-1,2,4-triazol-3-ylmethyl)-1,3-thiazolidine-2,4-dione following General Procedure F.

$^1$H NMR (400 MHz, CD$_3$OD): δ 8.24 (s, 1H), 8.07 (s, 1H), 8.01 (s, 1H), 7.73 (d, 1H), 7.55 (dd, 1H), 7.39 (d, 1H), 7.33-7.37 (m, 1H), 6.67 (d, 1H), 5.82 (s, 2H), 3.70 (s, 2H), 2.42 (s, 3H).

LC/MS: mass calcd. for C$_{23}$H$_{16}$ClF$_3$N$_6$O$_2$S: 532.07. found 533.1 [M+H]$^+$

Example 87

2-[(5Z)-5-({1-[2,4-Bis(trifluoromethyl)benzyl]-1H-indazol-5-yl}methylidene)-2,4-dioxo-1,3-thiazolidin-3-yl]-N-sulfamoylacetamide

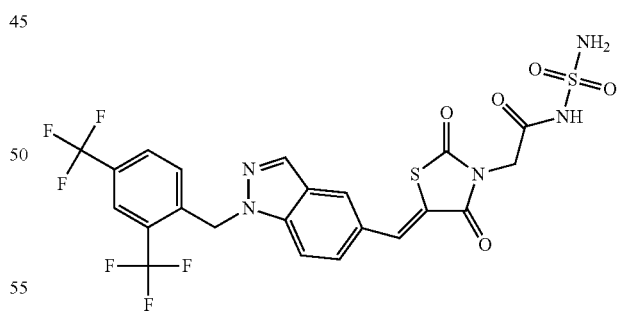

2-[(5Z)-5-({1-[2,4-Bis(trifluoromethyl)benzyl]-1H-indazol-5-yl}methylidene)-2,4-dioxo-1,3-thiazolidin-3-yl]-N-sulfamoylacetamide was prepared from {5-[1-(2,4-bis-trifluoromethylbenzyl)-1H-indazol-5-ylmethylene]-2,4-dioxothiazolidin-3-yl}acetic acid (Example 59) and sulfamide following General Procedure L.

$^1$H NMR (400 MHz, DMSO-d$_6$): δ 8.39 (s, 1H), 8.20 (s, 1H), 8.13 (s, 1H), 8.10 (s, 1H), 7.96 (d, 1H), 7.83 (d, 1H), 7.67-7.74 (m, 1H), 7.59 (s, 2H), 6.91 (d, 1H), 5.97 (s, 2H), 4.37 (s, 2H).

LC/MS: mass calcd. for $C_{22}H_{16}F_6N_6O_6S_2$: 607.04. found 607.8 [M+H]$^+$ Example 88

2-[(5Z)-5-({1-[2,4-Bis(trifluoromethyl)benzyl]-1H-indazol-5-yl}methylidene)-2,4-dioxo-1,3-thiazolidin-3-yl]-N-(dimethylsulfamoyl)acetamide

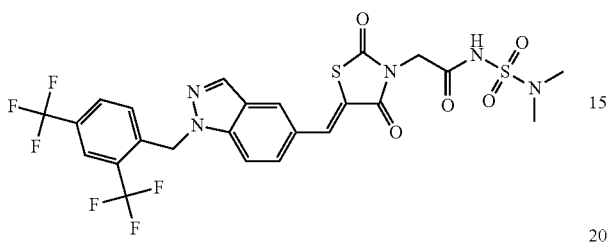

2-[(5Z)-5-({1-[2,4-Bis(trifluoromethyl)benzyl]-1H-indazol-5-yl}methylidene)-2,4-dioxo-1,3-thiazolidin-3-yl]-N-(dimethylsulfamoyl)acetamide was prepared from {5-[1-(2,4-bis-trifluoromethylbenzyl)-1H-indazol-5-ylmethylene]-2,4-dioxo-1,3-thiazolidin-3-yl}acetic acid (Example 59) and N,N-dimethylsulfamide following General Procedure L.

$^1$H NMR (400 MHz, CDCl$_3$): δ 8.27 (s, 1H), 8.07 (s, 1H), 8.01 (d, 2H), 7.66 (d, 1H), 7.56 (dd, 1H), 7.40 (d, 1H), 6.83 (d, 1H), 5.91 (s, 2H), 4.47 (s, 2H), 3.84 (br. s., 3H), 2.88-2.98 (m, 6H).

LC/MS: mass calcd. for $C_{24}H_{19}F_6N_5O_5S_2$: 635.07. found 635.9 [M+H]$^+$ Example 89

1-[(5Z)-5-({1-[4-Chloro-2-(trifluoromethyl)benzyl]-1H-indazol-5-yl}methylidene)-2,4-dioxo-1,3-thiazolidin-3-yl]cyclopropanecarboxylic acid

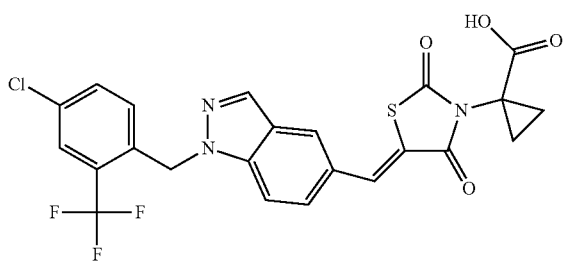 [SMILES: O=C1S/C(=C\c2ccc3c(cnn3Cc3ccc(Cl)cc3C(F)(F)F)c2)C(=O)N1C1(C(=O)O)CC1]

(A) Methyl 1-(2,4-dioxo-1,3-thiazolidin-3-yl)cyclopropanecarboxylate was prepared from methyl-aminocyclopropanecarboxylate following General Procedure D.
(B) Methyl 1-(5-{[1-(4-chloro-2-trifluoromethylbenzyl)-1H-indazol-5-yl]methylene}-2,4-dioxo-1,3-thiazolidin-3-yl)cyclopropanecarboxylate was prepared from [4-chloro-2-(trifluoromethyl)benzyl]-1H-indazol-5-carbaldehyde (from Example 1) and methyl 1-(2,4-dioxo-1,3-thiazolidin-3-yl)cyclopropanecarboxylate following General Procedure F.
(C) 1-[(5Z)-5-({1-[4-Chloro-2-(trifluoromethyl)benzyl]-1H-indazol-5-yl}methylidene)-2,4-dioxo-1,3-thiazolidin-3-yl]cyclopropanecarboxylic acid was prepared from methyl 1-(5-{[1-(4-chloro-2-trifluoromethylbenzyl)-1H-indazol-5-yl]methylene}-2,4-dioxo-1,3-thiazolidin-3-yl)cyclopropanecarboxylate following General Procedure O.

$^1$H NMR (400 MHz, CDCl$_3$): δ 8.21 (s, 1H), 8.01 (s, 1H), 7.95 (s, 1H), 7.71 (d, 1H), 7.50 (dd, 1H), 7.34 (d, 2H), 6.67 (d, 1H), 5.79 (s, 2H), 1.91-2.00 (m, 2H), 1.50-1.59 (m, 2H).

LC/MS: mass calcd. for $C_{23}H_{15}ClF_3N_3O_4S$: 521.04. found 521.9 [M+H]$^+$ Example 90

(5Z)-5-({1-[4-Chloro-2-(trifluoromethyl)benzyl]-1H-indazol-5-yl}methylidene)-3-(1H-1,2,4-triazol-3-ylmethyl)-1,3-thiazolidine-2,4-dione

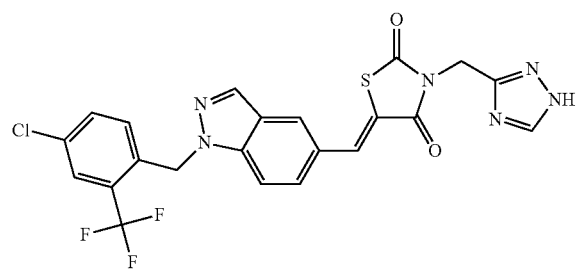 [SMILES: O=C1S/C(=C\c2ccc3c(cnn3Cc3ccc(Cl)cc3C(F)(F)F)c2)C(=O)N1Cc1nc[nH]n1]

(A) 3-(1H-1,2,4-triazol-3-ylmethyl)-1,3-thiazolidine-2,4-dione was prepared from 3-aminomethyl-(1H)-1,2,4-triazole following General Procedure D.
(B) (5Z)-5-({1-[4-Chloro-2-(trifluoromethyl)benzyl]-1H-indazol-5-yl}methylidene)-3-(1H-1,2,4-triazol-3-ylmethyl)-1,3-thiazolidine-2,4-dione was prepared from [4-chloro-2-(trifluoromethyl)benzyl]-1H-indazol-5-carbaldehyde (from Example 1) and 3-(1H-1,2,4-triazol-3-ylmethyl)-1,3-thiazolidine-2,4-dione following General Procedure F.

$^1$H NMR (400 MHz, CD$_3$OD): δ 8.16-8.31 (m, 1H), 8.15-8.23 (m, 1H), 8.01-8.07 (m, 1H), 7.99-8.13 (m, 1H), 7.74 (br. s., 1H), 7.54-7.64 (m, 1H), 7.36-7.47 (m, 2H), 6.59-6.76 (m, 1H), 5.83 (br. s., 2H), 5.02-5.15 (m, 2H).

LC/MS: mass calcd. for $C_{22}H_{14}ClF_3N_6O_2S$: 518.05. found 519.1 [M+H]$^+$ Example 91

1-{2-[(5Z)-5-({1-[4-Chloro-2-(trifluoromethyl)benzyl]-1H-indazol-5-yl}methylidene)-2,4-dioxo-1,3-thiazolidin-3-yl]ethoxy}guanidine

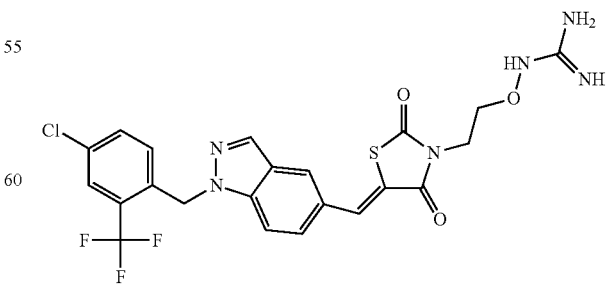

(A) Bis(1,1-dimethylethyl) [({[2-(2,4-dioxo-1,3-thiazolidin-3-yl)ethyl]oxy}amino)methylidene]biscarbamate was prepared from bis(1,1-dimethylethyl) ({[(2-amino-ethyl)oxy]amino}methylidene)-biscarbamate following General Procedure D.

(B) Bis(1,1-dimethylethyl) [{[(2-{(5Z)-5-[(1-{[4-chloro-2-(trifluoromethyl)phenyl]methyl}-1H-indazol-5-yl)methylidene]-2,4-dioxo-1,3-thiazolidin-3-yl}ethyl)oxy]amino}methylidene]biscarbamate was prepared from [4-chloro-2-(trifluoromethyl)benzyl]-1H-indazol-5-carbaldehyde (from Example 1) and bis(1,1-dimethylethyl) [({[2-(2,4-dioxo-1,3-thiazolidin-3-yl)ethyl]oxy}amino)methylidene]biscarbamate following General Procedure F.

(C) 1-{2-[(5Z)-5-({1-[4-Chloro-2-(trifluoromethyl)benzyl]-1H-indazol-5-yl}methylidene)-2,4-dioxo-1,3-thiazolidin-3-yl]ethoxy}guanidine was prepared from bis(1,1-dimethylethyl) [{[(2-{(5Z)-5-[(1-{[4-chloro-2-(trifluoromethyl)phenyl]methyl}-1H-indazol-5-yl)methylidene]-2,4-dioxo-1,3-thiazolidin-3-yl}ethyl)oxy]amino}methylidene]biscarbamate following General Procedure M.

$^1$H NMR (400 MHz, CDCl$_3$): δ 8.24 (s, 1H), 7.97-8.06 (m, 2H), 7.73 (d, 1H), 7.53 (dd, 1H), 7.38 (d, 2H), 6.66 (d, 1H), 5.81 (s, 2H), 4.04 (s, 4H).

LC/MS: mass calcd. for C$_{22}$H$_{18}$ClF$_3$N$_6$O$_3$S: 538.08. found 539.0 [M+H]$^+$ Example 92

(5Z)-5-({1-[4-Chloro-2-(trifluoromethyl)benzyl]-1H-indazol-5-yl}methylidene)-3-(1,3-thiazol-2-ylmethyl)-1,3-thiazolidine-2,4-dione

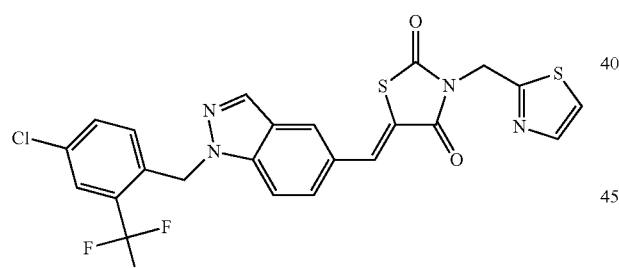

(5Z)-5-({1-[4-Chloro-2-(trifluoromethyl)benzyl]-1H-indazol-5-yl}methylidene)-3-(1,3-thiazol-2-ylmethyl)-1,3-thiazolidine-2,4-dione was prepared from [(5Z)-5-({1-[4-chloro-2-(trifluoromethyl)benzyl]-1H-indazol-5-yl}methylidene)-2,4-dioxo-1,3-thiazolidine (from Example 1) and thiazol-2-yl-methanol following General Procedure J.

$^1$H NMR (400 MHz, CDCl$_3$): δ 8.22 (s, 1H), 8.08 (s, 1H), 7.98 (s, 1H), 7.77 (d, 1H), 7.72 (d, 1H), 7.51 (dd, 1H), 7.31-7.38 (m, 3H), 6.68 (d, 1H), 5.80 (s, 2H), 5.27 (s, 2H).

LC/MS: mass calcd. for C$_{23}$H$_{14}$ClF$_3$N$_4$O$_2$S$_2$: 534.02. found 535.1 [M+H]$^+$ Example 93

(5Z)-5-({1-[4-Chloro-2-(trifluoromethyl)benzyl]-1H-indazol-5-yl}methylidene)-3-(1,3-thiazol-4-ylmethyl)-1,3-thiazolidine-2,4-dione

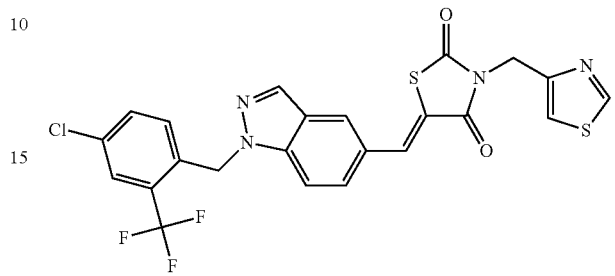

(5Z)-5-({1-[4-Chloro-2-(trifluoromethyl)benzyl]-1H-indazol-5-yl}methylidene)-3-(1,3-thiazol-4-ylmethyl)-1,3-thiazolidine-2,4-dione was prepared from [(5Z)-5-({1-[4-chloro-2-(trifluoromethyl)benzyl]-1H-indazol-5-yl}methylidene)-2,4-dioxo-1,3-thiazolidine (from Example 1) and thiazol-4-yl-methanol following General Procedure J.

$^1$H NMR (400 MHz, CDCl$_3$): δ 8.79 (d, 1H), 8.21 (s, 1H), 8.06 (s, 1H), 7.96 (s, 1H), 7.72 (d, 1H), 7.51 (dd, 1H), 7.31-7.39 (m, 3H), 6.67 (d, 1H), 5.79 (s, 2H), 5.12 (s, 2H).

LC/MS: mass calcd. for C$_{23}$H$_{14}$ClF$_3$N$_4$O$_2$S$_2$: 534.02. found 535.1 [M+H]$^+$ Example 94

(5Z)-5-({1-[4-Chloro-2-(trifluoromethyl)benzyl]-1H-indazol-5-yl}methylidene)-3-(1,3-thiazol-5-ylmethyl)-1,3-thiazolidine-2,4-dione

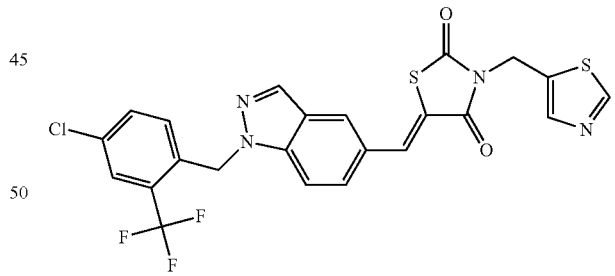

(5Z)-5-({1-[4-Chloro-2-(trifluoromethyl)benzyl]-1H-indazol-5-yl}methylidene)-3-(1,3-thiazol-5-ylmethyl)-1,3-thiazolidine-2,4-dione was prepared from [(5Z)-5-({1-[4-chloro-2-(trifluoromethyl)benzyl]-1H-indazol-5-yl}methylidene)-2,4-dioxo-1,3-thiazolidine (from Example 1) and thiazol-5-ylmethanol following General Procedure J.

$^1$H NMR (400 MHz, CDCl$_3$): δ 8.77 (s, 1H), 8.22 (d, 1H), 8.05 (s, 1H), 7.99 (d, 1H), 7.94-7.97 (m, 1H), 7.72 (d, 1H), 7.49 (dd, 1H), 7.30-7.38 (m, 2H), 6.68 (d, 1H), 5.79 (s, 2H), 5.14 (s, 2H).

LC/MS: mass calcd. for C$_{23}$H$_{14}$ClF$_3$N$_4$O$_2$S$_2$: 534.02. found 535.1 [M+H]$^+$

Example 95

(5Z)-5-({1-[4-Chloro-2-(trifluoromethyl)benzyl]-1H-indazol-5-yl}methylidene)-3-[(3R)-piperidin-3-ylmethyl]-1,3-thiazolidine-2,4-dione

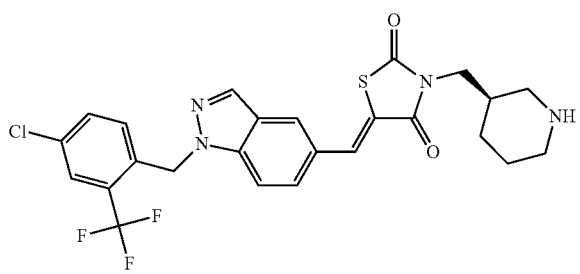 [SMILES: O=C1S/C(=C\c2ccc3c(cnn3Cc3ccc(Cl)cc3C(F)(F)F)c2)C(=O)N1C[C@@H]1CCCNC1]

(A) 1,1-Dimethylethyl (3R)-3-(5-{[1-(4-chloro-2-trifluoromethylbenzyl)-1H-indazol-5-yl]methylene}-2,4-dioxo-1,3-thiazolidin-3-ylmethyl)piperidine-1-carboxylate was prepared from [(5Z)-5-({1-[4-chloro-2-(trifluoromethyl)benzyl]-1H-indazol-5-yl}methylidene)-2,4-dioxo-1,3-thiazolidine (from Example 1) and 1,1-dimethylethyl (3R)-3-hydroxymethylpiperidine-1-carboxylate following General Procedure J.

(B) (5Z)-5-({1-[4-Chloro-2-(trifluoromethyl)benzyl]-1H-indazol-5-yl}methylidene)-3-[(3R)-piperidin-3-ylmethyl]-1,3-thiazolidine-2,4-dione was prepared from 1,1-dimethylethyl (3R)-3-(5-{[1-(4-chloro-2-trifluoromethylbenzyl)-1H-indazol-5-yl]methylene}-2,4-dioxo-1,3-thiazolidin-3-ylmethyl)piperidine-1-carboxylate following General Procedure M.

$^1$H NMR (400 MHz, CDCl$_3$): δ 8.21 (s, 1H), 8.01 (s, 1H), 7.95 (s, 1H), 7.71 (d, 1H), 7.49 (dd, 1H), 7.34 (d, 2H), 6.68 (d, 1H), 5.78 (s, 2H), 3.71 (d, 2H), 3.34 (t, 2H), 2.80 (td, 1H), 2.65 (t, 1H), 2.23-2.39 (m, 1H), 1.72-1.99 (m, 3H), 1.24-1.38 (m, 2H).

LC/MS: mass calcd. for C$_{25}$H$_{22}$ClF$_3$N$_4$O$_2$S: 534.11. found 535.2 [M+H]$^+$

Example 96

(5Z)-5-({1-[4-Chloro-2-(trifluoromethyl)benzyl]-1H-indazol-5-yl}methylidene)-3-[(3S)-piperidin-3-ylmethyl]-1,3-thiazolidine-2,4-dione

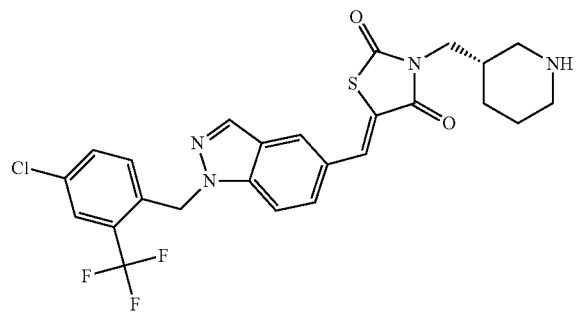 [SMILES: O=C1S/C(=C\c2ccc3c(cnn3Cc3ccc(Cl)cc3C(F)(F)F)c2)C(=O)N1C[C@H]1CCCNC1]

(A) 1,1-Dimethylethyl (3S)-3-(5-{[1-(4-chloro-2-trifluoromethylbenzyl)-1H-indazol-5-yl]methylene}-2,4-dioxo-1,3-thiazolidin-3-ylmethyl)piperidine-1-carboxylate was prepared from [(5Z)-5-({1-[4-chloro-2-(trifluoromethyl)benzyl]-1H-indazol-5-yl}methylidene)-2,4-dioxo-1,3-thiazolidine (from Example 1) and 1,1-dimethylethyl (3S)-3-hydroxymethylpiperidine-1-carboxylate following General Procedure J.

(B) (5Z)-5-({1-[4-Chloro-2-(trifluoromethyl)benzyl]-1H-indazol-5-yl}methylidene)-3-[(3S)-piperidin-3-ylmethyl]-1,3-thiazolidine-2,4-dione was prepared from 1,1-dimethylethyl (3S)-3-(5-{[1-(4-chloro-2-trifluoromethylbenzyl)-1H-indazol-5-yl]methylene}-2,4-dioxo-1,3-thiazolidin-3-ylmethyl)piperidine-1-carboxylate following General Procedure M.

$^1$H NMR (400 MHz, CDCl$_3$): δ 8.21 (s, 1H), 8.01 (s, 1H), 7.96 (s, 1H), 7.72 (d, 1H), 7.50 (dd, 1H), 7.35 (d, 2H), 6.68 (d, 1H), 5.79 (s, 2H), 3.71 (d, 2H), 3.31 (t, 2H), 2.77 (td, 1H), 2.63 (t, 1H), 2.29 (br. s., 1H), 1.70-1.95 (m, 3H), 1.25-1.38 (m, 2H).

LC/MS: mass calcd. for C$_{25}$H$_{22}$ClF$_3$N$_4$O$_2$S: 534.11. found 535.2 [M+H]$^+$

Example 97

4-[(5Z)-5-({1-[4-Chloro-2-(trifluoromethyl)benzyl]-1H-indazol-5-yl}methylidene)-2,4-dioxo-1,3-thiazolidin-3-yl]butanoic acid

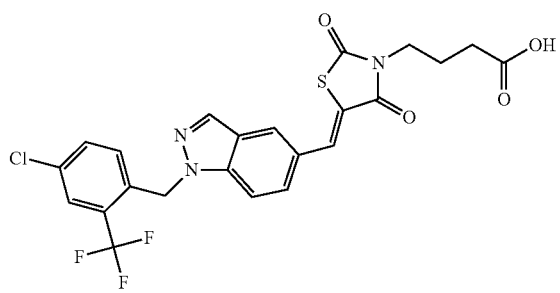 [SMILES: O=C(O)CCCN1C(=O)S/C(=C\c2ccc3c(cnn3Cc3ccc(Cl)cc3C(F)(F)F)c2)C1=O]

(A) 1,1-Dimethylethyl 4-(5-{[1-(4-chloro-2-trifluoromethylbenzyl)-1H-indazol-5-yl]methylene}-2,4-dioxo-1,3-thiazolidin-3-yl)butyrate was prepared from [(5Z)-5-({1-[4-chloro-2-(trifluoromethyl)benzyl]-1H-indazol-5-yl}methylidene)-2,4-dioxo-1,3-thiazolidine (from Example 1) and tert-butyl 4-bromobutyrate following General Procedure H.

(B) 4-[(5Z)-5-({1-[4-Chloro-2-(trifluoromethyl)benzyl]-1H-indazol-5-yl}methylidene)-2,4-dioxo-1,3-thiazolidin-3-yl]butanoic acid was prepared from 1,1-dimethylethyl 4-(5-{[1-(4-chloro-2-trifluoromethylbenzyl)-1H-indazol-5-yl]methylene}-2,4-dioxo-1,3-thiazolidin-3-yl)butyrate following General Procedure M.

$^1$H NMR (400 MHz, CD$_3$OD): δ 8.27 (s, 1H), 8.02-8.09 (m, 2H), 7.75 (d, 1H), 7.64-7.69 (m, 1H), 7.60 (dd, 1H), 7.48 (d, 1H), 7.42 (dd, 1H), 6.67 (d, 1H), 5.84 (s, 2H), 3.85 (t, 2H), 2.39 (t, 2H), 2.01 (t, 2H).

LC/MS: mass calcd. for C$_{23}$H$_{17}$ClF$_3$N$_3$O$_4$S: 523.06. found 523.9 [M+H]$^+$

Example 98

(5Z)-5-({1-[4-Chloro-2-(trifluoromethyl)benzyl]-1H-indazol-5-yl}methylidene)-3-[(3R)-thiomorpholin-3-ylmethyl]-1,3-thiazolidine-2,4-dione

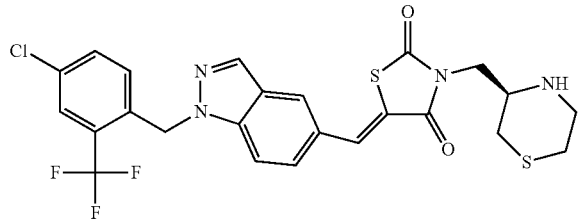 [SMILES: O=C1S/C(=C\c2ccc3c(cnn3Cc3ccc(Cl)cc3C(F)(F)F)c2)C(=O)N1C[C@@H]1CSCCN1]

(A) A mixture of (3R)-thiomorpholine-3-carboxylic acid (1.36 mmol) and BH$_3$-DMS (20.4 mmol) in THF (5 mL) was stirred at rt for 12 h. The reaction was then cooled to 0° C. and quenched by the dropwise addition of water until bubbling ceased. K$_2$CO$_3$ (1 g) was added and after stirring for 1 h, the reaction was extracted with EtOAc. The organic layer was extracted with brine, dried (Na$_2$SO$_4$) and concentrated in vacuo to afford crude (3R)-thiomorpholin-3-yl-methanol, which was used directly without further purification.

(B) (5Z)-5-({1-[4-Chloro-2-(trifluoromethyl)benzyl]-1H-indazol-5-yl}methylidene)-3-[(3R)-thiomorpholin-3-ylmethyl]-1,3-thiazolidine-2,4-dione was prepared from [(5Z)-5-({1-[4-chloro-2-(trifluoromethyl)benzyl]-1H-indazol-5-yl}methylidene)-2,4-dioxo-1,3-thiazolidine (from Example 1) and (3R)-thiomorpholin-3-yl-methanol following General Procedure J.

$^1$H NMR (400 MHz, CDCl$_3$): δ 8.23 (s, 1H), 8.03 (s, 1H), 7.98 (s, 1H), 7.72 (s, 1H), 7.51 (d, 1H), 7.37 (d, 2H), 6.68 (d, 1H), 5.80 (s, 2H), 4.28 (dd, 1H), 3.94 (dd, 1H), 3.70-3.83 (m, 2H), 3.40 (br. s., 1H), 3.17-3.29 (m, 1H), 2.83-3.06 (m, 3H).

LC/MS: mass calcd. for C$_{24}$H$_{20}$ClF$_3$N$_4$O$_2$S$_2$: 552.07. found 553.2 [M+H]$^+$

Example 99

(5Z)-5-({1-[4-Chloro-2-(trifluoromethyl)benzyl]-1H-indazol-5-yl}methylidene)-3-(1H-indol-5-ylmethyl)-1,3-thiazolidine-2,4-dione

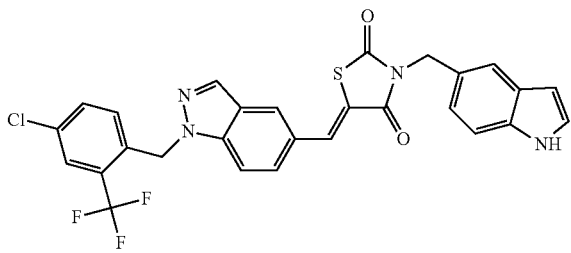 [SMILES: O=C1S/C(=C\c2ccc3c(cnn3Cc3ccc(Cl)cc3C(F)(F)F)c2)C(=O)N1Cc1ccc2[nH]ccc2c1]

(5Z)-5-({1-[4-Chloro-2-(trifluoromethyl)benzyl]-1H-indazol-5-yl}methylidene)-3-(1H-indol-5-ylmethyl)-1,3-thiazolidine-2,4-dione was prepared from [(5Z)-5-({1-[4-chloro-2-(trifluoromethyl)benzyl]-1H-indazol-5-yl}methylidene)-2,4-dioxo-1,3-thiazolidine (from Example 1) and (1H-indol-5-yl)methanol following General Procedure J.

$^1$H NMR (400 MHz, CD$_3$OD): δ 9.59 (br. s., 1H), 8.22 (d, 1H), 8.02 (s, 1H), 7.94-7.99 (m, 1H), 7.73-7.78 (m, 1H), 7.72 (d, 1H), 7.51 (dd, 1H), 7.32-7.40 (m, 3H), 7.29 (dd, 1H), 7.19-7.26 (m, 1H), 6.64 (d, 1H), 6.46-6.54 (m, 1H), 5.79 (s, 2H), 5.01 (s, 2H).

LC/MS: mass calcd. for C$_{28}$H$_{18}$ClF$_3$N$_4$O$_2$S: 566.08. found 567.1 [M+H]$^+$

Example 100

(5Z)-3-[(trans-3-Aminocyclobutyl)methyl]-5-({1-[4-chloro-2-(trifluoromethyl)benzyl]-1H-indazol-5-yl}methylidene)-1,3-thiazolidine-2,4-dione

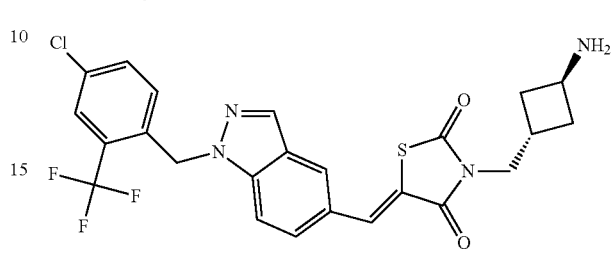

(A) 1,1-Dimethylethyl trans-3-[5-{[1-(4-chloro-2-trifluoromethylbenzyl)-1H-indazol-5-yl]methylene}-2,4-dioxo-1,3-thiazolidin-3-ylmethyl]cyclobutylcarbamate was prepared from [(5Z)-5-({1-[4-chloro-2-(trifluoromethyl)benzyl]-1H-indazol-5-yl}methylidene)-2,4-dioxo-1,3-thiazolidine (from Example 1) and 1,1-dimethylethyl trans-(3-hydroxymethylcyclobutyl)carbamate following General Procedure J.

(B) (5Z)-3-[(trans-3-Aminocyclobutyl)methyl]-5-({1-[4-chloro-2-(trifluoromethyl)benzyl]-1H-indazol-5-yl}methylidene)-1,3-thiazolidine-2,4-dione was prepared from 1,1-dimethylethyl trans-3-[5-{[1-(4-chloro-2-trifluoromethylbenzyl)-1H-indazol-5-yl]methylene}-2,4-dioxo-1,3-thiazolidin-3-ylmethyl]cyclobutylcarbamate following General Procedure M.

$^1$H NMR (400 MHz, CDCl$_3$): δ 8.19 (s, 1H), 7.97 (s, 1H), 7.93 (s, 1H), 7.70 (d, 1H), 7.47 (d, 1H), 7.32 (d, 2H), 6.66 (d, 1H), 5.76 (s, 2H), 4.32 (br. s., 3H), 3.85 (d, 2H), 3.71-3.82 (m, 1H), 2.76 (ddd, 1H), 2.14-2.27 (m, 2H), 2.00-2.14 (m, 2H).

LC/MS: mass calcd. for C$_{24}$H$_{20}$ClF$_3$N$_4$O$_2$S: 520.09. found 520.9 [M+H]$^+$

Example 101

(5Z)-3-(Azetidin-3-ylmethyl)-5-({1-[4-chloro-2-(trifluoromethyl)benzyl]-1H-indazol-5-yl}methylidene)-1,3-thiazolidine-2,4-dione

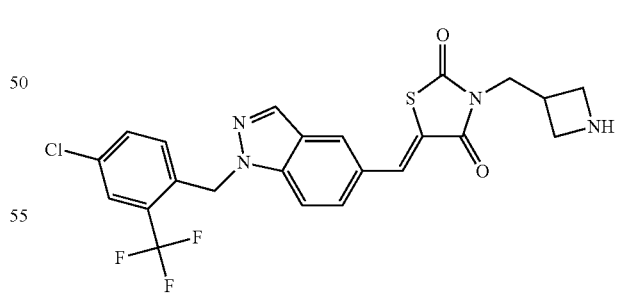

(A) 1,1-Dimethylethyl 3-(5-{[1-(4-chloro-2-trifluoromethylbenzyl)-1H-indazol-5-yl]methylene}-2,4-dioxo-1,3-thiazolidin-3-ylmethyl)azetidine-1-carboxylate was prepared from [(5Z)-5-({1-[4-chloro-2-(trifluoromethyl)benzyl]-1H-indazol-5-yl}methylidene)-2,4-dioxo-1,3-thiazolidine (from Example 1) and 1,1-dimethylethyl 3-hydroxymethylazetidine-1-carboxylate following General Procedure J.

(B) (5Z)-3-(Azetidin-3-ylmethyl)-5-({1-[4-chloro-2-(trifluoromethyl)benzyl]-1H-indazol-5-yl}methylidene)-1,3-thiazolidine-2,4-dione was prepared from 1,1-dimethylethyl 3-(5-{[1-(4-chloro-2-trifluoromethyl benzyl)-1H-indazol-5-yl]methylene}-2,4-dioxo-1,3-thiazolidin-3-ylmethyl)azetidine-1-carboxylate following General Procedure M.

$^1$H NMR (400 MHz, CDCl$_3$): δ 8.19-8.27 (m, 1H), 7.99-8.09 (m, 1H), 7.92-7.99 (m, 1H), 7.65-7.76 (m, 1H), 7.47-7.55 (m, 1H), 7.30-7.40 (m, 2H), 5.79 (s, 2H), 3.89-4.11 (m, 2H), 3.77-3.89 (m, 1H), 3.64-3.77 (m, 1H), 3.39-3.64 (m, 2H), 2.96-3.39 (m, 2H).

LC/MS: mass calcd. for C$_{23}$H$_{18}$ClF$_3$N$_4$O$_2$S: 506.08. found 507.1 [M+H]$^+$

Example 102

(5Z)-3-Azetidin-3-yl-5-({1-[4-chloro-2-(trifluoromethyl)benzyl]-1H-indazol-5-yl}methylidene)-1,3-thiazolidine-2,4-dione

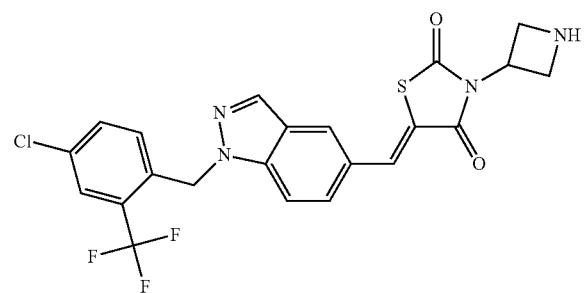 [SMILES: O=C1S/C(=C\c2ccc3c(cnn3Cc3ccc(Cl)cc3C(F)(F)F)c2)C(=O)N1C1CNC1]

(A) 1,1-Dimethylethyl 3-(5-{[1-(4-chloro-2-trifluoromethylbenzyl)-1H-indazol-5-yl]methylene}-2,4-dioxo-1,3-thiazolidin-3-yl)azetidine-1-carboxylate was prepared from [(5Z)-5-({1-[4-chloro-2-(trifluoromethyl)benzyl]-1H-indazol-5-yl}methylidene)-2,4-dioxo-1,3-thiazolidine (from Example 1) and 1,1-dimethylethyl 3-hydroxyazetidine-1-carboxylate following General Procedure J.

(B) (5Z)-3-Azetidin-3-yl-5-({1-[4-chloro-2-(trifluoromethyl)benzyl]-1H-indazol-5-yl}methylidene)-1,3-thiazolidine-2,4-dione was prepared from 1,1-dimethylethyl 3-(5-{[1-(4-chloro-2-trifluoromethylbenzyl)-1H-indazol-5-yl]methylene}-2,4-dioxo-1,3-thiazolidin-3-yl)azetidine-1-carboxylate following General Procedure M.

$^1$H NMR (400 MHz, CDCl$_3$): δ 8.21 (s, 1H), 8.03 (s, 1H), 7.92-7.99 (m, 1H), 7.72 (d, 1H), 7.44-7.53 (m, 1H), 7.29-7.38 (m, 2H), 6.68 (d, 1H), 5.79 (s, 2H), 5.31-5.36 (m, 1H), 4.53 (dd, 2H), 4.16 (t, 2H).

LC/MS: mass calcd. for C$_{22}$H$_{16}$ClF$_3$N$_4$O$_2$S: 492.06. found 493.0 [M+H]$^+$

Example 103

1-{2-[(5Z)-5-({1-[2,4-Bis(trifluoromethyl)benzyl]-1H-indazol-5-yl}methylidene)-2,4-dioxo-1,3-thiazolidin-3-yl]ethoxy}guanidine

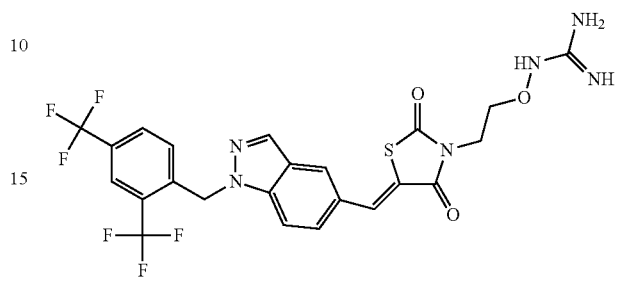

(A) Bis(1,1-dimethylethyl) [{[(2-{(5Z)-5-[(1-{[2,4-bis(trifluoromethyl)phenyl]methyl}-1H-indazol-5-yl)methylidene]-2,4-dioxo-1,3-thiazolidin-3-yl}ethyl)oxy]amino}methylidene]biscarbamate was prepared from [(5Z)-5-({1-[2,4-bis-(trifluoromethyl)benzyl]-1H-indazol-5-yl}methylidene)-2,4-dioxo-1,3-thiazolidine (from Example 6) and bis(1,1-dimethylethyl) [({[2-(2,4-dioxo-1,3-thiazolidin-3-yl)ethyl]oxy}amino)methylidene]-biscarbamate (from Example 91) following General Procedure F.

(B) 1-{2-[(5Z)-5-({1-[2,4-Bis(trifluoromethyl)benzyl]-1H-indazol-5-yl}methylidene)-2,4-dioxo-1,3-thiazolidin-3-yl]ethoxy}guanidine was prepared from bis(1,1-dimethylethyl) [{[(2-{(5Z)-5-[(1-{[2,4-bis(trifluoromethyl)-phenyl]methyl}-1H-indazol-5-yl)methylidene]-2,4-dioxo-1,3-thiazolidin-3-yl}ethyl)oxy]amino}methylidene]biscarbamate following General Procedure M.

$^1$H NMR (400 MHz, CDCl$_3$): δ 8.20 (s, 1H), 7.97 (d, 2H), 7.92 (s, 1H), 7.61 (d, 1H), 7.42-7.48 (m, 1H), 7.31 (d, 1H), 6.81 (d, 1H), 5.83 (s, 2H), 4.07-4.14 (m, 2H), 3.97-4.07 (m, 2H).

LC/MS: mass calcd. for C$_{23}$H$_{18}$F$_6$N$_6$O$_3$S: 572.11. found 573.1 [M+H]$^+$

Example 104

(5Z)-5-({1-[4-Chloro-2-(trifluoromethyl)benzyl]-1H-indazol-5-yl}methylidene)-3-[2-(1,4-diazepan-1-yl)ethyl]-1,3-thiazolidine-2,4-dione

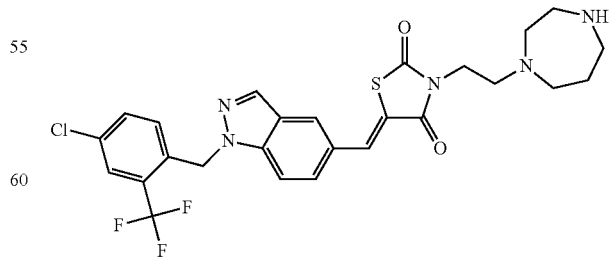

(A) 1,1-Dimethylethyl 4-(2-[5-{[1-(4-chloro-2-trifluoromethylbenzyl)-1H-indazol-5-yl]methylene}-2,4-dioxo-1,3-thiazolidin-3-yl]ethyl)-[1,4]diazepane-1-carboxylate was prepared from [(5Z)-5-({1-[4-chloro-2-(trifluoromethyl)benzyl]-1H-indazol-5-yl}methylidene)-2,4-dioxo-1,3-thiazolidine (from Example 1), 1-bromo-2-chloroethane and 1,1-dimethylethyl[1,4]diazepane-1-carboxylate following General Procedure G.

(B) (5Z)-5-({1-[4-Chloro-2-(trifluoromethyl)benzyl]-1H-indazol-5-yl}methylidene)-3-[2-(1,4-diazepan-1-yl)ethyl]-1,3-thiazolidine-2,4-dione was prepared from 1,1-dimethylethyl 4-(2-[5-{[1-(4-chloro-2-trifluoromethylbenzyl)-1H-indazol-5-yl]methylene}-2,4-dioxo-1,3-thiazolidin-3-yl]ethyl)-[1,4]diazepane-1-carboxylate following General Procedure M.

$^1$H NMR (400 MHz, CDCl$_3$): δ 8.18 (s, 1H), 8.12 (s, 1H), 7.93 (s, 1H), 7.71 (d, 1H), 7.60 (d, 1H), 7.32 (dd, 1H), 7.28 (d, 1H), 6.63 (d, 1H), 5.78 (s, 2H), 4.01 (br. s., 2H), 3.80 (br. s., 2H), 3.61 (br. s., 1H), 3.37 (br. s., 2H), 3.16 (br. s., 2H), 2.07-2.33 (m, 2H), 1.77 (br. s., 3H).

LC/MS: mass calcd. for C$_{26}$H$_{25}$ClF$_3$N$_5$O$_2$S: 563.14. found 564.1 [M+H]$^+$ Example 105

(5Z)-3-{[trans-3-Aminocyclohexyl]methyl}-5-({1-[4-chloro-2-(trifluoromethyl)benzyl]-1H-indazol-5-yl}methylidene)-1,3-thiazolidine-2,4-dione

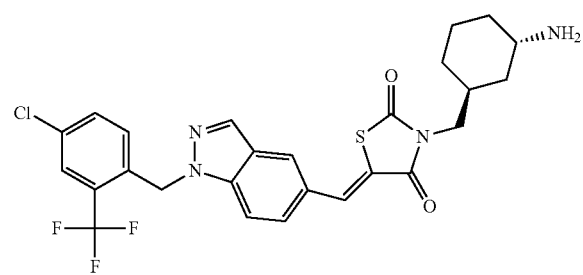 [SMILES: N[C@H]1CCC[C@H](CN2C(=O)S/C(=C\c3ccc4c(cnn4Cc4ccc(Cl)cc4C(F)(F)F)c3)C2=O)C1]

(A) 1,1-Dimethylethyl trans-3-(5-{[1-(4-chloro-2-trifluoromethylbenzyl)-1H-indazol-5-yl]methylene}-2,4-dioxo-1,3-thiazolidin-3-ylmethyl)cyclohexylcarbamate was prepared from [(5Z)-5-({1-[4-chloro-2-(trifluoromethyl)benzyl]-1H-indazol-5-yl}methylidene)-2,4-dioxo-1,3-thiazolidine (from Example 1) and 1,1-dimethylethyl trans-(3-hydroxymethylcyclohexyl)carbamate following General Procedure J.

(B) (5Z)-3-{[trans-3-Aminocyclohexyl]methyl}-5-({1-[4-chloro-2-(trifluoromethyl)benzyl]-1H-indazol-5-yl}methylidene)-1,3-thiazolidine-2,4-dione was prepared from 1,1-dimethylethyl trans-3-(5-{[1-(4-chloro-2-trifluoromethylbenzyl)-1H-indazol-5-yl]methylene}-2,4-dioxo-1,3-thiazolidin-3-ylmethyl)cyclohexylcarbamate following General Procedure M.

$^1$H NMR (400 MHz, CDCl$_3$): δ 8.18 (s, 1H), 7.95 (s, 1H), 7.91 (s, 1H), 7.70 (d, 1H), 7.45 (dd, 1H), 7.27-7.35 (m, 2H), 6.66 (d, 1H), 5.76 (s, 2H), 3.69 (d, 1H), 3.60 (br. s., 1H), 2.31 (br. s., 1H), 1.85 (br. s., 2H), 1.55-1.67 (m, 6H).

LC/MS: mass calcd. for C$_{26}$H$_{24}$ClF$_3$N$_4$O$_2$S: 548.13. found 549.0 [M+H]$^+$ Example 106

(5Z)-3-{[trans-4-(Aminomethyl)cyclohexyl]methyl}-5-({1-[4-chloro-2-(trifluoromethyl)benzyl]-1H-indazol-5-yl}methylidene)-1,3-thiazolidine-2,4-dione

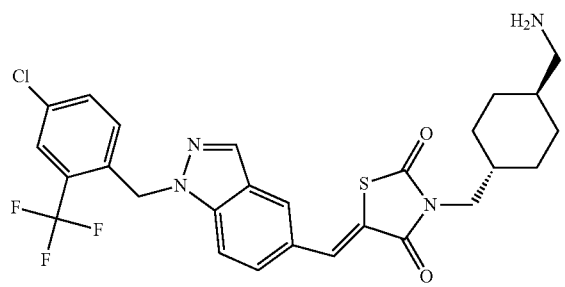 [SMILES: NC[C@H]1CC[C@H](CN2C(=O)S/C(=C\c3ccc4c(cnn4Cc4ccc(Cl)cc4C(F)(F)F)c3)C2=O)CC1]

(A) 1,1-Dimethylethyl trans-[4-(5-{[1-(4-chloro-2-trifluoromethylbenzyl)-1H-indazol-5-yl]methylene}-2,4-dioxo-1,3-thiazolidin-3-ylmethyl)-cyclohexylmethyl]carbamate was prepared from [(5Z)-5-({1-[4-chloro-2-(trifluoromethyl)benzyl]-1H-indazol-5-yl}methylidene)-2,4-dioxo-1,3-thiazolidine (from Example 1) and 1,1-dimethylethyl trans-(4-hydroxymethylcyclohexylmethyl)carbamate following General Procedure J.

(B) (5Z)-3-{[trans-4-(Aminomethyl)cyclohexyl]methyl}-5-({1-[4-chloro-2-(trifluoromethyl)benzyl]-1H-indazol-5-yl}methylidene)-1,3-thiazolidine-2,4-dione was prepared from 1,1-dimethylethyl trans-[4-(5-{[1-(4-chloro-2-trifluoromethylbenzyl)-1H-indazol-5-yl]methylene}-2,4-dioxo-1,3-thiazolidin-3-ylmethyl)cyclohexylmethyl]carbamate following General Procedure M.

$^1$H NMR (400 MHz, CDCl$_3$): δ 8.22 (s, 1H), 8.01 (s, 1H), 7.97 (s, 1H), 7.72 (d, 1H), 7.52 (dd, 1H), 7.31-7.39 (m, 2H), 6.67 (d, 1H), 5.80 (s, 2H), 3.63 (d, 2H), 2.75 (d, 2H), 1.72-1.90 (m, 5H), 1.52-1.66 (m, 1H), 1.24-1.34 (m, 3H), 0.90-1.17 (m, 3H).

LC/MS: mass calcd. for C$_{27}$H$_{26}$ClF$_3$N$_4$O$_2$S: 562.14. found 563.0 [M+H]$^+$ Example 107

(5Z)-3-[(2R)-2-Amino-2-cyclohexylethyl]-5-({1-[4-chloro-2-(trifluoromethyl)benzyl]-1H-indazol-5-yl}methylidene)-1,3-thiazolidine-2,4-dione

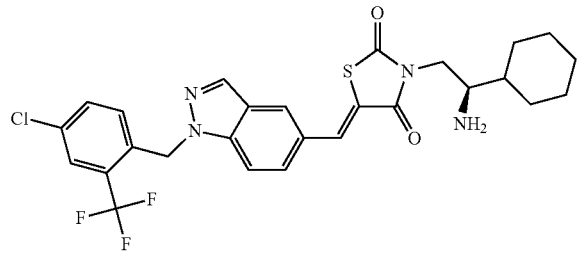 [SMILES: N[C@@H](CN1C(=O)S/C(=C\c2ccc3c(cnn3Cc3ccc(Cl)cc3C(F)(F)F)c2)C1=O)C1CCCCC1]

(A) 1,1-Dimethylethyl (2R)-2-{5-[(1-(4-chloro-2-trifluoromethylbenzyl)-1H-indazol-5-yl)methylene]-2,4-dioxo-1,3-thiazolidin-3-yl}-1-cyclohexylethyl)-carbamate was prepared from [(5Z)-5-({1-[4-chloro-2-(trifluoromethyl)benzyl]-1H-indazol-5-yl}methylidene)-2,4-dioxo-1,3-thiazolidine (from Example 1) and 1,1-dimethylethyl (1R)-1-cyclohexyl-2-hydroxyethylcarbamate following General Procedure J.

(B) (5Z)-3-[(2R)-2-Amino-2-cyclohexylethyl]-5-({1-[4-chloro-2-(trifluoromethyl)benzyl]-1H-indazol-5-yl}methylidene)-1,3-thiazolidine-2,4-dione was prepared from 1,1-dimethylethyl (2R)-2-{5-[(1-(4-chloro-2-trifluoromethylbenzyl)-1H-indazol-5-yl)methylene]-2,4-dioxo-1,3-thiazolidin-3-yl}-1-cyclohexylethyl)carbamate following General Procedure M.

$^1$H NMR (400 MHz, DMSO-d$_6$): δ 8.38 (s, 1H), 8.20 (s, 1H), 8.11 (s, 1H), 7.90 (d, 2H), 7.82 (d, 1H), 7.64-7.74 (m, 2H), 6.82 (d, 1H), 5.88 (s, 2H), 3.85 (d, 2H), 3.23-3.30 (m, 1H), 1.57-1.89 (m, 6H), 1.06-1.28 (m, 5H).

LC/MS: mass calcd. for C$_{27}$H$_{26}$ClF$_3$N$_4$O$_2$S: 562.14. found 563.0 [M+H]$^+$ Example 108

(5Z)-5-({1-[4-Chloro-2-(trifluoromethyl)benzyl]-1H-indazol-5-yl}methylidene)-3-(2-pyridin-4-ylethyl)-1,3-thiazolidine-2,4-dione

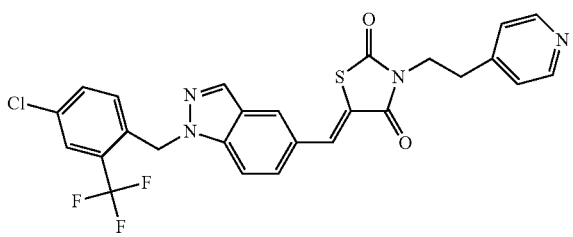 [SMILES: O=C1S/C(=C\c2ccc3c(cnn3Cc3ccc(Cl)cc3C(F)(F)F)c2)C(=O)N1CCc1ccncc1]

(A) 3-(2-Pyridin-4-ylethyl)-1,3-thiazolidine-2,4-dione was prepared from 4-(2-aminoethyl)pyridine following General Procedure D.

(B) (5Z)-5-({1-[4-Chloro-2-(trifluoromethyl)benzyl]-1H-indazol-5-yl}methylidene)-3-(2-pyridin-4-ylethyl)-1,3-thiazolidine-2,4-dione was prepared from [4-chloro-2-(trifluoromethyl)benzyl]-1H-indazol-5-carbaldehyde (from Example 1) and 3-(2-pyridin-4-ylethyl)-1,3-thiazolidine-2,4-dione following General Procedure F.

$^1$H NMR (400 MHz, CDCl$_3$): δ 8.73 (d, 2H), 8.23 (s, 1H), 8.00 (s, 1H), 7.97 (s, 1H), 7.72 (d, 1H), 7.62 (d, 2H), 7.46-7.54 (m, 1H), 7.31-7.40 (m, 2H), 6.68 (d, 1H), 5.80 (s, 2H), 4.13 (t, 2H), 3.23 (t, 2H).

LC/MS: mass calcd. for C$_{26}$H$_{18}$ClF$_3$N$_4$O$_2$S: 542.08. found 543.2 [M+H]$^+$ Example 109

(5Z)-5-({1-[4-Chloro-2-(trifluoromethyl)benzyl]-1H-indazol-5-yl}methylidene)-3-(2-pyridin-3-ylethyl)-1,3-thiazolidine-2,4-dione

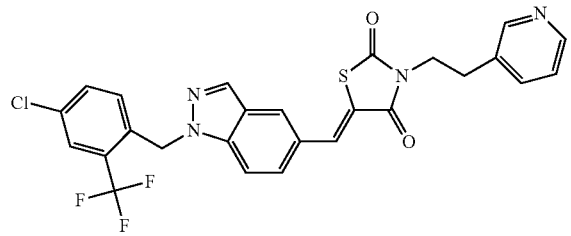 [SMILES: O=C1S/C(=C\c2ccc3c(cnn3Cc3ccc(Cl)cc3C(F)(F)F)c2)C(=O)N1CCc1cccnc1]

(A) 3-(2-Pyridin-3-ylethyl)-1,3-thiazolidine-2,4-dione was prepared from 3-(2-aminoethyl)pyridine following General Procedure D.

(B) (5Z)-5-({1-[4-Chloro-2-(trifluoromethyl)benzyl]-1H-indazol-5-yl}methylidene)-3-(2-pyridin-3-ylethyl)-1,3-thiazolidine-2,4-dione was prepared from [4-chloro-2-(trifluoromethyl)benzyl]-1H-indazol-5-carbaldehyde (from Example 1) and 3-(2-pyridin-3-ylethyl)-1,3-thiazolidine-2,4-dione following General Procedure F.

$^1$H NMR (400 MHz, CDCl$_3$): δ 8.49-8.60 (m, 2H), 8.22 (s, 1H), 8.00 (s, 1H), 7.96 (s, 1H), 7.64-7.75 (m, 2H), 7.50 (dd, 1H), 7.29-7.40 (m, 3H), 6.67 (d, 1H), 5.80 (s, 2H), 4.03 (t, 2H), 3.04 (t, 2H).

LC/MS: mass calcd. for C$_{26}$H$_{18}$ClF$_3$N$_4$O$_2$S: 542.08. found 543.3 [M+H]$^+$ Example 110

(5Z)-5-({1-[4-Chloro-2-(trifluoromethyl)benzyl]-1H-indazol-5-yl}methylidene)-3-{2-[(5-nitropyridin-2-yl)amino]ethyl}-1,3-thiazolidine-2,4-dione

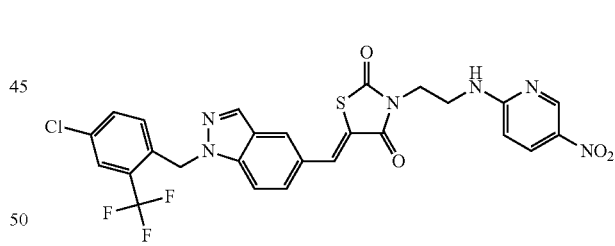

(A) 3-[2-(5-Nitropyridin-2-ylamino)ethyl]-1,3-thiazolidine-2,4-dione was prepared from 2-(2-aminoethylamino)-5-nitropyridine following General Procedure D.

(B) (5Z)-5-({1-[4-Chloro-2-(trifluoromethyl)benzyl]-1H-indazol-5-yl}methylidene)-3-{2-[(5-nitropyridin-2-yl)amino]ethyl}-1,3-thiazolidine-2,4-dione was prepared from [4-chloro-2-(trifluoromethyl)benzyl]-1H-indazol-5-carbaldehyde (from Example 1) and 3-[2-(5-nitropyridin-2-ylamino)-ethyl]-1,3-thiazolidine-2,4-dione following General Procedure F.

$^1$H NMR (400 MHz, CDCl$_3$): δ 8.93 (d, 1H), 8.23 (s, 1H), 8.12 (d, 1H), 7.92-8.05 (m, 2H), 7.72 (d, 1H), 7.50 (dd, 1H), 7.34-7.40 (m, 2H), 6.66 (d, 1H), 6.43 (d, 1H), 5.80 (s, 2H), 4.05 (t, 2H), 3.73-3.87 (m, 2H).

LC/MS: mass calcd. for $C_{26}H_{18}ClF_3N_6O_4S$: 602.08. found 603.1 $[M+H]^+$ Example 111

(5Z)-5-({1-[4-Chloro-2-(trifluoromethyl)benzyl]-1H-indazol-5-yl}methylidene)-3-(2-pyrrolidin-1-ylethyl)-1,3-thiazolidine-2,4-dione

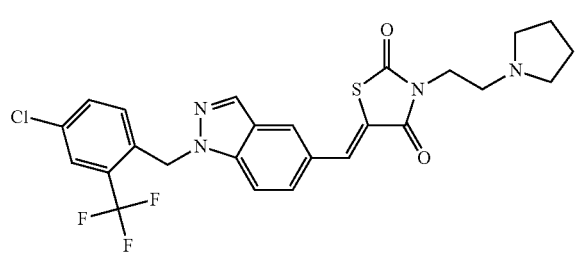 [SMILES: O=C1S/C(=C\c2ccc3c(cnn3Cc3ccc(Cl)cc3C(F)(F)F)c2)C(=O)N1CCN1CCCC1]

(5Z)-5-({1-[4-Chloro-2-(trifluoromethyl)benzyl]-1H-indazol-5-yl}methylidene)-3-(2-pyrrolidin-1-ylethyl)-1,3-thiazolidine-2,4-dione was prepared from [(5Z)-5-({1-[4-chloro-2-(trifluoromethyl)benzyl]-1H-indazol-5-yl}methylidene)-2,4-dioxo-1,3-thiazolidine (from Example 1) and 1-(2-bromoethyl)pyrrolidine hydrobromide following General Procedure H.

$^1$H NMR (400 MHz, CDCl$_3$): δ 8.21 (s, 1H), 8.01 (s, 1H), 7.96 (s, 1H), 7.71 (d, 1H), 7.51 (dd, 1H), 7.29-7.39 (m, 2H), 6.67 (d, 1H), 5.79 (s, 2H), 3.92 (t, 2H), 2.78 (t, 2H), 2.61 (br. s., 4H), 1.70-1.90 (m, 4H).

LC/MS: mass calcd. for $C_{25}H_{22}ClF_3N_4O_2S$: 534.11. found 535.3 $[M+1]^+$ Example 112

(5Z)-3-(1-Azabicyclo[2.2.2]oct-3-yl)-5-({1-[4-chloro-2-(trifluoromethyl)benzyl]-1H-indazol-5-yl}methylidene)-1,3-thiazolidine-2,4-dione

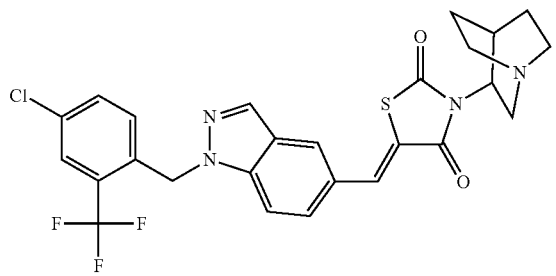 [SMILES: O=C1S/C(=C\c2ccc3c(cnn3Cc3ccc(Cl)cc3C(F)(F)F)c2)C(=O)N1C1CN2CCC1CC2]

(5Z)-3-(1-Azabicyclo[2.2.2]oct-3-yl)-5-({1-[4-chloro-2-(trifluoromethyl)benzyl]-1H-indazol-5-yl}methylidene)-1,3-thiazolidine-2,4-dione was prepared from [(5Z)-5-({1-[4-chloro-2-(trifluoromethyl)benzyl]-1H-indazol-5-yl}methylidene)-2,4-dioxo-1,3-thiazolidine (from Example 1) and 3-hydroxy-1-azabicyclo[2.2.2]octane following General Procedure J.

$^1$H NMR (400 MHz, CDCl$_3$): δ 8.22 (s, 1H), 7.99 (s, 1H), 7.96 (s, 1H), 7.72 (d, 1H), 7.51 (dd, 1H), 7.35 (d, 2H), 6.68 (d, 1H), 5.80 (s, 2H), 4.51-4.65 (m, 1H), 3.98 (dd, 1H), 3.34-3.47 (m, 1H), 3.32-3.60 (m, 1H), 3.12 (t, 1H), 2.77-3.04 (m, 3H), 1.90-2.00 (m, 1H), 1.65-1.88 (m, 2H), 1.46 (d, 1H).

LC/MS: mass calcd. for $C_{26}H_{22}ClF_3N_4O_2S$: 546.11 found 547.4 $[M+1]^+$

Example 113

(5Z)-5-({1-[4-Chloro-2-(trifluoromethyl)benzyl]-1H-indazol-5-yl}methylidene)-3-piperidin-4-yl-1,3-thiazolidine-2,4-dione

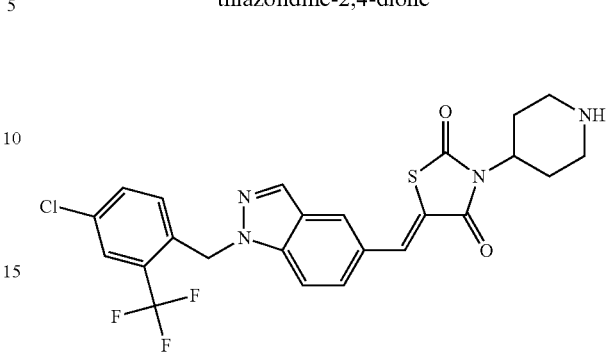

(A) 1,1-Dimethylethyl 4-{(5Z)-5-[(1-{[4-chloro-2-(trifluoromethyl)phenyl]-methyl}-1H-indazol-5-yl)methylidene]-2,4-dioxo-1,3-thiazolidin-3-yl}piperidine-1-carboxylate was prepared from (5Z)-5-({1-[4-chloro-2-(trifluoromethyl)benzyl]-1H-indazol-5-yl}methylidene)-2,4-dioxo-1,3-thiazolidine (from Example 1) and 4-hydroxypiperidine-1-carboxylic acid tert-butyl ester following General Procedure J.

(B) (5Z)-5-({1-[4-Chloro-2-(trifluoromethyl)benzyl]-1H-indazol-5-yl}methylidene)-3-piperidin-4-yl-1,3-thiazolidine-2,4-dione was prepared by the deprotection of 1,1-dimethylethyl 4-{(5Z)-5-[(1-{[4-chloro-2-(trifluoromethyl)phenyl]-methyl}-1H-indazol-5-yl)methylidene]-2,4-dioxo-1,3-thiazolidin-3-yl}piperidine-1-carboxylate following General Procedure M.

$^1$H NMR (400 MHz, CDCl$_3$): δ 8.21 (s, 1H), 7.99 (s, 1H), 7.95 (s, 1H), 7.72 (d, 1H), 7.51 (dd, 1H), 7.35 (d, 2H), 6.68 (d, 1H), 5.80 (s, 2H), 4.36-4.47 (m, 1H), 3.24 (d, 2H), 2.71 (td, 2H), 2.34-2.48 (m, 2H), 1.76 (br. s., 1H), 1.69 (dd, 2H).

LC/MS: mass calcd. for $C_{24}H_{20}ClF_3N_4O_2S$: 520.09. found 521.4 $[M+1]^+$ Example 114

(5Z)-5-({1-[4-Chloro-2-(trifluoromethyl)benzyl]-1H-indazol-5-yl}methylidene)-3-[(3S)-pyrrolidin-3-yl]-1,3-thiazolidine-2,4-dione

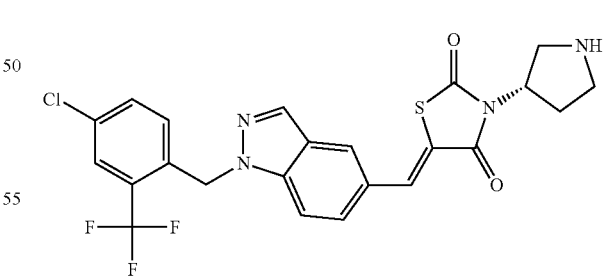

(A) 1,1-Dimethylethyl (3S)-3-{(5Z)-5-[(1-{[4-chloro-2-(trifluoromethyl)phenyl]-methyl}-1H-indazol-5-yl)methylidene]-2,4-dioxo-1,3-thiazolidin-3-yl}pyrrolidine-1-carboxylate was prepared from (5Z)-5-({1-[4-chloro-2-(trifluoromethyl)benzyl]-1H-indazol-5-yl}methylidene)-2,4-dioxo-1,3-thiazolidine (from Example 1) and (3R)-3-pyrrolidine-1-carboxylic acid tert-butyl ester following General Procedure J.

(B) (5Z)-5-({1-[4-Chloro-2-(trifluoromethyl)benzyl]-1H-indazol-5-yl}methylidene)-3-[(3S)-pyrrolidin-3-yl]-1,3-thiazolidine-2,4-dione was prepared by the deprotection of 1,1-dimethylethyl (3S)-3-{(5Z)-5-[(1-{[4-chloro-2-(trifluoromethyl)phenyl]-methyl}-1H-indazol-5-yl)methylidene]-2,4-dioxo-1,3-thiazolidin-3-yl}pyrrolidine-1-carboxylate following General Procedure M.

$^1$H NMR (400 MHz, CDCl$_3$): δ 8.22 (s, 1H), 7.99 (s, 1H), 7.96 (s, 1H), 7.72 (d, 1H), 7.50 (dd, 1H), 7.31-7.38 (m, 2H), 6.68 (d, 1H), 5.80 (s, 2H), 4.93-5.04 (m, 1H), 3.39 (t, 1H), 3.19-3.30 (m, 1H), 3.10 (br. s., 1H), 2.83 (br. s., 1H), 2.15-2.26 (m, 1H), 2.11 (br. s., 1H), 1.93-2.07 (m, 1H).

LC/MS: mass calcd. for C$_{23}$H$_{18}$ClF$_3$N$_4$O$_2$S: 506.08. found 507.4 [M+1]$^+$ Example 115

(5Z)-5-({1-[4-Chloro-2-(trifluoromethyl)benzyl]-1H-indazol-5-yl}methylidene)-3-[2-(3-hydroxyazetidin-1-yl)ethyl]-1,3-thiazolidine-2,4-dione

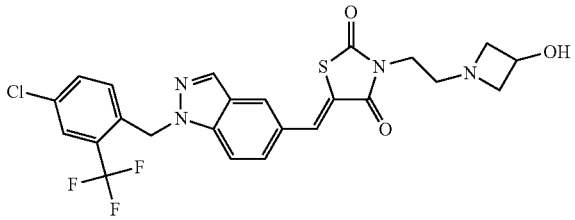 [SMILES: O=C1S/C(=C\c2ccc3c(cnn3Cc3ccc(Cl)cc3C(F)(F)F)c2)C(=O)N1CCN1CC(O)C1]

(5Z)-5-({1-[4-Chloro-2-(trifluoromethyl)benzyl]-1H-indazol-5-yl}-methylidene)-3-[2-(3-hydroxyazetidin-1-yl)ethyl]-1,3-thiazolidine-2,4-dione was prepared from [(5Z)-5-({1-[4-chloro-2-(trifluoromethyl)benzyl]-1H-indazol-5-yl}methylidene)-2,4-dioxo-1,3-thiazolidine (from Example 1), 1-bromo-2-chloroethane and 3-hydroxyazetidine hydrochloride following General Procedure G.

$^1$H NMR (400 MHz, CDCl$_3$): δ 8.17 (s, 1H), 8.11 (s, 1H), 7.87 (s, 1H), 7.71 (d, 1H), 7.59 (d, 1H), 7.30-7.35 (m, 2H), 6.63 (d, 1H), 5.78 (s, 2H), 4.70 (br. s., 1H), 4.38 (br. s., 2H), 4.00-4.09 (m, 4H), 3.12 (dd, 2H), 2.50 (br. s., 1H).

LC/MS: mass calcd. for C$_{24}$H$_{20}$ClF$_3$N$_4$O$_3$S: 536.09. found 537.4 [M+1]$^+$ Example 116

(5Z)-5-({1-[4-Chloro-2-(trifluoromethyl)benzyl]-1H-indazol-5-yl}methylidene)-3-[2-(3,3-difluoropyrrolidin-1-yl)ethyl]-1,3-thiazolidine-2,4-dione

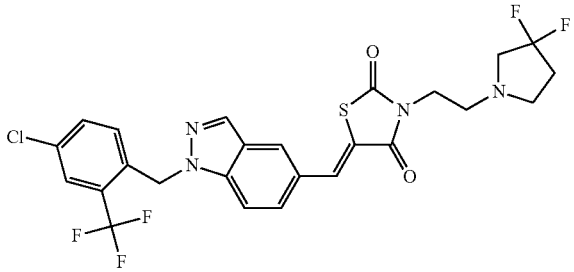 [SMILES: O=C1S/C(=C\c2ccc3c(cnn3Cc3ccc(Cl)cc3C(F)(F)F)c2)C(=O)N1CCN1CCC(F)(F)C1]

(5Z)-5-({1-[4-Chloro-2-(trifluoromethyl)benzyl]-1H-indazol-5-yl}methylidene)-3-[2-(3,3-difluoropyrrolidin-1-yl)ethyl]-1,3-thiazolidine-2,4-dione was prepared from [(5Z)-5-({1-[4-chloro-2-(trifluoromethyl)benzyl]-1H-indazol-5-yl}methylidene)-2,4-dioxo-1,3-thiazolidine (from Example 1), 1-bromo-2-chloroethane and 3,3-difluoropyrrolidine hydrochloride following General Procedure G.

$^1$H NMR (400 MHz, CDCl$_3$): δ 8.18 (s, 1H), 8.12 (s, 1H), 7.93 (br. s., 1H), 7.71 (d, 1H), 7.60 (d, 1H), 7.27-7.36 (m, 2H), 6.64 (d, 1H), 5.79 (s, 2H), 4.03 (d, 2H), 3.89-4.00 (m, 1H), 3.83 (t, 2H), 3.74 (br. s., 1H), 3.11-3.21 (m, 2H), 2.44 (dd, 2H).

LC/MS: mass calcd. for C$_{25}$H$_{20}$ClF$_5$N$_4$O$_2$S: 570.09. found 571.4 [M+1]$^+$ Example 117

(5Z)-3-[2-(4-Acetylpiperazin-1-yl)ethyl]-5-({1-[4-chloro-2-(trifluoromethyl)benzyl]-1H-indazol-5-yl}methylidene)-1,3-thiazolidine-2,4-dione

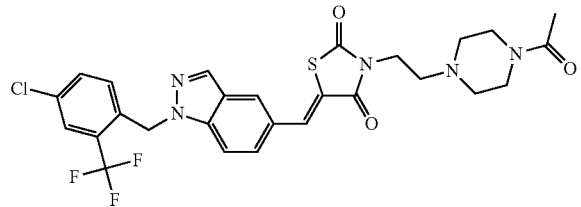 [SMILES: CC(=O)N1CCN(CCN2C(=O)S/C(=C\c3ccc4c(cnn4Cc4ccc(Cl)cc4C(F)(F)F)c3)C2=O)CC1]

(5Z)-3-[2-(4-Acetylpiperazin-1-yl)ethyl]-5-({1-[4-chloro-2-(trifluoromethyl)benzyl]-1H-indazol-5-yl}methylidene)-1,3-thiazolidine-2,4-dione was prepared from [(5Z)-5-({1-[4-chloro-2-(trifluoromethyl)benzyl]-1H-indazol-5-yl}methylidene)-2,4-dioxo-1,3-thiazolidine (from Example 1), 1-bromo-2-chloroethane and 1-acetylpiperazine following General Procedure G.

$^1$H NMR (400 MHz, CDCl$_3$): δ 8.18 (s, 1H), 8.11 (s, 1H), 7.91 (s, 1H), 7.71 (d, 1H), 7.59 (d, 1H), 7.32 (dd, 1H), 7.28 (d, 2H), 6.64 (d, 1H), 5.79 (s, 2H), 4.00 (br. s., 2H), 3.74 (br. s., 4H), 3.59 (br. s., 4H), 3.17 (t, 2H), 2.14 (s, 3H).

LC/MS: mass calcd. for C$_{27}$H$_{25}$ClF$_3$N$_5$O$_3$S: 591.13. found 592.5 [M+1]$^+$ Example 118

(5Z)-5-({1-[4-Chloro-2-(trifluoromethyl)benzyl]-1H-indazol-5-yl}methylidene)-3-(1-ethylpiperidin-4-yl)-1,3-thiazolidine-2,4-dione

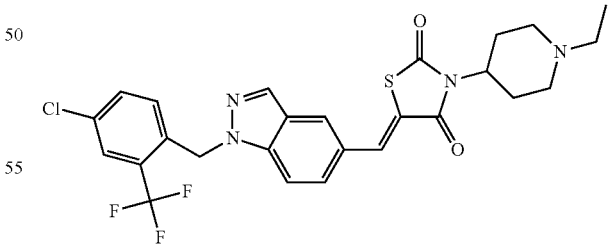

(5Z)-5-({1-[4-Chloro-2-(trifluoromethyl)benzyl]-1H-indazol-5-yl}methylidene)-3-(1-ethylpiperidin-4-yl)-1,3-thiazolidine-2,4-dione was prepared from (5Z)-5-({1-[4-chloro-2-(trifluoromethyl)benzyl]-1H-indazol-5-yl}methylidene)-3-piperidin-4-yl-1,3-thiazolidine-2,4-dione (Example 113) and ethyl iodide at rt following General Procedure S.

$^1$H NMR (400 MHz, CDCl$_3$): δ 8.22 (s, 1H), 7.99 (s, 1H), 7.95 (s, 1H), 7.72 (s, 1H), 7.47-7.54 (m, 1H), 7.35 (d, 2H), 6.67 (d, 1H), 5.80 (s, 2H), 4.21-4.35 (m, 1H), 3.10 (d, 2H), 2.54-2.68 (m, 2H), 2.46 (q, 2H), 1.96-2.10 (m, 2H), 1.59-1.73 (m, 2H), 1.11 (t, 3H).

LC/MS: mass calcd. for $C_{26}H_{24}ClF_3N_4O_2S$: 548.13. found 549.5 $[M+1]^+$

Example 119

(5Z)-5-({1-[4-Chloro-2-(trifluoromethyl)benzyl]-1H-indazol-5-yl}methylidene)-3-[(3S)-1-ethylpyrrolidin-3-yl]-1,3-thiazolidine-2,4-dione

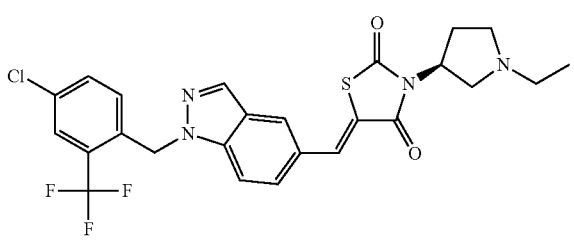 [SMILES: CCN1CC[C@H](N2C(=O)S/C(=C\c3ccc4c(cnn4Cc4ccc(Cl)cc4C(F)(F)F)c3)C2=O)C1]

(5Z)-5-({1-[4-Chloro-2-(trifluoromethyl)benzyl]-1H-indazol-5-yl}methylidene)-3-[(3S)-1-ethylpyrrolidin-3-yl]-1,3-thiazolidine-2,4-dione was prepared from (5Z)-5-({1-[4-chloro-2-(trifluoromethyl)benzyl]-1H-indazol-5-yl}methylidene)-3-[(3S)-pyrrolidin-3-yl]-1,3-thiazolidine-2,4-dione (Example 114) and ethyl iodide at rt following General Procedure S.

$^1$H NMR (400 MHz, $CDCl_3$): δ 8.21 (s, 1H), 7.99 (s, 1H), 7.95 (s, 1H), 7.72 (d, 1H), 7.50 (dd, 1H), 7.35 (d, 2H), 6.68 (d, 1H), 5.80 (s, 2H), 5.00-5.13 (m, 1H), 3.12 (t, 1H), 2.96-3.05 (m, 1H), 2.73 (q, 1H), 2.53-2.68 (m, 3H), 2.16-2.28 (m, 2H), 1.13 (t, 3H).

LC/MS: mass calcd. for $C_{25}H_{22}ClF_3N_4O_2S$: 534.11. found 535.4 $[M+1]^+$

Example 120

(5Z)-3-(2-Azetidin-1-ylethyl)-5-({1-[4-chloro-2-(trifluoromethyl)benzyl]-1H-indazol-5-yl}methylidene)-1,3-thiazolidine-2,4-dione

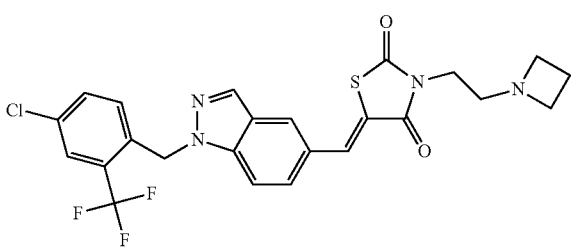 [SMILES: O=C1S/C(=C\c2ccc3c(cnn3Cc3ccc(Cl)cc3C(F)(F)F)c2)C(=O)N1CCN1CCC1]

(5Z)-3-(2-Azetidin-1-ylethyl)-5-({1-[4-chloro-2-(trifluoromethyl)benzyl]-1H-indazol-5-yl}methylidene)-1,3-thiazolidine-2,4-dione was prepared from [(5Z)-5-({1-[4-chloro-2-(trifluoromethyl)benzyl]-1H-indazol-5-yl}methylidene)-2,4-dioxo-1,3-thiazolidine (from Example 1), 1-bromo-2-chloroethane and azetidine hydrochloride following General Procedure G.

$^1$H NMR (400 MHz, $CDCl_3$): δ 8.17 (s, 1H), 8.11 (s, 1H), 7.87 (s, 1H), 7.70 (d, 1H), 7.55-7.62 (m, 1H), 7.32 (dd, 1H), 7.28 (d, 1H), 6.62 (d, 1H), 5.79 (s, 2H), 4.17 (br. s., 4H), 4.00-4.08 (m, 2H), 3.07-3.17 (m, 2H), 2.32 (quin, 2H).

LC/MS: mass calcd. for $C_{24}H_{20}ClF_3N_4O_2S$: 520.09. found 521.4 $[M+1]^+$

Example 121

(5Z)-5-({1-[4-Chloro-2-(trifluoromethyl)benzyl]-1H-indazol-5-yl}methylidene)-3-{[(2S)-1-methylpyrrolidin-2-yl]methyl}-1,3-thiazolidine-2,4-dione

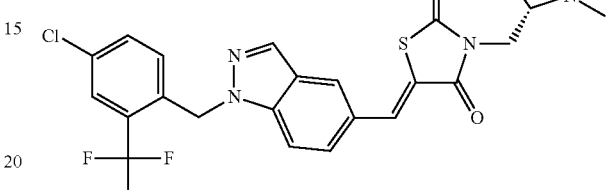

(5Z)-5-({1-[4-Chloro-2-(trifluoromethyl)benzyl]-1H-indazol-5-yl}methylidene)-3-{[(2S)-1-methylpyrrolidin-2-yl]methyl}-1,3-thiazolidine-2,4-dione was prepared from [(5Z)-5-({1-[4-chloro-2-(trifluoromethyl)benzyl]-1H-indazol-5-yl}methylidene)-2,4-dioxo-1,3-thiazolidine (from Example 1) and (2S)-2-hydroxymethyl-1-methylpyrrolidine following General Procedure J.

$^1$H NMR (400 MHz, $CDCl_3$): δ 8.22 (s, 1H), 8.01 (s, 1H), 7.92-7.99 (m, 1H), 7.72 (d, 1H), 7.46-7.56 (m, 1H), 7.30-7.39 (m, 2H), 6.67 (d, 1H), 5.80 (s, 2H), 3.71-3.89 (m, 2H), 3.08 (t, 1H), 2.53-2.64 (m, 1H), 2.45 (s, 3H), 2.20-2.29 (m, 1H), 1.77-1.95 (m, 2H), 1.63-1.77 (m, 2H).

LC/MS: mass calcd. for $C_{25}H_{22}ClF_3N_4O_2S$: 534.11. found 535.4 $[M+1]^+$

Example 122

[(5Z)-5-({1-[4-Fluoro-2-(trifluoromethyl)benzyl]-1H-indazol-5-yl}methylidene)-2,4-dioxo-1,3-thiazolidin-3-yl]acetic acid

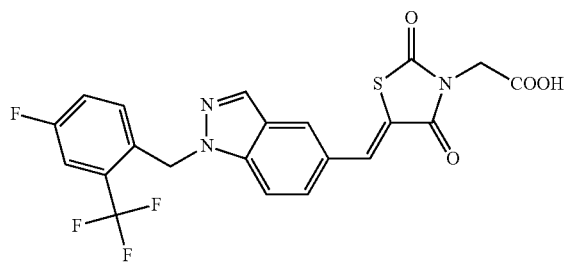 [SMILES: O=C(O)CN1C(=O)S/C(=C\c2ccc3c(cnn3Cc3ccc(F)cc3C(F)(F)F)c2)C1=O]

[(5Z)-5-({1-[4-Fluoro-2-(trifluoromethyl)benzyl]-1H-indazol-5-yl}methylidene)-2,4-dioxo-1,3-thiazolidin-3-yl]acetic acid was prepared from [(5Z)-5-({1-[4-fluoro-2-(trifluoromethyl)benzyl]-1H-indazol-5-yl}methylidene)-2,4-dioxo-1,3-thiazolidine (from Example 5) and tert-butyl bromoacetate following General Procedure I.

$^1$H NMR (400 MHz, $CDCl_3$): δ 8.26 (s, 1H), 8.08 (s, 1H), 7.99 (s, 1H), 7.51-7.57 (m, 1H), 7.45 (dd, 1H), 7.38 (d, 1H), 7.09 (td, 1H), 6.75 (dd, 1H), 5.82 (s, 2H), 4.98 (br. s., 3H), 4.58 (s, 2H).

LC/MS: mass calcd. for $C_{21}H_{13}F_4N_3O_4S$, 479.06. found 480.3 $[M+1]^+$

Example 123

(5Z)-5-({1-[4-Chloro-2-(trifluoromethyl)benzyl]-1H-indazol-5-yl}methylidene)-3-(2-methoxyethyl)-1,3-thiazolidine-2,4-dione

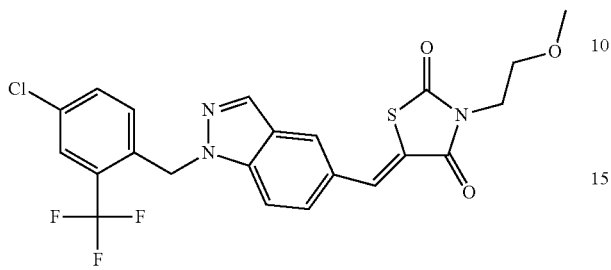

(5Z)-5-({1-[4-Chloro-2-(trifluoromethyl)benzyl]-1H-indazol-5-yl}methylidene)-3-(2-methoxyethyl)-1,3-thiazolidine-2,4-dione was prepared from [(5Z)-5-({1-[4-chloro-2-(trifluoromethyl)benzyl]-1H-indazol-5-yl}methylidene)-2,4-dioxo-1,3-thiazolidine (from Example 1) and 2-bromoethyl methyl ether following General Procedure H.

$^1$H NMR (400 MHz, CDCl$_3$): δ 8.23 (br. s., 1H), 8.03 (s, 1H), 7.97 (s, 1H), 7.72 (d, 1H), 7.52 (d, 1H), 7.35 (d, 2H), 6.67 (d, 1H), 5.80 (5, 2H), 3.99 (t, 2H), 3.65 (t, 2H), 3.37 (5, 3H).

LC/MS: mass calcd. for C$_{22}$H$_{17}$ClF$_3$N$_3$O$_3$S: 495.06. found 496.3 [M+1]$^+$

Example 124

(5Z)-5-({1-[4-Chloro-2-(trifluoromethyl)benzyl]-1H-indazol-5-yl}methylidene)-3-piperidin-3-yl-1,3-thiazolidine-2,4-dione

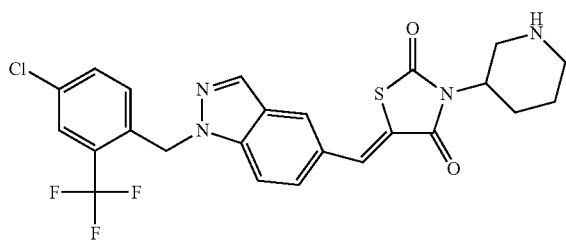 [SMILES: O=C1S/C(=C\c2ccc3c(cnn3Cc3ccc(Cl)cc3C(F)(F)F)c2)C(=O)N1C1CCCNC1]

(A) 1,1-Dimethylethyl 3-(2,4-dioxo-1,3-thiazolidin-3-yl)piperidine-1-carboxylate was prepared from 1,1-dimethylethyl 3-aminopiperidine-1-carboxylate following General Procedure D.

(B) 1,1-Dimethylethyl 3-{(5Z)-5-[(1-{[4-chloro-2-(trifluoromethyl)phenyl]-methyl}-1H-indazol-5-yl)methylidene]-2,4-dioxo-1,3-thiazolidin-3-yl}piperidine-1-carboxylate was prepared from [4-chloro-2-(trifluoromethyl)benzyl]-1H-indazol-5-carbaldehyde (from Example 1) and 1,1-dimethylethyl 3-(2,4-dioxo-1,3-thiazolidin-3-yl)piperidine-1-carboxylate following General Procedure F.

(C) (5Z)-5-({1-[4-Chloro-2-(trifluoromethyl)benzyl]-1H-indazol-5-yl}methylidene)-3-piperidin-3-yl-1,3-thiazolidine-2,4-dione was prepared by the deprotection of 1,1-dimethylethyl 3-{(5Z)-5-[(1-{[4-chloro-2-(trifluoromethyl)phenyl]methyl}-1H-indazol-5-yl)methylidene]-2,4-dioxo-1,3-thiazolidin-3-yl}piperidine-1-carboxylate following General Procedure M.

$^1$H NMR (400 MHz, CDCl$_3$): δ 8.21 (s, 1H), 7.98 (s, 1H), 7.95 (s, 1H), 7.72 (d, 1H), 7.47-7.53 (m, 1H), 7.35 (d, 2H), 6.68 (d, 1H), 5.80 (s, 2H), 4.27-4.43 (m, 1H), 3.42 (t, 1H), 2.93-3.10 (m, 2H), 2.63 (td, 1H), 2.36-2.51 (m, 1H), 1.85 (d, 2H), 1.50-1.65 (m, 1H).

LC/MS: mass calcd. for C$_{24}$H$_{20}$ClF$_3$N$_4$O$_2$S: 520.09. found 521.3 [M+1]$^+$

Example 125

(5Z)-5-({1-[4-Chloro-2-(trifluoromethyl)benzyl]-1H-indazol-5-yl}methylidene)-3-[(3R)-tetrahydrofuran-3-yl]-1,3-thiazolidine-2,4-dione

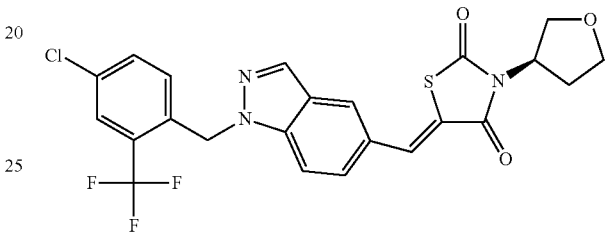

(A) [(3R)-Tetrahydrofuran-3-yl]-1,3-thiazolidine-2,4-dione was prepared from (3R)-3-aminotetrahydrofuran following General Procedure D.

(B) (5Z)-5-({1-[4-Chloro-2-(trifluoromethyl)benzyl]-1H-indazol-5-yl}methylidene)-3-[(3R)-tetrahydrofuran-3-yl]-1,3-thiazolidine-2,4-dione was prepared from [4-chloro-2-(trifluoromethyl)benzyl]-1H-indazol-5-carbaldehyde (from Example 1) and [(3R)-tetrahydrofuran-3-yl]-1,3-thiazolidine-2,4-dione following General Procedure F.

$^1$H NMR (400 MHz, CDCl$_3$): δ 8.23 (s, 1H), 8.01 (s, 1H), 7.96 (s, 1H), 7.72 (d, 1H), 7.51 (d, 1H), 7.31-7.39 (m, 2H), 6.68 (d, 1H), 5.80 (s, 2H), 5.01-5.14 (m, 1H), 4.21 (q, 1H), 4.03-4.10 (m, 1H), 3.97-4.02 (m, 1H), 3.89-3.96 (m, 1H), 2.32-2.45 (m, 1H), 2.18-2.32 (m, 1H).

LC/MS: mass calcd. for C$_{23}$H$_{17}$ClF$_3$N$_3$O$_3$S: 507.06. found 508.3 [M+1]$^+$

Example 126

2-[(5Z)-5-({1-[4-Chloro-2-(trifluoromethyl)benzyl]-1H-indazol-5-yl}methylidene)-2,4-dioxo-1,3-thiazolidin-3-yl]-N-(methylsulfonyl)acetamide

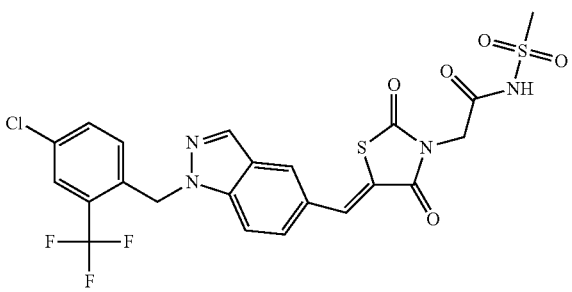 [SMILES: CS(=O)(=O)NC(=O)CN1C(=O)S/C(=C\c2ccc3c(cnn3Cc3ccc(Cl)cc3C(F)(F)F)c2)C1=O]

2-[(5Z)-5-({1-[4-Chloro-2-(trifluoromethyl)benzyl]-1H-indazol-5-yl}methylidene)-2,4-dioxo-1,3-thiazolidin-3-yl]-N-(methylsulfonyl)-acetamide was prepared from [(5Z)-5-({1-[4-chloro-2-(trifluoromethyl)-benzyl]-1H-indazol-5-yl}methylidene)-2,4-dioxo-1,3-thiazolidin-3-yl]acetic acid (Example 4) following General Procedure L using methanesulfonic acid amide in place of the sulfamide.

$^1$H NMR (400 MHz, DMSO-$d_6$): δ 12.34 (br. s., 1H), 8.36 (s, 1H), 8.19 (s, 1H), 8.12 (s, 1H), 7.87 (d, 1H), 7.80 (d, 1H), 7.69 (d, 1H), 7.61-7.67 (m, 1H), 6.76 (d, 1H), 5.86 (s, 2H), 4.45 (s, 2H), 3.25 (s, 3H).

LC/MS: mass calcd for $C_{22}H_{16}ClF_3N_4O_6S_2$: 572.02. found 573.2 [M+1]$^+$

Example 127

(5Z)-5-({1-[4-Chloro-2-(trifluoromethyl)benzyl]-1H-indazol-5-yl}methylidene)-3-methyl-1,3-thiazolidine-2,4-dione

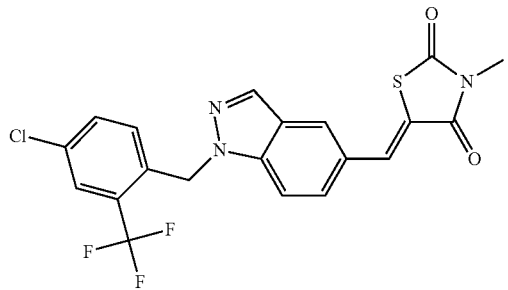 [SMILES: CN1C(=O)S/C(=C\c2ccc3c(cnn3Cc3ccc(Cl)cc3C(F)(F)F)c2)C1=O]

(5Z)-5-({1-[4-Chloro-2-(trifluoromethyl)benzyl]-1H-indazol-5-yl}methylidene)-3-methyl-1,3-thiazolidine-2,4-dione was prepared from [(5Z)-5-({1-[4-chloro-2-(trifluoromethyl)benzyl]-1H-indazol-5-yl}methylidene)-2,4-dioxo-1,3-thiazolidine (from Example 1) and methyl alcohol following General Procedure J.

$^1$H NMR (400 MHz, CDCl$_3$): δ 8.22 (s, 1H), 8.04 (s, 1H), 7.97 (s, 1H), 7.72 (s, 1H), 7.50-7.56 (m, 1H), 7.35 (dd, 2H), 6.67 (d, 1H), 5.80 (s, 2H), 3.27 (s, 3H).

LC/MS: mass calcd. for $C_{20}H_{13}ClF_3N_3O_2S$: 451.04. found 452.3 [M+1]$^+$

Example 128

(5Z)-5-({1-[4-Chloro-2-(trifluoromethyl)benzyl]-1H-indazol-5-yl}methylidene)-3-(8-methyl-8-azabicyclo[3.2.1]oct-3-yl)-1,3-thiazolidine-2,4-dione

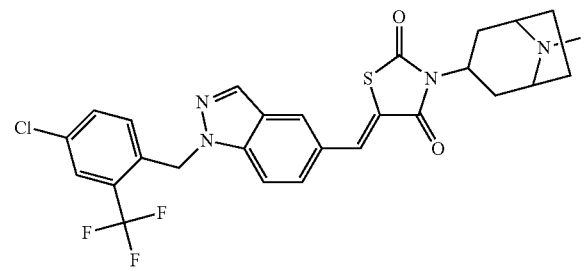 [SMILES: CN1C2CCC1CC(N1C(=O)S/C(=C\c3ccc4c(cnn4Cc4ccc(Cl)cc4C(F)(F)F)c3)C1=O)C2]

(5Z)-5-({1-[4-Chloro-2-(trifluoromethyl)benzyl]-1H-indazol-5-yl}methylidene)-3-(8-methyl-8-azabicyclo[3.2.1]oct-3-yl)-1,3-thiazolidine-2,4-dione was prepared from [(5Z)-5-({1-[4-chloro-2-(trifluoromethyl)-benzyl]-1H-indazol-5-yl}methylidene)-2,4-dioxo-1,3-thiazolidine (from Example 1) and endo-3-hydroxy-8-methyl-8-azabicyclo[3.2.1]octane] following General Procedure J.

$^1$H NMR (400 MHz, CDCl$_3$): δ 8.21 (s, 1H), 7.97 (s, 1H), 7.95 (s, 1H), 7.72 (d, 1H), 7.50 (dd, 1H), 7.35 (s, 1H), 7.33 (s, 1H), 6.68 (d, 1H), 5.79 (s, 2H), 4.59-4.75 (m, 1H), 3.31 (br. s., 2H), 2.66 (td, 2H), 2.51 (s, 3H), 2.06-2.17 (m, 2H), 1.66-1.79 (m, 2H), 1.32-1.44 (m, 2H).

LC/MS: mass calcd. for $C_{27}H_{24}ClF_3N_4O_2S$: 560.13. found 561.4 [M+1]$^+$

Example 129

(5Z)-5-({1-[4-Chloro-2-(trifluoromethyl)benzyl]-1H-indazol-5-yl}methylidene)-3-[2-(methylsulfonyl)ethyl]-1,3-thiazolidine-2,4-dione

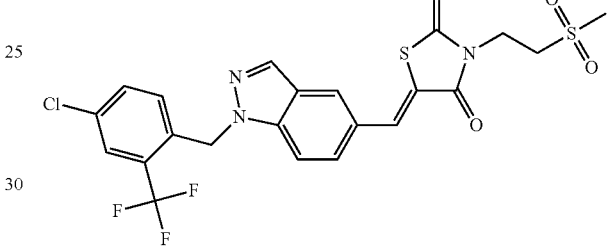

(5Z)-5-({1-[4-Chloro-2-(trifluoromethyl)benzyl]-1H-indazol-5-yl}methylidene)-3-[2-(methylsulfonyl)ethyl]-1,3-thiazolidine-2,4-dione was prepared from [(5Z)-5-({1-[4-chloro-2-(trifluoromethyl)benzyl]-1H-indazol-5-yl}methylidene)-2,4-dioxo-1,3-thiazolidine (from Example 1) and 2-(methylsulfonyl)ethyl alcohol following General Procedure J.

$^1$H NMR (400 MHz, CDCl$_3$): δ 8.22 (s, 1H), 8.06 (s, 1H), 7.97 (s, 1H), 7.72 (s, 1H), 7.51 (d, 1H), 7.32-7.39 (m, 2H), 6.68 (d, 1H), 5.80 (s, 2H), 4.26 (t, 2H), 3.43 (t, 2H), 3.05 (s, 3H).

LC/MS: mass calcd. for $C_{22}H_{17}ClF_3N_3O_4S_2$: 543.03. found 544.4 [M+1]$^+$

Example 130

(5Z)-5-({1-[4-Chloro-2-(trifluoromethyl)benzyl]-1H-indazol-5-yl}methylidene)-3-(piperidin-4-ylmethyl)-1,3-thiazolidine-2,4-dione

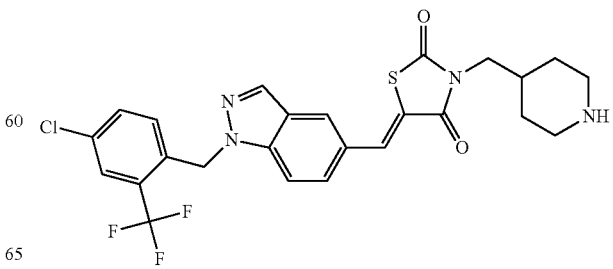

(A) 1,1-Dimethylethyl 4-[{(5Z)-5-[(1-{[4-chloro-2-(trifluoromethyl)phenyl]-methyl}-1H-indazol-5-yl)methylidene]-2,4-dioxo-1,3-thiazolidin-3-yl}methyl]piperidine-1-carboxylate was prepared from (5Z)-5-({1-[4-chloro-2-(trifluoromethyl)benzyl]-1H-indazol-5-yl}methylidene)-2,4-dioxo-1,3-thiazolidine (from Example 1) and 1,1-dimethylethyl 4-hydroxymethylpiperidine-1-carboxylate following General Procedure J.

(B) (5Z)-5-({1-[4-Chloro-2-(trifluoromethyl)benzyl]-1H-indazol-5-yl}methylidene)-3-(piperidin-4-ylmethyl)-1,3-thiazolidine-2,4-dione was prepared from 1,1-dimethylethyl 4-[{(5Z)-5-[(1-{[4-chloro-2-(trifluoromethyl)phenyl]methyl}-1H-indazol-5-yl)methylidene]-2,4-dioxo-1,3-thiazolidin-3-yl}methyl]piperidine-1-carboxylate following General Procedure M.

$^1$H NMR (400 MHz, CDCl$_3$): δ 8.21 (s, 1H), 8.01 (s, 1H), 7.96 (s, 1H), 7.71 (d, 1H), 7.48-7.53 (m, 1H), 7.31-7.38 (m, 2H), 6.67 (d, 1H), 5.79 (s, 2H), 3.66 (d, 2H), 3.13 (d, 2H), 2.60 (td, 2H), 2.45 (br. s., 1H), 1.95 (td, 1H), 1.67 (d, 2H), 1.25-1.36 (m, 2H).

LC/MS: mass calcd. for C$_{25}$H$_{22}$ClF$_3$N$_4$O$_2$S: 534.11. found 535.4 [M+1]$^+$ Example 131

(5Z)-5-({1-[4-Chloro-2-(trifluoromethyl)benzyl]-1H-indazol-5-yl}methylidene)-3-[2-(2-oxo-1,3-oxazolidin-3-yl)ethyl]-1,3-thiazolidine-2,4-dione

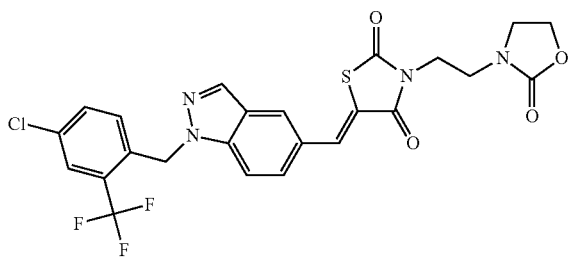 [SMILES: O=C1OCCN1CCN1C(=O)S/C(=C\c2ccc3c(cnn3Cc3ccc(Cl)cc3C(F)(F)F)c2)C1=O]

(5Z)-5-({1-[4-Chloro-2-(trifluoromethyl)benzyl]-1H-indazol-5-yl}methylidene)-3-[2-(2-oxo-1,3-oxazolidin-3-yl)ethyl]-1,3-thiazolidine-2,4-dione was prepared from [(5Z)-5-({1-[4-chloro-2-(trifluoromethyl)benzyl]-1H-indazol-5-yl}methylidene)-2,4-dioxo-1,3-thiazolidine (from Example 1) and 3-(2-hydroxyethyl)1,3-oxazolidin-2-one following General Procedure J.

$^1$H NMR (400 MHz, CDCl$_3$): δ 8.21 (s, 1H), 8.02 (s, 1H), 7.96 (s, 1H), 7.72 (s, 1H), 7.50 (d, 1H), 7.35 (s, 1H), 7.33 (s, 1H), 6.65 (d, 1H), 5.80 (s, 2H), 4.33 (t, 2H), 3.97 (t, 2H), 3.71 (t, 2H), 3.61 (t, 2H).

LC/MS: mass calcd. for C$_{24}$H$_{18}$ClF$_3$N$_4$O$_4$S: 550.07. found 551.4 [M+1]$^+$ Example 132

(5Z)-3-[(3S)-1-Azabicyclo[2.2.2]oct-3-yl]-5-({1-[4-chloro-2-(trifluoromethyl)benzyl]-1H-indazol-5-yl}methylidene)-1,3-thiazolidine-2,4-dione

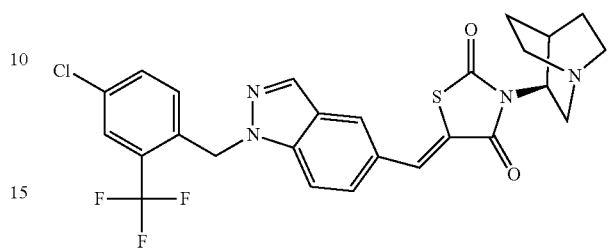

(5Z)-3-[(3S)-1-Azabicyclo[2.2.2]oct-3-yl]-5-({1-[4-chloro-2-(trifluoromethyl)benzyl]-1H-indazol-5-yl}methylidene)-1,3-thiazolidine-2,4-dione was prepared from [(5Z)-5-({1-[4-chloro-2-(trifluoromethyl)benzyl]-1H-indazol-5-yl}methylidene)-2,4-dioxo-1,3-thiazolidine (from Example 1) and (3R)-3-hydroxy-1-azabicyclo[2.2.2]octane following General Procedure J.

$^1$H NMR (400 MHz, CDCl$_3$): δ 8.24 (s, 1H), 8.05 (s, 1H), 7.98 (s, 1H), 7.73 (d, 1H), 7.51 (d, 1H), 7.33-7.41 (m, 2H), 6.71 (d, 1H), 5.80 (s, 2H), 4.88 (br. s., 1H), 4.42 (br. s., 1H), 3.89 (br. s., 1H), 3.62 (br. s., 1H), 3.40 (br. s., 3H), 1.98-2.25 (m, 4H), 1.89 (br. s., 1H).

LC/MS: mass calcd. for C$_{26}$H$_{22}$ClF$_3$N$_4$O$_2$S: 546.11. found 547.4 [M+1]$^+$ Example 133

(5Z)-5-({1-[4-Chloro-2-(trifluoromethyl)benzyl]-1H-indazol-5-yl}methylidene)-3-(1-methylazetidin-3-yl)-1,3-thiazolidine-2,4-dione

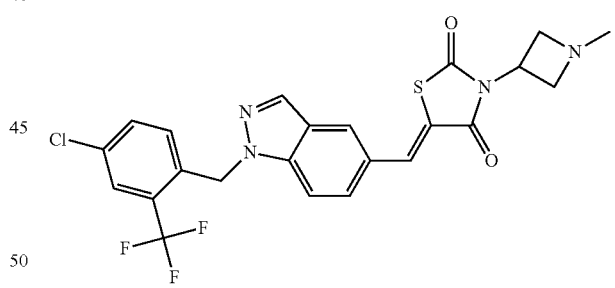

(A) 1,1-Dimethylethyl 3-{(5Z)-5-[(1-{[4-chloro-2-(trifluoromethyl)phenyl]-methyl}-1H-indazol-5-yl)methylidene]-2,4-dioxo-1,3-thiazolidin-3-yl}azetidine-1-carboxylate was prepared from (5Z)-5-({1-[4-chloro-2-(trifluoromethyl)benzyl]-1H-indazol-5-yl}methylidene)-2,4-dioxo-1,3-thiazolidine (from Example 1) and 1,1-dimethylethyl 3-hydroxy-azetidine-1-carboxylate following General Procedure J.

(B) (5Z)-5-({1-[4-Chloro-2-(trifluoromethyl)benzyl]-1H-indazol-5-yl}methylidene)-3-[azetidin-3-yl]-1,3-thiazolidine-2,4-dione was prepared by the deprotection of 1,1-dimethylethyl 3-{(5Z)-5-[(1-{[4-chloro-2-(trifluoromethyl)phenyl]-methyl}-1H-indazol-5-yl)methylidene]-2,4-dioxo-1,3-thiazolidin-3-yl}azetidine-1-carboxylate following General Procedure M.

(C) (5Z)-5-({1-[4-Chloro-2-(trifluoromethyl)benzyl]-1H-indazol-5-yl}methylidene)-3-(1-methylazetidin-3-yl)-1,3-thiazolidine-2,4-dione was prepared from (5Z)-5-({1-[4-chloro-2-(trifluoromethyl)benzyl]-1H-indazol-5-yl}methylidene)-3-[azetidin-3-yl]-1,3-thiazolidine-2,4-dione and formaldehyde following General Procedure R.

$^1$H NMR (400 MHz, CDCl$_3$): δ 8.24 (s, 1H), 8.08 (s, 1H), 7.98 (s, 1H), 7.72 (s, 1H), 7.50 (d, 1H), 7.30-7.43 (m, 2H), 6.70 (d, 1H), 5.80 (s, 2H), 5.48-5.57 (m, 1H), 4.75-4.85 (m, 2H), 4.56 (t, 2H), 3.15 (s, 3H).

LC/MS: mass calcd. for C$_{23}$H$_{18}$ClF$_3$N$_4$O$_2$S: 506.08. found 507.4 [M+1]$^+$ Example 134

(5Z)-5-({1-[4-Chloro-2-(trifluoromethyl)benzyl]-1H-indazol-5-yl}methylidene)-3-[(1-methylpiperidin-4-yl)methyl]-1,3-thiazolidine-2,4-dione

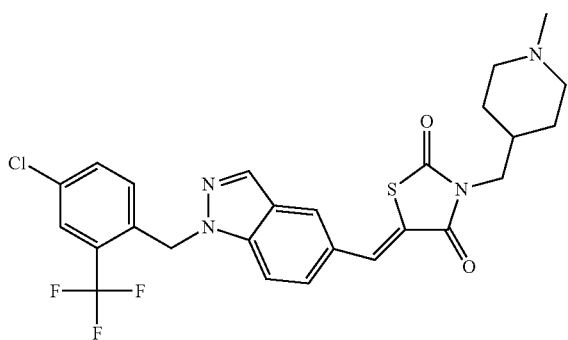 [SMILES: CN1CCC(CN2C(=O)S/C(=C\c3ccc4c(cnn4Cc4ccc(Cl)cc4C(F)(F)F)c3)C2=O)CC1]

(5Z)-5-({1-[4-Chloro-2-(trifluoromethyl)benzyl]-1H-indazol-5-yl}methylidene)-3-[(1-methylpiperidin-4-yl)methyl]-1,3-thiazolidine-2,4-dione was prepared from (5Z)-5-({1-[4-chloro-2-(trifluoromethyl)benzyl]-1H-indazol-5-yl}methylidene)-3-(piperidin-4-ylmethyl)-1,3-thiazolidine-2,4-dione (Example 130) and formaldehyde following General Procedure R.

$^1$H NMR (400 MHz, CDCl$_3$): δ 11.50 (br. s., 1H), 8.24 (s, 1H), 8.04 (d, 1H), 7.98 (s, 1H), 7.73 (s, 1H), 7.52 (d, 1H), 7.33-7.41 (m, 2H), 6.70 (d, 1H), 5.81 (s, 2H), 4.20 (br. s., 2H), 3.74 (br. s., 2H), 2.84 (s, 3H), 2.67 (br. s., 2H), 1.67-2.21 (m, 5H).

LC/MS: mass calcd. for C$_{26}$H$_{24}$ClF$_3$N$_4$O$_2$S: 548.13. found 549.4 [M+1]$^+$ Example 135

(5Z)-5-({1-[4-Chloro-2-(trifluoromethyl)benzyl]-1H-indazol-5-yl}methylidene)-3-(1-methylpiperidin-4-yl)-1,3-thiazolidine-2,4-dione

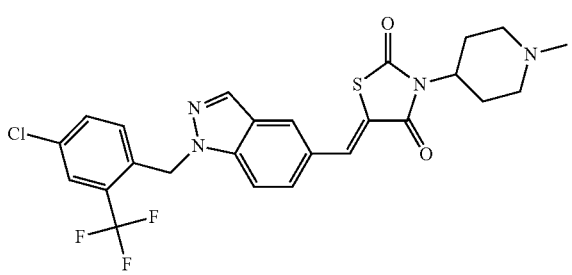 [SMILES: CN1CCC(N2C(=O)S/C(=C\c3ccc4c(cnn4Cc4ccc(Cl)cc4C(F)(F)F)c3)C2=O)CC1]

(5Z)-5-({1-[4-Chloro-2-(trifluoromethyl)benzyl]-1H-indazol-5-yl}methylidene)-3-(1-methylpiperidin-4-yl)-1,3-thiazolidine-2,4-dione was prepared from (5Z)-5-({1-[4-chloro-2-(trifluoromethyl)benzyl]-1H-indazol-5-yl}methylidene)-3-piperidin-4-yl-1,3-thiazolidine-2,4-dione (Example 113) and formaldehyde following General Procedure R.

$^1$H NMR (400 MHz, CDCl$_3$): δ 8.21 (s, 1H), 7.98 (s, 1H), 7.95 (s, 1H), 7.72 (d, 1H), 7.47-7.53 (m, 1H), 7.35 (s, 1H), 7.33 (s, 1H), 6.67 (d, 1H), 5.79 (s, 2H), 4.27 (tq, 1H), 2.99 (d, 2H), 2.63 (qd, 2H), 2.32 (s, 3H), 2.00-2.14 (m, 2H), 1.66 (d, 2H).

LC/MS: mass calcd. for C$_{25}$H$_{22}$ClF$_3$N$_4$O$_2$S: 534.11. found 535.4 [M+1]$^+$ Example 136

(5Z)-5-({1-[4-Chloro-2-(trifluoromethyl)benzyl]-1H-indazol-5-yl}methylidene)-3-(1-methylpiperidin-3-yl)-1,3-thiazolidine-2,4-dione

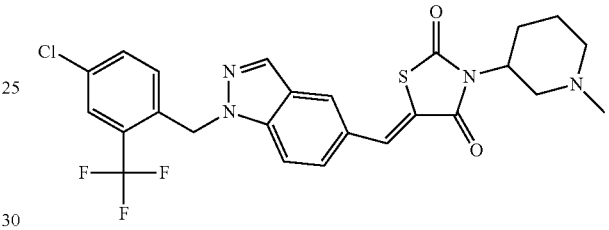

(5Z)-5-({1-[4-Chloro-2-(trifluoromethyl)benzyl]-1H-indazol-5-yl}methylidene)-3-(1-methylpiperidin-3-yl)-1,3-thiazolidine-2,4-dione was prepared from (5Z)-5-({1-[4-chloro-2-(trifluoromethyl)benzyl]-1H-indazol-5-yl}methylidene)-3-piperidin-3-yl-1,3-thiazolidine-2,4-dione (Example 124) and formaldehyde following General Procedure R.

$^1$H NMR (400 MHz, CDCl$_3$): δ 8.21 (s, 1H), 7.98 (s, 1H), 7.95 (s, 1H), 7.72 (d, 1H), 7.46-7.53 (m, 1H), 7.35 (s, 1H), 7.33 (s, 1H), 6.67 (d, 1H), 5.79 (s, 2H), 4.49-4.60 (m, 1H), 2.68-2.87 (m, 2H), 2.33 (s, 3H), 2.17-2.30 (m, 1H), 1.92-2.01 (m, 1H), 1.62-1.89 (m, 4H).

LC/MS: mass calcd. for C$_{25}$H$_{22}$ClF$_3$N$_4$O$_2$S: 534.11, 535.4 found [M+1]$^+$ Example 137

(5Z)-5-({1-[4-Chloro-2-(trifluoromethyl)benzyl]-1H-indazol-5-yl}methylidene)-3-(pyridin-2-ylmethyl)-1,3-thiazolidine-2,4-dione

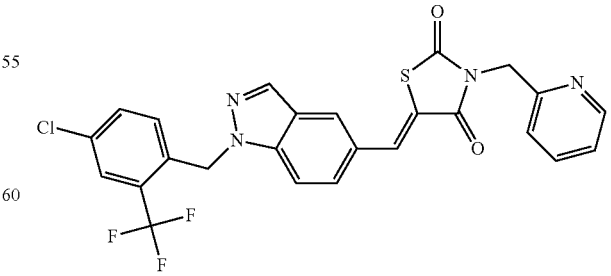

(5Z)-5-({1-[4-Chloro-2-(trifluoromethyl)benzyl]-1H-indazol-5-yl}methylidene)-3-(pyridin-2-ylmethyl)-1,3-thiazolidine-2,4-dione was prepared from [(5Z)-5-({1-[4-chloro-2-

(trifluoromethyl)benzyl]-1H-indazol-5-yl}methylidene)-2,4-dioxo-1,3-thiazolidine (from Example 1) and 2-(bromomethyl)pyridine hydrobromide following General Procedure H.

¹H NMR (400 MHz, CDCl₃): δ 8.56 (d, 1H), 8.22 (s, 1H), 8.06 (s, 1H), 7.97 (s, 1H), 7.71 (d, 1H), 7.67 (td, 1H), 7.52 (dd, 1H), 7.32-7.40 (m, 2H), 7.30 (d, 1H), 7.20 (dd, 1H), 6.67 (d, 1H), 5.79 (s, 2H), 5.08 (s, 2H).

LC/MS: mass calcd. for $C_{25}H_{16}ClF_3N_4O_2S$: 528.06. found 529.4 [M+1]⁺

Example 138

(5Z)-5-({1-[4-Chloro-2-(trifluoromethyl)benzyl]-1H-indazol-5-yl}methylidene)-3-[(3-hydroxyisoxazol-5-yl)methyl]-1,3-thiazolidine-2,4-dione

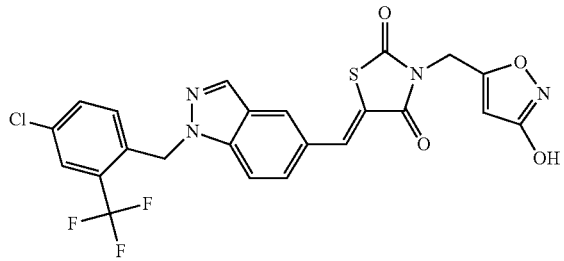 [SMILES: O=C1S/C(=C\c2ccc3c(cnn3Cc3ccc(Cl)cc3C(F)(F)F)c2)C(=O)N1Cc1cc(O)no1]

(5Z)-5-({1-[4-Chloro-2-(trifluoromethyl)benzyl]-1H-indazol-5-yl}methylidene)-3-[(3-hydroxyisoxazol-5-yl)methyl]-1,3-thiazolidine-2,4-dione was prepared from [(5Z)-5-({1-[4-chloro-2-(trifluoromethyl)benzyl]-1H-indazol-5-yl}methylidene)-2,4-dioxo-1,3-thiazolidine (from Example 1) and 5-chloromethyl-3-hydroxyisoxazole following General Procedure H.

¹H NMR (400 MHz, CDCl₃): δ 8.24 (s, 1H), 8.07 (s, 1H), 7.99 (s, 1H), 7.73 (d, 1H), 7.50-7.55 (m, 1H), 7.33-7.41 (m, 2H), 6.67 (d, 1H), 5.95 (s, 1H), 5.81 (s, 2H), 4.92 (s, 2H).

LC/MS: mass calcd. for $C_{23}H_{14}ClF_3N_4O_4S$: 534.04. found 535.4 [M+1]⁺

Example 139

(5Z)-5-({1-[4-Chloro-2-(trifluoromethyl)benzyl]-1H-indazol-5-yl}methylidene)-3-[(1-methyl-1H-imidazol-5-yl)methyl]-1,3-thiazolidine-2,4-dione

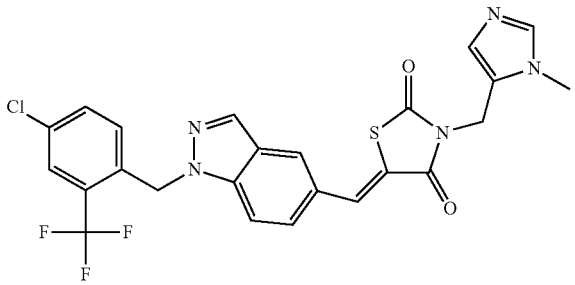 [SMILES: Cn1cncc1CN1C(=O)S/C(=C\c2ccc3c(cnn3Cc3ccc(Cl)cc3C(F)(F)F)c2)C1=O]

(5Z)-5-({1-[4-Chloro-2-(trifluoromethyl)benzyl]-1H-indazol-5-yl}methylidene)-3-[(1-methyl-1H-imidazol-5-yl)methyl]-1,3-thiazolidine-2,4-dione was prepared from [(5Z)-5-({1-[4-chloro-2-(trifluoromethyl)benzyl]-1H-indazol-5-yl}methylidene)-2,4-dioxo-1,3-thiazolidine (from Example 1) and 5-hydroxymethyl-1-methyl-1H-imidazole following General Procedure J.

¹H NMR (400 MHz, CDCl₃): δ 8.22 (s, 1H), 8.03 (s, 1H), 7.95 (s, 1H), 7.72 (d, 1H), 7.46-7.53 (m, 1H), 7.41 (s, 1H), 7.36 (s, 1H), 7.34 (s, 1H), 7.22 (s, 1H), 6.68 (d, 1H), 5.79 (s, 2H), 4.90 (s, 2H), 3.78 (s, 3H).

LC/MS: mass calcd. for $C_{24}H_{17}ClF_3N_5O_2S$: 531.07. found 532.4 [M+1]⁺

Example 140

(5Z)-5-({1-[4-Chloro-2-(trifluoromethyl)benzyl]-1H-indazol-5-yl}methylidene)-3-[2-(1-methylpyrrolidin-2-yl)ethyl]-1,3-thiazolidine-2,4-dione

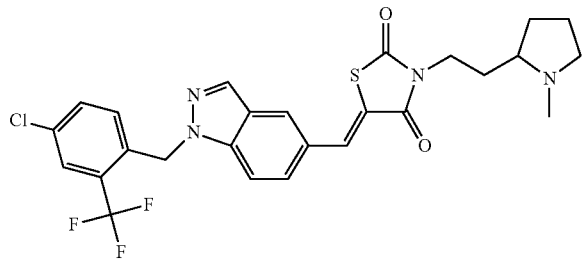 [SMILES: CN1CCCC1CCN1C(=O)S/C(=C\c2ccc3c(cnn3Cc3ccc(Cl)cc3C(F)(F)F)c2)C1=O]

(5Z)-5-({1-[4-Chloro-2-(trifluoromethyl)benzyl]-1H-indazol-5-yl}methylidene)-3-[2-(1-methylpyrrolidin-2-yl)ethyl]-1,3-thiazolidine-2,4-dione was prepared from [(5Z)-5-({1-[4-chloro-2-(trifluoromethyl)benzyl]-1H-indazol-5-yl}methylidene)-2,4-dioxo-1,3-thiazolidine (from Example 1) and 2-(2-chloroethyl)-1-methylpyrrolidine following General Procedure H.

¹H NMR (400 MHz, CDCl₃): δ 12.29 (br. s., 1H), 8.23 (d, 1H), 8.04 (s, 1H), 7.98 (s, 1H), 7.72 (s, 1H), 7.47-7.54 (m, 1H), 7.33-7.40 (m, 2H), 6.69 (d, 1H), 5.80 (s, 2H), 3.88-4.02 (m, 1H), 3.81 (dt, 1H), 2.90 (s, 3H), 2.13-2.33 (m, 7H), 2.06 (br. s., 2H).

LC/MS: mass calcd. for $C_{26}H_{24}ClF_3N_4O_2S$: 548.13. found 549.5 [M+1]⁺

Example 141

Ethyl (1R,2R)-2-[(5Z)-5-({1-[4-chloro-2-(trifluoromethyl)benzyl]-1H-indazol-5-yl}methylidene)-2,4-dioxo-1,3-thiazolidin-3-yl]cyclopentanecarboxylate

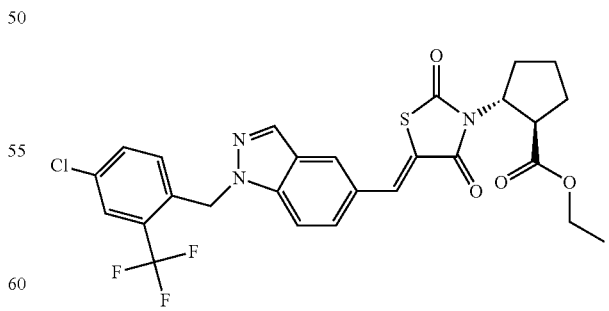

Ethyl (1R,2R)-2-[(5Z)-5-({1-[4-chloro-2-(trifluoromethyl)benzyl]-1H-indazol-5-yl}methylidene)-2,4-dioxo-1,3-thiazolidin-3-yl]cyclopentanecarboxylate was prepared from [(5Z)-5-({1-[4-chloro-2-(trifluoromethyl)benzyl]-1H-indazol-5-yl}methylidene)-2,4-dioxo-1,3-thiazolidine (from Example 1) and ethyl (1R,2S)-2-hydroxycyclopentanecarboxylate following General Procedure J.

¹H NMR (400 MHz, CDCl₃): δ 8.22 (s, 1H), 8.00 (s, 1H), 7.96 (s, 1H), 7.72 (d, 1H), 7.51 (d, 1H), 7.36 (s, 1H), 7.34 (s, 1H), 6.68 (d, 1H), 5.80 (s, 2H), 4.97 (q, 1H), 4.04-4.18 (m, 2H), 3.51 (q, 1H), 2.14-2.29 (m, 2H), 1.90-2.10 (m, 3H), 1.72-1.85 (m, 1H), 1.20 (t, 3H).

LC/MS: mass calcd. for $C_{27}H_{23}ClF_3N_3O_4S$: 577.10. found 578.4 $[M+1]^+$

Example 142

(1R,2R)-2-[(5Z)-5-({1-[4-Chloro-2-(trifluoromethyl)benzyl]-1H-indazol-5-yl}methylidene)-2,4-dioxo-1,3-thiazolidin-3-yl]cyclopentanecarboxylic acid

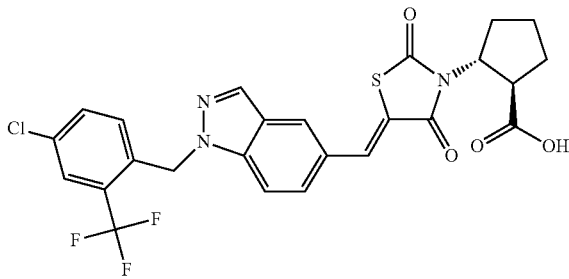 [SMILES: O=C(O)[C@@H]1CCC[C@H]1N1C(=O)S/C(=C\c2ccc3c(cnn3Cc3ccc(Cl)cc3C(F)(F)F)c2)C1=O]

(1R,2R)-2-[(5Z)-5-({1-[4-Chloro-2-(trifluoromethyl)benzyl]-1H-indazol-5-yl}methylidene)-2,4-dioxo-1,3-thiazolidin-3-yl]cyclopentanecarboxylic acid was prepared by hydrolysis of ethyl (1R,2R)-2-[(5Z)-5-({1-[4-chloro-2-(trifluoromethyl)benzyl]-1H-indazol-5-yl}methylidene)-2,4-dioxo-1,3-thiazolidin-3-yl]cyclopentanecarboxylate (Example 141) following General Procedure O.

¹H NMR (400 MHz, CDCl₃): δ 8.21 (s, 1H), 7.99 (s, 1H), 7.95 (s, 1H), 7.72 (d, 1H), 7.47-7.52 (m, 1H), 7.35 (s, 1H), 7.33 (s, 1H), 6.67 (d, 1H), 5.80 (s, 2H), 5.04 (q, 1H), 3.60 (q, 1H), 2.22-2.33 (m, 1H), 2.12-2.22 (m, 1H), 1.92-2.12 (m, 3H), 1.73-1.87 (m, 1H).

LC/MS: mass calcd. for $C_{25}H_{19}ClF_3N_3O_4S$: 549.07. found 550.4 $[M+1]^+$

Example 143

(5Z)-5-({1-[4-Chloro-2-(trifluoromethyl)benzyl]-1H-indazol-5-yl}methylidene)-3-[(3S)-1-methylpyrrolidin-3-yl]-1,3-thiazolidine-2,4-dione

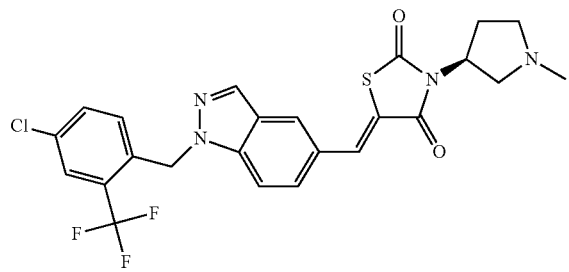 [SMILES: CN1CC[C@H](N2C(=O)S/C(=C\c3ccc4c(cnn4Cc4ccc(Cl)cc4C(F)(F)F)c3)C2=O)C1]

(5Z)-5-({1-[4-Chloro-2-(trifluoromethyl)benzyl]-1H-indazol-5-yl}methylidene)-3-[(3S)-1-methylpyrrolidin-3-yl]-1,3-thiazolidine-2,4-dione was prepared from (5Z)-5-({1-[4-chloro-2-(trifluoromethyl)benzyl]-1H-indazol-5-yl}methylidene)-3-[(3S)-pyrrolidin-3-yl]-1,3-thiazolidine-2,4-dione (Example 114) and formaldehyde following General Procedure R.

¹H NMR (400 MHz, CDCl₃): δ 8.20 (s, 1H), 7.98 (s, 1H), 7.94 (s, 1H), 7.71 (d, 1H), 7.47-7.53 (m, 1H), 7.35 (s, 1H), 7.32 (s, 1H), 6.67 (d, 1H), 5.78 (s, 2H), 5.00-5.12 (m, 1H), 3.02 (t, 1H), 2.84-2.94 (m, 1H), 2.76 (q, 1H), 2.67 (t, 1H), 2.42 (s, 3H), 2.16-2.27 (m, 2H).

LC/MS: mass calcd. for $C_{24}H_{20}ClF_3N_4O_2S$: 520.09. found 521.4 $[M+1]^+$

Example 144

(5Z)-5-({1-[4-Chloro-2-(trifluoromethyl)benzyl]-1H-indazol-5-yl}methylidene)-3-[(3R)-1-methylpyrrolidin-3-yl]-1,3-thiazolidine-2,4-dione

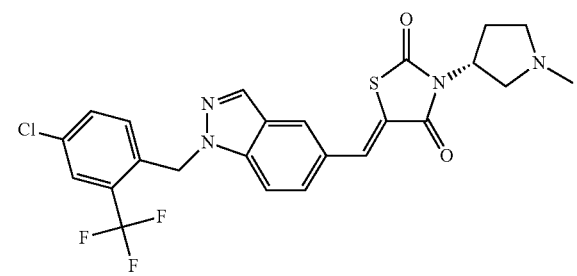 [SMILES: CN1CC[C@@H](N2C(=O)S/C(=C\c3ccc4c(cnn4Cc4ccc(Cl)cc4C(F)(F)F)c3)C2=O)C1]

(A) 1,1-Dimethylethyl (3R)-3-{(5Z)-5-[(1-{[4-chloro-2-(trifluoromethyl)phenyl]-methyl}-1H-indazol-5-yl)methylidene]-2,4-dioxo-1,3-thiazolidin-3-yl}pyrrolidine-1-carboxylate was prepared from (5Z)-5-({1-[4-chloro-2-(trifluoromethyl)benzyl]-1H-indazol-5-yl}methylidene)-2,4-dioxo-1,3-thiazolidine (from Example 1) and 1,1-dimethylethyl (3S)-3-pyrrolidine-1-carboxylate following General Procedure J.

(B) (5Z)-5-({1-[4-Chloro-2-(trifluoromethyl)benzyl]-1H-indazol-5-yl}methylidene)-3-[(3R)-pyrrolidin-3-yl]-1,3-thiazolidine-2,4-dione was prepared by the deprotection of 1,1-dimethylethyl (3R)-3-{(5Z)-5-[(1-{[4-chloro-2-(trifluoromethyl)phenyl]methyl}-1H-indazol-5-yl)methylidene]-2,4-dioxo-1,3-thiazolidin-3-yl}pyrrolidine-1-carboxylate following General Procedure M.

(C) (5Z)-5-({1-[4-Chloro-2-(trifluoromethyl)benzyl]-1H-indazol-5-yl}methylidene)-3-[(3R)-1-methylpyrrolidin-3-yl]-1,3-thiazolidine-2,4-dione was prepared from (5Z)-5-({1-[4-chloro-2-(trifluoromethyl)benzyl]-1H-indazol-5-yl}methylidene)-3-[(3R)-pyrrolidin-3-yl]-1,3-thiazolidine-2,4-dione and formaldehyde following General Procedure R.

¹H NMR (400 MHz, CDCl₃): δ 8.21 (s, 1H), 7.99 (s, 1H), 7.95 (s, 1H), 7.72 (d, 1H), 7.47-7.53 (m, 1H), 7.36 (s, 1H), 7.33 (s, 1H), 6.68 (d, 1H), 5.80 (s, 2H), 5.01-5.14 (m, 1H), 3.03 (t, 1H), 2.91 (td, 1H), 2.78 (q, 1H), 2.69 (t, 1H), 2.43 (s, 3H), 2.16-2.32 (m, 2H).

LC/MS: mass calcd. for $C_{24}H_{20}ClF_3N_4O_2S$: 520.09. found 521.4 $[M+1]^+$

Example 145

(5Z)-5-({1-[4-Chloro-2-(trifluoromethyl)benzyl]-1H-indazol-5-yl}methylidene)-3-[(2S)-pyrrolidin-2-ylmethyl]-1,3-thiazolidine-2,4-dione

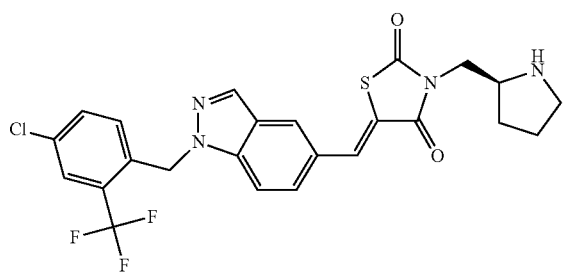 [SMILES: O=C1S/C(=C\c2ccc3c(cnn3Cc3ccc(Cl)cc3C(F)(F)F)c2)C(=O)N1C[C@@H]1CCCN1]

(A) 1,1-Dimethylethyl (2S)-2-[{(5Z)-5-[(1-{[4-chloro-2-(trifluoromethyl)phenyl]-methyl}-1H-indazol-5-yl)methylidene]-2,4-dioxo-1,3-thiazolidin-3-yl}methyl]pyrrolidine-1-carboxylate was prepared from (5Z)-5-({1-[4-chloro-2-(trifluoromethyl)benzyl]-1H-indazol-5-yl}methylidene)-2,4-dioxo-1,3-thiazolidine (from Example 1) and 1,1-dimethylethyl (2S)-2-(hydroxymethyl)piperidine-1-carboxylate following General Procedure J.

(B) (5Z)-5-({1-[4-Chloro-2-(trifluoromethyl)benzyl]-1H-indazol-5-yl}methylidene)-3-[(2S)-pyrrolidin-2-ylmethyl]-1,3-thiazolidine-2,4-dione was prepared from 1,1-dimethylethyl (2S)-2-[{(5Z)-5-[(1-{[4-chloro-2-(trifluoromethyl)phenyl]methyl}-1H-indazol-5-yl)methylidene]-2,4-dioxo-1,3-thiazolidin-3-yl}methyl]pyrrolidine-1-carboxylate following General Procedure M.

$^1$H NMR (400 MHz, CDCl$_3$): δ 8.21 (s, 1H), 8.01 (s, 1H), 7.95 (s, 1H), 7.71 (s, 1H), 7.50 (d, 1H), 7.36 (br. s., 1H), 7.34 (br. s., 1H), 6.67 (d, 1H), 5.79 (s, 2H), 3.76 (d, 2H), 3.48-3.57 (m, 1H), 3.02 (dt, 1H), 2.89 (dt, 1H), 1.79-1.97 (m, 3H), 1.67-1.79 (m, 1H), 1.38-1.53 (m, 1H).

LC/MS: mass calcd. for C$_{24}$H$_{20}$ClF$_3$N$_4$O$_2$S: 520.09. found 521.4 [M+1]$^+$

Example 146

{4-[(5Z)-5-({1-[4-Chloro-2-(trifluoromethyl)benzyl]-1H-indazol-5-yl}methylidene)-2,4-dioxo-1,3-thiazolidin-3-yl]piperidin-1-yl}acetic acid

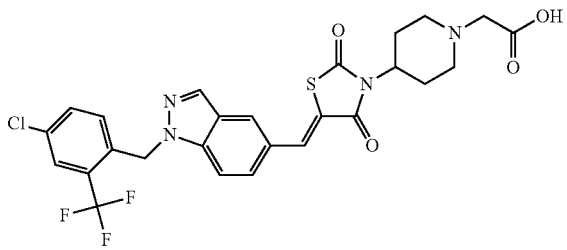 [SMILES: O=C(O)CN1CCC(N2C(=O)S/C(=C\c3ccc4c(cnn4Cc4ccc(Cl)cc4C(F)(F)F)c3)C2=O)CC1]

1,1-Dimethylethyl {4-[(5Z)-5-({1-[4-chloro-2-(trifluoromethyl)benzyl]-1H-indazol-5-yl}methylidene)-2,4-dioxo-1,3-thiazolidin-3-yl]piperidin-1-yl}acetate was prepared from (5Z)-5-({1-[4-chloro-2-(trifluoromethyl)benzyl]-1H-indazol-5-yl}methylidene)-3-piperidin-4-yl-1,3-thiazolidine-2,4-dione (Example 113) and tert-butyl bromoacetate using the same methods as described by Procedure I.

$^1$H NMR (400 MHz, CDCl$_3$): δ 10.13 (br. s., 2H), 8.15 (s, 1H), 7.93 (s, 1H), 7.87 (s, 1H), 7.69 (s, 1H), 7.41 (d, 1H), 7.26-7.33 (m, 2H), 6.64 (d, 1H), 5.72 (br. s., 2H), 4.60 (br. s., 1H), 3.98 (br. s., 4H), 3.24 (br. s., 2H), 3.03 (br. s., 2H), 2.02 (br. s., 2H).

LC/MS: mass calcd. for C$_{26}$H$_{22}$ClF$_3$N$_4$O$_4$S: 578.1. found 579.4 [M+1]$^+$

Example 147

(5Z)-5-({1-[4-Chloro-2-(trifluoromethyl)benzyl]-1H-indazol-5-yl}methylidene)-3-[1-(2-methoxyethyl)piperidin-4-yl]-1,3-thiazolidine-2,4-dione

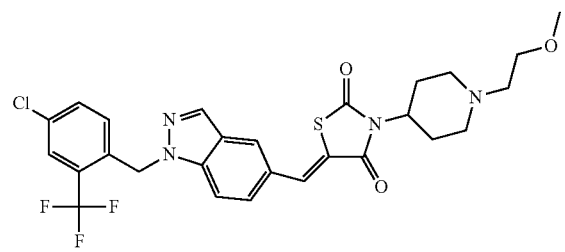 [SMILES: COCCN1CCC(N2C(=O)S/C(=C\c3ccc4c(cnn4Cc4ccc(Cl)cc4C(F)(F)F)c3)C2=O)CC1]

(5Z)-5-({1-[4-Chloro-2-(trifluoromethyl)benzyl]-1H-indazol-5-yl}methylidene)-3-[1-(2-methoxyethyl)piperidin-4-yl]-1,3-thiazolidine-2,4-dione was prepared from (5Z)-5-({1-[4-chloro-2-(trifluoromethyl)benzyl]-1H-indazol-5-yl}methylidene)-3-piperidin-4-yl-1,3-thiazolidine-2,4-dione (Example 113) and 2-bromoethyl methyl ether following General Procedure S.

$^1$H NMR (400 MHz, CDCl$_3$): δ 8.21 (s, 1H), 7.98 (s, 1H), 7.94 (s, 1H), 7.71 (d, 1H), 7.46-7.53 (m, 1H), 7.35 (s, 1H), 7.33 (s, 1H), 6.67 (d, 1H), 5.79 (s, 2H), 4.28 (ddd, 1H), 3.53 (t, 2H), 3.37 (s, 3H), 3.10 (d, 2H), 2.55-2.71 (m, 4H), 2.15 (t, 2H), 1.64 (d, 2H).

LC/MS: mass calcd. for C$_{27}$H$_{26}$ClF$_3$N$_4$O$_3$S: 578.14. found 579.5 [M+1]$^+$

Example 148

(5Z)-5-({1-[4-Chloro-2-(trifluoromethyl)benzyl]-1H-indazol-5-yl}methylidene)-3-[1-(2-hydroxyethyl)piperidin-4-yl]-1,3-thiazolidine-2,4-dione

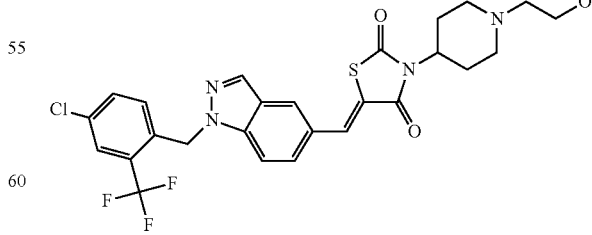

(5Z)-5-({1-[4-Chloro-2-(trifluoromethyl)benzyl]-1H-indazol-5-yl}methylidene)-3-[1-(2-hydroxyethyl)piperidin-4-yl]-1,3-thiazolidine-2,4-dione was prepared from (5Z)-5-({1-[4-chloro-2-(trifluoromethyl)benzyl]-1H-indazol-5- yl}methylidene)-3-piperidin-4-yl-1,3-thiazolidine-2,4-dione (Example 113) and 2-bromoethanol following General Procedure S.

$^1$H NMR (400 MHz, CDCl$_3$): δ 8.21 (s, 1H), 7.98 (s, 1H), 7.96 (s, 1H), 7.72 (d, 1H), 7.47-7.54 (m, 1H), 7.36 (s, 1H), 7.34 (s, 1H), 6.68 (d, 1H), 5.79 (s, 2H), 4.32 (tt, 1H), 3.62 (t, 2H), 3.05 (d, 2H), 2.51-2.67 (m, 4H), 2.21 (t, 2H), 1.62-1.75 (m, 2H).

LC/MS: mass calcd. for C$_{26}$H$_{24}$ClF$_3$N$_4$O$_3$S: 564.12. found 565.2 [M+1]$^+$ Example 149

(5Z)-5-({1-[4-Chloro-2-(trifluoromethyl)benzyl]-1H-indazol-5-yl}methylidene)-3-{1-[2-(methylsulfonyl)ethyl]piperidin-4-yl}-1,3-thiazolidine-2,4-dione

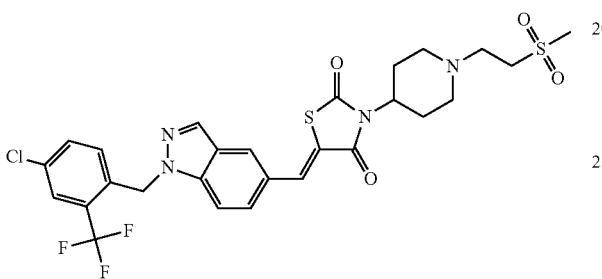

(5Z)-5-({1-[4-Chloro-2-(trifluoromethyl)benzyl]-1H-indazol-5-yl}methylidene)-3-{1-[2-(methylsulfonyl)ethyl]piperidin-4-yl}-1,3-thiazolidine-2,4-dione was prepared from (5Z)-5-({1-[4-chloro-2-(trifluoromethyl)-1H-indazol-5-yl}methylidene)-3-piperidin-4-yl-1,3-thiazolidine-2,4-dione (Example 113) and 2-(methylsulfonyl)ethyl methanesulfonate (prepared following General the methods described in PCT Int, Appl. 2006047277) following General Procedure S.

$^1$H NMR (400 MHz, CDCl$_3$): δ 8.22 (s, 1H), 7.99 (s, 1H), 7.97 (s, 1H), 7.72 (d, 1H), 7.47-7.54 (m, 1H), 7.33-7.40 (m, 2H), 6.67 (d, 1H), 5.80 (s, 2H), 4.32 (ddd, 1H), 3.18 (t, 2H), 3.10 (s, 3H), 3.06 (d, 2H), 2.91 (t, 2H), 2.56 (qd, 2H), 2.21 (t, 2H), 1.71 (d, 2H).

LC/MS: mass calcd. for C$_{27}$H$_{26}$ClF$_3$N$_4$O$_4$S$_2$: 626.1. found 627.5 [M+1]$^+$ Example 150

(5Z)-5-({1-[4-Chloro-2-(trifluoromethyl)benzyl]-1H-indazol-5-yl}methylidene)-3-[1-(2,2,2-trifluoroethyl)piperidin-4-yl]-1,3-thiazolidine-2,4-dione

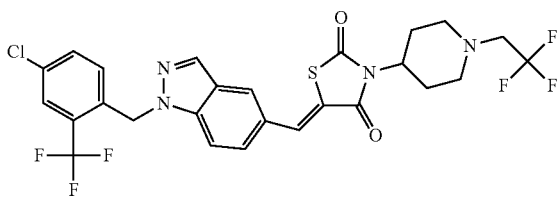 [SMILES: O=C1S/C(=C\c2ccc3c(cnn3Cc3ccc(Cl)cc3C(F)(F)F)c2)C(=O)N1C1CCN(CC(F)(F)F)CC1]

(5Z)-5-({1-[4-Chloro-2-(trifluoromethyl)benzyl]-1H-indazol-5-yl}methylidene)-3-[1-(2,2,2-trifluoroethyl)piperidin-4-yl]-1,3-thiazolidine-2,4-dione was prepared from (5Z)-5-({1-[4-chloro-2-(trifluoromethyl)benzyl]-1H-indazol-5-yl}methylidene)-3-piperidin-4-yl-1,3-thiazolidine-2,4-dione (Example 113) and 2,2,2-trifluoroethyl trifluoromethanesulfonate following General Procedure S.

$^1$H NMR (400 MHz, CDCl$_3$): δ 8.21 (s, 1H), 7.97-8.01 (m, 1H), 7.95 (s, 1H), 7.72 (d, 1H), 7.50 (dd, 1H), 7.36 (s, 1H), 7.34 (s, 1H), 6.68 (d, 1H), 5.79 (s, 2H), 4.30 (ddd, 1H), 2.99-3.16 (m, 4H), 2.47-2.70 (m, 4H), 1.64 (d, 2H).

LC/MS: mass calcd. for C$_{26}$H$_{21}$ClF$_6$N$_4$O$_2$S: 602.1. found 603.5 [M+1]$^+$ Example 151

[(2S)-2-{[(5Z)-5-({1-[4-Chloro-2-(trifluoromethyl)benzyl]-1H-indazol-5-yl}methylidene)-2,4-dioxo-1,3-thiazolidin-3-yl]methyl}pyrrolidin-1-yl]acetic acid

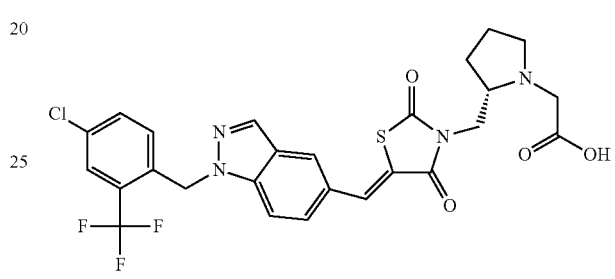

[(2S)-2-{[(5Z)-5-({1-[4-Chloro-2-(trifluoromethyl)benzyl]-1H-indazol-5-yl}methylidene)-2,4-dioxo-1,3-thiazolidin-3-yl]methyl}pyrrolidin-1-yl]acetic acid was prepared from (5Z)-5-({1-[4-chloro-2-(trifluoromethyl)benzyl]-1H-indazol-5-yl}methylidene)-3-[(2S)-pyrrolidin-2-ylmethyl]-1,3-thiazolidine-2,4-dione (Example 145) and tert-butyl bromoacetate using the same methods as described by Procedure I.

$^1$H NMR (400 MHz, CDCl$_3$): δ 8.96 (br. s., 2H), 8.20 (br. s., 1H), 8.00 (br. s., 1H), 7.91 (br. s., 1H), 7.71 (s, 1H), 7.45 (d, 1H), 7.32 (m, 2H), 6.66 (d, 1H), 5.76 (s, 2H), 3.81-4.55 (m, 6H), 3.37 (br. s., 1H), 1.91-2.45 (m, 4H).

LC/MS: mass calcd. for C$_{26}$H$_{22}$ClF$_3$N$_4$O$_4$S: 578.1. found 579.5 [M+1]$^+$ Example 152

(5Z)-5-({1-[4-Chloro-2-(trifluoromethyl)benzyl]-1H-indazol-5-yl}methylidene)-3-{[(2S)-1-(2-methoxyethyl)pyrrolidin-2-yl]methyl}-1,3-thiazolidine-2,4-dione

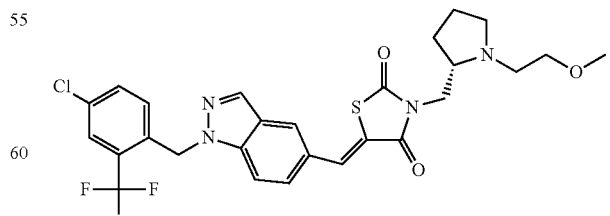

(5Z)-5-({1-[4-Chloro-2-(trifluoromethyl)benzyl]-1H-indazol-5-yl}methylidene)-3-{[(2S)-1-(2-methoxyethyl)pyrrolidin-2-yl]methyl}-1,3-thiazolidine-2,4-dione was prepared from (5Z)-5-({1-[4-chloro-2-(trifluoromethyl)benzyl]-1H-indazol-5-yl}methylidene)-3-[(2S)-pyrrolidin-2-ylmethyl]-1,3-thiazolidine-2,4-dione (Example 145) and 2-bromoethyl methyl ether following General Procedure S.

$^1$H NMR (400 MHz, CDCl$_3$): δ 8.24 (br. s., 1H), 8.05 (br. s., 1H), 7.97 (s, 1H), 7.72 (d, 1H), 7.51 (d, 1H), 7.31-7.39 (m, 2H), 6.70 (d, 1H), 5.80 (br. s., 2H), 4.26 (br. s., 2H), 3.86 (m, 3H), 3.68 (br. s., 2H), 3.51 (br. s., 2H), 3.40 (br. s., 3H), 3.22 (br. s., 1H), 2.20 (d, 2H), 2.06 (br. s., 1H).

LC/MS: mass calcd. for C$_{27}$H$_{26}$ClF$_3$N$_4$O$_3$S: 578.14. found 579.5 [M+1]$^+$

Example 153

(5Z)-5-({1-[4-Chloro-2-(trifluoromethyl)benzyl]-1H-indazol-5-yl}methylidene)-3-{[(2S)-1-(2-hydroxyethyl)pyrrolidin-2-yl]methyl}-1,3-thiazolidine-2,4-dione

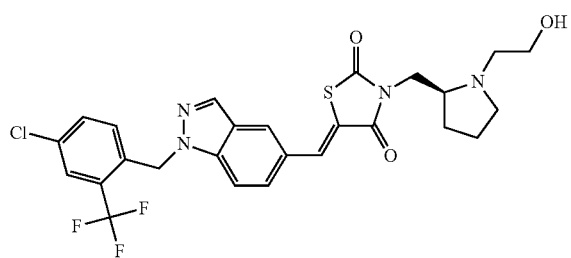 [SMILES: O=C1S/C(=C\c2ccc3c(cnn3Cc3ccc(Cl)cc3C(F)(F)F)c2)C(=O)N1C[C@@H]1CCCN1CCO]

(5Z)-5-({1-[4-Chloro-2-(trifluoromethyl)benzyl]-1H-indazol-5-yl}methylidene)-3-{[(2S)-1-(2-hydroxyethyl)pyrrolidin-2-yl]methyl}-1,3-thiazolidine-2,4-dione was prepared from (5Z)-5-({1-[4-chloro-2-(trifluoromethyl)benzyl]-1H-indazol-5-yl}methylidene)-3-[(2S)-pyrrolidin-2-ylmethyl]-1,3-thiazolidine-2,4-dione (Example 145) and 2-bromoethanol following General Procedure S.

$^1$H NMR (400 MHz, CDCl$_3$): δ 8.23 (s, 1H), 8.05 (br. s., 1H), 7.97 (s, 1H), 7.72 (s, 1H), 7.50 (d, 1H), 7.31-7.39 (m, 2H), 6.70 (d, 1H), 5.80 (s, 2H), 3.90-4.35 (m, 5H), 3.70 (br. s., 2H), 3.48 (br. s., 2H), 2.95-3.28 (m, 2H), 2.11-2.36 (m, 2H).

LC/MS: mass calcd. for C$_{26}$H$_{24}$ClF$_3$N$_4$O$_3$S: 564.12. found 565.4 [M+1]$^+$

Example 154

3-[(2S)-2-Aminobutyl]-(5Z)-5-({1-[4-chloro-2-(trifluoromethyl)benzyl]-1H-indazol-5-yl}methylidene)-1,3-thiazolidine-2,4-dione

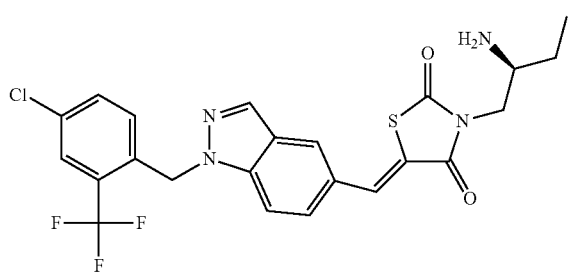 [SMILES: CC[C@H](N)CN1C(=O)S/C(=C\c2ccc3c(cnn3Cc3ccc(Cl)cc3C(F)(F)F)c2)C1=O]

(A) 3-[(2S)-2-(tert-butyloxycarbonyl)aminobutyl]-5-({1-[4-chloro-2-(trifluoromethyl)benzyl]-1H-indazol-5-yl}methylidene)-1,3-thiazolidine-2,4-dione was prepared from [(5Z)-5-({1-[4-chloro-2-(trifluoromethyl)benzyl]-1H-indazol-5-yl}methylidene)-2,4-dioxo-1,3-thiazolidine (from Example 1) and [(2S)-2-(tert-butyloxycarbonyl)amino]butan-1-ol following General Procedure J.

(B) 3-[(2S)-2-Aminobutyl]-(5Z)-5-({1-[4-chloro-2-(trifluoromethyl)benzyl]-1H-indazol-5-yl}methylidene)-1,3-thiazolidine-2,4-dione was prepared from 3[(2S)-2-(tert-butyloxycarbonyl)aminobutyl]-5-({1-[4-chloro-2-(trifluoromethyl)benzyl]-1H-indazol-5-yl}methylidene)-1,3-thiazolidine-2,4-dione following General Procedure M.

$^1$H NMR (400 MHz, CDCl$_3$): δ 8.22 (s, 1H), 8.02 (s, 1H), 7.97 (s, 1H), 7.72 (d, 1H), 7.51 (dd, 1H), 7.36 (s, 1H), 7.34 (s, 1H), 6.68 (d, 1H), 5.80 (s, 2H), 3.64-3.80 (m, 2H), 3.05 (br. s., 1H), 1.50-1.66 (m, 1H), 1.17-1.41 (m, 3H), 0.96-1.06 (m, 3H).

LC/MS: mass calcd. for C$_{23}$H$_{20}$ClF$_3$N$_4$O$_2$S: 508.09. found 509.3 [M+1]$^+$

Example 155

3-[(2S)-2-Aminopropyl]-(5Z)-5-({1-[4-chloro-2-(trifluoromethyl)benzyl]-1H-indazol-5-yl}methylidene)-1,3-thiazolidine-2,4-dione

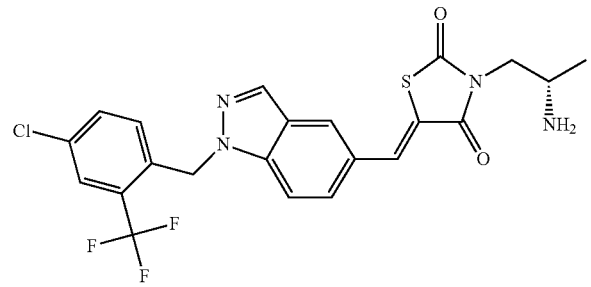 [SMILES: C[C@H](N)CN1C(=O)S/C(=C\c2ccc3c(cnn3Cc3ccc(Cl)cc3C(F)(F)F)c2)C1=O]

(A) 3-[(2S)-2-(tert-butyloxycarbonyl)aminopropyl]-5-({1-[4-chloro-2-(trifluoromethyl)benzyl]-1H-indazol-5-yl}methylidene)-1,3-thiazolidine-2,4-dione was prepared from [(5Z)-5-({1-[4-chloro-2-(trifluoromethyl)benzyl]-1H-indazol-5-yl}methylidene)-2,4-dioxo-1,3-thiazolidine (from Example 1) and [(2S)-2-(tert-butyloxycarbonyl)amino]propan-1-ol following General Procedure J.

(B) 3-[(2S)-2-Aminopropyl]-(5Z)-5-({1-[4-chloro-2-(trifluoromethyl)benzyl]-1H-indazol-5-yl}methylidene)-1,3-thiazolidine-2,4-dione was prepared from 3-[(2S)-2-(tert-butyloxycarbonyl)aminopropyl]-5-({1-[4-chloro-2-(trifluoromethyl)benzyl]-1H-indazol-5-yl}methylidene)-1,3-thiazolidine-2,4-dione following General Procedure M.

$^1$H NMR (400 MHz, CDCl$_3$): δ 8.22 (s, 1H), 8.03 (s, 1H), 7.97 (s, 1H), 7.72 (d, 1H), 7.51 (dd, 1H), 7.30-7.39 (m, 2H), 6.68 (d, 1H), 5.80 (s, 2H), 3.69 (d, 2H), 3.32 (m, 1H), 1.22-1.39 (m, 2H), 1.17 (d, 3H).

LC/MS: mass calcd. for C$_{22}$H$_{18}$ClF$_3$N$_4$O$_2$S, 494.08. found 495.3 [M+1]$^+$

Example 156

N-[(1S)-1-{[(5Z)-5-({1-[4-Chloro-2-(trifluoromethyl)benzyl]-1H-indazol-5-yl}methylidene)-2,4-dioxo-1,3-thiazolidin-3-yl]methyl}propyl]methanesulfonamide

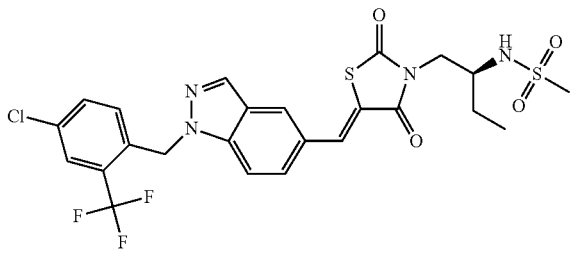 [SMILES: CC[C@@H](CN1C(=O)S/C(=C\c2ccc3c(cnn3Cc3ccc(Cl)cc3C(F)(F)F)c2)C1=O)NS(C)(=O)=O]

N-[(1S)-1-{[(5Z)-5-({1-[4-Chloro-2-(trifluoromethyl)benzyl]-1H-indazol-5-yl}methylidene)-2,4-dioxo-1,3-thiazolidin-3-yl]methyl}propyl]methanesulfonamide was prepared from 3-[(2S)-2-aminobutyl]-(5Z)-5-({1-[4-chloro-2-(trifluoromethyl)benzyl]-1H-indazol-5-yl}methylidene)-1,3-thiazolidine-2,4-dione (Example 154) and methanesulfonyl chloride following General Procedure U.

$^1$H NMR (400 MHz, CDCl$_3$): δ 8.21 (s, 1H), 8.04 (s, 1H), 7.98 (s, 1H), 7.72 (d, 1H), 7.52 (dd, 1H), 7.35 (s, 1H), 7.33 (s, 1H), 6.65 (d, 1H), 5.80 (s, 2H), 4.64 (d, 1H), 3.67-3.92 (m, 3H), 2.91 (s, 3H), 1.66-1.81 (m, 1H), 1.48-1.65 (m, 1H), 1.09 (t, 3H).

LC/MS: mass calcd. for $C_{24}H_{22}ClF_3N_4O_4S_2$: 586.07. found 587.4 [M+1]$^+$

Example 157

N-{(1S)-2-[(5Z)-5-({1-[4-Chloro-2-(trifluoromethyl)benzyl]-1H-indazol-5-yl}methylidene)-2,4-dioxo-1,3-thiazolidin-3-yl]-1-methylethyl}methanesulfonamide

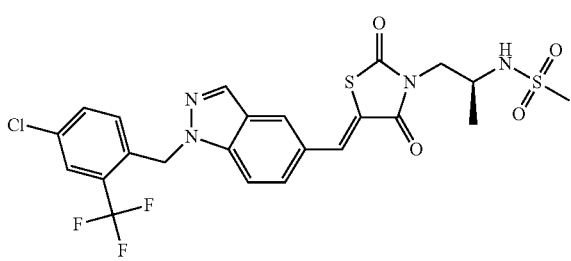 [SMILES: C[C@@H](CN1C(=O)S/C(=C\c2ccc3c(cnn3Cc3ccc(Cl)cc3C(F)(F)F)c2)C1=O)NS(C)(=O)=O]

N-[(1S)-1-{[(5Z)-5-({1-[4-Chloro-2-(trifluoromethyl)benzyl]-1H-indazol-5-yl}methylidene)-2,4-dioxo-1,3-thiazolidin-3-yl]-1-methylethyl}methanesulfonamide was prepared from 3-[(2S)-2-aminopropyl]-(5Z)-5-({1-[4-chloro-2-(trifluoromethyl)benzyl]-1H-indazol-5-yl}methylidene)-1,3-thiazolidine-2,4-dione (Example 155) and methanesulfonyl chloride following General Procedure U.

$^1$H NMR (400 MHz, CDCl$_3$): δ 8.22 (s, 1H), 8.05 (s, 1H), 7.98 (s, 1H), 7.72 (d, 1H), 7.52 (dd, 1H), 7.36 (s, 1H), 7.34 (s, 1H), 6.66 (d, 1H), 5.80 (s, 2H), 4.68 (d, 1H), 3.90-3.99 (m, 1H), 3.82-3.90 (m, 1H), 3.70-3.80 (m, 1H), 2.91 (s, 3H), 1.35 (d, 3H).

LC/MS: mass calcd. for $C_{23}H_{20}ClF_3N_4O_4S_2$: 572.06. found 573.4 [M+1]$^+$

Example 158

N-{2-[(5Z)-5-({1-[4-Chloro-2-(trifluoromethyl)benzyl]-1H-indazol-5-yl}methylidene)-2,4-dioxo-1,3-thiazolidin-3-yl]ethyl}methanesulfonamide

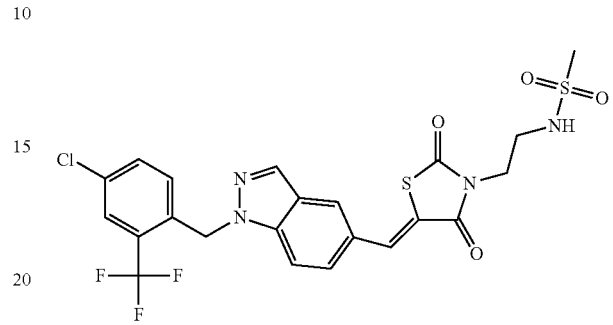

N-{2-[(5Z)-5-({1-[4-Chloro-2-(trifluoromethyl)benzyl]-1H-indazol-5-yl}methylidene)-2,4-dioxo-1,3-thiazolidin-3-yl]ethyl}methanesulfonamide was prepared from 3-(2-aminoethyl)-(5Z)-5-({1-[4-chloro-2-(trifluoromethyl)benzyl]-1H-indazol-5-yl}methylidene)-1,3-thiazolidine-2,4-dione (Example 49) and methanesulfonyl chloride following General Procedure U.

$^1$H NMR (400 MHz, CDCl$_3$): δ 8.23 (s, 1H), 8.05 (s, 1H), 7.99 (s, 1H), 7.72 (d, 1H), 7.52 (dd, 1H), 7.33-7.41 (m, 2H), 6.66 (d, 1H), 5.80 (s, 2H), 3.95 (t, 2H), 3.46 (t, 2H), 3.42 (br. s., 1H), 2.96 (s, 3H).

LC/MS: mass calcd. for $C_{22}H_{18}ClF_3N_4O_4S_2$: 558.04. found 559.3 [M+1]$^+$

Example 159

(5Z)-5-({1-[4-Chloro-2-(trifluoromethyl)benzyl]-1H-indazol-5-yl}methylidene)-3-({(2S)-1-[2-(methylsulfonyl)ethyl]pyrrolidin-2-yl}methyl)-1,3-thiazolidine-2,4-dione

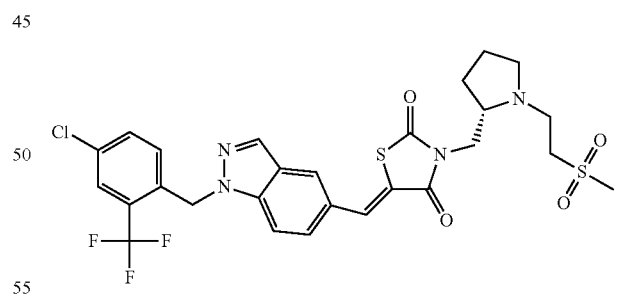

(5Z)-5-({1-[4-Chloro-2-(trifluoromethyl)benzyl]-1H-indazol-5-yl}methylidene)-3-({(2S)-1-[2-(methylsulfonyl)ethyl]pyrrolidin-2-yl}methyl)-1,3-thiazolidine-2,4-dione was prepared from (5Z)-5-({1-[4-chloro-2-(trifluoromethyl)benzyl]-1H-indazol-5-yl}methylidene)-3-[(2S)-pyrrolidin-2-ylmethyl]-1,3-thiazolidine-2,4-dione (Example 145) and 2-(methylsulfonyl)ethyl methanesulfonate (prepared as described in WO 2006/047277) following General Procedure S.

$^1$H NMR (400 MHz, CDCl$_3$): δ 8.14 (s, 1H), 8.12 (s, 1H), 7.60-7.75 (m, 2H), 7.33 (dd, 1H), 7.19-7.25 (m, 2H), 6.62 (d,

1H), 5.78 (s, 2H), 4.05-4.18 (m, 1H), 3.87-3.99 (m, 1H), 3.61 (dt, 1H), 3.41 (ddd, 1H), 3.15-3.32 (m, 2H), 2.90-3.13 (m, 2H), 2.80 (s, 3H), 2.09-2.25 (m, 2H), 1.93-2.07 (m, 1H), 1.45-1.65 (m, 2H).

LC/MS: mass calcd. for $C_{27}H_{26}ClF_3N_4O_4S_2$: 626.1. found 627.4 $[M+1]^+$

Example 160

N-tert-Butyl-1-[(5Z)-5-({1-[4-chloro-2-(trifluoromethyl)benzyl]-1H-indazol-5-yl}methylidene)-2,4-dioxo-1,3-thiazolidin-3-yl]methanesulfonamide

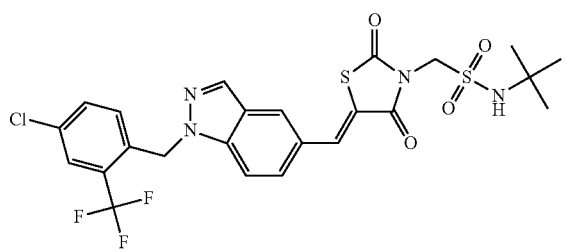 [SMILES: CC(C)(C)NS(=O)(=O)CN1C(=O)S/C(=C\c2ccc3c(cnn3Cc3ccc(Cl)cc3C(F)(F)F)c2)C1=O]

N-tert-Butyl-1-[(5Z)-5-({1-[4-chloro-2-(trifluoromethyl)benzyl]-1H-indazol-5-yl}methylidene)-2,4-dioxo-1,3-thiazolidin-5-yl]methanesulfonamide was prepared from [(5Z)-5-({1-[4-chloro-2-(trifluoromethyl)benzyl]-1H-indazol-5-yl}methylidene)-2,4-dioxo-1,3-thiazolidine (from Example 1) and N-tert-butyl-1-chloromethanesulfonamide following General Procedure H.

$^1$H NMR (400 MHz, CDCl$_3$): δ 8.23 (s, 1H), 8.09 (s, 1H), 7.97 (s, 1H), 7.72 (d, 1H), 7.50 (dd, 1H), 7.30-7.40 (m, 2H), 6.69 (d, 1H), 5.80 (s, 2H), 5.05 (s, 2H), 4.33 (s, 1H), 1.45 (s, 9H).

LC/MS: mass calcd. for $C_{24}H_{22}ClF_3N_4O_4S_2$: 586.07. found 587.1 $[M+1]^+$

Example 161

(5Z)-3-[(2S)-2-Amino-2-phenylethyl]-5-({1-[4-chloro-2-(trifluoromethyl)benzyl]-1H-indazol-5-yl}methylidene)-1,3-thiazolidine-2,4-dione

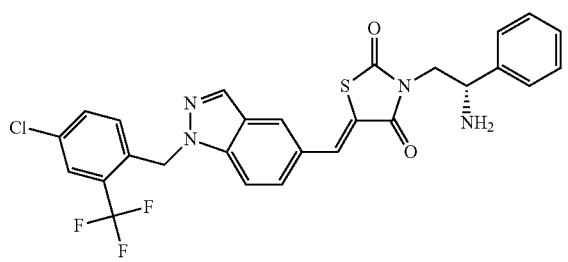 [SMILES: N[C@H](CN1C(=O)S/C(=C\c2ccc3c(cnn3Cc3ccc(Cl)cc3C(F)(F)F)c2)C1=O)c1ccccc1]

(A) (5Z)-3-[(2S)-2-(tert-butyloxycarbonyl)amino-2-phenylethyl]-5-({1-[4-chloro-2-(trifluoromethyl)benzyl]-1H-indazol-5-yl}methylidene)-1,3-thiazolidine-2,4-dione was prepared from [(5Z)-5-({1-[4-chloro-2-(trifluoromethyl)benzyl]-1H-indazol-5-yl}methylidene)-2,4-dioxo-1,3-thiazolidine (from Example 1) and [(2S)-2-(tert-butyloxycarbonyl)amino]-2-phenylethan-1-ol following General Procedure J.

(B) (5Z)-3-[(2S)-2-Amino-2-phenylethyl]-5-({1-[4-chloro-2-(trifluoromethyl)benzyl]-1H-indazol-5-yl}methylidene)-1,3-thiazolidine-2,4-dione was prepared from (5Z)-3-[(2S)-2-(tert-butyloxycarbonyl)amino-2-phenylethyl]-5-({1-[4-chloro-2-(trifluoromethyl)benzyl]-1H-indazol-5-yl}methylidene)-1,3-thiazolidine-2,4-dione following General Procedure M.

$^1$H NMR (400 MHz, CDCl$_3$): δ 8.21 (s, 1H), 8.01 (s, 1H), 7.96 (s, 1H), 7.71 (s, 1H), 7.47-7.54 (m, 1H), 7.27-7.46 (m, 7H), 6.67 (d, 1H), 5.79 (s, 2H), 4.36 (dd, 1H), 3.81-4.03 (m, 2H), 1.70 (br. s., 2H).

LC/MS: mass calcd. for $C_{27}H_{20}ClF_3N_4O_2S$: 556.09. found 557.2 $[M+1]^+$

Example 162

(5Z)-3-[(2S)-2-Amino-3-methylbutyl]-5-({1-[4-chloro-2-(trifluoromethyl)benzyl]-1H-indazol-5-yl}methylidene)-1,3-thiazolidine-2,4-dione

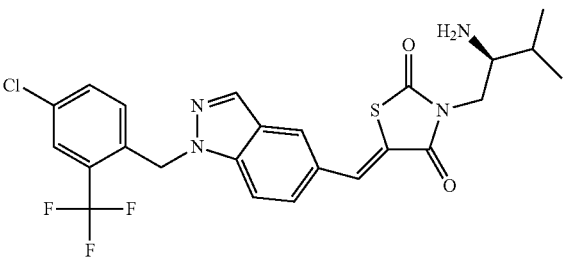 [SMILES: CC(C)[C@H](N)CN1C(=O)S/C(=C\c2ccc3c(cnn3Cc3ccc(Cl)cc3C(F)(F)F)c2)C1=O]

(A) (5Z)-3-[(2S)-2-(tert-butyloxycarbonyl)amino-3-methylbutyl]-5-({1-[4-chloro-2-(trifluoromethyl)benzyl]-1H-indazol-5-yl}methylidene)-1,3-thiazolidine-2,4-dione was prepared from [(5Z)-5-({1-[4-chloro-2-(trifluoromethyl)benzyl]-1H-indazol-5-yl}methylidene)-2,4-dioxo-1,3-thiazolidine (from Example 1) and [(2S)-2-(tert-butyloxycarbonyl)amino]-3-methylbutan-1-ol following General Procedure J.

(B) (5Z)-3-[(2S)-2-Amino-3-methylbutyl]-5-({1-[4-chloro-2-(trifluoromethyl)benzyl]-1H-indazol-5-yl}methylidene)-1,3-thiazolidine-2,4-dione was prepared from (5Z)-3-[(2S)-2-(tert-butyloxycarbonyl)amino-3-methylbutyl]-5-({1-[4-chloro-2-(trifluoromethyl)benzyl]-1H-indazol-5-yl}methylidene)-1,3-thiazolidine-2,4-dione following General Procedure M.

$^1$H NMR (400 MHz, CDCl$_3$): δ 8.21 (s, 1H), 8.02 (s, 1H), 7.96 (s, 1H), 7.71 (s, 1H), 7.51 (d, 1H), 7.35 (s, 1H), 7.33 (s, 1H), 6.67 (d, 1H), 5.79 (s, 2H), 3.66-3.80 (m, 2H), 2.96 (dt, 1H), 1.63-1.78 (m, 1H), 1.45 (br. s., 2H), 1.01 (d, 3H), 0.98 (d, 3H).

LC/MS: mass calcd. for $C_{24}H_{22}ClF_3N_4O_2S$: 522.11. found 523.2 $[M+1]^+$

Example 163

(5Z)-5-({1-[4-Chloro-2-(trifluoromethyl)benzyl]-1H-indazol-5-yl}methylidene)-3-(2-piperazin-1-ylethyl)-1,3-thiazolidine-2,4-dione

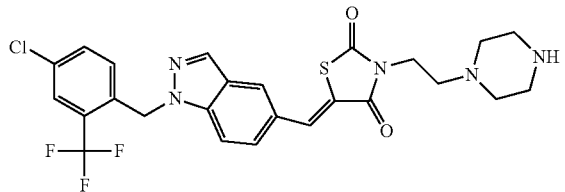 [SMILES: O=C1S/C(=C\c2ccc3c(cnn3Cc3ccc(Cl)cc3C(F)(F)F)c2)C(=O)N1CCN1CCNCC1]

(A) 1,1-Dimethylethyl 4-[{(5Z)-5-[(1-{[4-chloro-2-(trifluoromethyl)phenyl]-methyl}-1H-indazol-5-yl)methylidene]-2,4-dioxo-1,3-thiazolidin-3-yl}-ethyl]piperazine-1-carboxylate was prepared from (5Z)-5-({1-[4-chloro-2-(trifluoromethyl)benzyl]-1H-indazol-5-yl}methylidene)-2,4-dioxo-1,3-thiazolidine (from Example 1) and 1,1-dimethylethyl 4-(2-hydroxyethyl)piperazine-1-carboxylate following General Procedure J.

(B) (5Z)-5-({1-[4-Chloro-2-(trifluoromethyl)benzyl]-1H-indazol-5-yl}methylidene)-3-(2-piperazin-1-ylethyl)-1,3-thiazolidine-2,4-dione was prepared from 1,1-dimethylethyl 4-[{(5Z)-5-[(1-{[4-chloro-2-(trifluoromethyl)phenyl]methyl}-1H-indazol-5-yl)methylidene]-2,4-dioxo-1,3-thiazolidin-3-yl}ethyl]piperazine-1-carboxylate following General Procedure M.

$^1$H NMR (400 MHz, CDCl$_3$): δ 8.22 (s, 1H), 8.01 (s, 1H), 7.97 (s, 1H), 7.71 (s, 1H), 7.52 (dd, 1H), 7.29-7.40 (m, 2H), 6.67 (d, 1H), 5.80 (s, 2H), 3.90 (t, 2H), 2.76-2.90 (m, 4H), 2.62 (t, 2H), 2.49 (br. s., 4H), 1.74 (br. s., 1H).

LC/MS: mass calcd. for C$_{25}$H$_{23}$ClF$_3$N$_5$O$_2$S: 549.12. found 550.2 [M+1]$^+$

Example 164

(5Z)-5-({1-[4-Chloro-2-(trifluoromethyl)benzyl]-1H-indazol-5-yl}methylidene)-3-(2-piperidin-4-ylethyl)-1,3-thiazolidine-2,4-dione

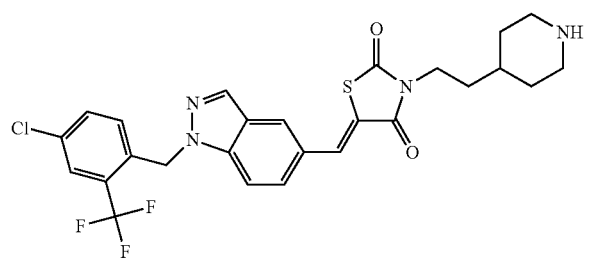 [SMILES: O=C1S/C(=C\c2ccc3c(cnn3Cc3ccc(Cl)cc3C(F)(F)F)c2)C(=O)N1CCC1CCNCC1]

(A) 1,1-Dimethylethyl 4-[{(5Z)-5-[(1-{[4-chloro-2-(trifluoromethyl)phenyl]-methyl}-1H-indazol-5-yl)methylidene]-2,4-dioxo-1,3-thiazolidin-3-yl}-ethyl]piperidine-1-carboxylate was prepared from (5Z)-5-({1-[4-chloro-2-(trifluoromethyl)benzyl]-1H-indazol-5-yl}methylidene)-2,4-dioxo-1,3-thiazolidine (from Example 1) and 1,1-dimethylethyl 4-(2-hydroxyethyl)piperidine-1-carboxylate following General Procedure J.

(B) (5Z)-5-({1-[4-Chloro-2-(trifluoromethyl)benzyl]-1H-indazol-5-yl}methylidene)-3-(2-piperidin-4-ylethyl)-1,3-thiazolidine-2,4-dione was prepared from 1,1-dimethylethyl 4-[{(5Z)-5-[(1-{[4-chloro-2-(trifluoromethyl)phenyl]methyl}-1H-indazol-5-yl)methylidene]-2,4-dioxo-1,3-thiazolidin-3-yl}ethyl]piperidine-1-carboxylate following General Procedure M.

$^1$H NMR (400 MHz, CDCl$_3$): δ 8.21 (s, 1H), 8.01 (s, 1H), 7.96 (s, 1H), 7.71 (s, 1H), 7.51 (d, 1H), 7.30-7.39 (m, 2H), 6.68 (d, 1H), 5.80 (s, 2H), 3.80 (t, 2H), 3.08 (d, 2H), 2.60 (br. s., 2H), 1.78 (br. s., 3H), 1.62 (q, 2H), 1.34-1.51 (m, 1H), 1.10-1.30 (m, 2H).

LC/MS: mass calcd. for C$_{26}$H$_{24}$ClF$_3$N$_4$O$_2$S: 548.13. found 549.2 [M+1]$^+$

Example 165

1-[(5Z)-5-({1-[4-Chloro-2-(trifluoromethyl)benzyl]-1H-indazol-5-yl}methylidene)-2,4-dioxo-1,3-thiazolidin-3-yl]methanesulfonamide

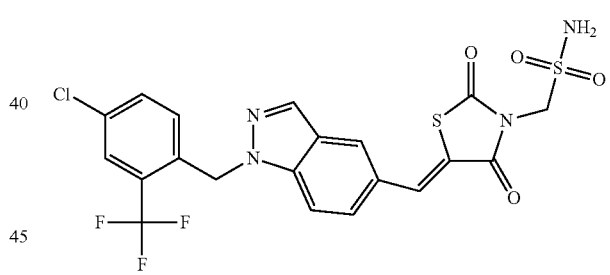

1-[(5Z)-5-({1-[4-Chloro-2-(trifluoromethyl)benzyl]-1H-indazol-5-yl}methylidene)-2,4-dioxo-1,3-thiazolidin-3-yl]methanesulfonamide was prepared from N-tert-butyl-1-[(5Z)-5-({1-[4-chloro-2-(trifluoromethyl)-benzyl]-1H-indazol-5-yl}methylidene)-2,4-dioxo-1,3-thiazolidin-3-yl]methanesulfonamide (Example 160) using the same method as described in General Procedure M, but at a reaction temperature of 50° C.

$^1$H NMR (400 MHz, CDCl$_3$): δ 8.24 (s, 1H), 8.10 (s, 1H), 7.99 (s, 1H), 7.73 (d, 1H), 7.52 (d, 1H), 7.33-7.42 (m, 2H), 6.69 (d, 1H), 5.80 (s, 2H), 5.10 (s, 2H).

LC/MS: mass calcd. for C$_{20}$H$_{13}$ClF$_3$N$_4$O$_4$S$_2$: 530.01. found 531.1 [M+1]$^+$

Example 166

N-({[(5Z)-5-({1-[4-Chloro-2-(trifluoromethyl)benzyl]-1H-indazol-5-yl}methylidene)-2,4-dioxo-1,3-thiazolidin-3-yl]methyl}sulfonyl)acetamide

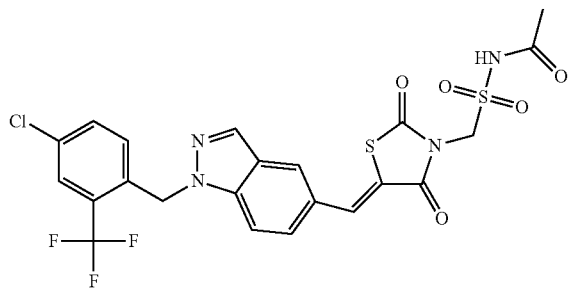 [SMILES: CC(=O)NS(=O)(=O)CN1C(=O)S/C(=C\c2ccc3c(cnn3Cc3ccc(Cl)cc3C(F)(F)F)c2)C1=O]

N-({[(5Z)-5-({1-[4-Chloro-2-(trifluoromethyl)benzyl]-1H-indazol-5-yl}methylidene)-2,4-dioxo-1,3-thiazolidin-3-yl]methyl}sulfonyl)acetamide was prepared from 1-[(5Z)-5-({1-[4-chloro-2-(trifluoromethyl)benzyl]-1H-indazol-5-yl}methylidene)-2,4-dioxo-1,3-thiazolidin-3-yl]methanesulfonamide (Example 165) following General Procedure V.

$^1$H NMR (400 MHz, DMSO-d$_6$): δ 12.04 (br. s., 1H), 8.37 (s, 1H), 8.21 (s, 1H), 8.19 (s, 1H), 7.87 (d, 1H), 7.78-7.83 (m, 1H), 7.68-7.73 (m, 1H), 7.64 (dd, 1H), 6.78 (d, 1H), 5.86 (s, 2H), 5.22 (s, 2H), 1.98 (s, 3H).

LC/MS: mass calcd. for C$_{22}$H$_{16}$ClF$_3$N$_4$O$_6$S$_2$: 572.02. found 573.0 [M+1]$^+$

Example 167

(5Z)-3-[(2R)-2-Amino-3-hydroxypropyl]-5-({1-[4-chloro-2-(trifluoromethyl)benzyl]-1H-indazol-5-yl}methylidene)-1,3-thiazolidine-2,4-dione

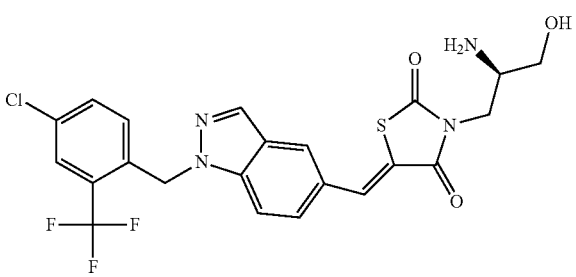 [SMILES: N[C@@H](CO)CN1C(=O)S/C(=C\c2ccc3c(cnn3Cc3ccc(Cl)cc3C(F)(F)F)c2)C1=O]

(A) 1,1-Dimethylethyl (4R)-4-[{(5Z)-5-[(1-{[4-Chloro-2-(trifluoromethyl)phenyl]-methyl}-1H-indazol-5-yl)methylidene]-2,4-dioxo-1,3-thiazolidin-3-yl}-methyl]-2,2-dimethyloxazolidine-3-carboxylate was prepared from (5Z)-5-({1-[4-chloro-2-(trifluoromethyl)benzyl]-1H-indazol-5-yl}methylidene)-2,4-dioxo-1,3-thiazolidine (from Example 1) and 1,1-dimethylethyl (4R)-4-hydroxymethyl-2,2-dimethyloxazolidine-3-carboxylate following General Procedure J.

(B) (5Z)-3-[(2R)-2-Amino-3-hydroxypropyl]-5-({1-[4-chloro-2-(trifluoromethyl)benzyl]-1H-indazol-5-yl}methylidene)-1,3-thiazolidine-2,4-dione was prepared from 1,1-dimethylethyl (4R)-4-[{(5Z)-5-[(1-{[4-chloro-2-(trifluoromethyl)phenyl]methyl}-1H-indazol-5-yl)methylidene]-2,4-dioxo-1,3-thiazolidin-3-yl}methyl]-2,2-dimethyloxazolidine-3-carboxylate following General Procedure M.

$^1$H NMR (400 MHz, CDCl$_3$): δ 8.22 (s, 1H), 8.04 (s, 1H), 7.97 (s, 1H), 7.71 (d, 1H), 7.47-7.54 (m, 1H), 7.30-7.39 (m, 2H), 6.68 (d, 1H), 5.79 (s, 2H), 3.83 (d, 2H), 3.42-3.60 (m, 2H), 3.20 (t, 1H), 2.17 (s, 1H), 2.01 (s, 2H).

LC/MS: mass calcd. for C$_{22}$H$_{18}$ClF$_3$N$_4$O$_3$S: 510.07. found 511.2 [M+1]$^+$

Example 168

(5Z)-3-[(2S)-2-Amino-3-methoxypropyl]-5-({1-[4-chloro-2-(trifluoromethyl)benzyl]-1H-indazol-5-yl}methylidene)-1,3-thiazolidine-2,4-dione

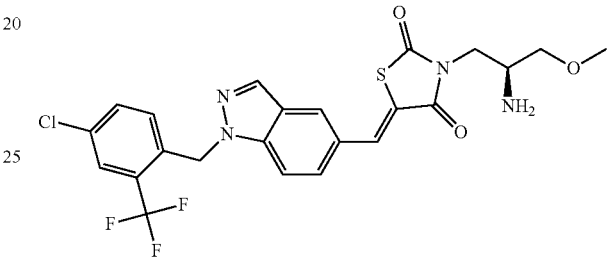

(A) To a solution of 1,1-dimethylethyl (4R)-4-hydroxymethyl-2,2-dimethyloxazolidine-3-carboxylate (1 mmol) in DMF (5 mL) was added sodium hydride (1.1 equiv), and the mixture was stirred at rt for 30 min. Iodomethane (1.2 equiv) was then added and the mixture was stirred for 1 h. The reaction was diluted with EtOAc, extracted with water (3×), dried (anhydrous Na$_2$SO$_4$) and concentrated to afford 1,1-dimethylethyl (4R)-4-methoxymethyl-2,2-dimethyl-oxazolidine-3-carboxylate.

(B) A solution of 1,1-dimethylethyl (4R)-4-methoxymethyl-2,2-dimethyloxazolidine-3-carboxylate (0.95 mmol) and p-toluenesulfonic acid (2 equiv) in methanol (5 mL) was stirred at rt for 5 h. The reaction was concentrated in vacuo and the resultant residue was purified by silica gel chromatography (EtOAc/hexane) to afford 1,1-dimethylethyl (1S)-(2-hydroxy-1-methoxymethylethyl)carbamate.

(C) (5Z)-3-[(2S)-2-tert-butoxycarbonylamino-3-methoxypropyl]-5-({1-[4-chloro-2-(trifluoromethyl)benzyl]-1H-indazol-5-yl}methylidene)-1,3-thiazolidine-2,4-dione was prepared from (5Z)-5-({1-[4-chloro-2-(trifluoromethyl)-benzyl]-1H-indazol-5-yl}methylidene)-2,4-dioxo-1,3-thiazolidine (from Example 1) and 1,1-dimethylethyl (1S)-(2-hydroxy-1-methoxymethylethyl)-carbamate following General Procedure J.

(D) (5Z)-3-[(2S)-2-Amino-3-methoxypropyl]-5-({1-[4-chloro-2-(trifluoromethyl)benzyl]-1H-indazol-5-yl}methylidene)-1,3-thiazolidine-2,4-dione was prepared from (5Z)-3-[(2S)-2-tert-butoxycarbonylamino-3-methoxypropyl]-5-({1-[4-chloro-2-(trifluoromethyl)benzyl]-1H-indazol-5-yl}methylidene)-1,3-thiazolidine-2,4-dione following General Procedure M.

$^1$H NMR (400 MHz, CDCl$_3$): δ 8.22 (s, 1H), 8.02 (s, 1H), 7.97 (s, 1H), 7.72 (d, 1H), 7.47-7.55 (m, 1H), 7.35 (d, 2H), 6.68 (d, 1H), 5.80 (s, 2H), 3.78-3.83 (m, 2H), 3.48 (s, 3H), 3.29-3.45 (m, 5H).

LC/MS: mass calcd. for $C_{23}H_{20}ClF_3N_4O_3S$: 524.09. found 525.2 [M+1]$^+$

Example 169

(5Z)-3-(2-Amino-3,3,3-trifluoropropyl)-5-({1-[4-chloro-2-(trifluoromethyl)benzyl]-1H-indazol-5-yl}methylidene)-1,3-thiazolidine-2,4-dione

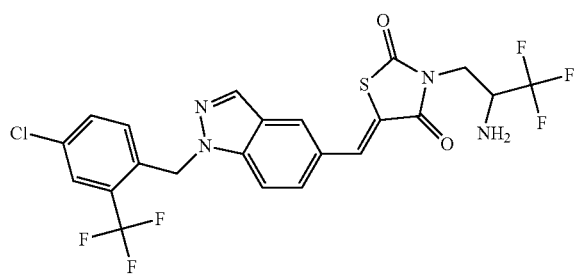 [SMILES: NC(CN1C(=O)S/C(=C\c2ccc3c(cnn3Cc3ccc(Cl)cc3C(F)(F)F)c2)C1=O)C(F)(F)F]

(A) 1,1-Dimethylethyl [2-{(5Z)-5-[(1-{[4-chloro-2-(trifluoromethyl)phenyl]-methyl}-1H-indazol-5-yl)methylidene]-2,4-dioxo-1,3-thiazolidin-3-yl}-1-(trifluoromethyl)ethyl]carbamate was prepared from [(5Z)-5-({1-[4-chloro-2-(trifluoromethyl)benzyl]-1H-indazol-5-yl}methylidene)-2,4-dioxo-1,3-thiazolidine (from Example 1) and 2-tert-butoxycarbonylamino-3,3,3-trifluoropropanol following General Procedure J.

(B) (5Z)-3-(2-Amino-3,3,3-trifluoropropyl)-5-({1-[4-chloro-2-(trifluoromethyl)benzyl]-1H-indazol-5-yl}methylidene)-1,3-thiazolidine-2,4-dione was prepared by the deprotection of 1,1-dimethylethyl [2-{(5Z)-5-[(1-{[4-chloro-2-(trifluoromethyl)phenyl]methyl}-1H-indazol-5-yl)methylidene]-2,4-dioxo-1,3-thiazolidin-3-yl}-1-(trifluoromethyl)ethyl]-carbamate following General Procedure M.

$^1$H NMR (400 MHz, CDCl$_3$): δ 8.22 (s, 1H), 8.05 (s, 1H), 7.97 (s, 1H), 7.72 (d, 1H), 7.48-7.55 (m, 1H), 7.30-7.40 (m, 2H), 6.68 (d, 1H), 5.80 (s, 2H), 3.96 (d, 2H), 3.62-3.75 (m, 1H).

LC/MS: mass calcd. for $C_{22}H_{15}ClF_6N_4O_2S$: 548.05. found 549.1 [M+1]$^+$

Example 170

(5Z)-5-({1-[4-Chloro-2-(trifluoromethyl)benzyl]-1H-indazol-5-yl}methylidene)-3-[(3S)-morpholin-3-ylmethyl]-1,3-thiazolidine-2,4-dione

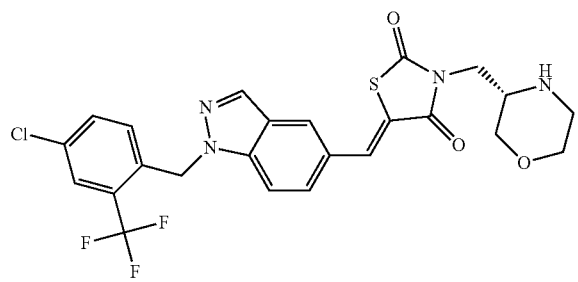 [SMILES: O=C1S/C(=C\c2ccc3c(cnn3Cc3ccc(Cl)cc3C(F)(F)F)c2)C(=O)N1C[C@H]1COCCN1]

(A) 1,1-Dimethylethyl (3S)-3-[{(5Z)-5-[(1-{[4-chloro-2-(trifluoromethyl)phenyl]-methyl}-1H-indazol-5-yl) methylidene]-2,4-dioxo-1,3-thiazolidin-3-yl}methyl] morpholine-1-carboxylate was prepared from (5Z)-5-({1-[4-chloro-2-(trifluoromethyl)benzyl]-1H-indazol-5-yl}methylidene)-2,4-dioxo-1,3-thiazolidine (from Example 1) and 1,1-dimethylethyl (3S)-3-(hydroxymethyl)morpholine-1-carboxylate following General Procedure J.

(B) (5Z)-5-({1-[4-Chloro-2-(trifluoromethyl)benzyl]-1H-indazol-5-yl}methylidene)-3-[(3S)-morpholin-3-ylmethyl]-1,3-thiazolidine-2,4-dione was prepared from 1,1-dimethylethyl (3S)-3-[{(5Z)-5-[(1-{[4-chloro-2-(trifluoromethyl)phenyl]-methyl}-1H-indazol-5-yl) methylidene]-2,4-dioxo-1,3-thiazolidin-3-yl}methyl] morpholine-1-carboxylate following General Procedure M.

$^1$H NMR (400 MHz, CDCl$_3$): δ 8.22 (s, 1H), 8.02 (s, 1H), 7.96 (s, 1H), 7.72 (d, 1H), 7.45-7.54 (m, 1H), 7.31-7.39 (m, 2H), 6.68 (d, 1H), 5.79 (s, 2H), 3.67-3.90 (m, 4H), 3.48-3.58 (m, 1H), 3.27-3.38 (m, 1H), 3.13-3.23 (m, 1H), 2.82-3.02 (m, 2H), 1.72 (br. s., 1H).

LC/MS: mass calcd. for $C_{24}H_{20}ClF_3N_4O_3S$: 536.09. found 537.1 [M+1]$^+$

Example 171

Methyl [(5Z)-5-({1-[(1S)-5-chloro-2,3-dihydro-1H-inden-1-yl]-1H-indazol-5-yl}methylidene)-2,4-dioxo-1,3-thiazolidin-3-yl]acetate

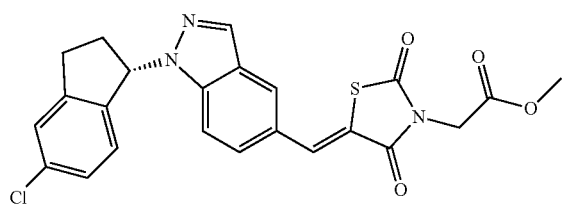 [SMILES: COC(=O)CN1C(=O)S/C(=C\c2ccc3c(cnn3[C@H]3CCc4cc(Cl)ccc43)c2)C1=O]

(A) To a mixture of 5-chloroindan-1-one (3.13 mmol) and (2S)-2-[([1,3,2]dioxaborolan-2-yloxy)diphenylmethyl]pyrrolidine (0.31 mmol, prepared following General the procedure described in *Eur. J. Org. Chem.* 1999, 1775-1786) in THF (10 mL) was added BH$_3$.DMS complex (0.7 equiv). The mixture was stirred at rt for 3 h, and diluted with EtOAc. The organic solution was extracted with water (3×), dried (Na$_2$SO$_4$) and concentrated. The resultant residue was purified by silica gel chromatography (EtOAc/hexane) to afford (1R)-5-chloro-2,3-dihydro-1H-inden-1-ol.

(B) (1S)-(5-chloroindan-1-yl)-1H-indazole-5-carbonitrile was prepared from 1H-indazole-5-carbonitrile and (1R)-5-chloro-2,3-dihydro-1H-inden-1-ol following General Procedure W.

(C) To a cooled solution (−78° C.) of (1S)-(5-chloroindan-1-yl)-1H-indazole-5-carbonitrile (1 mmol) in anhydrous toluene (10 mL) under nitrogen was added DIBAL (1M in hexanes, 2 equiv) in dropwise fashion. The mixture was stirred at (−78° C.) for 3 h, and then allowed to warm to rt. Acetic acid (1 mL) was added slowly followed by water (10 mL). The mixture was stirred for 10 min and then diluted with EtOAc. The organic layer was washed with brine, dried (anhydrous $Na_2SO_4$) and concentrated. The resultant residue was purified by silica gel chromatography (EtOAc/hexane) to afford (1S)-(5-chloroindan-1-yl)-1H-indazole-5-carbaldehyde.

(D) Methyl (2,4-dioxo-1,3-thiazolidin-3-yl)acetate was prepared from methyl 2-aminoacetate following General Procedure D.

(E) Methyl [(5Z)-5-({1-[(1S)-5-chloro-2,3-dihydro-1H-inden-1-yl]-1H-indazol-5-yl}methylidene)-2,4-dioxo-1,3-thiazolidin-3-yl]acetate was prepared from (1S)-(5-chloroindan-1-yl)-1H-indazole-5-carbaldehyde and methyl (2,4-dioxo-1,3-thiazolidin-3-yl)acetate following General Procedure F.

$^1$H NMR (400 MHz, $CDCl_3$): δ 8.13 (s, 1H), 8.06 (s, 1H), 7.94 (s, 1H), 7.44-7.49 (m, 1H), 7.37 (s, 1H), 7.29 (d, 1H), 7.14 (d, 1H), 6.90 (d, 1H), 6.24 (t, 1H), 4.51 (s, 2H), 3.80 (s, 3H), 3.29 (ddd, 1H), 3.08 (dt, 1H), 2.73-2.86 (m, 1H), 2.51-2.63 (m, 1H).

LC/MS: mass calcd. for $C_{23}H_{18}ClN_3O_4S$: 467.07. found 468.3 $[M+1]^+$

Example 172

(5Z)-5-({1-[(1S)-5-Chloro-2,3-dihydro-1H-inden-1-yl]-1H-indazol-5-yl}methylidene)-3-(2-pyrrolidin-1-ylethyl)-1,3-thiazolidine-2,4-dione

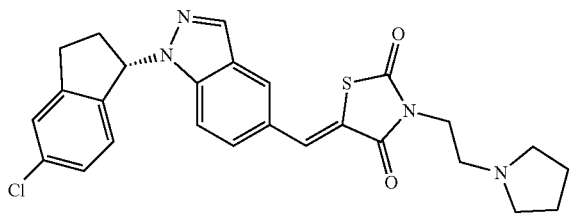 [SMILES: O=C1S/C(=C\c2ccc3c(cnn3[C@H]3CCc4cc(Cl)ccc43)c2)C(=O)N1CCN1CCCC1]

(A) 3-(2-Pyrrolidin-1-ylethyl)-1,3-thiazolidine-2,4-dione was prepared from 2-pyrrolidin-1-yl-ethylamine following General Procedure D.

(B) (5Z)-5-({1-[(1S)-5-Chloro-2,3-dihydro-1H-inden-1-yl]-1H-indazol-5-yl}methylidene)-3-(2-pyrrolidin-1-ylethyl)-1,3-thiazolidine-2,4-dione was prepared from (1S)-(5-chloroindan-1-yl)-1H-indazole-5-carbaldehyde (from Example 171) and 3-(2-pyrrolidin-1-yl-ethyl)-1,3-thiazolidine-2,4-dione following General Procedure F.

$^1$H NMR (400 MHz, $CDCl_3$): δ 8.11 (s, 1H), 8.00 (s, 1H), 7.92 (s, 1H), 7.41-7.50 (m, 1H), 7.37 (s, 1H), 7.29 (d, 1H), 7.13 (d, 1H), 6.89 (d, 1H), 6.23 (t, 1H), 3.92 (t, 2H), 3.29 (ddd, 1H), 3.07 (dt, 1H), 2.71-2.87 (m, 3H), 2.49-2.67 (m, 5H), 1.77 (br. s., 4H).

LC/MS: mass calcd. for $C_{26}H_{25}ClN_4O_2S$: 492.14. found 493.1 $[M+1]^+$

Example 173

[(5Z)-5-({1-[(1S)-5-Chloro-2,3-dihydro-1H-inden-1-yl]-1H-indazol-5-yl}methylidene)-2,4-dioxo-1,3-thiazolidin-3-yl]acetic acid

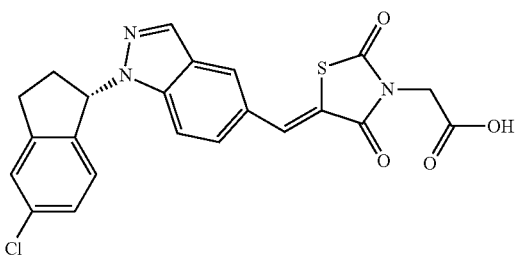 [SMILES: O=C(O)CN1C(=O)S/C(=C\c2ccc3c(cnn3[C@H]3CCc4cc(Cl)ccc43)c2)C1=O]

[(5Z)-5-({1-[(1S)-5-Chloro-2,3-dihydro-1H-inden-1-yl]-1H-indazol-5-yl}methylidene)-2,4-dioxo-1,3-thiazolidin-3-yl]acetic acid was prepared from methyl [(5Z)-5-({1-[(1S)-5-chloro-2,3-dihydro-1H-inden-1-yl]-1H-indazol-5-yl}methylidene)-2,4-dioxo-1,3-thiazolidin-3-yl]acetate (Example 171) following General Procedure O.

$^1$H NMR (400 MHz, $CDCl_3$): δ 8.15 (br. s., 1H), 8.06 (s, 1H), 7.94 (s, 1H), 7.46 (d, 1H), 7.37 (s, 1H), 7.22-7.31 (m, 2H), 7.14 (d, 1H), 6.89 (d, 1H), 6.25 (t, 1H), 4.54 (s, 2H), 3.21-3.35 (m, 1H), 3.07 (dt, 1H), 2.80 (dt, 1H), 2.45-2.63 (m, 1H).

LC/MS: mass calcd. for $C_{22}H_{16}ClN_3O_4S$: 453.06. found 454.0 $[M+1]^+$

Example 174

(5Z)-3-[trans-2-Aminocyclohexyl]-5-({1-[4-chloro-2-(trifluoromethyl)benzyl]-1H-indazol-5-yl}methylidene)-1,3-thiazolidine-2,4-dione

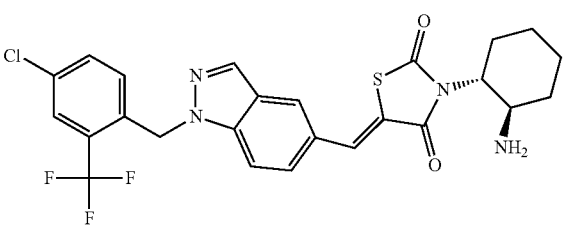 [SMILES: N[C@@H]1CCCC[C@H]1N1C(=O)S/C(=C\c2ccc3c(cnn3Cc3ccc(Cl)cc3C(F)(F)F)c2)C1=O]

(A) 1,1-Dimethylethyl trans-[2-(2,4-dioxo-thiazolidin-3-yl)cyclohexyl]-carbamate was prepared from 1,1-dimethylethyl trans-(2-aminocyclohexyl)carbamate following General Procedure D.

(B) (5Z)-3-[trans-2-Aminocyclohexyl]-5-({1-[4-chloro-2-(trifluoromethyl)benzyl]-1H-indazol-5-yl}methylidene)-1,3-thiazolidine-2,4-dione was prepared from [4-chloro-2-(trifluoromethyl)benzyl]-1H-indazol-5-carbaldehyde (from Example 1) and 1,1-dimethylethyl trans-[2-(2,4-dioxo-thiazolidin-3-yl)cyclohexyl]carbamate following General Procedure F.

$^1$H NMR (400 MHz, $CDCl_3$): δ 8.21 (s, 1H), 7.99 (s, 1H), 7.96 (s, 1H), 7.72 (d, 1H), 7.51 (d, 1H), 7.36 (s, 1H), 7.33 (s, 1H), 6.68 (d, 1H), 5.80 (s, 2H), 3.90-4.03 (m, 1H), 3.44 (br. s., 1H), 2.15-2.32 (m, 1H), 1.99-2.11 (m, 1H), 1.84 (d, 1H), 1.77 (d, 2H), 1.30-1.48 (m, 2H), 1.07-1.29 (m, 3H).

LC/MS: mass calcd. for $C_{25}H_{22}ClF_3N_4O_2S$: 534.11. found 535.2 [M+1]$^+$ Example 175

(5Z)-5-({1-[4-Chloro-2-(trifluoromethyl)benzyl]-1H-indazol-5-yl}methylidene)-3-(2,2,6,6-tetramethylpiperidin-4-yl)-1,3-thiazolidine-2,4-dione

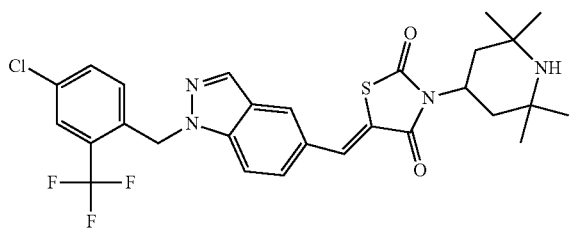 [SMILES: CC1(C)CC(N2C(=O)S/C(=C\c3ccc4c(cnn4Cc4ccc(Cl)cc4C(F)(F)F)c3)C2=O)CC(C)(C)N1]

(A) 3-(2,2,6,6-Tetramethylpiperidin-4-yl)-1,3-thiazolidine-2,4-dione was prepared from 4-amino-2,2,6,6-tetramethylpiperidine following General Procedure D.

(B) (5Z)-5-({1-[4-Chloro-2-(trifluoromethyl)benzyl]-1H-indazol-5-yl}methylidene)-3-(2,2,6,6-tetramethylpiperidin-4-yl)-1,3-thiazolidine-2,4-dione was prepared from [4-chloro-2-(trifluoromethyl)benzyl]-1H-indazol-5-carbaldehyde (from Example 1) and 3-(2,2,6,6-tetramethylpiperidin-4-yl)-1,3-thiazolidine-2,4-dione following General Procedure F.

$^1$H NMR (400 MHz, CDCl$_3$): δ 8.22 (s, 1H), 8.00 (s, 1H), 7.96 (s, 1H), 7.72 (s, 1H), 7.51 (d, 1H), 7.36 (br. s., 1H), 7.34 (br. s., 1H), 6.68 (d, 1H), 5.80 (s, 2H), 4.80-4.93 (m, 1H), 2.63 (br. s., 2H), 1.67 (dd, 2H), 1.50 (br. s., 6H), 1.41 (br. s., 6H).

LC/MS: mass calcd. for $C_{28}H_{28}ClF_3N_4O_2S$: 576.16. found 577.1 [M+1]$^+$ Example 176

(5Z)-3-(trans-4-Aminocyclohexyl)-5-({1-[4-chloro-2-(trifluoromethyl)benzyl]-1H-indazol-5-yl}methylidene)-1,3-thiazolidine-2,4-dione

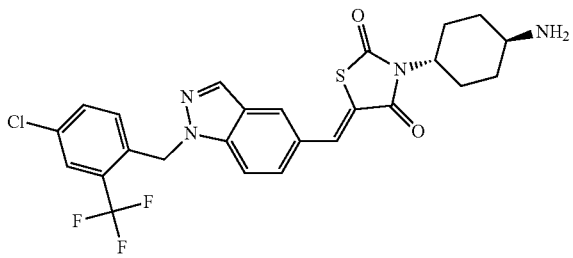 [SMILES: N[C@H]1CC[C@H](N2C(=O)S/C(=C\c3ccc4c(cnn4Cc4ccc(Cl)cc4C(F)(F)F)c3)C2=O)CC1]

(A) 1,1-Dimethylethyl trans-[4-(2,4-dioxo-1,3-thiazolidin-3-yl)cyclohexyl]-carbamate was prepared from 1,1-dimethylethyl trans-(4-aminocyclohexyl)carbamate following General Procedure D.

(B) (5Z)-3-(trans-4-Aminocyclohexyl)-5-({1-[4-chloro-2-(trifluoromethyl)benzyl]-1H-indazol-5-yl}methylidene)-1,3-thiazolidine-2,4-dione was prepared from [4-chloro-2-(trifluoromethyl)benzyl]-1H-indazol-5-carbaldehyde (from Example 1) and 1,1-dimethylethyl trans-[4-(2,4-dioxo-1,3-thiazolidin-3-yl)cyclohexyl]carbamate following General Procedure F.

$^1$H NMR (400 MHz, CDCl$_3$): δ 8.21 (s, 1H), 7.97 (s, 1H), 7.95 (s, 1H), 7.72 (d, 1H), 7.50 (d, 1H), 7.35 (s, 1H), 7.33 (s, 1H), 6.68 (d, 1H), 5.79 (s, 2H), 4.23-4.36 (m, 1H), 2.81 (br. s., 1H), 2.37 (qd, 2H), 1.98 (br. s., 1H), 1.72 (d, 2H), 1.43 (br. s., 3H), 1.18-1.35 (m, 2H).

LC/MS: mass calcd. for $C_{25}H_{22}ClF_3N_4O_2S$: 534.11. found 535.2 [M+1]$^+$ Example 177

Methyl [(5Z)-5-({1-[(1R)-5-chloro-2,3-dihydro-1H-inden-1-yl]-1H-indazol-5-yl}methylidene)-2,4-dioxo-1,3-thiazolidin-3-yl]acetate

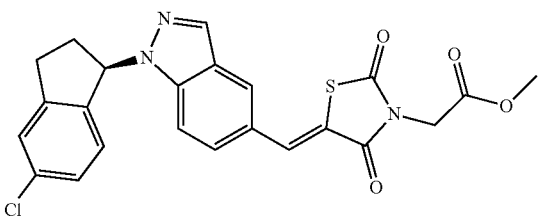 [SMILES: COC(=O)CN1C(=O)S/C(=C\c2ccc3c(cnn3[C@@H]3CCc4cc(Cl)ccc43)c2)C1=O]

Methyl [(5Z)-5-({1-[(1R)-5-chloro-2,3-dihydro-1H-inden-1-yl]-1H-indazol-5-yl}methylidene)-2,4-dioxo-1,3-thiazolidin-3-yl]acetate was prepared in a similar fashion as Example 171, using the isomeric catalyst, (2R)-2-[([1,3,2]dioxaborolan-2-yloxy)diphenylmethyl]pyrrolidine, in Step A.

$^1$H NMR (400 MHz, CDCl$_3$): δ 8.12 (s, 1H), 8.06 (s, 1H), 7.94 (s, 1H), 7.47 (dd, 1H), 7.37 (s, 1H), 7.28 (d, 1H), 7.14 (d, 1H), 6.89 (d, 1H), 6.24 (t, 1H), 4.51 (s, 2H), 3.80 (s, 3H), 3.29 (ddd, 1H), 3.08 (dt, 1H), 2.72-2.88 (m, 1H), 2.50-2.65 (m, 1H).

LC/MS: mass calcd. for $C_{23}H_{18}ClN_3O_4S$: 467.07. found 468.2 [M+1]$^+$

Example 178

(5Z)-5-({1-[(1R)-5-Chloro-2,3-dihydro-1H-inden-1-yl]-1H-indazol-5-yl}methylidene)-3-(2-pyrrolidin-1-ylethyl)-1,3-thiazolidine-2,4-dione

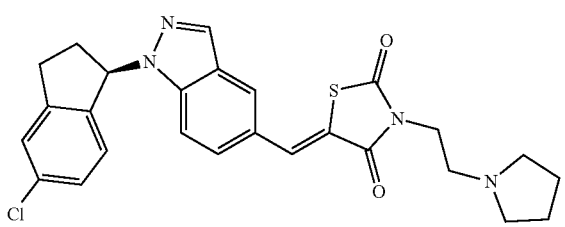 [SMILES: O=C1S/C(=C\c2ccc3c(cnn3[C@@H]3CCc4cc(Cl)ccc43)c2)C(=O)N1CCN1CCCC1]

(5Z)-5-({1-[(1R)-5-Chloro-2,3-dihydro-1H-inden-1-yl]-1H-indazol-5-yl}methylidene)-3-(2-pyrrolidin-1-ylethyl)-1,3-thiazolidine-2,4-dione was prepared by the method described for Example 172, using the isomeric (1R)-(5-chloroindan-1-yl)-1H-indazole-5-carbaldehyde and 3-(2-pyrrolidin-1-ylethyl)-1,3-thiazolidine-2,4-dione following General Procedure F.

¹H NMR (400 MHz, CDCl₃): δ 8.11 (s, 1H), 8.01 (s, 1H), 7.92 (s, 1H), 7.46 (dd, 1H), 7.36 (s, 1H), 7.25-7.31 (m, 1H), 7.13 (d, 1H), 6.89 (d, 1H), 6.23 (t, 1H), 3.93 (t, 2H), 3.29 (ddd, 1H), 3.07 (dt, 1H), 2.73-2.86 (m, 3H), 2.47-2.70 (m, 5H), 1.79 (br. s., 4H).

LC/MS: mass calcd. for C₂₆H₂₅ClN₄O₂S: 492.14. found 493.2 [M+1]⁺

Example 179

[(5Z)-5-({1-[(1R)-5-Chloro-2,3-dihydro-1H-inden-1-yl]-1H-indazol-5-yl}methylidene)-2,4-dioxo-1,3-thiazolidin-3-yl]acetic acid

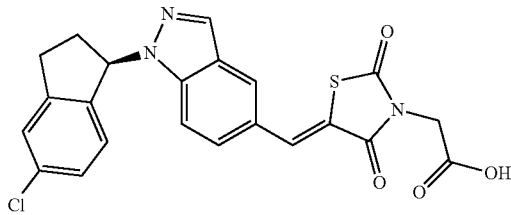 [SMILES: O=C(O)CN1C(=O)S/C(=C\c2ccc3c(cnn3[C@@H]3CCc4cc(Cl)ccc43)c2)C1=O]

[(5Z)-5-({1-[(1R)-5-Chloro-2,3-dihydro-1H-inden-1-yl]-1H-indazol-5-yl}methylidene)-2,4-dioxo-1,3-thiazolidin-3-yl]acetic acid was prepared from methyl [(5Z)-5-({1-[(1R)-5-chloro-2,3-dihydro-1H-inden-1-yl]-1H-indazol-5-yl}methylidene)-2,4-dioxo-1,3-thiazolidin-3-yl]acetate (Example 177) following General Procedure O.

¹H NMR (400 MHz, CDCl₃): δ 8.17 (br. s., 1H), 8.07 (s, 1H), 7.95 (s, 1H), 7.47 (d, 1H), 7.37 (s, 1H), 7.22-7.26 (m, 1H), 7.14 (d, 1H), 6.90 (d, 1H), 6.26 (br. s., 1H), 4.56 (s, 2H), 4.34 (br. s., 3H), 3.21-3.34 (m, 1H), 3.08 (dt, 1H), 2.80 (dd, 1H), 2.54 (dd, 1H).

LC/MS: mass calcd. for C₂₂H₁₆ClN₃O₄S: 453.06. found 454.1 [M+1]⁺

Example 180

Methyl (4R)-4-[(5Z)-5-({1-[4-chloro-2-(trifluoromethyl)benzyl]-1H-indazol-5-yl}methylidene)-2,4-dioxo-1,3-thiazolidin-3-yl]-L-prolinate

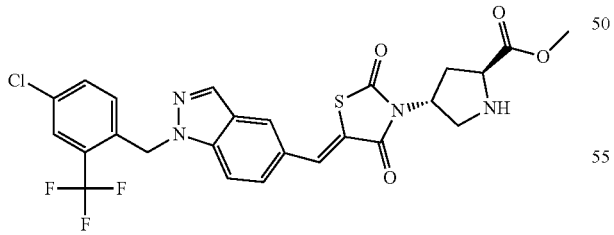

(A) Methyl (4R)-4-[(5Z)-5-({1-[4-chloro-2-(trifluoromethyl)benzyl]-1H-indazol-5-yl}methylidene)-2,4-dioxo-1,3-thiazolidin-3-yl]-1-tert-butoxycarbonyl-L-prolinate was prepared from [(5Z)-5-({1-[4-chloro-2-(trifluoromethyl)benzyl]-1H-indazol-5-yl}methylidene)-2,4-dioxo-1,3-thiazolidine (from Example 1) and methyl (4S)-4-hydroxy-1-tert-butoxycarbonyl-L-prolinate following General Procedure J.

(B) Methyl (4R)-4-[(5Z)-5-({1-[4-chloro-2-(trifluoromethyl)benzyl]-1H-indazol-5-yl}methylidene)-2,4-dioxo-1,3-thiazolidin-3-yl]-L-prolinate was prepared from methyl (4R)-4-[(5Z)-5-({1-[4-chloro-2-(trifluoromethyl)benzyl]-1H-indazol-5-yl}methylidene)-2,4-dioxo-1,3-thiazolidin-3-yl]-1-tert-butoxycarbonyl-L-prolinate following General Procedure M.

¹H NMR (400 MHz, CDCl₃): δ 8.22 (s, 1H), 8.00 (s, 1H), 7.96 (s, 1H), 7.72 (d, 1H), 7.47-7.53 (m, 1H), 7.36 (br. s., 1H), 7.34 (br. s., 1H), 6.68 (d, 1H), 5.80 (s, 2H), 5.03 (br. s., 1H), 4.27 (br. s., 1H), 3.77 (s, 3H), 3.40 (br. s., 1H), 3.26 (br. s., 1H), 2.45-2.57 (m, 1H), 2.24-2.36 (m, 1H).

LC/MS: mass calcd. for C₂₅H₂₀ClF₃N₄O₄S: 564.08. found 565.2 [M+1]⁺

Example 181

(4R)-4-[(5Z)-5-({1-[4-Chloro-2-(trifluoromethyl)benzyl]-1H-indazol-5-yl}methylidene)-2,4-dioxo-1,3-thiazolidin-3-yl]-L-proline

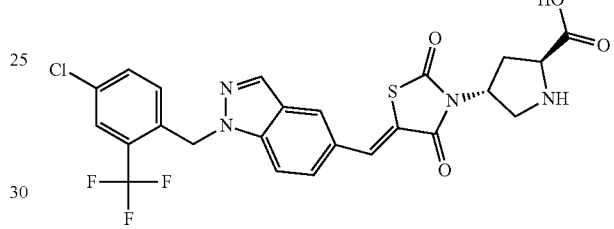

(4R)-4-[(5Z)-5-({1-[4-Chloro-2-(trifluoromethyl)benzyl]-1H-indazol-5-yl}methylidene)-2,4-dioxo-1,3-thiazolidin-3-yl]-L-proline was prepared from methyl (4R)-4-[(5Z)-5-({1-[4-chloro-2-(trifluoromethyl)benzyl]-1H-indazol-5-yl}methylidene)-2,4-dioxo-1,3-thiazolidin-3-yl]-L-prolinate (Example 180) following General Procedure O.

¹H NMR (400 MHz, CDCl₃): δ 8.09 (s, 1H), 7.92 (br. s., 1H), 7.81 (br. s., 1H), 7.68 (s, 1H), 7.36 (d, 1H), 7.30 (br. s., 1H), 7.21 (d, 1H), 6.62 (d, 1H), 5.67 (br. s., 2H), 5.30-5.42 (m, 1H), 5.05 (br. s., 1H), 4.06 (br. s., 1H), 3.84-3.98 (m, 1H), 2.79 (br. s., 2H).

LC/MS: mass calcd. for C₂₄H₁₈ClF₃N₄O₄S: 550.07. found 551.1 [M+1]⁺

Example 182

(5Z)-5-({1-[4-Chloro-2-(trifluoromethyl)benzyl]-1H-indazol-5-yl}methylidene)-3-{[(2S,4R)-4-hydroxypyrrolidin-2-yl]methyl}-1,3-thiazolidine-2,4-dione

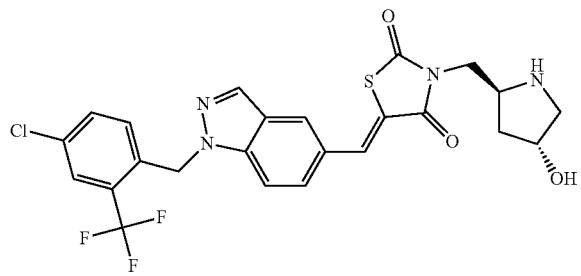 [SMILES: O=C1S/C(=C\c2ccc3c(cnn3Cc3ccc(Cl)cc3C(F)(F)F)c2)C(=O)N1C[C@@H]1C[C@@H](O)CN1]

(A) 1,1-Dimethylethyl (2S,4R)-4-(tert-butyldimethylsilanyloxy)-2-(2,4-dioxo-1,3-thiazolidin-3-ylmethyl)pyrrolidine-1-carboxylate was prepared from 1,1-dimethylethyl (2S,4R)-4-[(tert-butyldimethylsilanyl)oxy]-2-hydroxymethylpyrrolidine-1-carboxylate following General Procedure C.

(B) To a solution of 1,1-dimethylethyl (2S,4R)-4-(tert-butyldimethylsilanyloxy)-2-[(2,4-dioxo-1,3-thiazolidin-3-yl)methyl]pyrrolidine-1-carboxylate (1.16 mmol) in THF (10 mL) was added TBAF (1M in THF, 1.5 mmol) slowly at 0° C. After stirring at rt for 1 h, the reaction was concentrated in vacuo and the resultant residue was purified by silica gel chromatography (EtOAc/hexane) to afford 1,1-dimethylethyl (2S,4R)-2-[(2,4-dioxo-1-3-thiazolidin-3-yl)methyl]-4-hydroxypyrrolidine-1-carboxylate.

(C) (5Z)-5-({1-[4-Chloro-2-(trifluoromethyl)benzyl]-1H-indazol-5-yl}methylidene)-3-{[(2S,4R)-4-hydroxypyrrolidin-2-yl]methyl}-1,3-thiazolidine-2,4-dione was prepared from [4-chloro-2-(trifluoromethyl)benzyl]-1H-indazol-5-carbaldehyde (from Example 1) and 1,1-dimethylethyl (2S,4R)-2-[(2,4-dioxo-1-3-thiazolidin-3-yl)methyl]-4-hydroxypyrrolidine-1-carboxylate following General Procedure F.

$^1$H NMR (400 MHz, CDCl$_3$): δ 8.22 (s, 1H), 8.02 (s, 1H), 7.96 (s, 1H), 7.72 (d, 1H), 7.48-7.54 (m, 1H), 7.36 (s, 1H), 7.34 (s, 1H), 6.67 (d, 1H), 5.80 (s, 2H), 4.48 (t, 1H), 3.67-3.86 (m, 3H), 3.11 (dd, 1H), 2.90 (d, 1H), 1.89-1.99 (m, 1H), 1.84 (br. s., 1H), 1.69 (ddd, 1H).

LC/MS: mass calcd. for C$_{24}$H$_{20}$ClF$_3$N$_4$O$_3$S: 536.09. found 537.3 [M+1]$^+$ Example 183

(5Z)-5-({1-[4-Chloro-2-(trifluoromethyl)benzyl]-1H-indazol-5-yl}methylidene)-3-[(2S)-morpholin-2-ylmethyl]-1,3-thiazolidine-2,4-dione

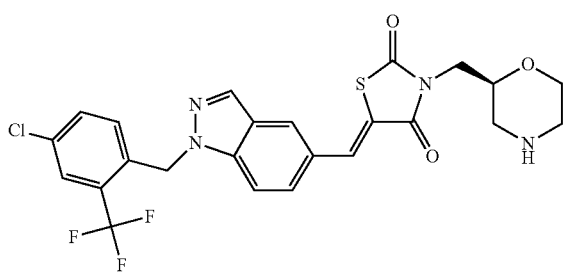 [SMILES: O=C1S/C(=C\c2ccc3c(cnn3Cc3ccc(Cl)cc3C(F)(F)F)c2)C(=O)N1C[C@@H]1CNCCO1]

(A) 1,1-Dimethylethyl (2S)-2-[{(5Z)-5-[(1-{[4-chloro-2-(trifluoromethyl)phenyl]methyl}-1H-indazol-5-yl)methylidene]-2,4-dioxo-1,3-thiazolidin-3-yl}methyl]morpholine-4-carboxylate was prepared from (5Z)-5-({1-[4-chloro-2-(trifluoromethyl)benzyl]-1H-indazol-5-yl}methylidene)-2,4-dioxo-1,3-thiazolidine (from Example 1) and 1,1-dimethylethyl (2S)-2-(hydroxymethyl)morpholine-4-carboxylate following General Procedure J.

(B) (5Z)-5-({1-[4-Chloro-2-(trifluoromethyl)benzyl]-1H-indazol-5-yl}methylidene)-3-[(2S)-morpholin-2-ylmethyl]-1,3-thiazolidine-2,4-dione was prepared from 1,1-dimethylethyl (2S)-2-[{(5Z)-5-[(1-{[4-chloro-2-(trifluoromethyl)phenyl]methyl}-1H-indazol-5-yl)methylidene]-2,4-dioxo-1,3-thiazolidin-3-yl}methyl]morpholine-4-carboxylate following General Procedure M.

$^1$H NMR (400 MHz, CDCl$_3$): δ 8.22 (s, 1H), 8.03 (s, 1H), 7.97 (s, 1H), 7.72 (d, 1H), 7.48-7.55 (m, 1H), 7.32-7.39 (m, 2H), 6.68 (d, 1H), 5.80 (s, 2H), 3.92-4.02 (m, 1H), 3.89 (d, 1H), 3.74-3.84 (m, 1H), 3.67 (dd, 1H), 3.53 (td, 1H), 2.84-3.02 (m, 2H), 2.75-2.84 (m, 1H), 2.67 (t, 1H), 1.62 (br. s., 1H).

LC/MS: mass calcd. for C$_{24}$H$_{20}$ClF$_3$N$_4$O$_3$S: 536.09. found 537.2 [M+1]$^+$ Example 184

(5Z)-5-({1-[4-Chloro-2-(trifluoromethyl)benzyl]-1H-indazol-5-yl}methylidene)-3-{[(2S,4R)-4-fluoropyrrolidin-2-yl]methyl}-1,3-thiazolidine-2,4-dione

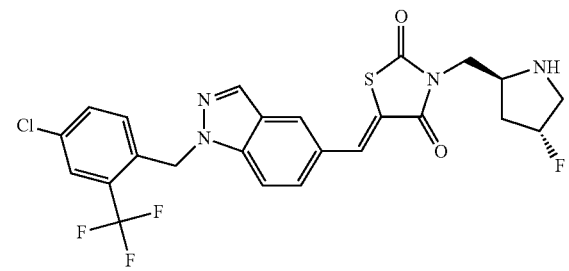 [SMILES: O=C1S/C(=C\c2ccc3c(cnn3Cc3ccc(Cl)cc3C(F)(F)F)c2)C(=O)N1C[C@@H]1C[C@@H](F)CN1]

(A) A solution of 1,1-dimethylethyl (2S,4R)-4-fluoro-2-carboxypyrrolidine-1-carboxylate (3 mmol) and BH$_3$.DMS complex (2 equiv) in THF (10 mL) was stirred at 67° C. for 16 h. After cooling to rt, the mixture was diluted with EtOAc, extracted successively with 1N NaOH solution and brine, dried (Na$_2$SO$_4$) and concentrated. The resultant residue was purified by silica gel chromatography (EtOAc/hexane) to afford 1,1-dimethylethyl (2S,4R)-4-fluoro-2-(hydroxymethyl)pyrrolidine-1-carboxylate.

(B) 1,1-Dimethylethyl (2S,4R)-2-[{(5Z)-5-[(1-{[4-chloro-2-(trifluoromethyl)phenyl]methyl}-1H-indazol-5-yl)methylidene]-2,4-dioxo-1,3-thiazolidin-3-yl}methyl]-4-fluoropyrrolidine-1-carboxylate was prepared from (5Z)-5-({1-[4-chloro-2-(trifluoromethyl)benzyl]-1H-indazol-5-yl}methylidene)-2,4-dioxo-1,3-thiazolidine (from Example 1) and 1,1-dimethylethyl (2S,4R)-4-fluoro-2-(hydroxymethyl)pyrrolidine-1-carboxylate following General Procedure J.

(C) (5Z)-5-({1-[4-Chloro-2-(trifluoromethyl)benzyl]-1H-indazol-5-yl}methylidene)-3-{[(2S,4R)-4-fluoropyrrolidin-2-yl]methyl}-1,3-thiazolidine-2,4-dione was prepared from 1,1-dimethylethyl (2S,4R)-2-[{(5Z)-5-[(1-{[4-chloro-2-(trifluoromethyl)phenyl]methyl}-1H-indazol-5-yl)methylidene]-2,4-dioxo-1,3-thiazolidin-3-yl}methyl]-4-fluoropyrrolidine-1-carboxylate following General Procedure M.

$^1$H NMR (400 MHz, CDCl$_3$): δ 8.22 (s, 1H), 8.03 (s, 1H), 7.97 (s, 1H), 7.72 (s, 1H), 7.51 (d, 1H), 7.37 (br. s., 1H), 7.34 (br. s., 1H), 6.68 (d, 1H), 5.80 (s, 2H), 5.25 (dt, 1H), 3.67-3.91 (m, 3H), 3.02-3.28 (m, 2H), 2.14-2.33 (m, 1H), 1.94-2.11 (m, 1H), 1.59-1.81 (m, 1H).

LC/MS: mass calcd. for C$_{24}$H$_{19}$ClF$_4$N$_4$O$_2$S: 538.09. found 539.2 [M+1]$^+$

Example 185

2-[(5Z)-5-({1-[4-Fluoro-2-(trifluoromethyl)benzyl]-1H-indazol-5-yl}methylidene)-2,4-dioxo-1,3-thiazolidin-3-yl]-N-(methylsulfonyl)acetamide

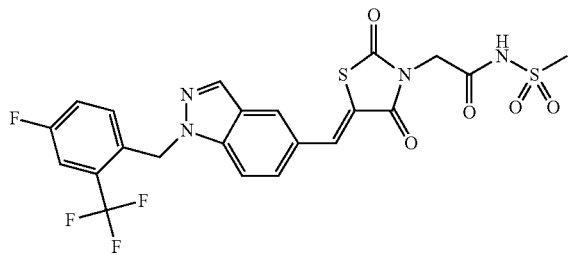 [SMILES: CS(=O)(=O)NC(=O)CN1C(=O)S/C(=C\c2ccc3c(cnn3Cc3ccc(F)cc3C(F)(F)F)c2)C1=O]

2-[(5Z)-5-({1-[4-Fluoro-2-(trifluoromethyl)benzyl]-1H-indazol-5-yl}methylidene)-2,4-dioxo-1,3-thiazolidin-3-yl]-N-(methylsulfonyl)-acetamide was prepared from [(5Z)-5-({1-[4-fluoro-2-(trifluoromethyl)-benzyl]-1H-indazol-5-yl}methylidene)-2,4-dioxo-1,3-thiazolidin-3-yl]acetic acid (Example 122) following General Procedure L using methanesulfonic acid amide in place of the sulfamide.

$^1$H NMR (400 MHz, DMSO-$d_6$): δ 8.38 (s, 1H), 8.21 (s, 1H), 8.15 (s, 1H), 7.83 (d, 1H), 7.68-7.76 (m, 2H), 7.46 (td, 1H), 6.88 (dd, 1H), 5.87 (s, 2H), 4.45 (s, 2H), 4.11 (br. s., 1H), 3.24 (s, 3H).

LC/MS: mass calcd. for $C_{22}H_{16}F_4N_4O_6S_2$: 556.05. found 557.3 [M+1]$^+$

Example 186

(5Z)-5-({1-[4-Chloro-2-(trifluoromethyl)benzyl]-1H-indazol-5-yl}methylidene)-3-{[(2S,4R)-4-hydroxy-1-(2-hydroxyethyl)pyrrolidin-2-yl]methyl}-1,3-thiazolidine-2,4-dione

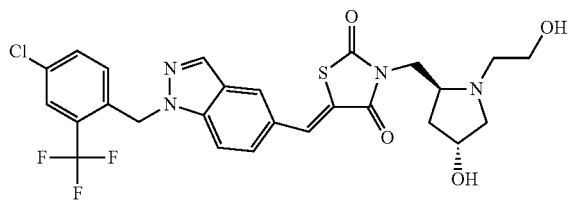 [SMILES: O=C1S/C(=C\c2ccc3c(cnn3Cc3ccc(Cl)cc3C(F)(F)F)c2)C(=O)N1C[C@@H]1C[C@@H](O)CN1CCO]

(5Z)-5-({1-[4-Chloro-2-(trifluoromethyl)benzyl]-1H-indazol-5-yl}methylidene)-3-{[(2S,4R)-4-hydroxy-1-(2-hydroxyethyl)pyrrolidin-2-yl]methyl}-1,3-thiazolidine-2,4-dione was prepared from (5Z)-5-({1-[4-chloro-2-(trifluoromethyl)benzyl]-1H-indazol-5-yl}methylidene)-3-{[(2S,4R)-4-hydroxypyrrolidin-2-yl]methyl}-1,3-thiazolidine-2,4-dione (Example 182) and 2-bromoethanol following General Procedure S.

$^1$H NMR (400 MHz, CDCl$_3$): δ 8.22 (s, 1H), 8.03 (s, 1H), 7.97 (s, 1H), 7.72 (d, 1H), 7.51 (d, 1H), 7.36 (br. s., 1H), 7.34 (br. s., 1H), 6.67 (d, 1H), 5.80 (s, 2H), 4.42 (br. s., 1H), 3.74-3.91 (m, 2H), 3.59-3.70 (m, 2H), 3.42 (dd, 1H), 3.25-3.34 (m, 1H), 3.09-3.20 (m, 1H), 2.75 (br. s., 1H), 2.70 (dt, 1H), 2.43 (dd, 1H), 1.83-1.98 (m, 2H).

LC/MS: mass calcd. for $C_{26}H_{24}ClF_3N_4O_4S$: 580.12. found 581.3 [M+1]$^+$

Example 187

(5Z)-5-({1-[4-Chloro-2-(trifluoromethyl)benzyl]-1H-indazol-5-yl}methylidene)-3-{[(2S)-4-(2-hydroxyethyl)morpholin-2-yl]methyl}-1,3-thiazolidine-2,4-dione

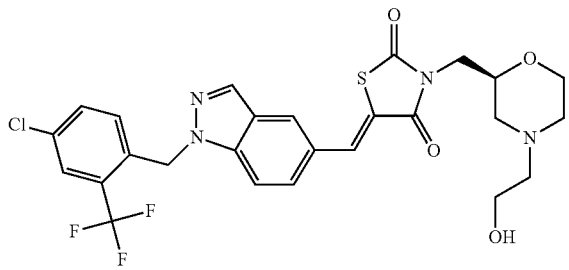 [SMILES: O=C1S/C(=C\c2ccc3c(cnn3Cc3ccc(Cl)cc3C(F)(F)F)c2)C(=O)N1C[C@@H]1CN(CCO)CCO1]

(5Z)-5-({1-[4-Chloro-2-(trifluoromethyl)benzyl]-1H-indazol-5-yl}methylidene)-3-{[(2S)-4-(2-hydroxyethyl)morpholin-2-yl]methyl}-1,3-thiazolidine-2,4-dione was prepared from (5Z)-5-({1-[4-chloro-2-(trifluoromethyl)benzyl]-1H-indazol-5-yl}methylidene)-3-[(2)-morpholin-2-ylmethyl]-1,3-thiazolidine-2,4-dione and 2-bromoethanol following General Procedure S.

$^1$H NMR (400 MHz, CDCl$_3$): δ 8.22 (s, 1H), 8.03 (s, 1H), 7.97 (s, 1H), 7.72 (d, 1H), 7.48-7.54 (m, 1H), 7.36 (s, 1H), 7.34 (s, 1H), 6.67 (d, 1H), 5.80 (s, 2H), 3.85-4.03 (m, 3H), 3.70 (dd, 1H), 3.59-3.67 (m, 1H), 3.51 (t, 2H), 2.86 (d, 1H), 2.72 (d, 1H), 2.54-2.64 (m, 2H), 2.18-2.32 (m, 1H), 2.03 (t, 1H), 1.60 (br. s., 1H).

LC/MS: mass calcd. for $C_{26}H_{24}ClF_3N_4O_4S$: 580.12. found 581.3 [M+1]$^+$

Example 188

(5Z)-5-({1-[4-Chloro-2-(trifluoromethyl)benzyl]-1H-indazol-5-yl}methylidene)-3-{[(2S,4R)-4-hydroxy-1-(2-methoxyethyl)pyrrolidin-2-yl]methyl}-1,3-thiazolidine-2,4-dione

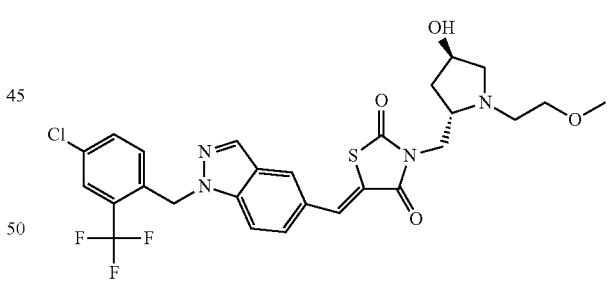

(5Z)-5-({1-[4-Chloro-2-(trifluoromethyl)benzyl]-1H-indazol-5-yl}methylidene)-3-{[(2S,4R)-4-hydroxy-1-(2-methoxyethyl)pyrrolidin-2-yl]methyl}-1,3-thiazolidine-2,4-dione was prepared from (5Z)-5-({1-[4-chloro-2-(trifluoromethyl)benzyl]-1H-indazol-5-yl}methylidene)-3-{[(2S,4R)-4-hydroxypyrrolidin-2-yl]methyl}-1,3-thiazolidine-2,4-dione (Example 182) and 2-bromoethyl methyl ether following General Procedure S.

$^1$H NMR (400 MHz, CDCl$_3$): δ 8.25 (s, 1H), 8.13 (s, 1H), 7.81 (d, 1H), 7.70 (d, 1H), 7.32 (d, 1H), 7.23 (d, 1H), 7.15 (s, 1H), 6.59 (d, 1H), 5.77 (s, 2H), 4.67 (t, 1H), 4.24 (td, 1H), 4.08-4.18 (m, 1H), 3.92 (dd, 1H), 3.84 (dd, 1H), 3.43-3.55 (m, 2H), 3.24 (s, 3H), 3.12 (d, 1H), 2.81 (t, 2H), 2.19 (dd, 1H), 2.08 (br. s., 1H), 1.57 (m, 1H).

Example 189

(5Z)-5-({1-[4-Chloro-2-(trifluoromethyl)benzyl]-1H-indazol-5-yl}methylidene)-3-{[(2S)-4-(2-methoxyethyl)morpholin-2-yl]methyl}-1,3-thiazolidine-2,4-dione

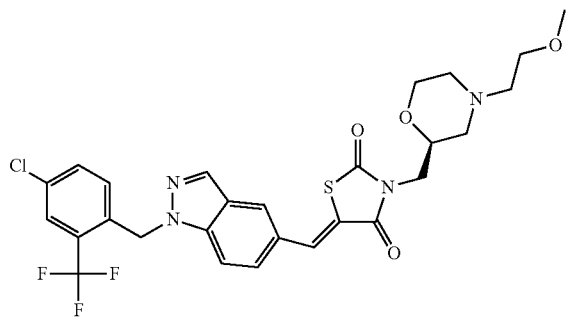 [SMILES: COCCN1CCO[C@H](CN2C(=O)S/C(=C\c3ccc4c(cnn4Cc4ccc(Cl)cc4C(F)(F)F)c3)C2=O)C1]

(5Z)-5-({1-[4-Chloro-2-(trifluoromethyl)benzyl]-1H-indazol-5-yl}methylidene)-3-{[(2S)-4-(2-methoxyethyl)morpholin-2-yl]methyl}-1,3-thiazolidine-2,4-dione was prepared from (5Z)-5-({1-[4-chloro-2-(trifluoromethyl)benzyl]-1H-indazol-5-yl}methylidene)-3-[(2S)-morpholin-2-ylmethyl]1,3-thiazolidine-2,4-dione (Example 183) and 2-bromoethyl methyl ether following General Procedure S.

$^1$H NMR (400 MHz, CDCl$_3$): δ 8.22 (s, 1H), 8.03 (s, 1H), 7.97 (s, 1H), 7.72 (d, 1H), 7.48-7.55 (m, 1H), 7.36 (s, 1H), 7.34 (s, 1H), 6.67 (d, 1H), 5.80 (s, 2H), 3.84-4.05 (m, 3H), 3.60-3.74 (m, 2H), 3.51 (t, 2H), 3.36 (s, 3H), 2.86 (d, 1H), 2.72 (d, 1H), 2.54-2.63 (m, 2H), 2.17-2.30 (m, 1H), 2.03 (t, 1H).

LC/MS: mass calcd. for C$_{27}$H$_{26}$ClF$_3$N$_4$O$_4$S: 594.13. found 595.3 [M+1]$^+$

Example 190

(5Z)-5-({1-[4-Chloro-2-(trifluoromethyl)benzyl]-1H-indazol-5-yl}methylidene)-3-{[(2S,4R)-4-fluoro-1-(2-methoxyethyl)pyrrolidin-2-yl]methyl}-1,3-thiazolidine-2,4-dione

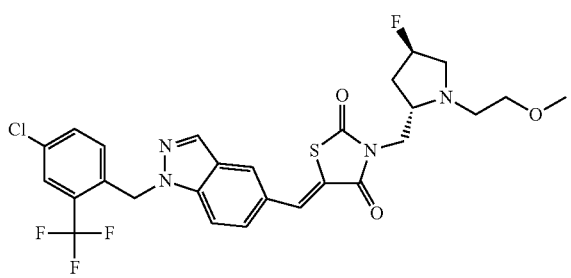 [SMILES: COCCN1C[C@H](F)C[C@H]1CN1C(=O)S/C(=C\c2ccc3c(cnn3Cc3ccc(Cl)cc3C(F)(F)F)c2)C1=O]

(5Z)-5-({1-[4-Chloro-2-(trifluoromethyl)benzyl]-1H-indazol-5-yl}methylidene)-3-{[(2S,4R)-4-fluoro-1-(2-methoxyethyl)pyrrolidin-2-yl]methyl}-1,3-thiazolidine-2,4-dione was prepared from (5Z)-5-({1-[4-chloro-2-(trifluoromethyl)benzyl]-1H-indazol-5-yl}methylidene)-3-{[(2S,4R)-4-fluoropyrrolidin-2-yl]methyl}-1,3-thiazolidine-2,4-dione (Example 184) and 2-bromoethyl methyl ether following General Procedure S.

$^1$H NMR (400 MHz, CDCl$_3$): δ 8.25 (s, 1H), 8.13 (s, 1H), 7.81 (d, 1H), 7.70 (s, 1H), 7.28-7.36 (m, 1H), 7.24 (d, 1H), 7.16 (s, 1H), 6.59 (d, 1H), 5.78 (s, 2H), 5.29-5.48 (dt, 1H), 4.11-4.28 (m, 2H), 3.86-4.09 (m, 2H), 3.43-3.54 (m, 2H), 3.30-3.42 (m, 1H), 3.24 (s, 3H), 2.81 (t, 2H), 2.49 (ddd, 1H), 1.46-1.72 (m, 1H).

LC/MS: mass calcd. for C$_{27}$H$_{25}$ClF$_4$N$_4$O$_3$S: 596.13. found 597.3 [M+1]$^+$

Example 191

(5Z)-5-({1-[4-Chloro-2-(trifluoromethyl)benzyl]-1H-indazol-5-yl}methylidene)-3-{[(2S,4R)-4-hydroxy-1-methylpyrrolidin-2-yl]methyl}-1,3-thiazolidine-2,4-dione

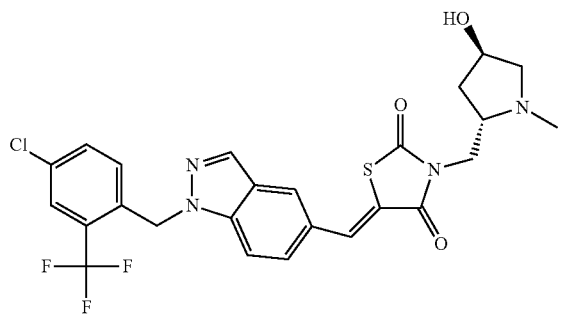 [SMILES: CN1C[C@H](O)C[C@H]1CN1C(=O)S/C(=C\c2ccc3c(cnn3Cc3ccc(Cl)cc3C(F)(F)F)c2)C1=O]

(5Z)-5-({1-[4-Chloro-2-(trifluoromethyl)benzyl]-1H-indazol-5-yl}methylidene)-3-{[(2S,4R)-4-hydroxy-1-methylpyrrolidin-2-yl]methyl}-1,3-thiazolidine-2,4-dione was prepared from (5Z)-5-({1-[4-chloro-2-(trifluoromethyl)benzyl]-1H-indazol-5-yl}methylidene)-3-{[(2S,4R)-4-hydroxypyrrolidin-2-yl]methyl}-1,3-thiazolidine-2,4-dione and formaldehyde following General Procedure R.

$^1$H NMR (400 MHz, CDCl$_3$): δ 8.22 (s, 1H), 8.01 (s, 1H), 7.96 (s, 1H), 7.72 (d, 1H), 7.51 (d, 1H), 7.36 (br. s., 1H), 7.34 (br. s., 1H), 6.67 (d, 1H), 5.80 (s, 2H), 4.35-4.46 (m, 1H), 3.85-3.93 (m, 1H), 3.75 (dd, 1H), 3.45 (dd, 1H), 2.87 (qd, 1H), 2.49 (s, 3H), 2.29 (dd, 1H), 1.98 (dd, 1H), 1.85 (ddd, 1H), 1.72 (br. s., 1H).

LC/MS: mass calcd. for C$_{25}$H$_{22}$ClF$_3$N$_4$O$_3$S: 550.11. found 551.3 [M+1]$^+$

Example 192

(5Z)-5-({1-[4-Chloro-2-(trifluoromethyl)benzyl]-1H-indazol-5-yl}methylidene)-3-{[(2S)-4-methylmorpholin-2-yl]methyl}-1,3-thiazolidine-2,4-dione

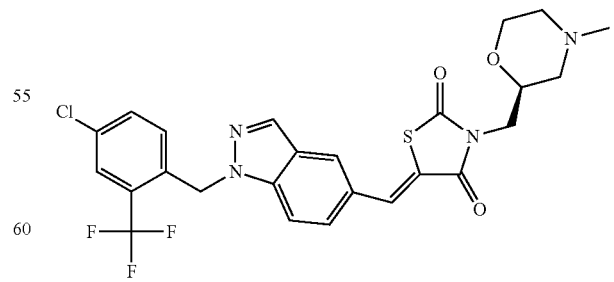

(5Z)-5-({1-[4-Chloro-2-(trifluoromethyl)benzyl]-1H-indazol-5-yl}methylidene)-3-{[(2S)-4-methylmorpholin-2-yl]methyl}-1,3-thiazolidine-2,4-dione was prepared from (5Z)-5-({1-[4-chloro-2-(trifluoromethyl)-benzyl]-1H-indazol-5- yl}methylidene)-3-[(2S)-morpholin-2-ylmethyl]-1,3-thiazolidine-2,4-dione (Example 183) and formaldehyde following General Procedure R.

$^1$H NMR (400 MHz, CDCl$_3$): δ 8.22 (s, 1H), 8.03 (s, 1H), 7.97 (s, 1H), 7.72 (s, 1H), 7.51 (d, 1H), 7.36 (br. s., 1H), 7.34 (br. s., 1H), 6.67 (d, 1H), 5.80 (s, 2H), 3.96-4.05 (m, 1H), 3.84-3.95 (m, 2H), 3.71 (dd, 1H), 3.60 (td, 1H), 2.75 (d, 1H), 2.60 (d, 1H), 2.30 (s, 3H), 2.18 (td, 1H), 1.90-2.02 (m, 1H).

LC/MS: mass calcd. for C$_{25}$H$_{22}$ClF$_3$N$_4$O$_3$S: 550.11. found 551.3 [M+1]$^+$ Example 193

(5Z)-5-({1-[4-Chloro-2-(trifluoromethyl)benzyl]-1H-indazol-5-yl}methylidene)-3-{[(2S,4R)-4-fluoro-1-methylpyrrolidin-2-yl]methyl}-1,3-thiazolidine-2,4-dione

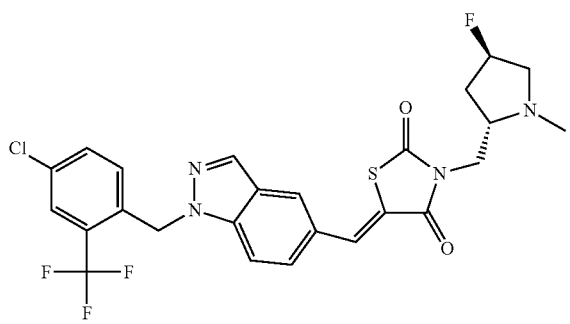 [SMILES: CN1C[C@H](F)C[C@H]1CN1C(=O)S/C(=C\c2ccc3c(cnn3Cc3ccc(Cl)cc3C(F)(F)F)c2)C1=O]

(5Z)-5-({1-[4-Chloro-2-(trifluoromethyl)benzyl]-1H-indazol-5-yl}methylidene)-3-{[(2S,4R)-4-fluoro-1-methylpyrrolidin-2-yl]methyl}-1,3-thiazolidine-2,4-dione was prepared from (5Z)-5-({1-[4-chloro-2-(trifluoromethyl)benzyl]-1H-indazol-5-yl}methylidene)-3-{[(2S,4R)-4-fluoropyrrolidin-2-yl]methyl}-1,3-thiazolidine-2,4-dione (Example 184) and formaldehyde following General Procedure R.

$^1$H NMR (400 MHz, CDCl$_3$): δ 8.22 (s, 1H), 8.02 (s, 1H), 7.97 (s, 1H), 7.72 (d, 1H), 7.51 (d, 1H), 7.31-7.40 (m, 2H), 6.68 (d, 1H), 5.80 (s, 2H), 4.99-5.21 (dt, 1H), 3.93 (dd, 1H), 3.77 (dd, 1H), 3.46-3.63 (m, 1H), 2.83-2.96 (m, 1H), 2.54-2.67 (m, 1H), 2.51 (s, 3H), 2.10-2.24 (m, 1H), 1.76-1.96 (m, 1H).

LC/MS: mass calcd. for C$_{25}$H$_{21}$ClF$_4$N$_4$O$_2$S: 552.1. found 553.3 [M+1]$^+$ Example 194

(5Z)-3-[(1-Aminocyclopropyl)methyl]-5-({1-[4-chloro-2-(trifluoromethyl)benzyl]-1H-indazol-5-yl}methylidene)-1,3-thiazolidine-2,4-dione

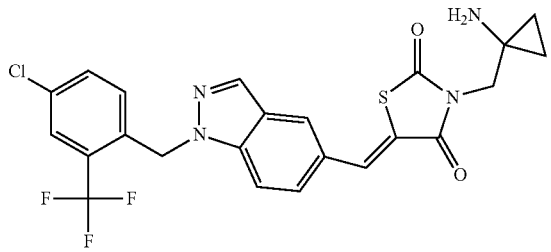 [SMILES: NC1(CN2C(=O)S/C(=C\c3ccc4c(cnn4Cc4ccc(Cl)cc4C(F)(F)F)c3)C2=O)CC1]

(A) (5Z)-3-{[1-(tert-Butoxycarbonylamino)cyclopropyl]methyl}-5-({1-[4-chloro-2-(trifluoromethyl)benzyl]-1H-indazol-5-yl}methylidene)-1,3-thiazolidine-2,4-dione was prepared from [(5Z)-5-({1-[4-chloro-2-(trifluoromethyl)-benzyl]-1H-indazol-5-yl}methylidene)-2,4-dioxo-1,3-thiazolidine (from Example 1) and [1-(tert-butoxycarbonylamino)cyclopropyl]methanol following General Procedure J.

(B) (5Z)-3-[(1-Aminocyclopropyl)methyl]-5-({1-[4-chloro-2-(trifluoromethyl)benzyl]-1H-indazol-5-yl}methylidene)-1,3-thiazolidine-2,4-dione was prepared from (5Z)-3-{[1-(tert-butoxycarbonylamino)-cyclopropyl]methyl}-5-({1-[4-chloro-2-(trifluoromethyl)benzyl]-1H-indazol-5-yl}methylidene)-1,3-thiazolidine-2,4-dione following General Procedure M.

$^1$H NMR (400 MHz, CDCl$_3$): δ 8.22 (s, 1H), 8.04 (s, 1H), 7.97 (s, 1H), 7.72 (d, 1H), 7.49-7.55 (m, 1H), 7.32-7.39 (m, 2H), 6.69 (d, 1H), 5.80 (s, 2H), 3.83 (s, 2H), 1.77 (br. s., 2H), 0.76-0.83 (m, 2H), 0.66-0.71 (m, 2H).

LC/MS: mass calcd. for C$_{23}$H$_{18}$ClF$_3$N$_4$O$_2$S: 506.08. found 507.4 [M+1]$^+$ Example 195

(5Z)-5-({1-[2,4-Bis(trifluoromethyl)benzyl]-1H-indazol-5-yl}methylidene)-3-[(2S)-morpholin-2-ylmethyl]-1,3-thiazolidine-2,4-dione

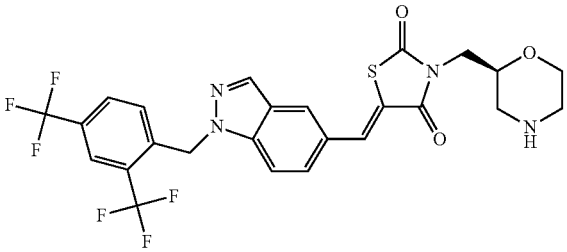 [SMILES: O=C1S/C(=C\c2ccc3c(cnn3Cc3ccc(C(F)(F)F)cc3C(F)(F)F)c2)C(=O)N1C[C@@H]1CNCCO1]

(A) 1,1-Dimethylethyl (2S)-2-[{(5Z)-5-[(1-{[2,4-bis(trifluoromethyl)phenyl]methyl}-1H-indazol-5-yl)methylidene]-2,4-dioxo-1,3-thiazolidin-3-yl}methyl]morpholine-4-carboxylate was prepared from (5Z)-5-({1-[2,4-bis(trifluoromethyl)benzyl]-1H-indazol-5-yl}methylidene)-2,4-dioxo-1,3-thiazolidine (from Example 6) and 1,1-dimethylethyl (2S)-2-(hydroxymethyl)morpholine-4-carboxylate following General Procedure J.

(B) (5Z)-5-({1-[2,4-Bis(trifluoromethyl)benzyl]-1H-indazol-5-yl}methylidene)-3-[(2S)-morpholin-2-ylmethyl]-1,3-thiazolidine-2,4-dione was prepared from 1,1-dimethylethyl (2S)-2-[{(5Z)-5-[(1-{[2,4-bis(trifluoromethyl)phenyl]-methyl}-1H-indazol-5-yl)methylidene]-2,4-dioxo-1,3-thiazolidin-3-yl}methyl]morpholine-4-carboxylate following General Procedure M.

$^1$H NMR (400 MHz, CDCl$_3$): δ 8.25 (s, 1H), 8.03 (s, 1H), 7.99 (s, 2H), 7.64 (d, 1H), 7.53 (d, 1H), 7.36 (d, 1H), 6.83 (d, 1H), 5.89 (s, 2H), 3.97 (dd, 1H), 3.89 (d, 1H), 3.76-3.86 (m, 1H), 3.68 (dd, 1H), 3.53 (td, 1H), 2.97 (d, 1H), 2.85-2.94 (m, 1H), 2.76-2.84 (m, 1H), 2.67 (dd, 1H).

LC/MS: mass calcd. for C$_{25}$H$_{20}$F$_6$N$_4$O$_3$S: 570.12. found 571.4 [M+1]$^+$

Example 196

(5Z)-5-({1-[2,4-Bis(trifluoromethyl)benzyl]-1H-indazol-5-yl}methylidene)-3-[(3S)-morpholin-3-ylmethyl]-1,3-thiazolidine-2,4-dione

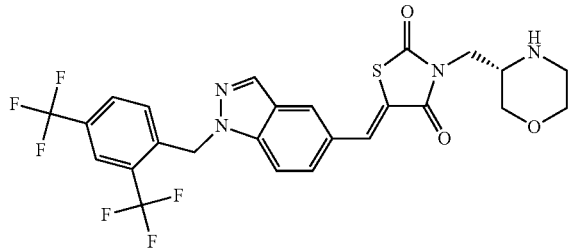 [SMILES: O=C1S/C(=C\c2ccc3c(cnn3Cc3ccc(C(F)(F)F)cc3C(F)(F)F)c2)C(=O)N1C[C@H]1COCCN1]

(A) 1,1-Dimethylethyl (3S)-3-[{(5Z)-5-[(1-{[2,4-bis(trifluoromethyl)phenyl]methyl}-1H-indazol-5-yl)methylidene]-2,4-dioxo-1,3-thiazolidin-3-yl}methyl]morpholine-4-carboxylate was prepared from (5Z)-5-({1-[2,4-bis(trifluoromethyl)benzyl]-1H-indazol-5-yl}methylidene)-2,4-dioxo-1,3-thiazolidine (from Example 6) and 1,1-dimethylethyl (3S)-3-(hydroxymethyl)morpholine-4-carboxylate following General Procedure J.

(B) (5Z)-5-({1-[2,4-Bis(trifluoromethyl)benzyl]-1H-indazol-5-yl}methylidene)-3-[(3S)-morpholin-3-ylmethyl]-1,3-thiazolidine-2,4-dione was prepared from 1,1-dimethylethyl (3S)-3-[{(5Z)-5-[(1-{[2,4-bis(trifluoromethyl)phenyl]-methyl}-1H-indazol-5-yl)methylidene]-2,4-dioxo-1,3-thiazolidin-3-yl}methyl]morpholine-4-carboxylate following General Procedure M.
$^1$H NMR (400 MHz, CDCl$_3$): δ 8.25 (s, 1H), 8.04 (s, 1H), 7.99 (s, 2H), 7.64 (d, 1H), 7.53 (d, 1H), 7.36 (d, 1H), 6.84 (d, 1H), 5.90 (s, 2H), 3.68-3.88 (m, 4H), 3.47-3.58 (m, 1H), 3.33 (dd, 1H), 3.13-3.24 (m, 1H), 2.83-3.01 (m, 2H).
LC/MS: mass calcd. for $C_{25}H_{20}F_6N_4O_3S$: 570.12. found 571.5 [M+1]$^+$

Example 197

(5Z)-5-({1-[2,4-Bis(trifluoromethyl)benzyl]-1H-indazol-5-yl}methylidene)-3-[(3R)-morpholin-3-ylmethyl]-1,3-thiazolidine-2,4-dione

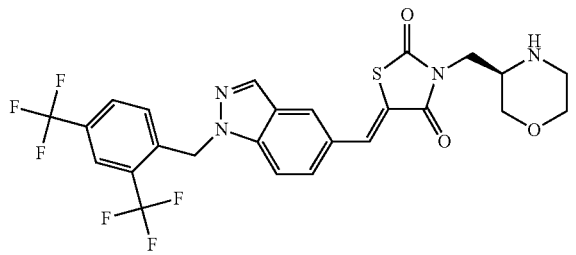 [SMILES: O=C1S/C(=C\c2ccc3c(cnn3Cc3ccc(C(F)(F)F)cc3C(F)(F)F)c2)C(=O)N1C[C@@H]1COCCN1]

(A) 1,1-Dimethylethyl (3R)-3-[{(5Z)-5-[(1-{[2,4-bis(trifluoromethyl)phenyl]methyl}-1H-indazol-5-yl)methylidene]-2,4-dioxo-1,3-thiazolidin-3-yl}methyl]morpholine-4-carboxylate was prepared from (5Z)-5-({1-[2,4-bis(trifluoromethyl)benzyl]-1H-indazol-5-yl}methylidene)-2,4-dioxo-1,3-thiazolidine (from Example 6) and 1,1-dimethylethyl (3R)-3-(hydroxymethyl)morpholine-4-carboxylate following General Procedure J.

(B) (5Z)-5-({1-[2,4-Bis(trifluoromethyl)benzyl]-1H-indazol-5-yl}methylidene)-3-[(3R)-morpholin-3-ylmethyl]-1,3-thiazolidine-2,4-dione was prepared from 1,1-dimethylethyl (3R)-3-[{(5Z)-5-[(1-{[2,4-bis(trifluoromethyl)phenyl]-methyl}-1H-indazol-5-yl)methylidene]-2,4-dioxo-1,3-thiazolidin-3-yl}methyl]morpholine-4-carboxylate following General Procedure M.
$^1$H NMR (400 MHz, CDCl$_3$): δ 8.25 (s, 1H), 8.04 (s, 1H), 7.99 (s, 2H), 7.64 (d, 1H), 7.49-7.56 (m, 1H), 7.36 (d, 1H), 6.84 (d, 1H), 5.90 (s, 2H), 3.68-3.87 (m, 4H), 3.48-3.58 (m, 1H), 3.33 (dd, 1H), 3.12-3.23 (m, 1H), 2.83-3.00 (m, 2H).
LC/MS: mass calcd. for $C_{25}H_{20}F_6N_4O_3S$: 570.12. found 571.4 [M+1]$^+$

Example 198

(5Z)-5-({1-[4-Chloro-2-(trifluoromethyl)benzyl]-1H-indazol-5-yl}methylidene)-3-[(3R)-morpholin-3-ylmethyl]-1,3-thiazolidine-2,4-dione

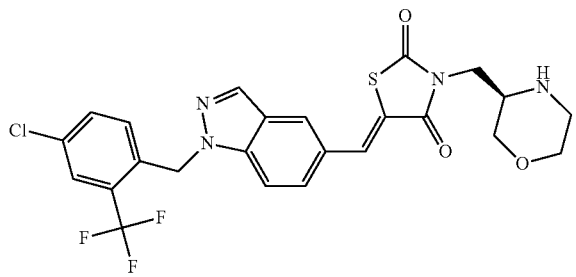 [SMILES: O=C1S/C(=C\c2ccc3c(cnn3Cc3ccc(Cl)cc3C(F)(F)F)c2)C(=O)N1C[C@@H]1COCCN1]

(A) 1,1-Dimethylethyl (3R)-3-[{(5Z)-5-[(1-{[2-chloro-4-(trifluoromethyl)phenyl]methyl}-1H-indazol-5-yl)methylidene]-2,4-dioxo-1,3-thiazolidin-3-yl}methyl]morpholine-4-carboxylate was prepared from (5Z)-5-({1-[2-chloro-4-(trifluoromethyl)benzyl]-1H-indazol-5-yl}methylidene)-2,4-dioxo-1,3-thiazolidine (from Example 1) and 1,1-dimethylethyl (3R)-3-(hydroxymethyl)morpholine-4-carboxylate following General Procedure J.

(B) (5Z)-5-({1-[2-Chloro-4-(trifluoromethyl)benzyl]-1H-indazol-5-yl}methylidene)-3-[(3R)-morpholin-3-ylmethyl]-1,3-thiazolidine-2,4-dione was prepared from 1,1-dimethylethyl (3R)-3-[{(5Z)-5-[(1-{[2-chloro-4-(trifluoromethyl)phenyl]methyl}-1H-indazol-5-yl)methylidene]-2,4-dioxo-1,3-thiazolidin-3-yl}methyl]morpholine-4-carboxylate following General Procedure M.
$^1$H NMR (400 MHz, CDCl$_3$): δ 8.22 (s, 1H), 8.03 (s, 1H), 7.97 (s, 1H), 7.72 (d, 1H), 7.48-7.54 (m, 1H), 7.32-7.39 (m, 2H), 6.68 (d, 1H), 5.80 (s, 2H), 3.69-3.88 (m, 4H), 3.48-3.58 (m, 1H), 3.33 (dd, 1H), 3.13-3.23 (m, 1H), 2.83-3.01 (m, 2H).
LC/MS: mass calcd. for $C_{24}H_{20}ClF_3N_4O_3S$: 536.09. found 537.4 [M+1]$^+$

Example 199

(5Z)-5-({1-[4-Chloro-2-(trifluoromethyl)benzyl]-1H-indazol-5-yl}methylidene)-3-(cis-4-fluoropiperidin-3-yl)-1,3-thiazolidine-2,4-dione

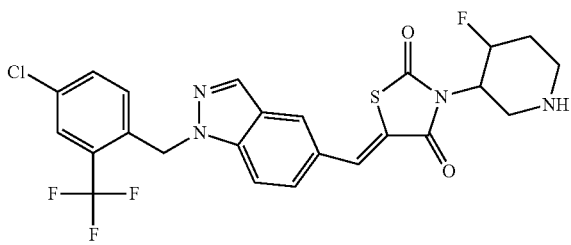 [SMILES: O=C1S/C(=C\c2ccc3c(cnn3Cc3ccc(Cl)cc3C(F)(F)F)c2)C(=O)N1C1CNCCC1F]

(A) 1,1-Dimethylethyl cis-3-[(5Z)-5-[(1-[4-chloro-2-(trifluoromethyl)benzyl]-1H-indazol-5-yl)methylidene]-2,4-dioxo-1,3-thiazolidin-3-yl]-4-fluoropiperidine-1-carboxylate was prepared from (5Z)-5-({1-[2-chloro-4-(trifluoromethyl)benzyl]-1H-indazol-5-yl}methylidene)-2,4-dioxo-1,3-thiazolidine (from Example 1) and 1,1-dimethylethyl trans-3-hydroxy-4-fluoropiperidine-1-carboxylate (prepared as described in US 2007/249589) following General Procedure W.

(B) (5Z)-5-({1-[4-Chloro-2-(trifluoromethyl)benzyl]-1H-indazol-5-yl}methylidene)-3-(cis-4-fluoropiperidin-3-yl)-1,3-thiazolidine-2,4-dione was prepared from 1,1-dimethylethyl cis-3-[(5Z)-5-[(1-[4-chloro-2-(trifluoromethyl)benzyl]-1H-indazol-5-yl)methylidene]-2,4-dioxo-1,3-thiazolidin-3-yl]-4-fluoropiperidine-1-carboxylate following General Procedure M.

$^1$H NMR (400 MHz, CDCl$_3$): δ 8.21 (s, 1H), 7.95 (s, 1H), 7.72 (d, 1H), 7.65 (s, 1H), 7.45-7.50 (m, 1H), 7.30-7.38 (m, 2H), 6.66 (d, 1H), 5.80 (s, 2H), 4.83-5.04 (m, 2H), 4.08-4.20 (m, 2H), 3.99-4.08 (m, 1H), 3.81-3.91 (m, 1H), 2.27-2.40 (m, 1H), 2.02-2.13 (m, 1H).

LC/MS: mass calcd. for C$_{24}$H$_{19}$ClF$_4$N$_4$O$_2$S: 538.08. found 539.5 [M+1]$^+$

Example 200

(5Z)-5-({1-[2,4-Bis(trifluoromethyl)benzyl]-1H-indazol-5-yl}methylidene)-3-(cis-4-fluoropiperidin-3-yl)-1,3-thiazolidine-2,4-dione

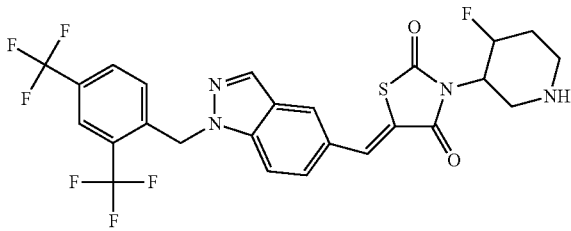 [SMILES: O=C1S/C(=C\c2ccc3c(cnn3Cc3ccc(C(F)(F)F)cc3C(F)(F)F)c2)C(=O)N1C1CNCCC1F]

(A) 1,1-Dimethylethyl cis-3-[(5Z)-5-[([2,4-bis(trifluoromethyl)benzyl]-1H-indazol-5-yl)methylidene]-2,4-dioxo-1,3-thiazolidin-3-yl]-4-fluoropiperidine-1-carboxylate was prepared from (5Z)-5-({1-[2,4-bis(trifluoromethyl)benzyl]-1H-indazol-5-yl}methylidene)-2,4-dioxo-1,3-thiazolidine (from Example 6) and 1,1-dimethylethyl trans-3-hydroxy-4-fluoropiperidine-1-carboxylate (prepared as described in US 2007/249589) following General Procedure W.

(B) (5Z)-5-({1-[2,4-bis(trifluoromethyl)benzyl]-1H-indazol-5-yl}methylidene)-3-(cis-4-fluoropiperidin-3-yl)-1,3-thiazolidine-2,4-dione was prepared from 1,1-dimethylethyl cis-3-[(5Z)-5-[(1-[2,4-bis(trifluoromethyl)benzyl]-1H-indazol-5-yl)methylidene]-2,4-dioxo-1,3-thiazolidin-3-yl]-4-fluoropiperidine-1-carboxylate following General Procedure M.

$^1$H NMR (400 MHz, CDCl$_3$): δ 8.23 (s, 1H), 7.99 (s, 1H), 7.97 (s, 1H), 7.61-7.69 (m, 2H), 7.49 (d, 1H), 7.33 (d, 1H), 6.82 (d, 1H), 5.89 (s, 2H), 4.93 (dd, 1H), 4.09-4.21 (m, 3H), 4.03 (d, 1H), 3.80-3.92 (m, 1H), 2.48 (br. s., 1H), 2.26-2.41 (m, 1H), 1.97-2.16 (m, 1H).

LC/MS: mass calcd. for C$_{25}$H$_{19}$F$_7$N$_4$O$_2$S: 572.11. found 573.5 [M+1]$^+$

Example 201

(5Z)-5-({1-[4-Chloro-2-(trifluoromethyl)benzyl]-1H-indazol-5-yl}methylidene)-3-(cis-3-fluoropiperidin-4-yl)-1,3-thiazolidine-2,4-dione

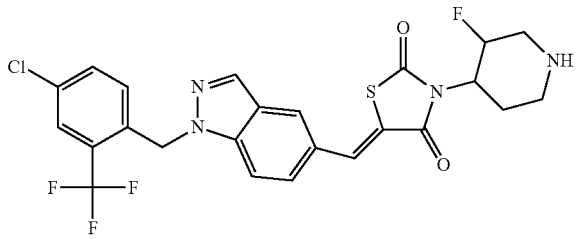 [SMILES: O=C1S/C(=C\c2ccc3c(cnn3Cc3ccc(Cl)cc3C(F)(F)F)c2)C(=O)N1C1CCNCC1F]

(A) 1,1-Dimethylethyl cis-4-[(5Z)-5-[(1-[4-chloro-2-(trifluoromethyl)benzyl]-1H-indazol-5-yl)methylidene]-2,4-dioxo-1,3-thiazolidin-3-yl]-3-fluoropiperidine-1-carboxylate was prepared from (5Z)-5-({1-[2-chloro-4-(trifluoromethyl)benzyl]-1H-indazol-5-yl}methylidene)-2,4-dioxo-1,3-thiazolidine (from Example 1) and 1,1-dimethylethyl trans-4-hydroxy-3-fluoropiperidine-1-carboxylate (prepared as described in US 2007/249589) following General Procedure J.

(B) (5Z)-5-({1-[4-Chloro-2-(trifluoromethyl)benzyl]-1H-indazol-5-yl}methylidene)-3-(cis-3-fluoropiperidin-4-yl)-1,3-thiazolidine-2,4-dione was prepared from 1,1-dimethylethyl cis-4-[(5Z)-5-[(1-[4-chloro-2-(trifluoromethyl)benzyl]-1H-indazol-5-yl)methylidene]-2,4-dioxo-1,3-thiazolidin-3-yl]-3-fluoropiperidine-1-carboxylate following General Procedure M.

$^1$H NMR (400 MHz, CDCl$_3$): δ 8.22 (s, 1H), 8.00 (s, 1H), 7.96 (s, 1H), 7.72 (d, 1H), 7.48-7.54 (m, 1H), 7.36 (s, 1H), 7.34 (s, 1H), 6.68 (d, 1H), 5.80 (s, 2H), 4.57-4.75 (m, 1H), 4.40-4.56 (m, 1H), 3.25-3.46 (m, 2H), 3.18 (qd, 1H), 2.83-3.03 (m, 1H), 2.72 (t, 1H), 1.88 (br. s., 1H), 1.72 (d, 1H).

LC/MS: mass calcd. for C$_{24}$H$_{19}$ClF$_4$N$_4$O$_2$S: 538.08. found 539.5 [M+1]$^+$

Example 202

(5Z)-5-({1-[4-Chloro-2-(trifluoromethyl)benzyl]-1H-indazol-5-yl}methylidene)-3-[(3R,8aS)-hexahydro-1H-pyrrolo[2,1-c][1,4]oxazin-3-ylmethyl]-1,3-thiazolidine-2,4-dione

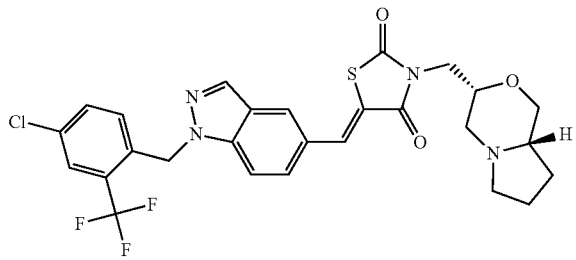 [SMILES: O=C1S/C(=C\c2ccc3c(cnn3Cc3ccc(Cl)cc3C(F)(F)F)c2)C(=O)N1C[C@H]1CN2CCC[C@H]2CO1]

(5Z)-5-({1-[4-Chloro-2-(trifluoromethyl)benzyl]-1H-indazol-5-yl}methylidene)-3-[(3R,8aS)-hexahydro-1H-pyrrolo[2,1-c][1,4]oxazin-3-ylmethyl]-1,3-thiazolidine-2,4-dione was prepared from [(5Z)-5-({1-[4-chloro-2-(trifluoromethyl)benzyl]-1H-indazol-5-yl}methylidene)-2,4-dioxo-1,3-thiazolidine (from Example 1) and [(3R,8aS)-hexahydro-1H-pyrrolo[2,1-c][1,4]oxazin-3-yl]methanol (prepared as described in WO 2004/006846) following General Procedure J.

$^1$H NMR (400 MHz, CDCl$_3$): δ 8.22 (s, 1H), 8.01 (s, 1H), 7.96 (s, 1H), 7.72 (d, 1H), 7.51 (d, 1H), 7.36 (s, 1H), 7.33 (s, 1H), 6.67 (d, 1H), 5.80 (s, 2H), 4.69 (dd, 1H), 4.09-4.20 (m, 1H), 3.69-3.87 (m, 2H), 3.56 (dd, 1H), 3.03 (t, 1H), 2.91 (d, 1H), 2.48 (dd, 1H), 2.04-2.20 (m, 2H), 1.67-1.89 (m, 3H), 1.41-1.54 (m, 1H).

LC/MS: mass calcd. for C$_{27}$H$_{24}$ClF$_3$N$_4$O$_3$S: 576.12. found 577.5 [M+1]$^+$

Example 203

(5Z)-5-({1-[4-Chloro-2-(trifluoromethyl)benzyl]-1H-indazol-5-yl}methylidene)-3-[(3S,8aS)-hexahydro-1H-pyrrolo[2,1-c][1,4]oxazin-3-ylmethyl]-1,3-thiazolidine-2,4-dione

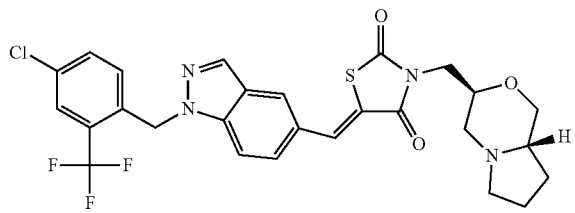 [SMILES: O=C1S/C(=C\c2ccc3c(cnn3Cc3ccc(Cl)cc3C(F)(F)F)c2)C(=O)N1C[C@@H]1CN2CCC[C@H]2CO1]

(5Z)-5-({1-[4-Chloro-2-(trifluoromethyl)benzyl]-1H-indazol-5-yl}methylidene)-3-[(3S,8aS)-hexahydro-1H-pyrrolo[2,1-c][1,4]oxazin-3-ylmethyl]-1,3-thiazolidine-2,4-dione was prepared from [(5Z)-5-({1-[4-chloro-2-(trifluoromethyl)benzyl]-1H-indazol-5-yl}methylidene)-2,4-dioxo-1,3-thiazolidine (from Example 1) and [(3S,8aS)-hexahydro-1H-pyrrolo[2,1-c][1,4]oxazin-3-yl]methanol (prepared as described in WO 2004/006846) following General Procedure J.

$^1$H NMR (400 MHz, CDCl$_3$): δ 8.22 (s, 1H), 8.03 (s, 1H), 7.97 (s, 1H), 7.72 (s, 1H), 7.52 (d, 1H), 7.31-7.38 (m, 2H), 6.67 (d, Hz, 1H), 5.80 (s, 2H), 3.94-4.05 (m, 2H), 3.83-3.92 (m, 1H), 3.76 (dd, 1H), 3.27 (t, 1H), 3.02-3.13 (m, 2H), 2.04-2.24 (m, 3H), 1.67-1.88 (m, 3H), 1.21-1.38 (m, 1H).

LC/MS: mass calcd. for C$_{27}$H$_{24}$ClF$_3$N$_4$O$_3$S: 576.12. found 577.5 [M+1]$^+$

Example 204

(5Z)-5-({1-[4-Chloro-2-(trifluoromethyl)benzyl]-1H-indazol-5-yl}methylidene)-3-[(3R,9aS)-hexahydro-1H-[1,4]oxazino[3,4-c][1,4]oxazin-3-ylmethyl]-1,3-thiazolidine-2,4-dione

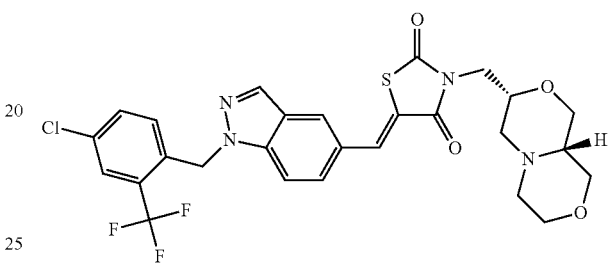

(5Z)-5-({1-[4-Chloro-2-(trifluoromethyl)benzyl]-1H-indazol-5-yl}methylidene)-3-[(3R,9aS)-hexahydro-1H-[1,4]oxazino[3,4-c][1,4]oxazin-3-ylmethyl]-1,3-thiazolidine-2,4-dione was prepared from [(5Z)-5-({1-[4-chloro-2-(trifluoromethyl)benzyl]-1H-indazol-5-yl}methylidene)-2,4-dioxo-1,3-thiazolidine (from Example 1) and [(3R,9aS)-hexahydro-1H-[1,4]oxazino[3,4-c][1,4]oxazin-3-yl]methanol (prepared as described in WO 2004/006846) following General Procedure J.

$^1$H NMR (400 MHz, CDCl$_3$): δ 8.22 (s, 1H), 7.99-8.05 (m, 1H), 7.94-7.98 (m, 1H), 7.72 (d, 1H), 7.51 (d, 1H), 7.36 (s, 1H), 7.34 (s, 1H), 6.68 (d, 1H), 5.80 (s, 2H), 3.52-4.03 (m, 6H), 3.12-3.44 (m, 3H), 2.54-2.68 (m, 3H), 2.29-2.48 (m, 2H).

LC/MS: mass calcd. for C$_{27}$H$_{24}$ClF$_3$N$_4$O$_4$S: 592.12. found 593.6 [M+1]$^+$

Example 205

(5Z)-5-({1-[4-Chloro-2-(trifluoromethyl)benzyl]-1H-indazol-5-yl}methylidene)-3-[(3S,9aS)-hexahydro-1H-[1,4]oxazino[3,4-c][1,4]oxazin-3-ylmethyl]-1,3-thiazolidine-2,4-dione

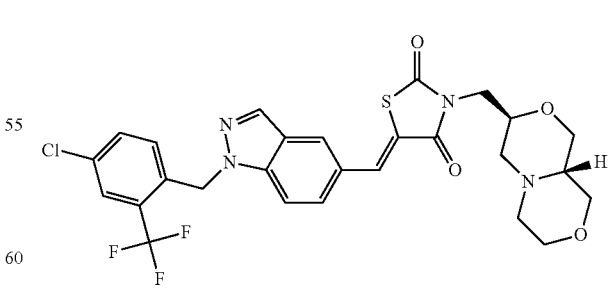

(5Z)-5-({1-[4-Chloro-2-(trifluoromethyl)benzyl]-1H-indazol-5-yl}methylidene)-3-[(3S,9aS)-hexahydro-1H-[1,4]oxazino[3,4-c][1,4]oxazin-3-ylmethyl]-1,3-thiazolidine-2,4-dione was prepared from [(5Z)-5-({1-[4-chloro-2-(trifluoromethyl)benzyl]-1H-indazol-5-yl}methylidene)-2, 4-dioxo-1,3-thiazolidine (from Example 1) and [(3S,9aS)-hexahydro-1H-[1,4]oxazino[3,4-c][1,4]oxazin-3-yl]methanol (prepared as described in PCT Int. Appl. 2004006846) following General Procedure J.

$^1$H NMR (400 MHz, CDCl$_3$): δ 8.22 (s, 1H), 8.03 (s, 1H), 7.97 (s, 1H), 7.72 (d, 1H), 7.52 (d, 1H), 7.31-7.38 (m, 2H), 6.68 (d, 1H), 5.80 (s, 2H), 3.91-3.99 (m, 2H), 3.84 (dd, 1H), 3.60-3.79 (m, 4H), 3.18 (dt, 2H), 2.75 (d, 1H), 2.63 (d, 1H), 2.33-2.49 (m, 2H), 2.13-2.23 (m, 1H).

LC/MS: mass calcd. for C$_{27}$H$_{24}$ClF$_3$N$_4$O$_4$S: 592.12. found 593.6 [M+1]$^+$

Example 206

(5Z)-5-({1-[4-Chloro-2-(trifluoromethyl)benzyl]-1H-indazol-5-yl}methylidene)-3-[(1S,9aR)-octahydro-2H-quinolizin-1-ylmethyl]-1,3-thiazolidine-2,4-dione

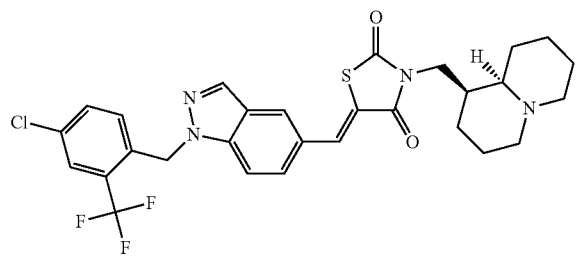 [SMILES: O=C1S/C(=C\c2ccc3c(cnn3Cc3ccc(Cl)cc3C(F)(F)F)c2)C(=O)N1C[C@@H]1CCCN2CCCC[C@H]12]

(5Z)-5-({1-[4-Chloro-2-(trifluoromethyl)benzyl]-1H-indazol-5-yl}methylidene)-3-[(1S,9aR)-octahydro-2H-quinolizin-1-ylmethyl]-1,3-thiazolidine-2,4-dione was prepared from [(5Z)-5-({1-[4-chloro-2-(trifluoromethyl)benzyl]-1H-indazol-5-yl}methylidene)-2,4-dioxo-1,3-thiazolidine (from Example 1) and [(1S,9aR)-octahydro-2H-quinolizin-1-yl]methanol following General Procedure J.

$^1$H NMR (400 MHz, CDCl$_3$): δ 8.21 (s, 1H), 7.99 (s, 1H), 7.95 (s, 1H), 7.71 (d, 1H), 7.50 (d, 1H), 7.35 (s, 1H), 7.33 (s, 1H), 6.67 (d, 1H), 5.79 (s, 2H), 4.17-4.28 (m, 1H), 3.84 (dd, 1H), 2.88 (dd, 2H), 1.89-2.19 (m, 5H), 1.81 (d, 1H), 1.42-1.67 (m, 6H), 1.19-1.41 (m, 2H).

LC/MS: mass calcd. for C$_{29}$H$_{28}$ClF$_3$N$_4$O$_2$S: 588.16. found 589.5 [M+1]$^+$

Example 207

(5Z)-5-({1-[2,4-Bis(trifluoromethyl)benzyl]-1H-indazol-5-yl}methylidene)-3-[(1S,9aR)-octahydro-2H-quinolizin-1-ylmethyl]-1,3-thiazolidine-2,4-dione

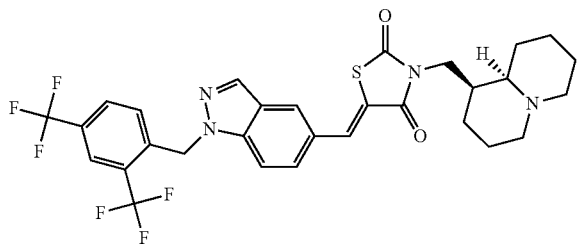 [SMILES: O=C1S/C(=C\c2ccc3c(cnn3Cc3ccc(C(F)(F)F)cc3C(F)(F)F)c2)C(=O)N1C[C@@H]1CCCN2CCCC[C@H]12]

(5Z)-5-({1-[2,4-Bis(trifluoromethyl)benzyl]-1H-indazol-5-yl}methylidene)-3-[(1S,9aR)-octahydro-2H-quinolizin-1-yl methyl]-1,3-thiazolidine-2,4-dione was prepared from [(5Z)-5-({1-[2,4-bis(trifluoromethyl)benzyl]-1H-indazol-5-yl}methylidene)-2,4-dioxo-1,3-thiazolidine (from Example 6) and [(1S,9aR)-octahydro-2H-quinolizin-1-yl]methanol following General Procedure J.

$^1$H NMR (400 MHz, CDCl$_3$): δ 8.24 (s, 1H), 7.95-8.03 (m, 3H), 7.63 (d, 1H), 7.52 (d, 1H), 7.35 (d, 1H), 6.82 (d, 1H), 5.89 (s, 2H), 4.17-4.26 (m, 1H), 3.79-3.92 (m, 1H), 2.87 (d, 2H), 1.88-2.14 (m, 5H), 1.81 (d, 1H), 1.22-1.69 (m, 8H).

LC/MS: mass calcd. for C$_{30}$H$_{28}$F$_6$N$_4$O$_2$S: 622.18. found 623.5 [M+1]$^+$

Example 208

(5Z)-5-({1-[2,4-Bis(trifluoromethyl)benzyl]-1H-indazol-5-yl}methylidene)-3-[(3R,8aS)-hexahydro-1H-pyrrolo[2,1-c][1,4]oxazin-3-ylmethyl]-1,3-thiazolidine-2,4-dione

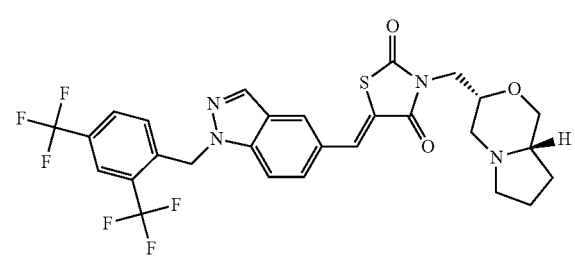 [SMILES: O=C1S/C(=C\c2ccc3c(cnn3Cc3ccc(C(F)(F)F)cc3C(F)(F)F)c2)C(=O)N1C[C@H]1CN2CCC[C@H]2CO1]

(5Z)-5-({1-[2,4-Bis(trifluoromethyl)benzyl]-1H-indazol-5-yl}methylidene)-3-[(3R,8aS)-hexahydro-1H-pyrrolo[2,1-c][1,4]oxazin-3-ylmethyl]-1,3-thiazolidine-2,4-dione was prepared from [(5Z)-5-({1-[2,4-bis(trifluoromethyl)benzyl]-1H-indazol-5-yl}methylidene)-2,4-dioxo-1,3-thiazolidine (from Example 6) and [(3R,8aS)-hexahydro-1H-pyrrolo[2,1-c][1,4]oxazin-3-yl]methanol (prepared as described in WO 2004/006846) following General Procedure J.

$^1$H NMR (400 MHz, CDCl$_3$): δ 8.25 (s, 1H), 8.02 (s, 1H), 7.99 (d, 2H), 7.64 (d, 1H), 7.53 (d, 1H), 7.35 (d, 1H), 6.83 (d, 1H), 5.89 (s, 2H), 4.68 (dd, 1H), 4.10-4.22 (m, 1H), 3.70-3.90 (m, 2H), 3.56 (dd, 1H), 2.99-3.10 (m, 1H), 2.87-2.96 (m, 1H), 2.50 (dd, 1H), 2.02-2.24 (m, 2H), 1.56-1.90 (m, 3H), 1.38-1.56 (m, 1H).

LC/MS: mass calcd. for C$_{28}$H$_{24}$F$_6$N$_4$O$_3$S: 610.15. found 611.5 [M+1]$^+$

Example 209

Methyl [(5Z)-5-({1-[4-chloro-2-(trifluoromethyl)benzyl]-1H-indazol-5-yl}methylidene)-2,4-dioxo-1,3-thiazolidin-3-yl](tetrahydro-2H-pyran-4-yl)acetate

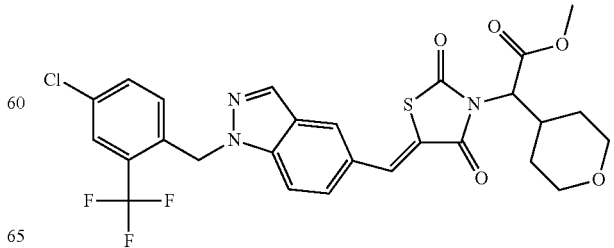

(A) Methyl 2-(2,4-dioxothiazolidin-3-yl)-2-(tetrahydro-2H-pyran-4-yl)acetate was prepared from methyl 2-amino-2-(tetrahydro-2H-pyran-4-yl)acetate following General Procedure D.

(B) Methyl [(5Z)-5-({1-[4-chloro-2-(trifluoromethyl)benzyl]-1H-indazol-5-yl}methylidene)-2,4-dioxo-1,3-thiazolidin-3-yl](tetrahydro-2H-pyran-4-yl)acetate was prepared from [4-chloro-2-(trifluoromethyl)benzyl]-1H-indazol-5-carbaldehyde (from Example 1) and methyl 2-(2,4-dioxothiazolidin-3-yl)-2-(tetrahydro-2H-pyran-4-yl)acetate following General Procedure F.

$^1$H NMR (400 MHz, CD$_3$OD): δ 8.29 (s, 1H), 8.13 (s, 1H), 8.09 (s, 1H), 7.80 (d, 1H), 7.56-7.69 (m, 2H), 7.49 (dd, 1H), 6.70 (d, 1H), 5.87 (s, 2H), 4.80 (d, 1H), 3.86-3.99 (m, 2H), 3.72 (s, 3H), 3.37-3.51 (m, 2H), 2.56-2.70 (m, 1H), 2.12-2.21 (m, 1H), 1.36-1.50 (m, 2H), 1.19-1.35 (m, 1H).

LCMS: mass calcd. for C$_{27}$H$_{23}$ClF$_3$N$_3$O$_5$S: 593.1. found 593.9 [M+H]$^+$ Example 210

Methyl (2S)-3-tert-butoxy-2-[(5Z)-5-({1-[4-chloro-2-(trifluoromethyl)benzyl]-1H-indazol-5-yl}methylidene)-2,4-dioxo-1,3-thiazolidin-3-yl]propanoate

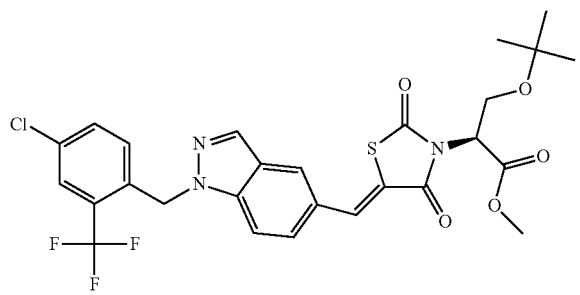 [SMILES: COC(=O)[C@H](COC(C)(C)C)N1C(=O)S/C(=C\c2ccc3c(cnn3Cc3ccc(Cl)cc3C(F)(F)F)c2)C1=O]

(A) Methyl (2S)-3-tert-butoxy-2-(2,4-dioxo-1,3-thiazolidin-3-yl)propanoate was prepared from methyl (2S)-2-amino-3-tert-butoxypropanoate following General Procedure D.

(B) Methyl (2S)-3-tert-butoxy-2-[(5Z)-5-({1-[4-chloro-2-(trifluoromethyl)-benzyl]-1H-indazol-5-yl}methylidene)-2,4-dioxo-1,3-thiazolidin-3-yl]propanoate was prepared from [4-chloro-2-(trifluoromethyl)benzyl]-1H-indazol-5-carbaldehyde (from Example 1) and methyl (2S)-3-tert-butoxy-2-(2,4-dioxo-1,3-thiazolidin-3-yl)propanoate following General Procedure F.

$^1$H NMR (400 MHz, CDCl$_3$): δ 8.22 (s, 1H), 8.03 (s, 1H), 7.98 (s, 1H), 7.72 (d, 1H), 7.53 (dd, 1H), 7.37-7.33 (m, 2H), 6.67 (d, 1H), 5.80 (s, 2H), 5.02 (t, 1H), 4.01 (d, 2H), 3.78 (s, 3H), 1.14 (s, 9H).

LCMS: mass calcd. for C$_{27}$H$_{25}$ClF$_3$N$_3$O$_5$S: 595.12. found 539.8 [M-tert-Bu+2H]$^+$ Example 211

Ethyl 2-[(5Z)-5-({1-[4-chloro-2-(trifluoromethyl)benzyl]-1H-indazol-5-yl}methylidene)-2,4-dioxo-1,3-thiazolidin-3-yl]-3-(pyridin-2-yl)propanoate

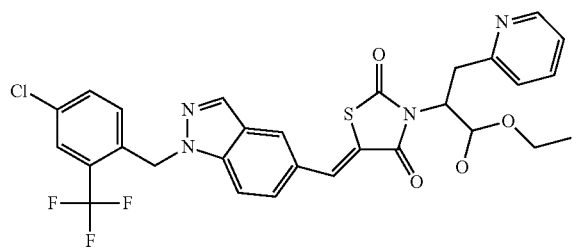 [SMILES: CCOC(O)C(Cc1ccccn1)N1C(=O)S/C(=C\c2ccc3c(cnn3Cc3ccc(Cl)cc3C(F)(F)F)c2)C1=O]

(A) Ethyl 2-(2,4-dioxo-1,3-thiazolidin-3-yl)-3-(pyridin-2-yl)propanoate was prepared from ethyl 2-amino-3-(pyridin-2-yl)propanoate following General Procedure D.

(B) Ethyl 2-[(5Z)-5-({1-[4-chloro-2-(trifluoromethyl)benzyl]-1H-indazol-5-yl}methylidene)-2,4-dioxo-1,3-thiazolidin-3-yl]-3-(pyridin-2-yl)propanoate was prepared from [4-chloro-2-(trifluoromethyl)benzyl]-1H-indazol-5-carbaldehyde (from Example 1) and ethyl 2-(2,4-dioxo-1,3-thiazolidin-3-yl)-3-(pyridin-2-yl)propanoate following General Procedure F.

$^1$H NMR (400 MHz, CD$_3$OD): δ 8.42 (d, 1H), 8.27 (s, 1H), 8.07 (s, 1H), 7.97 (s, 1H), 7.80 (d, 1H), 7.72 (td, 1H), 7.55-7.63 (m, 2H), 7.48 (dd, 1H), 7.30 (d, 1H), 7.24 (dd, 1H), 6.69 (d, 1H), 5.86 (s, 2H), 5.49 (dd, 1H), 4.19-4.31 (m, 2H), 3.64-3.72 (m, 1H), 3.50-3.61 (m, 1H), 1.23-1.30 (m, 3H).

LCMS: mass calcd. for C$_{29}$H$_{22}$ClF$_3$N$_4$O$_4$S: 614.10. found 614.8 [M+H]$^+$ Example 212

Methyl (2R)-3-tert-butoxy-2-[(5Z)-5-({1-[4-chloro-2-(trifluoromethyl)benzyl]-1H-indazol-5-yl}methylidene)-2,4-dioxo-1,3-thiazolidin-3-yl]propanoate

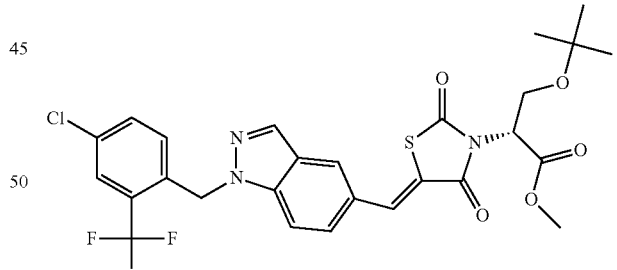

(A) Methyl (2R)-3-tert-butoxy-2-(2,4-dioxo-1,3-thiazolidin-3-yl)propanoate was prepared from methyl (2R)-2-amino-3-tert-butoxypropanoate following General Procedure D.

(B) Methyl (2R)-3-tert-butoxy-2-[(5Z)-5-({1-[4-chloro-2-(trifluoromethyl)-benzyl]-1H-indazol-5-yl}methylidene)-2,4-dioxo-1,3-thiazolidin-3-yl]propanoate was prepared from [4-chloro-2-(trifluoromethyl)benzyl]-1H-indazol-5-carbaldehyde (from Example 1) and methyl (2R)-3-tert-butoxy-2-(2,4-dioxo-1,3-thiazolidin-3-yl)propanoate following General Procedure F.

¹H NMR (400 MHz, CDCl₃): δ 8.23 (s, 1H), 8.03 (s, 1H), 7.99 (s, 1H), 7.72 (d, 1H), 7.53 (dd, 1H), 7.31-7.39 (m, 2H), 6.67 (d, 1H), 5.81 (s, 2H), 5.02 (t, 1H), 3.94-4.05 (m, 4H), 3.76 (s, 3H), 1.14 (s, 9H).

LCMS: mass calcd. for $C_{27}H_{25}ClF_3N_3O_5S$: 595.12. found 539.8 [M-tert-Bu+2H]⁺

Example 213

Methyl 4-[(5Z)-5-({1-[4-chloro-2-(trifluoromethyl)benzyl]-1H-indazol-5-yl}methylidene)-2,4-dioxo-1,3-thiazolidin-3-yl]-1-methylpiperidine-4-carboxylate

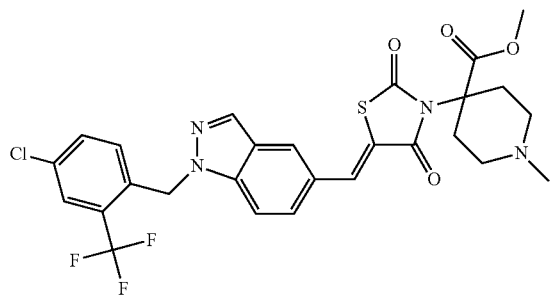 [SMILES: COC(=O)C1(N2C(=O)S/C(=C\c3ccc4c(cnn4Cc4ccc(Cl)cc4C(F)(F)F)c3)C2=O)CCN(C)CC1]

(A) Methyl 4-(2,4-dioxo-1,3-thiazolidin-3-yl)-1-methylpiperidine-4-carboxylate was prepared from methyl 4-amino-1-methylpiperidine-4-carboxylate following General Procedure D.

(B) Methyl 4-[(5Z)-5-({1-[4-chloro-2-(trifluoromethyl)benzyl]-1H-indazol-5-yl}methylidene)-2,4-dioxo-1,3-thiazolidin-3-yl]-1-methylpiperidine-4-carboxylate was prepared from [4-chloro-2-(trifluoromethyl)benzyl]-1H-indazol-5-carbaldehyde (from Example 1) and methyl 4-(2,4-dioxo-1,3-thiazolidin-3-yl)-1-methylpiperidine-4-carboxylate following General Procedure F.

¹H NMR (400 MHz, CD₃OD): δ 8.28 (s, 1H), 8.10 (s, 1H), 8.02 (s, 1H), 7.80 (d, 1H), 7.56-7.66 (m, 2H), 7.49 (dd, 1H), 6.70 (d, 1H), 5.86 (s, 2H), 3.77 (s, 3H), 2.94-3.18 (m, 6H), 2.61 (s, 3H), 2.35-2.47 (m, 2H).

LCMS: mass calcd. for $C_{27}H_{24}ClF_3N_4O_4S$: 592.12. found 593.3 [M+H]⁺

Example 214

Methyl 2-[(5Z)-5-({1-[4-chloro-2-(trifluoromethyl)benzyl]-1H-indazol-5-yl}methylidene)-2,4-dioxo-1,3-thiazolidin-3-yl]-3-(1-methyl-1H-imidazol-4-yl)propanoate

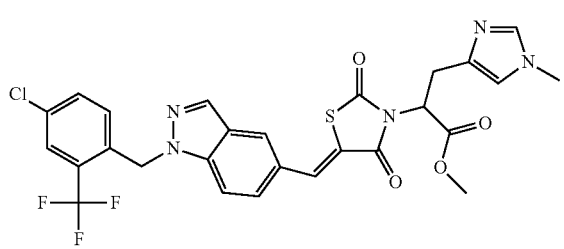 [SMILES: COC(=O)C(Cc1cn(C)cn1)N1C(=O)S/C(=C\c2ccc3c(cnn3Cc3ccc(Cl)cc3C(F)(F)F)c2)C1=O]

(A) Methyl 2-(2,4-dioxo-1,3-thiazolidin-3-yl)-3-(1-methyl-1H-imidazol-4-yl)propanoate was prepared from methyl 2-amino-3-(1-methyl-1H-imidazol-4-yl)propanoate following General Procedure D.

(B) Methyl 2-[(5Z)-5-({1-[4-chloro-2-(trifluoromethyl)benzyl]-1H-indazol-5-yl}methylidene)-2,4-dioxo-1,3-thiazolidin-3-yl]-3-(1-methyl-1H-imidazol-4-yl)propanoate was prepared from [4-chloro-2-(trifluoromethyl)benzyl]-1H-indazol-5-carbaldehyde (from Example 1) and methyl 2-(2,4-dioxo-1,3-thiazolidin-3-yl)-3-(1-methyl-1H-imidazol-4-yl)propanoate following General Procedure F.

¹H NMR (400 MHz, CD₃OD): δ 8.80 (s, 1H), 8.29 (s, 1H), 8.12 (s, 1H), 8.08 (s, 1H), 7.80 (d, 1H), 7.57-7.67 (m, 2H), 7.49 (dd, 1H), 7.43 (s, 1H), 6.72 (d, 1H), 5.87 (s, 2H), 5.38 (dd, 1H), 3.86 (s, 3H), 3.79 (s, 3H), 3.58-3.67 (m, 1H), 3.42-3.55 (m, 1H).

LCMS: mass calcd. for $C_{27}H_{21}ClF_3N_5O_4S$: 603.10. found 603.8 [M+H]⁺

Example 215 tert-Butyl 4-{1-[(5Z)-5-({1-[4-chloro-2-(trifluoromethyl)benzyl]-1H-indazol-5-yl}methylidene)-2,4-dioxo-1,3-thiazolidin-3-yl]-2-methoxy-2-oxoethyl}piperidine-1-carboxylate

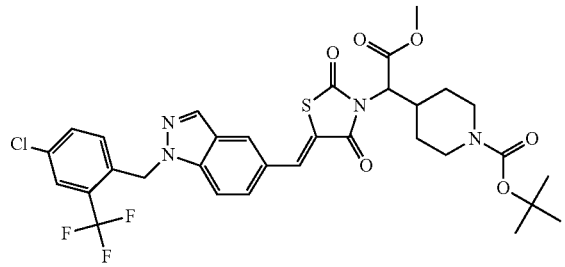 [SMILES: COC(=O)C(C1CCN(C(=O)OC(C)(C)C)CC1)N1C(=O)S/C(=C\c2ccc3c(cnn3Cc3ccc(Cl)cc3C(F)(F)F)c2)C1=O]

(A) tert-Butyl 4-[(2,4-dioxo-1,3-thiazolidin-3-yl)methoxycarbonylmethyl]-piperidine-1-carboxylate was prepared from tert-butyl 4-(amino-methoxycarbonylmethyl)piperidine-1-carboxylate following General Procedure D.

(B) tert-Butyl 4-{1-[(5Z)-5-({1-[4-chloro-2-(trifluoromethyl)benzyl]-1H-indazol-5-yl}methylidene)-2,4-dioxo-1,3-thiazolidin-3-yl]-2-methoxy-2-oxoethyl}piperidine-1-carboxylate was prepared from [4-chloro-2-(trifluoromethyl)benzyl]-1H-indazol-5-carbaldehyde (from Example 1) and tert-butyl 4-[(2,4-dioxo-1,3-thiazolidin-3-yl)methoxycarbonylmethyl]-piperidine-1-carboxylate following General Procedure F.

¹H NMR (400 MHz, CDCl₃): δ 8.23 (s, 1H), 8.04 (s, 1H), 7.97 (s, 1H), 7.72 (d, 1H), 7.50 (d, 1H), 7.37 (d, 2H), 6.66-6.73 (m, 1H), 5.80 (s, 2H), 4.72 (d, 1H), 4.02-4.26 (m, 2H), 3.75 (s, 3H), 2.50-2.85 (m, 3H), 2.15-2.26 (m, 1H), 1.45-1.50 (m, 1H), 1.44 (s, 9H), 1.13-1.29 (m, 1H).

LCMS: mass calcd. for $C_{32}H_{32}ClF_3N_4O_6S$: 692.17. found 593.2 [M-t-BuO₂C+H]⁺

Example 216

2-[(5Z)-5-({1-[4-Chloro-2-(trifluoromethyl)benzyl]-1H-indazol-5-yl}methylidene)-2,4-dioxo-1,3-thiazolidin-3-yl]-3-pyridin-2-ylpropanoic acid

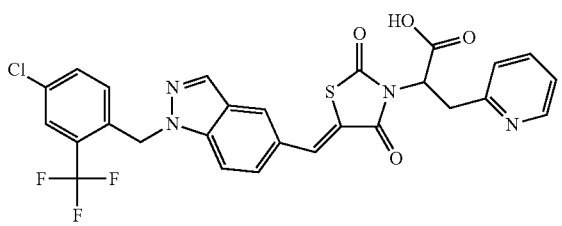 [SMILES: O=C(O)C(Cc1ccccn1)N1C(=O)S/C(=C\c2ccc3c(cnn3Cc3ccc(Cl)cc3C(F)(F)F)c2)C1=O]

2-[(5Z)-5-({1-[4-Chloro-2-(trifluoromethyl)benzyl]-1H-indazol-5-yl}methylidene)-2,4-dioxo-1,3-thiazolidin-3-yl]-3-pyridin-2-ylpropanoic acid was prepared from ethyl 2-[(5Z)-5-({1-[4-chloro-2-(trifluoromethyl)benzyl]-1H-indazol-5-yl}methylidene)-2,4-dioxo-1,3-thiazolidin-3-yl]-3-pyridin-2-ylpropanoate (Example 211) following General Procedure O.

$^1$H NMR (400 MHz, DMSO-$d_6$): δ 8.54 (d, 1H), 8.35 (s, 1H), 8.15 (s, 1H), 8.05 (s, 1H), 7.90-7.99 (m, 1H), 7.87 (d, 1H), 7.79 (d, 1H), 7.65 (ddd, 2H), 7.48-7.58 (m, 1H), 7.41 (br. s., 1H), 6.76 (d, 1H), 5.85 (s, 2H), 5.46 (dd, 1H), 3.44-3.70 (m, 2H).

LCMS: mass calcd. for $C_{27}H_{18}ClF_3N_4O_4S$: 586.07. found 587.3 [M+H]$^+$

Example 217

Methyl 2-[(5Z)-5-({1-[4-chloro-2-(trifluoromethyl)benzyl]-1H-indazol-5-yl}methylidene)-2,4-dioxo-1,3-thiazolidin-3-yl]-3-pyridin-3-ylpropanoate

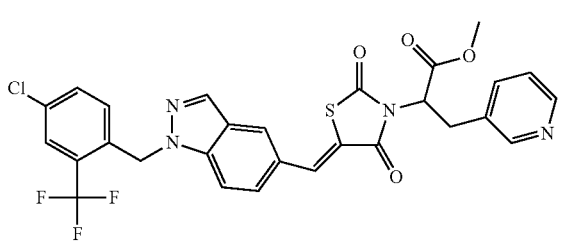 [SMILES: COC(=O)C(Cc1cccnc1)N1C(=O)S/C(=C\c2ccc3c(cnn3Cc3ccc(Cl)cc3C(F)(F)F)c2)C1=O]

(A) Methyl 2-(2,4-dioxo-1,3-thiazolidin-3-yl)-3-(pyridin-3-yl)propanoate was prepared from methyl 2-amino-3-(pyridin-3-yl)propanoate following General Procedure D.

(B) Methyl 2-[(5Z)-5-({1-[4-chloro-2-(trifluoromethyl)benzyl]-1H-indazol-5-yl}methylidene)-2,4-dioxo-1,3-thiazolidin-3-yl]-3-(pyridin-2-yl)propanoate was prepared from [4-chloro-2-(trifluoromethyl)benzyl]-1H-indazol-5-carbaldehyde (from Example 1) and methyl 2-(2,4-dioxo-1,3-thiazolidin-3-yl)-3-(pyridin-3-yl)propanoate following General Procedure F.

$^1$H NMR (400 MHz, CD$_3$OD): δ 8.34-8.40 (m, 2H), 8.25 (s, 1H), 8.03 (s, 1H), 7.95 (s, 1H), 7.78 (d, 1H), 7.73 (d, 1H), 7.55 (s, 2H), 7.44-7.47 (m, 1H), 7.33 (dd, 1H), 6.68 (d, 1H), 5.83 (s, 2H), 5.41 (dd, 1H), 3.80 (s, 3H), 3.57-3.66 (m, 1H), 3.44 (dd, 1H).

LCMS: mass calcd. for $C_{28}H_{20}ClF_3N_4O_4S$: 600.08. found 600.8 [M+H]$^+$

Example 218

1-[(5Z)-5-({1-[4-Chloro-2-(trifluoromethyl)benzyl]-1H-indazol-5-yl}methylidene)-2,4-dioxo-1,3-thiazolidin-3-yl]cyclohexanecarboxylic acid

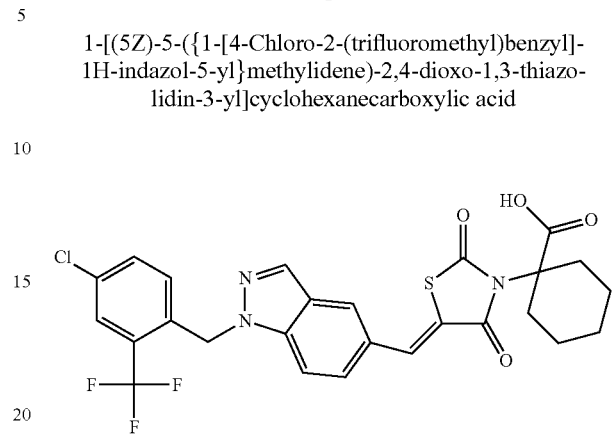

(A) Methyl 1-(2,4-dioxo-1,3-thiazolidin-3-yl)-cyclohexanecarboxylate was prepared from methyl 1-aminocyclohexanecarboxylate following General Procedure D.

(B) Methyl 1-[(5Z)-5-({1-[4-chloro-2-(trifluoromethyl)benzyl]-1H-indazol-5-yl}methylidene)-2,4-dioxo-1,3-thiazolidin-3-yl]cyclohexanecarboxylate was prepared from [4-chloro-2-(trifluoromethyl)benzyl]-1H-indazol-5-carbaldehyde (from Example 1) and methyl 1-(2,4-dioxo-1,3-thiazolidin-3-yl)cyclohexanecarboxylate following General Procedure F.

(C) 1-[(5Z)-5-({1-[4-Chloro-2-(trifluoromethyl)benzyl]-1H-indazol-5-yl}methylidene)-2,4-dioxo-1,3-thiazolidin-3-yl]cyclohexanecarboxylic acid was prepared from methyl 1-[(5Z)-5-({1-[4-chloro-2-(trifluoromethyl)benzyl]-1H-indazol-5-yl}methylidene)-2,4-dioxo-1,3-thiazolidin-3-yl]cyclohexanecarboxylate following General Procedure O.

$^1$H NMR (400 MHz, DMSO-$d_6$): δ 8.37 (s, 1H), 8.15 (s, 1H), 8.03 (s, 1H), 7.89 (d, 1H), 7.81 (d, 1H), 7.62-7.70 (m, 2H), 6.78 (d, 1H), 5.87 (s, 3H), 2.63-2.75 (m, 2H), 1.93-2.05 (m, 2H), 1.66 (d, 2H), 1.38-1.55 (m, 4H).

LCMS: mass calcd. for $C_{26}H_{21}ClF_3N_3O_4S$: 563.09. found 564.2 [M+H]$^+$

Example 219

[(5Z)-5-({1-[4-Chloro-2-(trifluoromethyl)benzyl]-1H-indazol-5-yl}methylidene)-2,4-dioxo-1,3-thiazolidin-3-yl](tetrahydro-2H-pyran-4-yl)acetic acid

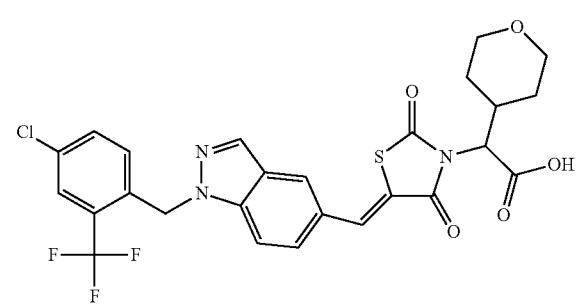 [SMILES: O=C(O)C(C1CCOCC1)N1C(=O)S/C(=C\c2ccc3c(cnn3Cc3ccc(Cl)cc3C(F)(F)F)c2)C1=O]

[(5Z)-5-({1-[4-Chloro-2-(trifluoromethyl)benzyl]-1H-indazol-5-yl}methylidene)-2,4-dioxo-1,3-thiazolidin-3-yl](tetrahydro-2H-pyran-4-yl)acetic acid was prepared from methyl [(5Z)-5-({1-[4-chloro-2-(trifluoromethyl)benzyl]-1H-indazol-5-yl}methylidene)-2,4-dioxo-1,3-thiazolidin-3-yl](tetrahydro-2H-pyran-4-yl)acetate (Example 209) following General Procedure O.

$^1$H NMR (400 MHz, DMSO-d$_6$): δ 8.38 (s, 1H), 8.21 (s, 1H), 8.16 (s, 1H), 7.89 (d, 1H), 7.82 (d, 1H), 7.62-7.74 (m, 2H), 6.79 (d, 1H), 5.87 (s, 2H), 4.69 (d, 1H), 3.75-3.89 (m, 2H), 3.21-3.31 (m, 2H), 2.09 (d, 1H), 1.26-1.43 (m, 3H), 1.13 (dd, 1H).

LCMS: mass calcd. for C$_{26}$H$_{21}$ClF$_3$N$_3$O$_5$S: 579.08. found 621.2 [M+MeCN+H]$^+$ Example 220

4-[(5Z)-5-({1-[4-Chloro-2-(trifluoromethyl)benzyl]-1H-indazol-5-yl}methylidene)-2,4-dioxo-1,3-thiazolidin-3-yl]-1-methylpiperidine-4-carboxylic acid

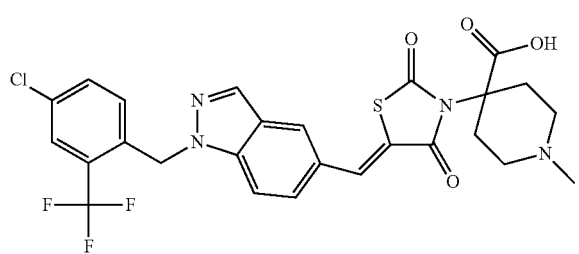 [SMILES: CN1CCC(C(=O)O)(N2C(=O)S/C(=C\c3ccc4c(cnn4Cc4ccc(Cl)cc4C(F)(F)F)c3)C2=O)CC1]

4-[(5Z)-5-({1-[4-Chloro-2-(trifluoromethyl)benzyl]-1H-indazol-5-yl}methylidene)-2,4-dioxo-1,3-thiazolidin-3-yl]-1-methylpiperidine-4-carboxylic acid was prepared from methyl 4-[(5Z)-5-({1-[4-chloro-2-(trifluoromethyl)benzyl]-1H-indazol-5-yl}methylidene)-2,4-dioxo-1,3-thiazolidin-3-yl]-1-methylpiperidine-4-carboxylate (Example 213) following General Procedure O.

$^1$H NMR (400 MHz, DMSO-d$_6$): δ 8.38 (s, 1H), 8.17 (s, 1H), 8.07 (s, 1H), 7.89 (d, 1H), 7.81 (d, 1H), 7.61-7.71 (m, 2H), 6.79 (d, 1H), 5.87 (s, 3H), 3.62-3.79 (m, 7H), 2.63-2.76 (m, 2H), 2.14 (dt, 2H).

LCMS: mass calcd. for C$_{26}$H$_{22}$ClF$_3$N$_4$O$_4$S: 578.10. found 579.8[M+H]$^+$ Example 221

(2S)-2-[(5Z)-5-({1-[4-Chloro-2-(trifluoromethyl)benzyl]-1H-indazol-5-yl}methylidene)-2,4-dioxo-1,3-thiazolidin-3-yl]-3-hydroxypropanoic acid

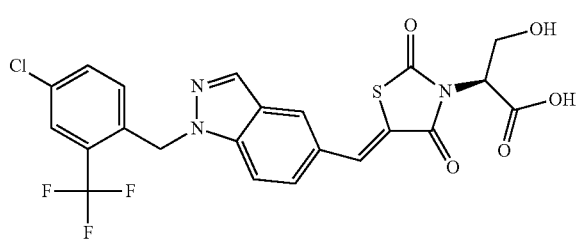 [SMILES: O=C(O)[C@H](CO)N1C(=O)S/C(=C\c2ccc3c(cnn3Cc3ccc(Cl)cc3C(F)(F)F)c2)C1=O]

(2S)-2-[(5Z)-5-({1-[4-Chloro-2-(trifluoromethyl)benzyl]-1H-indazol-5-yl}methylidene)-2,4-dioxo-1,3-thiazolidin-3-yl]-3-hydroxypropanoic acid was prepared from methyl (2S)-3-tert-butoxy-2-[(5Z)-5-({1-[4-chloro-2-(trifluoromethyl)benzyl]-1H-indazol-5-yl}methylidene)-2,4-dioxo-1,3-thiazolidin-3-yl]propanoate (Example 210) following General Procedure O.

$^1$H NMR (400 MHz, DMSO-d$_6$): δ 8.38 (s, 1H), 8.20 (s, 1H), 8.13 (s, 1H), 7.89 (d, 1H), 7.79-7.85 (m, 1H), 7.59-7.75 (m, 2H), 6.79 (d, 1H), 5.88 (s, 2H), 5.02 (dd, 1H), 3.91-4.09 (m, 2H).

LCMS: mass calcd. for C$_{22}$H$_{16}$ClF$_3$N$_3$O$_6$S: 525.04. found 526.1 [M+H]$^+$ Example 222

(2R)-2-[(5Z)-5-({1-[4-Chloro-2-(trifluoromethyl)benzyl]-1H-indazol-5-yl}methylidene)-2,4-dioxo-1,3-thiazolidin-3-yl]-3-hydroxypropanoic acid

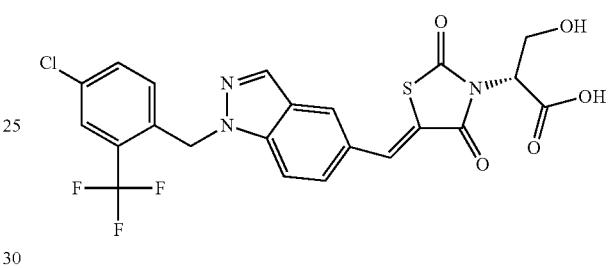

(2R)-2-[(5Z)-5-({1-[4-Chloro-2-(trifluoromethyl)benzyl]-1H-indazol-5-yl}methylidene)-2,4-dioxo-1,3-thiazolidin-3-yl]-3-hydroxypropanoic acid was prepared from methyl (2R)-3-tert-butoxy-2-[(5Z)-5-({1-[4-chloro-2-(trifluoromethyl)benzyl]-1H-indazol-5-yl}methylidene)-2,4-dioxo-1,3-thiazolidin-3-yl]propanoate (Example 212) following General Procedure O.

$^1$H NMR (400 MHz, DMSO-d$_6$): δ 8.38 (s, 1H), 8.20 (s, 1H), 8.13 (s, 1H), 7.89 (d, 1H), 7.79-7.85 (m, 1H), 7.71 (dd, 1H), 7.67 (dd, 1H), 6.79 (d, 1H), 5.88 (s, 2H), 5.02 (dd, 1H), 3.91-4.08 (m, 2H).

LCMS: mass calcd. for C$_{22}$H$_{16}$ClF$_3$N$_3$O$_6$S: 525.04. found 526.3 [M+H]$^+$ Example 223

2-[(5Z)-5-({1-[4-Chloro-2-(trifluoromethyl)benzyl]-1H-indazol-5-yl}methylidene)-2,4-dioxo-1,3-thiazolidin-3-yl]-3-(1-methyl-1H-imidazol-4-yl)propanoic acid

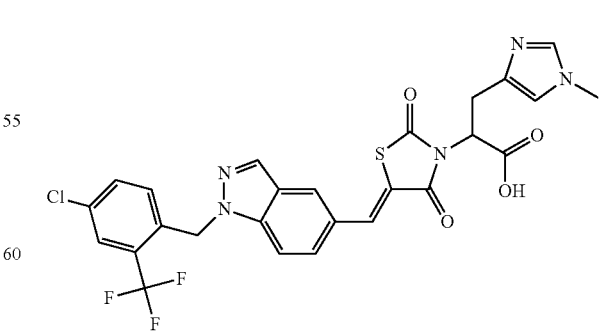

2-[(5Z)-5-({1-[4-Chloro-2-(trifluoromethyl)benzyl]-1H-indazol-5-yl}methylidene)-2,4-dioxo-1,3-thiazolidin-3-yl]-3-(1-methyl-1H-imidazol-4-yl)propanoic acid was prepared from methyl 2-[(5Z)-5-({1-[4-chloro-2-(trifluoromethyl) benzyl]-1H-indazol-5-yl}methylidene)-2,4-dioxo-1,3-thiazolidin-3-yl]-3-(1-methyl-1H-imidazol-4-yl)propanoate (Example 214) following General Procedure O.

$^1$H NMR (400 MHz, CD$_3$OD): δ 8.90 (s, 1H), 8.36 (s, 1H), 8.18 (s, 1H), 8.10 (s, 1H), 7.80 (d, 1H), 7.79-7.88 (m, 1H), 7.64-7.68 (m, 2H), 7.48 (s, 1H), 6.78 (d, 1H), 5.87 (s, 2H), 5.23 (dd, 1H), 3.76 (s, 3H), 3.51-3.58 (m, 1H), 3.38-3.45 (m, 1H).

LCMS: mass calcd. for C$_{26}$H$_{19}$ClF$_3$N$_5$O$_4$S: 589.08. found 590.3 [M+H]$^+$ Example 224

[(5Z)-5-({1-[4-Chloro-2-(trifluoromethyl)benzyl]-1H-indazol-5-yl}methylidene)-2,4-dioxo-1,3-thiazolidin-3-yl](piperidin-4-yl)acetic acid

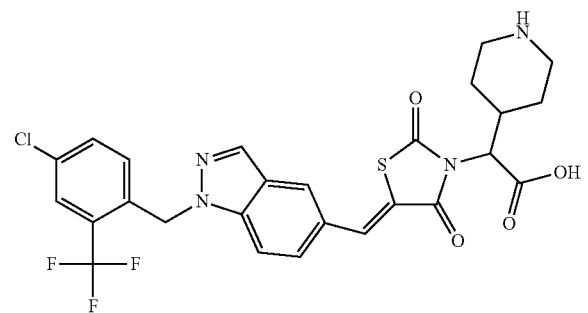 [SMILES: O=C(O)C(C1CCNCC1)N1C(=O)S/C(=C\c2ccc3c(cnn3Cc3ccc(Cl)cc3C(F)(F)F)c2)C1=O]

[(5Z)-5-({1-[4-Chloro-2-(trifluoromethyl)benzyl]-1H-indazol-5-yl}methylidene)-2,4-dioxo-1,3-thiazolidin-3-yl](piperidin-4-yl)acetic acid was prepared from 1,1-dimethylethyl 4-{1-[(5Z)-5-({1-[4-chloro-2-(trifluoromethyl)benzyl]-1H-indazol-5-yl}methylidene)-2,4-dioxo-1,3-thiazolidin-3-yl]-2-methoxy-2-oxoethyl}piperidine-1-carboxylate (Example 215) following General Procedure O.

$^1$H NMR (400 MHz, CDCl$_3$): δ 8.39 (s, 1H), 8.22 (s, 1H), 8.18 (s, 1H), 7.90 (d, 1H), 7.83 (d, 1H), 6.66-6.73 (m, 2H), 6.82 (d, 2H), 5.80 (s, 2H), 4.81 (d, 1H), 3.21-3.56 (m, 2H), 2.86-2.96 (m, 2H), 2.32-2.55 (m, 1H), 2.26-2.29 (m, 1H), 1.64-1.68 (m, 1H), 1.49-1.52 (m, 1H), 1.30-1.33 (m, 1H).

LCMS: mass calcd. for C$_{26}$H$_{22}$ClF$_3$N$_4$O$_4$S: 578.10. found 579.3 [M+H]$^+$ Example 225

2-[(5Z)-5-({1-[4-Chloro-2-(trifluoromethyl)benzyl]-1H-indazol-5-yl}methylidene)-2,4-dioxo-1,3-thiazolidin-3-yl]-3-pyridin-3-ylpropanoic acid

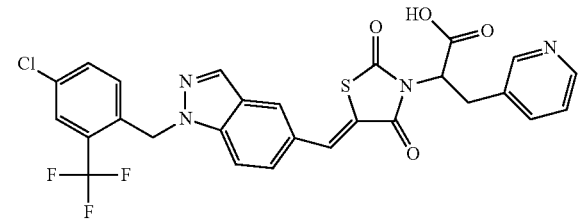 [SMILES: O=C(O)C(Cc1cccnc1)N1C(=O)S/C(=C\c2ccc3c(cnn3Cc3ccc(Cl)cc3C(F)(F)F)c2)C1=O]

2-[(5Z)-5-({1-[4-Chloro-2-(trifluoromethyl)benzyl]-1H-indazol-5-yl}methylidene)-2,4-dioxo-1,3-thiazolidin-3-yl]-3-pyridin-3-ylpropanoic acid was prepared from methyl 2-[(5Z)-5-({1-[4-chloro-2-(trifluoromethyl)-benzyl]-1H-indazol-5-yl}methylidene)-2,4-dioxo-1,3-thiazolidin-3-yl]-3-pyridin-3-ylpropanoate (Example 217) following General Procedure O.

$^1$H NMR (400 MHz, DMSO-d$_6$): δ 8.85 (s, 1H), 8.76 (d, 1H), 8.41 (d, 1H), 8.37 (s, 1H), 8.17 (s, 1H), 8.08 (s, 1H), 7.87-7.95 (m, 2H), 7.81 (d, 1H), 7.66 (dd, 2H), 6.79 (d, 1H), 5.87 (s, 2H), 5.46 (dd, 1H), 3.69 (dd, 1H), 3.45 (dd, 1H).

LCMS: mass calcd. for C$_{27}$H$_{18}$ClF$_3$N$_4$O$_4$S: 586.07. found 587.3 [M+H]$^+$ Example 226

Methyl 4-[(5Z)-5-({1-[4-chloro-2-(trifluoromethyl) benzyl]-1H-indazol-5-yl}methylidene)-2,4-dioxo-1, 3-thiazolidin-3-yl]tetrahydro-2H-pyran-4-carboxylate

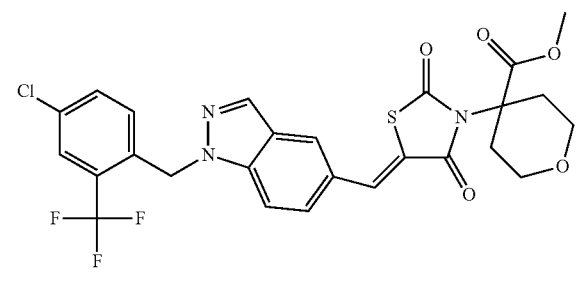 [SMILES: COC(=O)C1(N2C(=O)S/C(=C\c3ccc4c(cnn4Cc4ccc(Cl)cc4C(F)(F)F)c3)C2=O)CCOCC1]

(A) Methyl 4-(2,4-dioxo-1,3-thiazolidin-3-yl)tetrahydropyran-4-carboxylate was prepared from methyl 4-aminotetrahydropyran-4-carboxylate following General Procedure D.

(B) Methyl 4-[(5Z)-5-({1-[4-chloro-2-(trifluoromethyl) benzyl]-1H-indazol-5-yl}methylidene)-2,4-dioxo-1,3-thiazolidin-3-yl]tetrahydro-2H-pyran-4-carboxylate was prepared from [4-chloro-2-(trifluoromethyl)benzyl]-1H-indazol-5-carbaldehyde (from Example 1) and methyl 4-(2,4-dioxo-1,3-thiazolidin-3-yl)tetrahydropyran-4-carboxylate following General Procedure F.

$^1$H NMR (400 MHz, CDCl$_3$): δ 8.22 (s, 1H), 7.92-7.97 (m, 2H), 7.72 (d, 1H), 7.49 (dd, 1H), 7.31-7.40 (m, 2H), 6.69 (d, H), 5.80 (s, 2H), 3.72-3.93 (m, 7H), 2.86 (ddd, 2H), 2.31 (ddd, 2H).

LCMS: mass calcd. for C$_{26}$H$_{21}$ClF$_3$N$_3$O$_5$S: 579.08. found 580.2 [M+H]$^+$ Example 227

4-[(5Z)-5-({1-[4-Chloro-2-(trifluoromethyl)benzyl]-1H-indazol-5-yl}methylidene)-2,4-dioxo-1,3-thiazolidin-3-yl]tetrahydro-2H-pyran-4-carboxylic acid

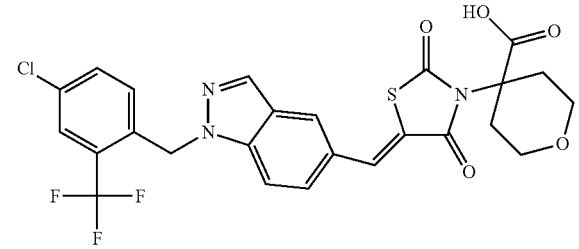

4-[(5Z)-5-({1-[4-Chloro-2-(trifluoromethyl)benzyl]-1H-indazol-5-yl}methylidene)-2,4-dioxo-1,3-thiazolidin-3-yl]tetrahydro-2H-pyran-4-carboxylic acid was prepared from methyl 4-[(5Z)-5-({1-[4-chloro-2-(trifluoromethyl)benzyl]-1H-indazol-5-yl}methylidene)-2,4-dioxo-1,3-thiazolidin-3-yl]tetrahydro-2H-pyran-4-carboxylate (Example 226) following General Procedure O.

$^1$H NMR (400 MHz, CD$_3$OD): δ 8.26 (s, 1H), 8.04 (s, 1H), 7.95 (s, 1H), 7.78 (d, 1H), 7.53-7.60 (m, 2H), 7.46 (dd, 1H), 6.67 (d, 1H), 5.84 (s, 2H), 3.89 (qd, 2H), 3.67-3.77 (m, 2H), 2.76-2.87 (m, 2H), 2.20-2.32 (m, 2H).

LCMS: mass calcd. for C$_{25}$H$_{19}$ClF$_3$N$_3$O$_5$S: 565.07. found 566.3 [M+H]$^+$ Example 228

2-[(5Z)-5-({1-[4-Chloro-2-(trifluoromethyl)benzyl]-1H-indazol-5-yl}methylidene)-2,4-dioxo-1,3-thiazolidin-3-yl]-3-piperidin-4-ylpropanoic acid

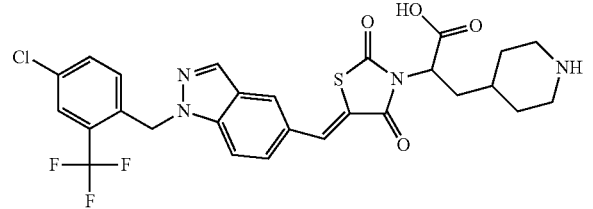 [SMILES: O=C(O)C(CC1CCNCC1)N1C(=O)S/C(=C\c2ccc3c(cnn3Cc3ccc(Cl)cc3C(F)(F)F)c2)C1=O]

(A) 1,1-Dimethylethyl 4-[2-(2,4-dioxo-1,3-thiazolidin-3-yl)-2-ethoxycarbonylethyl]piperidine-1-carboxylate was prepared from 1,1-dimethylethyl 4-(2-amino-2-ethoxycarbonylethyl)piperidine-1-carboxylate following General Procedure D.

(B) Ethyl 2-[(5Z)-5-({1-[4-chloro-2-(trifluoromethyl)benzyl]-1H-indazol-5-yl}methylidene)-2,4-dioxo-1,3-thiazolidin-3-yl]-3-(piperidin-4-yl)-propanoate was prepared from [4-chloro-2-(trifluoromethyl)benzyl]-1H-indazol-5-carbaldehyde (from Example 1) and 1,1-dimethylethyl 4-[2-(2,4-dioxo-1,3-thiazolidin-3-yl)-2-ethoxycarbonylethyl]piperidine-1-carboxylate following General Procedure F.

(C) 2-[(5Z)-5-({1-[4-Chloro-2-(trifluoromethyl)benzyl]-1H-indazol-5-yl}methylidene)-2,4-dioxo-1,3-thiazolidin-3-yl]-3-piperidin-4-ylpropanoic acid was prepared from ethyl 2-[(5Z)-5-({1-[4-chloro-2-(trifluoromethyl)benzyl]-1H-indazol-5-yl}methylidene)-2,4-dioxo-1,3-thiazolidin-3-yl]-3-(piperidin-4-yl)propanoate following General Procedure O.

$^1$H NMR (400 MHz, CD$_3$OD): δ 8.29 (s, 1H), 8.13 (s, 1H), 8.09 (s, 1H), 7.81 (d, 1H), 7.57-7.69 (m, 2H), 7.49 (dd, 1H), 6.72 (d, 1H), 5.87 (s, 2H), 5.12 (dd, 1H), 3.32-3.44 (m, 2H), 2.88-3.01 (m, 2H), 2.22-2.35 (m, 1H), 2.08-2.20 (m, 2H), 1.83-1.93 (m, 1H), 1.53-1.64 (m, 1H), 1.31-1.51 (m, 2H).

LCMS: mass calcd. for C$_{27}$H$_{24}$ClF$_3$N$_4$O$_4$S: 592.12. found 634.3 [M+MeCN+H]$^+$ Example 229

2-[(5Z)-5-({1-[4-Chloro-2-(trifluoromethyl)benzyl]-1H-indazol-5-yl}methylidene)-2,4-dioxo-1,3-thiazolidin-3-yl]-3-(1H-imidazol-4-yl)propanoic acid

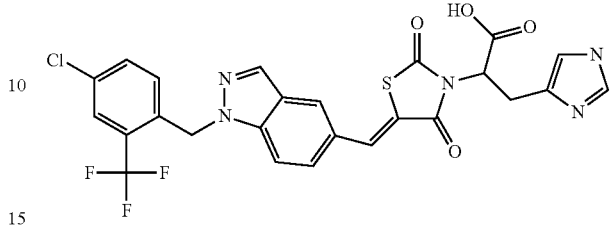

(A) Methyl 3-(1-dimethylsulfamoyl-1H-imidazol-4-yl)-2-(2,4-dioxo-1-3-thiazolidin-3-yl)-propanoate was prepared from methyl 2-amino-3-(1-dimethylsulfamoyl-1H-imidazol-4-yl)-propanoate following General Procedure D.

(B) Methyl 2-[(5Z)-5-({1-[4-chloro-2-(trifluoromethyl)benzyl]-1H-indazol-5-yl}methylidene)-2,4-dioxo-1,3-thiazolidin-3-yl]-3-(1H-imidazol-4-yl)propanoate was prepared from [4-chloro-2-(trifluoromethyl)benzyl]-1H-indazol-5-carbaldehyde (from Example 1) and methyl 3-(1-dimethylsulfamoyl-1H-imidazol-4-yl)-2-(2,4-dioxo-1-3-thiazolidin-3-yl)propanoate following General Procedure F.

(C) 2-[(5Z)-5-({1-[4-Chloro-2-(trifluoromethyl)benzyl]-1H-indazol-5-yl}methylidene)-2,4-dioxo-1,3-thiazolidin-3-yl]-3-(1H-imidazol-4-yl)propanoic acid was prepared from methyl 2-[(5Z)-5-({1-[4-chloro-2-(trifluoromethyl)benzyl]-1H-indazol-5-yl}methylidene)-2,4-dioxo-1,3-thiazolidin-3-yl]-3-(1H-imidazol-4-yl)propanoate following General Procedure O.

$^1$H NMR (400 MHz, CD$_3$OD): δ 8.82 (d, 1H), 8.28 (s, 1H), 8.11 (s, 1H), 8.06 (s, 1H), 7.80 (d, 1H), 7.55-7.68 (m, 2H), 7.49 (dd, 1H), 7.40 (s, 1H), 6.71 (d, 1H), 5.86 (s, 2H), 5.35 (dd, 1H), 3.52-3.70 (m, 2H).

LCMS: mass calcd. for C$_{25}$H$_{17}$ClF$_3$N$_5$O$_4$S: 575.06. found 576.2 [M+H]$^+$ Example 230

4-[(5Z)-5-({1-[4-Chloro-2-(trifluoromethyl)benzyl]-1H-indazol-5-yl}methylidene)-2,4-dioxo-1,3-thiazolidin-3-yl]piperidine-4-carboxylic acid

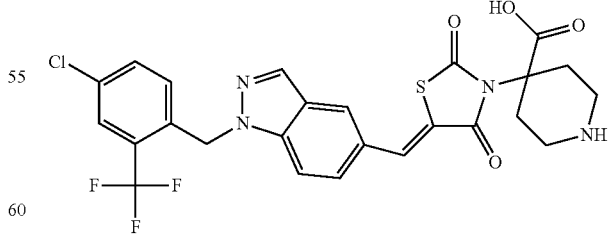

(A) 1,1-Dimethylethyl 4-(2,4-dioxo-1,3-thiazolidin-3-yl)-4-methoxycarbonyl-piperidine-1-carboxylate was prepared from 1,1-dimethylethyl 4-amino-4-methoxycarbonylpiperidine-1-carboxylate following General Procedure D.

(B) Methyl 4-[(5Z)-5-({1-[4-Chloro-2-(trifluoromethyl) benzyl]-1H-indazol-5-yl}methylidene)-2,4-dioxo-1,3-thiazolidin-3-yl]piperidine-4-carboxylate was prepared from [4-chloro-2-(trifluoromethyl)benzyl]-1H-indazol-5-carbaldehyde (from Example 1) and 1,1-dimethylethyl 4-(2,4-dioxo-1,3-thiazolidin-3-yl)-4-methoxycarbonylpiperidine-1-carboxylate following General Procedure F.

(C) 4-[(5Z)-5-({1-[4-Chloro-2-(trifluoromethyl)benzyl]-1H-indazol-5-yl}methylidene)-2,4-dioxo-1,3-thiazolidin-3-yl]piperidine-4-carboxylic acid was prepared from methyl 4-[(5Z)-5-({1-[4-chloro-2-(trifluoromethyl)-benzyl]-1H-indazol-5-yl}methylidene)-2,4-dioxo-1,3-thiazolidin-3-yl]piperidine-4-carboxylate following General Procedure O.

$^1$H NMR (400 MHz, CD$_3$OD): δ 8.28 (s, 1H), 8.08 (s, 1H), 8.01 (s, 1H), 7.79 (d, 1H), 7.55-7.65 (m, 2H), 7.48 (dd, 1H), 6.70 (d, 1H), 5.85 (s, 2H), 3.30-3.53 (m, 4H), 3.03-3.18 (m, 2H), 2.42-2.59 (m, 2H).

LCMS: mass calcd. for C$_{25}$H$_{20}$ClF$_3$N$_4$O$_4$S: 564.08. found 606.3 [M+MeCN+H]$^+$ Example 231

(5Z)-3-[(2-Amino-1H-imidazol-4-yl)methyl]-5-({1-[4-chloro-2-(trifluoromethyl)benzyl]-1H-indazol-5-yl}methylidene)-1,3-thiazolidine-2,4-dione

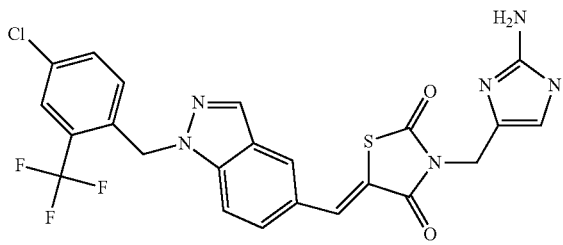 [SMILES: Nc1nc(CN2C(=O)S/C(=C\c3ccc4c(cnn4Cc4ccc(Cl)cc4C(F)(F)F)c3)C2=O)c[nH]1]

(A) (5Z)-3-(3-bromo-2-oxoprop-1-yl)-5-({1-[4-chloro-2-(trifluoromethyl)-benzyl]-1H-indazol-5-yl}methylidene)-1,3-thiazolidine-2,4-dione was prepared from [(5Z)-5-({1-[4-chloro-2-(trifluoromethyl) benzyl]-1H-indazol-5-yl}methylidene)-2,4-dioxo-1,3-thiazolidine (from Example 1) and 1,3-dibromopropan-2-one following General Procedure S.

(B) A mixture of (5Z)-3-(3-bromo-2-oxoprop-1-yl)-5-({1-[4-chloro-2-(trifluoromethyl)benzyl]-1H-indazol-5-yl}methylidene)-1,3-thiazolidine-2,4-dione (0.114 mmol) and tert-butoxycarbonylguanidine (1.26 mmol) in THF (2 mL) was stirred at rt. After 6 h, the reaction was concentrated and the residue was purified by silica gel chromatography (hexanes/EtOAc) to afford (5Z)-3-[(2-tert-butoxycarbonylamino-1H-imidazol-4-yl)methyl]-5-({1-[4-chloro-2-(trifluoromethyl)benzyl]-1H-indazol-5-yl}methylidene)-1,3-thiazolidine-2,4-dione.

(C) (5Z)-3-[(2-Amino-1H-imidazol-4-yl)methyl]-5-({1-[4-chloro-2-(trifluoromethyl)benzyl]-1H-indazol-5-yl}methylidene)-1,3-thiazolidine-2,4-dione was prepared from (5Z)-3-[(2-tert-butoxycarbonylamino-1H-imidazol-4-yl)methyl]-5-({1-[4-chloro-2-(trifluoromethyl)benzyl]-1H-indazol-5-yl}methylidene)-1,3-thiazolidine-2,4-dione following General Procedure M.

$^1$H NMR (400 MHz, CD$_3$OD): δ 8.25 (s, 1H), 8.06 (s, 1H), 8.05 (s, 1H), 7.78 (d, 1H), 7.53-7.63 (m, 2H), 7.46 (dd, 1H), 6.85 (s, 1H), 6.68 (d, 1H), 5.84 (s, 2H), 4.81 (s, 2H).

LCMS: mass calcd. for C$_{23}$H$_{16}$ClF$_3$N$_6$O$_2$S: 532.07. found 574.3 [M+MeCN+H]$^+$ Example 232

Methyl 1-[(5Z)-5-({1-[4-chloro-2-(trifluoromethyl) benzyl]-1H-indazol-5-yl}methylidene)-2,4-dioxo-1,3-thiazolidin-3-yl]cyclopentanecarboxylate

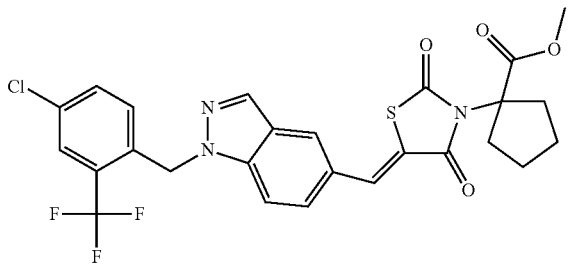 [SMILES: COC(=O)C1(N2C(=O)S/C(=C\c3ccc4c(cnn4Cc4ccc(Cl)cc4C(F)(F)F)c3)C2=O)CCCC1]

(A) Methyl 1-(2,4-dioxo-1,3-thiazolidin-3-yl)cyclopentanecarboxylate was prepared from methyl 1-aminocyclopentanecarboxylate following General Procedure D.

(B) Methyl 1-[(5Z)-5-({1-[4-chloro-2-(trifluoromethyl) benzyl]-1H-indazol-5-yl}methylidene)-2,4-dioxo-1,3-thiazolidin-3-yl]cyclopentanecarboxylate was prepared from [4-chloro-2-(trifluoromethyl)benzyl]-1H-indazol-5-carbaldehyde (from Example 1) and methyl 1-(2,4-dioxo-1,3-thiazolidin-3-yl)cyclopentanecarboxylate following General Procedure F.

$^1$H NMR (400 MHz, CDCl$_3$): δ 8.22 (s, 1H), 7.94 (m, 2H), 7.72 (d, 1H), 7.49 (dd, 1H), 7.34 (d, 2H), 6.68 (d, 1H), 5.80 (s, 2H), 3.75 (s, 3H), 2.38-2.61 (m, 4H), 1.75-1.89 (m, 4H).

LCMS: mass calcd. for C$_{26}$H$_{21}$ClF$_3$N$_3$O$_4$S: 563.09. found 605.4 [M+MeCN+H]$^+$ Example 233

Methyl 1-[(5Z)-5-({1-[4-chloro-2-(trifluoromethyl) benzyl]-1H-indazol-5-yl}methylidene)-2,4-dioxo-1,3-thiazolidin-3-yl]cyclobutanecarboxylate

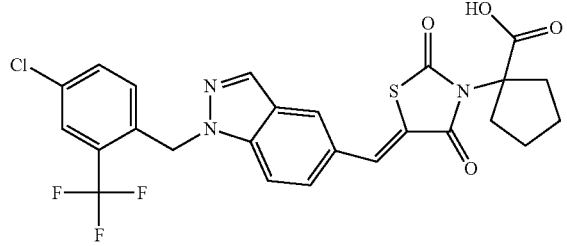 [SMILES: O=C1S/C(=C\c2ccc3c(cnn3Cc3ccc(Cl)cc3C(F)(F)F)c2)C(=O)N1C1(C(=O)O)CCCC1]

1-[(5Z)-5-({1-[4-Chloro-2-(trifluoromethyl)benzyl]-1H-indazol-5-yl}methylidene)-2,4-dioxo-1,3-thiazolidin-3-yl] cyclopentanecarboxylic acid was prepared from methyl 1-[(5Z)-5-({1-[4-chloro-2-(trifluoromethyl)benzyl]-1H-indazol-5-yl}methylidene)-2,4-dioxo-1,3-thiazolidin-3-yl]cyclopentanecarboxylate (Example 232) following General Procedure O.

$^1$H NMR (400 MHz, DMSO-d$_6$): δ 8.37 (s, 1H), 8.29 (br. s., 1H), 8.15 (s, 1H), 8.03 (s, 1H), 7.89 (d, 1H), 7.81 (d, 1H), 7.63-7.70 (m, 2H), 6.78 (d, 1H), 5.87 (s, 2H), 2.33-2.55 (m, 4H), 1.71-1.81 (m, 4H).

LCMS: mass calcd. for C$_{26}$H$_{19}$ClF$_3$N$_3$O$_4$S: 549.07. found 550.4 [M+H]$^+$

Example 234

Methyl 1-[(5Z)-5-({1-[4-chloro-2-(trifluoromethyl)benzyl]-1H-indazol-5-yl}methylidene)-2,4-dioxo-1,3-thiazolidin-3-yl]cyclobutanecarboxylate

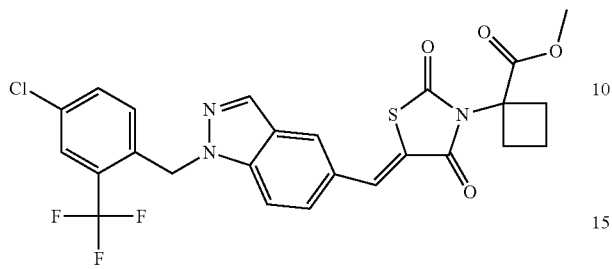

(A) Methyl 1-(2,4-dioxo-1,3-thiazolidin-3-yl)cyclobutanecarboxylate was prepared from methyl 1-amino-cyclobutanecarboxylate following General Procedure D.

(B) Methyl 1-[(5Z)-5-({1-[4-chloro-2-(trifluoromethyl)benzyl]-1H-indazol-5-yl}methylidene)-2,4-dioxo-1,3-thiazolidin-3-yl]cyclobutanecarboxylate was prepared from [4-chloro-2-(trifluoromethyl)benzyl]-1H-indazol-5-carbaldehyde (from Example 1) and methyl 1-(2,4-dioxo-1,3-thiazolidin-3-yl)cyclobutanecarboxylate following General Procedure F.

$^1$H NMR (400 MHz, CDCl$_3$): δ 8.22 (s, 1H), 7.95 (s, 2H), 7.72 (d, 1H), 7.50 (dd, 1H), 7.35 (d, 2H), 6.67 (d, 1H), 5.80 (s, 2H), 3.81 (s, 3H), 2.76-2.96 (m, 4H), 2.34-2.47 (m, 1H), 1.91-2.03 (m, 1H).

LCMS: mass calcd. for $C_{25}H_{19}ClF_3N_3O_4S$: 549.07. found 550.4 [M+H]$^+$

Example 235

1-[(5Z)-5-({1-[4-Chloro-2-(trifluoromethyl)benzyl]-1H-indazol-5-yl}methylidene)-2,4-dioxo-1,3-thiazolidin-3-yl]cyclobutanecarboxylic acid

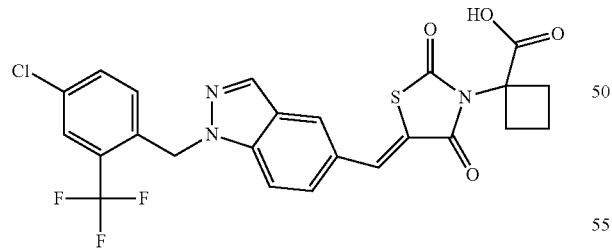

1-[(5Z)-5-({1-[4-Chloro-2-(trifluoromethyl)benzyl]-1H-indazol-5-yl}methylidene)-2,4-dioxo-1,3-thiazolidin-3-yl]cyclobutanecarboxylic acid was prepared from methyl 1-[(5Z)-5-({1-[4-chloro-2-(trifluoromethyl)-benzyl]-1H-indazol-5-yl}methylidene)-2,4-dioxo-1,3-thiazolidin-3-yl]cyclobutanecarboxylate (Example 234) following General Procedure O.

$^1$H NMR (400 MHz, CD$_3$OD): δ 8.23 (s, 1H), 7.98 (s, 1H), 7.86 (s, 1H), 7.76 (d, 1H), 7.51 (s, 2H), 7.43 (dd, 1H), 6.65 (d, 1H), 5.80 (s, 2H), 2.73-2.89 (m, 4H), 2.35-2.42 (m, 1H), 1.93-2.01 (m, 1H).

LCMS: mass calcd. for $C_{24}H_{17}ClF_3N_3O_4S$: 535.06. found 536.4 [M+H]$^+$

Example 236 tert-Butyl {2-[(5Z)-5-({1-[4-chloro-2-(trifluoromethyl)benzyl]-1H-indazol-5-yl}methylidene)-2,4-dioxo-1,3-thiazolidin-3-yl]ethoxy}acetate

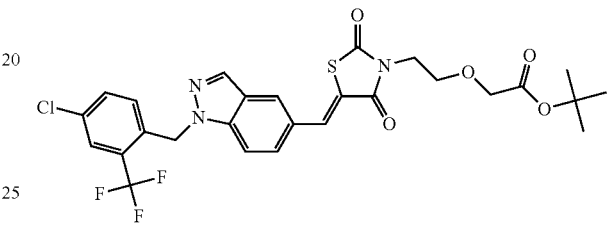

(A) [(5Z)-5-({1-[4-Chloro-2-(trifluoromethyl)benzyl]-1H-indazol-5-yl}methylidene)-3-[2-(tetrahydropyran-2-yloxy)ethyl]-2,4-dioxo-1,3-thiazolidine was prepared from [(5Z)-5-({1-[4-chloro-2-(trifluoromethyl)-benzyl]-1H-indazol-5-yl}methylidene)-2,4-dioxo-1,3-thiazolidine (from Example 1) and 2-(tetrahydropyran-2-yloxy)ethanol following General Procedure C.

(B) A solution of [(5Z)-5-({1-[4-chloro-2-(trifluoromethyl)benzyl]-1H-indazol-5-yl}methylidene)-3-[2-(tetrahydropyran-2-yloxy)ethyl]-2,4-dioxo-1,3-thiazolidine (0.45 mmol) and TsOH.H$_2$O (cat.) in MeOH (6 mL) was stirred for 1 h, then concentrated to dryness. The residue was taken up in EtOAc (10 mL), extracted with sat'd aq. NaHCO$_3$, dried (Na$_2$SO$_4$) and concentrated in vacuo to afford [(5Z)-5-({1-[4-chloro-2-(trifluoromethyl)benzyl]-1H-indazol-5-yl}methylidene)-3-(2-hydroxy-ethyl)-2,4-dioxo-1,3-thiazolidine as white solid.

(C) To a cooled solution (−78° C.) of [(5Z)-5-({1-[4-chloro-2-(trifluoromethyl)-benzyl]-1H-indazol-5-yl}methylidene)-3-(2-hydroxyethyl)-2,4-dioxo-1,3-thiazolidine (0.415 mmol) in THF (10 mL) was added a solution of LiHDMS (1.0M in THF; 0.415 mmol) in dropwise fashion. After stirring for 30 min, tert-butyl bromoacetate (0.498 mmol) was added and the reaction mixture was allowed to gradually warm to 0° C. The reaction was quenched by the addition of sat'd aq. NH$_4$Cl (few drops) and the mixture was concentrated in vacuo, and the resultant residue was purified by silica gel chromatography (hexanes/EtOAc) to afford tert-butyl {2-[(5Z)-5-({1-[4-chloro-2-(trifluoromethyl)benzyl]-1H-indazol-5-yl}methylidene)-2,4-dioxo-1,3-thiazolidin-3-yl]ethoxy}acetate.

$^1$H NMR (400 MHz, CDCl$_3$): δ 8.35 (s, 1H), 8.20 (s, 1H), 8.15 (s, 1H), 7.67-7.73 (m, 2H), 7.29-7.37 (m, 2H), 6.69 (d, 1H), 5.80 (s, 2H), 4.28-4.38 (m, 2H), 4.04-4.11 (m, 2H), 3.81-3.95 (m, 2H), 1.33 (s, 9H).

LCMS: mass calcd. for $C_{27}H_{25}ClF_3N_3O_5S$: 595.12. found 597.4 [M+H]$^+$

Example 237

{2-[(5Z)-5-({1-[4-Chloro-2-(trifluoromethyl)benzyl]-1H-indazol-5-yl}methylidene)-2,4-dioxo-1,3-thiazolidin-3-yl]ethoxy}acetic acid

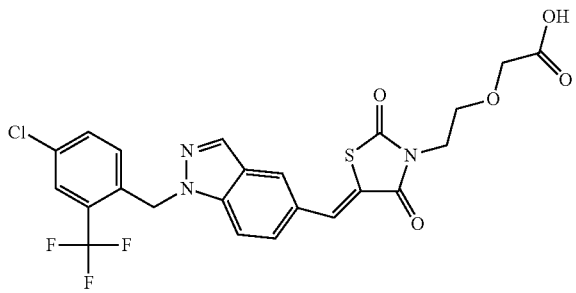 [SMILES: O=C(O)COCCN1C(=O)S/C(=C\c2ccc3c(cnn3Cc3ccc(Cl)cc3C(F)(F)F)c2)C1=O]

{2-[(5Z)-5-({1-[4-Chloro-2-(trifluoromethyl)benzyl]-1H-indazol-5-yl}methylidene)-2,4-dioxo-1,3-thiazolidin-3-yl]ethoxy}acetic acid was prepared from tert-butyl {2-[(5Z)-5-({1-[4-chloro-2-(trifluoromethyl)benzyl]-1H-indazol-5-yl}methylidene)-2,4-dioxo-1,3-thiazolidin-3-yl]ethoxy}acetate (Example 236) following General Procedure M.

$^1$H NMR (400 MHz, CD$_3$OD): δ 8.28 (s, 1H), 8.25 (s, 2H), 7.76-7.84 (m, 2H), 7.45-7.57 (m, 2H), 6.67 (d, 1H), 5.86 (s, 2H), 4.24-4.31 (m, 2H), 4.16-4.24 (m, H), 3.74 (s, 2H).

LCMS: mass calcd. for C$_{23}$H$_{17}$ClF$_3$N$_3$O$_5$S: 539.05. found 539.4 [M]$^+$

Example 238

Methyl {(5Z)-5-[(1-{[2,4-bis(trifluoromethyl)phenyl]methyl}-1H-indol-5-yl)methylidene]-2,4-dioxo-1,3-thiazolidin-3-yl}acetate

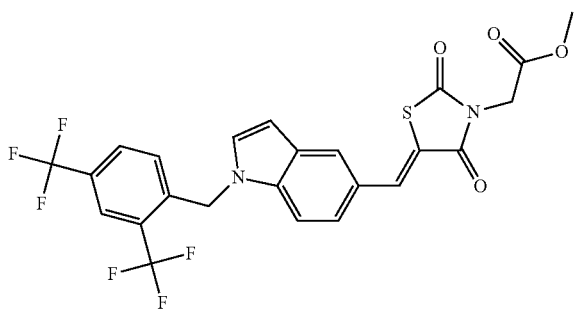 [SMILES: COC(=O)CN1C(=O)S/C(=C\c2ccc3c(ccn3Cc3ccc(C(F)(F)F)cc3C(F)(F)F)c2)C1=O]

(A) [2,4-bis-(trifluoromethyl)benzyl]-1H-indol-5-carbaldehyde was prepared from 2,4-bis-(trifluoromethyl)benzyl bromide and 1H-indol-5-carbaldehyde following General Procedure A.
(B) [(5Z)-5-({1-[2,4-bis-(trifluoromethyl)benzyl]-1H-indol-5-yl}methylidene)-2,4-dioxo-1,3-thiazolidine was prepared from [2,4-bis-(trifluoromethyl)-benzyl]-1H-indol-5-carbaldehyde following General Procedure E.
(C) Methyl {(5Z)-5-[(1-{[2,4-bis(trifluoromethyl)phenyl]methyl}-1H-indol-5-yl)methylidene]-2,4-dioxo-1,3-thiazolidin-3-yl}acetate was prepared from [(5Z)-5-({1-[2,4-bis-(trifluoromethyl)benzyl]-1H-indol-5-yl}methylidene)-2,4-dioxo-1,3-thiazolidine and methyl bromoacetate following General Procedure H.

$^1$H NMR (400 MHz, CDCl$_3$): δ 8.09 (s, 1H), 7.99 (s, 1H), 7.89 (s, 1H), 7.61 (d, 1H), 7.36 (d, 1H), 7.19-7.24 (m, 2H), 6.76 (d, 1H), 6.64 (d, 1H), 5.63 (s, 2H), 4.51 (s, 2H), 3.79 (s, 3H).

LC/MS: mass calcd. for C$_{24}$H$_{16}$F$_6$N$_2$O$_4$S: 542.07. found 543.4 [M+H]$^+$

Example 239

(5Z)-5-[(1-{[2,4-Bis(trifluoromethyl)phenyl]methyl}-1H-indol-5-yl)methylidene]-3-[3-(dimethylamino)propyl]-1,3-thiazolidine-2,4-dione

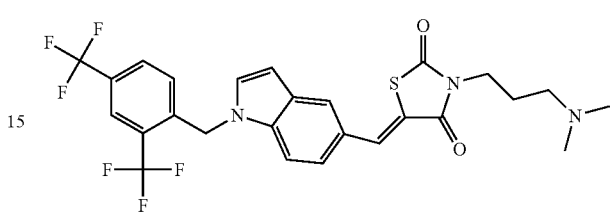

(5Z)-5-[(1-{[2,4-Bis(trifluoromethyl)phenyl]methyl}-1H-indol-5-yl)methylidene]-3-[3-(dimethylamino)propyl]-1,3-thiazolidine-2,4-dione was prepared from [(5Z)-5-({1-[2,4-bis-(trifluoromethyl)benzyl]-1H-indol-5-yl}methylidene)-2,4-dioxo-1,3-thiazolidine (from Example 238) and 3-(dimethylamino)propyl chloride hydrochloride following General Procedure H.

$^1$H NMR (400 MHz, CDCl$_3$): δ 7.97 (s, 1H), 7.92 (s, 1H), 7.82 (s, 1H), 7.54 (d, 1H), 7.29 (d, 1H), 7.10-7.17 (m, 2H), 6.68 (d, 1H), 6.58 (d, 1H), 5.56 (s, 2H), 3.75 (t, 2H), 2.27 (t, 2H), 2.15 (s, 6H), 1.71-1.83 (m, 3H).

LC/MS: mass calcd. for C$_{26}$H$_{23}$F$_6$N$_3$O$_2$S: 555.14. found 556.4 [M+H]$^+$

Example 240

(5Z)-5-[(1-{[2,4-Bis(trifluoromethyl)phenyl]methyl}-1H-indol-5-yl)methylidene]-3-[2-(dimethylamino)ethyl]-1,3-thiazolidine-2,4-dione

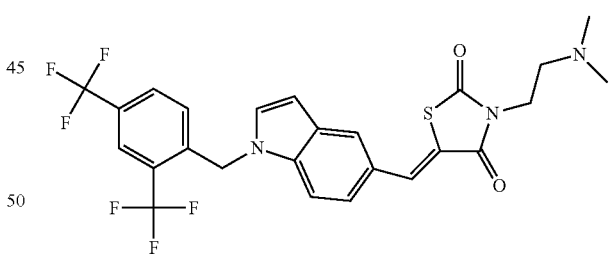

(5Z)-5-[(1-{[2,4-Bis(trifluoromethyl)phenyl]methyl}-1H-indol-5-yl)methylidene]-3-[2-(dimethylamino)ethyl]-1,3-thiazolidine-2,4-dione was prepared from [(5Z)-5-({1-[2,4-bis-(trifluoromethyl)benzyl]-1H-indol-5-yl}methylidene)-2,4-dioxo-1,3-thiazolidine (from Example 238) and 2-(dimethylamino)ethyl chloride hydrochloride following General Procedure H.

$^1$H NMR (400 MHz, CDCl$_3$): δ 7.97 (s, 1H), 7.92 (s, 1H), 7.81 (s, 1H), 7.50-7.57 (m, 1H), 7.27 (s, 1H), 7.11-7.16 (m, 2H), 6.68 (d, 1H), 6.58 (s, 1H), 5.55 (s, 2H), 3.81 (t, 2H), 2.51 (t, 2H), 2.22 (s, 6H).

LC/MS: mass calcd. for C$_{25}$H$_{21}$F$_6$N$_3$O$_2$S: 541.13. found 542.4 [M+H]$^+$

Example 241

(5Z)-5-[(1-{[2,4-Bis(trifluoromethyl)phenyl]methyl}-1H-indol-5-yl)methylidene]-3-(2-morpholin-4-yl-2-oxoethyl)-1,3-thiazolidine-2,4-dione

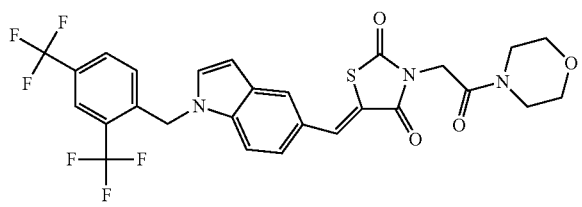 [SMILES: O=C(CN1C(=O)S/C(=C\c2ccc3c(ccn3Cc3ccc(C(F)(F)F)cc3C(F)(F)F)c2)C1=O)N1CCOCC1]

(5Z)-5-[(1-{[2,4-Bis(trifluoromethyl)phenyl]methyl}-1H-indol-5-yl)methylidene]-3-(2-morpholin-4-yl-2-oxoethyl)-1,3-thiazolidine-2,4-dione was prepared from [(5Z)-5-({1-[2,4-bis-(trifluoromethyl)benzyl]-1H-indol-5-yl}methylidene)-2,4-dioxo-1,3-thiazolidine (from Example 238) and 4-bromoacetyl morpholine following General Procedure H.

$^1$H NMR (400 MHz, CDCl$_3$): δ 8.01 (s, 1H), 7.92 (s, 1H), 7.82 (s, 1H), 7.51-7.58 (m, 1H), 7.26-7.33 (m, 1H), 7.16 (d, 2H), 6.65-6.72 (m, 1H), 6.55-6.61 (m, 1H), 5.56 (s, 2H), 4.48 (s, 2H), 3.71 (br. s., 2H), 3.65 (br. s., 2H), 3.54-3.60 (m, 2H), 3.46 (br. s., 2H).

LC/MS: mass calcd. for $C_{27}H_{21}F_6N_3O_4S$: 597.12. found 598.4 [M+H]$^+$

Example 242

(5Z)-5-[(1-{[2,4-Bis(trifluoromethyl)phenyl]methyl}-1H-indol-5-yl)methylidene]-3-(2-hydroxyethyl)-1,3-thiazolidine-2,4-dione

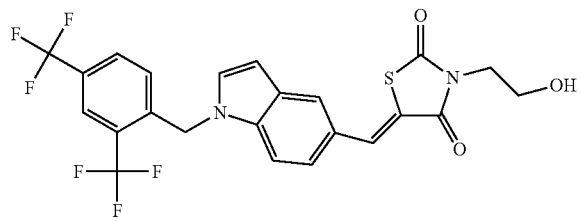 [SMILES: O=C1S/C(=C\c2ccc3c(ccn3Cc3ccc(C(F)(F)F)cc3C(F)(F)F)c2)C(=O)N1CCO]

(5Z)-5-[(1-{[2,4-Bis(trifluoromethyl)phenyl]methyl}-1H-indol-5-yl)methylidene]-3-(2-hydroxyethyl)-1,3-thiazolidine-2,4-dione was prepared from [(5Z)-5-({1-[2,4-bis-(trifluoromethyl)benzyl]-1H-indol-5-yl}methylidene)-2,4-dioxo-1,3-thiazolidine (from Example 238) and 2-bromoethanol following General Procedure H.

$^1$H NMR (400 MHz, CDCl$_3$): δδ 7.94 (s, 1H), 7.87 (s, 1H), 7.76 (s, 1H), 7.48 (d, 1H), 7.19-7.26 (m, 1H), 7.06-7.12 (m, 2H), 6.63 (d, 1H), 6.52 (d, 1H), 5.50 (s, 2H), 3.83-3.91 (m, 2H), 3.77 (br. s., 2H), 1.99 (br. s., 1H).

LC/MS: mass calcd. for $C_{23}H_{16}F_6N_2O_3S$: 514.08. found 515.3 [M+H]$^+$

Example 243

(5Z)-5-[(1-{[4-Chloro-2-(trifluoromethyl)phenyl]methyl}-1H-indol-5-yl)methylidene]-3-[2-(dimethylamino)ethyl]-1,3-thiazolidine-2,4-dione

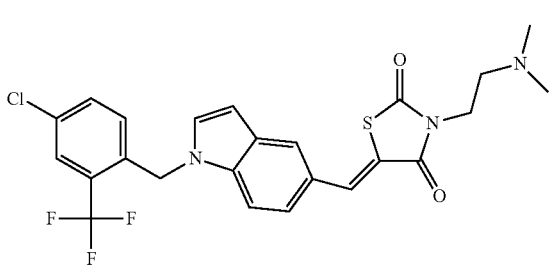 [SMILES: CN(C)CCN1C(=O)S/C(=C\c2ccc3c(ccn3Cc3ccc(Cl)cc3C(F)(F)F)c2)C1=O]

(A) [4-Chloro-2-(trifluoromethyl)benzyl]-1H-indol-5-carbaldehyde was prepared from 4-chloro-2-(trifluoromethyl)benzyl bromide and 1H-indol-5-carbaldehyde following General Procedure A.

(B) [(5Z)-5-({1-[4-Chloro-2-(trifluoromethyl)benzyl]-1H-indol-5-yl}methylidene)-2,4-dioxo-1,3-thiazolidine was prepared from [4-chloro-2-(trifluoromethyl)benzyl]-1H-indol-5-carbaldehyde following General Procedure E.

(C) (5Z)-5-[(1-{[4-Chloro-2-(trifluoromethyl)phenyl}methyl]-1H-indol-5-yl)methylidene]-3-[2-(dimethylamino)ethyl]-1,3-thiazolidine-2,4-dione was prepared from [(5Z)-5-({1-[4-chloro-2-(trifluoromethyl)benzyl]-1H-indol-5-yl}methylidene)-2,4-dioxo-1,3-thiazolidine and 2-(dimethylamino)ethyl chloride hydrochloride following General Procedure H.

$^1$H NMR (400 MHz, CDCl$_3$): δ 8.03 (s, 1H), 7.86 (s, 1H), 7.72 (d, 1H), 7.29-7.37 (m, 2H), 7.18-7.24 (m, 2H), 6.72 (d, 1H), 6.48 (d, 1H), 5.52 (s, 2H), 3.87 (t, 2H), 2.58 (t, 2H), 2.29 (s, 6H).

LC/MS: mass calcd. for $C_{24}H_{21}ClF_3N_3O_2S$: 507.10. found 508.3 [M+H]$^+$

Example 244

(5Z)-5-[(1-{[4-Chloro-2-(trifluoromethyl)phenyl}methyl]-1H-indol-5-yl)methylidene]-3-[3-(dimethylamino)propyl]-1,3-thiazolidine-2,4-dione

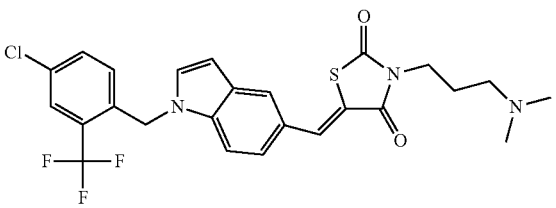 [SMILES: CN(C)CCCN1C(=O)S/C(=C\c2ccc3c(ccn3Cc3ccc(Cl)cc3C(F)(F)F)c2)C1=O]

(5Z)-5-[(1-{[4-Chloro-2-(trifluoromethyl)phenyl]methyl}-1H-indol-5-yl)methylidene]-3-[3-(dimethylamino)propyl]-1,3-thiazolidine-2,4-dione was prepared from [(5Z)-5-({1-[4-chloro-2-(trifluoromethyl)benzyl]-1H-indol-5-yl}methylidene)-2,4-dioxo-1,3-thiazolidine (from Example 243) and 3-(dimethylamino)propyl chloride hydrochloride following General Procedure H.

¹H NMR (400 MHz, CDCl₃): δ 8.03 (s, 1H), 7.87 (s, 1H), 7.72 (s, 1H), 7.34 (d, 1H), 7.31 (d, 1H), 7.18-7.24 (m, 2H), 6.72 (d, H), 6.48 (d, 1H), 5.52 (s, 2H), 3.82 (t, 2H), 2.34 (t, 2H), 2.22 (s, 6H), 1.78-1.89 (m, 3H).

LC/MS: mass calcd. for $C_{25}H_{23}ClF_3N_3O_2S$: 521.12. found 522.3 $[M+H]^+$

Example 245

(5Z)-5-[(1-{[4-Chloro-2-(trifluoromethyl)phenyl]methyl}-1H-indol-5-yl)methylidene]-3-[3-(4-methylpiperazin-1-yl)propyl]-1,3-thiazolidine-2,4-dione

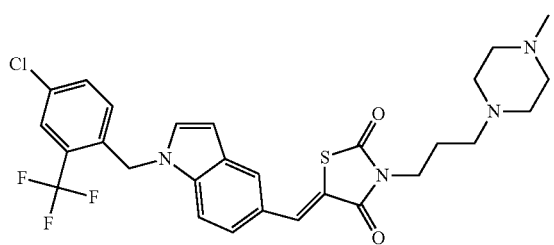 [SMILES: CN1CCN(CCCN2C(=O)S/C(=C\c3ccc4c(ccn4Cc4ccc(Cl)cc4C(F)(F)F)c3)C2=O)CC1]

(5Z)-5-[(1-{[4-Chloro-2-(trifluoromethyl)phenyl]methyl}-1H-indol-5-yl)methylidene]-3-[3-(4-methylpiperazin-1-yl)propyl]-1,3-thiazolidine-2,4-dione was prepared from [(5Z)-5-({1-[4-chloro-2-(trifluoromethyl)-benzyl]-1H-indol-5-yl}methylidene)-2,4-dioxo-1,3-thiazolidine (from Example 243) and 4-(3-chloropropyl)-1-methylpiperazine dihydrochloride following General Procedure H.

¹H NMR (400 MHz, CDCl₃): δ 8.03 (s, 1H), 7.87 (s, 1H), 7.72 (d, 1H), 7.35 (d, 1H), 7.31 (d, 1H), 7.17-7.24 (m, 2H), 6.72 (d, 1H), 6.49 (d, 1H), 5.53 (s, 2H), 3.84 (t, 2H), 2.43 (m, 10H), 2.22 (s, 3H), 1.86 (t, 2H).

LC/MS: mass calcd. for $C_{28}H_{28}ClF_3N_4O_2S$: 576.16. found 577.2 $[M+H]^+$

Example 246

4-({5-[(Z)-{3-[2-(Dimethylamino)ethyl]-2,4-dioxo-1,3-thiazolidin-5-ylidene}methyl]-1H-indol-1-yl}methyl)-3-(trifluoromethyl)benzonitrile

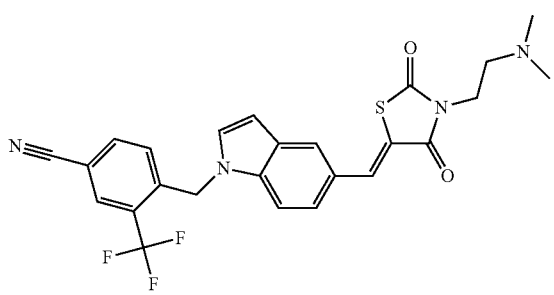 [SMILES: CN(C)CCN1C(=O)S/C(=C\c2ccc3c(ccn3Cc3ccc(C#N)cc3C(F)(F)F)c2)C1=O]

(A) A mixture of 4-methyl-3-trifluoromethylbenzonitrile (4 mmol), N-bromosuccinimide (4.2 mmol) and benzoyl peroxide (0.1 mmol) in CCl₄ (10 mL) was refluxed for 5 h. After cooling to rt, the mixture was filtered and the filtrate was concentrated in vacuo. Purification of the resultant residue by silica gel chromatography (hexane/EtOAc) provided 4-bromomethyl-3-trifluoromethylbenzonitrile as an oil.

(B) [4-Cyano-2-(trifluoromethyl)benzyl]-1H-indol-5-carbaldehyde was prepared from 1H-indol-5-carbaldehyde and 4-bromomethyl-3-trifluoromethylbenzonitrile following General Procedure A.

(C) [(5Z)-5-({1-[4-Cyano-2-(trifluoromethyl)benzyl]-1H-indol-5-yl}-methylidene)-2,4-dioxo-1,3-thiazolidine was prepared from [4-cyano-2-(trifluoromethyl)benzyl]-1H-indol-5-carbaldehyde following General Procedure E.

(D) 4-({5-[(Z)-{3-[2-(Dimethylamino)ethyl]-2,4-dioxo-1,3-thiazolidin-5-ylidene}methyl]-1H-indol-1-yl}methyl)-3-(trifluoromethyl)benzonitrile was prepared from [(5Z)-5-({1-[4-cyano-2-(trifluoromethyl)benzyl]-1H-indol-5-yl}methylidene)-2,4-dioxo-1,3-thiazolidine and 3-(dimethylamino)propyl chloride hydrochloride following General Procedure H.

¹H NMR (400 MHz, CDCl₃): δ 8.03 (s, 2H), 7.87 (s, 1H), 7.59-7.67 (m, 1H), 7.33 (s, 1H), 7.21 (d, 1H), 7.17 (d, 1H), 6.75 (d, 6.62 (d, 1H), 5.62 (s, 2H), 3.88 (t, 2H), 2.59 (t, 2H), 2.29 (s, 6H).

LC/MS: mass calcd. for $C_{25}H_{21}F_3N_4O_2S$: 498.13. found 499.3 $[M+H]^+$

Example 247

4-({5-[(Z)-{3-[3-(Dimethylamino)propyl]-2,4-dioxo-1,3-thiazolidin-5-ylidene}methyl]-1H-indol-1-yl}methyl)-3-(trifluoromethyl)benzonitrile

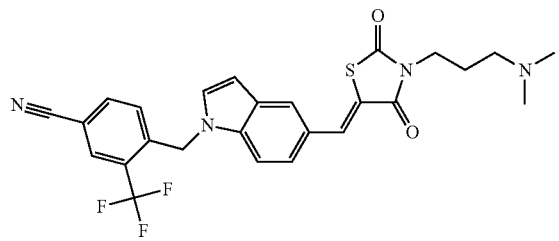 [SMILES: CN(C)CCCN1C(=O)S/C(=C\c2ccc3c(ccn3Cc3ccc(C#N)cc3C(F)(F)F)c2)C1=O]

4-({5-[(Z)-{3-[3-(Dimethylamino)propyl]-2,4-dioxo-1,3-thiazolidin-5-ylidene}methyl]-1H-indol-1-yl}methyl)-3-(trifluoromethyl)benzonitrile was prepared from [(5Z)-5-({1-[4-cyano-2-(trifluoromethyl)benzyl]-1H-indol-5-yl}methylidene)-2,4-dioxo-1,3-thiazolidine (from Example 246) and 3-(dimethylamino)propyl chloride hydrochloride following General Procedure H.

¹H NMR (400 MHz, CDCl₃): δ 8.03 (s, 2H), 7.88 (s, 1H), 7.60-7.67 (m, 1H), 7.34 (d, 1H), 7.21 (d, 1H), 7.18 (d, 1H), 6.76 (d, 1H), 6.62 (d, 1H), 5.62 (s, 2H), 3.82 (t, 2H), 2.34 (t, 2H), 2.22 (s, 6H), 1.84 (m, 2H).

LC/MS: mass calcd. for $C_{26}H_{23}F_3N_4O_2S$: 512.15. found 513.3 $[M+H]^+$

Example 248

1-{2-[(5Z)-5-({1-[2,4-Bis(trifluoromethyl)benzyl]-1H-indol-5-yl}methylidene)-2,4-dioxo-1,3-thiazolidin-3-yl]ethyl}-D-proline

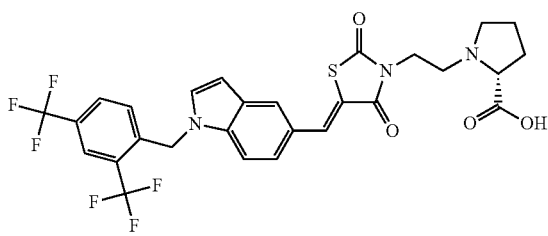 [SMILES: O=C(O)[C@H]1CCCN1CCN1C(=O)S/C(=C\c2ccc3c(ccn3Cc3ccc(C(F)(F)F)cc3C(F)(F)F)c2)C1=O]

1-{2-[(5Z)-5-({1-[2,4-Bis(trifluoromethyl)benzyl]-1H-indol-5-yl}methylidene)-2,4-dioxo-1,3-thiazolidin-3-yl]ethyl}-D-proline was prepared from [(5Z)-5-({1-[2,4-bis-(trifluoromethyl)benzyl]-1H-indol-5-yl}methylidene)-2,4-dioxo-1,3-thiazolidine (from Example 238), 2-bromo-1-chloroethane and (D)-proline following General Procedure G.

$^1$H NMR (400 MHz, CD$_3$OD): δ 7.87-8.02 (m, 4H), 1H), 7.60-7.76 (m, 1H), 7.31-7.50 (m, 2H), 7.06-7.23 (m, 1H), 6.58-6.76 (m, 2H), 5.63-5.73 (m, 2H), 4.19-4.39 (m, 1H), 3.44-4.03 (m, 4H), 2.87-3.27 (m, 2H), 2.08 (m, 4H).

LC/MS: mass calcd. for C$_{28}$H$_{23}$F$_6$N$_3$O$_4$S: 611.13. found 612.3 [M+H]$^+$

Example 249

(5Z)-5-[(1-{[4-Fluoro-2-(trifluoromethyl)phenyl]methyl}-1H-indol-5-yl)methylidene]-3-(2-morpholin-4-ylethyl)-1,3-thiazolidine-2,4-dione

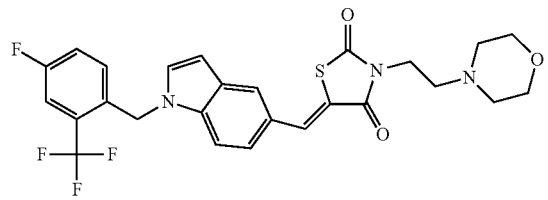 [SMILES: O=C1S/C(=C\c2ccc3c(ccn3Cc3ccc(F)cc3C(F)(F)F)c2)C(=O)N1CCN1CCOCC1]

(A) [4-Fluoro-2-(trifluoromethyl)benzyl]-1H-indol-5-carbaldehyde was prepared from 4-fluoro-2-(trifluoromethyl)benzyl bromide and 1H-indol-5-carbaldehyde following General Procedure A.

(B) [(5Z)-5-({1-[4-Fluoro-2-(trifluoromethyl)benzyl]-1H-indol-5-yl}methylidene)-2,4-dioxo-1,3-thiazolidine was prepared from [4-fluoro-2-(trifluoromethyl)-benzyl]-1H-indol-5-carbaldehyde following General Procedure E.

(C) (5Z)-5-[(1-{[4-Fluoro-2-(trifluoromethyl)phenyl]methyl}-1H-indol-5-yl)methylidene]-3-(2-morpholin-4-ylethyl)-1,3-thiazolidine-2,4-dione was prepared from [(5Z)-5-({1-[4-fluoro-2-(trifluoromethyl)benzyl]-1H-indol-5-yl}methylidene)-2,4-dioxo-1,3-thiazolidine and 4-(2-chloroethyl)-morpholine hydrochloride following General Procedure H.

$^1$H NMR (400 MHz, CDCl$_3$): δ 8.03 (s, 1H), 7.87 (d, 1H), 7.45 (dd, 1H), 7.35 (dd, 1H), 7.24 (d, 1H), 7.20 (d, 1H), 7.04 (m, 1H), 6.71 (dd, 1H), 6.54 (dd, 1H), 5.53 (s, 2H), 3.89 (t, 2H), 3.66 (t, 4H), 2.63 (t, 2H), 2.51 (t, 4H).

LC/MS: mass calcd. for C$_{26}$H$_{23}$F$_4$N$_3$O$_3$S: 533.14. found 534.4 [M+H]$^+$

Example 250

(5Z)-3-[2-(Dimethylamino)ethyl]-5-[(1-{[4-fluoro-2-(trifluoromethyl)phenyl]methyl}-1H-indol-5-yl)methylidene]-1,3-thiazolidine-2,4-dione

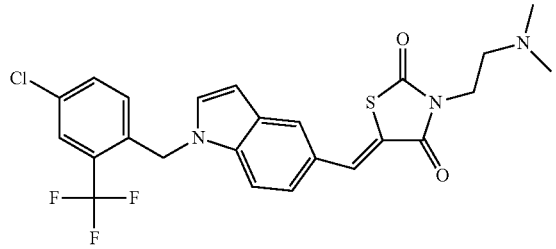 [SMILES: CN(C)CCN1C(=O)S/C(=C\c2ccc3c(ccn3Cc3ccc(Cl)cc3C(F)(F)F)c2)C1=O]

(5Z)-3-[2-(Dimethylamino)ethyl]-5-[(1-{[4-fluoro-2-(trifluoromethyl)-phenyl]methyl}-1H-indol-5-yl)methylidene]-1,3-thiazolidine-2,4-dione was prepared from [(5Z)-5-({1-[4-fluoro-2-(trifluoromethyl)benzyl]-1H-indol-5-yl}methylidene)-2,4-dioxo-1,3-thiazolidine (from Example 249) and 2-(dimethylamino)ethyl chloride hydrochloride following General Procedure H.

$^1$H NMR (400 MHz, CDCl$_3$): δ 8.03 (s, 1H), 7.85 (d, 1H), 7.45 (dd, 1H), 7.33 (dd, 1H), 7.22 (d, 1H), 7.19 (d, 1H), 7.04 (m, 1H), 6.70 (d, 1H), 6.54 (m, 1H), 5.52 (s, 2H), 3.87 (t, 2H), 2.58 (t, 2H), 2.29 (s, 6H).

LC/MS: mass calcd. for C$_{24}$H$_{21}$F$_4$N$_3$O$_2$S: 491.13. found 492.4 [M+H]$^+$

Example 251

(5Z)-5-[(1-{[4-Fluoro-2-(trifluoromethyl)phenyl]methyl}-1H-indol-5-yl)methylidene]-3-[2-(methyloxy)ethyl]-1,3-thiazolidine-2,4-dione

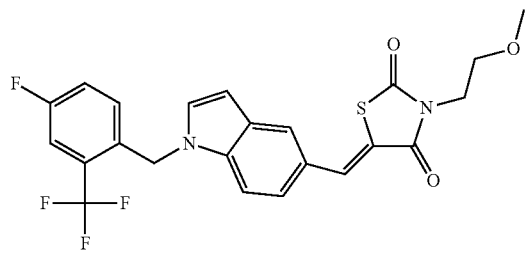 [SMILES: COCCN1C(=O)S/C(=C\c2ccc3c(ccn3Cc3ccc(F)cc3C(F)(F)F)c2)C1=O]

(5Z)-5-[(1-{[4-Fluoro-2-(trifluoromethyl)phenyl]methyl}-1H-indol-5-yl)methylidene]-3-[2-(methyloxy)ethyl]-1,3-thiazolidine-2,4-dione was prepared from [(5Z)-5-({1-[4-fluoro-2-(trifluoromethyl)benzyl]-1H-indol-5-yl}methylidene)-2,4-dioxo-1,3-thiazolidine (from Example 249) and 2-bromoethyl methyl ether following General Procedure H.

$^1$H NMR (400 MHz, CDCl$_3$): δ 8.05 (s, 1H), 7.87 (s, 1H), 7.45 (d, 1H), 7.35 (d, 1H), 7.23 (d, 1H), 7.20 (d, 1H), 7.05 (m, 1H), 6.71 (d, 1H), 6.55 (dd, 1H), 5.53 (s, 2H), 3.98 (t, 2H), 3.65 (t, 2H), 3.36 (s, 3H).

LC/MS: mass calcd. for $C_{23}H_{18}F_4N_2O_3S$: 478.10. found 479.3 $[M+H]^+$

Example 252

(5Z)-3-[3-(Dimethylamino)propyl]-5-[(1-{[4-fluoro-2-(trifluoromethyl)phenyl]-methyl}-1H-indol-5-yl)methylidene]-1,3-thiazolidine-2,4-dione

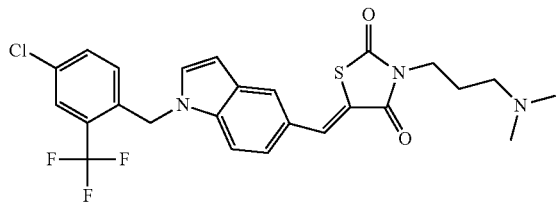 [SMILES: CN(C)CCCN1C(=O)S/C(=C\c2ccc3c(ccn3Cc3ccc(Cl)cc3C(F)(F)F)c2)C1=O]

(5Z)-3-[3-(Dimethylamino)propyl]-5-[(1-{[4-fluoro-2-(trifluoromethyl)phenyl]-methyl}-1H-indol-5-yl)methylidene]-1,3-thiazolidine-2,4-dione was prepared from [(5Z)-5-({1-[4-fluoro-2-(trifluoromethyl)benzyl]-1H-indol-5-yl}methylidene)-2,4-dioxo-1,3-thiazolidine (from Example 249) and 3-(dimethylamino)propyl chloride hydrochloride following General Procedure H.

$^1$H NMR (400 MHz, CDCl$_3$): δ 8.03 (s, 1H), 7.87 (s, 1H), 7.45 (dd, 1H), 7.35 (d, 1H), 7.23 (d, 1H), 7.20 (d, 1H), 7.05 (m, 1H), 6.71 (d, 1H), 6.54 (dd, 1H), 5.52 (s, 2H), 3.82 (t, 2H), 2.34 (t, 2H), 2.22 (s, 6H), 1.84 (m, 2H).

LC/MS: mass calcd. for $C_{26}H_{23}F_4N_3O_2S$: 505.14. found 506.3 $[M+H]^+$

Example 253

[(5Z)-5-({1-[4-Chloro-2-(trifluoromethyl)benzyl]-1H-indol-5-yl}methylidene)-2,4-dioxo-1,3-thiazolidin-3-yl]acetic acid

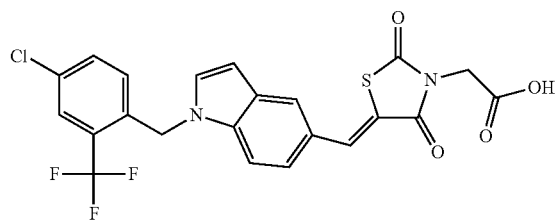

[(5Z)-5-({1-[4-Chloro-2-(trifluoromethyl)benzyl]-1H-indol-5-yl}methylidene)-2,4-dioxo-1,3-thiazolidin-3-yl]acetic acid was prepared from [(5Z)-5-({1-[4-chloro-2-(trifluoromethyl)benzyl]-1H-indol-5-yl}methylidene)-2,4-dioxo-1,3-thiazolidine (from Example 243) following General Procedure I.

$^1$H NMR (400 MHz, DMSO-d$_6$): δ 7.94 (s, 1H), 7.90 (s, 1H), 7.83 (d, 1H), 7.56 (dd, 1H), 7.52 (d, 1H), 7.35 (m, 2H), 6.69 (d, 1H), 6.44 (d, 1H), 5.61 (s, 2H), 3.89 (s, 2H).

LC/MS: mass calcd. for $C_{22}H_{14}ClF_3N_2O_4S$: 494.03. found 495.2 $[M+H]^+$

Example 254

(5Z)-5-({1-[4-Chloro-2-(trifluoromethyl)benzyl]-1H-indol-5-yl}methylidene)-3-(2-morpholin-4-yl-ethyl)-1,3-thiazolidine-2,4-dione

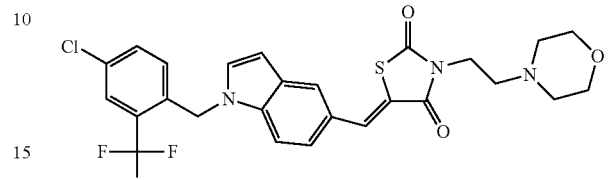

(5Z)-5-({1-[4-Chloro-2-(trifluoromethyl)benzyl]-1H-indol-5-yl}methylidene)-3-(2-morpholin-4-ylethyl)-1,3-thiazolidine-2,4-dione was prepared from [(5Z)-5-({1-[4-chloro-2-(trifluoromethyl)benzyl]-1H-indol-5-yl}methylidene)-2,4-dioxo-1,3-thiazolidine (from Example 243) and 4-(2-chloroethyl)morpholine hydrochloride following General Procedure H.

$^1$H NMR (400 MHz, CDCl$_3$): δ 8.03 (s, 1H), 7.88 (d, 1H), 7.72 (d, 1H), 7.35 (dd, 1H), 7.31 (dd, 1H), 7.22 (d, 1H), 7.20 (d, 1H), 6.72 (dd, 1H), 6.48 (d, 1H), 5.53 (s, 2H), 3.89 (t, 2H), 3.66 (t, 4H), 2.64 (t, 2H), 2.52 (br, 4H).

LC/MS: mass calcd. for $C_{26}H_{23}ClF_3N_3O_3S$: 549.11. found 550.4 $[M+H]^+$

Example 255

[(5Z)-5-({1-[4-Fluoro-2-(trifluoromethyl)benzyl]-1H-indol-5-yl}methylidene)-2,4-dioxo-1,3-thiazolidin-3-yl]acetic acid

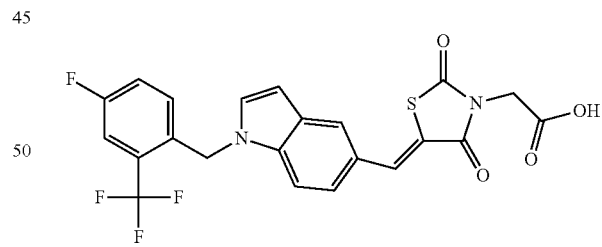

[(5Z)-5-({1-[4-Fluoro-2-(trifluoromethyl)benzyl]-1H-indol-5-yl}methylidene)-2,4-dioxo-1,3-thiazolidin-3-yl]acetic acid was prepared from [(5Z)-5-({1-[4-fluoro-2-(trifluoromethyl)benzyl]-1H-indol-5-yl}methylidene)-2,4-dioxo-1,3-thiazolidine (from Example 249) following General Procedure I.

$^1$H NMR (400 MHz, CDCl$_3$): δ 8.10 (s, 1H), 7.88 (s, 1H), 7.46 (dd, 1H), 7.35 (d, 1H), 7.24 (d, 1H), 7.21 (d, 1H), 7.05 (m, 1H), 6.72 (d, 1H), 6.55 (dd, 1H), 5.53 (s, 2H), 4.56 (s, 2H).

LC/MS: mass calcd. for $C_{22}H_{14}F_4N_2O_4S$: 478.06. found 479.3 $[M+H]^+$

Example 256

(5Z)-5-({1-[4-Chloro-2-(trifluoromethyl)benzyl]-1H-indol-5-yl}methylidene)-3-[(3S)-morpholin-3-ylmethyl]-1,3-thiazolidine-2,4-dione

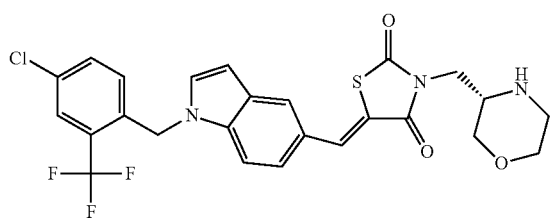 [SMILES: O=C1S/C(=C\c2ccc3c(ccn3Cc3ccc(Cl)cc3C(F)(F)F)c2)C(=O)N1C[C@H]1COCCN1]

(A) 1,1-Dimethylethyl (3S)-3-[{(5Z)-5-[(1-{[4-chloro-2-(trifluoromethyl)phenyl]-methyl}-1H-indol-5-yl)methylidene]-2,4-dioxo-1,3-thiazolidin-3-yl}methyl]morpholine-1-carboxylate was prepared from (5Z)-5-({1-[4-chloro-2-(trifluoromethyl)benzyl]-1H-indol-5-yl}methylidene)-2,4-dioxo-1,3-thiazolidine (from Example 243) and 1,1-dimethylethyl (3S)-3-(hydroxymethyl)morpholine-1-carboxylate following General Procedure J.

(B) (5Z)-5-({1-[4-Chloro-2-(trifluoromethyl)benzyl]-1H-indol-5-yl}methylidene)-3-[(3S)-morpholin-3-ylmethyl]-1,3-thiazolidine-2,4-dione was prepared from 1,1-dimethylethyl (3S)-3-[{(5Z)-5-[(1-{[4-chloro-2-(trifluoromethyl)-phenyl]methyl}-1H-indol-5-yl)methylidene]-2,4-dioxo-1,3-thiazolidin-3-yl}methyl]morpholine-1-carboxylate following General Procedure M.

$^1$H NMR (400 MHz, CDCl$_3$): δ 8.06 (s, 1H), 7.87 (d, 1H), 7.73 (d, 1H), 7.34 (dd, 1H), 7.32 (dd, 1H), 7.22 (d, 1H), 7.21 (s, 1H), 6.72 (d, 1H), 6.49 (d, 1H), 5.53 (s, 2H), 3.83 (dd, 1H), 3.69-3.81 (3H), 3.53 (m, 1H), 3.33 (dd, 1H), 3.17 (m, 1H), 2.85-2.99 (2H).

LC/MS: mass calcd. for C$_{25}$H$_{21}$ClF$_3$N$_3$O$_3$S: 535.09. found 536.4 [M+H]$^+$

Example 257

1-{2-[(5Z)-5-({1-[4-Chloro-2-(trifluoromethyl)benzyl]-1H-indol-5-yl}methylidene)-2,4-dioxo-1,3-thiazolidin-3-yl]ethoxy}guanidine

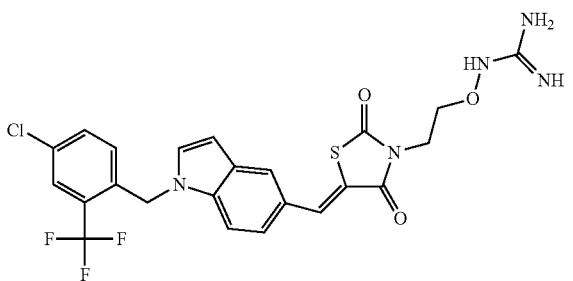

(A) Bis(1,1-dimethylethyl) [{[(2-{(5Z)-5-[(1-{[4-chloro-2-(trifluoromethyl)-phenyl]methyl}-1H-indol-5-yl)methylidene]-2,4-dioxo-1,3-thiazolidin-3-yl}ethyl)oxy]amino}methylidene]biscarbamate was prepared from [4-chloro-2-(trifluoromethyl)benzyl]-1H-indol-5-carbaldehyde (from Example 1) and bis(1,1-dimethylethyl) [({[2-(2,4-dioxo-1,3-thiazolidin-3-yl)ethyl]oxy}amino)methylidene]biscarbamate (from Example 91) following General Procedure F.

(B) 1-{2-[(5Z)-5-({1-[4-Chloro-2-(trifluoromethyl)benzyl]-1H-indol-5-yl}methylidene)-2,4-dioxo-1,3-thiazolidin-3-yl]ethoxy}guanidine was prepared from bis(1,1-dimethylethyl) [{[(2-{(5Z)-5-[(1-{[4-chloro-2-(trifluoromethyl)phenyl]methyl}-1H-indol-5-yl)methylidene]-2,4-dioxo-1,3-thiazolidin-3-yl}ethyl)oxy]amino}methylidene]biscarbamate following General Procedure M.

$^1$H NMR (400 MHz, CDCl$_3$): δ 7.98 (s, 1H), 7.77 (s, 1H), 7.70 (d, 1H), 7.49 (br. s., 2H), 7.21-7.29 (m, 2H), 7.09-7.19 (m, 2H), 6.67 (d, 1H), 6.45 (d, 1H), 5.44 (s, 2H), 4.08 (br. s., 2H), 4.01 (br. s., 2H).

LC/MS: mass calcd. for C$_{23}$H$_{19}$ClF$_3$N$_5$O$_3$S: 537.08. found 538.0 [M+H]$^+$

Example 258

(5Z)-5-({1-[4-Chloro-2-(trifluoromethyl)benzyl]-1H-benzotriazol-5-yl}methylidene)-3-(2-pyrrolidin-1-ylethyl)-1,3-thiazolidine-2,4-dione

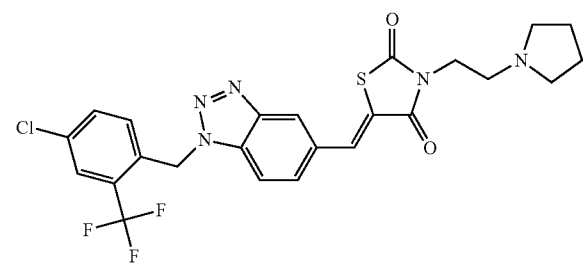 [SMILES: O=C1S/C(=C\c2ccc3c(c2)nnn3Cc2ccc(Cl)cc2C(F)(F)F)C(=O)N1CCN1CCCC1]

(A) Reaction of methyl benzotriazole-5-carboxylate and 4-chloro-2-trifluoromethylbenzyl bromide following General Procedure A afforded an isomeric product mixture composed of three regioisomers. Partial purification by silica gel chromatography (hexane/EtOAc) provided a mixture of methyl 1-(4-chloro-2-trifluoromethylbenzyl)-1H-benzotriazole-5-carboxylate and methyl 3-(4-chloro-2-trifluoromethylbenzyl)-3H-benzotriazole-5-carboxylate, which was used without further purification.

(B) To a cooled (0° C.) solution of methyl 1-(4-chloro-2-trifluoromethylbenzyl)-1H-benzotriazole-5-carboxylate and methyl 3-(4-chloro-2-trifluoromethylbenzyl)-3H-benzotriazole-5-carboxylate (8.11 mmol) in THF (40 mL) was added LAH (20.3 mmol) portionwise. After 30 min, the cold reaction was quenched by adding a minimal volume of sat'd aq. MgSO$_4$. Excess anhydrous MgSO$_4$ powder was then added and after stirring vigorously for 1 h, the mixture was filtered and concentrated under reduced pressure. Purification of the residual pale yellow oil by silica gel chromatography (hexanes/EtOAc) provided [1-(4-chloro-2-trifluoromethylbenzyl)-1H-benzotriazol-5-yl]methanol as pale yellow solid.

(C) To a solution of [1-(4-chloro-2-trifluoromethylbenzyl)-1H-benzotriazol-5-yl]methanol (8.11 mmol) in DCM (40 mL) was added Dess-Martin periodinane (8.48 mmol) and the mixture was stirred at rt for 30 min. The reaction was then concentrated in vacuo and the resultant residue was treated with EtOAc, filtered and the filtrate was concentrated. Purification of the residual yellow oil by silica gel chromatography (hexanes/EtOAc) afforded 1-(4-chloro-2-trifluoromethylbenzyl)-1H-benzotriazole-5-carbaldehyde as white solid.

(D) (5Z)-5-({1-[4-Chloro-2-(trifluoromethyl)benzyl]-1H-benzotriazol-5-yl}methylidene)-3-(2-pyrrolidin-1-yl-ethyl)-1,3-thiazolidine-2,4-dione was prepared from 1-(4-chloro-2-trifluoromethylbenzyl)-1H-benzotriazole-5-carbaldehyde and 3-(2-pyrrolidin-1-ylethyl)-1,3-thiazolidine-2,4-dione (from Example 172) following General Procedure F.

$^1$H NMR (400 MHz, CD$_3$OD): δ 8.28 (s, 1H), 8.11 (s, 1H), 7.85 (d, 1H), 7.70-7.79 (m, 2H), 7.59 (dd, 1H), 7.02-7.07 (m, 1H), 6.16 (s, 2H), 4.07 (t, 2H), 3.19 (s, 4H), 2.00 (t, 4H).

LCMS: mass calcd. for C$_{24}$H$_{21}$ClF$_3$N$_5$O$_2$S: 535.11. found 536.1 [M+H]$^+$

Example 259

Ethyl [(5Z)-5-({1-[4-chloro-2-(trifluoromethyl)benzyl]-1H-benzotriazol-5-yl}methylidene)-2,4-dioxo-1,3-thiazolidin-3-yl]acetate

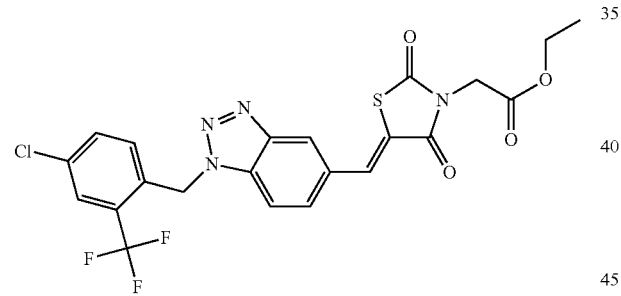

(A) A mixture of the potassium salt of thiazolidine-2,4-dione (from Example 65; 6.44 mmol) and ethyl bromoacetate (6.44 mmol) in acetone (7 mL) was refluxed for 4 h. After cooling to rt, the mixture was filtered and the filtrate was concentrated in vacuo to provide ethyl (2,4-dioxo-1,3-thiazolidin-3-yl)acetate as a colorless oil.

(B) Ethyl [(5Z)-5-({1-[4-chloro-2-(trifluoromethyl)benzyl]-1H-benzotriazol-5-yl}methylidene)-2,4-dioxo-1,3-thiazolidin-3-yl]acetate was prepared from 1-(4-chloro-2-trifluoromethylbenzyl)-1H-benzotriazole-5-carbaldehyde (from Example 258) and ethyl (2,4-dioxo-1,3-thiazolidin-3-yl)acetate following General Procedure F.

$^1$H NMR (400 MHz, CD$_3$OD): δ 8.46 (s, 1H), 8.23 (s, 1H), 7.96-7.94 (m, 2H), 7.85 (dd, 1H), 7.74 (dd, 1H), 7.14 (d, 1H), 6.19 (s, 2H), 4.53 (s, 2H), 4.19 (q, 2H), 1.22 (t, 2H).

LCMS: mass calcd. for C$_{22}$H$_{16}$ClF$_3$N$_4$O$_4$S: 524.05. found 566.0 [M+MeCN+H]$^+$

Example 260

[(5Z)-5-({1-[4-Chloro-2-(trifluoromethyl)benzyl]-1H-benzotriazol-5-yl}methylidene)-2,4-dioxo-1,3-thiazolidin-3-yl]acetic acid

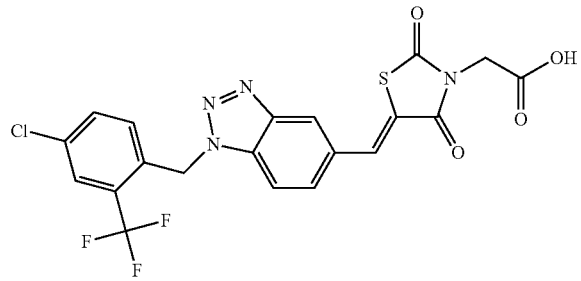 [SMILES: O=C(O)CN1C(=O)S/C(=C\c2ccc3c(c2)nnn3Cc2ccc(Cl)cc2C(F)(F)F)C1=O]

[(5Z)-5-({1-[4-Chloro-2-(trifluoromethyl)benzyl]-1H-benzotriazol-5-yl}methylidene)-2,4-dioxo-1,3-thiazolidin-3-yl]acetic acid was prepared from ethyl [(5Z)-5-({1-[4-chloro-2-(trifluoromethyl)benzyl]-1H-benzotriazol-5-yl}methylidene)-2,4-dioxo-1,3-thiazolidin-3-yl]acetate (Example 259) following General Procedure O.

$^1$H NMR (400 MHz, CD$_3$OD): δ 8.31 (s, 1H), 8.14 (s, 1H), 7.85 (d, 1H), 7.80-7.72 (m, 2H), 7.59 (dd, 1H), 7.04 (d, 1H), 6.16 (s, 2H), 4.55 (s, 2H).

LCMS: mass calcd. for C$_{20}$H$_{12}$ClF$_3$N$_4$O$_4$S: 496.02. found 538.0 [M+MeCN+H]$^+$

Example 261

Ethyl 4-[(5Z)-5-({1-[4-chloro-2-(trifluoromethyl)benzyl]-1H-benzotriazol-5-yl}methylidene)-2,4-dioxo-1,3-thiazolidin-3-yl]cyclohexanecarboxylate

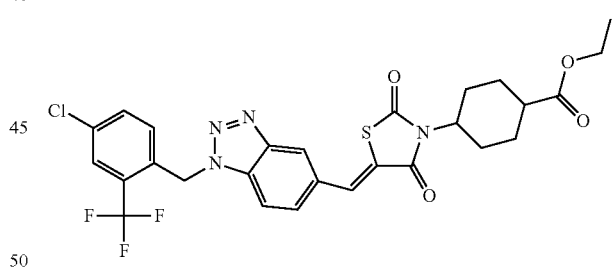

(A) [(5Z)-5-({1-[4-Chloro-2-(trifluoromethyl)benzyl]-1H-benzotriazol-5-yl}methylidene)-2,4-dioxo-1,3-thiazolidine was prepared from 1-(4-chloro-2-trifluoromethylbenzyl)-1H-benzotriazole-5-carbaldehyde (from Example 258) and thiazolidine-2,4-dione following General Procedure E.

(B) Ethyl 4-[(5Z)-5-({1-[4-chloro-2-(trifluoromethyl)benzyl]-1H-benzotriazol-5-yl}methylidene)-2,4-dioxo-1,3-thiazolidin-3-yl]cyclohexanecarboxylate was prepared from [(5Z)-5-({1-[4-chloro-2-(trifluoromethyl)benzyl]-1H-benzotriazol-5-yl}methylidene)-2,4-dioxo-1,3-thiazolidine and ethyl 4-hydroxycyclohexanecarboxylate following General Procedure J.

$^1$H NMR (400 MHz, CD$_3$OD): δ 8.26 (s, 1H), 7.98 (s, 1H), 7.98 (d, 1H), 7.58 (dd, 1H), 7.41 (d, 2H), 6.88 (d, 1H), 6.04 (s,

2H), 4.34-4.27 (m, 1H), 4.14 (q, 2H), 2.41-2.28 (m, 3H), 2.17-2.13 (m, 2H), 1.81-1.79 (m, 2H), 1.63-1.56 (m, 2H), 1.26 (t, 3H).

LCMS: mass calcd. for $C_{27}H_{24}ClF_3N_4O_4S$: 592.12. found 593.1 [M+H]$^+$

Example 262

(5Z)-5-({1-[4-Chloro-2-(trifluoromethyl)benzyl]-1H-benzotriazol-5-yl}methylidene)-3-(1H-1,2,3-triazol-4-ylmethyl)-1,3-thiazolidine-2,4-dione

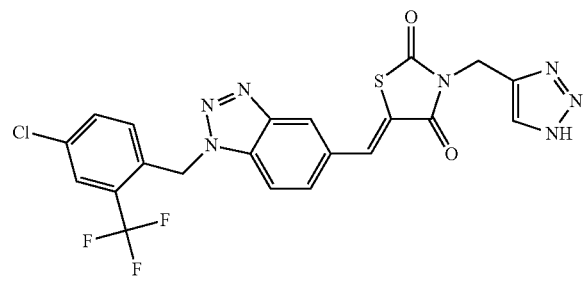 [SMILES: O=C1S/C(=C\c2ccc3c(c2)nnn3Cc2ccc(Cl)cc2C(F)(F)F)C(=O)N1Cc1c[nH]nn1]

(5Z)-5-({1-[4-Chloro-2-(trifluoromethyl)benzyl]-1H-benzotriazol-5-yl}methylidene)-3-(1H-1,2,3-triazol-4-ylmethyl)-1,3-thiazolidine-2,4-dione was prepared from 1-(4-chloro-2-trifluoromethylbenzyl)-1H-benzotriazole-5-carbaldehyde (from Example 258) and 3-(1H-[1,2,3]triazol-4-ylmethyl)-1,3-thiazolidine-2,4-dione (from Example 85) following General Procedure F.

$^1$H NMR (400 MHz, CD$_3$OD): δ 8.15 (s, 1H), 7.99 (s, 1H), 7.78-7.85 (m, 2H), 7.50-7.63 (m, 3H), 7.02 (d, 1H), 6.12 (s, 2H), 5.02 (s, 2H).

LCMS: mass calcd. for $C_{21}H_{13}ClF_3N_7O_2S$: 519.05. found 575 [M+MeCN+H]$^+$

Example 263

(5Z)-5-({1-[4-Chloro-2-(trifluoromethyl)benzyl]-1H-benzotriazol-5-yl}methylidene)-3-[(5-methyl-1H-1,2,4-triazol-3-yl)methyl]-1,3-thiazolidine-2,4-dione

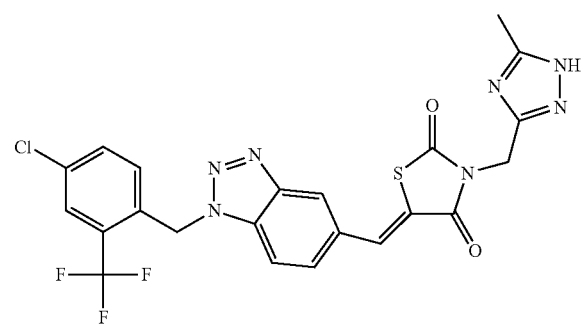 [SMILES: Cc1nc(CN2C(=O)S/C(=C\c3ccc4c(c3)nnn4Cc3ccc(Cl)cc3C(F)(F)F)C2=O)n[nH]1]

(5Z)-5-({1-[4-Chloro-2-(trifluoromethyl)benzyl]-1H-benzotriazol-5-yl}methylidene)-3-[(5-methyl-1H-1,2,4-triazol-3-yl)methyl]-1,3-thiazolidine-2,4-dione was prepared from 1-(4-chloro-2-trifluoromethylbenzyl)-1H-benzotriazole-5-carbaldehyde (from Example 258) and 3-(5-methyl-1H-[1,2,4]triazol-3-ylmethyl)-1,3-thiazolidine-2,4-dione (from Example 86) following General Procedure F.

$^1$H NMR (400 MHz, DMSO-d$_6$): δ 8.42 (s, 1H), 8.17 (s, 1H), 7.89-7.96 (m, 2H), 7.78-7.88 (m, 1H), 7.72 (dd, 1H), 7.12 (d, 1H), 6.16 (s, 2H), 4.81 (s., 2H), 2.28 (s, 3H).

LCMS: mass calcd. for $C_{22}H_{16}ClF_3N_7O_2S$: 533.06. found 534.1 [M+H]-F.

Example 264

(5Z)-5-({1-[4-Chloro-2-(trifluoromethyl)benzyl]-1H-benzotriazol-5-yl}methylidene)-3-(1H-1,2,4-triazol-3-ylmethyl)-1,3-thiazolidine-2,4-dione

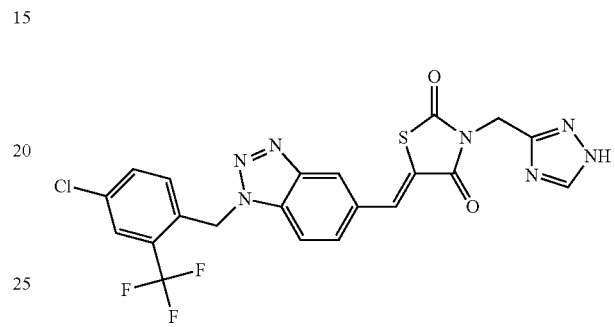

(5Z)-5-({1-[4-Chloro-2-(trifluoromethyl)benzyl]-1H-benzotriazol-5-yl}methylidene)-3-(1H-1,2,4-triazol-3-ylmethyl)-1,3-thiazolidine-2,4-dione was prepared from 1-(4-chloro-2-trifluoromethylbenzyl)-1H-benzotriazole-5-carbaldehyde (from Example 258) and 3-(1H-[1,2,4]triazol-3-ylmethyl)-1,3-thiazolidine-2,4-dione (from Example 90) following General Procedure F.

$^1$H NMR (400 MHz, DMSO-d$_6$): δ 8.45 (s, 1H), 8.20 (s, 1H), 7.94 (dd, 3H), 7.82-7.88 (m, 1H), 7.74 (dd, 1H), 7.05-7.25 (m, 1H), 6.19 (s, 2H), 4.93 (s, 2H).

LCMS: mass calcd. for $C_{21}H_{13}ClF_3N_7O_2S$: 519.05. found 562.2 [M+MeCN+H]$^+$

Example 265

(5Z)-5-({1-[4-Chloro-2-(trifluoromethyl)benzyl]-1H-benzotriazol-5-yl}methylidene)-3-(1H-tetrazol-5-ylmethyl)-1,3-thiazolidine-2,4-dione

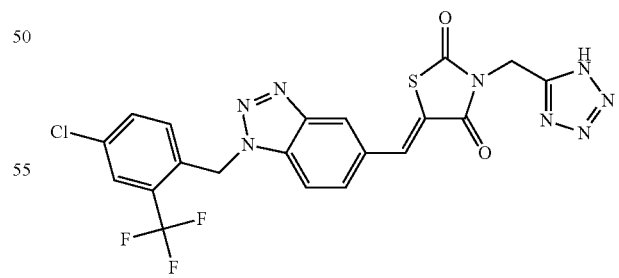

(5Z)-5-({1-[4-Chloro-2-(trifluoromethyl)benzyl]-1H-benzotriazol-5-yl}methylidene)-3-(1H-tetrazol-5-ylmethyl)-1,3-thiazolidine-2,4-dione was prepared from 1-(4-chloro-2-trifluoromethylbenzyl)-1H-benzotriazole-5-carbaldehyde (from Example 258) and 3-(1H-tetrazol-5-ylmethyl)-1,3-thiazolidine-2,4-dione (from Example 72) following General Procedure F.

¹H NMR (400 MHz, DMSO-d₆): δ 8.46 (s, 1H), 8.23 (s, 1H), 7.91-7.99 (m, 2H), 7.83-7.88 (m, 1H), 7.74 (dd, 1H), 7.15 (d, 1H), 6.19 (s, 2H), 5.21 (s, 2H).

LCMS: mass calcd. for $C_{20}H_{12}ClF_3N_8O_2S$: 520.04. found 521.0 [M+H]⁺

Example 266

4-[(5Z)-5-({1-[4-Chloro-2-(trifluoromethyl)benzyl]-1H-benzotriazol-5-yl}methylidene)-2,4-dioxo-1,3-thiazolidin-3-yl]cyclohexanecarboxylic acid

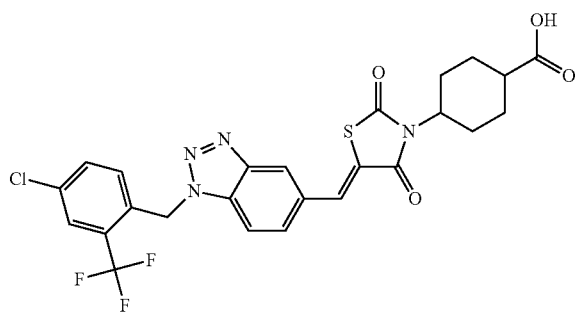 [SMILES: O=C(O)C1CCC(N2C(=O)S/C(=C\c3ccc4c(c3)nnn4Cc3ccc(Cl)cc3C(F)(F)F)C2=O)CC1]

4-[(5Z)-5-({1-[4-Chloro-2-(trifluoromethyl)benzyl]-1H-benzotriazol-5-yl}methylidene)-2,4-dioxo-1,3-thiazolidin-3-yl]cyclohexanecarboxylic acid was prepared from ethyl 4-[(5Z)-5-({1-[4-chloro-2-(trifluoromethyl)benzyl]-1H-benzotriazol-5-yl}methylidene)-2,4-dioxo-1,3-thiazolidin-3-yl]cyclohexane-carboxylate (Example 261) following General Procedure O.

¹H NMR (400 MHz, DMSO-d₆): δ 8.37-8.43 (m, 1H), 8.07-8.13 (m, 1H), 7.88-7.97 (m, 2H), 7.78-7.86 (m, 1H), 7.74 (dd, 1H), 7.13 (d, 1H), 6.17 (s, 2H), 4.07-4.25 (m, 1H), 2.11-2.24 (m., 3H), 2.01-2.05 (m, 2H), 1.71-1.82 (m, 2H), 1.35-1.65 (m, 2H).

LCMS: mass calcd. for $C_{25}H_{20}ClF_3N_4O_4S$: 564.08. found 606.3 [M+MeCN+H]⁺

Example 267

(5Z)-5-({1-[4-Chloro-2-(trifluoromethyl)benzyl]-1H-benzotriazol-5-yl}methylidene)-3-[(3S)-morpholin-3-ylmethyl]-1,3-thiazolidine-2,4-dione

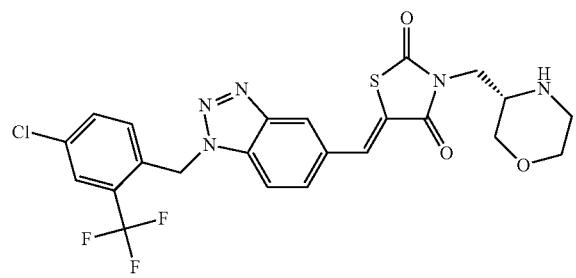 [SMILES: O=C1S/C(=C\c2ccc3c(c2)nnn3Cc2ccc(Cl)cc2C(F)(F)F)C(=O)N1C[C@H]1COCCN1]

(A) 1,1-Dimethylethyl (3S)-3-[{(5Z)-5-[(1-{[4-chloro-2-(trifluoromethyl)phenyl]-methyl}-1H-benzotriazol-5-yl)methylidene]-2,4-dioxo-1,3-thiazolidin-3-yl}methyl]morpholine-1-carboxylate was prepared from (5Z)-5-({1-[4-chloro-2-(trifluoromethyl)benzyl]-1H-benzotriazol-5-yl}methylidene)-2,4-dioxo-1,3-thiazolidine (from Example 261) and 1,1-dimethylethyl (3S)-3-(hydroxymethyl)morpholine-1-carboxylate following General Procedure J.

(B) (5Z)-5-({1-[4-Chloro-2-(trifluoromethyl)benzyl]-1H-benzotriazol-5-yl}methylidene)-3-[(3S)-morpholin-3-ylmethyl]-1,3-thiazolidine-2,4-dione was prepared from 1,1-dimethylethyl (3S)-3-[{(5Z)-5-[(1-{[4-chloro-2-(trifluoromethyl)phenyl]methyl}-1H-benzotriazol-5-yl)methylidene]-2,4-dioxo-1,3-thiazolidin-3-yl}methyl]morpholine-1-carboxylate following General Procedure M.

¹H NMR (400 MHz, CD₃OD): δ 8.31 (s, 1H), 8.16 (s, 1H), 7.86 (d, 1H), 7.70-7.81 (m, 2H), 7.60 (dd, 1H), 7.07 (d, 1H), 6.16 (s, 2H), 3.93-4.17 (m, 4H), 3.67-3.82 (m, 2H), 3.56-3.66 (m, 1H), 3.37-3.42 (m, 1H), 3.15-3.25 (m, 1H).

LCMS: mass calcd. for $C_{23}H_{19}ClF_3N_5O_3S$: 537.08. found 579.4 [M+MeCN+H]⁺

Example 268

2-[(5Z)-5-({1-[4-Chloro-2-(trifluoromethyl)benzyl]-1H-benzotriazol-5-yl}methylidene)-2,4-dioxo-1,3-thiazolidin-3-yl]-N-(pyrrolidin-1-ylsulfonyl)acetamide

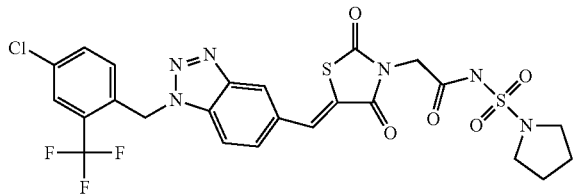 [SMILES: O=C(CN1C(=O)S/C(=C\c2ccc3c(c2)nnn3Cc2ccc(Cl)cc2C(F)(F)F)C1=O)NS(=O)(=O)N1CCCC1]

2-[(5Z)-5-({1-[4-chloro-2-(trifluoromethyl)benzyl]-1H-benzotriazol-5-yl}methylidene)-2,4-dioxo-1,3-thiazolidin-3-yl]-N-(pyrrolidin-1-ylsulfonyl)acetamide was prepared from [(5Z)-5-({1-[4-chloro-2-(trifluoromethyl)benzyl]-1H-benzotriazol-5-yl}methylidene)-2,4-dioxo-1,3-thiazolidin-3-yl]acetic acid (Example 260) and pyrrolidin-1-ylsulfonic acid amide following General Procedure L. The corresponding ethanolamine salt was prepared following General Procedure T.

¹H NMR (400 MHz, DMSO-d₆): δ 8.42 (s, 1H), 8.16 (s, 1H), 7.94 (br. d, 1H), 7.93 (d, 1H), 7.84 (dd, 1H), 7.73 (dd, 1H), 7.62 (br. s., 2H), 7.12 (d, 1H), 6.18 (s, 2H), 5.14 (t, 1H), 4.05 (s, 2H), 3.56 (q, 2H), 2.94-3.06 (m, 4H), 2.85 (t, 2H), 1.60 (ddd, 4H).

LCMS: mass calcd. for $C_{24}H_{20}ClF_3N_6O_6S_2$: 628.06. found 629.0 [M+H]⁺

Example 269

(5Z)-5-({1-[4-Chloro-2-(trifluoromethyl)benzyl]-1H-indazol-5-yl}methylidene)-3-[trans-2-(hydroxymethyl)piperidin-4-yl]-1,3-thiazolidine-2,4-dione

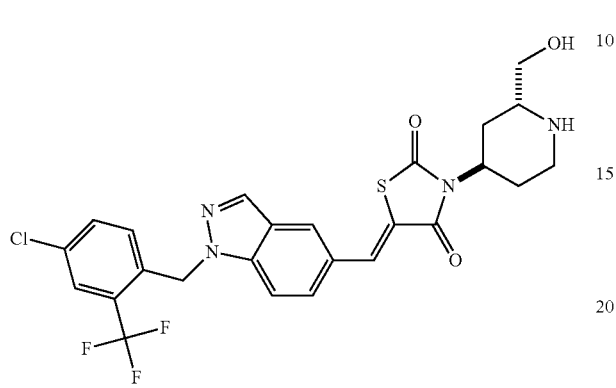

(A) To a solution of benzyl cis-4-hydroxy-2-methoxycarbonylpiperidine-1-carboxylate (2 mmol) in THF (10 mL) was added lithium borohydride (3 mmol) portionwise and the resulting mixture was stirred at rt for 16 h. AcOH (50% in water) was added slowly until the effervescence ceased. EtOAc was then added to dilute the mixture and the organic solution was extracted successively with sat. $NaHCO_3$ solution and brine, dried (anhydrous $Na_2SO_4$), and concentrated to afford benzyl cis-4-hydroxy-2-hydroxymethylpiperidine-1-carboxylate, which was used directly without further purification.

(B) A solution of benzyl cis-4-hydroxy-2-hydroxymethylpiperidine-1-carboxylate in methanol (200 mL) was hydrogenated (H-cube) using palladium on carbon (10%) as the catalyst cartridge at a speed of 1 mL/min. Evaporation of the solvent afforded cis-4-hydroxy-2-(hydroxymethyl)piperidine.

(C) To a solution of cis-4-hydroxy-2-(hydroxymethyl)piperidine (0.76 mmol) in MeOH/acetone (2 mL, 1:1, v/v) was added a drop of AcOH and the resulting solution was stirred at rt for 3 d. The reaction was concentrated in vacuo and the residue was purified by silica gel chromatography (EtOAc/MeOH) to afford cis-3,3-dimethylhexahydrooxazolo[3,4-a]pyridin-7-ol as colorless oil.

(D) (5Z)-5-({1-[4-Chloro-2-(trifluoromethyl)benzyl]-1H-indazol-5-yl}methylidene)-3-[trans-2-(hydroxymethyl)piperidin-4-yl]-1,3-thiazolidine-2,4-dione was prepared from [(5Z)-5-({1-[4-chloro-2-(trifluoromethyl)benzyl]-1H-indazol-5-yl}methylidene)-2,4-dioxo-1,3-thiazolidine (from Example 1) and cis-3,3-dimethylhexahydrooxazolo[3,4-a]pyridin-7-ol following General Procedure J. [During chromatographic purification (silica gel preparative TLC) the dimethyl ketal protection group was hydrolyzed.]

$^1$H NMR (400 MHz, $CDCl_3$): δ 8.21 (s, 1H), 7.98 (s, 1H), 7.95 (s, 1H), 7.72 (d, 1H), 7.50 (d, 1H), 7.36 (s, 1H), 7.33 (s, 1H), 6.68 (d, 1H), 5.79 (s, 2H), 4.55 (t, 1H), 3.88 (t, 1H), 3.39 (br. s., 1H), 3.07 (d, 1H), 2.81-3.00 (m, 2H), 2.62 (td, 1H), 2.32-2.49 (m, 1H), 1.56-1.78 (m, 2H).

LC/MS: mass calcd. for $C_{25}H_{22}ClF_3N_4O_3S$: 550.11. found 551.3 $[M+1]^+$

Example 270

(5Z)-5-({1-[4-Chloro-2-(trifluoromethyl)benzyl]-1H-indazol-5-yl}methylidene)-3-[trans-3-hydroxypiperidin-4-yl]-1,3-thiazolidine-2,4-dione

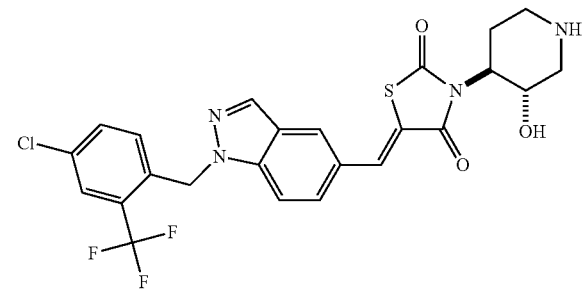

(A) To a solution of 1,1-dimethylethyl 3,6-dihydro-(2H)-pyridine-1-carboxylate (12.6 mmol) in DCM (100 mL) was added MCPBA (77%; 15.2 mmol) portionwise and the solution was stirred at rt for 16 h. The reaction was quenched by the addition of sat'd. aq. $Na_2S_2O_3$ (20 mL). After stirring for 20 min, the solution was extracted with DCM (2×100 mL). The organic layer was extracted successively with sat'd. aq. $NaHCO_3$ and brine, dried (anhydrous $Na_2SO_4$) and concentrated in vacuo. Purification of the resultant residue by silica gel chromatography (hexane/EtOAc) provided 1,1-dimethylethyl 7-oxa-3-azabicyclo[4.1.0]heptane-3-carboxylate as colorless oil.

(B) A mixture of 1,1-dimethylethyl 7-oxa-3-azabicyclo[4.1.0]heptane-3-carboxylate (5.03 mmol), thiazolidine-2,4-dione (5.13 mmol) and tetraethylammonium chloride (0.3 mmol) in DMF (1 mL) was prepared in a sealed vial and heated at 160° C. for 40 min in a microwave reactor. Upon cooling to rt, the reaction was diluted with EtOAc and extracted successively with water and brine, dried (anhydrous $Na_2SO_4$) and concentrated. Purification of the resultant residue by silica gel chromatography (hexane/EtOAc) provided both 1,1-dimethylethyl trans-4-(2,4-dioxo-1,3-thiazolidin-3-yl)-3-hydroxypiperidine-1-carboxylate and its regioisomer, 1,1-dimethylethyl trans-3-(2,4-dioxo-1,3-thiazolidin-3-yl)-4-hydroxy-piperidine-1-carboxylate.

(C) (5Z)-5-({1-[4-Chloro-2-(trifluoromethyl)benzyl]-1H-indazol-5-yl}methylidene)-3-[trans-3-hydroxypiperidin-4-yl]-1,3-thiazolidine-2,4-dione was prepared from [4-chloro-2-(trifluoromethyl)benzyl]-1H-indazol-5-carbaldehyde (from Example 1) and 1,1-dimethylethyl trans-4-(2,4-dioxo-1,3-thiazolidin-3-yl)-3-hydroxypiperidine-1-carboxylate following General Procedure F.

$^1$H NMR (400 MHz, $CDCl_3$): δ 8.19 (s, 1H), 7.94 (s, 1H), 7.91 (s, 1H), 7.71 (d, 1H), 7.46 (d, 1H), 7.29-7.36 (m, 2H), 6.67 (d, 1H), 5.78 (s, 2H), 4.38 (br. s., 1H), 4.25 (t, 1H), 3.39 (br. s., 1H), 3.16 (br. s., 1H), 2.47-2.81 (m, 2H), 2.32-2.47 (m, 1H), 1.89-2.09 (m, 2H), 1.83 (d, 1H).

LC/MS: mass calcd. for $C_{24}H_{20}ClF_3N_4O_3S$: 536.09. found 537.3 $[M+1]^+$

Example 271

(5Z)-5-({1-[2,4-Bis(trifluoromethyl)benzyl]-1H-indazol-5-yl}methylidene)-3-[trans-3-hydroxypiperidin-4-yl]-1,3-thiazolidine-2,4-dione

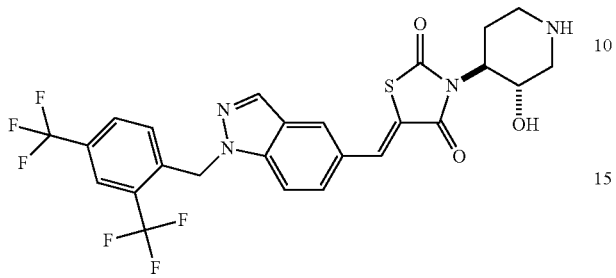

(5Z)-5-({1-[2,4-Bis(trifluoromethyl)benzyl]-1H-indazol-5-yl}methylidene)-3-[trans-3-hydroxypiperidin-4-yl]-1,3-thiazolidine-2,4-dione was prepared from [2,4-(trifluoromethyl)benzyl]-1H-indazol-5-carbaldehyde (from Example 6) and 1,1-dimethylethyl trans-4-(2,4-dioxo-thiazolidin-3-yl)-3-hydroxypiperidine-1-carboxylate (from Example 270) following General Procedure F.

$^1$H NMR (400 MHz, CDCl$_3$): δ 8.23 (s, 1H), 7.99 (s, 1H), 7.97 (s, 1H), 7.94 (s, 1H), 7.64 (d, 1H), 7.50 (d, 1H), 7.34 (d, 1H), 6.83 (d, 1H), 5.88 (s, 2H), 4.38 (td, 1H), 4.19-4.30 (m, 1H), 3.39 (dd, 1H), 3.15 (d, 1H), 2.63-2.74 (m, 1H), 2.53 (t, 1H), 2.40 (qd, 1H), 1.80 (br. s., 3H).

LC/MS: mass calcd. for $C_{25}H_{20}F_6N_4O_3S$: 570.12. found 571.4 $[M+1]^+$

Example 272

(5Z)-5-({1-[4-Fluoro-2-(trifluoromethyl)benzyl]-1H-indazol-5-yl}methylidene)-3-[trans-3-hydroxypiperidin-4-yl]-1,3-thiazolidine-2,4-dione

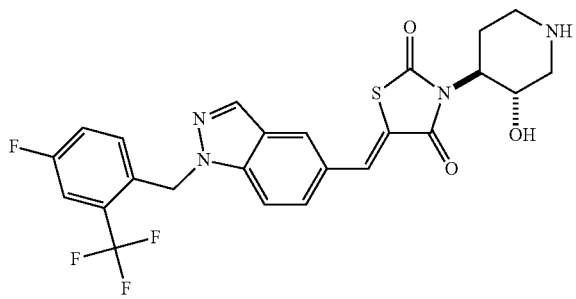

(5Z)-5-({1-[4-Fluoro-2-(trifluoromethyl)benzyl]-1H-indazol-5-yl}methylidene)-3-[trans-3-hydroxypiperidin-4-yl]-1,3-thiazolidine-2,4-dione was prepared from [4-fluoro-2-(trifluoromethyl)benzyl]-1H-indazol-5-carbaldehyde (from Example 5) and 1,1-dimethylethyl trans-4-(2,4-dioxo-1,3-thiazolidin-3-yl)-3-hydroxypiperidine-1-carboxylate (from Example 270) following General Procedure F.

$^1$H NMR (400 MHz, CDCl$_3$): δ 8.20 (s, 1H), 7.98 (s, 1H), 7.93 (s, 1H), 7.49 (d, 1H), 7.44 (dd, 1H), 7.35 (d, 1H), 7.04-7.13 (m, 1H), 6.76 (dd, 1H), 5.79 (s, 2H), 4.39 (br. s., 1H), 4.19-4.32 (m, 1H), 3.32-3.47 (m, 1H), 3.16 (br. s., 1H), 2.69 (br. s., 1H), 2.54 (br. s., 1H), 2.41 (d, 1H), 1.90 (br. s., 3H).

LC/MS: mass calcd. for $C_{24}H_{20}F_4N_4O_3S$: 520.12. found 521.4 $[M+1]^+$

Example 273

(5Z)-5-({1-[4-Chloro-2-(trifluoromethyl)benzyl]-1H-indazol-5-yl}methylidene)-3-(trans-3-fluoropiperidin-4-yl)-1,3-thiazolidine-2,4-dione

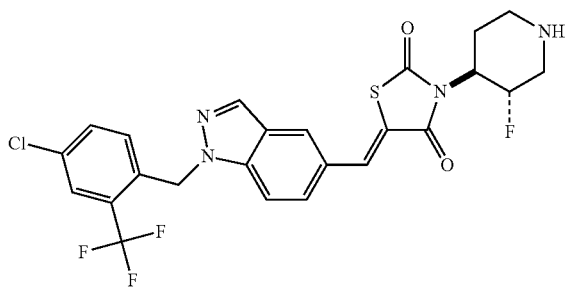

Preparation 1:
(A) To the solution of 1,1-dimethylethyl trans-4-(2,4-dioxo-1,3-thiazolidin-3-yl)-3-hydroxypiperidine-1-carboxylate (from Example 270, 0.68 mmol) in DCM (5 mL) in a plastic bottle was added bis(2-methoxyethyl)aminosulfur trifluoride (3 equiv) and a drop of ethanol. After stirring at rt for 3 h, the reaction was concentrated and the resultant residue was purified by silica gel chromatography (hexane/EtOAc) to provide 1,1-dimethylethyl trans-4-(2,4-dioxo-1,3-thiazolidin-3-yl)-3-fluoropiperidine-1-carboxylate as a pale yellow solid.

(B) (5Z)-5-({1-[4-Chloro-2-(trifluoromethyl)benzyl]-1H-indazol-5-yl}methylidene)-3-[trans-3-fluoropiperidin-4-yl]-1,3-thiazolidine-2,4-dione was prepared from [4-chloro-2-(trifluoromethyl)benzyl]-1H-indazol-5-carbaldehyde (from Example 1) and 1,1-dimethylethyl trans-4-(2,4-dioxo-1,3-thiazolidin-3-yl)-3-fluoropiperidine-1-carboxylate following General Procedure F.

Preparation 2:
(A) A mixture of 1,1-dimethylethyl 7-oxa-3-azabicyclo[4.1.0]heptane-3-carboxylate (from Example 270; 47.7 mmol), [(5Z)-5-({1-[4-chloro-2-(trifluoromethyl)benzyl]-1H-indazol-5-yl}methylidene)-2,4-dioxo-1,3-thiazolidine (from Example 1; 31.8 mmol) and magnesium perchlorate (23.9 mmol) in DMF (70 mL) was heated at 115° C. for 2-4 h. After cooling to rt, the mixture was slowly poured into water (300 mL) with vigorous stirring, and the resultant precipitate was filtered, thoroughly washed with water and dried to afford a mixture of 1,1-dimethylethyl trans-4-{(5Z)-5-[(1-{[4-chloro-2-(trifluoromethyl)phenyl]methyl}-1H-indazol-5-yl)methylidene]-2,4-dioxo-1,3-thiazolidin-3-yl}-3-hydroxypiperidine-1-carboxylate and the corresponding regioisomer, 1,1-dimethylethyl trans-3-{(5Z)-5-[(1-{[4-chloro-2-(trifluoromethyl)phenyl]methyl}-1H-indazol-5-yl)methylidene]-2,4-dioxo-1,3-thiazolidin-3-yl}-4-hydroxypiperidine-1-carboxylate in ratio of ~3.3:1.

(B) To an ice-cooled solution of the above mixture of 1,1-dimethylethyl trans-4-{(5Z)-5-[(1-{[4-chloro-2-(trifluoromethyl)phenyl]methyl}-1H-indazol-5-yl)methylidene]-2,4-dioxo-1,3-thiazolidin-3-yl}-3-hydroxypiperidine-1-carboxylate and the regioisomer, 1,1-dimethylethyl trans-3-{(5Z)-5-[(1-{[4-chloro-2-

(trifluoromethyl)phenyl]methyl}-1H-indazol-5-yl)methylidene]-2,4-dioxo-1,3-thiazolidin-3-yl}-4-hydroxypiperidine-1-carboxylate in DCM (350 mL) was slowly added bis(2-methoxyethyl)aminosulfur trifluoride (47.7 mmol). After stirring for 1 h, the solution was allowed to warm to rt and stir overnight. The reaction was then quenched with sat'd aq. NaHCO$_3$ and after separating phases, the organic phase was dried (Na$_2$SO$_4$) and concentrated to ~40 mL. The solution was loaded onto a silica gel column (Analogix, 200 g) and eluted with heptanes/DCM/EtOAc (40:57:3). Product-containing fractions were combined and concentrated to afford a crude product mixture as a pale yellow foam. Treatment of this foam with ether (~20 mL) led to product precipitation; additional ether (200 mL) was added portionwise with stirring and after cooling to ~5° C., the mixture was filtered through a glass fiber filter and washed with cold ether to afford 1,1-dimethylethyl trans-4-{(5Z)-5-[(1-{[4-chloro-2-(trifluoromethyl)phenyl]-methyl}-1H-indazol-5-yl)methylidene]-2,4-dioxo-1,3-thiazolidin-3-yl}-3-fluoropiperidine-1-carboxylate as an essentially white powder.

(C) (5Z)-5-({1-[4-Chloro-2-(trifluoromethyl)benzyl]-1H-indazol-5-yl}methylidene)-3-[trans-3-fluoropiperidin-4-yl]-1,3-thiazolidine-2,4-dione was prepared from 1,1-dimethylethyl trans-4-{(5Z)-5-[(1-{[4-chloro-2-(trifluoromethyl)phenyl]methyl}-1H-indazol-5-yl)methylidene]-2,4-dioxo-1,3-thiazolidin-3-yl}-3-fluoropiperidine-1-carboxylate following General Procedure M.

$^1$H NMR (400 MHz, CDCl$_3$): δ 8.22 (s, 1H), 8.02 (s, 1H), 7.96 (s, 1H), 7.72 (d, 1H), 7.47-7.56 (m, 1H), 7.36 (s, 1H), 7.34 (s, 1H), 6.68 (d, 1H), 5.80 (s, 2H), 5.10-5.33 (m, 1H), 4.40-4.55 (m, 1H), 3.52 (d, 1H), 3.14 (d, 1H), 2.68 (br. s., 2H), 2.43 (qd, 1H), 1.70-1.90 (m, 2H).

LC/MS: mass calcd. for C$_{24}$H$_{20}$ClF$_4$N$_4$O$_2$S: 538.09. found 539.3 [M+1]$^+$ Example 274

(5Z)-5-({1-[2,4-Bis(trifluoromethyl)benzyl]-1H-indazol-5-yl}methylidene)-3-(trans-3-fluoropiperidin-4-yl)-1,3-thiazolidine-2,4-dione

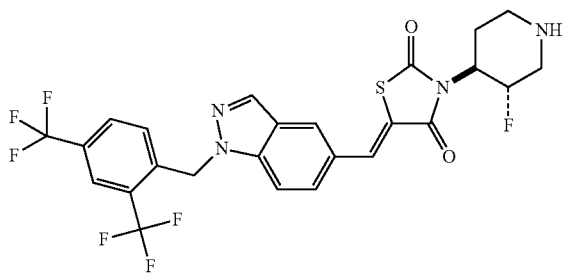

(5Z)-5-({1-[2,4-Bis(trifluoromethyl)benzyl]-1H-indazol-5-yl}methylidene)-3-[trans-3-fluoropiperidin-4-yl]-1,3-thiazolidine-2,4-dione was prepared from [2,4-bis(trifluoromethyl)benzyl]-1H-indazol-5-carbaldehyde (from Example 6) and 1,1-dimethylethyl trans-4-(2,4-dioxo-1,3-thiazolidin-3-yl)-3-fluoropiperidine-1-carboxylate (from Example 273) following General Procedure F.

$^1$H NMR (400 MHz, CDCl$_3$): δ 8.24 (s, 1H), 8.01 (s, 1H), 7.98 (d, 2H), 7.63 (d, 1H), 7.52 (d, 1H), 7.35 (d, 1H), 6.83 (d, 1H), 5.89 (s, 2H), 5.08-5.35 (m, 1H), 4.41-4.54 (m, 1H), 3.51 (d, 1H), 3.14 (d, 1H), 2.68 (br. s., 2H), 2.42 (qd, 1H), 1.91 (br. s., 1H), 1.84 (d, 1H).

LC/MS: mass calcd. for C$_{25}$H$_{19}$F$_7$N$_4$O$_2$S: 572.11. found 573.4 [M+1]$^+$ Example 275

(5Z)-5-({1-[4-Chloro-2-(trifluoromethyl)benzyl]-1H-indazol-5-yl}methylidene)-3-[trans-3-hydroxy-1-methylpiperidin-4-yl]-1,3-thiazolidine-2,4-dione

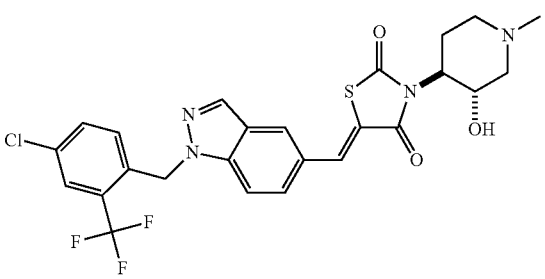

(5Z)-5-({1-[4-Chloro-2-(trifluoromethyl)benzyl]-1H-indazol-5-yl}methylidene)-3-[trans-3-hydroxy-1-methylpiperidin-4-yl]-1,3-thiazolidine-2,4-dione was prepared from (5Z)-5-({1-[4-chloro-2-(trifluoromethyl)benzyl]-1H-indazol-5-yl}methylidene)-3-[trans-3-hydroxypiperidin-4-yl]-1,3-thiazolidine-2,4-dione (Example 270) and formaldehyde following General Procedure R.

$^1$H NMR (400 MHz, CDCl$_3$): δ 8.20 (s, 1H), 7.96 (s, 1H), 7.92 (s, 1H), 7.72 (s, 1H), 7.48 (d, 1H), 7.30-7.38 (m, 2H), 6.67 (d, 1H), 5.78 (s, 2H), 4.53 (td, 1H), 4.06-4.19 (m, 1H), 3.17 (dd, 1H), 2.92 (d, 1H), 2.55 (qd, 1H), 2.35 (s, 3H), 2.04-2.15 (m, 1H), 1.97 (t, 1H), 1.74 (dt, 1H), 1.45 (br. s., 1H).

LC/MS: mass calcd. for C$_{25}$H$_{22}$ClF$_3$N$_4$O$_3$S: 550.11. found 551.3 [M+1]$^+$ Example 276

(5Z)-5-({1-[2,4-Bis(trifluoromethyl)benzyl]-1H-indazol-5-yl}methylidene)-3-[trans-3-hydroxy-1-methyl piperidin-4-yl]-1,3-thiazolidine-2,4-dione

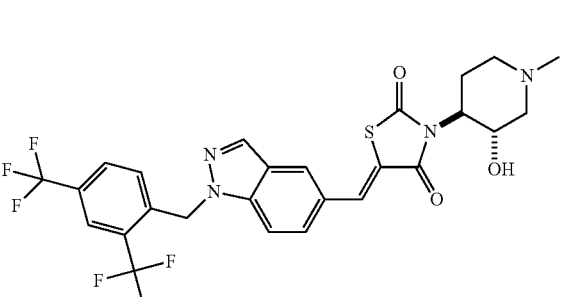

(5Z)-5-({1-[2,4-Bis(trifluoromethyl)benzyl]-1H-indazol-5-yl}methylidene)-3-[trans-3-hydroxy-1-methyl piperidin-4-yl]-1,3-thiazolidine-2,4-dione was prepared from (5Z)-5-({1-[2,4-bis(trifluoromethyl)benzyl]-1H-indazol-5-yl}methylidene)-3-[trans-3-hydroxypiperidin-4-yl]-1,3-thiazolidine-2,4-dione (Example 271) and formaldehyde following General Procedure R.

¹H NMR (400 MHz, CDCl₃): δ 8.23 (s, 1H), 7.99 (s, 1H), 7.97 (s, 1H), 7.94 (s, 1H), 7.63 (d, 1H), 7.50 (d, 1H), 7.34 (d, 1H), 6.82 (d, 1H), 5.88 (s, 2H), 4.52 (td, 1H), 4.05-4.17 (m, 1H), 3.17 (dd, 1H), 2.92 (d, 1H), 2.55 (qd, 1H), 2.34 (s, 3H), 2.06-2.16 (m, 1H), 1.97 (t, 1H), 1.74 (dd, 1H), 1.54 (br. s., 1H).

LC/MS: mass calcd. for $C_{26}H_{22}F_6N_4O_3S$: 584.13. found 585.4 [M+1]⁺

Example 277

(5Z)-5-({1-[4-Chloro-2-(trifluoromethyl)benzyl]-1H-indazol-5-yl}methylidene)-3-(trans-3-fluoro-1-methylpiperidin-4-yl)-1,3-thiazolidine-2,4-dione

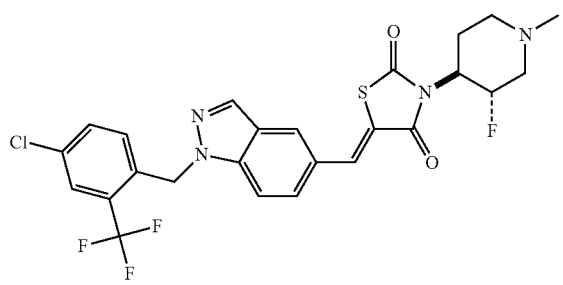

(5Z)-5-({1-[4-Chloro-2-(trifluoromethyl)benzyl]-1H-indazol-5-yl}methylidene)-3-[trans-3-fluoro-1-methylpiperidin-4-yl]-1,3-thiazolidine-2,4-dione was prepared from (5Z)-5-({1-[4-chloro-2-(trifluoromethyl)benzyl]-1H-indazol-5-yl}methylidene)-3-[trans-3-fluoropiperidin-4-yl]-1,3-thiazolidine-2,4-dione (Example 273) and formaldehyde following General Procedure R.

¹H NMR (400 MHz, CDCl₃): δ 8.22 (s, 1H), 8.01 (s, 1H), 7.96 (s, 1H), 7.72 (s, 1H), 7.51 (d, 1H), 7.36 (s, 1H), 7.34 (s, 1H), 6.68 (d, 1H), 5.80 (s, 2H), 5.25-5.48 (m, 1H), 4.28-4.42 (m, 1H), 3.24-3.36 (m, 1H), 2.85-2.96 (m, 1H), 2.56 (qd, 1H), 2.37 (s, 3H), 2.07-2.17 (m, 2H), 1.77 (dd, 1H).

LC/MS: mass calcd. for $C_{25}H_{21}ClF_4N_4O_2S$: 552.1. found 553.3 [M+1]⁺

Example 278

(5Z)-5-({1-[2,4-Bis(trifluoromethyl)benzyl]-1H-indazol-5-yl}methylidene)-3-(trans-3-fluoro-1-methylpiperidin-4-yl)-1,3-thiazolidine-2,4-dione

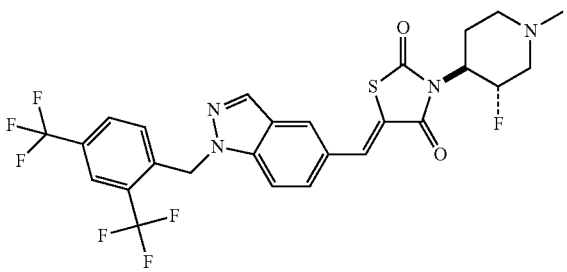

(5Z)-5-({1-[2,4-Bis(trifluoromethyl)benzyl]-1H-indazol-5-yl}methylidene)-3-[trans-3-fluoro-1-methylpiperidin-4-yl]-1,3-thiazolidine-2,4-dione was prepared from (5Z)-5-({1-[2,4-bis(trifluoromethyl)benzyl]-1H-indazol-5-yl}methylidene)-3-[trans-3-fluoropiperidin-4-yl]-1,3-thiazolidine-2,4-dione (Example 274) and formaldehyde following General Procedure R.

¹H NMR (400 MHz, CDCl₃): δ 8.25 (s, 1H), 8.02 (s, 1H), 7.98 (d, 2H), 7.64 (d, 1H), 7.52 (d, 1H), 7.36 (d, 1H), 6.83 (d, 1H), 5.89 (s, 2H), 5.24-5.49 (m, 1H), 4.29-4.44 (m, 1H), 3.25-3.36 (m, 1H), 2.86-2.97 (m, 1H), 2.45-2.67 (m, 1H), 2.37 (s, 3H), 2.06-2.19 (m, 2H), 1.71-1.82 (m, 1H).

LC/MS: mass calcd. for $C_{26}H_{21}F_7N_4O_2S$: 586.13. found 587.4 [M+1]⁺

Example 279

(5Z)-5-({1-[4-Chloro-2-(trifluoromethyl)benzyl]-1H-indazol-5-yl}methylidene)-3-[trans-4-hydroxypiperidin-3-yl]-1,3-thiazolidine-2,4-dione

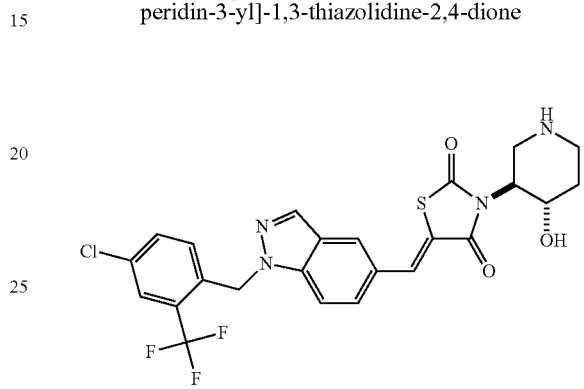

(5Z)-5-({1-[4-Chloro-2-(trifluoromethyl)benzyl]-1H-indazol-5-yl}methylidene)-3-[trans-4-hydroxypiperidin-3-yl]-1,3-thiazolidine-2,4-dione was prepared from [4-chloro-2-(trifluoromethyl)benzyl]-1H-indazol-5-carbaldehyde (from Example 1) and 1,1-dimethylethyl trans-3-(2,4-dioxo-1,3-thiazolidin-3-yl)-4-hydroxypiperidine-1-carboxylate (from Example 270) following General Procedure F.

¹H NMR (400 MHz, CDCl₃): δ 8.20 (s, 1H), 7.95 (s, 1H), 7.91 (s, 1H), 7.71 (d, 1H), 7.47 (d, 1H), 7.29-7.38 (m, 2H), 6.67 (d, 1H), 5.78 (s, 2H), 4.50 (td, 1H), 4.12-4.26 (m, 1H), 3.35 (br. s., 1H), 3.13 (br. s., 2H), 2.74 (br. s., 1H), 2.12-2.28 (m, 1H), 1.91-2.03 (m, 2H), 1.51 (d, 1H).

LC/MS: mass calcd. for $C_{24}H_{20}ClF_3N_4O_3S$: 536.09. found 537.4 [M+1]⁺

Example 280

(5Z)-5-({1-[2,4-Bis(trifluoromethyl)benzyl]-1H-indazol-5-yl}methylidene)-3-[trans-4-hydroxypiperidin-3-yl]-1,3-thiazolidine-2,4-dione

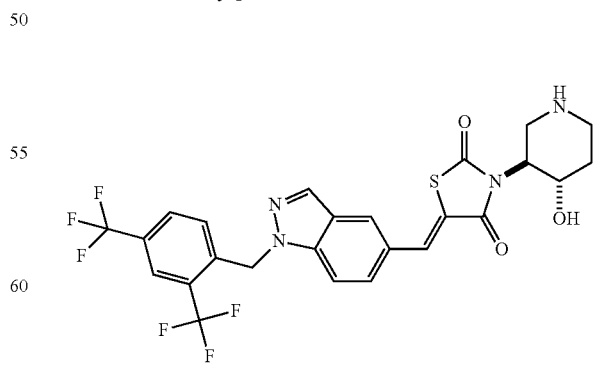

(5Z)-5-({1-[2,4-Bis(trifluoromethyl)benzyl]-1H-indazol-5-yl}methylidene)-3-[trans-4-hydroxypiperidin-3-yl]-1,3-thiazolidine-2,4-dione was prepared from [2,4-bis(trifluoromethyl)benzyl]-1H-indazol-5-carbaldehyde (from Example 6) and 1,1-dimethylethyl trans-3-(2,4-dioxo-1,3-thiazolidin-3-yl)-4-hydroxypiperidine-1-carboxylate (from Example 270) following General Procedure F.

$^1$H NMR (400 MHz, CDCl$_3$): δ 8.23 (s, 1H), 7.99 (s, 1H), 7.96 (s, 1H), 7.94 (s, 1H), 7.63 (d, 1H), 7.49 (d, 1H), 7.34 (d, 1H), 6.83 (d, 1H), 5.88 (s, 2H), 4.50 (td, 1H), 4.14-4.25 (m, 1H), 3.35 (t, 1H), 3.14 (d, 1H), 3.07 (dd, 1H), 2.74 (t, 1H), 2.19 (d, 1H), 1.43-1.59 (m, 1H).

LC/MS: mass calcd. for C$_{25}$H$_{20}$F$_6$N$_4$O$_3$S: 570.12. found 571.4 [M+1]$^+$ Example 281

(5Z)-5-({1-[4-Fluoro-2-(trifluoromethyl)benzyl]-1H-indazol-5-yl}methylidene)-3-[trans-4-hydroxypiperidin-3-yl]-1,3-thiazolidine-2,4-dione

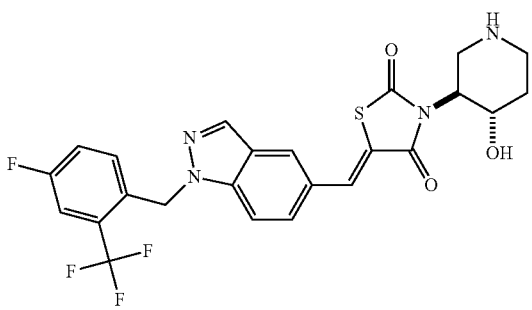

(5Z)-5-({1-[4-Fluoro-2-(trifluoromethyl)benzyl]-1H-indazol-5-yl}methylidene)-3-[trans-4-hydroxypiperidin-3-yl]-1,3-thiazolidine-2,4-dione was prepared from [4-fluoro-2-(trifluoromethyl)benzyl]-1H-indazol-5-carbaldehyde (from Example 5) and 1,1-dimethylethyl trans-3-(2,4-dioxo-1,3-thiazolidin-3-yl)-4-hydroxy-piperidine-1-carboxylate (from Example 270) following General Procedure F.

$^1$H NMR (400 MHz, CDCl$_3$): δ 8.21 (s, 1H), 7.98 (s, 1H), 7.94 (s, 1H), 7.49 (d, 1H), 7.45 (dd, 1H), 7.35 (d, 1H), 7.04-7.13 (m, 1H), 6.76 (dd, 1H), 5.79 (s, 2H), 4.50 (td, 1H), 4.09-4.24 (m, 1H), 3.34 (br. s., 1H), 3.13 (br. s., 2H), 2.74 (br. s., 1H), 2.18 (d, 1H), 1.63 (br. s., 2H), 1.49 (br. s., 1H).

LC/MS: mass calcd. for C$_{24}$H$_{20}$F$_4$N$_4$O$_3$S: 520.12. found 521.4 [M+1]$^+$ Example 282

(5Z)-5-({1-[4-Chloro-2-(trifluoromethyl)benzyl]-1H-indazol-5-yl}methylidene)-3-{2-[(3R)-3-(hydroxymethyl)piperazin-1-yl]ethyl}-1,3-thiazolidine-2,4-dione

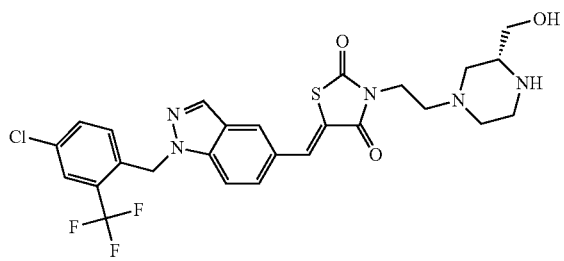 [SMILES: O=C1S/C(=C\c2ccc3c(cnn3Cc3ccc(Cl)cc3C(F)(F)F)c2)C(=O)N1CCN1CCN[C@@H](CO)C1]

(A) 1,1-Dimethylethyl 4-(2-[5-{[1-(4-Chloro-2-trifluoromethylbenzyl)-1H-indazol-5-yl]methylene}-2,4-dioxo-1,3-thiazolidin-3-yl]ethyl)-(2R)-2-hydroxymethylpiperazine-1-carboxylate was prepared from [(5Z)-5-({1-[4-chloro-2-(trifluoromethyl)benzyl]-1H-indazol-5-yl}methylidene)-2,4-dioxo-1,3-thiazolidine (from Example 1), 1-bromo-2-chloroethane and 1,1-dimethylethyl (2R)-2-hydroxymethylpiperazine-1-carboxylate following General Procedure G.

(B) (5Z)-5-({1-[4-Chloro-2-(trifluoromethyl)benzyl]-1H-indazol-5-yl}methylidene)-3-{2-[(3R)-3-(hydroxymethyl)piperazin-1-yl]ethyl}-1,3-thiazolidine-2,4-dione was prepared from 1,1-dimethylethyl 4-(2-[5-{[1-(4-chloro-2-trifluoromethylbenzyl)-1H-indazol-5-yl]methylene}-2,4-dioxo-1,3-thiazolidin-3-yl]ethyl)-(2R)-2-hydroxymethylpiperazine-1-carboxylate following General Procedure M.

$^1$H NMR (400 MHz, CD$_3$OD): δ 8.22 (s, 1H), 8.19 (s, 1H), 7.90 (s, 1H), 7.79 (d, 1H), 7.68 (dd, 1H), 7.44-7.51 (m, 2H), 6.65 (d, 1H), 5.84 (s, 2H), 3.91-4.06 (m, 2H), 3.78-3.91 (m, 1H), 3.61-3.78 (m, 1H), 3.43-3.56 (m, 3H), 3.37-3.43 (m, 2H), 3.25-3.37 (m, 4H).

LC/MS: mass calcd. for C$_{26}$H$_{25}$ClF$_3$N$_5$O$_3$S: 579.13. found 580.1 [M+H]$^+$ Example 283

(5Z)-5-({1-[4-Chloro-2-(trifluoromethyl)benzyl]-1H-indazol-5-yl}methylidene)-3-{2-[4-(1,2-dihydroxyethyl)piperidin-1-yl]ethyl}-1,3-thiazolidine-2,4-dione

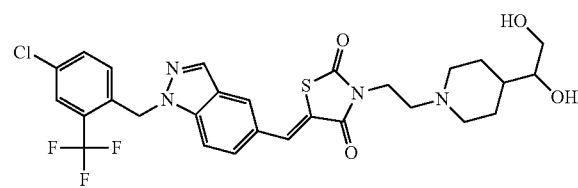 [SMILES: O=C1S/C(=C\c2ccc3c(cnn3Cc3ccc(Cl)cc3C(F)(F)F)c2)C(=O)N1CCN1CCC(C(O)CO)CC1]

(5Z)-5-({1-[4-Chloro-2-(trifluoromethyl)benzyl]-1H-indazol-5-yl}methylidene)-3-{2-[4-(1,2-dihydroxyethyl)piperidin-1-yl]ethyl}-1,3-thiazolidine-2,4-dione was prepared from [(5Z)-5-({1-[4-chloro-2-(trifluoromethyl)benzyl]-1H-indazol-5-yl}methylidene)-2,4-dioxo-1,3-thiazolidine (from Example 1), 1-bromo-2-chloroethane and 1-piperidin-4-ylethane-1,2-diol following General Procedure G.

$^1$H NMR (400 MHz, CD$_3$OD): δ 8.22 (s, 1H), 8.18 (s, 1H), 7.89 (s, 1H), 7.79 (d, 1H), 7.68 (dd, 1H), 7.44-7.51 (m, 2H), 6.64 (d, 1H), 5.85 (s, 2H), 4.43 (br. s., 1H), 3.86-4.07 (m, 2H), 3.71-3.86 (m, 1H), 3.56-3.70 (m, 1H), 3.45-3.56 (m, 1H), 3.36-3.45 (m, 2H), 3.19-3.26 (m, 2H), 2.99-3.16 (m, 2H), 2.80-2.99 (m, 1H), 1.81-2.02 (m, 1H), 1.65-1.80 (m, 2H).

LC/MS: mass calcd. for C$_{28}$H$_{28}$ClF$_3$N$_4$O$_4$S: 608.15. found 609.1 [M+H]$^+$

Example 284

(5Z)-3-[(trans-4-Aminocyclohexyl)methyl]-5-({1-[4-chloro-2-(trifluoromethyl)benzyl]-1H-indazol-5-yl}methylidene)-1,3-thiazolidine-2,4-dione

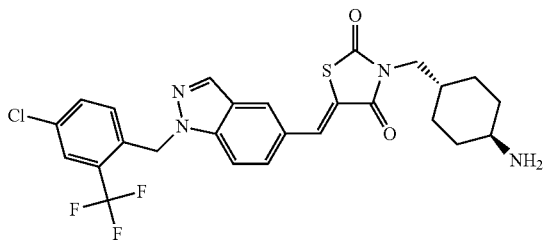 [SMILES: N[C@H]1CC[C@H](CN2C(=O)S/C(=C\c3ccc4c(cnn4Cc4ccc(Cl)cc4C(F)(F)F)c3)C2=O)CC1]

(A) 1,1-Dimethylethyl trans-[4-(5-{[1-(4-chloro-2-trifluoromethylbenzyl)-1H-indazol-5-yl]methylene}-2,4-dioxo-1,3-thiazolidin-3-ylmethyl)cyclohexyl]carbamate was prepared from [(5Z)-5-({1-[4-chloro-2-(trifluoromethyl)benzyl]-1H-indazol-5-yl}methylidene)-2,4-dioxo-1,3-thiazolidine (from Example 1) and 1,1-dimethylethyl trans-(4-hydroxymethylcyclohexyl)carbamate following General Procedure J.

(B) (5Z)-3-[(trans-4-Aminocyclohexyl)methyl]-5-({1-[4-chloro-2-(trifluoromethyl)benzyl]-1H-indazol-5-yl}methylidene)-1,3-thiazolidine-2,4-dione was prepared from 1,1-dimethylethyl trans-[4-(5-{[1-(4-chloro-2-trifluoromethylbenzyl)-1H-indazol-5-yl]methylene}-2,4-dioxo-1,3-thiazolidin-3-ylmethyl)cyclohexyl]carbamate following General Procedure M.

$^1$H NMR (400 MHz, CD$_3$OD): δ 8.27 (s, 1H), 8.09 (s, 1H), 8.04 (s, 1H), 7.80 (d, 1H), 7.54-7.66 (m, 2H), 7.48 (dd, 1H), 6.70 (d, 1H), 5.86 (s, 2H), 3.64 (d, 2H), 3.06 (s, 1H), 2.04-2.10 (m, 1H), 1.77-1.89 (m, 3H), 1.24-1.45 (m, 3H), 1.11-1.24 (m, 2H).

LC/MS: mass calcd. for C$_{26}$H$_{24}$ClF$_3$N$_4$O$_2$S: 548.13. found 548.9 [M+H]$^+$

Example 285

(5Z)-5-({1-[4-Chloro-2-(trifluoromethyl)benzyl]-1H-indazol-5-yl}methylidene)-3-(2-hydroxy-2-piperidin-4-ylethyl)-1,3-thiazolidine-2,4-dione

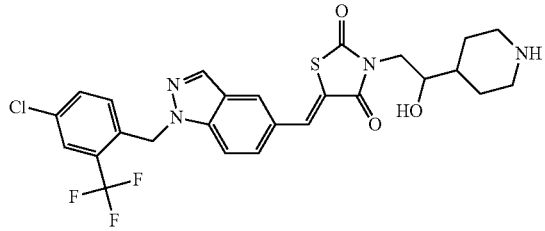 [SMILES: O=C1S/C(=C\c2ccc3c(cnn3Cc3ccc(Cl)cc3C(F)(F)F)c2)C(=O)N1CC(O)C1CCNCC1]

(A) 1,1-Dimethylethyl 4-[2-(5-{[1-(4-chloro-2-trifluoromethylbenzyl)-1H-indazol-5-yl]methylene}-2,4-dioxo-1,3-thiazolidin-3-yl)-1-hydroxyethyl]piperidine-1-carboxylate was prepared from [(5Z)-5-({1-[4-chloro-2-(trifluoromethyl)benzyl]-1H-indazol-5-yl}methylidene)-2,4-dioxo-1,3-thiazolidine (from Example 1) and 1,1-dimethylethyl 4-(1,2-dihydroxyethyl)piperidine-1-carboxylate following General Procedure J.

(B) (5Z)-5-({1-[4-Chloro-2-(trifluoromethyl)benzyl]-1H-indazol-5-yl}methylidene)-3-(2-hydroxy-2-piperidin-4-ylethyl)-1,3-thiazolidine-2,4-dione was prepared from 1,1-dimethylethyl 4-[2-(5-{[1-(4-chloro-2-trifluoromethylbenzyl)-1H-indazol-5-yl]methylene}-2,4-dioxo-1,3-thiazolidin-3-yl)-1-hydroxyethyl]piperidine-1-carboxylate following General Procedure M.

$^1$H NMR (400 MHz, CD$_3$OD): δ 8.28 (s, 1H), 8.04-8.12 (m, 2H), 7.77 (d, 1H), 7.62 (dd, 1H), 7.52 (d, 1H), 7.44 (dd, 1H), 6.69 (d, 1H), 5.86 (s, 2H), 3.85-3.97 (m, 1H), 3.73-3.85 (m, 2H), 3.39-3.49 (m, 2H), 2.89-3.04 (m, 2H), 2.11-2.22 (m, 1H), 1.89-2.01 (m, 1H), 1.57-1.80 (m, 3H).

LC/MS: mass calcd. for C$_{26}$H$_{24}$ClF$_3$N$_4$O$_3$S: 564.12. found 565.1 [M+H]$^+$

Example 286

(5Z)-5-({1-[4-Chloro-2-(trifluoromethyl)benzyl]-1H-indazol-5-yl}methylidene)-3-{[cis-4-hydroxypyrrolidin-2-yl]methyl}-1,3-thiazolidine-2,4-dione

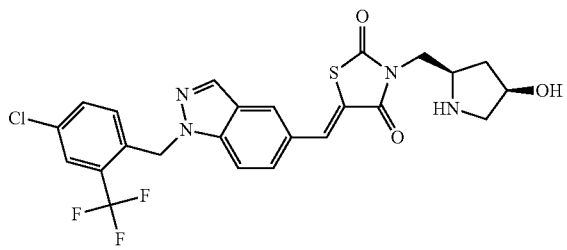 [SMILES: O=C1S/C(=C\c2ccc3c(cnn3Cc3ccc(Cl)cc3C(F)(F)F)c2)C(=O)N1C[C@H]1C[C@@H](O)CN1]

(A) 1,1-Dimethylethyl 2-(5-{[1-(4-chloro-2-trifluoromethylbenzyl)-1H-indazol-5-yl]methylene}-2,4-dioxo-1,3-thiazolidin-3-ylmethyl)-4-cis-hydroxypyrrolidine-1-carboxylate was prepared from [(5Z)-5-({1-[4-chloro-2-(trifluoromethyl)benzyl]-1H-indazol-5-yl}methylidene)-2,4-dioxo-1,3-thiazolidine (from Example 1) and 1,1-dimethylethyl cis-4-hydroxy-2-hydroxymethylpyrrolidine-1-carboxylate following General Procedure J.

(B) (5Z)-5-({1-[4-Chloro-2-(trifluoromethyl)benzyl]-1H-indazol-5-yl}methylidene)-3-{[cis-4-hydroxypyrrolidin-2-yl]methyl}-1,3-thiazolidine-2,4-dione was prepared from 1,1-dimethylethyl 2-(5-{[1-(4-chloro-2-trifluoromethylbenzyl)-1H-indazol-5-yl]methylene}-2,4-dioxo-1,3-thiazolidin-3-ylmethyl)-4-cis-hydroxypyrrolidine-1-carboxylate following General Procedure M.

$^1$H NMR (400 MHz, CD$_3$OD): δ 8.29 (s, 1H), 8.13 (s, 2H), 7.81 (d, 1H), 7.56-7.70 (m, 2H), 7.44-7.51 (m, 1H), 6.71 (d, 1H), 5.87 (s, 2H), 4.51-4.60 (m, 1H), 4.11-4.26 (m, 2H), 3.87-4.02 (m, 1H), 2.44-2.58 (m, 1H), 1.80-1.91 (m, 1H).

LC/MS: mass calcd. for C$_{24}$H$_{20}$ClF$_3$N$_4$O$_3$S: 536.09. found 537.2 [M+H]$^+$

Example 287

[(5Z)-5-({1-[4-Chloro-2-(trifluoromethyl)benzyl]-3-chloro-1H-indazol-5-yl}methylidene)-2,4-dioxo-1,3-thiazolidin-3-yl]acetic acid

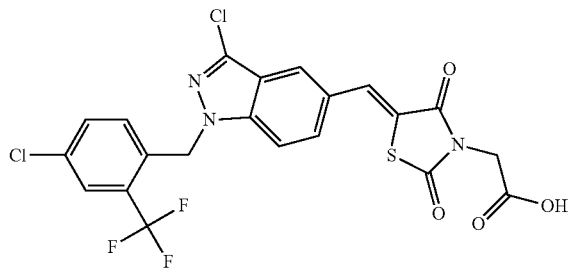 [SMILES: O=C(O)CN1C(=O)S/C(=C\c2ccc3c(c2)c(Cl)nn3Cc2ccc(Cl)cc2C(F)(F)F)C1=O]

(A) A solution of 1H-indazol-5-carbaldehyde (6.84 mmol) and N-chlorosuccinimide (7.53 mmol) in MeCN (25 mL) was refluxed for 12 h and then cooled to rt and concentrated. The resultant solid was washed extensively with water to provide crude 3-chloro-1H-indazol-5-carbaldehyde, which was used directly without further purification.

(B) 1-[4-Chloro-2-(trifluoromethyl)benzyl]-3-chloro-1H-indazol-5-carbaldehyde was prepared from 3-chloro-1H-indazol-5-carbaldehyde and 4-chloro-2-(trifluoromethyl)benzyl bromide following General Procedure B.

(C) [(5Z)-5-({1-[4-Chloro-2-(trifluoromethyl)benzyl]-3-chloro-1H-indazol-5-yl}methylidene)-2,4-dioxo-1,3-thiazolidine was prepared from [4-chloro-2-(trifluoromethyl)benzyl]-3-chloro-1H-indazol-5-carbaldehyde following General Procedure E.

(D) [(5Z)-5-({1-[4-Chloro-2-(trifluoromethyl)benzyl]-3-chloro-1H-indazol-5-yl}methylidene)-2,4-dioxo-1,3-thiazolidin-3-yl]acetic acid was prepared from [(5Z)-5-({1-[4-chloro-2-(trifluoromethyl)benzyl]-3-chloro-1H-indazol-5-yl}methylidene)-2,4-dioxo-1,3-thiazolidine following General Procedure I.

The corresponding ethanolamine salt was prepared following General Procedure T.

$^1$H NMR (400 MHz, DMSO-$d_6$) δ 8.11 (s, 1H), 8.05 (s, 1H), 7.93 (d, 1H), 7.90 (d, 1H), 7.76-7.85 (m, 1H), 7.53-7.76 (m, 3H), 6.96 (d, 1H), 5.86 (s, 2H), 5.29 (br. s., 1H), 3.91 (s, 2H), 3.55 (t, 2H), 2.83 (t, 2H).

LC/MS: mass calcd. for $C_{21}H_{12}Cl_2F_3N_3O_4S$: 530.31. found 530.0 [M]$^+$

Example 288

(5Z)-5-({1-[4-Chloro-2-(trifluoromethyl)benzyl]-1H-indazol-5-yl}methylidene)-3-hydroxy-1,3-thiazolidine-2,4-dione

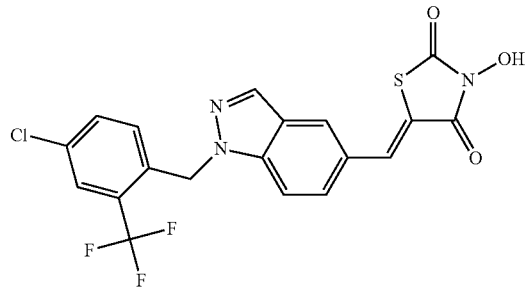 [SMILES: O=C1S/C(=C\c2ccc3c(cnn3Cc3ccc(Cl)cc3C(F)(F)F)c2)C(=O)N1O]

(A) 3-(Tetrahydropyran-2-yl)oxy-1,3-thiazolidine-2,4-dione was prepared from (tetrahydropyran-2-yl)oxyamine following General Procedure D.

(B) (5Z)-5-({1-[4-Chloro-2-(trifluoromethyl)benzyl]-1H-indazol-5-yl}methylidene)-3-hydroxy-1,3-thiazolidine-2,4-dione was prepared from [4-chloro-2-(trifluoromethyl)benzyl]-1H-indazol-5-carbaldehyde (from Example 1) and 3-(tetrahydropyran-2-yl)oxy-1,3-thiazolidine-2,4-dione following General Procedure F.

$^1$H NMR (400 MHz, CDCl$_3$): δ 8.23 (s, 1H), 8.06 (s, 1H), 7.97 (s, 1H), 7.72 (s, 1H), 7.51 (d, 1H), 7.36 (dd, 2H), 6.68 (d, 1H), 5.80 (s, 2H), 2.02 (br. s., 1H).

LC/MS: mass calcd. for $C_{19}H_{11}ClF_3N_3O_3S$: 453.02. found 454.2 [M+1]$^+$

Example 289

(5Z)-5-({1-[4-Chloro-2-(trifluoromethyl)benzyl]-1H-indazol-5-yl}methylidene)-3-(2-pyrrolidin-1-ylethoxy)-1,3-thiazolidine-2,4-dione

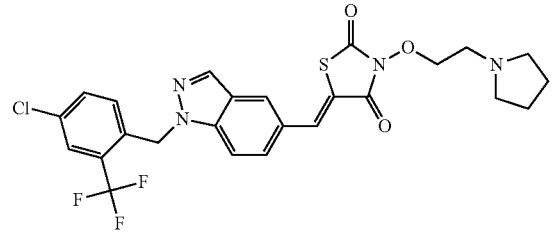 [SMILES: O=C1S/C(=C\c2ccc3c(cnn3Cc3ccc(Cl)cc3C(F)(F)F)c2)C(=O)N1OCCN1CCCC1]

To a solution of (5Z)-5-({1-[4-chloro-2-(trifluoromethyl)benzyl]-1H-indazol-5-yl}methylidene)-3-hydroxy-1,3-thiazolidine-2,4-dione (Example 288; 0.044 mmol), 1-(2-hydroxyethyl)pyrrolidine (1.5 equiv.) and triphenylphosphine (1.5 equiv.) in THF (5 mL) was added DIAD (1.5 equiv.) and the resultant solution was stirred overnight at rt. The mixture was then concentrated in vacuo, and the residue was purified by reverse phase HPLC (MeCN/water/formic acid) to provide (5Z)-5-({1-[4-chloro-2-(trifluoromethyl)benzyl]-1H-indazol-5-yl}methylidene)-3-(2-pyrrolidin-1-ylethoxy)-1,3-thiazolidine-2,4-dione.

$^1$H NMR (400 MHz, CDCl$_3$): δ 8.22 (s, 1H), 8.05 (s, 1H), 7.96 (s, 1H), 7.72 (s, 1H), 7.49 (d, 1H), 7.32-7.39 (m, 2H), 6.68 (d, 1H), 5.80 (s, 2H), 4.36 (t, 2H), 2.93 (t, 2H), 2.60 (br. s., 4H), 1.67-1.86 (m, 4H).

LC/MS: mass calcd. for $C_{25}H_{22}ClF_3N_4O_3S$: 550.1. found 551.3 [M+1]$^+$.

Example 290

(5Z)-5-({1-[4-Chloro-2-(trifluoromethyl)benzyl]-1H-benzotriazol-5-yl}methylidene)-3-hydroxy-1,3-thiazolidine-2,4-dione

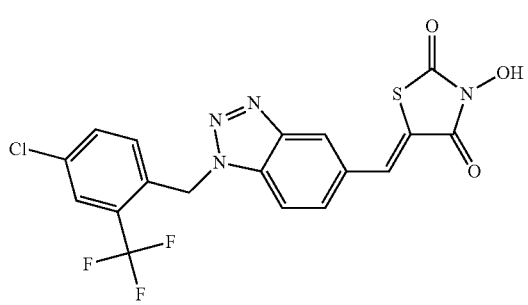 [SMILES: O=C1S/C(=C\c2ccc3c(c2)nnn3Cc2ccc(Cl)cc2C(F)(F)F)C(=O)N1O]

(5Z)-5-({1-[4-Chloro-2-(trifluoromethyl)benzyl]-1H-benzotriazol-5-yl}methylidene)-3-hydroxy-1,3-thiazolidine-2,4-dione was prepared from 1-(4-chloro-2-trifluoromethylbenzyl)-1H-benzotriazole-5-carbaldehyde (from Example 258) and 3-(tetrahydropyran-2-yl)oxy-1,3-thiazolidine-2,4-dione (from Example 288) following General Procedure F.

$^1$H NMR (400 MHz, DMF-$d_7$) δ 8.41 (s, 1H), 8.15 (s, 1H), 7.98 (d, 1H), 7.90 (d, 1H), 7.83 (dd, 1H), 7.71 (dd, 1H), 7.17 (d, 1H), 6.22 (s, 2H).

LC/MS: mass calcd. for $C_{18}H_{10}ClF_3N_4O_3S$: 454.82. found 496.0 [M+MeCN]$^+$.

Example 291

(5Z)-5-({1-[2,4-Bis(trifluoromethyl)benzyl]-1H-indazol-5-yl}methylidene)-3-hydroxy-1,3-thiazolidine-2,4-dione

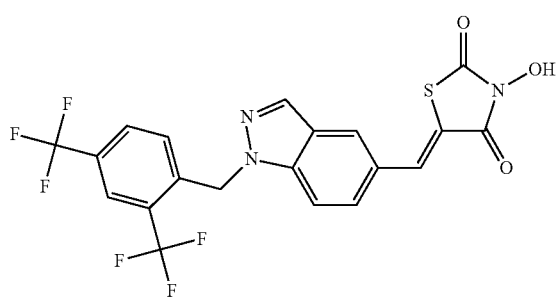 [SMILES: O=C1S/C(=C\c2ccc3c(cnn3Cc3ccc(C(F)(F)F)cc3C(F)(F)F)c2)C(=O)N1O]

(5Z)-5-({1-[2,4-Bis(trifluoromethyl)benzyl]-1H-indazol-5-yl}methylidene)-3-hydroxy-1,3-thiazolidine-2,4-dione was prepared from [2,4-bis(trifluoromethyl)benzyl]-1H-indazol-5-carbaldehyde (from Example 6) and 3-(tetrahydropyran-2-yl)oxy-1,3-thiazolidine-2,4-dione (from Example 288) following General Procedure F.

$^1$H NMR (400 MHz, CDCl$_3$) δ: 8.26 (s, 1H), 8.09 (s, 1H), 7.99 (s, 2H), 7.58-7.69 (m, 1H), 7.51 (dd, 1H), 7.33-7.42 (m, 1H), 6.84 (d, 1H), 5.90 (s, 2H).

LC/MS: mass calcd. for $C_{20}H_{11}F_6N_3O_3S$: 487.04. found 488.0 [M+H]$^+$.

Example 292

5-[1-(4-Chloro-2-trifluoromethyl benzyl)-1H-indazol-5-ylmethylene]-3-[(2S)-2-hydroxy-3-pyrrolidin-1-ylpropyl]thiazolidine-2,4-dione

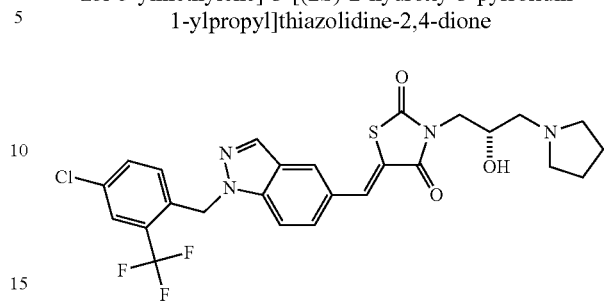

(A) 5-[1-(4-Chloro-2-trifluoromethylbenzyl)-1H-indazol-5-ylmethylene]-3-(R)-oxiranylmethylthiazolidine-2,4-dione was prepared from 5-[1-(4-chloro-2-trifluoromethylbenzyl)-1H-indazol-5-ylmethylene]thiazolidine-2,4-dione (from Example 1) and (S) 3-nitrobenzenesulfonic acid oxiranylmethyl ester following General Procedure X.

$^1$H NMR (400 MHz, CDCl$_3$) δ: 8.22 (s, 1H), 8.05 (s, 1H), 7.97 (s, 1H), 7.72 (s, 1H), 7.52-7.50 (m, 1H), 7.37-7.33 (m, 2H), 6.68 (d, 1H), 5.80 (s, 2H), 4.05-4.00 (m, 1H), 3.92-3.87 (m, 1H), 3.26 (br s, 1H), 2.85-2.83 (m, 1H), 2.71-2.69 (m, 1H).

LC/MS: mass calcd. for $C_{22}H_{15}ClF_3N_3O_3S$: 493.05. found 493.8 [M+H]$^+$.

(B) 5-[1-(4-Chloro-2-trifluoromethylbenzyl)-1H-indazol-5-ylmethylene]-3-[(2S)-2-hydroxy-3-pyrrolidin-1-ylpropyl]thiazolidine-2,4-dione was prepared from 5-[1-(4-chloro-2-trifluoromethylbenzyl)-1H-indazol-5-ylmethylene]-3-(R)-oxiranylmethylthiazolidine-2,4-dione and pyrrolidine following General Procedure X.

$^1$H NMR (400 MHz, CDCl$_3$) δ: 8.22 (s, 1H), 8.03 (s, 1H), 7.97 (s, 1H), 7.72 (s, 1H), 7.52-7.50 (m, 1H), 7.36-7.34 (m, 2H), 6.67 (d, 1H), 5.79 (s, 2H), 4.08-4.04 (m, 1H), 3.94-3.88 (m, 1H), 3.81-3.77 (m, 1H), 2.73-2.68 (m, 3H), 2.58-2.49 (m, 1H), 1.80 (br s, 4H).

LC/MS: mass calcd. for $C_{26}H_{24}ClF_3N_4O_3S$: 564.12. found 565.0 [M+H]$^+$.

Example 293

5-[1-(4-Chloro-2-trifluoromethyl benzyl)-1H-indazol-5-ylmethylene]-3-[(2S)-3-dimethylamino-2-hydroxypropyl]-thiazolidine-2,4-dione

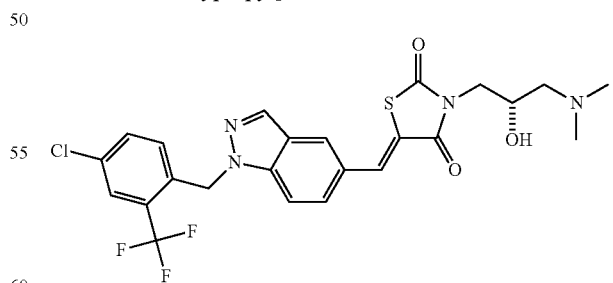

5-[1-(4-Chloro-2-trifluoromethylbenzyl)-1H-indazol-5-ylmethylene]-3-[(2S)-3-dimethylamino-2-hydroxypropyl]thiazolidine-2,4-dione was prepared from 5-[1-(4-chloro-2-trifluoromethyl benzyl)-1H-indazol-5-ylmethylene]-3-(R)-oxiranylmethylthiazolidine-2,4-dione (from Example 292) and dimethylamine following General Procedure X.

¹H NMR (400 MHz, CDCl₃) δ: 8.21 (s, 1H), 8.03 (s, 1H), 7.97 (s, 1H), 7.72 (s, 1H), 7.52-7.50 (m, 1H), 7.36-7.33 (m, 2H), 6.67 (d, 1H), 5.80 (s, 2H), 4.03-3.98 (m, 1H), 3.92-3.87 (m, 1H), 3.78-3.74 (m, 1H), 2.43-2.37 (m, 1H), 2.33-2.29 (m, 7H).

LC/MS: mass calcd. for C₂₄H₂₂ClF₃N₄O₃S: 538.11. found 539.1 [M+H]⁺.

Example 294

5-[1-(4-Chloro-2-trifluoromethylbenzyl)-1H-indazol-5-ylmethylene]-3-{(2R)-3-[(3R)-3-fluoropyrrolidin-1-yl]-2-hydroxypropyl}thiazolidine-2,4-dione

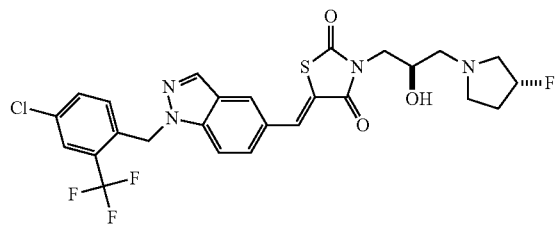 [SMILES: O=C1S/C(=C\c2ccc3c(cnn3Cc3ccc(Cl)cc3C(F)(F)F)c2)C(=O)N1C[C@H](O)CN1CC[C@@H](F)C1]

(A) 5-[1-(4-Chloro-2-trifluoromethylbenzyl)-1H-indazol-5-ylmethylene]-3-(S)-oxiranylmethylthiazolidine-2,4-dione was prepared from 5-[1-(4-chloro-2-trifluoromethylbenzyl)-1H-indazol-5-ylmethylene]thiazolidine-2,4-dione and (R) 3-nitrobenzenesulfonic acid oxiranylmethyl ester following General Procedure X.

LC/MS: mass calcd. for C₂₂H₁₅ClF₃N₃O₃S: 493.05. found 494.1 [M+H]⁺.

(B) 5-[1-(4-Chloro-2-trifluoromethylbenzyl)-1H-indazol-5-ylmethylene]-3-{(2R)-3-[(3R)-3-fluoropyrrolidin-1-yl]-2-hydroxypropyl}thiazolidine-2,4-dione was prepared from 5-[1-(4-chloro-2-trifluoromethylbenzyl)-1H-indazol-5-ylmethylene]-3-(S)-oxiranylmethylthiazolidine-2,4-dione and (3R)-3-fluoropyrrolidine following General Procedure X.

¹H NMR (400 MHz, CDCl₃) δ: 8.22 (s, 1H), 8.03 (s, 1H), 7.96 (s, 1H), 7.72 (s, 1H), 7.52-7.50 (m, 1H), 7.36-7.34 (m, 2H), 6.67 (d, 1H), 5.79 (s, 2H), 5.23 (br s, 0.5H), 5.09 (br s, 0.5H), 4.06-4.0 (m, 1H), 3.94-3.88 (m, 1H), 3.84-3.80 (m, 1H), 3.03-2.90 (m, 1H), 2.88-2.74 (m, 2H), 2.71-2.55 (m, 3H), 2.19-2.02 (m, 2H).

LC/MS: mass calcd. for C₂₆H₂₃ClF₄N₄O₃S: 582.11. found 583.0 [M+H]⁺.

Example 295

5-[1-(4-Chloro-2-trifluoromethyl benzyl)-1H-indazol-5-ylmethylene]-3-[(2R)-3-(2-fluoroethylamino)-2-hydroxypropyl]thiazolidine-2,4-dione

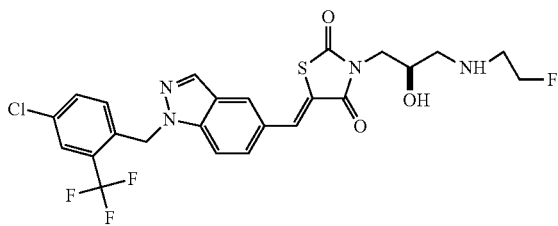 [SMILES: O=C1S/C(=C\c2ccc3c(cnn3Cc3ccc(Cl)cc3C(F)(F)F)c2)C(=O)N1C[C@H](O)CNCCF]

5-[1-(4-Chloro-2-trifluoromethylbenzyl)-1H-indazol-5-ylmethylene]-3-[(2R)-3-(2-fluoroethylamino)-2-hydroxypropyl]thiazolidine-2,4-dione was prepared from 5-[1-(4-chloro-2-trifluoromethylbenzyl)-1H-indazol-5-ylmethylene]-3-(S)-oxiranylmethylthiazolidine-2,4-dione (from Example 294) and 2-fluoroethylamine following General Procedure X.

¹H NMR (400 MHz, CDCl₃) δ: 8.22 (s, 1H), 8.04 (s, 1H), 7.97 (s, 1H), 7.72 (s, 1H), 7.52-7.50 (m, 1H), 7.36-7.33 (m, 2H), 6.68 (d, 1H), 5.80 (s, 2H), 4.59 (t, 1H), 4.47 (t, 1H), 3.99-3.95 (m, 1H), 3.92-3.90 (m, 1H), 3.84-3.79 (m, 1H), 2.99-2.97 (m, 1H), 2.92-2.89 (m, 1H), 2.86-2.82 (m, 1H), 2.71-2.66 (m, 1H).

LC/MS: mass calcd. for C₂₄H₂₁ClF₄N₄O₃S: 556.1. found 557.1 [M+H]⁺.

Example 296

5-[1-(4-Chloro-2-trifluoromethylbenzyl)-1H-indazol-5-ylmethylene]-3-(2-imidazol-1-yl-ethyl)thiazolidine-2,4-dione

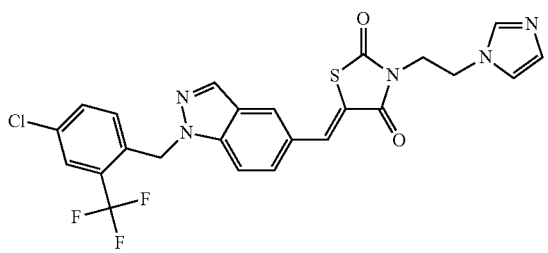 [SMILES: O=C1S/C(=C\c2ccc3c(cnn3Cc3ccc(Cl)cc3C(F)(F)F)c2)C(=O)N1CCn1ccnc1]

5-[1-(4-Chloro-2-trifluoromethylbenzyl)-1H-indazol-5-ylmethylene]-3-(2-imidazol-1-ylethyl)thiazolidine-2,4-dione was prepared from 5-[1-(4-chloro-2-trifluoromethylbenzyl)-1H-indazol-5-ylmethylene]thiazolidine-2,4-dione (from Example 1) and 2-imidazol-1-ylethanol following General Procedure J.

¹H NMR (400 MHz, CDCl₃) δ: 8.22 (s, 1H), 7.99 (s, 1H), 7.95 (s, 1H), 7.72 (s, 1H), 7.50-7.47 (m, 1H), 7.45 (s, 1H), 7.36-7.33 (m, 2H), 7.08 (s, 1H), 6.96 (s, 1H), 6.67 (d, 1H), 5.80 (s, 2H), 4.29 (t, 2H), 4.13 (t, 2H).

LC/MS: mass calcd. for C₂₄H₁₇ClF₃N₅O₂S: 531.07. found 532.0 [M+H]⁺.

Example 297

2-[(2S)-2-{[(5Z)-5-({1-[4-Chloro-2-(trifluoromethyl)benzyl]-1H-indazol-5-yl}methylidene)-2,4-dioxo-1,3-thiazolidin-3-yl]methyl}pyrrolidin-1-yl]acetamide

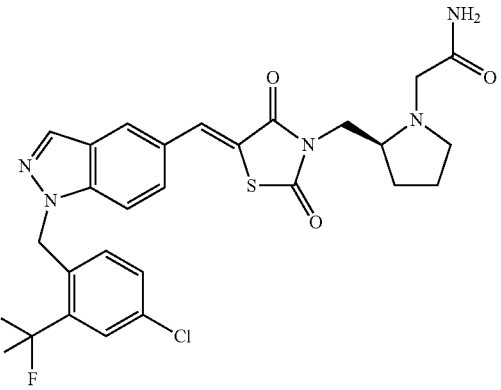

2-[(2S)-2-{[(5Z)-5-({1-[4-Chloro-2-(trifluoromethyl)benzyl]-1H-indazol-5-yl}methylidene)-2,4-dioxo-1,3-thiazolidin-3-yl]methyl}pyrrolidin-1-yl]acetamide was prepared from (5Z)-5-({1-[4-chloro-2-(trifluoromethyl)benzyl]-1H-indazol-5-yl}methylidene)-3-[(2S)-pyrrolidin-2-ylmethyl]-1,3-thiazolidine-2,4-dione (Example 145) and 2-bromoacetamide following General Procedure H.

$^1$H NMR (400 MHz, CD$_3$OD) δ: 8.29 (s, 1H), 8.09-8.15 (m, 2H), 7.80 (d, 1H), 7.62-7.68 (m, 1H), 7.60 (d, 1H), 7.45-7.51 (m, 1H), 6.71 (d, 1H), 5.86 (s, 2H), 4.43 (d, 1H), 4.25 (dd, 1H), 4.16 (dd, 1H), 4.01 (d, 1H), 3.81-3.91 (m, 1H), 2.26-2.38 (m, 1H), 2.06-2.17 (m, 2H), 1.84-1.97 (m, 1H), 1.26-1.34 ppm (m, 1H).

LC/MS: mass calcd. for C$_{26}$H$_{23}$ClF$_3$N$_5$O$_3$S: 578.02. found 578.1.

Example 298

2-[(2R)-2-{[(5Z)-5-({1-[4-Chloro-2-(trifluoromethyl)benzyl]-1H-indazol-5-yl}methylidene)-2,4-dioxo-1,3-thiazolidin-3-yl]methyl}pyrrolidin-1-yl]acetamide

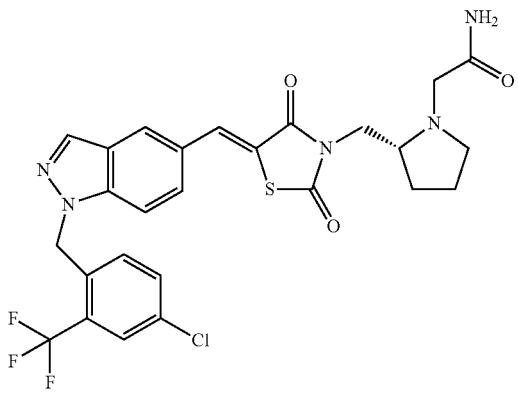 [SMILES: NC(=O)CN1CCC[C@@H]1CN1C(=O)S/C(=C\c2ccc3c(cnn3Cc3ccc(Cl)cc3C(F)(F)F)c2)C1=O]

(A) 1,1-Dimethylethyl (2R)-2-[{(5Z)-5-[(1-{[4-chloro-2-(trifluoromethyl)phenyl]-methyl}-1H-indazol-5-yl)methylidene]-2,4-dioxo-1,3-thiazolidin-3-yl]methyl}pyrrolidine-1-carboxylate was prepared from (5Z)-5-({1-[4-chloro-2-(trifluoromethyl)benzyl]-1H-indazol-5-yl}methylidene)-2,4-dioxo-1,3-thiazolidine (from Example 1) and 1,1-dimethylethyl (2R)-2-(hydroxymethyl)piperidine-1-carboxylate following General Procedure J.

(B) (5Z)-5-({1-[4-Chloro-2-(trifluoromethyl)benzyl]-1H-indazol-5-yl}methylidene)-3-[(2R)-pyrrolidin-2-ylmethyl]-1,3-thiazolidine-2,4-dione was prepared from 1,1-dimethylethyl (2R)-2-[{(5Z)-5-[(1-{[4-chloro-2-(trifluoromethyl)phenyl]methyl}-1H-indazol-5-yl)methylidene]-2,4-dioxo-1,3-thiazolidin-3-yl]methyl]pyrrolidine-1-carboxylate following General Procedure M.

(C) 2-[(2R)-2-{[(5Z)-5-({1-[4-Chloro-2-(trifluoromethyl)benzyl]-1H-indazol-5-yl}methylidene)-2,4-dioxo-1,3-thiazolidin-3-yl]methyl}pyrrolidin-1-yl]acetamide was prepared from (5Z)-5-({1-[4-chloro-2-(trifluoromethyl)benzyl]-1H-indazol-5-yl}methylidene)-3-[(2R)-pyrrolidin-2-ylmethyl]-1,3-thiazolidine-2,4-dione and 2-bromoacetamide following General Procedure H.

$^1$H NMR (400 MHz, CD$_3$OD) δ: 8.27 (s, 1H), 8.07-8.13 (m, 2H), 7.79 (d, 1H), 7.56-7.64 (m, 2H), 7.45-7.49 (m, 1H), 6.70 (d, 1H), 5.85 (s, 2H), 4.43 (d, 1H), 4.25 (dd, 1H), 4.16 (dd, 1H), 4.02 (d, 1H), 3.84-3.98 (m, 2H), 2.26-2.39 (m, 1H), 2.07-2.18 (m, 2H), 1.84-1.98 (m, 1H), 1.26-1.32 ppm (m, 1H).

LC/MS: mass calcd. for C$_{26}$H$_{23}$ClF$_3$N$_5$O$_3$S: 578.02. found 578.1.

Example 299

2-[(3R)-3-{[(5Z)-5-({1-[4-Chloro-2-(trifluoromethyl)benzyl]-1H-indazol-5-yl}methylidene)-2,4-dioxo-1,3-thiazolidin-3-yl]methyl}pyrrolidin-1-yl]acetamide

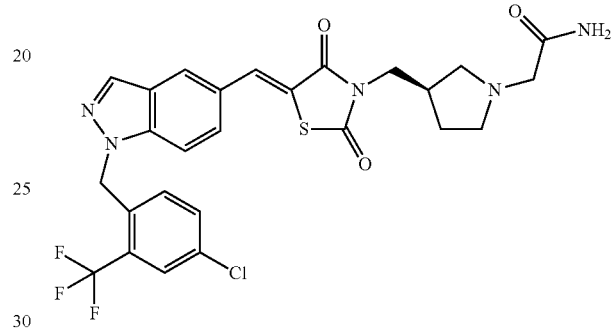

(A) 1,1-Dimethylethyl (3R)-3-[{(5Z)-5-[(1-{[4-chloro-2-(trifluoromethyl)phenyl]methyl}-1H-indazol-5-yl)methylidene]-2,4-dioxo-1,3-thiazolidin-3-yl}methyl]pyrrolidine-1-carboxylate was prepared from (5Z)-5-({1-[4-chloro-2-(trifluoromethyl)benzyl]-1H-indazol-5-yl}methylidene)-2,4-dioxo-1,3-thiazolidine (from Example 1) and 1,1-dimethylethyl (3R)-3-(hydroxymethyl)piperidine-1-carboxylate following General Procedure J.

(B) (5Z)-5-({1-[4-Chloro-2-(trifluoromethyl)benzyl]-1H-indazol-5-yl}methylidene)-3-[(3R)-pyrrolidin-3-ylmethyl]-1,3-thiazolidine-2,4-dione was prepared from 1,1-dimethylethyl (3R)-3-[{(5Z)-5-[(1-{[4-chloro-2-(trifluoromethyl)phenyl]methyl}-1H-indazol-5-yl)methylidene]-2,4-dioxo-1,3-thiazolidin-3-yl]methyl}pyrrolidine-1-carboxylate following General Procedure M.

(C) 2-[(3R)-3-{[(5Z)-5-({1-[4-Chloro-2-(trifluoromethyl)benzyl]-1H-indazol-5-yl}methylidene)-2,4-dioxo-1,3-thiazolidin-3-yl]methyl}pyrrolidin-1-yl]acetamide was prepared from (5Z)-5-({1-[4-chloro-2-(trifluoromethyl)benzyl]-1H-indazol-5-yl}methylidene)-3-[(3R)-pyrrolidin-3-ylmethyl]-1,3-thiazolidine-2,4-dione and 2-bromoacetamide following General Procedure H.

$^1$H NMR (400 MHz, CD$_3$OD) δ: 8.25-8.30 (m, 1H), 8.09-8.13 (m, 1H), 8.03-8.09 (m, 1H), 7.77-7.83 (m, 1H), 7.57-7.66 (m, 2H), 7.48 (dd, 1H), 6.66-6.74 (m, 1H), 5.86 (s, 2H), 4.62 (d, 1H), 4.47 (d, 1H), 4.26-4.36 (m, 1H), 3.81-4.10 (m, 4H), 3.55-3.66 (m, 1H), 2.96-3.07 (m, 1H), 2.52-2.72 (m, 1H), 2.29-2.42 (m, 1H), 2.05-2.18 ppm (m, 1H).

LC/MS: mass calcd. for C$_{26}$H$_{23}$ClF$_3$N$_5$O$_3$S: 578.02. found 578.0.

Example 300

(5Z)-5-({3-Chloro-1-[4-chloro-2-(trifluoromethyl)benzyl]-1H-indazol-5-yl}methylidene)-3-(2-pyrrolidin-1-ylethyl)-1,3-thiazolidine-2,4-dione

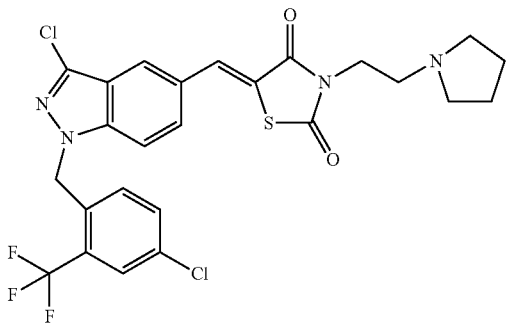 [SMILES: O=C1S/C(=C\c2ccc3c(c2)c(Cl)nn3Cc2ccc(Cl)cc2C(F)(F)F)C(=O)N1CCN1CCCC1]

(5Z)-5-({3-Chloro-1-[4-chloro-2-(trifluoromethyl)benzyl]-1H-indazol-5-yl}-methylidene)-3-(2-pyrrolidin-1-yl-ethyl)-1,3-thiazolidine-2,4-dione was prepared from [(5Z)-5-({3-chloro-1-[4-chloro-2-(trifluoromethyl)benzyl]-1H-indazol-5-yl}methylidene)-2,4-dioxo-1,3-thiazolidine (from Example 287) and 1-(2-hydroxyethyl)pyrrolidine following General Procedure J.

$^1$H NMR (400 MHz, CDCl$_3$) δ: 7.99 (s, 1H), 7.81 (s, 1H), 7.72 (d, 1H), 7.50 (dd, 1H), 7.40 (dd, 1H), 7.31 (d, 1H), 6.82 (d, 1H), 5.72 (s, 2H), 4.10 (t, 2H), 3.14-3.43 (m, 6H), 2.00-2.14 ppm (m, 4H).

LC/MS: mass calcd. for $C_{25}H_{21}Cl_2F_3N_4O_2S$: 569.44. found 569.1.

Example 301

(5Z)-5-({3-Chloro-1-[4-chloro-2-(trifluoromethyl)benzyl]-1H-indazol-5-yl}methylidene)-3-{[(2S)-1-methylpyrrolidin-2-yl]methyl}-1,3-thiazolidine-2,4-dione

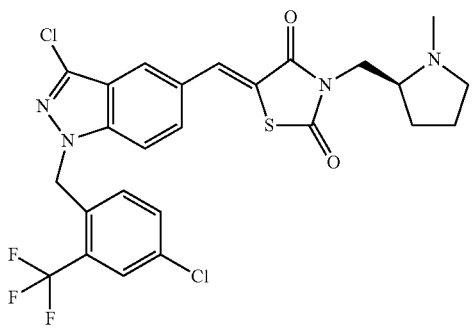 [SMILES: CN1CCC[C@H]1CN1C(=O)S/C(=C\c2ccc3c(c2)c(Cl)nn3Cc2ccc(Cl)cc2C(F)(F)F)C1=O]

(5Z)-5-({3-Chloro-1-[4-chloro-2-(trifluoromethyl)benzyl]-1H-indazol-5-yl}-methylidene)-3-{[(2S)-1-methylpyrrolidin-2-yl]methyl}-1,3-thiazolidine-2,4-dione was prepared from [(5Z)-5-({3-chloro-1-[4-chloro-2-(trifluoromethyl)benzyl]-1H-indazol-5-yl}methylidene)-2,4-dioxo-1,3-thiazolidine (from Example 287) and (2S)-(−)-1-methyl-2-pyrrolidinemethanol following General Procedure J.

$^1$H NMR (400 MHz, CDCl$_3$) δ: 8.01 (s, 1H), 7.85 (s, 1H), 7.71 (d, 1H), 7.53 (dd, 1H), 7.31-7.43 (m, 2H), 6.83 (d, 1H), 5.71 (s, 2H), 4.18-4.32 (m, 2H), 3.95-4.07 (m, 1H), 3.34-3.46 (m, 1H), 3.05 (s, 3H), 2.90-3.00 (m, 1H), 2.12-2.36 (m, 3H), 1.98-2.12 ppm (m, 1H).

LC/MS: mass calcd. for $C_{25}H_{21}Cl_2F_3N_4O_2S$: 569.44. found 569.2.

Example 302

4-[(5Z)-5-({3-Chloro-1-[4-chloro-2-(trifluoromethyl)benzyl]-1H-indazol-5-yl}-methylidene)-2,4-dioxo-1,3-thiazolidin-3-yl]cyclohexanecarboxylic acid

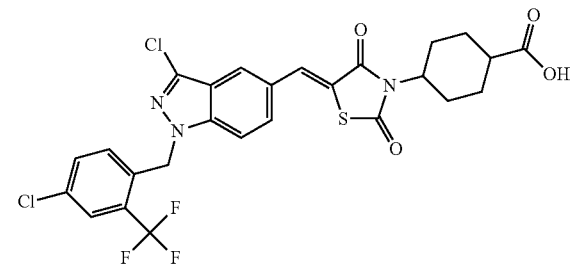 [SMILES: O=C(O)C1CCC(N2C(=O)S/C(=C\c3ccc4c(c3)c(Cl)nn4Cc3ccc(Cl)cc3C(F)(F)F)C2=O)CC1]

(A) 4-[(5Z)-5-({3-Chloro-1-[4-chloro-2-(trifluoromethyl)benzyl]-1H-indazol-5-yl}methylidene)-2,4-dioxo-1,3-thiazolidin-3-yl]cyclohexanecarboxylic acid ethyl ester was prepared from [(5Z)-5-({3-chloro-1-[4-chloro-2-(trifluoromethyl)benzyl]-1H-indazol-5-yl}methylidene)-2,4-dioxo-1,3-thiazolidine (from Example 287) and 4-hydroxycyclohexanecarboxylic acid ethyl ester following General Procedure J.

(B) 4-[(5Z)-5-({3-Chloro-1-[4-chloro-2-(trifluoromethyl)benzyl]-1H-indazol-5-yl}methylidene)-2,4-dioxo-1,3-thiazolidin-3-yl]cyclohexanecarboxylic acid was prepared from 4-[(5Z)-5-({3-chloro-1-[4-chloro-2-(trifluoromethyl)benzyl]-1H-indazol-5-yl}methylidene)-2,4-dioxo-1,3-thiazolidin-3-yl]cyclohexanecarboxylic acid ethyl ester following General Procedure O.

$^1$H NMR (400 MHz, DMSO-d$_6$): δ: 8.09 (s, 1H), 8.02 (s, 1H), 7.87-7.95 (m, 2H), 7.77 (dd, 1H), 7.70 (dd, 1H), 6.97 (d, 1H), 5.85 (s, 2H), 4.06-4.22 (m, 1H), 3.42 (t, 2H), 2.65 (t, 2H), 2.05-2.22 (m, 3H), 1.95-2.05 (m, 2H), 1.69-1.80 (m, 2H), 1.31-1.47 ppm (m, 2H).

LC/MS: mass calcd. for $C_{26}H_{20}Cl_2F_3N_3O_4S$: 598.43. found 598.0.

Example 303

(5Z)-5-({1-[4-Chloro-2-(trifluoromethyl)benzyl]-1H-indazol-5-yl}methylidene)-3-[(4-fluoropiperidin-4-yl)methyl]-1,3-thiazolidine-2,4-dione

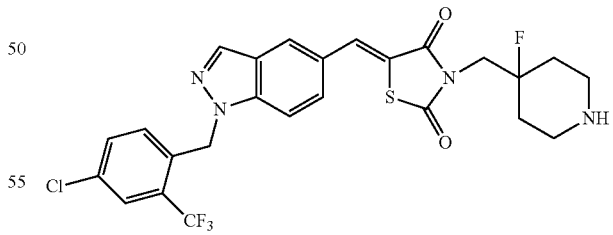

(A) 4-{5-[1-(4-Chloro-2-trifluoromethylbenzyl)-1H-indazol-5-ylmethylene]-2,4-dioxothiazolidin-3-ylmethyl}-4-fluoropiperidine-1-carboxylic acid tert-butyl ester was prepared from 5-[1-(4-chloro-2-trifluoromethylbenzyl)-1H-indazol-5-ylmethylene]thiazolidine-2,4-dione and 4-fluoro-4-hydroxymethyl-piperidine-1-carboxylic acid tert-butyl ester following General Procedure J.

LC/MS: mass calcd. for $C_{30}H_{29}ClF_4N_4O_4S$: 652.15. found 653.1 [M+H]$^+$ (B) (5Z)-5-({1-[4-Chloro-2-(trifluoromethyl)benzyl]-1H-indazol-5-yl}methylidene)-3-[(4-fluoropiperidin-4-yl)methyl]-1,3-thiazolidine-2,4-dione was prepared from 4-{5-[1-(4-chloro-2-trifluoromethylbenzyl)-1H-indazol-5-yl methylene]-2,4-dioxothiazolidin-3-ylmethyl}-4-fluoropiperidine-1-carboxylic acid tert-butyl ester following General Procedure N.

$^1$H NMR (400 MHz, DMSO-d$_6$): δ 9.11 (s, 1H), 8.95 (s, 1H), 8.38 (s, 1H), 8.19 (s, 1H), 8.12 (s, 1H), 7.90 (s, 1H), 7.82 (d, 1H), 7.70 (d, 1H), 7.67 (d, 1H), 6.79 (d, 1H), 5.88 (s, 2H), 3.95 (d, 2H), 3.26 (d, 2H), 3.00-2.89 (m, 2H), 2.07-1.93 (m, 4H).

LC/MS: mass calcd. for $C_{25}H_{21}ClF_4N_4O_2S$: 552.1. found 553.2 [M+H]$^+$.

Example 304

(5Z)-5-({1-[4-Chloro-2-(trifluoromethyl)benzyl]-1H-indazol-5-yl}methylidene)-3-[(4-fluoro-1-methylpiperidin-4-yl)methyl]-1,3-thiazolidine-2,4-dione

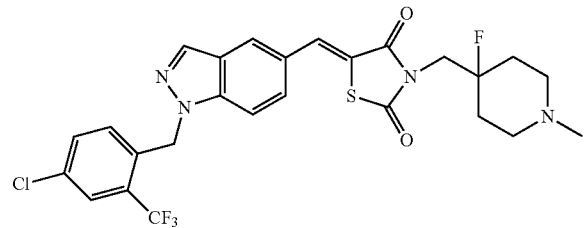 [SMILES: CN1CCC(F)(CN2C(=O)S/C(=C\c3ccc4c(cnn4Cc4ccc(Cl)cc4C(F)(F)F)c3)C2=O)CC1]

(5Z)-5-({1-[4-Chloro-2-(trifluoromethyl)benzyl]-1H-indazol-5-yl}-methylidene)-3-[(4-fluoro-1-methylpiperidin-4-yl)methyl]-1,3-thiazolidine-2,4-dione was prepared from (5Z)-5-({1-[4-chloro-2-(trifluoromethyl)benzyl]-1H-indazol-5-yl}methylidene)-3-[(4-fluoropiperidin-4-yl)methyl]-1,3-thiazolidine-2,4-dione (Example 303) following General Procedure R2.

$^1$H NMR (400 MHz, CDCl$_3$): δ 8.22 (s, 1H), 8.04 (s, 1H), 7.97 (s, 1H), 7.72 (s, 1H), 7.50 (d, 1H), 7.37-7.33 (m, 2H), 6.68 (d, 1H), 5.79 (s, 2H), 4.01 (d, 2H), 3.14 (d, 2H), 2.72 (t, 2H), 2.59 (s, 3H), 2.37-1.96 (m, 4H).

LC/MS: mass calcd. for $C_{26}H_{23}ClF_4N_4O_2S$: 566.1. found 567.3 [M+H]$^+$.

Example 305

(5Z)-5-({1-[4-Chloro-2-(trifluoromethyl)benzyl]-1H-indazol-5-yl}methylidene)-3-{[4-fluoro-1-(2-hydroxyethyl)piperidin-4-yl]methyl}-1,3-thiazolidine-2,4-dione

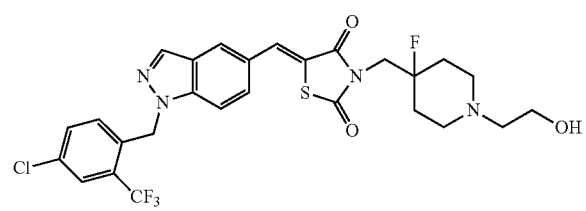 [SMILES: O=C1S/C(=C\c2ccc3c(cnn3Cc3ccc(Cl)cc3C(F)(F)F)c2)C(=O)N1CC1(F)CCN(CCO)CC1]

(5Z)-5-({1-[4-Chloro-2-(trifluoromethyl)benzyl]-1H-indazol-5-yl}methylidene)-3-{[4-fluoro-1-(2-hydroxyethyl)piperidin-4-yl]methyl}-1,3-thiazolidine-2,4-dione was prepared from (5Z)-5-({1-[4-chloro-2-(trifluoromethyl)benzyl]-1H-indazol-5-yl}methylidene)-3-[(4-fluoropiperidin-4-yl)methyl]-1,3-thiazolidine-2,4-dione (Example 303) and 2-bromoethanol following General Procedure S.

$^1$H NMR (400 MHz, CDCl$_3$): δ 8.23 (s, 1H), 8.05 (s, 1H), 7.97 (s, 1H), 7.72 (s, 1H), 7.52 (d, 1H), 7.37-7.33 (m, 2H), 6.68 (d, 1H), 5.80 (s, 2H), 3.96 (d, 2H), 3.61 (t, 2H), 2.77 (d, 2H), 2.57 (t, 2H), 2.40 (t, 2H), 1.89-1.72 (m, 4H).

LC/MS: mass calcd. for $C_{27}H_{25}ClF_4N_4O_3S$: 596.1. found 597.2 [M+H]$^+$.

Example 306

(5Z)-5-({1-[4-Chloro-2-(trifluoromethyl)benzyl]-1H-indazol-5-yl}methylidene)-3-[(1-ethyl-4-fluoropiperidin-4-yl)methyl]-1,3-thiazolidine-2,4-dione

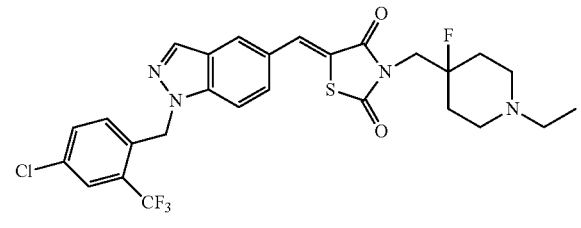 [SMILES: CCN1CCC(F)(CN2C(=O)S/C(=C\c3ccc4c(cnn4Cc4ccc(Cl)cc4C(F)(F)F)c3)C2=O)CC1]

(5Z)-5-({1-[4-Chloro-2-(trifluoromethyl)benzyl]-1H-indazol-5-yl}methylidene)-3-[(1-ethyl-4-fluoropiperidin-4-yl)methyl]-1,3-thiazolidine-2,4-dione was prepared from (5Z)-5-({1-[4-chloro-2-(trifluoromethyl)benzyl]-1H-indazol-5-yl}methylidene)-3-[(4-fluoropiperidin-4-yl)methyl]-1,3-thiazolidine-2,4-dione (Example 303) and acetaldehyde following General Procedure R2.

$^1$H NMR (400 MHz, CDCl$_3$): δ 8.21 (s, 1H), 8.04 (s, 1H), 7.96 (s, 1H), 7.72 (s, 1H), 7.50 (d, 1H), 7.38-7.34 (m, 2H), 6.68 (d, 1H), 5.79 (s, 2H), 4.04 (d, 2H), 3.38 (d, 2H), 3.00 (q, 2H), 2.87 (t, 2H), 2.63-2.06 (m, 4H), 1.43 (t, 3H).

LC/MS: mass calcd. for $C_{27}H_{25}ClF_4N_4O_2S$: 580.1. found 581.2 [M+H]$^+$.

Example 307

(5Z)-5-({1-[4-Chloro-2-(trifluoromethyl)benzyl]-1H-indazol-5-yl}methylidene)-3-{[4-fluoro-1-(1,1,1-d$_3$)methylpiperidin-4-yl]methyl}-1,3-thiazolidine-2,4-dione

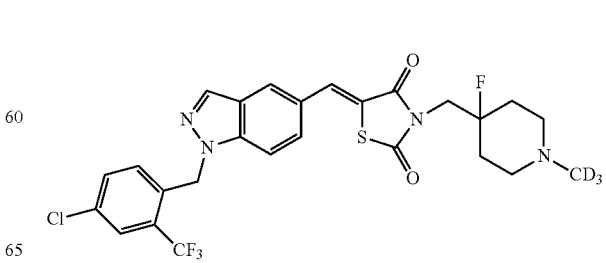

(5Z)-5-({1-[4-Chloro-2-(trifluoromethyl)benzyl]-1H-indazol-5-yl}methylidene)-3-{[4-fluoro-1-(1,1,1-d₃)methylpiperidin-4-yl]methyl}-1,3-thiazolidine-2,4-dione was prepared from (5Z)-5-({1-[4-chloro-2-(trifluoromethyl)benzyl]-1H-indazol-5-yl}methylidene)-3-[(4-fluoropiperidin-4-yl)methyl]-1,3-thiazolidine-2,4-dione (Example 303) and deuterated formaldehyde with deuterated sodium triacetoxyborohydride following General Procedure R2.

¹H NMR (400 MHz, CDCl₃): δ 8.22 (s, 1H), 8.04 (s, 1H), 7.97 (s, 1H), 7.72 (s, 1H), 7.50 (d, 1H), 7.37-7.33 (m, 2H), 6.68 (d, 1H), 5.79 (s, 2H), 3.95 (d, 2H), 2.71 (d, 2H), 2.29 (t, 2H), 1.91-1.82 (m, 4H).

LC/MS: mass calcd. for $C_{26}H_2OD_3ClF_4N_4O_2S$: 569.1. found 570.2 [M+H]⁺.

Example 308

(5Z)-3-[(4-Aminotetrahydro-2H-pyran-4-yl)methyl]-5-({1-[4-chloro-2-(trifluoromethyl)benzyl]-1H-indazol-5-yl}methylidene)-1,3-thiazolidine-2,4-dione

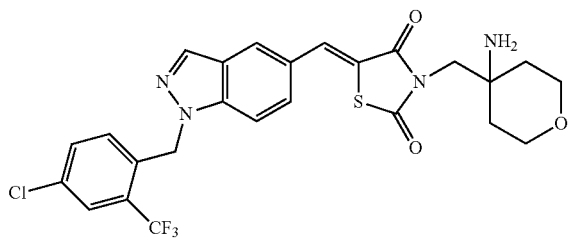 [SMILES: NC1(CN2C(=O)S/C(=C\c3ccc4c(cnn4Cc4ccc(Cl)cc4C(F)(F)F)c3)C2=O)CCOCC1]

(A) (4-{5-[1-(4-Chloro-2-trifluoromethylbenzyl)-1H-indazol-5-ylmethylene]-2,4-dioxothiazolidin-3-ylmethyl}tetrahydro-2H-pyran-4-yl)carbamic acid tert-butyl ester was prepared from 5-[1-(4-chloro-2-trifluoromethylbenzyl)-1H-indazol-5-ylmethylene]thiazolidine-2,4-dione and (4-hydroxymethyltetrahydro-2H-pyran-4-yl)carbamic acid tert-butyl ester following General Procedure J.

LC/MS: mass calcd. for $C_{30}H_{30}ClF_3N_4O_5S$: 650.15. found 651.1 [M+H]⁺.

(B) (5Z)-3-[(4-Aminotetrahydro-2H-pyran-4-yl)methyl]-5-({1-[4-chloro-2-(trifluoromethyl)benzyl]-1H-indazol-5-yl}methylidene)-1,3-thiazolidine-2,4-dione was prepared from (4-{5-[1-(4-chloro-2-trifluoromethylbenzyl)-1H-indazol-5-ylmethylene]-2,4-dioxothiazolidin-3-ylmethyl}tetrahydropyran-4-yl)carbamic acid tert-butyl ester following General Procedure N.

¹H NMR (400 MHz, DMSO-d₆): δ 8.39 (s, 1H), 8.20 (s, 1H), 8.18-8.10 (s, br, 3H), 7.90 (d, 1H), 7.83 (d, 1H), 7.71 (dd, 1H), 7.67 (dd, 1H), 6.82 (d, 1H), 5.87 (s, 2H), 3.99 (s, 2H), 3.83-3.65 (m, 4H), 1.82-1.72 (m, 4H).

LC/MS: mass calcd. for $C_{26}H_{22}ClF_3N_4O_3S$: 550.1. found 551.2 [M+H]⁺.

Example 309

Methyl (4-{[(5Z)-5-({1-[4-chloro-2-(trifluoromethyl)benzyl]-1H-indazol-5-yl}methylidene)-2,4-dioxo-1,3-thiazolidin-3-yl]methyl}tetrahydro-2H-pyran-4-yl)-carbamate

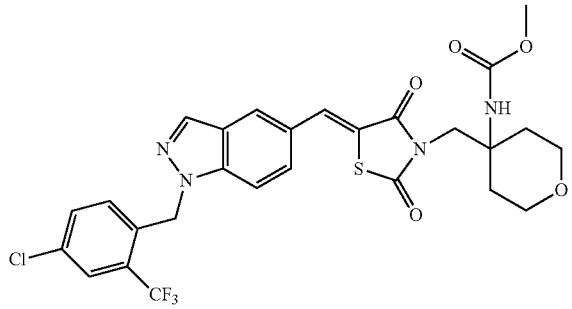 [SMILES: COC(=O)NC1(CN2C(=O)S/C(=C\c3ccc4c(cnn4Cc4ccc(Cl)cc4C(F)(F)F)c3)C2=O)CCOCC1]

Methyl (4-{[(5Z)-5-({1-[4-chloro-2-(trifluoromethyl)benzyl]-1H-indazol-5-yl}methylidene)-2,4-dioxo-1,3-thiazolidin-3-yl]methyl}tetrahydro-2H-pyran-4-yl)carbamate was prepared from (5Z)-3-[(4-aminotetrahydro-2H-pyran-4-yl)methyl]-5-({1-[4-chloro-2-(trifluoromethyl)benzyl]-1H-indazol-5-yl}methylidene)-1,3-thiazolidine-2,4-dione (Example 308) and methyl chloroformate following General Procedure R3.

¹H NMR (400 MHz, CDCl₃): δ 8.21 (s, 1H), 8.02 (s, 1H), 7.96 (s, 1H), 7.72 (s, 1H), 7.50 (d, 1H), 7.37-7.33 (m, 2H), 6.68 (d, 1H), 5.79 (s, 2H), 5.11 (d, 1H), 4.77 (d, 1H), 4.08-3.58 (m, 8H), 2.12-1.75 (m, 4H).

LC/MS: mass calcd. for $C_{27}H_{24}ClF_3N_4O_5S$: 608.1. found 609.2 [M+H]⁺.

Example 310

(5Z)-3-[(4-Aminotetrahydro-2H-pyran-4-yl)methyl]-5-({1-[2,4-bis(trifluoromethyl)benzyl]-1H-indazol-5-yl}methylidene)-1,3-thiazolidine-2,4-dione

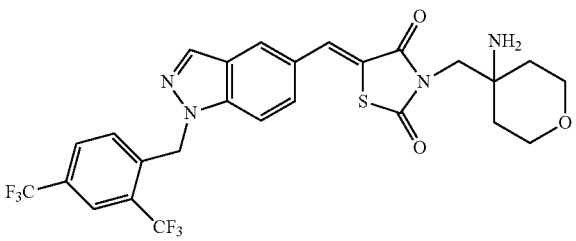 [SMILES: NC1(CN2C(=O)S/C(=C\c3ccc4c(cnn4Cc4ccc(C(F)(F)F)cc4C(F)(F)F)c3)C2=O)CCOCC1]

(A) (4-{5-[1-(2,4-Bis-trifluoromethylbenzyl)-1H-indazol-5-ylmethylene]-2,4-dioxothiazolidin-3-ylmethyl}tetrahydro-2H-pyran-4-yl)carbamic acid tert-butyl ester was prepared from 5-[1-(2,4-bis-trifluoromethylbenzyl)-1H-indazol-5-ylmethylene]thiazolidine-2,4-dione (from Example 6) and (4-hydroxymethyltetrahydro-2H-pyran-4-yl)carbamic acid tert-butyl ester following General Procedure J.

LC/MS: mass calcd. for $C_{31}H_{30}F_6N_4O_5S$: 684.18. found 685.2 [M+H]⁺.

(B) (5Z)-3-[(4-Aminotetrahydro-2H-pyran-4-yl)methyl]-5-({1-[2,4-bis(trifluoromethyl)benzyl]-1H-indazol-5- yl}methylidene)-1,3-thiazolidine-2,4-dione was prepared from (4-{5-[1-(2,4-bis-trifluoromethylbenzyl)-1H-indazol-5-yl methylene]-2,4-dioxothiazolidin-3-ylmethyl}tetrahydro-2H-pyran-4-yl)carbamic acid tert-butyl ester following General Procedure N.

$^1$H NMR (400 MHz, CDCl$_3$): δ 8.25 (s, 1H), 8.04 (s, 1H), 7.98 (s, br, 2H), 7.64 (d, 1H), 7.52 (d, 1H), 7.37 (d, 1H), 6.85 (d, 1H), 5.89 (s, 2H), 3.80-3.75 (m, 6H), 1.83-1.35 (m, 6H).

LC/MS: mass calcd. for C$_{26}$H$_{22}$F$_6$N$_4$O$_3$S: 584.1. found 585.2 [M+H]$^+$.

Example 311

N-(4-{[(5Z)-5-({1-[2,4-Bis(trifluoromethyl)benzyl]-1H-indazol-5-yl}methylidene)-2,4-dioxo-1,3-thiazolidin-3-yl]methyl}tetrahydro-2H-pyran-4-yl)cyclopropanecarboxamide

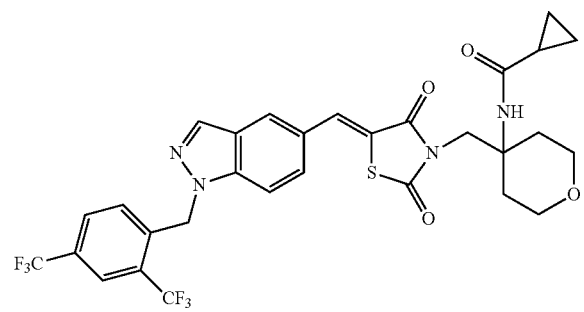 [SMILES: O=C(NC1(CN2C(=O)S/C(=C\c3ccc4c(cnn4Cc4ccc(C(F)(F)F)cc4C(F)(F)F)c3)C2=O)CCOCC1)C1CC1]

N-(4-{[(5Z)-5-({1-[2,4-Bis(trifluoromethyl)benzyl]-1H-indazol-5-yl}methylidene)-2,4-dioxo-1,3-thiazolidin-3-yl]methyl}tetrahydro-2H-pyran-4-yl)cyclopropane carboxamide was prepared from (5Z)-3-[(4-aminotetrahydro-2H-pyran-4-yl)methyl]-5-({1-[2,4-bis(trifluoromethyl)benzyl]-1H-indazol-5-yl}methylidene)-1,3-thiazolidine-2,4-dione (Example 310) and cyclopropanecarbonyl chloride following General Procedure R3.

$^1$H NMR (400 MHz, CDCl$_3$): δ 8.24 (s, 1H), 8.01 (s, 1H), 7.99 (s, 1H), 7.98 (s, 1H), 7.64 (d, 1H), 7.52 (d, 1H), 7.36 (d, 1H), 6.84 (d, 1H), 5.89 (s, 2H), 5.48 (s, 1H), 4.08 (s, 2H), 3.85-3.62 (m, 4H), 2.29-1.76 (m, 4H), 1.35-0.71 (m, 5H).

LC/MS: mass calcd. for C$_{30}$H$_{26}$F$_6$N$_4$O$_4$S: 652.2. found 653.3 [M+H]$^+$.

Example 312

(5Z)-3-[2-(4-Aminotetrahydro-2H-pyran-4-yl)ethyl]-5-({1-[4-chloro-2-(trifluoromethyl)benzyl]-1H-indazol-5-yl}methylidene)-1,3-thiazolidine-2,4-dione

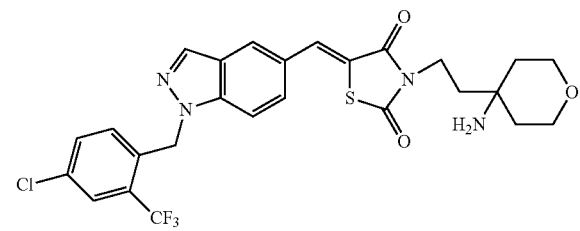 [SMILES: NC1(CCN2C(=O)S/C(=C\c3ccc4c(cnn4Cc4ccc(Cl)cc4C(F)(F)F)c3)C2=O)CCOCC1]

(A) [4-(2-{5-[1-(4-Chloro-2-trifluoromethylbenzyl)-1H-indazol-5-ylmethylene]-2,4-dioxothiazolidin-3-yl}ethyl)tetrahydro-2H-pyran-4-yl]carbamic acid tert-butyl ester was prepared from 5-[1-(4-chloro-2-trifluoromethylbenzyl)-1H-indazol-5-ylmethylene]thiazolidine-2,4-dione (from Example 1) and ([4-(2-hydroxyethyl)-tetrahydro-2H-pyran-4-yl]-carbamic acid tert-butyl ester following General Procedure J.

LC/MS: mass calcd. for C$_{31}$H$_{32}$ClF$_3$N$_4$O$_5$S: 664.17. found 665.3 [M+H]$^+$.

(B) (5Z)-3-[2-(4-Aminotetrahydro-2H-pyran-4-yl)ethyl]-5-({1-[4-chloro-2-(trifluoromethyl)benzyl]-1H-indazol-5-yl}methylidene)-1,3-thiazolidine-2,4-dione was prepared from [4-(2-{5-[1-(4-chloro-2-trifluoromethylbenzyl)-1H-indazol-5-ylmethylene]-2,4-dioxothiazolidin-3-yl}ethyl)tetrahydro-2H-pyran-4-yl]carbamic acid tert-butyl ester following General Procedure N.

$^1$H NMR (400 MHz, CDCl$_3$): δ 8.21 (s, 1H), 8.01 (s, 1H), 7.97 (s, 1H), 7.72 (s, 1H), 7.51 (d, 1H), 7.37-7.32 (m, 2H), 6.68 (d, 1H), 5.79 (s, 2H), 3.92 (s, 2H), 3.78-3.69 (m, 4H), 1.80-1.40 (m, 8H).

LC/MS: mass calcd. for C$_{26}$H$_{24}$ClF$_3$N$_4$O$_3$S: 564.1. found 565.2 [M+H]$^+$.

Example 313

(5Z)-3-[2-(4-Aminotetrahydro-2H-pyran-4-yl)ethyl]-5-({1-[2,4-bis(trifluoromethyl)benzyl]-1H-indazol-5-yl}methylidene)-1,3-thiazolidine-2,4-dione

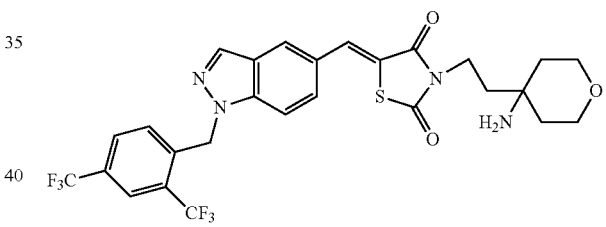

(A) [4-(2-{5-[1-(2,4-Bis-trifluoromethylbenzyl)-1H-indazol-5-ylmethylene]-2,4-dioxothiazolidin-3-yl}ethyl)tetrahydro-2H-pyran-4-yl]carbamic acid tert-butyl ester was prepared from 5-[1-(2,4-bis-trifluoromethylbenzyl)-1H-indazol-5-ylmethylene]thiazolidine-2,4-dione (from Example 6) and ([4-(2-hydroxyethyl)tetrahydro-2H-pyran-4-yl]carbamic acid tert-butyl ester following General Procedure J.

LC/MS: mass calcd. for C$_{32}$H$_{32}$F$_6$N$_4$O$_6$S: 698.20. found 699.2 [M+H]$^+$.

(B) (5Z)-3-[2-(4-Aminotetrahydro-2H-pyran-4-yl)ethyl]-5-({1-[2,4-bis(trifluoromethyl)benzyl]-1H-indazol-5-yl}methylidene)-1,3-thiazolidine-2,4-dione was prepared from [4-(2-{5-[1-(2,4-bis-trifluoromethylbenzyl)-1H-indazol-5-ylmethylene]-2,4-dioxothiazolidin-3-yl}ethyl)tetrahydro-2H-pyran-4-yl]carbamic acid tert-butyl ester following General Procedure N.

$^1$H NMR (400 MHz, DMSO-d$_6$): δ 8.40 (s, 1H), 8.29 (s, br, 3H), 8.20 (s, 1H), 8.13-8.10 (m, 2H), 7.98 (d, 1H), 7.85 (d, 1H), 7.70 (d, 1H), 6.94 (d, 1H), 5.99 (s, 2H), 3.83-3.75 (m, 4H), 3.54 (t, 2H), 2.06 (t, 2H), 1.78 (s, br, 4H).

LC/MS: mass calcd. for C$_{27}$H$_{24}$F$_6$N$_4$O$_3$S: 598.2. found 599.3 [M+H]$^+$.

Example 314

(5Z)-3-[(1-Aminocyclobutyl)methyl]-5-({1-[4-chloro-2-(trifluoromethyl)benzyl]-1H-indazol-5-yl}methylidene)-1,3-thiazolidine-2,4-dione

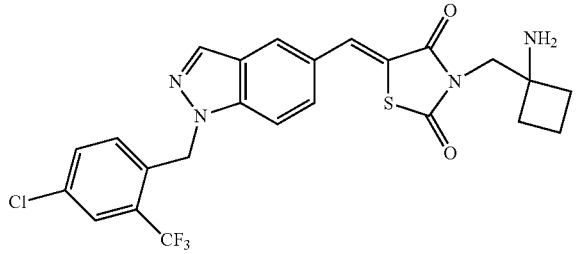 [SMILES: NC1(CN2C(=O)S/C(=C\c3ccc4c(cnn4Cc4ccc(Cl)cc4C(F)(F)F)c3)C2=O)CCC1]

(A) (1-{5-[1-(4-Chloro-2-trifluoromethylbenzyl)-1H-indazol-5-ylmethylene]-2,4-dioxothiazolidin-3-ylmethyl}cyclobutyl)carbamic acid tert-butyl ester was prepared from 5-[1-(4-chloro-2-trifluoromethylbenzyl)-1H-indazol-5-ylmethylene]thiazolidine-2,4-dione (from Example 1) and (1-hydroxymethylcyclobutyl)carbamic acid tert-butyl ester following General Procedure J.

LC/MS: mass calcd. for $C_{29}H_{28}ClF_3N_4O_4S$: 620.15. found 621.3 $[M+H]^+$.

(B) (5Z)-3-[(1-Aminocyclobutyl)methyl]-5-({1-[4-chloro-2-(trifluoromethyl)benzyl]-1H-indazol-5-yl}methylidene)-1,3-thiazolidine-2,4-dione was prepared from (1-{5-[1-(4-chloro-2-trifluoromethylbenzyl)-1H-indazol-5-ylmethylene]-2,4-dioxothiazolidin-3-ylmethyl}cyclobutyl)carbamic acid tert-butyl ester following General Procedure N.

$^1$H NMR (400 MHz, CDCl$_3$): δ 8.22 (s, 1H), 8.02 (s, 1H), 7.96 (s, 1H), 7.71 (s, 1H), 7.51 (d, 1H), 7.37-7.33 (m, 2H), 6.67 (d, 1H), 5.79 (s, 2H), 3.94 (d, 2H), 2.27-2.18 (m, 2H), 1.89-1.80 (m, 6H).

LC/MS: mass calcd. for $C_{24}H_{20}ClF_3N_4O_2S$: 520.1. found 521.2 $[M+H]^+$.

Example 315

(5Z)-5-({1-[4-Chloro-2-(trifluoromethyl)benzyl]-1H-indazol-5-yl}methylidene)-3-{[1-(dimethylamino)cyclobutyl]methyl}-1,3-thiazolidine-2,4-dione

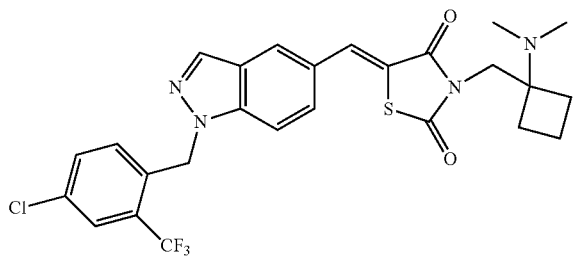 [SMILES: CN(C)C1(CN2C(=O)S/C(=C\c3ccc4c(cnn4Cc4ccc(Cl)cc4C(F)(F)F)c3)C2=O)CCC1]

(5Z)-5-({1-[4-Chloro-2-(trifluoromethyl)benzyl]-1H-indazol-5-yl}methylidene)-3-{[1-(dimethylamino)cyclobutyl]methyl}-1,3-thiazolidine-2,4-dione was prepared from (5Z)-3-[(1-aminocyclobutyl)methyl]-5-({1-[4-chloro-2-(trifluoromethyl)benzyl]-1H-indazol-5-yl}methylidene)-1,3-thiazolidine-2,4-dione (Example 314) following General Procedure R2.

$^1$H NMR (400 MHz, CDCl$_3$): δ 8.23 (s, 1H), 8.05 (s, 1H), 7.97 (s, 1H), 7.72 (s, 1H), 7.53 (d, 1H), 7.37-7.33 (m, 2H), 6.68 (d, 1H), 5.80 (s, 2H), 3.97 (d, 2H), 2.38 (s, 6H), 2.22-2.09 (m, 4H), 1.83-1.56 (m, 2H).

LC/MS: mass calcd. for $C_{26}H_{24}ClF_3N_4O_2S$: 548.1. found 549.3 $[M+H]^+$.

Example 316

(5Z)-5-({1-[4-Chloro-2-(trifluoromethyl)benzyl]-1H-indazol-5-yl}methylidene)-3-[(trans)-4-hydroxypyrrolidin-3-yl]-1,3-thiazolidine-2,4-dione

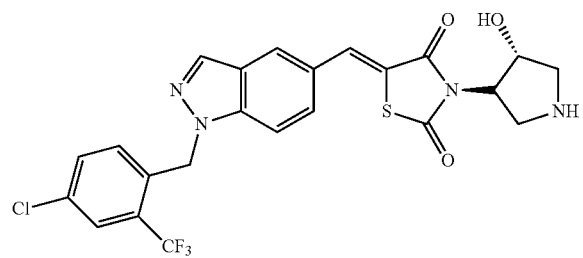

(A) To a solution of 2,5-dihydropyrrole-1-carboxylic acid tert-butyl ester (30 mmol) in DCM (50 mL) was added 40% MCPBA (1 equiv) and the resulting mixture was stirred at rt for 24 h. The solution was then extracted with aq. NaHCO$_3$, dried (Na$_2$SO$_4$) and concentrated. Purification of the residue by silica gel chromatography (1-30% EtOAc in heptanes) afforded 6-oxa-3-azabicyclo[3.1.0]hexane-3-carboxylic acid tert-butyl ester as a colorless oil.

(B) 3-{5-[1-(4-Chloro-2-trifluoromethylbenzyl)-1H-indazol-5-ylmethylene]-2,4-dioxothiazolidin-3-yl}-(trans)-4-hydroxypyrrolidine-1-carboxylic acid tert-butyl ester was prepared from 5-[1-(4-chloro-2-trifluoromethylbenzyl)-1H-indazol-5-ylmethylene]thiazolidine-2,4-dione (from Example 1) and 6-oxa-3-azabicyclo[3.1.0]hexane-3-carboxylic acid tert-butyl ester following a similar procedure as described for Example 270.

LC/MS: mass calcd. for $C_{28}H_{26}ClF_3N_4O_5S$: 622.13. found 623.1 $[M+H]^+$.

(C) (5Z)-5-({1-[4-Chloro-2-(trifluoromethyl)benzyl]-1H-indazol-5-yl}methylidene)-3-[(trans)-4-hydroxypyrrolidin-3-yl]-1,3-thiazolidine-2,4-dione was prepared from 3-{5-[1-(4-chloro-2-trifluoromethylbenzyl)-1H-indazol-5-ylmethylene]-2,4-dioxothiazolidin-3-yl}-4-hydroxypyrrolidine-1-carboxylic acid tert-butyl ester following General Procedure N.

$^1$H NMR (400 MHz, DMSO-d$_6$) for the HCl salt: δ 9.57 (s, 1H), 9.36 (s, 1H), 8.38 (s, 1H), δ 8.19 (s, 1H), 8.10 (s, 1H), 7.89 (d, 1H), 7.82 (d, 1H), 7.71-7.65 (m, 2H), 6.81 (d, 1H), 5.87 (s, 2H), 4.77-4.65 (m, 2H), 3.92-3.50 (m, 4H), 3.14 (m, 1H).

LC/MS: mass calcd. for $C_{23}H_{18}ClF_3N_4O_3S$: 522.1. found 523.2 $[M+H]^+$.

Example 317

(5Z)-5-({1-[4-Chloro-2-(trifluoromethyl)benzyl]-1H-indazol-5-yl}methylidene)-3-[(trans)-4-fluoropyrrolidin-3-yl]-1,3-thiazolidine-2,4-dione

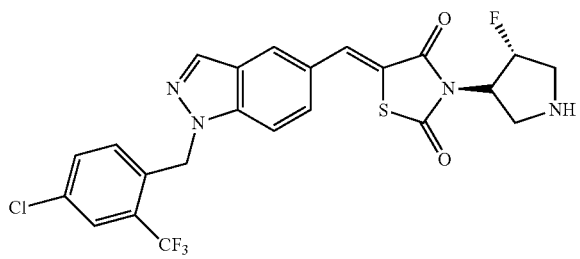

(A) 3-{5-[1-(4-Chloro-2-trifluoromethylbenzyl)-1H-indazol-5-ylmethylene]-2,4-dioxo-thiazolidin-3-yl}-4-fluoropyrrolidine-1-carboxylic acid tert-butyl ester was prepared from 3-{5-[1-(4-chloro-2-trifluoromethylbenzyl)-1H-indazol-5-ylmethylene]-2,4-dioxothiazolidin-3-yl}-4-hydroxypyrrolidine-1-carboxylic acid tert-butyl ester (from Example 316) following a similar procedure as described for Example 273.

LC/MS: mass calcd. for $C_{28}H_{25}ClF_4N_4O_4S$: 624.12. found 625.1 [M+H]$^+$.

(B) (5Z)-5-({1-[4-Chloro-2-(trifluoromethyl)benzyl]-1H-indazol-5-yl}methylidene)-3-[(trans)-4-fluoropyrrolidin-3-yl]-1,3-thiazolidine-2,4-dione was prepared from 3-{5-[1-(4-chloro-2-trifluoromethylbenzyl)-1H-indazol-5-ylmethylene]-2,4-dioxothiazolidin-3-yl}-4-fluoropyrrolidine-1-carboxylic acid tert-butyl ester following General Procedure N.

$^1$H NMR (400 MHz, DMSO-d$_6$) for the HCl salt: δ 9.95 (s, 2H), 8.38 (s, 1H), δ 8.20 (s, 1H), 8.11 (s, 1H), 7.89 (d, 1H), 7.82 (d, 1H), 7.70 (dd, 1H), 7.67 (dd, 1H), 6.81 (d, 1H), 5.88 (s, 2H), 5.74 (d, 1H), 5.06 (dt, 1H), 3.81-3.58 (m, 2H).

LC/MS: mass calcd. for $C_{23}H_{17}ClF_4N_4O_2S$: 524.1. found 525.3 [M+H]$^+$.

Example 318

(5Z)-5-({1-[4-Chloro-2-(trifluoromethyl)benzyl]-1H-indazol-5-yl}methylidene)-3-[(trans)-4-hydroxy-1-methylpyrrolidin-3-yl]-1,3-thiazolidine-2,4-dione

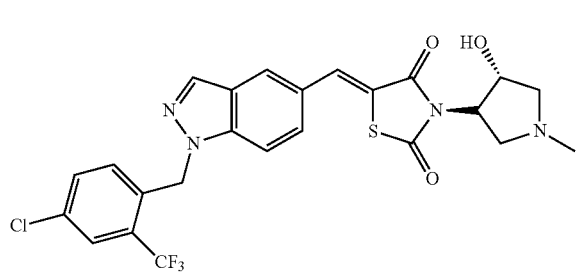

(5Z)-5-({1-[4-Chloro-2-(trifluoromethyl)benzyl]-1H-indazol-5-yl}methylidene)-3-[(trans)-4-hydroxy-1-methylpyrrolidin-3-yl]-1,3-thiazolidine-2,4-dione was prepared from (5Z)-5-({1-[4-Chloro-2-(trifluoromethyl)benzyl]-1H-indazol-5-yl}methylidene)-3-[(trans)-4-hydroxypyrrolidin-3-yl]-1,3-thiazolidine-2,4-dione (Example 316) following General Procedure R2.

$^1$H NMR (400 MHz, CDCl$_3$): δ 8.18 (s, 1H), 8.00 (s, 1H), 7.93 (s, 1H), 7.71 (s, 1H), 7.46 (d, 1H), 7.35-7.30 (m, 2H), 6.68 (d, 1H), 5.76 (s, 2H), 5.16 (t, 1H), 4.74 (br, 1H), 3.86 (t, 1H), 3.59-3.46 (m, 2H), 3.16 (t, 1H), 2.86 (s, 3H).

LC/MS: mass calcd. for $C_{24}H_{20}ClF_3N_4O_3S$: 536.1. found 537.3 [M+H]$^+$.

Example 319

(5Z)-5-({1-[4-Chloro-2-(trifluoromethyl)benzyl]-1H-indazol-5-yl}methylidene)-3-[(trans)-4-fluoro-1-methylpyrrolidin-3-yl]-1,3-thiazolidine-2,4-dione

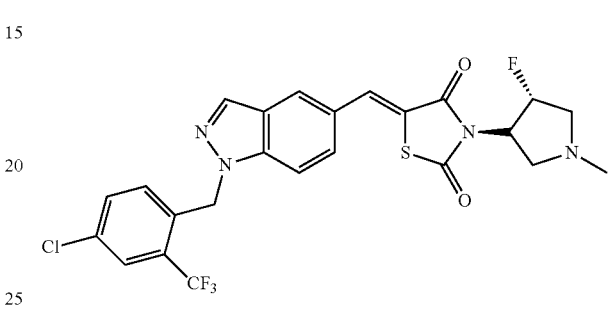

(5Z)-5-({1-[4-Chloro-2-(trifluoromethyl)benzyl]-1H-indazol-5-yl}methylidene)-3-[(trans)-4-fluoro-1-methylpyrrolidin-3-yl]-1,3-thiazolidine-2,4-dione was prepared from (5Z)-5-({1-[4-chloro-2-(trifluoromethyl)benzyl]-1H-indazol-5-yl}methylidene)-3-[(trans)-4-fluoropyrrolidin-3-yl]-1,3-thiazolidine-2,4-dione (Example 317) following General Procedure R2.

$^1$H NMR (400 MHz, CDCl$_3$): δ 8.22 (s, 1H), 8.02 (s, 1H), 7.96 (s, 1H), 7.72 (s, 1H), 7.50 (d, 1H), 7.37-7.33 (m, 2H), 6.69 (d, 1H), 5.79 (s, 2H), 5.49 (d, 1H), 5.08 (dt, 1H), 3.28-3.19 (m, 2H), 2.88 (ddd, 1H), 2.52 (t, 1H), 2.43 (s, 3H).

LC/MS: mass calcd. for $C_{24}H_{19}ClF_4N_4O_2S$: 538.1. found 39.2 [M+H]$^+$.

Example 320

(5Z)-5-({1-[4-Chloro-2-(trifluoromethyl)benzyl]-1H-indazol-5-yl}methylidene)-3-[(trans)-1-ethyl-4-fluoropyrrolidin-3-yl]-1,3-thiazolidine-2,4-dione

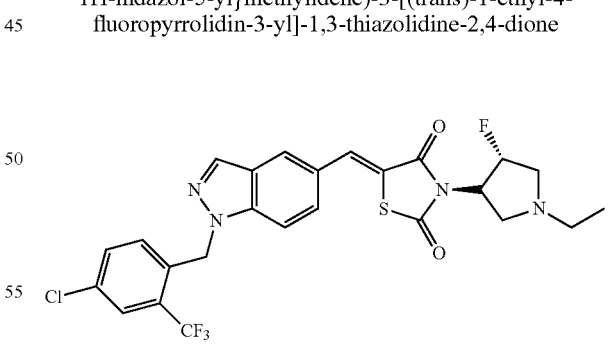

(5Z)-5-({1-[4-Chloro-2-(trifluoromethyl)benzyl]-1H-indazol-5-yl}methylidene)-3-[(trans)-1-ethyl-4-fluoropyrrolidin-3-yl]-1,3-thiazolidine-2,4-dione was prepared from (5Z)-5-({1-[4-chloro-2-(trifluoromethyl)benzyl]-1H-indazol-5-yl}methylidene)-3-[(trans)-4-fluoropyrrolidin-3-yl]-1,3-thiazolidine-2,4-dione (Example 317) and acetaldehyde (in place of formaldehyde) following General Procedure R2.

$^1$H NMR (400 MHz, CDCl$_3$): δ 8.22 (s, 1H), 8.02 (s, 1H), 7.96 (s, 1H), 7.72 (s, 1H), 7.50 (d, 1H), 7.37-7.33 (m, 2H), 6.69 (d, 1H), 5.79 (s, 2H), 5.51 (d, 1H), 5.08 (dt, 1H), 3.36-3.26 (m, 2H), 2.83 (ddd, 1H), 2.59 (q, 2H), 2.48 (t, 1H), 1.14 (t, 3H).

LC/MS: mass calcd. for $C_{25}H_{21}ClF_4N_4O_2S$: 552.1. found 553.2 $[M+H]^+$.

Example 321

(5Z)-5-({1-[4-Chloro-2-(trifluoromethyl)benzyl]-1H-indazol-5-yl}methylidene)-3-[(trans)-4-fluoro-1-(1-methylethyl)pyrrolidin-3-yl]-1,3-thiazolidine-2,4-dione

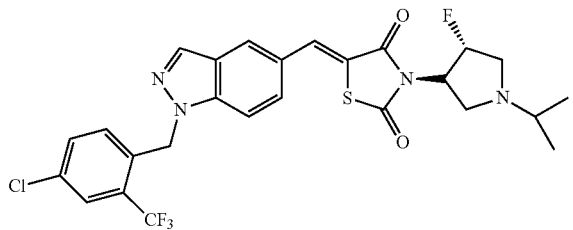

(5Z)-5-({1-[4-Chloro-2-(trifluoromethyl)benzyl]-1H-indazol-5-yl}methylidene)-3-[(trans)-4-fluoro-1-(1-methylethyl)pyrrolidin-3-yl]-1,3-thiazolidine-2,4-dione was prepared from (5Z)-5-({1-[4-chloro-2-(trifluoromethyl)benzyl]-1H-indazol-5-yl}methylidene)-3-[(trans)-4-fluoropyrrolidin-3-yl]-1,3-thiazolidine-2,4-dione (Example 317) and acetone (in place of formaldehyde) following General Procedure R2.

$^1$H NMR (400 MHz, CDCl$_3$): δ 8.22 (s, 1H), 8.02 (s, 1H), 7.96 (s, 1H), 7.72 (s, 1H), 7.50 (d, 1H), 7.37-7.33 (m, 2H), 6.69 (d, 1H), 5.79 (s, 2H), 5.52 (d, 1H), 5.08 (dt, 1H), 3.38-3.28 (m, 2H), 2.88 (ddd, 1H), 2.57-2.50 (m, 2H), 1.12 (t, 6H).

LC/MS: mass calcd. for $C_{26}H_{23}ClF_4N_4O_2S$: 566.1. found 567.2 $[M+H]^+$.

Example 322

(5Z)-5-({1-[4-Chloro-2-(trifluoromethyl)benzyl]-1H-indazol-5-yl}methylidene)-3-[(cis)-4-fluoropyrrolidin-3-yl]-1,3-thiazolidine-2,4-dione

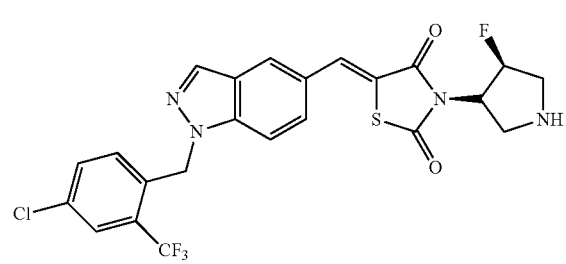

(A) A mixture of 6-oxa-3-aza-bicyclo[3.1.0]hexane-3-carboxylic acid tert-butyl ester (5.4 mmol, from Example 316) and triethylamine trihydrofluoride (5.4 mmol) was heated at 90° C. for 2 h, then cooled to rt. Aq. Na$_2$CO$_3$ was added and the mixture was extracted with EtOAc. The organic phase was dried (Na$_2$SO$_4$), concentrated and purified by silica gel chromatography (0-40% EtOAc in heptane) to afford (trans)-3-fluoro-4-hydroxypyrrolidine-1-carboxylic acid tert-butyl ester as a colorless oil.

(B) 3-{5-[1-(4-Chloro-2-trifluoromethylbenzyl)-1H-indazol-5-ylmethylene]-2,4-dioxothiazolidin-3-yl}-(cis)-4-fluoropyrrolidine-1-carboxylic acid tert-butyl ester was prepared from 5-[1-(4-chloro-2-trifluoromethylbenzyl)-1H-indazol-5-ylmethylene]thiazolidine-2,4-dione (from Example 1) and (trans)-3-fluoro-4-hydroxypyrrolidine-1-carboxylic acid tert-butyl ester following General Procedure J.

(C) (5Z)-5-({1-[4-Chloro-2-(trifluoromethyl)benzyl]-1H-indazol-5-yl}methylidene)-3-[(cis)-4-fluoropyrrolidin-3-yl]-1,3-thiazolidine-2,4-dione was prepared from 3-{5-[1-(4-chloro-2-trifluoromethylbenzyl)-1H-indazol-5-ylmethylene]-2,4-dioxothiazolidin-3-yl}-(cis)-4-fluoropyrrolidine-1-carboxylic acid tert-butyl ester following General Procedure N.

$^1$H NMR (400 MHz, CDCl$_3$): δ 8.22 (s, 1H), 8.01 (s, 1H), 7.96 (s, 1H), 7.72 (s, 1H), 7.50 (d, 1H), 7.37-7.33 (m, 2H), 6.68 (d, 1H), 5.79 (s, 2H), 5.13 (d, 1H), 5.00-4.88 (m, 1H), 3.81 (d, 1H), 3.48 (t, 1H), 3.00-2.83 (m, 2H), 2.40 (br, 1H).

LC/MS: mass calcd. for $C_{23}H_{17}ClF_4N_4O_2S$: 524.1. found 525.3 $[M+H]^+$.

Example 323

(5Z)-5-({1-[4-Chloro-2-(trifluoromethyl)benzyl]-1H-indazol-5-yl}methylidene)-3-[(cis)-4-fluoro-1-methylpyrrolidin-3-yl]-1,3-thiazolidine-2,4-dione

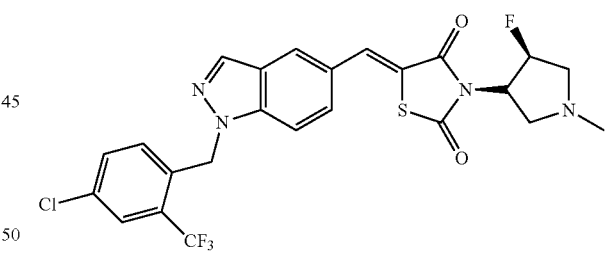

(5Z)-5-({1-[4-Chloro-2-(trifluoromethyl)benzyl]-1H-indazol-5-yl}methylidene)-3-[(cis)-4-fluoro-1-methylpyrrolidin-3-yl]-1,3-thiazolidine-2,4-dione was prepared from (5Z)-5-({1-[4-chloro-2-(trifluoromethyl)benzyl]-1H-indazol-5-yl}methylidene)-3-[(cis)-4-fluoropyrrolidin-3-yl]-1,3-thiazolidine-2,4-dione (Example 322) following General Procedure R2.

$^1$H NMR (400 MHz, CDCl$_3$): δ 8.22 (s, 1H), 8.00 (s, 1H), 7.96 (s, 1H), 7.72 (s, 1H), 7.50 (d, 1H), 7.37-7.33 (m, 2H), 6.67 (d, 1H), 5.79 (s, 2H), 5.28-5.09 (m, 1H), 4.94-4.84 (m, 1H), 3.60 (t, 1H), 3.29-3.20 (m, 1H), 3.02-2.84 (m, 2H), 2.49 (s, 3H).

LC/MS: mass calcd. for $C_{24}H_{19}ClF_4N_4O_2S$: 538.1. found 39.2 $[M+H]^+$.

Example 324

(5Z)-5-({1-[4-Chloro-2-(trifluoromethyl)benzyl]-1H-indazol-5-yl}methylidene)-3-[(cis)-1-ethyl-4-fluoropyrrolidin-3-yl]-1,3-thiazolidine-2,4-dione

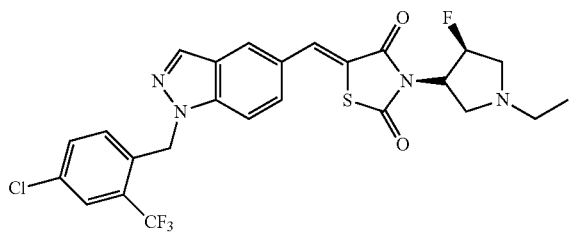

(5Z)-5-({1-[4-Chloro-2-(trifluoromethyl)benzyl]-1H-indazol-5-yl}methylidene)-3-[(cis)-1-ethyl-4-fluoropyrrolidin-3-yl]-1,3-thiazolidine-2,4-dione was prepared from (5Z)-5-({1-[4-chloro-2-(trifluoromethyl)benzyl]-1H-indazol-5-yl}methylidene)-3-[(cis)-4-fluoropyrrolidin-3-yl]-1,3-thiazolidine-2,4-dione (Example 322) and acetaldehyde (in place of formaldehyde) following General Procedure R2.

$^1$H NMR (400 MHz, CDCl$_3$): δ 8.22 (s, 1H), 8.00 (s, 1H), 7.95 (s, 1H), 7.71 (s, 1H), 7.50 (d, 1H), 7.37-7.33 (m, 2H), 6.67 (d, 1H), 5.79 (s, 2H), 5.33-5.14 (m, 1H), 4.95-4.84 (m, 1H), 3.64 (t, 1H), 3.48-3.38 (m, 1H), 3.18 (t, 1H), 2.95-2.65 (m, 3H), 1.16 (t, 3H).

LC/MS: mass calcd. for C$_{25}$H$_{21}$ClF$_4$N$_4$O$_2$S: 552.1. found 553.2 [M+H]$^+$.

Example 325

(5Z)-5-({1-[4-Chloro-2-(trifluoromethyl)benzyl]-1H-indazol-5-yl}methylidene)-3-[(3R,4S)-4-fluoro-1-(1-methylethyl)pyrrolidin-3-yl]-1,3-thiazolidine-2,4-dione

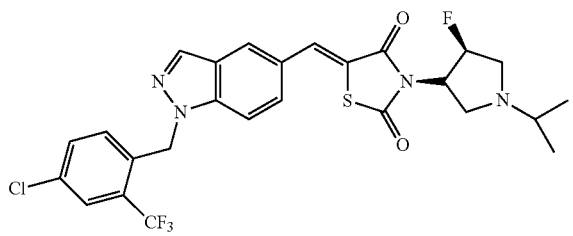

(5Z)-5-({1-[4-Chloro-2-(trifluoromethyl)benzyl]-1H-indazol-5-yl}methylidene)-3-[(3R,4S)-4-fluoro-1-(1-methylethyl)pyrrolidin-3-yl]-1,3-thiazolidine-2,4-dione was prepared from (5Z)-5-({1-[4-chloro-2-(trifluoromethyl)benzyl]-1H-indazol-5-yl}methylidene)-3-[(cis)-4-fluoropyrrolidin-3-yl]-1,3-thiazolidine-2,4-dione (Example 322) and acetone (in place of formaldehyde) following General Procedure R2.

$^1$H NMR (400 MHz, CDCl$_3$): δ 8.22 (s, 1H), 8.01 (s, 1H), 7.95 (s, 1H), 7.72 (s, 1H), 7.50 (d, 1H), 7.36-7.32 (m, 2H), 6.67 (d, 1H), 5.80 (s, 2H), 5.31-5.12 (m, 1H), 4.93-4.81 (m, 1H), 3.64 (t, 1H), 3.50-3.40 (m, 1H), 3.19 (t, 1H), 2.90 (ddd, 1H), 2.74 (m, 1H), 1.15 (t, 6H).

LC/MS: mass calcd. for C$_{26}$H$_{23}$ClF$_4$N$_4$O$_2$S: 566.1. found 567.2 [M+H]$^+$.

Example 326

(5Z)-5-({1-[4-Chloro-2-(trifluoromethyl)benzyl]-1H-indazol-5-yl}methylidene)-3-[(trans)-1-ethyl-3-fluoropiperidin-4-yl]-1,3-thiazolidine-2,4-dione

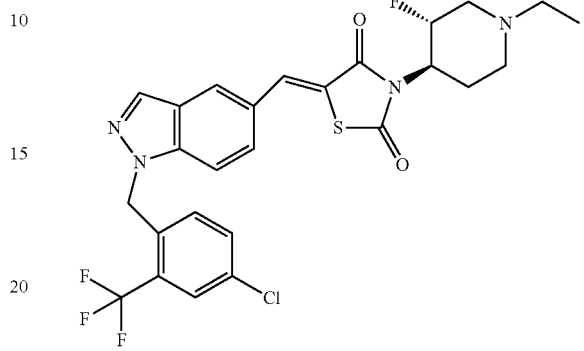

(5Z)-5-({1-[4-Chloro-2-(trifluoromethyl)benzyl]-1H-indazol-5-yl}methylidene)-3-[(trans)-1-ethyl-3-fluoropiperidin-4-yl]-1,3-thiazolidine-2,4-dione was prepared from (5Z)-5-({1-[4-chloro-2-(trifluoromethyl)benzyl]-1H-indazol-5-yl}methylidene)-3-[(trans)-3-fluoropiperidin-4-yl]-1,3-thiazolidine-2,4-dione (Example 273) and acetaldehyde (in place of formaldehyde) following General Procedure R2.

$^1$H NMR (400 MHz, CD$_3$OD): δ 8.28 (s, 1H), 8.11 (s, 1H), 8.08 (s, 1H), 7.80 (s, 1H), 7.61 (dd, 2H), 7.48 (d, 1H), 6.70 (d, 1H), 5.86 (s, 2H), 5.60 (m, 1H), 4.81 (m, 1H), 4.01 (d, 1H), 3.71 (d, 1H), 3.19-3.36 (4H), 2.78 (m, 1H), 2.24 (m, 1H), 1.41 (t, 3H).

LC/MS: mass calcd. for C$_{26}$H$_{23}$ClF$_4$N$_4$O$_2$S: 566.12. found 567.2 [M+H]$^+$.

Example 327

(5Z)-5-({1-[4-Chloro-2-(trifluoromethyl)benzyl]-1H-indazol-5-yl}methylidene)-3-[(trans)-3-fluoro-1-(2-hydroxyethyl)piperidin-4-yl]-1,3-thiazolidine-2,4-dione

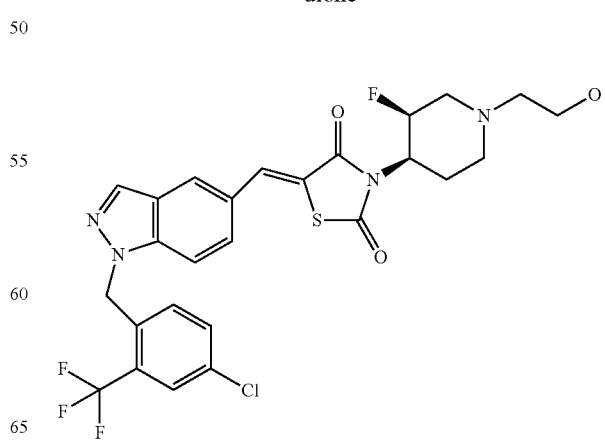

(5Z)-5-({1-[4-Chloro-2-(trifluoromethyl)benzyl]-1H-indazol-5-yl}methylidene)-3-[(trans)-3-fluoro-1-(2-hydroxyethyl)piperidin-4-yl]-1,3-thiazolidine-2,4-dione was prepared from (5Z)-5-({1-[4-chloro-2-(trifluoromethyl)benzyl]-1H-indazol-5-yl}methylidene)-3-[(trans)-3-fluoropiperidin-4-yl]-1,3-thiazolidine-2,4-dione (Example 273) and 2-bromoethanol following General Procedure S.

$^1$H NMR (400 MHz, CD$_3$OD): δ 8.29 (s, 1H), 8.13 (s, 1H), 8.11 (s, 1H), 7.80 (s, 1H), 7.66 (d, 1H), 7.60 (d, 1H), 7.49 (d, 1H), 6.71 (d, 1H), 5.87 (s, 2H), 5.62 (m, 1H), 4.80 (m, 1H), 4.07 (m, 1H), 3.92 (t, 2H), 3.79 (m, 1H), 3.39 (m, 2H), 3.31 (t, 2H), 2.80 (m, 1H), 2.22 (m, 1H).

LC/MS: mass calcd. for C$_{26}$H$_{23}$ClF$_4$N$_4$O$_3$S: 582.11. found 583.2 [M+H]$^+$.

Example 328

(5Z)-5-({1-[4-Chloro-2-(trifluoromethyl)benzyl]-1H-indazol-5-yl}methylidene)-3-[(trans)-3-fluoro-1-(1-methylethyl)piperidin-4-yl]-1,3-thiazolidine-2,4-dione

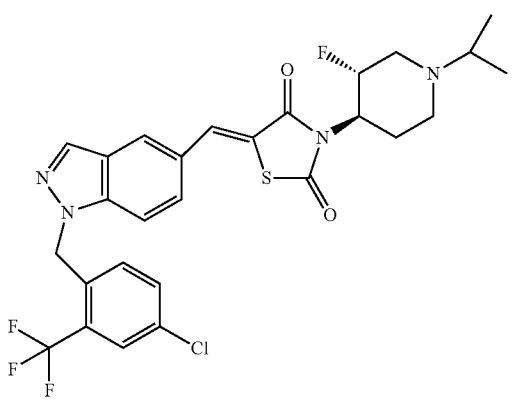

(5Z)-5-({1-[4-Chloro-2-(trifluoromethyl)benzyl]-1H-indazol-5-yl}methylidene)-3-[(trans)-3-fluoro-1-(1-methylethyl)piperidin-4-yl]-1,3-thiazolidine-2,4-dione was prepared from (5Z)-5-({1-[4-chloro-2-(trifluoromethyl)benzyl]-1H-indazol-5-yl}methylidene)-3-[(trans)-3-fluoropiperidin-4-yl]-1,3-thiazolidine-2,4-dione (Example 273) and acetone (in place of formaldehyde) following General Procedure R2.

$^1$H NMR (400 MHz, CD$_3$OD): δ 8.29 (s, 1H), 8.13 (s, 1H), 8.10 (s, 1H), 7.80 (d, 1H), 7.65 (dd, 1H), 7.60 (d, 1H), 7.49 (dd, 1H), 6.71 (d, 1H), 5.87 (s, 2H), 5.61 (m, 1H), 4.84 (m, 1H), 3.89 (m, 1H), 3.68 (m, 1H), 3.61 (m, 1H), 3.27-3.37 (2H), 2.77 (m, 1H), 2.24 (m, 1H), 1.42 (dd, 6H).

LC/MS: mass calcd. for C$_{27}$H$_{25}$ClF$_4$N$_4$O$_2$S: 580.13. found 581.25 [M+H]$^+$.

Example 329

(5Z)-5-({1-[4-Chloro-2-(trifluoromethyl)benzyl]-1H-indazol-5-yl}methylidene)-3-[(trans)-3-fluoro-1-(1,1,1-d$_3$)methylpiperidin-4-yl]-1,3-thiazolidine-2,4-dione

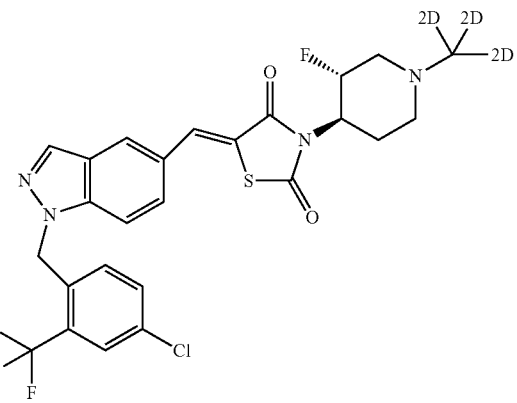

(5Z)-5-({1-[4-Chloro-2-(trifluoromethyl)benzyl]-1H-indazol-5-yl}methylidene)-3-[(trans)-3-fluoro-1-(1,1,1-d$_3$)methylpiperidin-4-yl]-1,3-thiazolidine-2,4-dione was prepared from (5Z)-5-({1-[4-chloro-2-(trifluoromethyl)benzyl]-1H-indazol-5-yl}methylidene)-3-[(trans)-3-fluoropiperidin-4-yl]-1,3-thiazolidine-2,4-dione (Example 273) and deuterated formaldehyde with deuterated sodium triacetoxyborohydride following General Procedure R2.

$^1$H NMR (400 MHz, CDCl$_3$): δ 8.22 (s, 1H), 8.00 (s, 1H), 7.96 (d, 1H), 7.71 (d, 1H), 7.50 (m, 1H), 7.34 (m, 2H), 6.67 (d, 1H), 5.79 (s, 2H), 5.35 (m, 1H), 4.38 (m, 1H), 2.94-3.56 (2H), 2.45-2.93 (2H), 2.13 (m, 1H), 1.78 (m, 1H).

LC/MS: mass calcd. for C$_{25}$H$_{18}$ClF$_4$N$_4$O$_2$SD$_3$: 555.12. found 556.20 [M+H]$^+$.

Example 330

(5Z)-5-({1-[2,4-Bis(trifluoromethyl)benzyl]-1H-indazol-5-yl}methylidene)-3-[(trans)-3-fluoro-1-(1,1,1-d$_3$)methylpiperidin-4-yl]-1,3-thiazolidine-2,4-dione

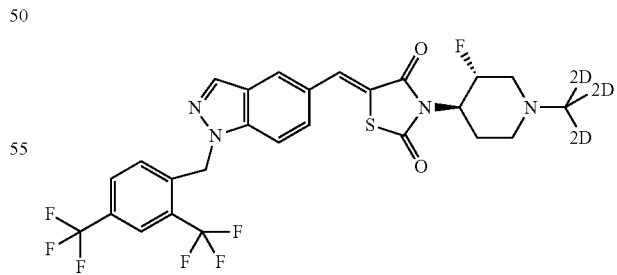

(5Z)-5-({1-[2,4-Bis(trifluoromethyl)benzyl]-1H-indazol-5-yl}methylidene)-3-[(trans)-3-fluoro-1-(1,1,1-d$_3$)methylpiperidin-4-yl]-1,3-thiazolidine-2,4-dione was prepared from (5Z)-5-({1-[2,4-bis(trifluoromethyl)benzyl]-1H-indazol-5-yl}-methylidene)-3-[(trans)-3-fluoropiperidin-4-yl]-1,3-thiazolidine-2,4-dione (Example 274) and deuterated formaldehyde with deuterated sodium triacetoxyborohydride following General Procedure R2.

$^1$H NMR (400 MHz, CD$_3$OD): δ 8.23 (s, 1H), 7.99-8.03 (3H), 7.73 (d, 1H), 7.54 (d, 2H), 6.81 (d, 1H), 5.89 (s, 2H), 5.57 (m, 1H), 4.75 (m, 1H), 3.94 (m, 1H), 3.64 (m, 1H), 3.53 (m, 1H), 2.68-3.09 (1H), 2.20 (m, 1H), 1.89 (m, 1H).

LC/MS: mass calcd. for C$_{26}$H$_{18}$F$_7$N$_4$O$_2$SD$_3$: 589.15. found 590.25 [M+H]$^+$.

Example 331

(5Z)-5-({1-[2,4-Bis(trifluoromethyl)benzyl]-1H-indazol-5-yl}methylidene)-3-[(trans)-3-fluoro-1-(1-methylethyl)piperidin-4-yl]-1,3-thiazolidine-2,4-dione

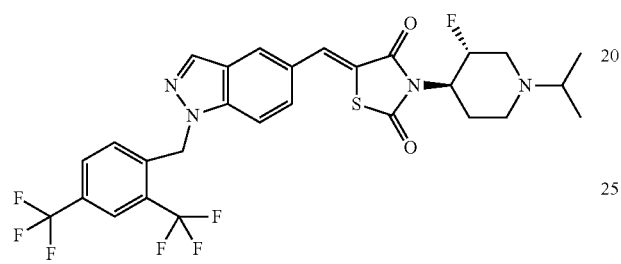

(5Z)-5-({1-[2,4-Bis(trifluoromethyl)benzyl]-1H-indazol-5-yl}methylidene)-3-[(cis/trans)-3-fluoro-1-(1-methylethyl)piperidin-4-yl]-1,3-thiazolidine-2,4-dione was prepared from (5Z)-5-({1-[2,4-bis(trifluoromethyl)benzyl]-1H-indazol-5-yl}methylidene)-3-[(trans)-3-fluoropiperidin-4-yl]-1,3-thiazolidine-2,4-dione (Example 274) and acetone (in place of formaldehyde) following General Procedure R2.

$^1$H NMR (400 MHz, CD$_3$OD): δ 8.29 (s, 1H), 8.07 (s, 1H), 8.05 (s, 1H), 8.04 (s, 1H), 7.78 (d, 1H), 7.59 (s, 2H), 6.86 (d, 1H), 5.95 (s, 2H), 5.68 (m, 1H), 4.85 (m, 1H), 3.92 (m, 1H), 3.72 (m, 1H), 3.63 (m, 1H), 3.30-3.40 (2H), 2.84 (m, 1H), 2.26 (m, 1H), 1.44 (d, 6H).

LC/MS: mass calcd. for C$_{28}$H$_{25}$F$_7$N$_4$O$_2$S: 614.16. found 615.30 [M+H]$^+$.

Example 332

(5Z)-5-({1-[4-Chloro-2-(trifluoromethyl)benzyl]-1H-indazol-5-yl}methylidene)-3-[(cis)-1-ethyl-3-fluoropiperidin-4-yl]-1,3-thiazolidine-2,4-dione

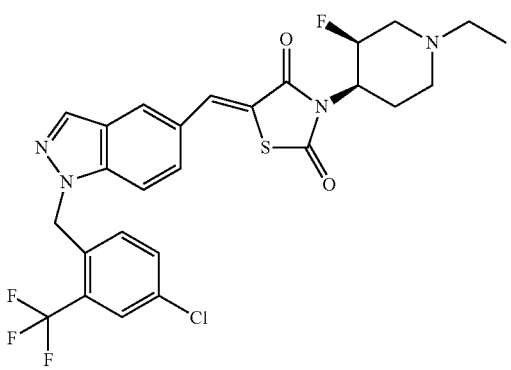 [SMILES: CCN1CC[C@@H](N2C(=O)S/C(=C\c3ccc4c(cnn4Cc4ccc(Cl)cc4C(F)(F)F)c3)C2=O)[C@@H](F)C1]

(5Z)-5-({1-[4-Chloro-2-(trifluoromethyl)benzyl]-1H-indazol-5-yl}methylidene)-3-[(cis)-1-ethyl-3-fluoropiperidin-4-yl]-1,3-thiazolidine-2,4-dione was prepared from (5Z)-5-({1-[4-chloro-2-(trifluoromethyl)benzyl]-1H-indazol-5-yl}methylidene)-3-[(cis)-3-fluoropiperidin-4-yl]-1,3-thiazolidine-2,4-dione (Example 201) and acetaldehyde (in place of formaldehyde) following General Procedure R2.

$^1$H NMR (400 MHz, CD$_3$OD): δ 8.28 (s, 1H), 8.10 (s, 1H), 8.05 (s, 1H), 7.80 (d, 1H), 7.63 (dd, 1H), 7.59 (d, 1H), 7.48 (dd, 1H), 6.70 (d, 1H), 5.86 (s, 2H), 5.20 (br, ½H), 5.08 (br, ½H), 4.76 (m, 1H), 3.93 (m, 1H), 3.75 (m, 1H), 3.62 (m, 1H), 3.54 (dd, 1H), 3.21-3.32 (3H), 2.18 (d, 1H), 1.37 (t, 3H).

LC/MS: mass calcd. for C$_{26}$H$_{23}$ClF$_4$N$_4$O$_2$S: 566.12. found 567.25 [M+H]$^+$.

Example 333

(5Z)-5-({1-[4-Chloro-2-(trifluoromethyl)benzyl]-3-methyl-1H-indazol-5-yl}methylidene)-3-[(trans)-3-fluoropiperidin-4-yl]-1,3-thiazolidine-2,4-dione

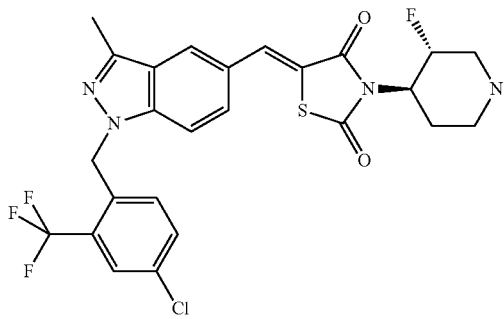 [SMILES: Cc1nn(Cc2ccc(Cl)cc2C(F)(F)F)c2ccc(/C=C3\SC(=O)N([C@@H]4CCNC[C@H]4F)C3=O)cc12]

(A) 4-{5-[1-(4-Chloro-2-trifluoromethylbenzyl)-3-methyl-1H-indazol-5-ylmethylene]-2,4-dioxothiazolidin-3-yl}-(trans)-3-fluoropiperidine-1-carboxylic acid tert-butyl ester was prepared from [(5Z)-5-({1-[4-chloro-2-(trifluoromethyl)-benzyl]-3-methyl-1H-indazol-5-yl}methylidene)-2,4-dioxo-1,3-thiazolidine (from Example 36) and (cis)-3-fluoro-4-hydroxypiperidine-1-carboxylic acid tert-butyl ester (prepared as described in U.S. Pat. Pub. No. 2007/0249589) following General Procedure J.

LC/MS: mass calcd. for C$_{30}$H$_{29}$ClF$_4$N$_4$O$_4$S: 652.15. found 653.1 [M+H]$^+$.

(B) (5Z)-5-({1-[4-Chloro-2-(trifluoromethyl)benzyl]-3-methyl-1H-indazol-5-yl}methylidene)-3-[(trans)-3-fluoropiperidin-4-yl]-1,3-thiazolidine-2,4-dione was prepared from 4-{5-[1-(4-chloro-2-trifluoromethylbenzyl)-3-methyl-1H-indazol-5-ylmethylene]-2,4-dioxothiazolidin-3-yl}-(trans)-3-fluoropiperidine-1-carboxylic acid tert-butyl ester following General Procedure N.

$^1$H NMR (400 MHz, CD$_3$OD): δ 8.11 (s, 1H), 8.04 (s, 1H), 7.79 (d, 1H), 7.64 (dd, 1H), 7.53 (d, 1H), 7.48 (dd, 1H), 6.70 (d, 1H), 5.78 (s, 2H), 5.54 (m, 1H), 4.80 (m, 1H), 3.83 (m, 1H), 3.54 (m, 1H), 3.23 (m, 2H), 2.72 (m, 1H), 2.62 (s, 3H), 2.19 (m, 1H).

LC/MS: mass calcd. for C$_{25}$H$_{21}$ClF$_4$N$_4$O$_2$S: 552.10. found 553.05 [M+H]$^+$.

Example 334

(5Z)-5-({1-[4-Chloro-2-(trifluoromethyl)benzyl]-3-methyl-1H-indazol-5-yl}-methylidene)-3-[(trans)-1-ethyl-3-fluoropiperidin-4-yl]-1,3-thiazolidine-2,4-dione

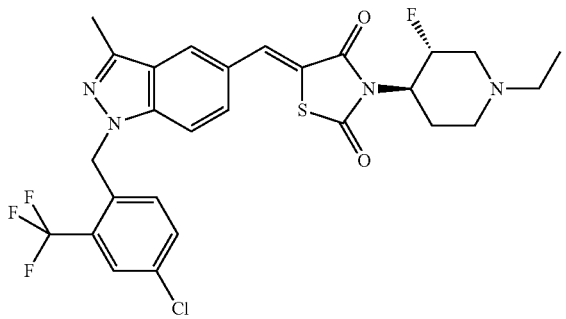 [SMILES: CCN1CC[C@@H](N2C(=O)S/C(=C\c3ccc4c(c3)c(C)nn4Cc3ccc(Cl)cc3C(F)(F)F)C2=O)[C@H](F)C1]

(5Z)-5-({1-[4-Chloro-2-(trifluoromethyl)benzyl]-3-methyl-1H-indazol-5-yl}methylidene)-3-[(trans)-1-ethyl-3-fluoropiperidin-4-yl]-1,3-thiazolidine-2,4-dione was prepared from (5Z)-5-({1-[4-chloro-2-(trifluoromethyl)benzyl]-3-methyl-1H-indazol-5-yl}methylidene)-3-[(trans)-3-fluoropiperidin-4-yl]-1,3-thiazolidine-2,4-dione (Example 333) and acetaldehyde following General Procedure R2.

$^1$H NMR (400 MHz, CD$_3$OD): δ 7.95 (s, 1H), 7.85 (s, 1H), 7.75 (d, 1H), 7.47 (d, 1H), 7.43 (d, 1H), 7.40 (d, 1H), 6.65 (d, 1H), 5.67 (s, 2H), 5.65 (m, 1H), 4.83 (m, 1H), 4.03 (m, 1H), 3.76 (m, 1H), 3.38 (q, 2H), 3.28 (m, 2H), 2.86 (m, 1H), 2.55 (s, 3H), 2.27 (m, 1H), 1.44 (t, 3H).

LC/MS: mass calcd. for C$_{27}$H$_{25}$ClF$_4$N$_4$O$_2$S: 580.13. found 581.10 [M+H]$^+$.

Example 335

(5Z)-5-({1-[4-Chloro-2-(trifluoromethyl)benzyl]-3-methyl-1H-indazol-5-yl}-methylidene)-3-[(trans)-3-fluoro-1-methylpiperidin-4-yl]-1,3-thiazolidine-2,4-dione

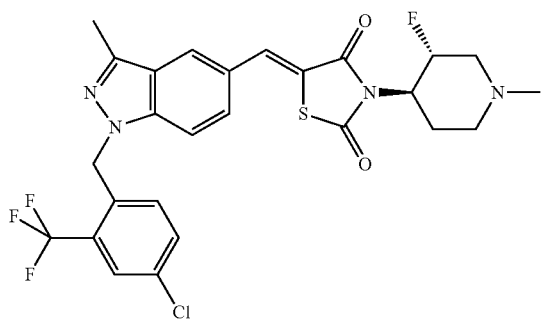 [SMILES: Cc1nn(Cc2ccc(Cl)cc2C(F)(F)F)c2ccc(/C=C3\SC(=O)N([C@@H]4CCN(C)C[C@H]4F)C3=O)cc12]

(5Z)-5-({1-[4-Chloro-2-(trifluoromethyl)benzyl]-3-methyl-1H-indazol-5-yl}methylidene)-3-[(trans)-3-fluoro-1-methylpiperidin-4-yl]-1,3-thiazolidine-2,4-dione was prepared from (5Z)-5-({1-[4-chloro-2-(trifluoromethyl)benzyl]-3-methyl-1H-indazol-5-yl}methylidene)-3-[(trans)-3-fluoropiperidin-4-yl]-1,3-thiazolidine-2,4-dione (Example 333) following General Procedure R2.

$^1$H NMR (400 MHz, CD$_3$OD): δ 7.94 (s, 1H), 7.84 (s, 1H), 7.74 (d, 1H), 7.45 (d, 1H), 7.41 (d, 1H), 7.38 (d, 1H), 6.64 (d, 1H), 5.66 (s, 2H), 5.65 (m, 1H), 4.81 (m, 1H), 3.99 (m, 1H), 3.71 (m, 1H), 3.33-3.44 (2H), 3.05 (s, 3H), 2.85 (m, 1H), 2.54 (s, 3H), 2.25 (m, 1H).

LC/MS: mass calcd. for C$_{26}$H$_{23}$ClF$_4$N$_4$O$_2$S: 566.12. found 567.15 [M+H]$^+$.

Example 336

(5Z)-5-({1-[2,4-Bis(trifluoromethyl)benzyl]-1H-indazol-5-yl}methylidene)-3-[(trans)-1-ethyl-3-fluoropiperidin-4-yl]-1,3-thiazolidine-2,4-dione

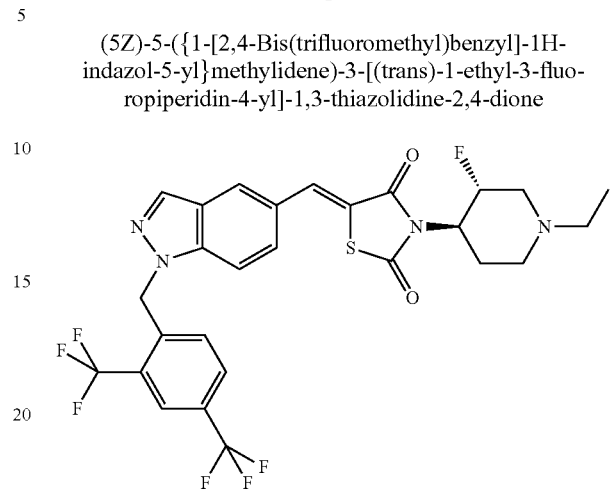

(5Z)-5-({1-[2,4-Bis(trifluoromethyl)benzyl]-1H-indazol-5-yl}methylidene)-3-[(trans)-1-ethyl-3-fluoropiperidin-4-yl]-1,3-thiazolidine-2,4-dione was prepared from (5Z)-5-({1-[2,4-bis(trifluoromethyl)benzyl]-1H-indazol-5-yl}methylidene)-3-[(cis/trans)-3-fluoropiperidin-4-yl]-1,3-thiazolidine-2,4-dione (Example 274) and acetaldehyde (in place of formaldehyde) following General Procedure R2.

$^1$H NMR (400 MHz, CD$_3$OD): δ 8.32 (s, 1H), 8.15 (s, 1H), 8.11 (s, 1H), 8.06 (s, 1H), 7.80 (d, 1H), 7.67 (dd, 1H), 7.63 (d, 1H), 6.89 (d, 1H), 5.99 (s, 2H), 5.57 (m, 1H), 4.82 (m, 1H), 4.01 (m, 1H), 3.70 (m, 1H), 3.16-3.36 (4H), 2.75 (m, 1H), 2.23 (m, 1H), 1.40 (t, 3H).

LC/MS: mass calcd. for C$_{27}$H$_{23}$F$_7$N$_4$O$_2$S: 600.14. found 601.20 [M+H]$^+$.

Example 337

(5Z)-5-({1-[4-Chloro-2-(trifluoromethyl)benzyl]-1H-indazol-5-yl}methylidene)-3-[2-(1,1-dioxido-1,2,5-thiadiazolidin-2-yl)ethyl]-1,3-thiazolidine-2,4-dione

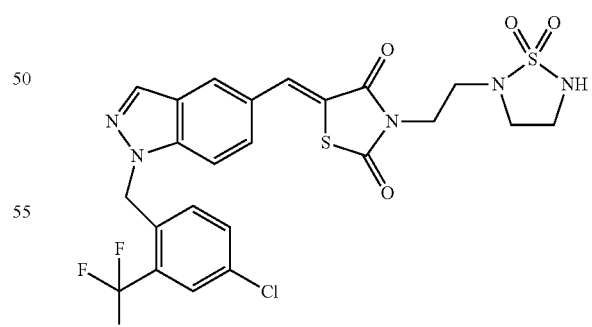

(A) (5Z)-5-({1-[4-Chloro-2-(trifluoromethyl)benzyl]-1H-indazol-5-yl}methylene)-3-(2-hydroxyethyl)thiazolidine-2,4-dione was prepared from [4-chloro-2-(trifluoromethyl)benzyl]-1H-indazol-5-carbaldehyde (from Example 1) and 3-(2-hydroxyethyl)thiazolidine-2,4-dione following General Procedure E.

(B) (5Z)-5-({1-[4-Chloro-2-(trifluoromethyl)benzyl]-1H-indazol-5-yl}methylidene)-3-[2-(1,1-dioxido-1,2,5-thiadiazolidin-2-yl)ethyl]-1,3-thiazolidine-2,4-dione was prepared from (5Z)-5-({1-[4-chloro-2-(trifluoromethyl)-1H-indazol-5-yl}methylene)-3-(2-hydroxyethyl)thiazolidine-2,4-dione and 1,1-dioxo-1$\lambda^6$-[1,2,5]thiadiazolidine-2-carboxylic acid tert-butyl ester (compound described in *Chemistry—A European Journal* 2004, 10(22), 5581-5606) according to General Procedure C followed by deprotection (Procedure M).

$^1$H NMR (400 MHz, DMSO-$d_6$): δ 8.38 (s, 1H), 8.18 (s, 1H), 8.09 (s, 1H), 7.89 (d, 1H), 7.82 (d, 1H), 7.63-7.73 (m, 2H), 7.18 (t, 1H), 6.77 (d, 1H), 5.88 (s, 2H), 3.87 (t, 2H), 3.17-3.29 (m, 6H).

LCMS: mass calcd. for $C_{23}H_{19}ClF_3N_6O_4S_2$: 586.0. found 585.9 [M]$^+$.

Example 338

{(trans)-4-[(5Z)-5-({1-[4-Chloro-2-(trifluoromethyl)benzyl]-1H-indazol-5-yl}-methylidene)-2,4-dioxo-1,3-thiazolidin-3-yl]-3-fluoropiperidin-1-yl}acetonitrile

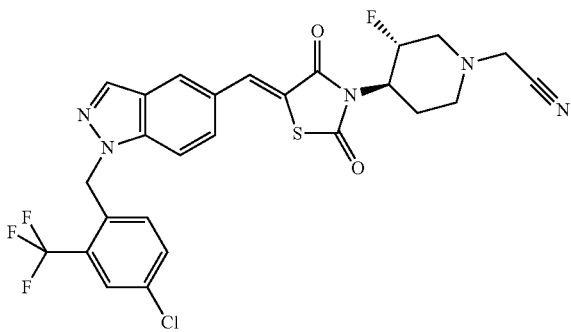 [SMILES: N#CCN1CC[C@@H](N2C(=O)S/C(=C\c3ccc4c(cnn4Cc4ccc(Cl)cc4C(F)(F)F)c3)C2=O)[C@H](F)C1]

{(cis/trans)-4-[(5Z)-5-({1-[4-Chloro-2-(trifluoromethyl)benzyl]-1H-indazol-5-yl}methylidene)-2,4-dioxo-1,3-thiazolidin-3-yl]-3-fluoropiperidin-1-yl}acetonitrile was prepared from (5Z)-5-({1-[4-chloro-2-(trifluoromethyl)benzyl]-1H-indazol-5-yl}methylidene)-3-[(trans)-3-fluoropiperidin-4-yl]-1,3-thiazolidine-2,4-dione (Example 273) and bromoacetonitrile following General Procedure S.

$^1$H NMR (400 MHz, CDCl$_3$): δ 8.22 (s, 1H), 8.02 (s, 1H), 7.96 (s, 1H), 7.72 (d, 1H), 7.50 (dd, 1H), 7.36 (dd, 1H), 7.34 (dd, 1H), 6.68 (d, 1H), 5.80 (s, 2H), 5.38 (m, 1H), 4.42 (m, 1H), 3.62 (m, 2H), 3.26 (m, 1H), 2.88 (m, 1H), 2.50-2.63 (3H), 1.86 (m, 1H).

LC/MS: mass calcd. for $C_{26}H_{20}ClF_4N_6O_2S$: 577.10. found 578.1 [M+H]$^+$.

Example 339

Methyl 5-{2-[(5Z)-5-({1-[4-chloro-2-(trifluoromethyl)benzyl]-1H-indazol-5-yl}-methylidene)-2,4-dioxo-1,3-thiazolidin-3-yl]ethyl}-1,2,5-thiadiazolidine-2-carboxylate 1,1-dioxide

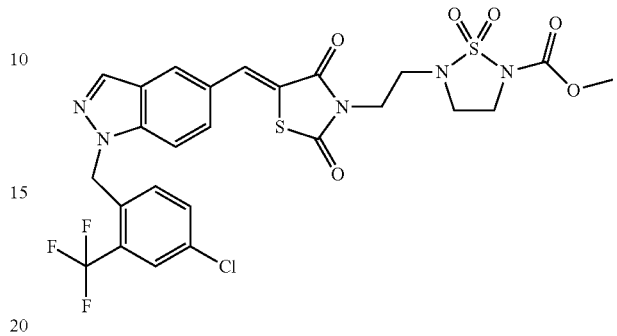

(A) To a solution of 1-methoxy-N-triethylammoniosulfonylmethanimidate (Burgess reagent, 12.3 mmol) in THF (10 mL) at 0° C. was added 2-aminoethanol (4.91 mmol). The reaction was allowed to warm to rt and then heated to 90° C. for 8 h. After cooling to rt, the reaction was quenched with saturated aq. NH$_4$Cl. The mixture was extracted with EtOAc and the organic layer was dried (Na$_2$SO$_4$) and concentrated to afford 1,1-dioxo-1$\lambda^6$-[1,2,5]thiadiazolidine-2-carboxylic acid methyl ester as colorless oil that was used without further purification.

(B) Methyl 5-{2-[(5Z)-5-({1-[4-chloro-2-(trifluoromethyl)benzyl]-1H-indazol-5-yl}methylidene)-2,4-dioxo-1,3-thiazolidin-3-yl]ethyl}-1,2,5-thiadiazolidine-2-carboxylate 1,1-dioxide was prepared from (5Z)-5-({1-[4-chloro-2-(trifluoromethyl)benzyl]-1H-indazol-5-yl}methylene)-3-(2-hydroxyethyl)thiazolidine-2,4-dione (from Example 340) and 1,1-dioxo-1$\lambda^6$-[1,2,5]thiadiazolidine-2-carboxylic acid methyl ester following General Procedure C.

$^1$H NMR (400 MHz, CDCl$_3$): δ 8.23 (s, 1H), 8.03 (s, 1H), 7.98 (s, 1H), 7.70-7.74 (m, 1H), 7.49-7.55 (m, 1H), 7.35 (d, 2H), 6.62-6.68 (m, 1H), 5.81 (s, 2H), 3.97-4.04 (m, 2H), 3.82-3.89 (m, 5H), 3.53-3.59 (m, 2H), 3.42 (m, 2H).

LCMS: mass calcd. for $C_{26}H_{21}ClF_3N_6O_6S_2$: 644.0. found 645.0 [M+H]$^+$.

Example 340

Methyl 5-{[(5Z)-5-({1-[4-chloro-2-(trifluoromethyl)benzyl]-1H-indazol-5-yl}-methylidene)-2,4-dioxo-1,3-thiazolidin-3-yl]acetyl}-1,2,5-thiadiazolidine-2-carboxylate 1,1-dioxide

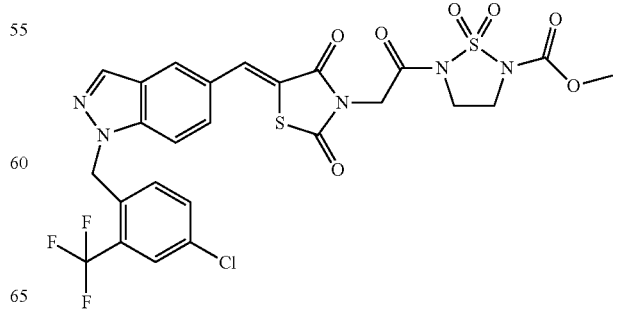

Methyl 5-{[(5Z)-5-({1-[4-chloro-2-(trifluoromethyl)benzyl]-1H-indazol-5-yl}-methylidene)-2,4-dioxo-1,3-thiazolidin-3-yl]acetyl}-1,2,5-thiadiazolidine-2-carboxylate 1,1-dioxide was prepared from [(5Z)-5-({1-[4-chloro-2-(trifluoromethyl)benzyl]-1H-indazol-5-yl}-methylidene)-2,4-dioxo-1,3-thiazolidin-3-yl]acetic acid (from Example 4) and 1,1-dioxo-1$\lambda^6$-[1,2,5]thiadiazolidine-2-carboxylic acid methyl ester (from Example 339) following General Procedure C.

$^1$H NMR (400 MHz, DMSO-$d_6$): δ 8.39 (s, 1H), 8.21-8.24 (m, 1H), 8.17 (s, 1H), 7.87-7.93 (m, 1H), 7.80-7.87 (m, 1H), 7.69-7.76 (m, 1H), 7.63-7.69 (m, 1H), 6.75-6.81 (m, 1H), 5.88 (s, 2H), 4.86 (s, 2H), 4.18-4.28 (m, 2H), 3.96-4.05 (m, 2H), 3.86 (s, 3H).

LCMS: mass calcd. for $C_{26}H_{19}ClF_3N_6O_7S_2$: 658.0. found 659.8 [M+H]$^+$.

Example 341

(5Z)-5-({1-[4-Chloro-2-(trifluoromethyl)benzyl]-1H-indazol-5-yl}methylidene)-3-(3-oxopiperidin-4-yl)-1,3-thiazolidine-2,4-dione

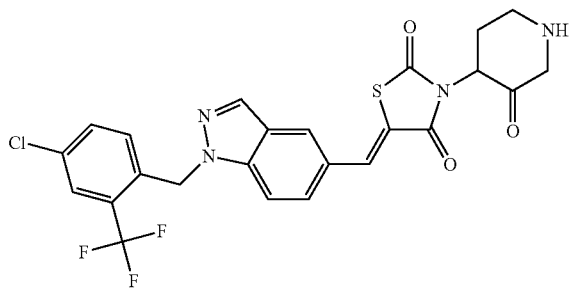 [SMILES: O=C1CNCCC1N1C(=O)S/C(=C\c2ccc3c(cnn3Cc3ccc(Cl)cc3C(F)(F)F)c2)C1=O]

(A) (5Z)-4-{5-[1-(4-chloro-2-trifluoromethylbenzyl)-1H-indazol-5-ylmethylene]-2,4-dioxothiazolidin-3-yl}-3-hydroxypiperidine-1-carboxylic acid tert-butyl ester was prepared from 1,1-dimethylethyl trans-4-(2,4-dioxo-1,3-thiazolidin-3-yl)-3-hydroxypiperidine-1-carboxylate (from Example 270) and [4-chloro-2-(trifluoromethyl)benzyl]-1H-indazol-5-carbaldehyde (from Example 1) following General Procedure F1.

(B) To a solution of (5Z)-4-{5-[1-(4-chloro-2-trifluoromethylbenzyl)-1H-indazol-5-ylmethylene]-2,4-dioxothiazolidin-3-yl}-3-hydroxypiperidine-1-carboxylic acid tert-butyl ester (0.13 mmol) in DCM (2 mL) was added Dess-Martin periodinane powder (0.16 mmol). The mixture was stirred at rt for 18 h, then purified by silica gel chromatography (0-30% EtOAc/hexanes). The product was obtained as pale yellow solid, which was treated with TFA/DCM following General Procedure M to afford the title compound.

$^1$H NMR (400 MHZ, CDCl$_3$): δ 8.20 (s, 1H), 8.02 (s, 1H), 7.97 (s, 1H), 7.75 (s, 1H), 7.55 (d, 1H), 7.29-7.36 (m, 2H), 6.65 (d, 1H), 5.80 (s, 2H), 5.05 (m, 1H), 3.71 (d, 1H), 3.48 (d, 1H), 3.35 (dd, 1H), 3.08 (dt, 1H), 2.32-2.47 (m, 1H), 2.25-2.34 (m, 1H), 2.18 (br.s, 1H).

LC/MS: mass calcd. for $C_{24}H_{18}ClF_3N_4O_3S$: 534.07. found 535.3 [M+1]$^+$.

Example 342

(5Z)-5-({1-[4-Chloro-2-(trifluoromethyl)benzyl]-1H-indazol-5-yl}methylidene)-3-(1-methyl-3-oxopiperidin-4-yl)-1,3-thiazolidine-2,4-dione

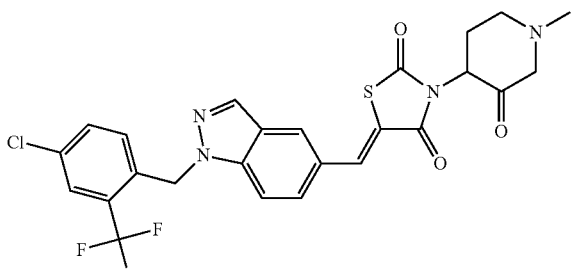

(5Z)-5-({1-[4-Chloro-2-(trifluoromethyl)benzyl]-1H-indazol-5-yl}methylidene)-3-(1-methyl-3-oxopiperidin-4-yl)-1,3-thiazolidine-2,4-dione was prepared from (5Z)-5-({1-[4-chloro-2-(trifluoromethyl)benzyl]-1H-indazol-5-yl}methylidene)-3-(3-oxopiperidin-4-yl)-1,3-thiazolidine-2,4-dione (Example 341) following General Procedure R.

$^1$H NMR (400 MHZ, CDCl$_3$): δ 8.22 (s, 1H), 8.01 (s, 1H), 7.96 (s, 1H), 7.72 (d, 1H), 7.51 (dd, 1H), 7.35 (d, 2H), 6.68 (d, 1H), 5.80 (s, 2H), 4.91 (dd, 1H), 3.48 (dd, 1H), 3.00-3.13 (m, 1H), 2.94 (d, 1H), 2.75-2.89 (m, 1H), 2.63 (dt, 1H), 2.42 (s, 3H), 2.15 (m, 1H).

LC/MS: mass calcd. for $C_{25}H_{20}ClF_3N_4O_3S$: 548.09. found 549.4 [M+1]$^+$.

Example 343

(5Z)-5-({1-[4-Chloro-2-(trifluoromethyl)benzyl]-1H-indazol-5-yl}methylidene)-3-(4-oxopiperidin-3-yl)-1,3-thiazolidine-2,4-dione

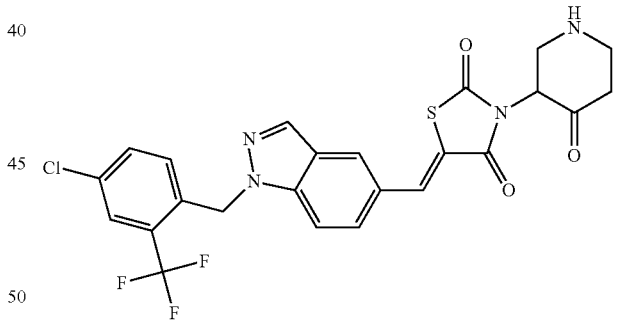

(A) (5Z)-3-{5-[1-(4-chloro-2-trifluoromethylbenzyl)-1H-indazol-5-ylmethylene]-2,4-dioxothiazolidin-3-yl}-4-hydroxypiperidine-1-carboxylic acid tert-butyl ester was prepared from 1,1-dimethylethyl trans-3-(2,4-dioxo-1,3-thiazolidin-3-yl)-4-hydroxypiperidine-1-carboxylate (from Example 270) and [4-chloro-2-(trifluoromethyl)benzyl]-1H-indazol-5-carbaldehyde (from Example 1) following General Procedure F1.

(B) To a solution of 3-{5-[1-(4-chloro-2-trifluoromethylbenzyl)-1H-indazol-5-ylmethylene]-2,4-dioxothiazolidin-3-yl}-4-hydroxypiperidine-1-carboxylic acid tert-butyl ester (0.2 mmol) in DCM (2 mL) was added Dess-Martin periodinane powder (0.25 mmol). The mixture was stirred at rt for 18 h, then purified by silica gel chromatography (0-30% EtOAc/hexanes). The product was obtained as pale yellow solid, which was treated with TFA/DCM following General Procedure M to afford the title compound.

$^1$H NMR (400 MHZ, CDCl$_3$): δ 8.21 (s, 1H), 7.99 (s, 1H), 7.95 (s, 1H), 7.71 (d, 1H), 7.49 (dd, 1H), 7.34 (d, 2H), 6.67 (d, 1H), 5.79 (s, 2H), 4.91 (dd, 1H), 3.58-3.70 (m, 1H), 3.45 (dd, 2H), 3.09 (td, 1H), 2.65-2.75 (m, 1H), 2.48-2.61 (m, 1H), 2.30 (br. s., 1H).

LC/MS: mass calcd. for C$_{24}$H$_{18}$ClF$_3$N$_4$O$_3$S: 534.07. found 535.3 [M+1]$^+$.

Example 344

(5Z)-5-({1-[4-Chloro-2-(trifluoromethyl)benzyl]-1H-indazol-5-yl}methylidene)-3-(1-methyl-4-oxopiperidin-3-yl)-1,3-thiazolidine-2,4-dione

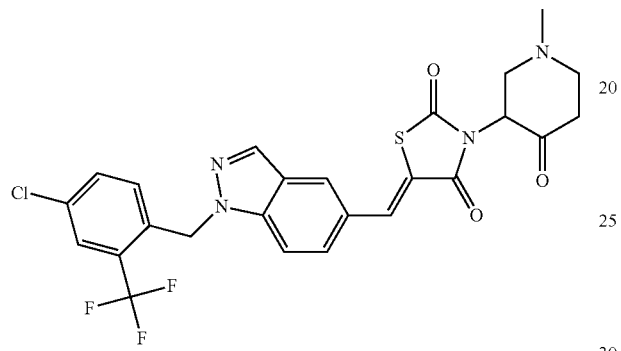

(5Z)-5-({1-[4-Chloro-2-(trifluoromethyl)benzyl]-1H-indazol-5-yl}methylidene)-3-(1-methyl-3-oxopiperidin-4-yl)-1,3-thiazolidine-2,4-dione was prepared from (5Z)-5-({1-[4-chloro-2-(trifluoromethyl)benzyl]-1H-indazol-5-yl}methylidene)-3-(4-oxopiperidin-3-yl)-1,3-thiazolidine-2,4-dione (Example 343) following General Procedure R.

$^1$H NMR (400 MHZ, CDCl$_3$): δ 8.22 (s, 1H), 8.00 (s, 1H), 7.96 (s, 1H), 7.72 (d, 1H), 7.50 (dd, 1H), 7.35 (d, 2H), 6.68 (d, 1H), 5.80 (s, 2H), 5.12 (dd, 1H), 3.04-3.19 (m, 3H), 2.54-2.81 (m, 3H), 2.48 (s, 3H).

LC/MS: mass calcd. for C$_{25}$H$_{20}$ClF$_3$N$_4$O$_3$S: 548.09. found 548.9 [M+1]$^+$.

Example 345

(5Z)-5-({1-[4-Chloro-2-(trifluoromethyl)benzyl]-1H-indazol-5-yl}methylidene)-3-(3,3-difluoropiperidin-4-yl)-1,3-thiazolidine-2,4-dione

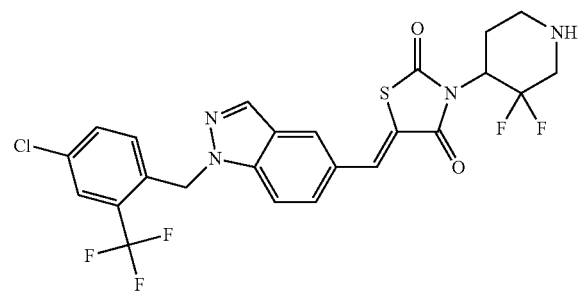 [SMILES: O=C1S/C(=C\c2ccc3c(cnn3Cc3ccc(Cl)cc3C(F)(F)F)c2)C(=O)N1C1CCNCC1(F)F]

To a solution of 4-{5-[1-(4-chloro-2-trifluoromethylbenzyl)-1H-indazol-5-ylmethylene]-2,4-dioxothiazolidin-3-yl}-3-oxopiperidine-1-carboxylic acid tert-butyl ester (0.08 mmol, from Example 341) in toluene (5 mL) in a plastic bottle was added bis(2-methoxyethyl)aminosulfur trifluoride (5 equiv) and a drop of ethanol. After stirring at 80° C. for 20 h, the reaction was concentrated and the resultant residue was purified by flash chromatography (20% EtOAc/Hexanes) to provide a pale yellow solid, which was treated with TFA/DCM following General Procedure M to afford the title compound.

$^1$H NMR (400 MHZ, CDCl$_3$): δ 8.22 (s, 1H), 8.03 (s, 1H), 7.97 (s, 1H), 7.72 (d, 1H), 7.47-7.54 (m, 1H), 7.32-7.39 (m, 2H), 6.68 (d, 1H), 5.80 (s, 2H), 4.63-4.82 (m, 1H), 3.23-3.41 (m, 3H), 3.06-3.20 (br.s., 1H), 2.88-3.05 (m, 1H), 2.69-2.82 (m, 1H), 1.89 (m, 1H).

LC/MS: mass calcd. for C$_{24}$H$_{18}$ClF$_5$N$_4$O$_2$S: 556.08. found 557.2 [M+1]$^+$.

Example 346

[(5Z)-5-({1-[4-Cyano-2-(trifluoromethyl)benzyl]-1H-indazol-5-yl}methylidene)-2,4-dioxo-1,3-thiazolidin-3-yl]acetic acid

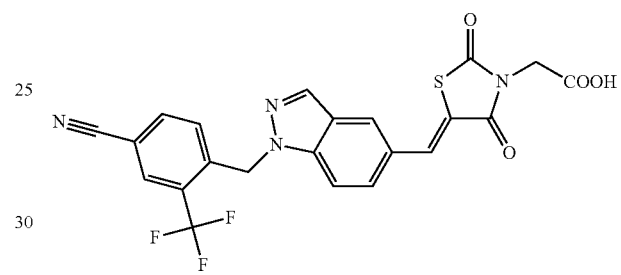

[(5Z)-5-({1-[4-Cyano-2-(trifluoromethyl)benzyl]-1H-indazol-5-yl}methylidene)-2,4-dioxo-1,3-thiazolidin-3-yl]acetic acid was prepared from [(5Z)-5-({1-[4-cyano-2-(trifluoromethyl)benzyl]-1H-indazol-5-yl}methylidene)-2,4-dioxo-1,3-thiazolidine (from Example 246) and tert-butyl bromoacetate following General Procedure I.

$^1$H NMR (400 MHZ, CDCl$_3$): δ 8.27 (s, 1H), 8.07 (s, 1H), 8.05 (s, 1H), 8.01 (s, 1H), 7.68 (d, 1H), 7.55 (dd, 1H), 7.37 (d, 1H), 6.82 (d, 1H), 5.90 (s, 2H), 4.49 (s, 2H).

LC/MS: mass calcd. for C$_{22}$H$_{13}$F$_3$N$_4$O$_4$S, 486.06. found 486.9 [M+1]$^+$.

Example 347

[(5Z)-5-({1-[4-Chloro-2-(trifluoromethyl)benzyl]-4-fluoro-1H-indazol-5-yl}methylidene)-2,4-dioxo-1,3-thiazolidin-3-yl]acetic acid

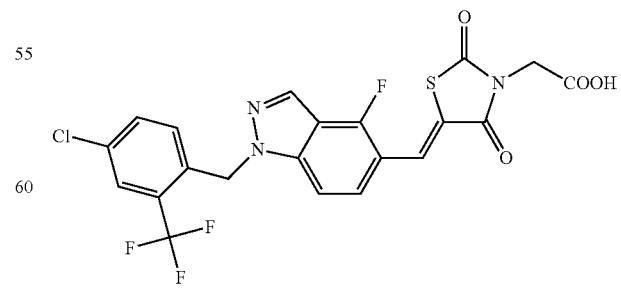

(A) To the solution of 3-fluoro-2-methylphenylamine (40 mmol) in toluene (50 mL) was added acetic anhydride (47 mmol). The mixture was heated to 100° C. for 1 h, then concentrated to give N-(3-fluoro-2-methylphenyl)acetamide as an off-white solid.

(B) To a solution of N-(3-Fluoro-2-methylphenyl)acetamide (39 mmol) in acetic acid (50 mL) was added bromine (40 mmol) in dropwise fashion. After stirring at rt for 2 days, the precipitated product was filtered, washed with water, and dried under high vacuum. N-(4-Bromo-3-fluoro-2-methylphenyl)acetamide was obtained as a white solid.

(C) N-(4-Bromo-3-fluoro-2-methylphenyl)acetamide (36 mmol) was suspended in 1,2 dichloroethane (150 mL) and acetic anhydride (108 mmol), potassium acetate (74 mmol), 18-Crown-6 (1.4 mmol) and isopentyl nitrite (79 mmol) were added sequentially. The mixture was heated at 65° C. for 24 h, cooled to rt and washed with sat. NaHCO3. The organic layer was dried (Na$_2$SO$_4$) and concentrated and the residue was purified by flash chromatography (0-20% EtOAc/hexanes). 1-(5-Bromo-4-fluoroindazol-1-yl)ethanone was obtained as a brown solid.

(D) A suspension of 1-(5-Bromo-4-fluoroindazol-1-yl)ethanone (13 mmol) in 10% HCl (40 mL) and methanol (10 mL) was heated at reflux until clear (ca. 1 h). The hot solution was filtered, cooled and pH was neutralized by the addition of NaOH solution (3N). The resultant white precipitate was collected via filtration and the solid was dried in vacuum to give 5-bromo-4-fluoro-1H-indazole.

(E) To a mixture of 5-bromo-4-fluoro-1H-indazole (4 mmol) and sodium hydride (4.3 mmol) in an Argon-purged round-bottom flask was added dry THF (10 mL) at rt. The mixture was stirred at rt for 15 min, during which time it became homogeneous (dark brown). The mixture was then cooled to −78° C., and a solution of n-butyllithium (8.7 mmol, 1.6 M in hexane) was added dropwise. After stirring for 1 h at −78° C., DMF (2 mL) was added dropwise and the mixture was allowed to warm to rt. After 3 h, the mixture was cooled to 0° C. and carefully treated with 1N HCl (20 mL). After a few minutes, solid sodium bicarbonate was added to basify the mixture to pH9-10. The aqueous solution was extracted with EtOAc(2×), and the organic layer was washed with brine, dried (Na$_2$SO$_4$) and concentrated. The residue was purified by flash chromatography (0-40% EtOAc/hexanes) to give 4-fluoro-1H-indazole-5-carbaldehyde.

(F) [4-Chloro-2-(trifluoromethyl)benzyl]-4-fluoro-1H-indazol-5-carbaldehyde was prepared from 4-fluoro-1H-indazole-5-carbaldehyde and 4-chloro-2-(trifluoromethyl)benzyl bromide following General Procedure A.

(G) [(5Z)-5-({1-[4-Chloro-2-(trifluoromethyl)benzyl]-4-fluoro-1H-indazol-5-yl}methylidene)-2,4-dioxo-1,3-thiazolidine was prepared from [4-chloro-2-(trifluoromethyl)benzyl]-4-fluoro-1H-indazol-5-carbaldehyde following General Procedure E.

(H) [(5Z)-5-({1-[4-Chloro-2-(trifluoromethyl)benzyl]-4-fluoro-1H-indazol-5-yl}methylidene)-2,4-dioxo-1,3-thiazolidin-3-yl]acetic acid was prepared from [(5Z)-5-({1-[4-chloro-2-(trifluoromethyl)benzyl]-4-fluoro-1H-indazol-5-yl}methylidene)-2,4-dioxo-1,3-thiazolidine and tert-butyl bromoacetate following General Procedure I.

$^1$H NMR (400 MHZ, CDCl$_3$): δ 8.30 (s, 1H), 8.27 (s, 1H), 7.73 (s, 1H), 7.48 (dd, 1H), 7.38 (d, 1H), 7.19 (d, 1H), 6.75 (d, 1H), 5.80 (s, 2H), 4.49 (s, 2H).

LC/MS: mass calcd. for C$_{21}$H$_{12}$ClF$_4$N$_3$O$_4$S, 513.02. found 513.8 [M+1]$^+$.

Example 348

[(5Z)-5-({1-[4-Chloro-2-(trifluoromethyl)benzyl]-6-fluoro-1H-indazol-5-yl}methylidene)-2,4-dioxo-1,3-thiazolidin-3-yl]acetic acid

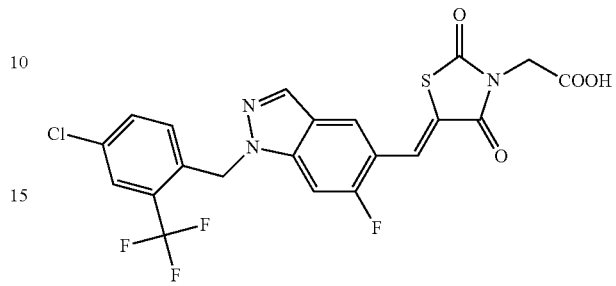

[(5Z)-5-({1-[4-Chloro-2-(trifluoromethyl)benzyl]-6-fluoro-1H-indazol-5-yl}-methylidene)-2,4-dioxo-1,3-thiazolidin-3-yl]acetic acid was prepared from 5-fluoro-2-methylphenylamine using similar methods as described in Example 347.

$^1$H NMR (400 MHZ, DMSO-d$_6$) δ 8.39 (s, 1H), 8.15 (d, 1H), 8.05 (s, 1H), 7.85-7.93 (m, 2H), 7.67 (d, 1H), 6.81 (d, 1H), 5.84 (s, 2H), 4.42 (s, 2H).

LC/MS: mass calcd. for C$_{21}$H$_{12}$ClF$_4$N$_3$O$_4$S, 513.02. found 514.2 [M+1]$^+$.

Example 349

(5Z)-5-({1-[4-Chloro-2-(trifluoromethyl)benzyl]-1H-indazol-5-yl}methylidene)-3-(4-methylpiperazin-1-yl)-1,3-thiazolidine-2,4-dione

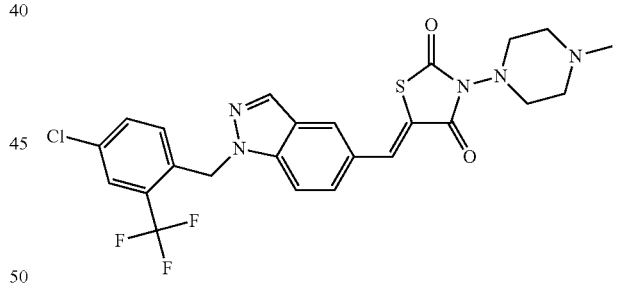

(A) 3-(4-Methylpiperazin-1-yl)-thiazolidine-2,4-dione was prepared from 4-methylpiperazin-1-ylamine following General Procedure Y.

(B) (5Z)-5-({1-[4-Chloro-2-(trifluoromethyl)benzyl]-1H-indazol-5-yl}methylidene)-3-(4-methylpiperazin-1-yl)-1,3-thiazolidine-2,4-dione was prepared from 3-(4-methyl-piperazin-1-yl)-thiazolidine-2,4-dione and [4-chloro-2-(trifluoromethyl)benzyl]-1H-indazol-5-carbaldehyde (from Example 1) following General Procedure E.

$^1$H NMR (400 MHZ, CDCl$_3$): δ 8.21 (s, 1H), 8.01 (s, 1H), 7.95 (s, 1H), 7.72 (d, 1H), 7.50 (dd, 1H), 7.34 (d, 2H), 6.68 (d, 1H), 5.79 (s, 2H), 3.42 (br. s., 4H), 2.65 (t, 4H), 2.35 (s, 3H).

LC/MS: mass calcd. for C$_{24}$H$_{21}$ClF$_3$N$_5$O$_2$S, 535.11. found 536.5 [M+1]$^+$.

Example 350

(5Z)-5-({1-[2,4-Bis(trifluoromethyl)benzyl]-1H-indazol-5-yl}methylidene)-3-(4-methylpiperazin-1-yl)-1,3-thiazolidine-2,4-dione

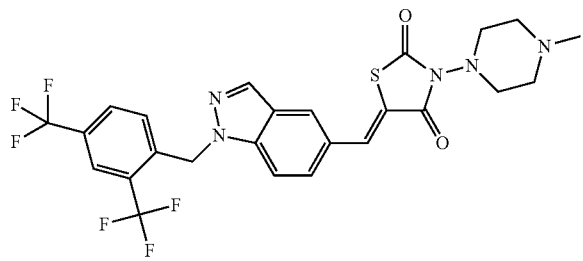 [SMILES: CN1CCN(N2C(=O)S/C(=C\c3ccc4c(cnn4Cc4ccc(C(F)(F)F)cc4C(F)(F)F)c3)C2=O)CC1]

(5Z)-5-({1-[2,4-Bis(trifluoromethyl)benzyl]-1H-indazol-5-yl}methylidene)-3-(4-methylpiperazin-1-yl)-1,3-thiazolidine-2,4-dione was prepared from 3-(4-methylpiperazin-1-yl)-thiazolidine-2,4-dione (from Example 349) and [2,4-bis(trifluoromethyl)benzyl]-1H-indazol-5-carbaldehyde (from Example 6) following General Procedure E.

$^1$H NMR (400 MHZ, CDCl$_3$): δ 8.24 (s, 1H), 8.01 (s, 1H), 7.98 (d, 2H), 7.64 (d, 1H), 7.51 (d, 1H), 7.35 (d, 1H), 6.84 (d, 1H), 5.89 (s, 2H), 3.43 (br. s., 4H), 2.65 (br. s., 4H), 2.35 (s, 3H).

LC/MS: mass calcd. for C$_{25}$H$_{21}$F$_6$N$_5$O$_2$S, 569.13. found 570.5 [M+1]$^+$.

Example 351

(5Z)-5-({1-[4-Chloro-2-(trifluoromethyl)benzyl]-1H-indazol-5-yl}methylidene)-3-piperazin-1-yl-1,3-thiazolidine-2,4-dione

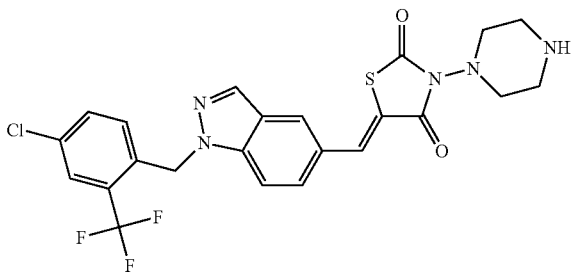 [SMILES: O=C1S/C(=C\c2ccc3c(cnn3Cc3ccc(Cl)cc3C(F)(F)F)c2)C(=O)N1N1CCNCC1]

(A) To a solution of piperazine-1-carboxylic acid tert-butyl ester (26 mmol) in DCM (130 mL) was added, in one portion, Diazald (4 eq.). After stirring at reflux for 12 h, the solution was cooled, concentrated and the residue was purified by flash chromatography (0-20% EtOAc/Heptane) to afford 4-nitrosopiperazine-1-carboxylic acid tert-butyl ester.

(B) To the solution of 4-nitrosopiperazine-1-carboxylic acid tert-butyl ester (7.4 mmol) in THF (100 mL) was added LAH (2.5 eq.) portionwise at 0° C. The solution was warmed to rt and stirred overnight, then quenched by the dropwise addition of a saturated solution of potassium sodium tartrate. The aqueous solution was extracted several times with DCM. The organic layer was dried (Na$_2$SO$_4$) and concentrated at 25° C. to afford 4-aminopiperazine-1-carboxylic acid tert-butyl ester as a white solid.

(C) 4-(2,4-Dioxothiazolidin-3-yl)piperazine-1-carboxylic acid tert-butyl ester was prepared from 4-aminopiperazine-1-carboxylic acid tert-butyl ester following General Procedure Y.

(D) ((5Z)-5-({1-[4-Chloro-2-(trifluoromethyl)benzyl]-1H-indazol-5-yl}methylidene)-3-piperazin-1-yl-1,3-thiazolidine-2,4-dione was prepared from 4-(2,4-dioxo-thiazolidin-3-yl)piperazine-1-carboxylic acid tert-butyl ester and [4-chloro-2-(trifluoromethyl)benzyl]-1H-indazol-5-carbaldehyde (from Example 1) following General Procedure F.

$^1$H NMR (400 MHZ, CDCl$_3$): δ 8.21 (s, 1H), 8.01 (s, 1H), 7.96 (s, 1H), 7.71 (d, 1H), 7.50 (dd, 1H), 7.32-7.38 (m, 2H), 6.68 (d, 1H), 5.79 (s, 2H), 3.34 (t, 4H), 3.07 (t, 4H).

LC/MS: mass calcd. for C$_{23}$H$_{19}$ClF$_3$N$_5$O$_2$S, 521.09. found 522.4 [M+1]$^+$.

Example 352

(5Z)-5-({1-[4-Chloro-2-(trifluoromethyl)benzyl]-1H-indazol-5-yl}methylidene)-3-[4-(2-methoxyethyl)piperazin-1-yl]-1,3-thiazolidine-2,4-dione

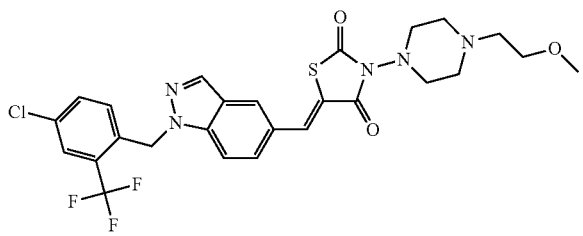 [SMILES: COCCN1CCN(N2C(=O)S/C(=C\c3ccc4c(cnn4Cc4ccc(Cl)cc4C(F)(F)F)c3)C2=O)CC1]

(5Z)-5-({1-[4-Chloro-2-(trifluoromethyl)benzyl]-1H-indazol-5-yl}methylidene)-3-[4-(2-methoxyethyl)piperazin-1-yl]-1,3-thiazolidine-2,4-dione was prepared from ((5Z)-5-({1-[4-chloro-2-(trifluoromethyl)benzyl]-1H-indazol-5-yl}methylidene)-3-piperazin-1-yl-1,3-thiazolidine-2,4-dione (Example 351) and 2-bromoethyl methyl ether following General Procedure S.

$^1$H NMR (400 MHZ, CDCl$_3$): δ 8.21 (s, 1H), 8.01 (s, 1H), 7.95 (s, 1H), 7.72 (d, 1H), 7.50 (dd, 1H), 7.36 (s, 1H), 7.33 (s, 1H), 6.68 (d, 1H), 5.79 (s, 2H), 3.53 (t, 2H), 3.43 (br. s., 4H), 3.37 (s, 3H), 2.73 (t, 4H), 2.65 (t, 2H).

LC/MS: mass calcd. for C$_{26}$H$_{25}$ClF$_3$N$_5$O$_3$S: 579.13. found 580.5 [M+H]$^+$.

Example 353

2-{4-[(5Z)-5-({1-[4-Chloro-2-(trifluoromethyl)benzyl]-1H-indazol-5-yl}methylidene)-2,4-dioxo-1,3-thiazolidin-3-yl]piperazin-1-yl}acetamide

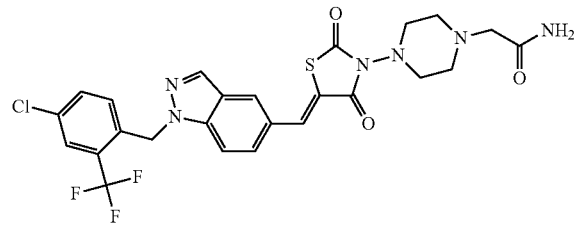 [SMILES: NC(=O)CN1CCN(N2C(=O)S/C(=C\c3ccc4c(cnn4Cc4ccc(Cl)cc4C(F)(F)F)c3)C2=O)CC1]

2-{4-[(5Z)-5-({1-[4-Chloro-2-(trifluoromethyl)benzyl]-1H-indazol-5-yl}methylidene)-2,4-dioxo-1,3-thiazolidin-3-yl]piperazin-1-yl}acetamide was prepared from ((5Z)-5-({1-[4-chloro-2-(trifluoromethyl)benzyl]-1H-indazol-5-yl}methylidene)-3-piperazin-1-yl-1,3-thiazolidine-2,4-dione (Example 351) and 2-bromoacetamide following General Procedure S.

$^1$H NMR (400 MHZ, CDCl$_3$): δ 8.22 (s, 1H), 8.02 (s, 1H), 7.96 (s, 1H), 7.72 (d, 1H), 7.50 (dd, 1H), 7.32-7.39 (m, 2H), 7.07 (br. s., 1H), 6.69 (d, 1H), 5.80 (s, 2H), 5.69 (br. s., 1H), 3.43 (br. s., 4H), 3.09 (s, 2H), 2.79 (t, 4H).

LC/MS: mass calcd. for $C_{25}H_{22}ClF_3N_6O_3S$: 578.11. found 579.5 $[M+H]^+$.

Example 354

(5Z)-5-({1-[4-Chloro-2-(trifluoromethyl)benzyl]-1H-indazol-5-yl}methylidene)-3-[4-(2-hydroxyethyl)piperazin-1-yl]-1,3-thiazolidine-2,4-dione

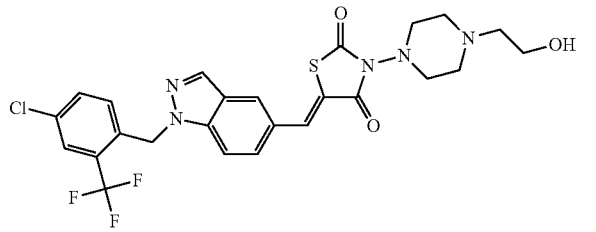 [SMILES: O=C1S/C(=C\c2ccc3c(cnn3Cc3ccc(Cl)cc3C(F)(F)F)c2)C(=O)N1N1CCN(CCO)CC1]

(5Z)-5-({1-[4-Chloro-2-(trifluoromethyl)benzyl]-1H-indazol-5-yl}methylidene)-3-[4-(2-hydroxyethyl)piperazin-1-yl]-1,3-thiazolidine-2,4-dione was prepared from ((5Z)-5-({1-[4-chloro-2-(trifluoromethyl)benzyl]-1H-indazol-5-yl}methylidene)-3-piperazin-1-yl-1,3-thiazolidine-2,4-dione (Example 351) and 2-bromoethanol following General Procedure S.

$^1$H NMR (400 MHZ, CDCl$_3$): δ 8.22 (s, 1H), 8.04 (s, 1H), 7.97 (s, 1H), 7.72 (d, 1H), 7.51 (dd, 1H), 7.36 (d, 2H), 6.69 (d, 1H), 5.80 (s, 2H), 3.64 (t, 2H), 3.43 (br. s., 4H), 2.75 (t, 4H), 2.62 (t, 2H).

LC/MS: mass calcd. for $C_{25}H_{23}ClF_3N_5O_3S$: 565.12. found 566.5 $[M+H]^+$.

Example 355

(5Z)-3-Amino-5-({1-[4-chloro-2-(trifluoromethyl)benzyl]-1H-indazol-5-yl}methylidene)-1,3-thiazolidine-2,4-dione

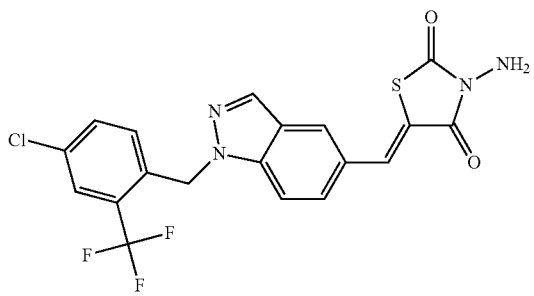 [SMILES: NN1C(=O)S/C(=C\c2ccc3c(cnn3Cc3ccc(Cl)cc3C(F)(F)F)c2)C1=O]

(A) (2,4-Dioxothiazolidin-3-yl)-carbamic acid tert-butyl ester was prepared from hydrazinecarboxylic acid tert-butyl ester following General Procedure Y.

(B) (5Z)-{5-[1-(4-Chloro-2-trifluoromethylbenzyl)-1H-indazol-5-ylmethylene]-2,4-dioxothiazolidin-3-yl}carbamic acid tert-butyl ester was prepared from (2,4-dioxothiazolidin-3-yl)carbamic acid tert-butyl ester and [4-chloro-2-(trifluoromethyl)benzyl]-1H-indazol-5-carbaldehyde (from Example 1) following General Procedure F1. The Boc group was removed by TFA/DCM following General Procedure M to afford the title compound.

$^1$H NMR (400 MHZ, CDCl$_3$): δ 8.23 (s, 1H), 8.10 (s, 1H), 7.98 (s, 1H), 7.72 (d, 1H), 7.52 (dd, 1H), 7.33-7.40 (m, 2H), 6.68 (d, 1H), 5.80 (s, 2H), 4.46 (s, 2H).

LC/MS: mass calcd. for $C_{19}H_{12}ClF_3N_4O_2S$, 452.03. found 453.3 $[M+1]^+$.

Example 356

N-[(5Z)-5-({1-[4-Chloro-2-(trifluoromethyl)benzyl]-1H-indazol-5-yl}methylidene)-2,4-dioxo-1,3-thiazolidin-3-yl]acetamide

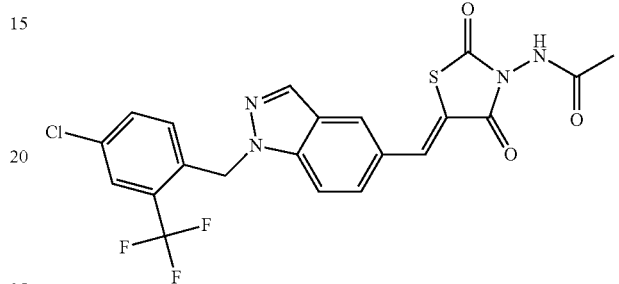

N-[(5Z)-5-({1-[4-Chloro-2-(trifluoromethyl)benzyl]-1H-indazol-5-yl}methylidene)-2,4-dioxo-1,3-thiazolidin-3-yl]acetamide was prepared from (5Z)-3-amino-5-({1-[4-chloro-2-(trifluoromethyl)benzyl]-1H-indazol-5-yl}methylidene)-1,3-thiazolidine-2,4-dione (Example 355) following General Procedure V.

$^1$H NMR (400 MHZ, DMSO-d$_6$): δ 10.91 (br. s., 1H), 8.37 (s, 1H), 8.21 (s, 1H), 8.17 (s, 1H), 7.87 (d, 1H), 7.81 (d, 1H), 7.71 (d, 1H), 7.64 (dd, 1H), 6.77 (d, 1H), 5.86 (s, 2H), 2.05 (s, 3H).

LC/MS: mass calcd. for $C_{21}H_{14}ClF_3N_4O_3S$, 494.04. found 495.3 $[M+1]^+$.

Example 357

(5Z)-5-({1-[2,4-Bis(trifluoromethyl)benzyl]-1H-indazol-5-yl}methylidene)-3-(methylamino)-1,3-thiazolidine-2,4-dione

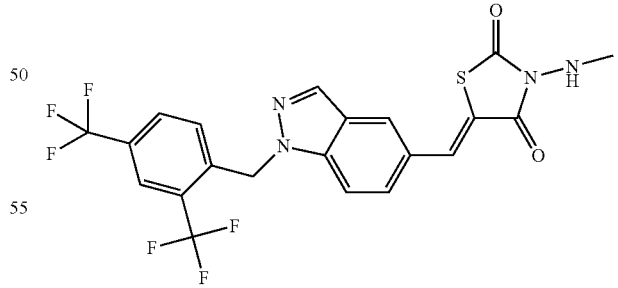

(A) 3-Methylaminothiazolidine-2,4-dione was prepared from methylhydrazine following General Procedure Y.

(B) (5Z)-5-({1-[2,4-Bis(trifluoromethyl)benzyl]-1H-indazol-5-yl}methylidene)-3-(methylamino)-1,3-thiazolidine-2,4-dione was prepared from 3-methylaminothiazolidine-2,4-dione and 2,4-bis(trifluoromethyl)benzyl]-1H-indazol-5-carbaldehyde (from Example 6) following General Procedure E.

<sup>1</sup>H NMR (400 MHZ, CDCl$_3$): δ 8.26 (s, 1H), 8.09 (s, 1H), 7.99 (s, 2H), 7.64 (d, 1H), 7.53 (dd, 1H), 7.37 (d, 1H), 6.84 (d, 1H), 5.90 (s, 2H), 4.89 (q, 1H), 2.84 (d, 3H).

LC/MS: mass calcd. for $C_{21}H_{14}F_6N_4O_2S$, 500.07. found 501.3 [M+1]$^+$.

Example 358

(5Z)-5-({1-[4-Chloro-2-(trifluoromethyl)benzyl]-1H-indazol-5-yl}methylidene)-3-(methylamino)-1,3-thiazolidine-2,4-dione

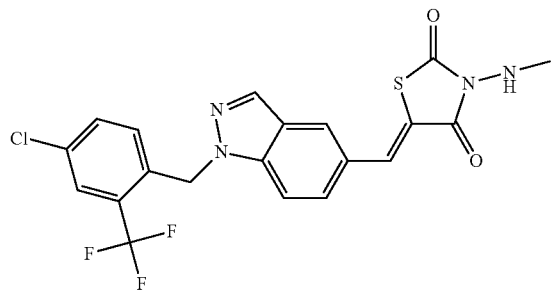 [SMILES: CNN1C(=O)S/C(=C\c2ccc3c(cnn3Cc3ccc(Cl)cc3C(F)(F)F)c2)C1=O]

(5Z)-5-({1-[4-Chloro-2-(trifluoromethyl)benzyl]-1H-indazol-5-yl}methylidene)-3-(methylamino)-1,3-thiazolidine-2,4-dione was prepared from 3-methylaminothiazolidine-2,4-dione (from Example 357) and [4-chloro-2-(trifluoromethyl)benzyl]-1H-indazol-5-carbaldehyde (from Example 1) following General Procedure E.

<sup>1</sup>H NMR (400 MHZ, CDCl$_3$): δ 8.23 (s, 1H), 8.09 (s, 1H), 7.98 (s, 1H), 7.72 (d, 1H), 7.51 (dd, 1H), 7.32-7.39 (m, 2H), 6.68 (d, 1H), 5.80 (s, 2H), 4.88 (q, 1H), 2.84 (d, 3H).

LC/MS: mass calcd. for $C_{20}H_{14}ClF_3N_4O_2S$, 466.05. found 467.3 [M+1]$^+$.

Example 359

(5Z)-5-({1-[4-Chloro-2-(trifluoromethyl)benzyl]-1H-indazol-5-yl}methylidene)-3-morpholin-4-yl-1,3-thiazolidine-2,4-dione

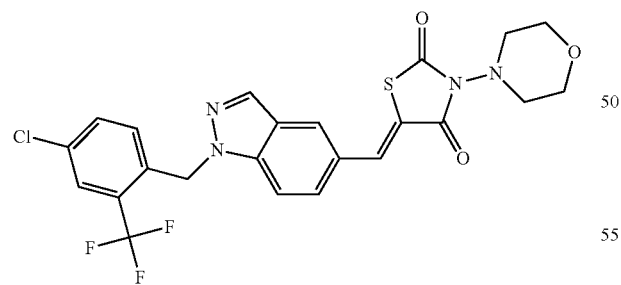

(A) 3-Morpholin-4-yl-thiazolidine-2,4-dione was prepared from morpholin-4-ylamine following General Procedure Y.

(B) (5Z)-5-({1-[4-Chloro-2-(trifluoromethyl)benzyl]-1H-indazol-5-yl}methylidene)-3-morpholin-4-yl-1,3-thiazolidine-2,4-dione was prepared from 3-morpholin-4-yl-thiazolidine-2,4-dione and [4-chloro-2-(trifluoromethyl)benzyl]-1H-indazol-5-carbaldehyde (from Example 1) following General Procedure F.

<sup>1</sup>H NMR (400 MHZ, CDCl$_3$): δ 8.22 (s, 1H), 8.02 (s, 1H), 7.96 (s, 1H), 7.72 (d, 1H), 7.50 (dd, 1H), 7.32-7.39 (m, 2H), 6.69 (d, 1H), 5.80 (s, 2H), 3.88 (t, 4H), 3.35-3.47 (m, 4H).

LC/MS: mass calcd. for $C_{23}H_{18}ClF_3N_4O_3S$, 522.07. found 523.4 [M+1]$^+$.

Example 360

N-[(5Z)-5-({1-[2,4-Bis(trifluoromethyl)benzyl]-1H-indazol-5-yl}methylidene)-2,4-dioxo-1,3-thiazolidin-3-yl]methanesulfonamide

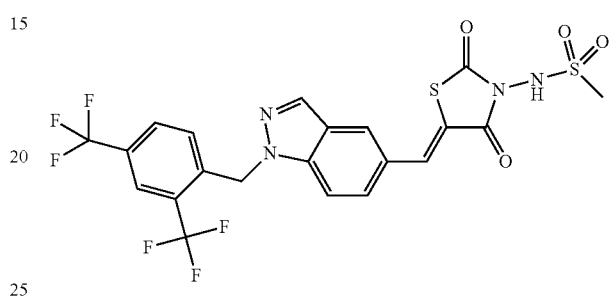

(A) N-(2,4-Dioxothiazolidin-3-yl)methanesulfonamide was prepared from methanesulfonyl hydrazide following General Procedure Y.

(B) N-[(5Z)-5-({1-[2,4-Bis(trifluoromethyl)benzyl]-1H-indazol-5-yl}methylidene)-2,4-dioxo-1,3-thiazolidin-3-yl]methanesulfonamide was prepared from N-(2,4-dioxo-thiazolidin-3-yl)-methanesulfonamide and 2,4-bis(trifluoromethyl)benzyl]-1H-indazol-5-carbaldehyde (from Example 6) following General Procedure E. The compound was made as an ethanolamine salt following General Procedure T.

<sup>1</sup>H NMR (400 MHZ, CDCl$_3$): δ 8.08 (s, 1H), 7.98 (s, 1H), 7.94 (s, 1H), 7.81 (s, 1H), 7.62 (d, 1H), 7.36-7.43 (m, 1H), 7.21 (d, 1H), 6.81 (d, 1H), 5.81 (s, 2H), 5.57 (br. s., 1H), 3.90-3.98 (m, 2H), 3.21-3.30 (m, 2H), 3.01 (s, 3H).

LC/MS: mass calcd. for $C_{21}H_{14}F_6N_4O_4S_2$, 564.04. found 565.4 [M+1]$^+$.

Example 361

N-[(5Z)-5-({1-[4-Chloro-2-(trifluoromethyl)benzyl]-1H-indazol-5-yl}methylidene)-2,4-dioxo-1,3-thiazolidin-3-yl]methanesulfonamide

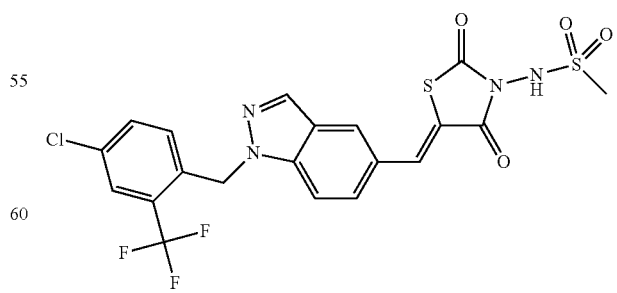

N-[(5Z)-5-({1-[4-Chloro-2-(trifluoromethyl)benzyl]-1H-indazol-5-yl}methylidene)-2,4-dioxo-1,3-thiazolidin-3-yl]methanesulfonamide was prepared from N-(2,4-dioxo-thiazolidin-3-yl)-methanesulfonamide (from Example 360) and [4-chloro-2-(trifluoromethyl)benzyl]-1H-indazol-5-carbaldehyde (from Example 1) following General Procedure E. The compound was made as an ethanolamine salt following General Procedure T.

$^1$H NMR (400 MHZ, CDCl$_3$): δ 8.02 (s, 1H), 7.90 (s, 1H), 7.75 (s, 1H), 7.70 (d, 1H), 7.29-7.39 (m, 2H), 7.16 (d, 1H), 6.63 (d, 1H), 6.23 (br. s., 4H), 5.69 (s, 2H), 3.96 (br. s., 2H), 3.28 (br. s., 2H), 2.97 (s, 3H).

LC/MS: mass calcd. for C$_{20}$H$_{14}$ClF$_3$N$_4$O$_4$S$_2$, 530.01. found 531.2 [M+1]$^+$.

Example 362

N-[(5Z)-5-({1-[4-Cyano-2-(trifluoromethyl)benzyl]-1H-indazol-5-yl}methylidene)-2,4-dioxo-1,3-thiazolidin-3-yl]methanesulfonamide

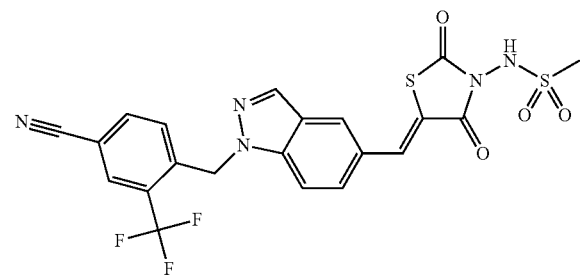 [SMILES: CS(=O)(=O)NN1C(=O)S/C(=C\c2ccc3c(cnn3Cc3ccc(C#N)cc3C(F)(F)F)c2)C1=O]

N-[(5Z)-5-({1-[4-Cyano-2-(trifluoromethyl)benzyl]-1H-indazol-5-yl}methylidene)-2,4-dioxo-1,3-thiazolidin-3-yl]methanesulfonamide was prepared from N-(2,4-dioxothiazolidin-3-yl)methanesulfonamide (from Example 360) and [4-cyano-2-(trifluoromethyl)benzyl]-1H-indazol-5-carbaldehyde (from Example 346) following General Procedure E.

$^1$H NMR (400 MHZ, DMSO-d$_6$) δ 10.91 (br. s., 1H), 8.42 (s, 1H), 8.39 (s, 1H), 8.24 (s, 1H), 8.22 (s, 1H), 8.04 (d, 1H), 7.86 (d, 1H), 7.74 (d, 1H), 6.85 (d, 1H), 5.98 (s, 2H), 3.21 (s, 3H).

LC/MS: mass calcd. for C$_{21}$H$_{14}$F$_3$N$_5$O$_4$S$_2$, 521.04. found 522.3 [M+1]$^+$.

Example 363

N-[(5Z)-5-({1-[4-Fluoro-2-(trifluoromethyl)benzyl]-1H-indazol-5-yl}methylidene)-2,4-dioxo-1,3-thiazolidin-3-yl]methanesulfonamide

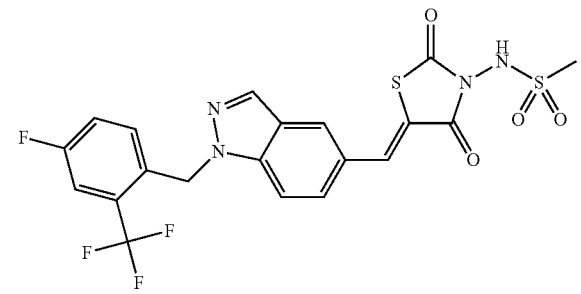 [SMILES: CS(=O)(=O)NN1C(=O)S/C(=C\c2ccc3c(cnn3Cc3ccc(F)cc3C(F)(F)F)c2)C1=O]

N-[(5Z)-5-({1-[4-Fluoro-2-(trifluoromethyl)benzyl]-1H-indazol-5-yl}methylidene)-2,4-dioxo-1,3-thiazolidin-3-yl]methanesulfonamide was prepared from N-(2,4-dioxothiazolidin-3-yl)methanesulfonamide (from Example 360) and [4-fluoro-2-(trifluoromethyl)benzyl]-1H-indazol-5-carbaldehyde (from Example 5) following General Procedure E.

$^1$H NMR (400 MHZ, DMSO-d$_6$) δ 10.90 (br. s., 1H), 8.38 (5, 1H), 8.22 (5, 2H), 7.84 (d, 1H), 7.68-7.76 (m, 2H), 7.40-7.51 (m, 1H), 6.88 (dd, 1H), 5.87 (5, 2H), 3.22 (5, 3H).

LC/MS: mass calcd. for C$_{20}$H$_{14}$F$_4$N$_4$O$_4$S$_2$, 514.04. found 514.9 [M+1]$^+$.

Example 364

N-[(5Z)-5-({1-[4-Bromo-2-(trifluoromethyl)benzyl]-1H-indazol-5-yl}methylidene)-2,4-dioxo-1,3-thiazolidin-3-yl]methanesulfonamide

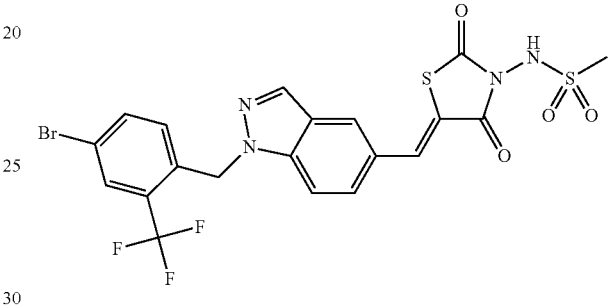

(A) [4-Bromo-2-(trifluoromethyl)benzyl]-1H-indazol-5-carbaldehyde was prepared from 4-bromo-2-(trifluoromethyl)benzyl bromide and 1H-indazol-5-carbaldehyde following General Procedure A.

(B) N-[(5Z)-5-({1-[4-Bromo-2-(trifluoromethyl)benzyl]-1H-indazol-5-yl}methylidene)-2,4-dioxo-1,3-thiazolidin-3-yl]methanesulfonamide was prepared from N-(2,4-dioxothiazolidin-3-yl)methanesulfonamide (from Example 360) and [4-bromo-2-(trifluoromethyl)benzyl]-1H-indazol-5-carbaldehyde following General Procedure E.

$^1$H NMR (400 MHZ, DMSO-d$_6$) δ 10.90 (br. s., 1H), 8.39 (s, 1H), 8.20-8.26 (m, 2H), 8.00 (d, 1H), 7.77-7.86 (m, 2H), 7.72 (dd, 1H), 6.71 (d, 1H), 5.86 (s, 2H), 3.21 (s, 3H).

LC/MS: mass calcd. for C$_{20}$H$_{14}$BrF$_3$N$_4$O$_4$S$_2$, 573.96. found 576.8 [M+1]$^+$.

Example 365

N-[(5Z)-5-({1-[4-Chloro-2-(trifluoromethyl)benzyl]-3-methyl-1H-indazol-5-yl}methylidene)-2,4-dioxo-1,3-thiazolidin-3-yl]methanesulfonamide

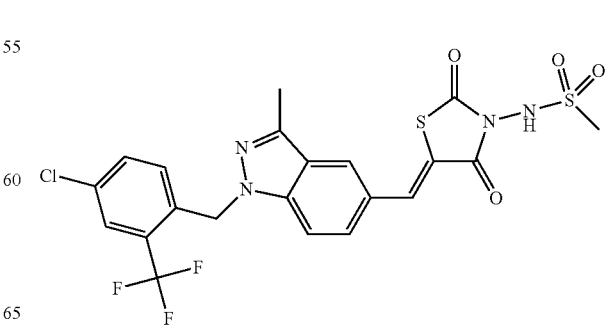

N-[(5Z)-5-({1-[4-Chloro-2-(trifluoromethyl)benzyl]-3-methyl-1H-indazol-5-yl}methylidene)-2,4-dioxo-1,3-thiazolidin-3-yl]methanesulfonamide was prepared from N-(2,4-dioxothiazolidin-3-yl)methanesulfonamide (from Example 360) and 1-[4-chloro-2-(trifluoromethyl)benzyl]-3-methyl-1H-indazol-5-carbaldehyde (from Example 36) following General Procedure E.

$^1$H NMR (400 MHZ, CDCl$_3$): δ 8.12 (s, 1H), 7.88 (s, 1H), 7.71 (s, 1H), 7.48 (d, 1H), 7.35 (d, 1H), 7.29 (d, 1H), 6.65 (d, 1H), 5.69 (s, 2H), 3.30 (s, 3H), 2.65 (s, 3H).

LC/MS: mass calcd. for C$_{21}$H$_{16}$ClF$_3$N$_4$O$_4$S$_2$, 544.03. found 545.3 [M+1]$^+$.

Example 366

N-[(5Z)-5-({3-Chloro-1-[4-chloro-2-(trifluoromethyl)benzyl]-1H-indazol-5-yl}methylidene)-2,4-dioxo-1,3-thiazolidin-3-yl]methanesulfonamide

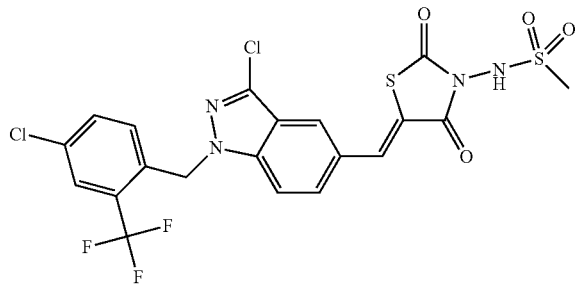

N-[(5Z)-5-({3-Chloro-1-[4-chloro-2-(trifluoromethyl)benzyl]-1H-indazol-5-yl}methylidene)-2,4-dioxo-1,3-thiazolidin-3-yl]methanesulfonamide was prepared from N-(2,4-dioxo-thiazolidin-3-yl)-methanesulfonamide (from Example 360) and 1-[4-chloro-2-(trifluoromethyl)benzyl]-3-chloro-1H-indazol-5-carbaldehyde (from Example 287) following General Procedure F.

$^1$H NMR (400 MHZ, CDCl$_3$): δ 8.13 (s, 1H), 7.90 (s, 1H), 7.72 (d, 1H), 7.55 (dd, 1H), 7.40 (dd, 1H), 7.36 (d, 1H), 6.85 (d, 1H), 5.73 (s, 2H), 3.30 (s, 3H).

LC/MS: mass calcd. for C$_{20}$H$_{13}$Cl$_2$F$_3$N$_4$O$_4$S$_2$, 563.97. found 565.1 [M+1]$^+$.

Example 367

N-[(5Z)-5-({1-[4-Chloro-2-(trifluoromethyl)benzyl]-3-iodo-1H-indazol-5-yl}methylidene)-2,4-dioxo-1,3-thiazolidin-3-yl]methanesulfonamide

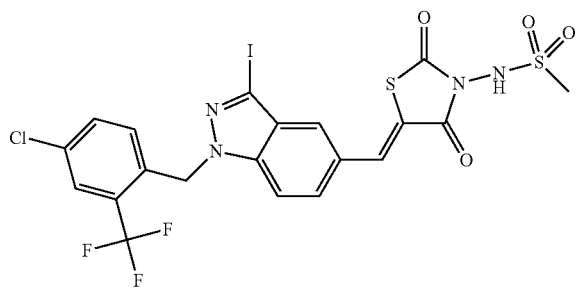

(A) To an ice-cooled solution of 1H-indazol-5-carbaldehyde (34 mmol) and KOH (37 mmol) in DMF (50 mL) was added I$_2$ (37 mmol) portionwise over 30 min. The mixture was allowed to warm to rt for 6 h. Water was added and then sat. Na$_2$S$_2$O$_3$ solution was added to quench excess I$_2$. The aqueous solution was extracted with EtOAc and the organic layer was dried (Na$_2$SO$_4$) and concentrated. The residue was purified by flash chromatography (EtOAc/hexane) to afford 3-iodo-1H-indazol-5-carbaldehyde.

(B) 1-[4-Chloro-2-(trifluoromethyl)benzyl]-3-iodo-1H-indazol-5-carbaldehyde was prepared from 3-iodo-1H-indazol-5-carbaldehyde and 4-chloro-2-(trifluoromethyl)benzyl bromide following General Procedure A.

(C) N-[(5Z)-5-({1-[4-Chloro-2-(trifluoromethyl)benzyl]-3-iodo-1H-indazol-5-yl}methylidene)-2,4-dioxo-1,3-thiazolidin-3-yl]methanesulfonamide was prepared from N-(2,4-dioxothiazolidin-3-yl)methanesulfonamide (from Example 360) and 1-[4-chloro-2-(trifluoromethyl)benzyl]-3-iodo-1H-indazol-5-carbaldehyde following General Procedure F.

$^1$H NMR (400 MHZ, CDCl$_3$): δ 8.14 (s, 1H), 7.72 (s, 2H), 7.55 (dd, 1H), 7.38 (dd, 1H), 7.34 (d, 1H), 6.78 (d, 1H), 5.80 (s, 2H), 3.30 (s, 3H).

LC/MS: mass calcd. for C$_{20}$H$_{13}$ClF$_3$IN$_4$O$_4$S$_2$, 655.91. found 656.7 [M+1]$^+$.

Example 368

N-[(5Z)-5-({1-[4-Chloro-2-(trifluoromethyl)benzyl]-3-fluoro-1H-indazol-5-yl}methylidene)-2,4-dioxo-1,3-thiazolidin-3-yl]methanesulfonamide (A) A suspension of 1-[4-Chloro-2-(trifluoromethyl)benzyl]-1H-indazol-5-carbaldehyde (0.9 mmol, from Example 1)) and SelectFluor® (2 eq., Aldrich) in CH$_3$CN (3 mL) was heated in a microwave reactor at 140° C. for 30 min. The solvent was evaporated and the residue was washed with DCM. The insoluble solid was discarded. The combined organic washings were concentrated and the residue was purified by flash chromatography (0-20% EtOAc/Hex) to afford 1-[4-chloro-2-(trifluoromethyl)benzyl]-3-fluoro-1H-indazol-5-carbaldehyde.

(B) N-[(5Z)-5-({1-[4-Chloro-2-(trifluoromethyl)benzyl]-3-fluoro-1H-indazol-5-yl}methylidene)-2,4-dioxo-1,3-thiazolidin-3-yl]methanesulfonamide was prepared from N-(2,4-dioxothiazolidin-3-yl)methanesulfonamide (from Example 360) and 1-[4-chloro-2-(trifluoromethyl)benzyl]-3-fluoro-1H-indazol-5-carbaldehyde following General Procedure F. The compound was converted to the corresponding ethanolamine salt following General Procedure T.

$^1$H NMR (400 MHZ, DMSO-d$_6$): δ 8.06 (s, 1H), 8.00 (s, 1H), 7.83-7.92 (m, 2H), 7.76 (d, 1H), 7.69 (d, 1H), 6.97 (d, 1H), 5.75 (s, 2H), 3.57 (t, 2H), 2.85 (t, 2H), 2.67 (s, 3H).

LC/MS: mass calcd. for C$_{20}$H$_{13}$ClF$_4$N$_4$O$_4$S$_2$, 548.00. found 548.9 [M+1]$^+$.

Example 369

N-[(5Z)-5-({1-[2,4-Bis(trifluoromethyl)benzyl]-3-cyano-1H-indazol-5-yl}-methylidene)-2,4-dioxo-1,3-thiazolidin-3-yl]methanesulfonamide

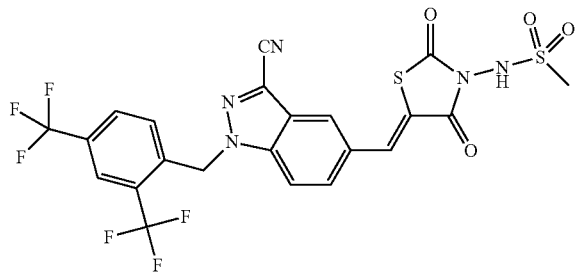 [SMILES: CS(=O)(=O)NN1C(=O)S/C(=C\c2ccc3c(c2)c(C#N)nn3Cc2ccc(C(F)(F)F)cc2C(F)(F)F)C1=O]

(A) 1-[2,4-Bis(trifluoromethyl)benzyl]-3-iodo-1H-indazol-5-carbaldehyde was prepared from 3-iodo-1H-indazol-5-carbaldehyde (from Example 367) and 2,4-bis-(trifluoromethyl)benzyl bromide following General Procedure A.

(B) A mixture of 1-[2,4-bis(trifluoromethyl)benzyl]-3-iodo-1H-indazol-5-carbaldehyde (2 mmol) and CuCN (5 mmol) in DMF (5 mL) was heated under microwave irradiation at 170° C. for 30 min. The mixture was partitioned between EtOAc and water. The EtOAc extracts were combined, washed with brine, dried ($Na_2SO_4$) and concentrated. The residue was purified by flash chromatography (EtOAc/hexanes 1:4 v/v) to afford 1-[2,4-bis(trifluoromethyl)benzyl]-3-cyano-1H-indazol-5-carbaldehyde as a white solid.

(C) N-[(5Z)-5-({1-[2,4-Bis(trifluoromethyl)benzyl]-3-cyano-1H-indazol-5-yl}methylidene)-2,4-dioxo-1,3-thiazolidin-3-yl]methanesulfonamide was prepared from N-(2,4-dioxothiazolidin-3-yl)methanesulfonamide (from Example 360) and 1-[2,4-bis(trifluoromethyl)benzyl]-3-cyano-1H-indazol-5-carbaldehyde following General Procedure F.

$^1$H NMR (400 MHZ, $CDCl_3$): δ 8.14 (s, 1H), 8.07 (s, 1H), 8.03 (s, 1H), 7.73 (d, 1H), 7.64 (dd, 1H), 7.52 (d, 1H), 7.03 (d, 1H), 5.95 (s, 2H), 3.30 (s, 3H).

LC/MS: mass calcd. for $C_{22}H_{13}F_6N_5O_4S_2$, 589.03. found 590.2 $[M+1]^+$.

Example 370

N-[(5Z)-5-({1-[4-Chloro-2-(trifluoromethyl)benzyl]-4-fluoro-1H-indazol-5-yl}methylidene)-2,4-dioxo-1,3-thiazolidin-3-yl]methanesulfonamide

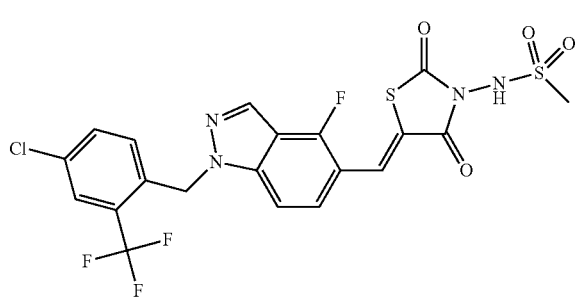 [SMILES: CS(=O)(=O)NN1C(=O)S/C(=C\c2ccc3c(cnn3Cc3ccc(Cl)cc3C(F)(F)F)c2F)C1=O]

N-[(5Z)-5-({1-[4-Chloro-2-(trifluoromethyl)benzyl]-4-fluoro-1H-indazol-5-yl}methylidene)-2,4-dioxo-1,3-thiazolidin-3-yl]methanesulfonamide was prepared from N-(2,4-dioxothiazolidin-3-yl)methanesulfonamide (from Example 360) and [4-chloro-2-(trifluoromethyl)benzyl]-4-fluoro-1H-indazol-5-carbaldehyde (from Example 347) following General Procedure E.

$^1$H NMR (400 MHZ, $CDCl_3$): δ 8.37 (s, 1H), 8.29 (s, 1H), 7.73 (d, 1H), 7.43-7.50 (m, 1H), 7.36-7.41 (m, 1H), 7.18 (d, 1H), 6.76 (d, 1H), 5.79 (s, 2H), 3.30 (s, 3H).

LC/MS: mass calcd. for $C_{20}H_{13}ClF_4N_4O_4S_2$, 548.00. found 548.9 $[M+1]^+$.

Example 371

N-[(5Z)-5-({1-[4-Chloro-2-(trifluoromethyl)benzyl]-6-fluoro-1H-indazol-5-yl}methylidene)-2,4-dioxo-1,3-thiazolidin-3-yl]methanesulfonamide

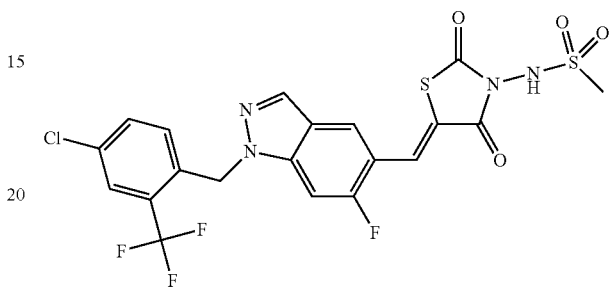

N-[(5Z)-5-({1-[4-Chloro-2-(trifluoromethyl)benzyl]-6-fluoro-1H-indazol-5-yl}methylidene)-2,4-dioxo-1,3-thiazolidin-3-yl]methanesulfonamide was prepared from N-(2,4-dioxothiazolidin-3-yl)methanesulfonamide (from Example 360) and [4-chloro-2-(trifluoromethyl)benzyl]-6-fluoro-1H-indazol-5-carbaldehyde (from Example 348) following General Procedure E.

$^1$H NMR (400 MHZ, DMSO-$d_6$): δ 8.38 (s, 1H), 8.11 (d, 1H), 7.96 (s, 1H), 7.83-7.91 (m, 2H), 7.67 (dd, 1H), 6.79 (d, 1H), 5.83 (s, 2H), 2.81 (s, 3H).

LC/MS: mass calcd. for $C_{20}H_{13}ClF_4N_4O_4S_2$, 548.00. found 548.9 $[M+1]^+$.

Example 372

N-[(5Z)-5-({1-[2,4-Bis(trifluoromethyl)benzyl]-1H-indazol-5-yl}methylidene)-2,4-dioxo-1,3-thiazolidin-3-yl]cyclopropanecarboxamide

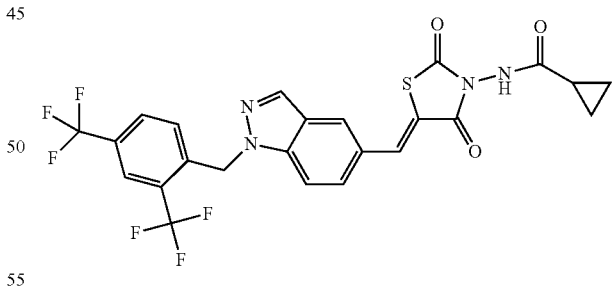

(A) Cyclopropanecarboxylic acid (2,4-dioxothiazolidin-3-yl)amide was prepared from cyclopropanecarboxylic acid hydrazide following General Procedure Y.

(B) N-[(5Z)-5-({1-[2,4-Bis(trifluoromethyl)benzyl]-1H-indazol-5-yl}methylidene)-2,4-dioxo-1,3-thiazolidin-3-yl]cyclopropanecarboxamide was prepared from cyclopropanecarboxylic acid (2,4-dioxothiazolidin-3-yl)amide and 2,4-bis(trifluoromethyl)benzyl]-1H-indazol-5-carbaldehyde (from Example 6) following General Procedure E.

$^1$H NMR (400 MHZ, DMSO-$d_6$): δ 8.40 (s, 1H), 8.22 (s, 1H), 8.16 (s, 1H), 8.11 (s, 1H), 7.96 (d, 1H), 7.84 (d, 1H), 7.71

(dd, 1H), 6.91 (d, 1H), 5.98 (br.s., 2H), 5.74 (s, 2H), 1.79 (m, 1H), 0.87-0.94 (m, 2H), 0.79 (m, 2H).

LC/MS: mass calcd. for $C_{24}H_{16}F_6N_4O_3S$, 554.08. found 554.9 $[M+1]^+$.

Example 373

N-[(5Z)-5-({1-[4-Chloro-2-(trifluoromethyl)benzyl]-1H-indazol-5-yl}methylidene)-2,4-dioxo-1,3-thiazolidin-3-yl]cyclopropanecarboxamide

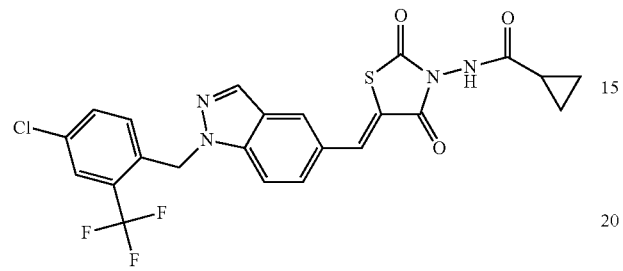

N-[(5Z)-5-({1-[4-Chloro-2-(trifluoromethyl)benzyl]-1H-indazol-5-yl}methylidene)-2,4-dioxo-1,3-thiazolidin-3-yl]cyclopropanecarboxamide was prepared from cyclopropanecarboxylic acid (2,4-dioxothiazolidin-3-yl)amide (Example 372) and 4-chloro-2-(trifluoromethyl)benzyl]-1H-indazol-5-carbaldehyde (from Example 1) following General Procedure E.

$^1$H NMR (400 MHZ, DMSO-$d_6$): δ 11.09 (br. s., 1H), 8.37 (s, 1H), 8.20 (s, 1H), 8.17 (s, 1H), 7.86-7.90 (m, 1H), 7.81 (d, 1H), 7.70 (dd, 1H), 7.64 (dd, 1H), 6.76 (d, 1H), 5.87 (s, 2H), 1.73-1.89 (m, 1H), 0.86-0.97 (m, 2H), 0.77 (m, 2H).

LC/MS: mass calcd. for $C_{23}H_{16}ClF_3N_4O_3S$, 520.06. found 520.8 $[M+1]^+$.

Example 374

N-[(5Z)-5-({1-[4-Chloro-2-(trifluoromethyl)benzyl]-4-fluoro-1H-indazol-5-yl}methylidene)-2,4-dioxo-1,3-thiazolidin-3-yl]methanesulfonamide

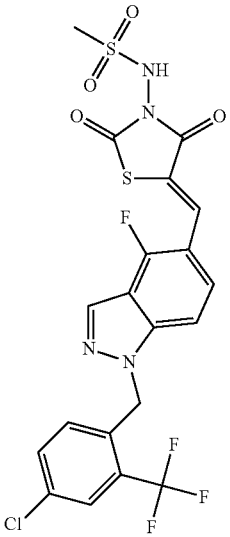 [SMILES: CS(=O)(=O)NN1C(=O)S/C(=C\c2ccc3c(cnn3Cc3ccc(Cl)cc3C(F)(F)F)c2F)C1=O]

N-[(5Z)-5-({1-[4-Chloro-2-(trifluoromethyl)benzyl]-4-fluoro-1H-indazol-5-yl}methylidene)-2,4-dioxo-1,3-thiazolidin-3-yl]methanesulfonamide was prepared from N-(2,4-dioxothiazolidin-3-yl)methanesulfonamide (from Example 360) and [4-Chloro-2-(trifluoromethyl)benzyl]-4-fluoro-1H-indazol-5-carbaldehyde (from Example 347) following General Procedure E.

$^1$H NMR (400 MHz, CDCl$_3$) δ 8.37 (s, 1H), 8.29 (s, 1H), 7.73 (d, 1H), 7.43-7.51 (m, 1H), 7.35-7.41 (m, 1H), 7.18 (d, 1H), 6.76 (s, 1H), 5.79 (s, 2H), 3.30 (s, 3H).

LC/MS: mass calcd. for $C_{20}H_{13}ClF_4N_4O_4S_2$: 548.00. found 549.3 $[M+1]^+$.

Example 375

2-[(5Z)-5-({3-Chloro-1-[4-chloro-2-(trifluoromethyl)benzyl]-1H-indazol-5-yl}methylidene)-2,4-dioxo-1,3-thiazolidin-3-yl]-N-(pyrrolidin-1-ylsulfonyl)acetamide

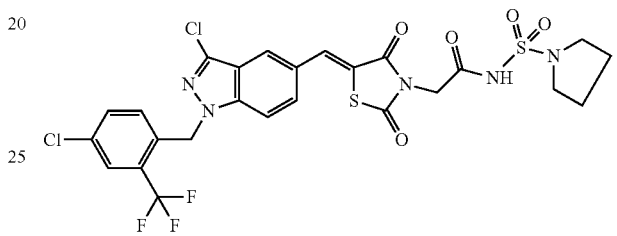

2-[(5Z)-5-({3-Chloro-1-[4-chloro-2-(trifluoromethyl)benzyl]-1H-indazol-5-yl}methylidene)-2,4-dioxo-1,3-thiazolidin-3-yl]-N-(pyrrolidin-1-ylsulfonyl)acetamide was prepared from [(5Z)-5-({1-[4-chloro-2-(trifluoromethyl)benzyl]-3-chloro-1H-indazol-5-yl}methylidene)-2,4-dioxo-1,3-thiazolidin-3-yl]acetic acid (Example 287) and pyrrolidin-1-ylsulfonic acid amide following Procedure L. The corresponding ethanolamine salt was prepared following General Procedure T.

$^1$H NMR (400 MHz, DMSO-$d_6$): δ 8.14 (s, 1H), 8.06 (s, 1H), 7.93 (d, 1H), 7.90 (d, 1H), 7.80 (dd, 1H), 7.69 (dd, 1H), 7.63 (d, 2H), 6.97 (d, 1H), 5.86 (s, 2H), 5.14 (t, 1H), 4.05 (s, 2H), 3.56 (q, 2H), 3.01 (br. s., 4H), 2.85 (t, 2H), 1.55-1.65 (m, 4H).

LC/MS: mass calcd. for $C_{25}H_{20}Cl_2F_3N_5O_5S$: 662.50. found 661.7 $[M]^+$.

Example 376

(2E)-4-[(5Z)-5-({1-[4-Chloro-2-(trifluoromethyl)benzyl]-1H-indazol-5-yl}methylidene)-2,4-dioxo-1,3-thiazolidin-3-yl]but-2-enoic acid

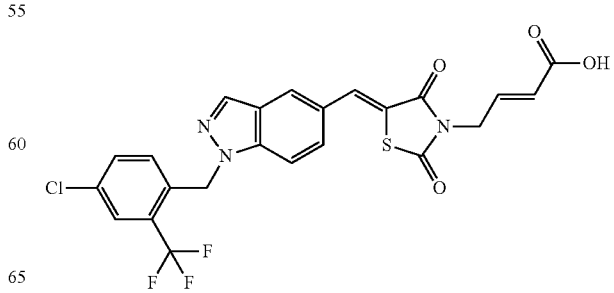

(A) (2E)-4-[(5Z)-5-({1-[4-Chloro-2-(trifluoromethyl)benzyl]-1H-indazol-5-yl}methylidene)-2,4-dioxo-1,3-thiazolidin-3-yl]but-2-enoic acid methyl ester was prepared from [(5Z)-5-({1-[4-chloro-2-(trifluoromethyl)benzyl]-1H-indazol-5-yl}methylidene)-2,4-dioxo-1,3-thiazolidine (from Example 1) and methyl 4-bromocrotonate following General Procedure S.

(B) (2E)-4-[(5Z)-5-({1-[4-Chloro-2-(trifluoromethyl)benzyl]-1H-indazol-5-yl}methylidene)-2,4-dioxo-1,3-thiazolidin-3-yl]but-2-enoic acid was obtained from (2E)-4-[(5Z)-5-({1-[4-chloro-2-(trifluoromethyl)benzyl]-1H-indazol-5-yl}methylidene)-2,4-dioxo-1,3-thiazolidin-3-yl]but-2-enoic acid methyl ester following General Procedure 0 and converted to the corresponding ethanolamine salt following General Procedure T.

$^1$H NMR (400 MHz, DMSO-$d_6$): δ 8.38 (d, 1H), 8.19 (s, 1H), 8.11 (s, 1H), 7.89 (d, 1H), 7.82 (d, 1H), 7.70 (dd, 1H), 7.66 (dd, 1H), 6.77 (d, 1H), 6.47 (dt, 1H), 5.87 (s, 2H), 5.73 (br. d., 1H), 4.36 (dd, 2H), 3.46 (t, 2H), 2.70 (t, 2H).

LC/MS: mass calcd. for $C_{23}H_{16}ClF_3N_3O_4S$: 521.91. found 521.8 [M]$^+$.

Example 377

4-{[(5Z)-5-({1-[4-Chloro-2-(trifluoromethyl)benzyl]-1H-indazol-5-yl}methylidene)-2,4-dioxo-1,3-thiazolidin-3-yl]methyl}benzoic acid

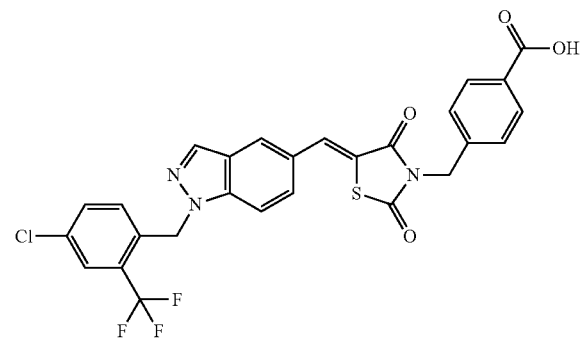 [SMILES: O=C(O)c1ccc(CN2C(=O)S/C(=C\c3ccc4c(cnn4Cc4ccc(Cl)cc4C(F)(F)F)c3)C2=O)cc1]

4-{[(5Z)-5-({1-[4-Chloro-2-(trifluoromethyl)benzyl]-1H-indazol-5-yl}methylidene)-2,4-dioxo-1,3-thiazolidin-3-yl]methyl}benzoic acid tert-butyl ester was prepared from [(5Z)-5-({1-[4-chloro-2-(trifluoromethyl)benzyl]-1H-indazol-5-yl}methylidene)-2,4-dioxo-1,3-thiazolidine (from Example 1) and tert-butyl 4-bromomethyl-benzoate (in place of tert-butyl bromoacetate) following General Procedure I, and converted to the corresponding ethanolamine salt following General Procedure T.

$^1$H NMR (400 MHz, DMSO-$d_6$): δ 2.77 (t, 5H) 3.51 (t, 5H) 4.87 (s, 2H) 5.87 (s, 2H) 6.77 (d, 1H) 7.29 (d, 2H) 7.66 (dd, 1H) 7.70 (dd, 1H) 7.78-7.87 (m, 3H) 7.89 (d, 1H) 8.13 (s, 1H) 8.19 (s, 1H) 8.38 (s, 1H).

LC/MS: mass calcd. for $C_{27}H_{17}ClF_3N_3O_4S$: 571.97. found 572.0 [M]$^+$.

Example 378

3-{[(5Z)-5-({1-[4-Chloro-2-(trifluoromethyl)benzyl]-1H-indazol-5-yl}methylidene)-2,4-dioxo-1,3-thiazolidin-3-yl]methyl}benzoic acid

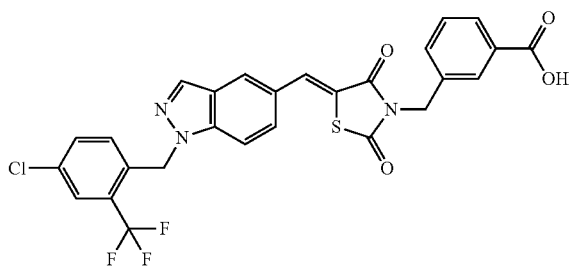 [SMILES: O=C(O)c1cccc(CN2C(=O)S/C(=C\c3ccc4c(cnn4Cc4ccc(Cl)cc4C(F)(F)F)c3)C2=O)c1]

(A) 3-{[(5Z)-5-({1-[4-Chloro-2-(trifluoromethyl)benzyl]-1H-indazol-5-yl}methylidene)-2,4-dioxo-1,3-thiazolidin-3-yl]methyl}benzoic acid methyl ester was prepared from [(5Z)-5-({1-[4-chloro-2-(trifluoromethyl)benzyl]-1H-indazol-5-yl}methylidene)-2,4-dioxo-1,3-thiazolidine (from Example 1) and methyl 3-bromomethylbenzoate following General Procedure S.

(B) 3-{[(5Z)-5-({1-[4-Chloro-2-(trifluoromethyl)benzyl]-1H-indazol-5-yl}methylidene)-2,4-dioxo-1,3-thiazolidin-3-yl]methyl}benzoic acid was prepared from 3-{[(5Z)-5-({1-[4-chloro-2-(trifluoromethyl)benzyl]-1H-indazol-5-yl}methylidene)-2,4-dioxo-1,3-thiazolidin-3-yl]methyl}benzoic acid methyl ester following General Procedure 0 and converted to the corresponding ethanolamine salt following General Procedure T.

$^1$H NMR (400 MHz, DMSO-$d_6$): δ 2.77 (t, 2H) 3.52 (t, 2H) 4.87 (s, 2H) 5.87 (s, 2H) 6.76 (d, 1H) 7.29-7.41 (m, 2H) 7.65 (dd, 1H) 7.70 (dd, 1H) 7.77-7.86 (m, 3H) 7.89 (d, 1H) 8.14 (s, 1H) 8.19 (s, 1H) 8.38 (s, 1H).

LC/MS: mass calcd. for $C_{27}H_{17}ClF_3N_3O_4S$: 571.97. found 572.0 [M]$^+$.

Example 379

2-{[(5Z)-5-({1-[4-Chloro-2-(trifluoromethyl)benzyl]-1H-indazol-5-yl}methylidene)-2,4-dioxo-1,3-thiazolidin-3-yl]methyl}benzoic acid

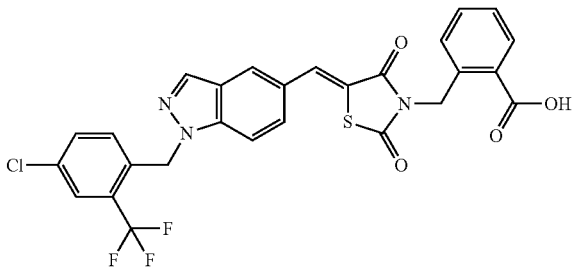 [SMILES: O=C(O)c1ccccc1CN1C(=O)S/C(=C\c2ccc3c(cnn3Cc3ccc(Cl)cc3C(F)(F)F)c2)C1=O]

(A) 2-{[(5Z)-5-({1-[4-Chloro-2-(trifluoromethyl)benzyl]-1H-indazol-5-yl}methylidene)-2,4-dioxo-1,3-thiazolidin-3-yl]methyl}benzoic acid methyl ester was prepared from

[(5Z)-5-({1-[4-chloro-2-(trifluoromethyl)benzyl]-1H-indazol-5-yl}methylidene)-2,4-dioxo-1,3-thiazolidine (from Example 1) and methyl 2-bromomethylbenzoate following General Procedure S.

(B) 2-{[(5Z)-5-({1-[4-Chloro-2-(trifluoromethyl)benzyl]-1H-indazol-5-yl}methylidene)-2,4-dioxo-1,3-thiazolidin-3-yl]methyl}benzoic acid was prepared from 2-{[(5Z)-5-({1-[4-chloro-2-(trifluoromethyl)benzyl]-1H-indazol-5-yl}methylidene)-2,4-dioxo-1,3-thiazolidin-3-yl]methyl}benzoic acid methyl ester following General Procedure 0 and converted to the corresponding ethanolamine salt following General Procedure T.

$^1$H NMR (400 MHz, DMSO-$d_6$): δ 2.83 (t, 2H) 3.57 (t, 2H) 5.30 (s, 2H) 5.88 (s, 2H) 6.78 (d, 1H) 6.83 (d, 1H) 7.16-7.32 (m, 2H) 7.67 (dd, 1H) 7.70-7.76 (m, 1H) 7.79 (dd, 1H) 7.81-7.86 (m, 1H) 7.90 (d, 1H) 8.14 (s, 1H) 8.21 (s, 1H) 8.39 (s, 1H).

LC/MS: mass calcd. for $C_{27}H_{17}ClF_3N_3O_4S$: 571.97. found 572.1 [M]$^+$.

Example 380

5-{[(5Z)-5-({1-[4-Chloro-2-(trifluoromethyl)benzyl]-1H-indazol-5-yl}methylidene)-2,4-dioxo-1,3-thiazolidin-3-yl]methyl}furan-2-carboxylic acid

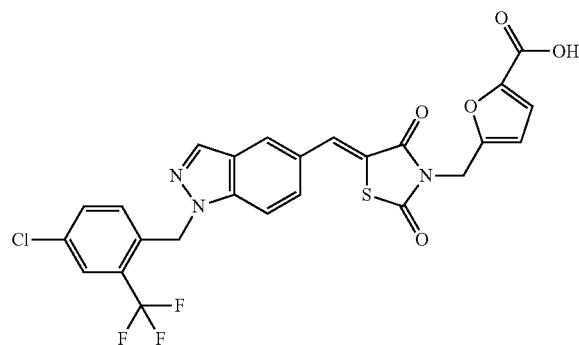 [SMILES: O=C(O)c1ccc(CN2C(=O)S/C(=C\c3ccc4c(cnn4Cc4ccc(Cl)cc4C(F)(F)F)c3)C2=O)o1]

(A) 5-{[(5Z)-5-({1-[4-Chloro-2-(trifluoromethyl)benzyl]-1H-indazol-5-yl}methylidene)-2,4-dioxo-1,3-thiazolidin-3-yl]methyl}furan-2-carboxylic acid methyl ester was prepared from [(5Z)-5-({1-[4-chloro-2-(trifluoromethyl)benzyl]-1H-indazol-5-yl}methylidene)-2,4-dioxo-1,3-thiazolidine (from Example 1) and methyl 5-chloromethylfuroate following General Procedure S (reaction time of 16 h).

(B) 5-{[(5Z)-5-({1-[4-Chloro-2-(trifluoromethyl)benzyl]-1H-indazol-5-yl}methylidene)-2,4-dioxo-1,3-thiazolidin-3-yl]methyl}furan-2-carboxylic acid was prepared from 5-{[(5Z)-5-({1-[4-chloro-2-(trifluoromethyl)benzyl]-1H-indazol-5-yl}methylidene)-2,4-dioxo-1,3-thiazolidin-3-yl]methyl}furan-2-carboxylic acid methyl ester following General Procedure 0 and converted to the corresponding ethanolamine salt following General Procedure T.

$^1$H NMR (400 MHz, DMSO-$d_6$): δ 8.38 (s, 1H), 8.18 (s, 1H), 8.13 (s, 1H), 7.89 (d, 1H), 7.82 (d, 1H), 7.70 (dd, 1H), 7.65 (dd, 1H), 7.46 (br. s., 1H), 6.76 (d, 1H), 6.54 (br. s., 1H), 6.35 (d, 1H), 5.87 (s, 2H), 5.27 (br. s., 1H), 4.82 (s, 2H), 3.55 (t, 2H), 2.82 (t, 2H).

LC/MS: mass calcd. for $C_{26}H_{16}ClF_3N_3O_6S$: 561.93. found 562.0 [M]$^+$.

Example 381

(5Z)-5-({1-[4-Chloro-2-(trifluoromethyl)benzyl]-1H-indazol-5-yl}methylidene)-3-[(3R,4R)-3-fluoropiperidin-4-yl]-1,3-thiazolidine-2,4-dione

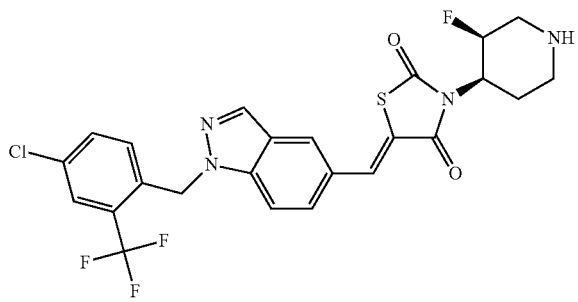 [SMILES: O=C1S/C(=C\c2ccc3c(cnn3Cc3ccc(Cl)cc3C(F)(F)F)c2)C(=O)N1[C@@H]1CCNC[C@@H]1F]

(A) 1,1-Dimethylethyl trans-4-{(5Z)-5-[(1-{[4-chloro-2-(trifluoromethyl)phenyl]methyl}-1H-indazol-5-yl)methylidene]-2,4-dioxo-1,3-thiazolidin-3-yl}-3-fluoropiperidine-1-carboxylate was prepared either from 1,1-dimethylethyl trans-4-(2,4-dioxo-1,3-thiazolidin-3-yl)-3-fluoropiperidine-1-carboxylate (from Example 273) and [4-chloro-2-(trifluoromethyl)benzyl]-1H-indazol-5-carbaldehyde (from Example 1) following General Procedure F1, or as described in Example 273, Preparation 2.

(B) Chiral resolution of 1,1-dimethylethyl trans-4-{(5Z)-5-[(1-{[4-chloro-2-(trifluoromethyl)phenyl]methyl}-1H-indazol-5-yl)methylidene]-2,4-dioxo-1,3-thiazolidin-3-yl}-3-fluoropiperidine-1-carboxylate was carried out on a 500 g Daicel Chiralcel® OD column (20 micron) eluting with ethanol to afford 1,1-dimethylethyl (3R,4R)-4-[(5Z)-5-({1-[4-chloro-2-(trifluoromethyl)benzyl]-1H-indazol-5-yl}methylidene)-2,4-dioxo-1,3-thiazolidin-3-yl]-3-fluoropiperidine-1-carboxylate (first isomer to elute) and 1,1-dimethylethyl (3S,4S)-4-[(5Z)-5-({1-[4-chloro-2-(trifluoromethyl)benzyl]-1H-indazol-5-yl}methylidene)-2,4-dioxo-1,3-thiazolidin-3-yl]-3-fluoropiperidine-1-carboxylate (second isomer to elute).

(C) (5Z)-5-({1-[4-Chloro-2-(trifluoromethyl)benzyl]-1H-indazol-5-yl}methylidene)-3-[(3R,4R)-3-fluoropiperidin-4-yl]-1,3-thiazolidine-2,4-dione was prepared from 1,1-dimethylethyl (3R,4R)-4-[(5Z)-5-({1-[4-chloro-2-(trifluoromethyl)benzyl]-1H-indazol-5-yl}methylidene)-2,4-dioxo-1,3-thiazolidin-3-yl]-3-fluoropiperidine-1-carboxylate following General Procedure M.

$^1$H NMR (400 MHz, CDCl$_3$): δ 1.74-1.89 (m, 1H) 2.43 (qd, 1H) 2.59-2.79 (m, 2H) 3.14 (d, 1H) 3.51 (dd, 1H) 4.40-4.57 (m, 1H) 5.22 (d. sxt., 1H) 5.80 (s, 2H) 6.68 (d, 1H) 7.32-7.41 (m, 2H) 7.51 (dd, 1H) 7.72 (d, 1H) 7.97 (s, 1H) 8.02 (s, 1H) 8.22 (s, 1H).

LC/MS: mass calcd. for $C_{24}H_{19}ClF_4N_4O_2S$: 538.95. found 539.0 [M]$^+$.

Example 382

(5Z)-5-({1-[4-Chloro-2-(trifluoromethyl)benzyl]-1H-indazol-5-yl}methylidene)-3-[(3S,4S)-3-fluoropiperidin-4-yl]-1,3-thiazolidine-2,4-dione

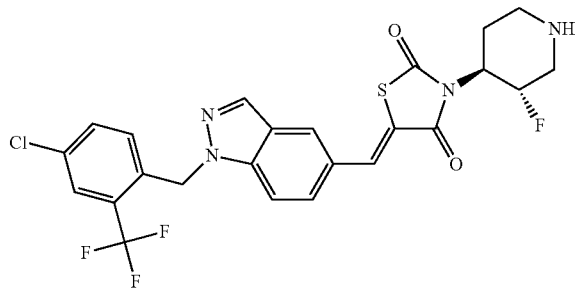 [SMILES: O=C1S/C(=C\c2ccc3c(cnn3Cc3ccc(Cl)cc3C(F)(F)F)c2)C(=O)N1[C@H]1CCNC[C@@H]1F]

(5Z)-5-({1-[4-Chloro-2-(trifluoromethyl)benzyl]-1H-indazol-5-yl}methylidene)-3-[(3S,4S)-3-fluoropiperidin-4-yl]-1,3-thiazolidine-2,4-dione was prepared from 1,1-dimethylethyl (3S,4S)-4-[(5Z)-5-({1-[4-chloro-2-(trifluoromethyl)benzyl]-1H-indazol-5-yl}methylidene)-2,4-dioxo-1,3-thiazolidin-3-yl]-3-fluoropiperidine-1-carboxylate (from Example 381) following General Procedure M.

$^1$H NMR (400 MHz, CDCl$_3$): δ 1.79-1.88 (m, 1H) 2.43 (qd, 1H) 2.61-2.74 (m, 2H) 3.14 (d, 1H) 3.51 (dd, 1H) 4.41-4.55 (m, 1H) 5.21 (d. sxt., 1H) 5.80 (s, 2H) 6.68 (d, 1H) 7.32-7.39 (m, 2H) 7.51 (dd, 1H) 7.72 (d, 1H) 7.97 (s, 1H) 8.02 (s, 1H) 8.22 (s, 1H).

LC/MS: mass calcd. for C$_{24}$H$_{19}$ClF$_4$N$_4$O$_2$S: 538.95. found 539.0 [M]$^+$.

Example 383

(5Z)-5-({1-[4-Chloro-2-(trifluoromethyl)benzyl]-1H-indazol-5-yl}methylidene)-3-[(3R,4R)-3-fluoro-1-methylpiperidin-4-yl]-1,3-thiazolidine-2,4-dione

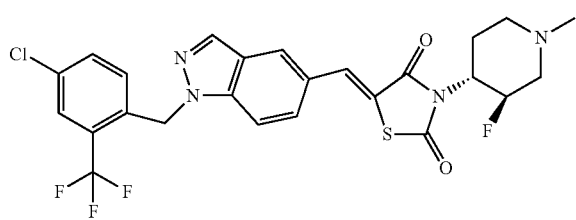 [SMILES: CN1CC[C@@H](N2C(=O)S/C(=C\c3ccc4c(cnn4Cc4ccc(Cl)cc4C(F)(F)F)c3)C2=O)[C@H](F)C1]

(5Z)-5-({1-[4-Chloro-2-(trifluoromethyl)benzyl]-1H-indazol-5-yl}methylidene)-3-[(3R,4R)-3-fluoro-1-methyl piperidin-4-yl]-1,3-thiazolidine-2,4-dione was prepared from (5Z)-5-({1-[4-chloro-2-(trifluoromethyl)benzyl]-1H-indazol-5-yl}methylidene)-3-[(3R,4R)-3-fluoropiperidin-4-yl]-1,3-thiazolidine-2,4-dione (from Example 381) and formaldehyde following General Procedure R.

$^1$H NMR (400 MHz, DMSO-d$_6$): δ 2.09-2.24 (m, 2H) 2.55-2.65 (m, 1H) 2.82 (br. s., 3H) 3.10-3.63 (m, 6H) 3.79-3.97 (m, 1H) 4.58-4.76 (m, 1H) 5.30-5.63 (m, 1H) 5.87 (s, 2H) 6.80 (d, 1H) 7.58-7.75 (m, 2H) 7.82 (d, 1H) 7.89 (s, 1H) 8.14 (s, 1H) 8.20 (s, 1H) 8.38 (s, 1H) 10.57 (br. s., 1H).

LC/MS: mass calcd. for C$_{26}$H$_{21}$ClF$_4$N$_4$O$_2$S: 552.98. found 553.0 [M]$^+$.

Example 384

(5Z)-5-({1-[4-Chloro-2-(trifluoromethyl)benzyl]-1H-indazol-5-yl}methylidene)-3-[(3S,4S)-3-fluoro-1-methylpiperidin-4-yl]-1,3-thiazolidine-2,4-dione

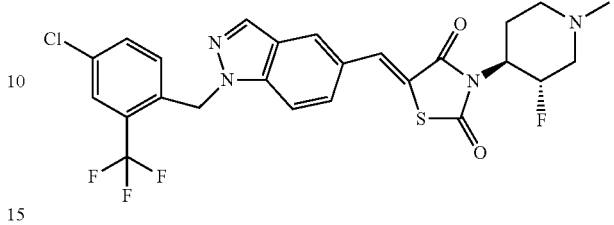

(5Z)-5-({1-[4-Chloro-2-(trifluoromethyl)benzyl]-1H-indazol-5-yl}methylidene)-3-[(3S,4S)-3-fluoro-1-methyl piperidin-4-yl]-1,3-thiazolidine-2,4-dione was prepared (5Z)-5-({1-[4-chloro-2-(trifluoromethyl)benzyl]-1H-indazol-5-yl}methylidene)-3-[(3S,4S)-3-fluoropiperidin-4-yl]-1,3-thiazolidine-2,4-dione (from Example 382) and formaldehyde following General Procedure R.

$^1$H NMR (400 MHz, DMSO-d$_6$): δ 2.05-2.25 (m, 1H) 2.55-2.66 (m, 1H) 2.81 (br. s., 3H) 3.07-3.61 (m, 5H) 3.88 (br. s., 1H) 4.56-4.81 (m, 1H) 5.30-5.65 (m, 1H) 5.87 (s, 2H) 6.80 (d, 1H) 7.59-7.75 (m, 2H) 7.82 (d, 1H) 7.89 (s, 1H) 8.14 (s, 1H) 8.20 (s, 1H) 8.38 (s, 1H) 10.72 (br. s., 1H).

LC/MS: mass calcd. for C$_{26}$H$_{21}$ClF$_4$N$_4$O$_2$S: 552.98. found 553.0 [M]$^+$.

Example 385

1-Chloro-N-{2-[(5Z)-5-({1-[4-chloro-2-(trifluoromethyl)benzyl]-1H-indazol-5-yl}-methylidene)-2,4-dioxo-1,3-thiazolidin-3-yl]-ethyl}methanesulfonamide

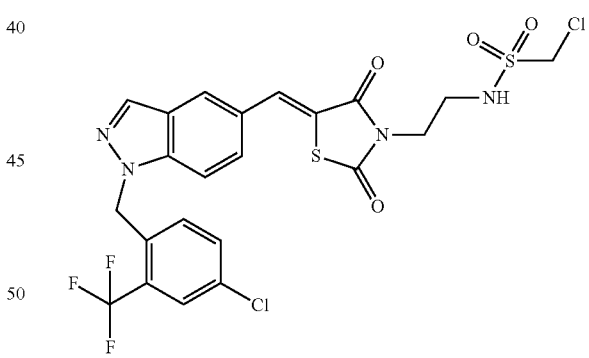

1-Chloro-N-{2-[(5Z)-5-({1-[4-chloro-2-(trifluoromethyl)benzyl]-1H-indazol-5-yl}-methylidene)-2,4-dioxo-1,3-thiazolidin-3-yl]ethyl}methanesulfonamide was prepared from 3-(2-aminoethyl)-(5Z)-5-({1-[4-chloro-2-(trifluoromethyl)benzyl]-1H-indazol-5-yl}methylidene)-1,3-thiazolidine-2,4-dione (from Example 49) and chloromethanesulfonyl chloride following General Procedure U.

$^1$H NMR (400 MHz, CDCl$_3$): δ 8.19 (s, 1H), 8.01 (s, 1H), 7.93 (s, 1H), 7.71 (d, 1H), 7.47 (d, 1H), 7.28-7.36 (m, 2H), 6.66 (d, 1H), 5.77 (s, 2H), 5.60 (t, 1H), 4.52 (s, 2H), 3.99 (t, 2H), 3.58 (q, 2H).

LCMS: mass calcd. for C$_{22}$H$_{17}$Cl$_2$F$_3$N$_4$O$_4$S$_2$: 593.4. found 594.9 [M+H]$^+$

Example 386

(5Z)-5-({1-[4-Chloro-2-(trifluoromethyl)benzyl]-1H-indazol-5-yl}methylidene)-3-[(3R,4R)-1-ethyl-3-fluoropiperidin-4-yl]-1,3-thiazolidine-2,4-dione

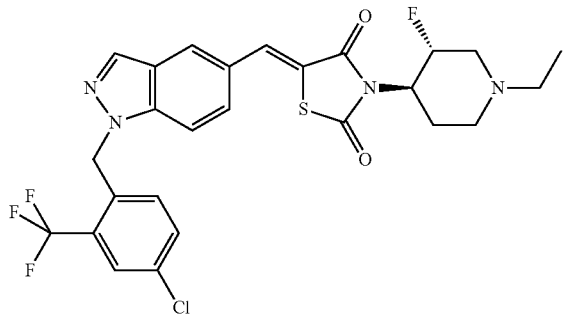 [SMILES: CCN1CC[C@@H](N2C(=O)S/C(=C\c3ccc4c(cnn4Cc4ccc(Cl)cc4C(F)(F)F)c3)C2=O)[C@H](F)C1]

(5Z)-5-({1-[4-Chloro-2-(trifluoromethyl)benzyl]-1H-indazol-5-yl}methylidene)-3-[(3R,4R)-1-ethyl-3-fluoropiperidin-4-yl]-1,3-thiazolidine-2,4-dione was prepared from (5Z)-5-({1-[4-chloro-2-(trifluoromethyl)benzyl]-1H-indazol-5-yl}methylidene)-3-[(3R,4R)-3-fluoropiperidin-4-yl]-1,3-thiazolidine-2,4-dione (Example 381) and acetaldehyde (in place of formaldehyde) following General Procedure R2.

$^1$H NMR (400 MHz, CDCl$_3$): δ 8.21 (s, 1H), 8.00 (s, 1H), 7.95 (s, 1H), 7.71 (s, 1H), 7.50 (d, 1H), 7.32-7.36 (2H), 6.67 (d, 1H), 5.79 (s, 2H), 5.36 (m, 1H), 4.37 (m, 1H), 3.38 (m, 1H), 2.99 (d, 1H), 2.46-2.61 (3H), 2.05-2.15 (2H), 1.78 (m, 1H), 1.11 (t, 3H).

LC/MS: mass calcd. for $C_{26}H_{23}ClF_4N_4O_2S$: 566.12. found 567.15 [M+H]$^+$.

Example 387

(5Z)-5-({1-[4-Chloro-2-(trifluoromethyl)benzyl]-1H-indazol-5-yl}methylidene)-3-[(3R,4R)-3-fluoro-1-(1-methylethyl)piperidin-4-yl]-1,3-thiazolidine-2,4-dione

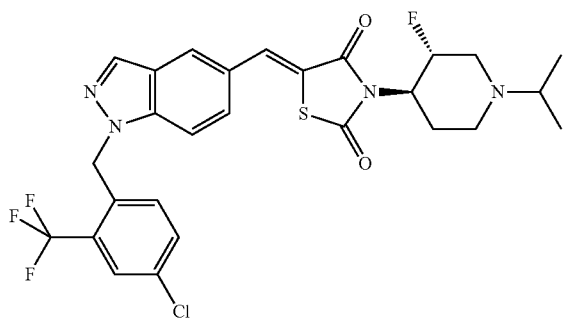 [SMILES: CC(C)N1CC[C@@H](N2C(=O)S/C(=C\c3ccc4c(cnn4Cc4ccc(Cl)cc4C(F)(F)F)c3)C2=O)[C@H](F)C1]

(5Z)-5-({1-[4-Chloro-2-(trifluoromethyl)benzyl]-1H-indazol-5-yl}methylidene)-3-[(3R,4R)-3-fluoro-1-(1-methylethyl)piperidin-4-yl]-1,3-thiazolidine-2,4-dione was prepared from (5Z)-5-({1-[4-chloro-2-(trifluoromethyl)benzyl]-1H-indazol-5-yl}methylidene)-3-[(3R,4R)-3-fluoropiperidin-4-yl]-1,3-thiazolidine-2,4-dione (Example 381) and acetone (in place of formaldehyde) following General Procedure R2.

$^1$H NMR (400 MHz, CDCl$_3$): δ 8.21 (s, 1H), 8.00 (s, 1H), 7.95 (s, 1H), 7.71 (d, 1H), 7.50 (d, 1H), 7.32-7.37 (2H), 6.68 (d, 1H), 5.79 (s, 2H), 5.30 (m, 1H), 4.34 (m, 1H), 3.30 (m, 1H), 2.81-2.93 (2H), 2.47 (ddd, 1H), 2.29 (dd, 1H), 2.25 (dd, 1H), 1.78 (m, 1H), 1.06 (d, 3H), 1.05 (d, 3H).

LC/MS: mass calcd. for $C_{27}H_{25}ClF_4N_4O_2S$: 580.13. found 581.10 [M+H]$^+$.

Example 388

{(3R,4R)-4-[(5Z)-5-({1-[4-Chloro-2-(trifluoromethyl)benzyl]-1H-indazol-5-yl}methylidene)-2,4-dioxo-1,3-thiazolidin-3-yl]-3-fluoropiperidin-1-yl}acetonitrile

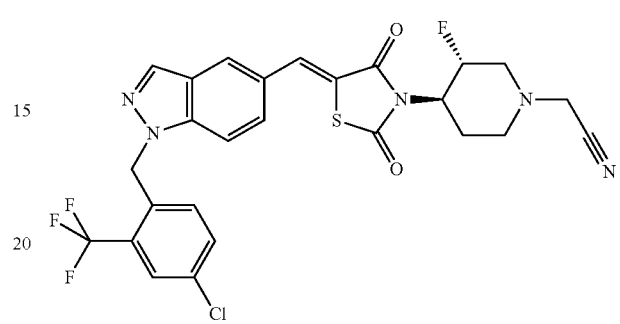

{(3R,4R)-4-[(5Z)-5-({1-[4-Chloro-2-(trifluoromethyl)benzyl]-1H-indazol-5-yl}methylidene)-2,4-dioxo-1,3-thiazolidin-3-yl]-3-fluoropiperidin-1-yl}acetonitrile was prepared from (5Z)-5-({1-[4-chloro-2-(trifluoromethyl)benzyl]-1H-indazol-5-yl}methylidene)-3-[(3R,4R)-3-fluoropiperidin-4-yl]-1,3-thiazolidine-2,4-dione (Example 381) and bromoacetonitrile following General Procedure S.

$^1$H NMR (400 MHz, CDCl$_3$): δ 8.22 (s, 1H), 8.01 (s, 1H), 7.96 (s, 1H), 7.72 (s, 1H), 7.50 (dd, 1H), 7.32-7.39 (2H), 6.68 (d, 1H), 5.79 (s, 2H), 5.38 (m, 1H), 4.41 (m, 1H), 3.63 (m, 2H), 3.27 (m, 1H), 2.88 (m, 1H), 2.50-2.65 (3H), 1.86 (m, 1H).

LC/MS: mass calcd. for $C_{26}H_{20}ClF_4N_5O_2S$: 577.10. found 578.0 [M+H]$^+$.

Example 389

N-{2-[(5Z)-5-({1-[4-Chloro-2-(trifluoromethyl)benzyl]-1H-indazol-5-yl}-methylidene)-2,4-dioxo-1,3-thiazolidin-3-yl]ethyl}acetamide

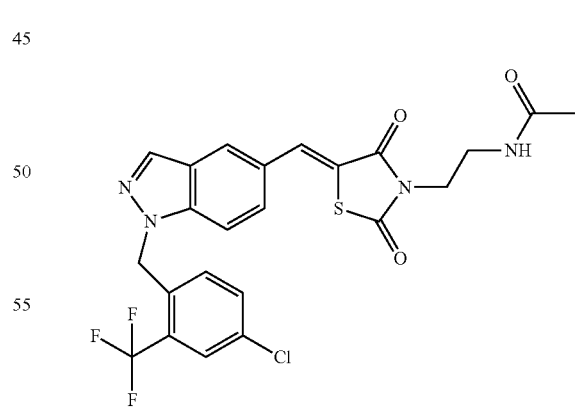

N-{2-[(5Z)-5-({1-[4-Chloro-2-(trifluoromethyl)benzyl]-1H-indazol-5-yl}methylidene)-2,4-dioxo-1,3-thiazolidin-3-yl]ethyl}acetamide was prepared from 3-(2-aminoethyl)-(5Z)-5-({1-[4-chloro-2-(trifluoromethyl)benzyl]-1H-indazol-5-yl}methylidene)-1,3-thiazolidine-2,4-dione (from Example 49) and acetic anhydride following General Procedure U.

$^1$H NMR (400 MHz, CD$_3$OD): δ 8.28 (s, 1H), 8.11 (s, 1H), 8.04 (s, 1H), 7.80 (d, 1H), 7.56-7.68 (m, 2H), 7.48 (dd, 1H), 6.69 (dd, 1H), 5.87 (s, 2H), 3.84-3.90 (m, 2H), 3.43-3.50 (m, 2H), 1.87 (s, 3H).

LCMS: mass calcd. for C$_{23}$H$_{18}$ClF$_3$N$_4$O$_3$S: 522.9. found 522.9 [M]$^+$.

Example 390

N-{2-[(5Z)-5-({1-[4-Chloro-2-(trifluoromethyl)benzyl]-1H-indazol-5-yl}-methylidene)-2,4-dioxo-1,3-thiazolidin-3-yl]ethyl}-2,2,2-trifluoroacetamide

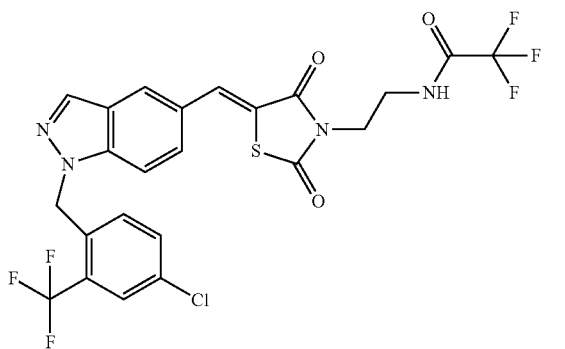 [SMILES: O=C1S/C(=C\c2ccc3c(cnn3Cc3ccc(Cl)cc3C(F)(F)F)c2)C(=O)N1CCNC(=O)C(F)(F)F]

N-{2-[(5Z)-5-({1-[4-Chloro-2-(trifluoromethyl)benzyl]-1H-indazol-5-yl}-methylidene)-2,4-dioxo-1,3-thiazolidin-3-yl]ethyl}-2,2,2-trifluoroacetamide was prepared from 3-(2-aminoethyl)-(5Z)-5-({1-[4-chloro-2-(trifluoromethyl)benzyl]-1H-indazol-5-yl}methylidene)-1,3-thiazolidine-2,4-dione (from Example 49) and trifluoroacetic anhydride following General Procedure U.

$^1$H NMR (400 MHz, CD$_3$OD): δ 9.45 (s, 1H), 8.28 (s, 1H), 8.11 (s, 1H), 8.5 (s, 1H), 7.80 (s, 1H), 7.56-7.69 (m, 2H), 7.49 (dd, 1H), 6.69 (dd, 1H), 5.87 (s, 2H), 3.89-4.01 (m, 2H), 3.54-3.62 (m, 2H).

LCMS: mass calcd. for C$_{23}$H$_{15}$ClF$_6$N$_4$O$_3$S: 576.9. found 577.0 [M]$^+$.

Example 391

N-{2-[(5Z)-5-({1-[4-Chloro-2-(trifluoromethyl)benzyl]-1H-indazol-5-yl}-methylidene)-2,4-dioxo-1,3-thiazolidin-3-yl]ethyl}benzenesulfonamide

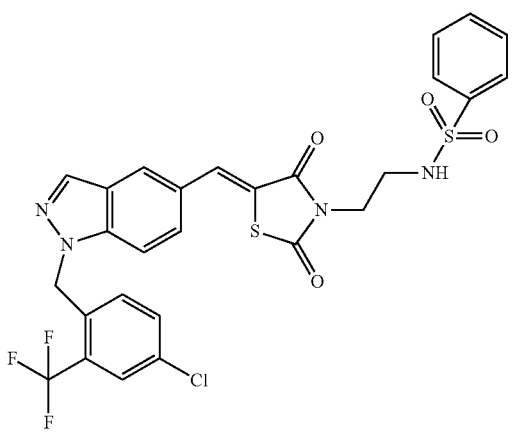 [SMILES: O=C1S/C(=C\c2ccc3c(cnn3Cc3ccc(Cl)cc3C(F)(F)F)c2)C(=O)N1CCNS(=O)(=O)c1ccccc1]

N-{2-[(5Z)-5-({1-[4-Chloro-2-(trifluoromethyl)benzyl]-1H-indazol-5-yl}methylidene)-2,4-dioxo-1,3-thiazolidin-3-yl]ethyl}benzenesulfonamide was prepared from 3-(2-aminoethyl)-(5Z)-5-({1-[4-chloro-2-(trifluoromethyl)benzyl]-1H-indazol-5-yl}methylidene)-1,3-thiazolidine-2,4-dione (from Example 49) and benzenesulfonyl chloride following General Procedure U.

$^1$H NMR (400 MHz, DMSO-d$_6$): δ 8.38 (s, 1H), 8.17 (s, 1H), 8.06 (s, 1H), 7.95 (t, 1H), 7.89 (dd, 1H), 7.80-7.84 (m, 1H), 7.74-7.78 (m, 2H), 7.66-7.71 (m, 2H), 7.63-7.66 (m, 1H), 7.58-7.63 (m, 2H), 6.77 (d, 1H), 5.87 (m, 2H), 3.71 (t, 2H), 3.04 (q, 2H).

LCMS: mass calcd. for C$_{27}$H$_{20}$ClF$_3$N$_4$O$_4$S$_2$: 621.1. found 620.9 [M]$^+$.

Example 392

N-{2-[(5Z)-5-({1-[4-Chloro-2-(trifluoromethyl)benzyl]-1H-indazol-5-yl}-methylidene)-2,4-dioxo-1,3-thiazolidin-3-yl]ethyl}-4-(trifluoromethyl)benzenesulfonamide

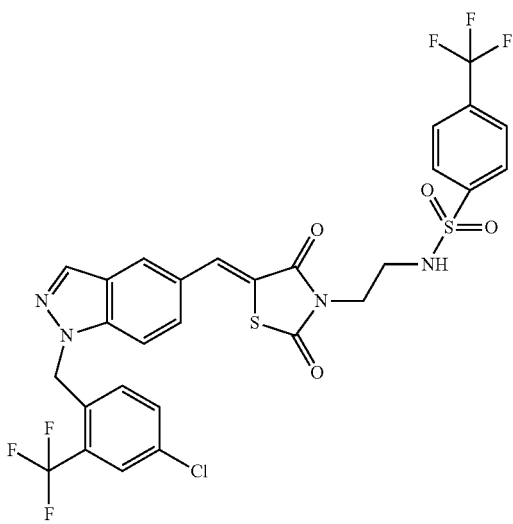 [SMILES: O=C1S/C(=C\c2ccc3c(cnn3Cc3ccc(Cl)cc3C(F)(F)F)c2)C(=O)N1CCNS(=O)(=O)c1ccc(C(F)(F)F)cc1]

N-{2-[(5Z)-5-({1-[4-Chloro-2-(trifluoromethyl)benzyl]-1H-indazol-5-yl}methylidene)-2,4-dioxo-1,3-thiazolidin-3-yl]ethyl}-4-(trifluoromethyl)benzenesulfonamide was prepared from 3-(2-aminoethyl)-(5Z)-5-({1-[4-chloro-2-(trifluoromethyl)benzyl]-1H-indazol-5-yl}methylidene)-1,3-thiazolidine-2,4-dione (from Example 49) and p-trifluoromethyl-benzenesulfonyl chloride following General Procedure U.

$^1$H NMR (400 MHz, CD$_3$OD): δ 8.34 (s, 1H), 8.29 (s, 1H), 8.10 (s, 1H), 7.99-8.03 (m, 1H), 7.95-7.99 (m, 1H), 7.81-7.86 (m, 1H), 7.80-7.81 (m, 1H), 7.64-7.69 (m, 1H), 7.60-7.64 (m, 1H), 7.46-7.51 (m, 1H), 7.39 (d, 1H), 7.08 (d, 1H), 6.68 (d, 1H), 5.87 (s, 2H), 3.83 (t, 2H), 3.27 (t, 2H).

LCMS: mass calcd. for C$_{28}$H$_{19}$ClF$_6$N$_4$O$_4$S$_2$: 689.1. found 688.9 [M]$^+$.

Example 393

N-{2-[(5Z)-5-({1-[4-Chloro-2-(trifluoromethyl)benzyl]-1H-indazol-5-yl}-methylidene)-2,4-dioxo-1,3-thiazolidin-3-yl]ethyl}methanesulfonamide

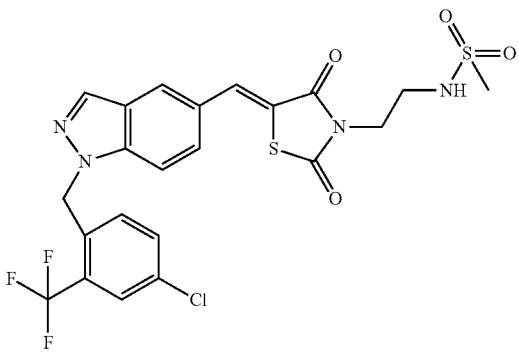 [SMILES: CS(=O)(=O)NCCN1C(=O)S/C(=C\c2ccc3c(cnn3Cc3ccc(Cl)cc3C(F)(F)F)c2)C1=O]

N-{2-[(5Z)-5-({1-[4-Chloro-2-(trifluoromethyl)benzyl]-1H-indazol-5-yl}methylidene)-2,4-dioxo-1,3-thiazolidin-3-yl]ethyl}methanesulfonamide was prepared from 3-(2-aminoethyl)-(5Z)-5-({1-[4-chloro-2-(trifluoromethyl)benzyl]-1H-indazol-5-yl}methylidene)-1,3-thiazolidine-2,4-dione (from Example 49) and methanesulfonyl chloride following General Procedure U.

$^1$H NMR (400 MHz, DMSO-d$_6$): δ 8.37 (s, 1H), 8.17 (s, 1H), 8.08 (s, 1H), 7.88-7.91 (m, 1H), 7.79-7.84 (m, 1H), 7.68-7.72 (m, 1H), 7.63-7.68 (m, 1H), 7.32 (t, 1H), 6.77 (d, 1H), 5.87 (s, 2H), 3.77 (t, 2H), 3.24 (q, 2H), 2.90 (s, 3H).

LCMS: mass calcd. for C$_{22}$H$_{18}$ClF$_3$N$_4$O$_4$S$_2$: 559.0. found 559.0 [M]$^+$.

Example 394

N-{2-[(5Z)-5-({1-[4-Chloro-2-(trifluoromethyl)benzyl]-1H-indazol-5-yl}-methylidene)-2,4-dioxo-1,3-thiazolidin-3-yl]ethyl}-2,2,2-trifluoro-N-methylacetamide

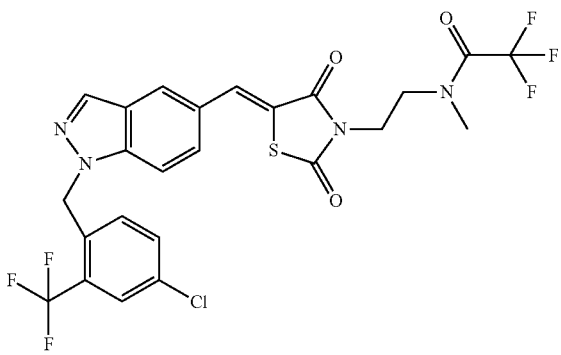 [SMILES: CN(CCN1C(=O)S/C(=C\c2ccc3c(cnn3Cc3ccc(Cl)cc3C(F)(F)F)c2)C1=O)C(=O)C(F)(F)F]

(A) (2-{5-[1-(4-Chloro-2-trifluoromethylbenzyl)-1H-indazol-5-ylmethylene]-2,4-dioxothiazolidin-3-yl}ethyl)methylcarbamic acid tert-butyl ester was prepared from [(5Z)-5-({1-[4-chloro-2-(trifluoromethyl)benzyl]-1H-indazol-5-yl}methylidene)-2,4-dioxo-1,3-thiazolidine (from Example 1) and tert-butyl N-(2-hydroxyethyl)-N-methylcarbamate following General Procedure J.

(B) 5-[1-(4-Chloro-2-trifluoromethylbenzyl)-1H-indazol-5-ylmethylene]-3-(2-methylaminoethyl)thiazolidine-2,4-dione was prepared by the deprotection of (2-{5-[1-(4-chloro-2-trifluoromethylbenzyl)-1H-indazol-5-ylmethylene]-2,4-dioxothiazolidin-3-yl}ethyl)methylcarbamic acid tert-butyl ester following General Procedure M.

(C) N-{2-[(5Z)-5-({1-[4-Chloro-2-(trifluoromethyl)benzyl]-1H-indazol-5-yl}methylidene)-2,4-dioxo-1,3-thiazolidin-3-yl]ethyl}-2,2,2-trifluoro-N-methylacetamide was prepared from 5-[1-(4-chloro-2-trifluoromethylbenzyl)-1H-indazol-5-ylmethylene]-3-(2-methylaminoethyl)thiazolidine-2,4-dione and trifluoroacetic anhydride following General Procedure U.

$^1$H NMR (400 MHz, CDCl$_3$): δ8.34 (s, 1H), 8.03-8.07 (m, 1H), 8.02 (s, 1H), 7.74 (d, 1H), 7.55-7.60 (dd, 1H), 7.33-7.42 (m, 2H), 6.60 (d, 1H), 5.85 (s, 2H), 4.04-4.10 (m, 2H), 3.78-3.85 (m, 2H), 3.24 (d, 3H).

LCMS: mass calcd. for C$_{24}$H$_{17}$ClF$_6$N$_4$O$_3$S: 590.9. found 590.9 [M]$^+$.

Example 395

N-{2-[(5Z)-5-({1-[4-Chloro-2-(trifluoromethyl)benzyl]-1H-indazol-5-yl}-methylidene)-2,4-dioxo-1,3-thiazolidin-3-yl]ethyl}-N-methyl-4-(trifluoromethyl)benzenesulfonamide

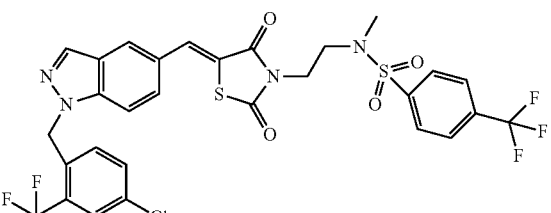

N-{2-[(5Z)-5-({1-[4-Chloro-2-(trifluoromethyl)benzyl]-1H-indazol-5-yl}methylidene)-2,4-dioxo-1,3-thiazolidin-3-yl]ethyl}-N-methyl-4-(trifluoromethyl)benzenesulfonamide was prepared from 5-[1-(4-chloro-2-trifluoromethylbenzyl)-1H-indazol-5-ylmethylene]-3-(2-methylaminoethyl)thiazolidine-2,4-dione (from Example 394) and p-trifluoromethylbenzenesulfonyl chloride following General Procedure U.

$^1$H NMR (400 MHz, CDCl$_3$): δ8.22 (s, 1H), 8.04 (s, 1H), 7.98 (s, 1H), 7.90 (d, 2H), 7.76 (d, 2H), 7.72 (d, 1H), 7.52 (dd, 1H), 7.32-7.38 (m, 2H), 6.65 (d, 1H), 5.80 (s, 2H), 3.96 (t, 2H), 3.38 (t, 2H), 2.94 (s, 3H).

LCMS: mass calcd. for C$_{29}$H$_{21}$ClF$_6$N$_4$O$_4$S$_2$: 703.1. found 703.0 [M]$^+$.

Example 396

N-{2-[(5Z)-5-({1-[4-Chloro-2-(trifluoromethyl)benzyl]-1H-indazol-5-yl}-methylidene)-2,4-dioxo-1,3-thiazolidin-3-yl]ethyl}-N-methylpyrrolidine-1-sulfonamide

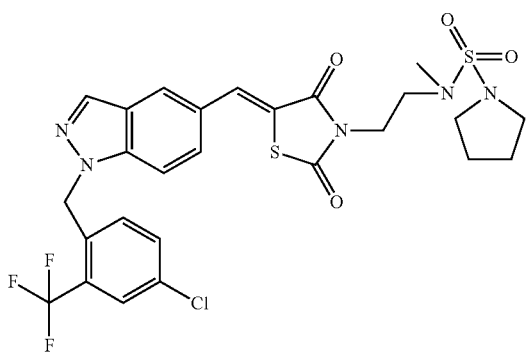 [SMILES: CN(CCN1C(=O)S/C(=C\c2ccc3c(cnn3Cc3ccc(Cl)cc3C(F)(F)F)c2)C1=O)S(=O)(=O)N1CCCC1]

N-{2-[(5Z)-5-({1-[4-Chloro-2-(trifluoromethyl)benzyl]-1H-indazol-5-yl}methylidene)-2,4-dioxo-1,3-thiazolidin-3-yl]ethyl}-N-methylpyrrolidine-1-sulfonamide was prepared from 5-[1-(4-chloro-2-trifluoromethylbenzyl)-1H-indazol-5-ylmethylene]-3-(2-methylaminoethyl)thiazolidine-2,4-dione (from Example 394) and pyrrolidine-1-sulfonyl chloride following General Procedure U.

$^1$H NMR (400 MHz, CDCl$_3$): δ 8.21 (s, 1H), 8.03 (s, 1H), 7.97 (s, 1H), 7.72 (d, 1H), 7.51 (dd, 1H), 7.34 (d, 2H), 6.66 (d, 1H), 5.80 (s, 2H), 3.95 (t, 2H), 3.50 (t, 2H), 3.20-3.27 (m, 4H), 2.91 (s, 3H), 1.87 (dt, 4H).

LCMS: mass calcd. for $C_{26}H_{25}ClF_3N_5O_4S_2$: 628.1. found 628.0 [M]$^+$.

Example 397

N-{2-[(5Z)-5-({1-[4-Chloro-2-(trifluoromethyl)benzyl]-1H-indazol-5-yl}methylidene)-2,4-dioxo-1,3-thiazolidin-3-yl]ethyl}-N-methylmethanesulfonamide

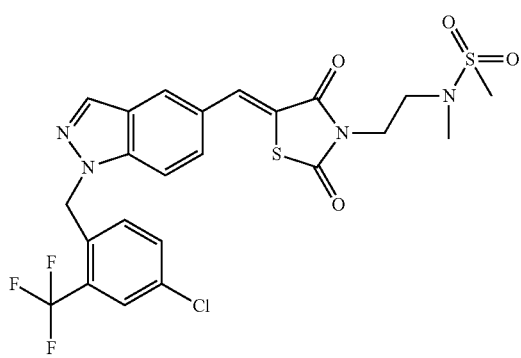 [SMILES: CN(CCN1C(=O)S/C(=C\c2ccc3c(cnn3Cc3ccc(Cl)cc3C(F)(F)F)c2)C1=O)S(C)(=O)=O]

N-{2-[(5Z)-5-({1-[4-Chloro-2-(trifluoromethyl)benzyl]-1H-indazol-5-yl}methylidene)-2,4-dioxo-1,3-thiazolidin-3-yl]ethyl}-N-methylmethane sulfonamide was prepared from 5-[1-(4-chloro-2-trifluoromethylbenzyl)-1H-indazol-5-ylmethylene]-3-(2-methylaminoethyl)thiazolidine-2,4-dione (from Example 394) and methanesulfonyl chloride following General Procedure U.

$^1$H NMR (400 MHz, CDCl$_3$): δ 8.21 (s, 1H), 8.03 (s, 1H), 7.97 (s, 1H), 7.72 (d, 1H), 7.51 (dd, 1H), 7.34 (d, 2H), 6.64 (d, 1H), 5.80 (s, 2H), 3.94-4.01 (m, 2H), 3.45-3.50 (m, 2H), 2.97 (s, 3H), 2.80 (s, 3H).

LCMS: mass calcd. for $C_{23}H_{20}ClF_3N_4O_4S_2$: 573.0. found 573.0 [M]$^+$.

Example 398

N-{2-[(5Z)-5-({1-[4-Chloro-2-(trifluoromethyl)benzyl]-1H-indazol-5-yl}methylidene)-2,4-dioxo-1,3-thiazolidin-3-yl]ethyl}morpholine-4-sulfonamide

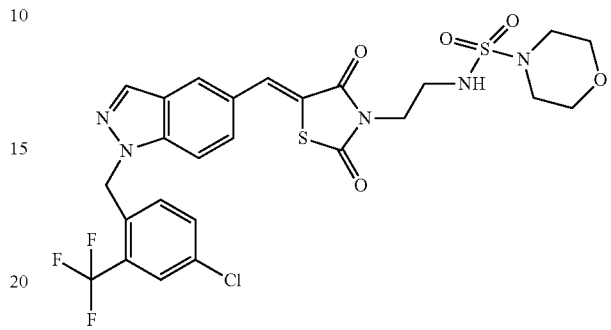

N-{2-[(5Z)-5-({1-[4-Chloro-2-(trifluoromethyl)benzyl]-1H-indazol-5-yl}methylidene)-2,4-dioxo-1,3-thiazolidin-3-yl]ethyl}morpholine-4-sulfonamide was prepared from 3-(2-aminoethyl)-(5Z)-5-({1-[4-chloro-2-(trifluoromethyl)benzyl]-1H-indazol-5-yl}methylidene)-1,3-thiazolidine-2,4-dione (from Example 49) and morpholine-4-sulfonyl chloride following General Procedure U.

$^1$H NMR (400 MHz, CD$_3$OD): δ 8.28 (s, 1H), 8.11 (d, 1H), 8.05 (m, 1H), 7.80 (d, 1H), 7.65 (dd, 1H), 7.59 (d, 1H), 7.48 (dd, 1H), 6.69 (d, 1H), 5.87 (s, 2H), 3.88 (t, 2H), 3.67-3.72 (m, 4H), 3.35 (t, 2H), 3.09 (m, 4H).

LCMS: mass calcd. for $C_{25}H_{23}ClF_3N_5O_5S_2$: 630.1. found 630.0 [M]$^+$.

Example 399

N-{2-[(5Z)-5-({1-[4-Chloro-2-(trifluoromethyl)benzyl]-1H-indazol-5-yl}methylidene)-2,4-dioxo-1,3-thiazolidin-3-yl]ethyl}pyrrolidine-1-sulfonamide

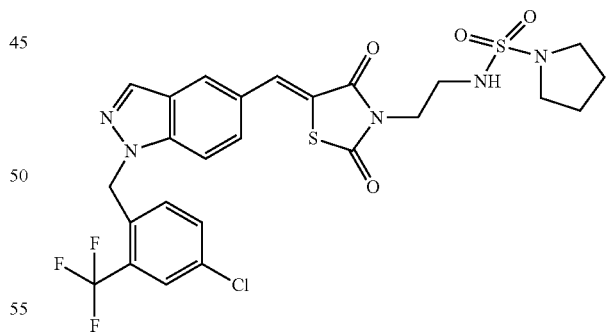

N-{2-[(5Z)-5-({1-[4-Chloro-2-(trifluoromethyl)benzyl]-1H-indazol-5-yl}methylidene)-2,4-dioxo-1,3-thiazolidin-3-yl]ethyl}pyrrolidine-1-sulfonamide was prepared from 3-(2-aminoethyl)-(5Z)-5-({1-[4-chloro-2-(trifluoromethyl)benzyl]-1H-indazol-5-yl}methylidene)-1,3-thiazolidine-2,4-dione (from Example 49) and pyrrolidine-1-sulfonyl chloride following General Procedure U $^1$H NMR (400 MHz, CD$_3$OD): δ 8.28 (s, 1H), 8.22 (s, 1H), 8.11 (dd, 1H), 8.06 (s, 1H), 7.80 (d, 1H), 7.65 (dd, 1H), 7.59

(d, 1H), 7.45-7.52 (m, 1H), 6.69 (d, 1H), 5.87 (m, 2H), 3.88 (t, 2H), 3.33 (t, 2H), 3.20-3.24 (m, 4H), 1.88 (m, 4H).

LCMS: mass calcd. for $C_{25}H_{23}ClF_3N_5O_4S_2$: 614.1. found 614.0 [M]+.

Example 400

(5Z)-3-[(2-Amino-1,3-thiazol-4-yl)methyl]-5-({1-[4-chloro-2-(trifluoromethyl)benzyl]-1H-indazol-5-yl}methylidene)-1,3-thiazolidine-2,4-dione

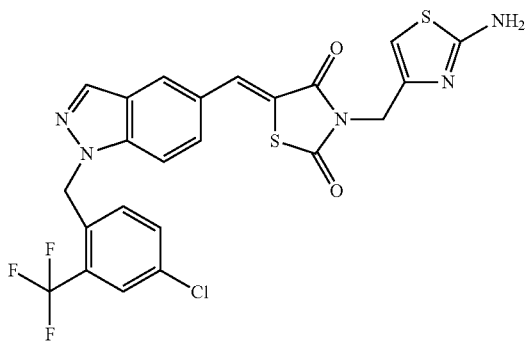 [SMILES: Nc1nc(CN2C(=O)S/C(=C\c3ccc4c(cnn4Cc4ccc(Cl)cc4C(F)(F)F)c3)C2=O)cs1]

(5Z)-3-[(2-Amino-1,3-thiazol-4-yl)methyl]-5-({1-[4-chloro-2-(trifluoromethyl)benzyl]-1H-indazol-5-yl}methylidene)-1,3-thiazolidine-2,4-dione was prepared from (5Z)-5-({1-[4-chloro-2-(trifluoromethyl)benzyl]-1H-indazol-5-yl}methylidene)-2,4-dioxo-1,3-thiazolidine (from Example 1) and 4-chloromethylthiazol-2-ylamine following General Procedure H.

$^1$H NMR (400 MHz, CDCl$_3$): δ 8.79 (d, 1H), 8.21 (s, 1H), 8.05 (s, 1H), 7.96 (s, 1H), 7.71 (d, 1H), 7.50 (dd, 1H), 7.31-7.40 (m, 2H), 6.67 (d, 1H), 5.79 (s, 2H), 5.12 (s, 2H).

LCMS: mass calcd. for $C_{23}H_{15}ClF_3N_5O_2S_2$: 550.0. found 550.1 [M]+.

Example 401

(5Z)-5-({1-[4-Chloro-2-(trifluoromethyl)benzyl]-1H-indazol-5-yl}methylidene)-3-(1,2,4-oxadiazol-3-ylmethyl)-1,3-thiazolidine-2,4-dione

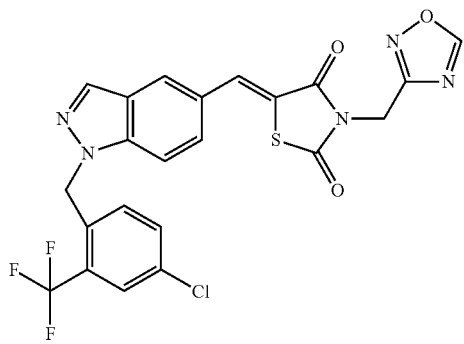 [SMILES: O=C1S/C(=C\c2ccc3c(cnn3Cc3ccc(Cl)cc3C(F)(F)F)c2)C(=O)N1Cc1ncon1]

(5Z)-5-({1-[4-Chloro-2-(trifluoromethyl)benzyl]-1H-indazol-5-yl}methylidene)-3-(1,2,4-oxadiazol-3-ylmethyl)-1,3-thiazolidine-2,4-dione was prepared from (5Z)-5-({1-[4-chloro-2-(trifluoromethyl)benzyl]-1H-indazol-5-yl}methylidene)-2,4-dioxo-1,3-thiazolidine (from Example 1) and 3-(chloromethyl)-1,2,4-oxadiazole following General Procedure H.

$^1$H NMR (400 MHz, CDCl$_3$): δ 8.21 (s, 1H), 8.04 (s, 1H), 7.96 (s, 1H), 7.72 (d, 1H), 7.51 (dd, 1H), 7.34 (d, 2H), 6.67 (d, 1H), 6.49 (s, 1H), 5.80 (s, 2H), 5.04 (s, 2H).

LCMS: mass calcd. for $C_{22}H_{13}ClF_3N_5O_3S$: 519.9. found 520.1 [M]+.

Example 402

(5Z)-5-({1-[4-Chloro-2-(trifluoromethyl)benzyl]-1H-indazol-5-yl}methylidene)-3-[(1-methyl-1H-imidazol-4-yl)methyl]-1,3-thiazolidine-2,4-dione

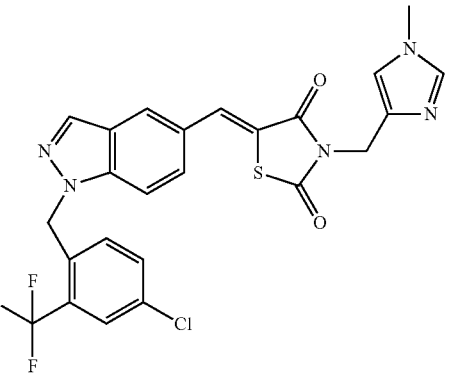

(5Z)-5-({1-[4-Chloro-2-(trifluoromethyl)benzyl]-1H-indazol-5-yl}methylidene)-3-[(1-methyl-1H-imidazol-4-yl)methyl]-1,3-thiazolidine-2,4-dione was prepared from (5Z)-5-({1-[4-chloro-2-(trifluoromethyl)benzyl]-1H-indazol-5-yl}methylidene)-2,4-dioxo-1,3-thiazolidine (from Example 1) and 4-(chloromethyl)-1-methyl-1H-imidazole hydrochloride following General Procedure H.

$^1$H NMR (400 MHz, CDCl$_3$): δ 8.21 (s, 1H), 8.03 (s, 1H), 7.94 (s, 1H), 7.71 (d, 1H), 7.49 (dd, 1H), 7.31-7.38 (m, 3H), 6.95 (s, 1H), 6.66 (d, 1H), 5.79 (s, 2H), 4.89 (s, 2H), 3.64 (s, 3H).

LCMS: mass calcd. for $C_{24}H_{17}ClF_3N_5O_2S$: 531.9. found 532.1 [M]+.

Example 403

(5Z)-5-({1-[4-Chloro-2-(trifluoromethyl)benzyl]-1H-indazol-5-yl}methylidene)-3-(1H-imidazol-2-ylmethyl)-1,3-thiazolidine-2,4-dione

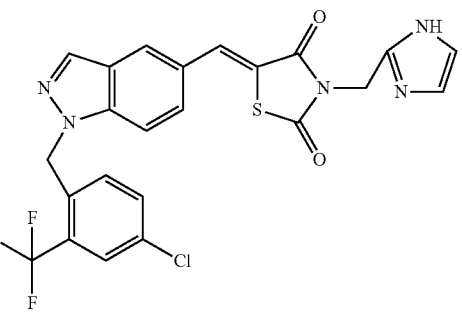

(5Z)-5-({1-[4-Chloro-2-(trifluoromethyl)benzyl]-1H-indazol-5-yl}methylidene)-3-(1H-imidazol-2-ylmethyl)-1,3-thiazolidine-2,4-dione was prepared from (5Z)-5-({1-[4-chloro-2-(trifluoromethyl)benzyl]-1H-indazol-5-yl}methylidene)-2,4-dioxo-1,3-thiazolidine (from Example 1) and 4-(chloromethyl)-1H-imidazole hydrochloride following General Procedure H.

$^1$H NMR (400 MHz, CDCl$_3$): δ 8.21 (s, 1H), 8.05 (s, 1H), 8.02 (s, 1H), 7.95 (s, 1H), 7.71 (d, 1H), 7.49 (dd, 1H), 7.35 (d, 2H), 7.04 (s, 2H), 6.68 (d, 1H), 5.79 (s, 2H), 5.06 (s, 2H).
LCMS: mass calcd. for C$_{23}$H$_{15}$ClF$_3$N$_5$O$_2$S: 517.9. found 518.0 [M]$^+$.

Example 404

(5Z)-5-({1-[4-Chloro-2-(trifluoromethyl)benzyl]-1H-indazol-5-yl}methylidene)-3-{[1-(1H-imidazol-2-ylmethyl)-1H-imidazol-2-yl]methyl}-1,3-thiazolidine-2,4-dione

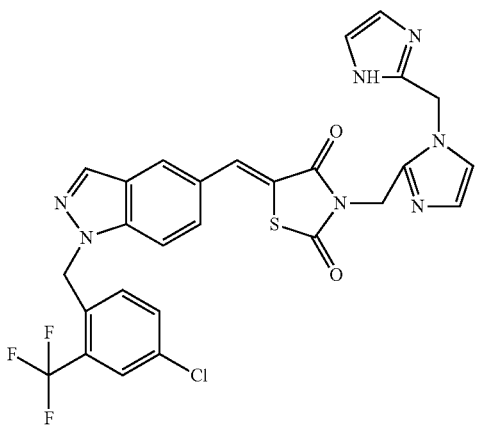 [SMILES: O=C1S/C(=C\c2ccc3c(cnn3Cc3ccc(Cl)cc3C(F)(F)F)c2)C(=O)N1Cc1nccn1Cc1ncc[nH]1]

(5Z)-5-({1-[4-chloro-2-(trifluoromethyl)benzyl]-1H-indazol-5-yl}methylidene)-3-{[1-(1H-imidazol-2-ylmethyl)-1H-imidazol-2-yl]methyl}-1,3-thiazolidine-2,4-dione was also isolated from the reaction described in Example 403.

$^1$H NMR (400 MHz, CD$_3$OD): δ 8.28 (s, 1H), 8.10 (s, 1H), 8.09 (s, 1H), 7.79 (d, 1H), 7.74 (d, 1H), 7.67 (d, 1H), 7.61 (d, 1H), 7.60 (s, 3H), 7.47 (dd, 1H), 6.71 (d, 1H), 6.11 (s, 2H), 5.86 (s, 2H), 5.38 (s, 2H).
LCMS: mass calcd. for C$_{27}$H$_{19}$ClF$_3$N$_7$O$_2$S: 598.0. found 597.9 [M]$^+$.

Example 405

(5Z)-5-({1-[4-Chloro-2-(trifluoromethyl)benzyl]-1H-indazol-5-yl}methylidene)-3-(1H-imidazol-4-ylmethyl)-1,3-thiazolidine-2,4-dione

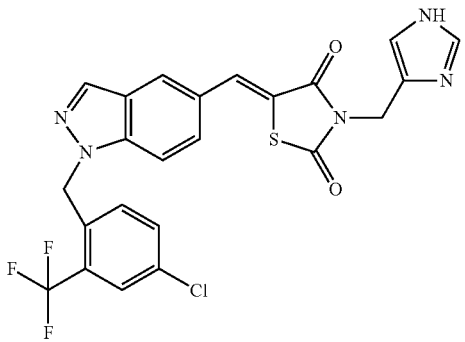

(5Z)-5-({1-[4-Chloro-2-(trifluoromethyl)benzyl]-1H-indazol-5-yl}-methylidene)-3-(1H-imidazol-4-ylmethyl)-1,3-thiazolidine-2,4-dione was prepared from (5Z)-5-({1-[4-chloro-2-(trifluoromethyl)benzyl]-1H-indazol-5-yl}methylidene)-2,4-dioxo-1,3-thiazolidine (from Example 1) and 2-(chloromethyl)-1H-imidazole hydrochloride following General Procedure H.

$^1$H NMR (400 MHz, CD$_3$OD): δ 8.27 (s, 1H), 8.09 (s, 1H), 8.06 (s, 1H), 7.97 (s, 2H), 7.79 (d, 1H), 7.70 (d, 1H), 7.63 (dd, 1H), 7.57 (d, 1H), 7.47 (dd, 1H), 7.12 (s, 1H), 6.68 (s, 1H), 5.86 (s, 2H).
LCMS: mass calcd. for C$_{23}$H$_{15}$ClF$_3$N$_5$O$_2$S: 517.9. found 518.1 [M]$^+$.

Example 406

[(5Z)-5-({1-[4-Chloro-2-(trifluoromethyl)benzyl]-3-fluoro-1H-indazol-5-yl}methylidene)-2,4-dioxo-1,3-thiazolidin-3-yl]acetic acid

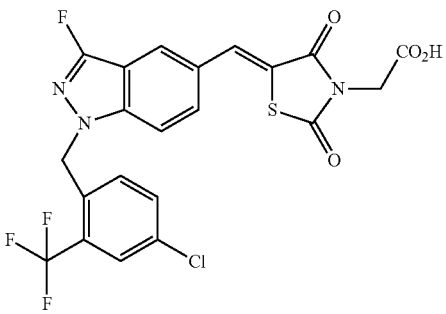 [SMILES: O=C(O)CN1C(=O)S/C(=C\c2ccc3c(c2)c(F)nn3Cc2ccc(Cl)cc2C(F)(F)F)C1=O]

(A) [(5Z)-5-({1-[4-Chloro-2-(trifluoromethyl)benzyl]-3-fluoro-1H-indazol-5-yl}methylidene)-2,4-dioxo-1,3-thiazolidin-3-yl]acetic acid was prepared from 1-(4-chloro-2-trifluoromethyl-benzyl)-3-fluoro-1H-indazole-5-carbaldehyde (from Example 368) and (2,4-dioxothiazolidin-3-yl)acetic acid following General Procedure F.

$^1$H NMR (400 MHz, CD$_3$OD): δ 8.29 (s, 1H), 8.12 (s, 1H), 8.08 (s, 1H), 7.80 (d, 1H), 7.65 (dd, 1H), 7.59 (d, 1H), 7.48 (dd, 1H), 6.69 (d, 1H), 5.87 (s, 2H), 4.96 (s, 2H).
LCMS: mass calcd. for C$_{21}$H$_{12}$ClF$_4$N$_3$O$_4$S: 513.9. found 513.9 [M]$^+$.

Example 407

[(5Z)-5-({3-Bromo-1-[4-chloro-2-(trifluoromethyl)benzyl]-1H-indazol-5-yl}methylidene)-2,4-dioxo-1,3-thiazolidin-3-yl]acetic acid

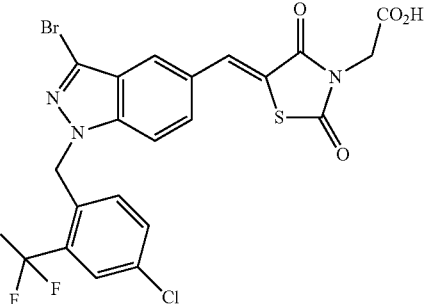

(A) A solution of 1H-Indazole-5-carbaldehyde (2.05 mmol) and N-bromosuccinimide (3.08 mmol) in DMF (8 mL) was stirred at rt for 3 h, then concentrated under reduced pressure. Chromatographic purification of the residue (silica gel, hexanes to hexanes:EtOAc, 1:1) afforded 3-bromo-1H-indazole-5-carbaldehyde as pale yellow solid.

(B) 3-Bromo-1-(4-chloro-2-trifluoromethylbenzyl)-1H-indazole-5-carbaldehyde was prepared from 3-bromo-1H-indazole-5-carbaldehyde and 4-chloro-2-(trifluoromethyl)benzyl bromide following General Procedure A.

(B) [(5Z)-5-({3-Bromo-1-[4-chloro-2-(trifluoromethyl)benzyl]-1H-indazol-5-yl}methylidene)-2,4-dioxo-1,3-thiazolidin-3-yl]acetic acid was prepared from 3-bromo-1-(4-chloro-2-trifluoromethylbenzyl)-1H-indazole-5-carbaldehyde and (2,4-dioxothiazolidin-3-yl)acetic acid following General Procedure F.

$^1$H NMR (400 MHz, CD$_3$OD): δ 8.27 (s, 1H), 8.10 (s, 1H), 7.98 (s, 1H), 7.80 (d, 1H), 7.63 (dd, 1H), 7.55 (d, 1H), 7.47 (dd, 1H), 6.68 (d, 1H), 5.86 (s, 2H), 5.03 (s, 2H).

LCMS: mass calcd. for C$_{21}$H$_{12}$BrClF$_3$N$_3$O$_4$S: 574.8. found 575.8 [M+H]$^+$.

Example 408

[(5Z)-5-({1-[4-Chloro-2-(trifluoromethyl)benzyl]-3-(4-fluorophenyl)-1H-indazol-5-yl}methylidene)-2,4-dioxo-1,3-thiazolidin-3-yl]acetic acid

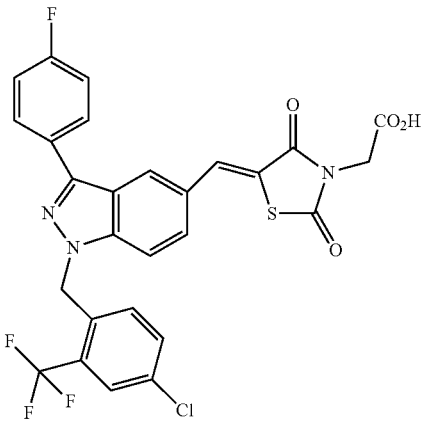 [SMILES: O=C(O)CN1C(=O)S/C(=C\c2ccc3c(c2)c(-c2ccc(F)cc2)nn3Cc2ccc(Cl)cc2C(F)(F)F)C1=O]

(A) A mixture of 3-bromo-1-(4-chloro-2-trifluoromethylbenzyl)-1H-indazole-5-carbaldehyde (0.311 mmol from Example 407), 4-fluorophenylboronic acid (0.498 mmol), Pd(dppf)Cl$_2$ dichloromethane complex (0.0311 mmol) and sodium carbonate (0.933 mmol) in DME/H$_2$O (4 mL; 4:1) under argon was stirred at 100° C. for 6 h, then concentrated. The residue was purified by chromatography (silica gel, hexanes to hexanes:EtOAc, 1:1) to afford 1-(4-chloro-2-trifluoromethylbenzyl)-3-(4-fluorophenyl)-1H-indazole-5-carbaldehyde as white solid.

(B) [(5Z)-5-({1-[4-Chloro-2-(trifluoromethyl)benzyl]-3-(4-fluorophenyl)-1H-indazol-5-yl}methylidene)-2,4-dioxo-1,3-thiazolidin-3-yl]acetic acid was prepared from 1-(4-chloro-2-trifluoromethylbenzyl)-3-(4-fluorophenyl)-1H-indazole-5-carbaldehyde and (2,4-dioxothiazolidin-3-yl)acetic acid following General Procedure F.

$^1$H NMR (400 MHz, CD$_3$OD): δ 8.28 (m, 1H), 8.08-8.15 (m, 2H), 7.80 (d, 1H), 7.57-7.68 (m, 2H), 7.48 (d, 2H), 7.46 (d, 2H), 7.03 (d, 2H), 6.69 (d, 1H), 5.86 (s, 2H), 4.84 (s, 2H).

LCMS: mass calcd. for C$_{27}$H$_{16}$ClF$_4$N$_3$O$_4$S: 590.0. found 589.9 [M]$^+$.

Example 409

(5Z)-5-({1-[4-Chloro-2-(trifluoromethyl)benzyl]-1H-indazol-5-yl}methylidene)-3-[(2,2-dioxido-1,2,3-oxathiazolidin-4-yl)methyl]-1,3-thiazolidine-2,4-dione

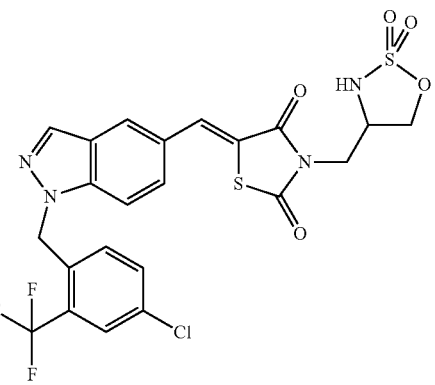

A solution of (5Z)-5-({1-[4-chloro-2-(trifluoromethyl)benzyl]-1H-indazol-5-yl}methylidene)-3-(2,3-dihydroxypropyl)-1,3-thiazolidine-2,4-dione (0.195 mmol, from Example 43) and N,N-diethyl-N-[[[(2,2,2-trichloroethoxy)carbonyl]amino]sulfonyl]ethanaminium, inner salt (0.488 mmol, prepared as described in Chemistry—A European Journal 2004, 10(22), 5581-5606) in THF (4 mL) was refluxed for 4 h, then concentrated under reduced pressure. The crude product was purified by flash chromatography to provide the Troc-protected material, which was then deprotected following General Procedure M to provide (5Z)-5-({1-[4-Chloro-2-(trifluoromethyl)benzyl]-1H-indazol-5-yl}methylidene)-3-[(2,2-dioxido-1,2,3-oxathiazolidin-4-yl)methyl]-1,3-thiazolidine-2,4-dione.

$^1$H NMR (400 MHz, CD$_3$OD): δ 8.12 (m, 1H), 7.77 (m, 1H), 7.72 (s, 1H), 7.45 (d, 1H), 7.31-7.42 (m, 2H), 6.59 (d, 1H), 5.81 (s, 2H), 3.88-4.01 (m, 1H), 3.71-3.82 (m, 1H), 3.47-3.64 (m, 2H), 3.35-3.44 (m, 1H).

LCMS: mass calcd. for C$_{22}$H$_{16}$ClF$_3$N$_4$O$_5$S$_2$: 573.0. found 575.1 [M+H]$^+$.

Example 410

(5Z)-5-({1-[4-Chloro-2-(trifluoromethyl)benzyl]-1H-indazol-5-yl}methylidene)-3-{[1-(methylsulfonyl)-1H-imidazol-2-yl]methyl}-1,3-thiazolidine-2,4-dione

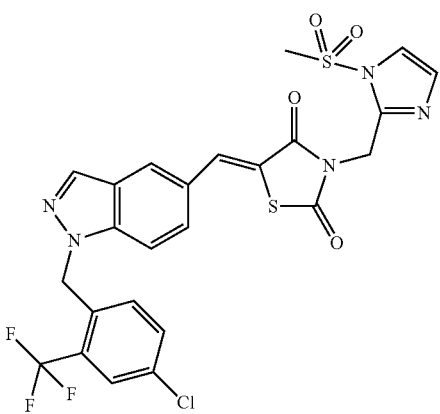 [SMILES: CS(=O)(=O)n1ccnc1CN1C(=O)S/C(=C\c2ccc3c(cnn3Cc3ccc(Cl)cc3C(F)(F)F)c2)C1=O]

(5Z)-5-({1-[4-Chloro-2-(trifluoromethyl)benzyl]-1H-indazol-5-yl}-methylidene)-3-{[1-(methylsulfonyl)-1H-imidazol-2-yl]methyl}-1,3-thiazolidine-2,4-dione was prepared from (5Z)-5-({1-[4-chloro-2-(trifluoromethyl)benzyl]-1H-indazol-5-yl}methylidene)-3-(1H-imidazol-2-ylmethyl)-1,3-thiazolidine-2,4-dione (from Example 403) and methanesulfonyl chloride following General Procedure U.

$^1$H NMR (400 MHz, CD$_3$OD): δ 8.29 (s, 1H), 8.14 (s, 2H), 7.80 (d, 1H), 7.58-7.67 (m, 2H), 7.55 (s, 2H), 7.49 (dd, 1H), 6.71 (d, 1H), 5.87 (s, 2H), 5.26 (s, 2H), 2.70 (s, 3H).

LCMS: mass calcd. for C$_{24}$H$_{17}$ClF$_3$N$_5$O$_4$S$_2$: 596.0. found 518.1 [M−SO$_2$Me]$^+$.

Example 411

(5Z)-5-({1-[4-Chloro-2-(trifluoromethyl)benzyl]-1H-indazol-5-yl}methylidene)-3-({1-[(trifluoromethyl)sulfonyl]-1H-imidazol-2-yl}methyl)-1,3-thiazolidine-2,4-dione

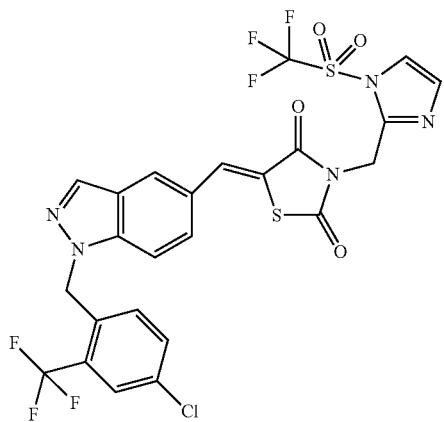 [SMILES: O=C1S/C(=C\c2ccc3c(cnn3Cc3ccc(Cl)cc3C(F)(F)F)c2)C(=O)N1Cc1nccn1S(=O)(=O)C(F)(F)F]

(5Z)-5-({1-[4-Chloro-2-(trifluoromethyl)benzyl]-1H-indazol-5-yl}methylidene)-3-({1-[(trifluoromethyl)sulfonyl]-1H-imidazol-2-yl}methyl)-1,3-thiazolidine-2,4-dione was prepared from (5Z)-5-({1-[4-chloro-2-(trifluoromethyl)benzyl]-1H-indazol-5-yl}methylidene)-3-(1H-imidazol-2-ylmethyl)-1,3-thiazolidine-2,4-dione (from Example 403) and trifluoromethanesulfonyl chloride following General Procedure U.

$^1$H NMR (400 MHz, CD$_3$OD): δ 8.29 (s, 1H), 8.14 (s, 2H), 7.98 (s, 1H), 7.80 (d, 1H), 7.59-7.68 (m, 2H), 7.55 (s, 1H), 7.48 (dd, 1H), 6.71 (d, 1H), 5.87 (s, 2H), 5.25 (s, 2H).

LCMS: mass calcd. for C$_{24}$H$_{14}$ClF$_6$N$_5$O$_4$S$_2$: 650.0. found 518.0 [M−SO$_2$CF$_3$]$^+$.

Example 412

(5Z)-5-({1-[4-Chloro-2-(trifluoromethyl)benzyl]-1H-indazol-5-yl}methylidene)-3-{[1-(pyrrolidin-1-ylsulfonyl)-1H-imidazol-2-yl]methyl}-1,3-thiazolidine-2,4-dione

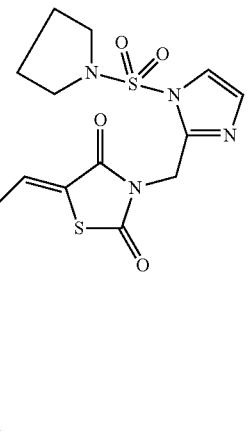

(5Z)-5-({1-[4-Chloro-2-(trifluoromethyl)benzyl]-1H-indazol-5-yl}methylidene)-3-{[1-(pyrrolidin-1-ylsulfonyl)-1H-imidazol-2-yl]methyl}-1,3-thiazolidine-2,4-dione was prepared from (5Z)-5-({1-[4-chloro-2-(trifluoromethyl)benzyl]-1H-indazol-5-yl}methylidene)-3-(1H-imidazol-2-ylmethyl)-1,3-thiazolidine-2,4-dione (from Example 403) and 1-pyrrolidinesulfonyl chloride following General Procedure U.

$^1$H NMR (400 MHz, CD$_3$OD): δ 8.29 (s, 1H), 8.14 (s, 2H), 7.98 (s, 1H), 7.80 (d, 1H), 7.58-7.67 (m, 2H), 7.54 (s, 2H), 7.48 (dd, 1H), 6.71 (d, 1H), 5.87 (s, 2H), 5.25 (s, 2H), 3.46-3.53 (m, 4H), 2.01-2.08 (m, 4H).

LCMS: mass calcd. for C$_{27}$H$_{22}$ClF$_3$N$_6$O$_4$S$_2$: 651.1. found 651.0 [M]$^+$.

Example 413

N-(4-{[(5Z)-5-({1-[4-Chloro-2-(trifluoromethyl)benzyl]-1H-indazol-5-yl}-methylidene)-2,4-dioxo-1,3-thiazolidin-3-yl]methyl}-1,3-thiazol-2-yl)acetamide

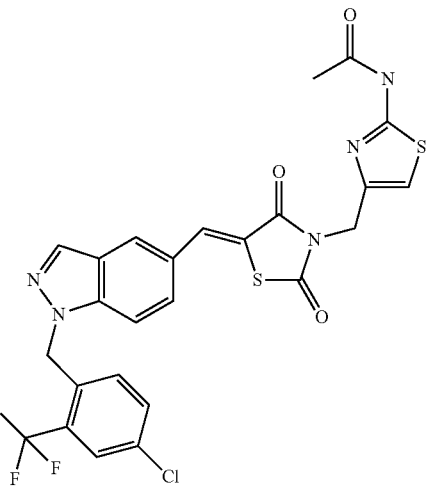

N-(4-{[(5Z)-5-({1-[4-Chloro-2-(trifluoromethyl)benzyl]-1H-indazol-5-yl}methylidene)-2,4-dioxo-1,3-thiazolidin-3-yl]methyl}-1,3-thiazol-2-yl)acetamide was prepared from (5Z)-3-[(2-amino-1,3-thiazol-4-yl)methyl]-5-({1-[4-chloro-2-(trifluoromethyl)benzyl]-1H-indazol-5-yl}methylidene)-1,3-thiazolidine-2,4-dione (from Example 400) and acetic anhydride following General Procedure U.

$^1$H NMR (400 MHz, DMSO-d$_6$): δ 8.45 (s, 1H), 8.20 (s, 1H), 7.72-7.79 (m, 2H), 7.67 (dd, 1H), 7.56 (d, 1H), 6.75 (m, 1H), 6.67 (d, 1H), 6.44 (m, 1H), 5.78 (m, 2H), 4.40 (s, 2H), 1.97 (d, 3H).

LCMS: mass calcd. for C$_{27}$H$_{17}$ClF$_3$N$_6$O$_3$S$_2$: 592.0. found 591.9 [M]$^+$.

Example 414

N-(4-{[(5Z)-5-({1-[4-Chloro-2-(trifluoromethyl)benzyl]-1H-indazol-5-yl}-methylidene)-2,4-dioxo-1,3-thiazolidin-3-yl]methyl}-1,3-thiazol-2-yl)-1,1,1-trifluoromethanesulfonamide

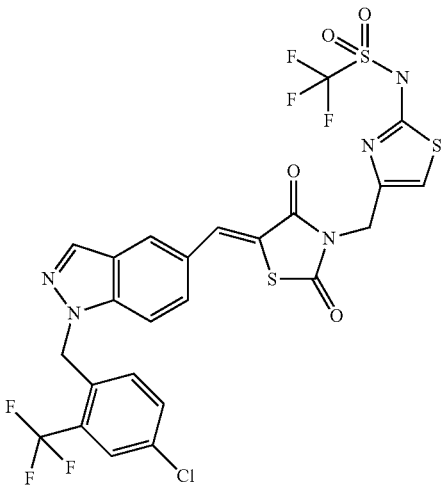 [SMILES: O=C1S/C(=C\c2ccc3c(cnn3Cc3ccc(Cl)cc3C(F)(F)F)c2)C(=O)N1Cc1csc(NS(=O)(=O)C(F)(F)F)n1]

N-(4-{[(5Z)-5-({1-[4-Chloro-2-(trifluoromethyl)benzyl]-1H-indazol-5-yl}methylidene)-2,4-dioxo-1,3-thiazolidin-3-yl]methyl}-1,3-thiazol-2-yl)-1,1,1-trifluoromethanesulfonamide was prepared from (5Z)-3-[(2-amino-1,3-thiazol-4-yl)methyl]-5-({1-[4-chloro-2-(trifluoromethyl)benzyl]-1H-indazol-5-yl}methylidene)-1,3-thiazolidine-2,4-dione (from Example 400) and trifluoromethanesulfonyl chloride following General Procedure U.

$^1$H NMR (400 MHz, CD$_3$OD): δ 8.34 (s, 1H), 8.14 (s, 1H), 8.01-8.06 (m, 2H), 7.81 (dd, 1H), 7.71 (dd, 1H), 7.63 (d, 1H), 7.51 (dd, 1H), 6.81 (d, 1H), 5.92 (s, 2H), 4.42 (s, 2H).

LCMS: mass calcd. for C$_{24}$H$_{14}$ClF$_6$N$_5$O$_4$S$_3$: 682.0. found 681.9 [M]$^+$.

Example 415

5-[1-(4-Chloro-2-trifluoromethylbenzyl)-1H-indazol-5-ylmethylene]-3-[2-(1,1-dioxo-1λ$^6$-[1,2,5]thiadiazolidin-2-yl)-2-oxoethyl]thiazolidine-2,4-dione

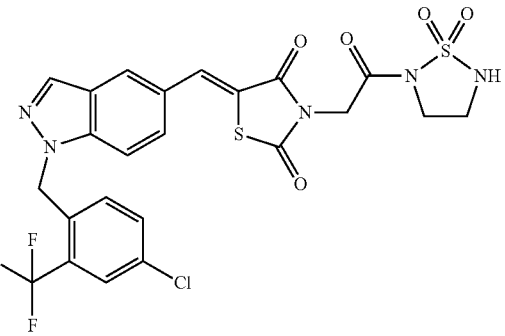

(A) tert-Butyl 5-{[(5Z)-5-({1-[4-chloro-2-(trifluoromethyl)benzyl]-1H-indazol-5-yl}methylidene)-2,4-dioxo-1,3-thiazolidin-3-yl]acetyl}-1,2,5-thiadiazolidine-2-carboxylate 1,1-dioxide was prepared from [(5Z)-5-({1-[4-chloro-2-(trifluoromethyl)benzyl]-1H-indazol-5-yl}methylidene)-2,4-dioxo-1,3-thiazolidin-3-yl]acetic acid (from Example 4) and 1,1-dioxo-1λ$^6$-[1,2,5]thiadiazolidine-2-carboxylic acid tert-butyl ester following General Procedure C.

(B) 5-[1-(4-Chloro-2-trifluoromethyl-benzyl)-1H-indazol-5-ylmethylene]-3-[2-(1,1-dioxo-1λ$^6$-[1,2,5]thiadiazolidin-2-yl)-2-oxoethyl]thiazolidine-2,4-dione was prepared from tert-butyl 5-{[(5Z)-5-({1-[4-chloro-2-(trifluoromethyl)benzyl]-1H-indazol-5-yl}methylidene)-2,4-dioxo-1,3-thiazolidin-3-yl]acetyl}-1,2,5-thiadiazolidine-2-carboxylate 1,1-dioxide following General Procedure M.

$^1$H NMR (400 MHz, DMSO-d$_6$): δ 8.39 (s, 1H), 8.22 (s, 1H), 8.17 (s, 1H), 7.89 (d, 1H), 7.83 (d, 1H), 7.72 (dd, 1H), 7.66 (dd, 1H), 6.78 (d, 1H), 5.88 (s, 2H), 4.76 (s, 2H).

LCMS: mass calcd. for C$_{23}$H$_{17}$ClF$_3$N$_6$O$_6$S$_2$: 600.0. found 599.8 [M]$^+$.

Example 416

[(5Z)-5-({1-[4-Chloro-2-(trifluoromethyl)benzyl]-3-cyano-1H-indazol-5-yl}-methylidene)-2,4-dioxo-1,3-thiazolidin-3-yl]acetic acid

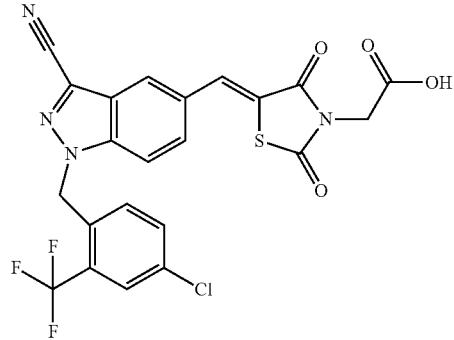 [SMILES: N#Cc1nn(Cc2ccc(Cl)cc2C(F)(F)F)c2ccc(/C=C3\SC(=O)N(CC(=O)O)C3=O)cc12]

(A) A mixture of 3-bromo-1-(4-chloro-2-trifluoromethyl-benzyl)-1H-indazole-5-carbaldehyde (0.479 mmol, from Example 407), Pd(dppf)Cl2 dichloromethane complex (0.0479 mmol), zinc cyanide (0.575 mmol), and sodium acetate (0.958 mmol) in DMF (6 mL) under argon was heated at 100° C. for 4 h, then concentrated under reduced pressure. Chromatographic purification of the residue (silica gel, hexanes to hexanes:EtOAc, 1:1) afforded 1-(4-Chloro-2-trifluoromethylbenzyl)-5-formyl-1H-indazole-3-carbonitrile as yellow solid.

(B) [(5Z)-5-({1-[4-Chloro-2-(trifluoromethyl)benzyl]-3-cyano-1H-indazol-5-yl}methylidene)-2,4-dioxo-1,3-thiazolidin-3-yl]acetic acid was prepared from 1-(4-chloro-2-trifluoromethyl-benzyl)-5-formyl-1H-indazole-3-carbonitrile and (2,4-dioxothiazolidin-3-yl)-acetic acid following General Procedure F.

$^1$H NMR (400 MHz, CD$_3$OD): δ 8.12 (s, 1H), 8.08 (s, 1H), 7.83 (d, 1H), 7.79 (s, 2H), 7.57 (dd, 1H), 6.95 (d, 1H), 5.98 (s, 2H), 4.30 (s, 2H).

LCMS: mass calcd. for C$_{22}$H$_{12}$ClF$_3$N$_4$O$_4$S: 520.9. found 519.8 [M]$^+$.

Example 417

[(5Z)-5-({3-Carbamoyl-1-[4-chloro-2-(trifluoromethyl)benzyl]-1H-indazol-5-yl}-methylidene)-2,4-dioxo-1,3-thiazolidin-3-yl]acetic acid

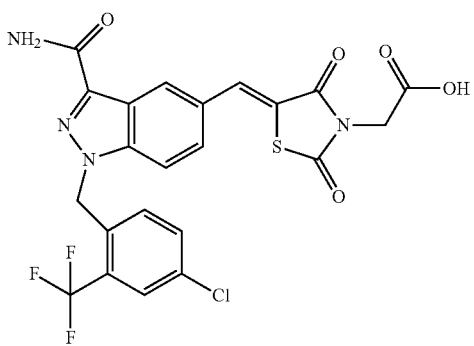 [SMILES: NC(=O)c1nn(Cc2ccc(Cl)cc2C(F)(F)F)c2ccc(/C=C3\SC(=O)N(CC(=O)O)C3=O)cc12]

[(5Z)-5-({3-carbamoyl-1-[4-chloro-2-(trifluoromethyl)benzyl]-1H-indazol-5-yl}methylidene)-2,4-dioxo-1,3-thiazolidin-3-yl]acetic acid was also isolated from the reaction described in Example 416.

$^1$H NMR (400 MHz, DMSO-d$_6$): δ 8.58 (s, 1H), 8.04 (s, 1H), 7.82 (d, 1H), 7.69 (dd, 1H), 7.63 (d, 1H), 7.53 (dd, 1H), 6.78 (d, 1H), 5.96 (s, 2H), 4.25 (s, 2H).

LCMS: mass calcd. for C$_{22}$H$_{14}$ClF$_3$N$_4$O$_6$S: 538.9. found 538.9 [M]$^+$.

Example 418

5-Chloro-N-{2-[(5Z)-5-({1-[4-chloro-2-(trifluoromethyl)benzyl]-1H-indazol-5-yl}methylidene)-2,4-dioxo-1,3-thiazolidin-3-yl]ethyl}-1,3-dimethyl-1H-pyrazole-4-sulfonamide

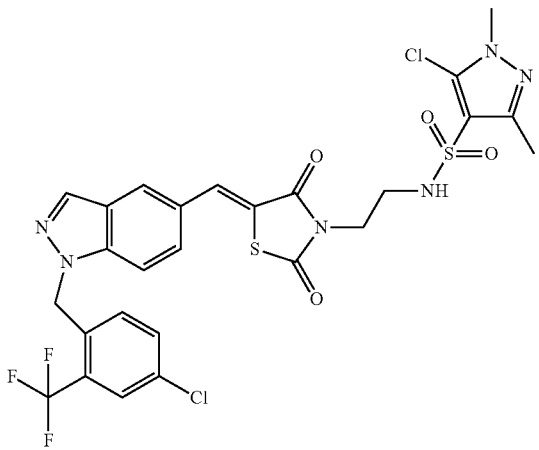 [SMILES: Cc1nn(C)c(Cl)c1S(=O)(=O)NCCN1C(=O)S/C(=C\c2ccc3c(cnn3Cc3ccc(Cl)cc3C(F)(F)F)c2)C1=O]

5-Chloro-N-{2-[(5Z)-5-({1-[4-chloro-2-(trifluoromethyl)benzyl]-1H-indazol-5-yl}methylidene)-2,4-dioxo-1,3-thiazolidin-3-yl]ethyl}-1,3-dimethyl-1H-pyrazole-4-sulfonamide was prepared from 3-(2-aminoethyl)-(5Z)-5-({1-[4-chloro-2-(trifluoromethyl)benzyl]-1H-indazol-5-yl}methylidene)-1,3-thiazolidine-2,4-dione (from Example 49) and 5-chloro-1,3-dimethyl-1H-pyrazole-4-sulfonyl chloride following General Procedure U.

$^1$H NMR (400 MHz, CD$_3$OD): δ 8.28 (d, 1H), 8.11 (s, 1H), 8.02 (d, 1H), 7.80 (s, 1H), 7.56-7.67 (m, 2H), 7.45-7.52 (m, 1H), 6.69 (t, 1H), 5.87 (s, 2H), 3.93-3.98 (m, 2H), 3.77-3.84 (m, 2H), 3.56-3.61 (m, 1H), 2.32 (s, 3H), 2.03 (s, 3H).

LCMS: mass calcd. for C$_{26}$H$_{21}$Cl$_2$F$_3$N$_6$O$_4$S$_2$: 673.5. found 672.8 [M]$^+$.

Example 419

N-{2-[(5Z)-5-({1-[4-Chloro-2-(trifluoromethyl)benzyl]-1H-indazol-5-yl}-methylidene)-2,4-dioxo-1,3-thiazolidin-3-yl]ethyl}-3,5-dimethylisoxazole-4-sulfonamide

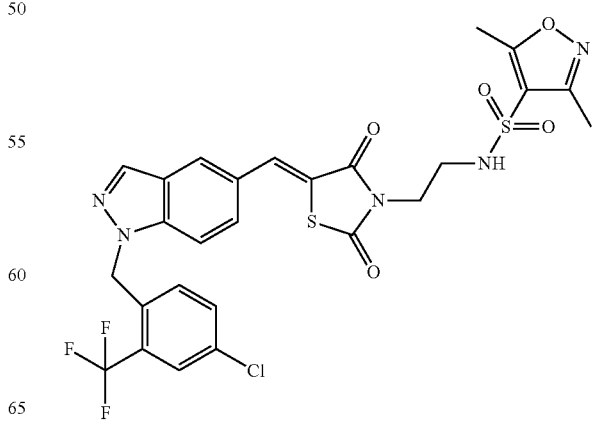

499

N-{2-[(5Z)-5-({1-[4-Chloro-2-(trifluoromethyl)benzyl]-1H-indazol-5-yl}methylidene)-2,4-dioxo-1,3-thiazolidin-3-yl]ethyl}-3,5-dimethylisoxazole-4-sulfonamide was prepared from 3-(2-aminoethyl)-(5Z)-5-({1-[4-chloro-2-(trifluoromethyl)benzyl]-1H-indazol-5-yl}methylidene)-1,3-thiazolidine-2,4-dione (from Example 49) and 3,5-dimethylisoxazole-4-sulfonyl chloride following General Procedure U.

$^1$H NMR (400 MHz, CD$_3$OD): δ 8.28 (s, 1H), 8.10 (s, 1H), 8.03 (d, 1H), 7.80 (d, 1H), 7.56-7.65 (m, 2H), 7.47 (dd, 1H), 6.68 (d, 1H), 5.86 (s, 2H), 3.94 (t, 2H), 3.82 (t, 2H), 3.55-3.62 (m, 1H), 2.58 (s, 3H), 2.33 (s, 3H).

LCMS: mass calcd. for C$_{26}$H$_{21}$ClF$_3$N$_5$O$_5$S$_2$: 640.1. found 639.9 [M]$^+$.

Example 420

N-[5-({2-[(5Z)-5-({1-[4-Chloro-2-(trifluoromethyl)benzyl]-1H-indazol-5-yl}-methylidene)-2,4-dioxo-1,3-thiazolidin-3-yl]ethyl}sulfamoyl)-4-methyl-1,3-thiazol-2-yl]acetamide

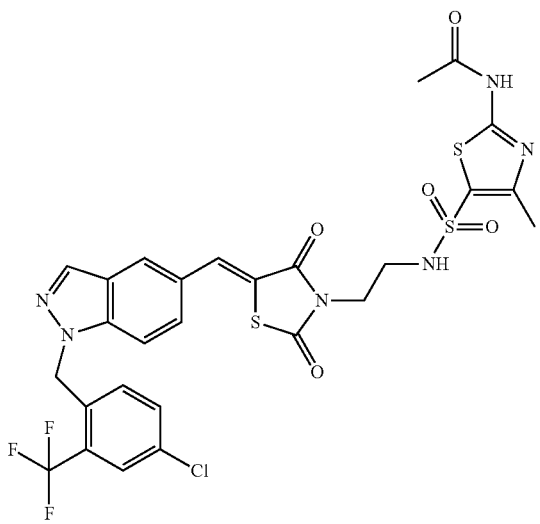 [SMILES: CC(=O)Nc1nc(C)c(S(=O)(=O)NCCN2C(=O)S/C(=C\c3ccc4c(cnn4Cc4ccc(Cl)cc4C(F)(F)F)c3)C2=O)s1]

N-[5-({2-[(5Z)-5-({1-[4-Chloro-2-(trifluoromethyl)benzyl]-1H-indazol-5-yl}methylidene)-2,4-dioxo-1,3-thiazolidin-3-yl]ethyl}sulfamoyl)-4-methyl-1,3-thiazol-2-yl]acetamide was prepared from 3-(2-aminoethyl)-(5Z)-5-({1-[4-chloro-2-(trifluoromethyl)benzyl]-1H-indazol-5-yl}methylidene)-1,3-thiazolidine-2,4-dione (from Example 49) and 2-acetamido-4-methyl-5-thiazolesulfonyl chloride following General Procedure U.

$^1$H NMR (400 MHz, CDCl$_3$): δ 8.27 (s, 1H), 8.03 (s, 1H), 8.00 (s, 1H), 7.74 (d, 1H), 7.57 (dd, 1H), 7.45 (d, 1H), 7.39 (dd, 1H), 6.66 (d, 1H), 5.84 (s, 2H), 3.88 (t, 3H), 3.36 (t, 3H), 2.52 (s, 3H), 2.03 (s, 3H).

LCMS: mass calcd. for C$_{27}$H$_{22}$ClF$_3$N$_6$O$_5$S$_3$: 699.2. found 698.8 [M]$^+$.

Example 421

5-({2-[(5Z)-5-({1-[4-Chloro-2-(trifluoromethyl)benzyl]-1H-indazol-5-yl}-methylidene)-2,4-dioxo-1,3-thiazolidin-3-yl]ethyl}sulfamoyl)furan-2-carboxylic acid

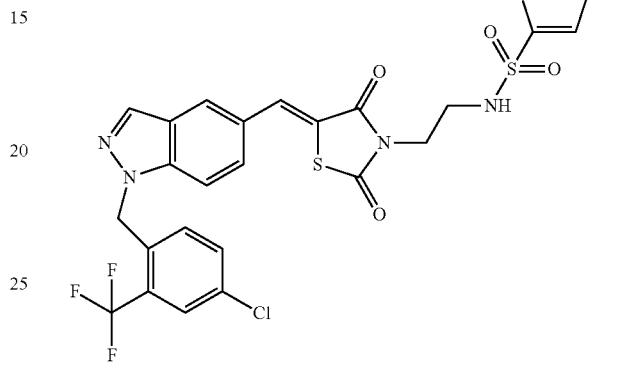

(A) Methyl 5-({2-[(5Z)-5-({1-[4-Chloro-2-(trifluoromethyl)benzyl]-1H-indazol-5-yl}methylidene)-2,4-dioxo-1,3-thiazolidin-3-yl]ethyl}sulfamoyl)furan-2-carboxylate was prepared from 3-(2-aminoethyl)-(5Z)-5-({1-[4-chloro-2-(trifluoromethyl)benzyl]-1H-indazol-5-yl}methylidene)-1,3-thiazolidine-2,4-dione (from Example 49) and methyl 5-(chlorosulfonyl)-2-furoate following General Procedure U.

(B) 5-({2-[(5Z)-5-({1-[4-Chloro-2-(trifluoromethyl)benzyl]-1H-indazol-5-yl}methylidene)-2,4-dioxo-1,3-thiazolidin-3-yl]ethyl}sulfamoyl)furan-2-carboxylic acid was prepared from methyl 5-({2-[(5Z)-5-({1-[4-chloro-2-(trifluoromethyl)benzyl]-1H-indazol-5-yl}methylidene)-2,4-dioxo-1,3-thiazolidin-3-yl]ethyl}sulfamoyl)furan-2-carboxylate following General Procedure O.

$^1$H NMR (400 MHz, CD$_3$OD): δ 8.26 (s, 1H), 8.06 (s, 1H), 8.01 (s, 1H), 7.78 (d, 1H), 7.52-7.63 (m, 2H), 7.46 (dd, 1H), 7.31 (d, 1H), 7.23 (d, 1H), 6.67 (d, 1H), 5.84 (s, 2H), 4.31 (t, 2H), 4.19 (t, 2H).

LCMS: mass calcd. for C$_{26}$H$_{18}$ClF$_3$N$_4$O$_7$S$_2$: 655.02. found 656.0 [M+H]$^+$.

D) General Administration, Formulation, and Dosages

The present compounds are ERR-α inverse agonists and are therefore useful in treating or inhibiting the progression of ERR-α mediated conditions including but not limited to ankylosing spondylitis, artherosclerosis, arthritis (such as rheumatoid arthritis, infectious arthritis, childhood arthritis, psoriatic arthritis, reactive arthritis), bone-related diseases (including those related to bone formation), breast cancer (including those unresponsive to anti-estrogen therapy), cardiovascular disorders, cartilage-related disease (such as cartilage injury/loss, cartilage degeneration, and those related to cartilage formation), chondrodysplasia, chondrosarcoma, chronic back injury, chronic bronchitis, chronic inflammatory airway disease, chronic obstructive pulmonary disease, diabetes, disorders of energy homeostasis, gout, pseudogout, lipid disorders, metabolic syndrome, multiple myeloma, obesity, osteoarthritis, osteogenesis imperfecta, osteolytic bone metastasis, osteomalacia, osteoporosis, Paget's disease, periodontal disease, polymyalgia rheumatica, Reiter's syndrome, repetitive stress injury, hyperglycemia, elevated blood glucose level, and insulin resistance and other disorders, diseases, or conditions related thereto.

The invention features a method for treating a subject with an ERR-α mediated disease, said method comprising administering to the subject a therapeutically effective amount of a pharmaceutical composition comprising a compound of the invention. In particular, the invention also provides a method for treating or inhibiting the progression of breast cancer, arthritis, inflammatory airway disease, or metabolic disorders, and associated symptoms or complications thereof in a subject, wherein the method comprises administering to the subject a therapeutically effective amount of a pharmaceutical composition comprising a compound of the invention.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "*Design of Prodrugs*", ed. H. Bundgaard, Elsevier, 1985.

Some of the crystalline forms for the compounds may exist as polymorphs and as such are intended to be included in the present invention. In addition, some of the compounds may form solvates with water (i.e., hydrates) or common organic solvents, and such solvates are intended to be encompassed within the scope of this invention.

Where the processes for the preparation of the compounds according to the invention give rise to mixtures of stereoisomers, these isomers may be separated by conventional techniques such as preparative chromatography. The compounds may be prepared in racemic form or as individual enantiomers or diasteromers by either stereospecific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. It is to be understood that all stereoisomers, racemic mixtures, diastereomers, cis-trans isomers, and enantiomers thereof are encompassed within the scope of the present invention.

E) Use

1. Dosages

Those of skill in the treatment of disorders, diseases, or conditions mediated by ERR-α can determine the effective daily amount from the test results presented hereinafter and other information. The exact dosage and frequency of administration depends on the particular compound of invention used, the particular condition being treated, the severity of the condition being treated, the age, weight and general physical condition of the particular patient as well as other medication the patient may be taking, as is well known to those skilled in the art. Furthermore, it is evident that said effective daily amount may be lowered or increased depending on the response of the treated patient and/or depending on the evaluation of the physician prescribing the compounds of the instant invention. The effective daily amount ranges mentioned herein are therefore only guidelines in practicing the present invention.

Preferably, the method for the treatment of the ERR-α disorders described in the present invention using any of the compounds as defined herein, the dosage form will contain a pharmaceutically acceptable carrier containing between from about 0.1 mg to about 5000 mg; particularly from about 0.5 mg to about 1000 mg; and, more particularly, from about 1 mg to about 100 mg of the compound, and may be constituted into any form suitable for the mode of administration selected. The dosages, however, may be varied depending upon the requirement of the subjects, the severity of the condition being treated and the compound being employed. The use of either daily administration or post-periodic dosing may be employed.

The pharmaceutical compositions herein will contain, per unit dosage unit, e.g., tablet, capsule, powder, injection, suppository, teaspoonful and the like, of from about 0.001 mg/kg/day to about 10 mg/kg/day (particularly from about 0.01 mg/kg/day to about 1 mg/kg/day; and, more particularly, from about 0.1 mg/kg/day to about 0.5 mg/kg/day) and may be given at a dosage of from about 0.001 mg/kg/day to about 30 mg/kg/day (particularly from about 0.01 mg/kg/day to about 2 mg/kg/day, more particularly from about 0.1 mg/kg/day to about 1 mg/kg/day and even more particularly from about 0.5 mg/kg/day to about 1 mg/kg/day).

Preferably these compositions are in unit dosage forms from such as tablets, pills, capsules, dry powders for reconstitution or inhalation, granules, lozenges, sterile parenteral solutions or suspensions, metered aerosol or liquid sprays, drops, ampoules, autoinjector devices or suppositories for administration by oral, intranasal, sublingual, intraocular, transdermal, parenteral, rectal, vaginal, dry powder inhaler or other inhalation or insufflation means. Alternatively, the composition may be presented in a form suitable for once-weekly or once-monthly administration; for example, an insoluble salt of the active compound, such as the decanoate salt, may be adapted to provide a depot preparation for intramuscular injection.

For preparing solid pharmaceutical compositions such as tablets, the principal active ingredient is mixed with a pharmaceutical carrier, e.g. conventional tableting ingredients such as diluents, binders, adhesives, disintegrants, lubricants, antiadherents and gildants. Suitable diluents include, but are not limited to, starch (i.e. corn, wheat, or potato starch, which may be hydrolized), lactose (granulated, spray dried or anhydrous), sucrose, sucrose-based diluents (confectioner's sugar; sucrose plus about 7 to 10 weight percent invert sugar; sucrose plus about 3 weight percent modified dextrins; sucrose plus invert sugar, about 4 weight percent invert sugar, about 0.1 to 0.2 weight percent cornstarch and magnesium stearate), dextrose, inositol, mannitol, sorbitol, microcrystalline cellulose (i.e. AVICEL™ microcrystalline cellulose available from FMC Corp.), dicalcium phosphate, calcium sulfate dihydrate, calcium lactate trihydrate and the like. Suitable binders and adhesives include, but are not limited to acacia gum, guar gum, tragacanth gum, sucrose, gelatin, glucose, starch, and cellulosics (i.e. methylcellulose, sodium carboxymethylcellulose, ethylcellulose, hydroxypropylmethylcellulose, hydroxypropylcellulose, and the like), water soluble or dispersible binders (i.e. alginic acid and salts thereof, magnesium aluminum silicate, hydroxyethylcellulose [i.e. TYLOSE™ available from Hoechst Celanese], polyethylene glycol, polysaccharide acids, bentonites, polyvinylpyrrolidone, polymethacrylates and pregelatinized starch) and the like. Suitable disintegrants include, but are not limited to, starches (corn, potato, etc.), sodium starch glycolates, pregelatinized starches, clays (magnesium aluminum silicate), celluloses (such as crosslinked sodium carboxymethylcellulose and microcrystalline cellulose), alginates, pregelatinized starches (i.e. corn starch, etc.), gums (i.e. agar, guar, locust bean, karaya, pectin, and tragacanth gum), crosslinked polyvinylpyrrolidone and the like. Suitable lubricants and antiadherents include, but are not limited to, stearates (magnesium, calcium and sodium), stearic acid, talc waxes, stearowet, boric acid, sodium chloride, DL-leucine, carbowax 4000, carbowax 6000, sodium oleate, sodium benzoate, sodium acetate, sodium lauryl sulfate, magnesium lauryl sulfate and the like. Suitable gildants include, but are not limited to, talc, cornstarch, silica (i.e. CAB-O-SIL™ silica available from Cabot, SYLOID™ silica available from W.R. Grace/Davison, and AEROSIL™ silica available from Degussa) and the like. Sweeteners and flavorants may be added to chewable solid dosage forms to improve the palatability of the oral dosage form. Additionally, colorants and coatings may be added or applied to the solid dosage form for ease of identification of the drug or for aesthetic purposes. These carriers are formulated with the pharmaceutical active to provide an accurate, appropriate dose of the pharmaceutical active with a therapeutic release profile.

Generally these carriers are mixed with the pharmaceutical active to form a solid preformulation composition containing a homogeneous mixture of the pharmaceutical active form of the present invention, or a pharmaceutically acceptable salt thereof. Generally the preformulation will be formed by one of three common methods: (a) wet granulation, (b) dry granulation and (c) dry blending. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.1 mg to about 500 mg of the active ingredient of the present invention. The tablets or pills containing the novel compositions may also be formulated in multilayer tablets or pills to provide a sustained or provide dual-release products. For example, a dual release tablet or pill can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric materials such as shellac, cellulose acetate (i.e. cellulose acetate phthalate, cellulose acetate trimetllitate), polyvinyl acetate phthalate, hydroxypropyl methylcellulose phthalate, hydroxypropyl methylcellulose acetate succinate, methacrylate and ethylacrylate copolymers, methacrylate and methyl methacrylate copolymers and the like. Sustained release tablets may also be made by film coating or wet granulation using slightly soluble or insoluble substances in solution (which for a wet granulation acts as the binding agents) or low melting solids a molten form (which in a wet granulation may incorporate the active ingredient). These materials include natural and synthetic polymers waxes, hydrogenated oils, fatty acids and alcohols (i.e. beeswax, carnauba wax, cetyl alcohol, cetylstearyl alcohol, and the like), esters of fatty acids metallic soaps, and other acceptable materials that can be used to granulate, coat, entrap or otherwise limit the solubility of an active ingredient to achieve a prolonged or sustained release product.

The liquid forms in which the novel compositions of the present invention may be incorporated for administration orally or by injection include, but are not limited to aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable suspending agents for aqueous suspensions, include synthetic and natural gums such as, acacia, agar, alginate (i.e. propylene alginate, sodium alginate and the like), guar, karaya, locust bean, pectin, tragacanth, and xanthan gum, cellulosics such as sodium carboxymethylcellulose, methylcellulose, hydroxymethylcellulose, hydroxyethylcellulose, hydroxypropyl cellulose and hydroxypropyl methylcellulose, and combinations thereof, synthetic polymers such as polyvinyl pyrrolidone, carbomer (i.e. carboxypolymethylene), and polyethylene glycol; clays such as bentonite, hectorite, attapulgite or sepiolite; and other pharmaceutically acceptable suspending agents such as lecithin, gelatin or the like. Suitable surfactants include but are not limited to sodium docusate, sodium lauryl sulfate, polysorbate, octoxynol-9, nonoxynol-10, polysorbate 20, polysorbate 40, polysorbate 60, polysorbate 80, polyoxamer 188, polyoxamer 235 and combinations thereof. Suitable deflocculating or dispersing agent include pharmaceutical grade lecithins. Suitable flocculating agent include but are not limited to simple neutral electrolytes (i.e. sodium chloride, potassium, chloride, and the like), highly charged insoluble polymers and polyelectrolyte species, water soluble divalent or trivalent ions (i.e. calcium salts, alums or sulfates, citrates and phosphates (which can be used jointly in formulations as pH buffers and flocculating agents). Suitable preservatives include but are not limited to parabens (i.e. methyl, ethyl, n-propyl and n-butyl), sorbic acid, thimerosal, quaternary ammonium salts, benzyl alcohol, benzoic acid, chlorhexidine gluconate, phenylethanol and the like. There are many liquid vehicles that may be used in liquid pharmaceutical dosage forms, however, the liquid vehicle that is used in a particular dosage form must be compatible with the suspending agent(s). For example, nonpolar liquid vehicles such as fatty esters and oils liquid vehicles are best used with suspending agents such as low HLB (Hydrophile-Lipophile Balance) surfactants, stearalkonium hectorite, water insoluble resins, water insoluble film forming polymers and the like. Conversely, polar liquids such as water, alcohols, polyols and glycols are best used with suspending agents such as higher HLB surfactants, clays silicates, gums, water soluble cellulosics, water soluble polymers and the like. For parenteral administration, sterile suspensions and solutions are desired. Liquid forms useful for parenteral administration include sterile solutions, emulsions and suspensions. Isotonic preparations which generally contain suitable preservatives are employed when intravenous administration is desired.

Furthermore, compounds of the present invention can be administered in an intranasal dosage form via topical use of suitable intranasal vehicles or via transdermal skin patches, the composition of which are well known to those of ordinary skill in that art. To be administered in the form of a transdermal delivery system, the administration of a therapeutic dose will, of course, be continuous rather than intermittent throughout the dosage regimen.

Compounds of the present invention can also be administered in the form of liposome delivery systems, such as small unilamellar vesicles, large unilamellar vesicles, multilamellar vesicles and the like. Liposomes can be formed from a variety of phospholipids, such as cholesterol, stearylamine, phosphatidylcholines and the like.

The daily dose of a pharmaceutical composition of the present invention may be varied over a wide range from about 0.1 mg to about 5000 mg; preferably, the dose will be in the range of from about 1 mg to about 100 mg per day for an average human. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 or 500 milligrams of the active ingredient for the symptomatic adjustment of the dosage to the subject to be treated. Advantageously, a compound of the present invention may be administered in a single daily dose or the total daily dosage may be administered in divided doses of two, three or four times daily.

It is also apparent to one skilled in the art that the therapeutically effective dose for active compounds of the invention or a pharmaceutical composition thereof will vary according to the desired effect. Therefore, optimal dosages to be administered may be readily determined by those skilled in the art, and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

Compounds of this invention may be administered in any of the foregoing compositions and dosage regimens or by means of those compositions and dosage regimens established in the art whenever use of the compounds of the invention as ERR-α inverse agonists is required for a subject in need thereof.

2. Formulations

To prepare the pharmaceutical compositions of this invention, one or more compounds of Formula (I) or salt thereof as the active ingredient, is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

The compounds of the present invention may be formulated into various pharmaceutical forms for administration purposes. Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

3. Combination Therapy

The compounds of the present invention may be used in combination with one or more pharmaceutically active agents. These agents include ERR-α antagonists, glucokinase modulators, anti-diabetic agents, other lipid lowering agents, direct thrombin inhibitor (DTI), as well as lipid lowering agents such as statin drugs and the fibrates.

ERR-α antagonists include, for example, all the compounds disclosed in US-2006-0014812-A1, particularly those of the formula

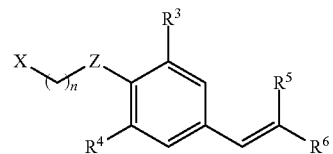

wherein:
n is 0 or 1;
Z is —O—, —S—, >NH, or >NR$^a$ where R$^a$ is alkyl, cycloalkyl, phenyl, or heterocycloalkyl;
X is an aryl or heteroaryl group;
R$^3$ is —H or —O-alkyl unsubstituted or substituted with one or more substituents independently selected from the group consisting of —OH, halo, —CN, —O-alkyl, and —N(R$^w$)R$^x$ where R$^w$ and R$^x$ are each independently —H or alkyl;
R$^4$ is selected from the group consisting of —H, halo, —O-alkyl, —CN, —NO$_2$, and —COON; and
R$^5$ and R$^6$ are each independently —CN; —COOH; or a moiety selected from the group consisting of —COO-alkyl, —(C=O)alkyl, —(S=O)$_m$-aryl where m is 0, 1, or 2, cycloalkyl, heterocycloalkyl, —(C=O)phenyl, heteroaryl, and —(C=O)heterocycloalkyl; or R$^5$ and R$^6$ taken together with the carbon to which they are attached form an optionally benzofused heterocycloalkyl or cycloalkyl moiety;
wherein each such moiety is unsubstituted or substituted with one or more substituents independently selected from the group consisting of: —OH; =O; =S; alkyl optionally substituted with —OH, —O-alkyl, phenyl, —NH$_2$, —NH(alkyl), —N(alkyl)$_2$, halo, —CF$_3$, —COOH, or —COO-alkyl; —O-alkyl; phenyl; —O-phenyl; benzyl; —O-benzyl; cycloalkyl; —O-cycloalkyl; —CN; —NO$_2$; —N(R$^y$)R$^z$ where R$^y$ and R$^z$ are each independently —H, alkyl, or —(C=O)alkyl, or R$^y$ and R$^z$ taken together with the nitrogen to which they are attached form a heterocycloalkyl wherein one carbon ring atom is optionally replaced with >O, >NH or >N-alkyl and where one carbon ring atom is optionally substituted with —OH or =O; —(C=O)N(R$^y$)R$^z$; —(N—R$^t$)SO$_2$alkyl where R$^t$ is —H or alkyl; —(C=O) alkyl; —(S=O)$_n$)alkyl where n is 0, 1 or 2; —SO$_2$N (R$^y$)R$^z$ where R$^y$ and R$^z$ are as defined above; —SCF$_3$; halo; —CF$_3$; —OCF$_3$; —COOH; and —COOalkyl;
or a pharmaceutically acceptable salt, pharmaceutically acceptable prodrug, or pharmaceutically active metabolite of such compound.

Anti-obesity agents can be classified into several categories based upon the mechanism of action. These agents include selective serotonin reuptake inhibitors (SSRIs), serotonin agonists, serotonin and norepinephrine reuptake inhibitors, pancreatic lipase inhibitors, β3-adrenoreceptor agonists, NPY antagonists, melanocortin receptor agonists, leptin-targeted agents, CB1 antagonists (e.g. Rimonabant), monoamine reuptake inhibitors (e.g. Sibutramine), and lipase inhibitors (e.g. Orlistat).

Serotonin agonist agents such as dexfenfluramine and fenfluramine were reported to cause cardiac valvular abnormalities when used at the prescribed dosage in combination with phentermine. Selective serotonin reuptake inhibitors (SSRIs) are generally used for the treatment of depression. These agents include fluoxetine (Prozac), paroxetine, fluvoxamine and sertraline.

Representative serotonin modulators are listed below:

(A) Selective serotonin reuptake inhibitors (SSRIs)
1. Citalopram (1-(3-(dimethylamino)propyl)-1-(4-fluorophenyl)-1,3-dihydro-5-isobenzofurancarbonitrile, also known as citalopram hydrobromide (USAN), nitalopram, nitalapram, ZD 211, LU 10171, Lu10-171, LU 10171-B, CIPRAMIL, SEROPRAM, CIPRAM, ELOPRAM, LUPRAM, SEPRAM, PRISDAL, or CELEXA);
2. Fluoxetine (benzenepropanamine, N-Methyl-gamma-[4-(trifluoromethyl)phenoxy]-, (±) hydrochloride, also known as LY 110140, RENEURON, SARAFEM, or PROZAC);
3. Fluvoxamine (5-methoxy-1-(4-(trifluoromethyl)phenyl)-1-pentanone (E)-O-(2-aminoethyl)oxime, also known as fluvoxamine maleate (USAN), DU 23000, MK 264, SME 3110, FEVARIN, FLOXYFRAL, LUVOX, DUMYROX, DUMIROX, FLAVOXYL, FAVERIN, or DEPROMEL);
4. Indeloxazine ((+, −)-2-((indel-7-yloxy)methyl)morpholine, also known as ideloxazine, YM 08054, CI-874, ELEN, or NOIN);
5. Paroxetine hydrochloride ((3S,4R)-3-((1,3-benzodioxol-5-yloxy)methyl)-4-(4-fluorophenyl)piperidine hydrochloride, or piperidine, 3-((1,3-benzodioxol-5-yloxy)methyl)-4-(4-fluorophenyl)-, (3S-trans)-, also known as FR 7051, FG-7051, BRL 29060, BRL 29060A, NNC 207051, SI 211103, CASBOL, SEROXAT, AROPAX, PAXIL, TAGONIS, FROSINOR, DEROXAT, SEREUPIN, MOTIVAN, or PAXIL CR);
6. Sertraline (1-naphthalenamine, 4-(3,4-dichlorophenyl)-1,2,3,4-tetrahydro-N-methyl-, (1S-cis)- or 1-Naphthalenamine, 4-(3,4-dichlorophenyl)-1,2,3,4-tetrahydro-N-methyl-, (1S-cis), also known as CP 51974, CP 51974 01, AREMIS, BESITRAN, GLADEM, LUSTRAL, SERAD, SERLAIN, SERLIFT, TATIG, or ZOLOFT);
7. Tianeptine (7-((3-chloro-6,11-dihydro-6-methyldibenzo(c,f)(1,2)thiazepin-11-yl)amino)heptanoic acid S,S-dioxide, also known as S 1574, or STABLON);
8. Centpropazine (1-(p-propionylphenoxy)-3-(Nsup(4)-henylpiperazynyl)propan-2-ol);
9. Paroxetine (GEOMATRIX drug delivery system) (piperidine,3-((1,3-benzodioxol-5-yloxy)methyl)-4-(4-fluorophenyl)-, (3S-trans)-, also known as paroxetine, GEOMATRIX, PAXIL CR);
10. Escitalopram ((1S)-1-(3-(dimethylamino)propyl)-1-(4-fluorophenyl)-1,3-dihydro-5-isobenzofuran carbonitrile, or 5-Isobenzofurancarbonitrile, 1-(3-(dimethylamino)propyl)-1-(4-fluorophenyl)-1,3-dihydro, (S)—, also known as escitalopram, xalate (USAN), citalopram, (S)(+)-citalopram, LU 26042, LU 26054, Lu26-054, or CIPRALEX);
11. Litoxetine (4-[(2-Naphthalenyl)methoxy]piperidine, also known as SL 810385);
12. (S)-Fluoxetine ((S)—N-methyl-gamma-(4-(trifluoromethyl)phenoxy)benzenepropanamine);
13. Cericlamine ((+,−)-3,4-dichloro-beta-(dimethylamino)-beta-methylbenzenepropanol, also known as JO 1017(+,−), JO 1239(−), or JO 1240(—F));
14. Dapoxetine ((+)-(S)—N,N-dimethyl-alpha-(2-(1-naphthyl-oxy)ethyl)benzylamine HCl, also known as LY-210448 or LY-243917);
15. 6-Nitroquipazine derivatives;
16. Series of substituted 6-nitroquipazines (Pharmaprojects No. 3391);
17. AAL 13 (2-(4-(3-chloropropyl)-1-piperazinyl)quinoline);
18. Depression therapy (by Vita Invest, Spain);
19. DUP 631 ($C_{13}H_{23}NO_2S$);
20. FI 4503 (by Ferrer, Spain);
21. Series of indolylcyclohexylamines (Pharmaprojects No. 6443, American Home Products);
22. LY 280253 (N-Methyl-N-[3-[4-(methylthio)phenoxy)-3-phenylpropyl]amine);
23. LY 285974 (by Lilly);
24. Omiloxetine (Ethanone,2-((3R,4S)-3-((1,3-benzodioxol-5-yloxy)methyl)-4-(4-fluorophenyl)-1-piperidinyl)-1-(4-fluorophenyl)-, rel-, also known as FI-4500, FI-4501, FI-4503); and
25. WF 31 (8-Methyl-2beta-propanoyl-3beta-(4-(1-methylethyl)-phenyl)-8-azabicyclo[3.2.1]);

(B) Serotonin agonists and partial agonists
1. Dexfenfluramine; and
2. Fenfluramine;

(C) Serotonin reuptake inhibitor with serotonin agonist activity
1. EMD-68843 (2-benzofurancarboxamide, 5-(4-(4-(5-cyano-1H-indol-3-yl)butyl)-1-piperazinyl)-, also known as SB-659746-A);
2. OPC-14523 (2(1H)-quinolinone, 1-(3-(4-(3-chlorophenyl)-1-piperazinyl)propyl)-3,4-dihydro-5-methoxy);
3. Vilazodone (5-{4-[4-(5-Cyano-3-indolyl)-butyl]-1-piperazinyl}-benzofuran-2-carboxamide, also known as EMD 68843 or SB 659746A);
4. Series of condensed thiazoles (3-(benzo (b) thiophen-3-yl)-5,6-dihydroimidazo (2,1-b)thiazolemonohydrobromide dihydrate, Pharmaprojects No. 5274, Abbott); and
5. VN-2222 (VN-8522, by Vita Invest, Spain).

Preferred examples of serotonin modulators include selective serotonin reuptake inhibitors such as Citalopram, Fluoxetine, Fluvoxamine, Indeloxazine, Paroxetine hydrochloride, Sertraline, Tianeptine, Centpropazine, Paroxetine, Escitalopram, and Litoxetine.

The following are also anti-obesity agents useful in the combination therapies of the present invention:

(A) Amylin and amylin analogs
1. Pramlintide (I-Lysyl-I-cysteinyl-I-asparaginyl-I-threonyl-I-alanyl-I-threonyl-I-cysteinyl-I-alanyl-I-threonyl-I-glutaminyl-I-arginyl-I-leucyl-I-alanyl-I-asparaginyl-I-phenylalanyl-I-leucyl-I-valyl-I-histidyl-I-seryl-I-seryl-I-asparaginyl-I-asparaginyl-I-phenylalanylglycyl-I-prolyl-I-isoleucyl-I-leucyl-I-prolyl-I-prolyl-I-threonyl-I-asparaginyl-I-valylglycyl-I-seryl-I-asparaginyl-I-threonyl-I-tyrosinamide cyclic (2-7)-disulfide, also known as pramlintide acetate, AC 137, ACO 137, AC 0137, SYMLIN, Tripro-amylin, or NORMYLIN);
2. Amylin agonists;
3. ACO 253 (AC 253, GG 747, GR 1150747A, or ANTAM);

(B) Ciliary neurotrophic factors (CNTF)
1. AXOKINE;
2. PEG-AXOKINE;
3. Peptide mimic of ciliary neurotrophic factor (CNTF mimic, also known as MYELOS);
4. Ciliary neurotrophic factor (CNTF by Fidia, Italy);

(C) Glucagon-like peptide-1
1. AC-2993 (also known as exendin-4, AC-2993 LAR, Medisord Exendin, AC-2993, Medisorb, or extendin-4, Amylin);
2. Exendin 4 (His-Gly-Glu-Gly-Thr-Phe-Thr-Ser-Asp-Leu-Ser-Lys-Gln-Met-Glu-Glu-Glu-Ala-V-al-Arg-Leu-Phe-Ile-Glu-Trp-Leu-Lys-Asn-Gly-Gly-Pro-Ser-Ser-Gly-Ala-Pro-Pro-Pro-Ser-amide, also known as AC 2993, AC 2993 LAR, Medisord Exendin, or AC-2993, Medisorb);
3. GLP-1 (Glucagon-like peptide-17-36 amide);
4. Glucagon-like peptide-1 oral transmucosal formulation;
5. Exendin 3 (His-Ser-Asp-Gly-Thr-Phe-Thr-Ser-Asp-Leu-Ser-Lys-Gln-Met-Glu-Glu-Glu-Ala-V-al-Arg-Leu-Phe-Ile-Glu-Trp-Leu-Lys-Asn-Gly-Gly-Pro-Ser-Ser-Gly-Ala-Pro-Pro-Pro-Ser-amide);

(D) Leptin & leptin mimetics
1. Leptin (2nd-generation);
2. Leptin agonists;
3. Leptin expression modulators;
4. Leptin signalling pathway modulators;
5. Leptin modulator;
6. Leptin (by IC Innovations, UK);
7. Leptin receptor, Monoclonal antibodies;
8. Recombinant native leptin;
9. LY-355101;
10. Leptin, Amylin (E) Melanocortin receptor agonist (MC4)
1. HP-228 (Glycinamide, N-acetyl-L-norleucyl-L-glutaminyl-L-histidyl-D-phenylalanyl-L-arginyl-D-tryptophyl-);
2. Melanocortin-4 receptor agonist (by Palatin, USA);
3. Melanocortin 4 agonist (by Pharmacopeia, Roche);
4. MC-4 agonists (by Millennium, Chiron)
5. Melanocortin-4 agonist (by Melacure Therapeutics, Sweden);
6. Melanocortin receptor modulators (Pharmaprojects No. 5224, Neurocrine Biosciences, US);
7. Pharmaprojects No. 5967, Trega/Novartis;

(F) NPY antagonists
1. AXC 0216;
2. AXC 1829;
3. SA-0204 (Neuropeptide Y antagonist, Apoptosis stimulator, Lipid metabolism modulator);
4. Alpha-trinositol (D-myo-Inositol, 1,2,6-tris(dihydrogen phosphate), also known as PP-56);
5. H 40922 (H 409/22);
6. BMS-192548 (1,11(4H,5H)-naphthacenedione,2-acetyl-4-a,12a-dihydro-3,4a,10,12,12a-pentahydroxy-8-methoxy-, TAN 1612 isomer);
7. Alanex (1,4-bis{(4-amino-6-methoxyphenylamino-1,2-dihydro-1,3,5-triazin-2-yl)-4-phenoxymethyl}benzene, Neuropeptide Y derivatives);
8. PD-160170 (6-(2-isopropyl-benzenesulfonyl)-5-nitroquinolin-8-ylamine);
9. 2,4-Diaminopyridine derivatives (6-(5-ethyl-1,3,4-thiadiazol-2-ylthiomethyl)-4-morpholino-2-(3-(2-propenyloxycarbonylamino) benzylamino)pyridine, Pharmaprojects No. 5618, Banyu/Merck);
10. Arpromidine analogs;
11. Neuropeptide Y antagonist (Pharmaprojects No. 4990, Pfizer);
12. 4 Methyl substituted benzimidazoles (NPY-1 antagonist, NPY-2 antagonist);
13. LY-366337 (Neuropeptide Y1 antagonist);
14. S-2501, S-25579, S-25584, S-25585, S-19528, S-34354 (all Neuropeptide Y1/5 antagonists);
15. Neuropeptide Y antagonist (subtypes 1 and 5) and Galanin receptor antagonist (Pharmaprojects No. 4897, Bristol-Myers Squibb);
16. Benzylamine derivatives (1-arylpiperazinyl-1-alkyloxyphenyl-4-alkylcycloalkanes);
17. J-104870 (Neuropeptide Y1 antagonist, Appetite suppressant);
18. LY-357897 (Neuropeptide Y1 antagonist);
19. Neuropeptide Y1 antagonist (Pfizer/Neurogen);
20. SR-120107A (Neuropeptide Y1 antagonist);
21. BIBO-3304 ((R)—N-((4-(aminocarbonylaminomethyl)-phenyl)methyl)-N2-(diphenylacetyl)-argininamide trifluoroacetate);
22. BIBP 3226 ((R)—N-(4-((aminoiminomethyl)amino)-1-((((4-hydroxyphenyl)methyl)amino)carbonyl)butyl)-alpha-phenylbenzeneacetamide, or benzeneacetamide, N-((1R)-4-((aminoiminomethyl)amino)-1-((((4-hydroxyphenyl)methyl)amino) carbonyl)butyl)-alpha-phenyl-);
23. SR 120819A (benzenepropanamide, N-(1-((4-((((4-((dimethylamino)methyl)cyclohexyl)methyl)amino)iminomethyl)phenyl)methyl)-2-oxo-2-(1-pyrrolidinyl)ethyl)-alpha-((2-naphthalenylsulfonyl)amino)-, (alphaR-(N(R*(cis)), alphaR*))-);
24. NGD-95-1 (CP-422935, NGD 951);
25. Compounds with benzazepine nuclei (Neuropeptide Y1 antagonist);
26. Neuropeptide Y1 antagonist (by Yamanouchi Pharmaceutical);
27. GI-264879A (Neuropeptide Y1 antagonist);
28. GW-1229 ([2',4],[2,4']homodimer of Ile-Glu-Pro-Dpr-Tyr-Arg-Leu-Arg-Tyr-CONH2, where Dpr is diaminopropionic acid, also known as 1229U91, MN-24, GR-231118);
29. BIIE-0246 (Cyclopentaneacetamide, N-[(1S)-4-[(aminoiminomethyl)amino]-1-[[[2-(3,5-dioxo-1,2-diphenyl-1,2,4-triazolidin-4-yl)ethyl]amino]carbonyl]butyl]-1-[2-[4-(6,11-dihydro-6-oxo-5H-dibenz[b,e]azepin-11-yl)-1-piperazinyl]-2-oxoethyl]-);
30. Neuropeptide Y2 antagonist (by Neurogen, USA);
31. Amide derivatives (Neuropeptide Y5 antagonist);
32. Neuropeptide Y agonist and antagonist—subtypes 1 and 5 (Schering-Plough)
33. N-(sulfonamido)alkyl-[3a,4,5,9b-tetrahydro-1H-benzo[e]indol-2-yl]amine (RWJPRI);
34. Neuropeptide Y5 antagonist (by Novartis);
35. Neuropeptide Y5 antagonist (by Pfizer/Neurogen);
36. Pyrrolo[3,2-d]pyrimidine based neuropeptide Y5 antagonists;
37. CGP-71683 (Pharmaprojects No. 5651, CGP-71683A);
38. Neuropeptide Y5 agonist/antagonist (Pharmaprojects No. 5664, Bayer);

(G) Histamine H3 receptor antagonists
1. GT-2331 (3-((1R,2R)-2-(5,5-dimethyl-1-hexynyl)cyclopropyl)-1H-imidazole, also known as PERCEPTIN);
2. Ciproxifan (Cyclopropyl-(4-(3-1H-imidazol-4-yl)propyloxy)phenyl)methanone, also known as BP 2359 or Compound 359);
3. Compound 421 (imidazoylpropanol derivative, INSERM (France)/Bioprojet);
4. FUB 181(3-(4-chlorophenyl)propyl-3-(1H-imidazol-4-yl)propyl ether);
5. GR 175737 (3-((4-chlorophenyl)methyl)-5-(2-(1H-imidazol-4-yl)ethyl)-1,2-oxadiazole);
6. GT 2227 (4-(6-cyclohexyl-3(Z)-hexenyl)imidazole maleate);

7. GT 2394 ((1R,2R)-(trans-2-Imidazol-4-ylcyclopropyl)(cyclohexylmethoxy)carboxamide);
8. GT-2016 (piperidine, 1-(5-cyclohexyl-1-oxopentyl)-4-(1H-imidazol-4-yl)-),
9. Imoproxifan (1-(4-(3-(1H-imidazol-4-yl)propoxy)phenyl)ethan-1-one oxime);
10. Impentamine (by Berlin Free University);
11. Abbott Laboratories H3 antagonist for Attention deficit Hyperactivity Disorder (ADHD);
12. Gliatech (USA) H3 antagonist for eating disorder;
13. Series of novel carbamates as derivatives of 3-(1H-imidazol-4-yl)propanol with an N-alkyl chain;
14. Series of analogs with a neutral linker leading to 4-(1H-imidazol-4-ylmethyl)benzene;
15. Urea, N-4-(1H-imidazol-4-ylmethyl)phenylmethyl-N'-(3,5-dichlorophenyl)-, monohydrochloride;
16. Sch-50971 (1H-imidazole, 4-[(3R,4R)-4-methyl-3-pyrrolidinyl]-);
17. Thioperamide (N-cyclohexyl-4-(1H-imidazol-4-yl)-1-piperidinecarbothioamide, also known as MR 12842);
18. UCL-1283 (by University College London);
19. UCL-1390 (4-(3-(1H-imidazol-4-yl)propoxy)benzonitrile);
20. UCL-1409 ((phenoxyalkyl)imidazoles);
21. UCL-1972 (by University College London);
22. Verongamine (benzenepropanamide, 3-bromo-.alpha.-(hydroxyimino)-N-[2-(1H-imidazol-4-yl)ethyl]-4-methoxy-, (E)-);
23. VUF-9153 (Carbamimidothioic acid, [(4-chlorophenyl)methyl]-, 3-(1H-imidazol-4-yl)propyl ester, also known as Clobenpropit);

(H) Pancreatic lipase inhibitors
1. Orlistat (L-Leucine, N-formyl-, 1-((3-hexyl-4-oxo-2-oxetanyl)methyl)dodecyl ester, (2S-(2alpha(R*), 3beta))-, or N-formyl-L-leucine(2S-(2alpha (R*), 3beta))-1-((3-hexyl-4-oxo-2-oxetanyl)methyl)dodecyl ester, also known as Orlipastat, RO 180647, Tetrahydrolipstatin (THL), XENICAL, or ZENICAL);
2. ATL 962 (also known as AZM 119 or Alizyme);
3. GelTex (Anti-obesity therapeutics);
4. AZM-131 (by Yakurigaku Chuo Kenkyusho/Institute of Food Research);
5. RED 103004 (XiMed Group (United Kingdom)/BioClin);

(I) Alpha melanocyte stimulating hormone analogues
1. Melanotan II (acetyl-norleucyl-aspartyl-histidyl-D-phenylalanyl-arginyl-tryptophyl-lysinamide C-4.2-N-6.7-lactam, also known as MT II);
2. MBU-23, MBU-23, MBU-24, MBU-27, MBU-28 and MBU-29 (all described in WO 009827113);
3. MSH fusion toxin (also known as DAB389MSH, anti-melanoma, chimaera)
4. SHU-9119 (L-Lysinamide, N-acetyl-L-norleucyl-L-.alpha.-aspartyl-L-histidyl-3-(2-naphthalenyl)-D-alanyl-L-arginyl-L-tryptophyl-, (2.fwdarw.7)-lactam, also known as MBX 36)
5. SHU-9005 (a substituted derivative of alpha-MSH)
6. ZYC-200 (alpha-MSH, Schepens/ZYCOS with BIOTOPE expression cassette system)

(J) Mixed serotonin reuptake inhibitor with serotonin or alpha adrenergic antagonist activity
1. Nefazodone (2-(3-(4-(3-chlorophenyl)-1-piperazinyl)propyl)-5-ethyl-2,4-dihydro-4-(2-phenoxyethyl)-3H-1,2,4-triazol-3-one, also known as MJ 13754, MS13754, BMY 13754, BMY 137541, SERZONE, DUTONIN, RESERIL, NEFADAR, NIFEREL, MENFAZONA, RULIVAN, DEPREFAX, or SERZONIL);
2. YM 992 ((S)-2-(((7-fluoro-2,3-dihydro-1H-inden-4-yl)oxy)methyl)morpholine hydrochloride, or (S)-2-(((7-fluoro-2,3-dihydro-1H-inden-4-yl)oxy)methyl)morpholine hydrochloride, also known as YM 35992);
3. A 80426 ((R)—N-methyl-N-((1,2,3,4-tetrahydro-5-methoxy-1-naphthalenyl)methyl)-6-benzofuranethanamine);
4. 5-HT1A antagonist (by Vita-Invest, Spain);
5. Nefazodone metabolite (by Sepracor, USA);
6. Serotonin reuptake inhibitors/serotonin 1A antagonists (Wyeth-Ayerst)

(K) Appetite-suppressants acting through adrenergic mechanisms
1. benzphetamine;
2. phenmetrazine;
3. phentermine;
4. diethylpropion;
5. mazindol;
6. sibutramine;
7. phenylpropanolamine;
8. ephedrine (L) Mixed serotonin & dopamine reuptake inhibitors
1. BL-1834 (1-propanamine, 3-dibenz(b,e)oxepin-11(6H)-ylidene-N,N-dimethyl);
2. NS-2389 or NS-2347 (GW-650250A, GW 650250);
3. (R)-Sibutramine;
4. NS-2359 (by NeuroSearch, Denmark);
5. RTI-112 or RTI-113 or RTI-177 (8-Azabicyclo(3.2.1)octane-2-carboxylic acid,3-(4-chloro-3-methylphenyl)-8-methyl-, methyl ester, hydrochloride, (1R,2S,3S,5S));
6. BSF-74681(Abbott);
7. Hyperforin trimethoxybenzoate (IDN-5491);

(M) Mixed serotonin reuptake inhibitors and dopamine antagonist
1. SLV-310 (Solvay, Belgium);
2. EMD 86006 (3-(2-(3-(4-fluorophenyl)benzylamino)ethoxy)benzonitrile);
3. SLV 301 (by Solvay);

(N) Norepinephrine & serotonin reuptake inhibitors (NSRI)
1. Milnacipran (Cyclopropanecarboxamide, 2-(aminomethyl)-N,N-diethyl-1-phenyl-, cis-(+/−)-, or (+)-cis-2-(Aminomethyl)-N-diethyl-1-phenyl cyclopropane carboxamide hydrochloride, also known as F-2207, F-2641, TN-912, DALCIPRAN, IXEL, MIDACIPRAN, MIDALCIPRAN, MILNACIPRAN SR, TOLEDOMIN);
2. Tramadol, Purdue (cyclohexanol, 2-((dimethylamino)methyl)-1-(3-methoxyphenyl)-, cis-(+/−), also known as TRAMADOL, Tramadol, CR, or Toray);
3. Milnacipran (drug delivery system, sustained release);
4. Duloxetine ((S)—N-methyl-gamma-(1-naphthalenyloxy)-2-thiophenepropanamine, or (+)-(S)—N-Methyl-gamma-(1-naphthyloxy)-2-thiophene-propylamine hydrochloride, also known as LY 248686, duloxetine oxalate, LY-223332, LY-223743, LY-223994, LY-227750, LY-227942, LY-228993, LY-248686, LY-264452, LY-264453, LY-267826"
5. Naltrexone+tramadol (morphinan-6-one,17-(cyclopropylmethyl)-4,5-epoxy-3,14-dihydroxy-, (5alpha)-, mix with cyclohexanol, 2-((dimethylamino)methyl)-1-(3-methoxyphenyl)-, cis-(+/−)-, also known as PTI-601, tramadol+naltrexone, Pain T)
6. (S) sibutramine ((S)-1-(4-chlorophenyl)-N,N-dimethyl-alpha-(2-methylpropyl)cyclobutanemethanamine);
7. Tramadol, Labopharm (cyclohexanol, 2-((dimethylamino)methyl)-1-(3-methoxyphenyl)-, cis-(+/−), also known as tramadol, Contramid);

8. F 98214TA (by FAES, Spain);
9. S 33005 ((−)-1-(1-Dimethylaminomethyl-5-methoxybenzocyclobutan-1-yl)cyclopentanol);
10. Tacrine analogues, SIDR;

(O) Serotonin, norepinephrine and dopamine reuptake inhibitors
1. Sibutramine (cyclobutanemethanamine,1-(4-chlorophenyl)-N,N-dimethyl-alpha-(2-methylpropyl)-, or 1-(4-chlorophenyl)-N,N-dimethyl-alpha-(2-methylpropyl)cyclobutanemethanamine hydrochloride monohydrate, also known as Sibutramine hydrochloride monohydrate, BTS-54354, BTS-54505, BTS-54524, KES-524, MERIDIA, REDUCTIL, RADUCTIL, REDUCTASE, PLENTY, ECTIVA);
2. Venlafaxine (cyclohexanol, 1-[2-(dimethylamino)-1-(4-methoxyphenyl)ethyl], also known as WY 45030, WY 45651, WY 45655, DOBUPAL, EFECTIN, EFEXOR, EFFEXOR, ELAFAX, VANDRAL, TREVILOR);
3. Venlafaxine XR (cyclohexanol, 1-(2-(dimethylamino)-1-(4-methoxyphenyl)ethyl)-, hydrochloride, also known as EFFEXOR XR, I EFFEXOR ER, EFFEXOR XL, EFFEXOR LP, DOBUPAL RETARD, VANDRAL RETARD, EFFEXOR-EXEL 75, EFEXOR XR, EFEXOR DEPOT, ELAFAX XR);
4. Venlafaxine (drug delivery system, OROS oral controlled release, also known as venlafaxine, OROS, or EFEXOR XR)
5. (+)-Desmethylsibutramine (also known as DDMS, Didesmethylsibutramine-Sepracor);
6. BTS-74398 (1-[1-(3,4-Dichlorophenyl)cyclobutyl]-2-(3-dimethylaminopropylthio)ethanone, Abbott Pharmaprojects No. 6247);
7. Desmethylvenlafaxine (by Sepracor);

(P) Appetite-suppressant agents acting through dopamine mechanisms
1. Apomorphine;

(Q) Selective norepinephrine (noradrenaline) reuptake inhibitors
1. Reboxetine ((2S)-rel-2-((R)-(2-ethoxyphenoxy)phenylmethyl)morpholine, or morpholine, 2-[(2-ethoxyphenoxy)phenylmethyl]-, (R,S)—, methanesulfonate, also known as reboxetine mesylate (USAN), FCE 20124, FCE 21684, PNU 155950E, EDRONAX, PROLIFT, VESTRA, IRENON, NOREBOX);
2. Tomoxetine ((gamma.R)—N-methyl-gamma-(2-methylphenoxy)benzenepropanamine, or (−)-N-Methyl-3-phenyl-3-(o-tolyloxy)propylamine hydrochloride, also known as LY 139603, LY 135252, LY 139602);
3. Hydroxynortriptyline ((E)-10-11-dihydro-5-(3-(methylamino)propylidene)-5H-dibenzo-(a,d)cyclohepten-10-ol);
4. LY 368975 ((R)—N-Methyl-3-[2-(methylsulfanyl)phenoxy]-3-phenylpropylamine hydrochloride);

(R) Combined norepinephrine and dopamine reuptake inhibitors
1. Bupropion (1-(3-chlorophenyl)-2-((1,1-dimethylethyl)amino)-1-propanone, also known as bupropion hydrochloride (USAN), bupropin, amfebutamone, BW 323U, WELLBUTRIN, QUOMEM, or ZYBAN);
2. GW 320659 ((2S-(2alpha,3alpha,5alpha))-2-(3,5-difluorophenyl)-3,5-dimethyl-2-morpholinol hydrochloride, also known as 1555, 1555U88, BW 1555U88);
3. Hydroxy bupropion (also known as bupropion, R—, or R-bupropion);
4. (−)Didesmethylsibutramine (also known as (S)-didesmethylsibutramine, desmethylsibutramine, (−)-DDMS or MERIDIA (urogenital));

(S) Mixed norepinephrine reuptake inhibitor and other neurotransmitter antagonists
1. Zotepine (2-((8-chlorodibenzo(b,f)thiepin-10-yl)oxy)-N,N-dimethylethylamine, also known as LODOPIN, NIPOLEPT, ZOLEPTIL, ZOPITE, SETOUS, MAJORPIN);
2. MCI-225 (4-(2-fluorophenyl)-2-methyl-6-(piperazin-1-yl)-3a,7a-dihydrothieno (2,3-d) pyrimidine, or 4-(2-Fluorophenyl)-6-methyl-2-piperazinothieno[2,3-d]pyrimidine hydrochloride hydrate);
3. A 75200 ((R*,R*)-(+,−)-3-phenyl-1-((6,7,8,9-tetrahydronaphtho-(1,2-d)-1,3-dioxol-6-yl)methyl)pyrrolidine);

(T) Combined serotonin reuptake inhibitors and sigma receptor antagonists
1. E-5296 (by Esteve, Spain);
2. E-6276 (by Esteve, Spain);
3. E-5842 (pyridine, 4-(4-fluorophenyl)-1,2,3,6-tetrahydro-1-(4-(1H-1,2,4-triazol-1-yl)butyl)-, 2-hydroxy-1,2,3-propanetricarboxylate (1:1));
4. E 5826 (citrate salt of E-5842);

(U) Other neurotransmitter modulators with serotonin or norepinephrine uptake inhibitor activity
1. Pirlindole (1H-pyrazino(3,2,1-jk)carbazole, 2,3,3a,4,5,6-hexahydro-8-methyl-, also known as CAS-125, Pyrazidol, pirazidol, LIFRIL, IMPLEMENTOR);
2. NS-2330 (by NeuroSearch, Denmark);
3. VAN-H36 (by Vita-Invest, Spain);
4. UR 1827 (2-(1-Benzylpiperidin-4-yl)-1-[4-(5-methylpyrimidin-4-ylamino)phenyl]-1-ethanone);

(V) C-75 (Fatty acid synthase inhibitor)

(W) S 15261 (L-4-(2-(2-(9-Fluorenyl)acetamido)ethyl)benzoic acid 2-(2-methoxy-2-(3-(trifluoromethyl)phenyl)ethylamino)ethyl ester)

(X) S 100B (Neurotrophic factor)

(Y) Stimulators of uncoupling protein function (z) Cholecystokinin agonists (AA) Androgens
1. dehydroepiandrosterone;
2. dehydroepiandrosterone derivatives (such as etiocholandione);

(BB) Testosterone (CC) Anabolic steroids (eg, oxandrolone)

(DD) Steroidal hormones (EE) Amylase inhibitors (FF) Enterostatin agonists/mimetics (GG) Orexin/hypocretin antagonists (HH) Urocortin antagonists (II) Bombesin agonists (JJ) Modulators of protein kinase A (KK) Corticotropin-releasing factor mimetics (LL) Cocaine- and amphetamine-regulated transcript mimetics (MM) Calcitonin-gene related peptide mimetics (NN) Nizatidine (Axid)

Other agents useful for the combination therapy of the present invention include glucokinase modulators include:

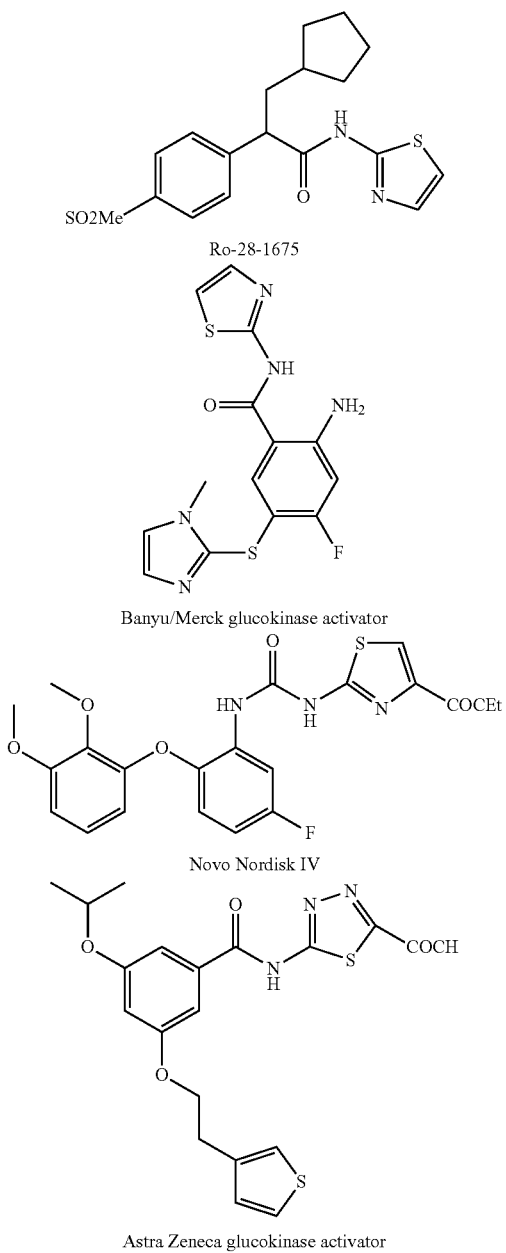

Ro-28-1675

Banyu/Merck glucokinase activator

Novo Nordisk IV

Astra Zeneca glucokinase activator

Anti-diabetic agents include RXR modulators such as:
(1) bexarotene (4-(1-(3,5,5,8,8-pentamethyl-5,6,7,8-tetrahydro-2-naphthalenyl)ethenyl)benzoic acid, known as TARGRETIN, TARGRETYN, TARGREXIN; also known as LGD 1069, LG 100069, LG 1069, LDG 1069, LG 69, RO 264455);
(2) 9-cis-retinoic acid;
(3) AGN-4326 (also known as ALRT-4204, AGN-4204, ALRT-326, ALRT-324, or LGD 1324);
(4) LGD 1324 (ALRT 324);
(5) LG 100754;
(6) LY-510929;
(7) LGD 1268 (6-(1,1,4,4,6-pentamethyl-1,2,3,4-tetrahydro-naphth-7-ylcycloprop-1-yl)nicotinic acid, known as ALRT 268 or LG 100268); and
(8) LG 100264.

Anti-diabetic agents also include thiazolidinedione and non-thiazolidinedione insulin sensitizers, which decrease peripheral insulin resistance by enhancing the effects of insulin at target organs and tissues.

The following agents are known to bind and activate the nuclear receptor peroxisome proliferator-activated receptor-gamma (PPARγ) which increases transcription of specific insulin-responsive genes. Examples of PPAR-gamma agonists are thiazolidinediones such as:
(1) rosiglitazone (2,4-thiazolidinedione,5-((4-(2-(methyl-2-pyridinylamino)ethoxy)phenyl)methyl)-, (Z)-2-butenedioate (1:1) or 5-((4-(2-(methyl-2-pyridinylamino)ethoxy)phenyl)methyl)-2,4-thiazolidinedione, known as AVANDIA; also known as BRL 49653, BRL 49653C, BRL 49653c, SB 210232, or rosiglitazone maleate);
(2) pioglitazone (2,4-thiazolidinedione, 5-((4-(2-(5-ethyl-2-pyridinyl)ethoxy)phenyl)methyl)-, monohydrochloride, (+−)- or 5-((4-(2-(5-ethyl-2-pyridyl)ethoxy)phenyl)methy)-2,4-thiazolidinedione, known as ACTOS, ZACTOS, or GLUSTIN; also known as AD 4833, U 72107, U 72107A, U 72107E, pioglitazone hydrochloride (USAN));
(3) troglitazone (5-((4-((3,4-dihydro-6-hydroxy-2,5,7,8-tetramethyl-2H-1-benzopyran-2-yl)methoxy)phenyl)methyl)-2,4-thiazolidinedione, known as NOSCAL, REZULIN, ROMOZIN, or PRELAY; also known as CI-991, CS 045, GR 92132, GR 92132×);
(4) isaglitazone ((+)-5-[[6-[(2-fluorophenyl)methoxy]-2-naphthalenyl]methyl]-2,4-thiazolidinedione or 5-((6-((2-fluorophenyl)methoxy)-2-naphthalenyl)methyl-2,4-thiazolidinedione or 5-(6-(2-fluorobenzyloxy) naphthalen-2-ylmethyl)thiazolidine-2,4-dione, also known as MCC-555 or neoglitazone); and
(5) 5-BTZD.

Additionally, the non-thiazolidinediones that act as insulin sensitizing agents include, but are not limited to:
(1) JT-501 (JTT 501, PNU-1827, PNU-716-MET-0096, or PNU 182716: isoxazolidine-3,5-dione, 4-((4-(2-phenyl-5-methyl)-1,3-oxazolyl)ethylphenyl-4) methyl-);
(2) KRP-297 (5-(2,4-dioxothiazolidin-5-ylmethyl)-2-methoxy-N-(4-(trifluoromethyl)benzyl)benzamide or 5-((2,4-dioxo-5-thiazolidinyl)methyl)-2-methoxy-N-((4-(trifluoromethyl)phenyl)methyl)benzamide); and
(3) Farglitazar (L-tyrosine, N-(2-benzoylphenyl)-o-(2-(5-methyl-2-phenyl-4-oxazolyl)ethyl)- or N-(2-benzoylphenyl)-O-(2-(5-methyl-2-phenyl-4-oxazolyl) ethyl)-L-tyrosine, or GW2570 or GI-262570).

Other anti-diabetic agents have also been shown to have PPAR modulator activity such as PPAR gamma, SPPAR gamma, and/or PPAR delta/gamma agonist activity. Examples are listed below:
(1) AD 5075;
(2) R 119702 ((+−)-5-(4-(5-Methoxy-1H-benzimidazol-2-ylmethoxy)benzyl)thiazolin-2,4-dione hydrochloride, or CI 1037 or CS 011);
(3) CLX-0940 (peroxisome proliferator-activated receptor alpha agonist/peroxisome proliferator-activated receptor gamma agonist);
(4) LR-90 (2,5,5-tris(4-chlorophenyl)-1,3-dioxane-2-carboxylic acid, PPARdelta/γ agonist);
(5) Tularik (PPARγ agonist);
(6) CLX-0921 (PPARγ agonist);
(7) CGP-52608 (PPAR agonist);
(8) GW-409890 (PPAR agonist);
(9) GW-7845 (PPAR agonist);
(10) L-764406 (PPAR agonist);
(11) LG-101280 (PPAR agonist);
(12) LM-4156 (PPAR agonist);

(13) Risarestat (CT-112);
(14) YM 440 (PPAR agonist);
(15) AR-H049020 (PPAR agonist);
(16) GW 0072 (4-(4-((2S,5S)-5-(2-(bis(phenylmethyl)amino)-2-oxoethyl)-2-heptyl-4-oxo-3-thiazolidinyl)butyl)benzoic acid);
(17) GW 409544 (GW-544 or GW-409544);
(18) NN 2344 (DRF 2593);
(19) NN 622 (DRF 2725);
(20) AR-H039242 (AZ-242);
(21) GW 9820 (fibrate);
(22) GW 1929 (N-(2-benzoylphenyl)-O-(2-(methyl-2-pyridinylamino)ethyl)-L-tyrosine, known as GW 2331, PPAR alpha/γ agonist);
(23) SB 219994 ((S)-4-(2-(2-benzoxazolylmethylamino)ethoxy)-alpha-(2,2,2-trifluoroethoxy)benzenepropanoic acid or 3-(4-(2-(N-(2-benzoxazolyl)-N-methylamino)ethoxy)phenyl)-2 (S)-(2,2,2-trifluoroethoxy) propionic acid or benzenepropanoic acid,4-(2-(2-benzoxazolylmethylamino)ethoxy)-alpha-(2,2,2-trifluoroethoxy)-, (alphaS)-, PPARalpha/γ agonist);
(24) L-796449 (PPAR alpha/γ agonist);
(25) Fenofibrate (Propanoic acid, 2-[4-(4-chlorobenzoyl)phenoxy]-2-methyl-, 1-methylethyl ester, known as TRICOR, LIPCOR, LIPANTIL, LIPIDIL MICRO PPAR alpha agonist);
(26) GW-9578 (PPAR alpha agonist);
(27) GW-2433 (PPAR alpha/γ agonist);
(28) GW-0207 (PPARγ agonist);
(29) LG-100641 (PPARγ agonist);
(30) LY-300512 (PPARγ agonist);
(31) NID525-209 (NID-525);
(32) VDO-52 (VDO-52);
(33) LG 100754 (peroxisome proliferator-activated receptor agonist);
(34) LY-510929 (peroxisome proliferator-activated receptor agonist);
(35) bexarotene (4-(1-(3,5,5,8,8-pentamethyl-5,6,7,8-tetrahydro-2-naphthalenyl)ethenyl)benzoic acid, known as TARGRETIN, TARGRETYN, TARGREXIN; also known as LGD 1069, LG 100069, LG 1069, LDG 1069, LG 69, RO 264455); and
(36) GW-1536 (PPAR alpha/γ agonist).

Other insulin sensitizing agents include, but are not limited to:
(1) INS-1 (D-chiro inositol or D-1,2,3,4,5,6-hexahydroxycyclohexane);
(2) protein tyrosine phosphatase 1 B (PTP-1B) inhibitors;
(3) glycogen synthase kinase-3 (GSK3) inhibitors;
(4) beta 3 adrenoceptor agonists such as ZD 2079 ((R)—N-(2-(4-(carboxymethyl)phenoxy)ethyl)-N-(2-hydroxy-2-phenethyl) ammonium chloride, also known as ICI D 2079) or AZ 40140;
(5) glycogen phosphorylase inhibitors;
(6) fructose-1,6-bisphosphatase inhibitors;
(7) chromic picolinate, vanadyl sulfate (vanadium oxysulfate);
(8) KP 102 (organo-vanadium compound);
(9) chromic polynicotinate;
(10) potassium channel agonist NN 414;
(11) YM 268 (5,5'-methylene-bis(1,4-phenylene)bismethylenebis(thiazolidine-2,4-dione);
(12) TS 971;
(13) T 174 ((+−)-5-(2,4-dioxothiazolidin-5-ylmethyl)-2-(2-naphthylmethyl)benzoxazole);
(14) SDZ PGU 693 ((+)-trans-2(S-((4-chlorophenoxy)methyl)-7alpha-(3,4-dichlorophenyl)tetrahydropyrrolo (2,1-b) oxazol-5(6H)-one);
(15) S 15261 ((−)-4-(2-((9H-fluoren-9-ylacetyl)amino) ethyl)benzoic acid 2-((2-methoxy-2-(3-(trifluoromethyl)phenyl)ethyl)amino)ethyl ester);
(16) AZM 134 (Alizyme);
(17) ARIAD;
(18) R 102380;
(19) PNU 140975 (1-(hydrazinoiminomethyl) hydrazino) acetic acid;
(20) PNU 106817 (2-(hydrazinoiminomethyl)hydrazino) acetic acid;
(21) NC 2100 (5-((7-(phenylmethoxy)-3-quinolinyl)methyl)-2,4-thiazolidinedione;
(22) MXC 3255;
(23) MBX 102;
(24) ALT 4037;
(25) AM 454;
(26) JTP 20993 (2-(4-(2-(5-methyl-2-phenyl-4-oxazolyl)ethoxy)benzyl)malonic acid dimethyl diester);
(27) Dexlipotam (5(R)-(1,2-dithiolan-3-yl)pentanoic acid, also known as (R)-alpha lipoic acid or (R)-thioctic acid);
(28) BM 170744 (2,2-Dichloro-12-(p-chlorophenyl)dodecanoic acid);
(29) BM 152054 (5-(4-(2-(5-methyl-2-(2-thienyl)oxazol-4-yl)ethoxy)benzothien-7-ylmethyl)thiazolidine-2,4-dione);
(30) BM 131258 (5-(4-(2-(5-methyl-2-phenyloxazol-4-yl)ethoxy)benzothien-7-ylmethyl)thiazolidine-2,4-dione);
(31) CRE 16336 (EML 16336);
(32) HQL 975 (3-(4-(2-(5-methyl-2-phenyloxazol-4-yl)ethoxy)phenyl)-2(S)-(propylamino)propionic acid);
(33) DRF 2189 (5-((4-(2-(1-Indolyl)ethoxy)phenyl)methyl)thiazolidine-2,4-dione);
(34) DRF 554158;
(35) DRF-NPCC;
(36) CLX 0100, CLX 0101, CLX 0900, or CLX 0901;
(37) IkappaB Kinase (IKK B) Inhibitors
(38) mitogen-activated protein kinase (MAPK) inhibitors p38 MAPK Stimulators
(39) phosphatidyl-inositide triphosphate
(40) insulin recycling receptor inhibitors
(41) glucose transporter 4 modulators
(42) TNF-α antagonists
(43) plasma cell differentiation antigen-1 (PC-1) Antagonists
(44) adipocyte lipid-binding protein (ALBP/aP2) inhibitors
(45) phosphoglycans
(46) Galparan;
(47) Receptron;
(48) islet cell maturation factor;
(49) insulin potentiating factor (IPF or insulin potentiating factor-1);
(50) somatomedin C coupled with binding protein (also known as IGF-BP3, IGF-BP3, SomatoKine);
(51) Diab II (known as V-411) or Glucanin, produced by Biotech Holdings Ltd. or Volque Pharmaceutical;
(52) glucose-6 phosphatase inhibitors;
(53) fatty acid glucose transport protein;
(54) glucocorticoid receptor antagonists; and
(55) glutamine:fructose-6-phosphate amidotransferase (GFAT) modulators.

Anti-diabetic agents can further include biguanides, which decreases liver glucose production and increases the uptake of glucose. Examples of biguanides include metformin such as:
(1) 1,1-dimethylbiguanide (e.g., Metformin—DepoMed, Metformin—Biovail Corporation, or METFORMIN GR (metformin gastric retention polymer)); and
(2) metformin hydrochloride (N,N-dimethylimidodicarbonimidic diamide monohydrochloride, also known as LA 6023, BMS 207150, GLUCOPHAGE, or GLUCOPHAGE XR.

Additionally, anti-diabetic agents include alpha-glucosidase inhibitors, which inhibit alpha-glucosidase. Alpha-glucosidase converts fructose to glucose, thereby delaying the digestion of carbohydrates. The undigested carbohydrates are subsequently broken down in the gut, reducing the postprandial glucose peak.

Examples of alpha-glucosidase inhibitors include, but are not limited to (1) acarbose (D-glucose, O-4,6-dideoxy-4-(((1S-(1alpha, 4alpha,5beta,6alpha))-4,5,6-trihydroxy-3-(hydroxymethyl)-2-cyclohexen-1-yl)amino)-alpha-D-glucopyranosyl-(1-4)-O-alpha-D-glucopyranosyl-(1-4)-, also known as AG-5421, Bay-g-542, BAY-g-542, GLUCOBAY, PRECOSE, GLUCOR, PRANDASE, GLUMIDA, or ASCAROSE);
(2) Miglitol (3,4,5-piperidinetriol, 1-(2-hydroxyethyl)-2-(hydroxymethyl)-, (2R (2alpha, 3beta, 4alpha, 5beta))- or (2R,3R,4R,5S)-1-(2-hydroxyethyl)-2-(hydroxymethyl-3,4,5-piperidinetriol, also known as BAY 1099, BAY M 1099, BAY-m-1099, BAYGLITOL, DIASTABOL, GLYSET, MIGLIBAY, MITOLBAY, PLUMAROL);
(3) CKD-711 (0-4-deoxy-4-((2,3-epoxy-3-hydroxymethyl-4,5,6-trihydroxycyclohexane-1-yl)amino)-alpha-b-glucopyranosyl-(1-4)-alpha-D-glucopyranosyl-(1-4)-D-glucopyranose);
(4) emiglitate (4-(2-((2R,3R,4R,5S)-3,4,5-trihydroxy-2-(hydroxymethyl)-1-piperidinyl)ethoxy)benzoic acid ethyl ester, also known as BAY o 1248 or MKC 542);
(5) MOR 14 (3,4,5-piperidinetriol, 2-(hydroxymethyl)-1-methyl-, (2R-(2alpha,3beta,4alpha,5beta))-, also known as N-methyldeoxynojirimycin or N-methylmoranoline); and
(6) Voglibose (3,4-dideoxy-4-((2-hydroxy-1-(hydroxymethyl)ethyl)amino)-2-C-(hydroxymethyl)-D-epi-inositol or D-epi-Inosito-1,3,4-dideoxy-4-((2-hydroxy-1-(hydroxymethyl)ethyl)amino)-2-C-(hydroxymethyl)-, also known as A 71100, AO 128, BASEN, GLUSTAT, VOGLISTAT.

Anti-diabetic agents also include insulins such as regular or short-acting, intermediate-acting, and long-acting insulins, non-injectable or inhaled insulin, tissue selective insulin, glucophosphokinin (D-chiroinositol), insulin analogues such as insulin molecules with minor differences in the natural amino acid sequence and small molecule mimics of insulin (insulin mimetics), and endosome modulators. Examples include, but are not limited to:
(1) Biota;
(2) LP 100;
(3) (SP-5-21)-oxobis(1-pyrrolidinecarbodithioato-S,S') vanadium;
(4) insulin aspart (human insulin (28B-L-aspartic acid) or B28-Asp-insulin, also known as insulin X14, INA-X14, NOVORAPID, NOVOMIX, or NOVOLOG);
(5) insulin detemir (Human 29B-(N-6-(1-oxotetradecyl)-L-lysine)-(1A-21A), (1B-29B)-Insulin or NN 304);
(6) insulin lispro ("28B-L-lysine-29B-L-proline human insulin, or Lys(B28), Pro(B29) human insulin analog, also known as lys-pro insulin, LY 275585, HUMALOG, HUMALOG MIX 75/25, or HUMALOG MIX 50/50);
(7) insulin glargine (human (A21-glycine, B31-arginine, B32-arginine) insulin HOE 901, also known as LANTUS, OPTISULIN);
(8) Insulin Zinc Suspension, extended (Ultralente), also known as HUMULIN U or ULTRALENTE;
(9) Insulin Zinc suspension (Lente), a 70% crystalline and 30% amorphous insulin suspension, also known as LENTE ILETIN II, HUMULIN L, or NOVOLIN L;
(10) HUMULIN 50/50 (50% isophane insulin and 50% insulin injection);
(11) HUMULIN 70/30 (70% isophane insulin NPH and 30% insulin injection), also known as NOVOLIN 70/30, NOVOLIN 70/30 PenFill, NOVOLIN 70/30 Prefilled;
(12) insulin isophane suspension such as NPH ILETIN II, NOVOLIN N, NOVOLIN N PenFill, NOVOLIN N Prefilled, HUMULIN N;
(13) regular insulin injection such as ILETIN II Regular, NOVOLIN R, VELOSULIN BR, NOVOLIN R PenFill, NOVOLIN R Prefilled, HUMULIN R, or Regular U-500 (Concentrated);
(14) ARIAD;
(15) LY 197535;
(16) L-783281; and
(17) TE-17411.

Anti-diabetic agents can also include insulin secretion modulators such as:
(1) glucagon-like peptide-1 (GLP-1) and its mimetics;
(2) glucose-insulinotropic peptide (GIP) and its mimetics;
(3) exendin and its mimetics;
(4) dipeptyl protease (DPP or DPPIV) inhibitors such as
(4a) DPP-728 or LAF 237 (2-pyrrolidinecarbonitrile,1-(((2-((5-cyano-2-pyridinyl)amino)ethyl)amino) acetyl), known as NVP-DPP-728, DPP-728A, LAF-237);
(4b) Sitagliptin, also known as Januvia;
(4c) P 3298 or P32/98 (di-(3N-((2S,3S)-2-amino-3-methylpentanoyl)-1,3-thiazolidine) fumarate);
(4d) TSL 225 (tryptophyl-1,2,3,4-tetrahydroisoquinoline-3-carboxylic acid);
(4e) Valine pyrrolidide (valpyr);
(4f) 1-aminoalkylisoquinolinone-4-carboxylates and analogues thereof;
(4g) SDZ 272-070 (1-(L-Valyl)pyrrolidine);
(4h) TMC-2A, TMC-2B, or TMC-2C;
(4i) Dipeptide nitriles (2-cyanopyrrolodides);
(4j) CD26 inhibitors; and
(4k) SDZ 274-444;
(5) glucagon antagonists such as AY-279955; and
(6) amylin agonists which include, but are not limited to, pramlintide (AC-137, Symlin, tripro-amylin or pramlintide acetate).

Well-known anti-diabetic agents include insulin, sulfonylureas, biguanides, meglitinides, AGI's (Alpha-Glucosidase Inhibitors; e.g., Glyset), PPAR alpha agonists, and PPAR gamma agonists, and dual PPAR alpha/gamma agonists.

Examples of lipid lowering agents include bile acid sequestrants, fibric acid derivatives, nicotinic acid, and HMGCoA reductase inhibitors. Specific examples include statins such as LIPITOR®, ZOCOR®, PRAVACHOL®, LESCOL®, and MEVACOR®, and pitavastatin (nisvastatin) (Nissan, Kowa Kogyo, Sankyo, Novartis) and extended release forms thereof, such as ADX-159 (extended release lovastatin), as well as Colestid, Locholest, Questran, Atromid, Lopid, and Tricor.

Examples of blood pressure lowering agents include antihypertensive agents, such as angiotensin-converting enzyme (ACE) inhibitors (Accupril, Altace, Captopril, Lotensin, Mavik, Monopril, Prinivil, Univasc, Vasotec, and Zestril), adrenergic blockers (such as Cardura, Dibenzyline, Hylorel, Hytrin, Minipress, and Minizide) alpha/beta adrenergic blockers (such as Coreg, Normodyne, and Trandate), calcium channel blockers (such as Adalat, Calan, Cardene, Cardizem, Covera-HS, Dilacor, DynaCirc, Isoptin, Nimotop, Norvace, Plendil, Procardia, Procardia XL, Sula, Tiazac, Vascor, and Verelan), diuretics, angiotensin II receptor antagonists (such as Atacand, Avapro, Cozaar, and Diovan), beta adrenergic blockers (such as Betapace, Blocadren, Brevibloc, Cartrol, Inderal, Kerlone, Lavatol, Lopressor, Sectral, Tenormin, Toprol-XL, and Zebeta), vasodilators (such as Deponit, Dilatrate, SR, Imdur, Ismo, Isordil, Isordil Titradose, Monoket, Nitro-Bid, Nitro-Dur, Nitrolingual Spray, Nitrostat, and Sorbitrate), and combinations thereof (such as Lexxel, Lotrel, Tarka, Teczem, Lotensin HCT, Prinzide, Uniretic, Vaseretic, Zestoretic).

In addition, a second ERR-α modulator, as described above in Sections B) and E), may also be utilized as a third antidiabetic agent, provided that it is different from the first ERR-α modulator.

F) Biological Example

TR-FRET Assay

Time-Resolved Fluorescence Resonance Energy Transfer (TR-FRET) experiments were performed to examine the functional response of ERR1 (also known as ERR-α or ERR-1) ligands. The TR-FRET assay described herein relied on the conformation of ERR1 for binding to a co-activator peptide: when a test compound binds to ERR1 and alters its conformation, it can disrupt the binding of the co-activator peptide. The components of this homogeneous secondary assay included: the $^6$His-tagged-ERR1LBD, a GST-labeled-hSRC2 co-activator polypeptide and a fluorescent donor/acceptor pair from CIS bio international htrf/bioassays (Bedford, Mass.) using both an α-GST Europium (Eu) Cryptate label and an α$^6$His-XL665 (allophycocyanin) fluorophore.

For TR-FRET measurements, the reaction was buffered in 25 mM Tris pH 8, 2.5 mM Hepes, 20 mM KCl, 1 mM DTT, and 0.05 mg/mL BSA (delipidated). The final concentrations of reagents were 6 nM of ERR1LBD, 6 nM GST-SRC-2 peptide, 30 nM Eu cryptate, and 7.5 nM a$^6$His-XL665. Reactions were allowed to reach equilibrium at 25° C. for 4-18 h before collecting data on the Analyst from LJL Biosystems (Molecular Devices Sunnyvale, Calif.). As a time-resolved method, the samples were excited at 340 nM and emission was collected for 1 ms at both 615 and 665 nm with delays of 400 and 75 µs, respectively. Dose response curves were fitted using a hyperbolic equation and the data reported is the average of 3 independent experiments.

TABLE II

| COMPOUND # | EC$_{50}$ TR-FRET (µM) |
| --- | --- |
| 1 | 0.130 |
| 2 | 0.185 |
| 3 | 0.043 |
| 4 | 0.009 |
| 5 | 0.180 |
| 6 | 0.035 |
| 7 | 0.033 |
| 8 | 0.008 |
| 9 | 0.004 |
| 10 | 0.008 |
| 11 | 0.027 |
| 12 | 0.072 |
| 13 | 0.043 |
| 14 | 0.100 |
| 15 | 0.062 |
| 16 | 0.071 |
| 17 | 0.046 |
| 18 | 0.020 |
| 19 | 0.009 |
| 20 | 0.014 |
| 21 | 0.009 |
| 22 | 0.008 |
| 23 | 0.045 |
| 24 | 0.012 |
| 25 | 0.016 |
| 26 | 0.067 |
| 27 | 0.027 |
| 28 | 0.014 |
| 29 | 0.095 |
| 30 | 0.096 |
| 31 | 0.019 |
| 32 | 0.015 |
| 33 | 0.185 |
| 34 | 0.023 |
| 35 | 0.023 |
| 36 | 0.028 |
| 37 | 0.290 |
| 38 | 0.025 |
| 39 | 0.043 |
| 40 | 0.054 |
| 41 | 0.009 |
| 42 | 0.046 |
| 43 | 0.016 |
| 44 | 0.072 |
| 45 | 0.047 |
| 46 | 0.019 |
| 47 | 0.017 |
| 48 | 0.019 |
| 49 | 0.025 |
| 50 | 0.040 |
| 51 | 0.026 |
| 52 | 0.027 |
| 53 | 0.039 |
| 54 | 0.037 |
| 55 | 0.101 |
| 56 | 0.022 |
| 57 | 0.059 |
| 58 | 0.044 |
| 59 | 0.026 |
| 60 | 0.057 |
| 61 | 0.269 |
| 62 | 0.019 |
| 63 | 0.020 |
| 64 | 0.485 |
| 65 | 0.050 |
| 66 | 0.016 |
| 67 | 0.620 |
| 68 | 0.124 |
| 69 | 0.023 |
| 70 | 0.048 |
| 71 | 0.087 |
| 72 | 0.013 |
| 73 | 0.012 |
| 74 | 0.110 |
| 75 | 0.127 |
| 76 | 0.014 |
| 77 | 0.028 |
| 78 | 0.041 |

TABLE II-continued

| COMPOUND # | EC$_{50}$ TR-FRET (µM) |
|---|---|
| 79 | 0.030 |
| 80 | 0.041 |
| 81 | 0.051 |
| 82 | 0.081 |
| 83 | 0.082 |
| 84 | 0.580 |
| 85 | 0.136 |
| 86 | 0.089 |
| 87 | 0.650 |
| 88 | 0.134 |
| 89 | 0.092 |
| 90 | 0.028 |
| 91 | 0.058 |
| 92 | 0.024 |
| 93 | 0.014 |
| 94 | 10.000 |
| 95 | 0.057 |
| 96 | 0.067 |
| 97 | 0.047 |
| 98 | 0.980 |
| 99 | >10 |
| 100 | 0.046 |
| 101 | 0.068 |
| 102 | 0.037 |
| 103 | 0.043 |
| 104 | 0.112 |
| 105 | 0.068 |
| 106 | 0.350 |
| 107 | 0.264 |
| 108 | 0.102 |
| 109 | 0.152 |
| 110 | 0.438 |
| 111 | 0.017 |
| 112 | 0.022 |
| 113 | 0.016 |
| 114 | 0.055 |
| 115 | 0.130 |
| 116 | 0.180 |
| 117 | 0.086 |
| 118 | 0.025 |
| 119 | 0.040 |
| 120 | 0.220 |
| 121 | 0.005 |
| 122 | 0.314 |
| 123 | 0.045 |
| 124 | 0.051 |
| 125 | 0.047 |
| 126 | 0.018 |
| 127 | 0.032 |
| 128 | 0.019 |
| 129 | 0.018 |
| 130 | 0.033 |
| 131 | 0.005 |
| 132 | 0.018 |
| 133 | 0.020 |
| 134 | 0.045 |
| 135 | 0.019 |
| 136 | 0.035 |
| 137 | 0.066 |
| 138 | 0.042 |
| 139 | 0.016 |
| 140 | 0.032 |
| 141 | 0.183 |
| 142 | 0.038 |
| 143 | 0.025 |
| 144 | 0.031 |
| 145 | 0.027 |
| 146 | 0.016 |
| 147 | 0.036 |
| 148 | 0.015 |
| 149 | 0.026 |
| 150 | 0.057 |
| 151 | 0.030 |
| 152 | 0.027 |
| 153 | 0.017 |
| 154 | 0.017 |
| 155 | 0.024 |
| 156 | 0.027 |
| 157 | 0.023 |
| 158 | 0.021 |
| 159 | 0.087 |
| 160 | 0.077 |
| 161 | 0.073 |
| 162 | 0.032 |
| 163 | 0.038 |
| 164 | 0.047 |
| 165 | 0.034 |
| 166 | 0.008 |
| 167 | 0.023 |
| 168 | 0.029 |
| 169 | 0.032 |
| 170 | 0.015 |
| 171 | 0.029 |
| 172 | 0.300 |
| 173 | 0.070 |
| 174 | 0.150 |
| 175 | 0.035 |
| 176 | 0.058 |
| 177 | 6.001 |
| 178 | 9.701 |
| 179 | 3.450 |
| 180 | 0.032 |
| 181 | 0.025 |
| 182 | 0.096 |
| 183 | 0.170 |
| 184 | 0.140 |
| 185 | 0.277 |
| 186 | 0.054 |
| 187 | 0.027 |
| 188 | 0.060 |
| 189 | 0.160 |
| 190 | 0.410 |
| 191 | 0.019 |
| 192 | 0.045 |
| 193 | 0.160 |
| 194 | 0.034 |
| 195 | 0.061 |
| 196 | 0.050 |
| 197 | 0.065 |
| 198 | 0.031 |
| 199 | 0.015 |
| 200 | 0.014 |
| 201 | 0.061 |
| 202 | 0.035 |
| 203 | 0.053 |
| 204 | 0.046 |
| 205 | 0.022 |
| 206 | 0.097 |
| 207 | 0.192 |
| 208 | 0.136 |
| 209 | 0.087 |
| 210 | 0.260 |
| 211 | 0.091 |
| 212 | 0.250 |
| 213 | 0.028 |
| 214 | 0.044 |
| 215 | 0.061 |
| 216 | 0.033 |
| 217 | 0.041 |
| 218 | 0.088 |
| 219 | 0.042 |
| 220 | 0.074 |
| 221 | 0.061 |
| 222 | 0.058 |
| 223 | 0.055 |
| 224 | 0.022 |
| 225 | 0.032 |
| 226 | 0.030 |
| 227 | 0.053 |
| 228 | 0.049 |
| 229 | 0.076 |
| 230 | 0.016 |

TABLE II-continued

TR-FRET data

| COMPOUND # | EC$_{50}$ TR-FRET (μM) |
|---|---|
| 231 | 0.046 |
| 232 | 0.107 |
| 233 | 0.057 |
| 234 | 0.099 |
| 235 | 0.045 |
| 236 | 0.111 |
| 237 | 0.098 |
| 238 | 1.800 |
| 239 | 0.100 |
| 240 | 0.070 |
| 241 | 0.100 |
| 242 | 0.100 |
| 243 | 0.050 |
| 244 | 0.050 |
| 245 | 0.050 |
| 246 | 0.500 |
| 247 | 0.300 |
| 248 | 0.290 |
| 249 | 0.350 |
| 250 | 0.200 |
| 251 | 0.350 |
| 252 | 0.100 |
| 253 | 0.120 |
| 254 | 0.320 |
| 255 | 1.020 |
| 256 | 0.110 |
| 257 | 0.074 |
| 258 | 0.024 |
| 259 | 0.022 |
| 260 | 0.041 |
| 261 | 0.124 |
| 262 | 0.024 |
| 263 | 0.016 |
| 264 | 0.016 |
| 265 | 0.040 |
| 266 | 0.029 |
| 267 | 0.011 |
| 268 | 0.046 |
| 269 | 0.067 |
| 270 | 0.025 |
| 271 | 0.038 |
| 272 | 0.153 |
| 273 | 0.034 |
| 274 | 0.088 |
| 275 | 0.023 |
| 276 | 0.029 |
| 277 | 0.058 |
| 278 | 0.071 |
| 279 | 0.022 |
| 280 | 0.034 |
| 281 | 0.170 |
| 282 | 0.361 |
| 283 | 0.527 |
| 284 | 0.129 |
| 285 | 0.038 |
| 286 | 0.456 |
| 287 | 0.022 |
| 288 | 0.016 |
| 289 | 0.017 |
| 290 | 0.029 |
| 291 | 0.047 |
| 292 | 0.049 |
| 293 | 0.035 |
| 294 | 0.063 |
| 295 | 0.066 |
| 296 | 0.017 |
| 297 | 0.076 |
| 298 | 0.049 |
| 299 | 0.037 |
| 300 | 0.007 |
| 301 | 0.015 |
| 302 | 0.002 |
| 303 | 0.026 |
| 304 | 0.007 |
| 305 | 0.003 |
| 306 | 0.071 |

TABLE II-continued

TR-FRET data

| COMPOUND # | EC$_{50}$ TR-FRET (μM) |
|---|---|
| 307 | 0.210 |
| 308 | 0.005 |
| 309 | 0.015 |
| 310 | 0.086 |
| 311 | 0.133 |
| 312 | 0.065 |
| 313 | 0.700 |
| 314 | 0.830 |
| 315 | 0.071 |
| 316 | 0.036 |
| 317 | 0.012 |
| 318 | 0.024 |
| 319 | 0.021 |
| 320 | 0.031 |
| 321 | 0.043 |
| 322 | 0.060 |
| 323 | 0.054 |
| 324 | 0.033 |
| 325 | 0.087 |
| 326 | 0.140 |
| 327 | 0.021 |
| 328 | 0.152 |
| 329 | 0.015 |
| 330 | 0.091 |
| 331 | 0.238 |
| 332 | 0.110 |
| 333 | 0.048 |
| 334 | 0.048 |
| 335 | 0.046 |
| 336 | 0.293 |
| 337 | 0.047 |
| 338 | 0.024 |
| 339 | 0.106 |
| 340 | 0.053 |
| 341 | 0.039 |
| 342 | 0.065 |
| 343 | 0.027 |
| 344 | 0.040 |
| 345 | 0.018 |
| 346 | 0.579 |
| 347 | 0.116 |
| 348 | 0.007 |
| 349 | 0.024 |
| 350 | 0.038 |
| 351 | 0.022 |
| 352 | 0.025 |
| 353 | 0.011 |
| 354 | 0.017 |
| 355 | 0.020 |
| 356 | 0.014 |
| 357 | 0.039 |
| 358 | 0.022 |
| 359 | 0.026 |
| 360 | 0.026 |
| 361 | 0.013 |
| 362 | 0.308 |
| 363 | 0.059 |
| 364 | 0.004 |
| 365 | 0.023 |
| 366 | 0.006 |
| 367 | 0.004 |
| 368 | 0.003 |
| 369 | 0.064 |
| 370 | 0.048 |
| 371 | 0.009 |
| 372 | 0.011 |
| 373 | 0.007 |
| 374 | 0.048 |
| 375 | 0.070 |
| 376 | 0.065 |
| 377 | 0.067 |
| 378 | 0.066 |
| 379 | 0.021 |
| 380 | 0.015 |
| 381 | 0.028 |
| 382 | 0.011 |

TABLE II-continued

TR-FRET data

| COMPOUND # | EC$_{50}$ TR-FRET (µM) |
| --- | --- |
| 383 | 0.023 |
| 384 | 0.022 |
| 385 | 0.039 |
| 386 | 0.042 |
| 387 | 0.123 |
| 388 | 0.034 |
| 389 | 0.026 |
| 390 | 0.064 |
| 391 | 0.215 |
| 392 | 0.215 |
| 393 | 0.032 |
| 394 | 0.122 |
| 395 | 0.460 |
| 396 | 0.112 |
| 397 | 0.023 |
| 398 | 0.010 |
| 399 | 0.079 |
| 400 | 0.062 |
| 401 | 0.036 |
| 402 | 0.048 |
| 403 | 0.020 |
| 404 | 0.021 |
| 405 | 0.048 |
| 406 | 0.013 |
| 407 | 0.007 |
| 408 | 0.153 |
| 409 | >10 |
| 410 | 0.025 |
| 411 | 0.029 |
| 412 | 0.038 |
| 413 | 0.312 |
| 414 | 0.109 |
| 415 | 0.012 |
| 416 | 0.035 |
| 417 | 0.050 |
| 418 | 0.083 |
| 419 | 0.115 |
| 420 | 0.028 |
| 421 | 0.034 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

Zucker fa/fa Rat Model Assay

Zucker fa/fa is a monogenic model of frank diabetes due to a mutation on the fa gene truncating the leptin receptor and preventing its interaction with its peptide hormone. This mutation results in a hyperphagic phenotype and the rodent develops obesity, hyperlipidemia, fasting hyperglycemia and insulin resistance. Zucker fa/fa male rats were received at four weeks of age and allowed to acclimate for one week. At five weeks of age the animals were single housed in cages in a temperature-controlled room with 12-hour light/dark cycle. The rats were allowed ad libitum access to water and food and throughout the study were maintained on a Purina 5008 diet. Animals were sorted based primarily on fed insulin levels and circulating triglycerides. Animals were dosed orally once a day (10 mg/kg) in the morning for 4 days. The vehicle used was either 20% HPβCD (Hydroxypropyl Beta Cyclodextrin) or 15% Vitamin E/30% PEG-400 (Polyethylene Glycol 400). Fed insulin and triglycerides were measured using blood collected from the tail vein at day 5. Serum plasma samples were prepared by centrifugation in EDTA (Ethylenediamine-tetraacetic acid) containing tubes, transferred into 96 well plates and stored at −80° C. Results are summarized in Table III.

TABLE III

Zucker fa/fa Rat Model data

| COMPOUND # | % Change Fed Insulin Levels | % Change Fed Triglyceride Levels |
| --- | --- | --- |
| 4 | −50 | −14 |
| 8 | −21 | −19 |
| 19 | −9 | 21 |
| 22 | −11 | 32 |
| 27 | 9 | 0 |
| 31 | −51 | −14 |
| 35 | −29 | −46 |
| 36 | −18 | −4 |
| 38 | −47 | 1 |
| 40 | −10 | −23 |
| 59 | −23 | −25 |
| 72 | −44 | −51 |
| 73 | −30 | −19 |
| 79 | −20 | 34 |
| 91 | −68 | −60 |
| 111 | −49 | −30 |
| 121 | −59 | −37 |
| 126 | −14 | 13 |
| 128 | −36 | 28 |
| 143 | −49 | −29 |
| 146 | −26 | −14 |
| 148 | −77 | −40 |
| 149 | −35 | 10 |
| 155 | −60 | −55 |
| 166 | −58 | −37 |
| 167 | −33 | −45 |
| 170 | −52 | −61 |
| 202 | −3 | −26 |
| 260 | −50 | −23 |
| 277 | −73 | −57 |
| 287 | −53 | −36 |
| 288 | −35 | −29 |
| 361 | −58 | −43 |
| 383 | −67 | −68 |
| 384 | −52 | −51 |

The invention claimed is:

1. A compound of Formula (I)

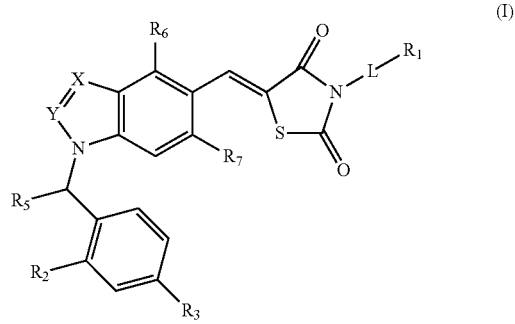

wherein
X is $CR_4$;
Y is N;
L is a bond;
$R^1$ is an optionally substituted heterocyclyl group;
$R_2$ is halo-substituted $C_{1-3}$alkyl, or alternatively $R_2$ is linked together to $R_5$ to form a cycloalkyl fused to the phenyl ring to which $R_2$ is shown attached;

$R_3$ is halo, cyano, halo-substituted $C_{1-3}$alkyl, or $C_{1-4}$alkoxyl;

$R_4$ is H, hydroxyl, halo, $C_{1-4}$alkyl, $C_{1-4}$alkoxyl, optionally substituted phenyl, cyano, or —C(O)NH$_2$;

$R_5$ is H, or alternatively $R_5$ is linked together to $R_2$ to form a cycloalkyl fused to the phenyl ring to which $R_2$ is shown attached;

$R_6$ is H or F; and $R_7$ is H or F;

or an enantiomer, diastereomer, cis-trans isomer, racemate, prodrug or pharmaceutically acceptable salt thereof.

2. The compound of claim 1 wherein

X is $CR_4$;

Y is N;

L is a bond;

$R_1$ is selected from

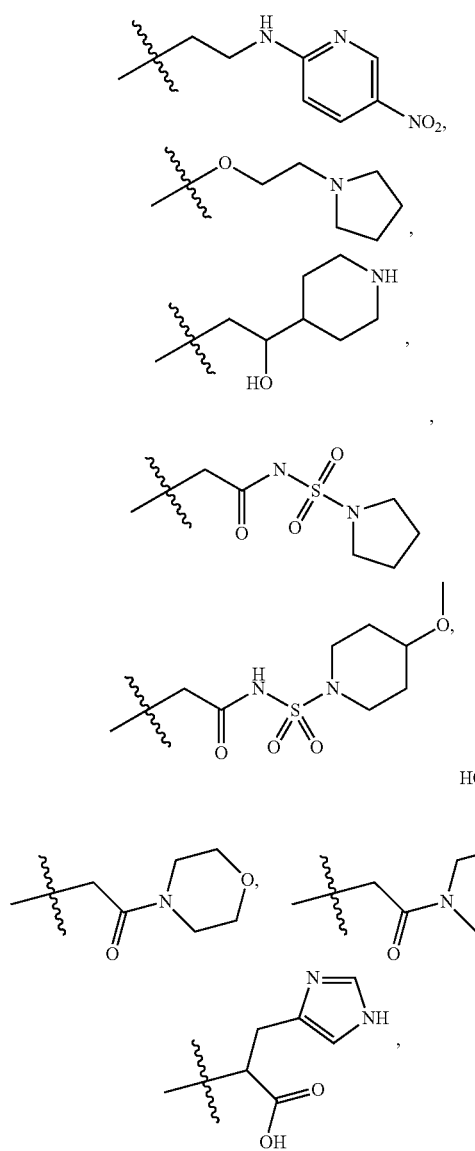

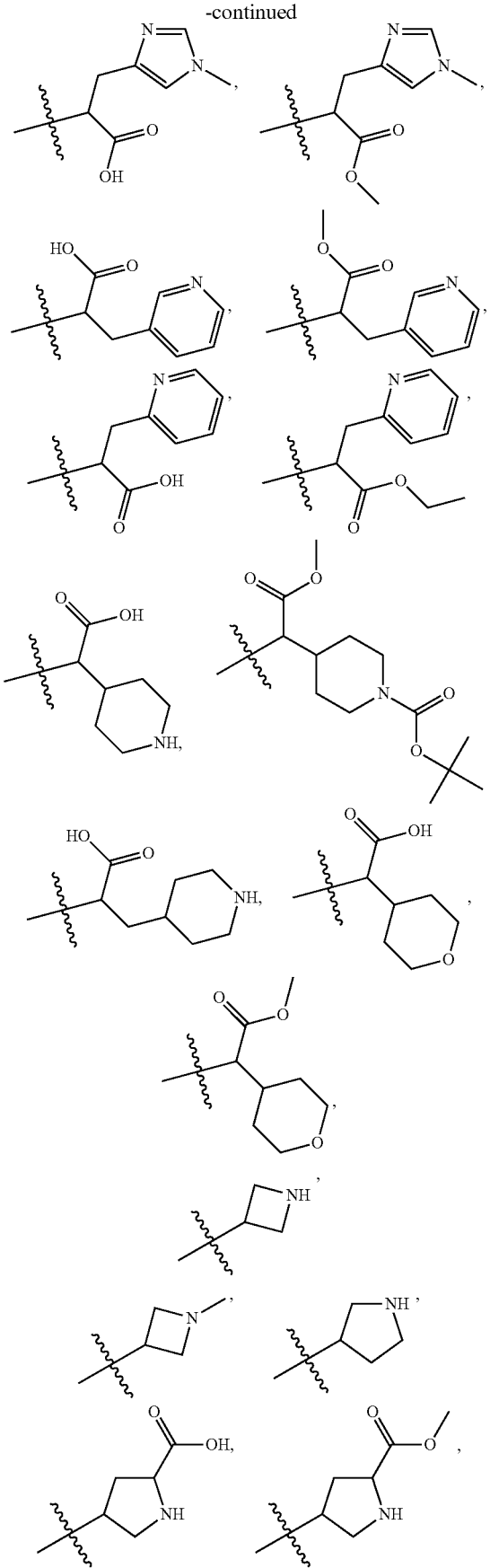

531
-continued
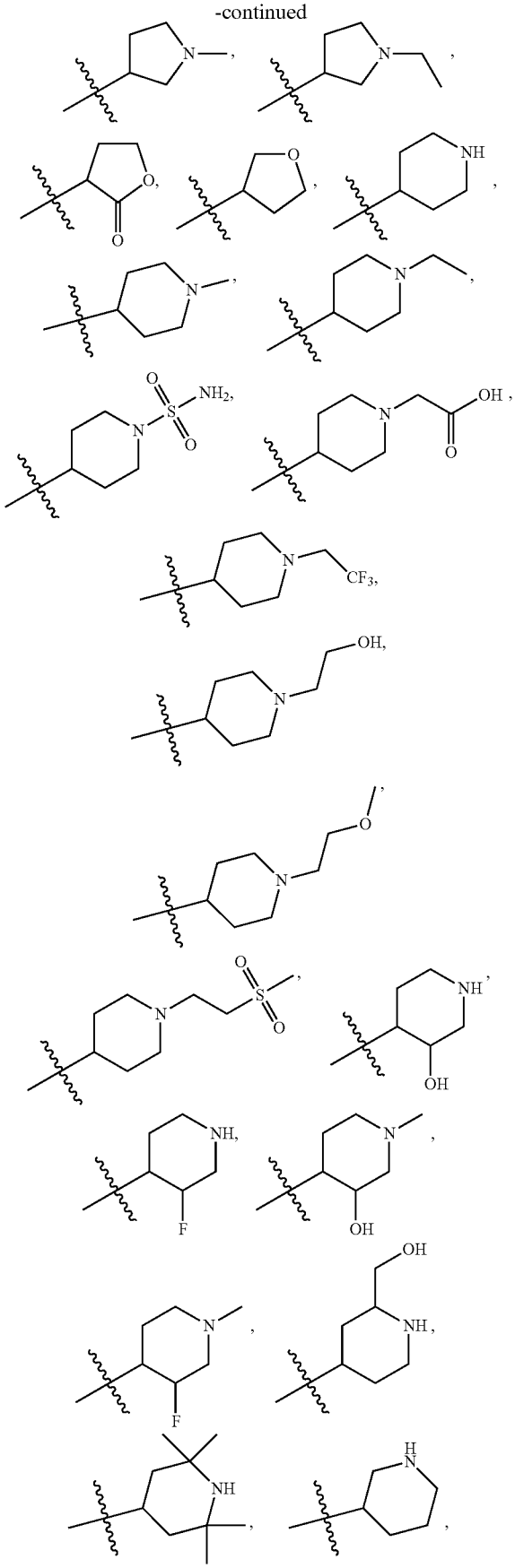
532
-continued
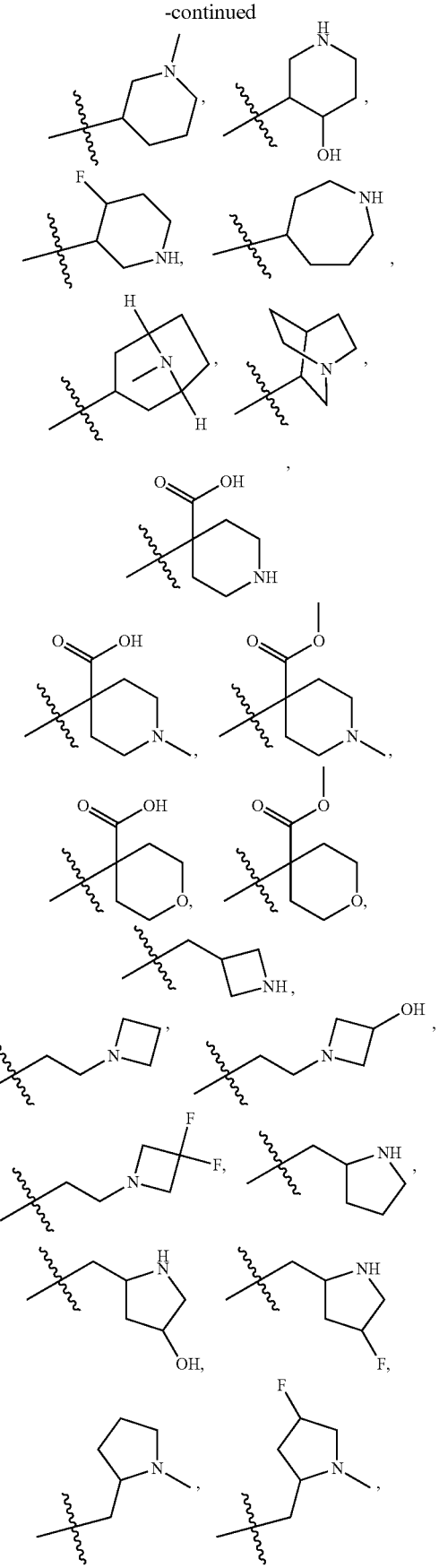

533
-continued
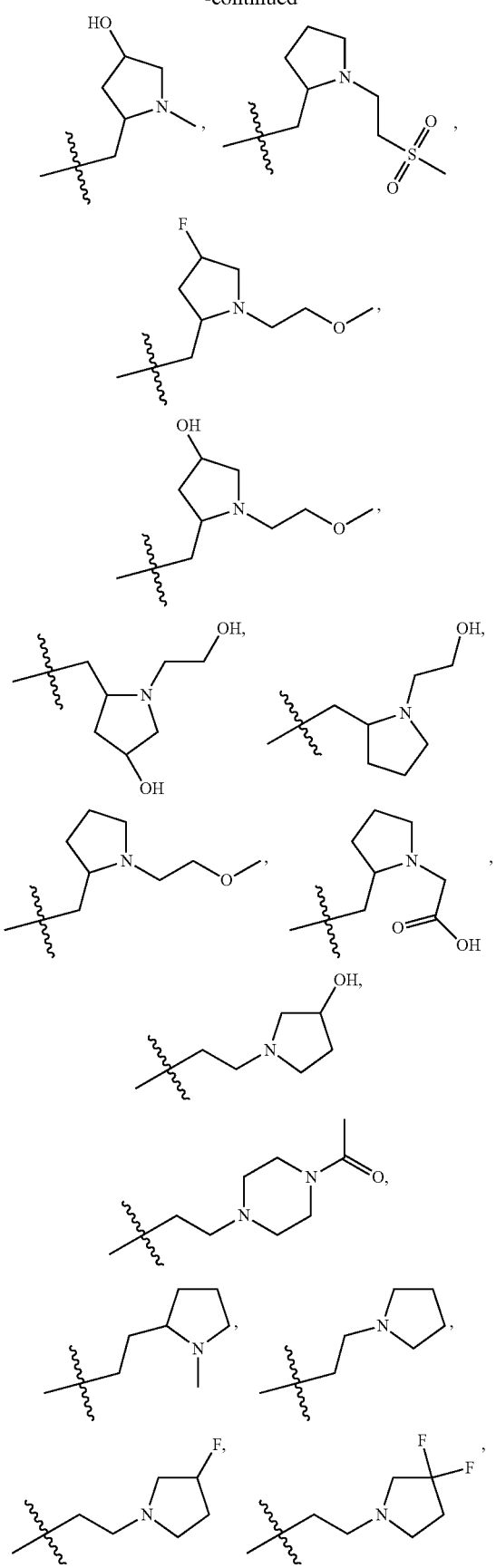
534
-continued
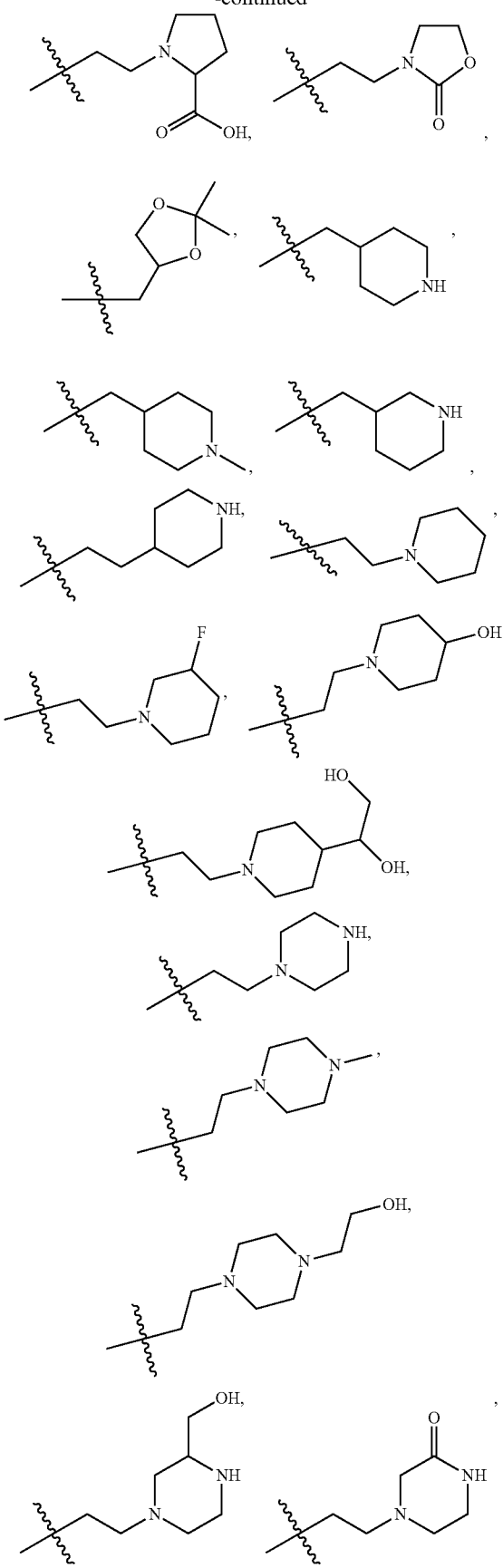

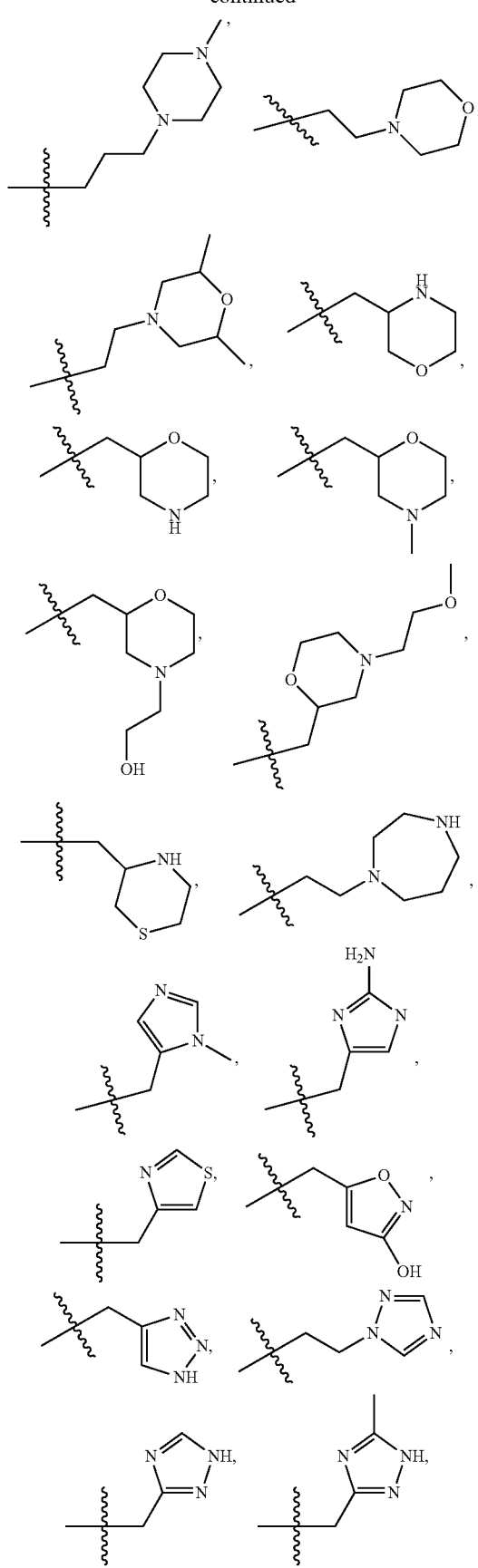
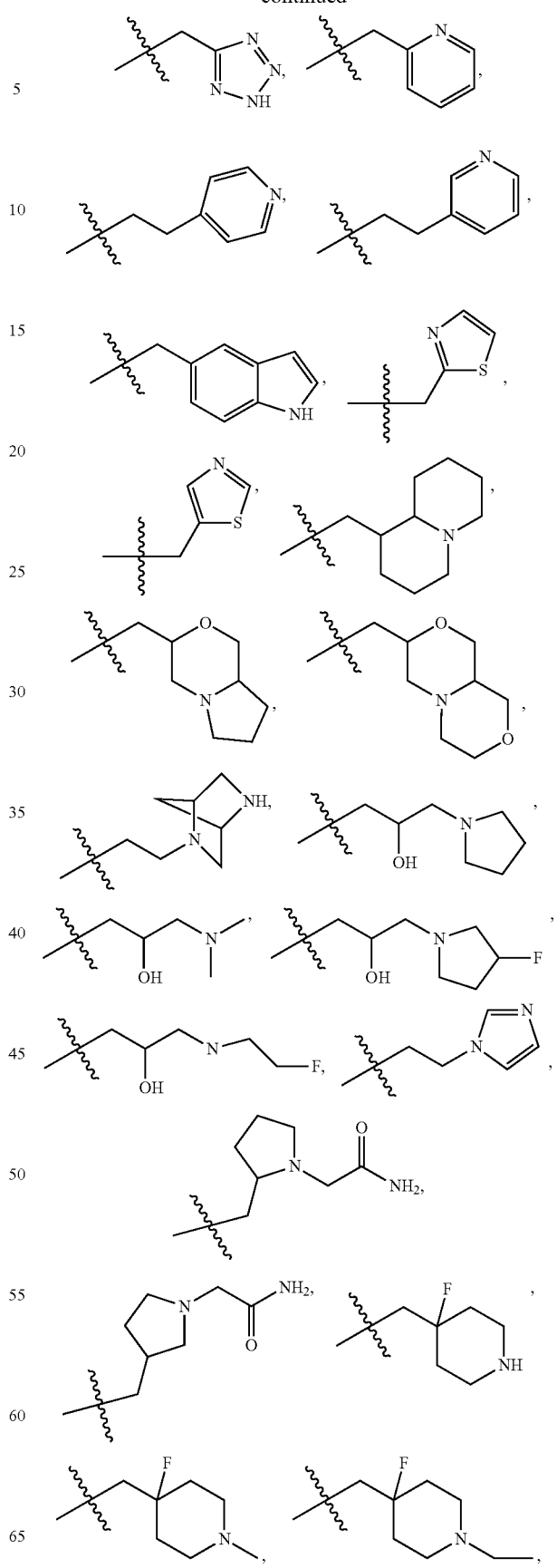

537
-continued
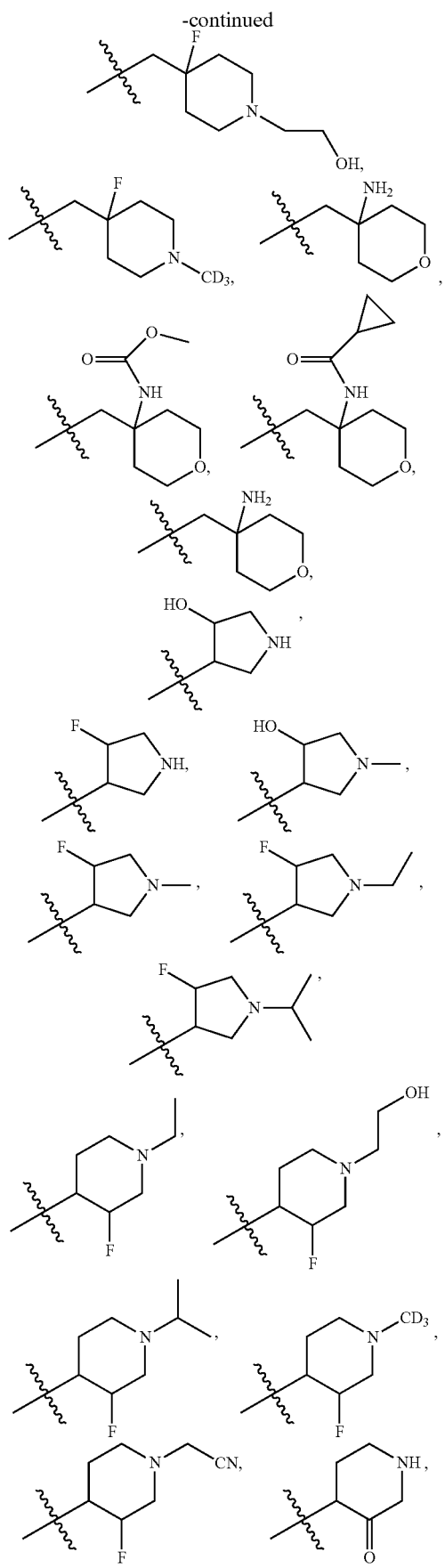
538
-continued
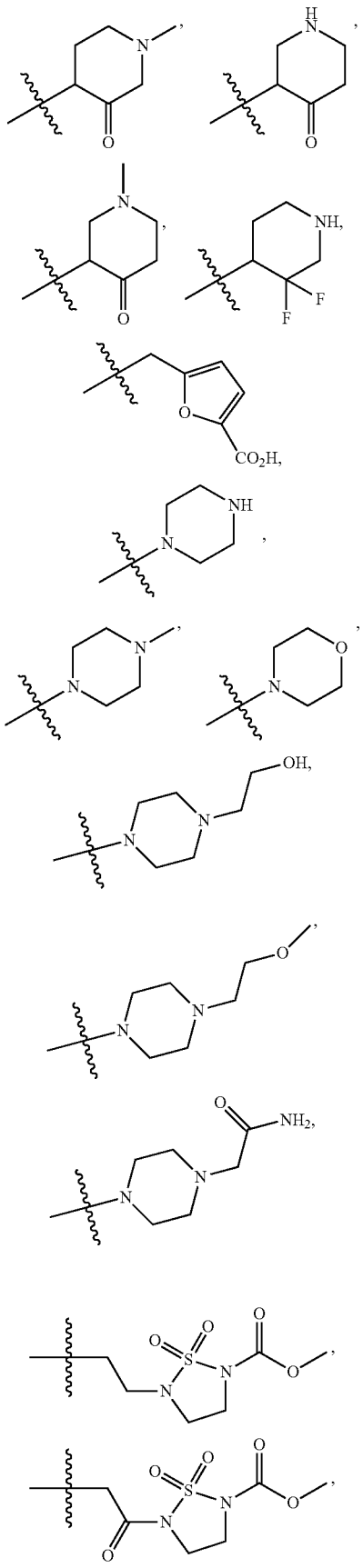

539
-continued

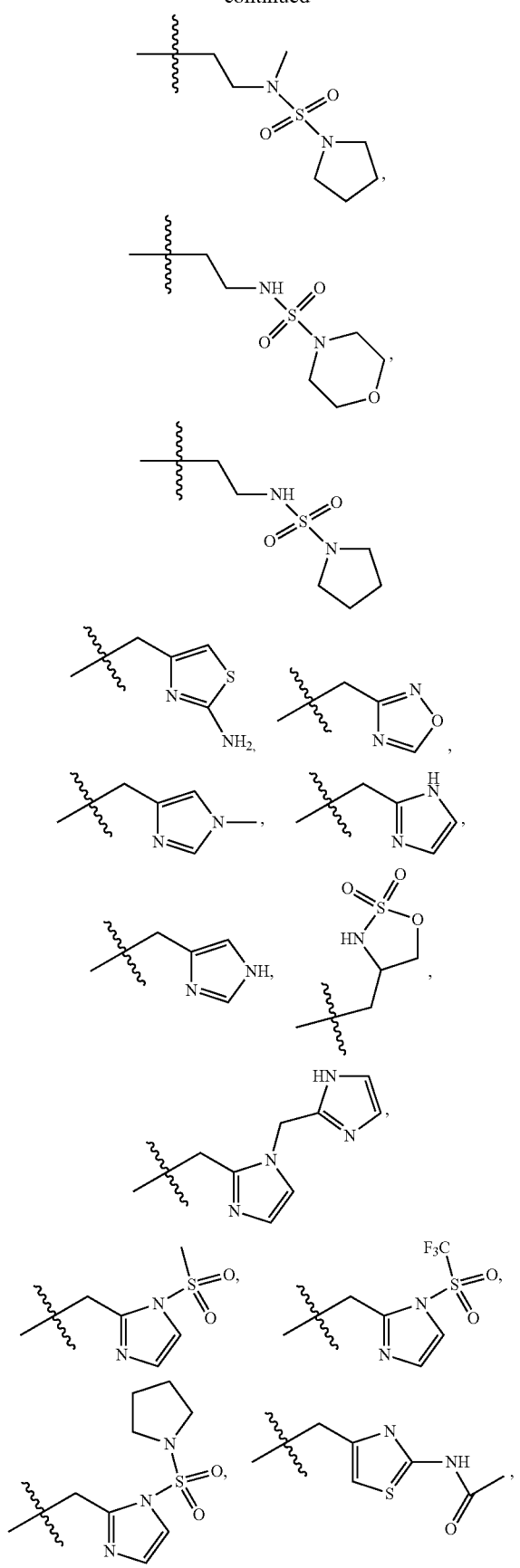

540
-continued

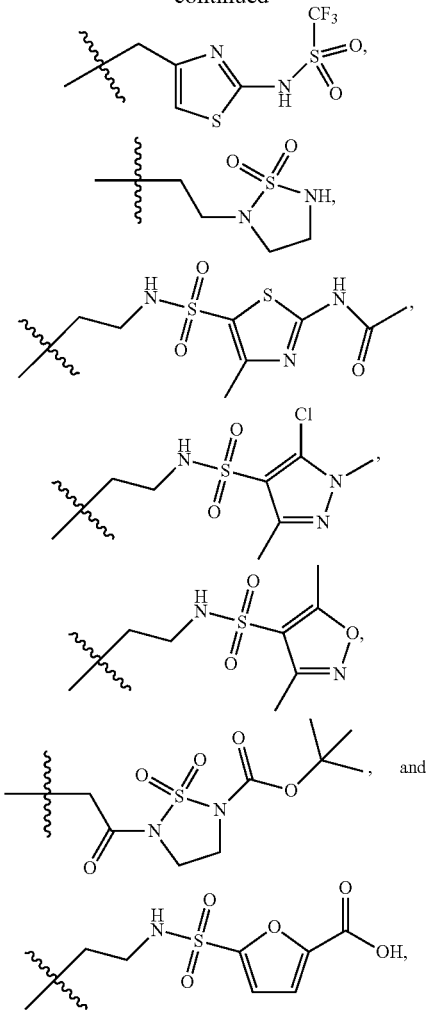

R$_2$ is halo-substituted C$_{1-3}$alkyl;
R$_3$ is halo or halo-substituted C$_{1-3}$alkyl;
R$_4$ is H or halo
R$_5$ is H;
R$_6$ is H or F; and
R$_7$ is H or F.

3. The compound of claim 2 wherein
X is CR$_4$;
Y is N;
L is a bond;
R$_2$ is CF$_3$;
R$_3$ is F, Cl, CF$_3$ or OCH$_3$;
R$_4$ is H, hydroxyl, Cl, OCH$_3$ or CH$_3$;
R$_5$ is H;
R$_6$ is H; and
R$_7$ is H.

4. The compound of claim 3 wherein
X is CR$_4$;
Y is N;
R$_3$ is C$_1$, CF$_3$ or OCH$_3$; and
R$_4$ is H, Cl, or CH$_3$.

5. The compound of claim 4 wherein
X is CR$_4$;
Y is N;
L is a bond;
R$_3$ is C$_1$, CF$_3$ or OCH$_3$; and
R$_4$ is H, Cl, or CH$_3$.

6. The compound of claim 3 wherein
X is $CR_4$;
Y is N;
L is a bond;
$R_3$ is $C_1$, $CF_3$ or $OCH_3$; and
$R_4$ is H, Cl, or $CH_3$.

7. The compound of claim 1 wherein
X is $CR_4$;
Y is N;
L is a bond;
$R_1$ is selected from

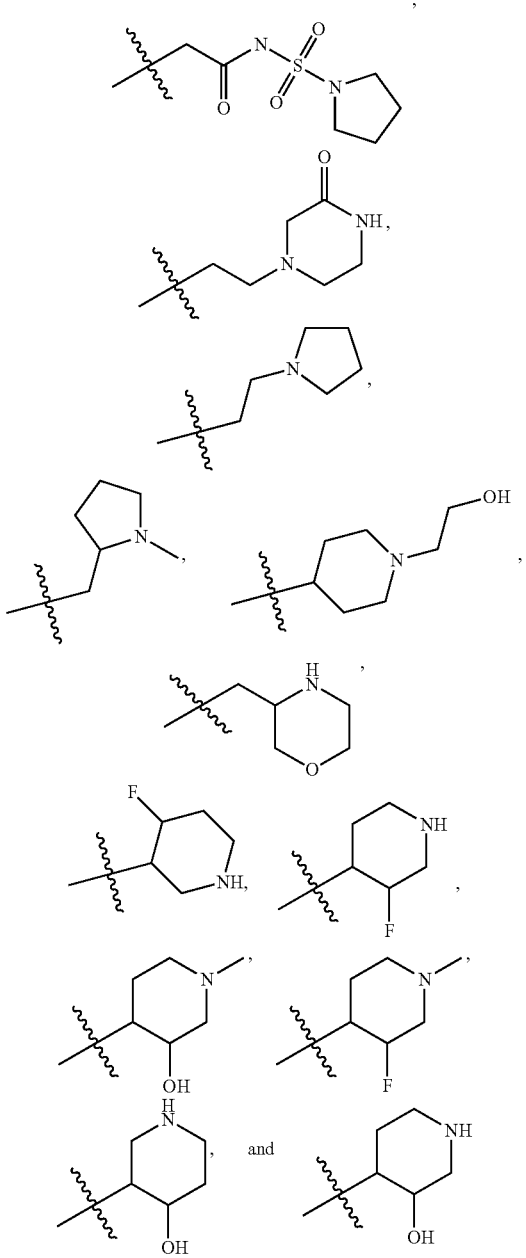

$R_2$ is halo-substituted $C_{1-3}$alkyl;
$R_3$ is halo or halo-substituted $C_{1-3}$alkyl;
$R_4$ is H or halo
$R_5$ is H;
$R_6$ is H or F; and
$R_7$ is H or F.

8. The compound of claim 7 wherein
X is $CR_4$;
Y is N;
L is a bond;
$R_2$ is $CF_3$;
$R_3$ is F, Cl, $CF_3$ or $OCH_3$;
$R_4$ is H, hydroxyl, Cl, $OCH_3$ or $CH_3$;
$R_5$ is H;
$R_6$ is H; and
$R_7$ is H.

9. The compound of claim 8 wherein
X is $CR_4$;
Y is N;
$R_3$ is $C_1$, $CF_3$ or $OCH_3$; and
$R_4$ is H, Cl, or $CH_3$.

10. The compound of claim 9 wherein
X is $CR_4$;
Y is N;
L is a bond;
$R_3$ is $C_1$, $CF_3$ or $OCH_3$; and
$R_4$ is H, Cl, or $CH_3$.

11. The compound of claim 8 wherein
X is $CR_4$;
Y is N;
L is a bond;
$R_3$ is $C_1$, $CF_3$ or $OCH_3$; and
$R_4$ is H, Cl, or $CH_3$.

12. The compound of claim 1 wherein
X is $CR_4$;
Y is N;
L is a bond;
$R_1$ is selected from

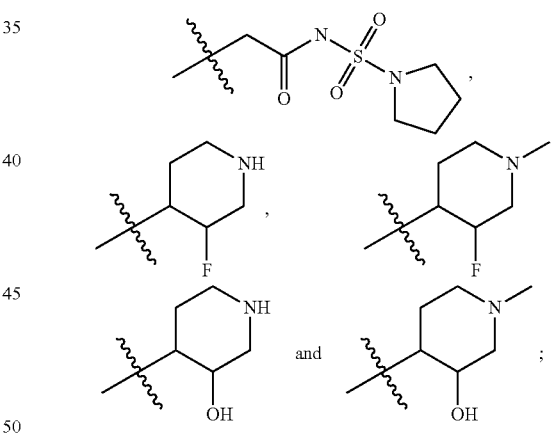

$R_2$ is halo-substituted $C_{1-3}$alkyl;
$R_3$ is halo or halo-substituted $C_{1-3}$alkyl;
$R_4$ is H or halo
$R_5$ is H;
$R_6$ is H or F; and
$R_7$ is H or F.

13. The compound of claim 12 wherein
X is $CR_4$;
Y is N;
L is a bond;
$R_2$ is $CF_3$;
$R_3$ is F, Cl, $CF_3$ or $OCH_3$;
$R_4$ is H, hydroxyl, Cl, $OCH_3$ or $CH_3$;
$R_5$ is H;
$R_6$ is H; and
$R_7$ is H.

14. The compound of claim 13 wherein
X is CR$_4$;
Y is N;
R$_3$ is C$_1$, CF$_3$ or OCH$_3$; and
R$_4$ is H, Cl, or CH$_3$.

15. The compound of claim 13 wherein
X is CR$_4$;
Y is N;
L is a bond;
R$_3$ is C$_1$, CF$_3$ or OCH$_3$; and
R$_4$ is H, Cl, or CH$_3$.

16. The compound of claim 13 wherein
X is CR$_4$;
Y is N;
L is a bond;
R$_3$ is C$_1$, CF$_3$ or OCH$_3$; and
R$_4$ is H, Cl, or CH$_3$.

17. The compound of claim 1 selected from
2-[(5Z)-5-({1-[4-Chloro-2-(trifluoromethyl)benzyl]-1H-indazol-5-yl}methylidene)-2,4-dioxo-1,3-thiazolidin-3-yl]-N-(pyrrolidin-1-ylsulfonyl)acetamide;
(5Z)-5-({1-[4-chloro-2-(trifluoromethyl)benzyl]-1H-indazol-5-yl}methylidene)-3-(trans-3-hydroxy-1-methylpiperidin-4-yl)-1,3-thiazolidine-2,4-dione;
(5Z)-5-({1-[4-chloro-2-(trifluoromethyl)benzyl]-1H-indazol-5-yl}methylidene)-3-(trans-3-fluoro-1-methylpiperidin-4-yl)-1,3-thiazolidine-2,4-dione;
(5Z)-5-({1-[4-chloro-2-(trifluoromethyl)benzyl]-1H-indazol-5-yl}methylidene)-3-(trans-3-hydroxypiperidin-4-yl)-1,3-thiazolidine-2,4-dione;
(5Z)-5-({1-[4-chloro-2-(trifluoromethyl)benzyl]-3-methyl-1H-indazol-5-yl}methylidene)-3-(trans-3-fluoropiperidin-4-yl)-1,3-thiazolidine-2,4-dione;
(5Z)-5-({1-[4-chloro-2-(trifluoromethyl)benzyl]-3-methyl-1H-indazol-5-yl}methylidene)-3-(trans-3-fluoro-1-methylpiperidin-4-yl)-1,3-thiazolidine-2,4-dione;
(5Z)-5-({1-[4-Chloro-2-(trifluoromethyl)benzyl]-1H-indazol-5-yl}methylidene)-3-[(3S)-morpholin-3-ylmethyl]-1,3-thiazolidine-2,4-dione;
(5Z)-5-({1-[2,4-Bis(trifluoromethyl)benzyl]-1H-indazol-5-yl}methylidene)-3-(cis-4-fluoropiperidin-3-yl)-1,3-thiazolidine-2,4-dione;
(5Z)-5-({1-[4-Chloro-2-(trifluoromethyl)benzyl]-1H-indazol-5-yl}methylidene)-3-(cis-4-fluoropiperidin-3-yl)-1,3-thiazolidine-2,4-dione;
(5Z)-5-({1-[4-Chloro-2-(trifluoromethyl)benzyl]-1H-indazol-5-yl}methylidene)-3-(2H-tetrazol-5-ylmethyl)-1,3-thiazolidine-2,4-dione;
(5Z)-5-({1-[4-Chloro-2-(trifluoromethyl)benzyl]-1H-indazol-5-yl}methylidene)-3-[1-(2-hydroxyethyl)piperidin-4-yl]-1,3-thiazolidine-2,4-dione;
(5Z)-5-({1-[4-Chloro-2-(trifluoromethyl)benzyl]-1H-indazol-5-yl}methylidene)-3-(2-pyrrolidin-1-ylethyl)-1,3-thiazolidine-2,4-dione;
(5Z)-5-({1-[4-Chloro-2-(trifluoromethyl)benzyl]-1H-indazol-5-yl}methylidene)-3-{[(2S)-1-methylpyrrolidin-2-yl]methyl}-1,3-thiazolidine-2,4-dione;
(5Z)-5-({1-[4-Chloro-2-(trifluoromethyl)benzyl]-1H-indazol-5-yl}methylidene)-3-(trans-4-hydroxypiperidin-3-yl)-1,3-thiazolidine-2,4-dione;
(5Z)-5-({1-[4-Chloro-2-(trifluoromethyl)benzyl]-1H-indazol-5-yl}methylidene)-3-(trans-3-fluoropiperidin-4-yl)-1,3-thiazolidine-2,4-dione;
(5Z)-5-({1-[4-Chloro-2-(trifluoromethyl)benzyl]-1H-indazol-5-yl}methylidene)-3-[(3R,4R)-3-fluoropiperidin-4-yl]-1,3-thiazolidine-2,4-dione;
(5Z)-5-({1-[4-Chloro-2-(trifluoromethyl)benzyl]-1H-indazol-5-yl}methylidene)-3-[(3S,4S)-3-fluoropiperidin-4-yl]-1,3-thiazolidine-2,4-dione;
(5Z)-5-({1-[4-Chloro-2-(trifluoromethyl)benzyl]-1H-indazol-5-yl}methylidene)-3-[(3R,4R)-3-fluoro-1-methylpiperidin-4-yl]-1,3-thiazolidine-2,4-dione;
(5Z)-5-({1-[4-Chloro-2-(trifluoromethyl)benzyl]-1H-indazol-5-yl}methylidene)-3-[(3S,4S)-3-fluoro-1-methylpiperidin-4-yl]-1,3-thiazolidine-2,4-dione; and
(5Z)-5-({1-[4-Chloro-2-(trifluoromethyl)benzyl]-1H-indazol-5-yl}methylidene)-3-[(trans)-3-fluoro-1-(2-hydroxyethyl)piperidin-4-yl]-1,3-thiazolidine-2,4-dione.

18. The compound of claim 1 selected from
(5Z)-5-({1-[4-Chloro-2-(trifluoromethyl)benzyl]-1H-indazol-5-yl}methylidene)-3-(morpholin-3-ylmethyl)-1,3-thiazolidine-2,4-dione;
(5Z)-5-({1-[4-chloro-2-(trifluoromethyl)benzyl]-1H-indazol-5-yl}methylidene)-3-(trans-3-hydroxy-1-methylpiperidin-4-yl)-1,3-thiazolidine-2,4-dione;
(5Z)-5-({1-[4-chloro-2-(trifluoromethyl)benzyl]-1H-indazol-5-yl}methylidene)-3-(trans-3-fluoro-1-methylpiperidin-4-yl)-1,3-thiazolidine-2,4-dione;
(5Z)-5-({1-[4-chloro-2-(trifluoromethyl)benzyl]-1H-indazol-5-yl}methylidene)-3-(trans-3-hydroxypiperidin-4-yl)-1,3-thiazolidine-2,4-dione;
(5Z)-5-({1-[4-chloro-2-(trifluoromethyl)benzyl]-3-methyl-1H-indazol-5-yl}methylidene)-3-(trans-3-fluoropiperidin-4-yl)-1,3-thiazolidine-2,4-dione;
(5Z)-5-({1-[4-chloro-2-(trifluoromethyl)benzyl]-3-methyl-1H-indazol-5-yl}methylidene)-3-(trans-3-fluoro-1-methyl piperidin-4-yl)-1,3-thiazolidine-2,4-dione;
(5Z)-5-({1-[4-Chloro-2-(trifluoromethyl)benzyl]-1H-indazol-5-yl}methylidene)-3-(trans-4-hydroxypiperidin-3-yl)-1,3-thiazolidine-2,4-dione;
(5Z)-5-({1-[4-Chloro-2-(trifluoromethyl)benzyl]-1H-indazol-5-yl}methylidene)-3-(trans-3-fluoropiperidin-4-yl)-1,3-thiazolidine-2,4-dione;
(5Z)-5-({1-[4-Chloro-2-(trifluoromethyl)benzyl]-1H-indazol-5-yl}methylidene)-3-[(3R,4R)-3-fluoropiperidin-4-yl]-1,3-thiazolidine-2,4-dione;
(5Z)-5-({1-[4-Chloro-2-(trifluoromethyl)benzyl]-1H-indazol-5-yl}methylidene)-3-[(3S,4S)-3-fluoropiperidin-4-yl]-1,3-thiazolidine-2,4-dione;
(5Z)-5-({1-[4-Chloro-2-(trifluoromethyl)benzyl]-1H-indazol-5-yl}methylidene)-3-[(3R,4R)-3-fluoro-1-methylpiperidin-4-yl]-1,3-thiazolidine-2,4-dione;
(5Z)-5-({1-[4-Chloro-2-(trifluoromethyl)benzyl]-1H-indazol-5-yl}methylidene)-3-[(3S,4S)-3-fluoro-1-methylpiperidin-4-yl]-1,3-thiazolidine-2,4-dione; and
(5Z)-5-({1-[4-Chloro-2-(trifluoromethyl)benzyl]-1H-indazol-5-yl}methylidene)-3-[(trans)-3-fluoro-1-(2-hydroxyethyl)piperidin-4-yl]-1,3-thiazolidine-2,4-dione.

19. The compound of claim 1 selected from
(5Z)-5-({1-[4-chloro-2-(trifluoromethyl)benzyl]-1H-indazol-5-yl}methylidene)-3-(trans-3-fluoro-1-methylpiperidin-4-yl)-1,3-thiazolidine-2,4-dione;
(5Z)-5-({1-[4-chloro-2-(trifluoromethyl)benzyl]-3-methyl-1H-indazol-5-yl}methylidene)-3-(trans-3-fluoropiperidin-4-yl)-1,3-thiazolidine-2,4-dione;
(5Z)-5-({1-[4-chloro-2-(trifluoromethyl)benzyl]-3-methyl-1H-indazol-5-yl}methylidene)-3-(trans-3-fluoro-1-methylpiperidin-4-yl)-1,3-thiazolidine-2,4-dione;
(5Z)-5-({1-[4-Chloro-2-(trifluoromethyl)benzyl]-1H-indazol-5-yl}methylidene)-3-(trans-3-fluoropiperidin-4-yl)-1,3-thiazolidine-2,4-dione;

(5Z)-5-({1-[4-Chloro-2-(trifluoromethyl)benzyl]-1H-indazol-5-yl}methylidene)-3-[(3R,4R)-3-fluoropiperidin-4-yl]-1,3-thiazolidine-2,4-dione;

(5Z)-5-({1-[4-Chloro-2-(trifluoromethyl)benzyl]-1H-indazol-5-yl}methylidene)-3-[(3S,4S)-3-fluoropiperidin-4-yl]-1,3-thiazolidine-2,4-dione;

(5Z)-5-({1-[4-Chloro-2-(trifluoromethyl)benzyl]-1H-indazol-5-yl}methylidene)-3-[(3R,4R)-3-fluoro-1-methylpiperidin-4-yl]-1,3-thiazolidine-2,4-dione;

(5Z)-5-({1-[4-Chloro-2-(trifluoromethyl)benzyl]-1H-indazol-5-yl}methylidene)-3-[(3S,4S)-3-fluoro-1-methylpiperidin-4-yl]-1,3-thiazolidine-2,4-dione; and (5Z)-5-({1-[4-Chloro-2-(trifluoromethyl)benzyl]-1H-indazol-5-yl}methylidene)-3-[(trans)-3-fluoro-1-(2-hydroxyethyl)piperidin-4-yl]-1,3-thiazolidine-2,4-dione.

20. A pharmaceutical composition comprising at least one compound of claim 1 and at least one pharmaceutically acceptable carrier.

21. A method of treating a subject suffering from or diagnosed with a disease, disorder, or condition mediated by ERR-α activity, comprising administering to the subject a therapeutically effective amount of at least one compound of claim 1.

22. A method according to claim 21, wherein the disease, disorder, or medical condition is selected from the group consisting of bone-related disease, bone formation, cartilage formation, cartilage loss, cartilage degeneration, cartilage injury, ankylosing spondylitis, chronic back injury, gout, osteoporosis, osteolytic bone metastasis, multiple myeloma, chondrosarcoma, chondrodysplasia, osteogenesis imperfecta, osteomalacia, Paget's disease, polymyalgia rheumatica, pseudogout, arthritis, rheumatoid arthritis, infectious arthritis, osteoarthritis, psoriatic arthritis, reactive arthritis, childhood arthritis, Reiter's syndrome, and repetitive stress injury.

23. A method according to claim 21, wherein the disease, disorder, or condition is selected from the group consisting of periodontal disease, chronic inflammatory airway disease, chronic bronchitis, and chronic obstructive pulmonary disease.

24. A method according to claim 21, wherein the disease, disorder, or condition is breast cancer.

25. A method according to claim 21, wherein the disease, disorder, or condition is selected from the group consisting of metabolic syndrome, obesity, disorders of energy homeostasis, diabetes, lipid disorders, cardiovascular disorders, atherosclerosis, hyperglycemia, elevated blood glucose level, and insulin resistance.

26. A method for ameliorating or inhibiting the progression of an ERR-α-mediated condition in a subject in need thereof, comprising administering to said subject a therapeutically effective amount of at least one compound according to claim 1.

27. A method for treating a prediabetic condition in a subject in need thereof, comprising administering to said subject a therapeutically effective amount of at least one compound according to claim 1.

28. A process for making a pharmaceutical composition comprising admixing any of the compounds according to claim 1 and a pharmaceutically acceptable carrier.

* * * * *